US012729213B2

(12) United States Patent
Wang et al.

(10) Patent No.: US 12,729,213 B2
(45) **Date of Patent: *Sep. 8, 2026**

(54) SMALL MOLECULE DEGRADERS OF STAT3

(71) Applicant: THE REGENTS OF THE UNIVERSITY OF MICHIGAN, Ann Arbor, MI (US)

(72) Inventors: Shaomeng Wang, Superior Township, MI (US); Haibin Zhou, Ann Arbor, MI (US); Renqi Xu, Ann Arbor, MI (US); Longchuan Bai, Ann Arbor, MI (US); Donna McEachern, Ann Arbor, MI (US); Jeanne Stuckey, Fenton, MI (US); Chao-Yie Yang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1250 days.

This patent is subject to a terminal disclaimer.

(21) Appl. No.: 17/442,666

(22) PCT Filed: Mar. 26, 2020

(86) PCT No.: PCT/US2020/024892

§ 371 (c)(1),
(2) Date: Sep. 24, 2021

(87) PCT Pub. No.: WO2020/198435

PCT Pub. Date: Oct. 1, 2020

(65) Prior Publication Data

US 2023/0083015 A1 Mar. 16, 2023

Related U.S. Application Data

(60) Provisional application No. 62/884,995, filed on Aug. 9, 2019, provisional application No. 62/823,949, filed on Mar. 26, 2019.

(51) Int. Cl.
*A61P 35/00* (2006.01)
*C07F 9/38* (2006.01)

(52) U.S. Cl.
CPC ............ *C07F 9/3882* (2013.01); *A61P 35/00* (2018.01)

(58) Field of Classification Search
CPC ...... C07F 9/3882; C07F 9/6561; A61P 35/00; A61K 31/675; A61K 45/06; A61K 2300/00; C07K 5/0812; C07K 5/0821; C07K 5/1024; C07D 401/14; C07D 405/14
See application file for complete search history.

(56) References Cited

U.S. PATENT DOCUMENTS

| | | | |
|---|---|---|---|
| 5,093,330 | A | 3/1992 | Caravatti et al. |
| 6,207,156 | B1 | 3/2001 | Kuchroo et al. |
| 6,808,710 | B1 | 10/2004 | Wood et al. |
| 6,984,720 | B1 | 1/2006 | Korman et al. |
| 7,595,048 | B2 | 9/2009 | Honjo et al. |
| 8,008,449 | B2 | 8/2011 | Korman et al. |
| 8,114,845 | B2 | 2/2012 | Langermann et al. |
| 8,217,149 | B2 | 7/2012 | Irving et al. |
| 8,522,156 | B2 | 8/2013 | Kumagai et al. |

(Continued)

FOREIGN PATENT DOCUMENTS

| | | | |
|---|---|---|---|
| WO | WO-2010/077589 | A2 | 7/2010 |
| WO | WO-2010/118309 | A2 | 10/2010 |

(Continued)

OTHER PUBLICATIONS

Anderson, A. C., "Tim-3: an emerging target in the cancer immunotherapy landscape" Cancer Immunology Research, (2014); 2(5):393-398.

(Continued)

*Primary Examiner* — Kara R. Mcmillian
*Assistant Examiner* — Sophia P Hirakis
(74) *Attorney, Agent, or Firm* — MARSHALL, GERSTEIN & BORUN LLP

(57) ABSTRACT

The present disclosure provides compounds represented by Formula I or Formula VIII: wherein $R^{1a}$, $R^{1b}$, M, A, E, $Q^A$, and $Q^B$ are as defined in the specification, and the salts and solvates thereof. Compounds of Formula I are degraders of STAT3 or degraders of STAT3 and STAT1. Compounds of Formula VIII are inhibitors of STAT3. STAT3 degraders and inhibitors are useful for the treatment of cancer and other diseases.

I

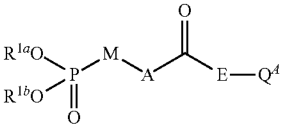

or

VIII

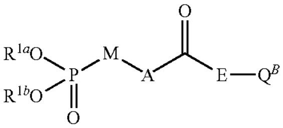

17 Claims, 63 Drawing Sheets

(56) References Cited

U.S. PATENT DOCUMENTS

| | | | | |
|---|---|---|---|---|
| 8,728,474 | B2 | 5/2014 | Honjo et al. | |
| 8,779,105 | B2 | 7/2014 | Korman et al. | |
| 8,900,587 | B2 | 12/2014 | Carven et al. | |
| 8,907,053 | B2 | 12/2014 | Sasikumar et al. | |
| 8,952,136 | B2 | 2/2015 | Carven et al. | |
| 9,073,994 | B2 | 7/2015 | Honjo et al. | |
| 9,084,776 | B2 | 7/2015 | Korman et al. | |
| 2007/0010428 | A1 | 1/2007 | McMurray et al. | |
| 2011/0150892 | A1 | 6/2011 | Thudium et al. | |
| 2013/0022623 | A1 | 1/2013 | Karsunky et al. | |
| 2013/0071403 | A1 | 3/2013 | Rolland et al. | |
| 2013/0309250 | A1 | 11/2013 | Cogswell et al. | |
| 2014/0093511 | A1 | 4/2014 | Lonberg et al. | |
| 2014/0286935 | A1 | 9/2014 | Hamblin et al. | |
| 2014/0341917 | A1 | 11/2014 | Nastri et al. | |
| 2015/0225457 | A1 | 8/2015 | Blumberg et al. | |
| 2015/0250853 | A1 | 9/2015 | Mak | |
| 2015/0259420 | A1 | 9/2015 | Triebel et al. | |
| 2022/0185831 | A1 | 6/2022 | Wang et al. | |
| 2023/0133504 | A1 * | 5/2023 | Reddy .................. | A61K 31/661 514/114 |
| 2023/0159573 | A1 * | 5/2023 | Wang ...................... | A61P 35/00 514/81 |

FOREIGN PATENT DOCUMENTS

| | | | |
|---|---|---|---|
| WO | WO-2015036499 | A1 | 3/2015 |
| WO | WO-2015/127548 | A1 | 9/2015 |
| WO | WO-2019/036815 | A1 | 2/2019 |
| WO | WO-2020/198435 | A1 | 10/2020 |
| WO | WO-2020/205467 | A1 | 10/2020 |
| WO | WO-2020/206424 | A1 | 10/2020 |
| WO | WO-2021/016333 | A1 | 1/2021 |
| WO | WO-2021/195481 | A1 | 9/2021 |
| WO | WO-2021188696 | A1 | 9/2021 |
| WO | WO-2022/182395 | A1 | 9/2022 |
| WO | WO-2023250058 | A1 | 12/2023 |
| WO | WO-2024148041 | A1 | 7/2024 |
| WO | WO-2024173291 | A1 | 8/2024 |
| WO | WO-2024173298 | A1 | 8/2024 |

OTHER PUBLICATIONS

Bai et al., "Targeted Degradation of BET Proteins in Triple-Negative Breast Cancer" Cancer Res., (2017); 77(9):2476-2487.

Banerjee et al., "Constitutive activation of STAT3 in breast cancer cells: A review" Int. J. Cancer, (2016); 138(11):2570-2578.

Betts, B.C. et al., "CD4+ T cell STAT3 phosphorylation precedes acute GVHD, and subsequent Th17 tissue invasion correlates with GVHD severity and therapeutic response," Journal of Leukocyte Biology, (Apr. 2015); 97:807-819.

Bingham et al., "Over one hundred solvates of sulfathiazole Electronic supplementary information (ESI) available: solvates and adducts of sulfathiazole," Chemical Communications, (Mar. 13, 2001); Issue 7, pp. 603-604.

Bondeson, D. P., et al., "Catalytic in vivo protein knockdown by small-molecule PROTACS", Nature Chemical Biology (2015); 11(8): 611-617.

Caira et al., "Preparation and Crystal Characterization of a Polymorph, a Monohydrate, and an Ethyl Acetate Solvate of the Antifungal Fluconazole" J. Pharm. Sci., (Mar. 2004); 93(3):601-611.

Fischer, E.S. et al., "Structure of the DDB1-CRBN E3 Ubiquitin ligase in complex with thalidomide", Nature (2014); 512(7512):49-53.

Haura et al., "Mechanisms of disease: Insights into the emerging role of signal transducers and activators of transcription in cancer" Nat Clin Pract Oncol, (Jun. 2005); 2(6):315-324. doi: 10.1038/ncponc0195.

Huang et al., "Role of LAG-3 in regulatory T cells" Immunity, (2004); 21(4):503-513.

Johnson et al., "Targeting the IL-6/JAK/STAT3 signalling axis in cancer" Nat Rev Clin Oncol, (Apr. 2018); 15(4):234-248. doi: 10.1038/nrclinonc.2018.8. Epub Feb. 6, 2018.

Kortylewski et al., "Targeting STAT3 affects melanoma on multiple fronts" Cancer Metastasis Rev, (Jun. 2005); 24(2):315-327. doi: 10.1007/s10555-005-1580-1.

Laurence, A. et al., "STAT3 transcription factor promotes instability of nTreg cells and limits generation of iTreg cells during acute murine graft-versus-host disease" Immunity, (Aug. 2012); 37(2):209-22. doi: 10.1016/j.immuni.2012.05.027.

Lüb et al., "IDO1 and IDO2 are expressed in human tumors: levo-but not dextro-1-methyl tryptophan inhibits tryptophan catabolism" Cancer Immunol. Immunother., (2009); 58(1):153-157.

Li et al., "Discovery of MD-224 as a First-in-Class, Highly Potent, and Efficacious Proteolysis Targeting Chimera Murine Double Minute 2 Degrader Capable of Achieving Complete and Durable Tumor Regression" J Med Chem, (Jan. 2019); 62(2):448-466. doi: 10.1021/acs.jmedchem.8b00909. Epub Dec. 10, 2018.

Lu, S.X. et al., "STAT-3 and ERK 1/2 phosphorylation are critical for T-cell alloactivation and graft-versus-host disease," Blood, (Dec. 15, 2008); 112(13):5254-5258, DOI 10.1182/blood-2008-03-147322.

Miklossy, G. et al., "Therapeutic modulators of STAT signalling for human diseases" Nature Reviews Drug Discovery, (2013); 12(8):611-629.

Morlacchi et al., "Synthesis and in Vitro Evaluation of a Peptidomimetic Inhibitor Targeting the Src Homology 2 (SH2) Domain of STAT6" ACS Med Chem Lett, (Dec. 4, 2013); 5(1):69-72. doi: 10.1021/ml4003919.

Naido et al., "Immune modulation for cancer therapy" British Journal of Cancer, (2014); 111(12):2214-2219.

Ngiow et al., "Anti-TIM3 antibody promotes T cell IFN-γ-mediated antitumor immunity and suppresses established tumors" Cancer Res, (May 2011); 71(10):3540-51. doi: 10.1158/0008-5472.CAN-11-0096. Epub Mar. 23, 2011.

Ngiow et al., "ProSpects for TIM3-Targeted Antitumor Immunotherapy" Cancer Res., (2011); 71(21):6567-6571.

Pardoll, "The blockade of immune checkpoints in cancer immunotherapy" Nat. Rev. Cancer, (2012); 12(4):252-264.

Qian et al., "Efficacy of levo-1-methyl tryptophan and dextro-1-methyl tryptophan in reversing indoleamine-2,3-dioxygenase-mediated arrest of T-cell proliferation in human epithelial ovarian cancer" Cancer Res., (2009); 69(13):5498-5504.

Qin et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression" J. Med. Chem., (2018); 61(15):6685-6704. HHS Public Access Author Manuscript; available in PMC Aug. 9, 2019; 48 pages.

Radojcic, V. et al., "STAT3 Signaling in CD4+ T Cells Is Critical for the Pathogenesis of Chronic Sclerodermatous Graft-Versus-Host Disease in a Murine Model," The Journal of Immunology, (2010); 184(2):764-774, https://doi.org/10.4049/jimmunol.0903006.

Raina, K. et al., "Chemical Inducers of Targeted Protein Degradation", Journal of Biological Chemistry (2010); 285(15):11057-11060.

Raina, K. et al., "PROTAC-induced BET protein degradation as a therapy for castration-resistant prostate cancer", Proceedings of the National Academy of Sciences (2016); 113(26):7124-7129.

Sakamoto, K.M. et al., "Protacs: Chimeric molecules that target proteins to the Skp1-Cullin-F box complex for ubiquitination and degradation", Proceedings of the National Academy of Sciences, (2001); 98(15):8554-8559.

Toure, M. et al., "Small-molecule PROTACS: new approaches to protein degradation", Angewandte Chemie International Edition (2016); 55(6):1966-1973.

Unanue, E.R. "Perspectives on anti-CD47 antibody treatment for experimental cancer" Proceedings of the National Academy of Sciences, (Jul. 2, 2013); 110(27):10886-10887.

Van Tonder et al., "Preparation and Physicochemical Characterization of 5 Niclosamide Solvates and 1 Hemisolvate," AAPS Pharm. Sci. Tech., (2004); 5(1):86-95.

(56) References Cited

OTHER PUBLICATIONS

Wang et al., "STAT3 inhibition, a novel approach to enhancing targeted therapy in human cancers (review)" Int J Onco, (Oct. 2012); 41(4):1181-1191. doi: 10.3892/ijo.2012.1568. Epub Jul. 24, 2012.
Yu et al., "The STATs of cancer—new molecular targets come of age" Nat Rev Cancer, (Feb. 2004); 4(2):97-105. doi: 10.1038/nrc1275.
Yue et al., "Targeting STAT3 in cancer: how successful are we?" Expert Opin Investig Drugs, (Jan. 2009); 18(1):45-56. doi: 10.1517/13543780802565791.
Zhou, B. et al., "Discovery of a Small-Molecule Degrader of Bromodomain and Extra-Terminal (BET) Proteins with Picomolar Cellular Potencies and Capable of Achieving Tumor Regression", Journal of Medicinal Chemistry (2018); 61(2): 462-481.
Bai et al., "A Potent and Selective Small-Molecule Degrader of STAT3 Achieves Complete Tumor Regression In Vivo.," Cancer Cell, vol. 36, No. 5, pp. 498-511.e17 (Nov. 2019).
Chen et al., "Structure-Based Design of Conformationally Constrained, Cell-Permeable STAT3 Inhibitors", ACS Medicinal Chemistry Letters, vol. 1, No. 2, pp. 85-89 (Mar. 2010).
Coleman et al., "Investigation of the Binding Determinants of Phosphopeptides Targeted to the Src Homology 2 Doman of the Signal Transducer and Activator of Transcription 3. Development of a High-Affinity Peptide Inhibitor," J. Med. Chem. 48, 6661-6670 (2005).
Debnath et al., "Small Molecule Inhibitors of Signal Transducer and Activator of Transcription 3 (Stat3) Protein," Journal of Medicinal Chemistry, vol. 55, No. 15, pp. 6645-6668 (May 2012).
International Preliminary Report on Patentability, mailed Oct. 14, 2021, for International Application No. PCT/US2020/025116 (10 pages).
International Preliminary Report on Patentability, mailed Oct. 6, 2022, for International Application No. PCT/US2021/024332 (9 total pages).
International Preliminary Report on Patentability, mailed Oct. 7, 2021, for International Application No. PCT/US2020/024892 (15 total pages).
International Search Report and Written Opinion, mailed Aug. 21, 2020, for International Application No. PCT/US2020/024892 (21 total pages).
International Search Report and Written Opinion, mailed Jun. 19, 2020, for International Application No. PCT/US2020/025116 (14 total pages).
International Search Report and Written Opinion, mailed Jun. 28, 2021, for International Application No. PCT/US2021/024332 (10 total pages).
Invitation to Pay Additional Fees and, Where Applicable, Protest Fee, mailed Jun. 24, 2020, for International Application No. PCT/US2020/024892 (17 total pages).
Mandal et al., "Conformationally Constrained Peptidomimetic Inhibitors of Signal Transducer and Activator of Transcription 3: Evaluation and Molecular Modeling," J. Med. Chem., 52, 2429-2442 (2009).
Mandal et al., "Potent and Selective Phosphopeptide Mimetic Prodrugs Targeted to the Src Homology 2 (SH2) Domain of Signal Transducer and Activator of Transcription 3," Journal of Medicinal Chemistry, vol. 54, No. 10, pp. 3549-3563 (Apr. 2011).
Mandal et al., "Structure-Affinity Relationships of Glutamine Mimics Incorporated into Phosphopeptides Targeted to the SH2 Domain of Signal Transducer and Activator of Transcription 3," J. Med. Chem., 52, 6126-6141, (2009).
Mandal et al., "Synthesis of Phosphatase-Stable, Cell-Permeable Peptidomimetic Prodrugs That Target the SH2 Domain of Stat3," Organic Letters, vol. 11, No. 15, pp. 3394-3397, (Jul. 2009).
Mandal et al., "Targeting the Src Homology 2 (SH2) Domain of Signal Transducer and Activator of Transcription 6 (STAT6) with Cell-Permeable, Phosphatase-Stable Phosphopeptide Mimics Potently Inhibits Tyr641 Phosphorylation and Transcriptional Activity," Journal of Medicinal Chemistry, 58, pp. 8970-8984 (2015).
Mandal et al., "Structure-Activity Studies of Phosphopeptidomimetic Prodrugs Targeting the Src Homology 2 (SH2) Domain of Signal Transducer and Activator of Transcription 3 (Stat3)", International Journal of Peptide Research and Therapeutics, vol. 19, No. 1, pp. 3-12, (Jul. 2012).
Ren et al., "identification of a High-Affinity Phosphopeptide Inhibitor of Stat3," Bioorganic and Medicinal Chemistry Letters, vol. 13, No. 4, pp. 633-636 (Feb. 2003).
Thérien et al., "Synthesis of a novel peptidic photoaffinity probe for the PTP-1B enzyme," Bioorganic & Medicinal Chemistry Letters, vol. 14, No. 9, pp. 2319-2322 (2004).
Yao et al., "Structure-based design and synthesis of small molecule protein-tyrosine phosphatase 1B inhibitors," Biooorganic & Medicinal Chemistry, vol. 6, No. 10, pp. 1799-1810 (Oct. 1998).
Yap et al., "Small-molecule inhibitors of dimeric transcription factors: Antagonism of protein-protein and protein-DNA interactions," MedChemComm., vol. 3, No. 5, p. 541 (Jan. 2012).
Zhou et al., "SD-91 as A Potent and Selective STAT3 Degrader Capable of Achieving Complete and Long-Lasting Tumor Regression," ACS Med Chem. Lett., 12, 6, 996-1004 (May 2021).
Zhou et al., "Structure-Based Discovery of SD-36 as a Potent, Selective and Efficacious PROTAC Degrader of STAT3 Protein," Journal of Medicinal Chemstiry, vol. 62, No. 24, pp. 11280-11300 (Nov. 2019).

* cited by examiner

| Cell Lines | Cell Type | $IC_{50}$ (μM) | |
|---|---|---|---|
| | | Cpd. No. 36 | Cpd. No. 200 |
| SU-DHL-1 | ALCL | 0.25 | >10 |
| SUP-M2 | ALCL | 0.13 | >10 |
| KI-JK | ALCL | 0.18 | >10 |
| Karpas-299 | ALCL | 0.98 | >10 |
| DEL | ALCL | 1.48 | >10 |
| SR786 | ALCL | >5 | >10 |
| SU-DHL-6 | nHL | >5 | >10 |
| Pfeiffer | DLCL | >5 | >10 |
| HDLM-2 | HL | >5 | >10 |
| Molm-16 | AML | 0.035 | 2.8 |
| OCI-AML-2 | AML | >5 | >10 |
| HL-60 | AML | >5 | >10 |
| Kasumi-1 | AML | >5 | >10 |
| KG-1 | AML | >5 | >10 |
| Molm-13 | AML | >5 | >10 |
| Mono-mac-6 | AML | >5 | >10 |
| OCI-M2 | AML | >5 | >10 |
| SKM-1 | AML | >5 | >10 |

Fig. 12

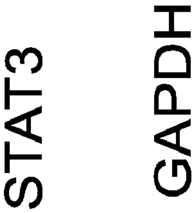
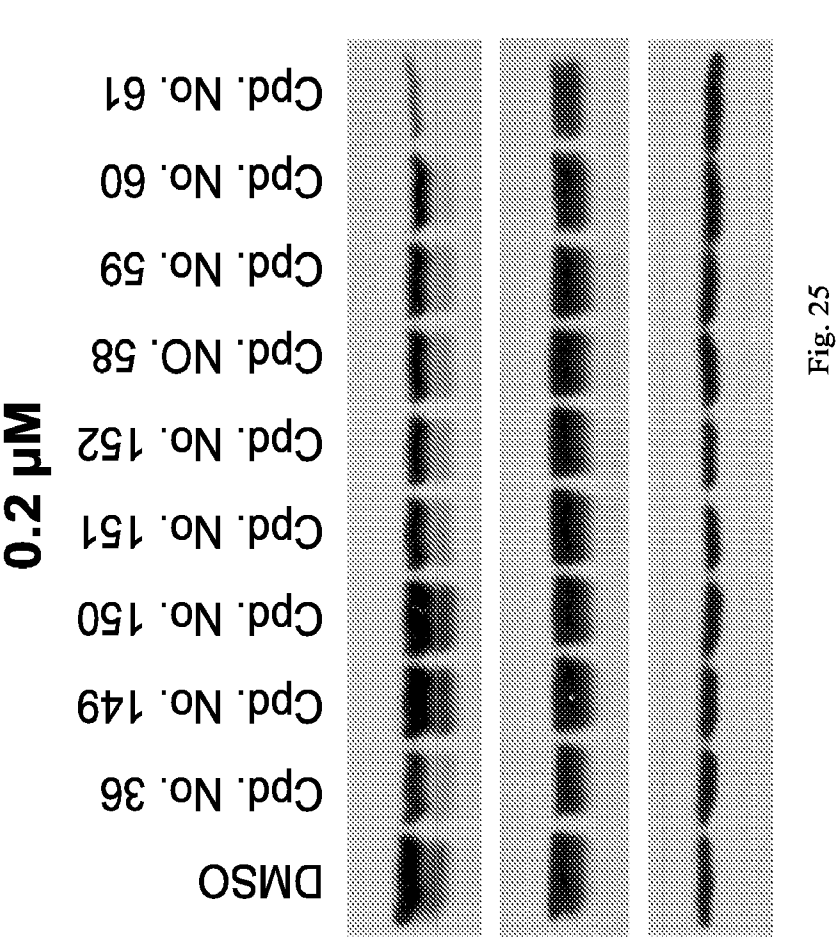
Fig. 25

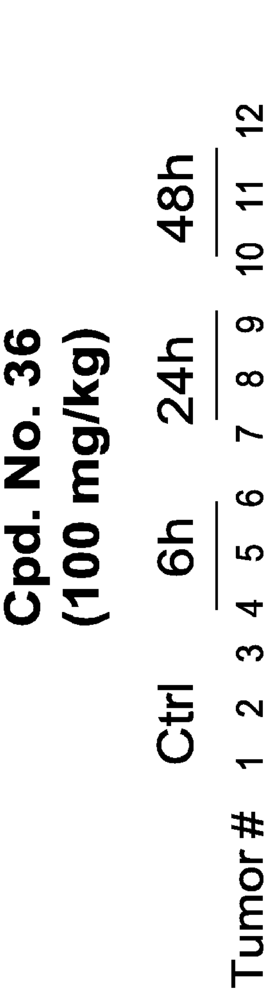
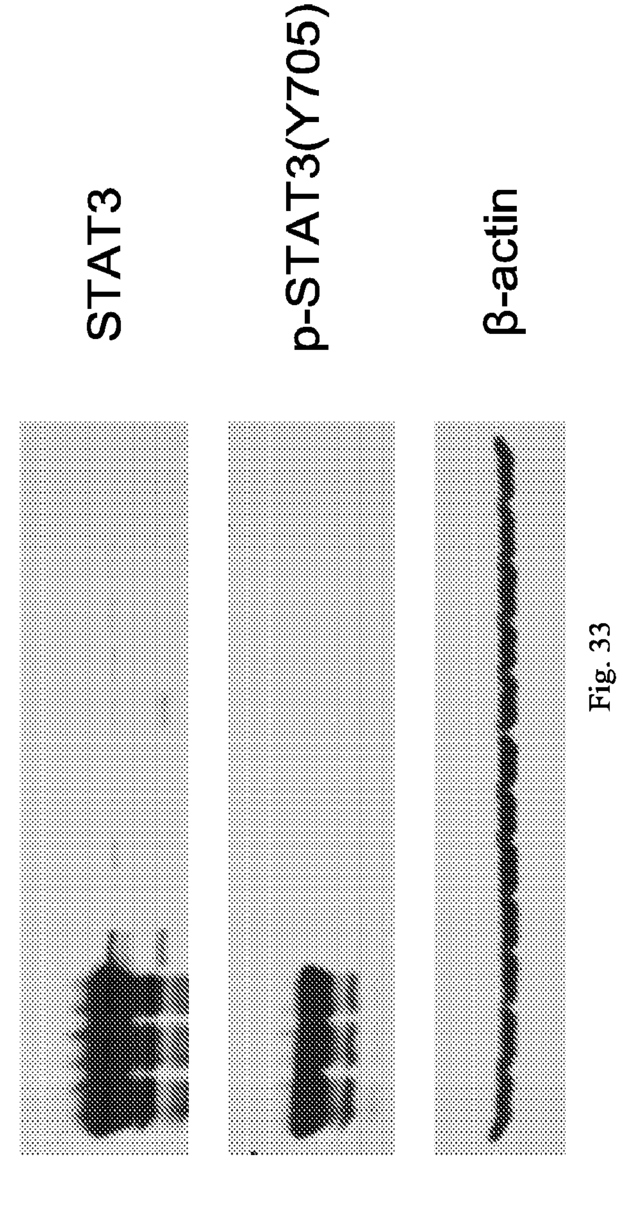
Fig. 33

Fig, 39

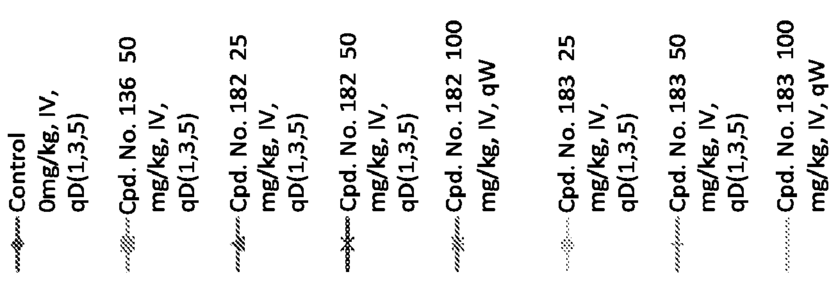
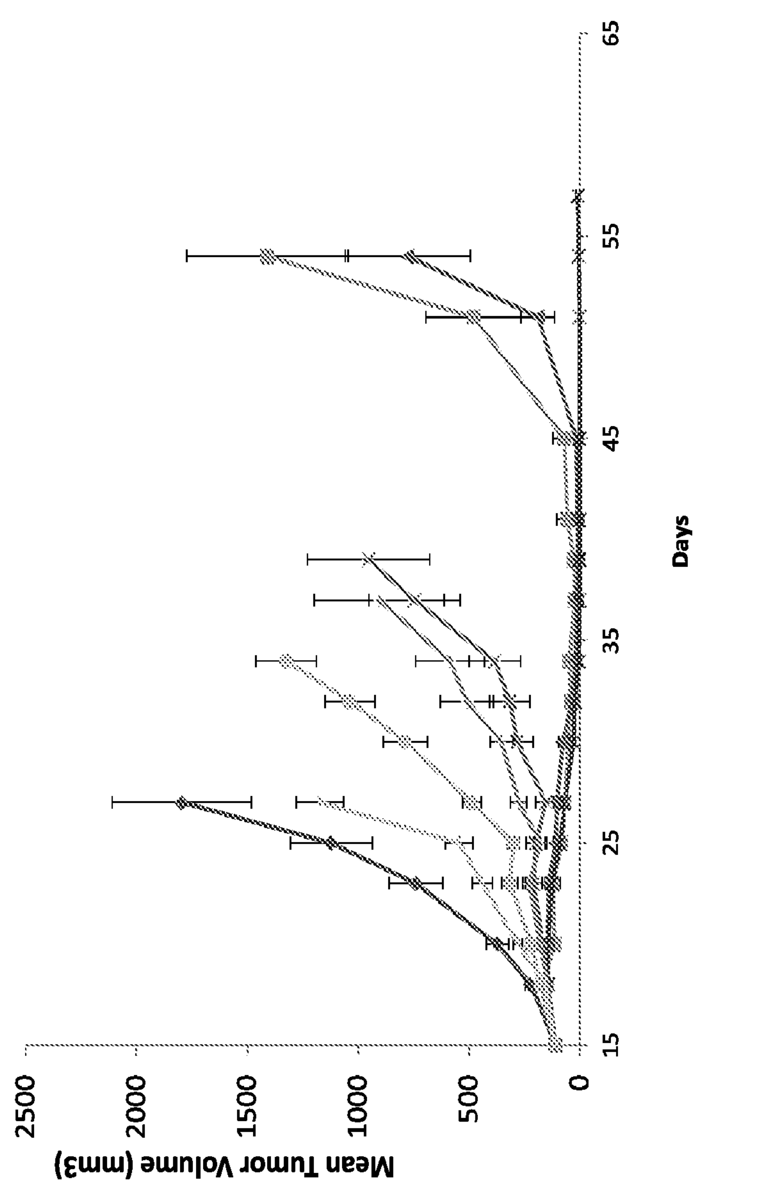
Fig. 47

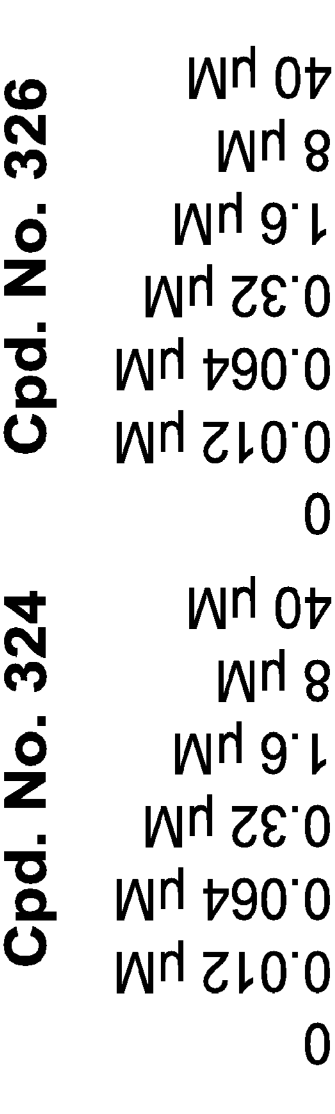
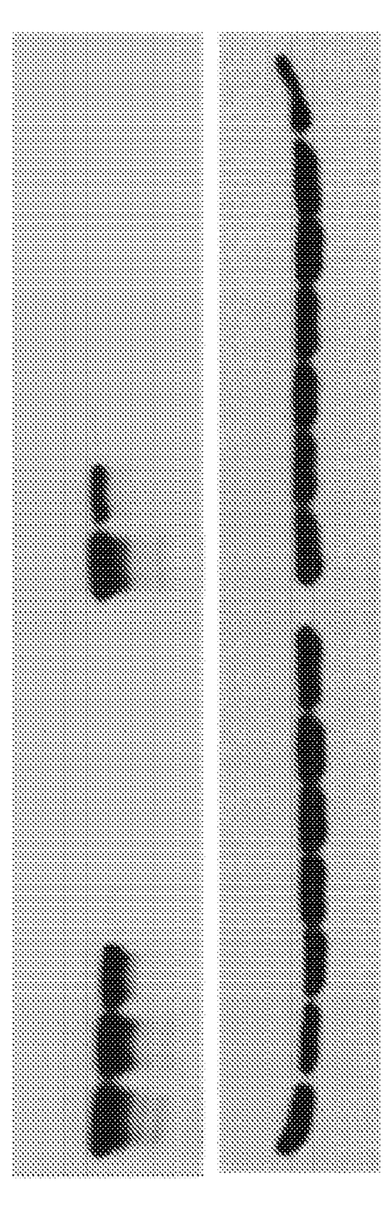
STAT3
β-actin
Fig. 55

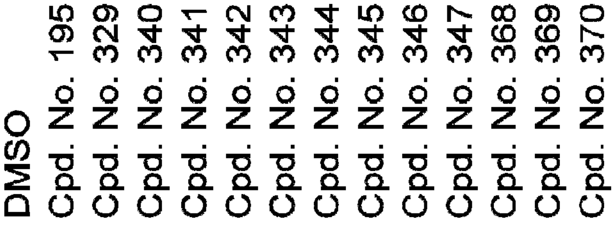
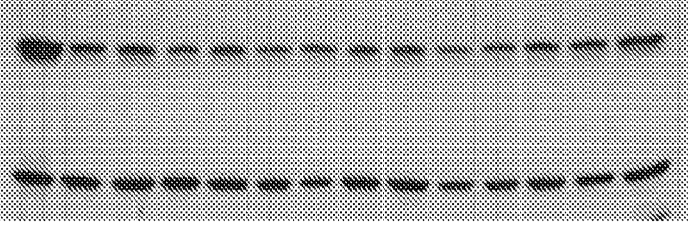
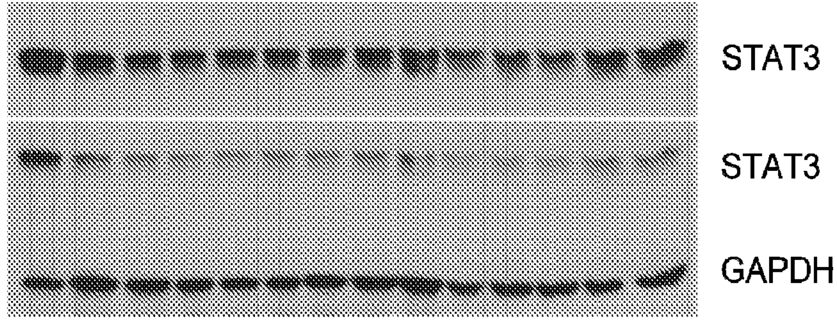
Fig. 63

SMALL MOLECULE DEGRADERS OF STAT3

STATEMENT OF GOVERNMENTAL INTEREST

This invention was made with government support under CA244509 awarded by the National Institutes of Health. The government has certain rights in the invention.

BACKGROUND OF THE INVENTION

Field of the Invention

The present disclosure provides STAT3 inhibitors, STAT3 degraders, methods and synthetic intermediates used to prepare STAT3 inhibitors and degraders, and therapeutic methods of treating conditions and diseases, e.g., cancer, wherein the inhibition or degradation of STAT3 protein provides a benefit.

Background

The signal transducer and activator of transcription (STAT) proteins play important roles in biological processes. For example, the abnormal activation of STAT signaling pathways is implicated in cancer, autoimmune diseases, rheumatoid arthritis, asthma, diabetes, and other human diseases. See, e.g., Miklossy et al., Nat Rev Drug Discov 12:611-629 (2013).

The STAT protein family is composed of seven members: STAT1, STAT2, STAT3, STAT4, STAT5A, STAT5B, and STAT6. Structurally, they share five domains: an amino-terminal domain, a coiled-coil domain, a DNA-binding domain, an SH2 domain, and a carboxy-terminal transactivation domain. The transactivation domain contains one or two amino acid residues that are crucial for the activity of the STAT protein. In particular, phosphorylation of a particular tyrosine residue promotes dimerization, whereas phosphorylation of a particular serine residue enhances transcriptional activation.

STAT proteins promote fundamental cellular processes, including cell growth and differentiation, development, apoptosis, immune responses, and inflammation. In particular, STAT3 function may be abnormal in the context of cancer, and this abnormality represents an underlying mechanism of STAT3 for promoting malignant transformation and progression. Constitutively active STAT3 is detected in numerous malignancies, including breast, melanoma, prostate, head and neck squamous cell carcinoma (HNSCC), multiple myeloma, pancreatic, ovarian, and brain tumors. Aberrant STAT3 signaling promotes tumorigenesis and tumor progression partly through dysregulating the expression of critical genes that control cell growth and survival, angiogenesis, migration, invasion, or metastasis. These genes include those that encode $p21^{WAF1/CIP2}$, cyclin D1, MYC, BCL-X, BCL-2, vascular endothelial growth factor (VEGF), matrix metalloproteinase 1 (MMP1), MMP7 and MMP9, and survivin. STAT3 may also play a role in the suppression of tumor immune surveillance. Consequently, the genetic and pharmacological modulation of persistently active STAT3 was shown to control the tumor phenotype and to lead to tumor regression in vivo.

Certain STAT3 inhibitors are disclosed in WO 2010/077589 A2. There exists a need in the art for STAT3 inhibitors and STAT3 degraders having physical and pharmacological properties that allow them to be used in therapeutic applications for treating disease.

BRIEF SUMMARY OF THE INVENTION

In one aspect, the present disclosure provides compounds represented by any one of Formulae I-IV, IV-A, V, V-A, VI, VI-A, VI-B, VI-C, VII, VII-A, VII-B, VII-C, VII-D, VII-E, XXII-XXIV, or XXVI, below, and the pharmaceutically acceptable salts and solvates, e.g., hydrates, thereof. These compounds are STAT3 degraders or synthetic intermediates that can be converted to STAT3 degraders. These compounds may also degrade STAT1. STAT3 and/or STAT3/STAT1 degraders are useful in treating or preventing diseases or conditions such as cancer wherein the degradation of STAT3 or STAT3 and STAT1 provides a benefit.

In another aspect, the present disclosure provides compounds represented by any one of Formulae VIII-XII, below, and the pharmaceutically acceptable salts and solvates, e.g., hydrates, thereof. These compounds are STAT3 inhibitors or synthetic intermediates that can be converted to STAT3 inhibitors. STAT3 inhibitors are useful in treating or preventing diseases or conditions such as cancer wherein the inhibition of STAT3 provides a benefit.

Compounds of Formulae I-IV, IV-A, V, V-A, VI, VI-A, VI-B, VI-C, VII, VII-A, VII-B, VII-C, VII-D, VII-E, VIII-XII, XXII-XXIV, or XXVI, and the pharmaceutically acceptable salts and solvates, e.g., hydrates, thereof, are collectively referred to as "Compounds of the Disclosure."

In another aspect, the present disclosure provides compounds represented by any one of Formulae XIII, XIII-A, XIII-B, XIII-C, XIII-D, XIII-E, XIV, or XV, below, and the pharmaceutically acceptable salts and solvates, e.g., hydrates, thereof. These compounds are phosphotyrosine mimetics that can be used as synthetic intermediates to prepare Compounds of the Disclosure.

In another aspect, the present disclosure provides compounds represented any one of Formulae XVI, XVI-A, XVII-XVIII or XXV, or Intermediate Formula 2, below, and the pharmaceutically acceptable salts and solvates, e.g., hydrates, thereof. These compounds are synthetic intermediates that can be used to prepare Compounds of the Disclosure.

Compounds of Formula XIII, XIII-A, XIII-B, XIII-C, XIII-D, XIII-E, XIV-XVI, XVI-A, XVII, XVIII, XXXIV-XXXIX, or Intermediate Formula 2, and the pharmaceutically acceptable salts and solvates, e.g., hydrates, thereof, are collectively referred to as "Intermediates of the Disclosure."

In another aspect, the present disclosure provides methods of treating or preventing a condition or disease by administering a therapeutically effective amount of a Compound of the Disclosure to a subject, e.g., a human patient, in need thereof. The disease or condition of interest that is treatable or preventable by inhibition or degradation of STAT3 is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, Compounds of the Disclosure may reduce the proliferation of unwanted cells by inducing apoptosis in those cells. In some embodiments, Compounds of the Disclosure are administered in combination with a second therapeutic agent.

In another aspect, the present disclosure provides a method of degrading, e.g., reducing the amount of, STAT3 in a subject, comprising administering to the subject a therapeutically effective amount of at least one Compound of the Disclosure having any one of Formulae I-IV, IV-A, V, V-A, VI, VI-A, VI-B, VI-C, VII, VII-A, VII-B, VII-C, VII-D, VII-E, or XXII-XXIV.

In another aspect, the present disclosure provides a method of degrading, e.g., reducing the amount of, STAT3 and STAT1 in a subject, comprising administering to the subject a therapeutically effective amount of at least one Compound of the Disclosure having any one of Formulae I-IV, IV-A, V, V-A, VI, VI-A, VI-B, VI-C, VII, VII-A, VII-B, VII-C, VII-D, VII-E, or XXII-XXIV.

In another aspect, the present disclosure provides a method of inhibiting STAT3 in a subject, comprising administering to the subject a therapeutically effective amount of at least one Compound of the Disclosure having any one of Formulae VIII-XII.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition or degradation of STAT3 provides a benefit, e.g., cancer, or degradation of STAT3 and STAT1 provides a benefit In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides Intermediates of the Disclosure for use in preparing Compounds of the Disclosure.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF DRAWINGS

FIG. 12 is a table showing that Cpd. No. 36 inhibits cell growth in ALCL and AML cell lines expressing high levels of STAT3.

FIG. 25 is an image showing the Western blot analysis of total STAT3 protein and phosphorylated STAT3 (Y705) protein in acute leukemia Molm-16 cells treated for 3 hours with Cpd. Nos. 36, 58, 59, 60, 61, 149, 150 151, and 152 at 0.2 μM.

FIG. 33 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. No. 36 at the concentration indicated.

FIG. 47 is a line graph showing the antitumor activity of Cpd. Nos. 136, 182, and 183 against Molm-16 xenograft tumors in mice at the doses and schedules indicated.

FIG. 55 is an image showing the Western blot analysis of the in vitro degradation of STAT3 in Molm-16 cells (DSMZ) at the doses indicated after treatment for 3-6 h with Cpd. Nos. 324 and 326.

FIG. 63 is two images showing the Western blot analysis of total STAT3 in SU-DHL-1 cells after treatment for 8 h with Cpd. Nos. 195, 329, 340, 341, 342, 343, 344, 345, 346, 347, 368, 369, and 370 at the concentrations indicated.

DETAILED DESCRIPTION OF THE INVENTION

I. Compounds of the Disclosure

Figure 1:
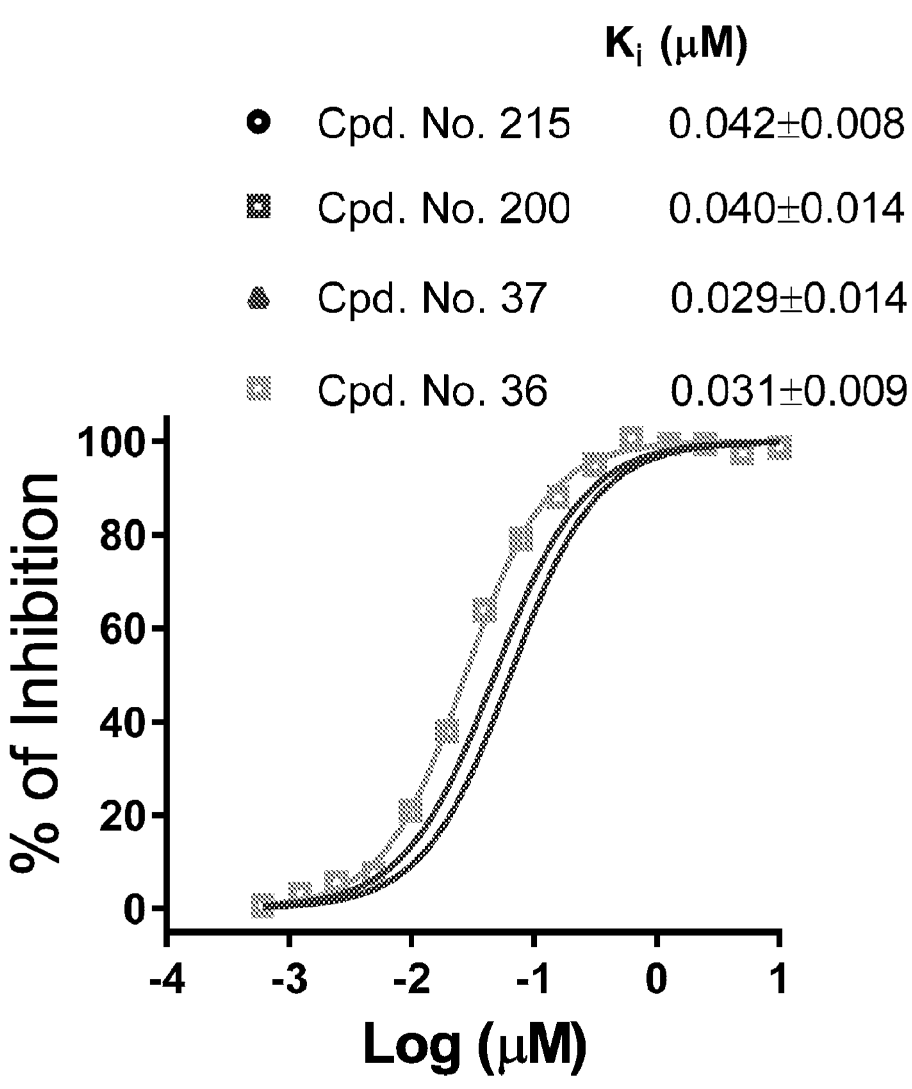
FIG. 1 is a line graph showing the binding affinities of Cpd. No. 215, Cpd. No. 36, Cpd. No. 37, and Cpd. No. 200 to recombinant STAT3 protein using a fluorescence-polarization assay.
Figure 2:
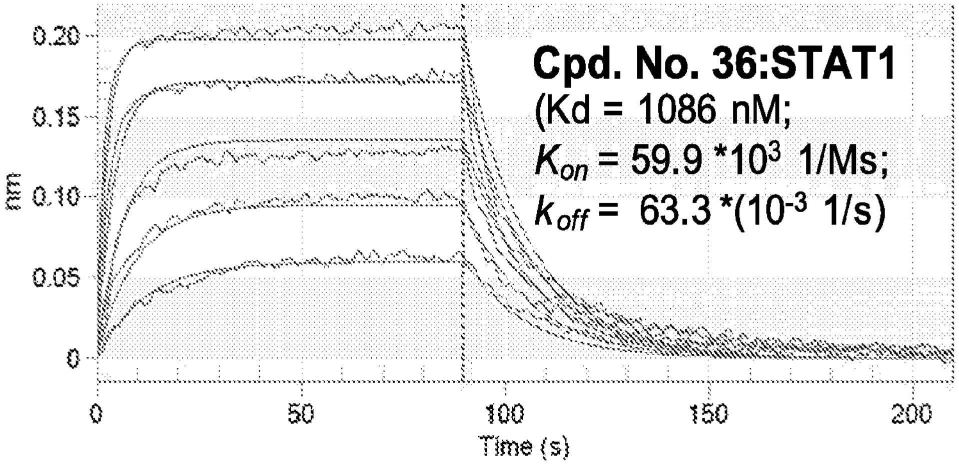
FIG. 2 is a line graph showing the binding affinities of Cpd. No. 36 to recombinant STAT1 protein using a BioLayer Interferometry (BLI) assay.
Figure 3:
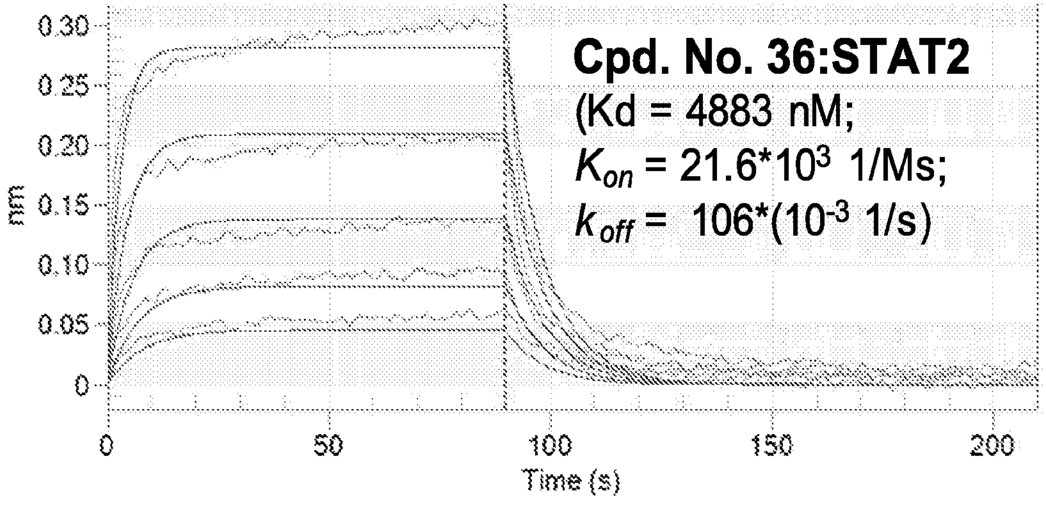
FIG. 3 is a line graph showing the binding affinities of Cpd. No. 36 to recombinant STAT2 protein using a BioLayer Interferometry (BLI) assay.
Figure 4:
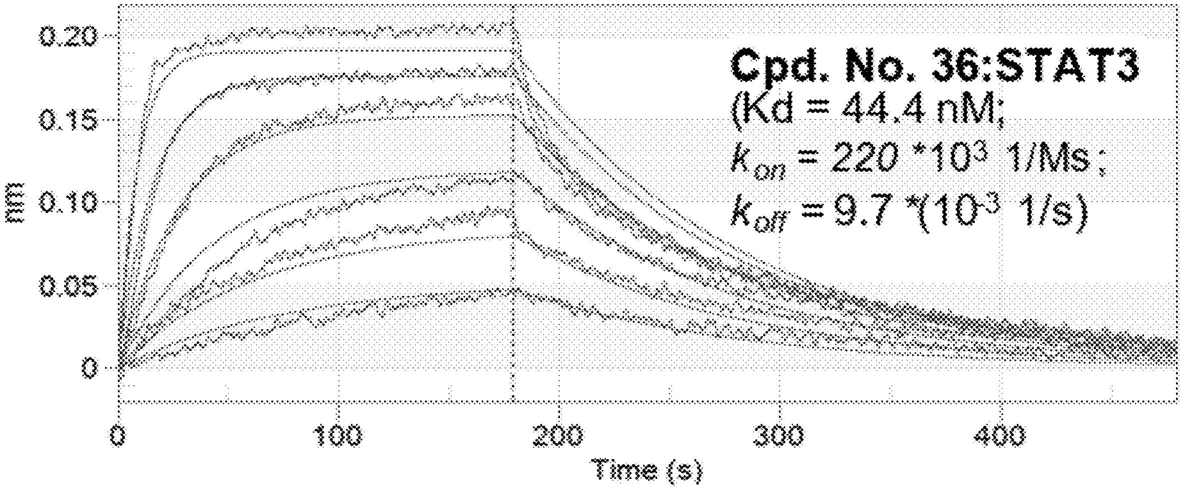
FIG. 4 is a line graph showing the binding affinities of Cpd. No. 36 to recombinant STAT3 protein using a BioLayer Interferometry (BLI) assay.
Figure 5:
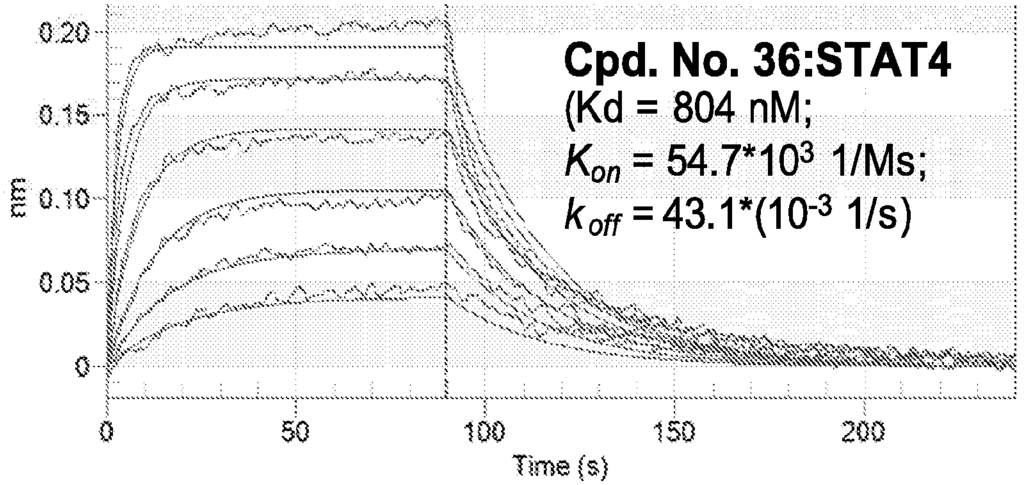
FIG. 5 is a line graph showing the binding affinities of Cpd. No. 36 to recombinant STAT4 protein using a BioLayer Interferometry (BLI) assay.
Figure 6:
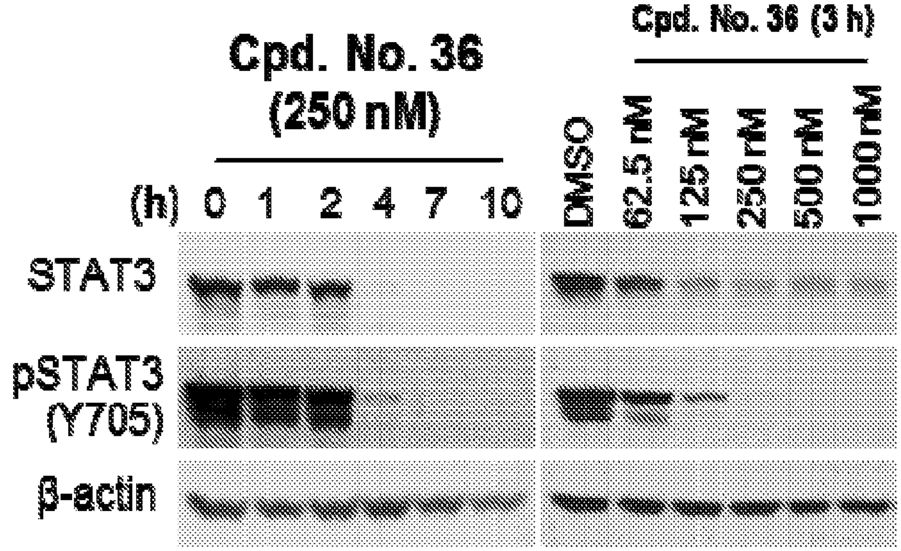
FIG. 6 is an image showing the Western blotting analysis of total STAT3 protein and phosphorylated STAT3 (Y705) in acute leukemia Molm-16 cells treated with Cpd. No. 36 at various time points and concentrations.
Figure 7:
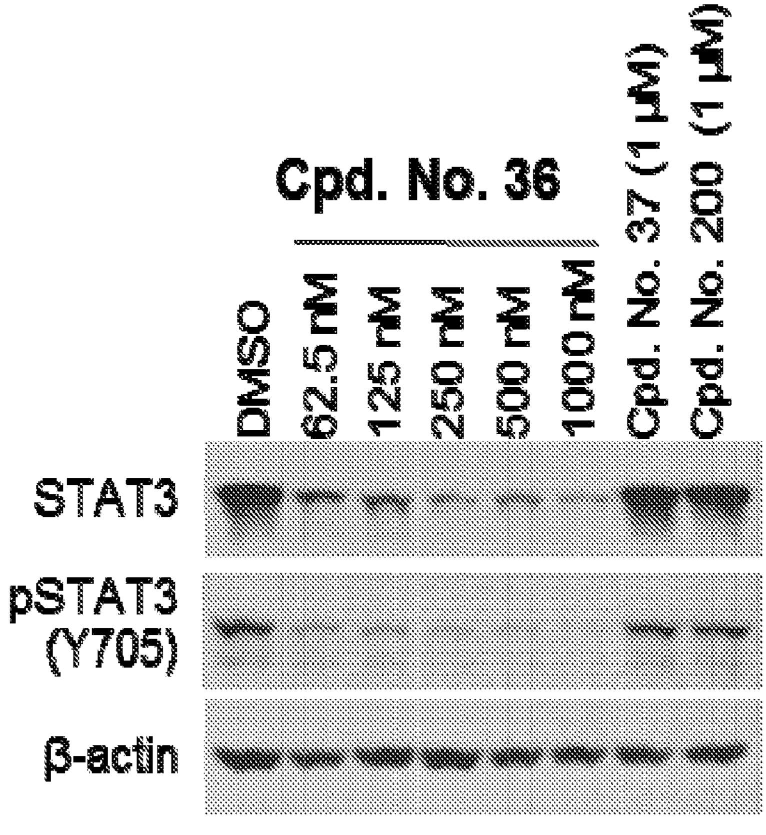
FIG. 7 is an image showing the Western blotting analysis of total STAT3 protein and phosphorylated STAT3 (Y705) in SU-DHL-1 cells treated with Cpd. Nos. 36, 37, and 200 at concentrations.
Figure 8:
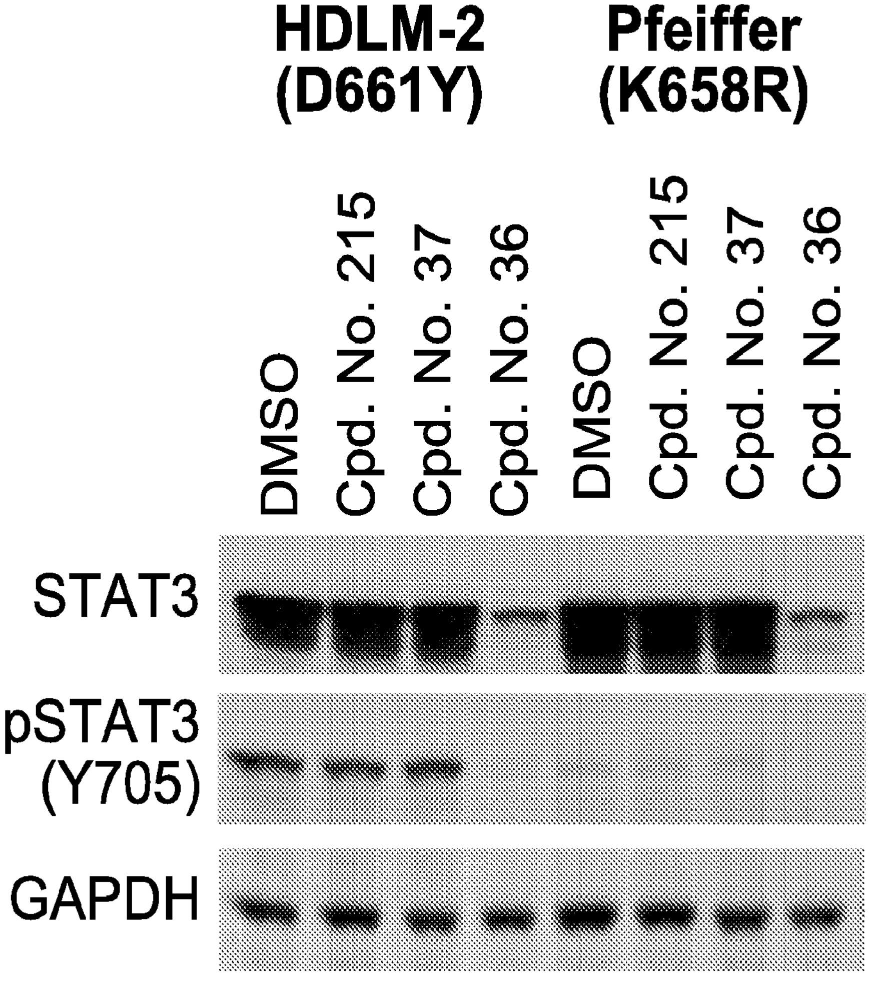
FIG. 8 is an image showing the Western blotting analysis of total STAT3 protein and phosphorylated STAT3 (Y705) in HDLM-2 and Pfeiffer cells treated with Cpd. Nos. 36, 37, and 215.
Figure 9:
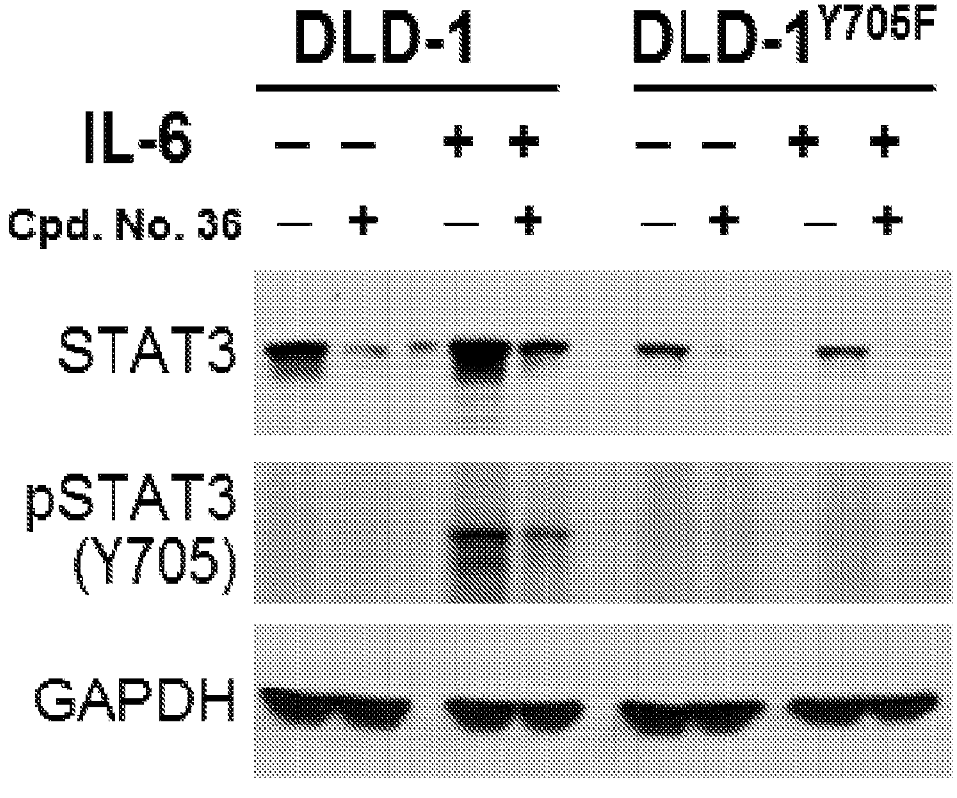
FIG. 9 is an image showing the Western blotting analysis of total STAT3 protein and phosphorylated STAT3 (Y705) in DLD-1 and DLD-1 (Y705F) cells treated with Cpd. No. 36 degrades mutated STAT3 proteins.
Figure 10:
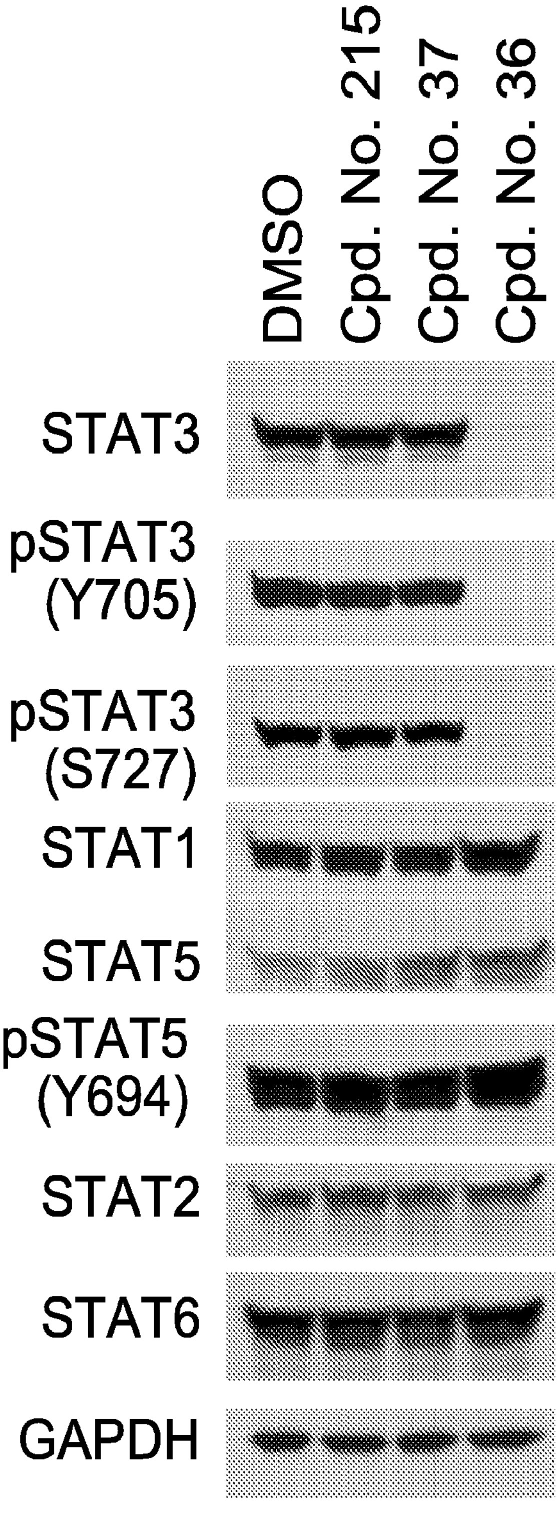
FIG. 10 is an image showing the Western blotting analysis of total STAT1, STAT2, STAT3, STAT5, and STAT6 protein in Molm-16 cells treated with Cpd. No. 36. Cpd. No. 36 specifically degrades STAT3 protein over other STAT members.
Figure 11:
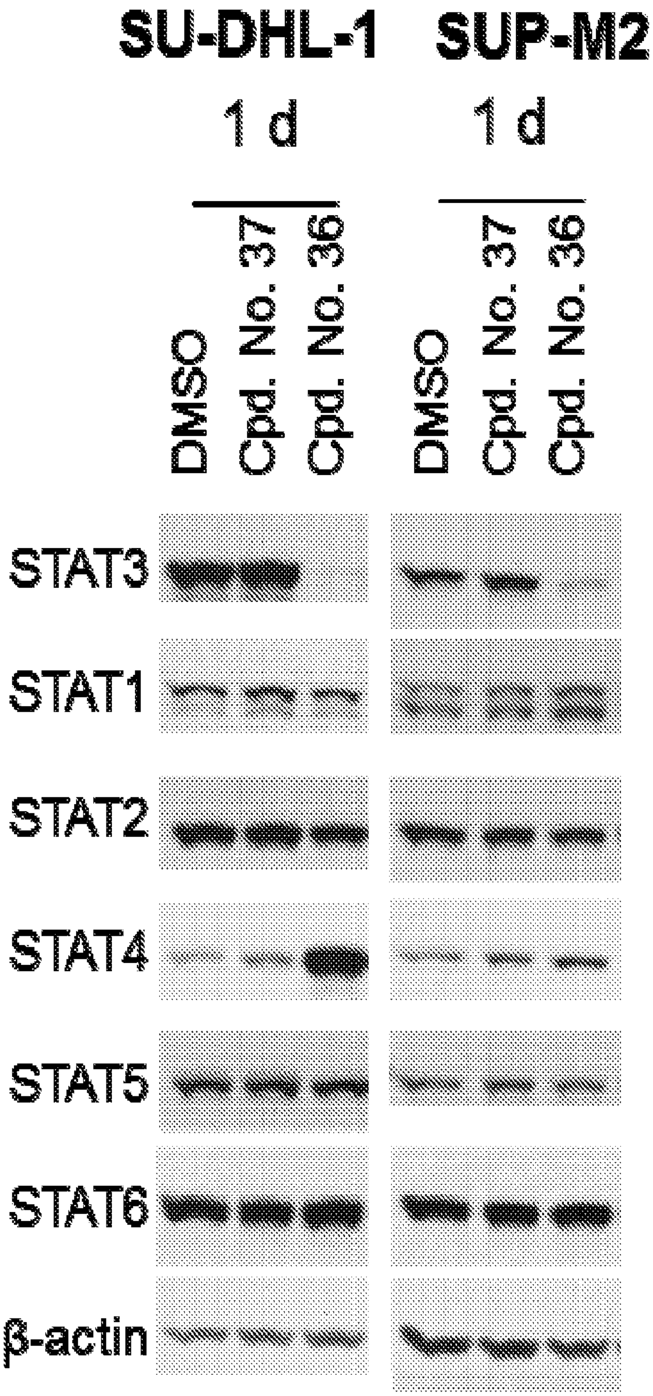
FIG. 11 is an image showing the Western blotting analysis of total STAT1, STAT2, STAT3, STAT4, STAT5, and STAT6 protein in SU-DHL-1 and SUP-M2 cells treated with Cpd. Nos. 36 and 37. Cpd. No. 36 specifically degrades STAT3 protein over other STAT members.
Figure 13:
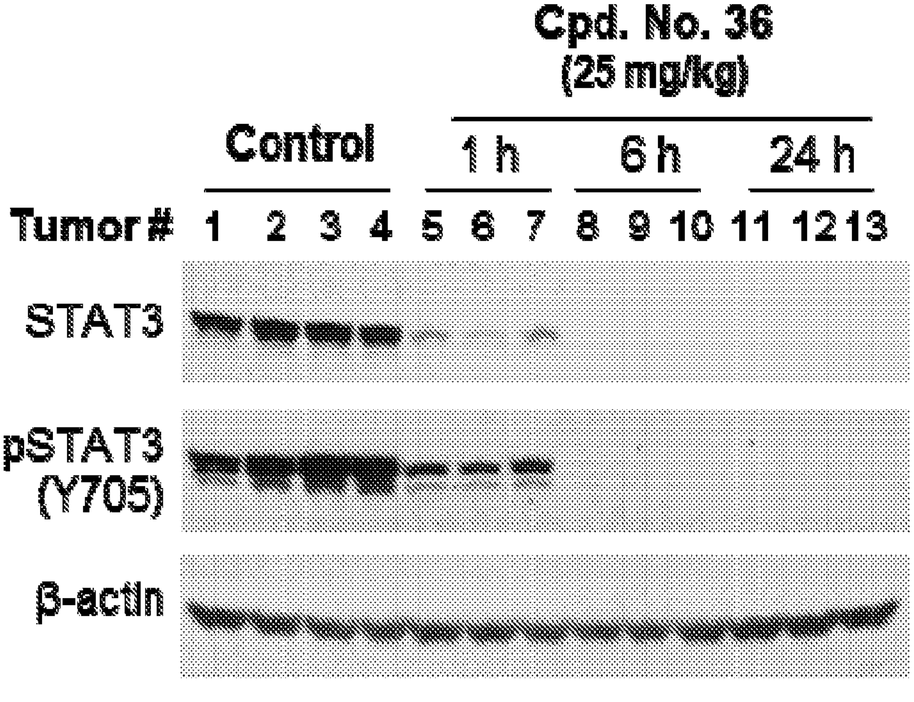
FIG. 13 is an image showing the Western blotting analysis of total STAT3 protein and phosphorylated STAT3 (Y705) in Molm-16 xenograft tumor tissue in mice treated intravenously with Cpd. No. 36.
Figure 14:
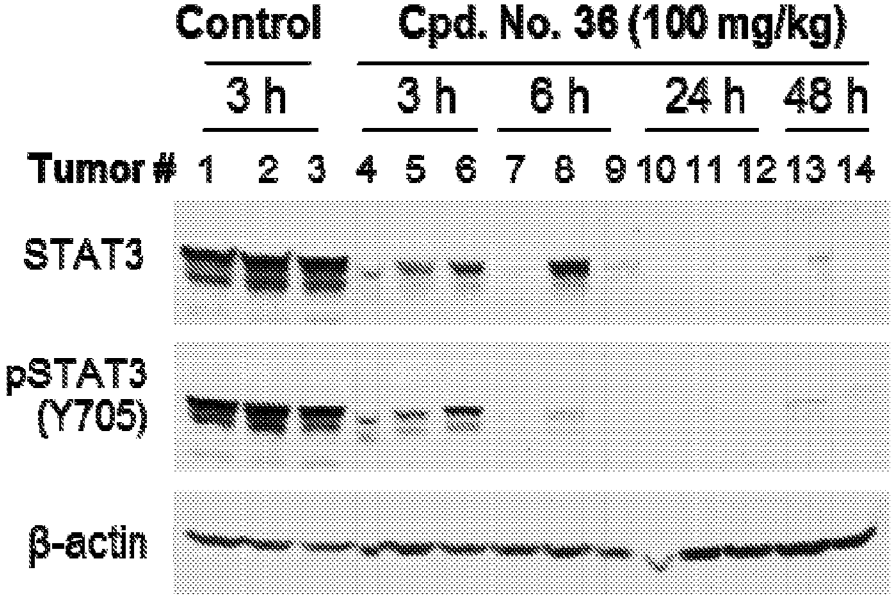
FIG. 14 is an image showing the Western blotting analysis of total STAT3 protein and phosphorylated STAT3 (Y705) in SU-DHL-1 xenograft tumor tissue in mice treated intravenously with Cpd. No. 36.
Figure 15:
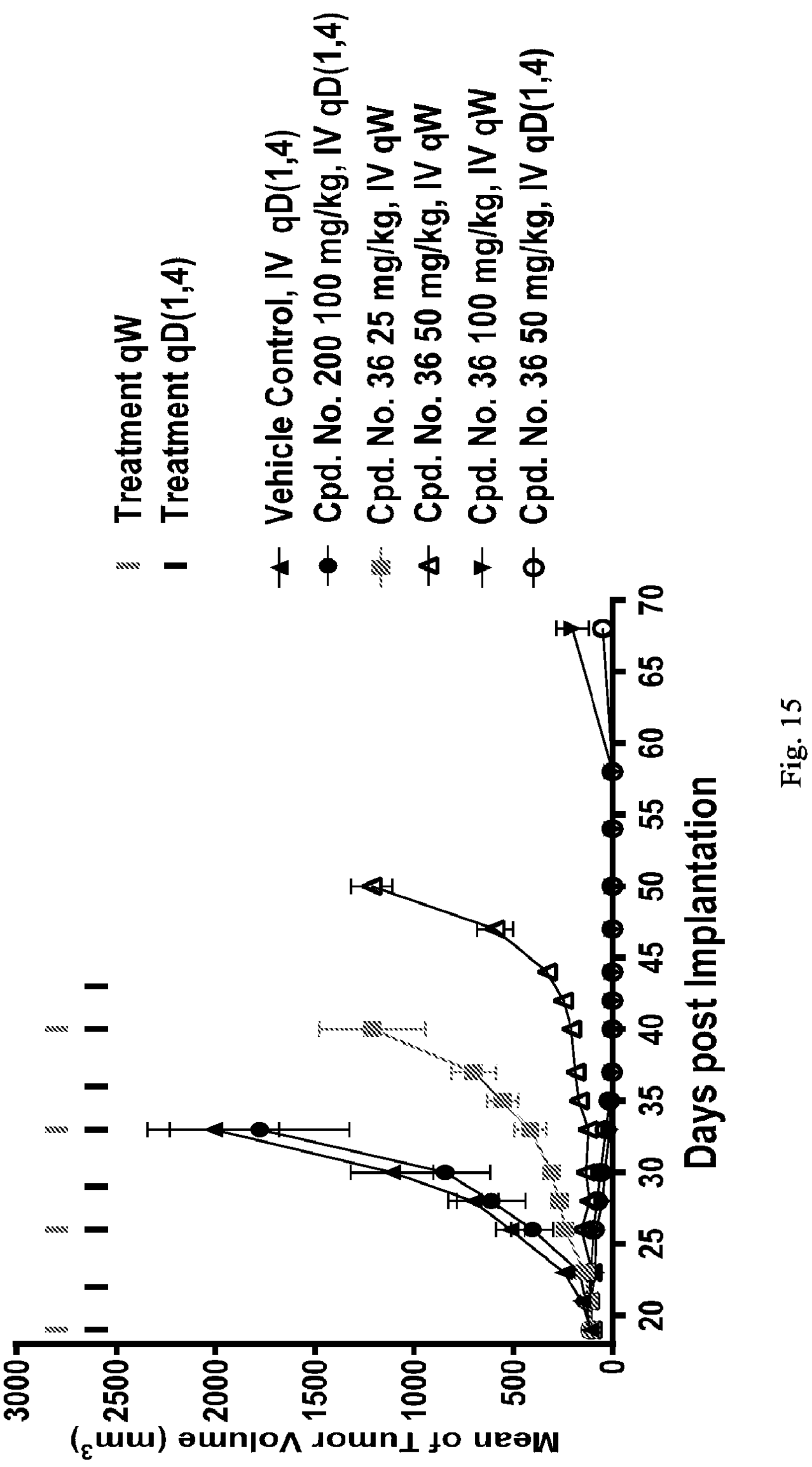
FIG. 15 is a line graph showing the antitumor activity of Cpd. No. 36 against Molm-16 xenograft tumors in mice.
Figure 16:
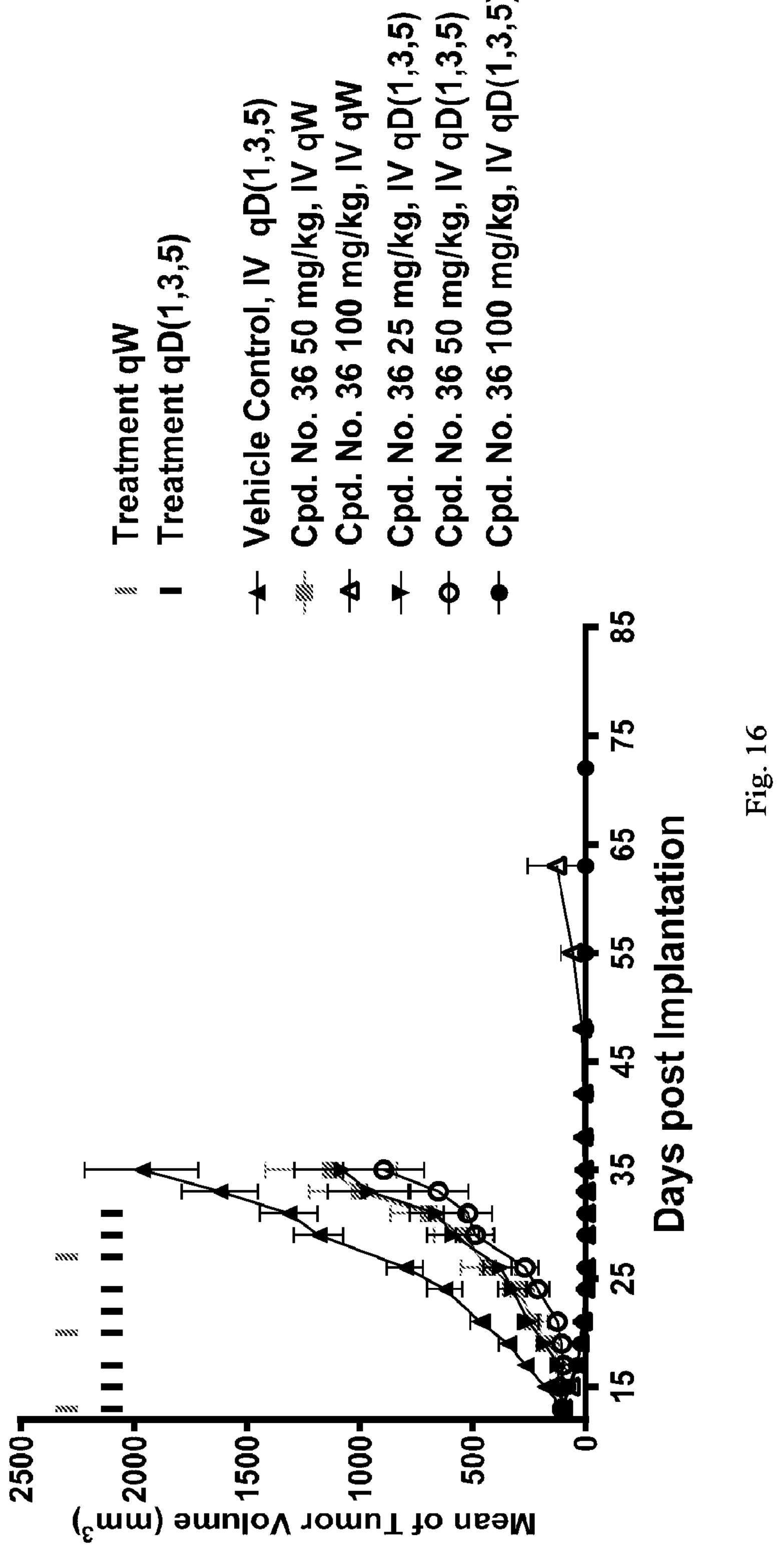
FIG. 16 is a line graph showing the antitumor activity of Cpd. No. 36 against SU-DHL-1 xenograft tumors in mice.
Figure 17:
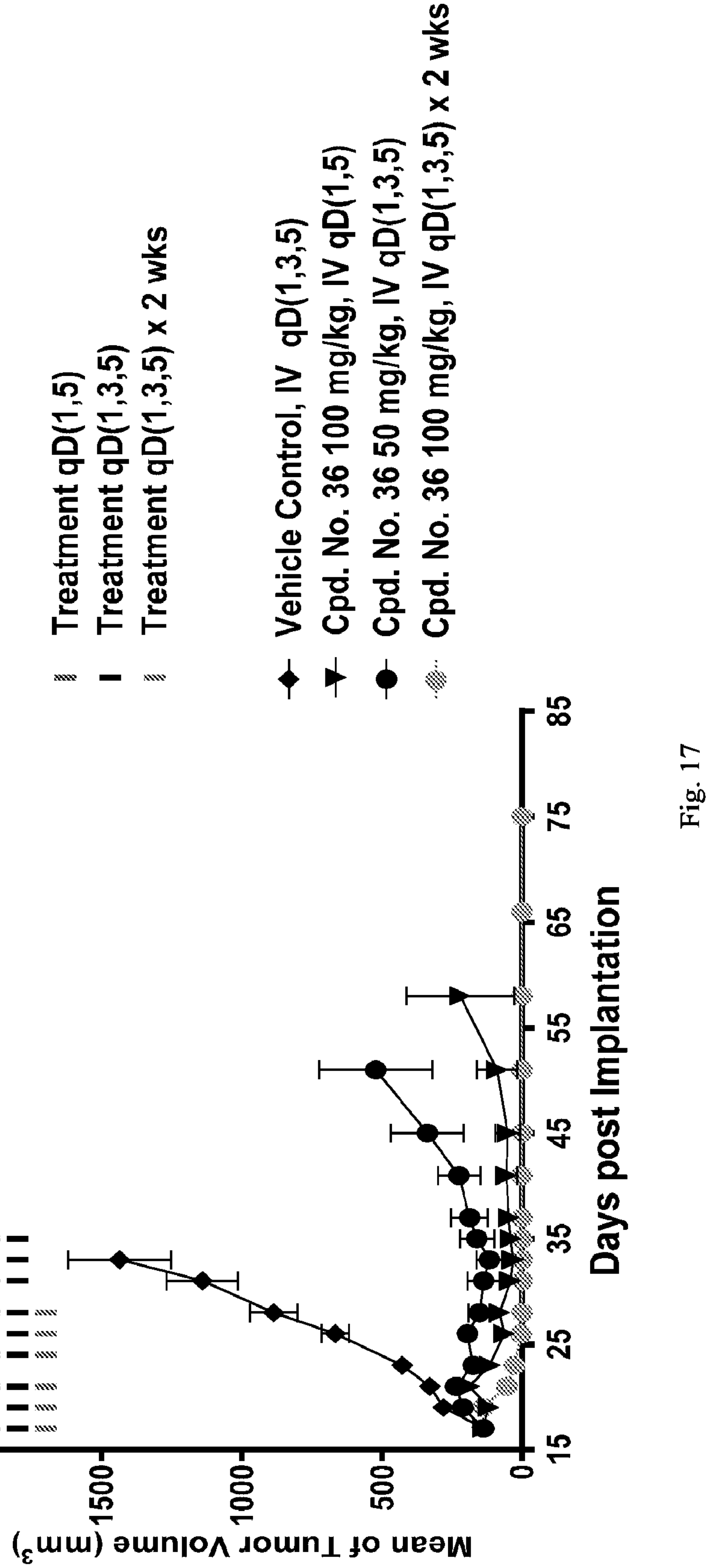
FIG. 17 is a line graph showing the antitumor activity of Cpd. No. 36 against SUP-M2 xenograft tumors in mice.
Figure 18:
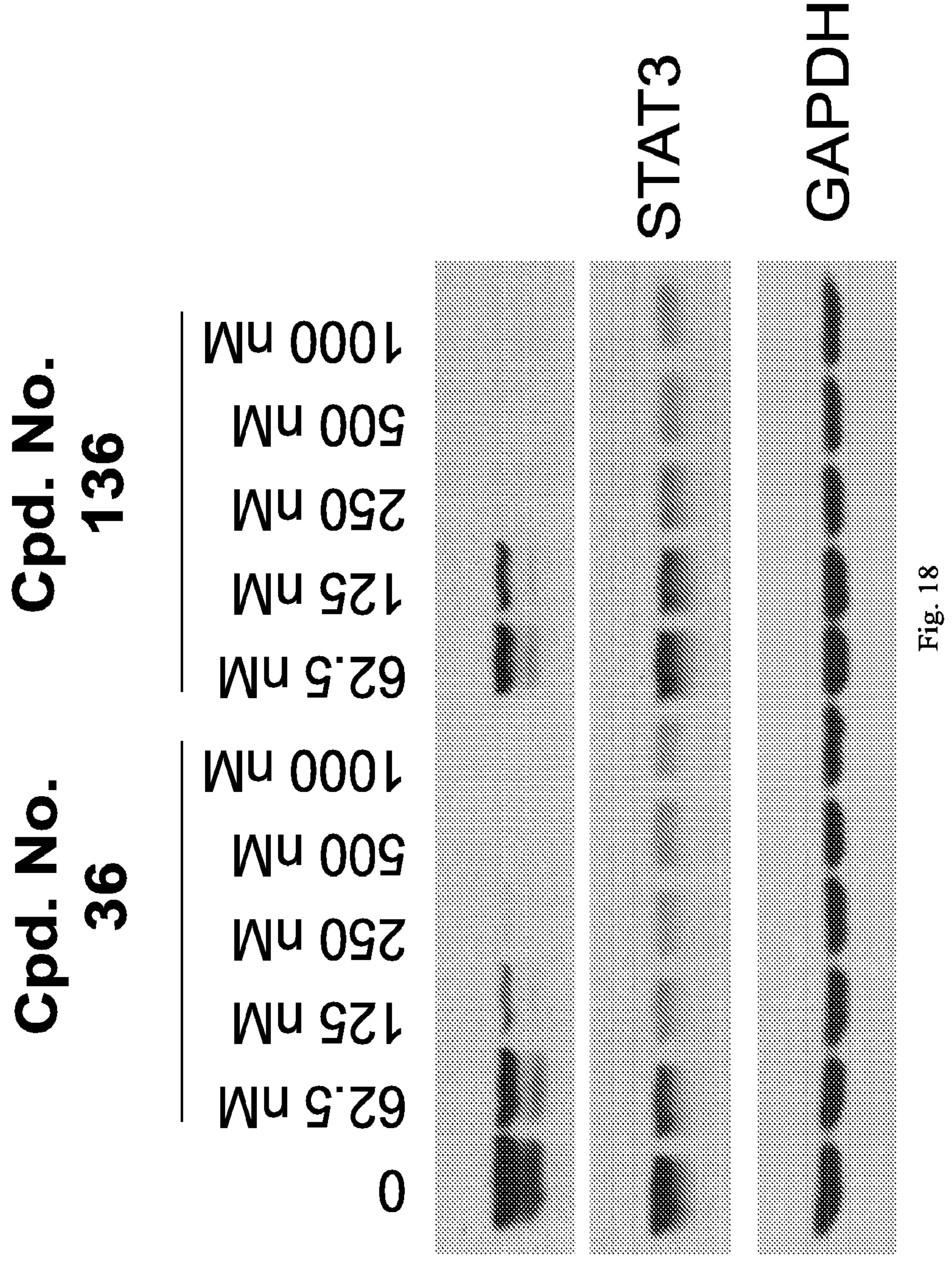
FIG. 18 is an image showing the Western blot analysis of total STAT3 protein and phosphorylated STAT3 (Y705) protein treated for 3 hours with Cpd. Nos. 36 and 136 at various concentrations.
Figure 19:
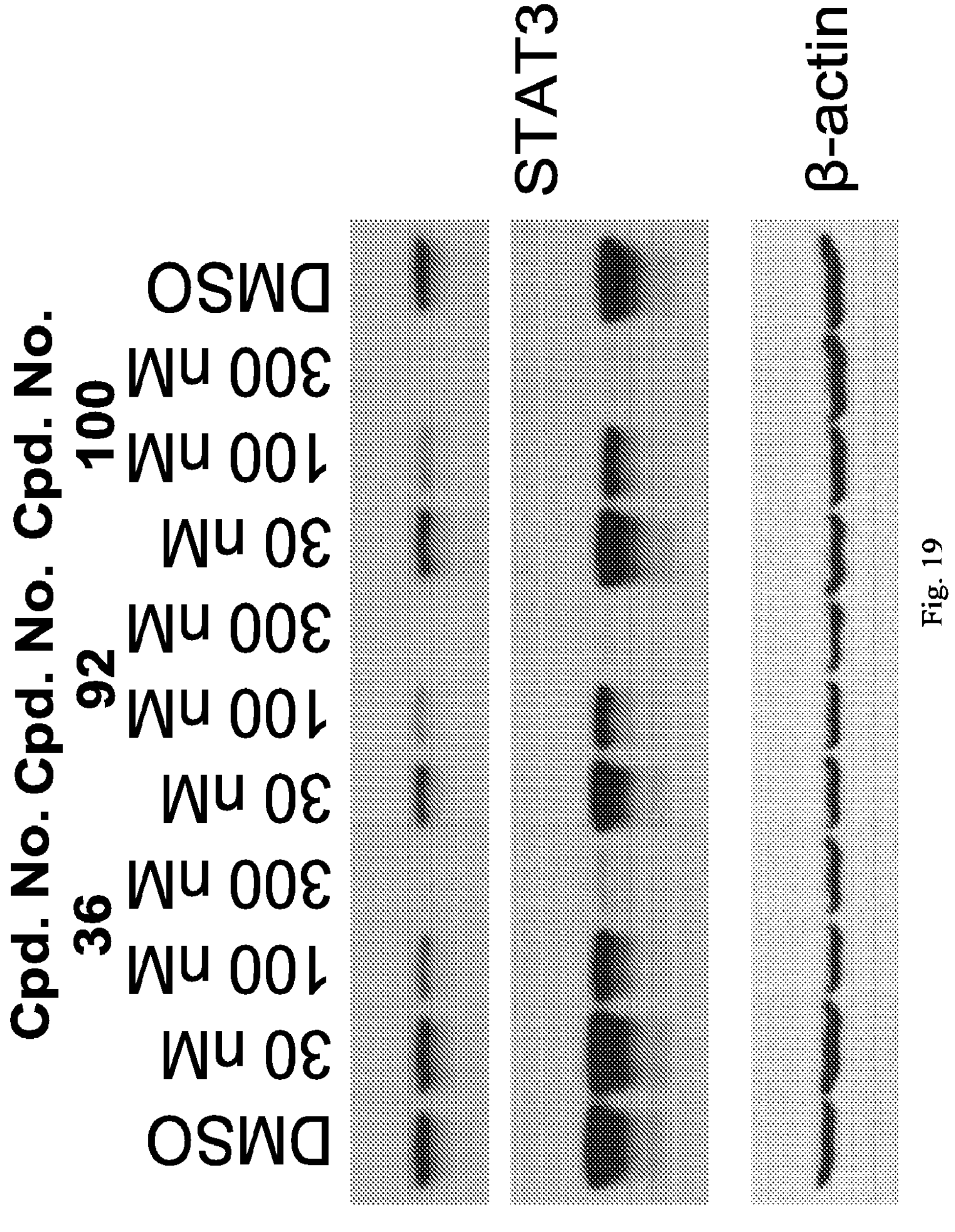
FIG. 19 is an image showing the Western blot analysis of total STAT3 protein in acute leukemia Molm-16 cells treated for 3 hours with Cpd. Nos. 36, 92, and 100 at various concentrations.
Figure 20:
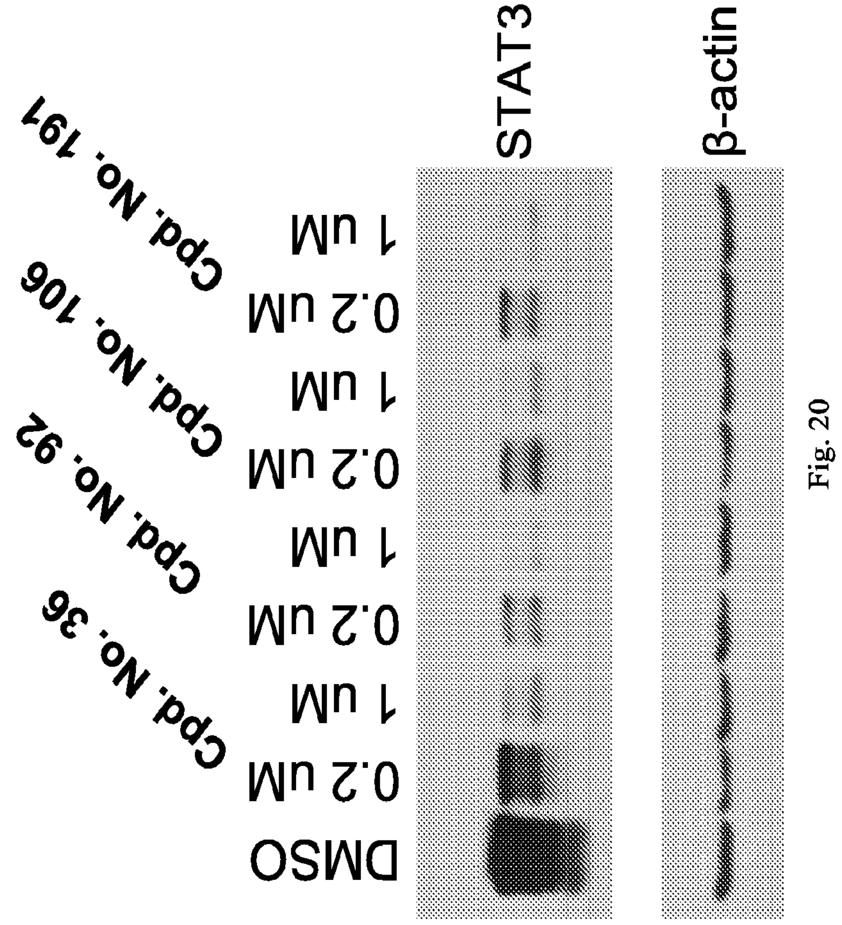
FIG. 20 is an image showing the Western blot analysis of total STAT3 protein in acute leukemia Molm-16 cells treated for 3 hours with Cpd. Nos. 36, 92, 106, and 191 at various concentrations.
Figure 21:
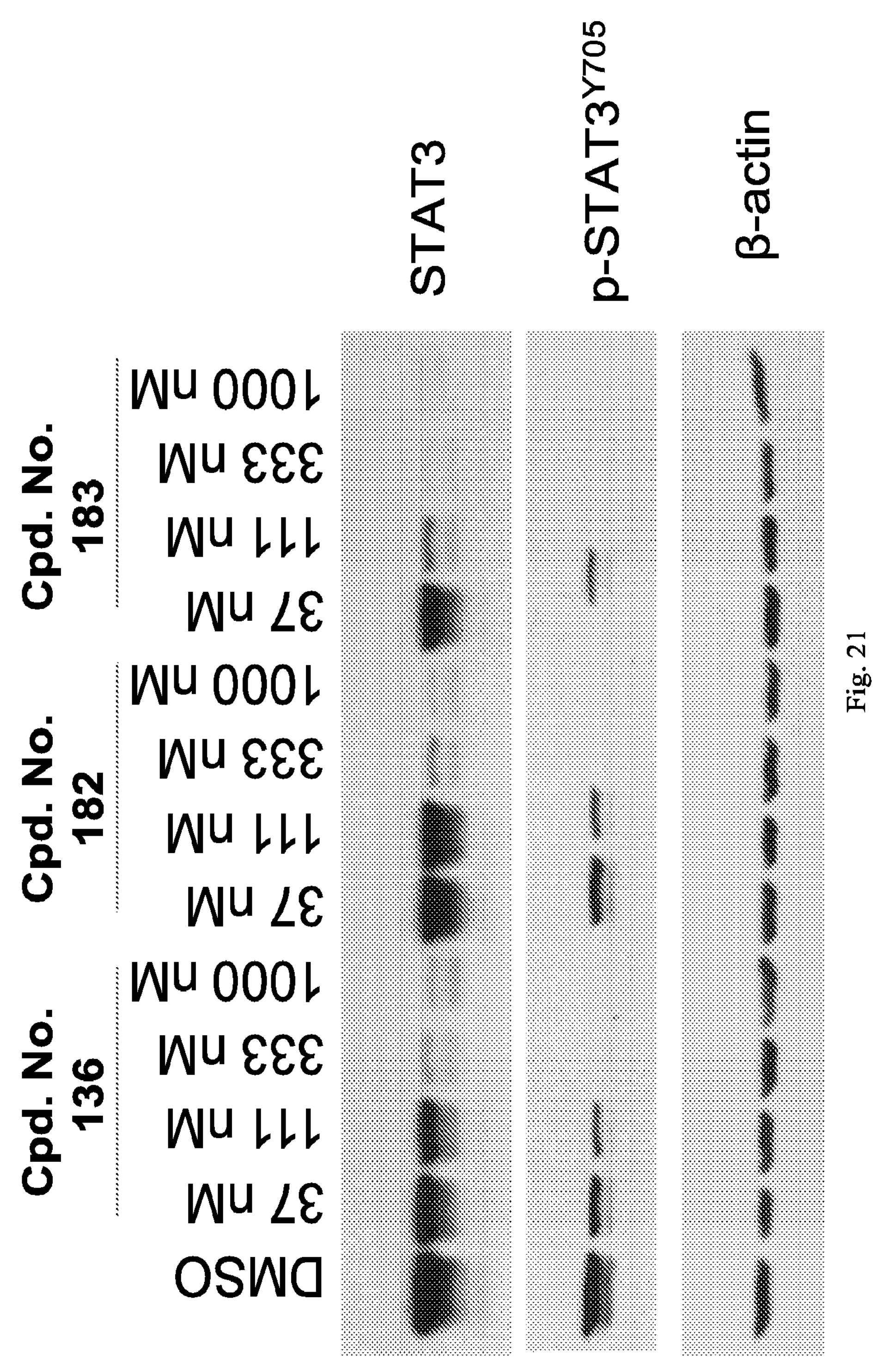
FIG. 21 is an image showing the Western blot analysis of total STAT3 protein and phosphorylated STAT3 (Y705) protein in acute leukemia Molm-16 cells treated for 3 hours with Cpd. No. 136, Cpd. No. 182, and Cpd. No. 183 at various concentrations.
Figure 22:
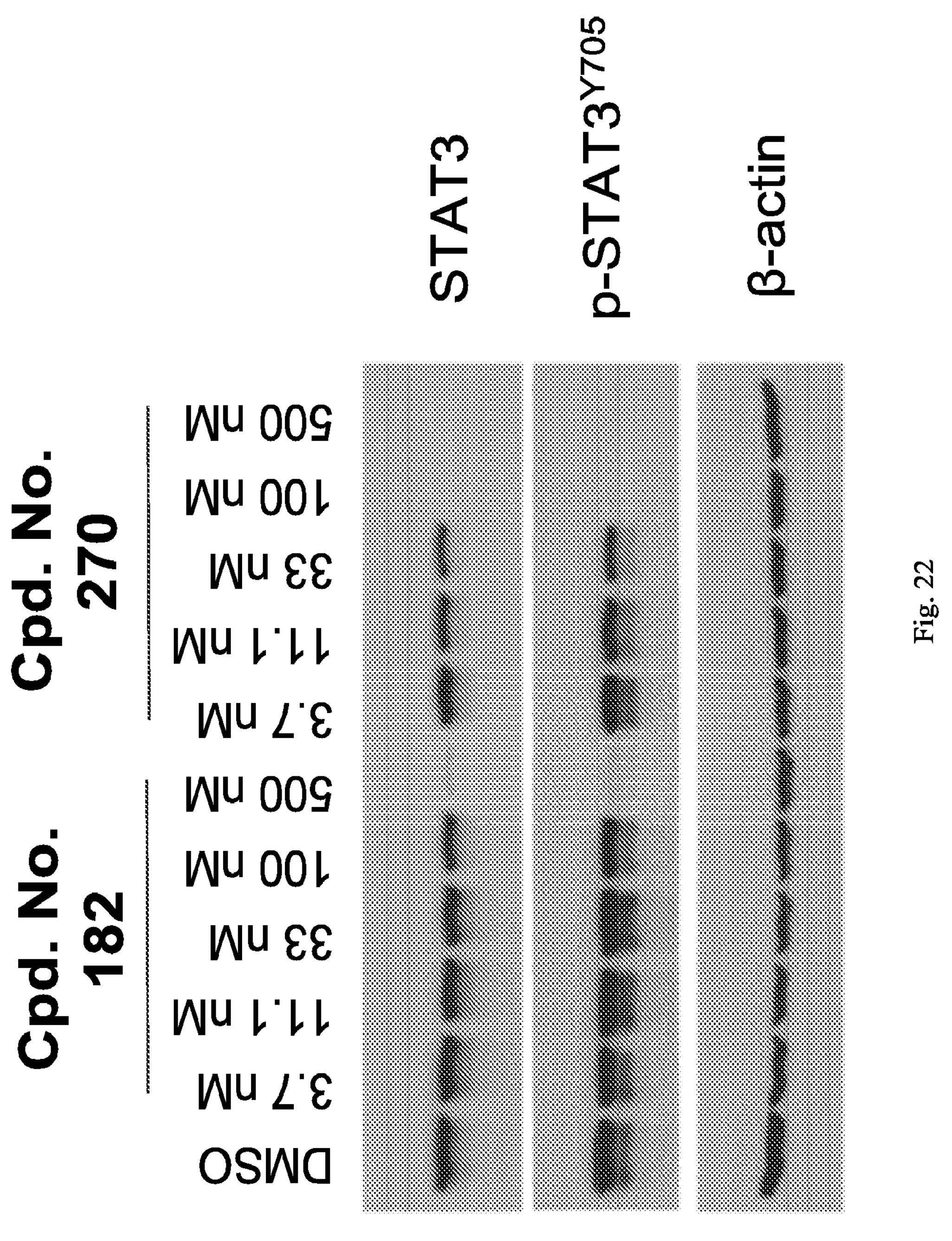
FIG. 22 is an image showing the Western blot analysis of total STAT3 protein and phosphorylated STAT3 (Y705) protein in acute leukemia Molm-16 cells treated for 3 hours with Cpd. Nos. 182 and Cpd. No. 270 at various concentrations.
Figure 23:
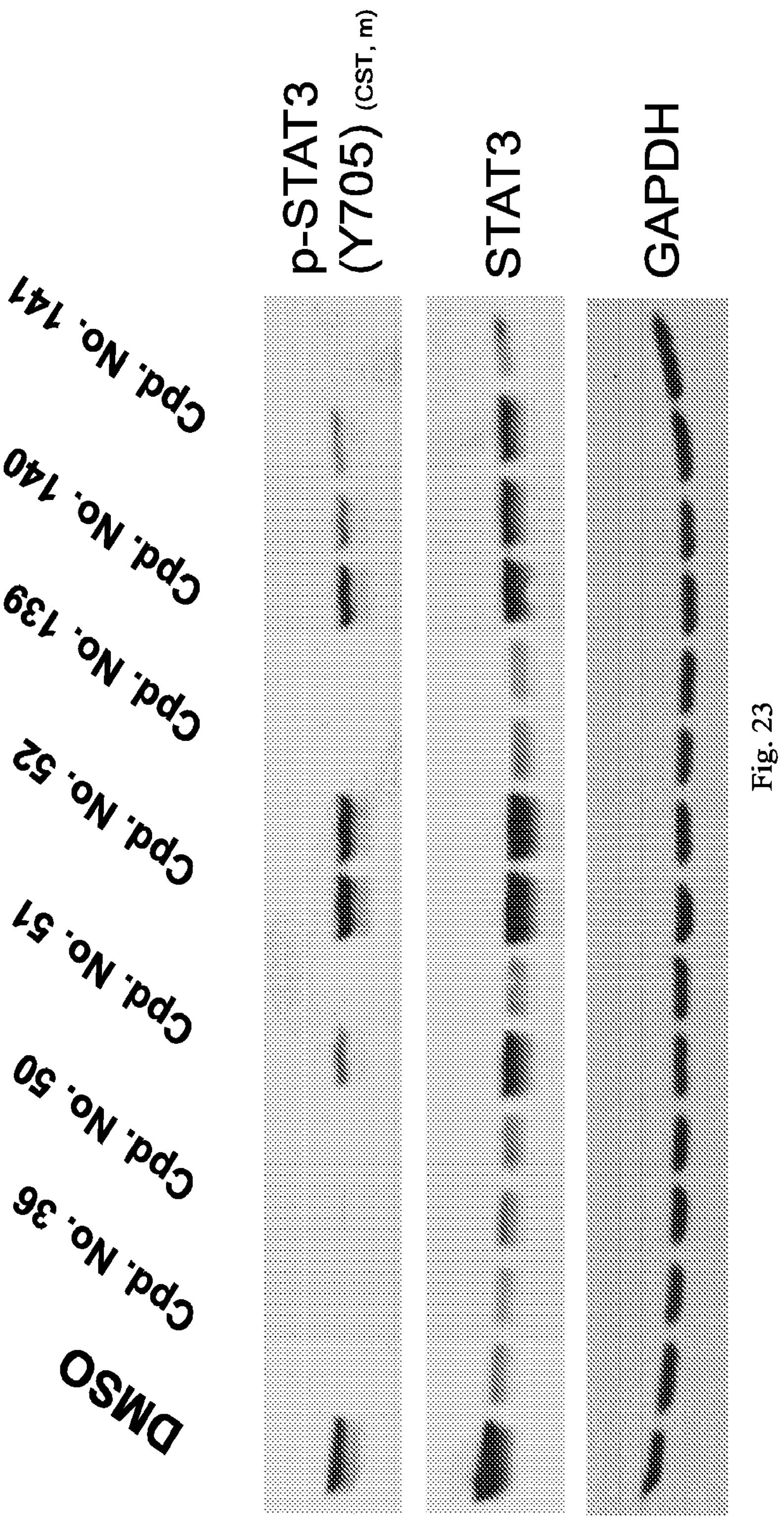
FIG. 23 is an image showing the Western blot analysis of total STAT3 protein and phosphorylated STAT3 (Y705) protein in acute leukemia Molm-16 cells treated for 3 hours with Cpd. Nos. 36, 50, 51, 52, 139, 140, and 141 at various concentrations.
Figure 24:
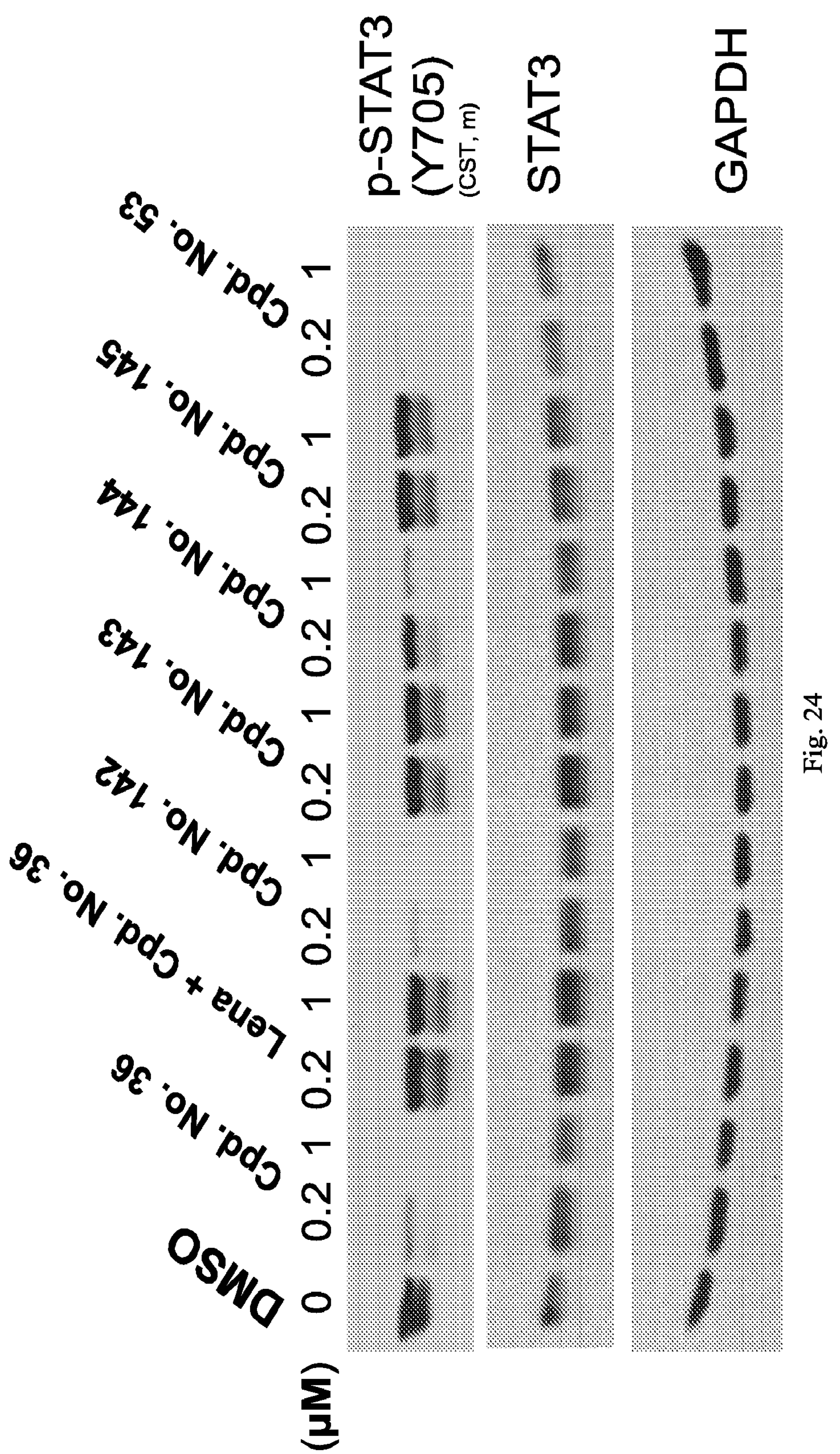
FIG. 24 is an image showing the Western blot analysis of total STAT3 protein and phosphorylated STAT3 (Y705) protein in acute leukemia Molm-16 cells treated for 2.5 hours with Cpd. Nos. 36, 53, 142, 143, 144, and 145, and Cpd. No. 36 plus lenalomide, at various concentrations.
Figure 26:
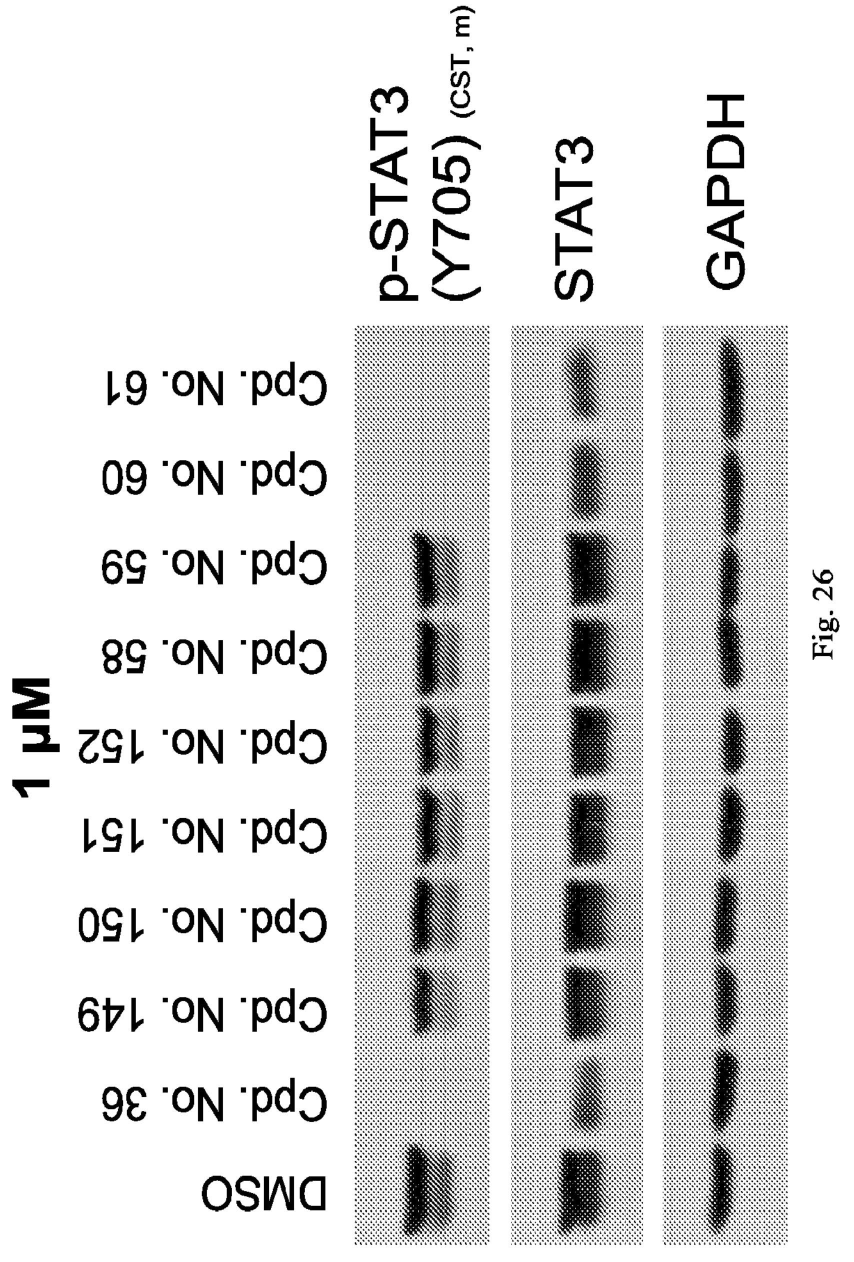
FIG. 26 is an image showing the Western blot analysis of total STAT3 protein and phosphorylated STAT3 (Y705) protein in acute leukemia Molm-16 cells treated for 3 hours with Cpd. Nos. 36, 58, 59, 60, 61, 149, 150 151, and 152 at 1.0 μM.
Figure 27:
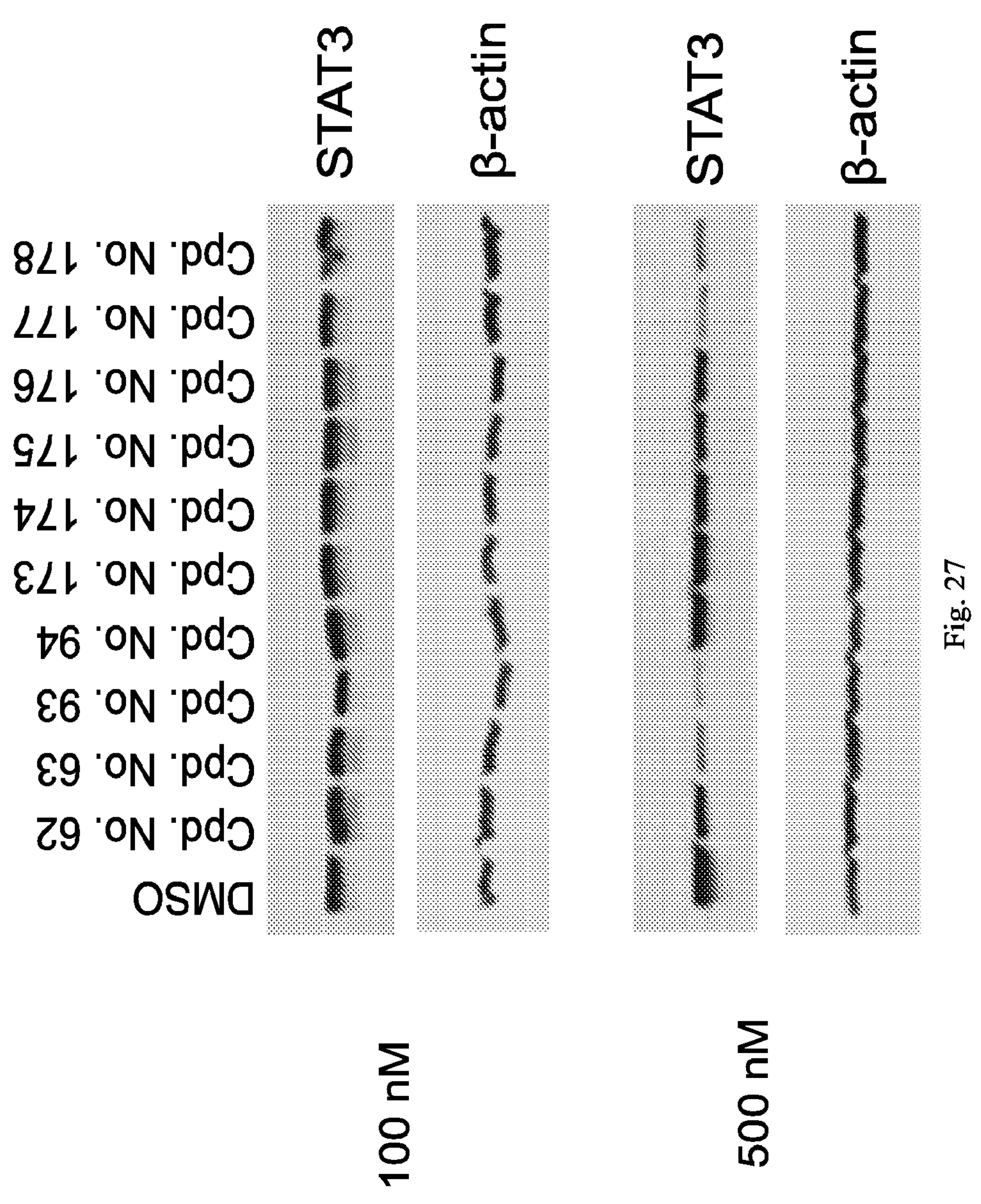
FIG. 27 is an image showing the Western blot analysis of total STAT3 protein and phosphorylated STAT3 (Y705) protein in acute leukemia Molm-16 cells treated for 2.5 hours with Cpd. Nos. 62, 63, 93, 94, 173, 174, 175, 176, 177, and 178 at 100 nM (top panels) or 500 nM (bottom panels).
Figure 28:
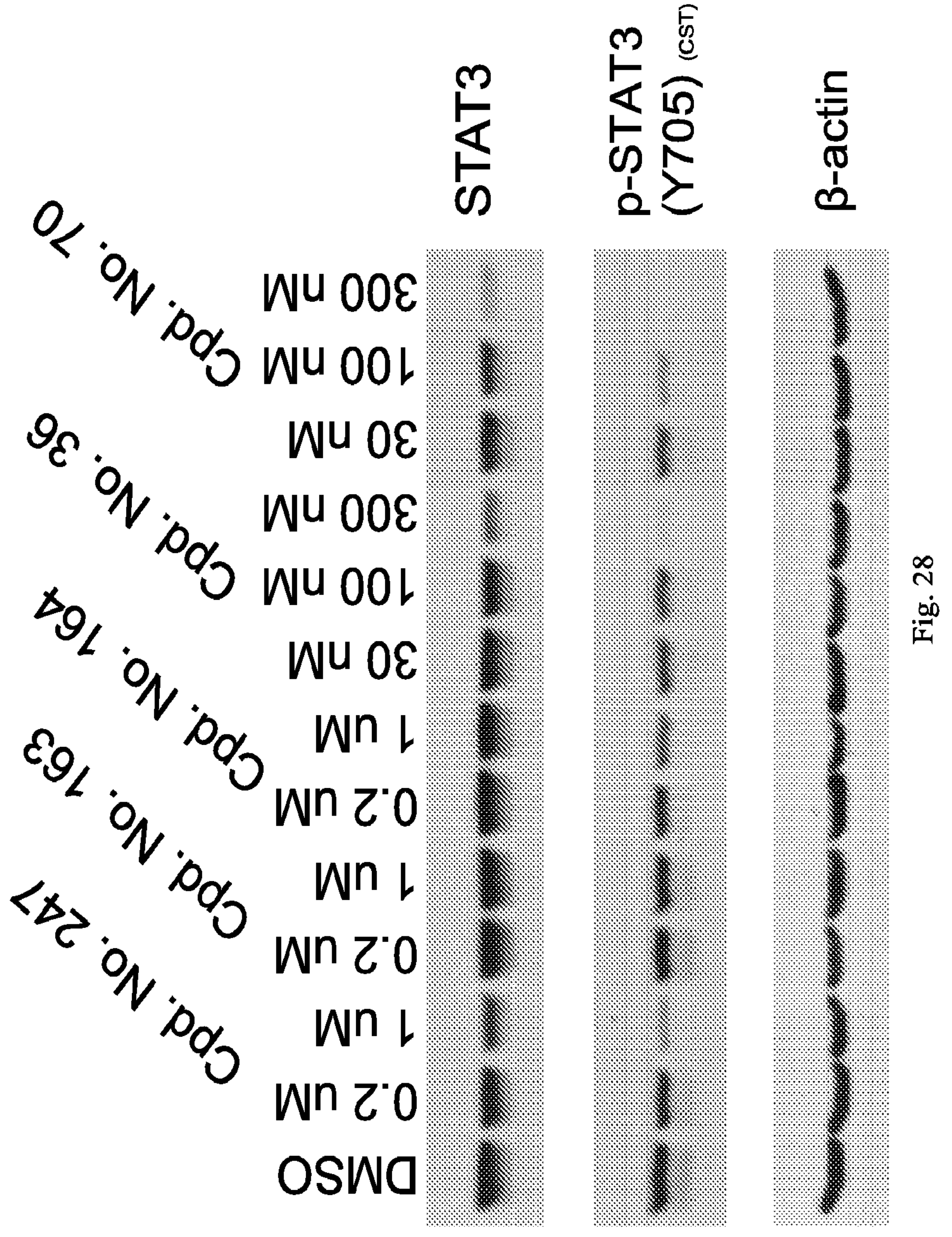
FIG. 28 is an image showing the Western blot analysis of total STAT3 protein and phosphorylated STAT3 (Y705) protein in acute leukemia Molm-16 cells treated for 2.5 hours with Cpd. Nos. 36, 70, 163, 164, and 247 at various concentrations.
Figure 29:
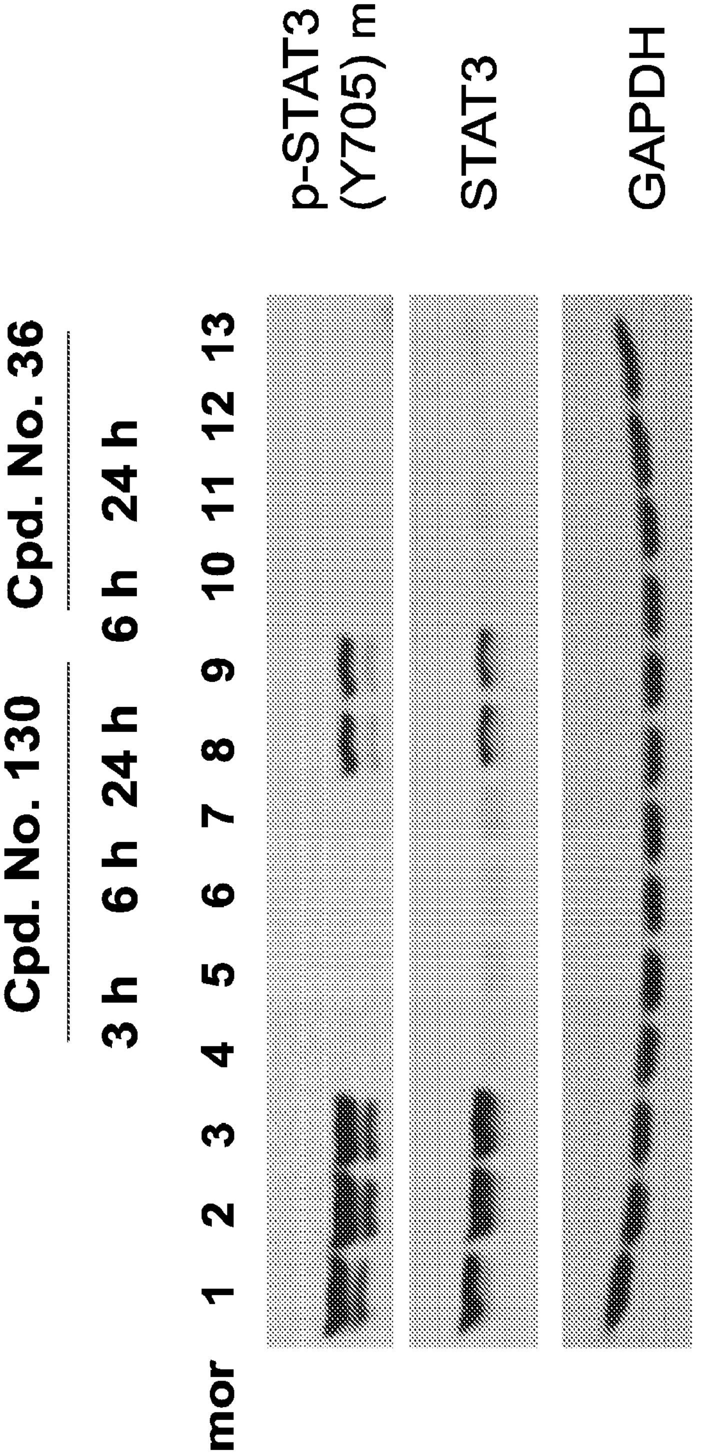
FIG. 29 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 36 and 130 at 25 mg/kg.
Figure 30:
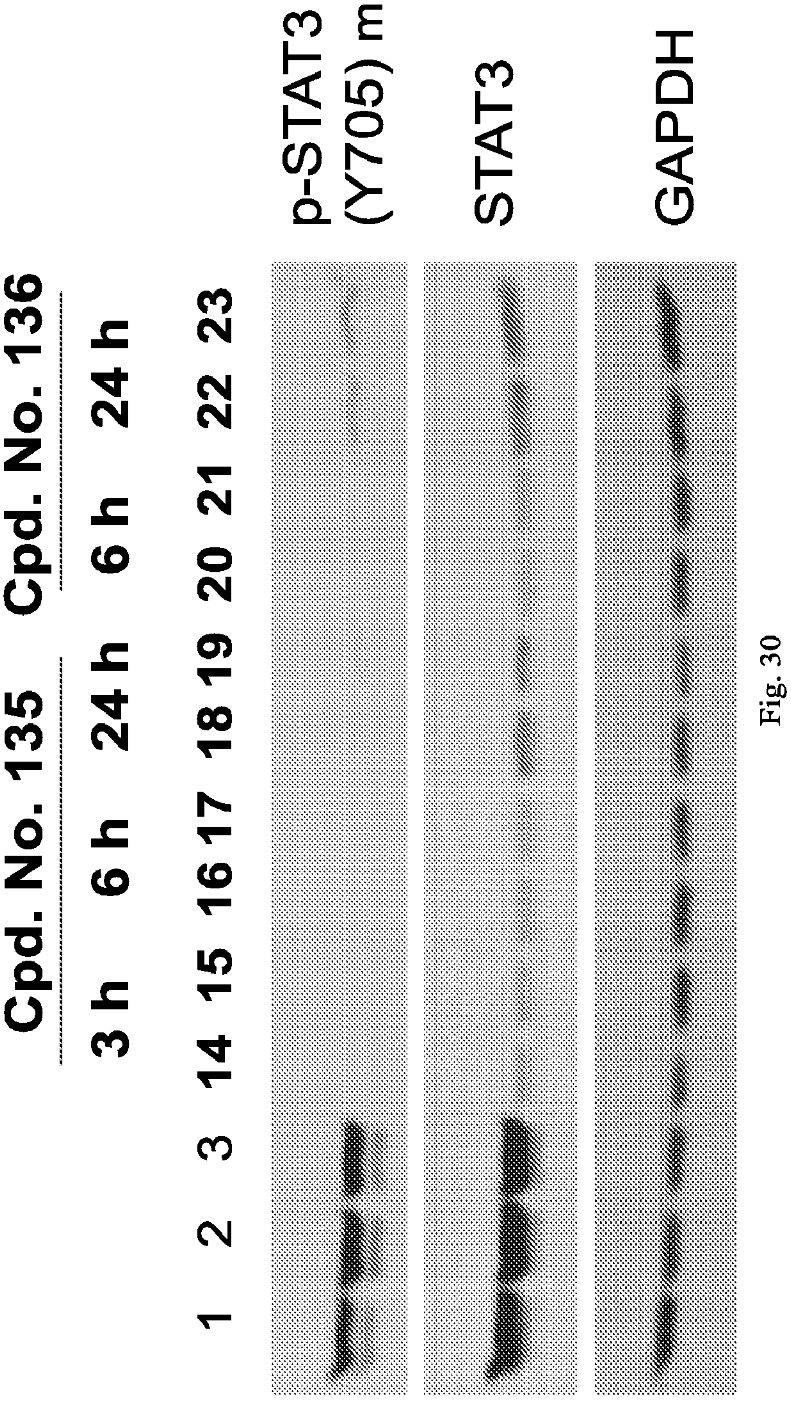
FIG. 30 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 135 and 136 at 25 mg/kg.
Figure 31:
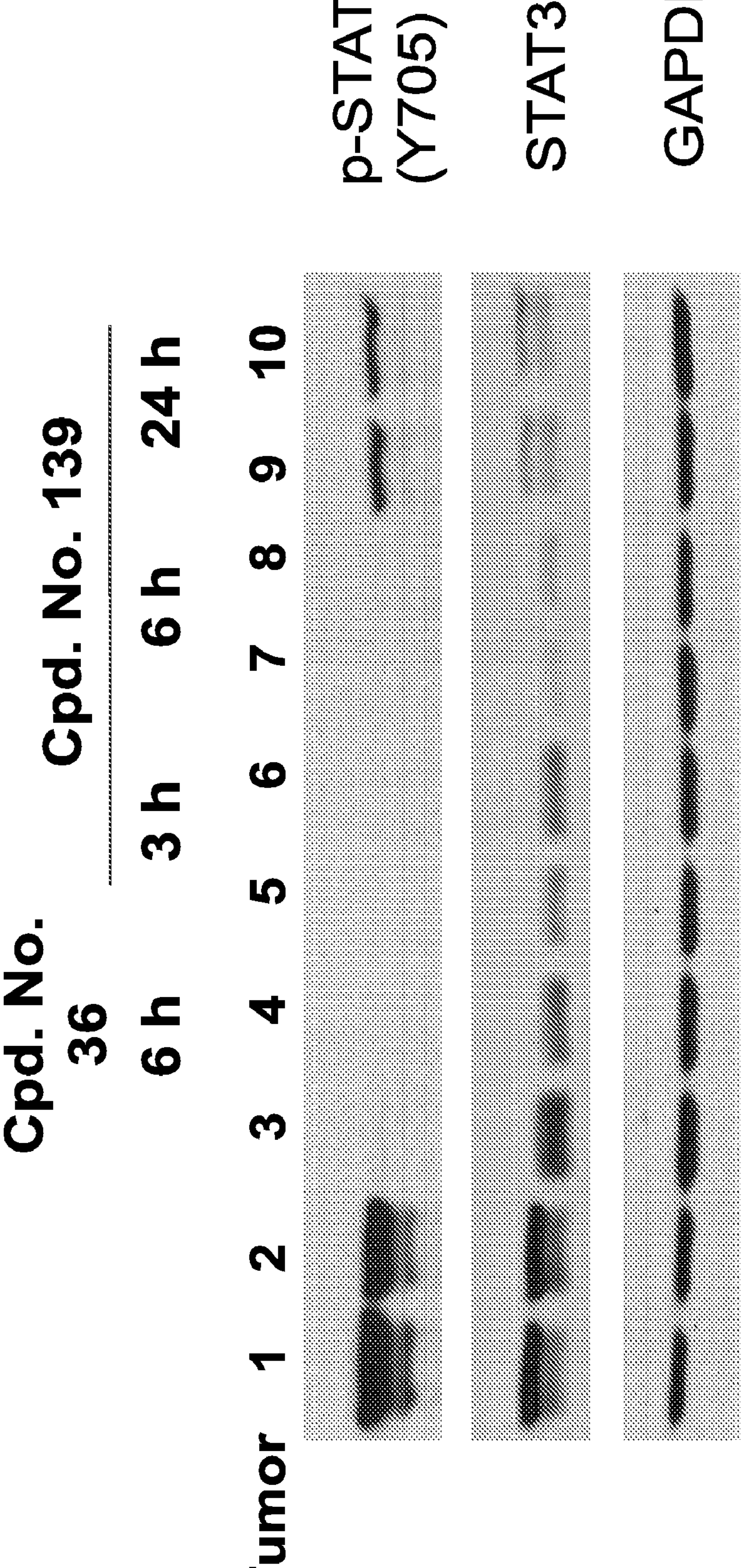
FIG. 31 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 36 and 139 at 25 mg/kg.
Figure 32:
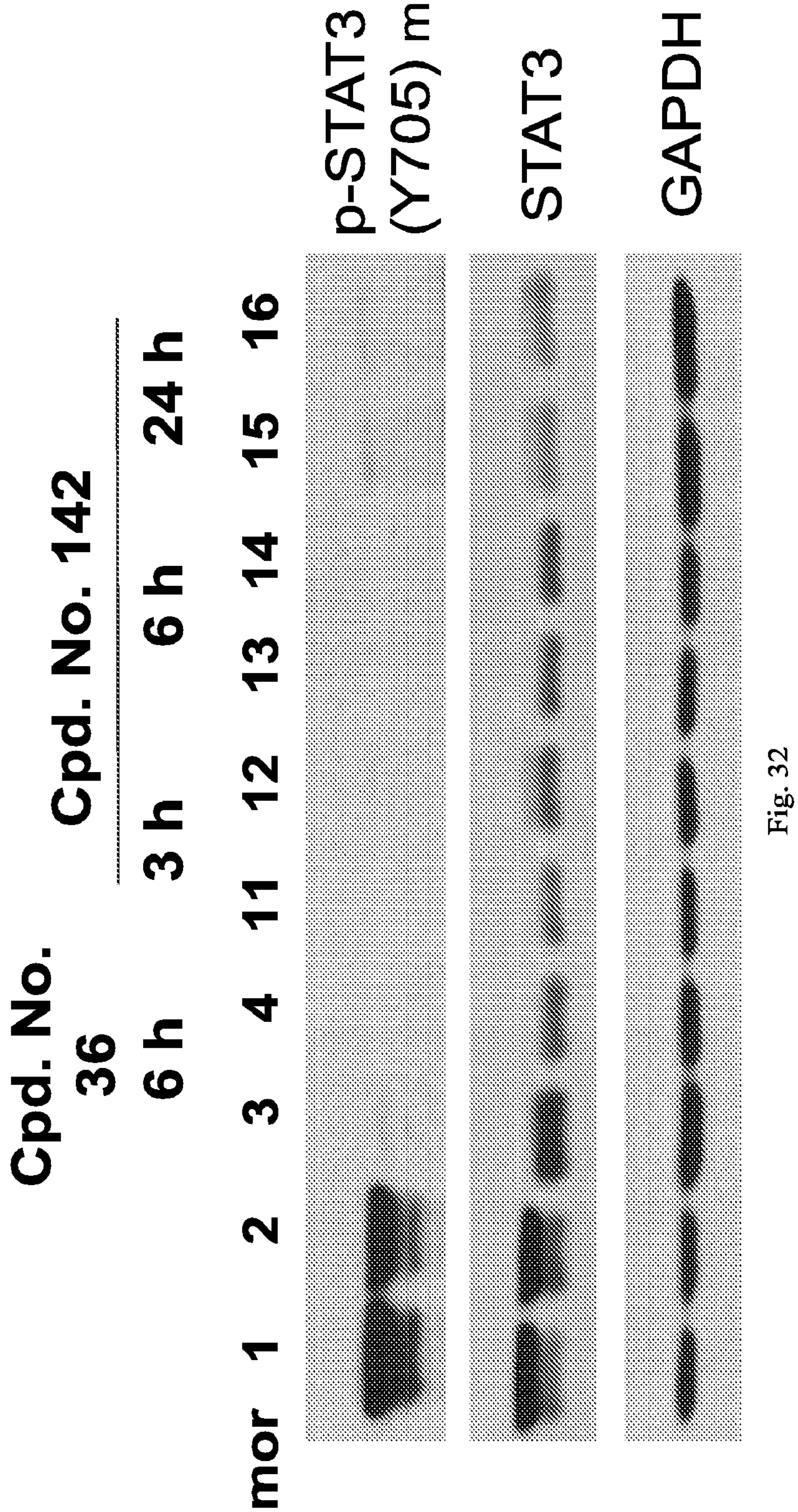
FIG. 32 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 36 and 142 at 25 mg/kg.
Figure 34:
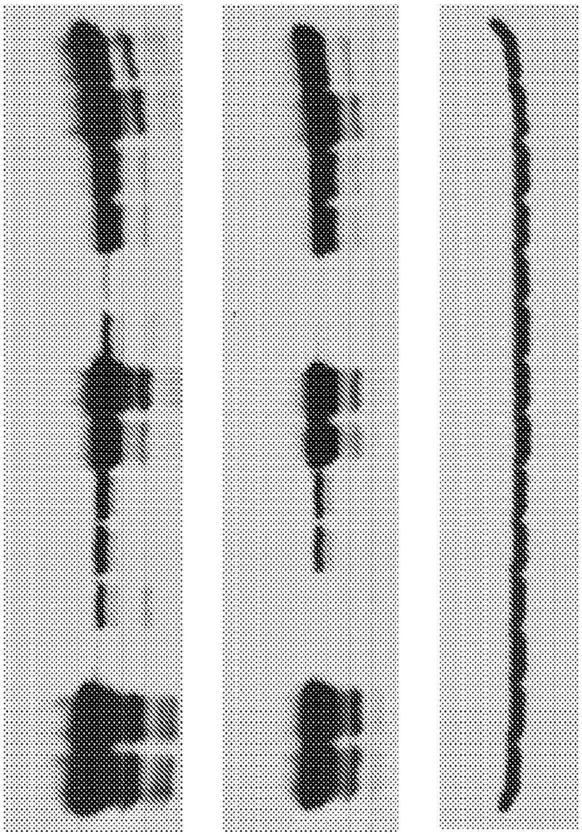
FIG. 34 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 182 and 183 at the concentrations indicated.
Figure 35:
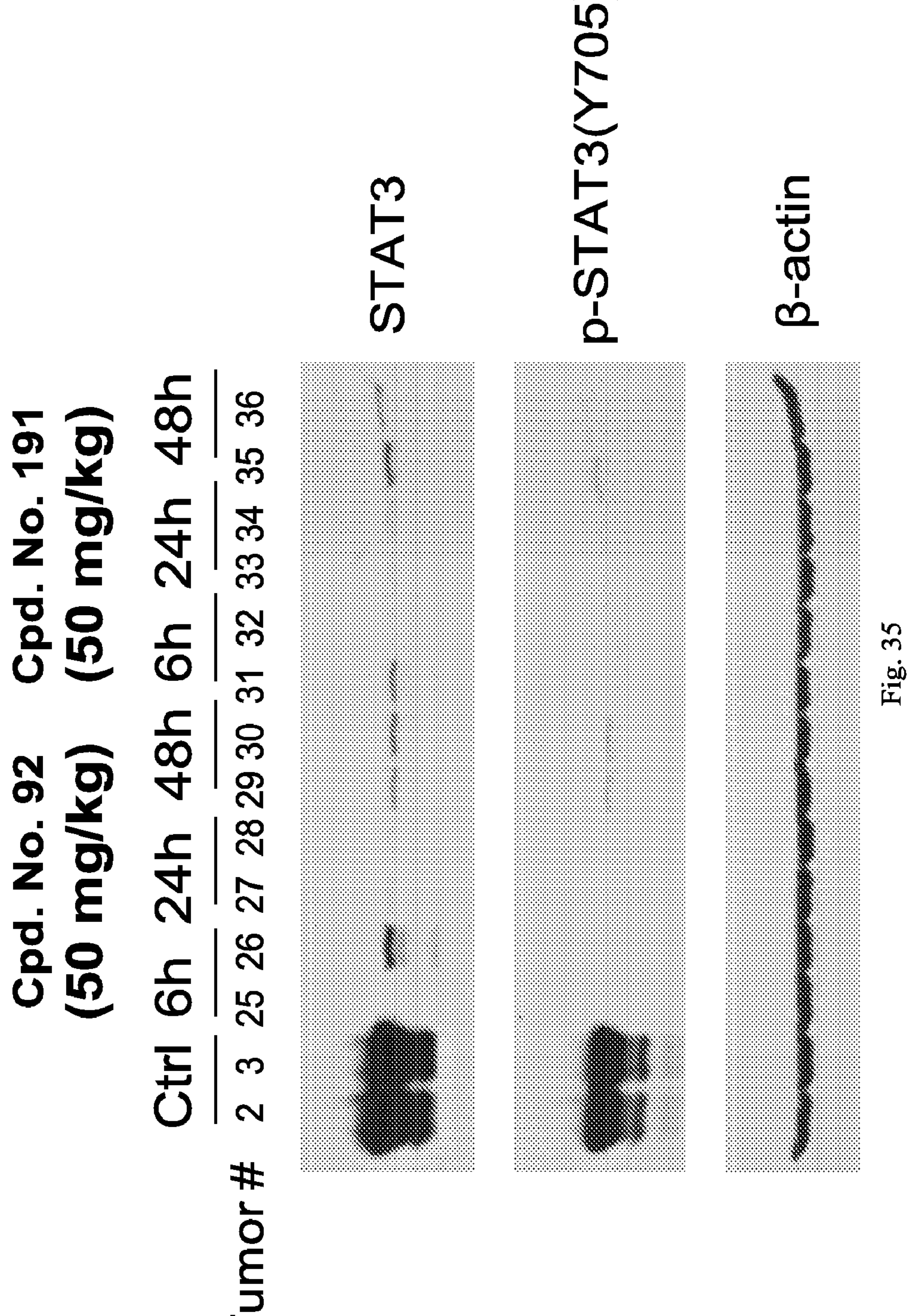
FIG. 35 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. Nos. 92 and 191 at the concentrations indicated.
Figure 36:
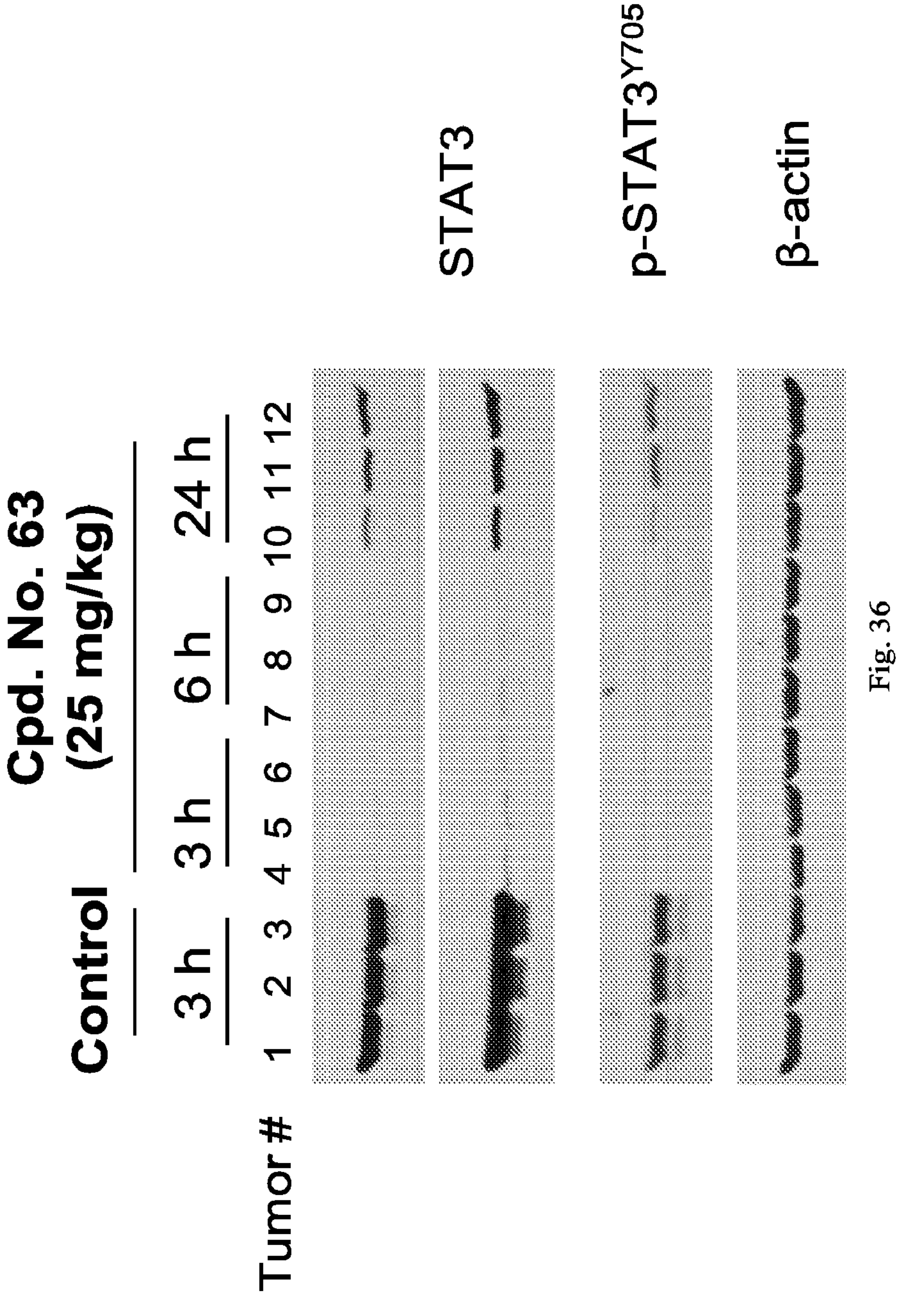
FIG. 36 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. No. 36 at the concentration indicated.
Figure 37:
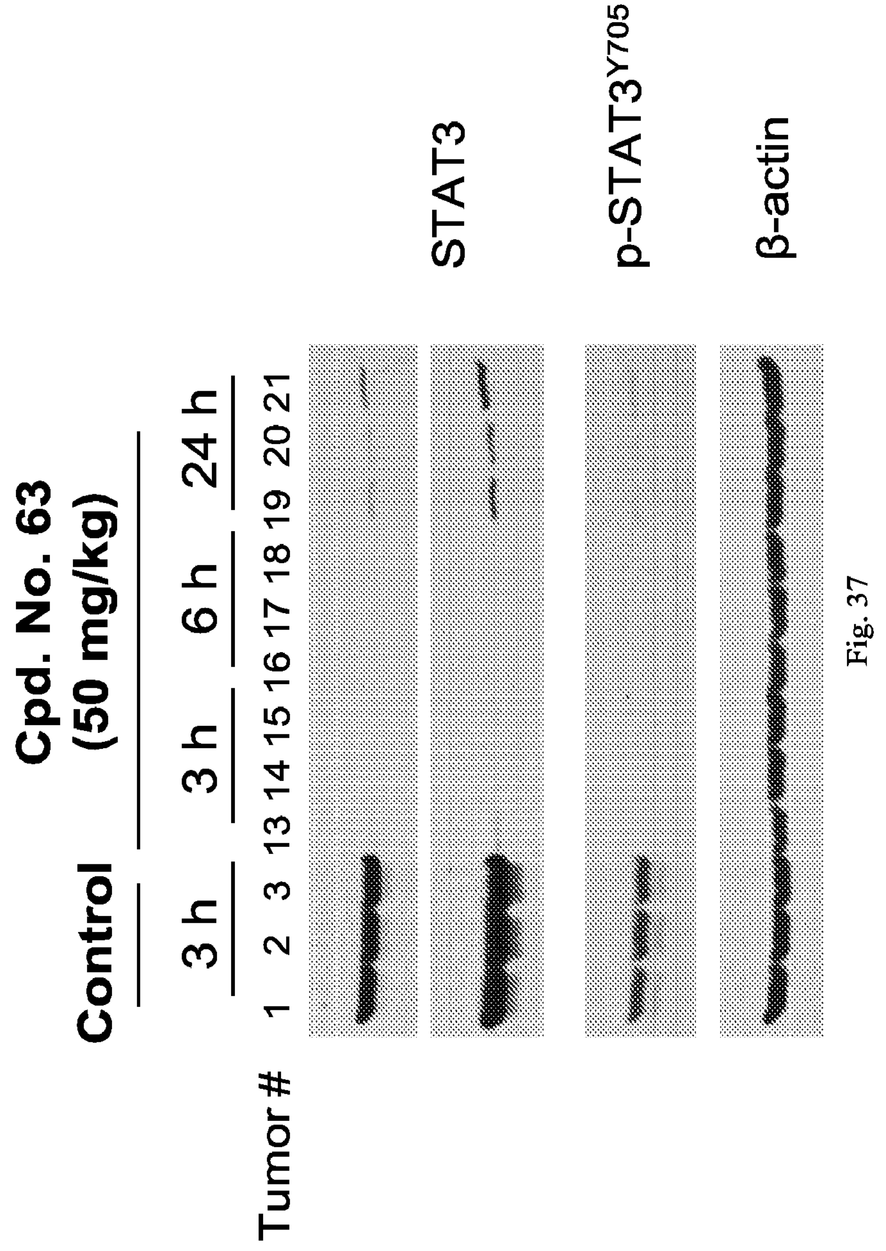
FIG. 37 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. No. 36 at the concentration indicated.
Figure 38:
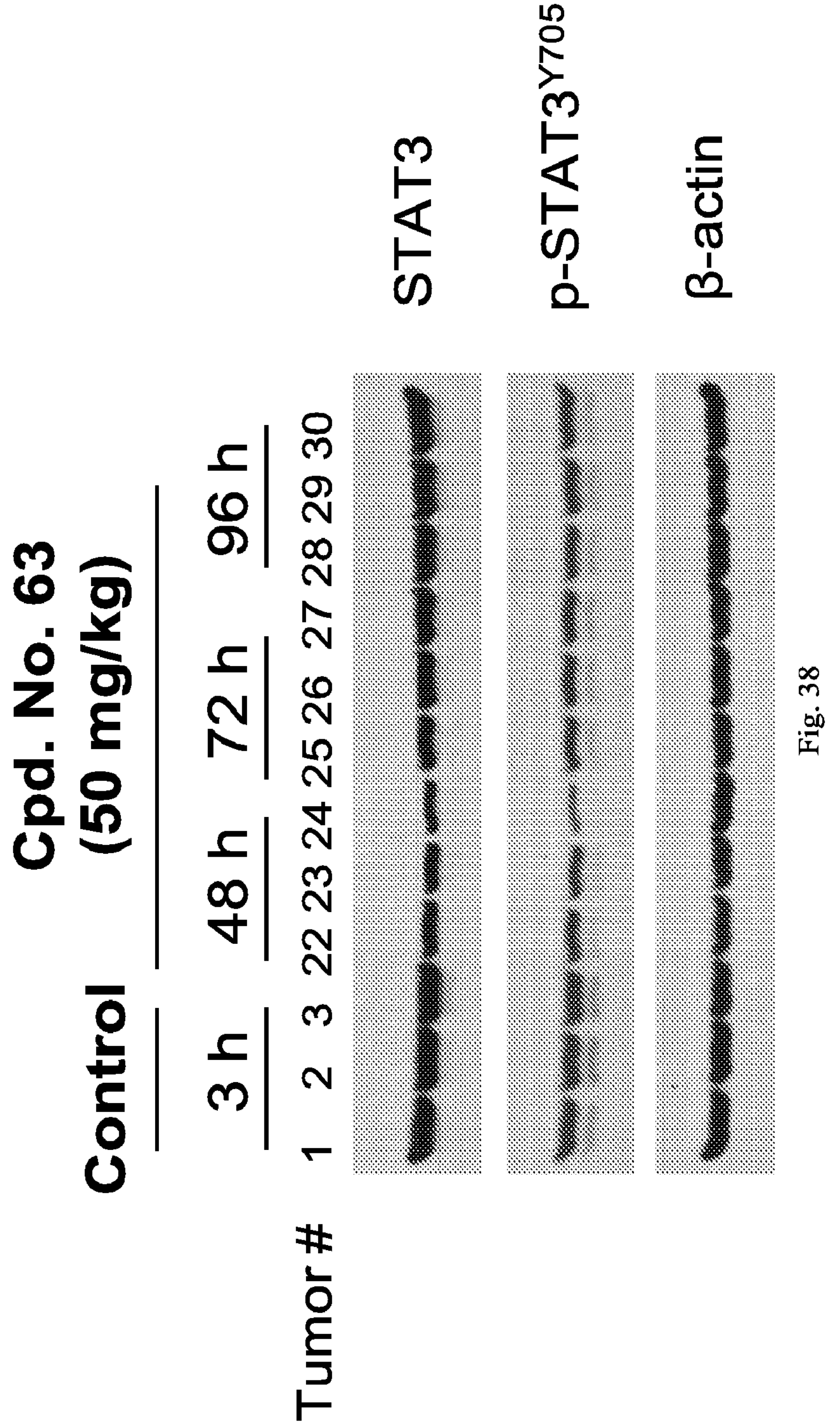
FIG. 38 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. No. 36 at the concentration indicated.
Figure 39:
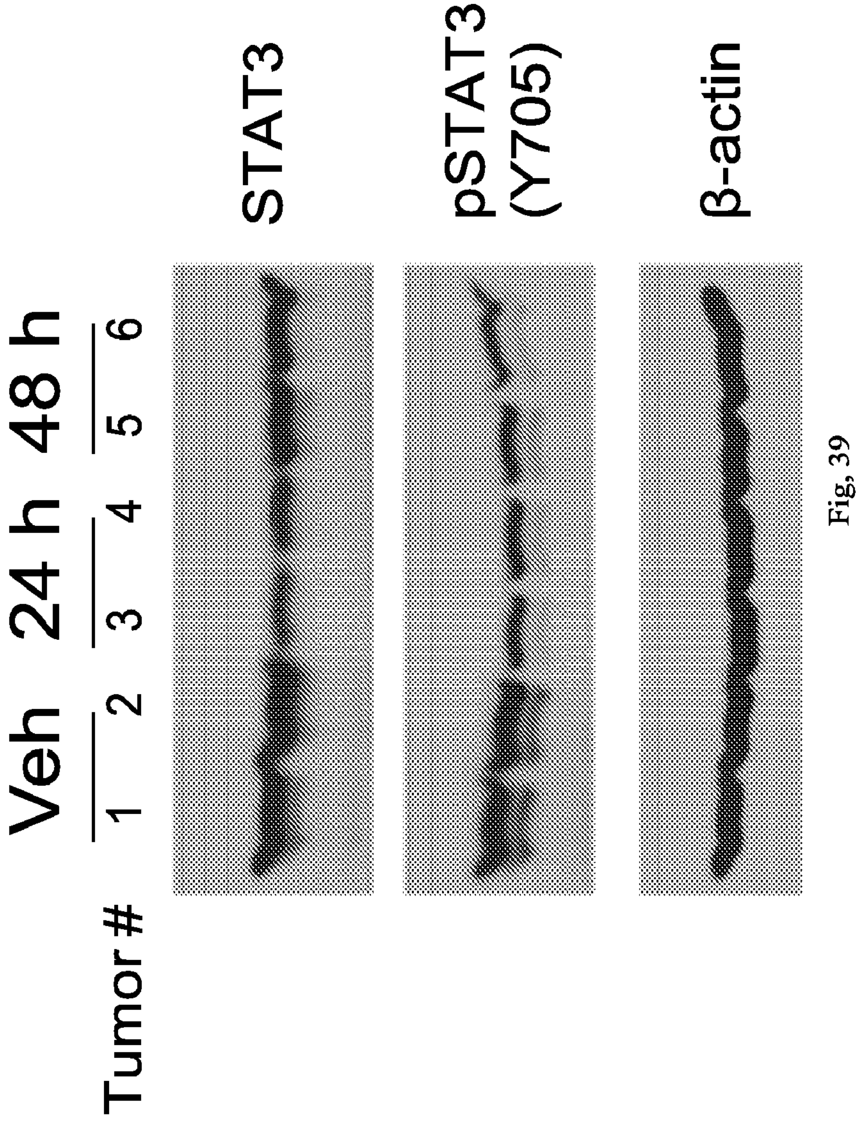
FIG. 39 is an image showing the Western blot analysis of total STAT3 protein and phosphorylated STAT3 (Y705) protein at the time points indicated in acute leukemia Molm-16 tumors in mice bearing Molm-16 tumors treated intravenously with Cpd. No. 270 at 50 mg/kg.
Figure 40:
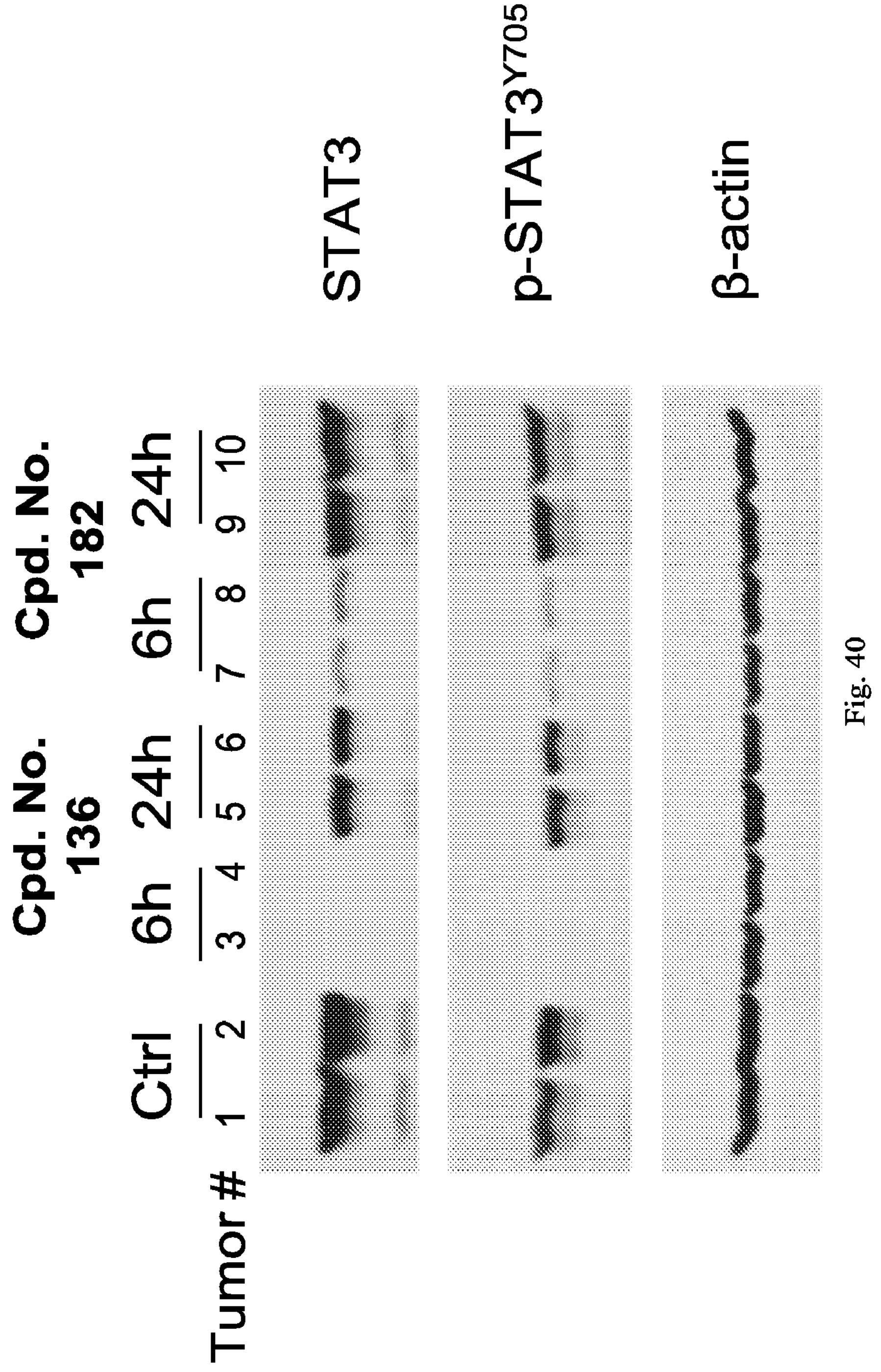
FIG. 40 is an image showing the Western blot analysis of total STAT3 protein and phosphorylated STAT3 (Y705) protein at the time points indicated in SU-DHL-1 tumors in mice bearing SU-DHL-1 tumors treated intravenously with Cpd. Nos. 136 and 182 at 50 mg/kg.
Figure 41:
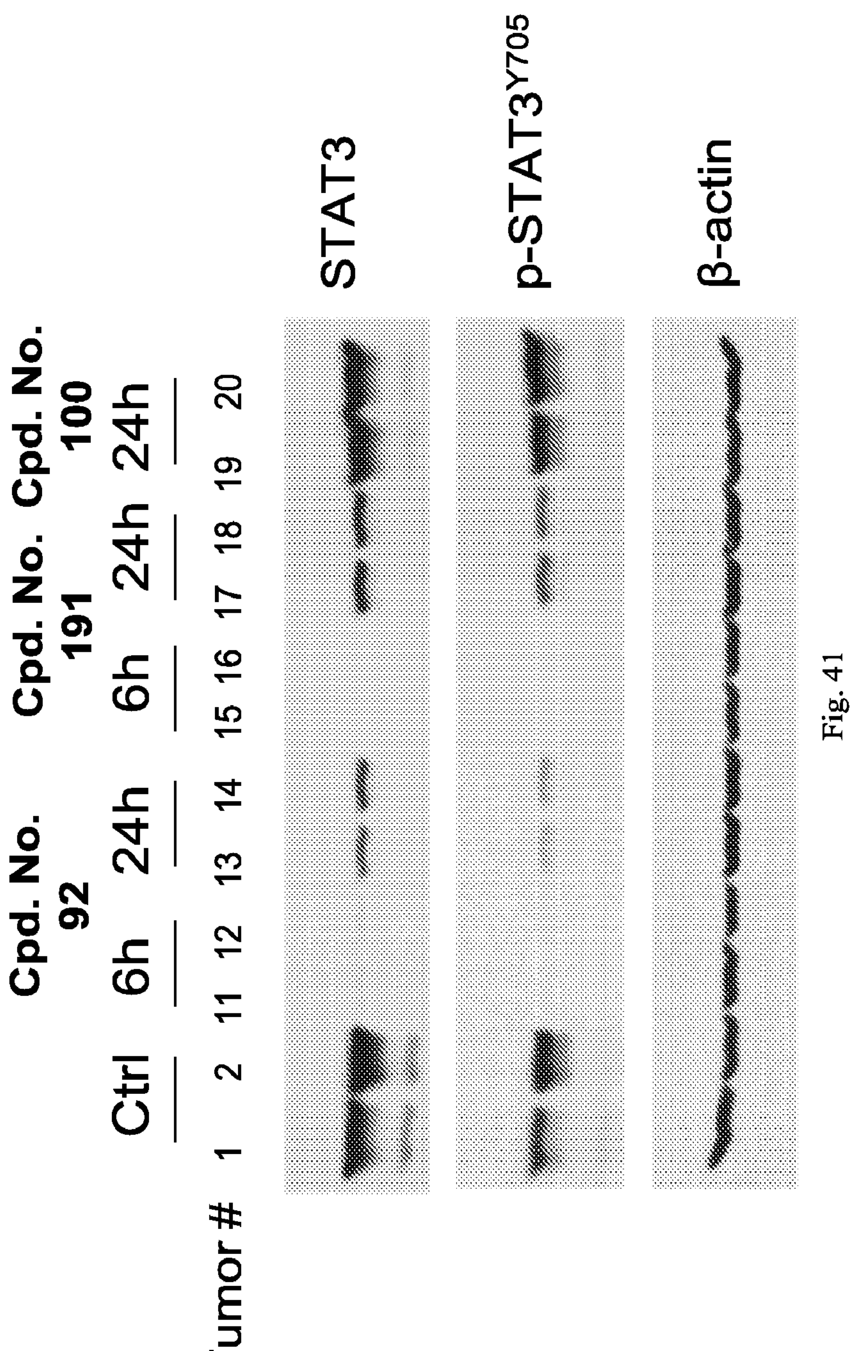
FIG. 41 is an image showing the Western blot analysis of total STAT3 protein and phosphorylated STAT3 (Y705) protein at the time points indicated in SU-DHL-1 tumors in mice bearing SU-DHL-1 tumors treated intravenously with Cpd. Nos. 92, 100, and 191 at 50 mg/kg.
Figure 42:
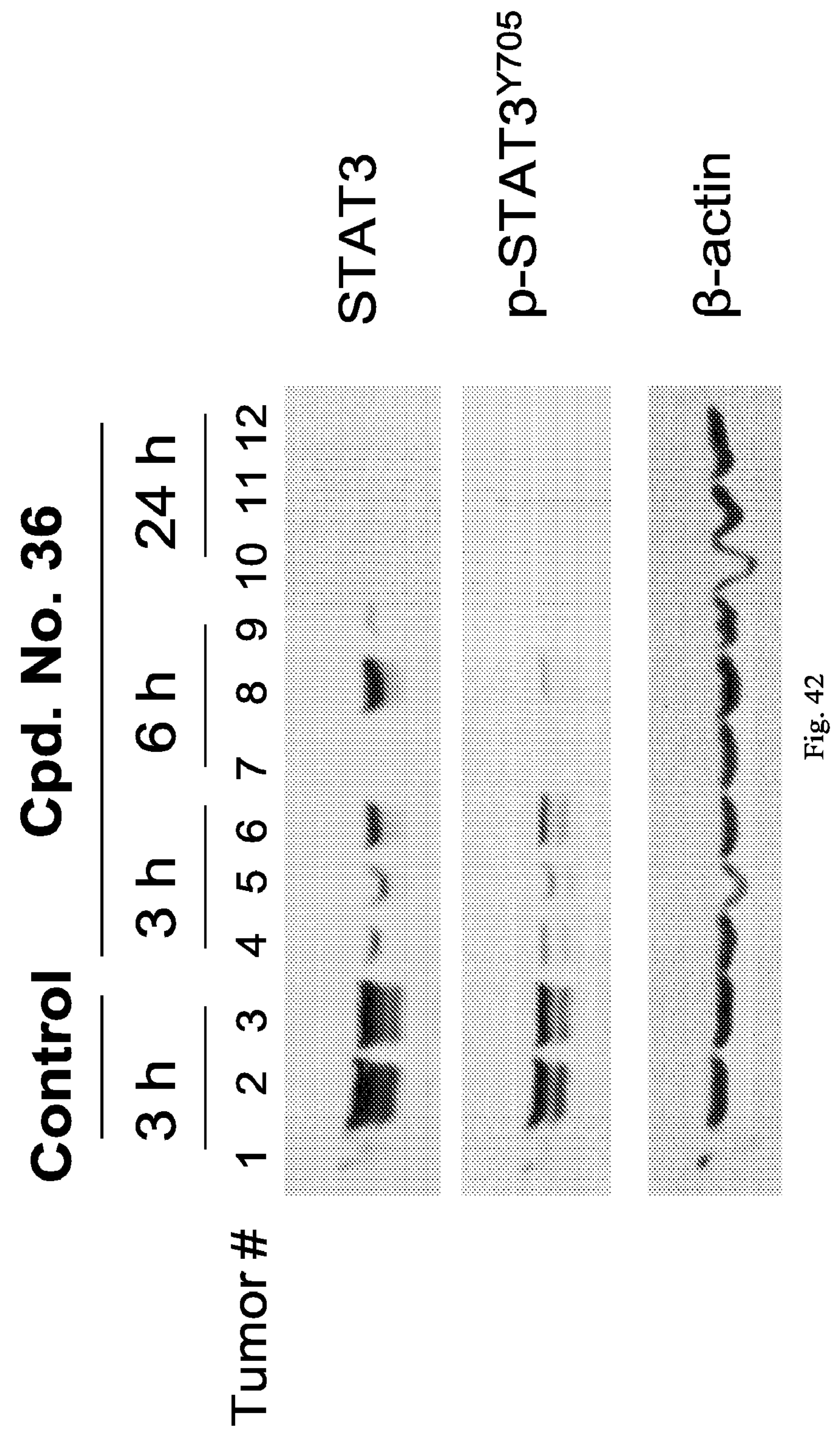
FIG. 42 is an image showing the Western blot analysis of total STAT3 protein and phosphorylated STAT3 (Y705) protein at the time points indicated in SU-DHL-1 tumors in mice bearing SU-DHL-1 tumors treated intravenously with Cpd. No. 36 at 100 mg/kg.
Figure 43:
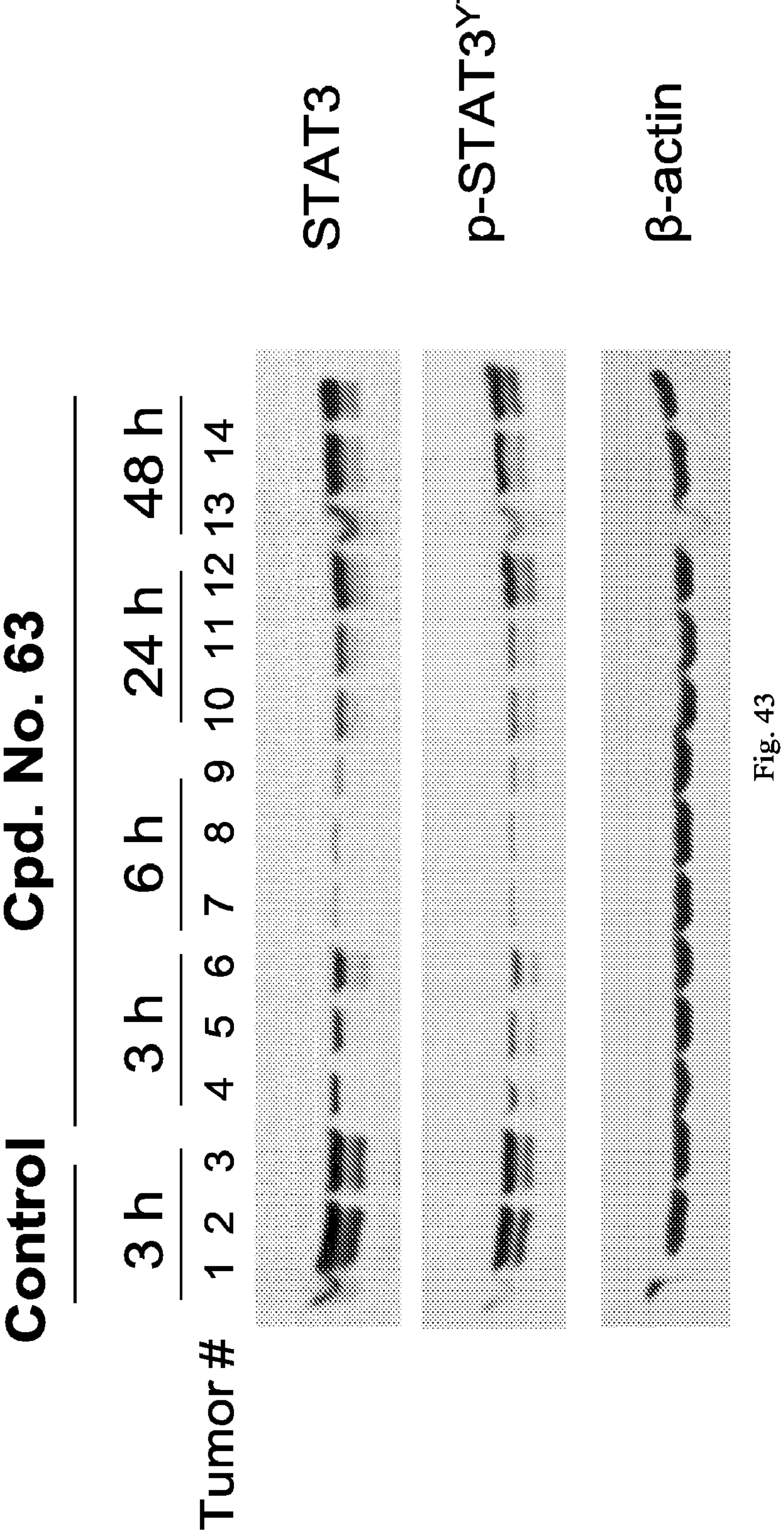
FIG. 43 is an image showing the Western blot analysis of total STAT3 protein and phosphorylated STAT3 (Y705) protein at the time points indicated in SU-DHL-1 tumors in mice bearing SU-DHL-1 tumors treated intravenously with Cpd. No. 63 at 100 mg/kg.
Figure 44:
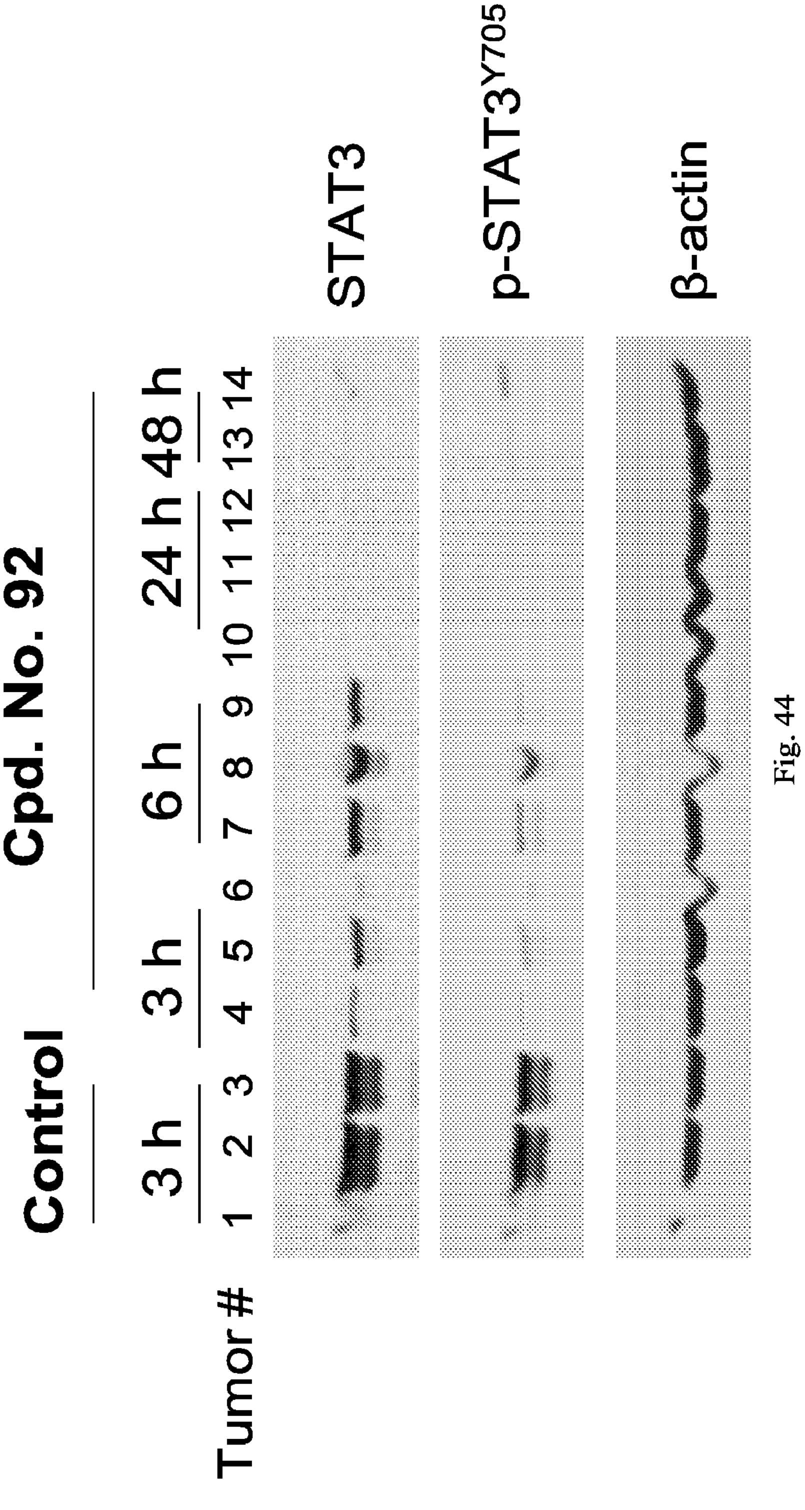
FIG. 44 is an image showing the Western blot analysis of total STAT3 protein and phosphorylated STAT3 (Y705) protein at the time points indicated in SU-DHL-1 tumors in mice bearing SU-DHL-1 tumors treated intravenously with Cpd. No. 92 at 100 mg/kg.
Figure 45:
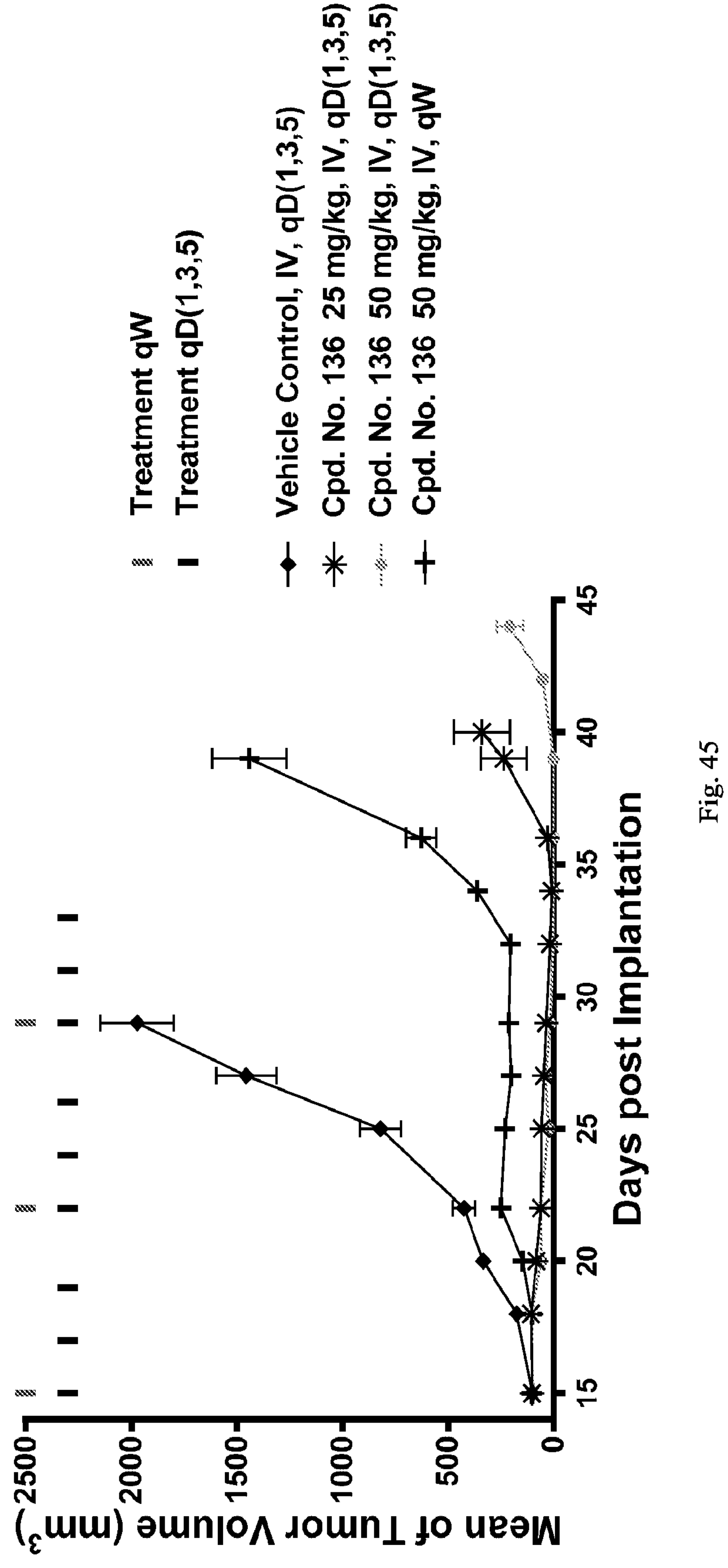
FIG. 45 is a line graph showing the antitumor activity of Cpd. No. 136 against Molm-16 xenograft tumors in mice at the doses and schedules indicated.
Figure 46:
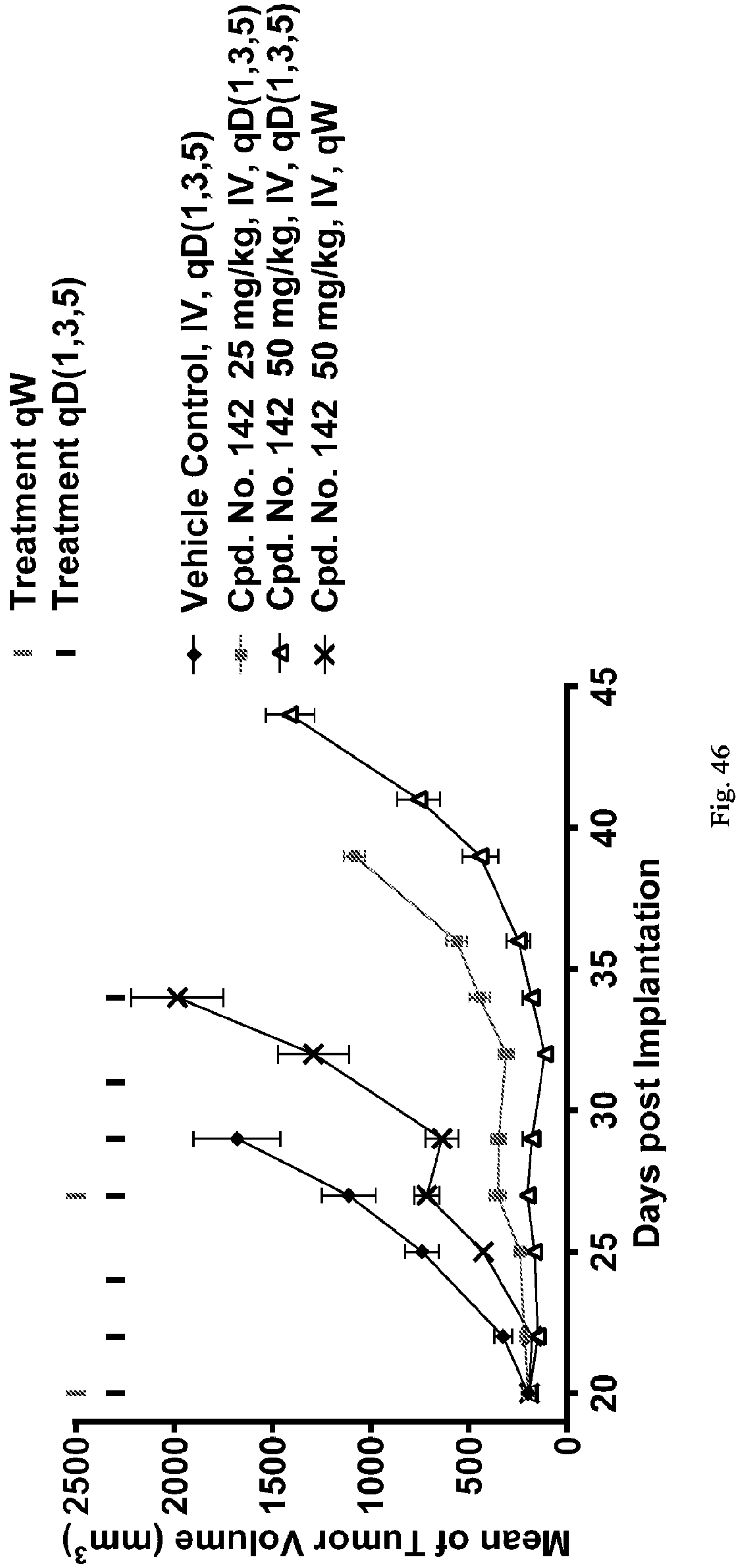
FIG. 46 is a line graph showing the antitumor activity of Cpd. No. 142 against Molm-16 xenograft tumors in mice at the doses and schedules indicated.
Figure 48:
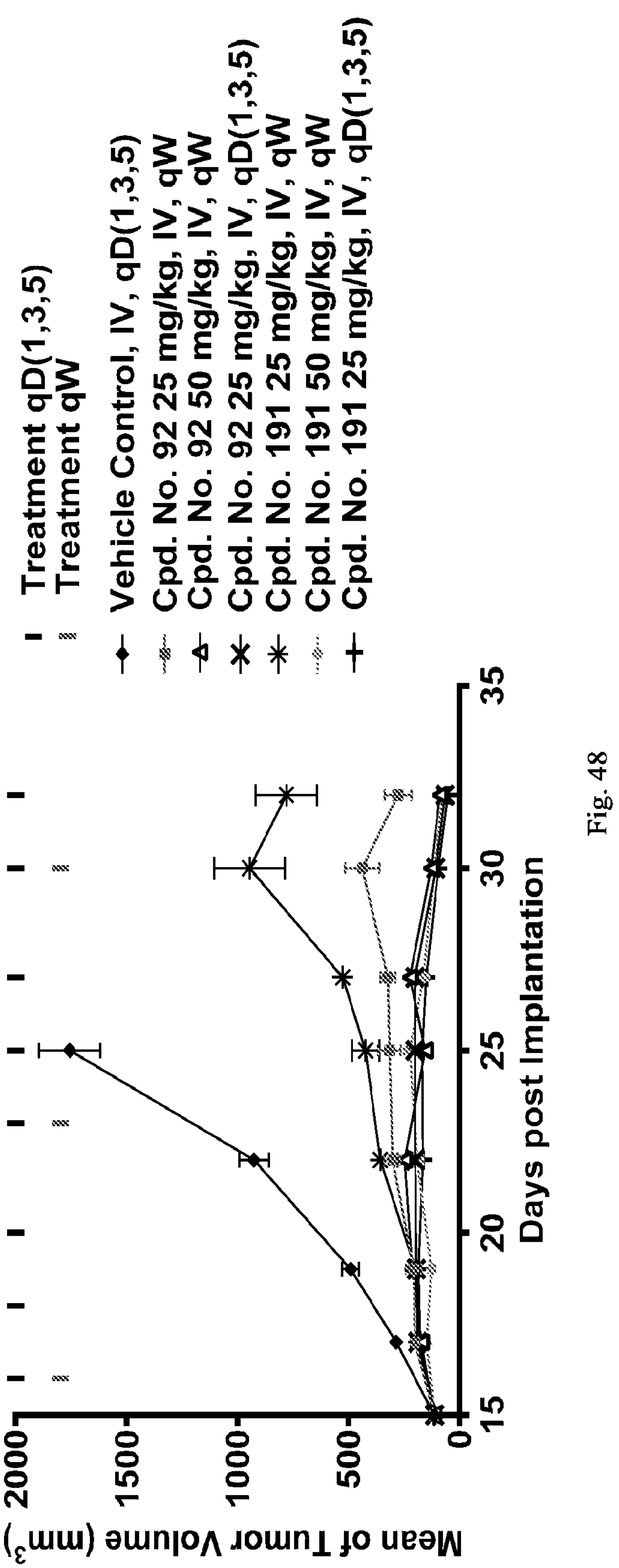
FIG. 48 is a line graph showing the antitumor activity of Cpd. Nos. 92 and 191 against Molm-16 xenograft tumors in mice at the doses and schedules indicated.
Figure 49:
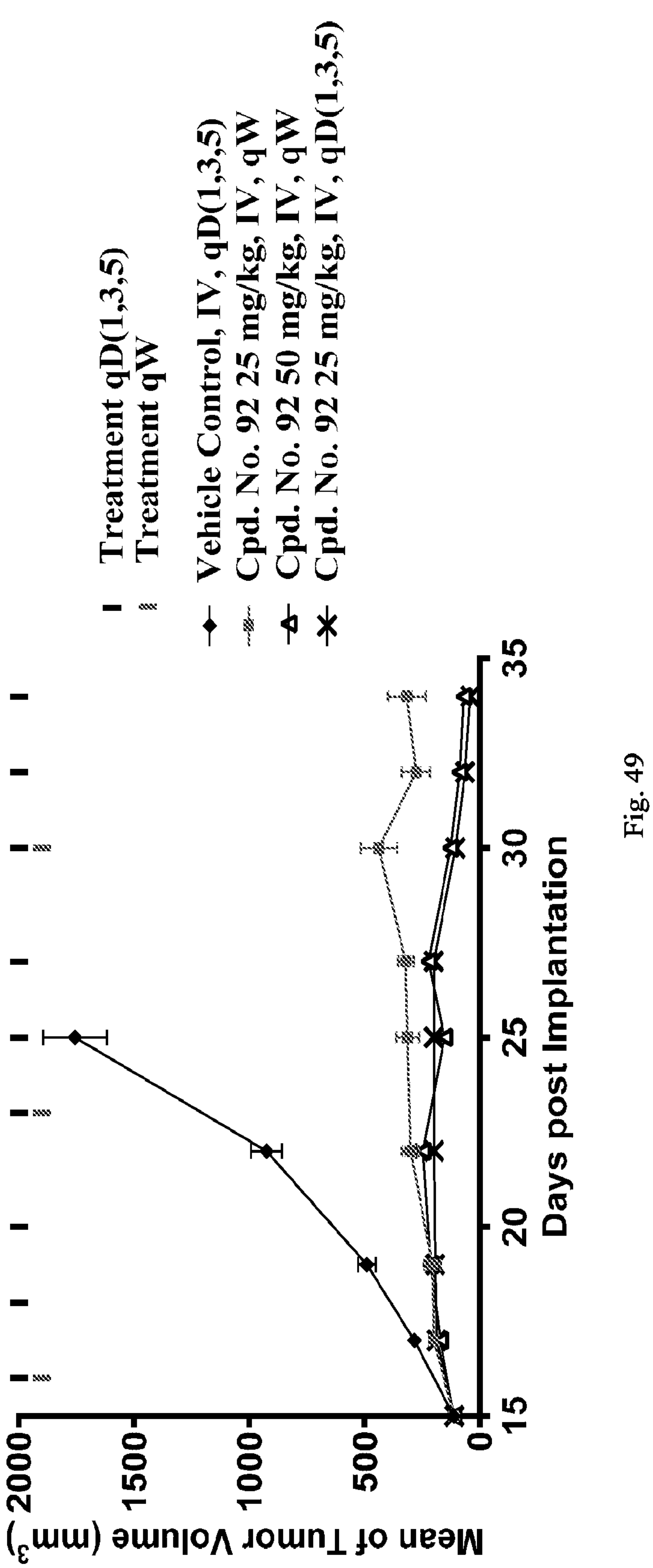
FIG. 49 is a line graph showing the antitumor activity of Cpd. No. 92 against Molm-16 xenograft tumors in mice at the doses and schedules indicated.
Figure 50:
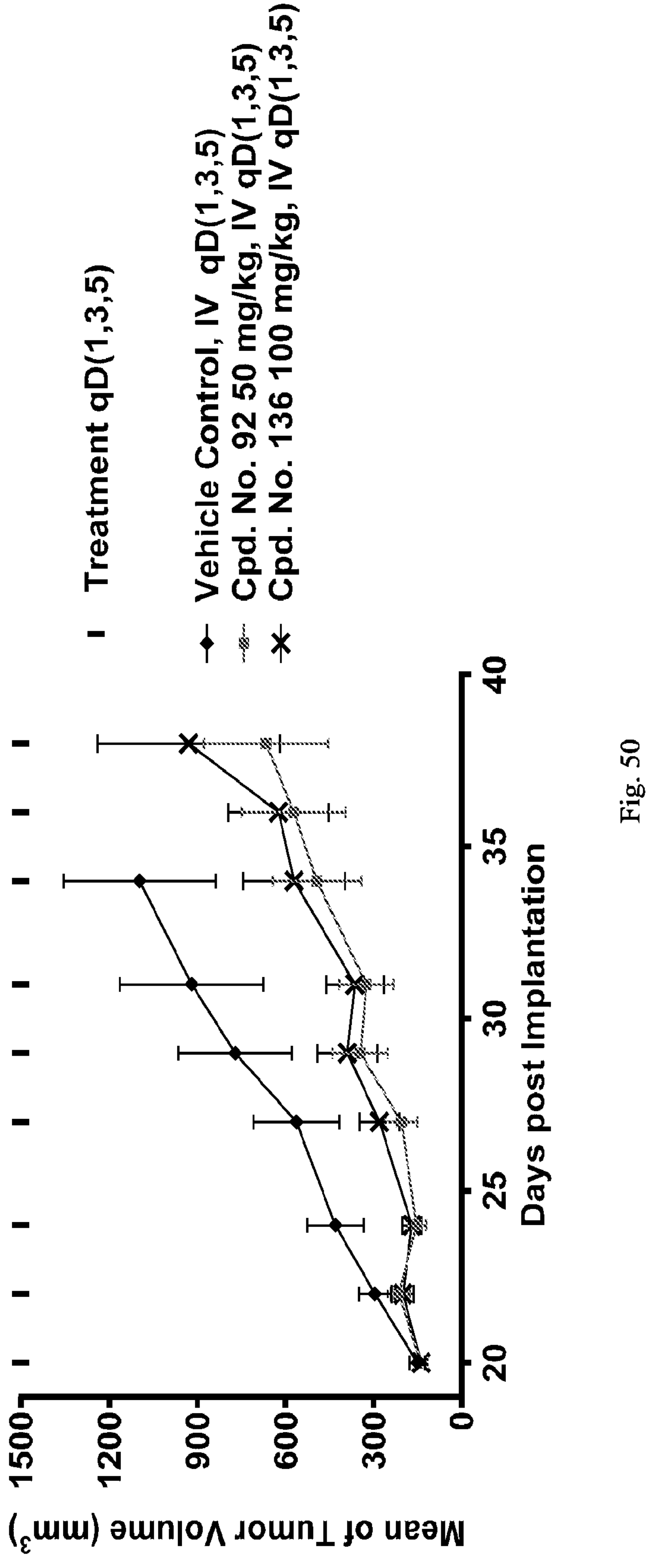
FIG. 50 is a line graph showing the antitumor activity of Cpd. Nos. 92 and 136 against SU-DHL-1 xenograft tumors in mice at the doses and schedules indicated.
Figure 51:
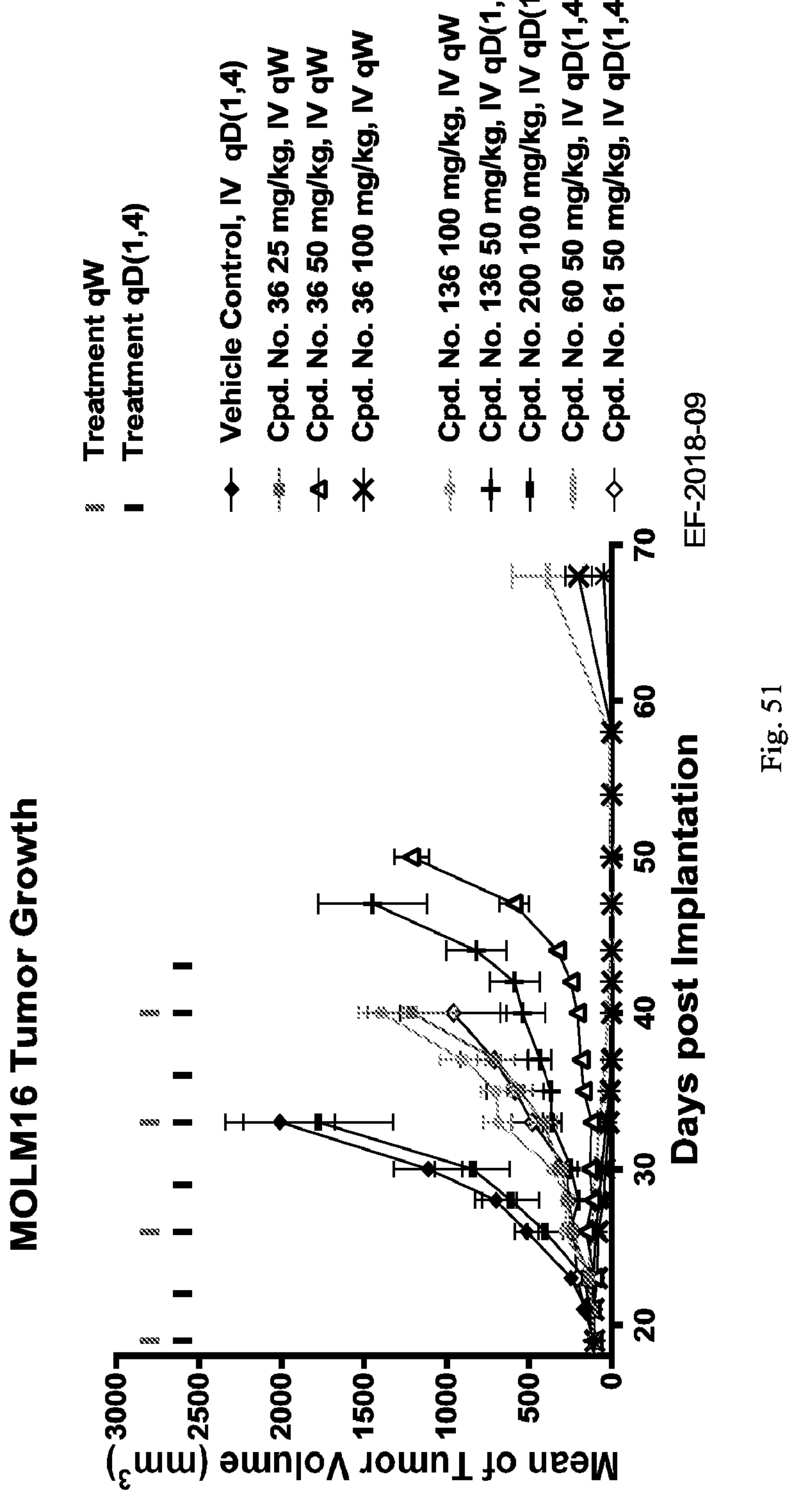
FIG. 51 is a line graph showing the antitumor activity of Cpd. Nos. 36, 60, 61, 136, and 200 against Molm-16 xenograft tumors in mice at the doses and schedules indicated.
Figure 52:
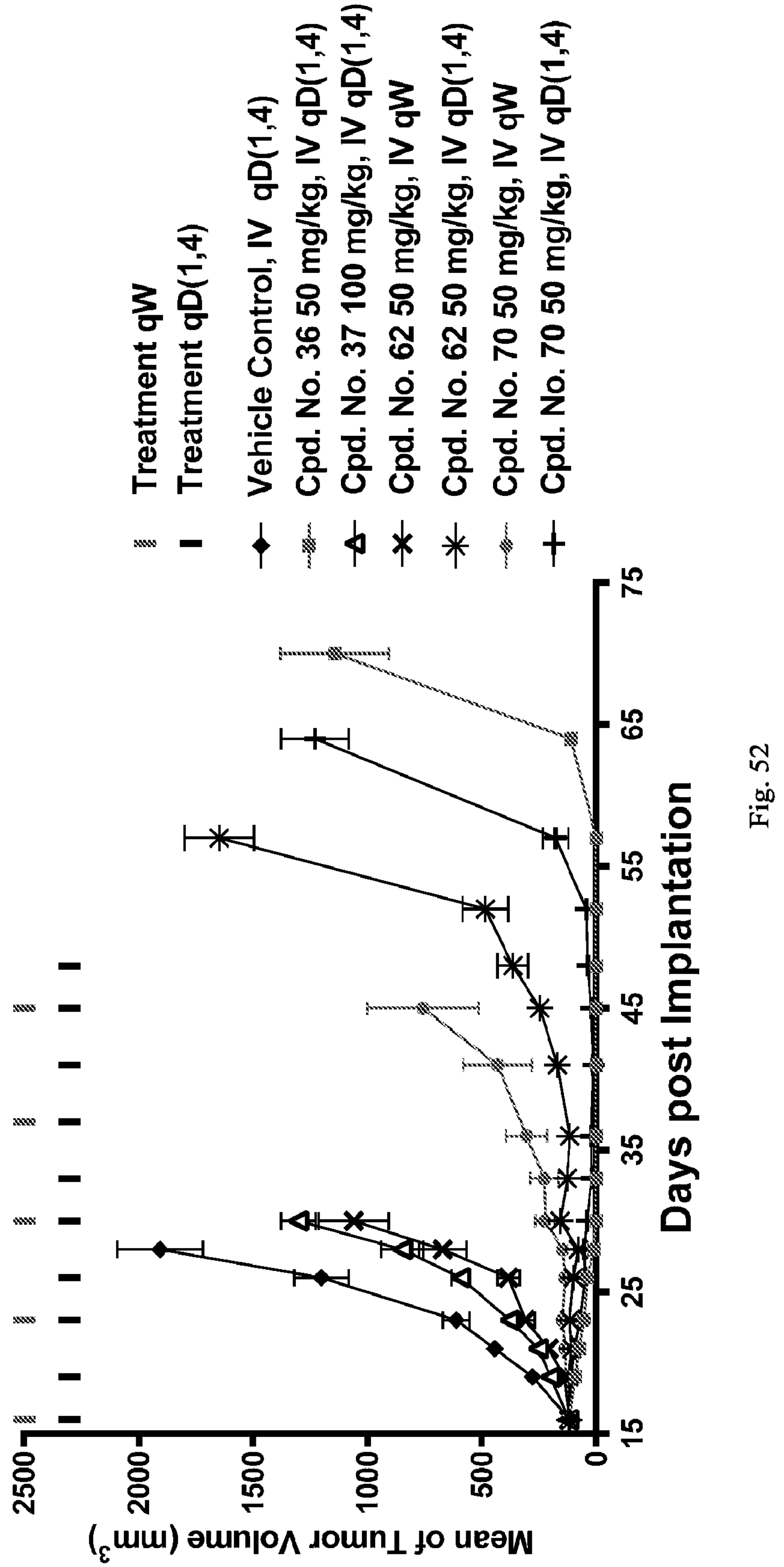
FIG. 52 is a line graph showing the antitumor activity of Cpd. Nos. 36, 37, 62, and 70 against Molm-16 xenograft tumors in mice at the doses and schedules indicated.
Figure 53:
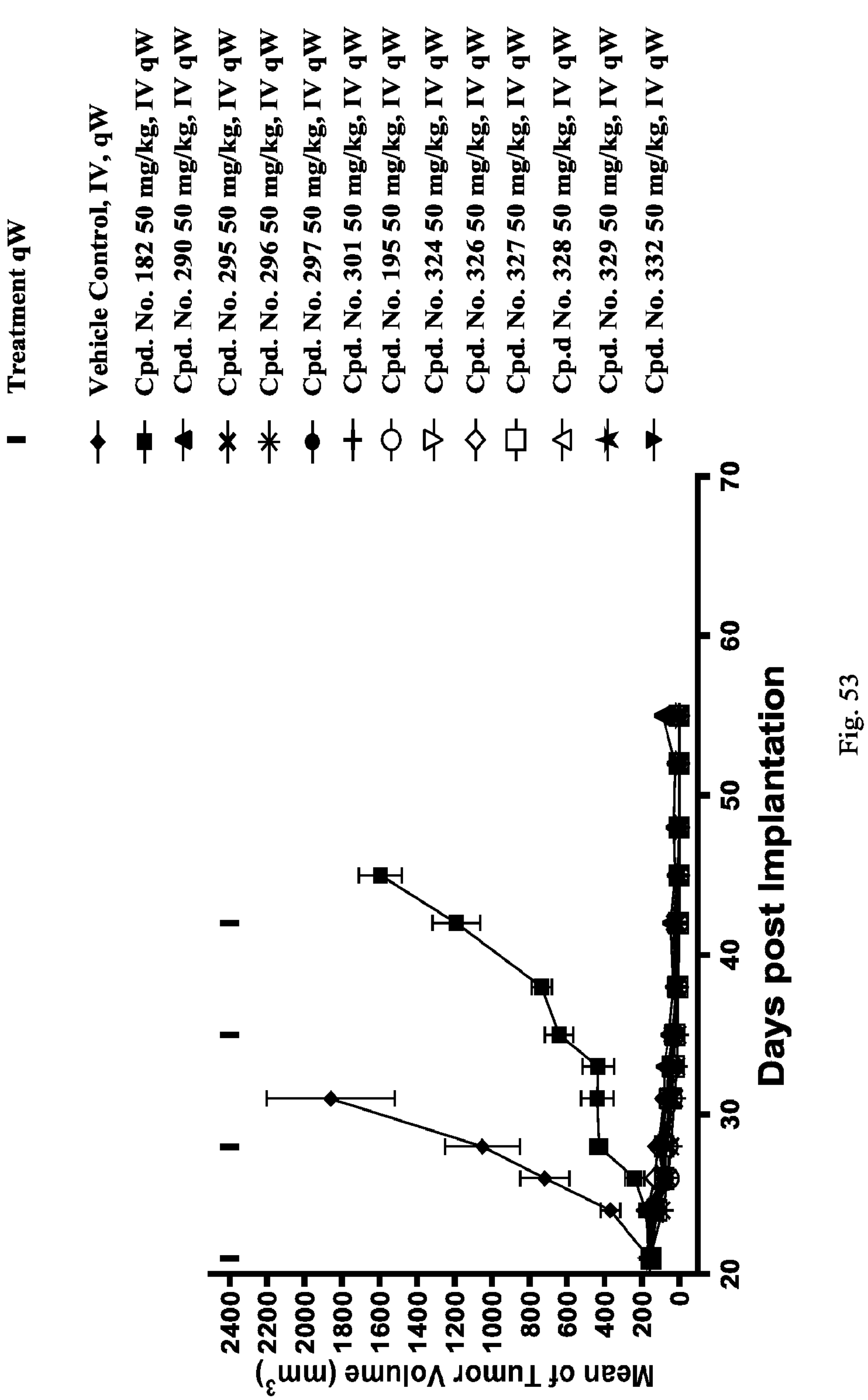
FIG. 53 is a line graph showing the antitumor activity of Cpd. Nos. 182, 195, 290, 295, 296, 297, 301, 324, 326, 327, 329, and 332 against Molm-16 xenograft tumors in mice at the doses and schedules indicated.
Figure 54:
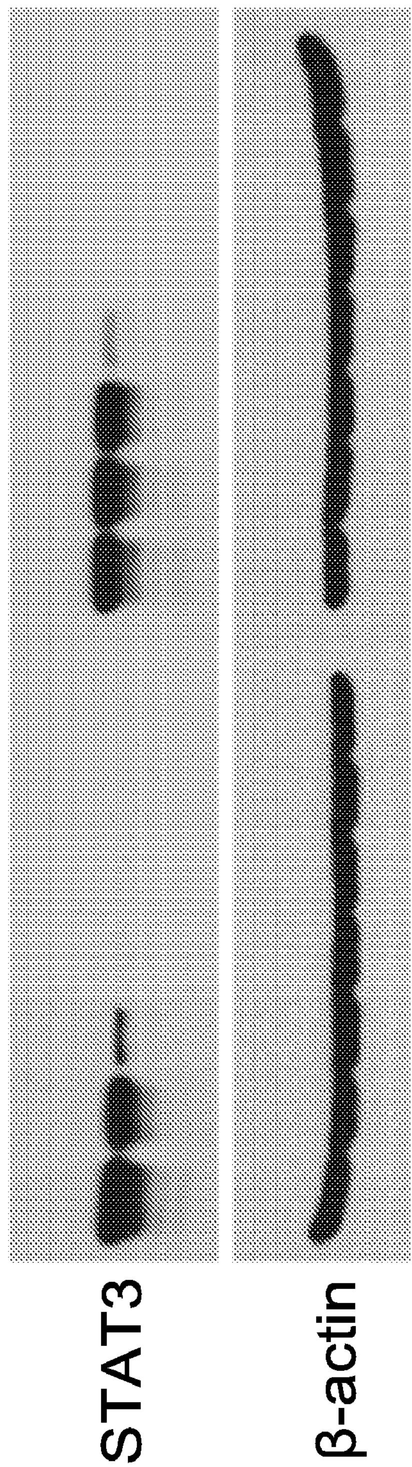
FIG. 54 is an image showing the Western blot analysis of the in vitro degradation of STAT3 in Molm-16 cells (DSMZ) at the doses indicated after treatment for 3-6 h with Cpd. Nos. 36 and 195.
Figure 56:
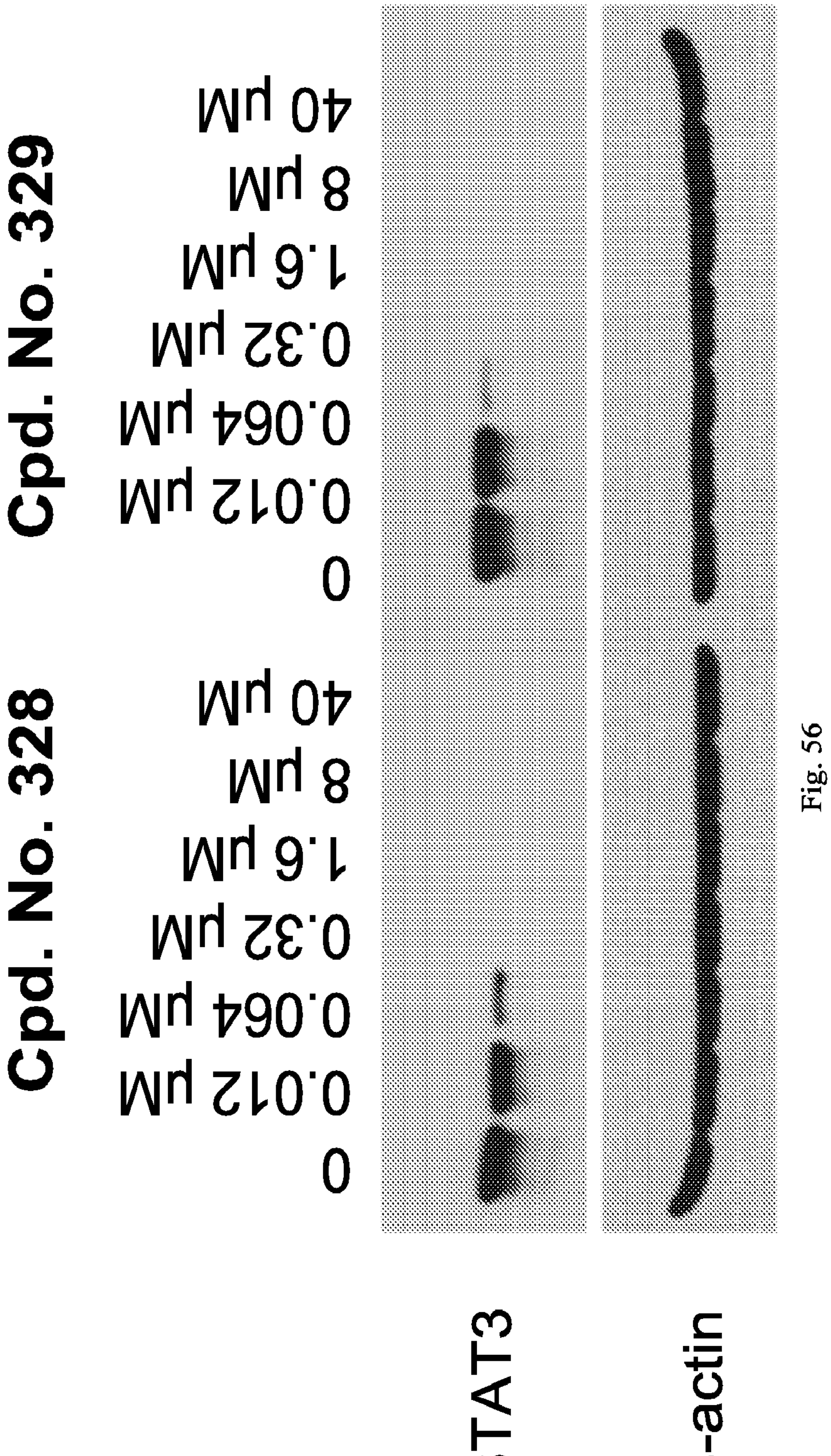
FIG. 56 is an image showing the Western blot analysis of the in vitro degradation of STAT3 in Molm-16 cells (DSMZ) at the doses indicated after treatment for 3-6 h with Cpd. Nos. 328 and 329.
Figure 57:
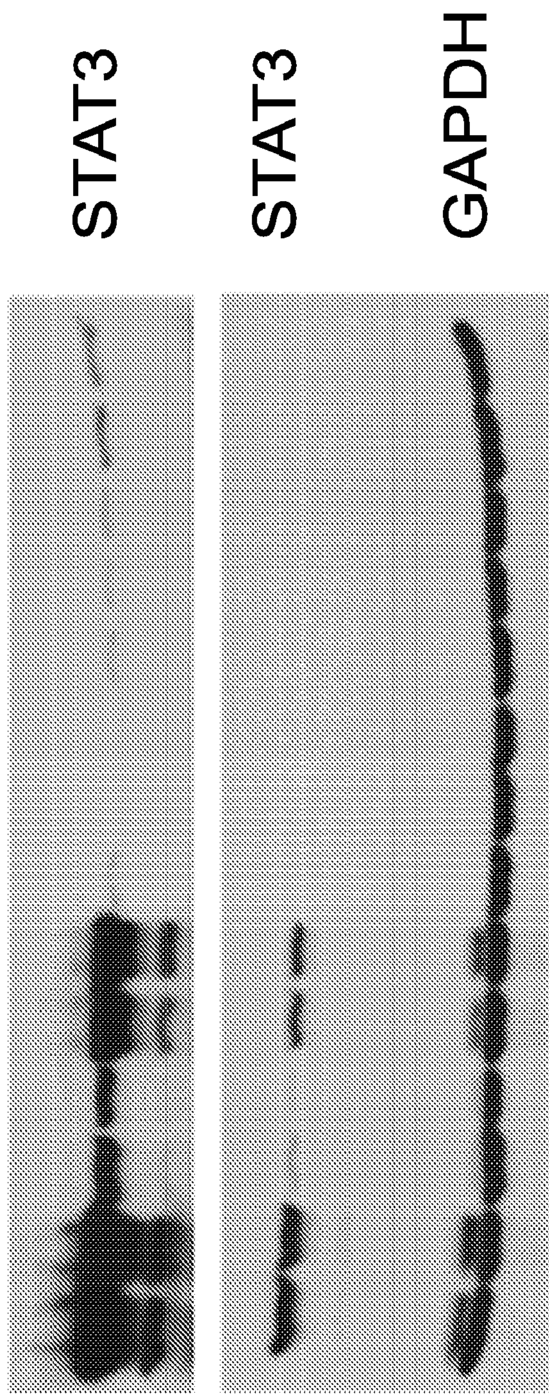
FIG. 57 is an image showing the Western blot analysis of STAT3 protein at the time points indicated in SCID mice bearing Molm-16 tumors treated intravenously with Cpd. Nos. 182, 195, and 324 at 25 mg/kg.
Figure 58:
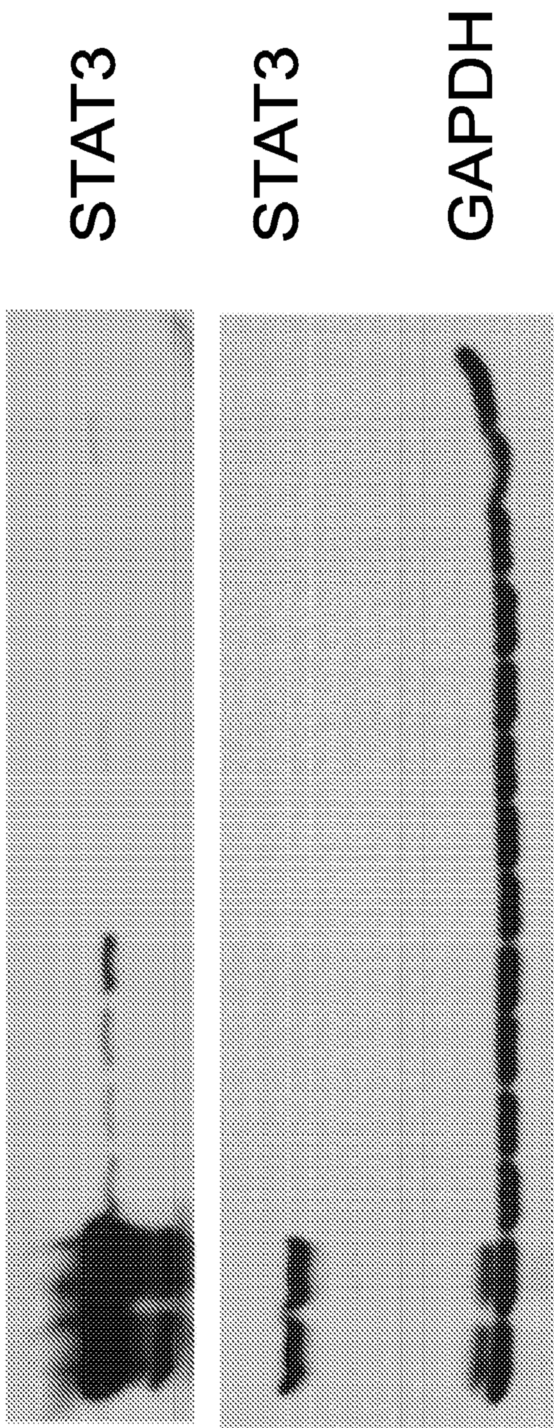
FIG. 58 is an image showing the Western blot analysis of STAT3 protein at the time points indicated in SCID mice bearing Molm-16 tumors treated intravenously with Cpd. Nos. 326, 328, and 329 at 25 mg/kg.
Figure 59:
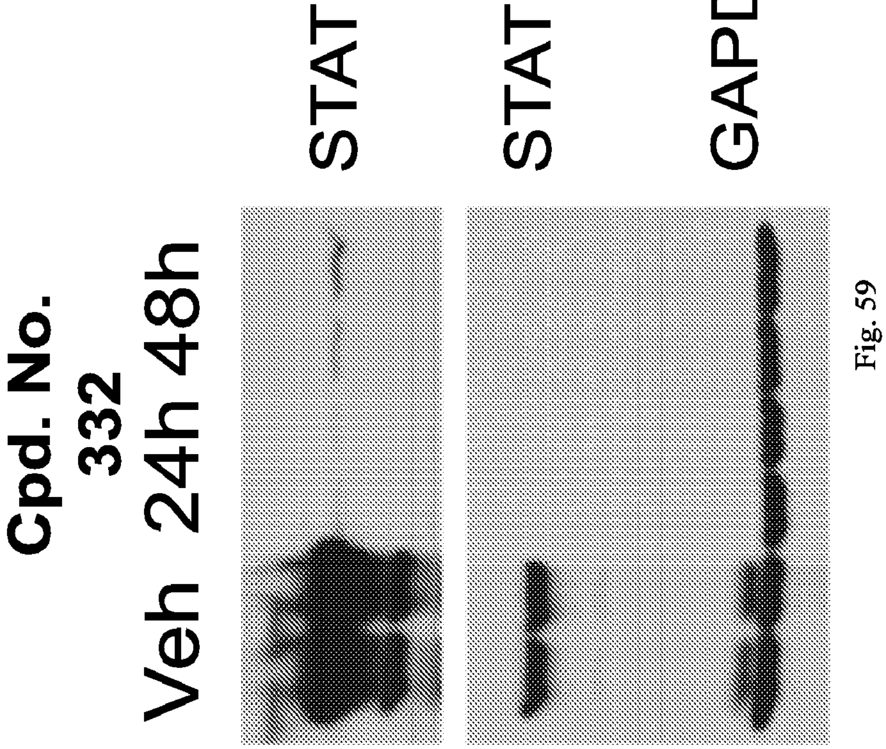
FIG. 59 is an image showing the Western blot analysis of STAT3 protein at the time points indicated in SCID mice bearing Molm-16 tumors treated intravenously with Cpd. No. 332 at 25 mg/kg.
Figure 60:
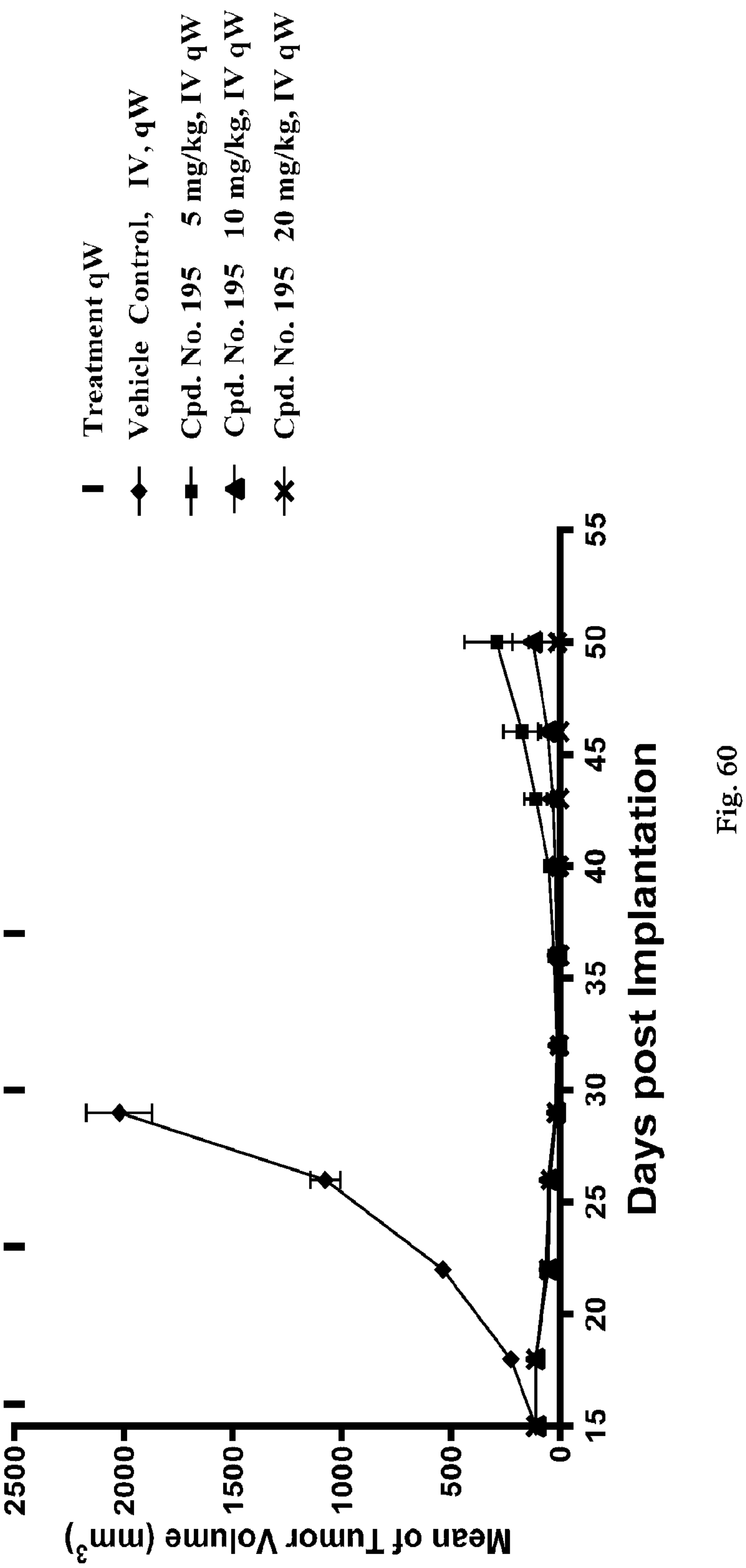
FIG. 60 is a line graph showing the antitumor activity of Cpd. No. 195 against Molm-16 xenograft tumors in mice at the doses and schedules indicated.
Figure 61:
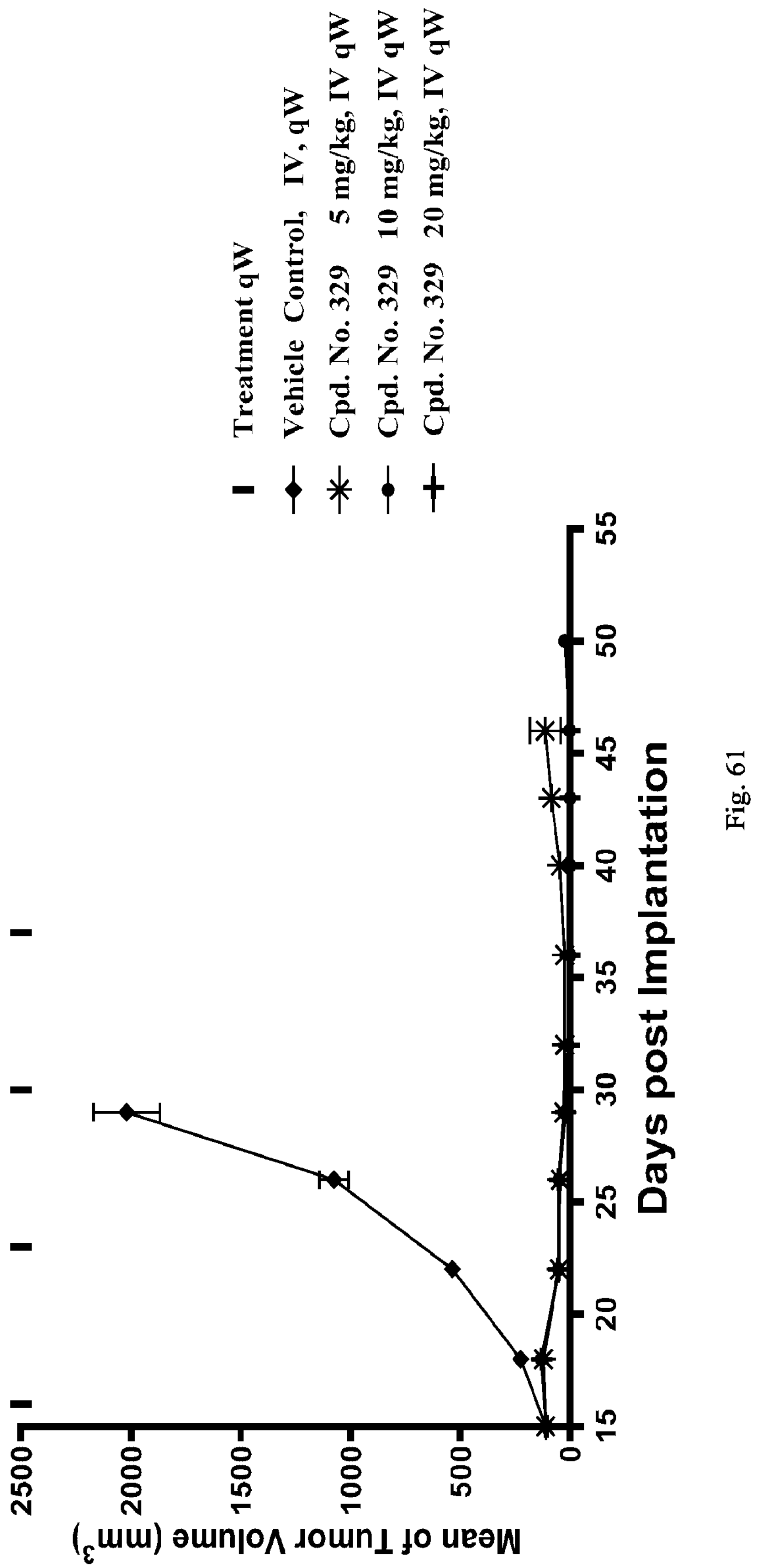
FIG. 61 is a line graph showing the antitumor activity of Cpd. No. 329 against Molm-16 xenograft tumors in mice at the doses and schedules indicated.
Figure 62:
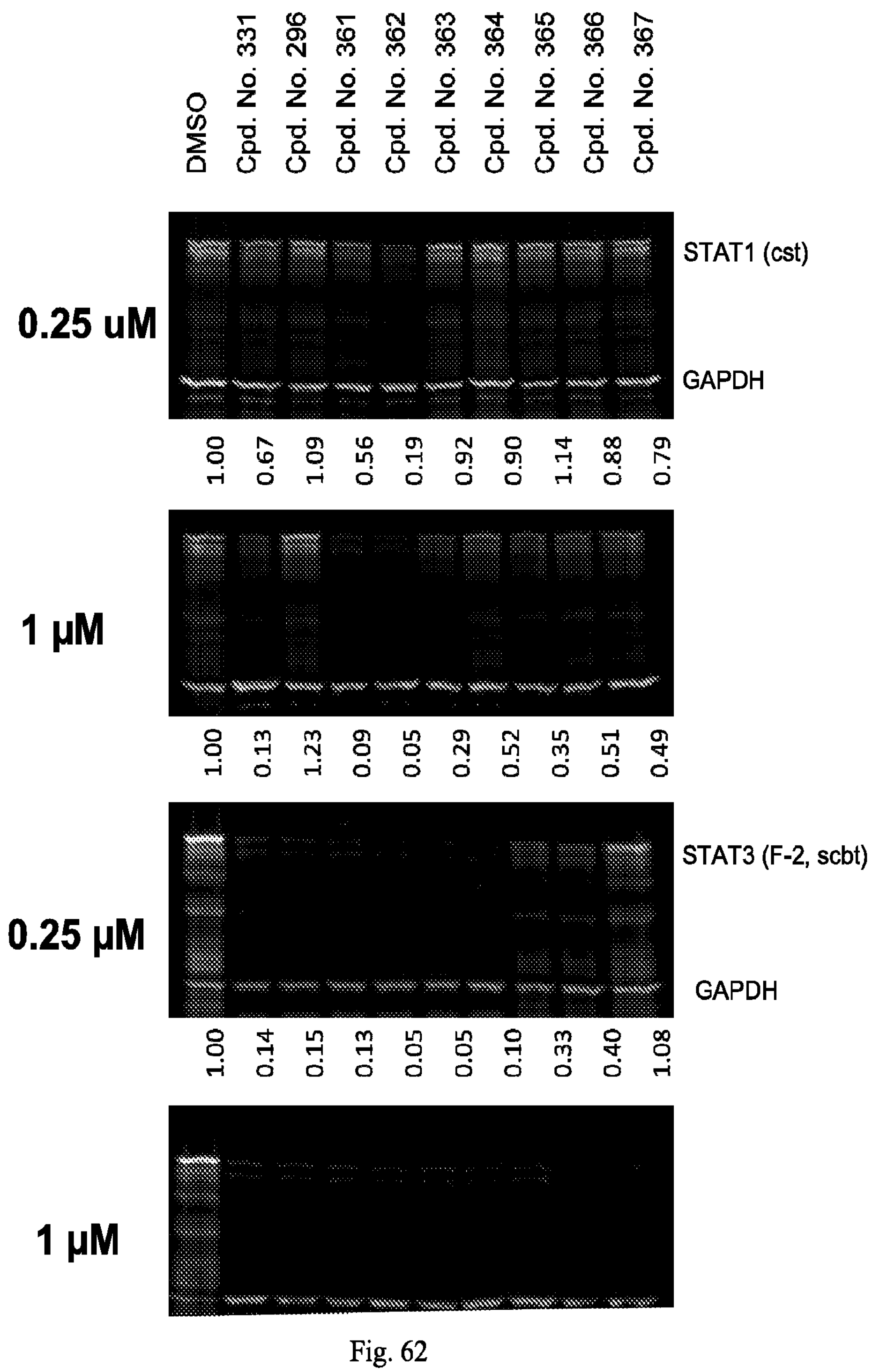
FIG. 62 is a series of four images showing the fluorescent immunoblotting analysis of STAT1 and STAT3 protein in Molm-16 cells after treatment for 4 h with Cpd. Nos. 331, 296, 361, 362, 363, 364, 365, 366, and 367 at the concentrations indicated.

Compounds of the Disclosure are STAT3 protein inhibitors, STAT3 protein degraders, synthetic intermediates that can be converted to STAT3 inhibitors, or synthetic intermediates that can be converted to STAT3 degraders. Compounds of the Disclosure may also degrade one or more additional STAT proteins, for example, STAT1. Thus, in some embodiments, Compounds of the Disclosure are dual STAT3/STAT1 degraders.

In one embodiment, Compounds of the Disclosure are compounds of Formula I:

I

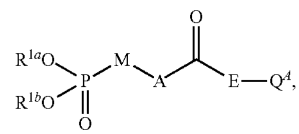

wherein:

$R^{1a}$ and $R^{1b}$ are independently selected from the group consisting of hydrogen $C_1$-$C_4$ alkyl, aralkyl, and $—CH_2OC(=O)R^{1e}$;

$R^{1e}$ is selected from the group consisting of $C_1$-$C_6$ alkyl, $C_3$-$C_6$ cycloalkyl, and $C_1$-$C_6$ alkoxy;

M is selected from the group consisting of —O— and $—C(R^{2a})(R^{2b})—$;

each $R^{2a}$ and $R^{2b}$ are independently selected from the group consisting of hydrogen and fluoro; or $R^{2a}$ and $R^{2b}$ taken together with the carbon atom to which they are attached form a —C(=O)— group;

A is selected from the group consisting of:

A-1

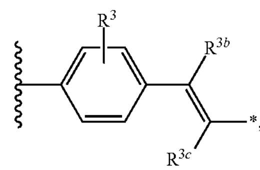

A-2

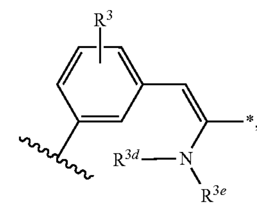

A-3

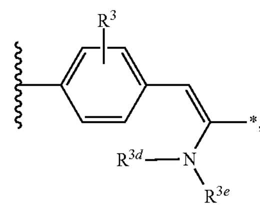

A-4

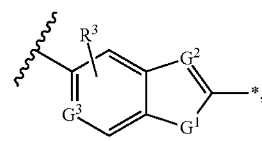

-continued

A-5

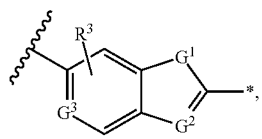

A-6

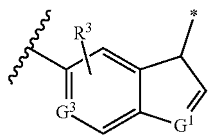

A-7

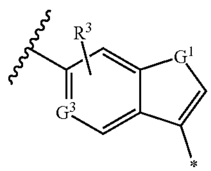

A-8

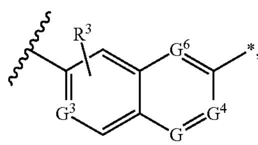

A-9

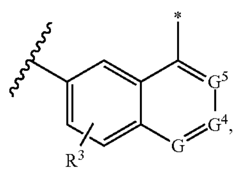

A-10

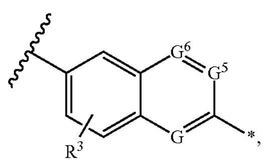

A-11

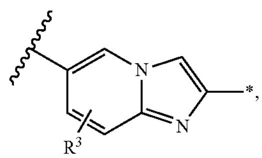

A-12

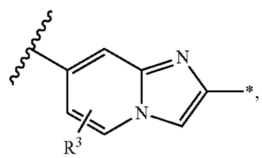

A-13

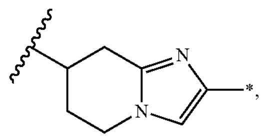

A-14

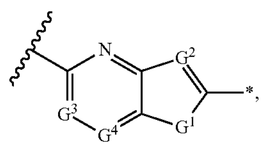

-continued

A-15

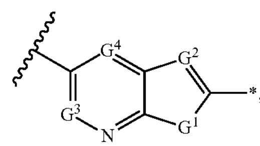

A-16

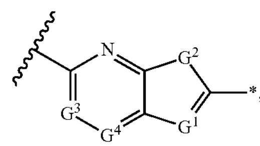

A-17

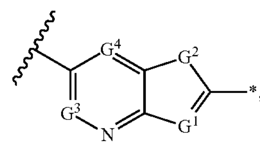

A-18

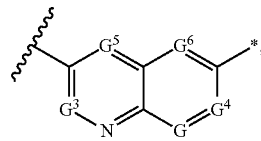

A-19

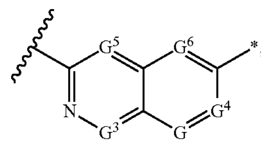

A-20

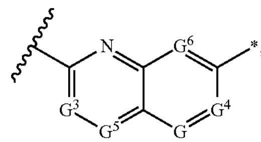

A-21

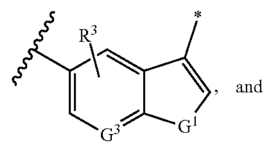

and

A-22

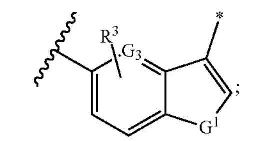

wherein the bond designated with an "*" is attached to —C(═O)-E-$Q^A$;

$G^1$ is selected from the group consisting of —O—, —S—, and —$NR^{17}$—;

$G^2$ is selected from the group consisting of —N═ and —$CR^{18a}$═;

$G^3$ is selected from the group consisting of —N═ and —$CR^{18b}$═;

$G^4$ is selected from the group consisting of —N═ and —$CR^{18c}$═;

$G^5$ is selected from the group consisting of —N═ and —$CR^{18d}$═;

$G^6$ is selected from the group consisting of —N═ and —$CR^{18e}$═;

G is selected from the group consisting of —N═ and —$CR^{18f}$═;

$R^3$ is selected from the group consisting of hydrogen, halo, $C_1$-$C_4$ alkyl, $C_3$-$C_6$ cycloalkyl, —C(═O)$R^{3a}$, and aralkyl;

$R^{3a}$ is $C_1$-$C_4$ alkyl;

$R^{3b}$ and $R^{3c}$ are independently selected from the group consisting of hydrogen and $C_1$-$C_4$ alkyl;

$R^{3d}$ is selected from the group consisting of hydrogen, $C_1$-$C_6$ alkyl, and —C(═O)$R^{3f}$;

$R^{3e}$ is selected from the group consisting of hydrogen and $C_1$-$C_4$ alkyl;

$R^{3f}$ is selected from the group consisting of $C_1$-$C_{12}$ alkyl, $C_1$-$C_6$ alkoxy, and aralkyloxy;

$R^{17}$ is selected from the group consisting of hydrogen, $C_1$-$C_4$ alkyl, $C_3$-$C_6$ cycloalkyl, aralkyl, and —C(═O) $R^{17a}$;

$R^{17a}$ is $C_1$-$C_4$ alkyl;

$R^{18a}$, $R^{18b}$, $R^{18c}$, $R^{18d}$, $R^{18e}$, and $R^{18f}$ are each independently selected from the group consisting of hydrogen, halo, and $C_1$-$C_4$ alkyl, E is:

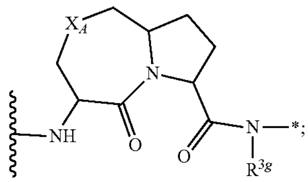

wherein the bond designated with an "*" is attached to $Q^A$;

$R^{3g}$ is selected from the group consisting of hydrogen and $C_1$-$C_4$ alkyl;

$X_A$ is selected from the group consisting of —N($R^8$)$CH_2$—, —$CH_2$N($R^8$)—, and —CH—$_2$$CH_2$—;

$R^8$ is selected from the group consisting of hydrogen, $C_1$-$C_6$ alkyl, $C_1$-$C_6$ haloalkyl, (heterocyclo)alkyl, —C(═O)$R^9$, alkylsulfonyl, and -L-B;

$R^9$ is selected from the group consisting of $C_1$-$C_6$ alkyl, amino, $C_1$-$C_6$ alkoxy, aralkyloxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

QA is selected from the group consisting of:

Q-1

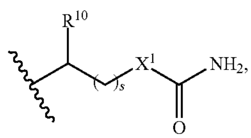

Q-2

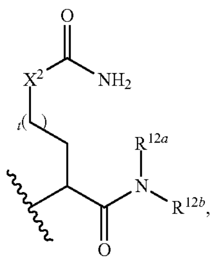

-continued

Q-3

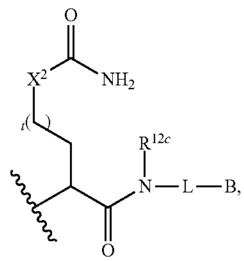

Q-4

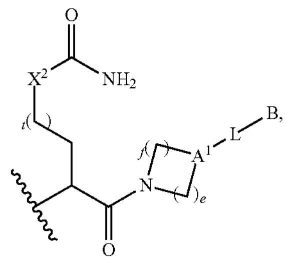

Q-5

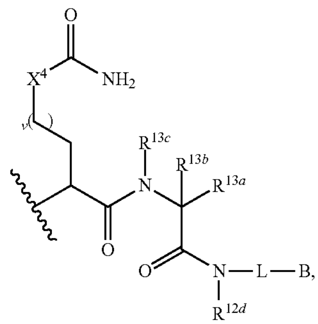

Q-6

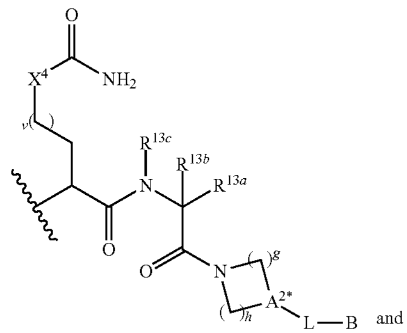

and

Q-7

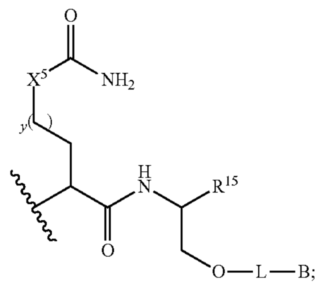

$X^1$ is selected from the group consisting of —$CH_2$—, —O—, and —N($R^{11a}$)—; or $X^1$ is absent;

$R^{10}$ is selected from the group consisting of hydrogen, $C_1$-$C_6$ alkyl, optionally substituted aralkyl, optionally substituted $C_3$-$C_6$ cycloalkyl, optionally substituted 4- to 8-membered heterocyclo, and optionally substituted aryl;

$R^{11a}$ is selected from the group consisting of hydrogen and $C_1$-$C_3$ alkyl;

s is 1, 2, 3, or 4;

$X^2$ is selected from the group consisting of —$CH_2$—, —O—, and —N($R^{11b}$)—; or $X^2$ is absent;

tis 0, 1, 2, 3, or 4;

$R^{11b}$ is selected from the group consisting of hydrogen and $C_1$-$C_3$ alkyl;

$R^{12a}$ is selected from the group consisting of hydrogen, $C_1$-$C_6$ alkyl, optionally substituted $C_2$-$C_6$ alkynyl, aralkyl, (heteroaryl)alkyl, optionally substituted $C_3$-$C_6$ cycloalkyl, optionally substituted 4- to 8-membered heterocyclo, optionally substituted aryl, (amido)(aryl)alkyl, (amino)(aryl)alkyl, (amino)(heteroaryl)alkyl, and (cycloalkyl)alkyl;

$R^{12b}$ is selected from the group consisting of hydrogen, $C_1$-$C_4$ alkyl, optionally substituted aryl, and aralkyl; or $R^{12a}$ and $R^{12b}$ taken together with the nitrogen atom to which they are attached form a 4- to 8-membered optionally substituted heterocyclo;

$R^{12c}$ is selected from the group consisting of hydrogen, $C_1$-$C_4$ alkyl, and aralkyl;

$A^1$ is selected from the group consisting of —C($R^{14a}$)— and —N—;

$R^{14a}$ is selected from the group consisting of hydrogen and $C_1$-$C_3$ alkyl;

e is 1, 2, or 3;

f is 1, 2, or 3;

$X^4$ is selected from the group consisting of —$CH_2$—, —O—, and —N($R^{11d}$)—; or $X^4$ is absent;

v is 0, 1, 2, 3, or 4;

$R^{11d}$ is selected from the group consisting of hydrogen and $C_1$-$C_3$ alkyl;

$R^{12d}$ is selected from the group consisting of hydrogen, $C_1$-$C_4$ alkyl, and aralkyl;

$R^{13a}$ is selected from the group consisting of hydrogen, $C_1$-$C_6$ alkyl, optionally substituted $C_3$-$C_{12}$ cycloalkyl, optionally substituted aryl, aralkyl, (heteroaryl)alkyl, (cycloalkyl)alkyl, and optionally substituted 5- to 9-membered heteroaryl;

$R^{13b}$ is selected from the group consisting of hydrogen and $C_1$-$C_4$ alkyl;

$R^{13c}$ is selected from the group consisting of hydrogen and $C_1$-$C_4$ alkyl; or $R^{13a}$ and $R^{13b}$ taken together form a $C_3$-$C_8$ optionally substituted cycloalkyl or $C_4$-$C_9$ optionally substituted heterocyclo; or $R^{13b}$ and $R^{13c}$ taken together form a 4- to 9-membered optionally substituted heterocyclo;

$A^{2*}$ is selected from the group consisting of —C($R^{14b}$)— and —N—;

$R^{14b}$ is selected from the group consisting of hydrogen and $C_1$-$C_3$ alkyl;

g is 1, 2, or 3;

h is 1, 2, or 3;

$X^5$ is selected from the group consisting of —$CH_2$—, —O—, and —N($R^{11e}$)—; or $X^5$ is absent;

y is 0, 1, 2, 3, or 4;

$R^{11e}$ is selected from the group consisting of hydrogen and $C_1$-$C_3$ alkyl;

$R^{15}$ is selected from the group consisting of hydrogen, $C_1$-$C_6$ alkyl, $C_3$-$C_8$ cycloalkyl, optionally substituted aryl, and optionally substituted 5- to 9-membered heteroaryl;

L is -$J^1$-$Y^1$-$J^2$-$Y^2$-$J^3$-Z—;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of —$(CH_2)_m$—, —C≡C—, —CH═CH—, —N($R^{16a}$)—, —C(═O)—, —S(═O)$_2$—, —C(═O)O—, —OC(═O)—, —C(═O)N($R^{16b}$)—, and —N($R^{16b}$)C(═O)—;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of —$(CH_2)_n$—, —C≡C—, —CH═CH—, —N($R^{16a}$)—, —C(═O)—, —S(═O)$_2$—, —C(═O)O—, —OC(═O)—, —C(═O)N($R^{16b}$), and —($R^{16b}$)C(═O)N—;

n is 0, 1, 2, 3, 4, 5, or 6;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of —$(CH_2)_d$—, —C≡C—, —CH═CH—, —C(═O)—, —O—, —S—, —N($R^{16c}$)—, —C(═O)N($R^{16d}$)—, —N($R^{16d}$)C(═O)—, —N($R^{16e}$)C(═O)$CH_2$O—, and —N($R^{16f}$)C(═O)$CH_2$N($R^{16g}$)—;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of:

B-1

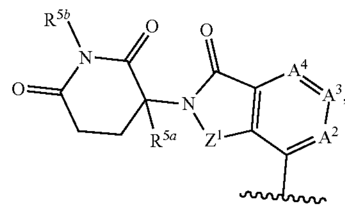

B-2

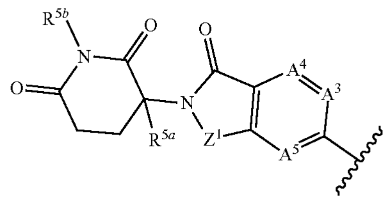

-continued

B-3

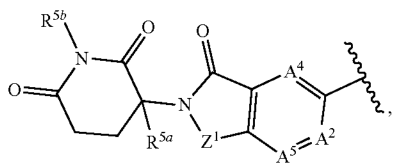

B-4

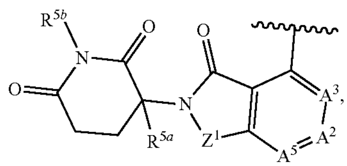

B-5

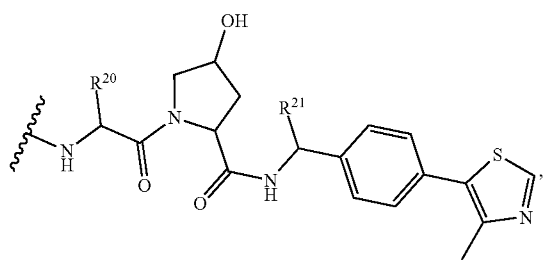

B-6

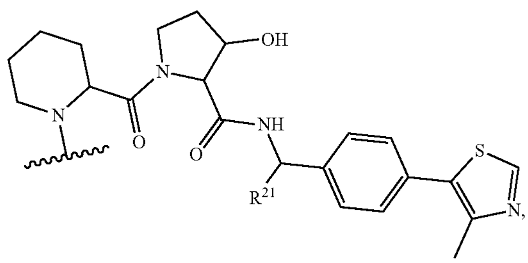

B-7

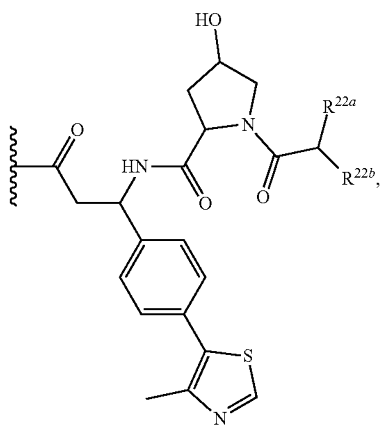

-continued

B-8

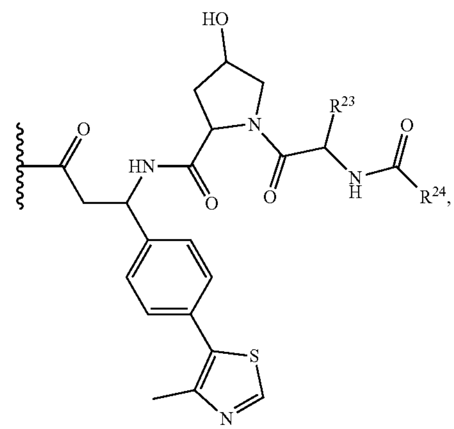

B-9

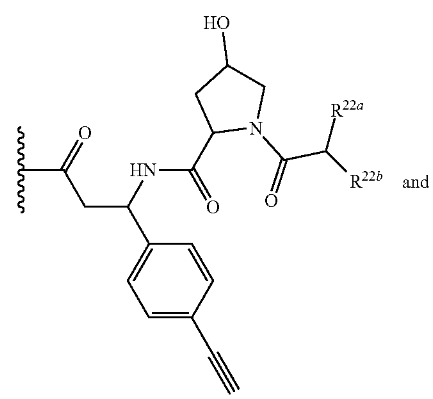

and

B-10

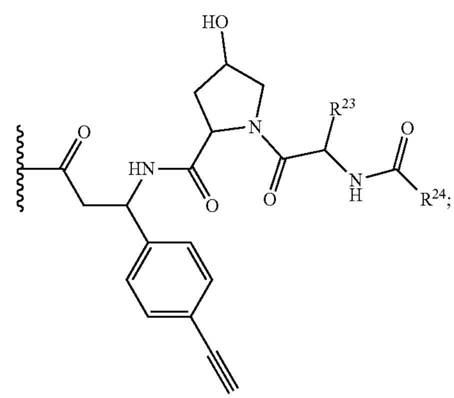

$A_5$ is selected from the group consisting of —C($R^{19a}$)= and —N=;

$A^2$ is selected from the group consisting of —C($R^{19b}$)= and —N=;

$A^3$ is selected from the group consisting of —C($R^{19c}$)= and —N=;

$A^4$ is selected from the group consisting of —C($R^{19d}$)= and —N=;

$Z^1$ is selected from the group consisting of —$CH_2$ and —C(=O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl; and $R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, or a pharmaceutically acceptable salt or solvate thereof.

In one embodiment, Compounds of the Disclosure are compounds of Formula I, with the provisos:

(1) when $X_A$ is —$CH_2CH_2$—, then $Q^A$ is selected from the group consisting of Q-3, Q-4, Q-5, Q-6, and Q-7;

(2) when $X_A$ is —$N(R^8)CH_2$— or —$CH_2N(R^8)$—, and $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, then $Q^A$ is selected from the group consisting of Q-3, Q-4, Q-5, Q-6, and Q-7;

(3) when $X_A$ is —$N(R^8)CH_2$— or —$CH_2N(R^8)$—, and $R^8$ is -L-B, then $Q^A$ is selected from the group consisting of Q-1 and Q-2, or a pharmaceutically acceptable salt or solvate thereof.

In another embodiment, Compounds of the Disclosure are compounds of Formula I, wherein $R^{1e}$ is $C_1$-$C_6$ alkyl, or a pharmaceutically acceptable salt or solvate thereof.

In another embodiment, Compounds of the Disclosure are compounds of Formula I, wherein $R^8$ is selected from the group consisting of hydrogen, $C_1$-$C_6$ alkyl, —C(═O)$R^9$, and -L-B, or a pharmaceutically acceptable salt or solvate thereof.

In another embodiment, Compounds of the Disclosure are compounds of Formula I, wherein $R^8$ is selected from the group consisting of hydrogen, $C_1$-$C_6$ alkyl, —C(═O)$R^9$, alkylsulfonyl, and -L-B, or a pharmaceutically acceptable salt or solvate thereof In another embodiment, Compounds of the Disclosure are compounds of Formula I, wherein $R^{13a}$ is selected from the group consisting of hydrogen, $C_1$-$C_6$ alkyl, optionally substituted $C_3$-$C_{12}$ cycloalkyl, optionally substituted aryl, aralkyl, and optionally substituted 5- to 9-membered heteroaryl, or a pharmaceutically acceptable salt or solvate thereof. In another embodiment, Compounds of the Disclosure are compounds of Formula I, wherein $R^{13a}$ is aralkyl.

In another embodiment, Compounds of the Disclosure are compounds of Formula I, wherein M is —O—, or a pharmaceutically acceptable salt or solvate thereof.

In another embodiment, Compounds of the Disclosure are compounds of Formula I, wherein M is —$C(R^{2a})(R^{2b})$—, or a pharmaceutically acceptable salt or solvate thereof.

In another embodiment, Compounds of the Disclosure are compounds of Formula II:

II

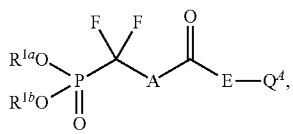

wherein $R^{1a}$, $R^{1b}$, A, E, and $Q^A$ are as defined in connection with Formula I, or a pharmaceutically acceptable salt or solvate thereof.

In another embodiment, Compounds of the Disclosure are compounds of Formula III:

III

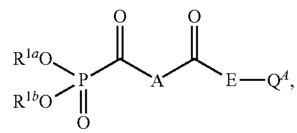

wherein $R^{1a}$, $R^{1b}$, A, E, and $Q^A$ are as defined in connection with Formula I, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-1, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-2, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-3, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-4, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-5, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-6, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-7, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-8, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-9, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-10, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-11, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-12, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-13, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-14, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-15, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-16, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-17, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-18, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-19, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-20, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-21, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is A-22, or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is selected from the group consisting of:

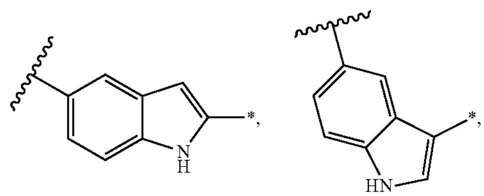

-continued

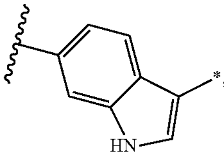
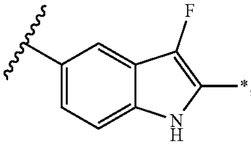
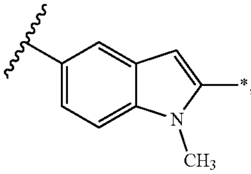
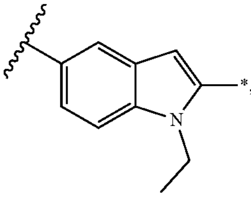
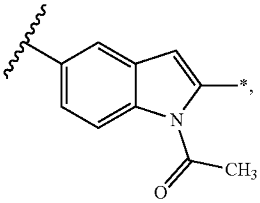
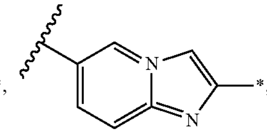
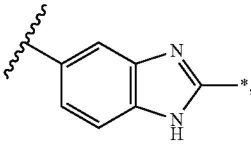
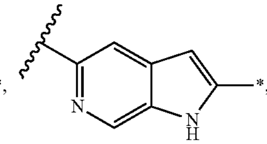
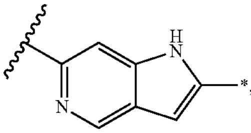
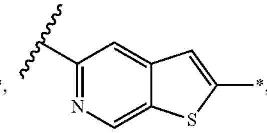
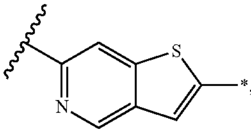
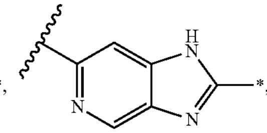
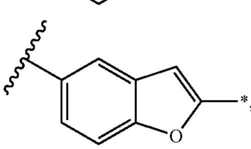
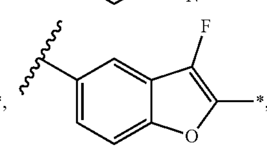
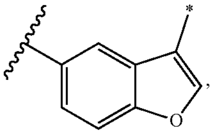
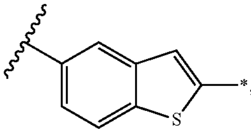
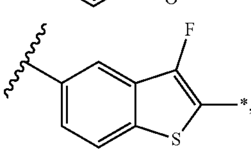
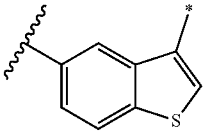
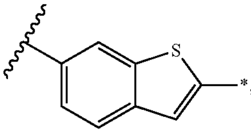
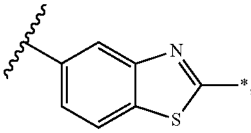
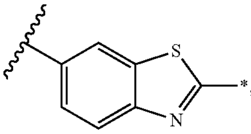
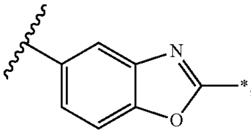

-continued

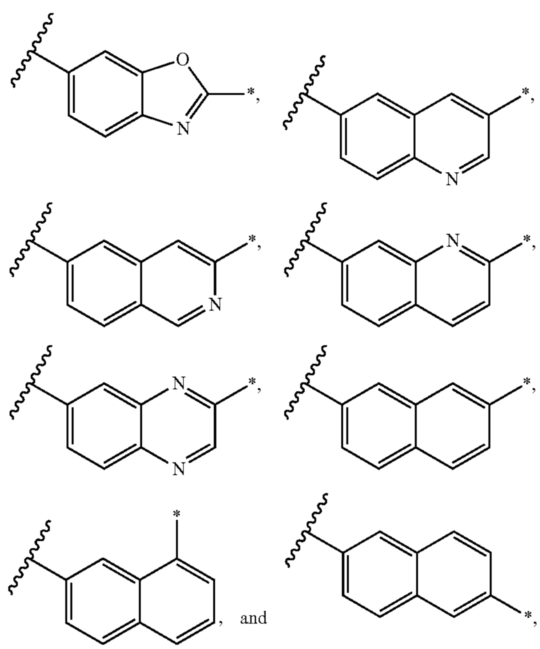

and or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is selected from the group consisting of:

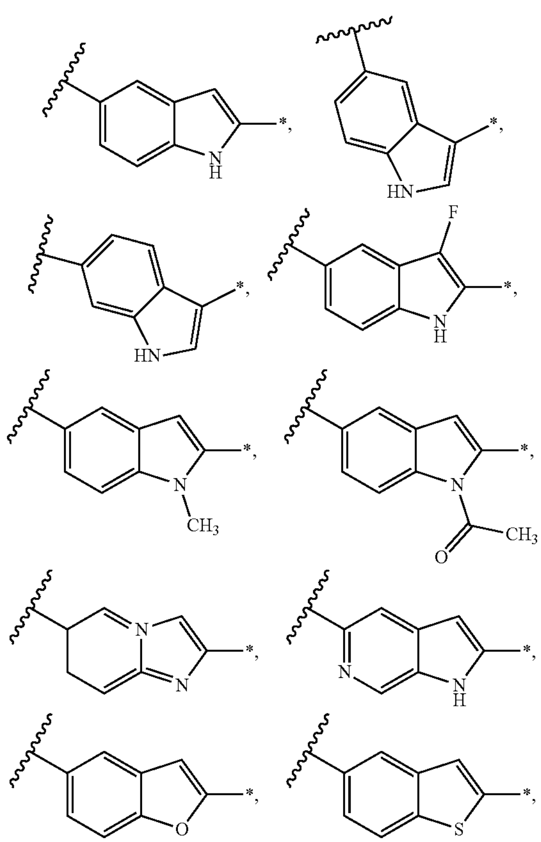

-continued

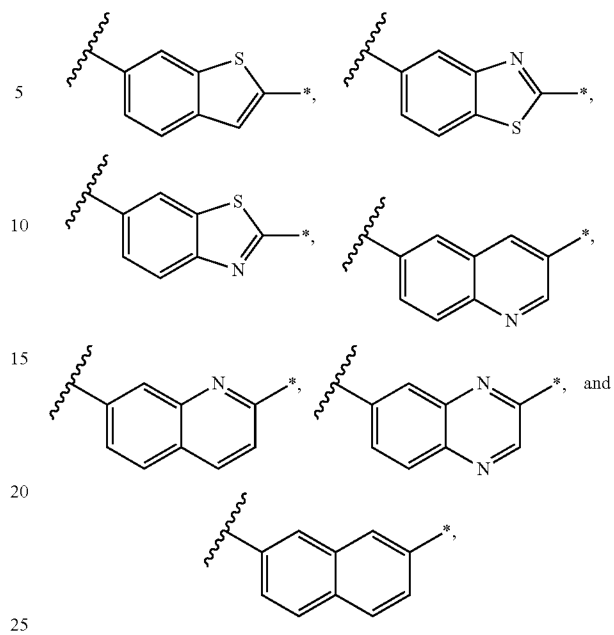

and or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is selected from the group consisting of:

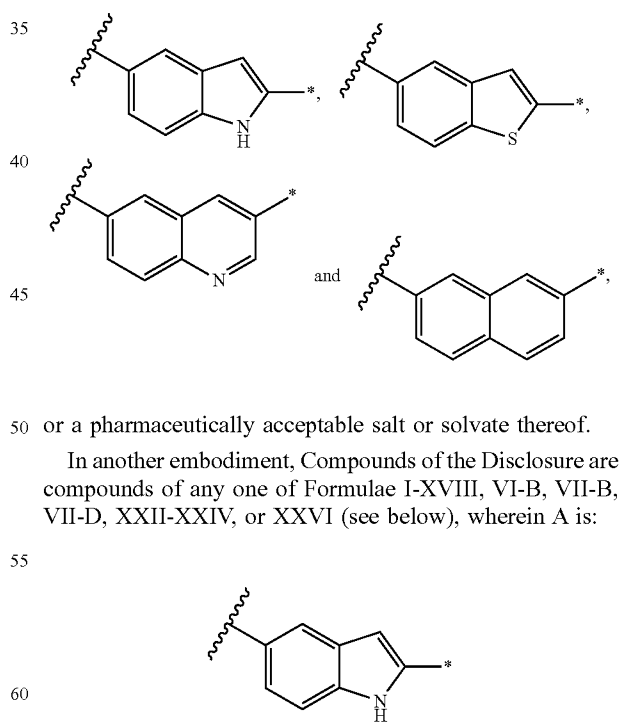

and or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is:

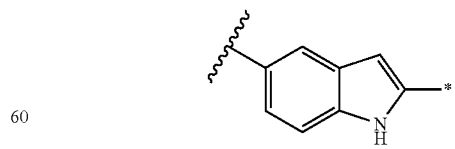

or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is:

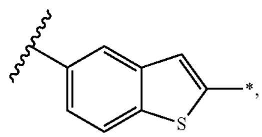

or a pharmaceutically acceptable salt or solvate thereof.

In another embodiment, Compounds of the Disclosure are compounds of any one of Formulae I-XVIII, VI-B, VII-B, VII-D, XXII-XXIV, or XXVI (see below), wherein A is:

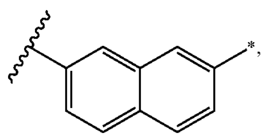

or a pharmaceutically acceptable salt or solvate thereof.

In another embodiment, Compounds of the Disclosure are compounds of any one of Formulae I-III, VIII-X, or XVI-XVIII (see below), wherein $R^{3g}$ is $C_1$-$C_4$ alkyl, or a pharmaceutically acceptable salt or solvate thereof.

In another embodiment, Compounds of the Disclosure are compounds of any one of Formulae I-III, VIII-X, or XVI-XVIII (see below), wherein $R^{3g}$ is hydrogen, or a pharmaceutically acceptable salt or solvate thereof.

In another embodiment, Compounds of the Disclosure are compounds of any one of Formulae I-III, VIII-X, or XVI-XVIII (see below), wherein E is:

E-1

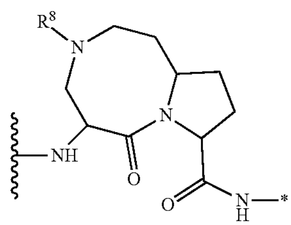

or a pharmaceutically acceptable salt or solvate thereof. In another embodiment, E-1 is selected from the group consisting of:

E-1-1

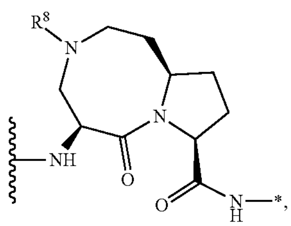

-continued

E-1-2

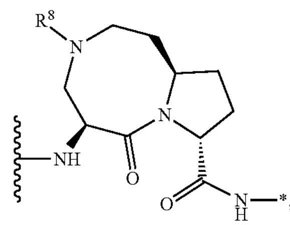

E-1-3

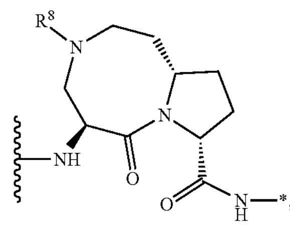

E-1-4

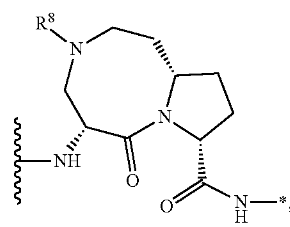

E-1-5

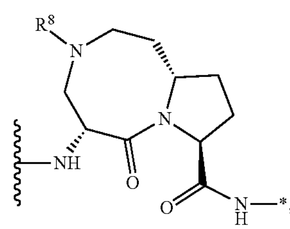

E-1-6

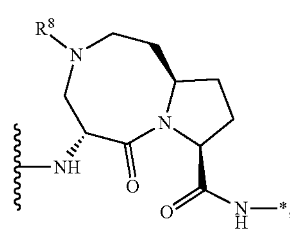

E-1-7

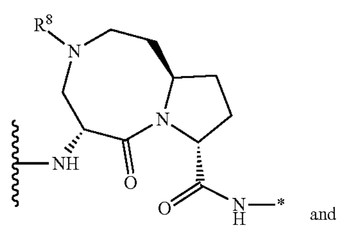

and

E-1-8

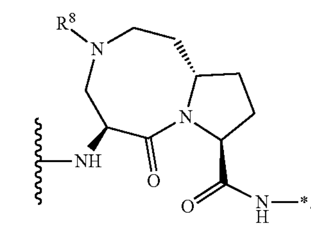

In another embodiment, E-1 is E-1-1. In another embodiment, E-1 is E-1-2. In another embodiment, E-1 is E-1-3. In another embodiment, E-1 is E-1-4. In another embodiment, E-1 is E-1-5. In another embodiment, E-1 is E-1-6. In another embodiment, E-1 is E-1-7. In another embodiment, E-1 is E-1-8.

In another embodiment, Compounds of the Disclosure are compounds of any one of Formulae I-III, VIII-X, or XVI-XVIII (see below), wherein E is:

E-2

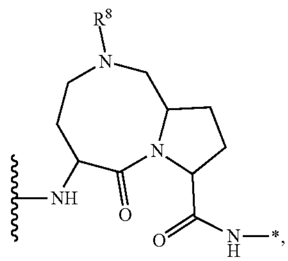

or a pharmaceutically acceptable salt or solvate thereof. In another embodiment, E-2 is selected from the group consisting of:

E-2-1

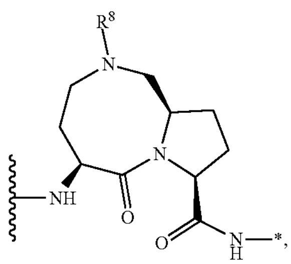

E-2-2

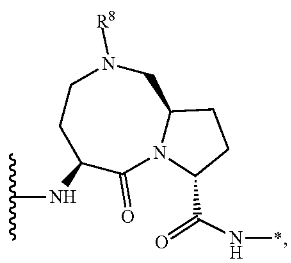

E-2-3

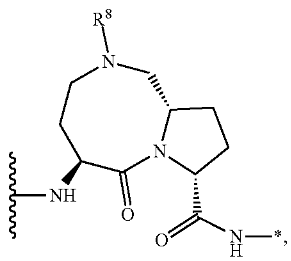

-continued

E-2-4

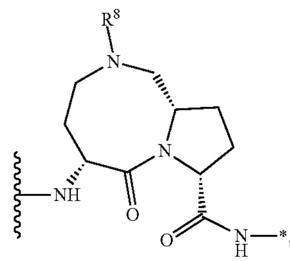

E-2-5

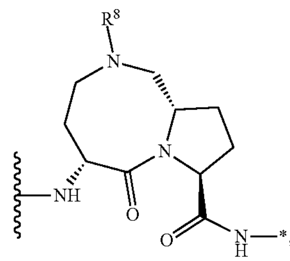

E-2-6

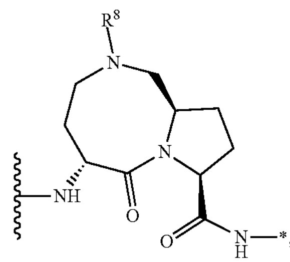

E-2-7

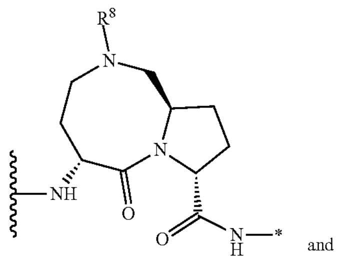

and

E-2-8

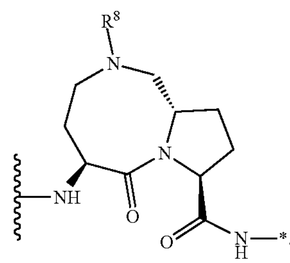

In another embodiment, E-2 is E-2-1. In another embodiment, E-2 is E-2-2. In another embodiment, E-2 is E-2-3. In another embodiment, E-2 is E-2-4. In another embodiment, E-2 is E-2-5. In another embodiment, E-2 is E-2-6. In another embodiment, E-2 is E-2-7. In another embodiment, E-2 is E-2-8.

In another embodiment, Compounds of the Disclosure are compounds of any one of Formulae I-III, VIII-X, or XVI-XVIII (see below), wherein E is:

E-3

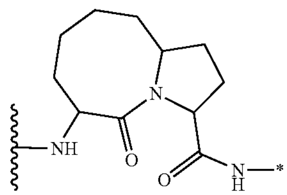

or a pharmaceutically acceptable salt or solvate thereof. In another embodiment, E-3 is selected from the group consisting of:

E-3-1

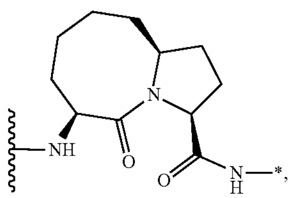

E-3-2

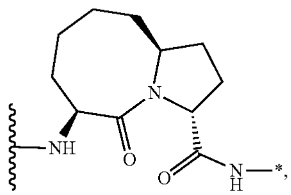

E-3-3

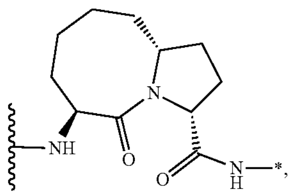

E-3-4

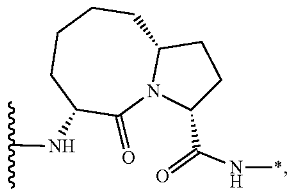

E-3-5

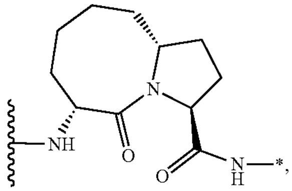

E-3-6

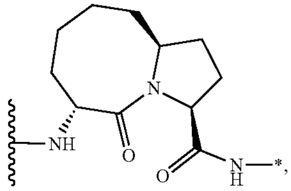

-continued

E-3-7

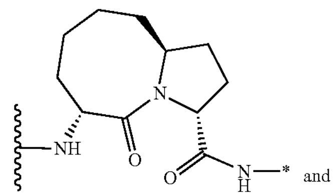

and

E-3-8

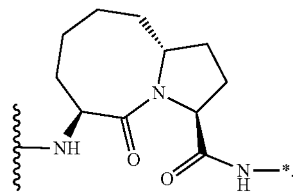

In another embodiment, E-3 is E-3-1. In another embodiment, E-3 is E-3-2. In another embodiment, E-3 is E-3-3. In another embodiment, E-3 is E-3-4. In another embodiment, E-3 is E-3-5. In another embodiment, E-3 is E-3-6. In another embodiment, E-3 is E-3-7. In another embodiment, E-3 is E-3-8.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is -L-B, $Q^A$ is Q-1, and $R^{10}$ is hydrogen, or a pharmaceutically acceptable salt or solvate thereof. In another embodiment, E is E-1-1. In another embodiment, E is E-2-1. In another embodiment, $X^1$ is selected from the group consisting of —$CH_2$— and —N(H)—. In another embodiment, $X^1$ is —$CH_2$—. In another embodiment, s is 0 or 1. In another embodiment, s is 0.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is -L-B, $Q^A$ is Q-2, or a pharmaceutically acceptable salt or solvate thereof. In another embodiment, E is E-1-1. In another embodiment, E is E-2-1. In another embodiment, Q-2 is:

Q-2-1

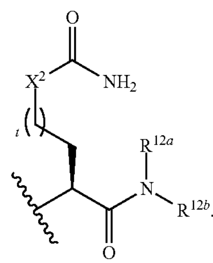

In another embodiment, $X^2$ is selected from the group consisting of —$CH_2$—, —O—, and —N(H)—. In another embodiment, $X^2$ is —$CH_2$—. In another embodiment, t is 0 or 1. In another embodiment, t is 0. In another embodiment, $R^{12b}$ is hydrogen, or a pharmaceutically acceptable salt or solvate thereof. In another embodiment, $R^{12a}$ is aralkyl, or a pharmaceutically acceptable salt or solvate thereof.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, and $Q^4$ is Q-3, or a pharmaceutically acceptable salt or solvate thereof. In another embodiment, E is E-1-1. In another embodiment, E is E-2-1. In another embodiment, $R^8$ is $C_1$-$C_4$ alkyl.

In another embodiment, Compounds of the Disclosure are compounds of any one of Formulae I-III, wherein E is E-3, E-3-1, E-3-2, E-3-3, E-3-4, E-3-5, E-3-6, E-3-7, or E-3-8; and $Q^4$ is Q-3, or a pharmaceutically acceptable salt or solvate thereof. In another embodiment, E is E-3-1.

In another embodiment, Compounds of the Disclosure are compounds of any one of Formulae I-III, wherein Q-3 is Q-3-1:

Q-3-1

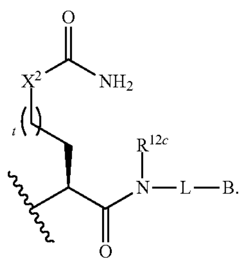

In another embodiment, $X^2$ is —$CH_2$—. In another embodiment, t is 0 or 1. In another embodiment, t is 0. In another embodiment, $R^{12c}$ is hydrogen.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, and $Q^4$ is Q-4, or a pharmaceutically acceptable salt or solvate thereof. In another embodiment, E is E-1-1. In another embodiment, E is E-2-1. In another embodiment, $R^8$ is $C_1$-$C_4$ alkyl, In another embodiment, Compounds of the Disclosure are compounds of any one of Formulae I-III, wherein E is E-3, E-3-1, E-3-2, E-3-3, E-3-4, E-3-5, E-3-6, E-3-7, or E-3-8; and $Q^4$ is Q-4, or a pharmaceutically acceptable salt or solvate thereof. In another embodiment, E is E-3-1.

In another embodiment, Compounds of the Disclosure are compounds of any one of Formulae I-III, wherein Q-4 is Q-4-1:

Q-4-1

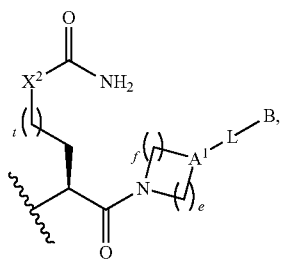

or a pharmaceutically acceptable salt or solvate thereof. In another embodiment, $X^2$ is —$CH_2$—. In another embodiment, t is 0 or 1. In another embodiment, t is 0. In another embodiment, f and e are each 1 or 2. In another embodiment, f and e are each 2. In another embodiment, $A^1$ is —C(H)—.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, and $Q^4$ is Q-5, or a pharmaceutically acceptable salt or solvate thereof. In another embodiment, E is E-1-1. In another embodiment, E is E-2-1. In another embodiment, $R^8$ is $C_1$-$C_4$ alkyl.

In another embodiment, Compounds of the Disclosure are compounds of any one of Formulae I-III, wherein E is E-3, E-3-1, E-3-2, E-3-3, E-3-4, E-3-5, E-3-6, E-3-7, or E-3-8; and $Q^4$ is Q-5, or a pharmaceutically acceptable salt or solvate thereof. In another embodiment, E is E-3-1.

In another embodiment, Compounds of the Disclosure are compounds of any one of Formulae I-III, wherein Q-5 is Q-5-1:

Q-5-1

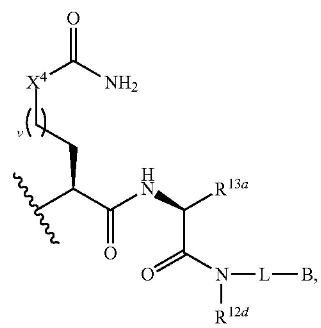

or a pharmaceutically acceptable salt or solvate thereof. In another embodiment, $X^4$ is —$CH_2$—. In another embodiment, v is 0 or 1. In another embodiment, v is 0. In another embodiment, $R^{12d}$ is hydrogen. In another embodiment, $R^{13a}$ is selected from the group consisting of optionally substituted $C_3$-$C_{12}$ cycloalkyl, aralkyl, and optionally substituted phenyl. In another embodiment, $R^{13a}$ is optionally substituted $C_3$-$C_6$ cycloalkyl. In another embodiment, $R^{13a}$ is optionally substituted phenyl. In another embodiment, $R^{13a}$ is aralkyl.

In another embodiment, Compounds of the Disclosure are compounds of any one of Formulae I-III, wherein Q-5 is Q-5-2:

Q-5-2

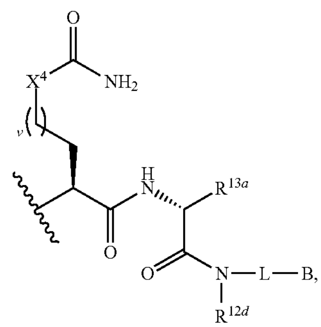

or a pharmaceutically acceptable salt or solvate thereof. In another embodiment, $X^4$ is —$CH_2$—. In another embodiment, v is 0 or 1. In another embodiment, v is 0. In another embodiment, $R^{12d}$ is hydrogen. In another embodiment, $R^{13a}$ is selected from the group consisting of optionally substituted $C_3$-$C_{12}$ cycloalkyl, aralkyl, and optionally substituted phenyl. In another embodiment, $R^{13a}$ is optionally substituted $C_3$-$C_6$ cycloalkyl. In another embodiment, $R^{13a}$ is optionally substituted phenyl. In another embodiment, $R^{13a}$ is aralkyl.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, and $Q^4$ is Q-6, or a pharmaceutically acceptable salt or solvate thereof. In another embodiment, E is E-1-1. In another embodiment, E is E-2-1. In another embodiment, $R^8$ is $C_1$-$C_4$ alkyl.

In another embodiment, Compounds of the Disclosure are compounds of any one of Formulae I-III, wherein E is E-3, E-3-1, E-3-2, E-3-3, E-3-4, E-3-5, E-3-6, E-3-7, or E-3-8; and $Q^4$ is Q-6, or a pharmaceutically acceptable salt or solvate thereof. In another embodiment, E is E-3-1.

In another embodiment, Compounds of the Disclosure are compounds of any one of Formulae I-III, wherein Q-6 is Q-6-1:

Q-6-1

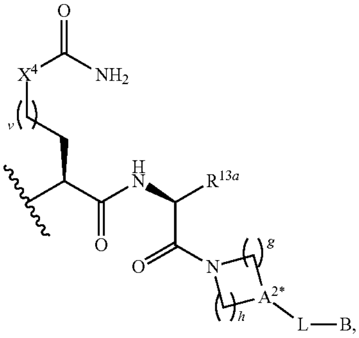

or a pharmaceutically acceptable salt or solvate thereof. In another embodiment, $X^4$ is —$CH_2$—. In another embodiment, v is 0 or 1. In another embodiment, v is 0. In another embodiment, $R^{13a}$ is selected from the group consisting of optionally substituted $C_3$-$C_{12}$ cycloalkyl, aralkyl, and optionally substituted phenyl. In another embodiment, $R^{13a}$ is optionally substituted $C_3$-$C_6$ cycloalkyl. In another embodiment, $R^{13a}$ is optionally substituted phenyl. In another embodiment, $R^{13a}$ is aralkyl. In another embodiment, g and h are each 1 or 2. In another embodiment, g and h are 2. In another embodiment, $A^{2*}$ is —C(H)—. In another embodiment, $A^{2*}$ is —N—. In another embodiment, Q-6-1 is Q-6-1-A or Q-6-1-B:

Q-6-1-A

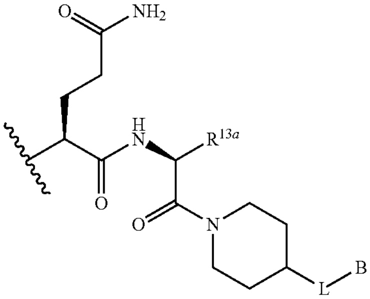

Q-6-1-B

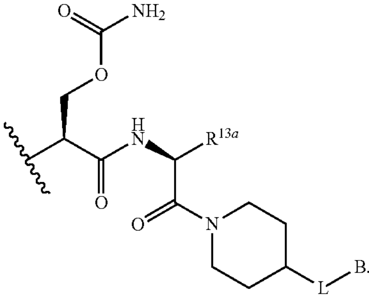

In another embodiment, Compounds of the Disclosure are compounds of any one of Formulae I-III, wherein Q-6 is Q-6-2:

Q-6-2

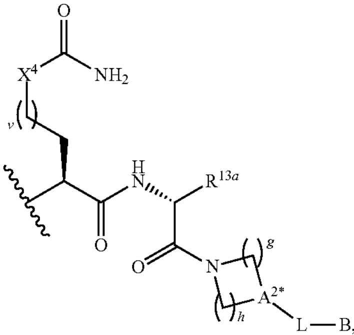

or a pharmaceutically acceptable salt or solvate thereof. In another embodiment, $X^4$ is —$CH_2$—. In another embodiment, v is 0 or 1. In another embodiment, v is 0. In another embodiment, $R^{13a}$ is selected from the group consisting of optionally substituted $C_3$-$C_{12}$ cycloalkyl, aralkyl, and optionally substituted phenyl. In another embodiment, $R^{13a}$ is optionally substituted $C_3$-$C_6$ cycloalkyl. In another embodiment, $R^{13a}$ is optionally substituted phenyl. In another embodiment, $R^{13a}$ is aralkyl. In another embodiment, g and h are each 1 or 2. In another embodiment, g and h are 2. In another embodiment, $A^{2*}$ is —C(H)—.

In another embodiment, Compounds of the Disclosure are compounds of any one of Formulae I-III, wherein E is E-1, E-1-1, E-1-2, E-1-3, E-1-4, E-1-5, E-1-6, E-1-7, E-1-8, E-2, E-2-1, E-2-2, E-2-3, E-2-4, E-2-5, E-2-6, E-2-7, or E-2-8, $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, and $Q^4$ is Q-7, or a pharmaceutically acceptable salt or solvate thereof. In another embodiment, E is E-1-1. In another embodiment, E is E-2-1. In another embodiment, $R^8$ is $C_1$-$C_4$ alkyl.

In another embodiment, Compounds of the Disclosure are compounds of any one of Formulae I-III, wherein E is E-3, E-3-1, E-3-2, E-3-3, E-3-4, E-3-5, E-3-6, E-3-7, or E-3-8; and $Q^A$ is Q-7, or a pharmaceutically acceptable salt or solvate thereof. In another embodiment, E is E-3-1.

In another embodiment, Compounds of the Disclosure are compounds of any one of Formulae I-III, wherein Q-7 is Q-7-1;

Q-7-1

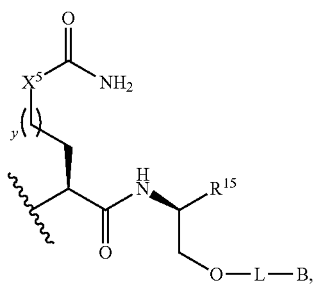

or a pharmaceutically acceptable salt or solvate thereof. In another embodiment, $X^5$ is —$CH_2$—. In another embodiment, y is 0 or 1. In another embodiment, y is 0. In another embodiment, $R^{15}$ is optionally substituted phenyl.

In another embodiment, Compounds of the Disclosure are compounds of any one of Formulae I-III, wherein Q-7 is Q-7-2;

Q-7-2

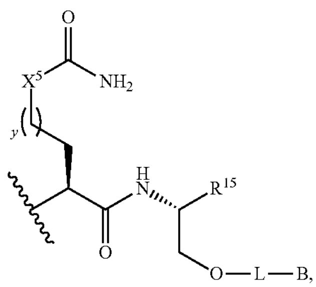

or a pharmaceutically acceptable salt or solvate thereof. In another embodiment, $X^5$ is —$CH_2$—. In another embodiment, y is 0 or 1. In another embodiment, y is 0. In another embodiment, $R^{15}$ is optionally substituted phenyl.

In another embodiment, Compounds of the Disclosure are compounds of any one of Formulae I-III or XVI-XVIII (see below) wherein, L is —$Y^1$-$J^2$-$Y^2$-$J^3$-Z—, or a pharmaceutically acceptable salt or solvate thereof. In another embodiment, L is —$Y^1$-$Y^2$-$J^3$-Z—. In another embodiment, L is —$Y^1$-$J^2$-$Y^2$—Z—. In another embodiment, L is —$Y^1$-$Y^2$—Z—. In another embodiment, $Y^1$ is selected from the group consisting of —$(CH_2)_m$— and —C(═O)—; m is 1, 2, or 3; $Y^2$ is —$(CH_2)_n$—; n is 1, 2, 3, 4, 5, or 6; and Z is selected from the group consisting of —$(CH_2)$—, —C≡C—, and —N(H)—.

In another embodiment, Compounds of the Disclosure are compounds of any one of Formulae I-III, XVI-XVIII, or XXIV (see below), wherein:

$R^8$ is -L-B;

L is selected from the group consisting of:

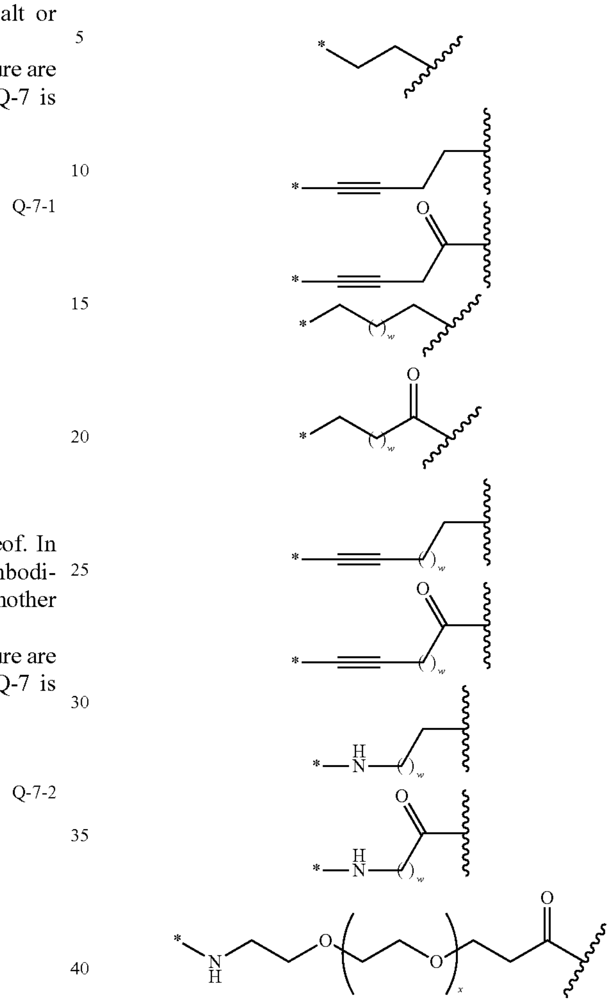

wherein the bond designated with an "*" is attached to B;

w is 1, 2, 3, 4, 5, 6, 7, 8, 9, 10, 11, or 12; and x is 1, 2, 3, 4, 5, or 6, or a pharmaceutically acceptable salt or solvate thereof.

In another embodiment, Compounds of the Disclosure are compounds of any one of Formulae I-III, XXII, or XXIII, wherein:

$R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$;

L is selected from the group consisting of:

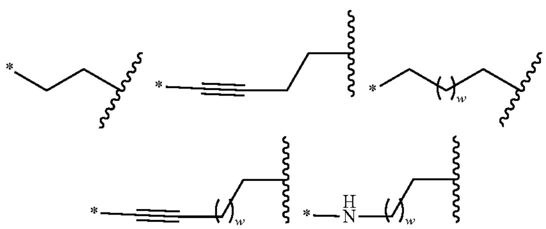

-continued

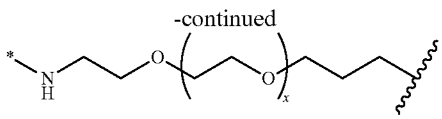

wherein the bond designated with an "*" is attached to B;

w is 1, 2, 3, 4, 5, 6, 7, 8, 9, 10, 11, or 12; and x is 1, 2, 3, 4, 5, or 6, or a pharmaceutically acceptable salt or solvate thereof.

In another embodiment, Compounds of the Disclosure are compounds of any one of Formulae I-III, XVI-XVIII, or XXII-XXIV (see below), wherein B is B-1, or a pharmaceutically acceptable salt or solvate thereof. In another embodiment, $R^{5b}$ is hydrogen. In another embodiment, $A^2$, $A^3$, and $A^4$ are —CH═. In another embodiment, $Z^1$ is —C(═O)—. In another embodiment, $Z^1$ is —$CH_2$—. In another embodiment, B-1 is:

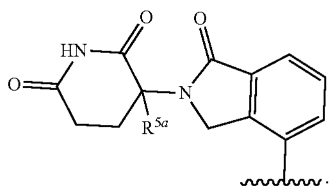

In another embodiment, B-1 is:

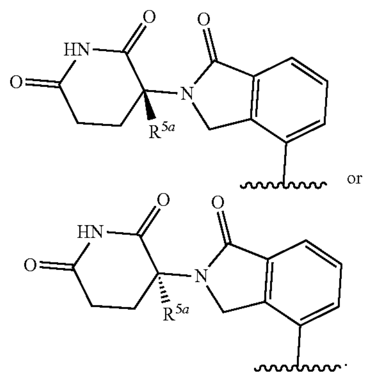

In another embodiment, $R^{5a}$ is fluoro. In another embodiment, $R^{5a}$ is deuterium. In another embodiment, $R^{5a}$ is hydrogen.

In another embodiment, Compounds of the Disclosure are compounds of any one of Formulae I-III, XVI-XVIII, or XXII-XXIV (see below), wherein B is B-2, or a pharmaceutically acceptable salt or solvate thereof.

In another embodiment, Compounds of the Disclosure are compounds of any one of Formulae I-III, XVI-XVIII, or XXII-XXIV (see below), wherein B is B-3, or a pharmaceutically acceptable salt or solvate thereof.

In another embodiment, Compounds of the Disclosure are compounds of any one of Formulae I-III, XVI-XVIII, or XXII-XXIV (see below), wherein B is B-4, or a pharmaceutically acceptable salt or solvate thereof.

In another embodiment, Compounds of the Disclosure are compounds of any one of Formulae I-III, XVI-XVIII, or XXII-XXIV (see below), wherein B is B-5, or a pharmaceutically acceptable salt or solvate thereof.

In another embodiment, Compounds of the Disclosure are compounds of any one of Formulae I-III, XVI-XVIII, or XXII-XXIV (see below), wherein B is B-6, or a pharmaceutically acceptable salt or solvate thereof.

In another embodiment, Compounds of the Disclosure are compounds of any one of Formulae I-III, XVI-XVIII, or XXII-XXIV (see below), wherein B is B-7, or a pharmaceutically acceptable salt or solvate thereof.

In another embodiment, Compounds of the Disclosure are compounds of any one of Formulae I-III, XVI-XVIII, or XXII-XXIV (see below), wherein B is B-8, or a pharmaceutically acceptable salt or solvate thereof.

In another embodiment, Compounds of the Disclosure are compounds of any one of Formulae I-III, XVI-XVIII, or XXII-XXIV (see below), wherein B is B-9, or a pharmaceutically acceptable salt or solvate thereof.

In another embodiment, Compounds of the Disclosure are compounds of any one of Formulae I-III, XVI-XVIII, or XXII-XXIV (see below), wherein B is B-10, or a pharmaceutically acceptable salt or solvate thereof.

In another embodiment, Compounds of the Disclosure are compounds of Formula IV:

IV

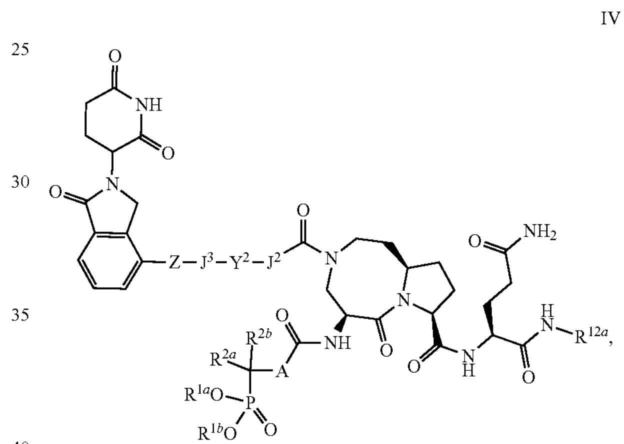

wherein $R^{1a}$, $R^{1b}$, $R^{2a}$, $R^{2b}$, $R^{12a}$, A, $J^2$, $J^3$, $Y^2$, and Z are as defined in connection with Formula I, or a pharmaceutically acceptable salt or solvate thereof.

In another embodiment, Compounds of the Disclosure are compounds of Formula V:

V

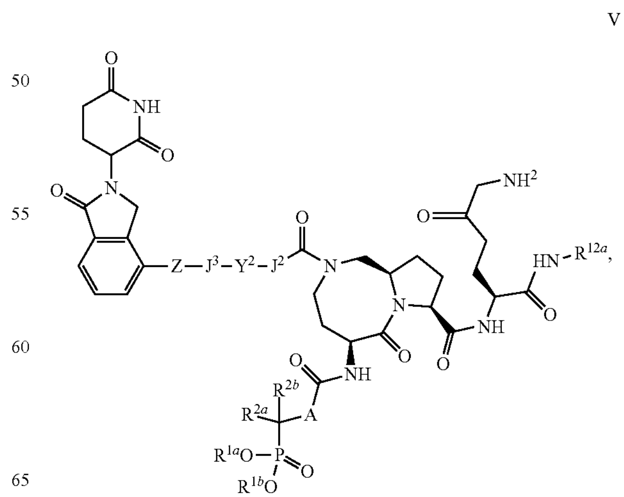

wherein $R^{1a}$, $R^{1b}$, $R^{2a}$, $R^{2b}$, $R^{12a}$, A, $J^2$, $J^3$, $Y^2$, and Z are as defined in connection with Formula I, or a pharmaceutically acceptable salt or solvate thereof.

In another embodiment, Compounds of the Disclosure are compounds of Formula IV-A:

IV-A

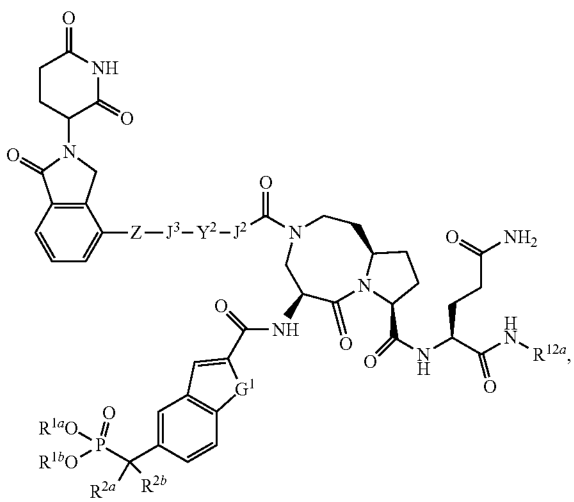

wherein $R^{1a}$, $R^{1b}$, $R^{2a}$, $R^{2b}$, $R^{12a}$, $G^1$, $J^2$, $J^3$, $Y^2$, and Z are as defined in connection with Formula I, or a pharmaceutically acceptable salt or solvate thereof.

In another embodiment, Compounds of the Disclosure are compounds of Formula V-A:

V-A

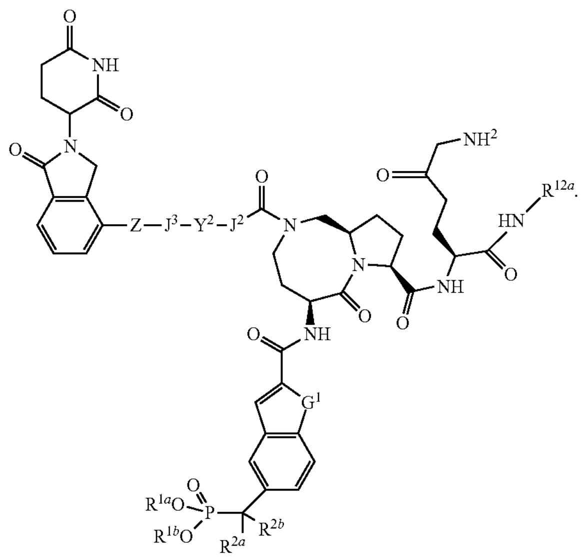

wherein $R^{1a}$, $R^{1b}$, $R^{2a}$, $R^{2b}$, $R^{12a}$, $G^1$, $J^2$, $J^3$, $Y^2$ and Z are as defined in connection with Formula I, or a pharmaceutically acceptable salt or solvate thereof.

In another embodiment, Compounds of the Disclosure are compounds of any one of Formulae IV, IV-A, V, or V-A, wherein $R^{12a}$ is aralkyl, or a pharmaceutically acceptable salt or solvate thereof. In another embodiment, $R^{12a}$ is:

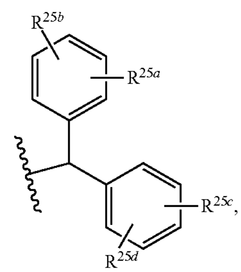

wherein $R^{25a}$, $R^{25b}$, $R^{25c}$, and $R^{25d}$ are each independently selected from the group consisting of hydrogen, halo, $C_1$-$C_4$ alkyl, and $C_1$-$C_4$ alkoxy.

In another embodiment, Compounds of the Disclosure are compounds of Formula IV-A or Formula V-A, wherein $G^1$ is —S—, or a pharmaceutically acceptable salt or solvate thereof.

In another embodiment, Compounds of the Disclosure are compounds of Formula IV-A or Formula V-A, wherein $G^1$ is —NH—, or a pharmaceutically acceptable salt or solvate thereof.

In another embodiment, Compounds of the Disclosure are compounds of any one of Formulae IV, IV-A, V, or V-A, wherein $R^{2a}$ and $R^{2b}$ are fluoro, or a pharmaceutically acceptable salt or solvate thereof.

In another embodiment, Compounds of the Disclosure are compounds of any one of Formulae IV, IV-A, V, or V-A, wherein $R^{2a}$ and $R^{2b}$ taken together with the carbon to which they are attached form a —C(═O)— group, or a pharmaceutically acceptable salt or solvate thereof.

In another embodiment, Compounds of the Disclosure are compounds of any one of Formulae IV, IV-A, V, or V-A, wherein $J^2$ is absent, $Y^2$ is $—(CH_2)_n—$, n is 3, 4, or 5, and $J^3$ is absent, or a pharmaceutically acceptable salt or solvate thereof.

In another embodiment, Compounds of the Disclosure are compounds of any one of Formulae IV, IV-A, V, or V-A, wherein Z is —C≡C—, or a pharmaceutically acceptable salt or solvate thereof.

In another embodiment, Compounds of the Disclosure are compounds of Formula VI:

VI

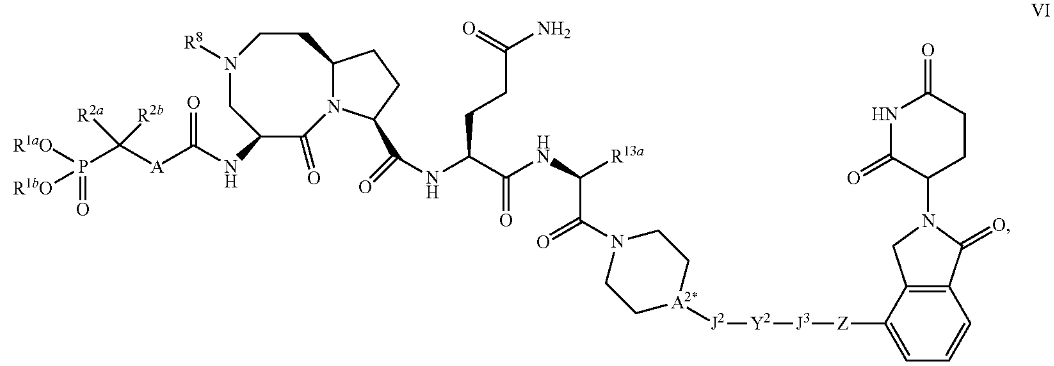

wherein $R^{1a}$, $R^{1b}$, $R^{2a}$, $R^{2b}$, $R^8$, $R^{13a}$, A, $A^{2*}$, $J^2$, $J^3$, $Y^2$, and Z are as defined in connection with Formula I, or a pharmaceutically acceptable salt or solvate thereof.

In another embodiment, Compounds of the Disclosure are compounds of Formula VII:

VII

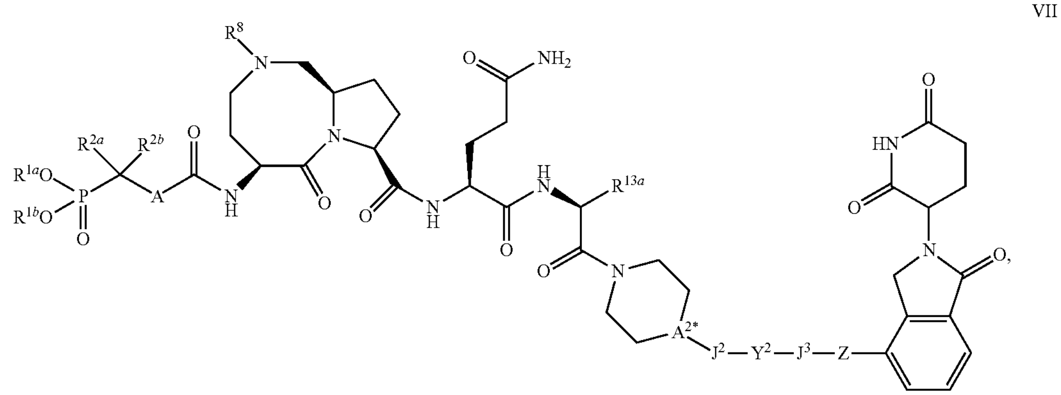

wherein $R^{1a}$, $R^{1b}$, $R^{2a}$, $R^{2b}$, $R^8$, $R^{13a}$, A, $A^{2*}$, $J^2$, $J^3$, $Y^2$, and Z are as defined in connection with Formula I, or a pharmaceutically acceptable salt or solvate thereof.

In another embodiment, Compounds of the Disclosure are compounds of Formula VI-A:

VI-A

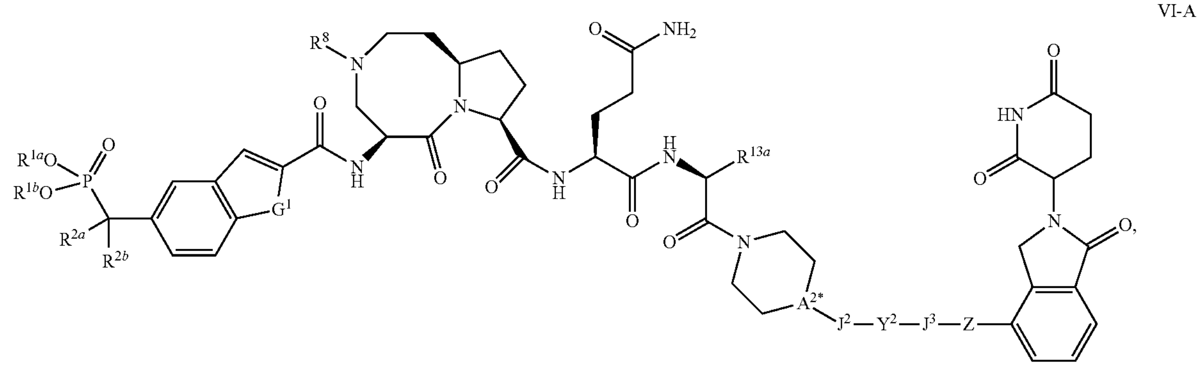

wherein $R^{1a}$, $R^{1b}$, $R^{2a}$, $R^{2b}$, $R^8$, $R^{13a}$, $A^{2*}$, $G^1$, $J^2$, $J^3$, $Y^2$, and Z are as defined in connection with Formula I, or a pharmaceutically acceptable salt or solvate thereof.

In another embodiment, Compounds of the Disclosure are compounds of Formula VII-A:

VII-A

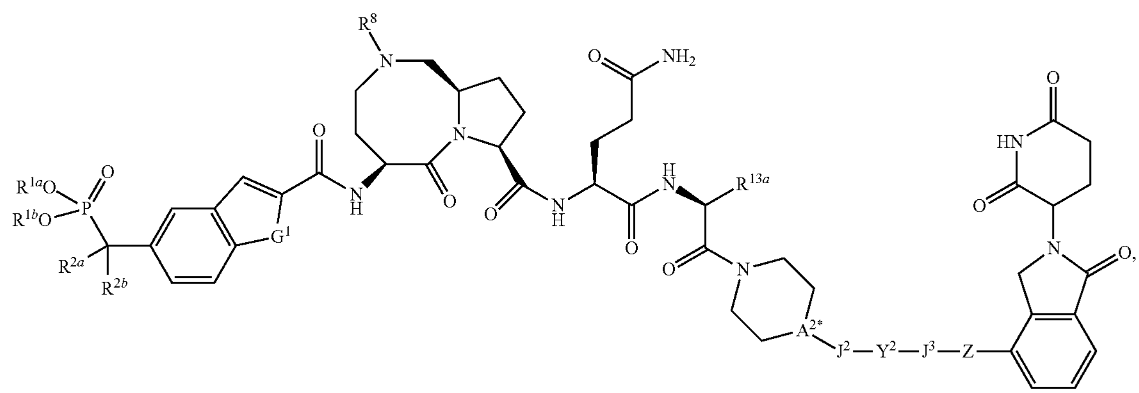

wherein $R^{1a}$, $R^{1b}$, $R^{2a}$, $R^{2b}$, $R^8$, $R^{13a}$, $A^{2*}$, $G^1$, $J^2$, $J^3$, $Y^2$, and Z are as defined in connection with Formula I, or a pharmaceutically acceptable salt or solvate thereof.

In another embodiment, Compounds of the Disclosure are compounds of Formula VI-B:

VI-B

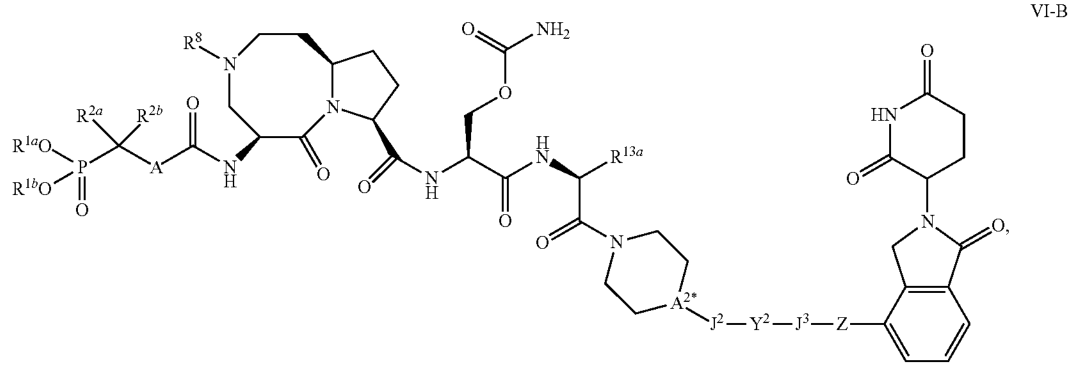

wherein $R^{1a}$, $R^{1b}$, $R^{2a}$, $R^{2b}$, $R^8$, $R^{13a}$, A, $A^{2*}$, $J^2$, $J^3$, $Y^2$, and Z are as defined in connection with Formula I, or a pharmaceutically acceptable salt or solvate thereof.

In another embodiment, Compounds of the Disclosure are compounds of Formula VII-B:

VII-B

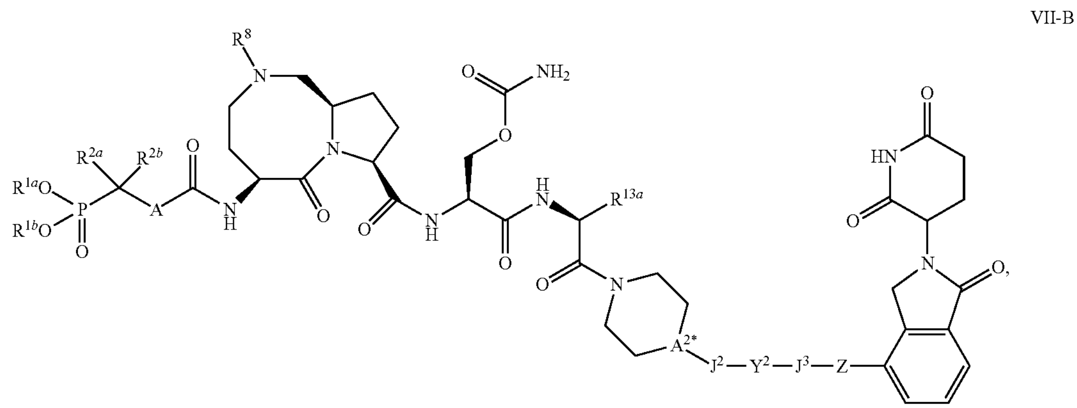

wherein $R^{1a}$, $R^{1b}$, $R^{2a}$, $R^{2b}$, $R^8$, $R^{13a}$, A, $A^{2*}$, $J^2$, $J^3$, $Y^2$, and Z are as defined in connection with Formula I, or a pharmaceutically acceptable salt or solvate thereof.

In another embodiment, Compounds of the Disclosure are compounds of Formula VI-C:

VI-C

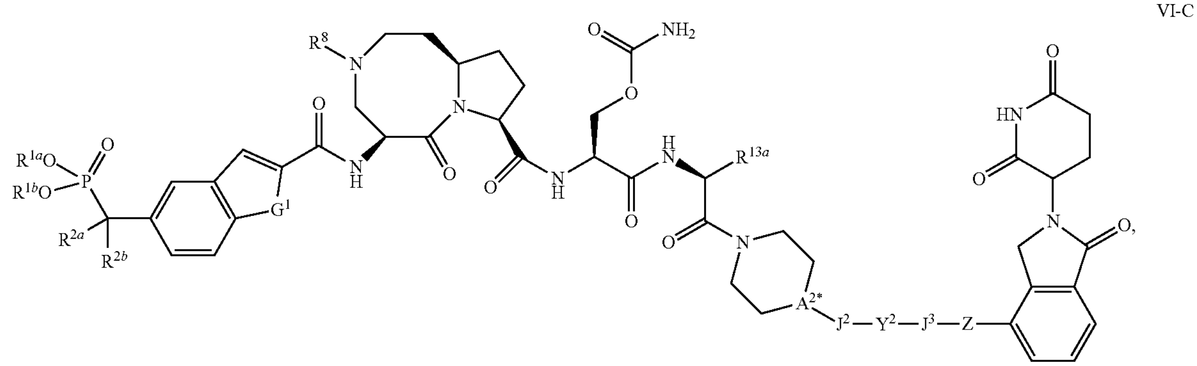

wherein $R^{1a}$, $R^{1b}$, $R^{2a}$, $R^{2b}$, $R^8$, $R^{13a}$, $A^{2*}$, $G^1$, $J^2$, $J^3$, $Y^2$, and Z are as defined in connection with Formula I, or a pharmaceutically acceptable salt or solvate thereof.

In another embodiment, Compounds of the Disclosure are compounds of Formula VII-C:

VII-C

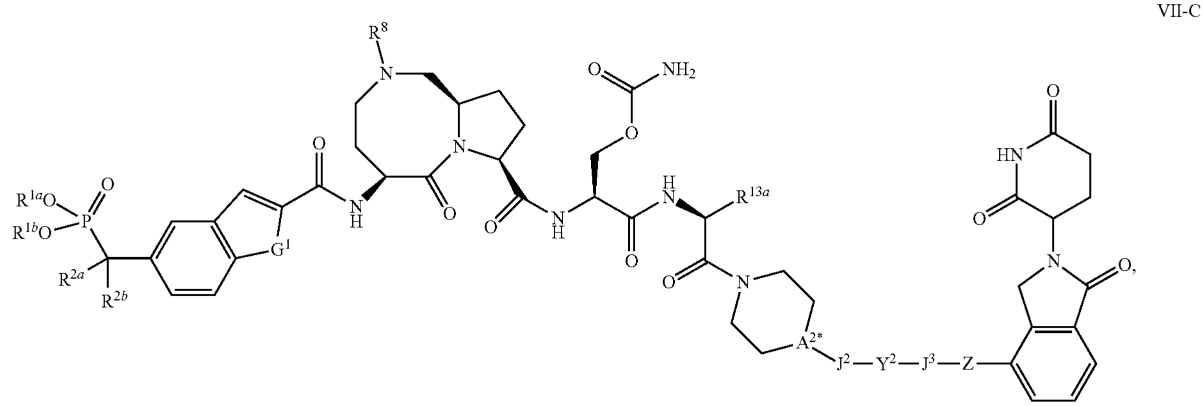

wherein $R^{1a}$, $R^{1b}$, $R^{2a}$, $R^{2b}$, $R^8$, $R^{13a}$, $A^{2*}$, $G^1$, $J^2$, $J^3$, $Y^2$, and Z are as defined in connection with Formula I, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein $R^{13a}$ is selected from the group consisting of optionally substituted cyclohexyl, aralkyl, (heteroaryl)alkyl, and optionally substituted phenyl, or a pharmaceutically acceptable salt or solvate thereof. In another embodiment, $R^{13a}$ is selected from the group consisting of optionally substituted cyclohexyl, aralkyl, and optionally substituted phenyl. In another embodiment, $R^{13a}$ is optionally substituted phenyl. In another embodiment, $R^{13a}$ is aralkyl. In another embodiment, $R^{13a}$ is (heteroaryl)alkyl. In another embodiment, Compounds of the Disclosure are compounds of any one of Formulae VI, VI-A, VI-B, IV-C, VII, VII-A, VII-B, or VII-C, wherein $R^8$ is selected from the group consisting of $C_1$-$C_4$ alkyl, $C_1$-$C_4$ haloalkyl, (heterocyclo)alkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy, or a pharmaceutically acceptable salt or solvate thereof. In another embodiment, $R^8$ is selected from the group consisting of $C_1$-$C_4$ alkyl, $C_1$-$C_4$ haloalkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy. In another embodiment, $R^8$ is $C_1$-$C_4$ alkyl. In another embodiment, $R^8$ is methyl. In another embodiment, $R^8$ is methyl, ethyl, isopropyl, —$CH_2CHF_2$, —$CH_2CF_3$, —C(═O)$OCH_3$, —C(═O)$CH_3$, —C(═O)$NHCH_3$, —C(═O)$N(CH_3)_2$, —S(═O)$_2$Me, —S(═O)$_2$Et, or —$SO_2$iPr. In another embodiment, $R^8$ is methyl, ethyl, —$CH_2CHF_2$, or —C(═O)$OCH_3$.

In another embodiment, Compounds of the Disclosure are compounds of any one of Formulae VI, VI-A, VI-B, IV-C, VII, VII-A, VII-B, or VII-C, wherein $A^{2*}$ is —CH—, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein $A^{2*}$ is —N—, or a pharmaceutically acceptable salt or solvate thereof.

In another embodiment, Compounds of the Disclosure are compounds of any one of Formulae VI-A, VI-C, VII-A, or VII-C, wherein $G^1$ is —S—, or a pharmaceutically acceptable salt or solvate thereof.

In another embodiment, Compounds of the Disclosure are compounds of any one of Formulae VI-A, VI-C, VII-A, or VII-C, wherein $G^1$ is —NH—, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein $R^{2a}$ and $R^{2b}$ are fluoro, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein $R^{2a}$ and $R^{2b}$ taken together with the carbon to which they are attached form a —C(═O)— group, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein $J^2$ is absent, $Y^2$ is $—(CH_2)_n—$, n is 2, 3, or 4, and $J^3$ is absent, or a pharmaceutically acceptable salt or solvate thereof.

In another embodiment, Compounds of the Disclosure are compounds of any one of Formulae VI, VI-A, VI-B, IV-C, VII, VII-A, VII-B, or VII-C, wherein Z is —C≡C—, or a pharmaceutically acceptable salt or solvate thereof.

In another embodiment, Compounds of the Disclosure are compounds of Formula VII-D:

VII-D

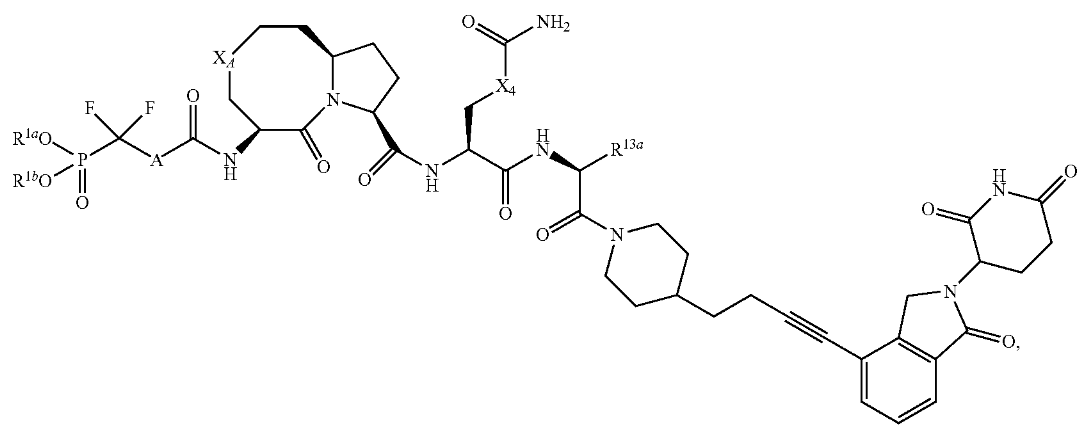

wherein $R^{1a}$, $R^{1b}$, $R^{13a}$, A, $X_A$, and $X^4$ are as defined in connection with Formula I, or a pharmaceutically acceptable salt or solvate thereof.

In another embodiment, Compounds of the Disclosure are compounds of Formula VII-D, wherein $X_A$ is $—N(R^8)CH_2—$; and $R^8$ is selected from the group consisting of hydrogen, $C_1$-$C_6$ alkyl, $C_1$-$C_6$ haloalkyl, (heterocyclo)alkyl, alkylsulfonyl, and $—C(═O)R^9$, or a pharmaceutically acceptable salt or solvate thereof. In another embodiment, $R^8$ is selected from the group consisting of $C_1$-$C_4$ alkyl, $C_1$-$C_4$ haloalkyl, and $—C(═O)R^9$; and $R^9$ is selected from the group consisting of $C_1$-$C_4$ alkyl, alkylamino, dialkylamino, and $C_1$-$C_4$ alkoxy. In another embodiment, $R^9$ is selected from the group consisting of $C_1$-$C_3$ alkyl, alkylamino, dialkylamino, and $C_1$-$C_3$ alkoxy. In another embodiment, $R^8$ is methyl, ethyl, isopropyl, $—CH_2CHF_2$, $—CH_2CF_3$, $—C(═O)OCH_3$, $—C(═O)CH_3$, $—C(═O)NHCH_3$, $—C(═O)N(CH_3)_2$, $—S(═O)_2Me$, $—S(═O)_2Et$, or $—SO_2iPr$. In another embodiment, $R^8$ is methyl, ethyl, $—CH_2CHF_2$, or $—C(═O)OCH_3$.

In another embodiment, Compounds of the Disclosure are compounds of Formula VII-D, wherein $X_A$ is $—CH_2N(R^8)—$; and $R^8$ is selected from the group consisting of hydrogen, $C_1$-$C_6$ alkyl, $C_1$-$C_6$ haloalkyl, (heterocyclo)alkyl, alkylsulfonyl, and $—C(═O)R^9$, or a pharmaceutically acceptable salt or solvate thereof. In another embodiment, $R^8$ is selected from the group consisting of $C_1$-$C_4$ alkyl, $C_1$-$C_4$ haloalkyl, and $—C(═O)R^9$; and $R^9$ is selected from the group consisting of $C_1$-$C_4$ alkyl, alkylamino, dialkylamino, and $C_1$-$C_4$ alkoxy. In another embodiment, $R^9$ is selected from the group consisting of $C_1$-$C_3$ alkyl, alkylamino, dialkylamino, and $C_1$-$C_3$ alkoxy. In another embodiment, $R^8$ is methyl, ethyl, isopropyl, $—CH_2CHF_2$, $—CH_2CF_3$, $—C(═O)OCH_3$, $—C(═O)CH_3$, $—C(═O)NHCH_3$, $—C(═O)N(CH_3)_2$, $—S(═O)_2Me$, $—S(═O)_2Et$, or $—SO_2iPr$. In another embodiment, $R^8$ is methyl, ethyl, $—CH_2CHF_2$, or $—C(═O)OCH_3$.

In another embodiment, Compounds of the Disclosure are compounds of Formula VII-D, wherein $X_A$ is $—CH_2CH_2—$, or a pharmaceutically acceptable salt or solvate thereof.

In another embodiment, Compounds of the Disclosure are compounds of Formula VII-D, wherein $X^4$ is $—CH_2—$, or a pharmaceutically acceptable salt or solvate thereof.

In another embodiment, Compounds of the Disclosure are compounds of Formula VII-D, wherein $X^4$ is —O—, or a pharmaceutically acceptable salt or solvate thereof.

In another embodiment, Compounds of the Disclosure are compounds of Formula VII-E:

VII-E

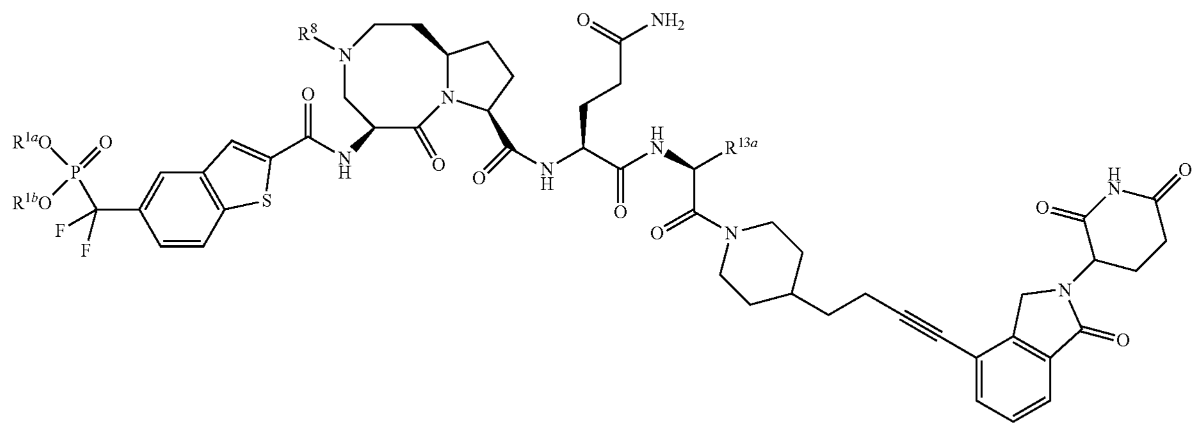

wherein $R^{1a}$, $R^{1b}$, $R^8$, and $R^{13a}$ are as defined in connection with Formula I, or a pharmaceutically acceptable salt or solvate thereof.

In another embodiment, Compounds of the Disclosure are compounds of Formula VII-E, wherein $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, or a pharmaceutically acceptable salt or solvate thereof. In another embodiment, $R^8$ is selected from the group consisting of $C_1$-$C_4$ alkyl, $C_1$-$C_4$ haloalkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy. In another embodiment, $R^9$ is selected from the group consisting of $C_1$-$C_3$ alkyl, alkylamino, dialkylamino, and $C_1$-$C_3$ alkoxy. In another embodiment, $R^8$ is methyl, ethyl, isopropyl, —$CH_2CHF_2$, —$CH_2CF_3$, —C(═O)$OCH_3$, —C(═O)$CH_3$, —C(═O)$NHCH_3$, —C(═O)$N(CH_3)_2$, —S(═O)$_2$Me, —S(═O)$_2$Et, or —$SO_2$iPr. In another embodiment, $R^8$ is methyl, ethyl, —$CH_2CHF_2$, or —C(═O)$OCH_3$.

In another embodiment, Compounds of the Disclosure are compounds of Formula VII-D or Formula VII-E wherein $R^{13a}$ is selected from the group consisting optionally substituted $C_3$-$C_{12}$ cycloalkyl, optionally substituted aryl, aralkyl, (heteroaryl)alkyl, (cycloalkyl)alkyl, and optionally substituted 5- to 9-membered heteroaryl, or a pharmaceutically acceptable salt or solvate thereof. In another embodiment, $R^{13a}$ is selected from the group consisting of:

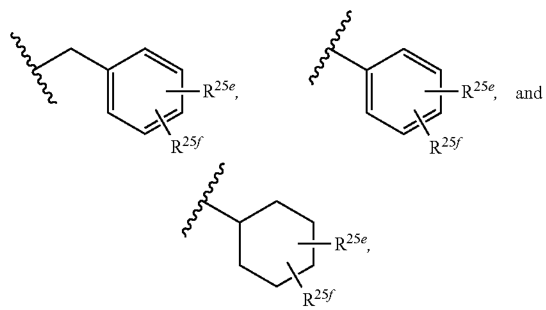

wherein $R^{25e}$ and $R^{25f}$ are independently selected from the group consisting of hydrogen, halo, $C_1$-$C_4$ alkyl, $C_1$-$C_4$ haloalkyl, and $C_1$-$C_4$ alkoxy.

In another embodiment, Compounds of the Disclosure are compounds of any one of Formulae I-IV, IV-A, V, V-A, VI, VI-A, VI-B, IV-C, VII, VII-A, VII-B, VII-C, VII-D, or VII-E, wherein $R^{1a}$ and $R^{1b}$ are $C_1$-$C_4$ alkyl, or a pharmaceutically acceptable salt or solvate thereof.

In another embodiment, Compounds of the Disclosure are compounds of any one of Formulae I-IV, IV-A, V, V-A, VI, VI-A, VI-B, IV-C, VII, VII-A, VII-B, VII-C, VII-D, or VII-E, wherein $R^{1a}$ and $R^{1b}$ are hydrogen, or a pharmaceutically acceptable salt or solvate thereof.

In another embodiment, Compounds of the Disclosure are compounds of any one of Formulae I-IV, IV-A, V, V-A, VI, VI-A, VI-B, IV-C, VII, VII-A, VII-B, VII-C, VII-D, or VII-E, wherein $R^{1a}$ and $R^{1b}$ are —$CH_2OC$(═O)$R^{1e}$; and each $R^{1e}$ is independently selected from the group consisting of $C_1$-$C_6$ alkyl and $C_1$-$C_6$ alkoxy. In another embodiment, each $R^{1e}$ is $C_1$-$C_6$ alkyl. In another embodiment, each $R^{1e}$ is $C_1$-$C_6$ alkoxy.

In another embodiment, Compounds of the Disclosure are compounds of any one of Formulae I-IV, IV-A, V, V-A, VI, VI-A, VI-B, IV-C, VII, VII-A, VII-B, VII-C, VII-D, or VII-E, wherein $R^{1a}$ and $R^{1b}$ are selected from the group consisting of:

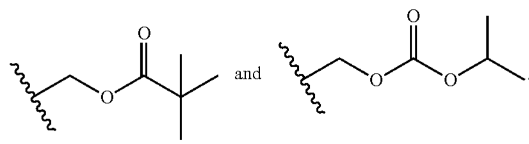

In another embodiment, Compounds of the Disclosure are compounds of any one of Formulae I, VI, VI-A, VI-B, IV-C, VII, VII-A, VII-B, VII-C, VII-D, or VII-E, wherein:

$R^{13a}$ is selected from the group consisting of:

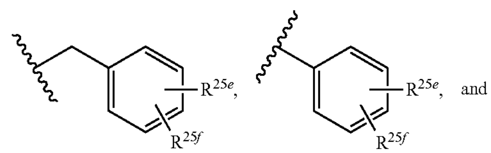

-continued

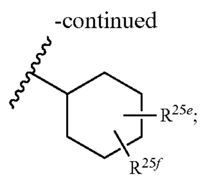

and $R^{25e}$ and $R^{25f}$ are independently selected from the group consisting of hydrogen, halo, $C_1$-$C_6$ alkyl, optionally substituted $C_3$-$C_6$ cycloalkyl, optionally substituted aryl, $C_1$-$C_4$ haloalkyl, $C_1$-$C_4$ alkoxy, carboxamido, sulfonamido, alkylsulfonyl, arylsulfonyl, —C(═O)$R^{57}$, —S(═O)$_2R^{58}$, and —N($R^{56c}$)S(═O)$_2R^{56d}$.

In another embodiment, Compounds of the Disclosure are compounds of any one of Formulae I, VI, VI-A, VI-B, IV-C, VII, VII-A, VII-B, VII-C, VII-D, or VII-E, wherein:

$R^{13a}$ is:

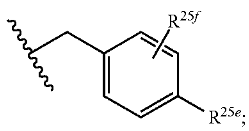

$R^{25e}$ is selected from the group consisting of hydrogen, halo, $C_1$-$C_6$ alkyl, —C(═O)N$R^{50c}R^{50d}$, $C_1$-$C_6$ alkylsulfonyl, arylsulfonyl, —N($R^{56c}$)S(═O)$_2R^{56d}$, and —S(═O)$_2R^{58}$, $R^{25f}$ is selected from the group consisting of hydrogen and halo;

$R^{50c}$ is selected from the group consisting of $C_1$-$C_6$ alkyl, optionally substituted $C_3$-$C_6$ cycloalkyl, optionally substituted 5- or 6-membered heterocyclo, optionally substituted phenyl, optionally substituted 5- to 9-membered heteroaryl, aralkyl, (heteroaryl)$C_1$-$C_4$ alkyl, and (heterocyclo)$C_1$-$C_4$ alkyl;

$R^{50d}$ is selected from the group consisting of hydrogen and $C_1$-$C_3$ alkyl; or $R^{50c}$ and $R^{50d}$ taken together with the nitrogen to which they are attached form a 3- to 8-membered optionally substituted heterocyclo group;

$R^{58}$ is optionally substituted $C_3$-$C_6$ cycloalkyl;

$R^{56c}$ is selected from the group consisting of hydrogen and $C_1$-$C_3$ alkyl; and $R^{56d}$ is selected from the group consisting of optionally substituted $C_3$-$C_6$ cycloalkyl, optionally substituted phenyl, and optionally substituted 5- to 9-membered heteroaryl.

In another embodiment, Compounds of the Disclosure are compounds of Formula XXII:

XXII

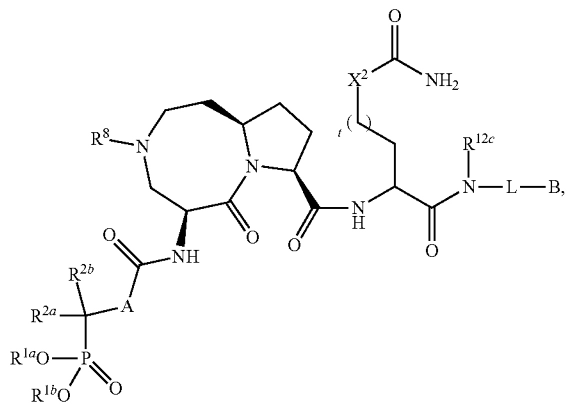

wherein:

$R^{1a}$ and $R^{1b}$ are independently selected from the group consisting of hydrogen $C_1$-$C_6$ alkyl, and aralkyl;

$R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, $R^{12c}$, A, $X^2$, t, L, and B are as defined in connection with Formula I, or a pharmaceutically acceptable salt or solvate thereof.

In another embodiment, Compounds of the Disclosure are compounds of Formula XXIII:

XXIII

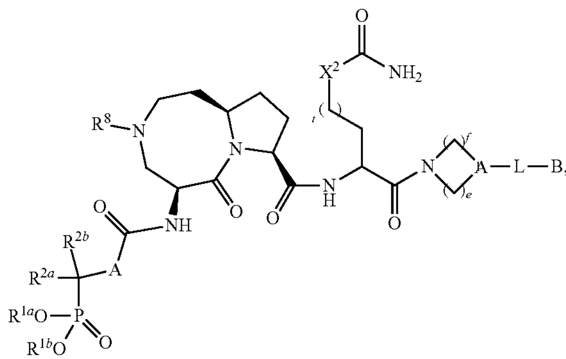

wherein:

$R^{1a}$ and $R^{1b}$ are independently selected from the group consisting of hydrogen $C_1$-$C_6$ alkyl, and aralkyl;

$R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, A, $A^1$, $X^2$, t, e, f, L, and B are as defined in connection with Formula I, or a pharmaceutically acceptable salt or solvate thereof.

In another embodiment, Compounds of the Disclosure are compounds of Formula XXIV:

XXIV

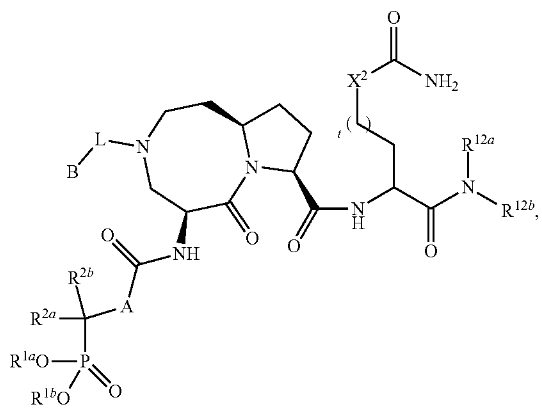

wherein $R^{1a}$ and $R^{1b}$ are independently selected from the group consisting of hydrogen $C_1$-$C_6$ alkyl, and aralkyl; and $R^{2a}$, $R^{2b}$, A, $X^2$, $R^{12a}$, $R^{12b}$, t, L, and B are as defined in connection with Formula I, or a pharmaceutically acceptable salt or solvate thereof.

In another embodiment, Compounds of the Disclosure are compounds of Formula XXVI:

XXVI

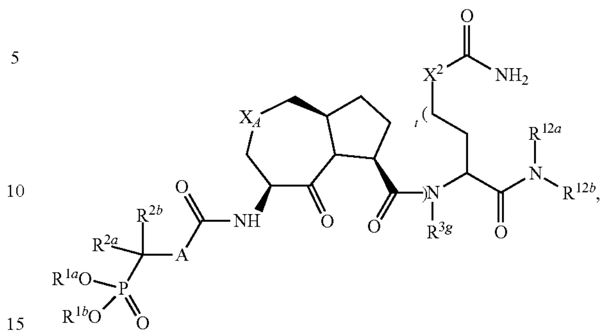

wherein $R^{1a}$ and $R^{1b}$ are independently selected from the group consisting of hydrogen, $C_1$-$C_6$ alkyl, and aralkyl; and $R^{2a}$, $R^{2b}$, A, $X_A$, $X^2$, t, $R^{3g}$, $R^{12a}$, and $R^{12b}$ as defined in connection with Formula I.

In another embodiment, Compounds of the Disclosure are the compounds of Formula I provided in Tables 1, 1A and IB, or a pharmaceutically acceptable salt or solvate thereof. In another embodiment, Compounds of the Disclosure are the compounds of Formula I provided in Tables 1 and 1A, or a pharmaceutically acceptable salt or solvate thereof. In another embodiment, Compounds of the Disclosure are the compounds of Formula I provided in Table 1, or a pharmaceutically acceptable salt or solvate thereof. In another embodiment, Compounds of the Disclosure are the compounds of Formula I provided in Table 1A, or a pharmaceutically acceptable salt or solvate thereof. In another embodiment, Compounds of the Disclosure are the compounds of Formula I provided in Table 1B, or a pharmaceutically acceptable salt or solvate thereof. The chemical names in Tables 1, 1A, and IB were generated by Chemdraw® Professional version 17.0.0.206 (121). In the event of any ambiguity between their chemical structure and chemical name, Compounds of the Disclosure are defined by their chemical structure.

TABLE 1

| Cpd. No. | Structure | Name |
| --- | --- | --- |
| 1 | 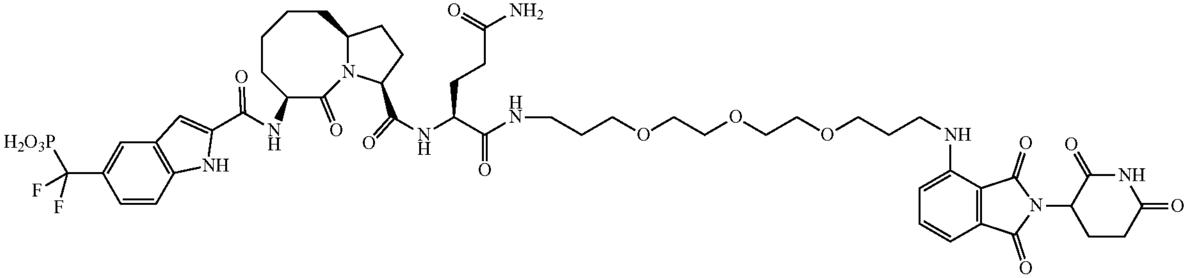 | ((2-(((3S,6S,10aS)-3-(((16S)-19-amino-1-((2-(2,6-dioxopiperidin-3-yl)-1,3-dioxoisoindolin-4-yl)amino)-15,19-dioxo-4,7,10-trioxa-14-azanonadecan-16-yl)carbamoyl)-5-oxodecahydropyrrolo[1,2-a]azocin-6-yl)carbamoyl)-1H-indol-5-yl)difluoromethyl) phosphonic acid |
| 2 | 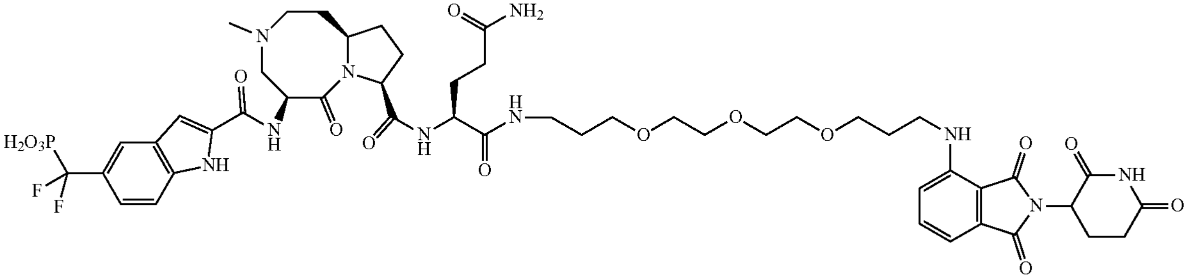 | ((2-(((5S,8S,10aR)-8-(((16S)-19-amino-1-((2-(2,6-dioxopiperidin-3-yl)-1,3-dioxoisoindolin-4-yl)amino)-15,19-dioxo-4,7,10-trioxa-14-azanonadecan-16-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 3 | 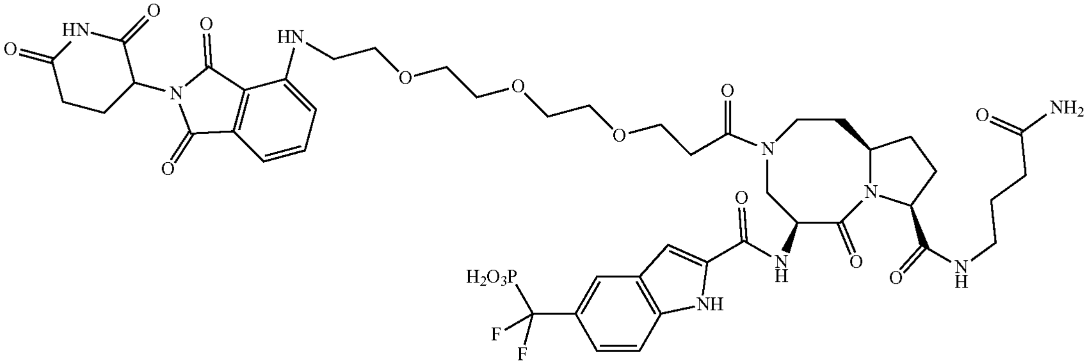 | ((2-(((5S,8S,10aR)-8-((4-amino-4-oxobutyl)carbamoyl)-3-(3-(2-(2-(2-((2-(2,6-dioxopiperidin-3-yl)-1,3-dioxoisoindolin-4-yl)amino)ethoxy)ethoxy)ethoxy)propanoyl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 4 | 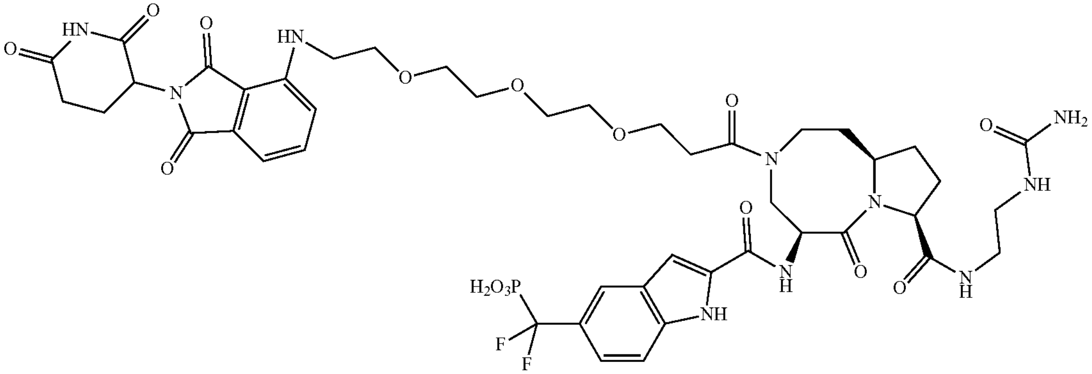 | ((2-(((5S,8S,10aR)-3-(3-(2-(2-(2-((2-(2,6-dioxopiperidin-3-yl)-1,3-dioxoisoindolin-4-yl)amino) ethoxy)ethoxy)ethoxy)propanoyl)-6-oxo-8-((2-ureidoethyl)carbamoyl)decahydropyrrolo[1,2-a][1,5]diazocin-5-yl)carbamoyl)-1H-indol-5-yl)difluoromethyl)phosphonic acid |
| 5 | 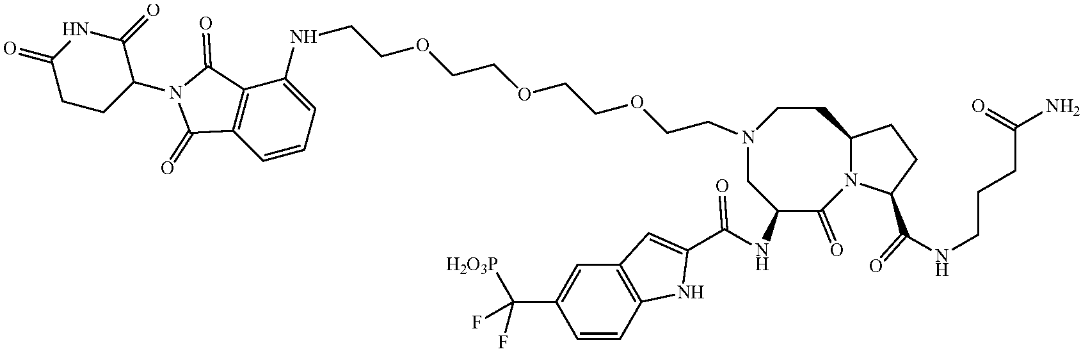 | ((2-(((5S,8S,10aR)-8-((4-amino-4-oxobutyl)carbamoyl)-3-(2-(2-(2-(2-((2-(2,6-dioxopiperidin-3-yl)-1,3-dioxoisoindolin-4-yl)amino)ethoxy)ethoxy)ethoxy)ethyl)-6-oxodecahydropyrrolo[1,2-a][1,5]diazocin-5-yl)carbamoyl)-1H-indol-5-yl)difluoromethyl) phosphonic acid |

TABLE 1-continued

| Cpd. No. | Structure | Name |
|---|---|---|
| 6 | 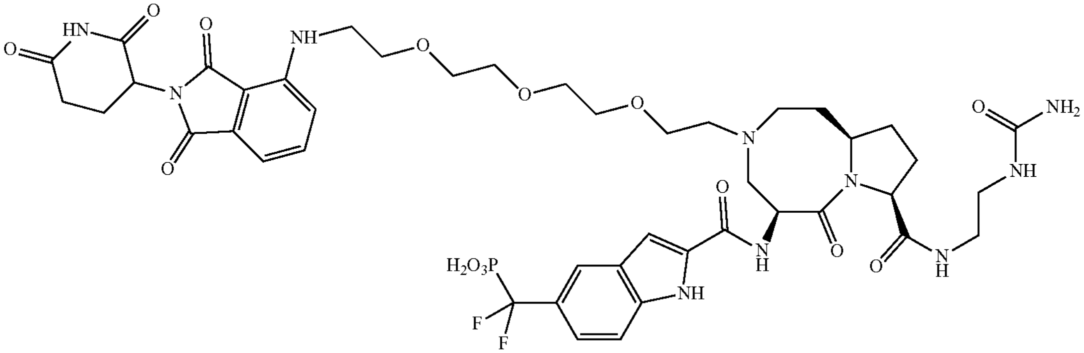 | ((2-(((5S,8S,10aR)-3-(2-(2-(2-(2-((2-(2,6-dioxopiperidin-3-yl)-1,3-dioxoisoindolin-4-yl)amino)ethoxy)ethoxy)ethoxy)ethyl)-6-oxo-8-((2-ureidoethyl)carbamoyl)decahydropyrrolo[1,2-a][1,5]diazocin-5-yl)carbamoyl)-1H-indol-5-yl)difluoromethyl)phosphonic acid |
| 7 | 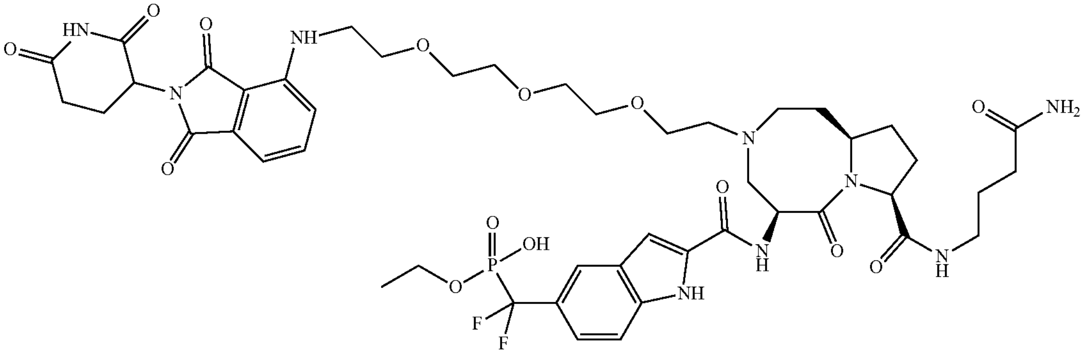 [SMILES: CCOP(=O)(O)C(F)(F)c1ccc2[nH]c(C(=O)N[C@H]3CN(CCOCCOCCOCCNc4cccc5c4C(=O)N(C4CCC(=O)NC4=O)C5=O)CC[C@H]4CC[C@@H](C(=O)NCCCC(N)=O)N4C3=O)cc2c1] | ethyl hydrogen ((2-(((5S,8S,10aR)-8-((4-amino-4-oxobutyl)carbamoyl)-3-(2-(2-(2-(2-((2-(2,6-dioxopiperidin-3-yl)-1,3-dioxoisoindolin-4-yl)amino)ethoxy)ethoxy)ethoxy)ethyl)-6-oxodecahydropyrrolo[1,2-a][1,5]diazocin-5-yl)carbamoyl)-1H-indol-5-yl)difluoromethyl)phosphonate |

TABLE 1-continued

| Cpd. No. | Structure | Name |
|---|---|---|
| 8 | 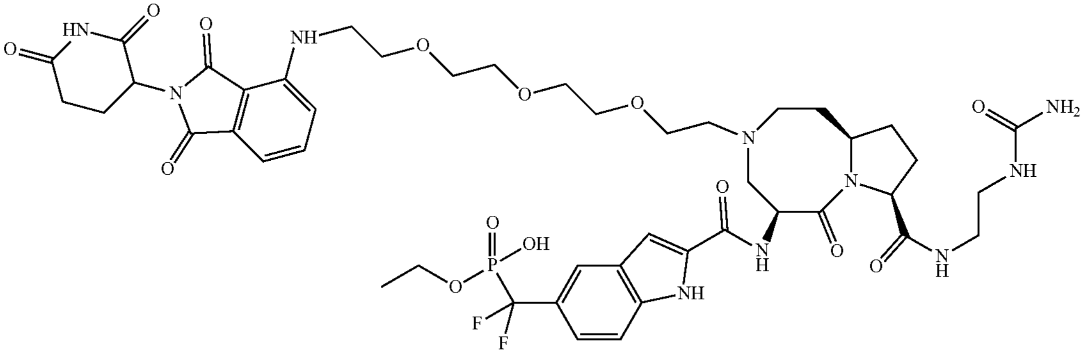 [SMILES: CCOP(=O)(O)C(F)(F)c1ccc2[nH]c(C(=O)N[C@H]3CN(CCOCCOCCOCCNc4cccc5c4C(=O)N(C4CCC(=O)NC4=O)C5=O)CC[C@H]4CC[C@@H](C(=O)NCCNC(N)=O)N4C3=O)cc2c1] | ethyl hydrogen ((2-(((5S,8S,10aR)-3-(2-(2-(2-(2-((2-(2,6-dioxopiperidin-3-yl)-1,3-dioxoisoindolin-4-yl)amino)ethoxy)ethoxy)ethoxy)ethyl)-6-oxo-8-((2-ureidoethyl)carbamoyl)decahydropyrrolo[1,2-a][1,5]diazocin-5-yl)carbamoyl)-1H-indol-5-yl)difluoromethyl)phosphonate |
| 9 | 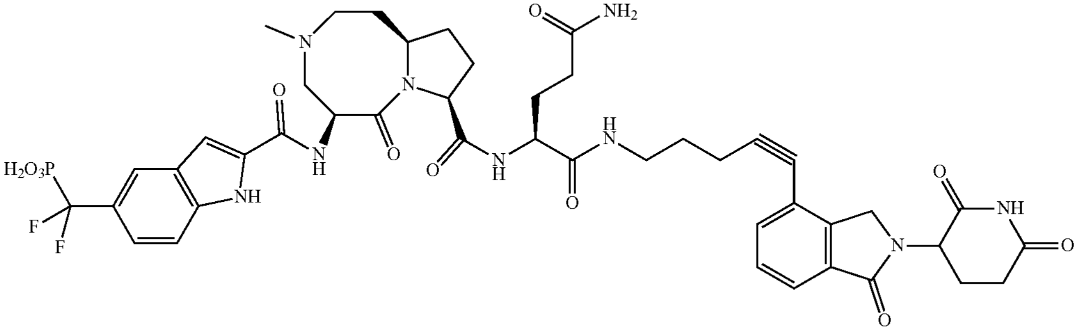 | ((2-(((5S,8S,10aR)-8-(((2S)-5-amino-1-((5-(2-(2,6-dioxopiperidin-3-yl)-1-oxoisoindolin-4-yl)pent-4-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 10 | 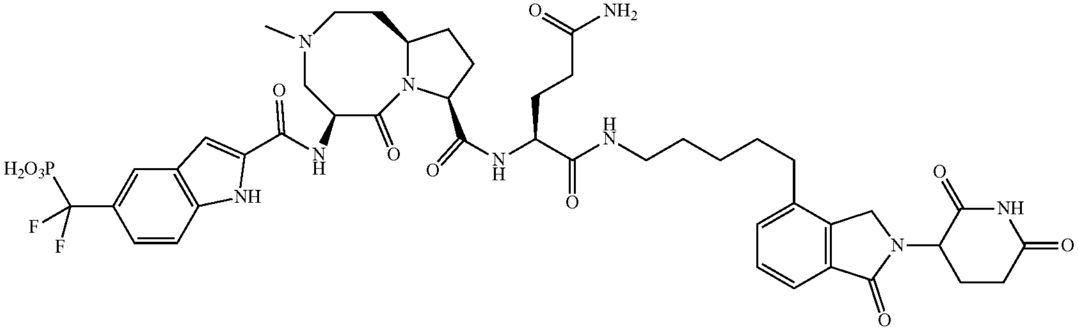 | ((2-(((5S,8S,10aR)-8-(((2S)-5-amino-1-((5-(2-(2,6-dioxopiperidin-3-yl)-1-oxoisoindolin-4-yl)pentyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 11 | 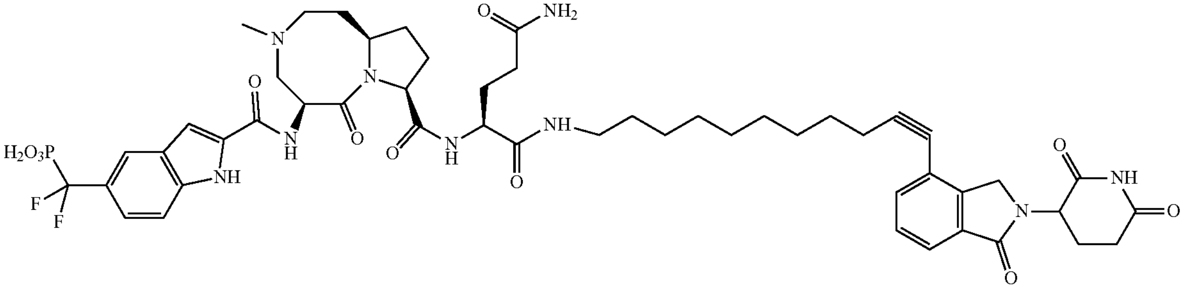 | ((2-(((5S,8S,10aR)-8-(((2S)-5-amino-1-((11-(2-(2,6-dioxopiperidin-3-yl)-1-oxoisoindolin-4-yl)undec-10-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 12 | 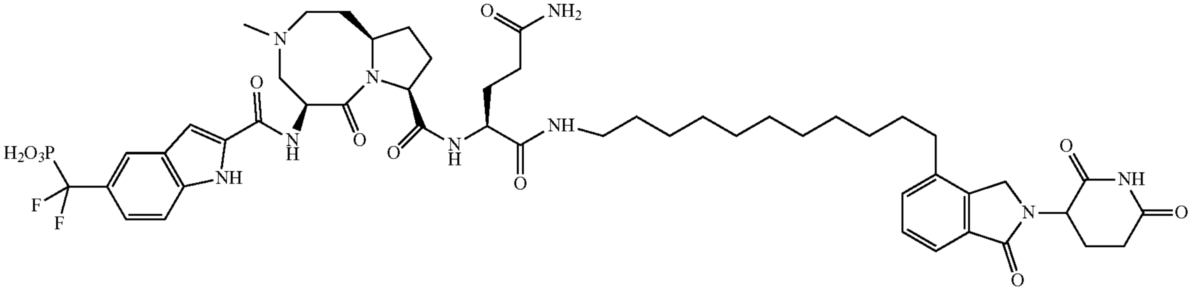 | ((2-(((5S,8S,10aR)-8-(((2S)-5-amino-1-((11-(2-(2,6-dioxopiperidin-3-yl)-1-oxoisoindolin-4-yl)undecyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 13 | 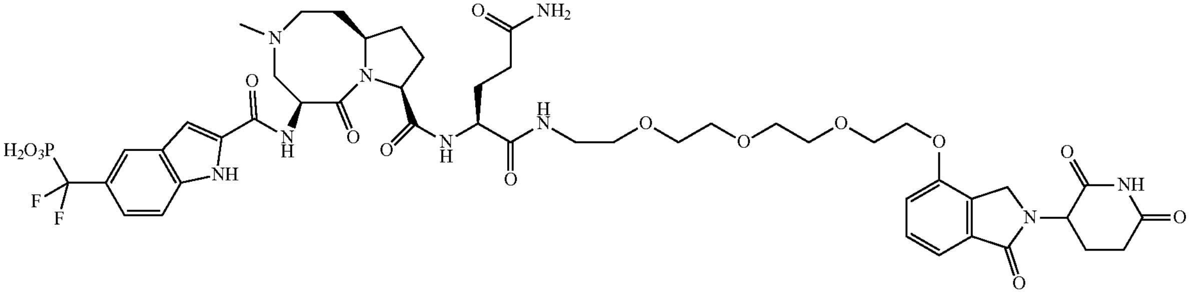 | ((2-(((5S,8S,10aR)-8-(((14S)-17-amino-1-((2-(2,6-dioxopiperidin-3-yl)-1-oxoisoindolin-4-yl)oxy)-13,17-dioxo-3,6,9-trioxa-12-azaheptadecan-14-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 14 | 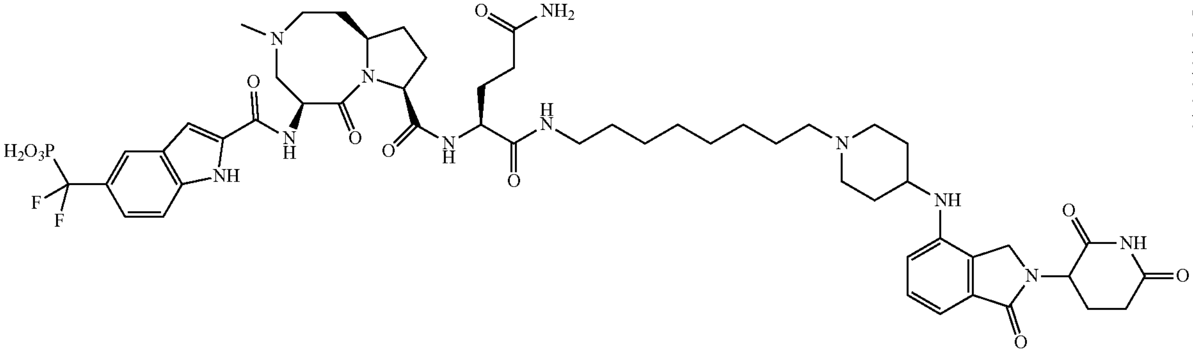 | ((2-(((5S,8S,10aR)-8-(((2S)-5-amino-1-((8-(4-((2-(2,6-dioxopiperidin-3-yl)-1-oxoisoindolin-4-yl)amino)piperidin-1-yl)octyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 15 | 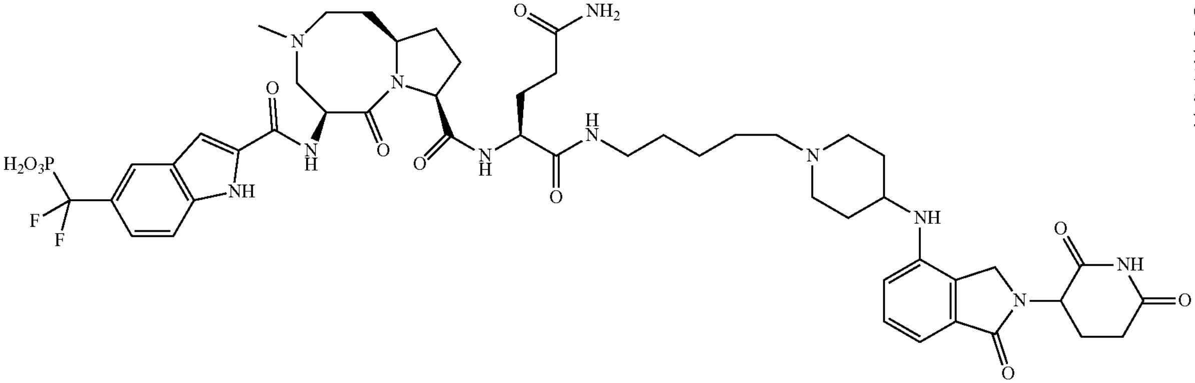 | ((2-(((5S,8S,10aR)-8-(((2S)-5-amino-1-((5-(4-((2-(2,6-dioxopiperidin-3-yl)-1-oxoisoindolin-4-yl)amino)piperidin-1-yl)pentyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 16 | 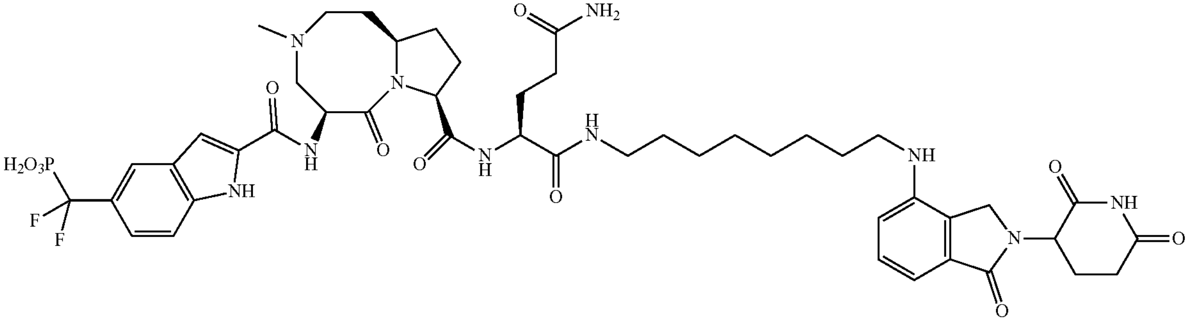 | ((2-(((5S,8S,10aR)-8-(((2S)-5-amino-1-((8-((2-(2,6-dioxopiperidin-3-yl)-1-oxoisoindolin-4-yl)amino)octyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 17 | 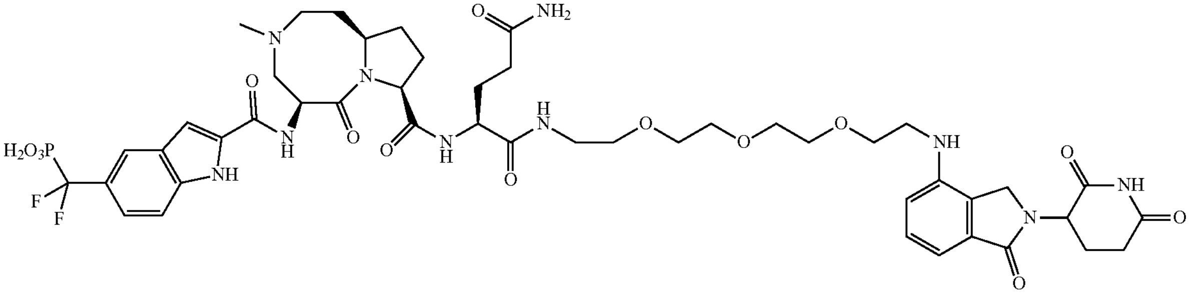 | ((2-(((5S,8S,10aR)-8-(((14S)-17-amino-1-((2-(2,6-dioxopiperidin-3-yl)-1-oxoisoindolin-4-yl)amino)-13,17-dioxo-3,6,9-trioxa-12-azaheptadecan-14-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 18 | 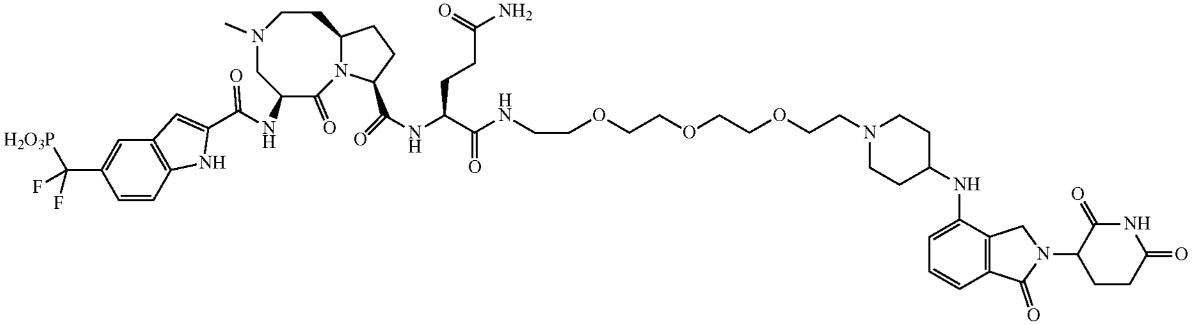 | ((2-(((5S,8S,10aR)-8-(((14S)-17-amino-1-(4-((2-(2,6-dioxopiperidin-3-yl)-1-oxoisoindolin-4-yl)amino)piperidin-1-yl)-13,17-dioxo-3,6,9-trioxa-12-azaheptadecan-14-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 19 | 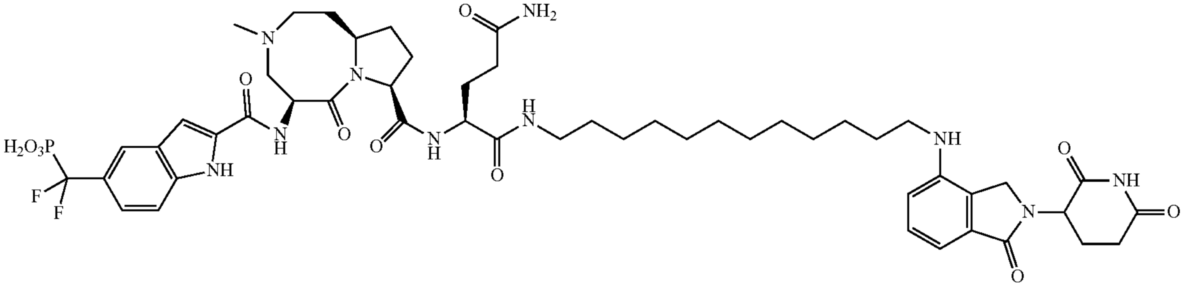 | ((2-(((5S,8S,10aR)-8-(((2S)-5-amino-1-((12-((2-(2,6-dioxopiperidin-3-yl)-1-oxoisoindolin-4-yl)amino)dodecyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 20 | 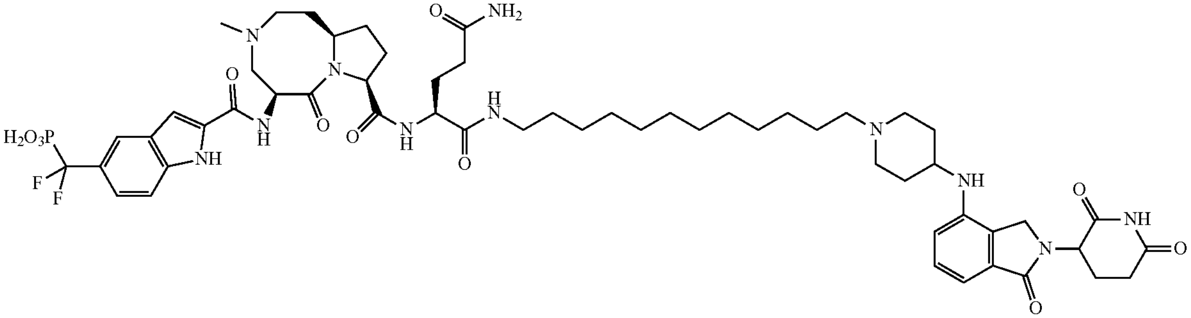 | ((2-(((5S,8S,10aR)-8-(((2S)-5-amino-1-((12-(4-((2-(2,6-dioxopiperidin-3-yl)-1-oxoisoindolin-4-yl)amino)piperidin-1-yl)dodecyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 21 | 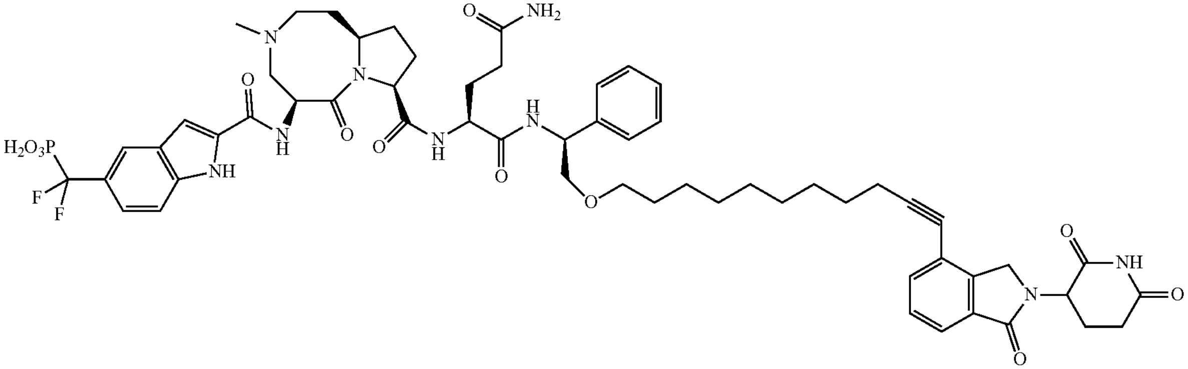 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 22 | 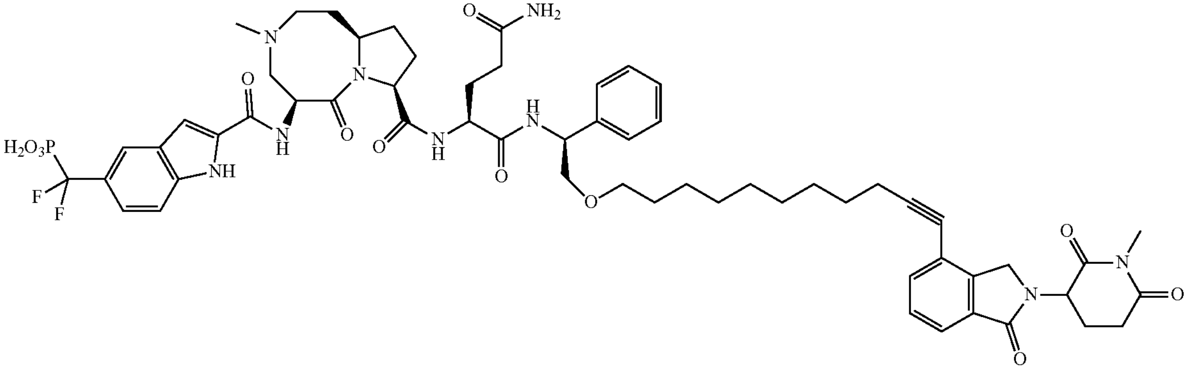 | ((2-(((5S,8S,10aR)-8-(((2S)-5-amino-1-(((1S)-2-((11-(2-(1-methyl-2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 23 | 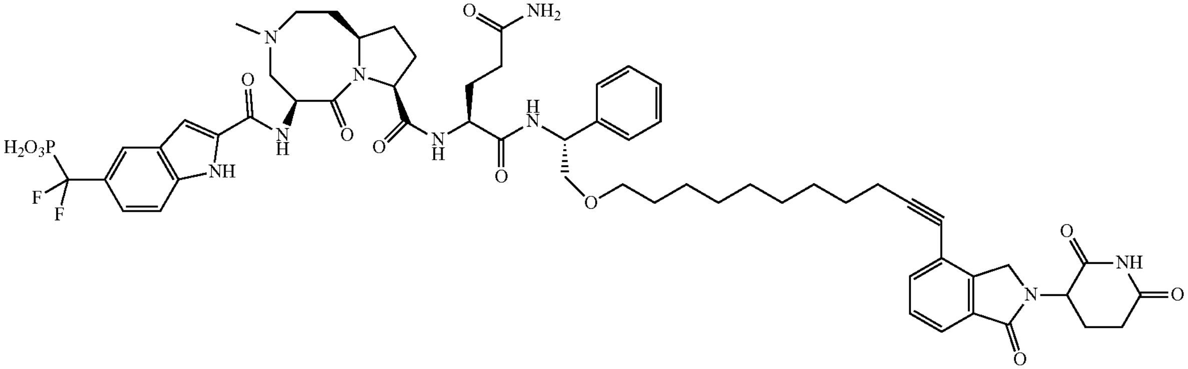 | ((2-(((5S,8S,10aR)-8-(((2S)-5-amino-1-(((1R)-2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 24 | 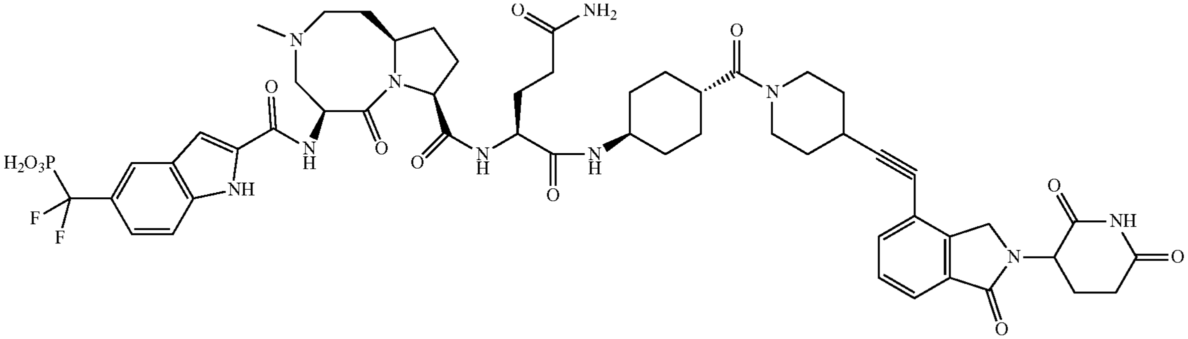 | ((2-(((5S,8S,10aR)-8-(((2S)-5-amino-1-(((1r,4S)-4-(4-((2-(2,6-dioxopiperidin-3-yl)-1-oxoisoindolin-4-yl)ethynyl)piperidine-1-carbonyl)cyclohexyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 25 | 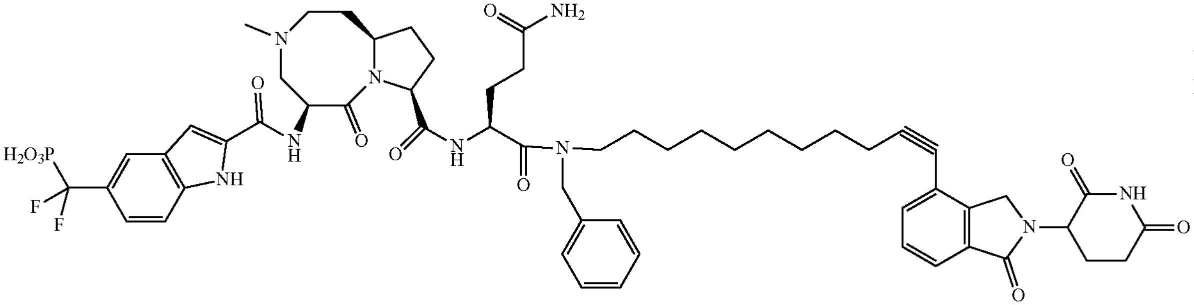 | ((2-(((5S,8S,10aR)-8-(((2S)-5-amino-1-(benzyl(11-(2-(2,6-dioxopiperidin-3-yl)-1-oxoisoindolin-4-yl)undec-10-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 26 | 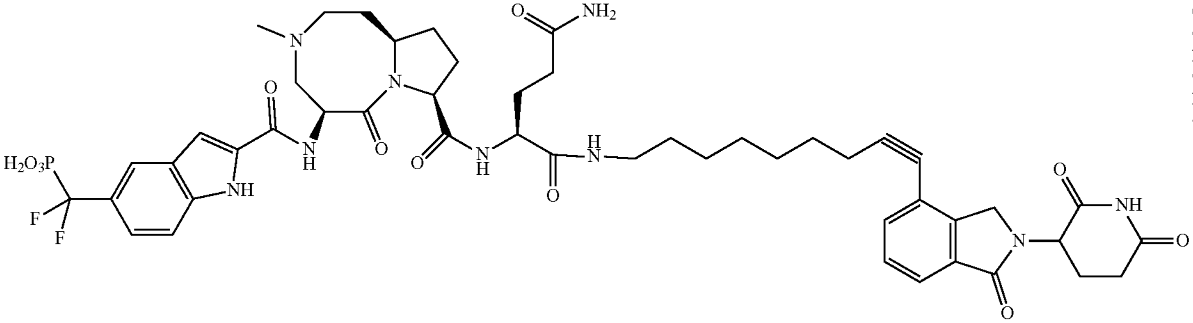 | ((2-(((5S,8S,10aR)-8-(((2S)-5-amino-1-((9-(2-(2,6-dioxopiperidin-3-yl)-1-oxoisoindolin-4-yl)non-8-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 27 | 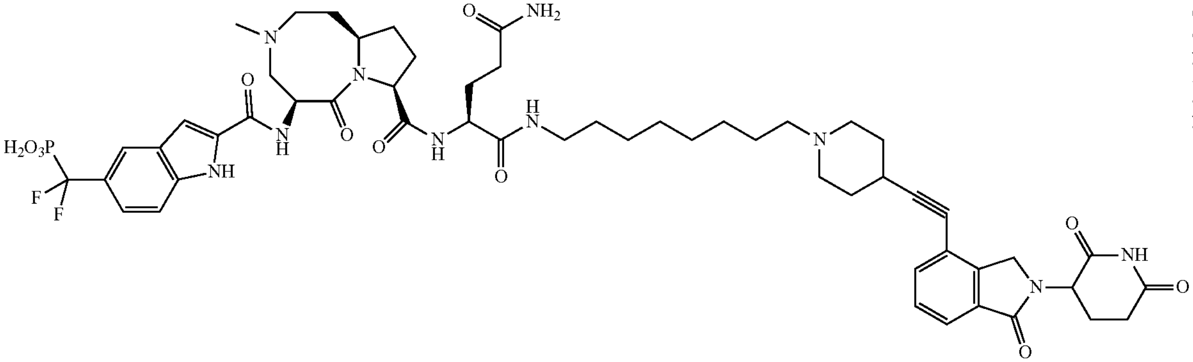 | ((2-(((5S,8S,10aR)-8-(((2S)-5-amino-1-((8-(4-((2-(2,6-dioxopiperidin-3-yl)-1-oxoisoindolin-4-yl)ethynyl)piperidin-1-yl)octyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 28 | 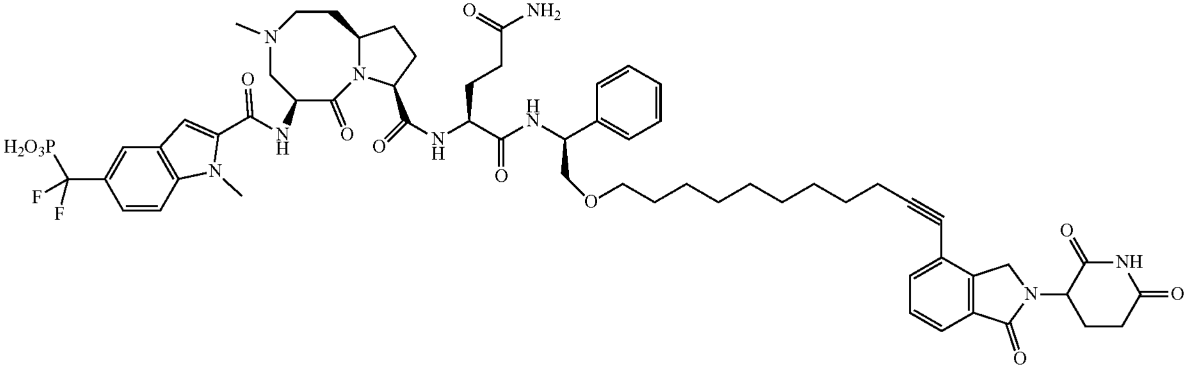 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1-methyl-1H-indol-5-yl)difluoromethyl)phosphonic acid |

TABLE 1-continued

| Cpd. No. | Structure | Name |
|---|---|---|
| 29 | 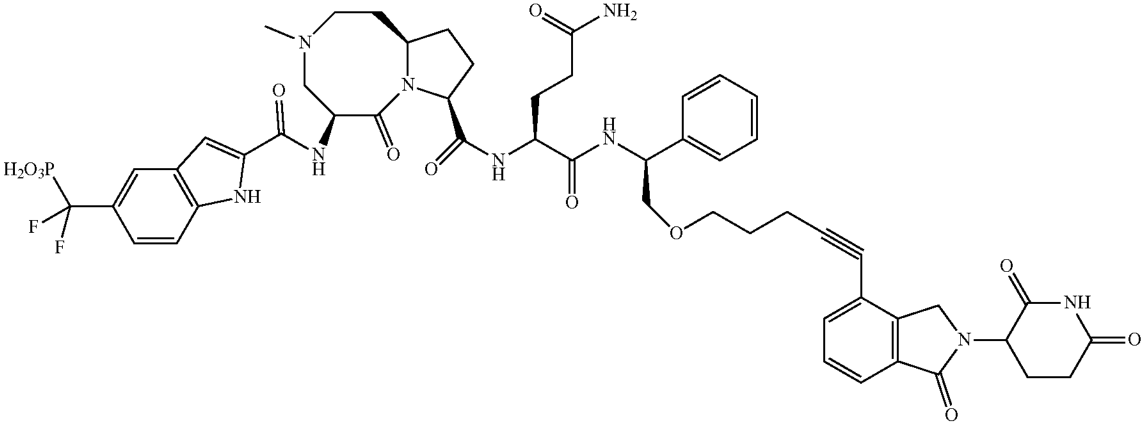 | ((2-(((5S,8S,10aR)-8-(((2S)-5-amino-1-(((1S)-2-((5-(2-(2,6-dioxopiperidin-3-yl)-1-oxoisoindolin-4-yl)pent-4-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 30 | 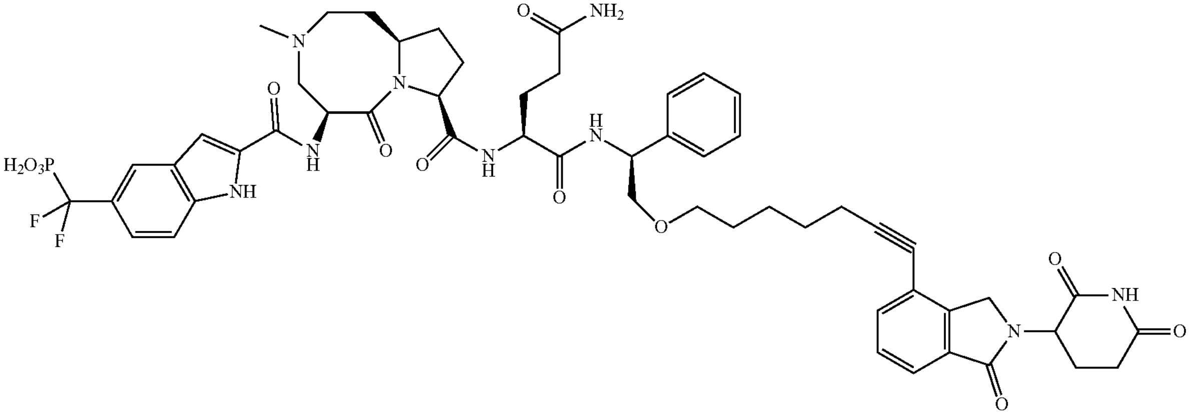 | ((2-(((5S,8S,10aR)-8-(((2S)-5-amino-1-(((1S)-2-((7-(2-(2,6-dioxopiperidin-3-yl)-1-oxoisoindolin-4-yl)hept-6-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 31 | 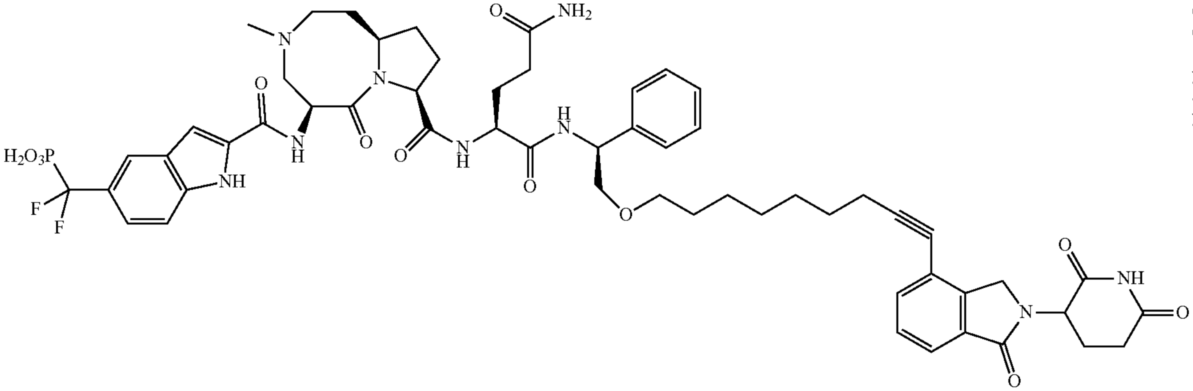 | ((2-(((5S,8S,10aR)-8-(((2S)-5-amino-1-(((1S)-2-((9-(2-(2,6-dioxopiperidin-3-yl)-1-oxoisoindolin-4-yl)non-8-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 32 | 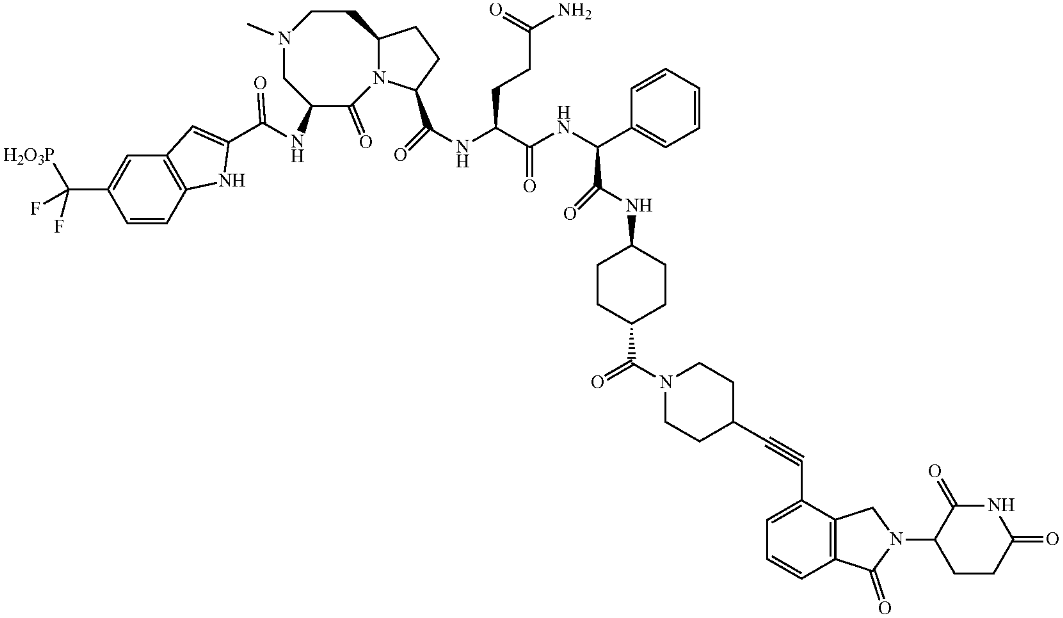 | ((2-(((5S,8S,10aR)-8-(((2S)-5-amino-1-(((1S)-2-(((1r,4S)-4-(4-((2-(2,6-dioxopiperidin-3-yl)-1-oxoisoindolin-4-yl)ethynyl)piperidine-1-carbonyl)cyclohexyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 33 | 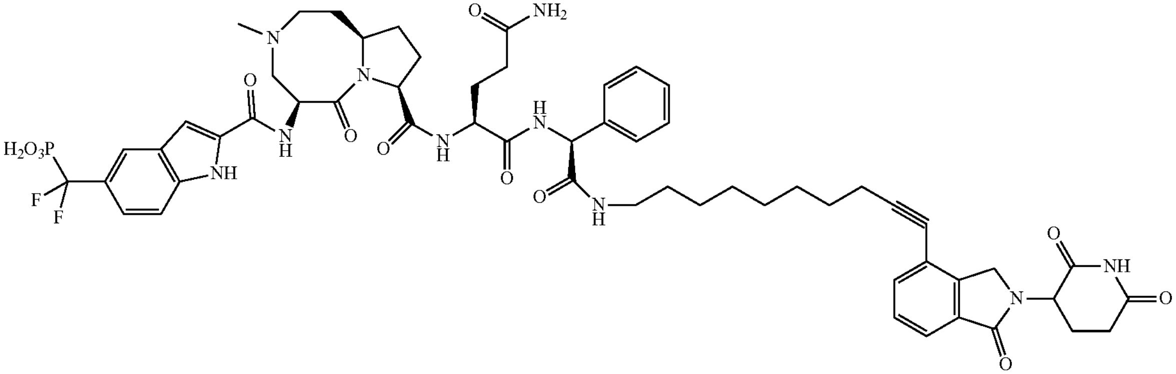 | ((2-(((5S,8S,10aR)-8-(((2S)-5-amino-1-(((1S)-2-((10-(2-(2,6-dioxopiperidin-3-yl)-1-oxoisoindolin-4-yl)dec-9-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 34 | 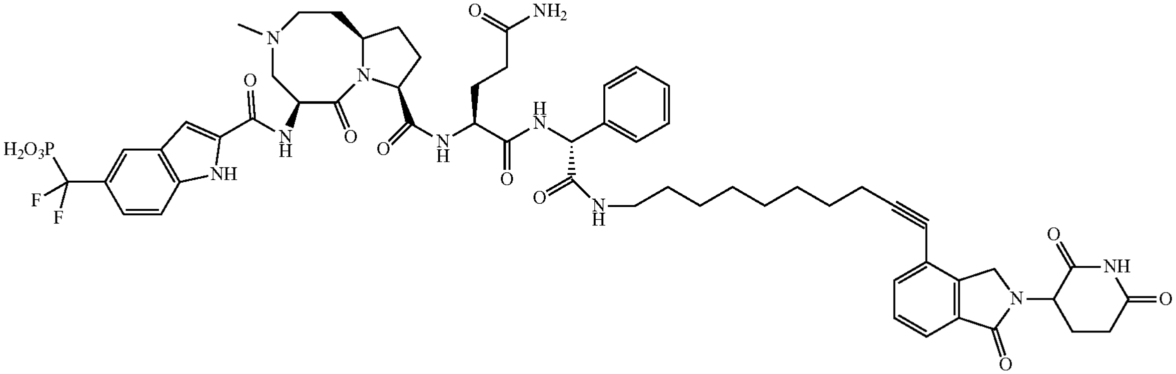 | ((2-(((5S,8S,10aR)-8-(((2S)-5-amino-1-(((1R)-2-((10-(2-(2,6-dioxopiperidin-3-yl)-1-oxoisoindolin-4-yl)dec-9-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 35 | 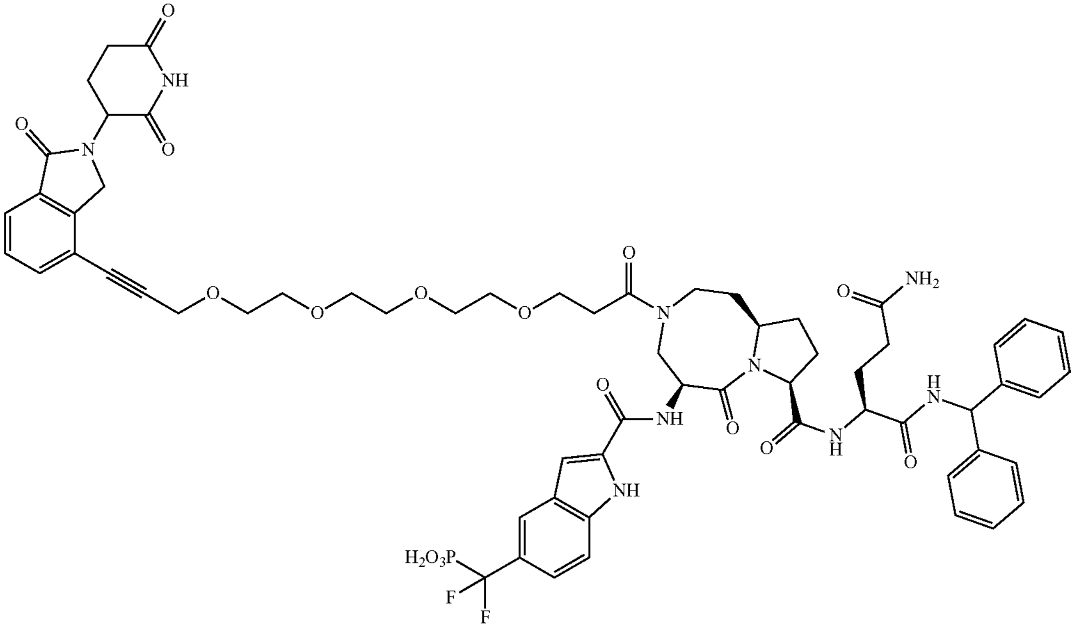 | ((2-(((5S,8S,10aR)-8-(((S)-5-amino-1-(benzhydrylamino)-1,5-dioxopentan-2-yl)carbamoyl)-3-(16-(2-(2,6-dioxopiperidin-3-yl)-1-oxoisoindolin-4-yl)-4,7,10,13-tetraoxahexadec-15-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 36 | 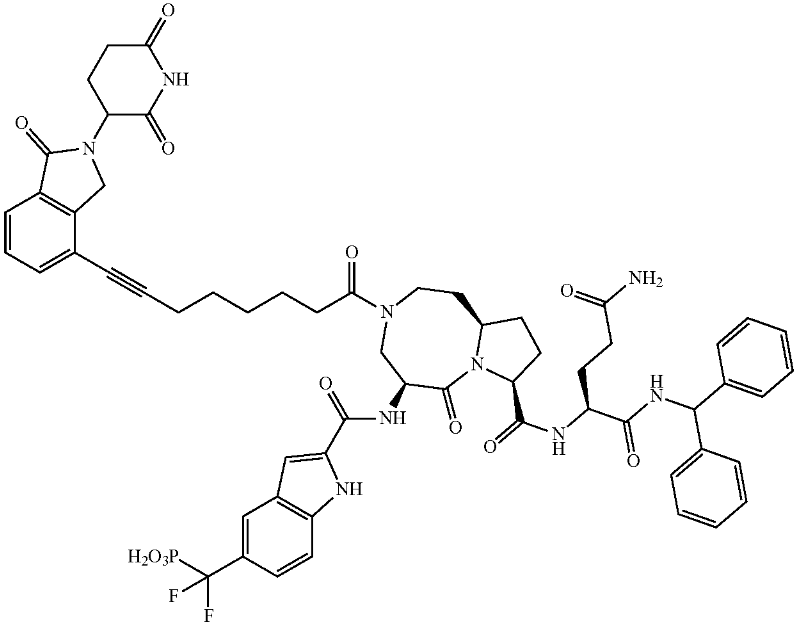 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 37 | 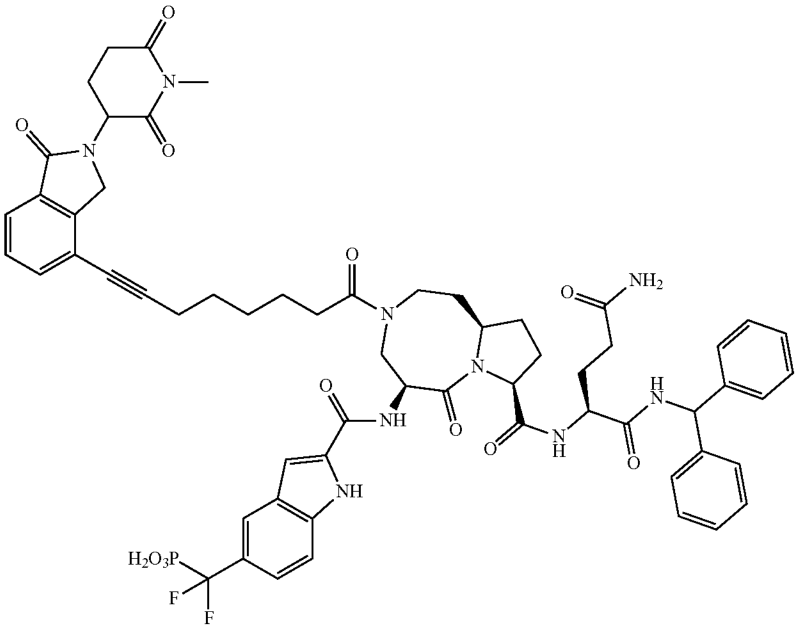 | ((2-(((5S,8S,10aR)-8-(((S)-5-amino-1-(benzhydrylamino)-1,5-dioxopentan-2-yl)carbamoyl)-3-(8-(2-(1-methyl-2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 37E | 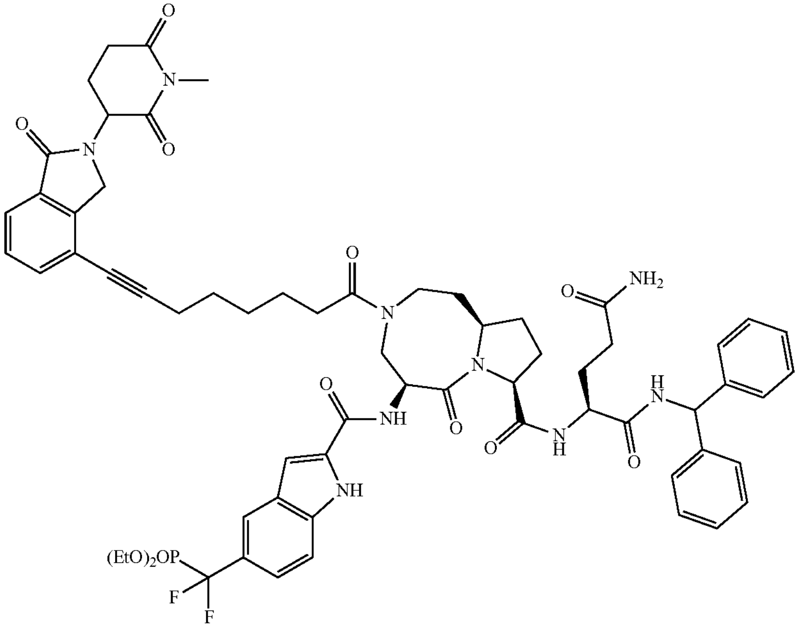 | diethyl ((2-(((5S,8S,10aR)-8-(((S)-5-amino-1-(benzhydrylamino)-1,5-dioxopentan-2-yl)carbamoyl)-3-(8-(2-(1-methyl-2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonate |

TABLE 1-continued

| Cpd. No. | Structure | Name |
|---|---|---|
| 38 | 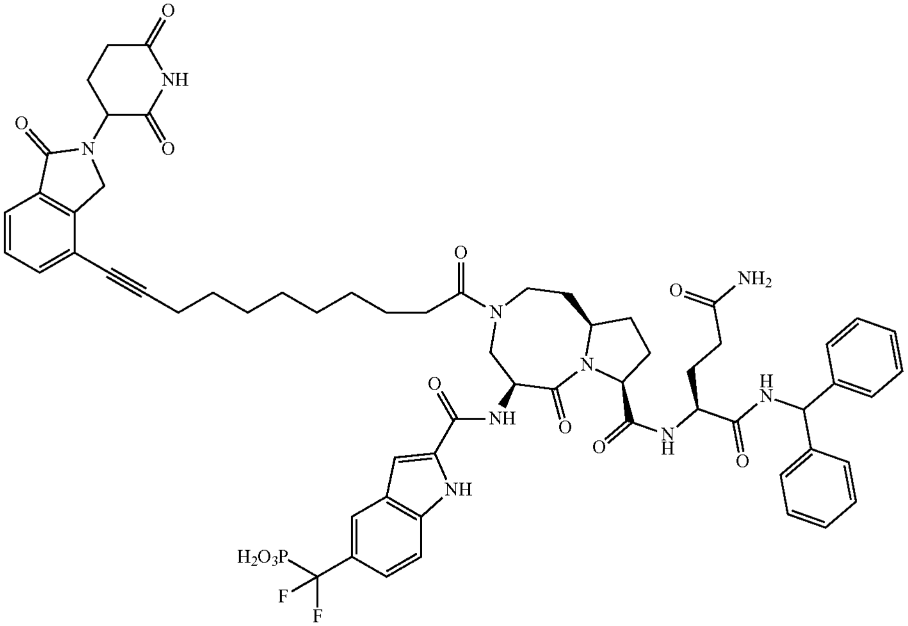 | ((2-(((5S,8S,10aR)-8-(((S)-5-amino-1-(benzhydrylamino)-1,5-dioxopentan-2-yl)carbamoyl)-3-(11-(2-(2,6-dioxopiperidin-3-yl)-1-oxoisoindolin-4-yl)undec-10-ynoyl)-6-oxodecahydropyrrolo[1,2-a][1,5]diazocin-5-yl)carbamoyl)-1H-indol-5-yl)difluoromethyl)phosphonic acid |
| 39 | 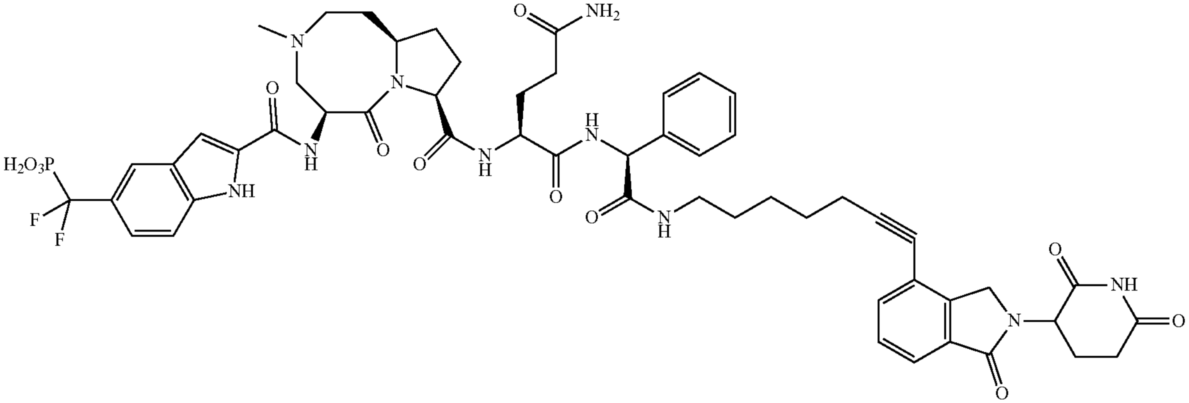 | ((2-(((5S,8S,10aR)-8-(((2S)-5-amino-1-(((1S)-2-((7-(2-(2,6-dioxopiperidin-3-yl)-1-oxoisoindolin-4-yl)hept-6-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 40 | 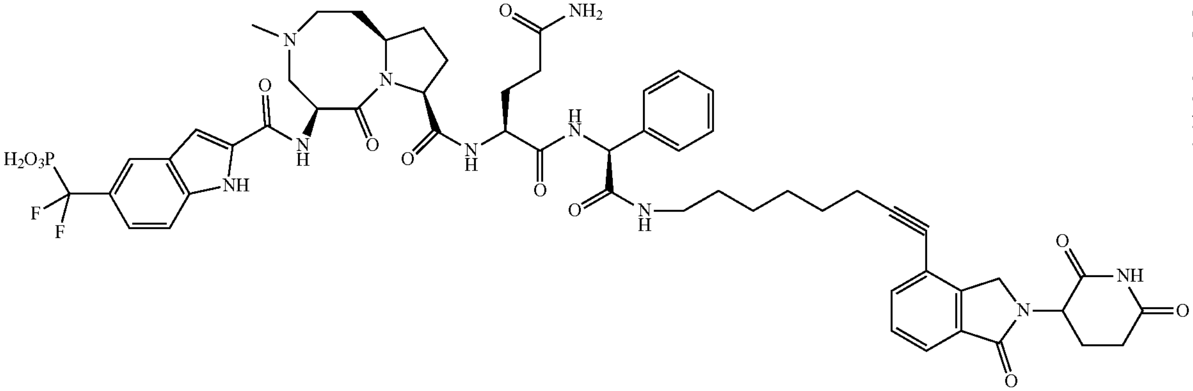 | ((2-(((5S,8S,10aR)-8-(((2S)-5-amino-1-(((1S)-2-((8-(2-(2,6-dioxopiperidin-3-yl)-1-oxoisoindolin-4-yl)oct-7-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 41 | 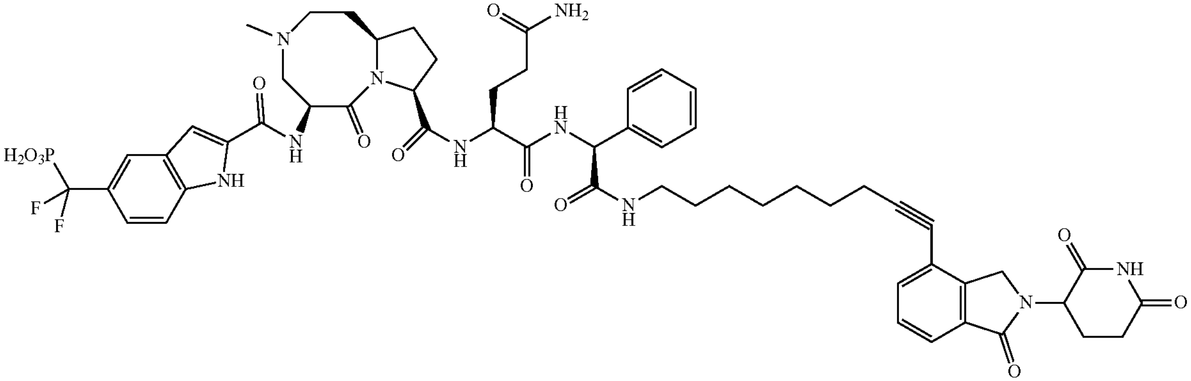 | ((2-(((5S,8S,10aR)-8-(((2S)-5-amino-1-(((1S)-2-((9-(2-(2,6-dioxopiperidin-3-yl)-1-oxoisoindolin-4-yl)non-8-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 42 | 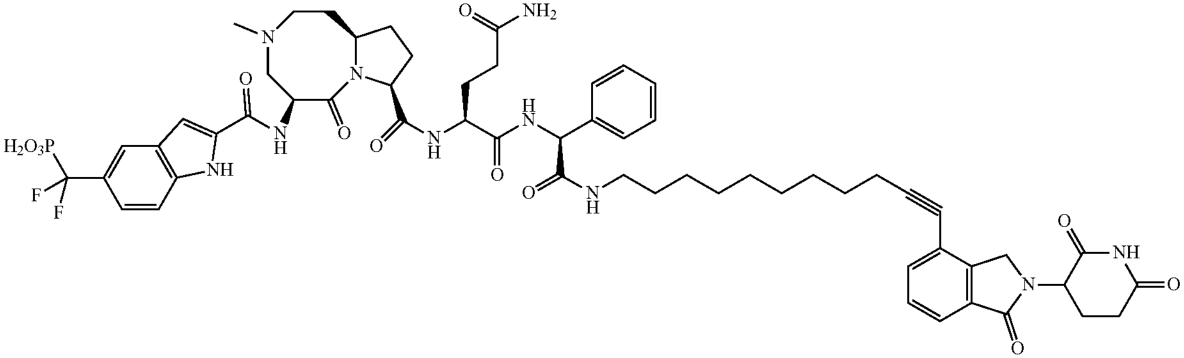 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 43 | 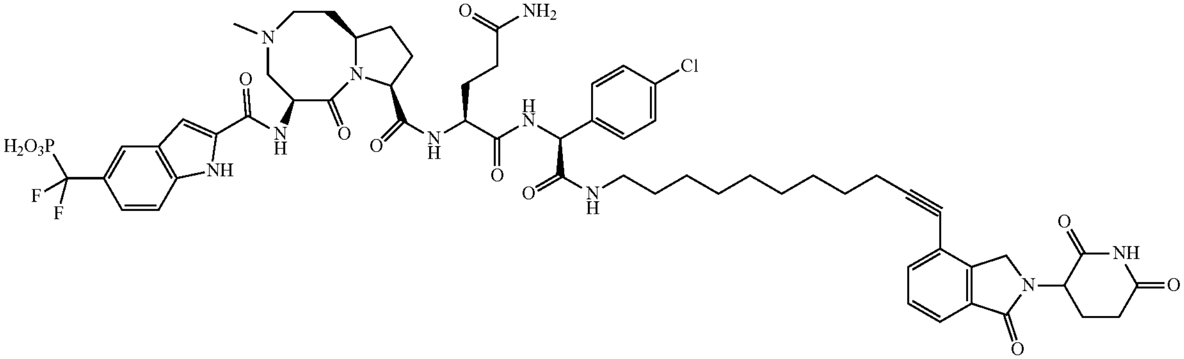 | ((2-(((5S,8S,10aR)-8-(((2S)-5-amino-1-(((1S)-1-(4-chlorophenyl)-2-((11-(2-(2,6-dioxopiperidin-3-yl)-1-oxoisoindolin-4-yl)undec-10-yn-1-yl)amino)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 44 | 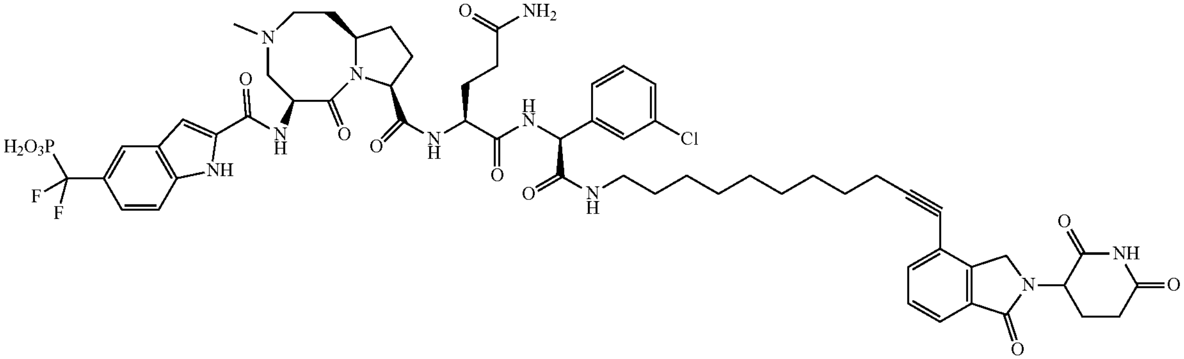 | ((2-(((5S,8S,10aR)-8-(((2S)-5-amino-1-(((1S)-1-(3-chlorophenyl)-2-((11-(2-(2,6-dioxopiperidin-3-yl)-1-oxoisoindolin-4-yl)undec-10-yn-1-yl)amino)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 47 | 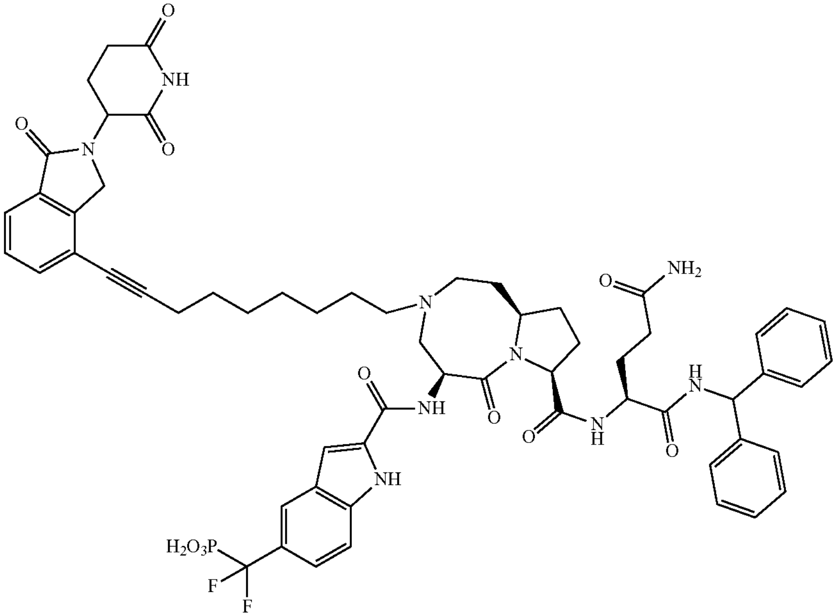 | ((2-(((5S,8S,10aR)-8-(((S)-5-amino-1-(benzhydrylamino)-1,5-dioxopentan-2-yl)carbamoyl)-3-(9-(2-(2,6-dioxopiperidin-3-yl)-1-oxoisoindolin-4-yl)non-8-yn-1-yl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 48 | 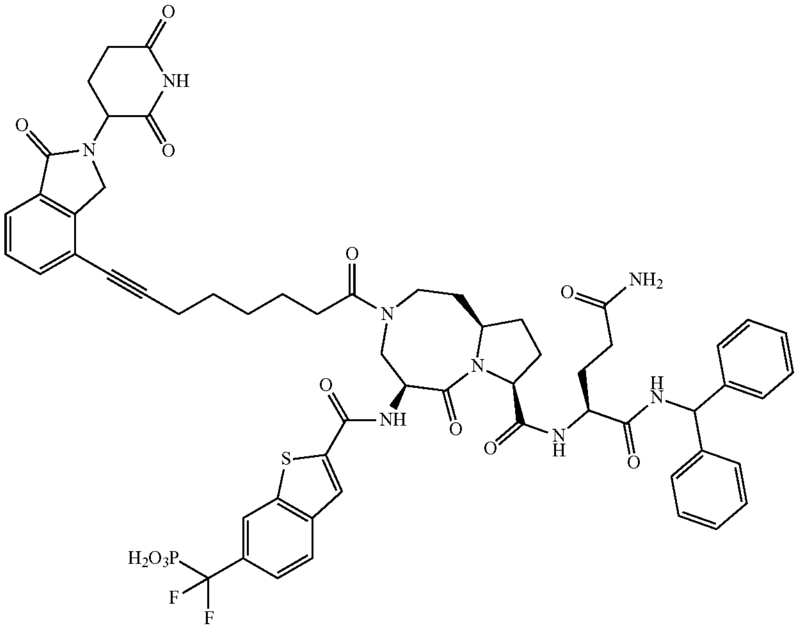 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-6-yl)difluoromethyl)phosphonic acid |

TABLE 1-continued
| Cpd. No. | Structure | Name |
|---|---|---|
| 49 | 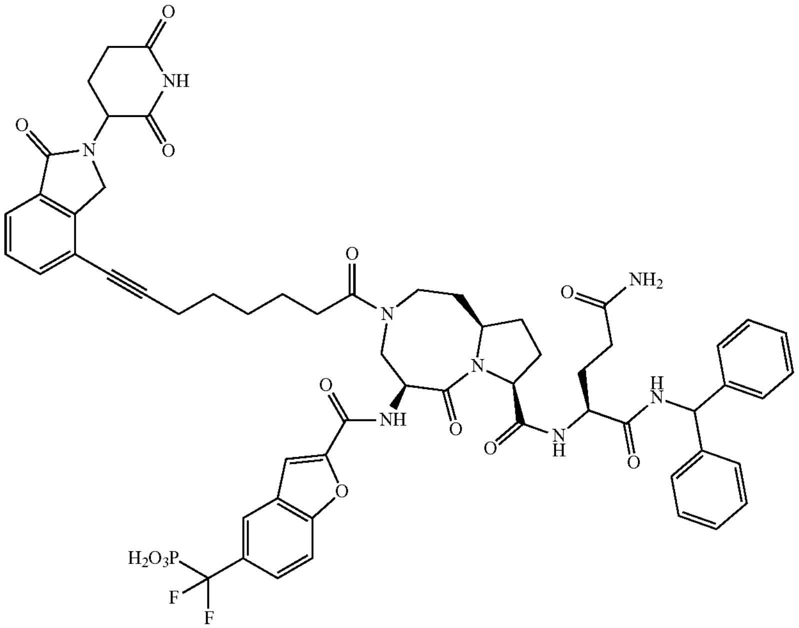 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzofuran-5-yl)difluoromethyl)phosphonic acid |

TABLE 1-continued
| Cpd. No. | Structure | Name |
|---|---|---|
| 50 | 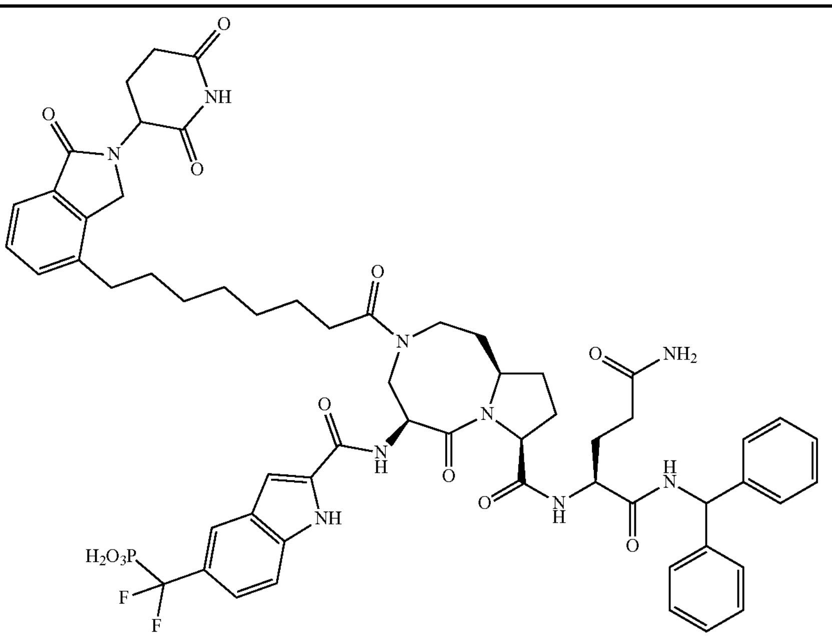 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)octanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 51 | 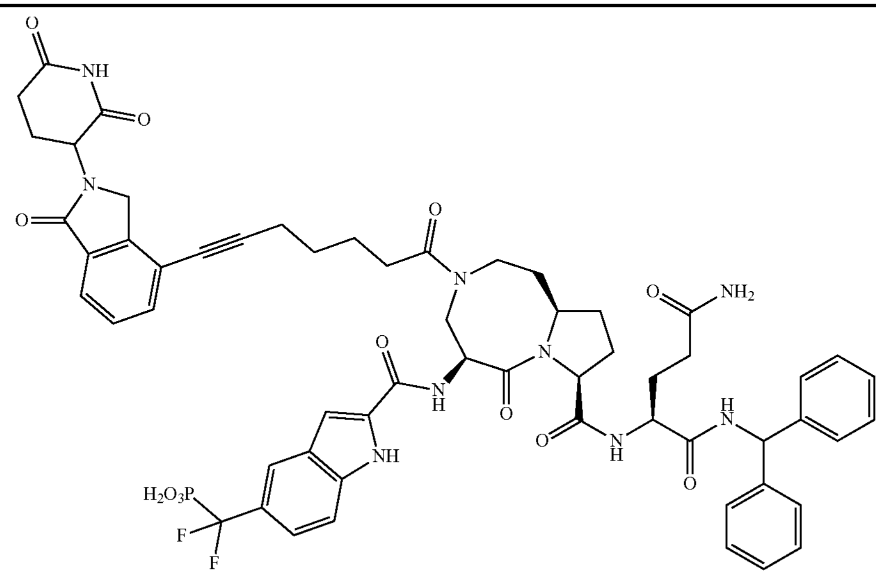 | ((2-(((5S,8S,10aR)-8-(((S)-5-amino-1-(benzhydrylamino)-1,5-dioxopentan-2-yl)carbamoyl)-3-(7-(2-(2,6-dioxopiperidin-3-yl)-1-oxoisoindolin-4-yl)hept-6-ynoyl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 52 | 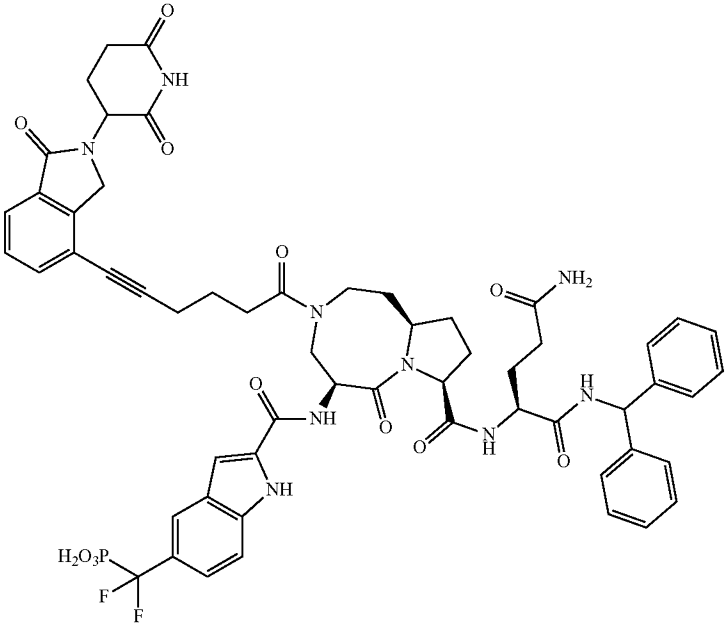 | ((2-(((5S,8S,10aR)-8-(((S)-5-amino-1-(benzhydrylamino)-1,5-dioxopentan-2-yl)carbamoyl)-3-(6-(2-(2,6-dioxopiperidin-3-yl)-1-oxoisoindolin-4-yl)hex-5-ynoyl)-6-oxodecahydropyrrolo[1,2-a][1,5]diazocin-5-yl)carbamoyl)-1H-indol-5-yl)difluoromethyl)phosphonic acid |
| 53 | 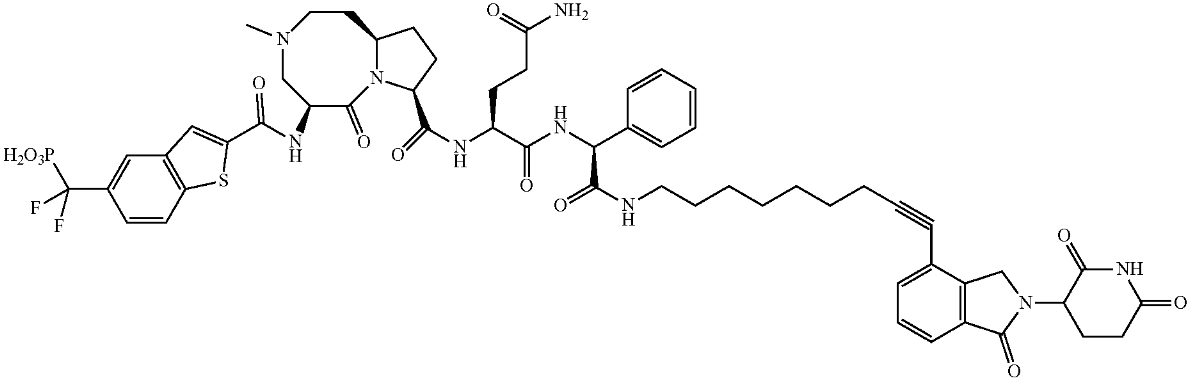 | ((2-(((5S,8S,10aR)-8-(((2S)-5-amino-1-(((1S)-2-((9-(2-(2,6-dioxopiperidin-3-yl)-1-oxoisoindolin-4-yl)non-8-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 54 | 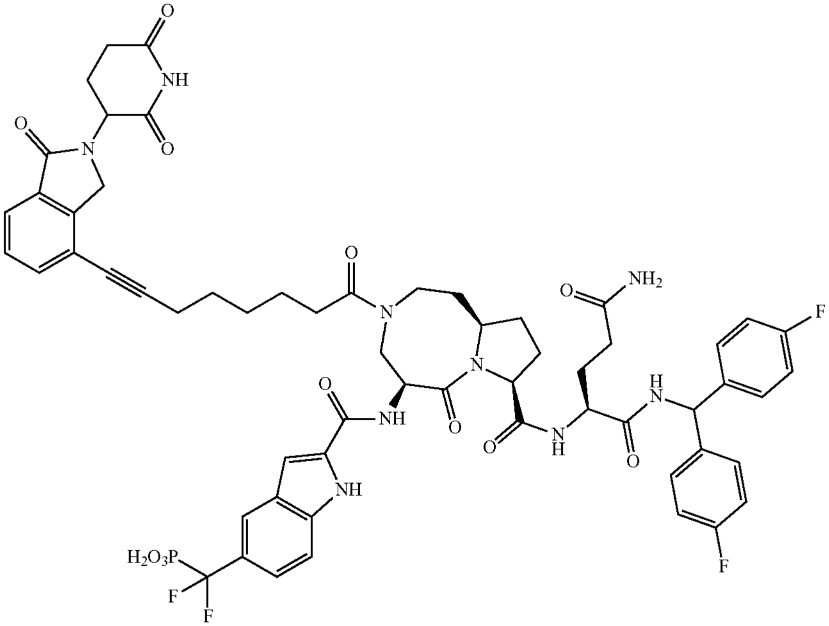 | ((2-(((5S,8S,10aR)-8-(((S)-5-amino-1-((bis(4-fluorophenyl)methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 55 | 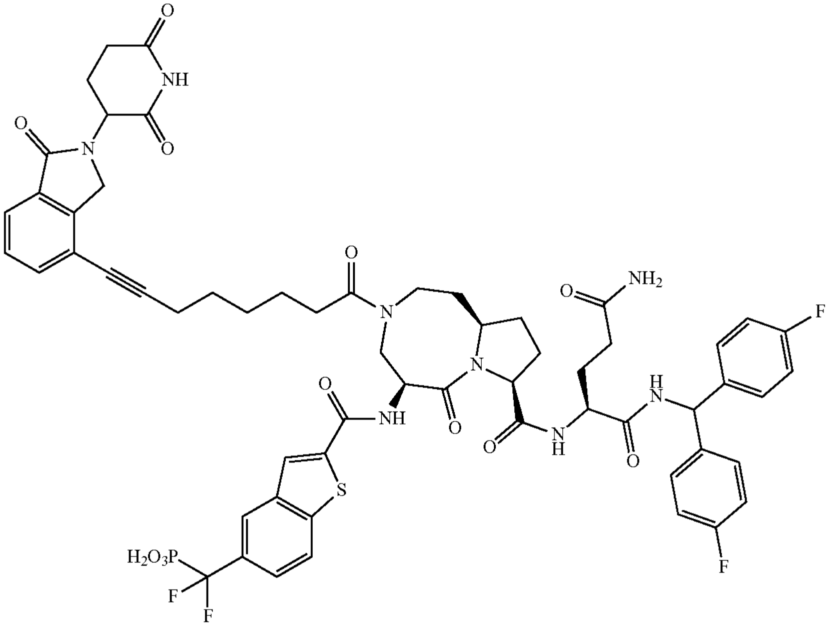 | ((2-(((5S,8S,10aR)-8-(((S)-5-amino-1-((bis(4-fluorophenyl)methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 56 | 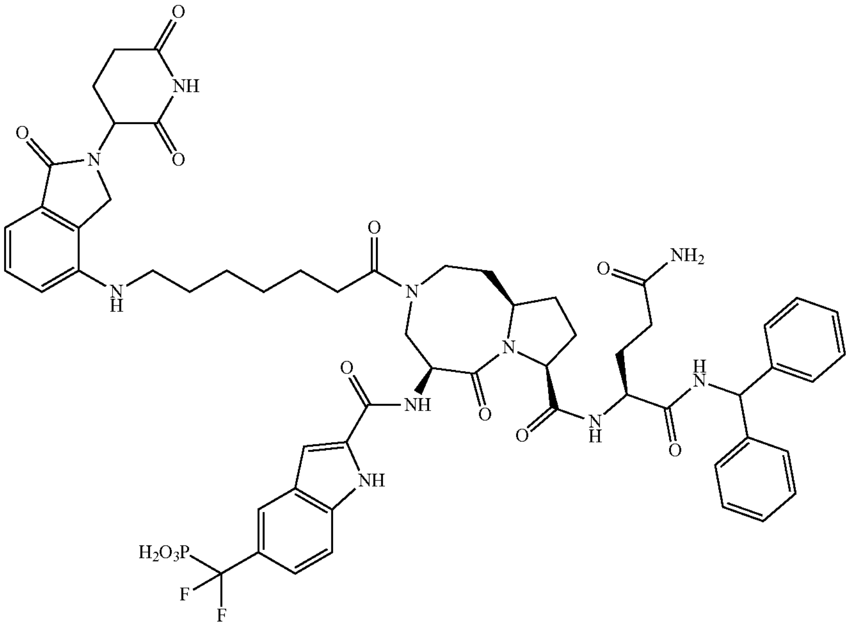 | ((2-(((5S,8S,10aR)-8-(((S)-5-amino-1-(benzhydrylamino)-1,5-dioxopentan-2-yl)carbamoyl)-3-(7-((2-(2,6-dioxopiperidin-3-yl)-1-oxoisoindolin-4-yl)amino)heptanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 57 | 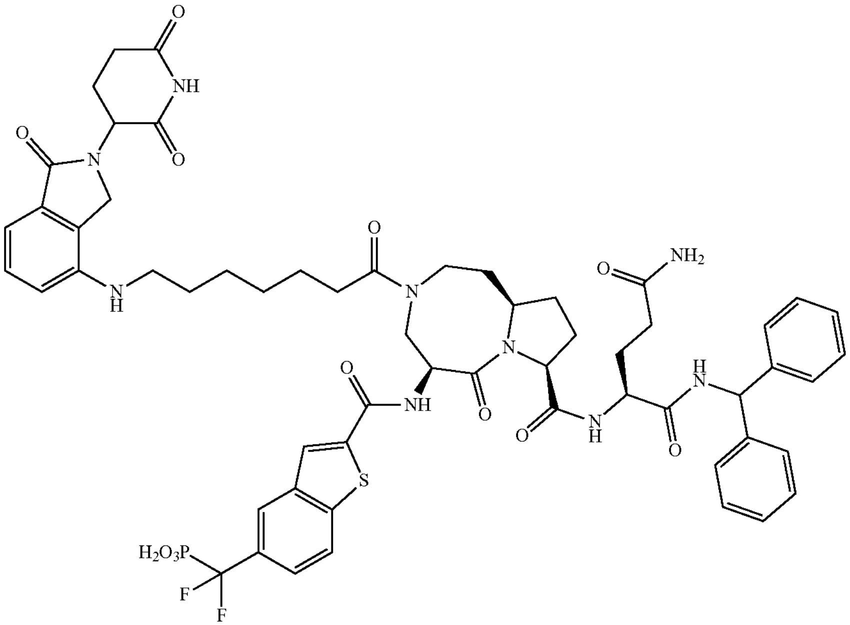 | ((2-(((5S,8S,10aR)-8-(((S)-5-amino-1-(benzhydrylamino)-1,5-dioxopentan-2-yl)carbamoyl)-3-(7-((2-(2,6-dioxopiperidin-3-yl)-1-oxoisoindolin-4-yl)amino)heptanoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 58 | 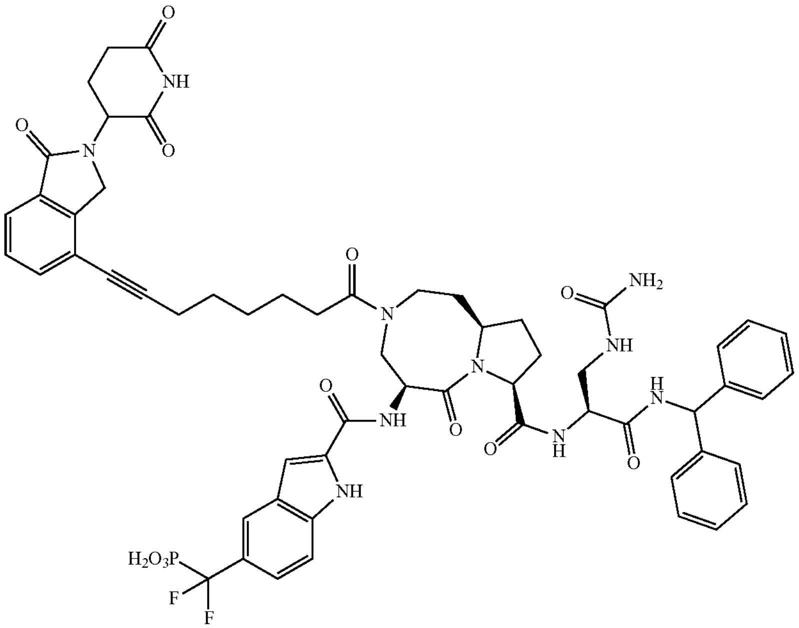 | ((2-(((5S,8S,10aR)-8-(((S)-1-(benzhydrylamino)-1-oxo-3-ureidopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 59 | 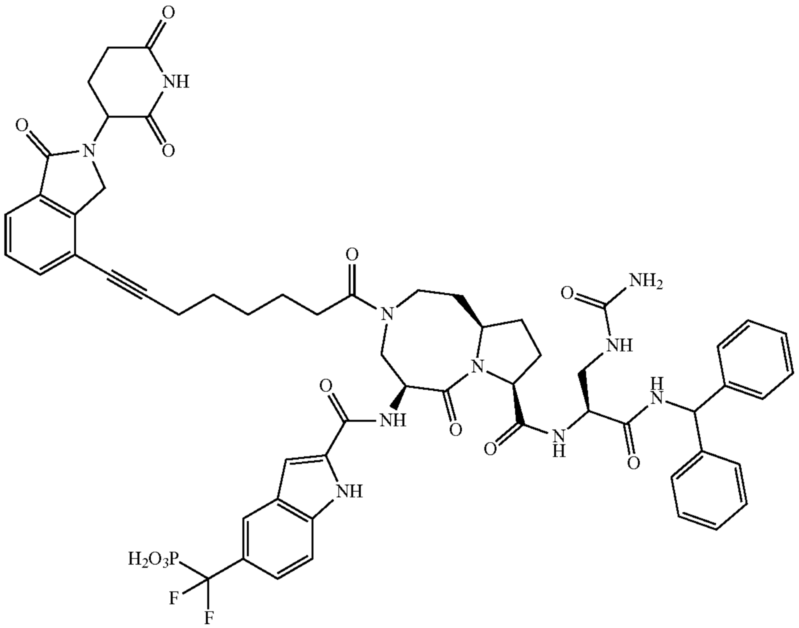 | ((2-(((5S,8S,10aR)-8-(((S)-1-(benzhydrylamino)-1-oxo-3-ureidopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 60 | 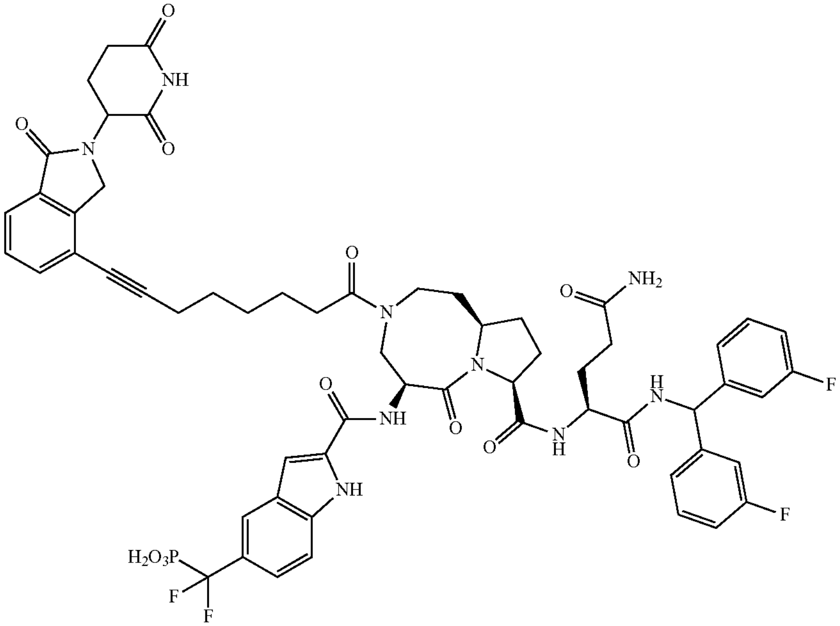 | ((2-(((5S,8S,10aR)-8-(((S)-5-amino-1-((bis(3-fluorophenyl)methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 61 | 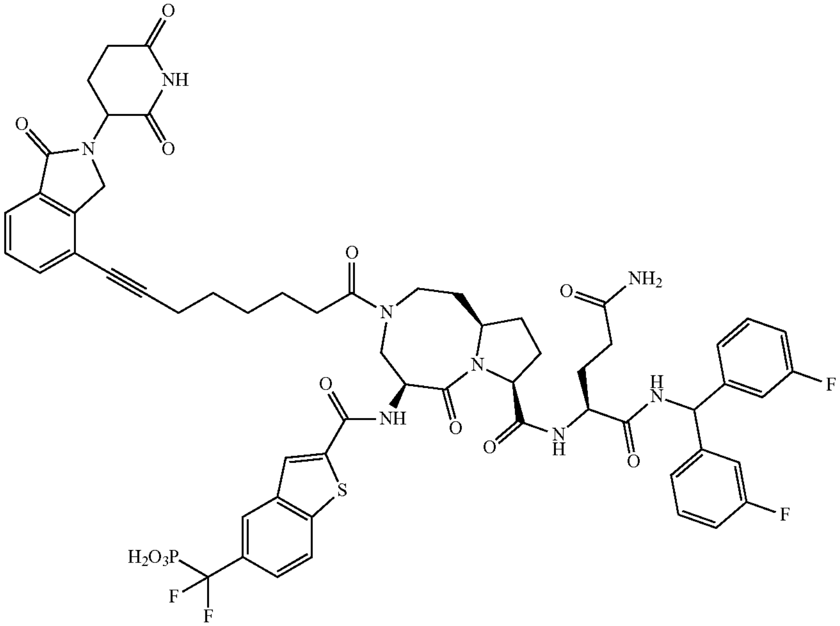 | ((2-(((5S,8S,10aR)-8-(((S)-5-amino-1-((bis(3-fluorophenyl)methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 62 | 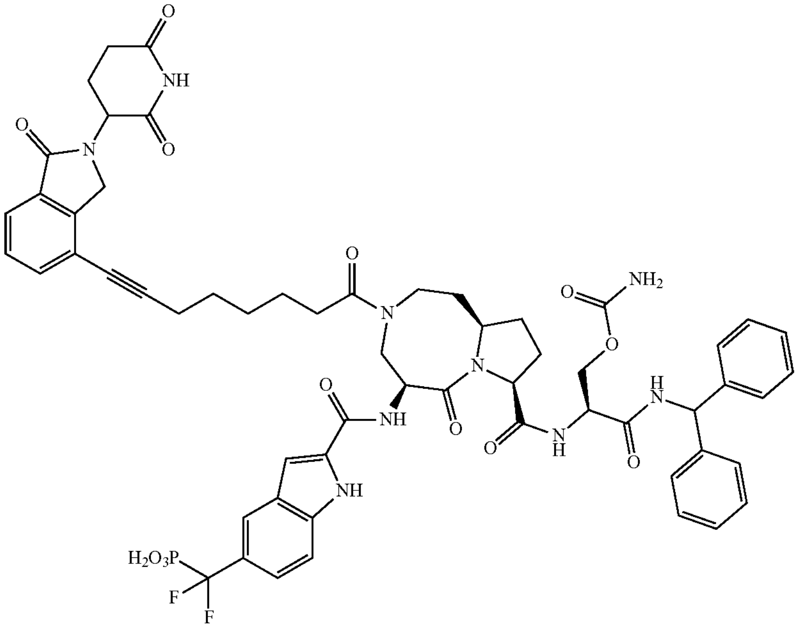 | ((2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 62E | 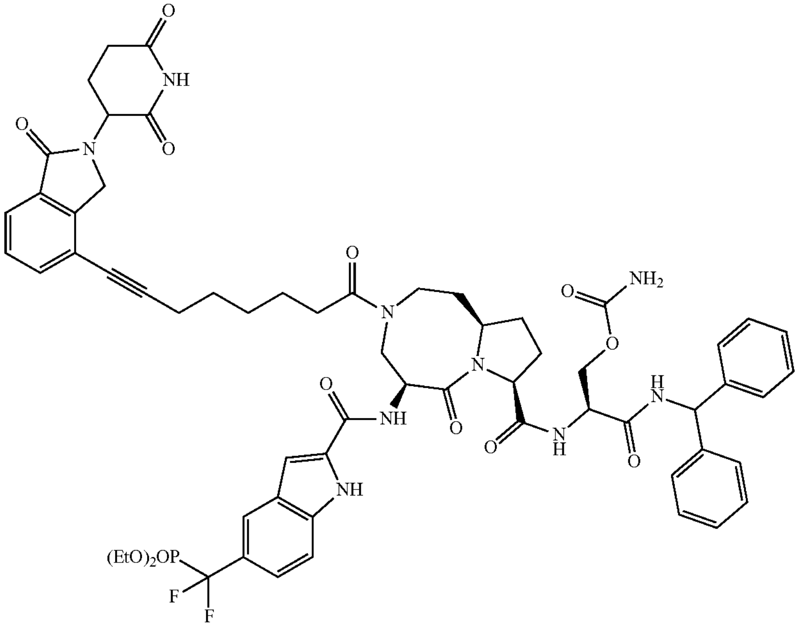 | (2S)-3-(benzhydrylamino)-2-((5S,8S,10aR)-5-(5-((diethoxyphosphoryl)difluoromethyl)-1H-indole-2-carboxamido)-3-(8-(2-(2,6-dioxopiperidin-3-yl)-1-oxoisoindolin-4-yl)oct-7-ynoyl)-6-oxodecahydropyrrolo[1,2-a][1,5]diazocine-8-carboxamido)-3-oxopropyl carbamate |

TABLE 1-continued
| Cpd. No. | Structure | Name |
|---|---|---|
| 63 | 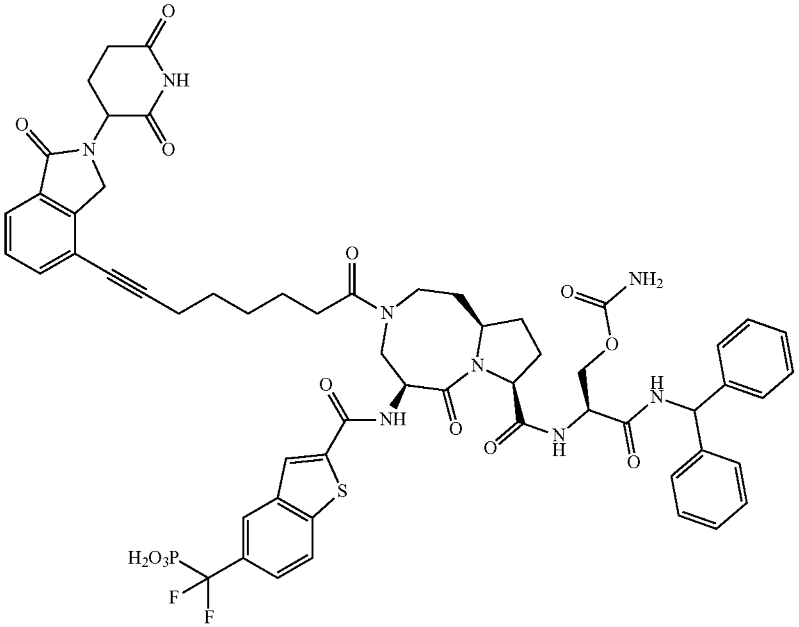 | ((2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 64 | 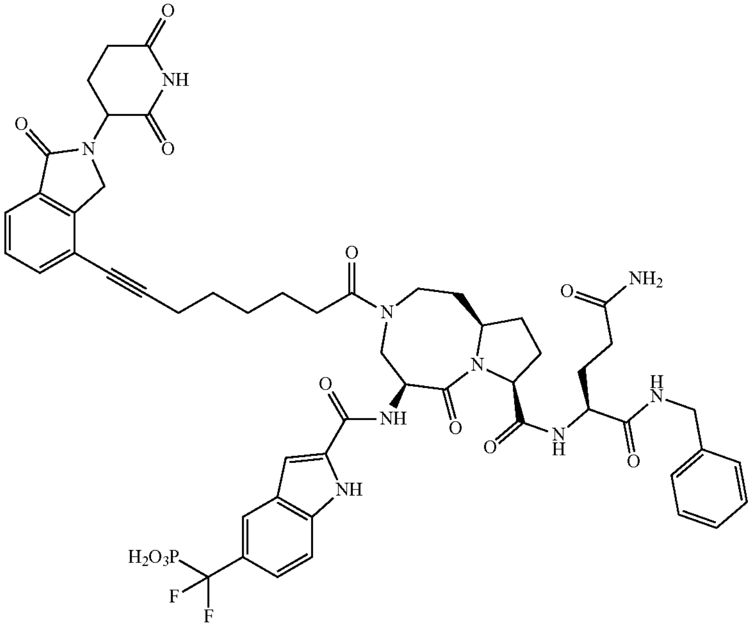 | ((2-(((5S,8S,10aR)-8-(((S)-5-amino-1-(benzylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 65 | 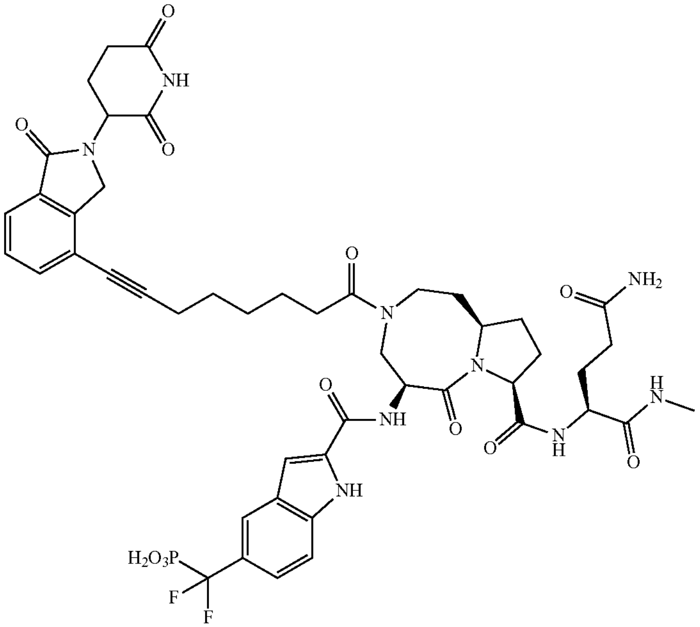 | ((2-(((5S,8S,10aR)-8-(((S)-5-amino-1-(methylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 66 | 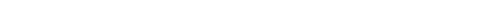 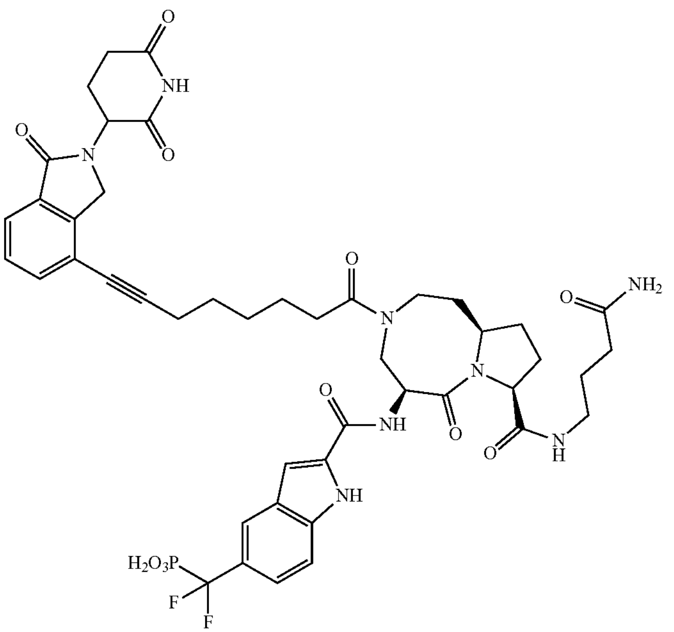 | ((2-(((5S,8S,10aR)-8-((4-amino-4-oxobutyl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 67 | 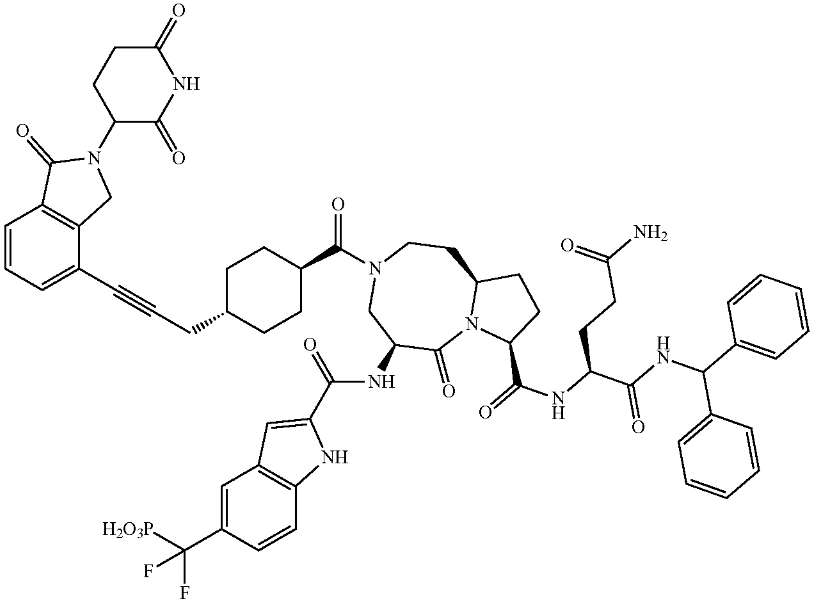 | ((2-(((5S,8S,10aR)-8-(((S)-5-amino-1-(benzhydrylamino)-1,5-dioxopentan-2-yl)carbamoyl)-3-((1r,4S)-4-(3-(2-(2,6-dioxopiperidin-3-yl)-1-oxoisoindolin-4-yl)prop-2-yn-1-yl)cyclohexane-1-carbonyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 68 | 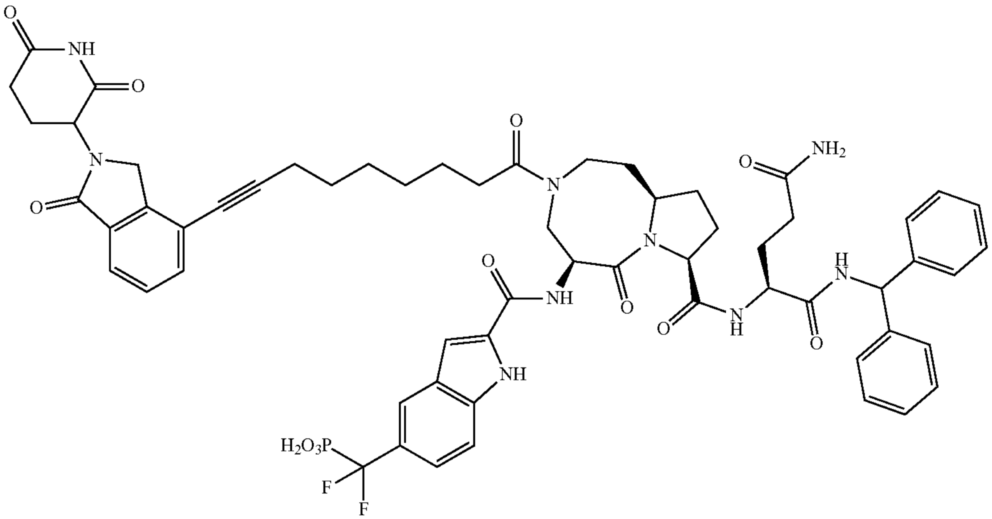 | ((2-(((5S,8S,10aR)-8-(((S)-5-amino-1-(benzhydrylamino)-1,5-dioxopentan-2-yl)carbamoyl)-3-(9-(2-(2,6-dioxopiperidin-3-yl)-1-oxoisoindolin-4-yl)non-8-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 69 | 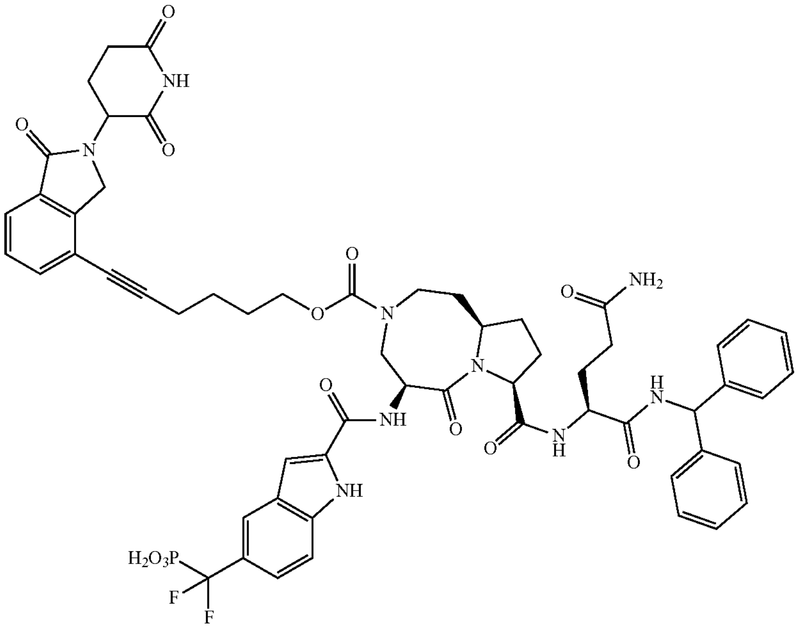 | ((2-(((5S,8S,10aR)-8-(((S)-5-amino-1-(benzhydrylamino)-1,5-dioxopentan-2-yl)carbamoyl)-3-(((6-(2-(2,6-dioxopiperidin-3-yl)-1-oxoisoindolin-4-yl)hex-5-yn-1-yl)oxy)carbonyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 69E | 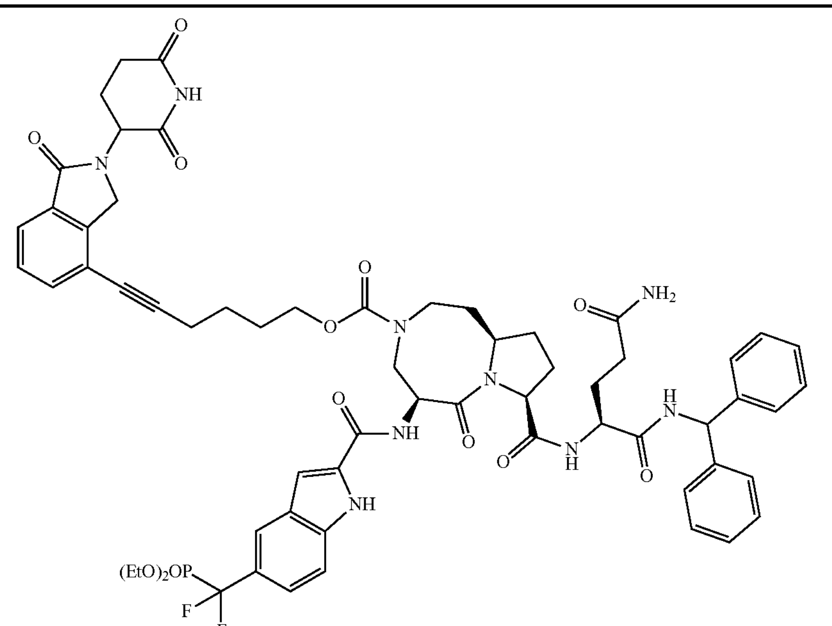 | 6-(2-(2,6-dioxopiperidin-3-yl)-1-oxoisoindolin-4-yl)hex-5-yn-1-yl (5S,8S,10aR)-8-(((S)-5-amino-1-(benzhydrylamino)-1,5-dioxopentan-2-yl)carbamoyl)-5-(5-((diethoxyphosphoryl)difluoromethyl)-1H-indole-2-carboxamido)-6-oxooctahydropyrrolo[1,2-a][1,5]diazocine-3(4H)-carboxylate |

TABLE 1-continued
| Cpd. No. | Structure | Name |
|---|---|---|
| 70 | 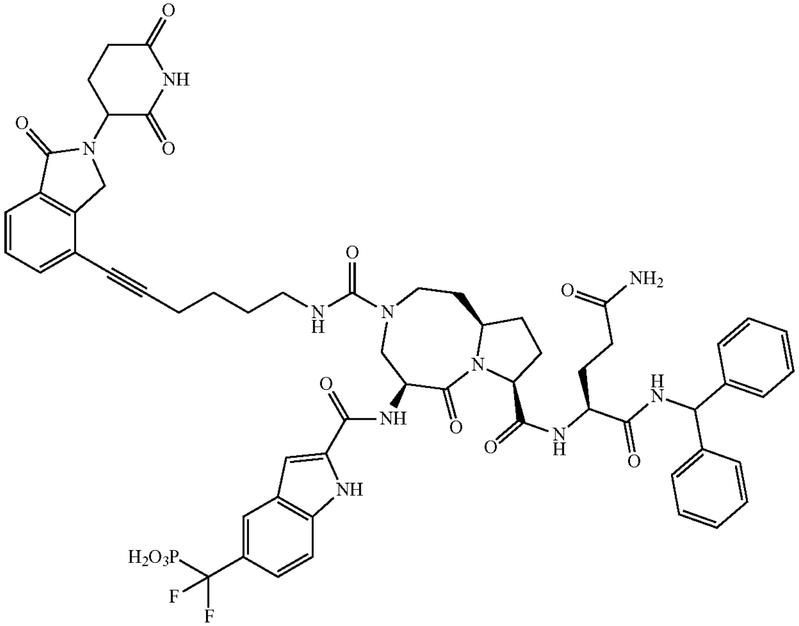 | ((2-(((5S,8S,10aR)-8-(((S)-5-amino-1-(benzhydrylamino)-1,5-dioxopentan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 70E | 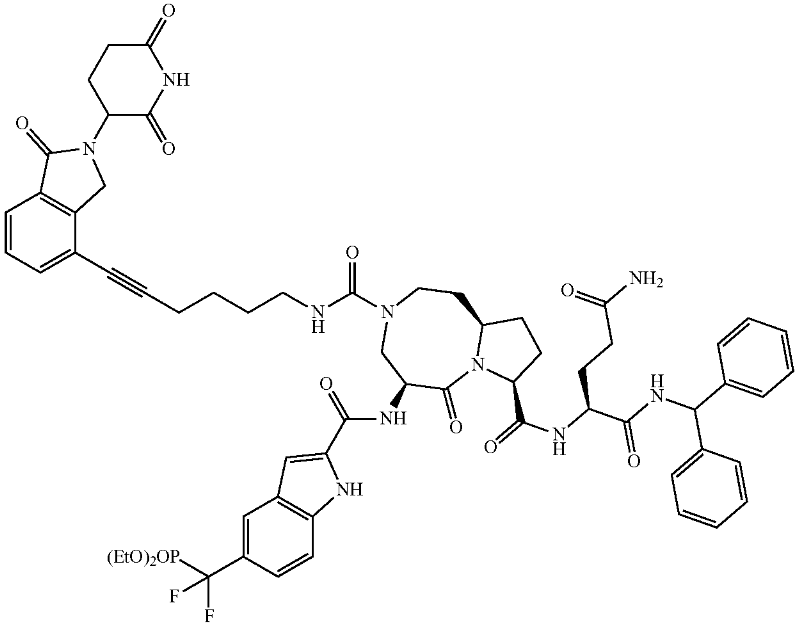 | diethyl ((2-(((5S,8S,10aR)-8-(((S)-5-amino-1-(benzhydrylamino)-1,5-dioxopentan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)-1H-indol-5-yl)difluoromethyl)phosphonate |

TABLE 1-continued
| Cpd. No. | Structure | Name |
|---|---|---|
| 71 | 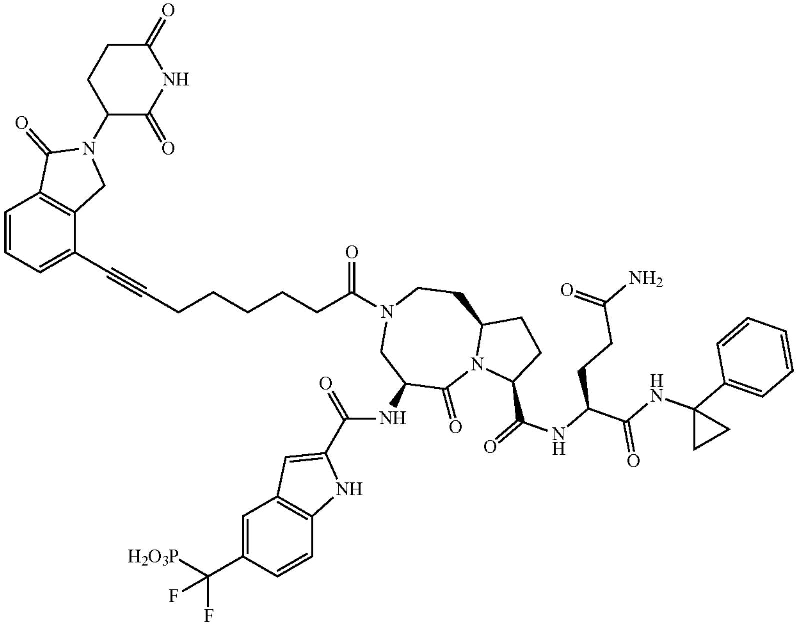 | ((2-(((5S,8S,10aR)-8-(((S)-5-amino-1,5-dioxo-1-((1-phenylcyclopropyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 72 | 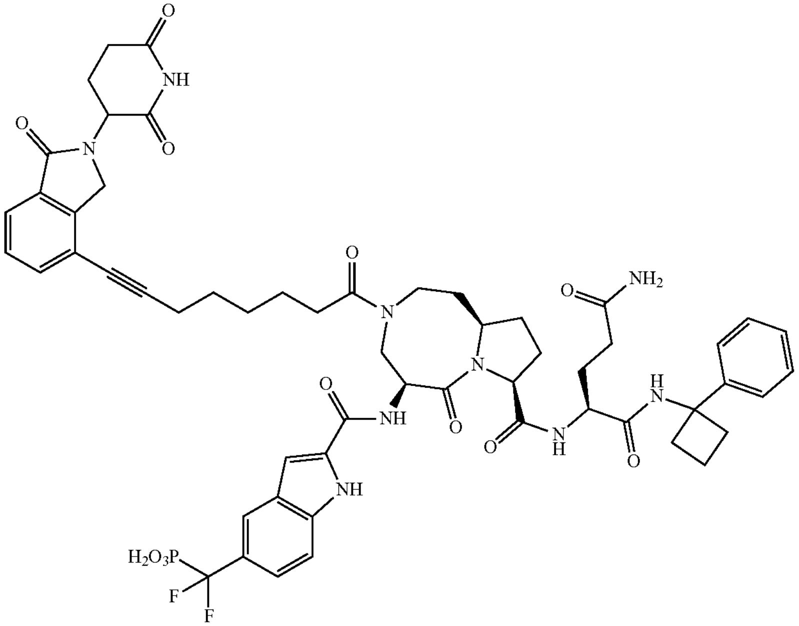 | ((2-(((5S,8S,10aR)-8-(((S)-5-amino-1,5-dioxo-1-((1-phenylcyclobutyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 73 | 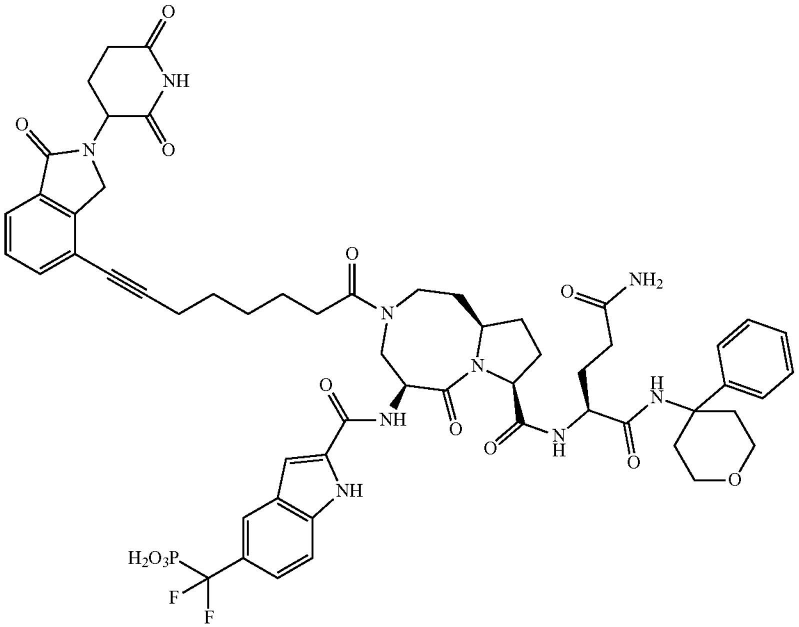 | ((2-(((5S,8S,10aR)-8-(((S)-5-amino-1,5-dioxo-1-((4-phenyltetrahydro-2H-pyran-4-yl)amino)pentan-2-yl)carbamoyl)-3-(8-(2-(2,6-dioxopiperidin-3-yl)-1-oxoisoindolin-4-yl)oct-7-ynoyl)-6-oxodecahydropyrro[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 74 | 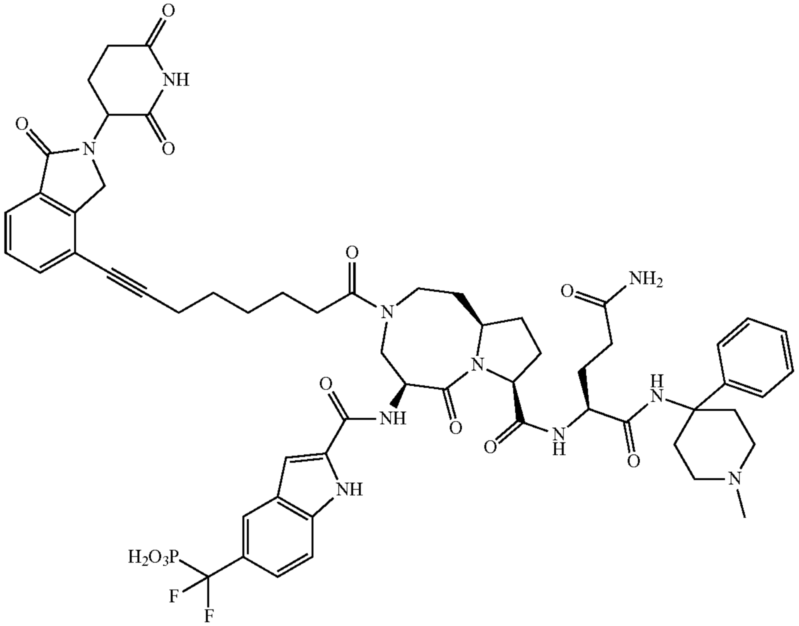 | ((2-(((5S,8S,10aR)-8-(((S)-5-amino-1-((1-methyl-4-phenylpiperidin-4-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 75 | 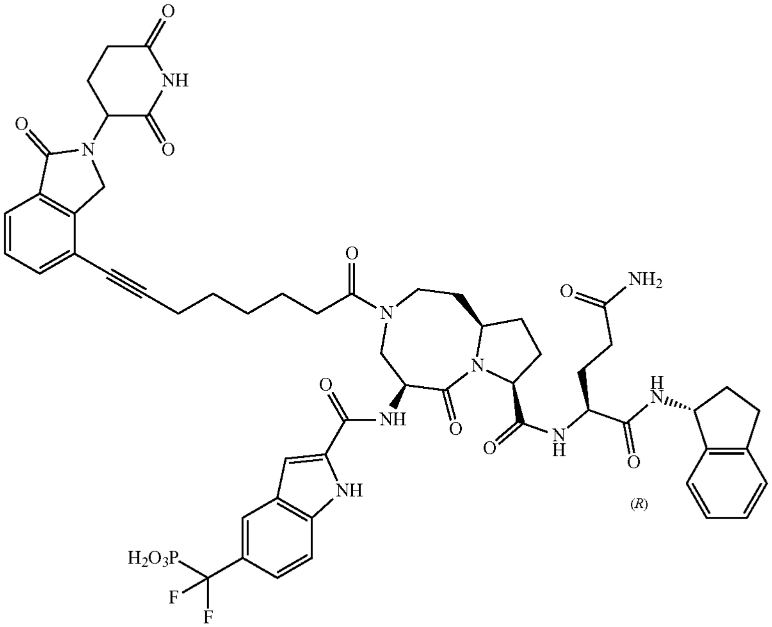 | ((2-(((5S,8S,10aR)-8-(((S)-5-amino-1-(((R)-2,3-dihydro-1H-inden-1-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 76 | 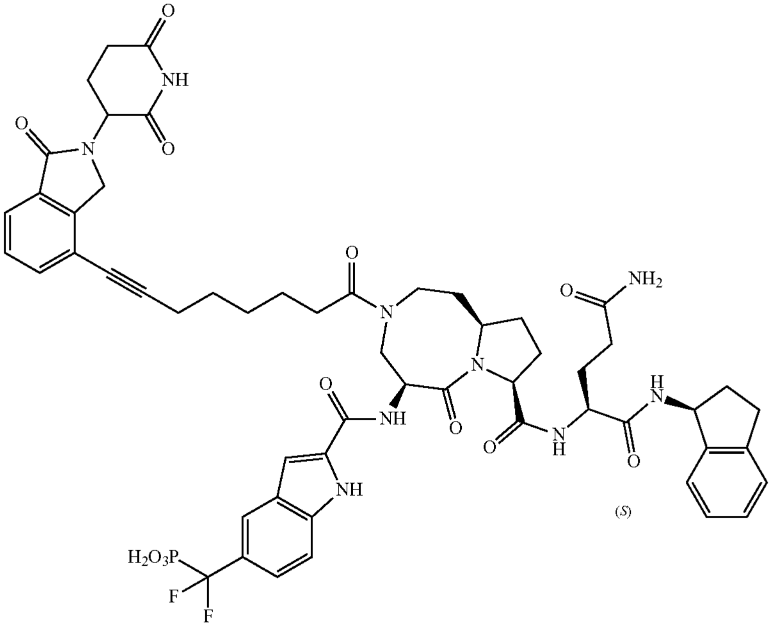 | ((2-(((5S,8S,10aR)-8-(((S)-5-amino-1-(((S)-2,3-dihydro-1H-inden-1-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 77 | 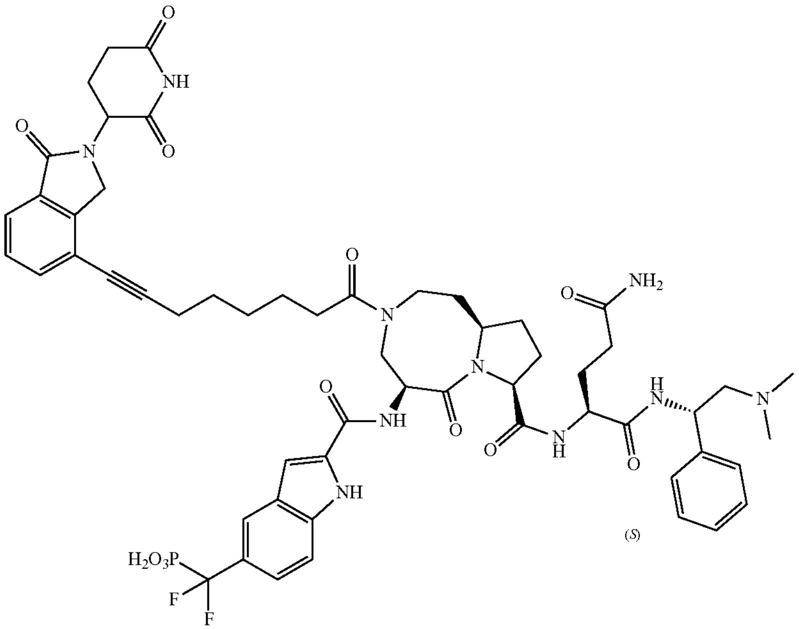 (S) | ((2-(((5S,8S,10aR)-8-(((S)-5-amino-1-(((S)-2-(dimethylamino)-1-phenylethyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 78 | 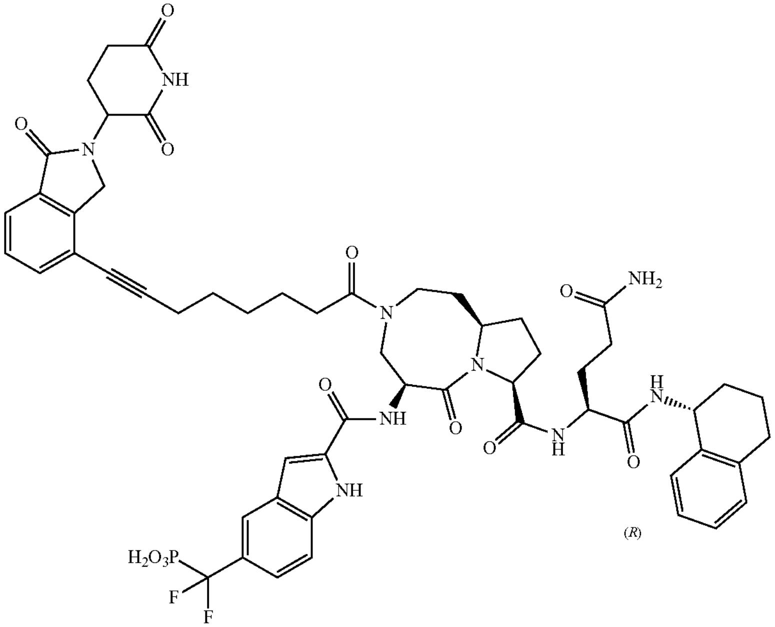 | ((2-(((5S,8S,10aR)-8-(((S)-5-amino-1,5-dioxo-1-(((R)-1,2,3,4-tetrahydronaphthalen-1-yl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 79 | 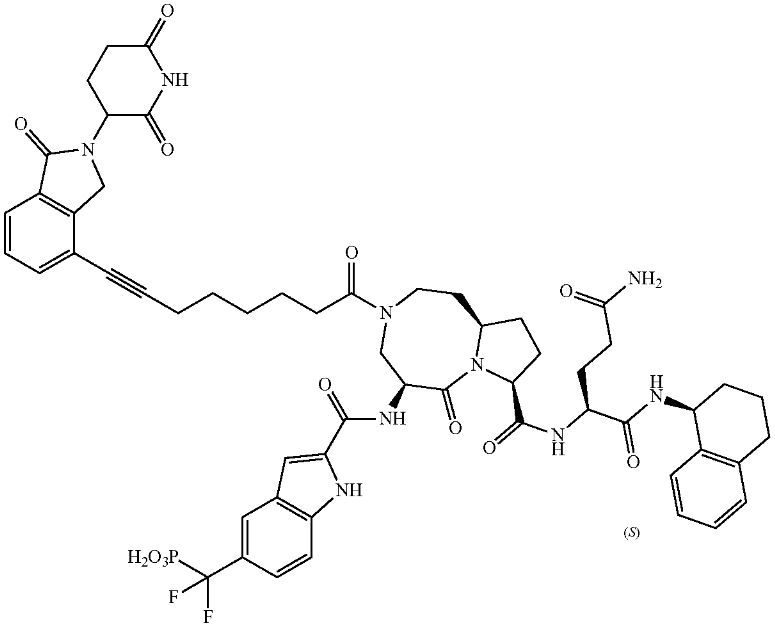 | ((2-(((5S,8S,10aR)-8-(((S)-5-amino-1,5-dioxo-1-(((S)-1,2,3,4-tetrahydronaphthalen-1-yl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 80 | 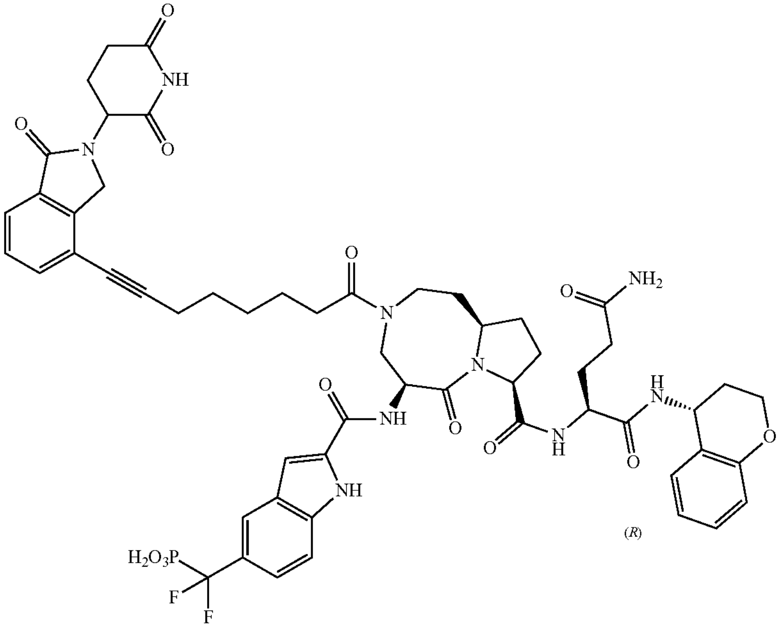 | ((2-(((5S,8S,10aR)-8-(((S)-5-amino-1-(((R)-chroman-4-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 81 | 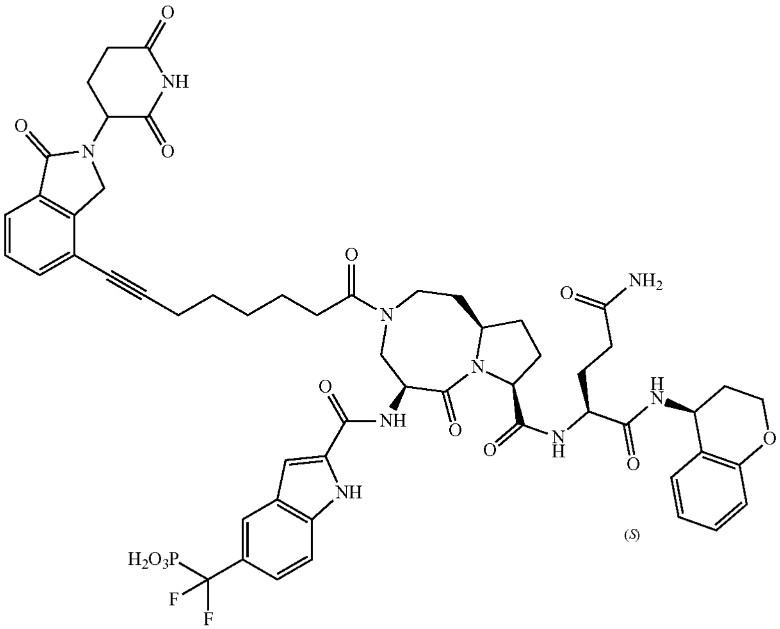 | ((2-(((5S,8S,10aR)-8-(((S)-5-amino-1-(((S)-chroman-4-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 82 | 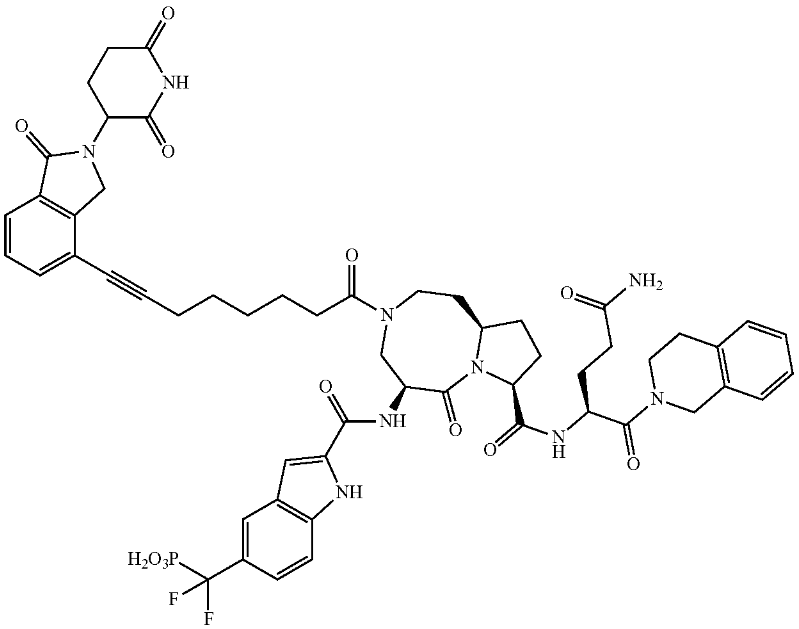 | ((2-(((5S,8S,10aR)-8-(((S)-5-amino-1-(3,4-dihydroisoquinolin-2(1H)-yl)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 83 | 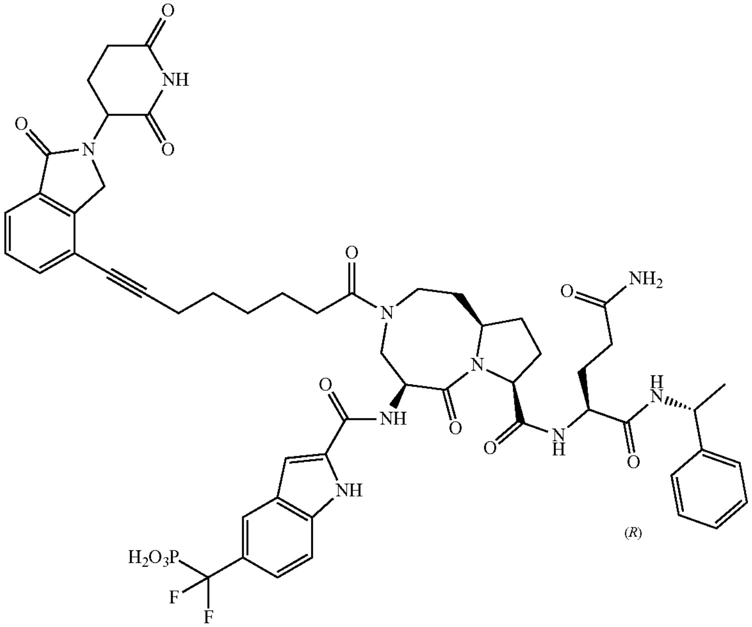 | ((2-(((5S,8S,10aR)-8-(((S)-5-amino-1,5-dioxo-1-(((R)-1-phenylethyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 84 | 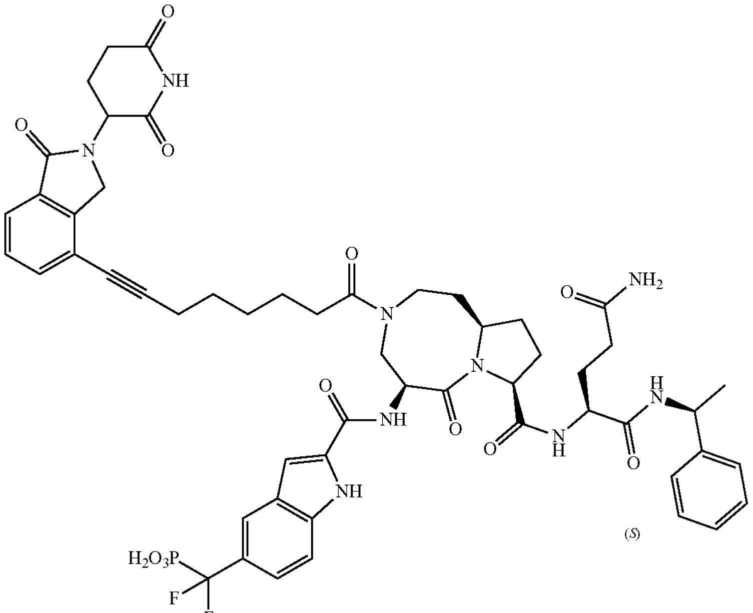 | ((2-(((5S,8S,10aR)-8-(((S)-5-amino-1,5-dioxo-1-(((S)-1-phenylethyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 85 | 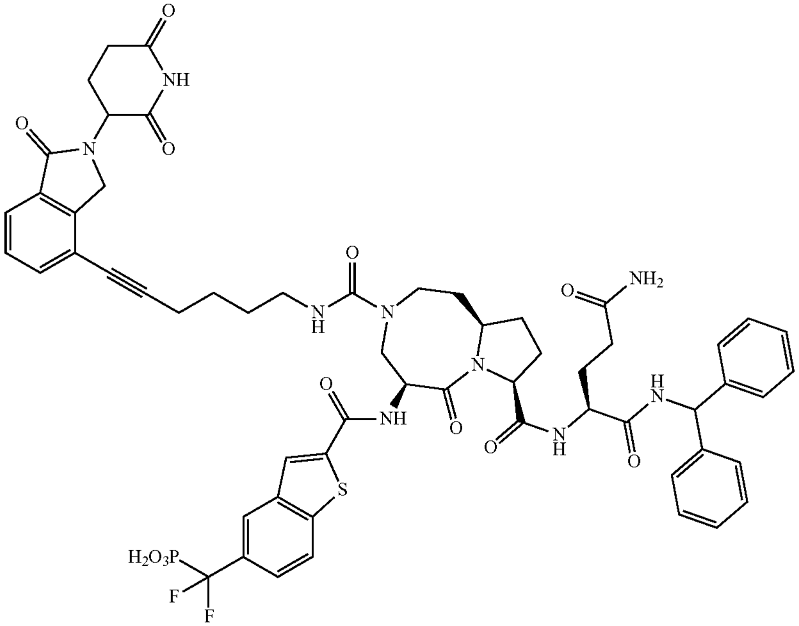 | ((2-(((5S,8S,10aR)-8-(((S)-5-amino-1-(benzhydrylamino)-1,5-dioxopentan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 86 | 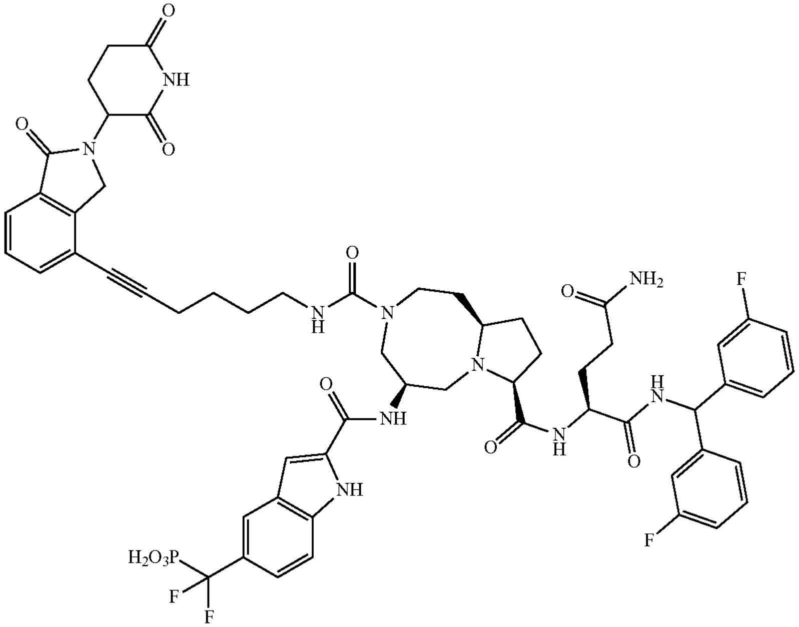 | ((2-(((5S,8S,10aR)-8-(((S)-5-amino-1-((bis(3-fluorophenyl)methyl)amino)-1,5-dioxopentan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 87 | 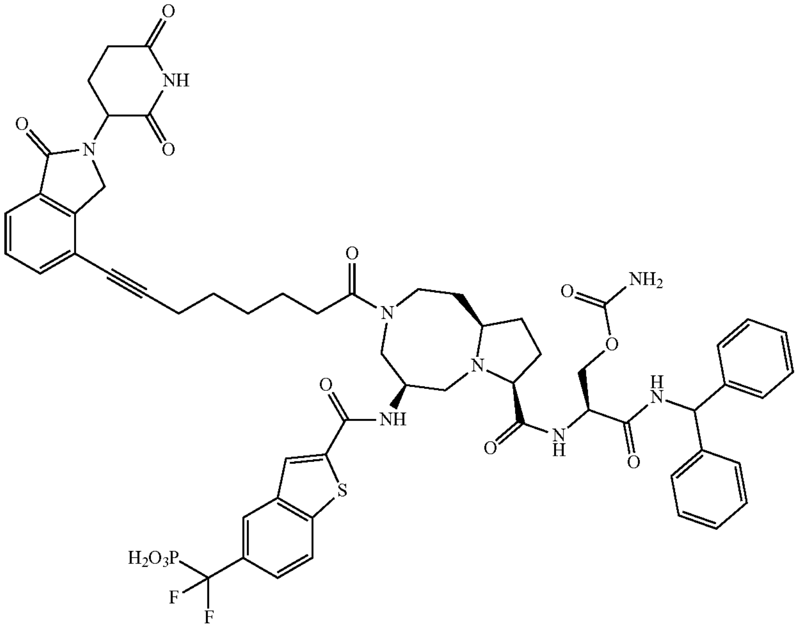 | ((2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 88 | 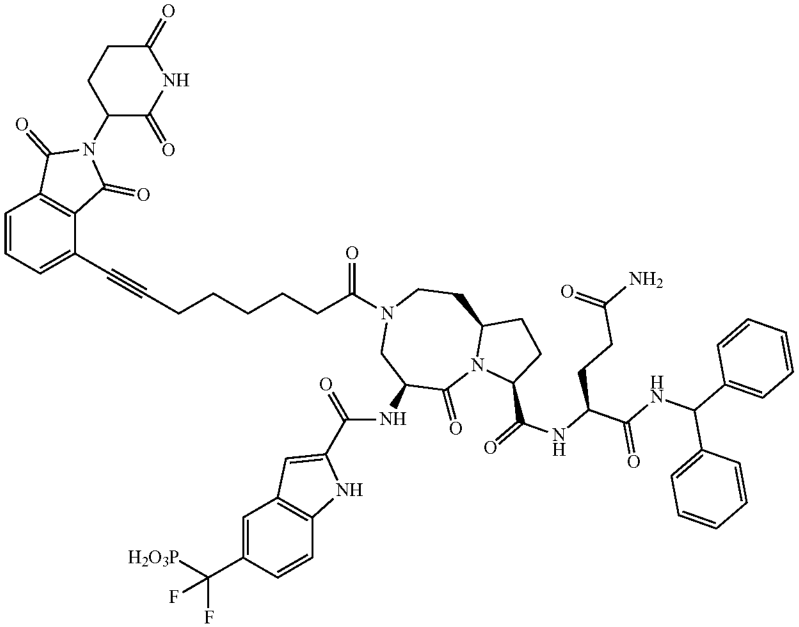 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1,3-dioxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 88E | 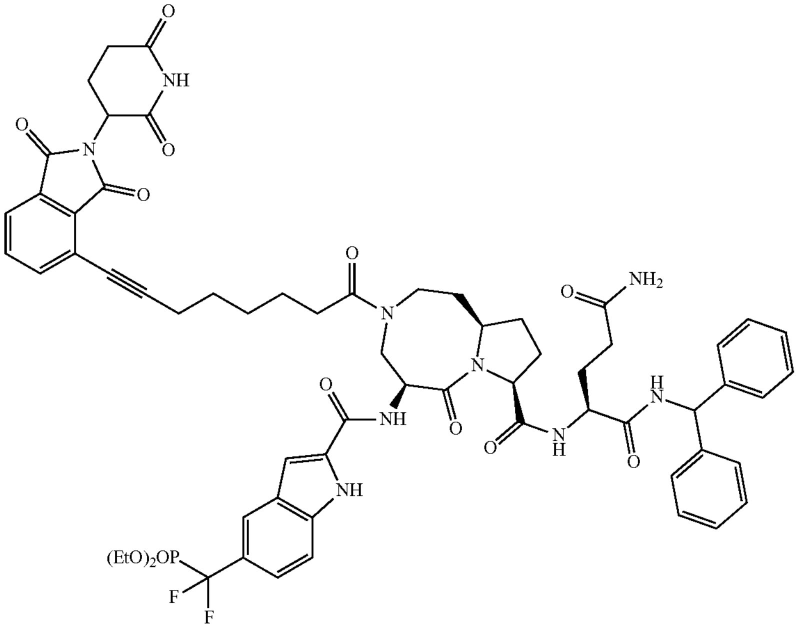 | diethyl ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1,3-dioxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonate |

TABLE 1-continued
| Cpd. No. | Structure | Name |
| --- | --- | --- |
| 89 | 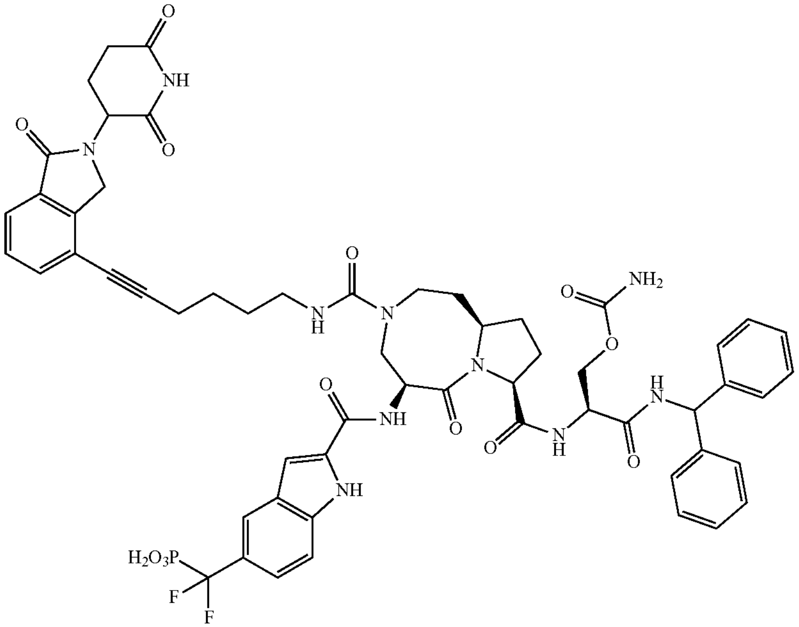 | ((2-(((5S,8S,10aR)-8-(((S)-1-(benzhydrylamino)-3-(carbamoyloxy)-1-oxopropan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 91 | 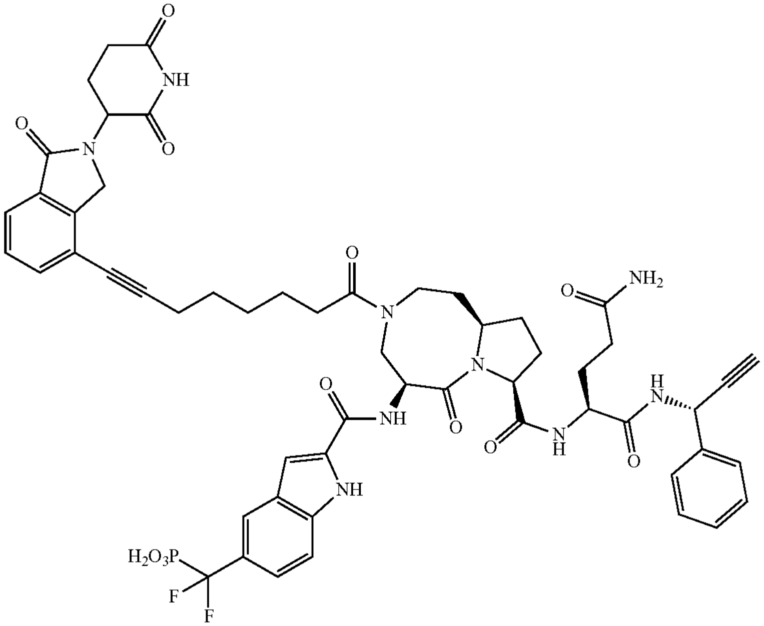 | ((2-(((5S,8S,10aR)-8-(((S)-5-amino-1,5-dioxo-1-(((R)-1-phenylprop-2-yn-1-yl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 92 | 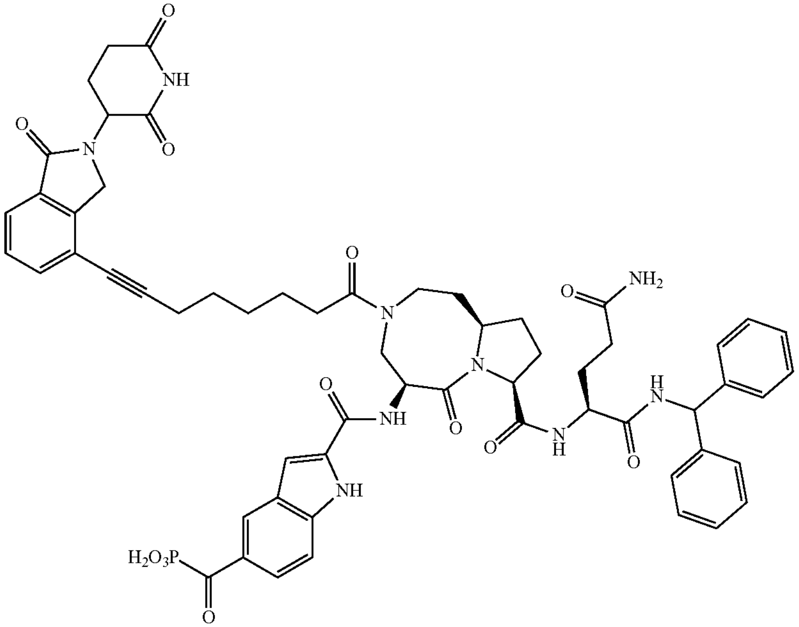 | (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indole-5-carbonyl)phosphonic acid |

TABLE 1-continued
| Cpd. No. | Structure | Name |
| --- | --- | --- |
| 93 | 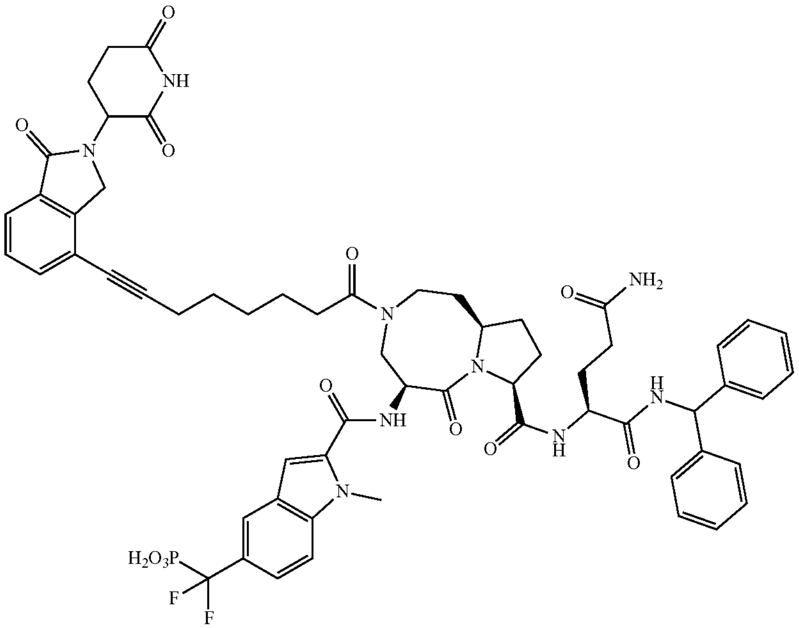 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1-methyl-1H-indol-5-yl)difluoromethyl)phosphonic acid |

TABLE 1-continued
| Cpd. No. | Structure | Name |
| --- | --- | --- |
| 94 | 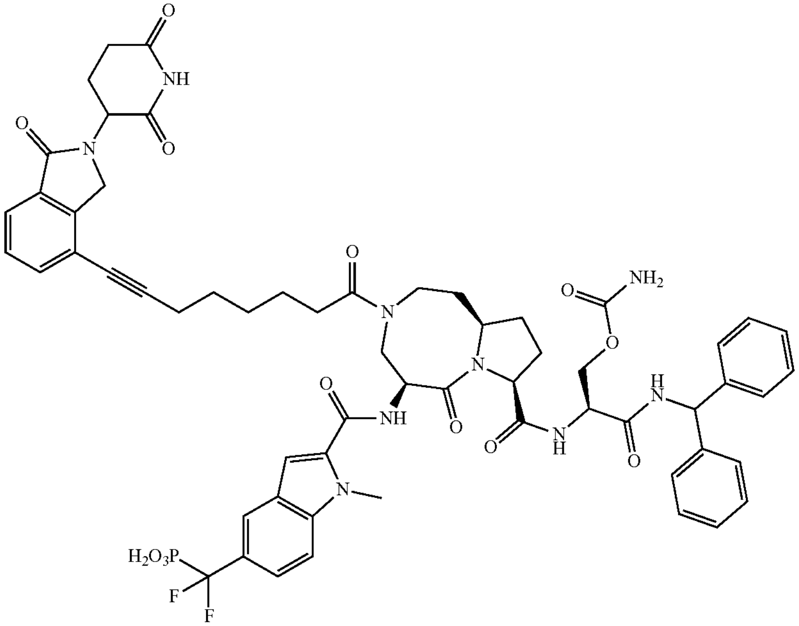 | ((2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1-methyl-1H-indol-5-yl)difluoromethyl)phosphonic acid |

TABLE 1-continued
| Cpd. No. | Structure | Name |
| --- | --- | --- |
| 95 | 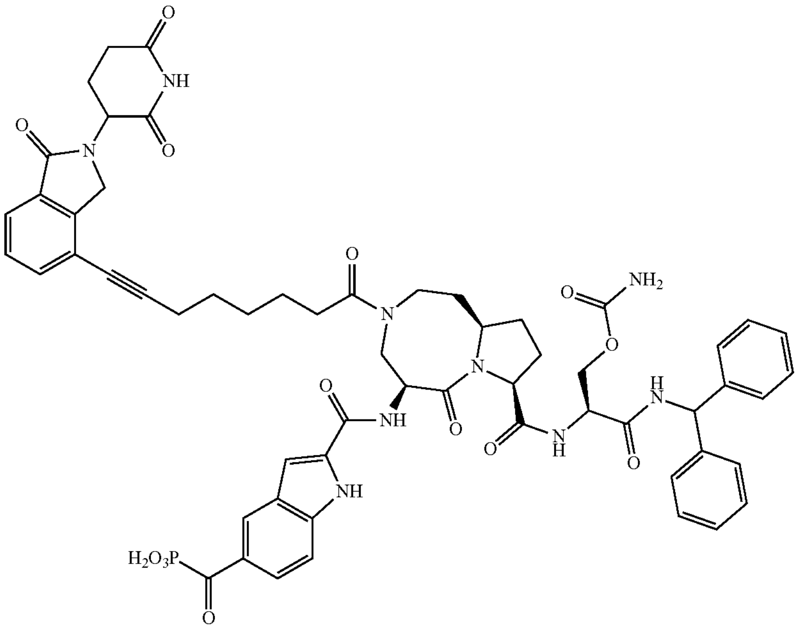 | (2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indole-5-carbonyl)phosphonic acid |

TABLE 1-continued
| Cpd. No. | Structure | Name |
|---|---|---|
| 96 | 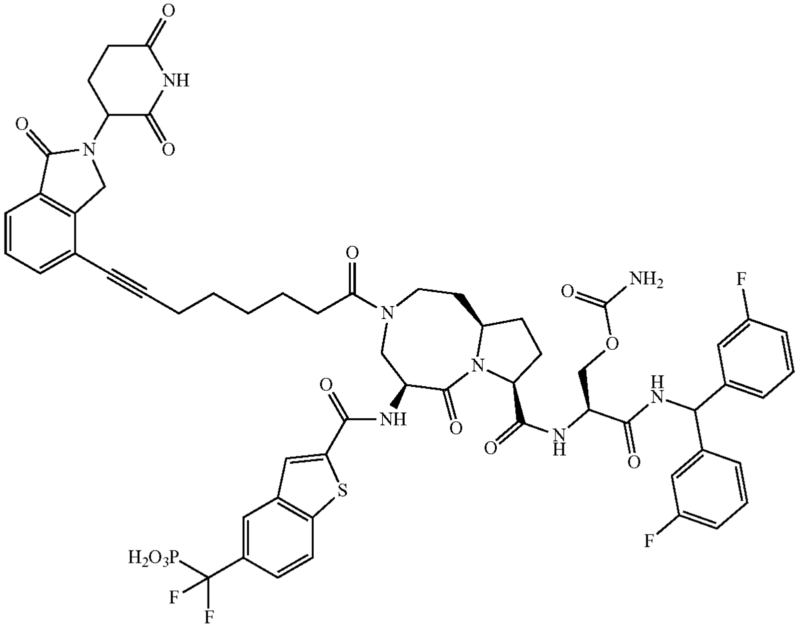 | ((2-(((5S,8S,10aR)-8-(((S)-1-((bis(3-fluorophenyl)methyl)amino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 97 | 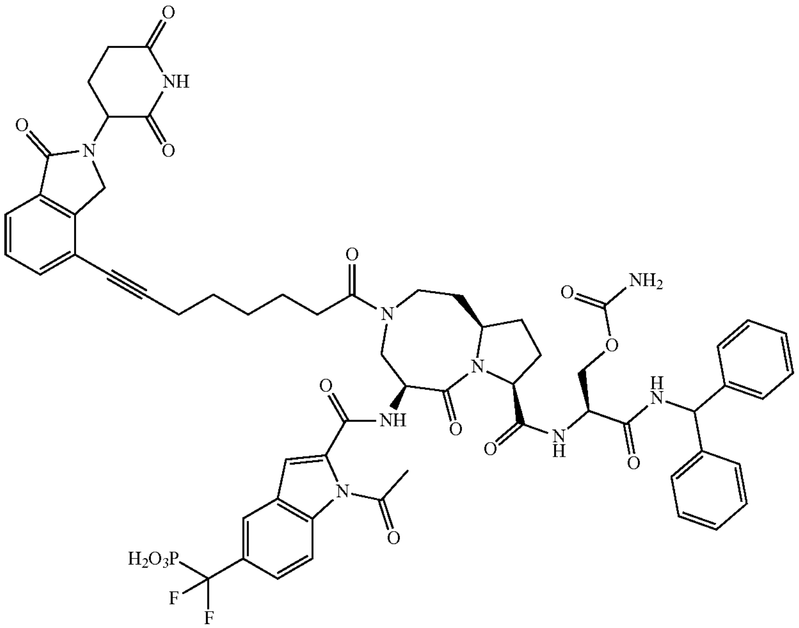 | ((1-acetyl-2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 98 | 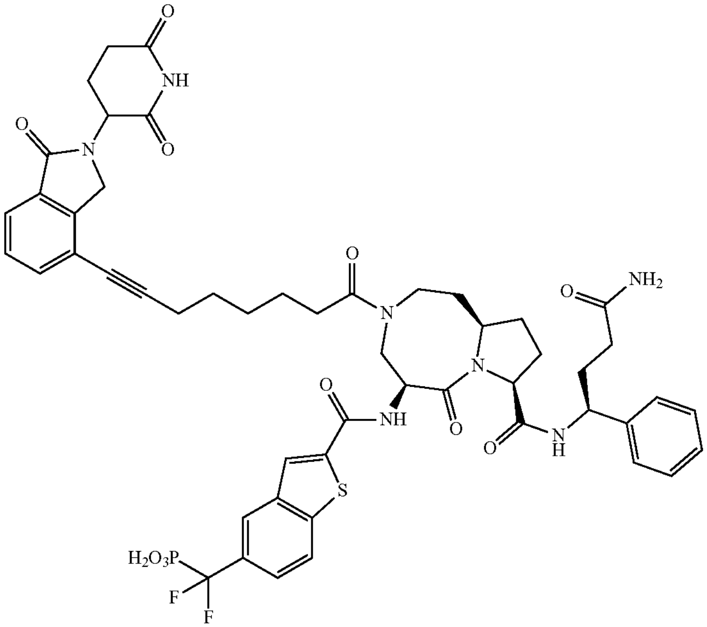 | ((2-(((5S,8S,10aR)-8-(((S)-4-amino-4-oxo-1-phenylbutyl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 99 | 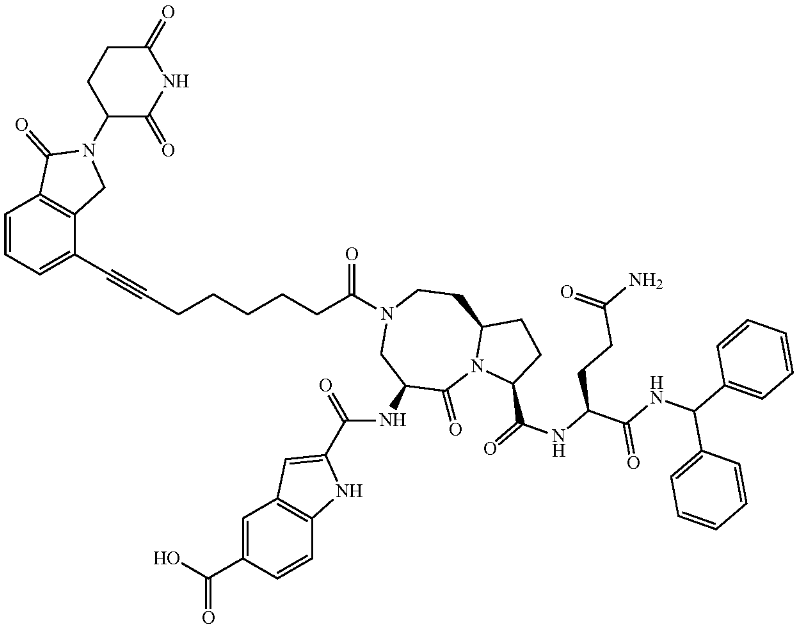 [SMILES: NC(=O)CC[C@H](NC(=O)[C@@H]1CC[C@@H]2CCN(C(=O)CCCCCC#Cc3cccc4c3CN(C3CCC(=O)NC3=O)C4=O)C[C@H](NC(=O)c3cc4cc(C(=O)O)ccc4[nH]3)C(=O)N21)C(=O)NC(c1ccccc1)c1ccccc1] | 2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indole-5-carboxylic acid |

TABLE 1-continued

| Cpd. No. | Structure | Name |
|---|---|---|
| 100 | 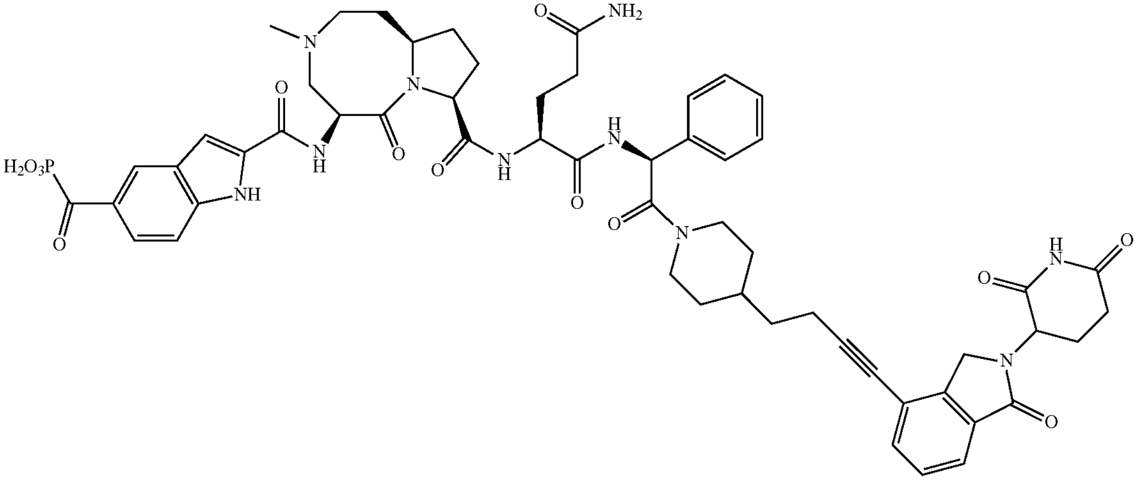 | (2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid |
| 101 | 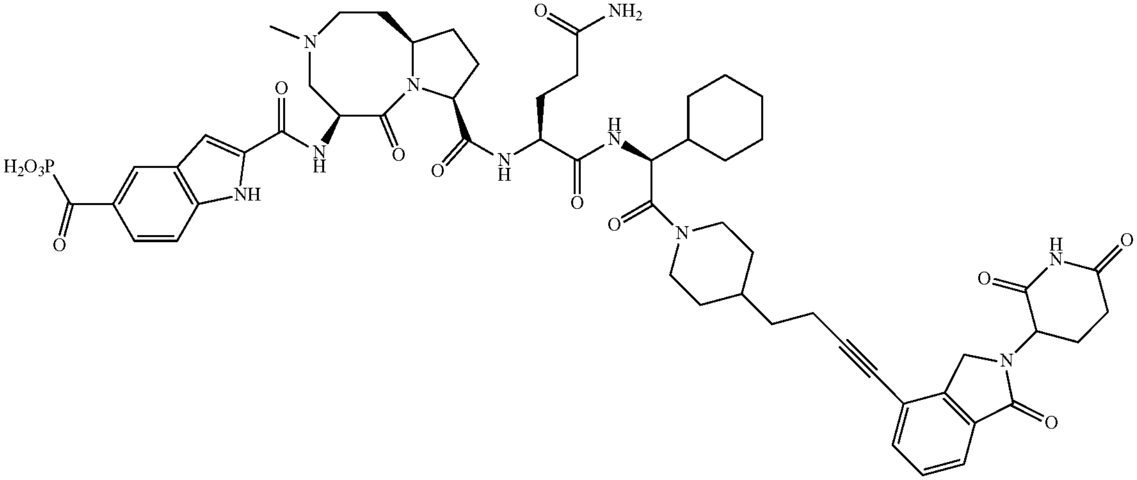 | (2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid |

TABLE 1-continued
| Cpd. No. | Structure | Name |
|---|---|---|
| 102 | 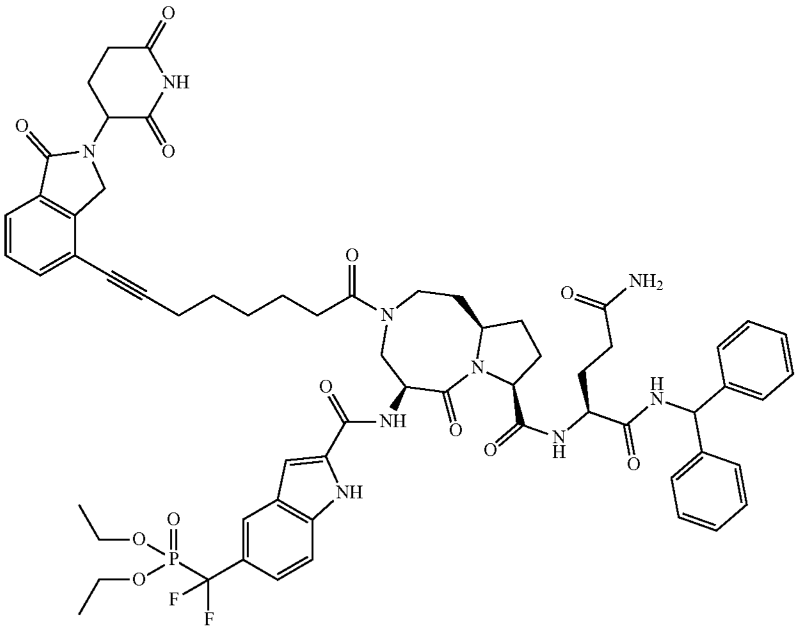 [SMILES: CCOP(=O)(OCC)C(F)(F)c1ccc2[nH]c(C(=O)N[C@H]3CN(C(=O)CCCCCC#Cc4cccc5c4CN(C4CCC(=O)NC4=O)C5=O)CC[C@H]4CC[C@@H](C(=O)N[C@@H](CCC(N)=O)C(=O)NC(c5ccccc5)c5ccccc5)N4C3=O)cc2c1] | diethyl ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonate |

TABLE 1-continued
| Cpd. No. | Structure | Name |
|---|---|---|
| 103 | 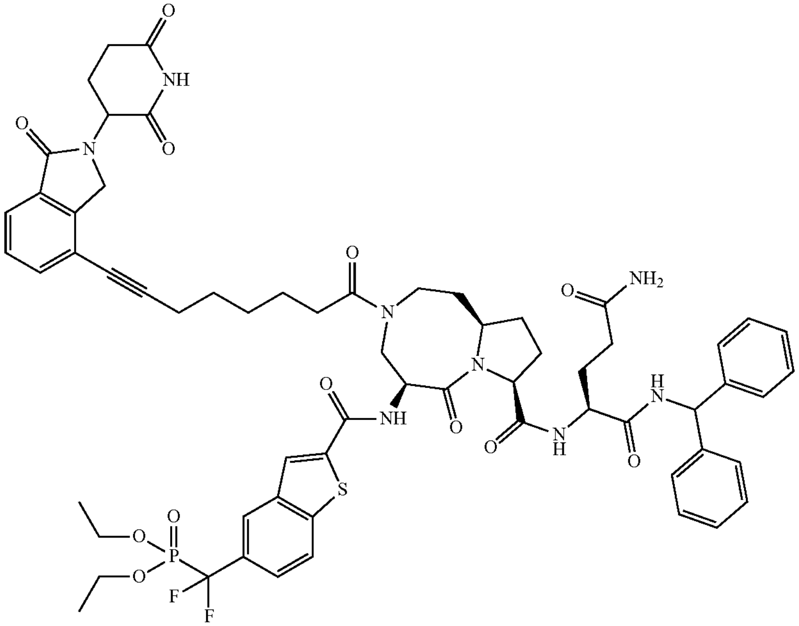 [SMILES: CCOP(=O)(OCC)C(F)(F)c1ccc2sc(C(=O)N[C@H]3CN(C(=O)CCCCCC#Cc4cccc5c4CN(C4CCC(=O)NC4=O)C5=O)CC[C@H]4CC[C@@H](C(=O)N[C@@H](CCC(N)=O)C(=O)NC(c5ccccc5)c5ccccc5)N4C3=O)cc2c1] | diethyl ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonate |

TABLE 1-continued
| Cpd. No. | Structure | Name |
| --- | --- | --- |
| 104 | 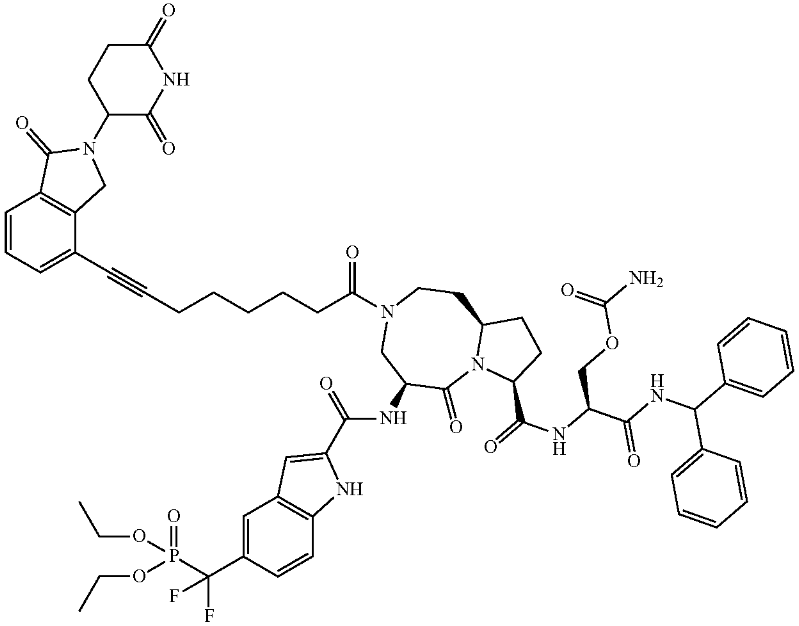 [SMILES: CCOP(=O)(OCC)C(F)(F)c1ccc2[nH]c(C(=O)N[C@H]3CN(C(=O)CCCCCC#Cc4cccc5c4CN(C4CCC(=O)NC4=O)C5=O)CC[C@H]4CC[C@@H](C(=O)N[C@@H](COC(N)=O)C(=O)NC(c5ccccc5)c5ccccc5)N4C3=O)cc2c1] | (2S)-3-(benzhydrylamino)-2-((5S,8S,10aR)-5-(5-((diethoxyphosphoryl)difluoromethyl)-1H-indole-2-carboxamido)-3-(8-(2-(2,6-dioxopiperidin-3-yl)-1-oxoisoindolin-4-yl)oct-7-ynoyl)-6-oxodecahydropyrrolo[1,2-a][1,5]diazocine-8-carboxamido)-3-oxopropyl carbamate |

TABLE 1-continued
| Cpd. No. | Structure | Name |
|---|---|---|
| 105 | 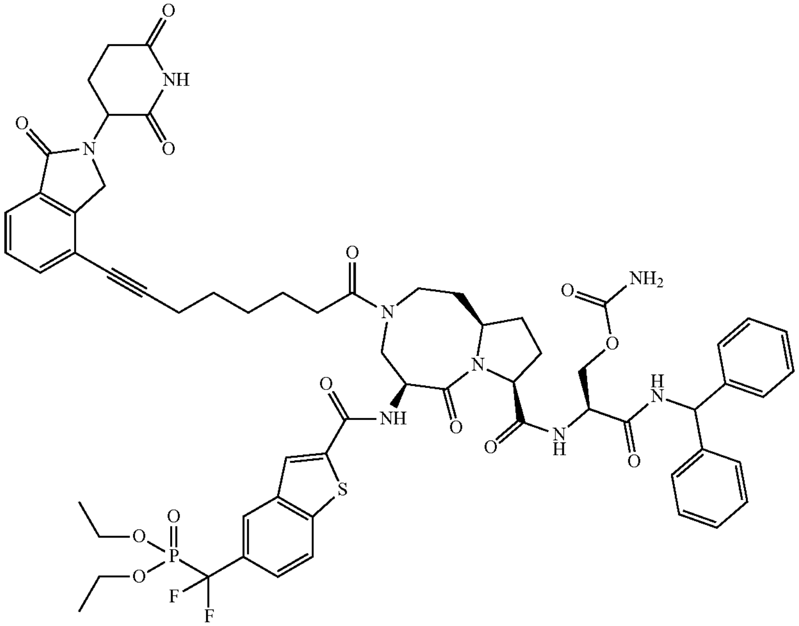 [SMILES: CCOP(=O)(OCC)C(F)(F)c1ccc2sc(C(=O)N[C@H]3CN(C(=O)CCCCCC#Cc4cccc5c4CN(C4CCC(=O)NC4=O)C5=O)CC[C@H]4CC[C@@H](C(=O)N[C@@H](COC(N)=O)C(=O)NC(c5ccccc5)c5ccccc5)N4C3=O)cc2c1] | (2S)-3-(benzhydrylamino)-2-((5S,8S,10aR)-5-(5-((diethoxyphosphoryl)difluoromethyl)benzo[b]thiophene-2-carboxamido)-3-(8-(2-(2,6-dioxopiperidin-3-yl)-1-oxoisoindolin-4-yl)oct-7-ynoyl)-6-oxodecahydropyrrolo[1,2-a][1,5]diazocine-8-carboxamido)-3-oxopropyl carbamate |

TABLE 1-continued
| Cpd. No. | Structure | Name |
| --- | --- | --- |
| 106 | 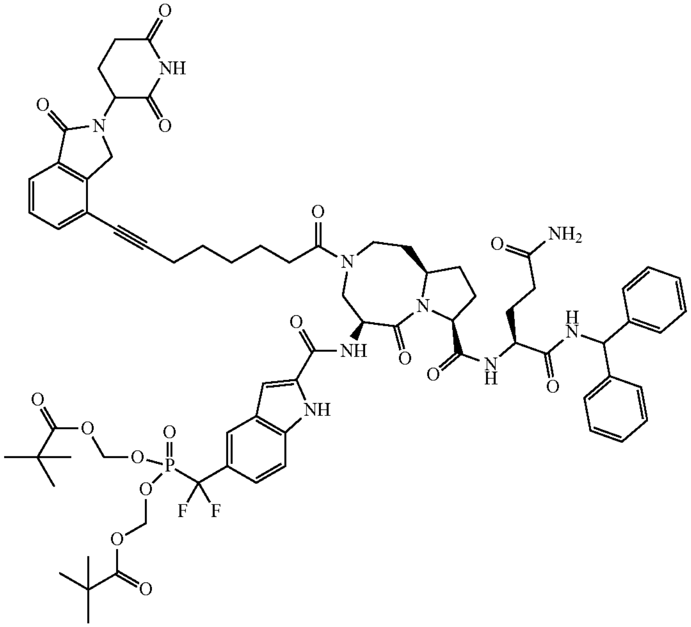 [SMILES: CC(C)(C)C(=O)OCOP(=O)(OCOC(=O)C(C)(C)C)C(F)(F)c1ccc2[nH]c(C(=O)N[C@H]3CN(C(=O)CCCCCC#Cc4cccc5c4CN(C4CCC(=O)NC4=O)C5=O)CC[C@H]4CC[C@@H](C(=O)N[C@@H](CCC(N)=O)C(=O)NC(c5ccccc5)c5ccccc5)N4C3=O)cc2c1] | ((((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphoryl)bis(oxy))bis(methylene) bis(2,2-dimethylpropanoate) |

TABLE 1-continued
| Cpd. No. | Structure | Name |
| --- | --- | --- |
| 107 | 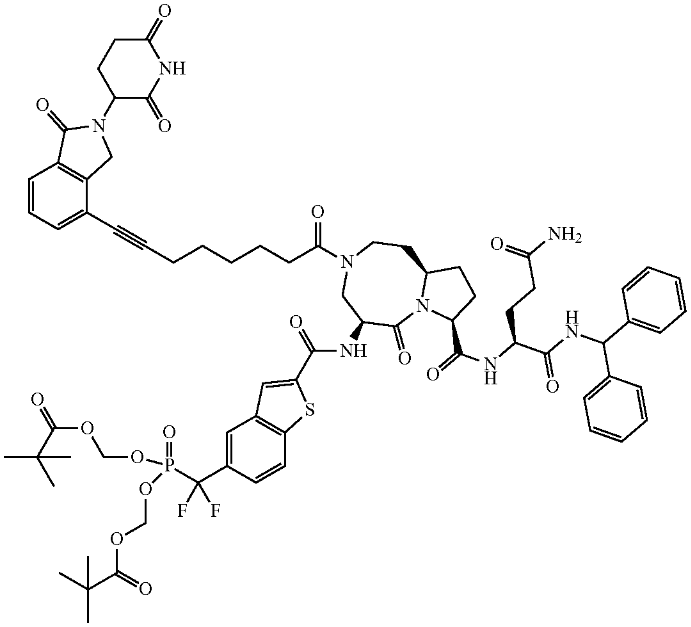 [SMILES: CC(C)(C)C(=O)OCOP(=O)(OCOC(=O)C(C)(C)C)C(F)(F)c1ccc2sc(C(=O)N[C@H]3CN(C(=O)CCCCCC#Cc4cccc5c4CN(C4CCC(=O)NC4=O)C5=O)CC[C@H]4CC[C@@H](C(=O)N[C@@H](CCC(N)=O)C(=O)NC(c5ccccc5)c5ccccc5)N4C3=O)cc2c1] | ((((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphoryl)bis(oxy))bis(methylene) bis(2,2-dimethylpropanoate) |

TABLE 1-continued

| Cpd. No. | Structure | Name |
|---|---|---|
| 108 | 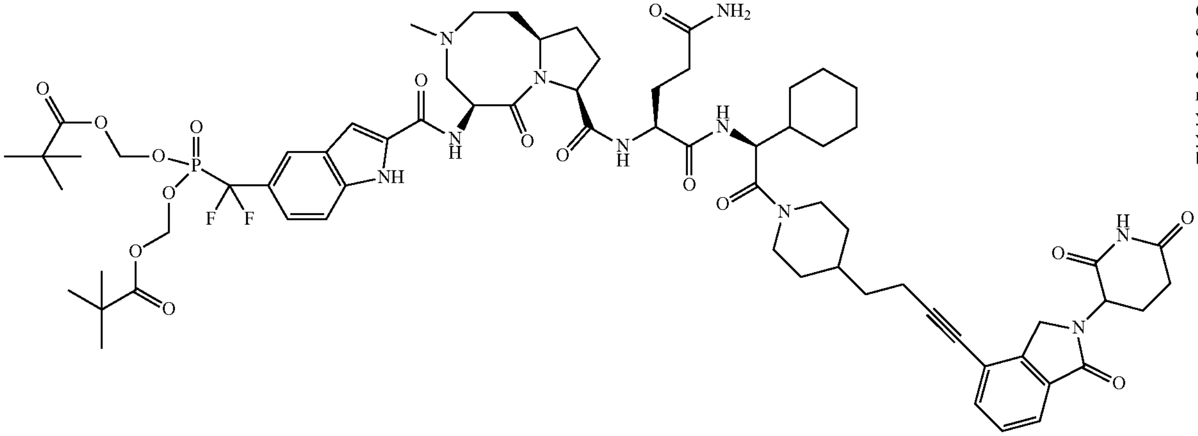 [SMILES: CN1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(OCOC(=O)C(C)(C)C)OCOC(=O)C(C)(C)C)ccc3[nH]2)C1] | ((((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphoryl)bis(oxy))bis(methylene) bis(2,2-dimethylpropanoate) |
| 109 | 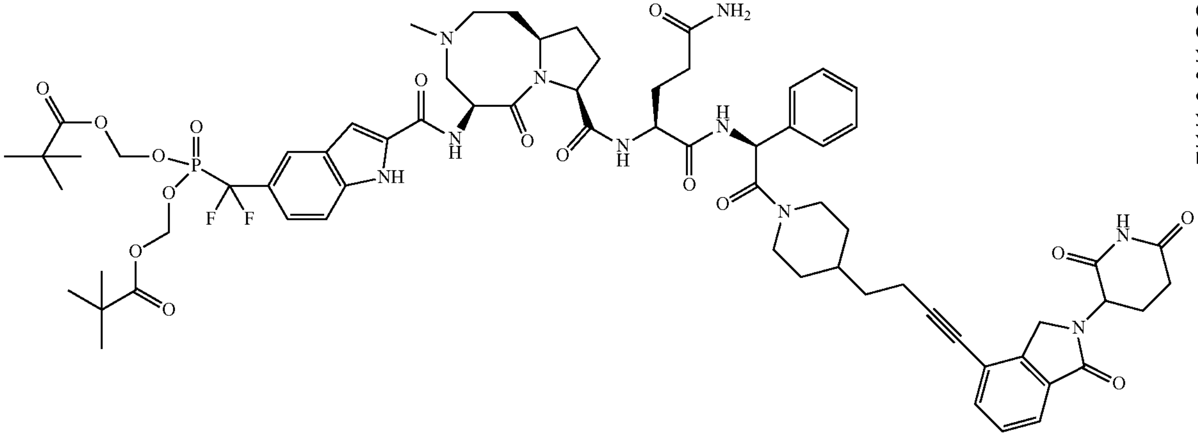 [SMILES: CN1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)c3ccccc3)N2C(=O)[C@@H](NC(=O)c2cc3cc(C(F)(F)P(=O)(OCOC(=O)C(C)(C)C)OCOC(=O)C(C)(C)C)ccc3[nH]2)C1] | ((((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphoryl)bis(oxy))bis(methylene) bis(2,2-dimethylpropanoate) |

TABLE 1-continued

| Cpd. No. | Structure | Name |
|---|---|---|
| 110 | 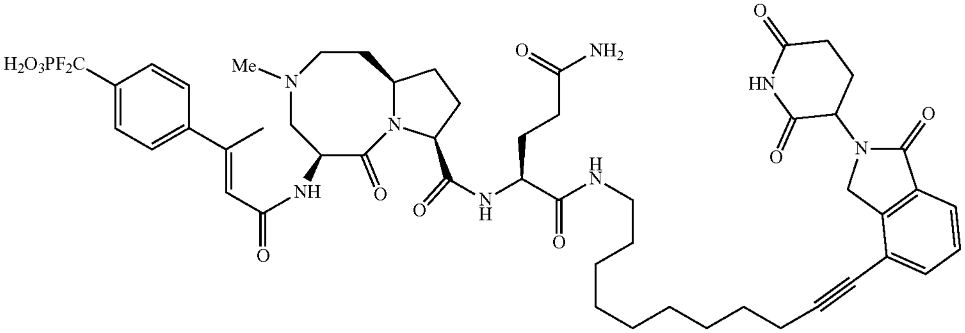 | ((4-((E)-4-(((5S,8S,10aR)-8-(((2S)-5-amino-1-((11-(2-(2,6-dioxopiperidin-3-yl)-1-oxoisoindolin-4-yl)undec-10-yn-1-yl)amino)-1,5-dioxopentan-2-yl)carbamoyl)-3-methyl-6-oxodecahydropyrrolo[1,2-a][1,5]diazocin-5-yl)amino)-4-oxobut-2-en-2-yl)phenyl)difluoromethyl)phosphonic acid |
| 111 | 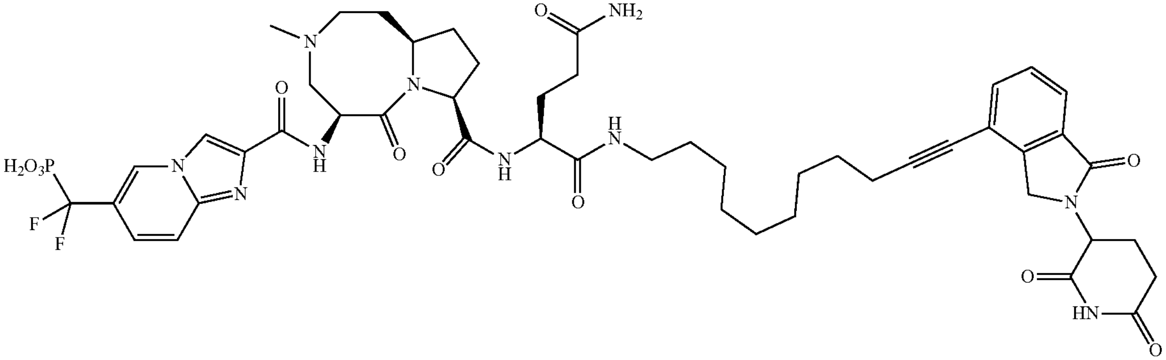 | ((2-(((5S,8S,10aR)-8-(((2S)-5-amino-1-((11-(2-(2,6-dioxopiperidin-3-yl)-1-oxoisoindolin-4-yl)undec-10-yn-1-yl)amino)-1,5-dioxopentan-2-yl)carbamoyl)-3-methyl-6-oxodecahydropyrrolo[1,2-a][1,5]diazocin-5-yl)carbamoyl)imidazo[1,2-a]pyridin-6-yl)difluoromethyl)phosphonic acid |
| 112 | 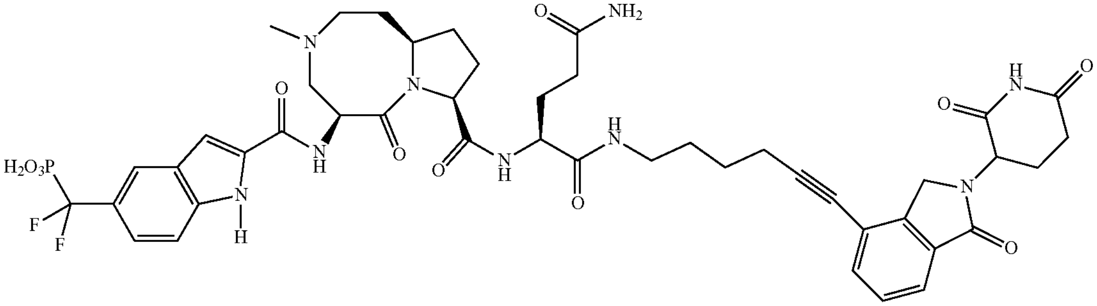 | ((2-(((5S,8S,10aR)-8-(((2S)-5-amino-1-((6-(2-(2,6-dioxopiperidin-3-yl)-1-oxoisoindolin-4-yl)hex-5-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 113 | 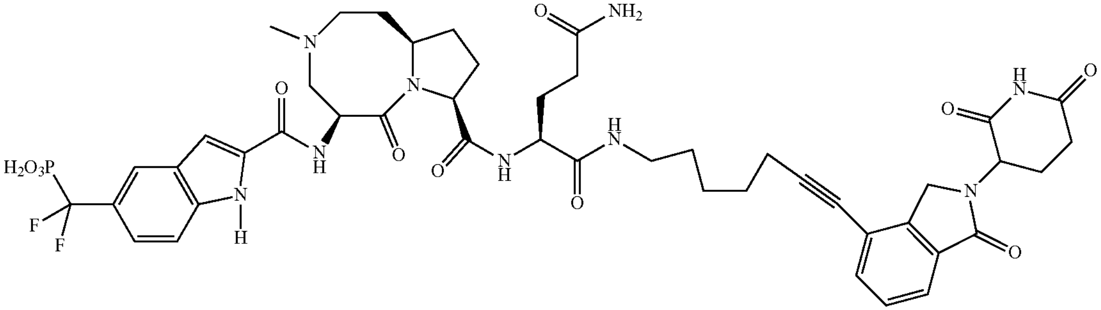 | ((2-(((5S,8S,10aR)-8-(((2S)-5-amino-1-((7-(2-(2,6-dioxopiperidin-3-yl)-1-oxoisoindolin-4-yl)hept-6-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 114 | 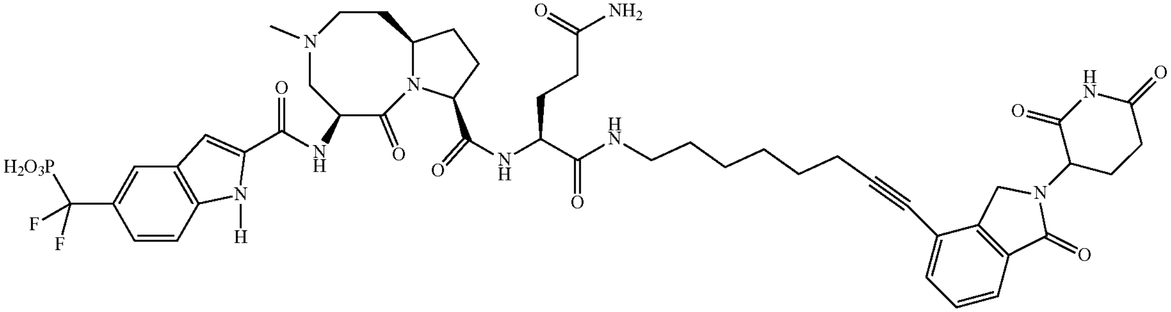 | ((2-(((5S,8S,10aR)-8-(((2S)-5-amino-1-((8-(2-(2,6-dioxopiperidin-3-yl)-1-oxoisoindolin-4-yl)oct-7-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 115 | 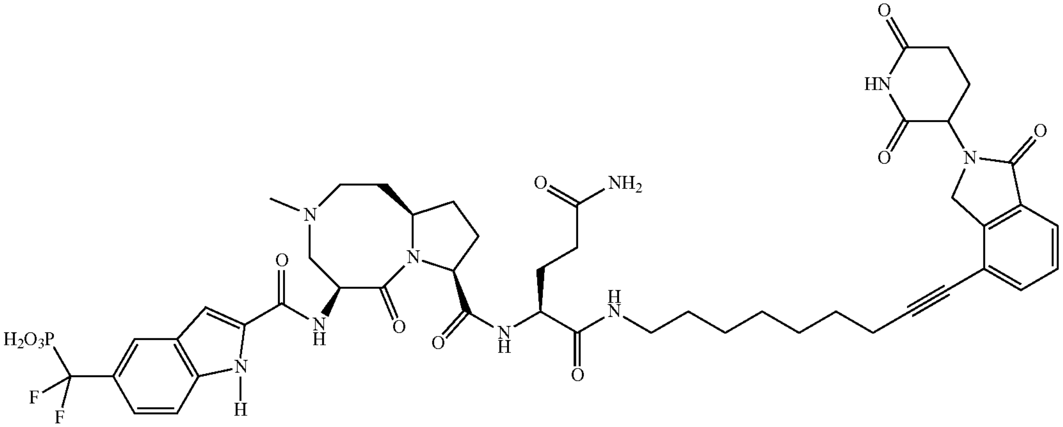 | ((2-(((5S,8S,10aR)-8-(((2S)-5-amino-1-((9-(2-(2,6-dioxopiperidin-3-yl)-1-oxoisoindolin-4-yl)non-8-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 116 | 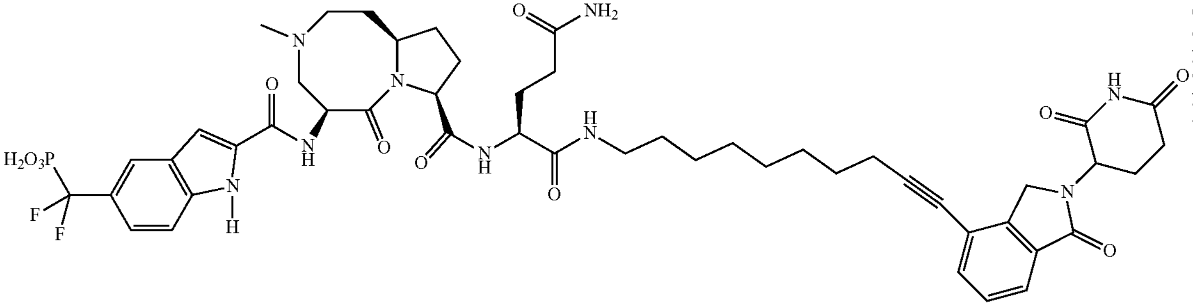 | ((2-(((5S,8S,10aR)-8-(((2S)-5-amino-1-((10-(2-(2,6-dioxopiperidin-3-yl)-1-oxoisoindolin-4-yl)dec-9-yn-1-yl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 117 | 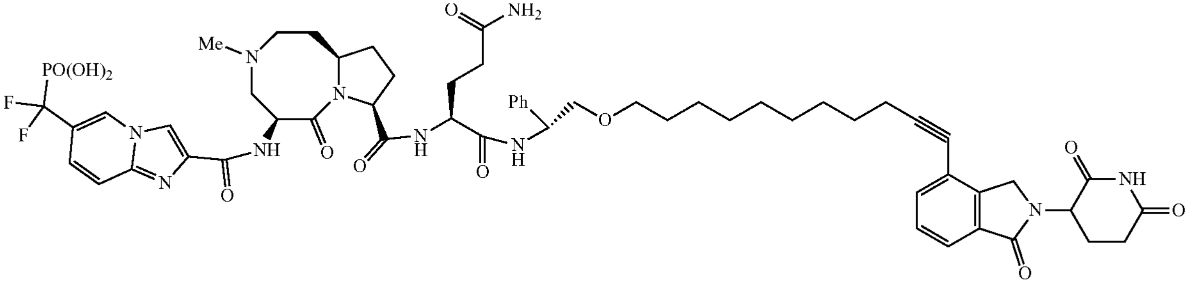 | ((2-(((5S,8S,10aR)-8-(((2S)-5-amino-1-((2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)imidazo[1,2-a]pyridin-6-yl)difluoromethyl)phosphonic acid |

TABLE 1-continued

| Cpd. No. | Structure | Name |
|---|---|---|
| 118 | 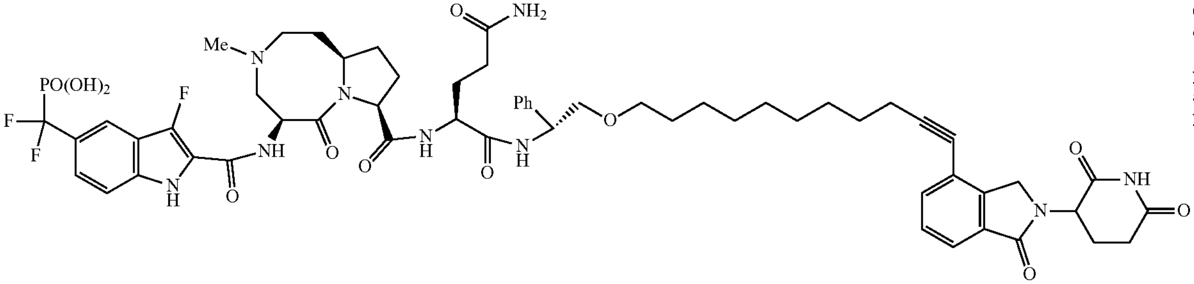 | ((2-(((5S,8S,10aR)-8-(((2S)-5-amino-1-((2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-3-fluoro-1H-indol-5-yl)difluoromethyl)phosphonic acid |
| 119 | 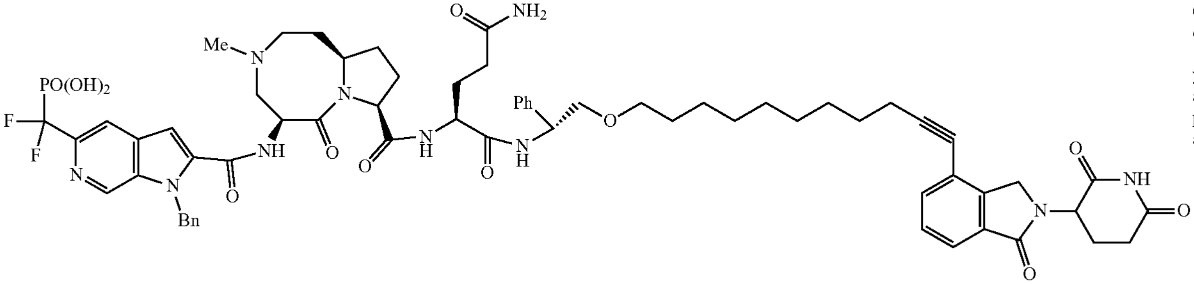 | ((2-(((5S,8S,10aR)-8-(((2S)-5-amino-1-((2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1-benzyl-1H-pyrrolo[2,3-c]pyridin-5-yl)difluoromethyl)phosphonic acid |
| 120 | 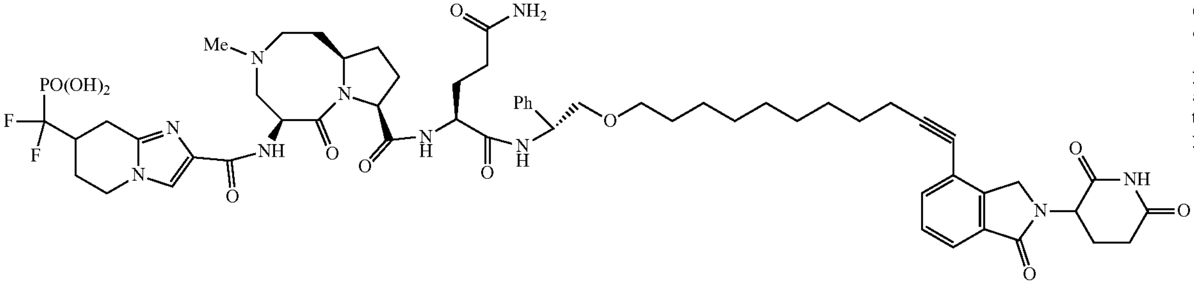 | ((2-(((5S,8S,10aR)-8-(((2S)-5-amino-1-((2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-5,6,7,8-tetrahydroimidazo[1,2-a]pyridin-7-yl)difluoromethyl)phosphonic acid |

TABLE 1-continued

| Cpd. No. | Structure | Name |
|---|---|---|
| 121 | 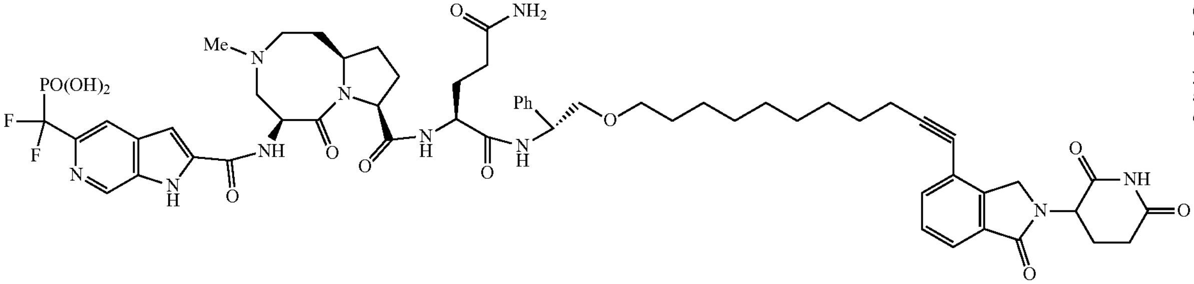 | ((2-(((5S,8S,10aR)-8-(((2S)-5-amino-1-((2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-pyrrolo[2,3-c]pyridin-5-yl)difluoromethyl)phosphonic acid |
| 122 | 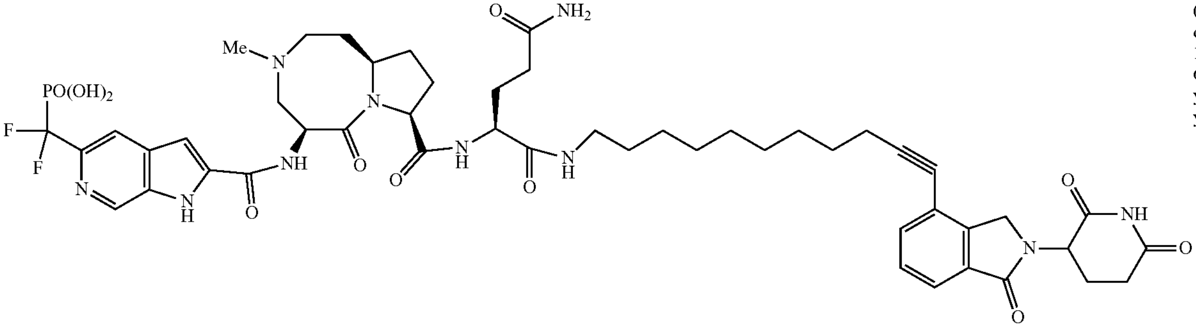 | ((2-(((5S,8S,10aR)-8-(((2S)-5-amino-1-((11-(2-(2,6-dioxopiperidin-3-yl)-1-oxoisoindolin-4-yl)undec-10-yn-1-yl)amino)-1,5-dioxopentan-2-yl)carbamoyl)-3-methyl-6-oxodecahydropyrrolo[1,2-a][1,5]diazocin-5-yl)carbamoyl)-1H-pyrrolo[2,3-c]pyridin-5-yl)difluoromethyl)phosphonic acid |
| 123 | 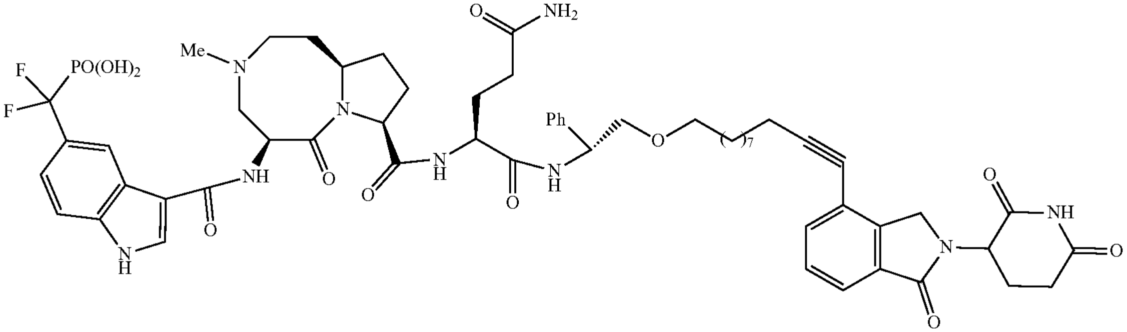 | ((3-(((5S,8S,10aR)-8-(((2S)-5-amino-1-((2-((5-(2-(2,6-dioxopiperidin-3-yl)-1-oxoisoindolin-4-yl)pent-4-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 124 | 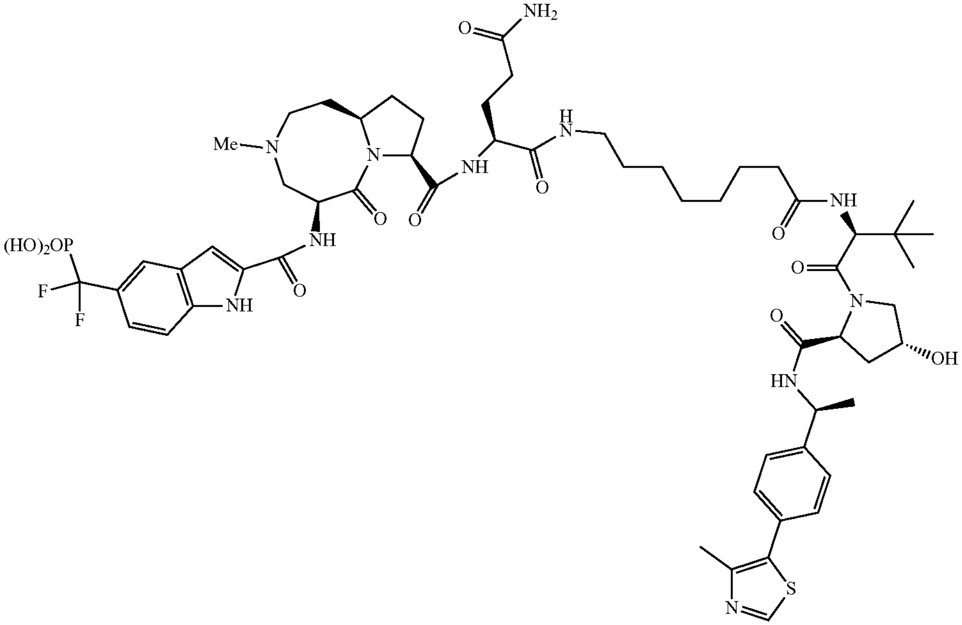 | ((2-(((5S,8S,10aR)-8-(((S)-5-amino-1-((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 125 | 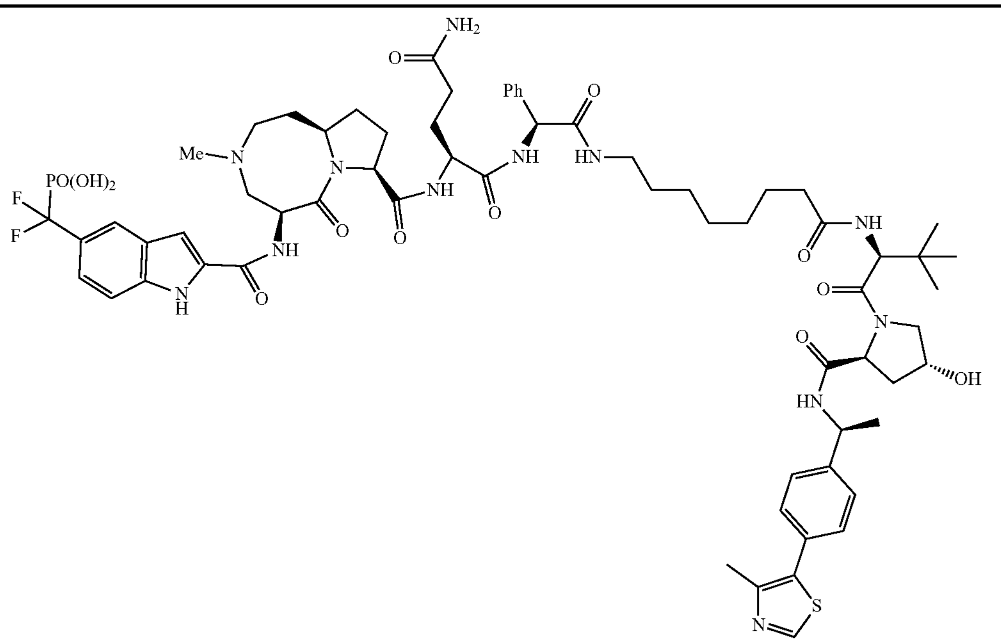 | ((2-(((5S,8S,10aR)-8-(((S)-5-amino-1-(((S)-2-((8-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-8-oxooctyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 126 | 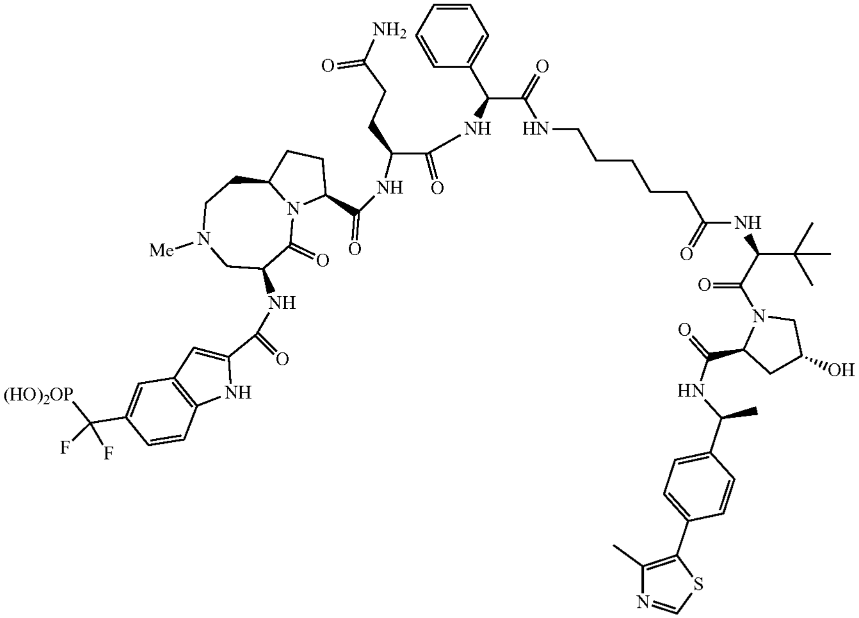 | ((2-(((5S,8S,10aR)-8-(((S)-5-amino-1-(((S)-2-((6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 127 | 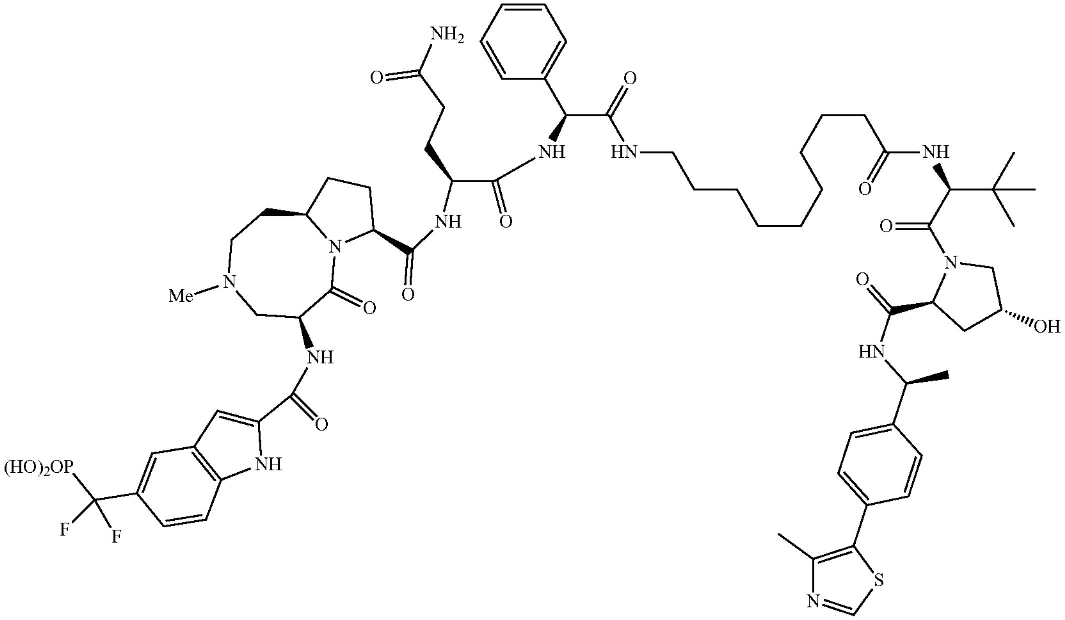 | ((2-(((5S,8S,10aR)-8-(((S)-5-amino-1-(((S)-2-((10-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-10-oxodecyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 128 | 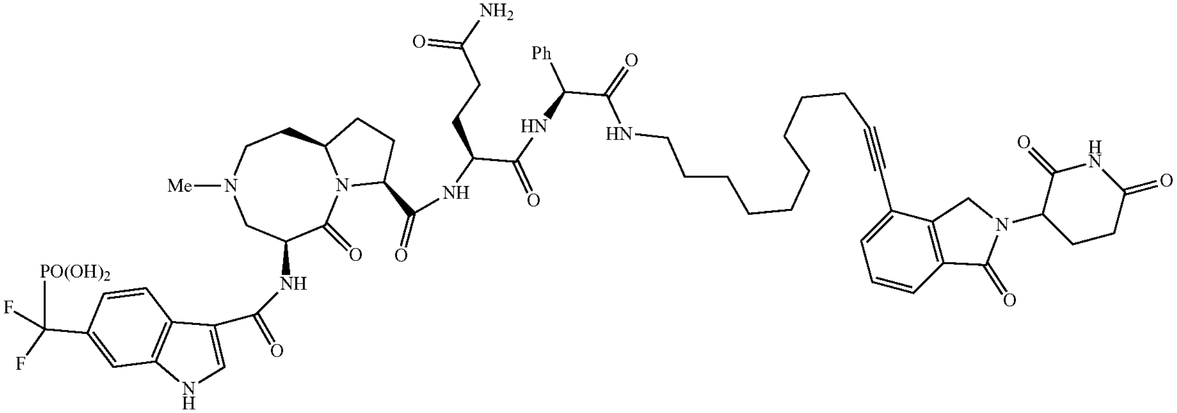 | ((3-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-6-yl)difluoromethyl)phosphonic acid |

TABLE 1-continued

| Cpd. No. | Structure | Name |
|---|---|---|
| 129 | 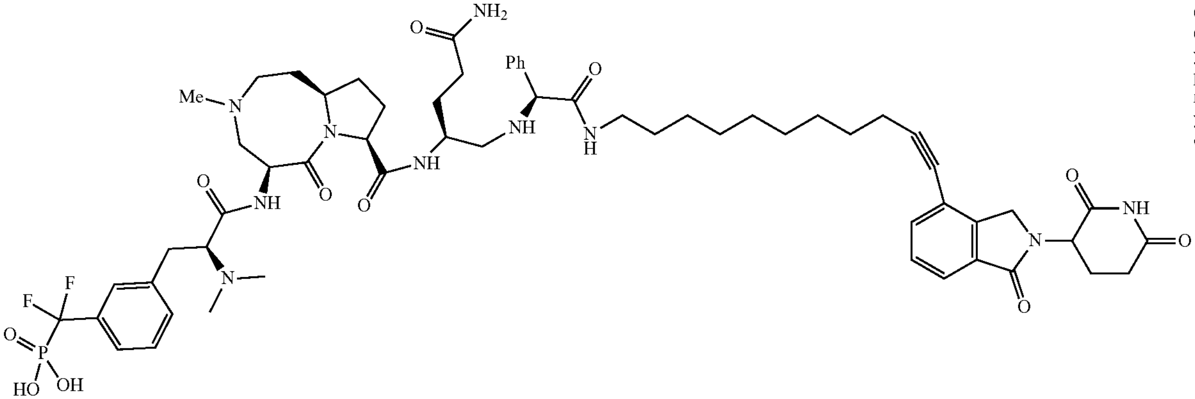 [SMILES: CN1CC[C@H]2CC[C@@H](C(=O)N[C@@H](CCC(N)=O)CN[C@H](C(=O)NCCCCCCCCCC#Cc3cccc4c3CN(C3CCC(=O)NC3=O)C4=O)c3ccccc3)N2C(=O)[C@@H](NC(=O)[C@H](Cc2cccc(C(F)(F)P(=O)(O)O)c2)N(C)C)C1] | ((3-((2S)-3-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-5-oxopentan-2-yl)carbamoyl)-3-methyl-6-oxodecahydropyrrolo[1,2-a][1,5]diazocin-5-yl)amino)-2-(dimethylamino)-3-oxopropyl)phenyl)difluoromethyl)phosphonic acid |
| 130 | 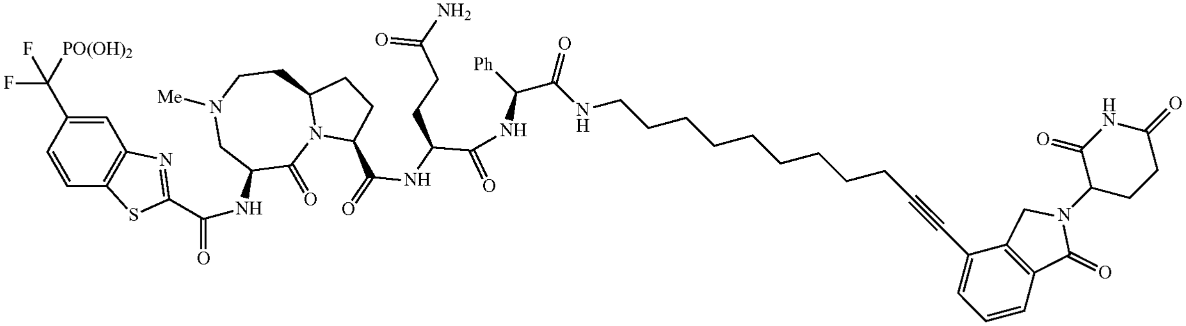 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzothiazol-5-yl)difluoromethyl)phosphonic acid |

TABLE 1-continued

| Cpd. No. | Structure | Name |
|---|---|---|
| 131 | 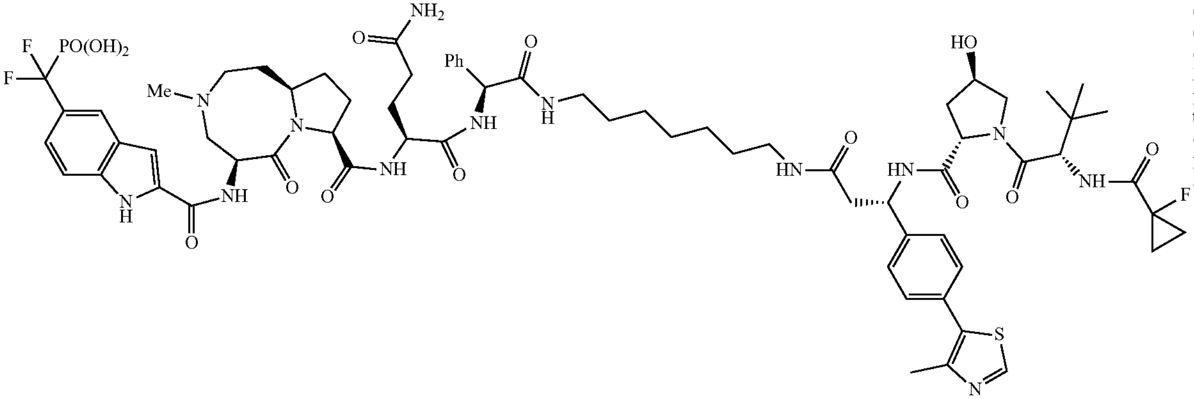 | ((2-(((5S,8S,10aR)-8-(((3S,16S,19S)-22-amino-1-((2S,4R)-1-((S)-2-(1-fluorocyclopropane-1-carboxamido)-3,3-dimethylbutanoyl)-4-hydroxypyrrolidin-2-yl)-3-(4-(4-methylthiazol-5-yl)phenyl)-1,5,15,18,22-pentaoxo-16-phenyl-2,6,14,17-tetraazadocosan-19-yl)carbamoyl)-3-methyl-6-oxodecahydropyrrolo[1,2-a][1,5]diazocin-5-yl)carbamoyl)-1H-indol-5-yl)difluoromethyl)phosphonic acid |
| 132 | 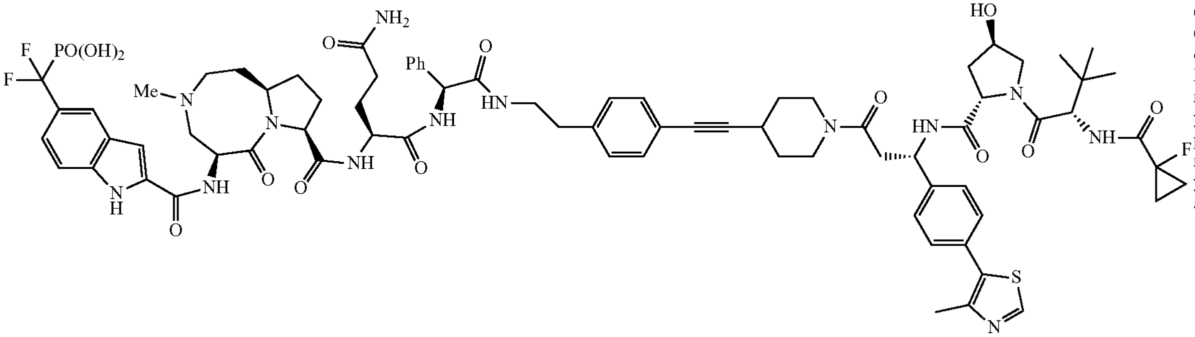 | ((2-(((5S,8S,10aR)-8-(((S)-5-amino-1-(((S)-2-((4-((1-((S)-3-((2S,4R)-1-((S)-2-(1-fluorocyclopropane-1-carboxamido)-3,3-dimethylbutanoyl)-4-hydroxypyrrolidine-2-carboxamido)-3-(4-(4-methylthiazol-5-yl)phenyl)propanoyl)piperidin-4-yl)ethynyl)phenethyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 133 | 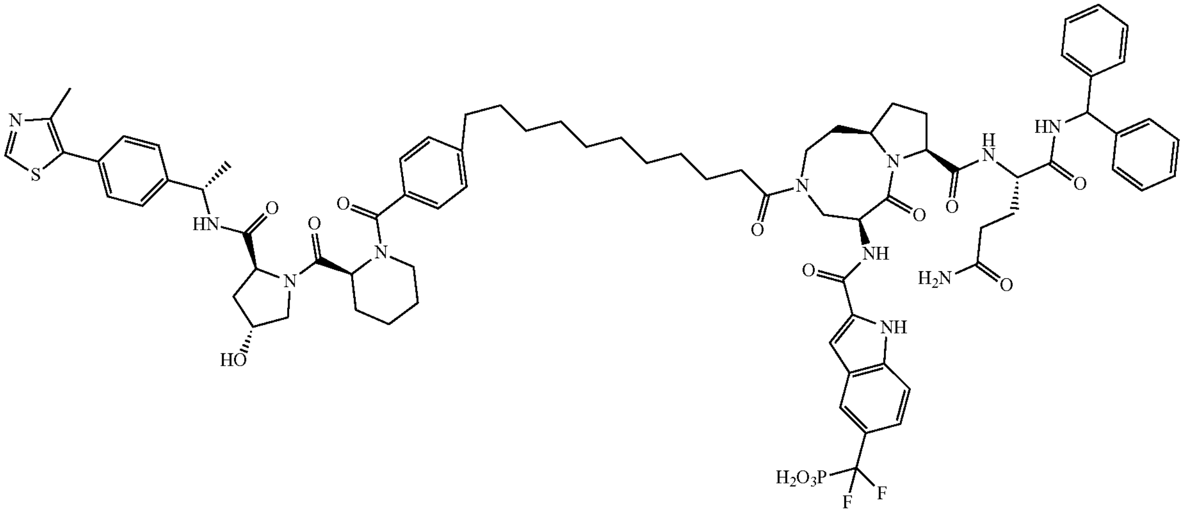 | ((2-(((5S,8S,10aR)-8-(((S)-5-amino-1-(benzhydrylamino)-1,5-dioxopentan-2-yl)carbamoyl)-3-(11-(4-((S)-2-((2S,4R)-4-hydroxy-2-(((S)-1-(4-(4-methylthiazol-5-yl)phenyl)ethyl)carbamoyl)pyrrolidine-1-carbonyl)piperidine-1-carbonyl)phenyl)undecanoyl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 134 | 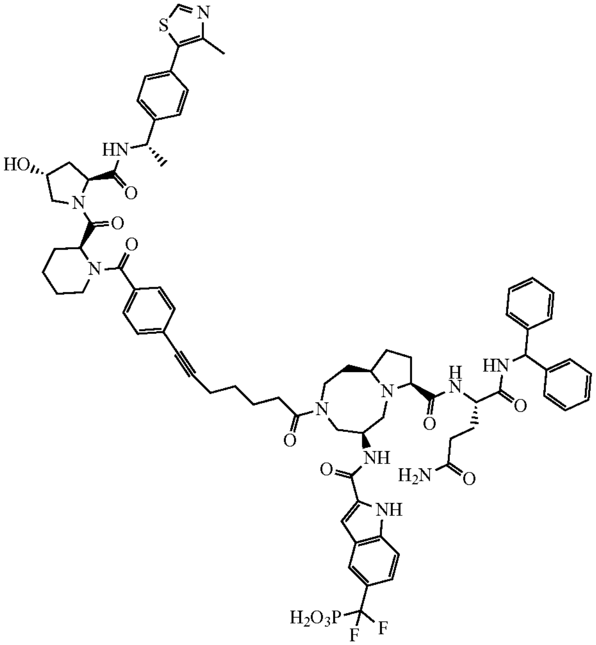 | ((2-(((5S,8S,10aR)-8-(((S)-5-amino-1-(benzhydrylamino)-1,5-dioxopentan-2-yl)carbamoyl)-3-(7-(4-((S)-2-((2S,4R)-4-hydroxy-2-(((S)-1-(4-(4-methylthiazol-5-yl)phenyl)ethyl)carbamoyl)pyrrolidine-1-carbonyl)piperidine-1-carbonyl)phenyl)hept-6-ynoyl)-6-oxodecahydropyrrolo[1,2-a][1,5]diazocin-5-yl)carbamoyl)-1H-indol-5-yl)difluoromethyl)phosphonic acid |
| 135 | 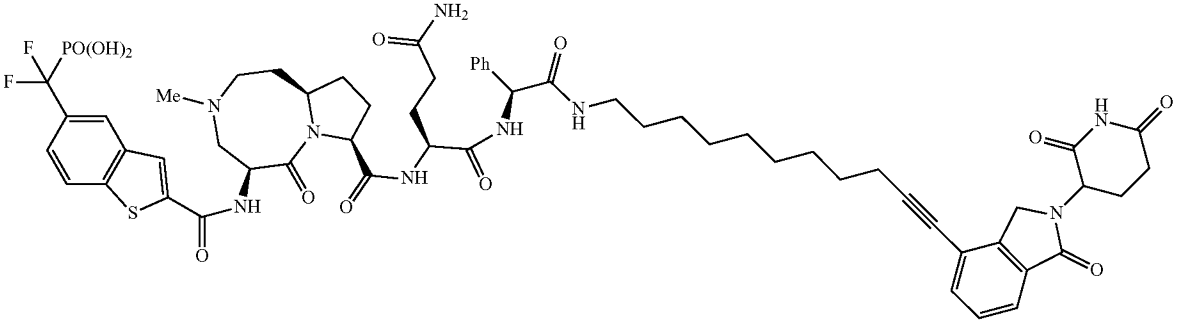 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 136 | 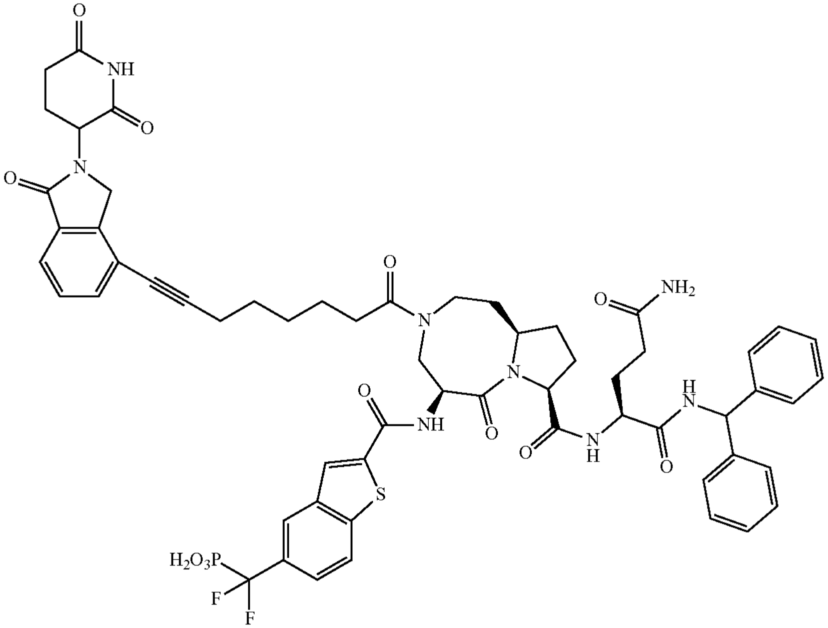 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 137 | 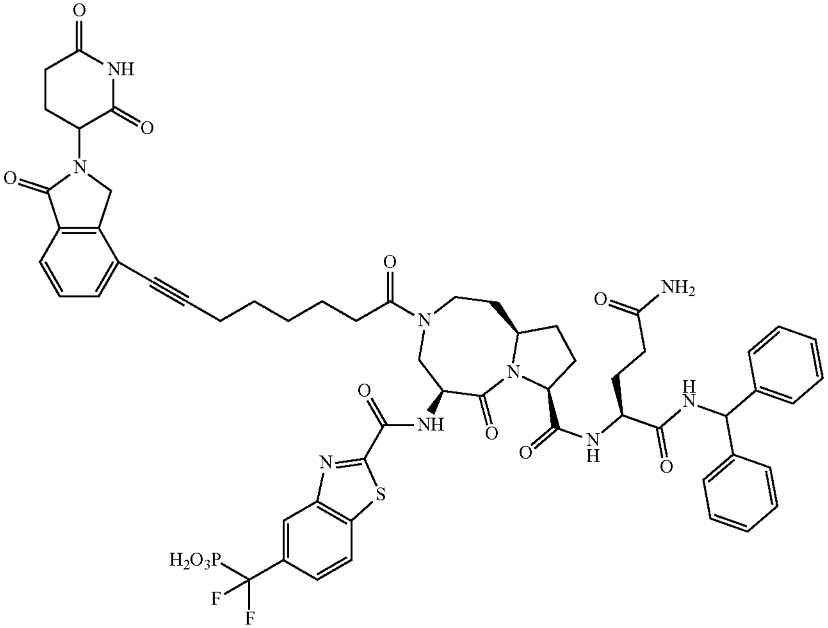 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzothiazol-5-yl)difluoromethyl)phosphonic acid |
| 138 | 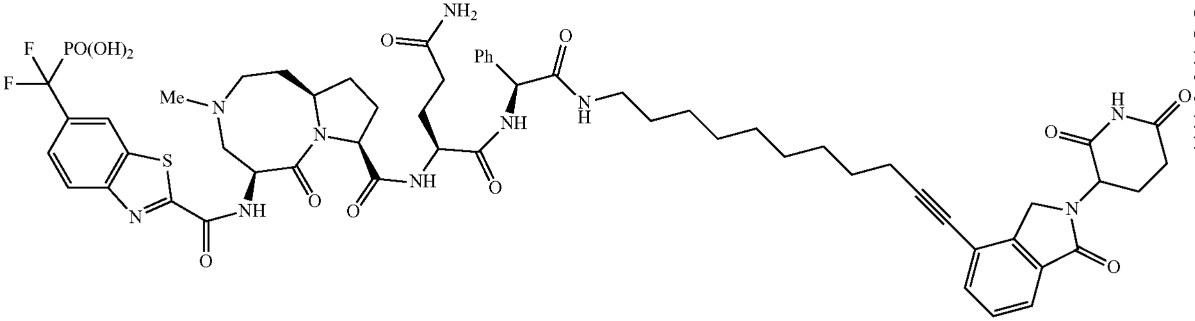 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzothiazol-6-yl)difluoromethyl)phosphonic acid |

TABLE 1-continued

| Cpd. No. | Structure | Name |
|---|---|---|
| 139 | 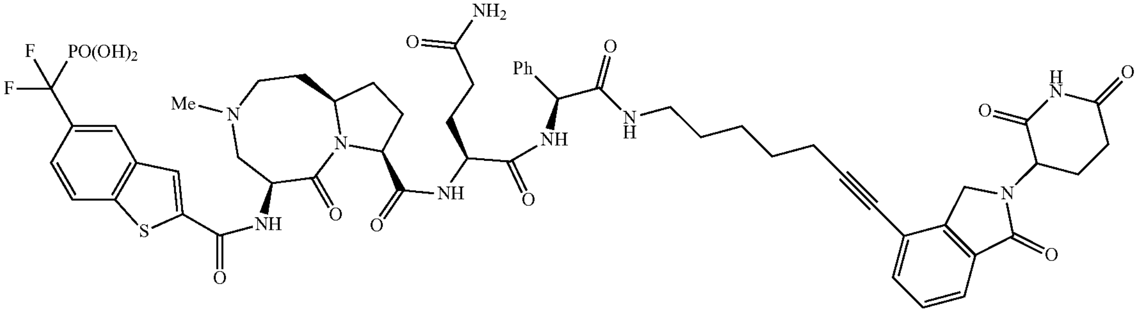 | ((2-(((5S,8S,10aR)-8-(((2S)-5-amino-1-(((1S)-2-((7-(2-(2,6-dioxopiperidin-3-yl)-1-oxoisoindolin-4-yl)hept-6-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 140 | 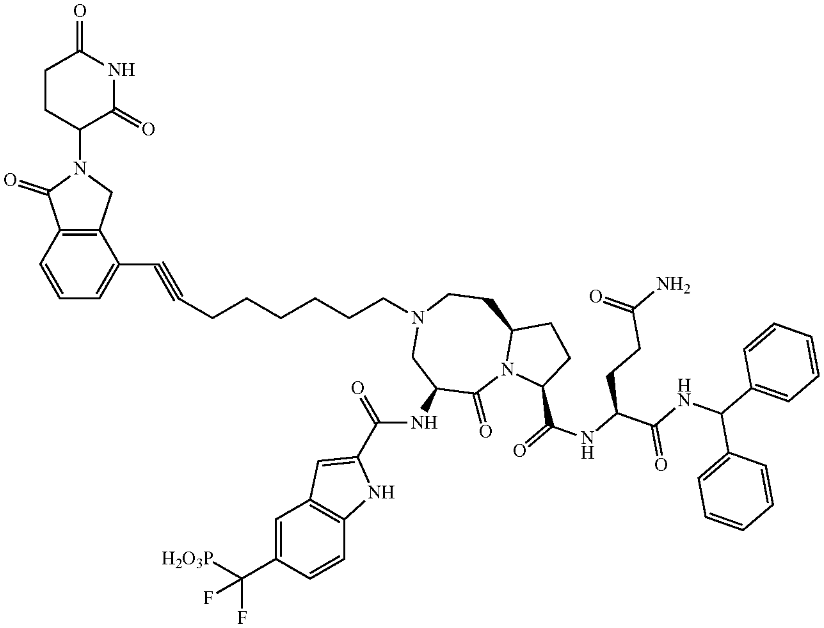 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-yn-1-yl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 141 | 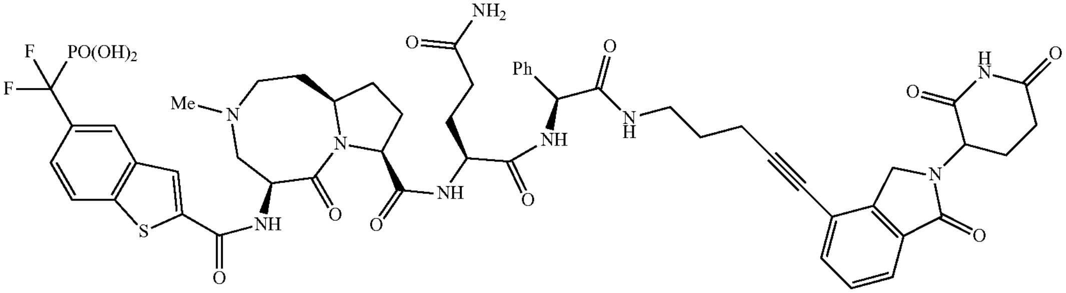 | ((2-(((5S,8S,10aR)-8-(((2S)-5-amino-1-(((1S)-2-((5-(2-(2,6-dioxopiperidin-3-yl)-1-oxoisoindolin-4-yl)pent-4-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 142 | 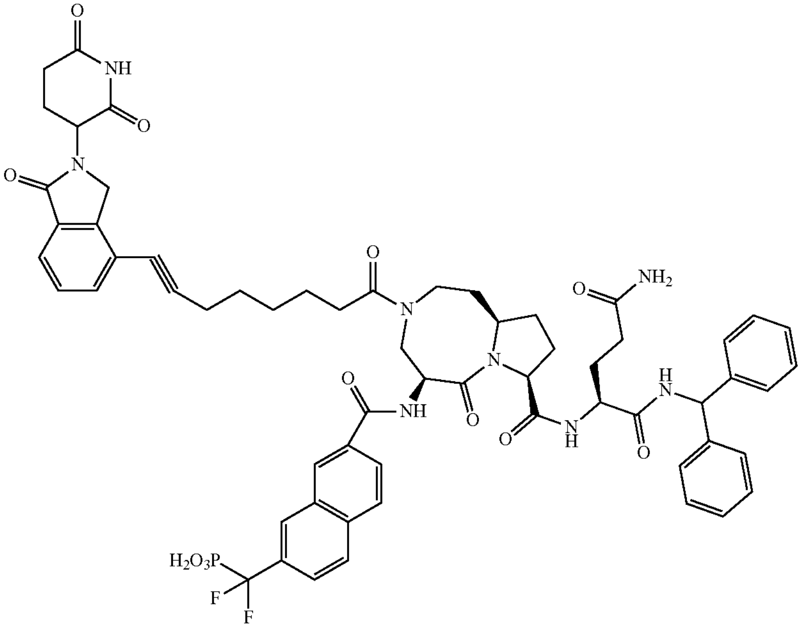 | ((7-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)naphthalen-2-yl)difluoromethyl)phosphonic acid |

TABLE 1-continued

| Cpd. No. | Structure | Name |
|---|---|---|
| 143 | 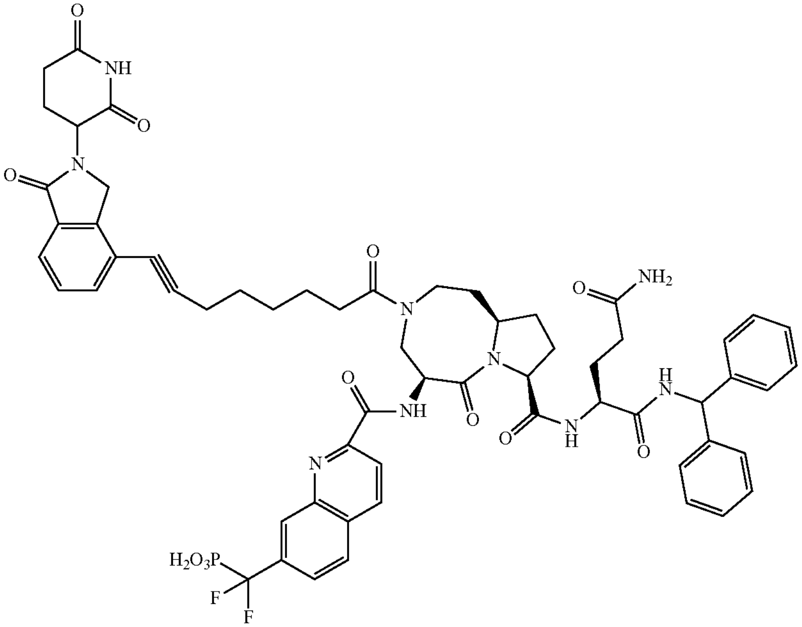 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)quinolin-7-yl)difluoromethyl)phosphonic acid |
| 144 | 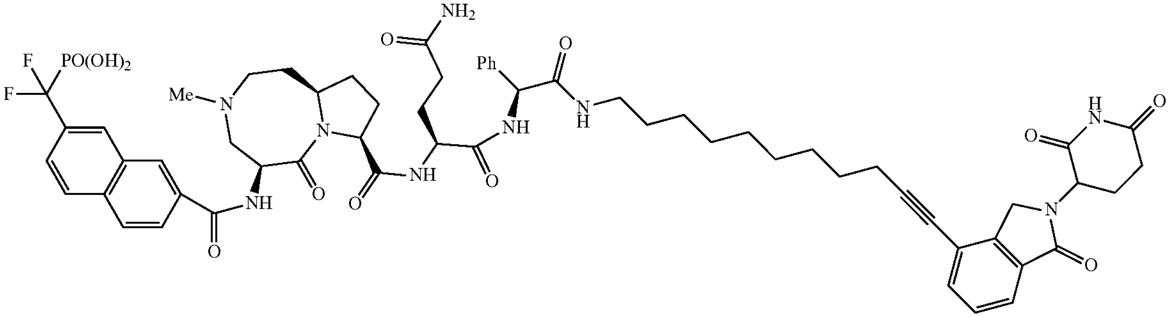 | ((7-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)naphthalen-2-yl)difluoromethyl)phosphonic acid |

TABLE 1-continued
| Cpd. No. | Structure | Name |
|---|---|---|
| 145 | 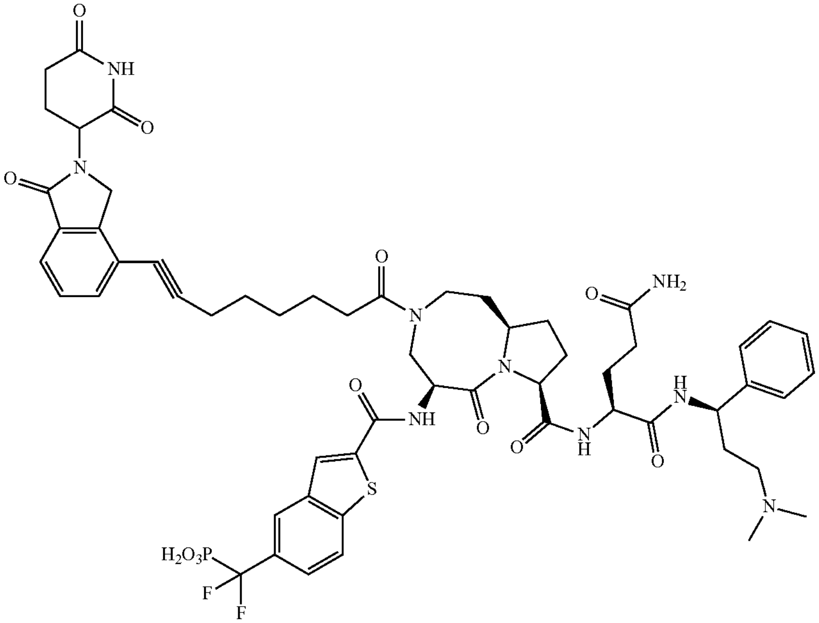 | ((2-(((5S,8S,10aR)-8-(((S)-5-amino-1-(((R)-3-(dimethylamino)-1-phenylpropyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 146 | 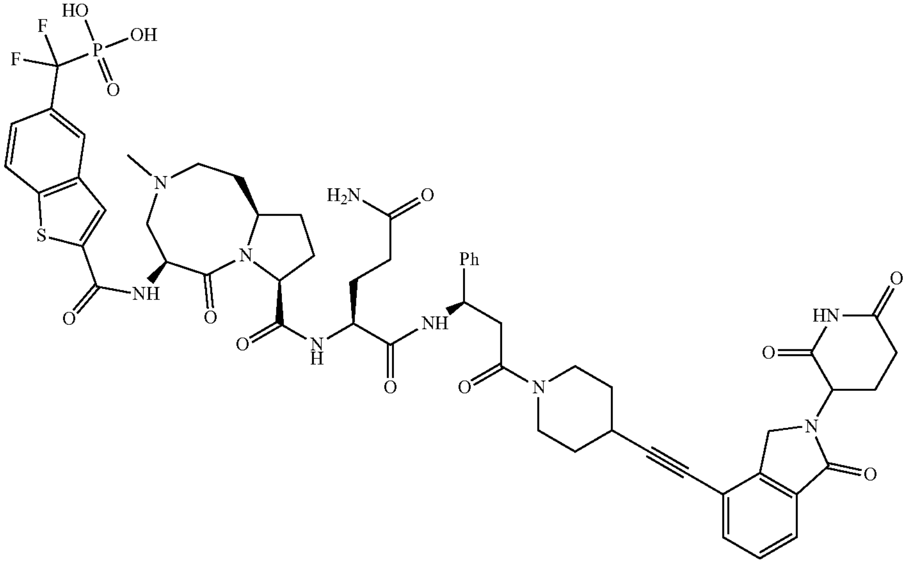 [SMILES: CN1CC[C@H]2CC[C@@H](C(=O)N[C@@H](CCC(N)=O)C(=O)N[C@H](CC(=O)N3CCC(C#Cc4cccc5c4CN(C4CCC(=O)NC4=O)C5=O)CC3)c3ccccc3)N2C(=O)[C@@H](NC(=O)c2cc3cc(C(F)(F)P(=O)(O)O)ccc3s2)C1] | ((2-(((5S,8S,10aR)-8-(((2S)-5-amino-1-(((1R)-3-(4-((2-(2,6-dioxopiperidin-3-yl)-1-oxoisoindolin-4-yl)ethynyl)piperidin-1-yl)-3-oxo-1-phenylpropyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 147 | 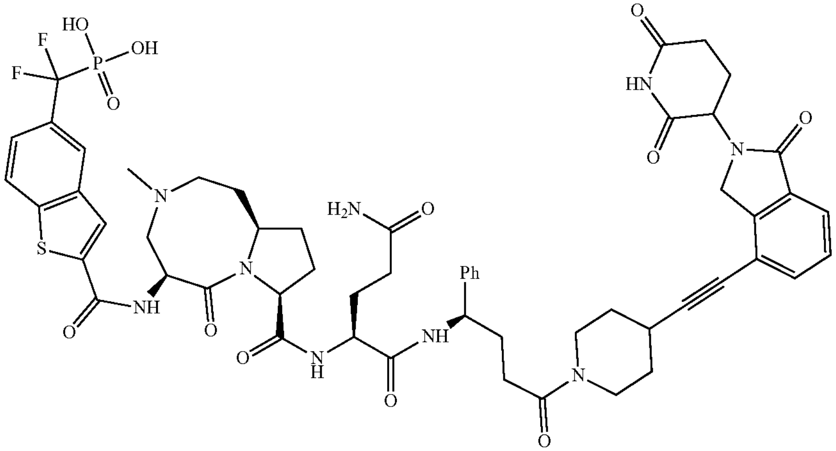 [SMILES: CN1CC[C@H]2CC[C@@H](C(=O)N[C@@H](CCC(N)=O)C(=O)N[C@H](CCC(=O)N3CCC(C#Cc4cccc5c4CN(C4CCC(=O)NC4=O)C5=O)CC3)c3ccccc3)N2C(=O)[C@@H](NC(=O)c2cc3cc(C(F)(F)P(=O)(O)O)ccc3s2)C1] | ((2-(((5S,8S,10aR)-8-(((2S)-5-amino-1-(((1R)-4-(4-((2-(2,6-dioxopiperidin-3-yl)-1-oxoisoindolin-4-yl)ethynyl)piperidin-1-yl)-4-oxo-1-phenylbutyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 148 | 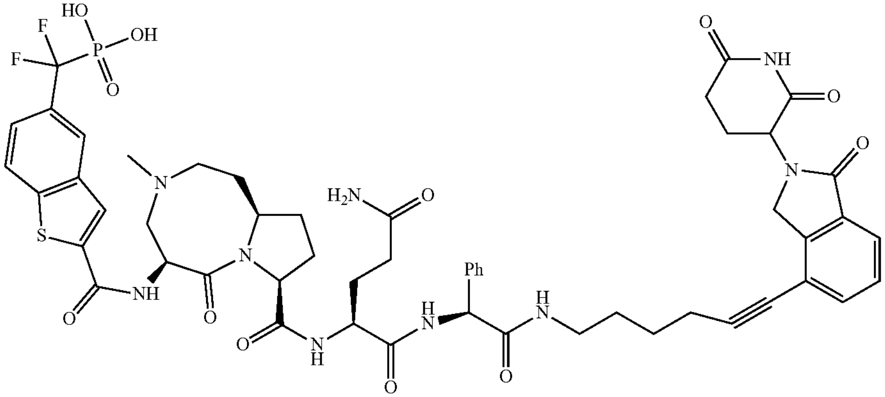 [SMILES: CN1CC[C@H]2CC[C@@H](C(=O)N[C@@H](CCC(N)=O)C(=O)N[C@H](C(=O)NCCCCC#Cc3cccc4c3CN(C3CCC(=O)NC3=O)C4=O)c3ccccc3)N2C(=O)[C@@H](NC(=O)c2cc3cc(C(F)(F)P(=O)(O)O)ccc3s2)C1] | ((2-(((5S,8S,10aR)-8-(((2S)-5-amino-1-(((1S)-2-((6-(2-(2,6-dioxopiperidin-3-yl)-1-oxoisoindolin-4-yl)hex-5-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 149 | 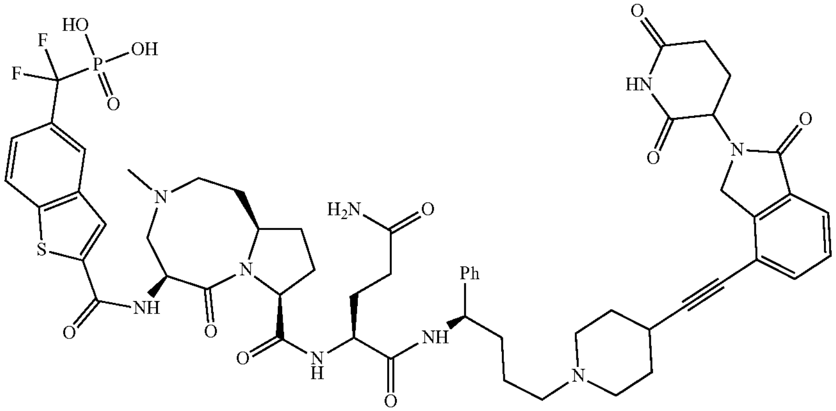 [SMILES: CN1CC[C@H]2CC[C@@H](C(=O)N[C@@H](CCC(N)=O)C(=O)N[C@H](CCCN3CCC(C#Cc4cccc5c4CN(C4CCC(=O)NC4=O)C5=O)CC3)c3ccccc3)N2C(=O)[C@@H](NC(=O)c2cc3cc(C(F)(F)P(=O)(O)O)ccc3s2)C1] | ((2-(((5S,8S,10aR)-8-(((2S)-5-amino-1-(((1R)-4-(4-((2-(2,6-dioxopiperidin-3-yl)-1-oxoisoindolin-4-yl)ethynyl)piperidin-1-yl)-1-phenylbutyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 150 | 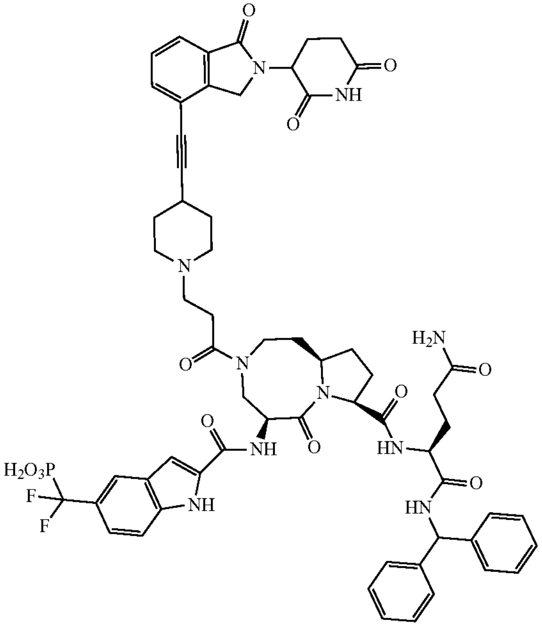 | ((2-(((5S,8S,10aR)-8-(((S)-5-amino-1-(benzhydrylamino)-1,5-dioxopentan-2-yl)carbamoyl)-3-(3-(4-((2-(2,6-dioxopiperidin-3-yl)-1-oxoisoindolin-4-yl)ethynyl)piperidin-1-yl)propanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 151 | 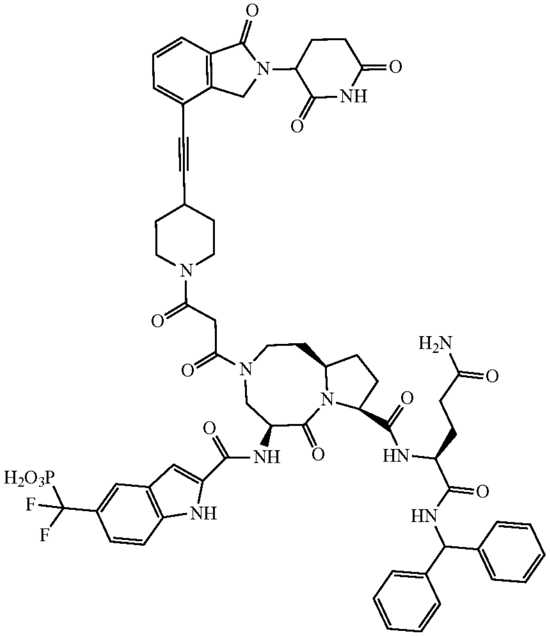 | ((2-(((5S,8S,10aR)-8-(((S)-5-amino-1-(benzhydrylamino)-1,5-dioxopentan-2-yl)carbamoyl)-3-(3-(4-((2-(2,6-dioxopiperidin-3-yl)-1-oxoisoindolin-4-yl)ethynyl)piperidin-1-yl)-3-oxopropanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 152 | 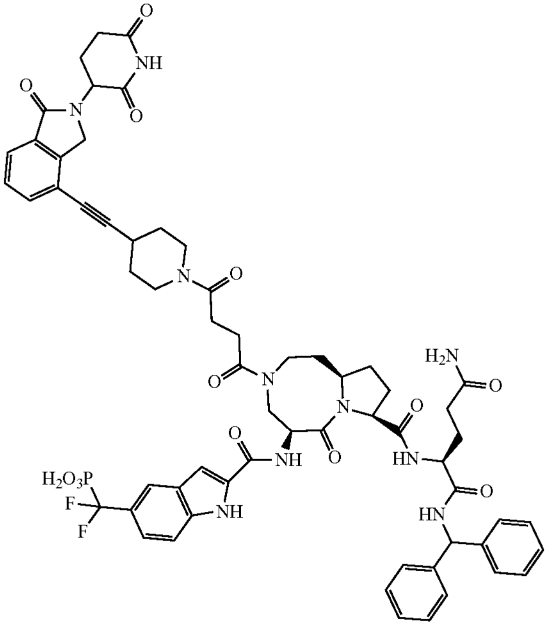 | ((2-(((5S,8S,10aR)-8-(((S)-5-amino-1-(benzhydrylamino)-1,5-dioxopentan-2-yl)carbamoyl)-3-(4-(4-((2-(2,6-dioxopiperidin-3-yl)-1-oxoisoindolin-4-yl)ethynyl)piperidin-1-yl)-4-oxobutanoyl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
|---|---|---|
| 153 | 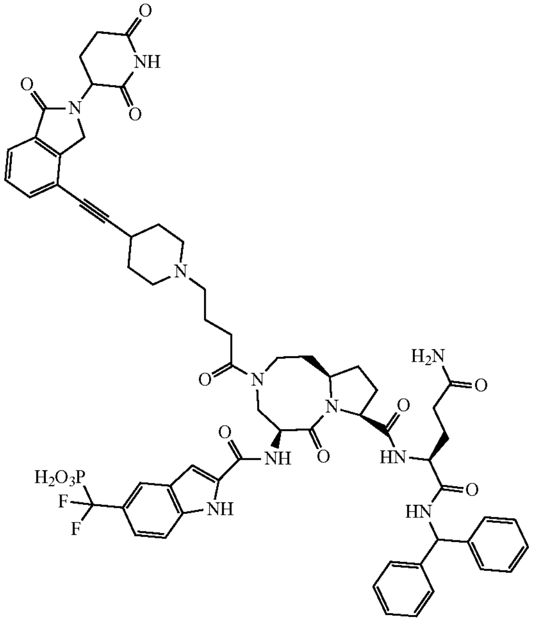 | ((2-(((5S,8S,10aR)-8-(((S)-5-amino-1-(benzhydrylamino)-1,5-dioxopentan-2-yl)carbamoyl)-3-(4-(4-((2-(2,6-dioxopiperidin-3-yl)-1-oxoisoindolin-4-yl)ethynyl)piperidin-1-yl)butanoyl)-6-oxodecahydropyrrolo[1,2-a][1,5]diazocin-5-yl)carbamoyl)-1H-indol-5-yl)difluoromethyl)phosphonic acid |
| 154 | 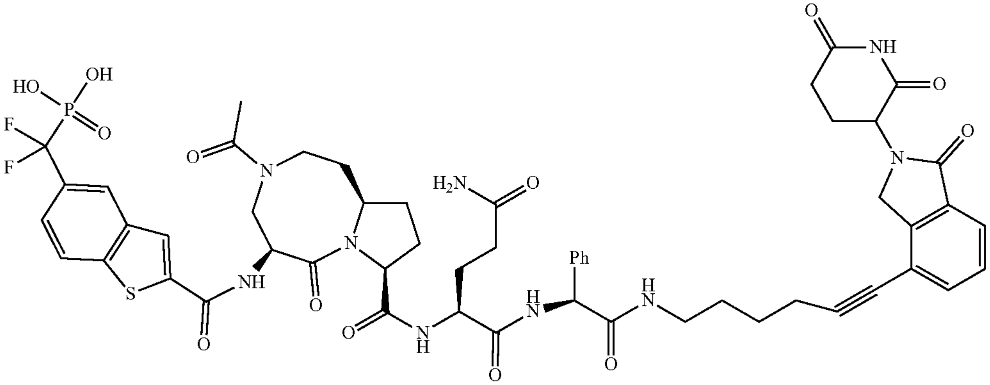 [SMILES: CC(=O)N1CC[C@H]2CC[C@@H](C(=O)N[C@@H](CCC(N)=O)C(=O)N[C@H](C(=O)NCCCCC#Cc3cccc4c3CN(C3CCC(=O)NC3=O)C4=O)c3ccccc3)N2C(=O)[C@@H](NC(=O)c2cc3cc(C(F)(F)P(=O)(O)O)ccc3s2)C1] | ((2-(((5S,8S,10aR)-3-acetyl-8-(((2S)-5-amino-1-(((1S)-2-((6-(2-(2,6-dioxopiperidin-3-yl)-1-oxoisoindolin-4-yl)hex-5-yn-1-yl)amino)-2-oxo-1-phenylethyl)amino)-1,5-dioxopentan-2-yl)carbamoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 155 | 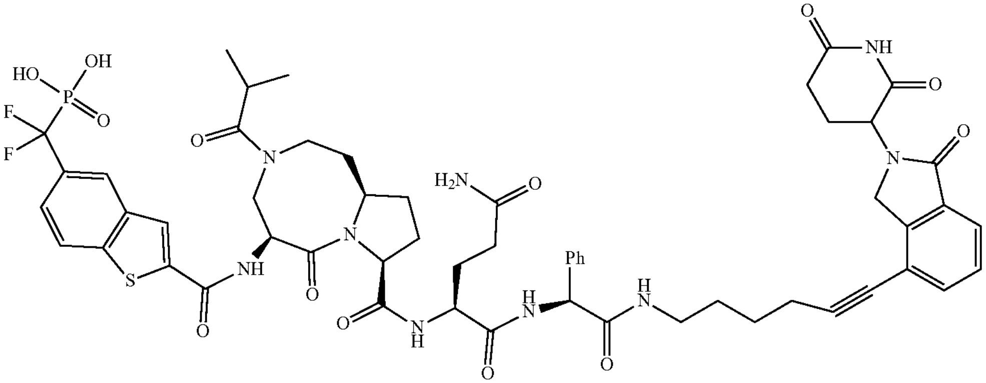 [SMILES: CC(C)C(=O)N1CC[C@H]2CC[C@@H](C(=O)N[C@@H](CCC(N)=O)C(=O)N[C@H](C(=O)NCCCCC#Cc3cccc4c3CN(C3CCC(=O)NC3=O)C4=O)c3ccccc3)N2C(=O)[C@@H](NC(=O)c2cc3cc(C(F)(F)P(=O)(O)O)ccc3s2)C1] | ((2-(((5S,8S,10aR)-8-(((2S)-5-amino-1-(((1S)-2-((6-(2-(2,6-dioxopiperidin-3-yl)-1-oxoisoindolin-4-yl)hex-5-yn-1-yl)amino)-2-oxo-1-phenylethyl)amino)-1,5-dioxopentan-2-yl)carbamoyl)-3-isobutyryl-6-oxodecahydropyrrolo[1,2-a][1,5]diazocin-5-yl)carbamoyl)benzo[b]thiophen-5-yl)difluoromethyl)phosphonic acid |
| 156 | 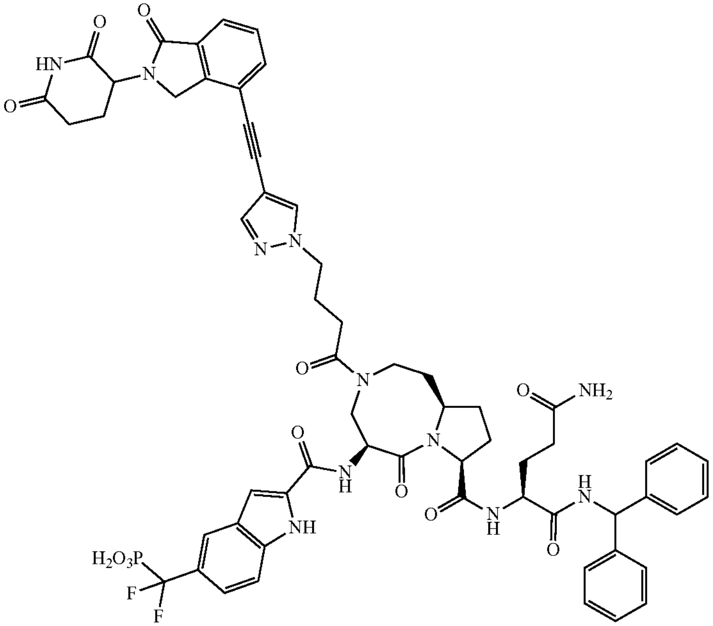 | ((2-(((5S,8S,10aR)-8-(((S)-5-amino-1-(benzhydrylamino)-1,5-dioxopentan-2-yl)carbamoyl)-3-(4-(4-((2-(2,6-dioxopiperidin-3-yl)-1-oxoisoindolin-4-yl)ethynyl)-1H-pyrazol-1-yl)butanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 157 | 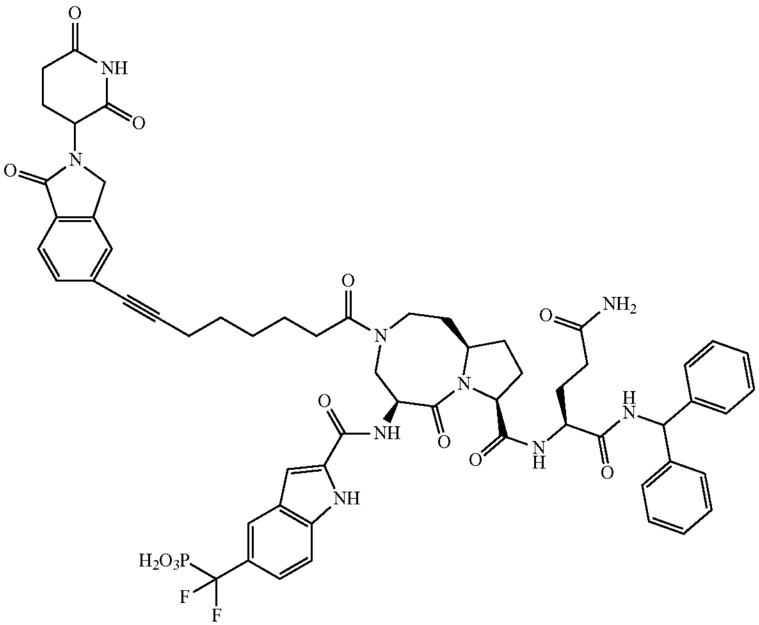 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-5-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 158 | 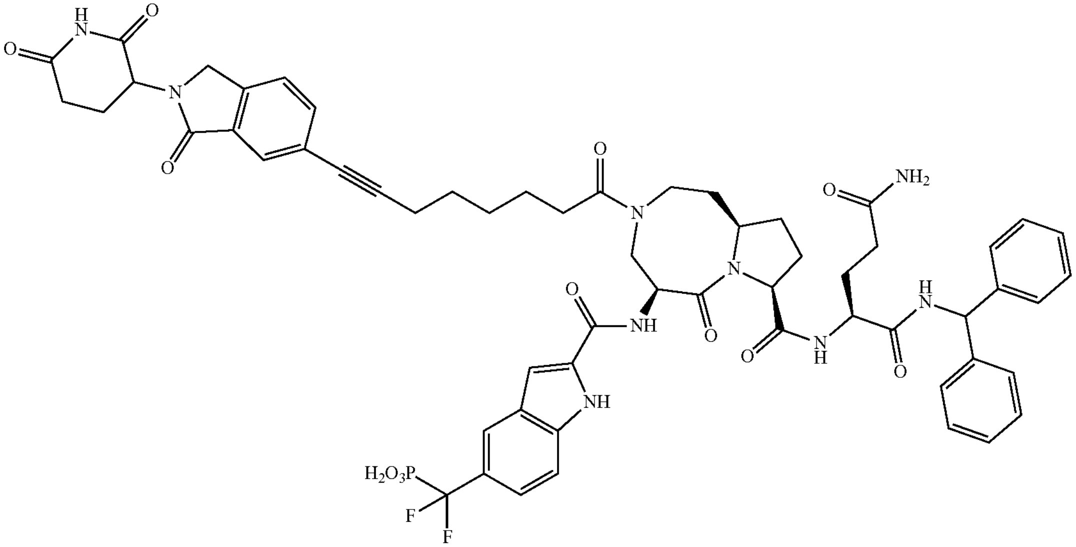 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-3-oxoisoindolin-5-yl)oct-7-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 159 | 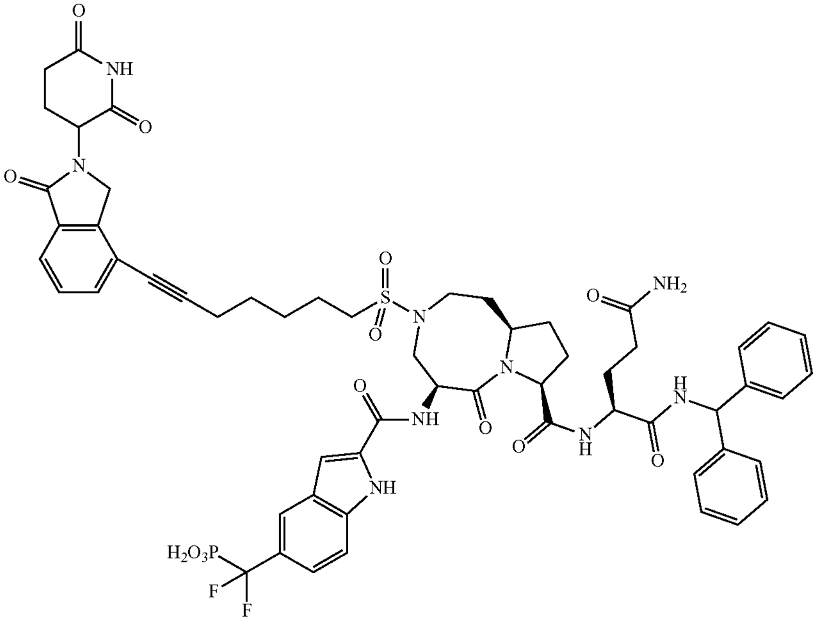 | ((2-(((5S,8S,10aR)-8-(((S)-5-amino-1-(benzhydrylamino)-1,5-dioxopentan-2-yl)carbamoyl)-3-((7-(2-(2,6-dioxopiperidin-3-yl)-1-oxoisoindolin-4-yl)hept-6-yn-1-yl)sulfonyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 160 | 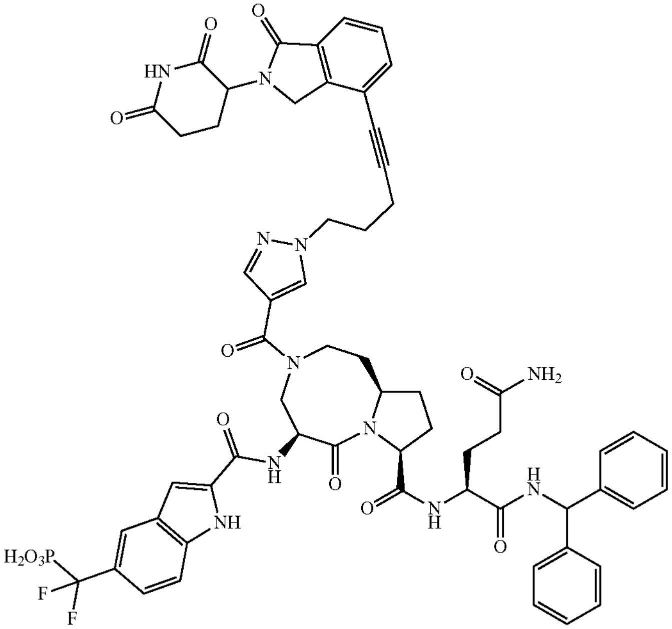 | ((2-(((5S,8S,10aR)-8-(((S)-5-amino-1-(benzhydrylamino)-1,5-dioxopentan-2-yl)carbamoyl)-3-(1-(5-(2-(2,6-dioxopiperidin-3-yl)-1-oxoisoindolin-4-yl)pent-4-yn-1-yl)-1H-pyrazole-4-carbonyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 161 | 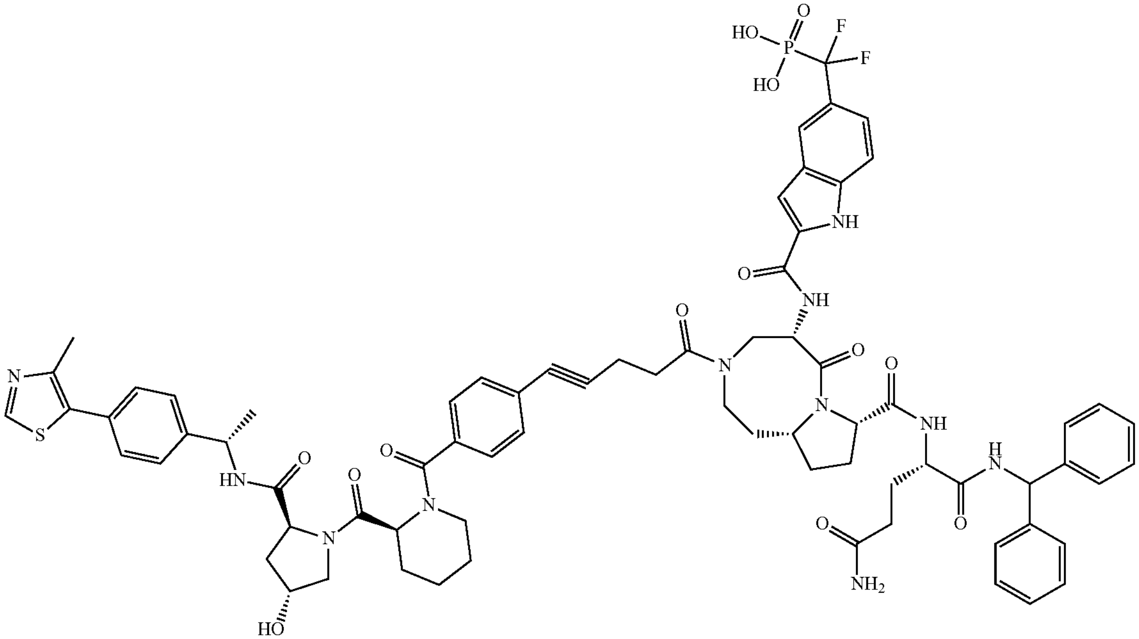 [SMILES: Cc1ncsc1-c1ccc([C@H](C)NC(=O)[C@@H]2C[C@@H](O)CN2C(=O)[C@@H]2CCCCN2C(=O)c2ccc(C#CCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(F)(F)P(=O)(O)O)ccc5[nH]4)C3)cc2)cc1] | ((2-(((5S,8S,10aR)-8-(((S)-5-amino-1-(benzhydrylamino)-1,5-dioxopentan-2-yl)carbamoyl)-3-(5-(4-((S)-2-((2S,4R)-4-hydroxy-2-(((S)-1-(4-(4-methylthiazol-5-yl)phenyl)ethyl)carbamoyl)pyrrolidine-1-carbonyl)piperidine-1-carbonyl)phenyl)pent-4-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 162 | 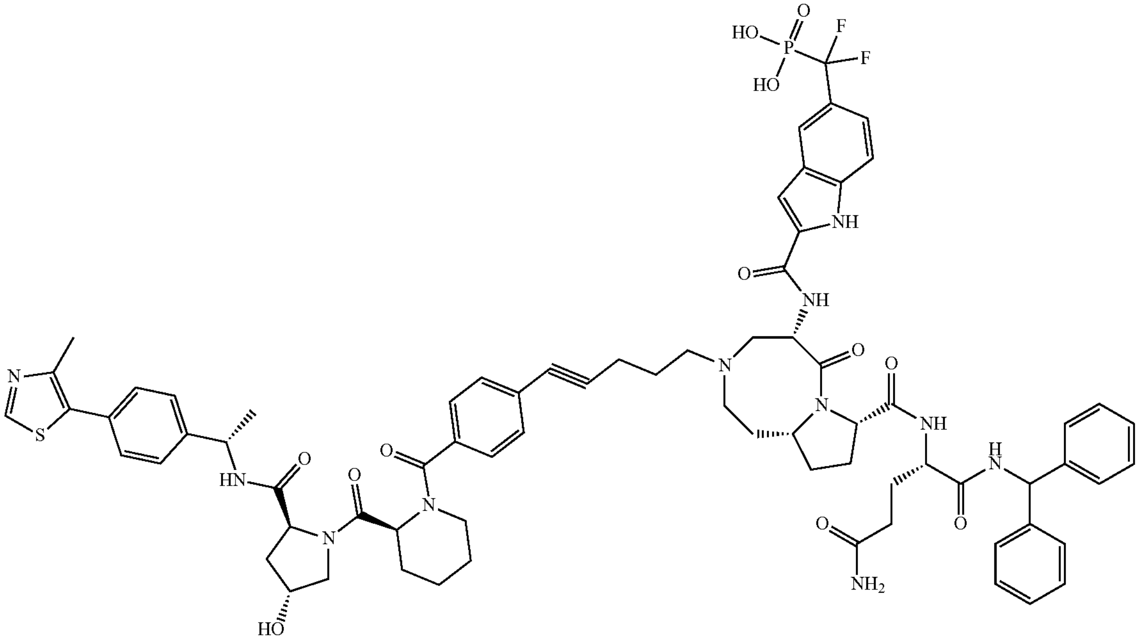 [SMILES: Cc1ncsc1-c1ccc([C@H](C)NC(=O)[C@@H]2C[C@@H](O)CN2C(=O)[C@@H]2CCCCN2C(=O)c2ccc(C#CCCCN3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(F)(F)P(=O)(O)O)ccc5[nH]4)C3)cc2)cc1] | ((2-(((5S,8S,10aR)-8-(((S)-5-amino-1-(benzhydrylamino)-1,5-dioxopentan-2-yl)carbamoyl)-3-(5-(4-((S)-2-((2S,4R)-4-hydroxy-2-(((S)-1-(4-(4-methylthiazol-5-yl)phenyl)ethyl)carbamoyl)pyrrolidine-1-carbonyl)piperidine-1-carbonyl)phenyl)pent-4-yn-1-yl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 163 | 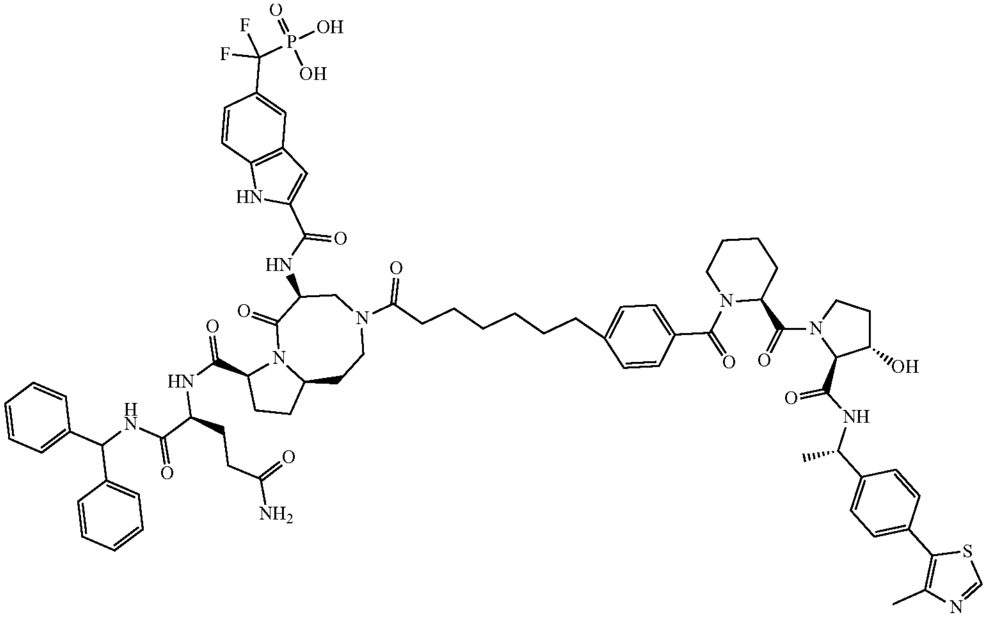 [SMILES: Cc1ncsc1-c1ccc([C@H](C)NC(=O)[C@@H]2[C@@H](O)CCN2C(=O)[C@@H]2CCCCN2C(=O)c2ccc(CCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(F)(F)P(=O)(O)O)ccc5[nH]4)C3)cc2)cc1] | ((2-(((5S,8S,10aR)-8-(((S)-5-amino-1-(benzhydrylamino)-1,5-dioxopentan-2-yl)carbamoyl)-3-(7-(4-((S)-2-((2S,3S)-3-hydroxy-2-(((S)-1-(4-(4-methylthiazol-5-yl)phenyl)ethyl)carbamoyl)pyrrolidine-1-carbonyl)piperidine-1-carbonyl)phenyl)heptanoyl)-6-oxodecahydropyrrolo[1,2-a][1,5]diazocin-5-yl)carbamoyl)-1H-indol-5-yl)difluoromethyl)phosphonic acid |
| 164 | 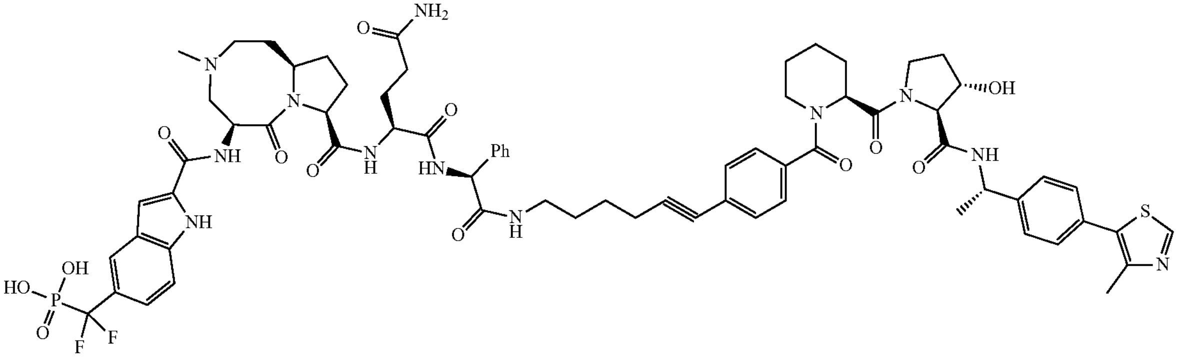 [SMILES: Cc1ncsc1-c1ccc([C@H](C)NC(=O)[C@@H]2[C@@H](O)CCN2C(=O)[C@@H]2CCCCN2C(=O)c2ccc(C#CCCCCNC(=O)[C@@H](NC(=O)[C@H](CCC(N)=O)NC(=O)[C@@H]3CC[C@@H]4CCN(C)C[C@H](NC(=O)c5cc6cc(C(F)(F)P(=O)(O)O)ccc6[nH]5)C(=O)N43)c3ccccc3)cc2)cc1] | ((2-(((5S,8S,10aR)-8-(((S)-5-amino-1-(((S)-2-((6-(4-((S)-2-((2S,3S)-3-hydroxy-2-(((S)-1-(4-(4-methylthiazol-5-yl)phenyl)ethyl)carbamoyl)pyrrolidine-1-carbonyl)piperidine-1-carbonyl)phenyl)hex-5-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 165 | 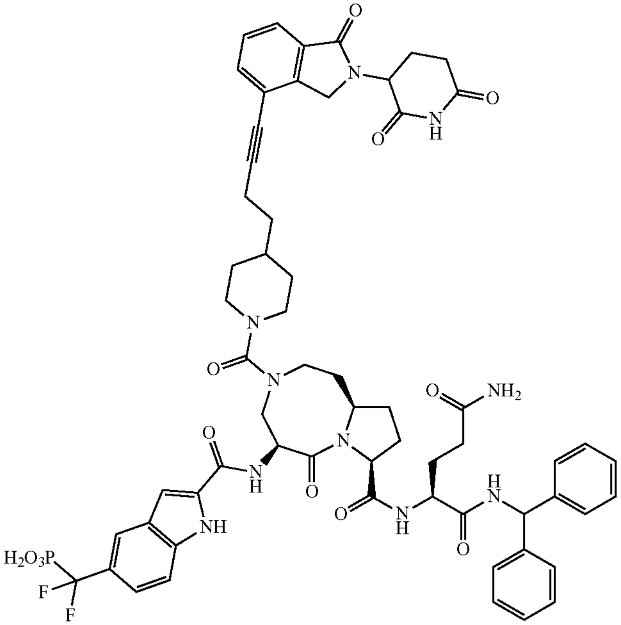 | ((2-(((5S,8S,10aR)-8-(((S)-5-amino-1-(benzhydrylamino)-1,5-dioxopentan-2-yl)carbamoyl)-3-(4-(4-(2-(2,6-dioxopiperidin-3-yl)-1-oxoisoindolin-4-yl)but-3-yn-1-yl)piperidine-1-carbonyl)-6-oxodecahydropyrrolo[1,2-a][1,5]diazocin-5-yl)carbamoyl)-1H-in-5-yl)difluoromethyl)phosphonic acid |

TABLE 1-continued
| Cpd. No. | Structure | Name |
|---|---|---|
| 166 | 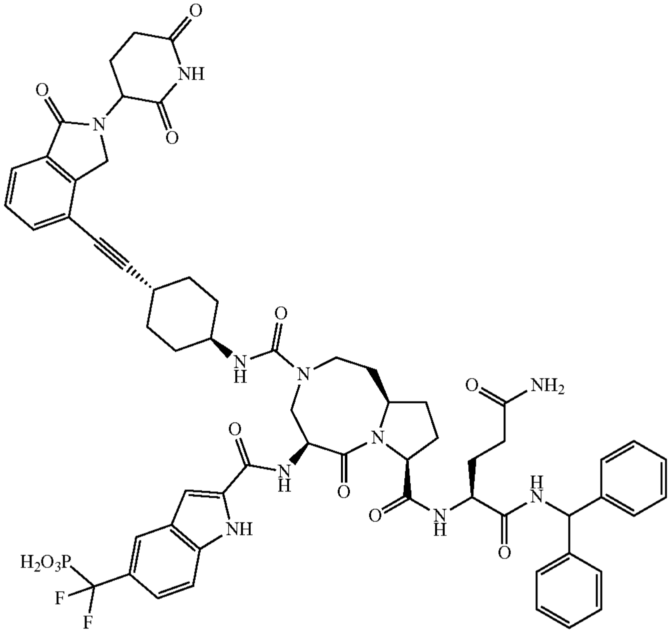 | ((2-(((5S,8S,10aR)-8-(((S)-5-amino-1-(benzhydrylamino)-1,5-dioxopentan-2-yl)carbamoyl)-3-(((1r,4S)-4-((2-(2,6-dioxopiperidin-3-yl)-1-oxoisoindolin-4-yl)ethynyl)cyclohexyl)carbamoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 167 | 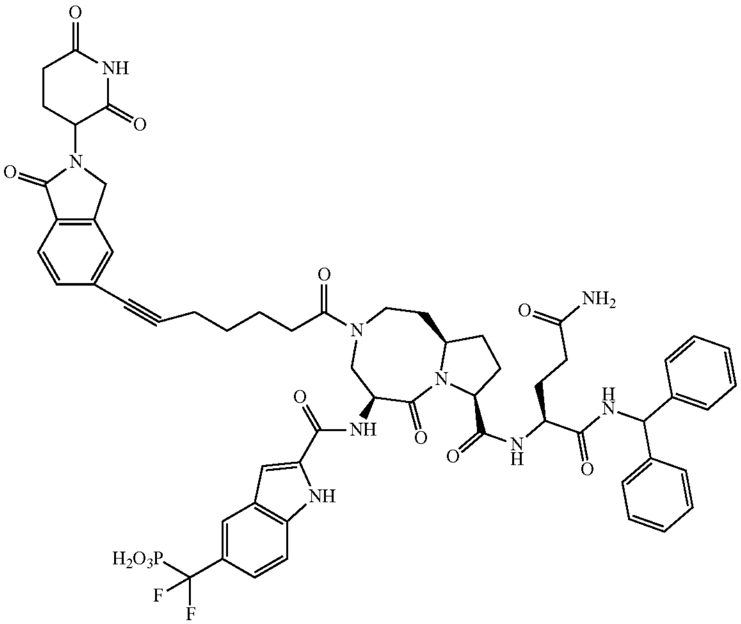 | ((2-(((5S,8S,10aR)-8-(((S)-5-amino-1-(benzhydrylamino)-1,5-dioxopentan-2-yl)carbamoyl)-3-(7-(2-(2,6-dioxopiperidin-3-yl)-1-oxoisoindolin-5-yl)hept-6-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 168 | 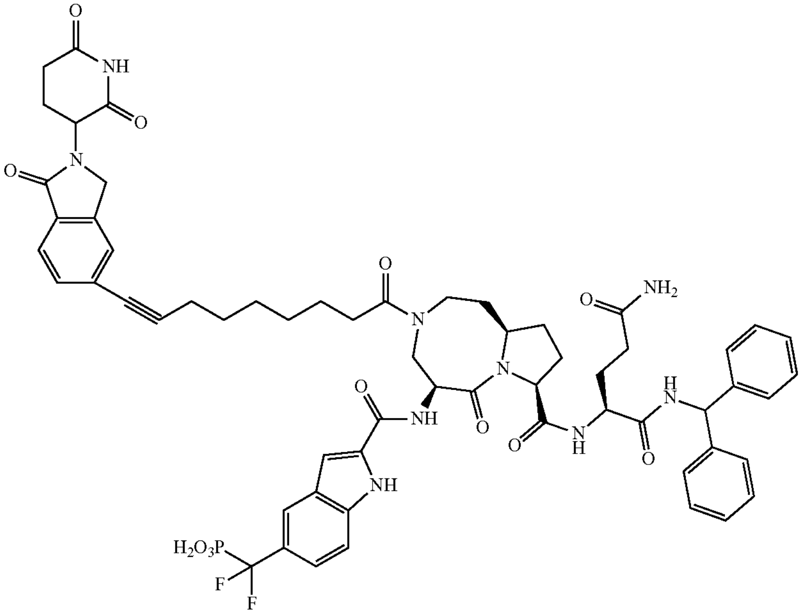 | ((2-(((5S,8S,10aR)-8-(((S)-5-amino-1-(benzhydrylamino)-1,5-dioxopentan-2-yl)carbamoyl)-3-(9-(2-(2,6-dioxopiperidin-3-yl)-1-oxoisoindolin-5-yl)non-8-ynoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 169 | 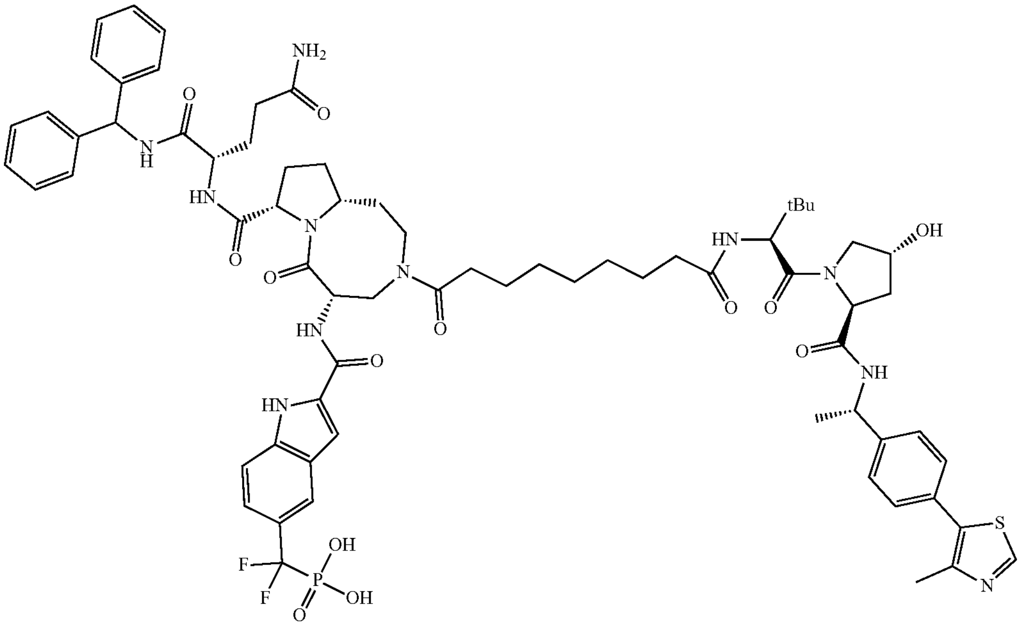 [SMILES: Cc1ncsc1-c1ccc([C@H](C)NC(=O)[C@@H]2C[C@@H](O)CN2C(=O)[C@@H](NC(=O)CCCCCCCC(=O)N2CC[C@H]3CC[C@@H](C(=O)N[C@@H](CCC(N)=O)C(=O)NC(c4ccccc4)c4ccccc4)N3C(=O)[C@@H](NC(=O)c3cc4cc(C(F)(F)P(=O)(O)O)ccc4[nH]3)C2)C(C)(C)C)cc1] | ((2-(((5S,8S,10aR)-8-(((S)-5-amino-1-(benzhydrylamino)-1,5-dioxopentan-2-yl)carbamoyl)-3-(9-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-9-oxononanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
|---|---|---|
| 170 | 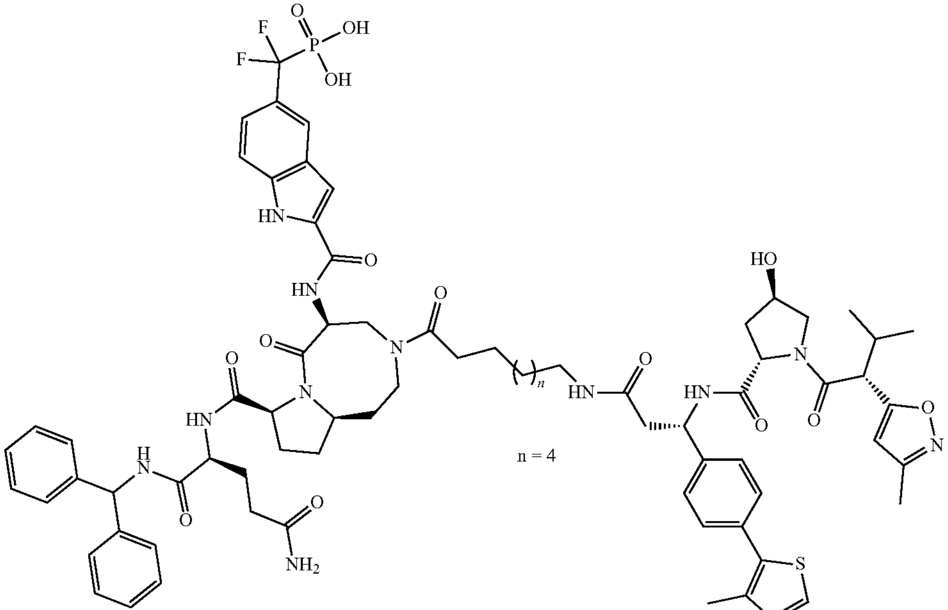 n = 4 | ((2-(((5S,8S,10aR)-8-(((S)-5-amino-1-(benzhydrylamino)-1,5-dioxopentan-2-yl)carbamoyl)-3-(5-((S)-3-((2S,4R)-4-hydroxy-1-((R)-3-methyl-2-(3-methylisoxazol-5-yl)butanoyl)pyrrolidine-2-carboxamido)-3-(4-(4-methylthiazol-5-yl)phenyl)propanamido)pentanoyl)-6-oxodecahydropyrrolo[1,2-a][1,5]diazocin-5-yl)carbamoyl)-1H-indol-5-yl)difluoromethyl)phosphonic acid |

TABLE 1-continued
| Cpd. No. | Structure | Name |
| --- | --- | --- |
| 171 | 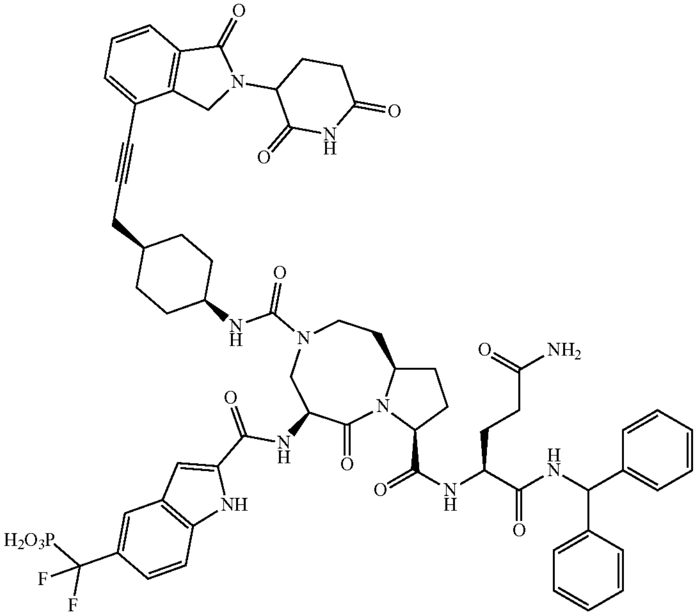 | ((2-(((5S,8S,10aR)-8-(((S)-5-amino-1-(benzhydrylamino)-1,5-dioxopentan-2-yl)carbamoyl)-3-(((1s,4R)-4-(3-(2-(2,6-dioxopiperidin-3-yl)-1-oxoisoindolin-4-yl)prop-2-yn-1-yl)cyclohexyl)carbamoyl)-6-oxodecahydropyrrolo[1,2-a][1,5]diazocin-5-yl)carbamoyl)-1H-indol-5-yl)difluoromethyl)phosphonic acid |

TABLE 1-continued

| Cpd. No. | Structure | Name |
| --- | --- | --- |
| 172 | 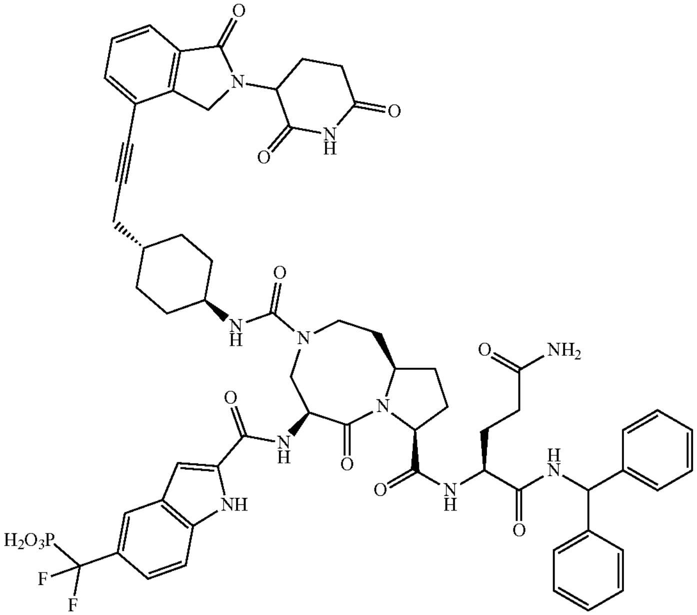 | ((2-(((5S,8S,10aR)-8-(((S)-5-amino-1-(benzhydrylamino)-1,5-dioxopentan-2-yl)carbamoyl)-3-(((1r,4S)-4-(3-(2-(2,6-dioxopiperidin-3-yl)-1-oxoisoindolin-4-yl)prop-2-yn-1-yl)cyclohexyl)carbamoyl)-6-oxodecahydropyrrolo[1,2-a][1,5]diazocin-5-yl)carbamoyl)-1H-indol-5-yl)difluoromethyl)phosphonic acid |
| 173 | 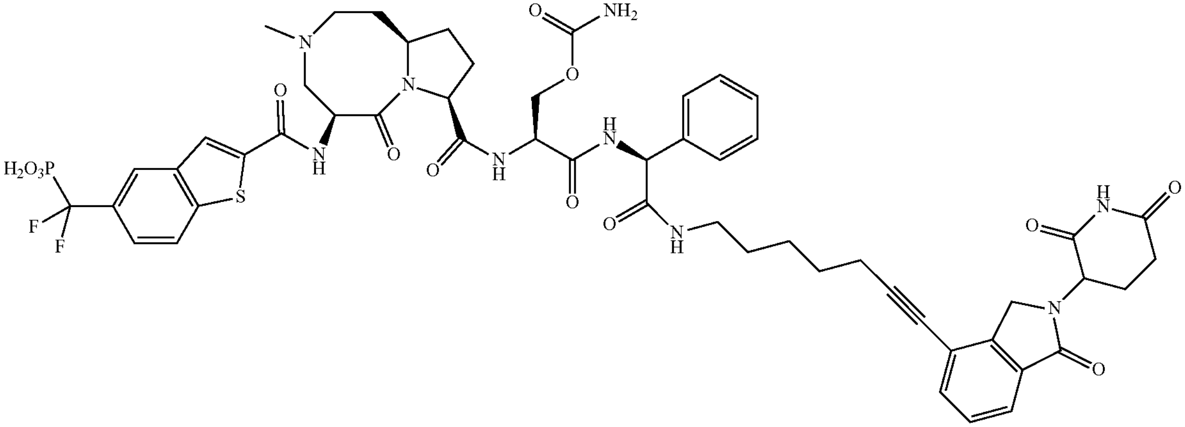 | ((2-(((5S,8S,10aR)-8-(((2S)-3-(carbamoyloxy)-1-(((1S)-2-((7-(2-(2,6-dioxopiperidin-3-yl)-1-oxoisoindolin-4-yl)hept-6-yn-1-yl)amino)-2-oxo-1-phenylethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 174 | 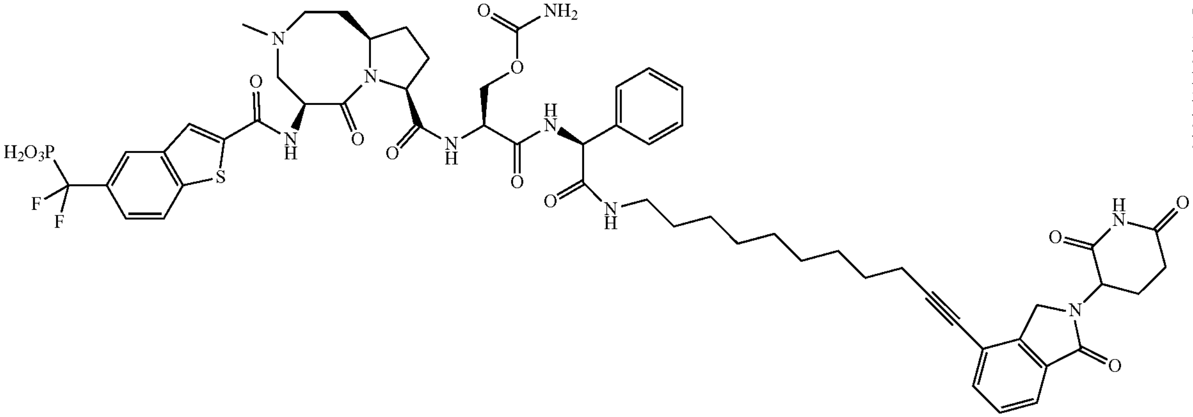 | ((2-(((5S,8S,10aR)-8-(((2S)-3-(carbamoyloxy)-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 175 | 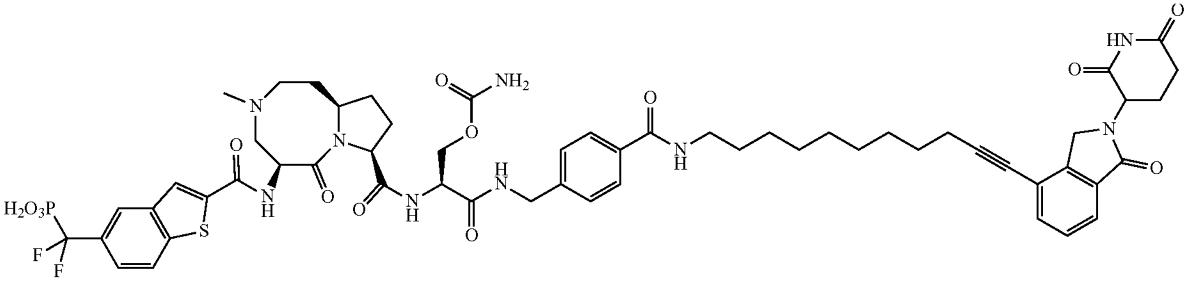 | ((2-(((5S,8S,10aR)-8-(((2S)-3-(carbamoyloxy)-1-((4-((11-(2-(2,6-dioxopiperidin-3-yl)-1-oxoisoindolin-4-yl)undec-10-yn-1-yl)carbamoyl)benzyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 176 | 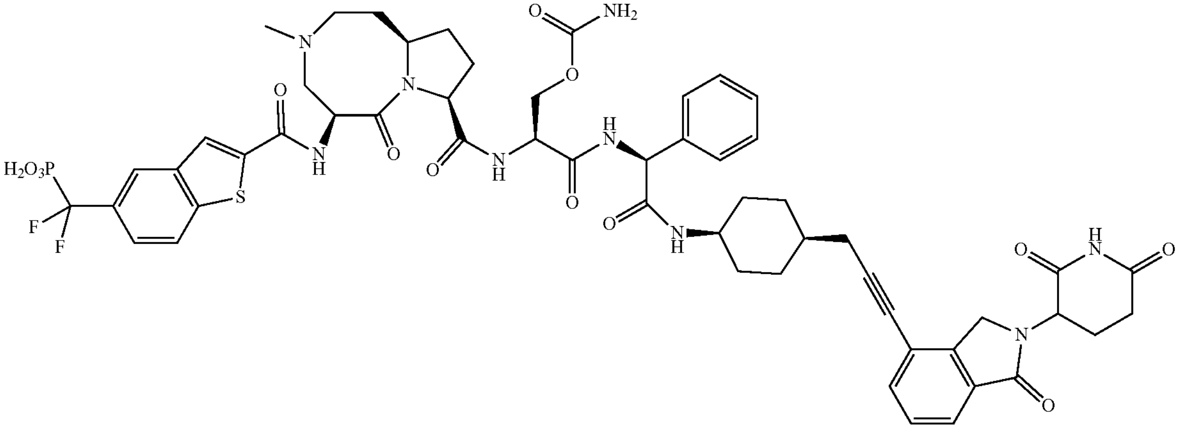 | ((2-(((5S,8S,10aR)-8-(((2S)-3-(carbamoyloxy)-1-(((1S)-2-(((1s,4R)-4-(3-(2-(2,6-dioxopiperidin-3-yl)-1-oxoisoindolin-4-yl)prop-2-yn-1-yl)cyclohexyl)amino)-2-oxo-1-phenylethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 177 | 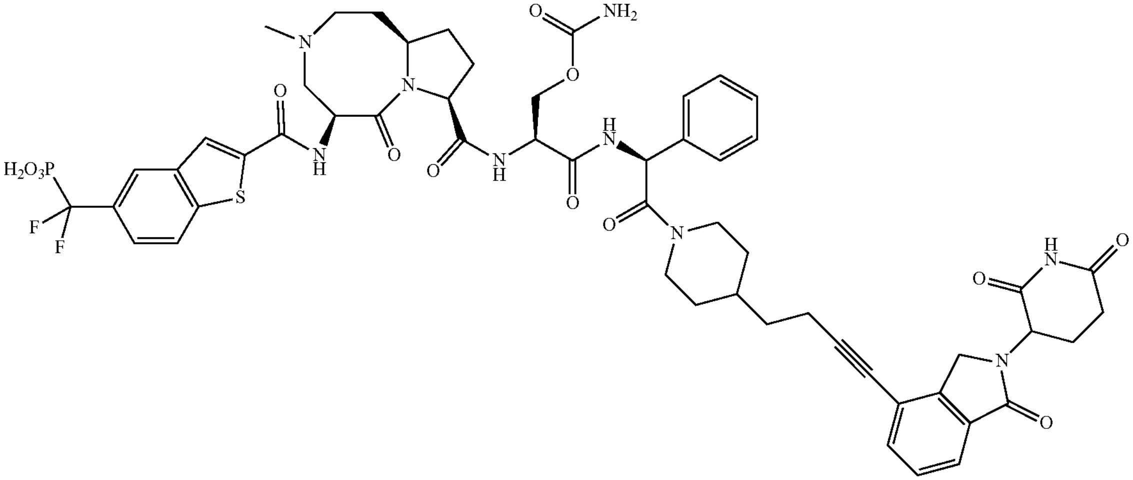 | ((2-(((5S,8S,10aR)-8-(((2S)-3-(carbamoyloxy)-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 178 | 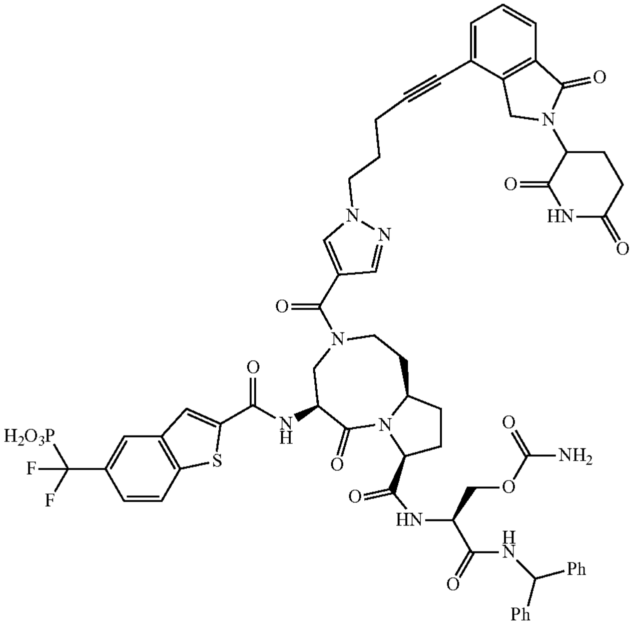 | ((2-(((5S,8S,10aR)-8-(((S)-1-(benzhydrylamino)-3-(carbamoyloxy)-1-oxopropan-2-yl)carbamoyl)-3-(1-(5-(2-(2,6-dioxopiperidin-3-yl)-1-oxoisoindolin-4-yl)pent-4-yn-1-yl)-1H-pyrazole-4-carbonyl)-6-oxodecahydropyrrolo[1,2-a][1,5]diazocin-5-yl)carbamoyl)benzo[b]thiophen-5-yl)difluoromethyl)phosphonic acid |
| 179 | 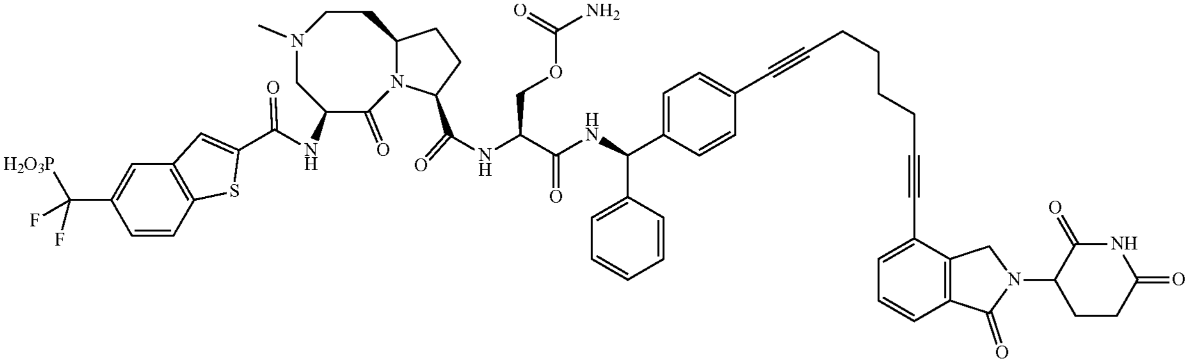 | ((2-(((5S,8S,10aR)-8-(((2S)-3-(carbamoyloxy)-1-(((1R)-(4-(8-(2-(2,6-dioxopiperidin-3-yl)-1-oxoisoindolin-4-yl)octa-1,7-diyn-1-yl)phenyl)(phenyl)methyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 180 | 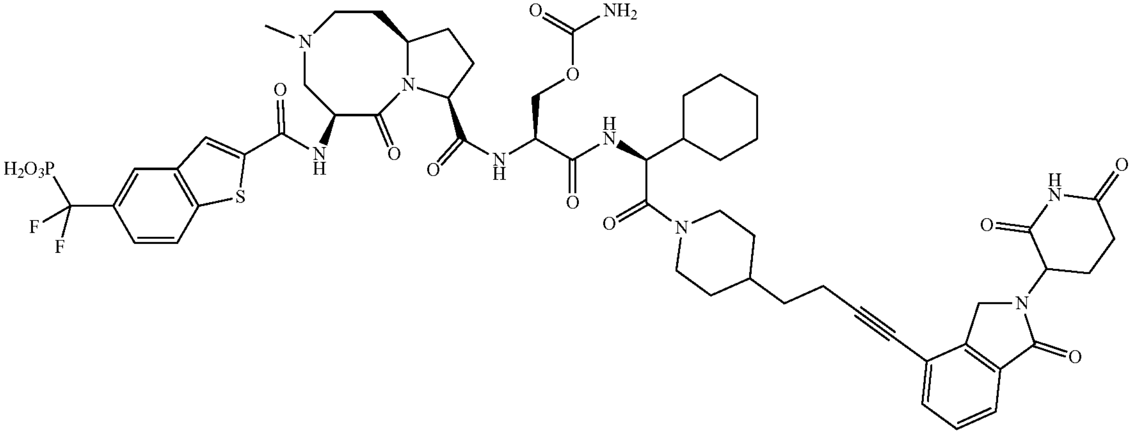 | ((2-(((5S,8S,10aR)-8-(((2S)-3-(carbamoyloxy)-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 181 | 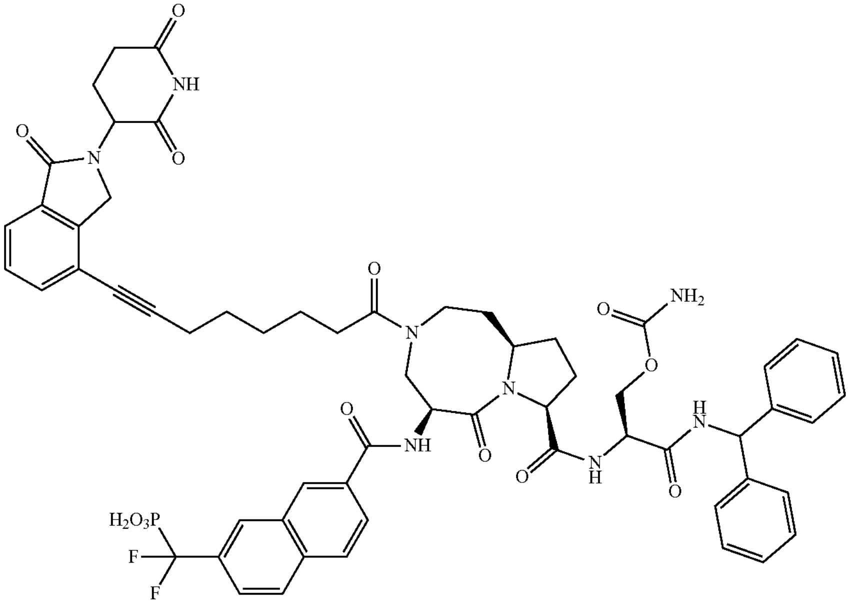 | ((7-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)naphthalen-2-yl)difluoromethyl)phosphonic acid |

TABLE 1-continued

| Cpd. No. | Structure | Name |
|---|---|---|
| 182 | 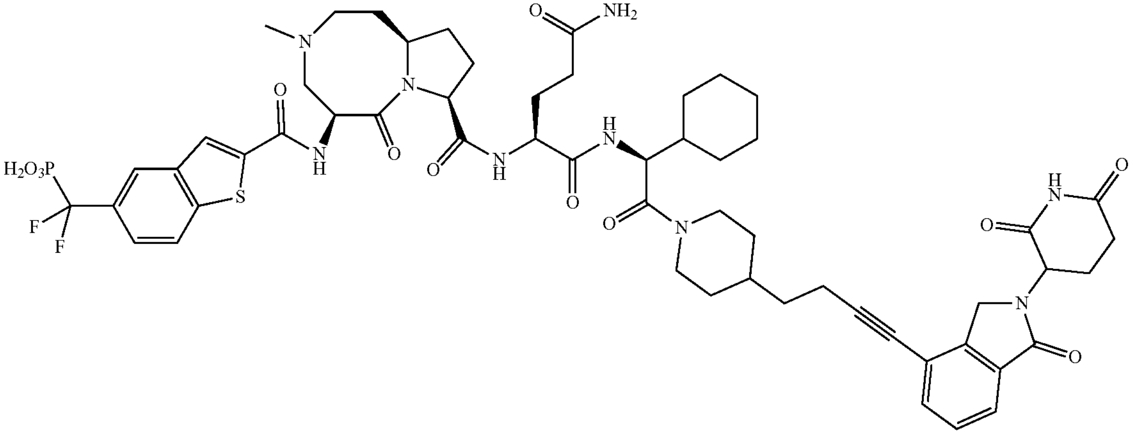 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 183 | 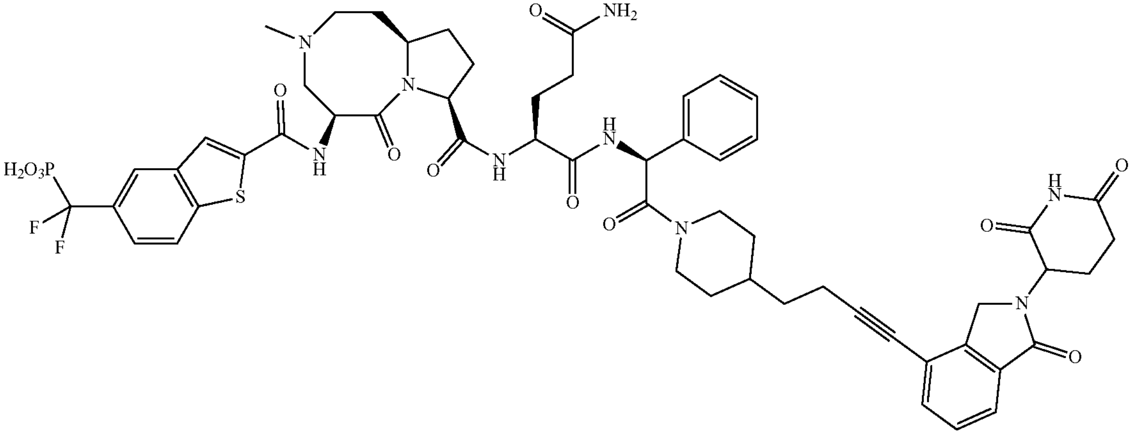 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 184 | 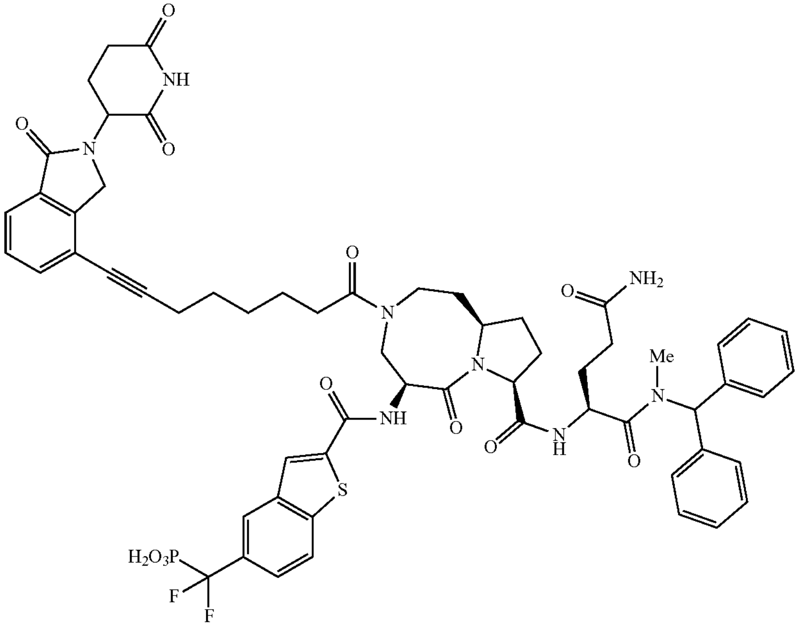 | ((2-(((5S,8S,10aR)-8-(((S)-5-amino-1-(benzhydryl(methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |
| 185 | 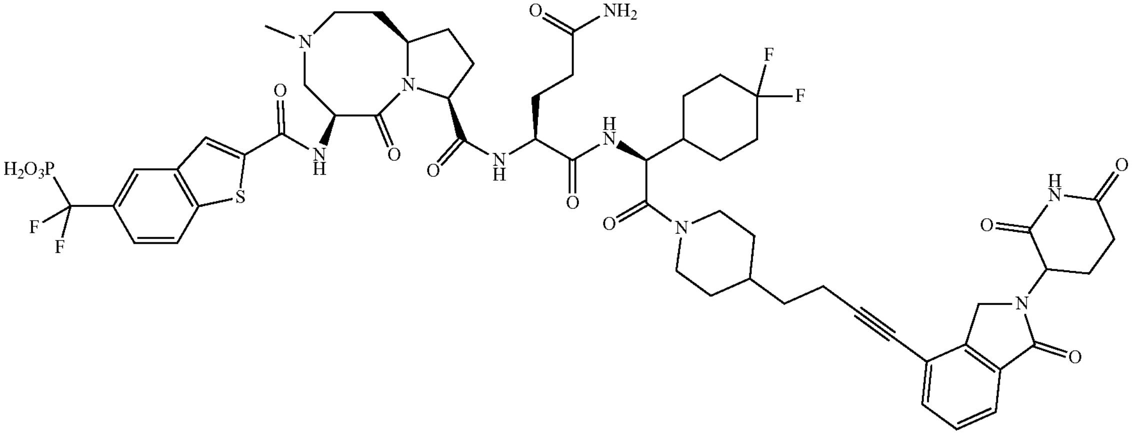 | ((2-(((5S,8S,10aR)-8-(((2S)-5-amino-1-(((1S)-1-(4,4-difluorocyclohexyl)-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 186 | 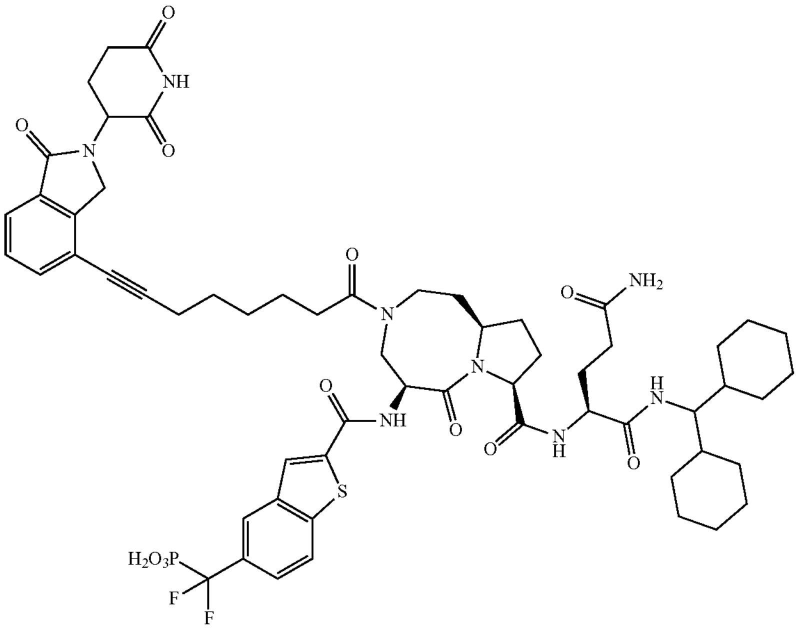 | ((2-(((5S,8S,10aR)-8-(((S)-5-amino-1-((dicyclohexylmethyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 187 | 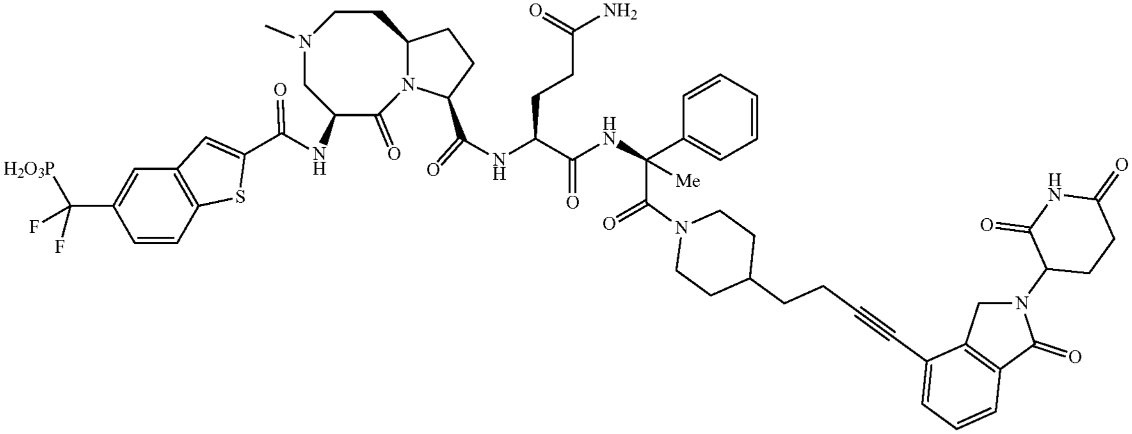 | ((2-(((5S,8S,10aR)-8-(((2S)-5-amino-1-((1-(4-(4-(2-(2,6-dioxopiperidin-3-yl)-1-oxoisoindolin-4-yl)but-3-yn-1-yl)piperidin-1-yl)-1-oxo-2-phenylpropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 188 | 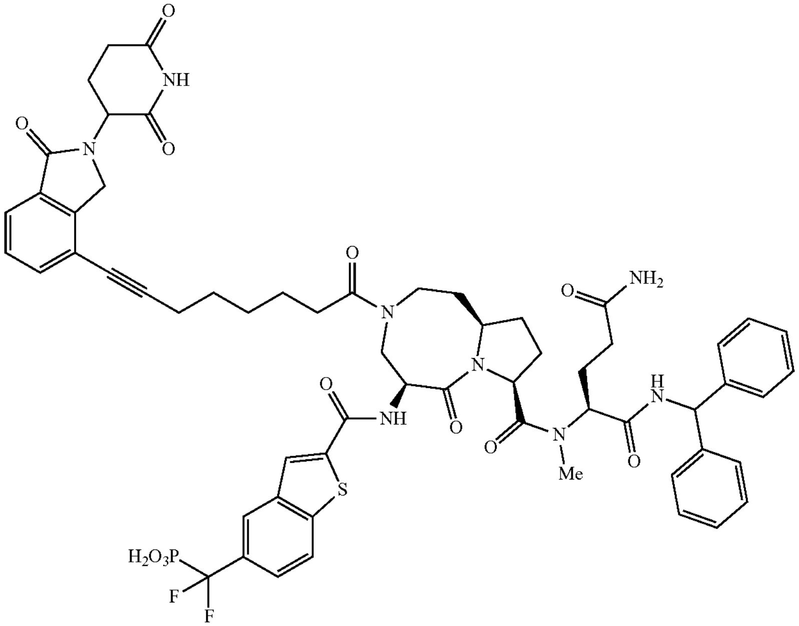 | ((2-(((5S,8S,10aR)-8-(((S)-5-amino-1-(benzhydrylamino)-1,5-dioxopentan-2-yl)(methyl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 189 | 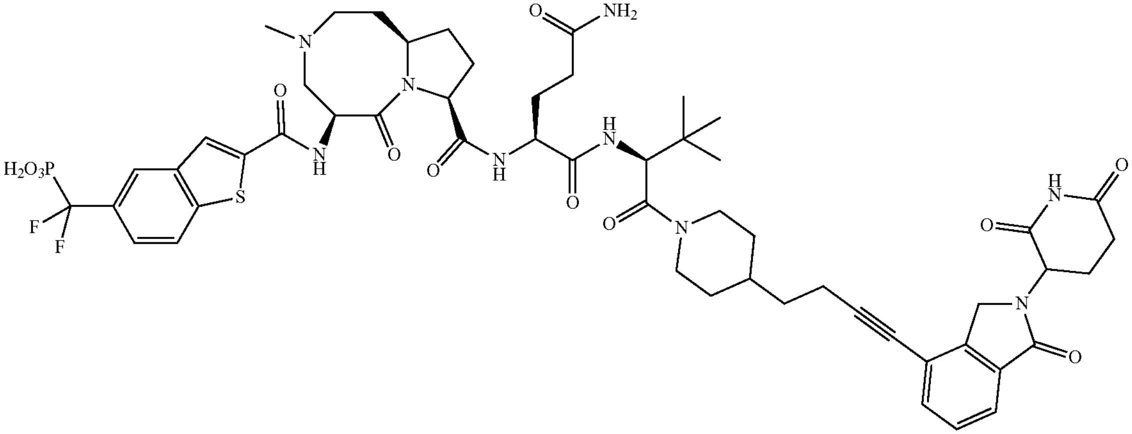 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3,3-dimethyl-1-oxobutan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 190 | 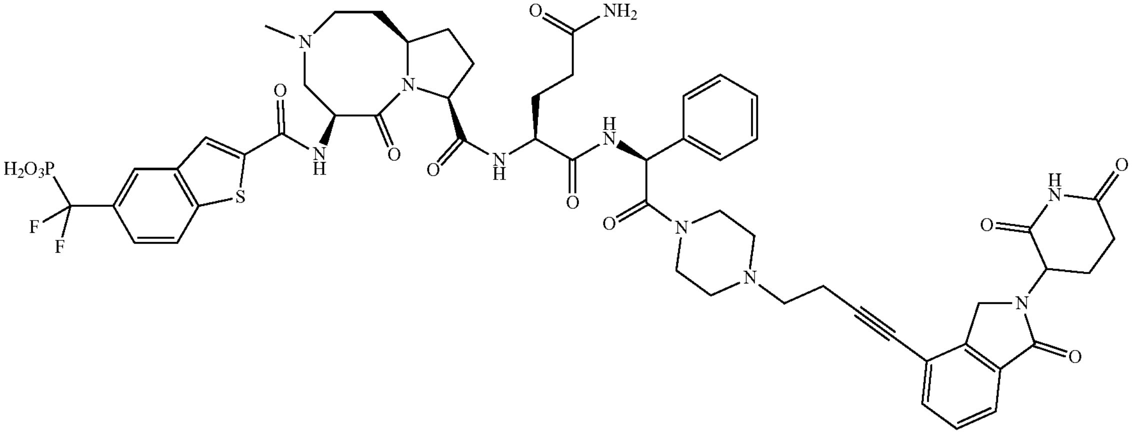 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperazin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 191 | 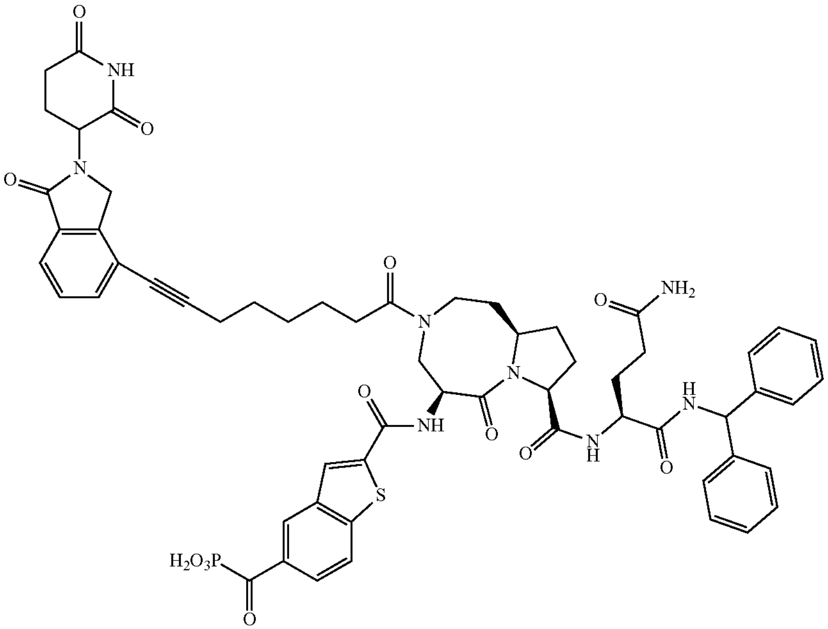 | (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophene-5-carbonyl)phosphonic acid |

TABLE 1-continued
| Cpd. No. | Structure | Name |
| --- | --- | --- |
| 191E | 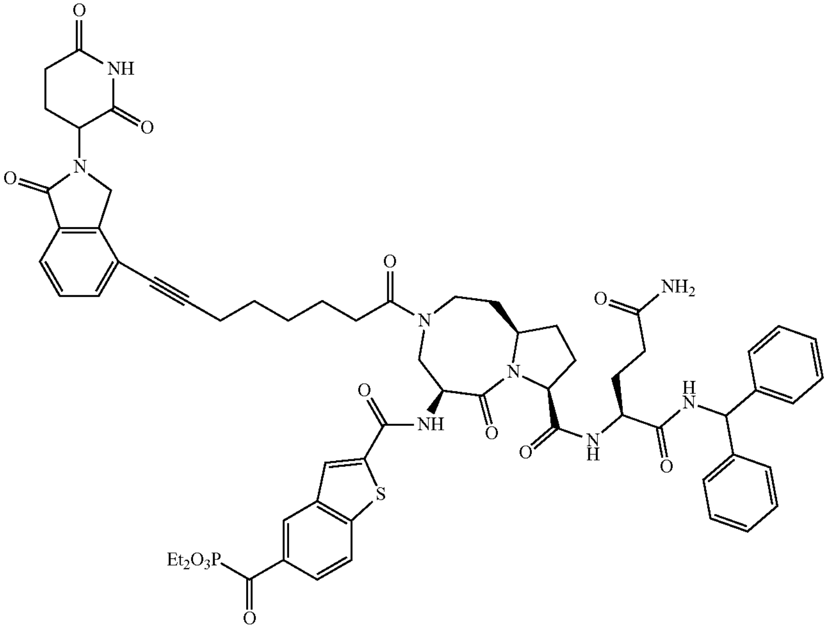 | (2S)-N1-benzhydryl-2-((5S,8S,10aR)-5-(5-(((diethyl-13-oxidaneyl)(11-oxidaneyl)phosphoryl)carbonyl)benzo[b]thiophene-2-carboxamido)-3-(8-(2-(2,6-dioxopiperidin-3-yl)-1-oxoisoindolin-4-yl)oct-7-ynoyl)-6-oxodecahydropyrrolo[1,2-a][1,5]diazocine-8-carboxamido)pentanediamide |

TABLE 1-continued

| Cpd. No. | Structure | Name |
|---|---|---|
| 192 | 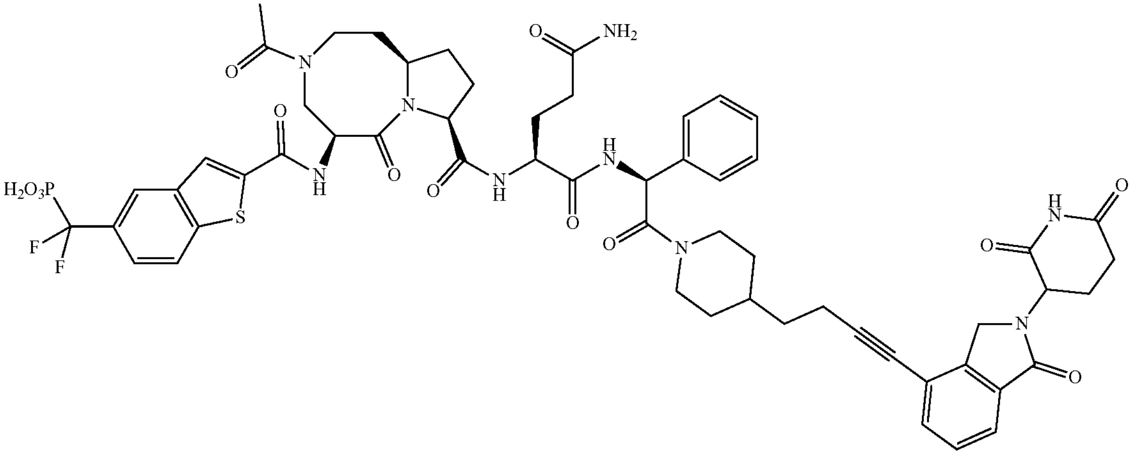 | ((2-(((5S,8S,10aR)-3-acetyl-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-6-oxodecahydropyrrolo[1,2-a][1,5]diazocin-5-yl)carbamoyl)benzo[b]thiophen-5-yl)difluoromethyl)phosphonic acid |
| 193 | 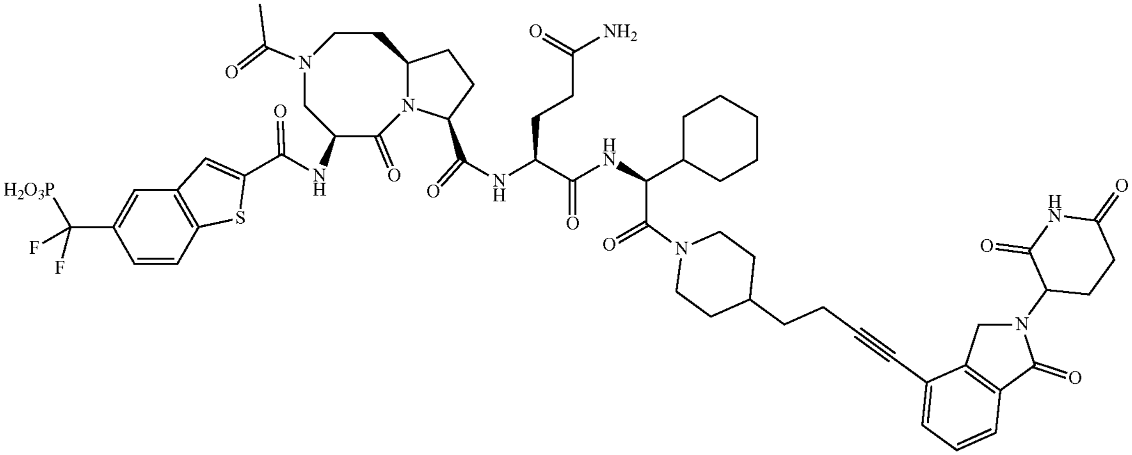 | ((2-(((5S,8S,10aR)-3-acetyl-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 194 | 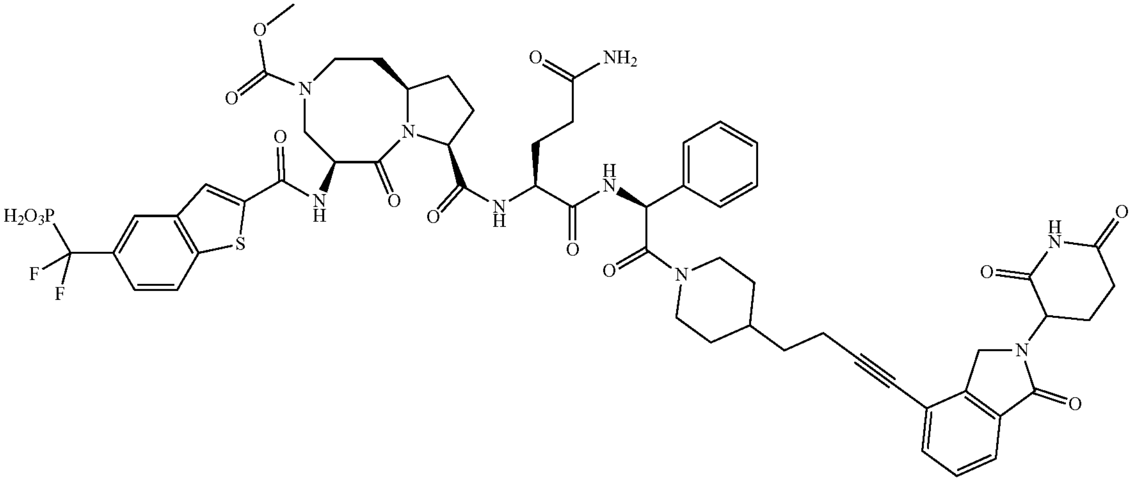 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 195 | 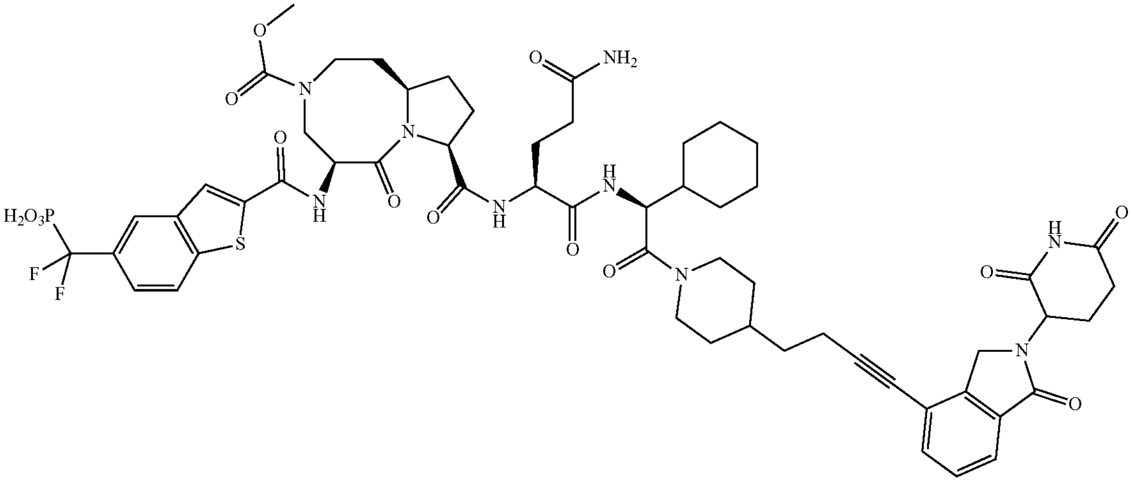 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 196 | 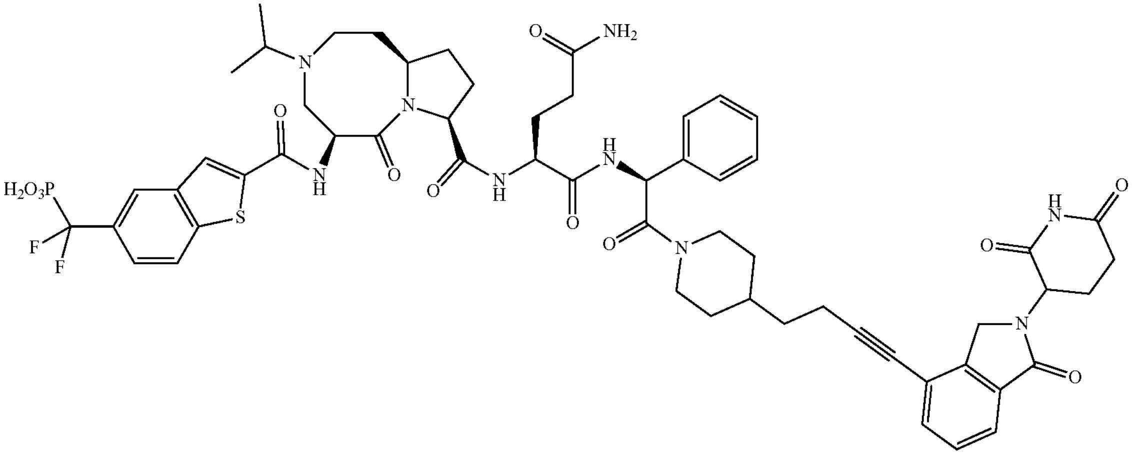 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-isopropyl-6-oxodecahydropyrrolo[1,2-a][1,5]diazocin-5-yl)carbamoyl)benzo[b]thiophen-5-yl)difluoromethyl)phosphonic acid |
| 197 | 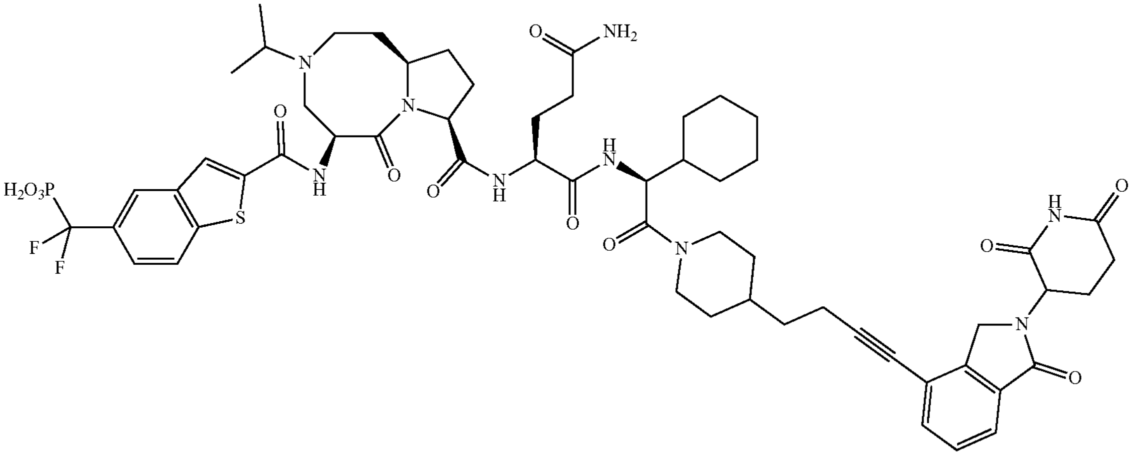 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-isopropyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 198 | 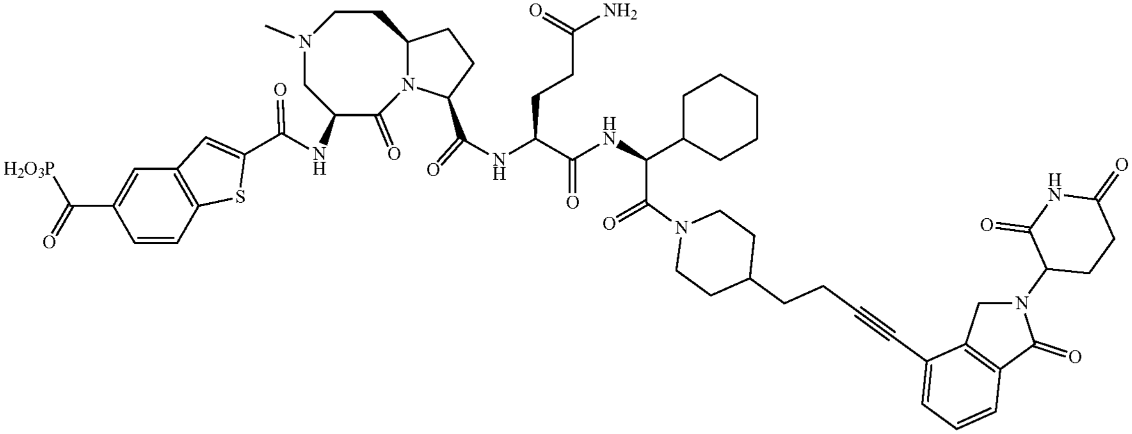 | (2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophene-5-carbonyl) phosphonic acid |
| 199 | 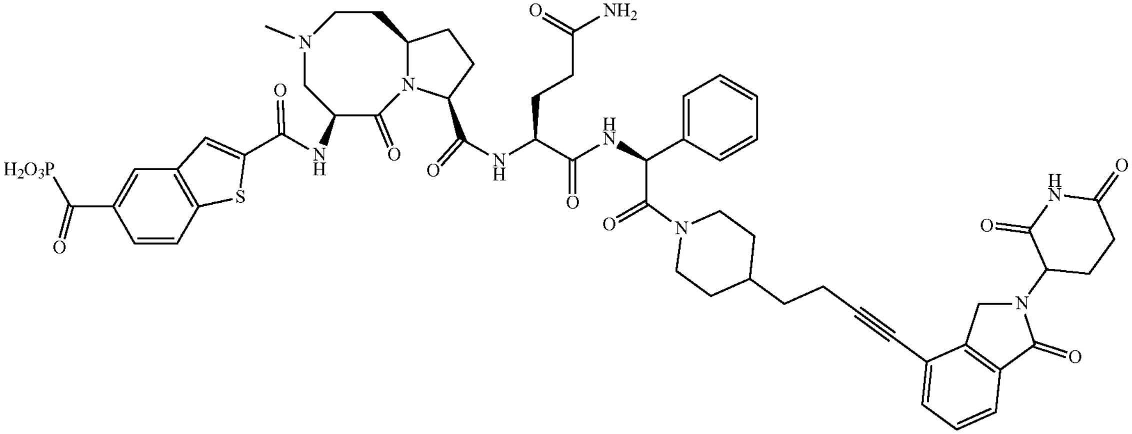 | (2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophene-5-carbonyl) phosphonic acid |

TABLE 1-continued

| Cpd. No. | Structure | Name |
| --- | --- | --- |
| 243 | 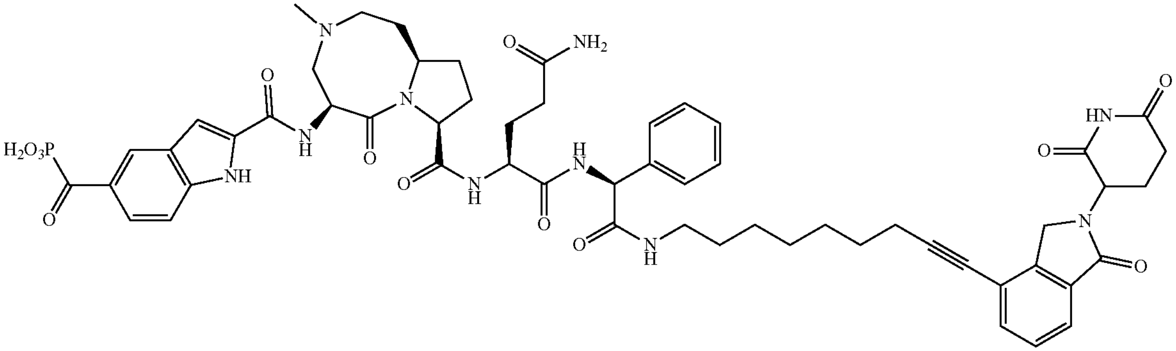 | (2-(((5S,8S,10aR)-8-(((2S)-5-amino-1-(((1S)-2-((9-(2-(2,6-dioxopiperidin-3-yl)-1-oxoisoindolin-4-yl)non-8-yn-1-yl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid |
| 244 | 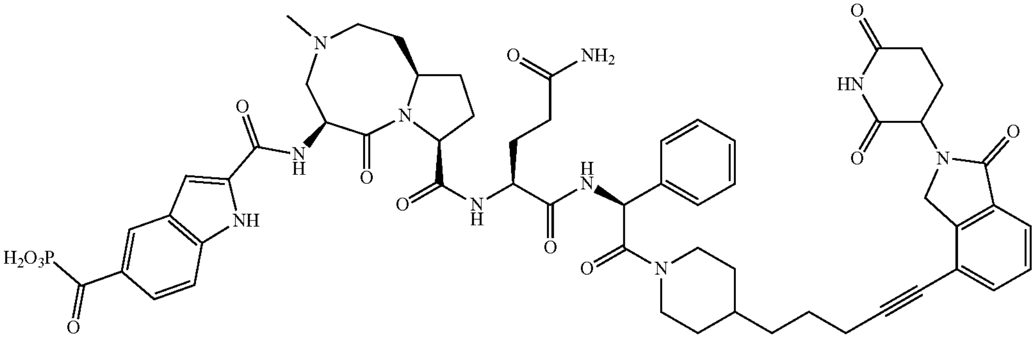 | (2-(((5S,8S,10aR)-8-(((2S)-5-amino-1-(((1S)-2-(4-(5-(2-(2,6-dioxopiperidin-3-yl)-1-oxoisoindolin-4-yl)pent-4-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid |
| 245 | 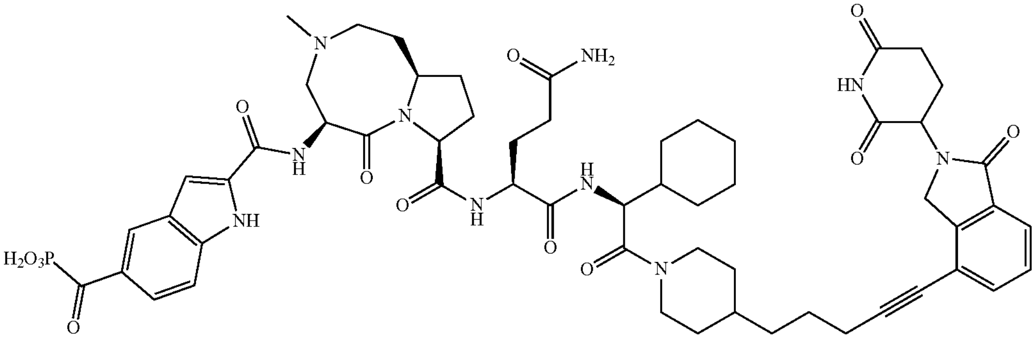 | (2-(((5S,8S,10aR)-8-(((2S)-5-amino-1-(((1S)-1-cyclohexyl-2-(4-(5-(2-(2,6-dioxopiperidin-3-yl)-1-oxoisoindolin-4-yl)pent-4-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid |

TABLE 1-continued

| Cpd. No. | Structure | Name |
| --- | --- | --- |
| 246 | 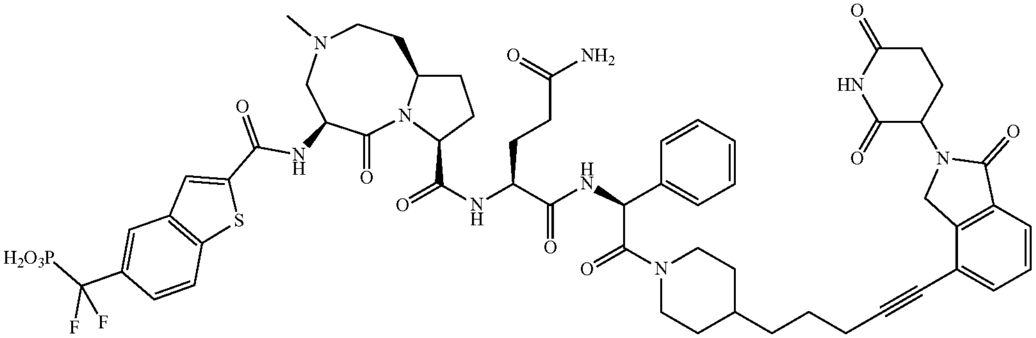 | ((2-(((5S,8S,10aR)-8-(((2S)-5-amino-1-(((1S)-2-(4-(5-(2-(2,6-dioxopiperidin-3-yl)-1-oxoisoindolin-4-yl)pent-4-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 247 | 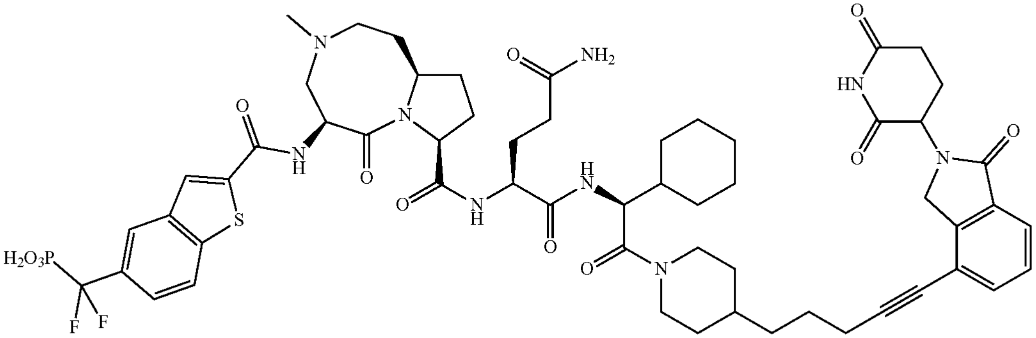 | ((2-(((5S,8S,10aR)-8-(((2S)-5-amino-1-(((1S)-1-cyclohexyl-2-(4-(5-(2-(2,6-dioxopiperidin-3-yl)-1-oxoisoindolin-4-yl)pent-4-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 248 | 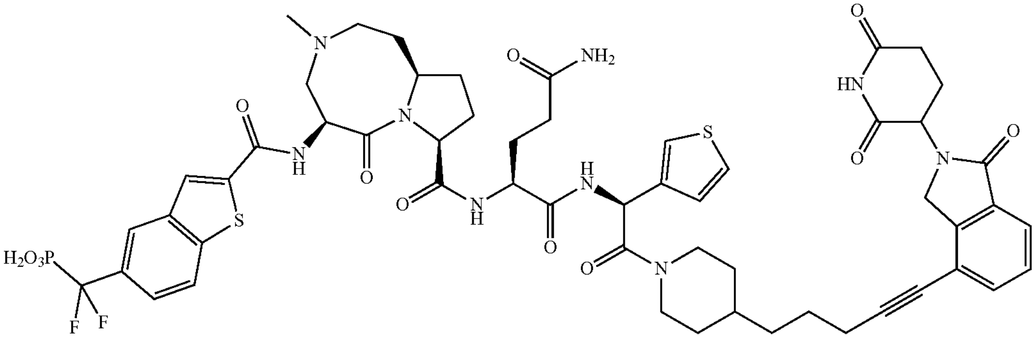 | ((2-(((5S,8S,10aR)-8-(((2S)-5-amino-1-(((1S)-2-(4-(5-(2-(2,6-dioxopiperidin-3-yl)-1-oxoisoindolin-4-yl)pent-4-yn-1-yl)piperidin-1-yl)-2-oxo-1-(thiophen-3-yl)ethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 249 | 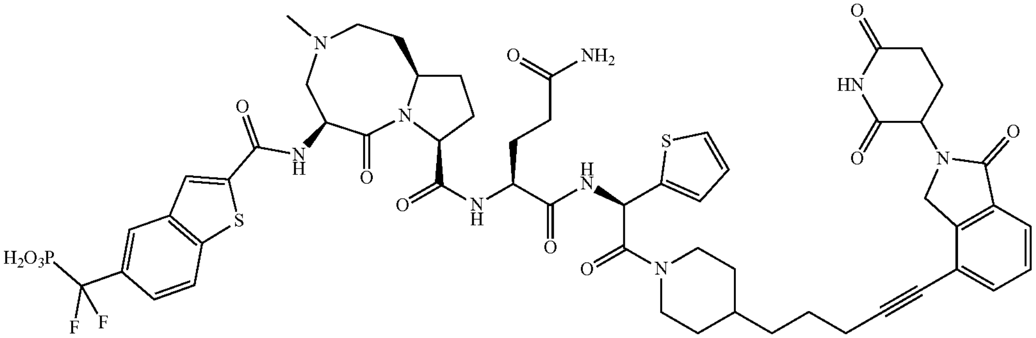 | ((2-(((5S,8S,10aR)-8-(((2S)-5-amino-1-(((1R)-2-(4-(5-(2-(2,6-dioxopiperidin-3-yl)-1-oxoisoindolin-4-yl)pent-4-yn-1-yl)piperidin-1-yl)-2-oxo-1-(thiophen-2-yl)ethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 250 | 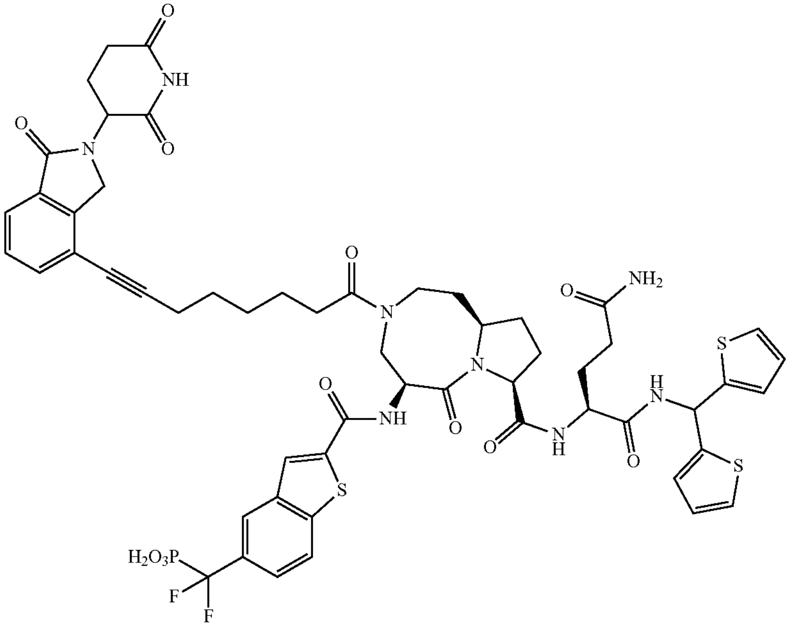 | ((2-(((5S,8S,10aR)-8-(((S)-5-amino-1-((di(thiophen-2-yl)methyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 251 | 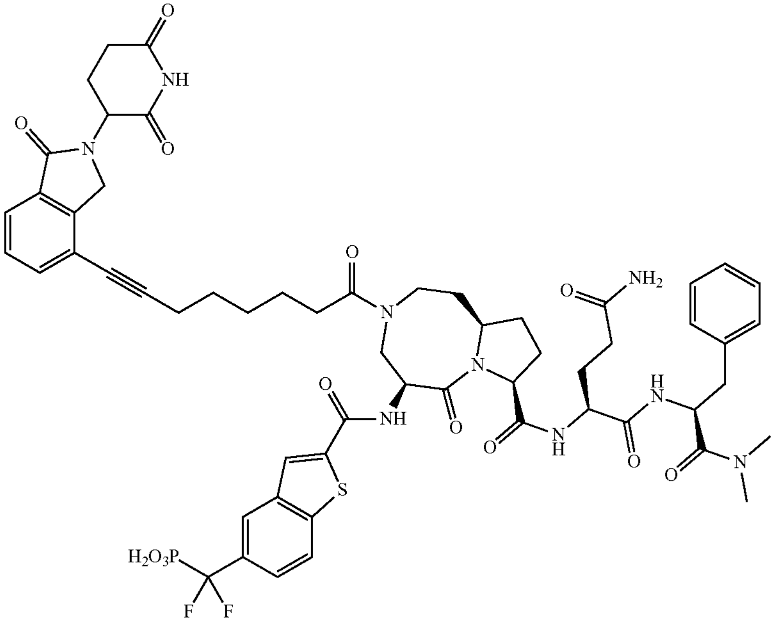 | ((2-(((5S,8S,10aR)-8-(((S)-5-amino-1-(((S)-1-(dimethylamino)-1-oxo-3-phenylpropan-2-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 252 | 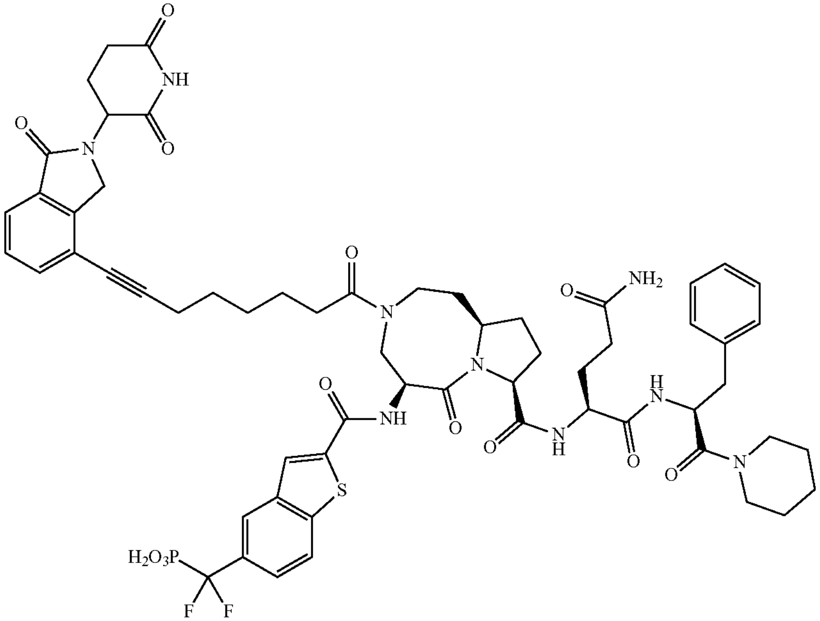 | ((2-(((5S,8S,10aR)-8-(((S)-5-amino-1,5-dioxo-1-(((S)-1-oxo-3-phenyl-iperidinedin-1-yl)propan-2-yl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
|---|---|---|
| 253 | 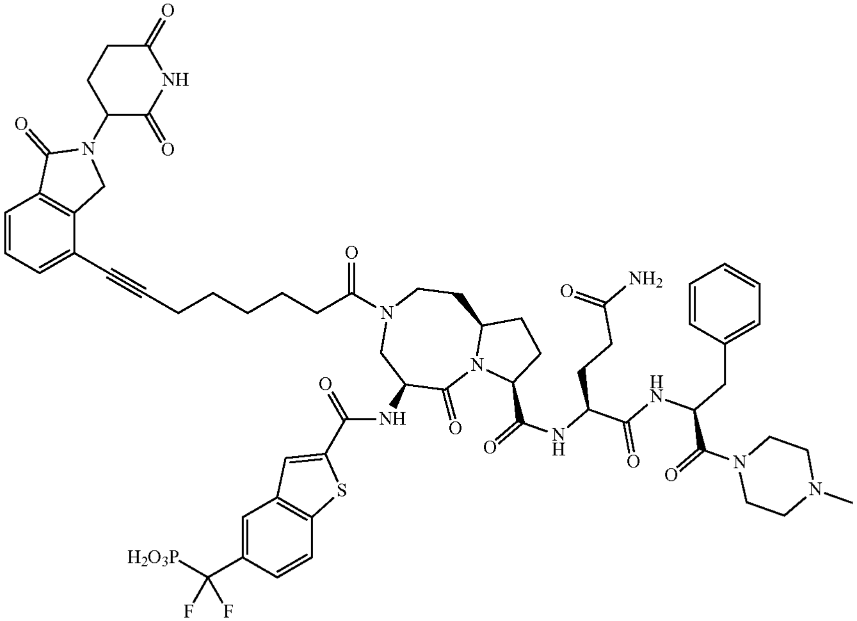 | ((2-(((5S,8S,10aR)-8-(((S)-5-amino-1-(((S)-1-(4-methylpiperazin-1-yl)-1-oxo-3-phenylpropan-2-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 254 | 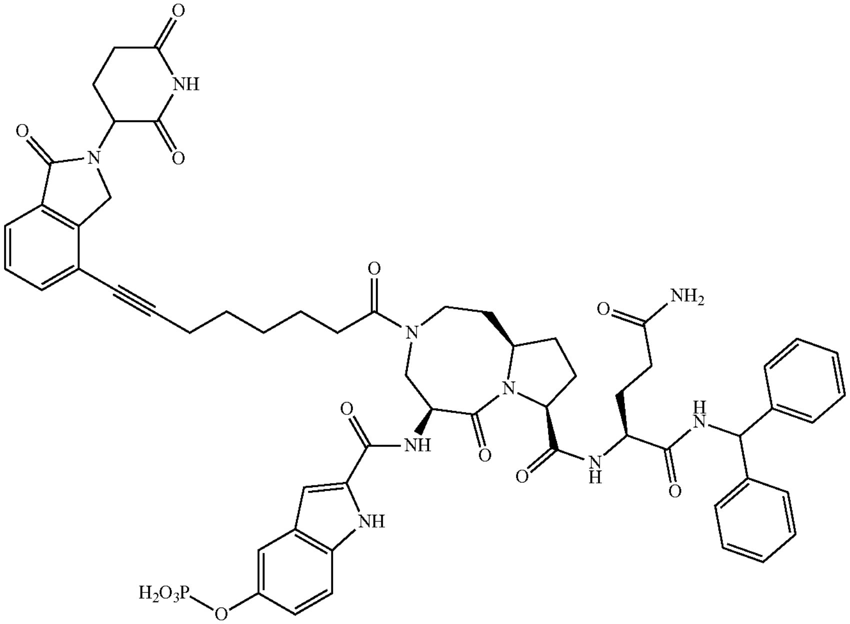 | 2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl dihydrogen phosphate |

TABLE 1-continued
| Cpd. No. | Structure | Name |
| --- | --- | --- |
| 255 | 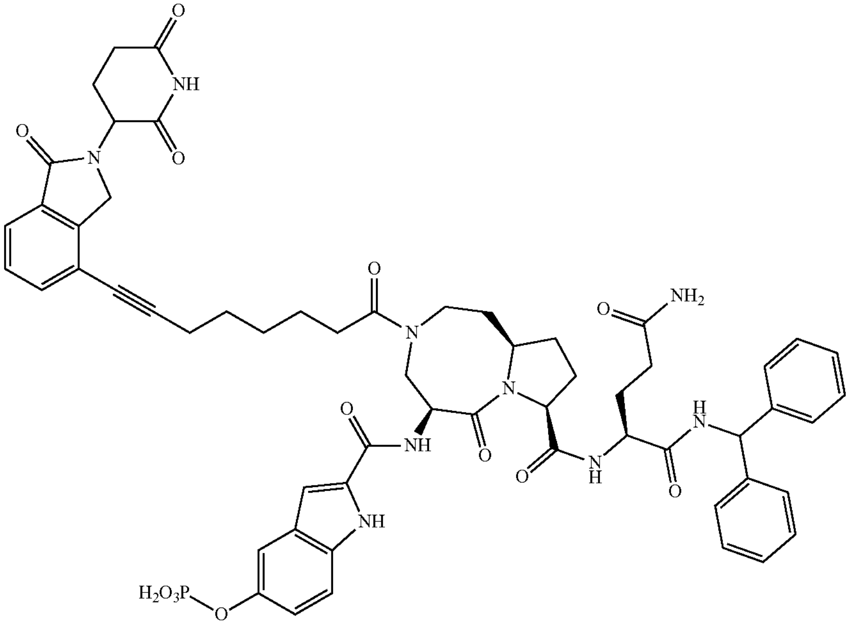 | ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)methyl)phosphonic acid |

TABLE 1-continued
| Cpd. No. | Structure | Name |
| --- | --- | --- |
| 256 | 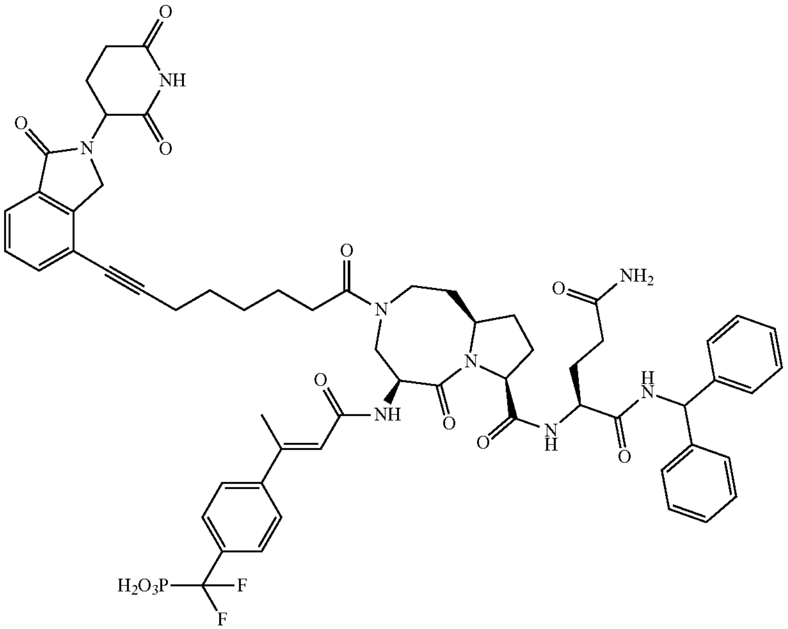 | ((4-((E)-4-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)amino)-4-oxobut-2-en-2-yl)phenyl)difluoromethyl)phosphonic acid |

TABLE 1-continued

| Cpd. No. | Structure | Name |
| --- | --- | --- |
| 257 | 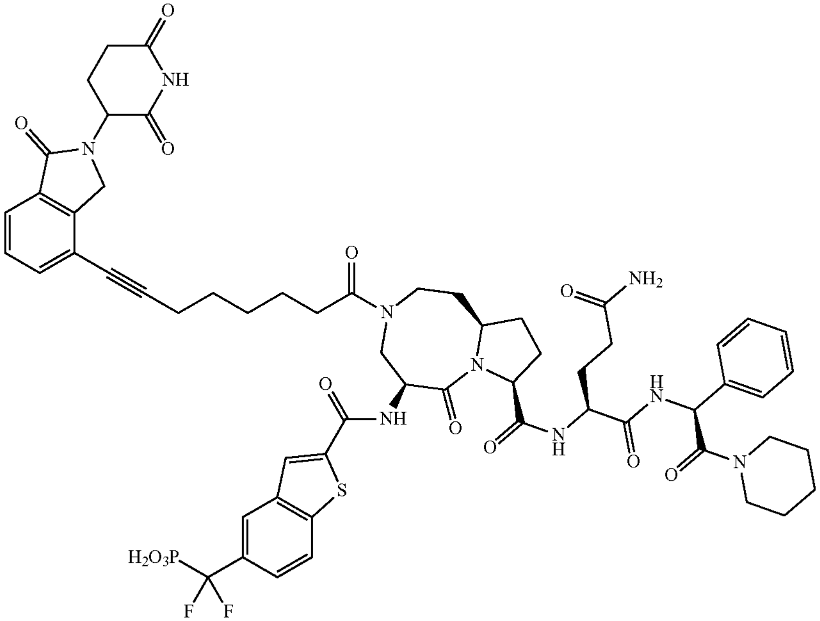 | ((2-(((5S,8S,10aR)-8-(((S)-5-amino-1,5-dioxo-1-(((S)-2-oxo-1-phenyl-iperidinedin-1-yl)ethyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |
| 258 | 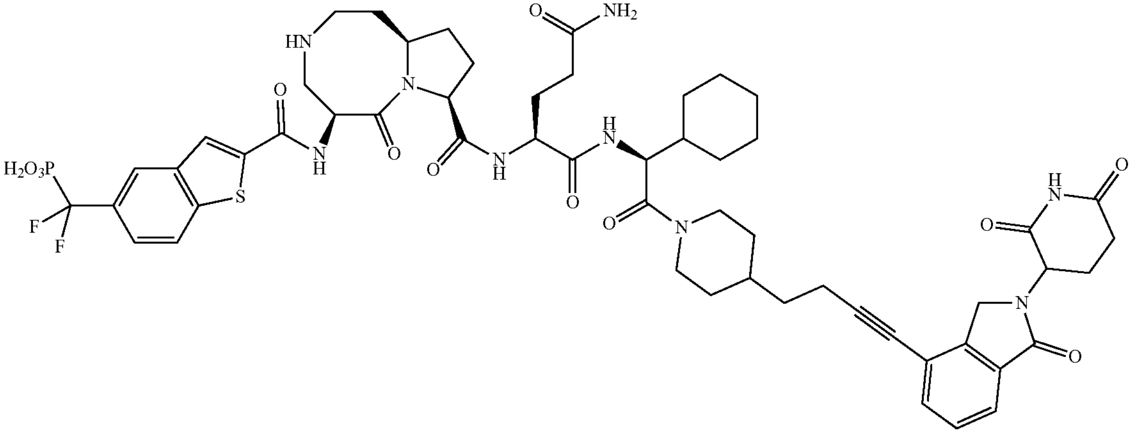 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 259 | 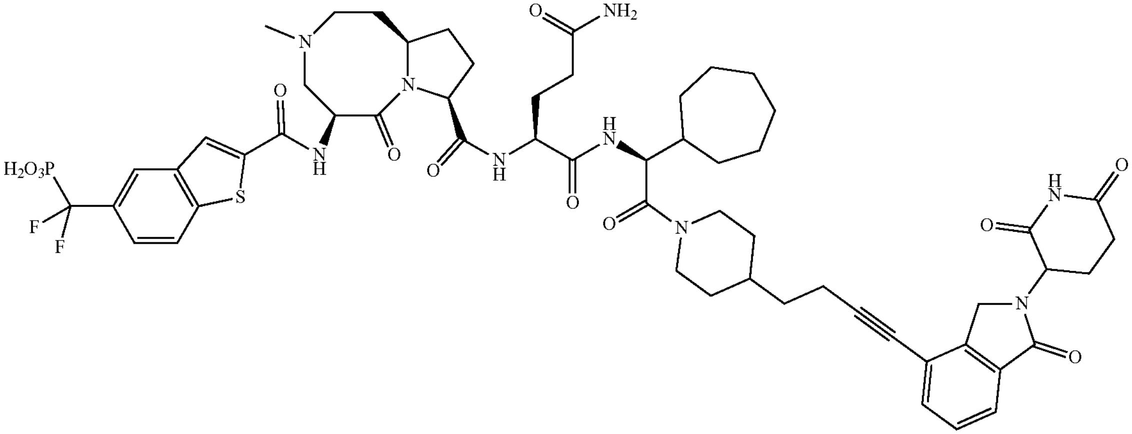 | ((2-(((5S,8S,10aR)-8-(((2S)-5-amino-1-(((1S)-1-cycloheptyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 260 | 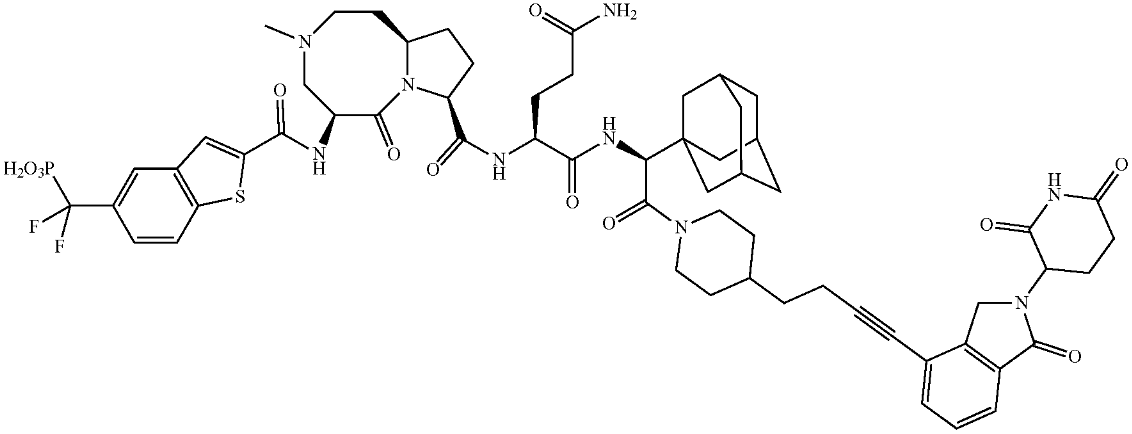 | ((2-(((5S,8S,10aR)-8-(((2S)-1-(((1S)-1-((1s,3R)-adamantan-1-yl)-2-(4-(4-(2-(2,6-dioxopiperidin-3-yl)-1-oxoisoindolin-4-yl)but-3-yn-1-yl)piperidin-1-yl)-2-oxoethyl)amino)-5-amino-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 261 | 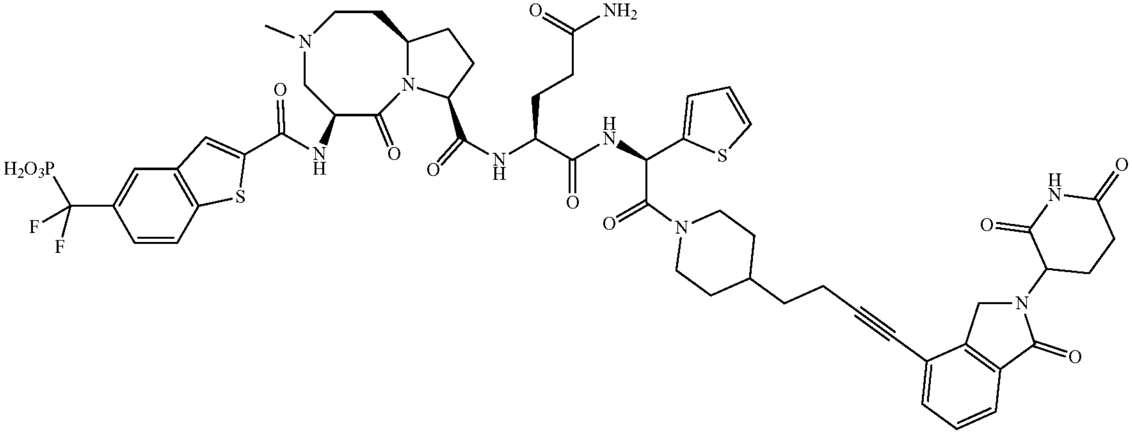 | ((2-(((5S,8S,10aR)-8-(((2S)-5-amino-1-(((1R)-2-(4-(4-(2-(2,6-dioxopiperidin-3-yl)-1-oxoisoindolin-4-yl)but-3-yn-1-yl)piperidin-1-yl)-2-oxo-1-(thiophen-2-yl)ethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 262 | 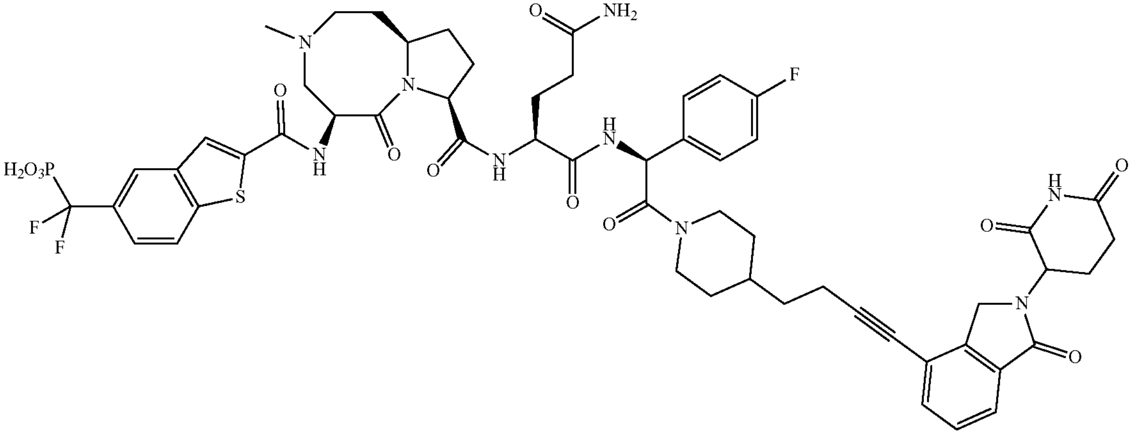 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-1-(4-fluorophenyl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 263 | 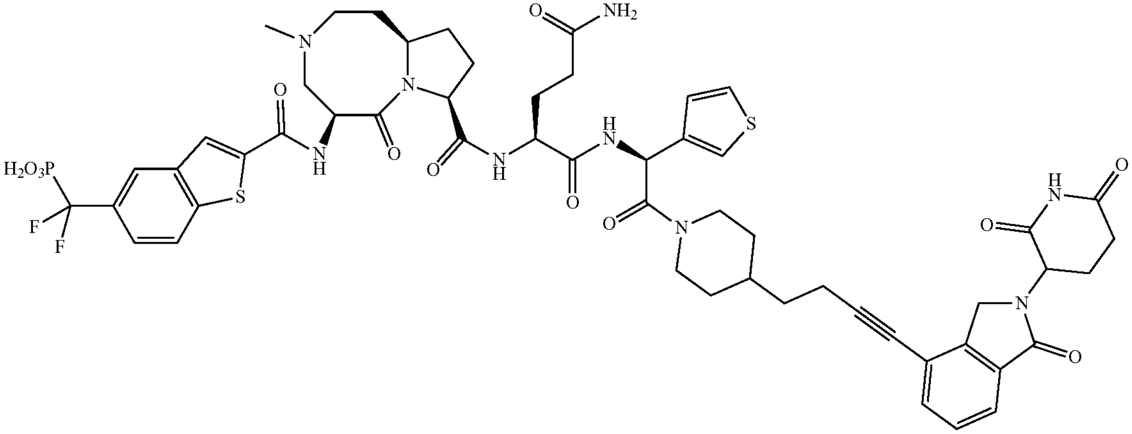 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-(thiophen-3-yl)ethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 264 | 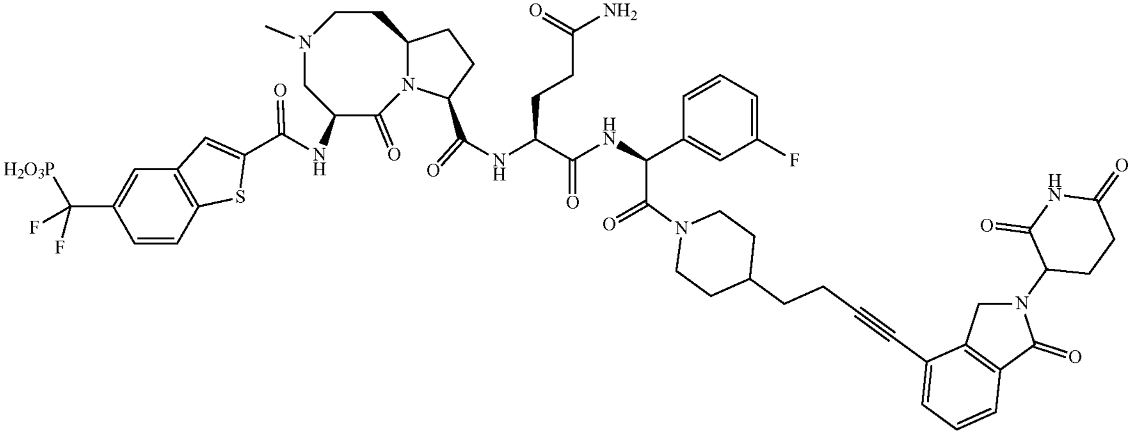 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-1-(3-fluorophenyl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 265 | 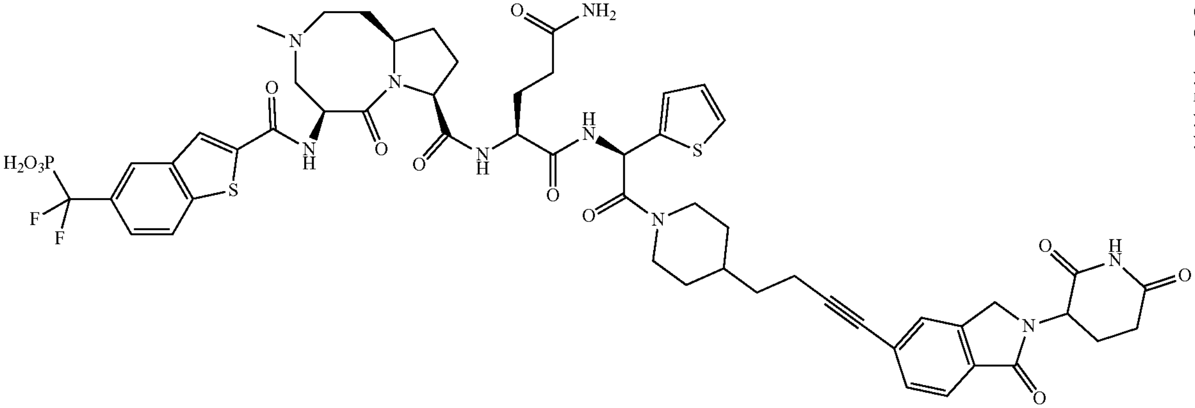 | ((2-(((5S,8S,10aR)-8-(((2S)-5-amino-1-(((1R)-2-(4-(4-(2-(2,6-dioxopiperidin-3-yl)-1-oxoisoindolin-5-yl)but-3-yn-1-yl)piperidin-1-yl)-2-oxo-1-(thiophen-2-yl)ethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 266 | 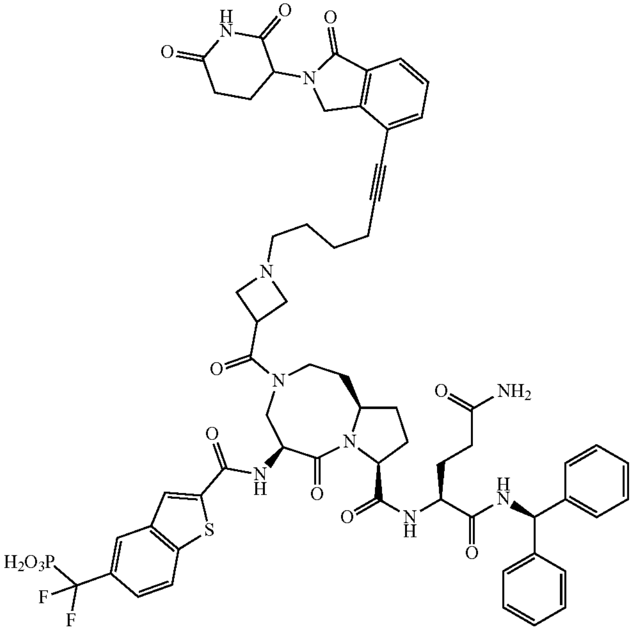 | ((2-(((5S,8S,10aR)-8-(((S)-5-amino-1-(benzhydrylamino)-1,5-dioxopentan-2-yl)carbamoyl)-3-(1-(6-(2-(2,6-dioxopiperidin-3-yl)-1-oxoisoindolin-4-yl)hex-5-yn-1-yl)azetidine-3-carbonyl)-6-oxodecahydropyrrolo[1,2-a][1,5]diazocin-5-yl)carbamoyl)benzo[b]thiophen-5-yl)difluoromethyl)phosphonic acid |

TABLE 1-continued
| Cpd. No. | Structure | Name |
| --- | --- | --- |
| 267 | 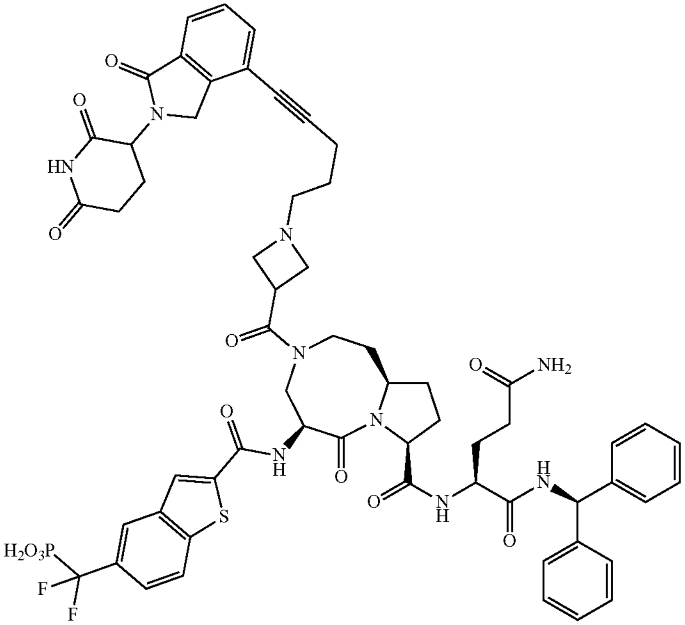 | ((2-(((5S,8S,10aR)-8-(((S)-5-amino-1-(benzhydrylamino)-1,5-dioxopentan-2-yl)carbamoyl)-3-(1-(5-(2-(2,6-dioxopiperidin-3-yl)-1-oxoisoindolin-4-yl)pent-4-yn-1-yl)azetidine-3-carbonyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 268 | 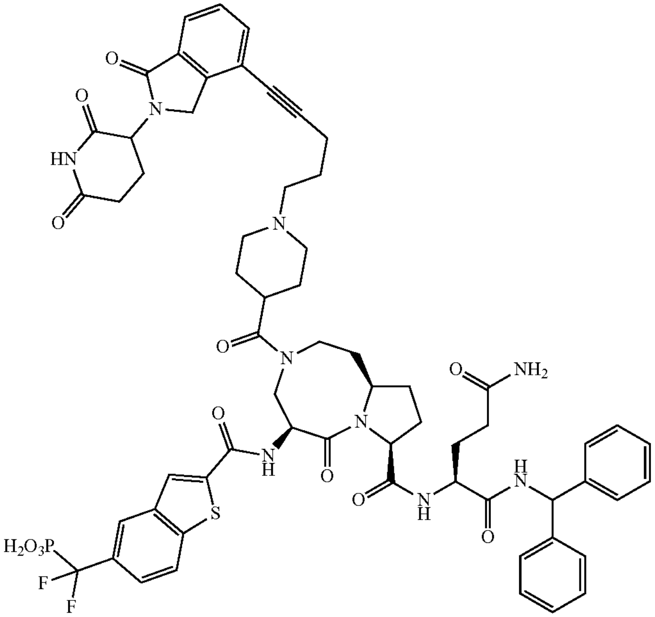 | ((2-(((5S,8S,10aR)-8-(((S)-5-amino-1-(benzhydrylamino)-1,5-dioxopentan-2-yl)carbamoyl)-3-(1-(5-(2-(2,6-dioxopiperidin-3-yl)-1-oxoisoindolin-4-yl)pent-4-yn-1-yl)piperidine-4-carbonyl)-6-oxodecahydropyrrolo[1,2-a][1,5]diazocin-5-yl)carbamoyl)benzo[b]thiophen-5-yl)difluoromethyl)phosphonic acid |
| 269 | 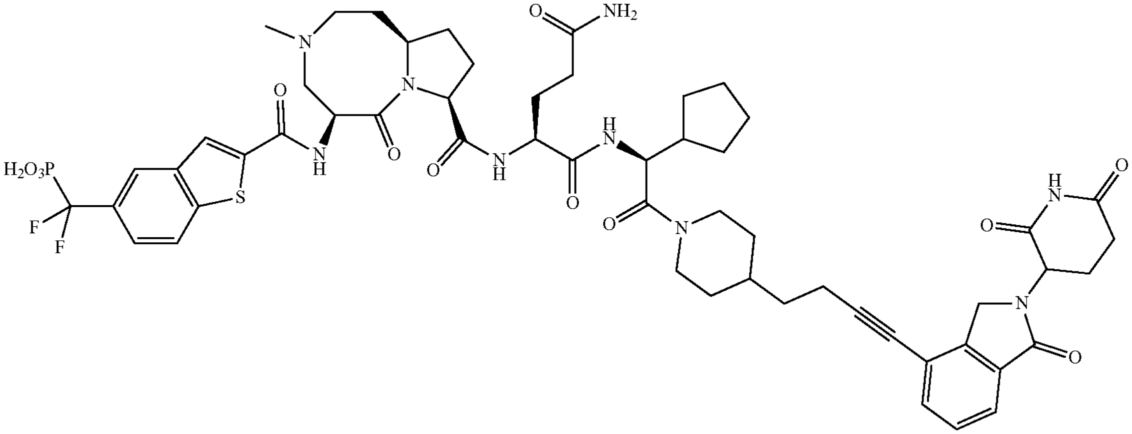 | ((2-(((5S,8S,10aR)-8-(((2S)-5-amino-1-(((1S)-1-cyclopentyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 270 | 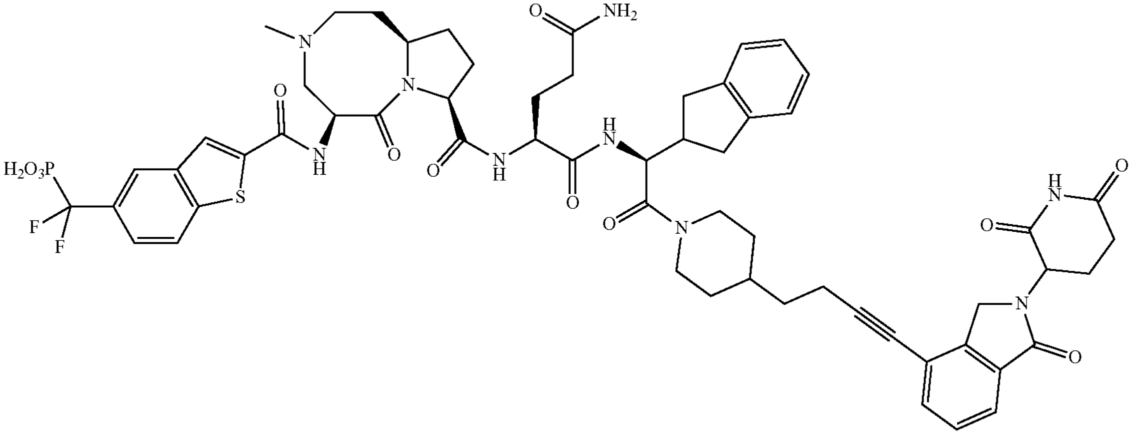 | ((2-(((5S,8S,10aR)-8-(((2S)-5-amino-1-(((1S)-1-(2,3-dihydro-1H-inden-2-yl)-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 271 | 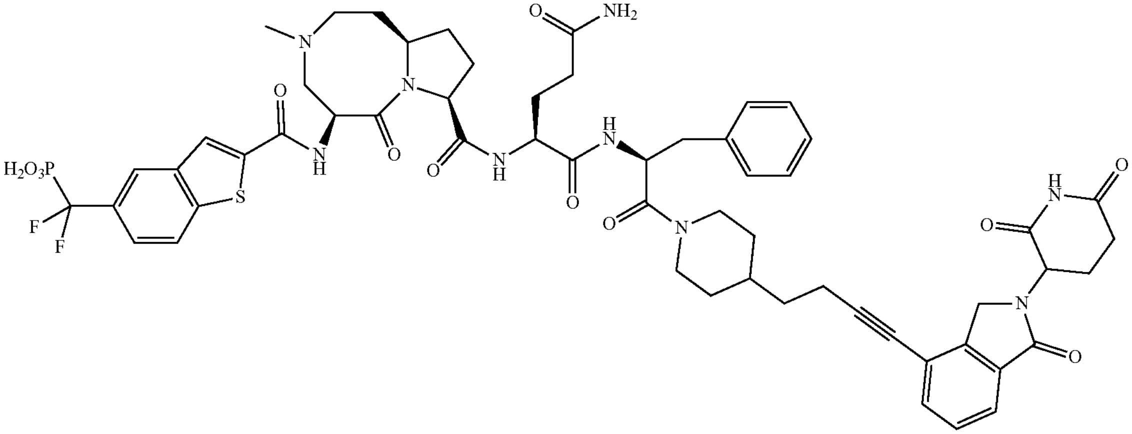 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-phenylpropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 272 | 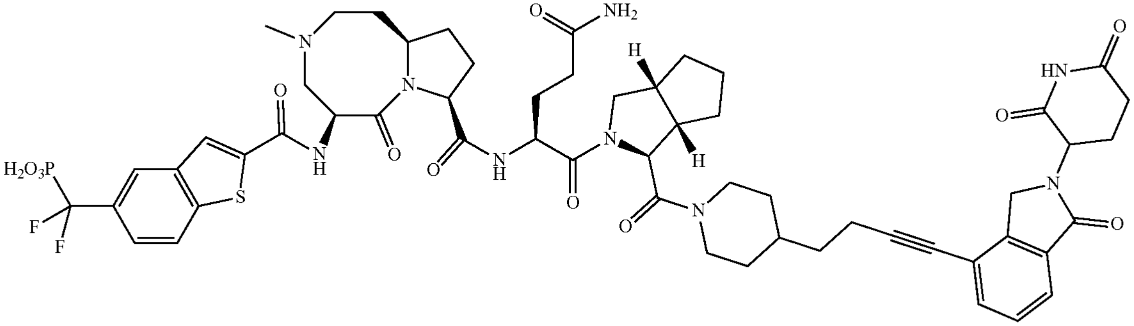 | ((2-(((5S,8S,10aR)-8-(((2S)-5-amino-1-((1S,3aR,6aS)-1-(4-(4-(2-(2,6-dioxopiperidin-3-yl)-1-oxoisoindolin-4-yl)but-3-yn-1-yl)piperidine-1-carbonyl)hexahydrocyclopenta[c]pyrrol-2(1H)-yl)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| F273 | 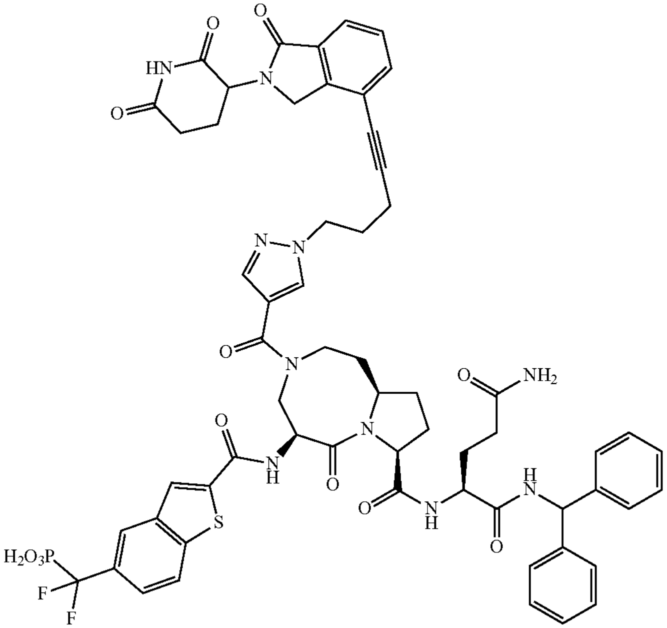 | ((2-(((5S,8S,10aR)-8-(((S)-5-amino-1-(benzhydrylamino)-1,5-dioxopentan-2-yl)carbamoyl)-3-(1-(5-(2-(2,6-dioxopiperidin-3-yl)-1-oxoisoindolin-4-yl)pent-4-yn-1-yl)-1H-pyrazole-4-carbonyl)-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
|---|---|---|
| 274 | 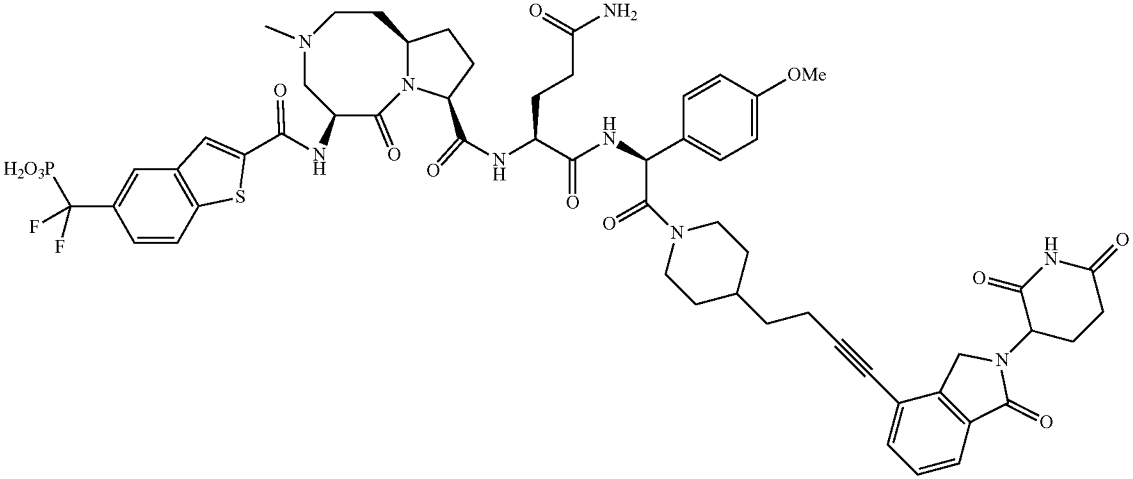 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-1-(4-methoxyphenyl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 275 | 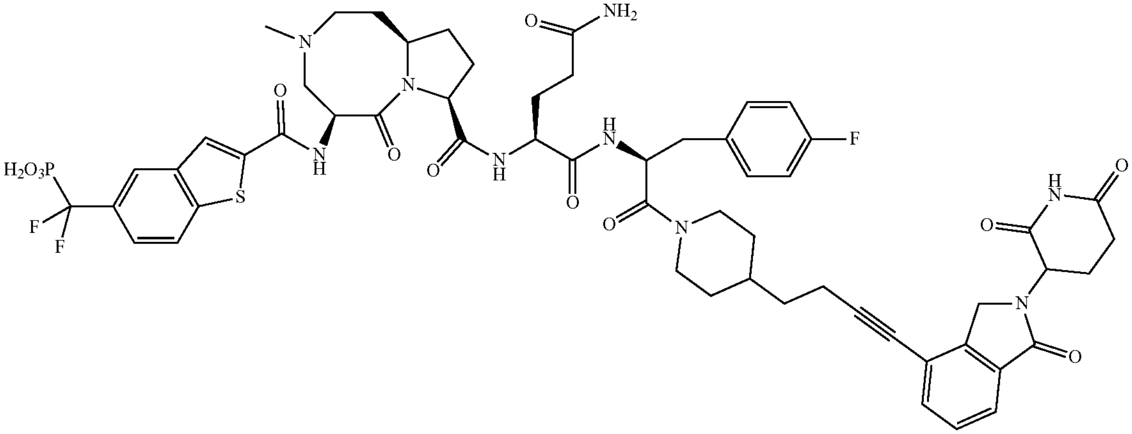 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 276 | 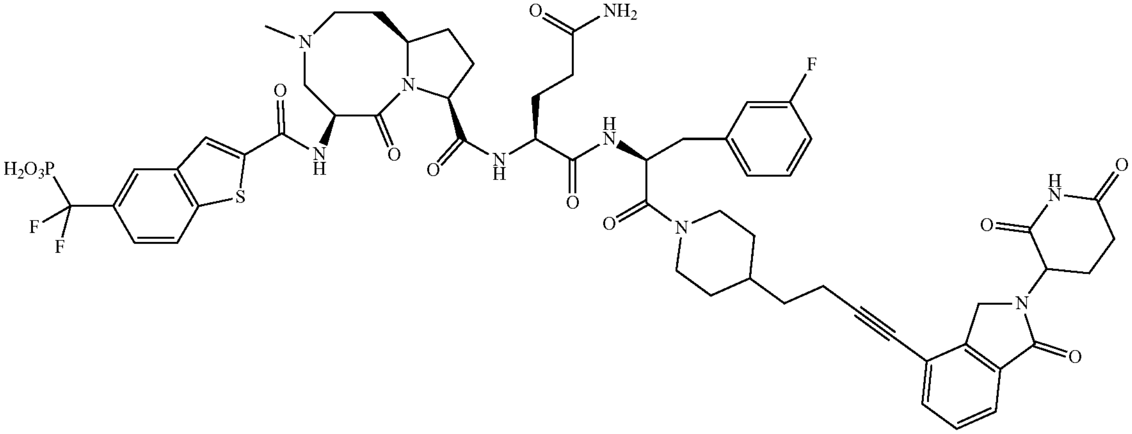 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(3-fluorophenyl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 277 | 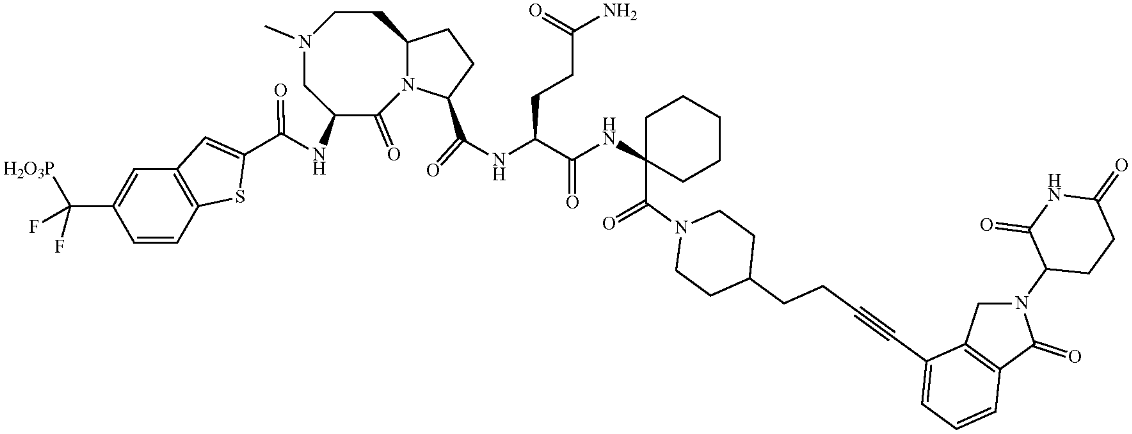 | ((2-(((5S,8S,10aR)-8-(((2S)-5-amino-1-((1-(4-(4-(2-(2,6-dioxopiperidin-3-yl)-1-oxoisoindolin-4-yl)but-3-yn-1-yl)piperidine-1-carbonyl)cyclohexyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1-continued

| Cpd. No. | Structure | Name |
| --- | --- | --- |
| 278 | 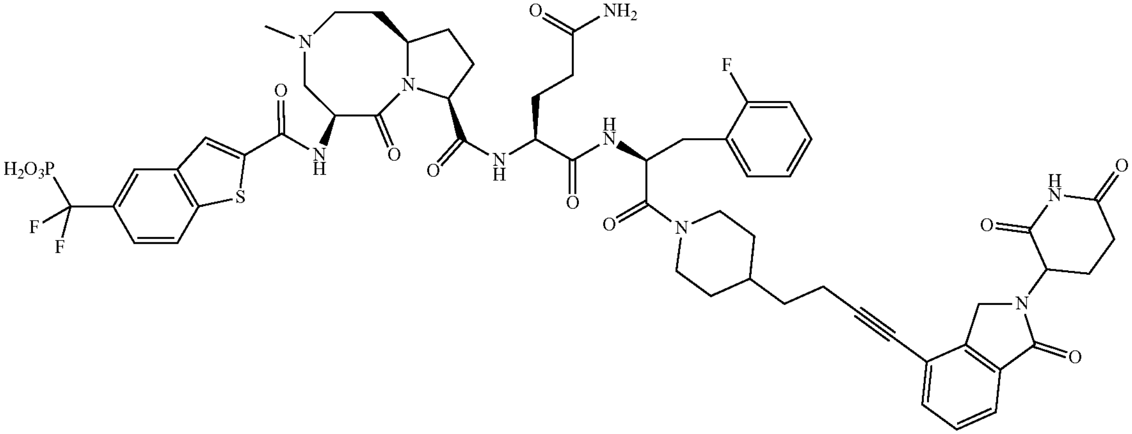 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(2-fluorophenyl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 279 | 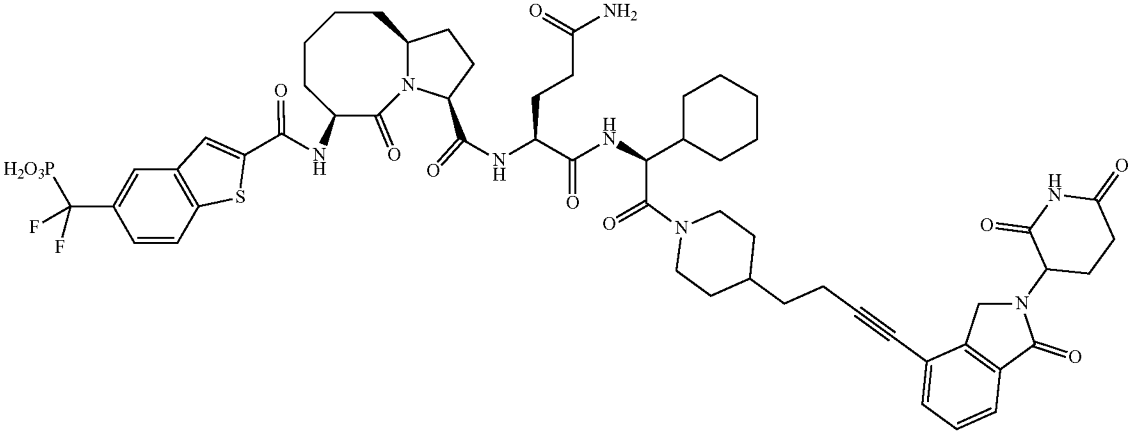 | ((2-(((3S,6S,10aS)-3-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |

TABLE 1-continued

| Cpd. No. | Structure | Name |
| --- | --- | --- |
| 280 | 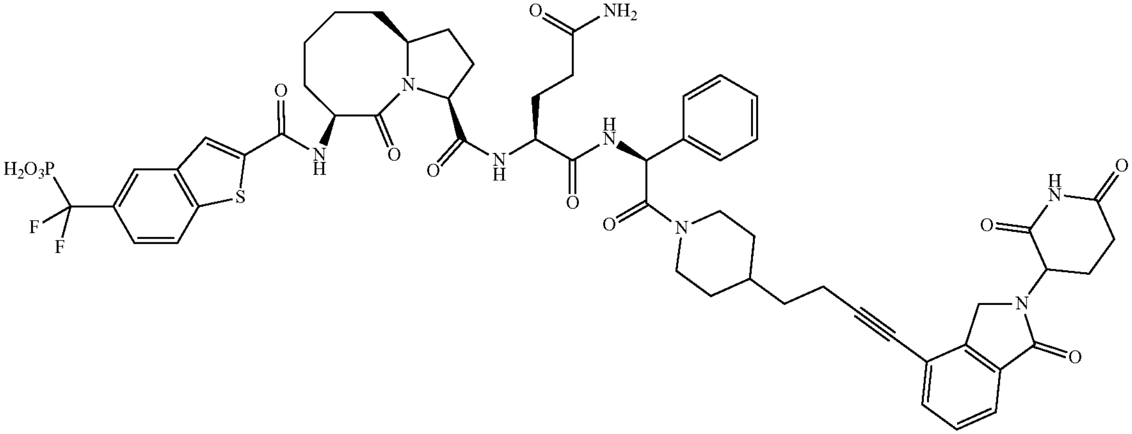 | ((2-(((3S,6S,10aS)-3-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |
| 281 | 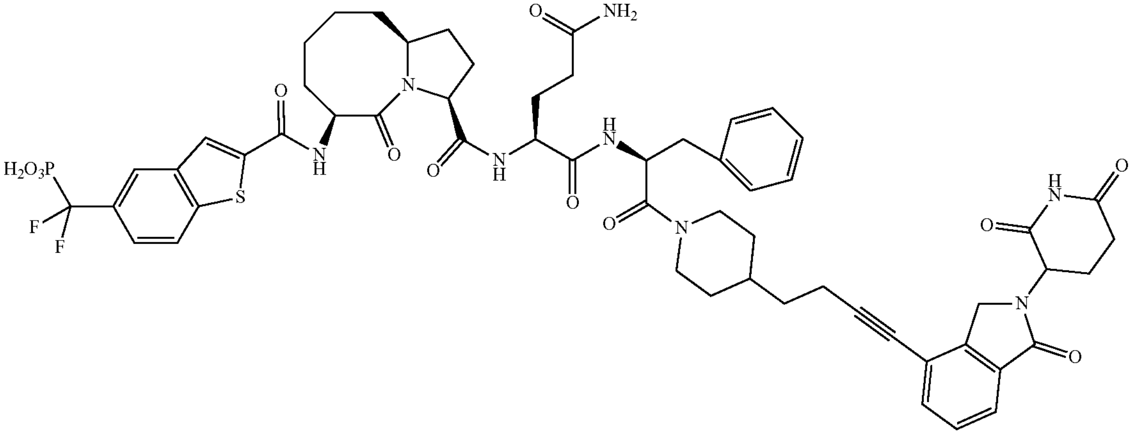 | ((2-(((3S,6S,10aS)-3-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-phenylpropan-2-yl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |

TABLE 1-continued

| Cpd. No. | Structure | Name |
| --- | --- | --- |
| 282 | 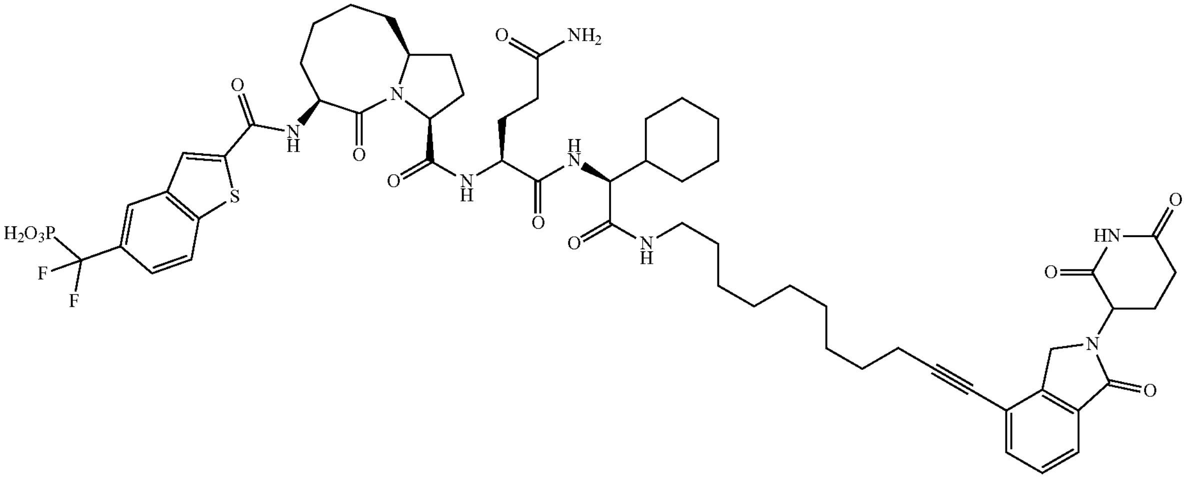 | ((2-(((3S,6S,10aS)-3-(((2S)-5-amino-1-(((1S)-1-cyclohexyl-2-((11-(2-(2,6-dioxopiperidin-3-yl)-1-oxoisoindolin-4-yl)undec-10-yn-1-yl)amino)-2-oxoethyl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |
| 283 | 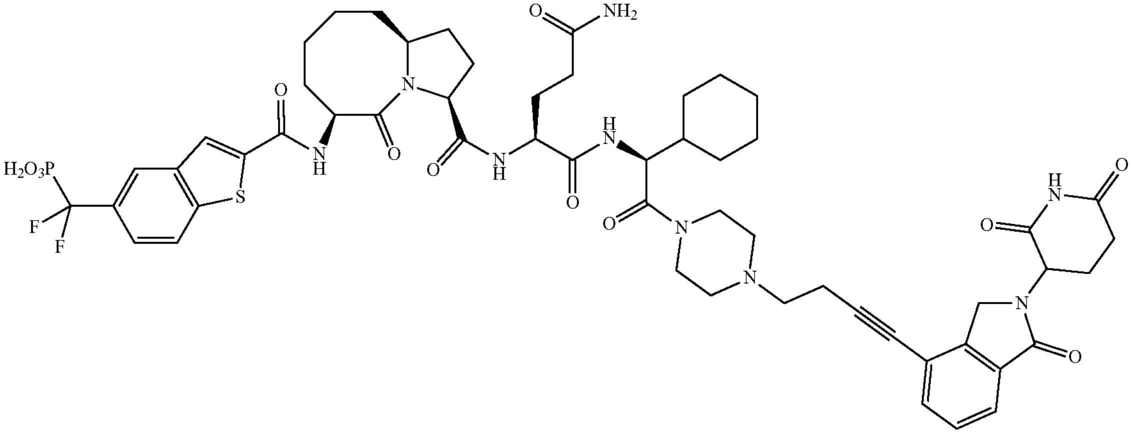 | ((2-(((3S,6S,10aS)-3-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperazin-1-yl)-2-oxoethyl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |

TABLE 1A

| Cpd. No. | Structure | Name |
|---|---|---|
| 284 | 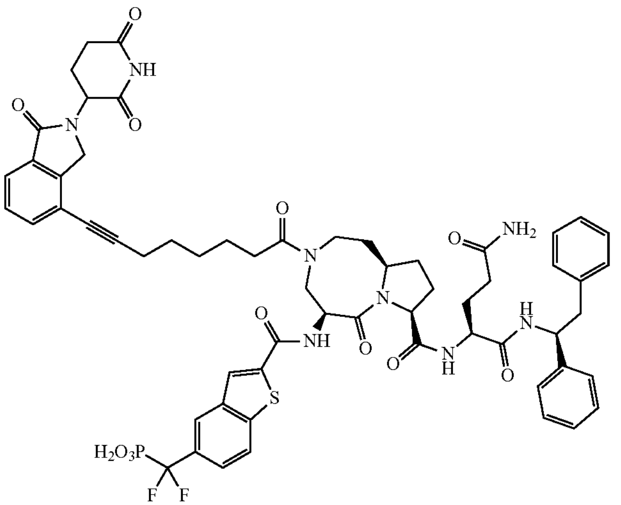 | ((2-(((5S,8S,10aR)-8-(((S)-5-amino-1-(((S)-1,2-diphenylethyl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |
| 285 | 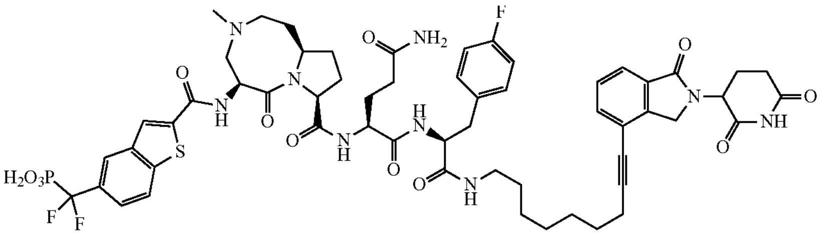 | ((2-(((5S,8S,10aR)-8-(((2S)-5-amino-1-(((2S)-1-((9-(2-(2,6-dioxopiperidin-3-yl)-1-oxoisoindolin-4-yl)non-8-yn-1-yl)amino)-3-(4-fluorophenyl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 286 | 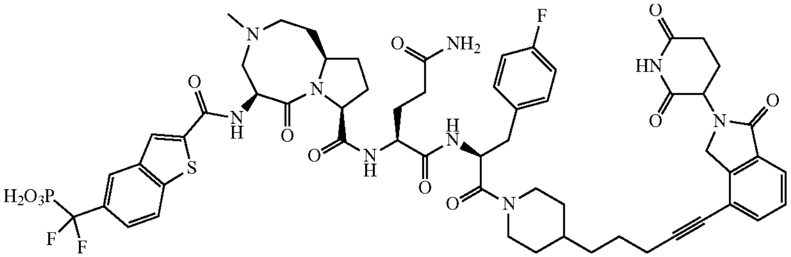 | ((2-(((5S,8S,10aR)-8-(((2S)-5-amino-1-(((2S)-1-(4-(5-(2-(2,6-dioxopiperidin-3-yl)-1-oxoisoindolin-4-yl)pent-4-yn-1-yl)piperidin-1-yl)-3-(4-fluorophenyl)-1-oxopropan-2-yl)amino)-1,5-dioxopentan-2-yl)carbamoyl)-3-methyl-6-oxodecahydropyrrolo[l,2-a][1,5]diazocin-5-yl)carbamoyl)benzo[b]thiophen-5-yl)difluoromethyl)phosphonic acid |
| 287 | 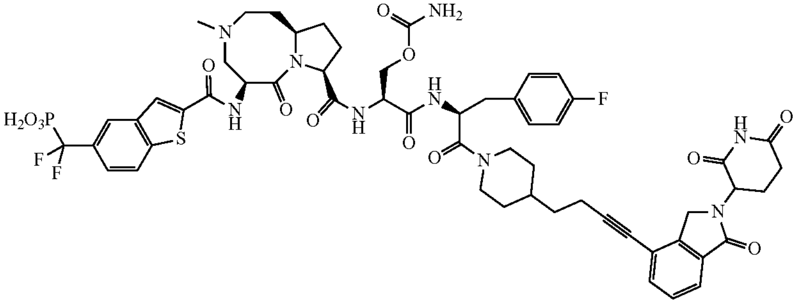 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 288 | 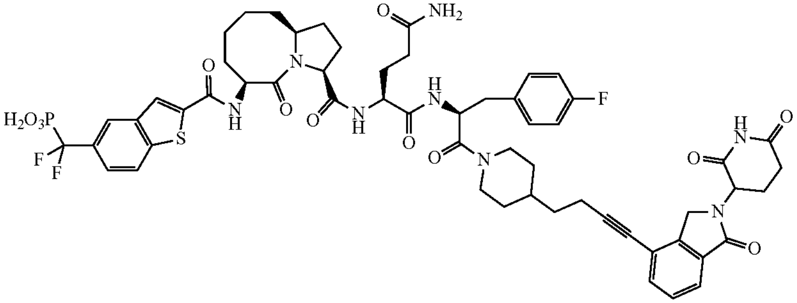 | ((2-(((3S,6S,10aS)-3-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |

TABLE 1A-continued

| Cpd. No. | Structure | Name |
|---|---|---|
| 289 | 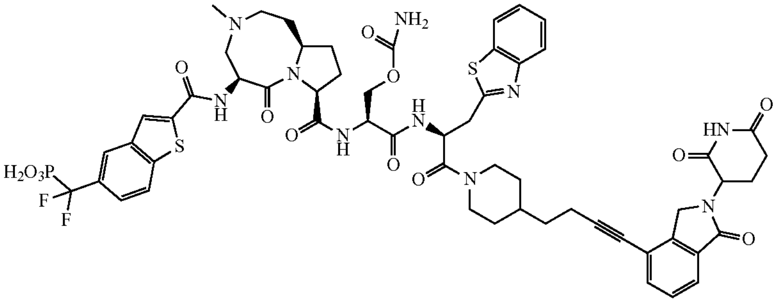 | ((2-(((5S,8S,10aR)-8-(((2S)-1-(((2S)-3-(benzo[d]thiazol-2-yl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-3-(carbamoyloxy)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 290 | 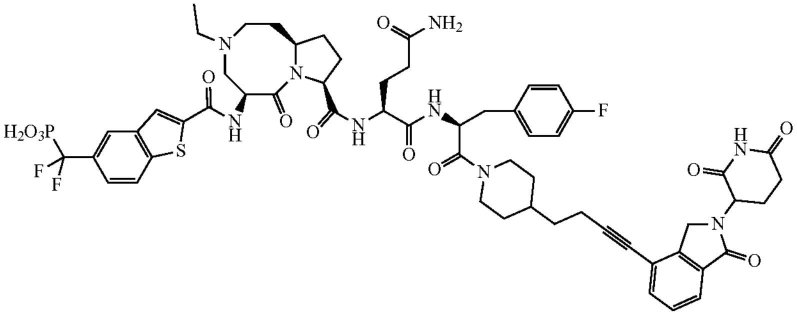 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 291 | 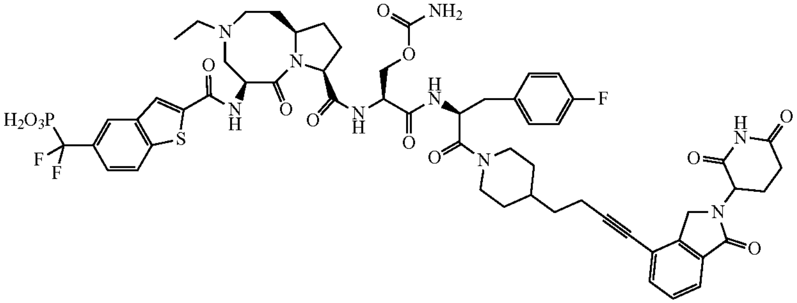 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1-oxopropan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 293 | 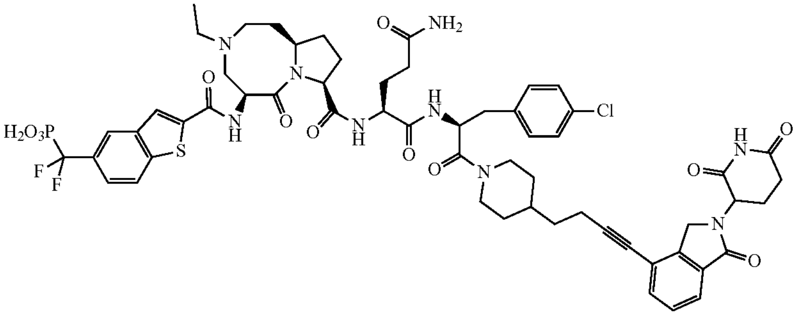 | ((2-(((5S,8S,10aR)-8-(((2S)-5-amino-1-(((2S)-3-(4-chlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 294 | 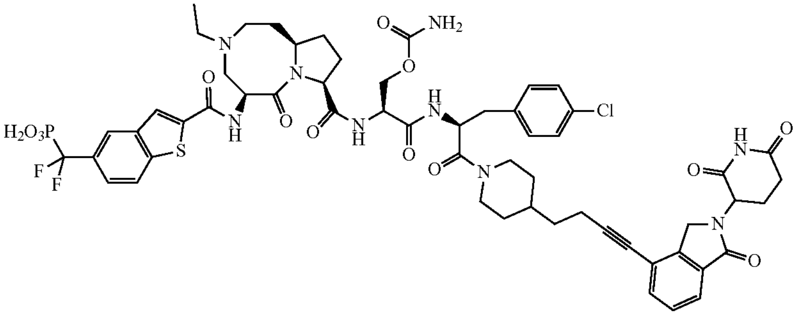 | ((2-(((5S,8S,10aR)-8-(((2S)-3-(carbamoyloxy)-1-(((2S)-3-(4-chlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 295 | 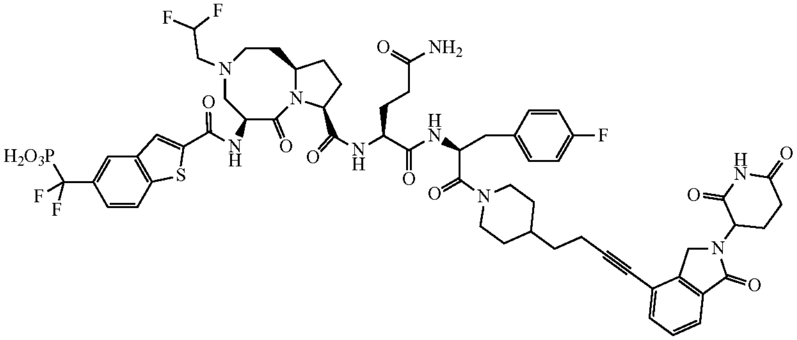 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 296 | 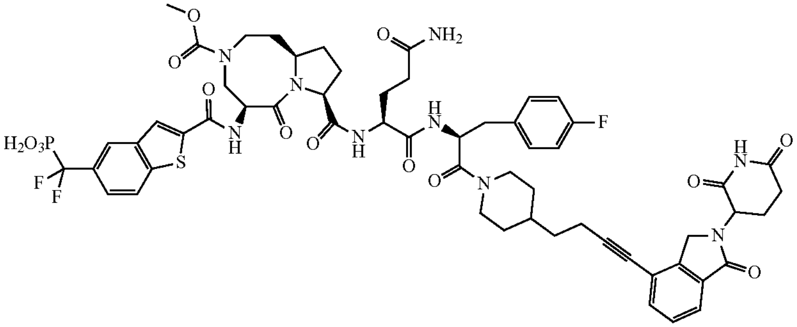 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 297 | 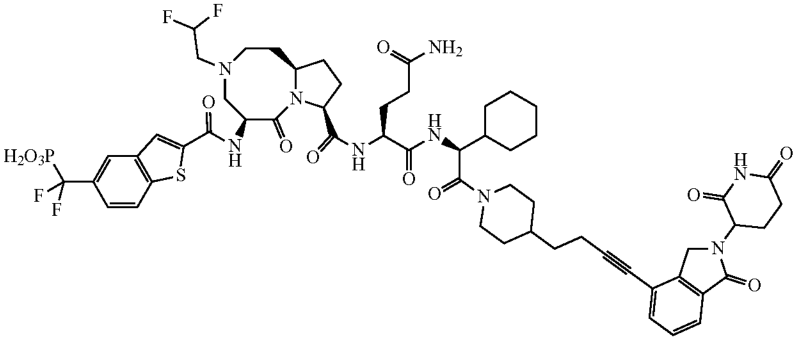 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl)phosphonic acid |
| 298 | 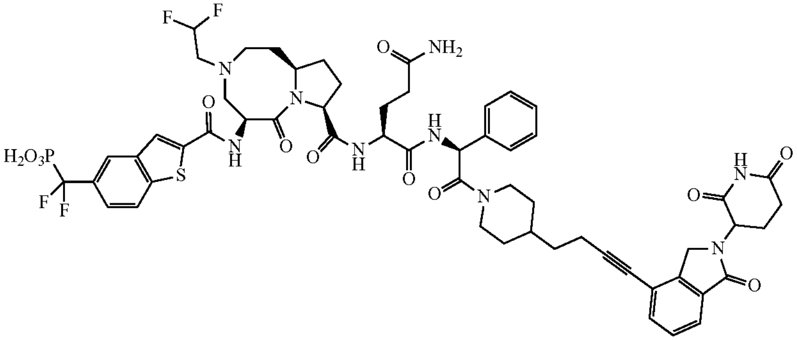 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 299 | 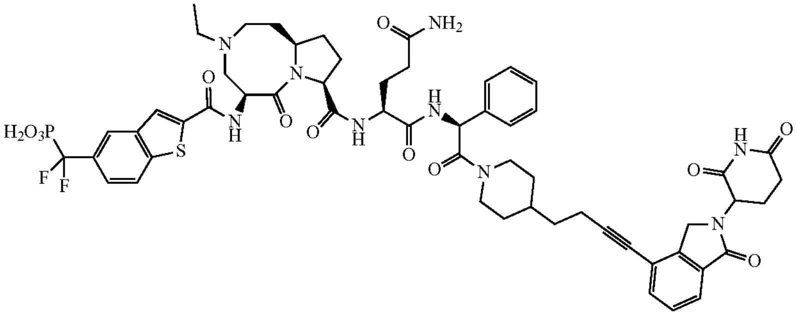 | ((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 300 | 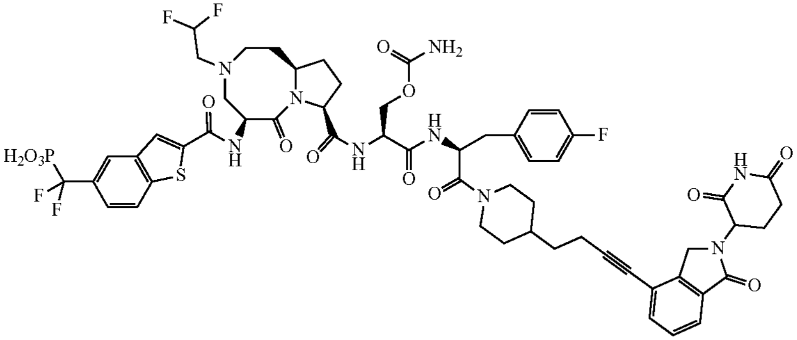 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1-oxopropan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl)phosphonic acid |
| 301 | 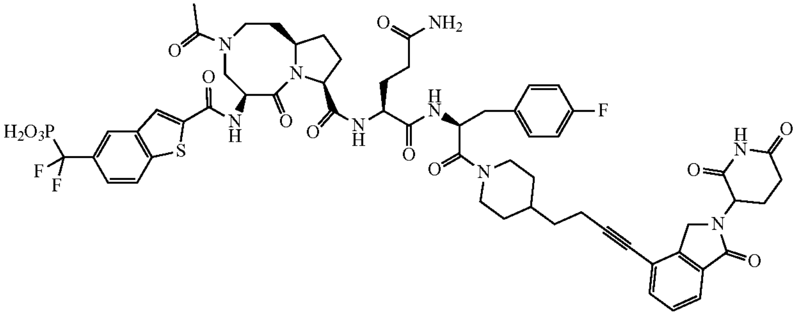 | ((2-(((5S,8S,10aR)-3-acetyl-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-6-oxodecahydropyrrolo[l,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 302 | 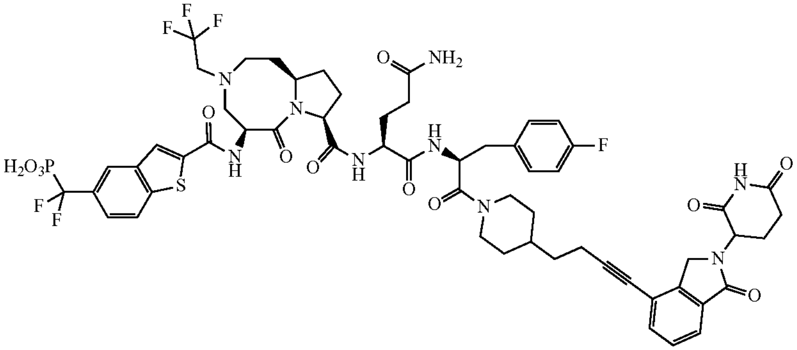 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-6-oxo-3-(2,2,2-trifluoroethyl)deca-hydropyrrolo[1,2-a][1,5]diazocin-5-yl)carbamoyl)benzo[b]thiophen-5-yl)difluoromethyl)phosphonic acid |
| 303 | 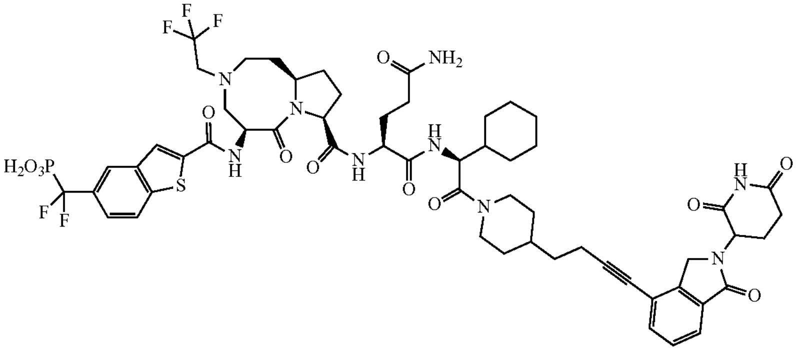 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-6-oxo-3-(2,2,2-trifluoroethyl)deca-hydropyrrolo[1,2-a][1,5]diazocin-5-yl)carbamoyl)benzo[b]thiophen-5-yl)difluoromethyl)phosphonic acid |
| 304 | 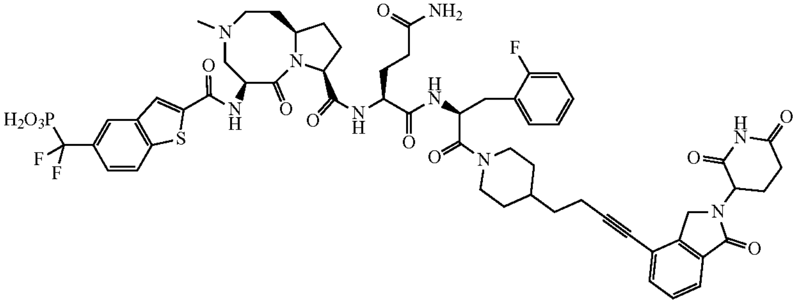 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-y1)-3-(2-fluorophenyl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 305 | 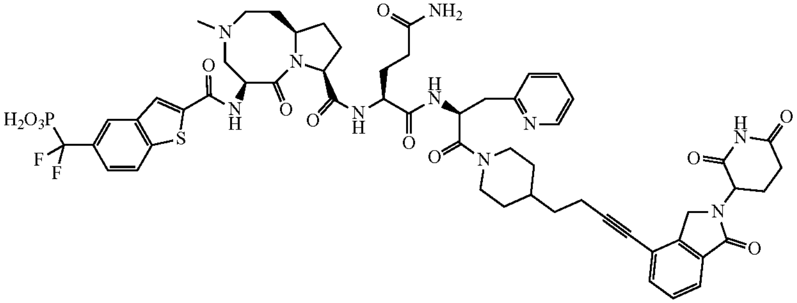 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(pyridin-2-yl)propan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 306 | 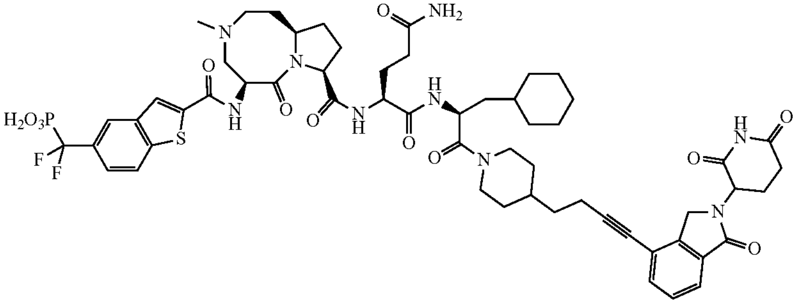 | ((2-(((5S,8S,10aR)-8-(((2S)-5-amino-1-(((2S)-3-cyclohexyl-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 307 | 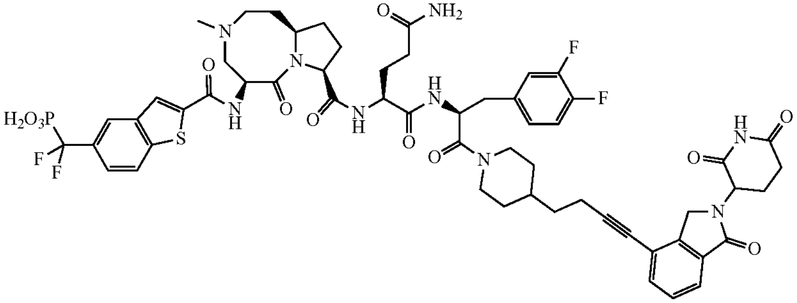 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 308 | 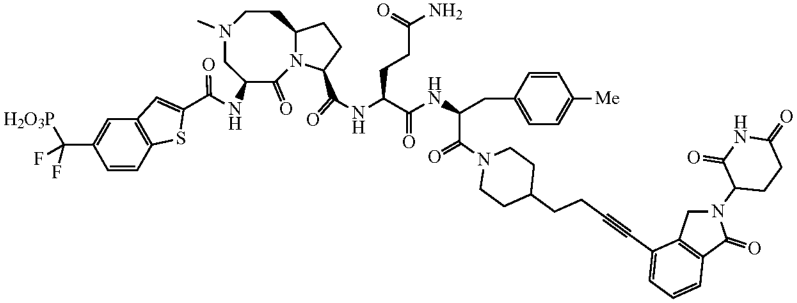 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(p-tolyl)propan-2-yl)amino)-1,5-dioxopentan-2-yl)carbamoyl)-3-methyl-6-oxodecahydropyrrolo1,2-a][1,5]diazocin-5-yl)carbamoyl)benzo[b]thiophen-5-yl)difluoromethyl)phosphonic acid |
| 309 | 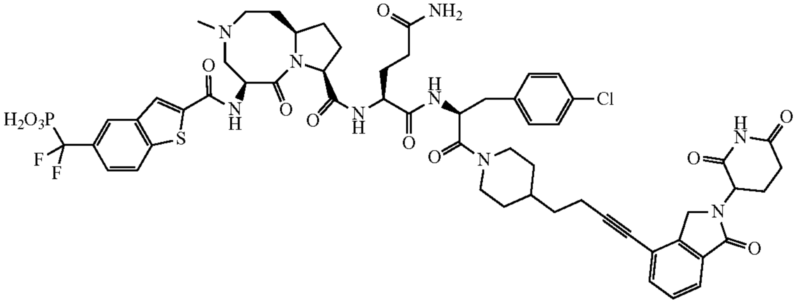 | ((2-(((5S,8S,10aR)-8-(((2S)-5-amino-1-(((2S)-3-(4-chlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b] thiophen-5-yl)difluoromethyl)phosphonic acid |
| 310 | 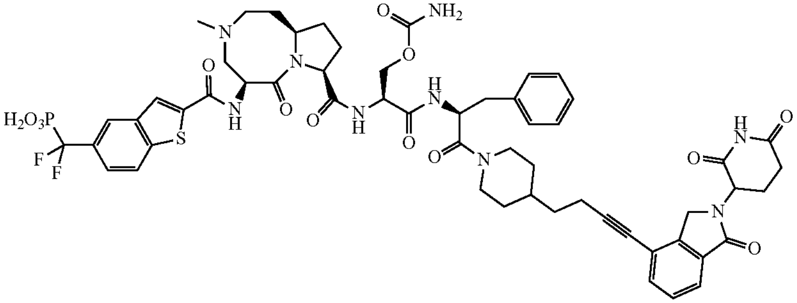 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-1-oxo-3-phenylpropan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 311 | 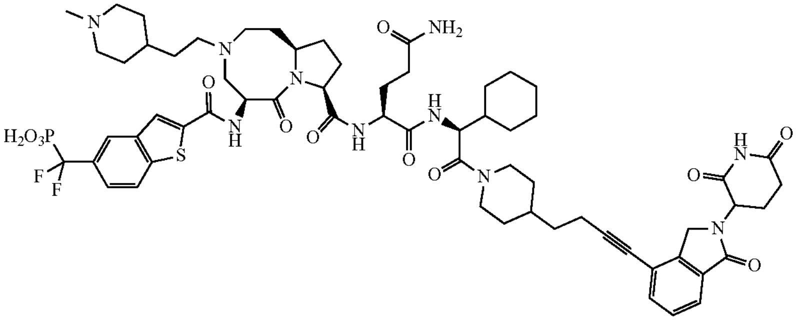 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(2-(1-methylpiperidin-4-yl)ethyl)-6-oxodecahydropyrrolo[1,2-a][1,5]diazocin-5-yl)carbamoyl)benzo[b]thiophen-5-yl)difluoromethyl)phosphonic acid |
| 312 | 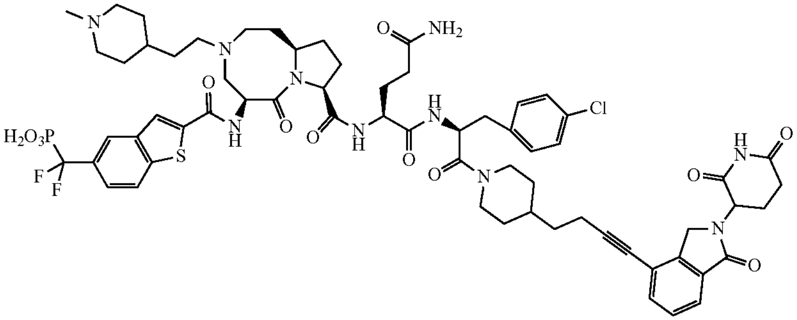 | ((2-(((5S,8S,10aR)-8-(((2S)-5-amino-1-(((2S)-3-(4-chlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(2-(1-methylpiperidin-4-yl)ethyl)-6-oxodecahydropyrrolo[1,2-a][1,5]diazocin-5-yl)carbamoyl)benzo[b]thiophen-5-yl)difluoromethyl)phosphonic acid |
| 313 | 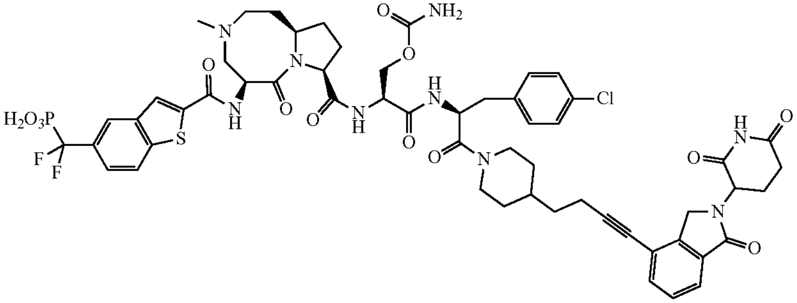 | ((2-(((5S,8S,10aR)-8-(((2S)-3-(carbamoyloxy)-1-(((2S)-3-(4-chlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 314 | 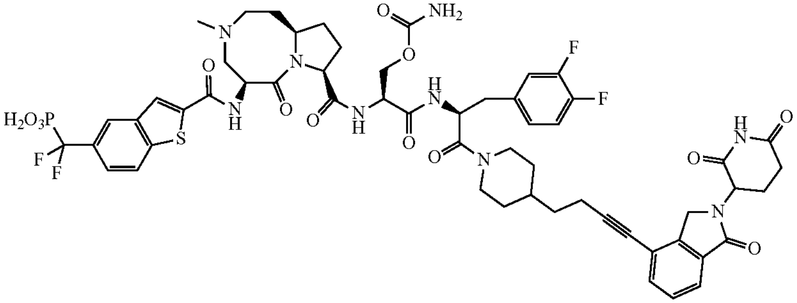 | ((2-(((5S,8S,10aR)-8-(((2S)-3-(carbamoyloxy)-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 315 | 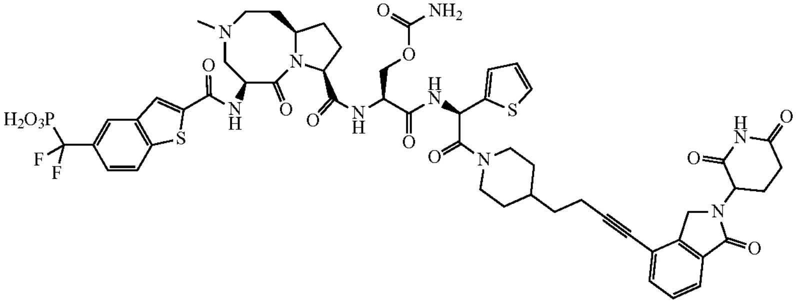 | ((2-(((5S,8S,10aR)-8-(((2S)-3-(carbamoyloxy)-1-(((1R)-2-(4-(4-(2-(2,6-dioxopiperidin-3-yl)1-oxoisoindolin-4-yl)but-3-yn-1-yl)piperidin-1-yl)-2-oxo-1-(thiophen-2-yl)ethyl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 316 | 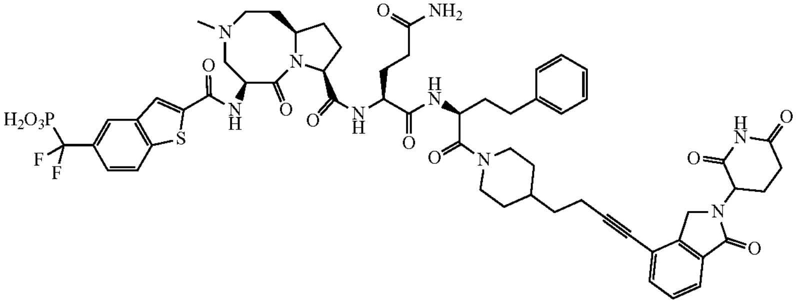 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-4-phenylbutan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 317 | 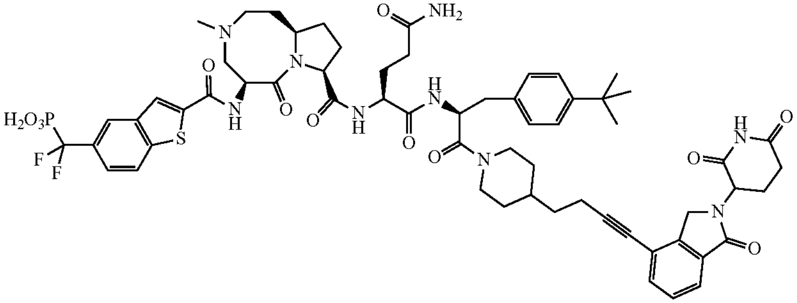 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 318 | 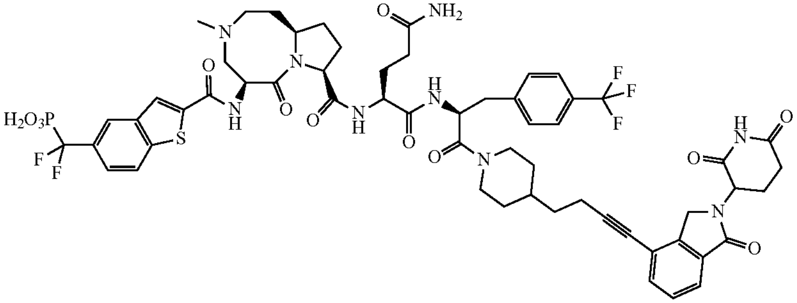 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-(trifluoromethyl)phenyl)propan-2-yl)amino)-1,5-dioxopentan-2-yl)carbamoyl)-3-methyl-6-oxodecahydropyrrolo1,2-a][1,5]diazocin-5-yl)carbamoyl)benzo[b]thiophen-5-yl) difluoromethyl)phosphonic acid |
| 319 | 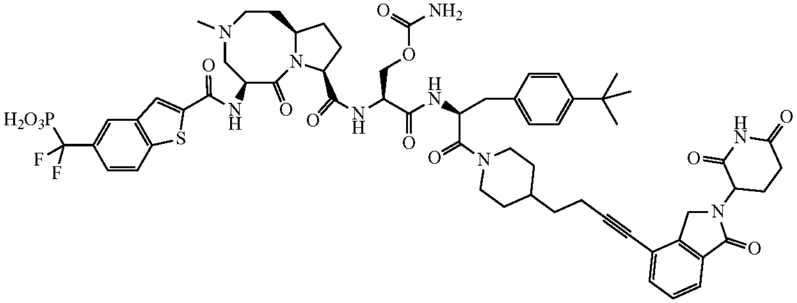 | ((2-(((5S,8S,10aR)-8-(((2S)-l-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-3-(carbamoyloxy)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 320 | 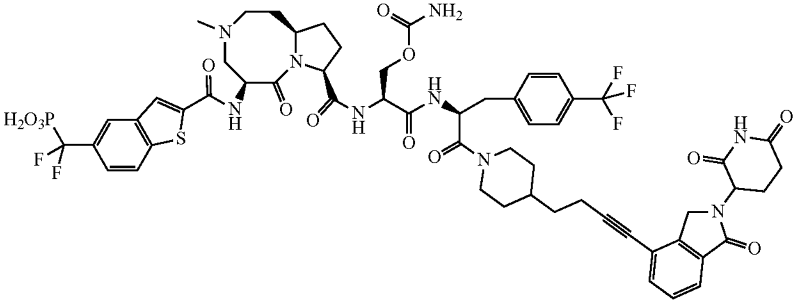 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-(trifluoromethyl)phenyl)propan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 321 | 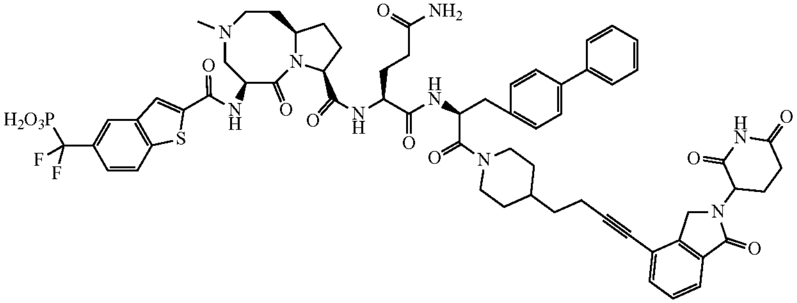 | ((2-(((5S,8S,10aR)-8-(((2S)-1-(((2S)-3-([1,1'-biphenyl]-4-yl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-5-amino-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 322 | 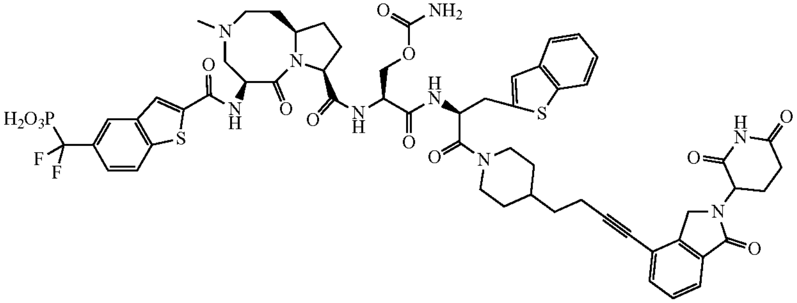 | ((2-(((5S,8S,10aR)-8-(((2S)-1-(((2S)-3-(benzo[b]thiophen-2-yl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-3-(carbamoyloxy)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 323 | 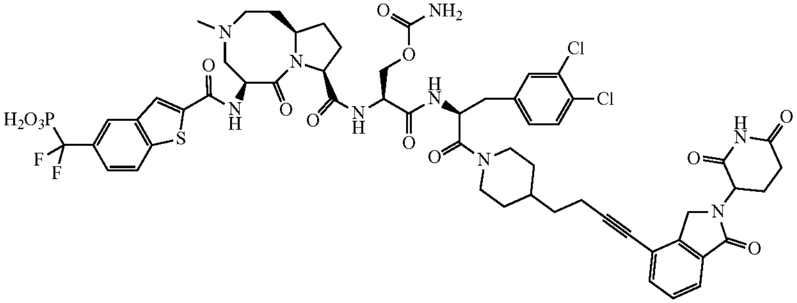 | ((2-(((5S,8S,10aR)-8-(((2S)-3-(carbamoyloxy)-1-(((2S)-3-(3,4-dichlorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |
| 324 | 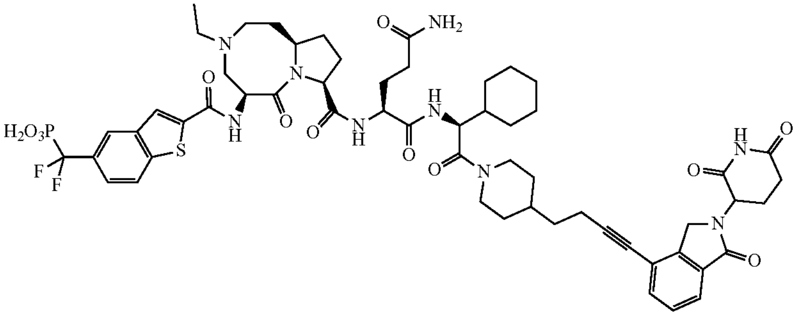 | ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 325 | 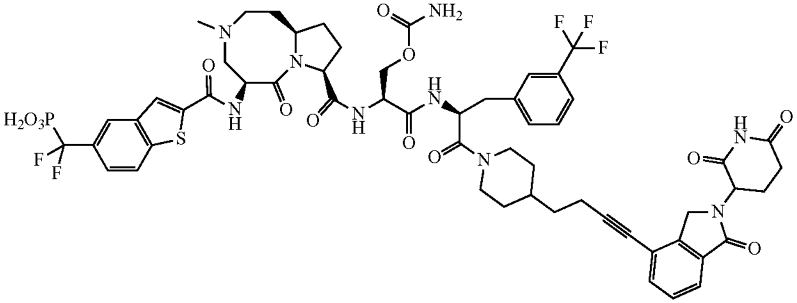 | ((2-(((5S,8S,10aR)-8-(((2S)-3-(carbamoyloxy)-1-(((2S)-1-(4-(4-(2-(2,6-dioxopiperidin-3-yl)-1-oxoisoindolin-4-yl)but-3-yn-1-yl)piperidin-1-yl)-1-oxo-3-(3-(trifluoromethyl)phenyl)propan-2-yl)amino)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 326 | 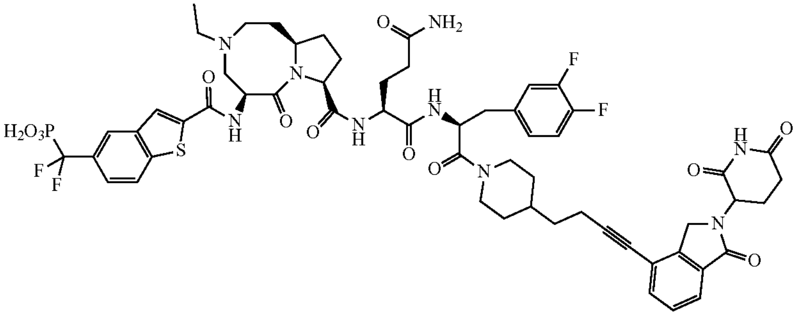 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 327 | 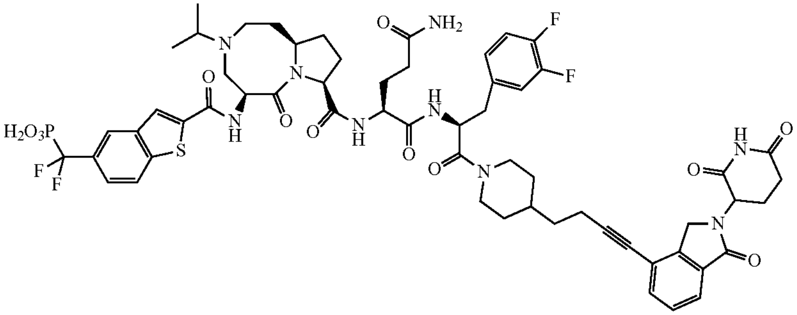 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-isopropyl-6-oxodecahydropyrrolo[1,2-a][1,5]diazocin-5-yl)carbamoyl)benzo[b]thiophen-5-yl)difluoromethyl)phosphonic acid |
| 328 | 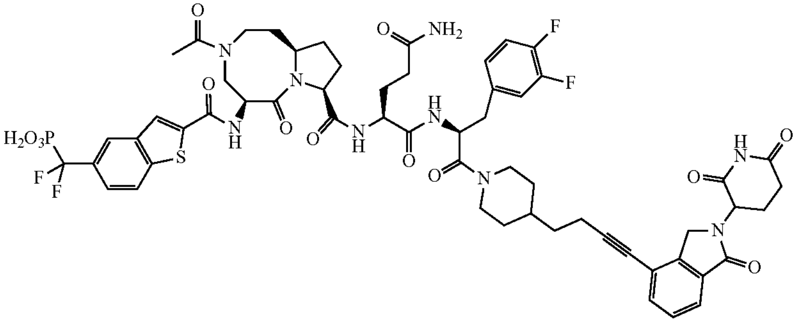 | ((2-(((5S,8S,10aR)-3-acetyl-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
|---|---|---|
| 329 | 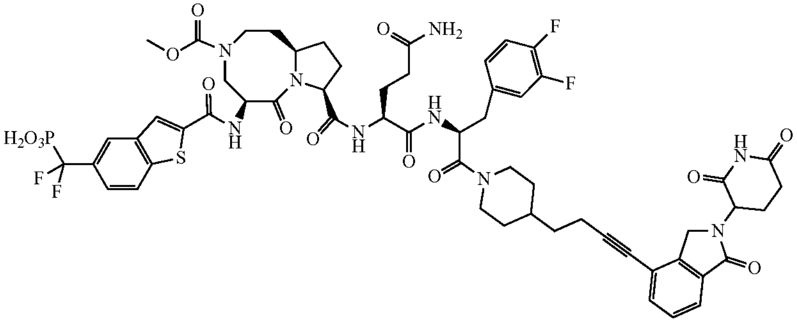 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 330 | 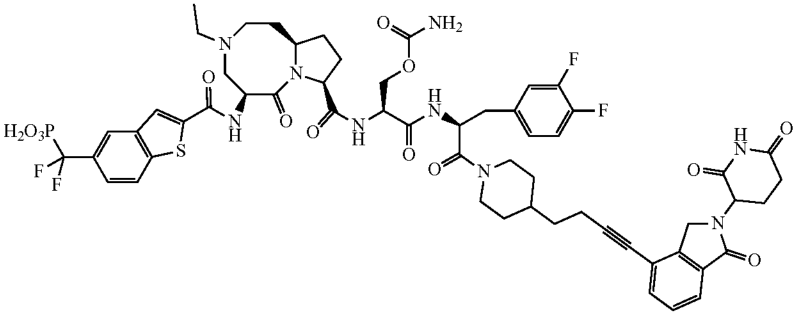 | ((2-(((5S,8S,10aR)-8-(((2S)-3-(carbamoyloxy)-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 331 | 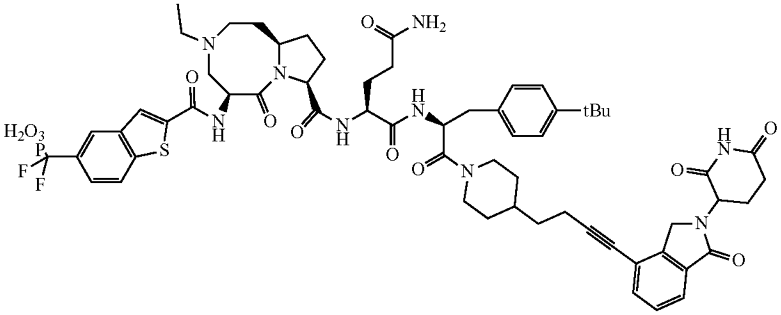 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1A-continued

| Cpd. No. | Structure | Name |
| --- | --- | --- |
| 332 | 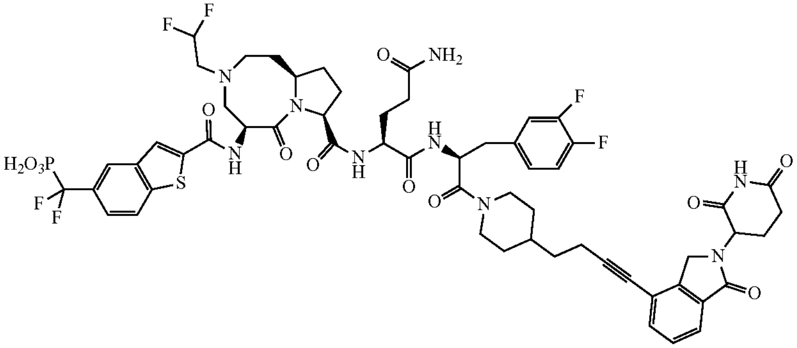 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl)phosphonic acid |
| 333 | 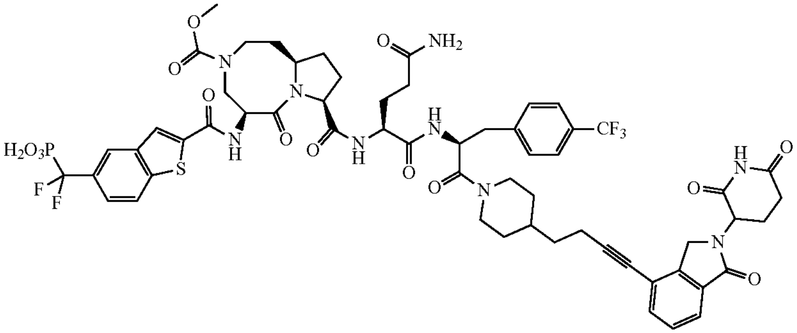 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-(trifluoromethyl)phenyl)propan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 334 | 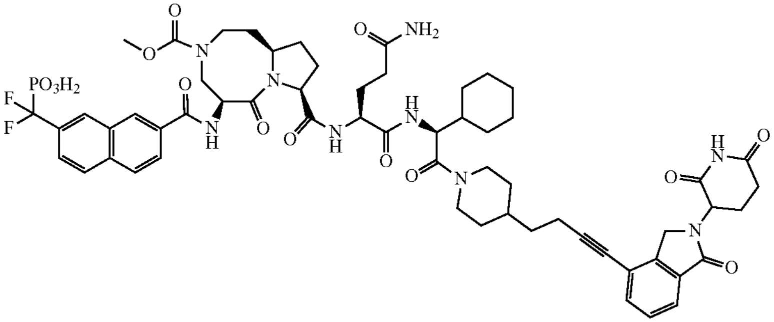 | ((7-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][l,5]diazocin-5-yl)carbamoyl)naphthalen-2-yl)difluoromethyl)phosphonic acid |

TABLE 1A-continued

| Cpd. No. | Structure | Name |
|---|---|---|
| 335 | 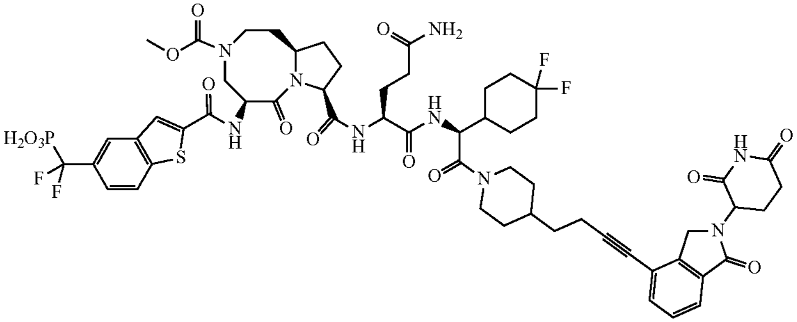 | ((2-(((5S,8S,10aR)-8-(((2S)-5-amino-1-((1S)-1-(4,4-difluorocyclohexyl)-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 336 | 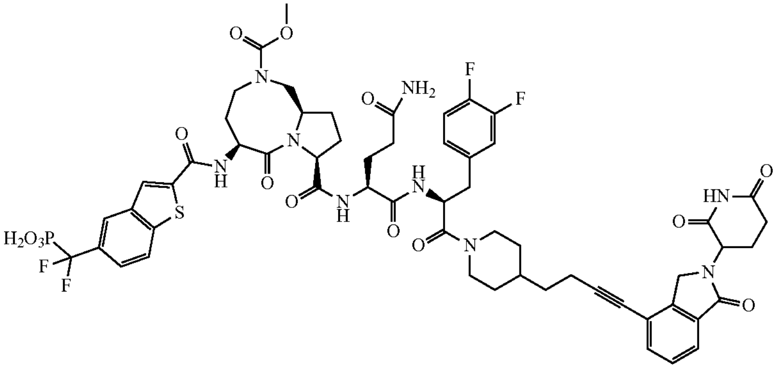 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-2-(methoxycarbonyl)-6-oxodecahydropyrrolo[1,2-a][1,4]diazocin-5-yl)carbamoyl)benzo[b]thiophen-5-yl)difluoromethyl)phosphonic acid |
| 337 | 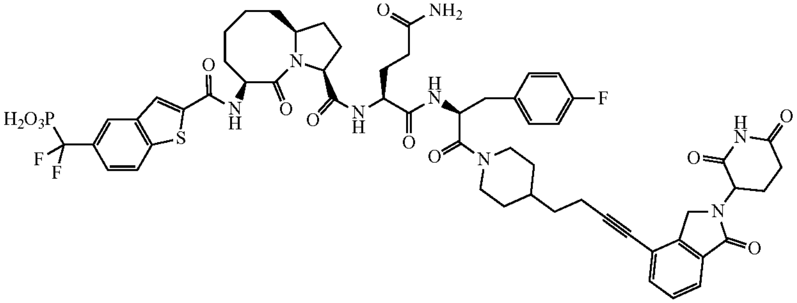 | ((2-(((3S,6S,10aS)-3-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-fluorophenyl)-1-oxopropan-2-yl)amino)-1,5-dioxopentan-2-yl)carbamoyl)-5-oxodecahydropyrrolo[1,2-a]azocin-6-yl)carbamoyl)benzo[b]thiophen-5-yl)difluoromethyl)phosphonic acid |

TABLE 1A-continued

| Cpd. No. | Structure | Name |
| --- | --- | --- |
| 339 | 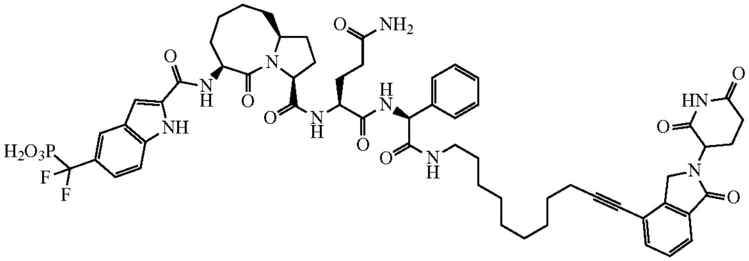 | ((2-(((3S,6S,10aS)-3-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-5-oxodecahydropyrrolo[1,2-a]azocin-6-yl)carbamoyl)-1H-indol-5-yl)difluoromethyl)phosphonic acid |
| 340 | 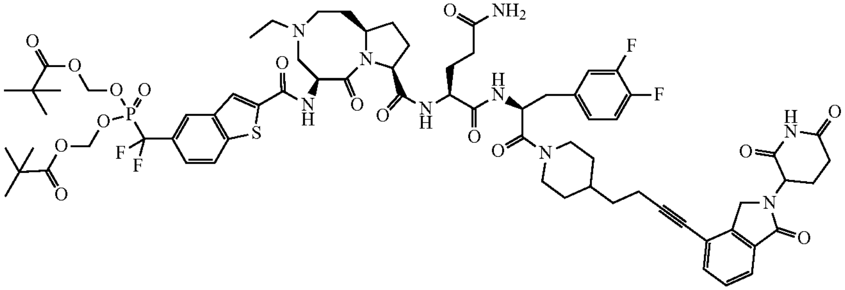 [SMILES: CCN1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(OCOC(=O)C(C)(C)C)OCOC(=O)C(C)(C)C)ccc3s2)C1] | ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphoryl)bis(oxy))bis(methylene) bis(2,2-dimethylpropanoate) |
| 341 | 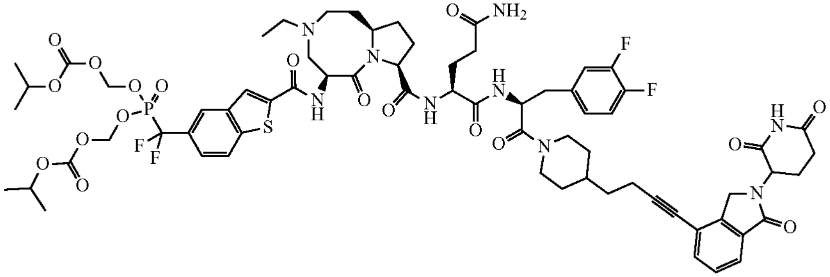 [SMILES: CCN1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(OCOC(=O)OC(C)C)OCOC(=O)OC(C)C)ccc3s2)C1] | ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphoryl)bis(oxy))bis(methylene) diisopropyl bis(carbonate) |

TABLE 1A-continued

| Cpd. No. | Structure | Name |
|---|---|---|
| 342 | 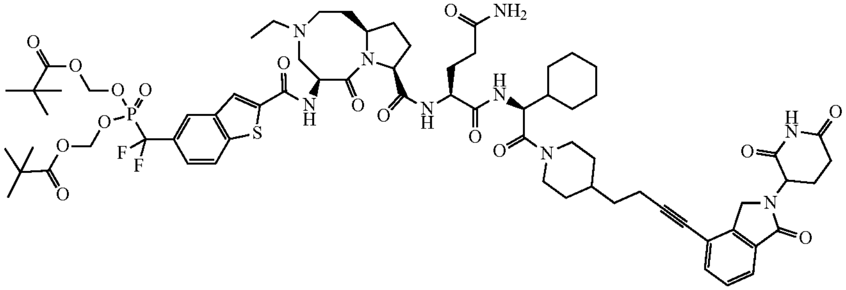 [SMILES: CCN1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(OCOC(=O)C(C)(C)C)OCOC(=O)C(C)(C)C)ccc3s2)C1] | ((((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphoryl)bis(oxy))bis(methylene) bis(2,2-dimethylpropanoate) |
| 343 | 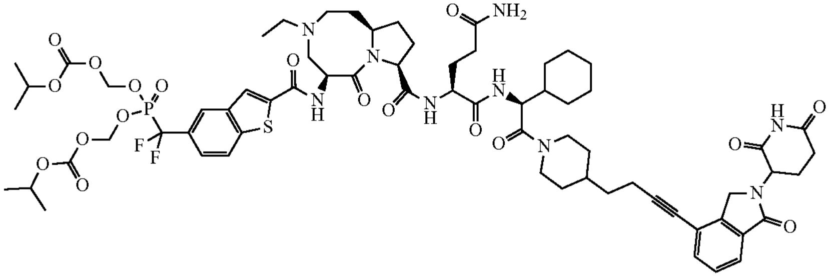 [SMILES: CCN1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(OCOC(=O)OC(C)C)OCOC(=O)OC(C)C)ccc3s2)C1] | ((((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphoryl)bis(oxy))bis(methylene) diisopropyl bis(carbonate) |
| 344 | 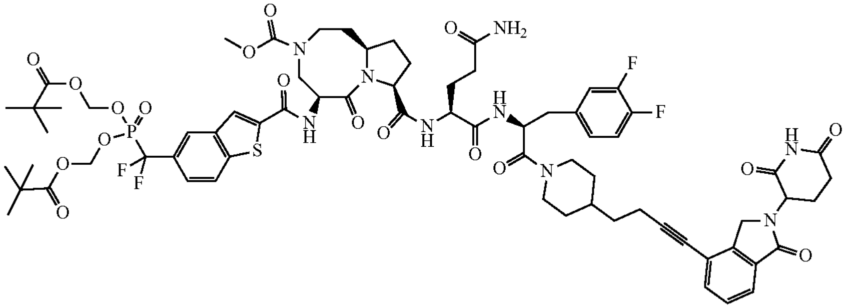 [SMILES: COC(=O)N1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(OCOC(=O)C(C)(C)C)OCOC(=O)C(C)(C)C)ccc3s2)C1] | ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphoryl)bis(oxy))bis(methylene) bis(2,2-dimethylpropanoate) |

TABLE 1A-continued

| Cpd. No. | Structure | Name |
|---|---|---|
| 345 | 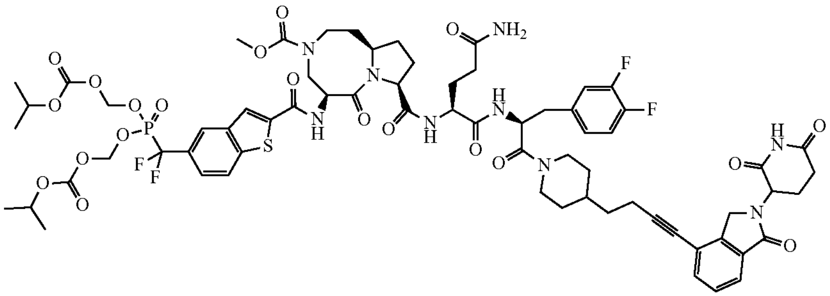 [SMILES: COC(=O)N1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(OCOC(=O)OC(C)C)OCOC(=O)OC(C)C)ccc3s2)C1] | methyl (5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-5-(5-((bis-(((isopropoxycarbonyl)oxy)methoxy)phosphoryl)difluoromethyl)benzo[b]thiophene-2-carboxamido)-6-oxooctahydropyrrolo[1,2-a][1,5]diazocine-3(4H)-carboxylate |
| 346 | 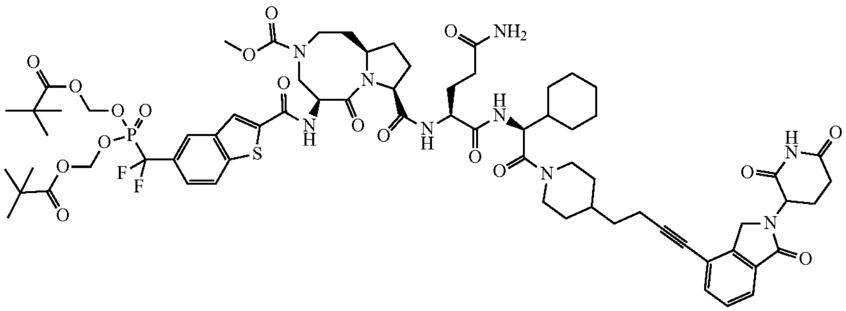 [SMILES: COC(=O)N1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(OCOC(=O)C(C)(C)C)OCOC(=O)C(C)(C)C)ccc3s2)C1] | ((((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]5-thiophen-yl)difluoromethyl)phosphoryl)bis(oxy))bis(methylene) bis(2,2-dimethylpropanoate) |
| 347 | 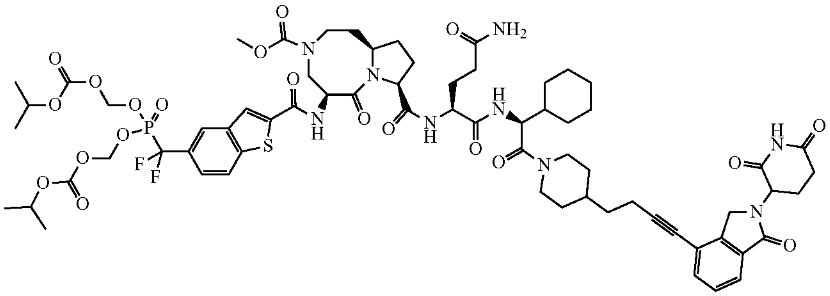 [SMILES: COC(=O)N1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(OCOC(=O)OC(C)C)OCOC(=O)OC(C)C)ccc3s2)C1] | methyl (5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-5-(5-((bis(((isopropoxycarbonyl)oxy)methoxy)phosphoryl)difluoromethyl)benzo[b]thiophene-2-carboxamido)-6-oxooctahydropyrrolo[1,2-a][1,5]diazocine-3(4H)-carboxylate |

TABLE 1A-continued
| Cpd. No. | Structure | Name |
|---|---|---|
| 348 | 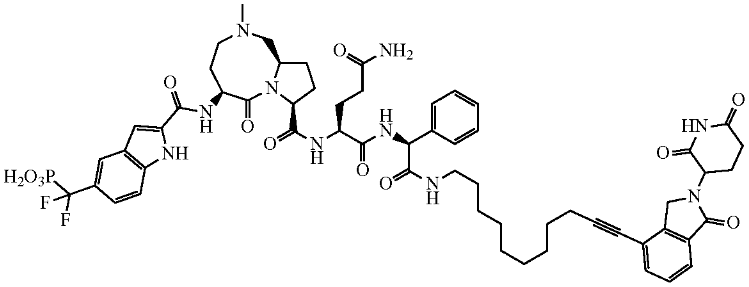 | ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)amino)-2-oxo-1-phenylethyl)amino)-1,5-dioxopentan-2-yl)carbamoyl)-2-methyl-6-oxodecahydropyrrolo[1,2-a][1,4]diazocin-5-yl)carbamoyl)-1H-indol-5-yl)difluoromethyl)phosphonic acid |

TABLE 1B
| Cpd. No. | Structure | Name |
|---|---|---|
| 349 | 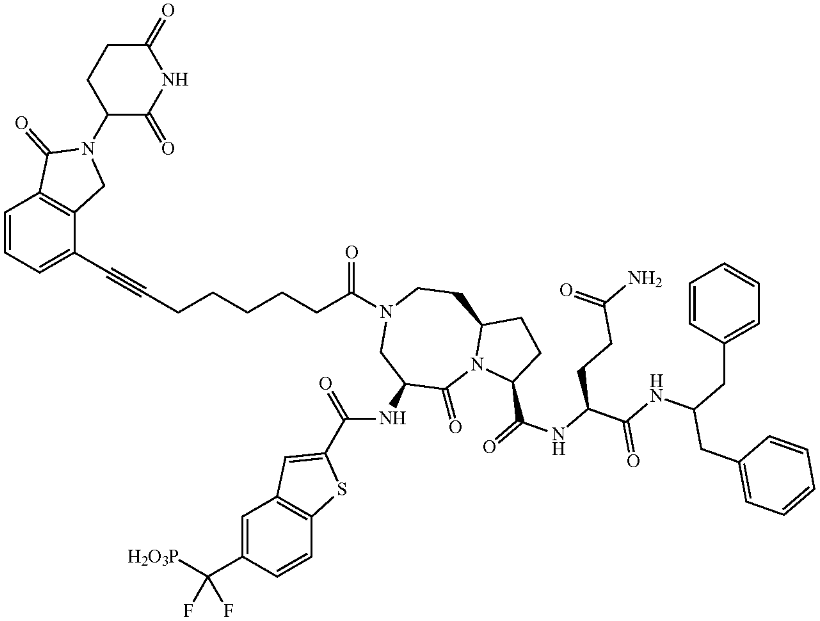 | ((2-(((5S,8S,10aR)-8-(((S)-5-amino-1-((1,3-diphenylpropan-2-yl)amino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 350 | 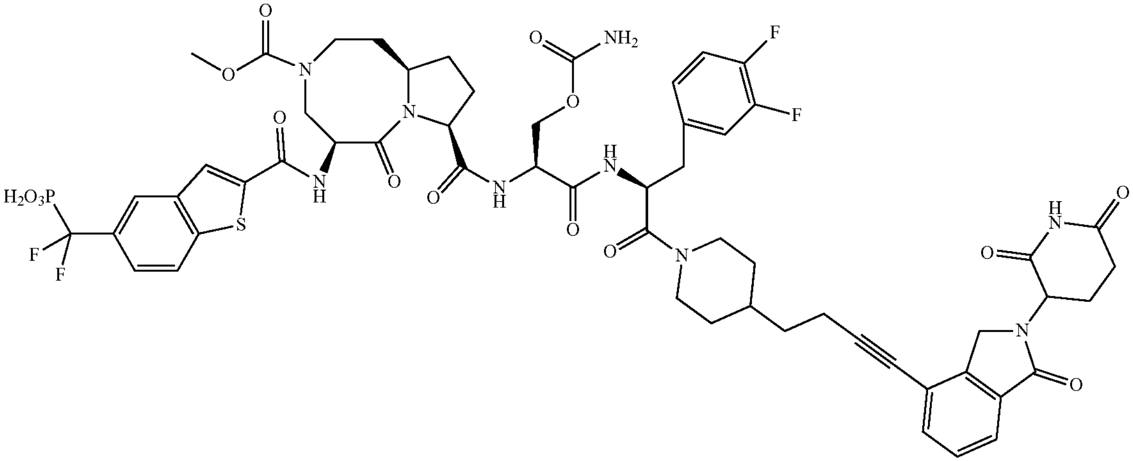 | ((2-(((5S,8S,10aR)-8-(((2S)-3-(carbamoyloxy)-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxopropan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |
| 351 | 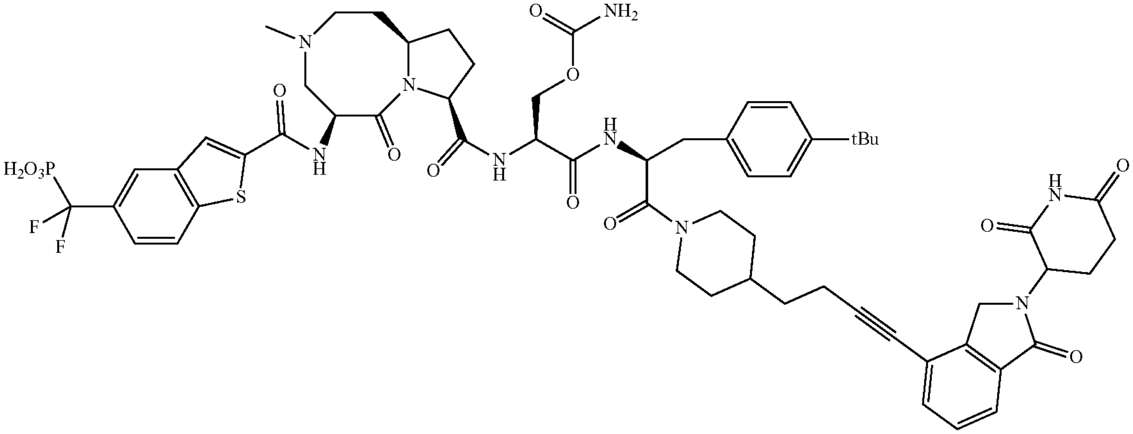 | ((2-(((5S,8S,10aR)-8-(((2S)-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-3-(carbamoyloxy)-1-oxopropan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 352 | 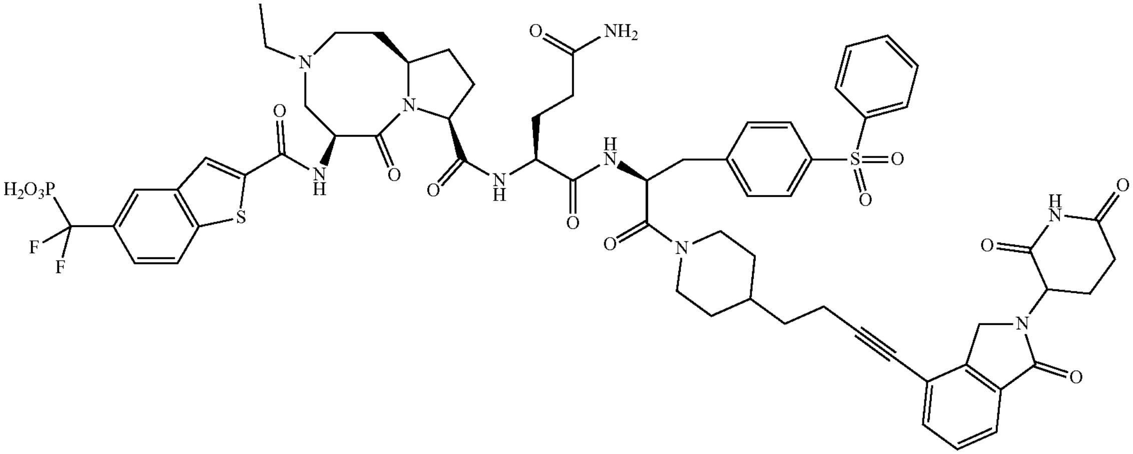 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-(phenylsulfonyl)phenyl)propan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 353 | 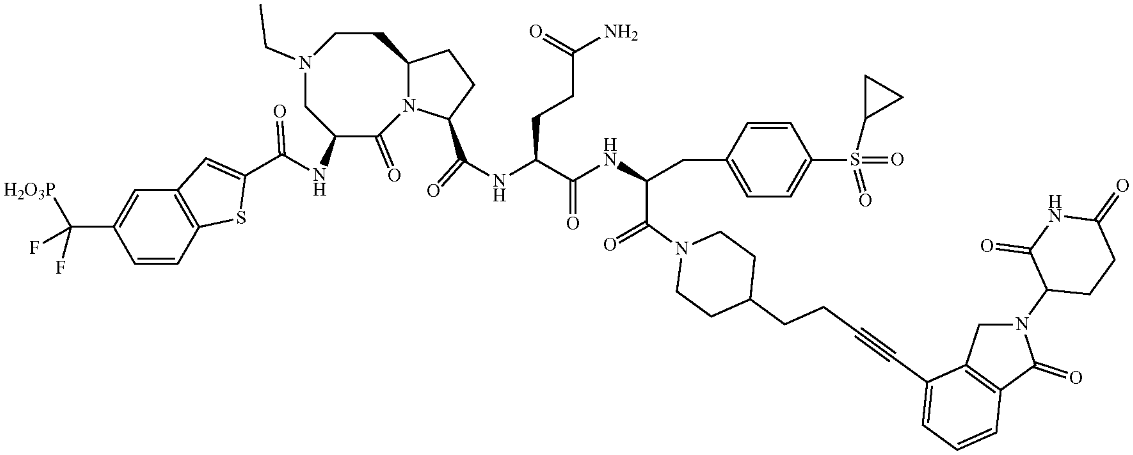 | ((2-(((5S,8S,10aR)-8-(((2S)-5-amino-1-(((2S)-3-(4-(cyclopropylsulfonyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 354 | 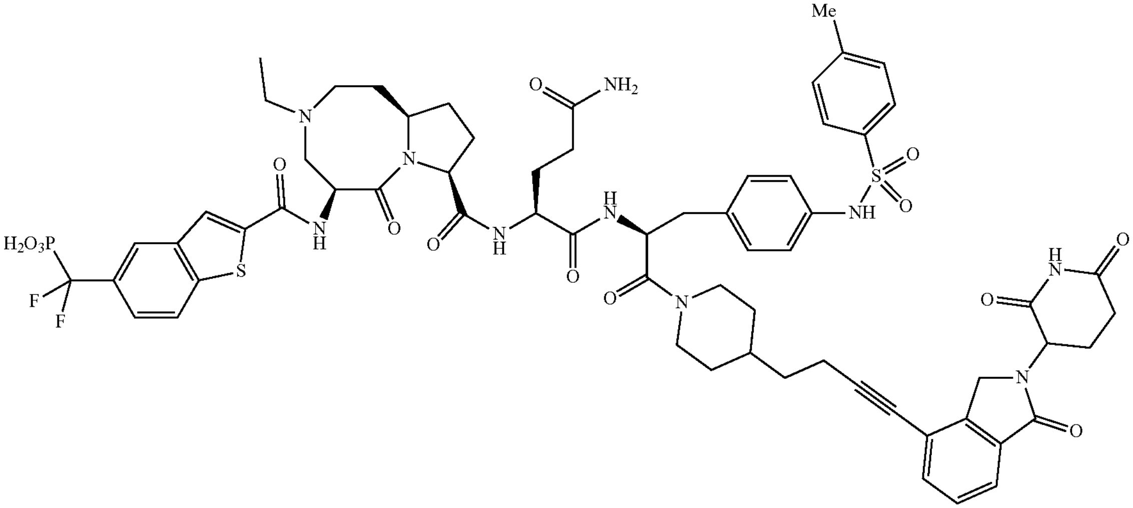 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-((4-methylphenyl)sulfonamido)phenyl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 355 | 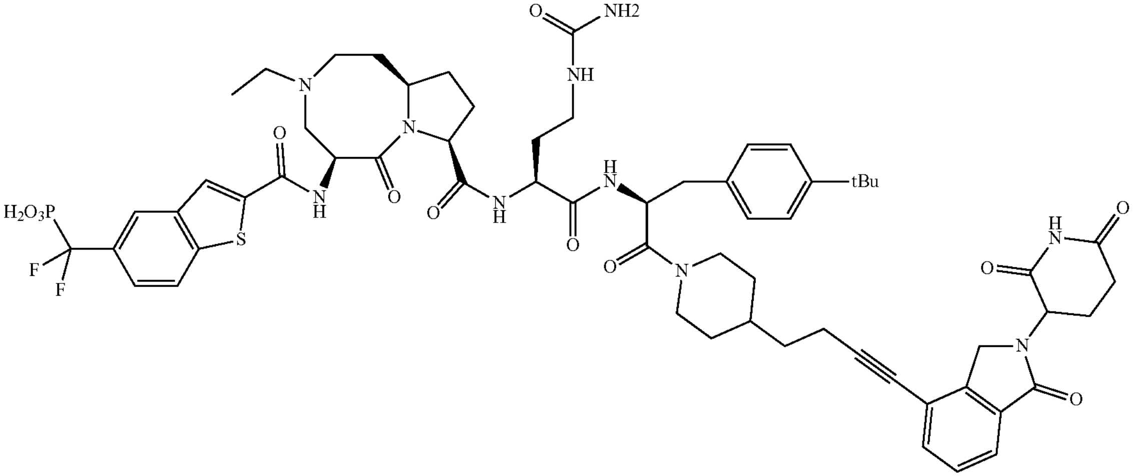 | ((2-(((5S,8S,10aR)-8-(((2S)-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxo-4-ureidobutan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
|---|---|---|
| 356 | 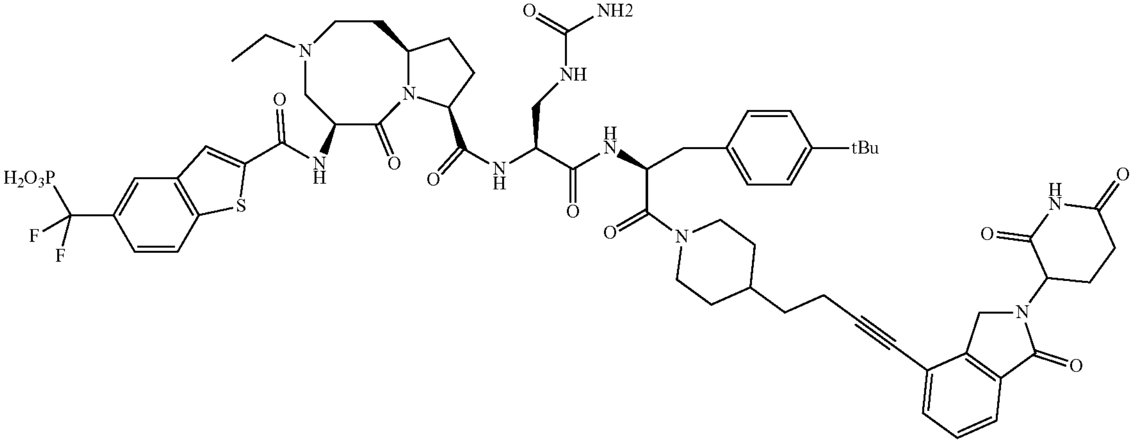 | ((2-(((5S,8S,10aR)-8-(((2S)-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1-oxo-3-ureidopropan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 357 | 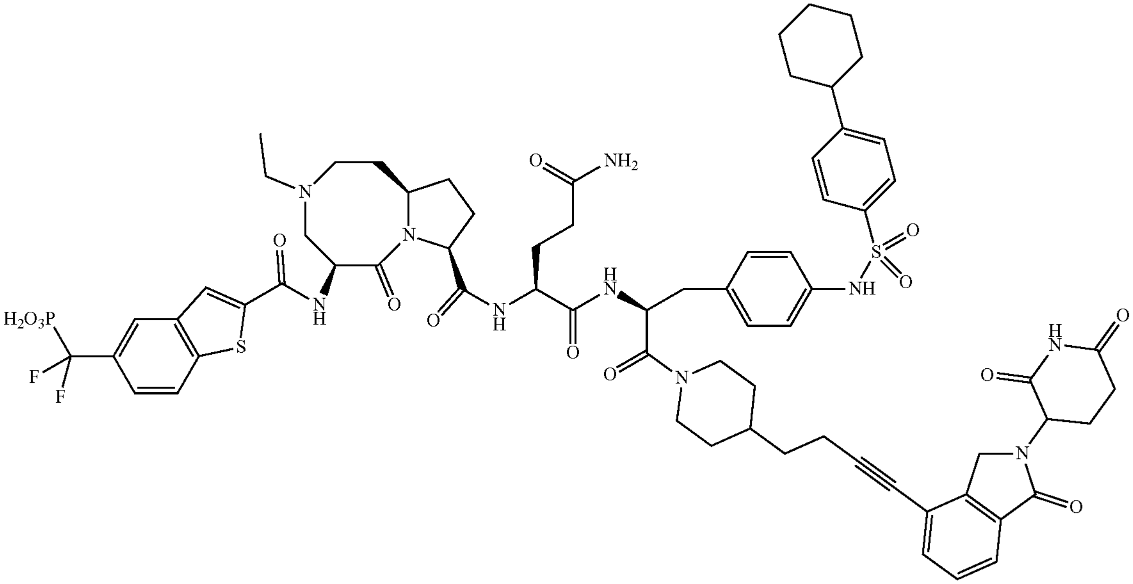 | ((2-(((5S,8S,10aR)-8-(((2S)-5-amino-1-(((2S)-3-(4-((4-cyclohexylphenyl)sulfonamido)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
|---|---|---|
| 358 | 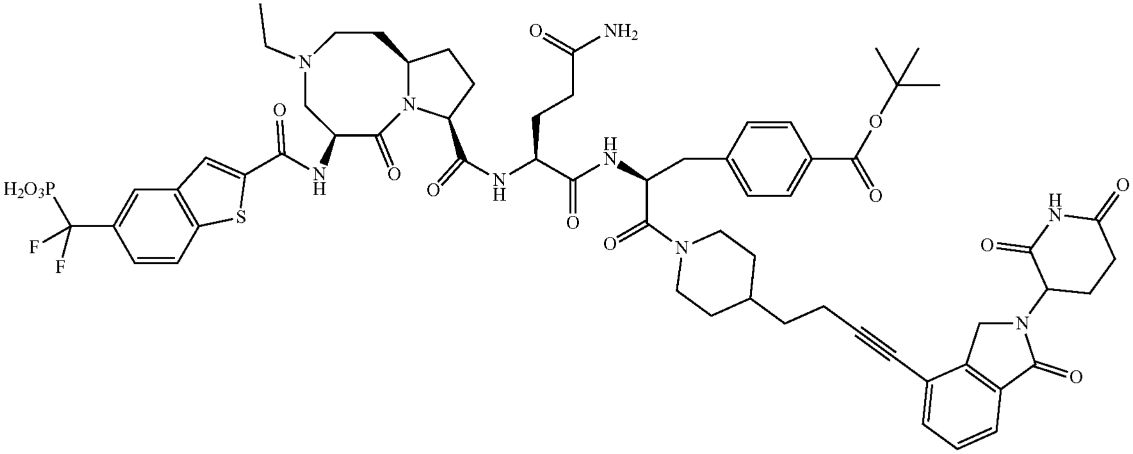 | ((2-(((5S,8S,10aR)-8-(((2S)-5-amino-1-(((2S)-3-(4-(tert-butoxycarbonyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 359 | 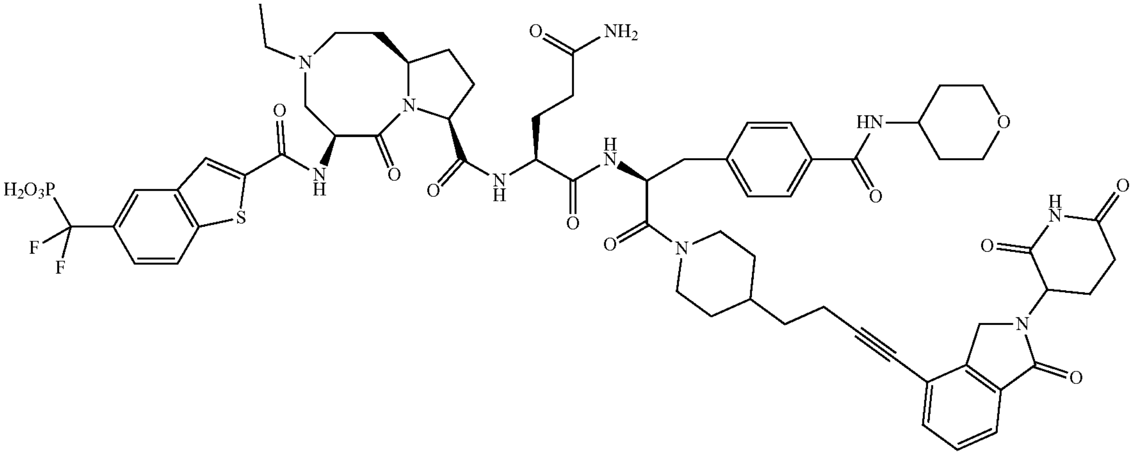 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-((tetrahydro-2H-pyran-4-yl)carbamoyl)phenyl)propan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 360 | 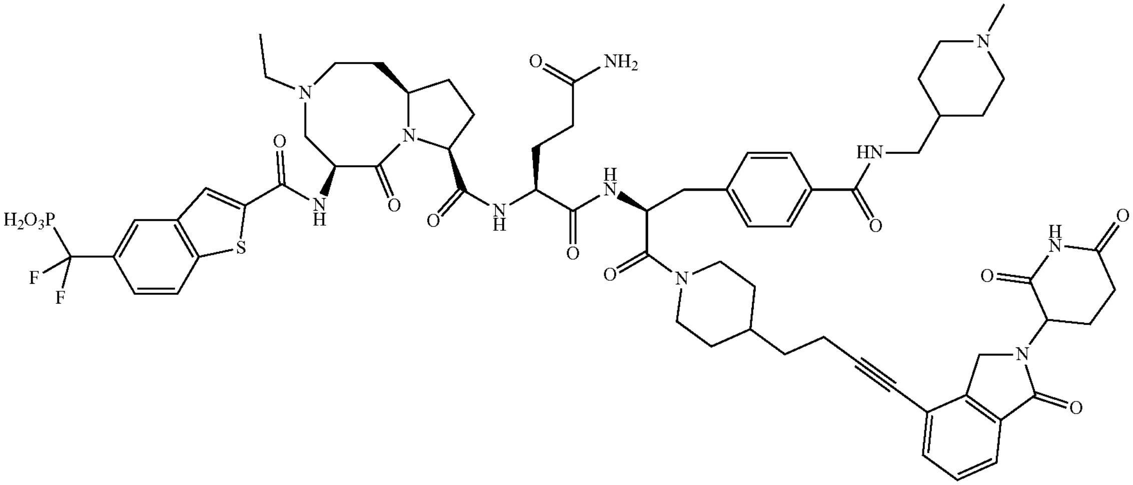 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-(((1-methylpiperidin-4-yl)methyl)carbamoyl)phenyl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic acid |
| 361 | 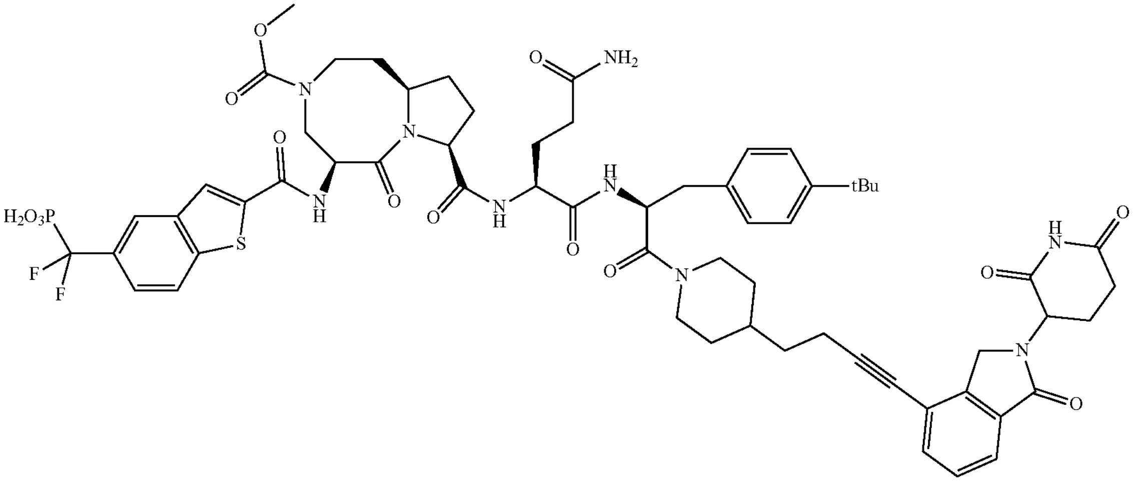 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 362 | 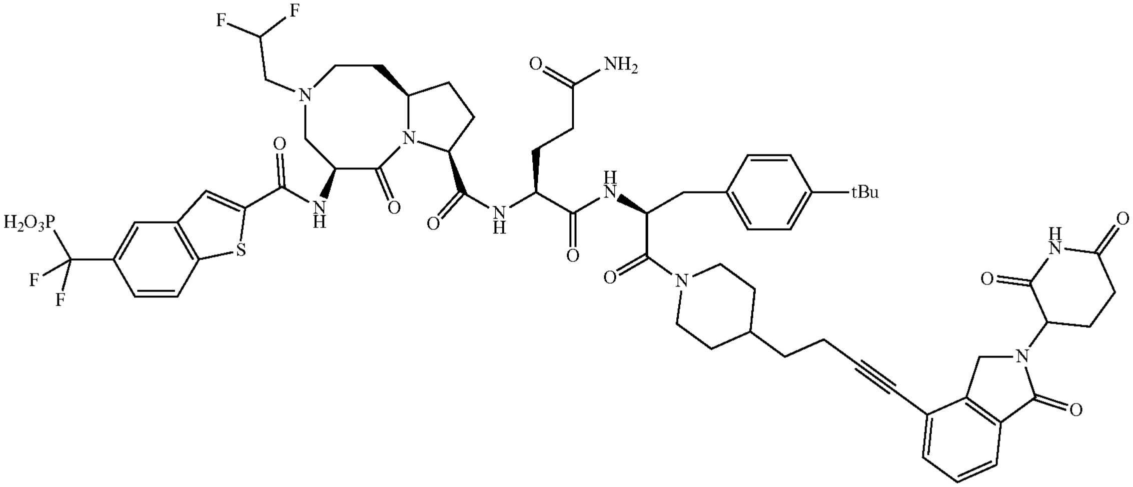 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(2,2-difluoroethyl)-6-oxodecahydropyrrolo[1,2-a][1,5]diazocin-5-yl)carbamoyl)benzo[b]thiophen-5-yl)difluoromethyl) phosphonic acid |
| 363 | 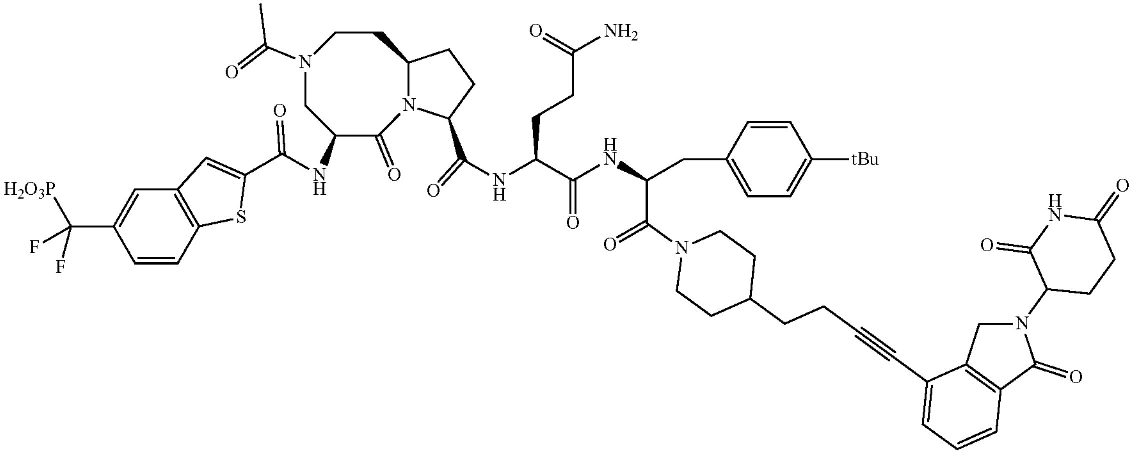 | ((2-(((5S,8S,10aR)-3-acetyl-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-6-oxodecahydropyrrolo [1,2-a][1,5]diazocin-5-yl)carbamoyl)benzo[b] thiophen-5-yl)difluoromethyl)phosphonic acid |

TABLE 1B-continued

| Cpd. No. | Structure | Name |
|---|---|---|
| 364 | 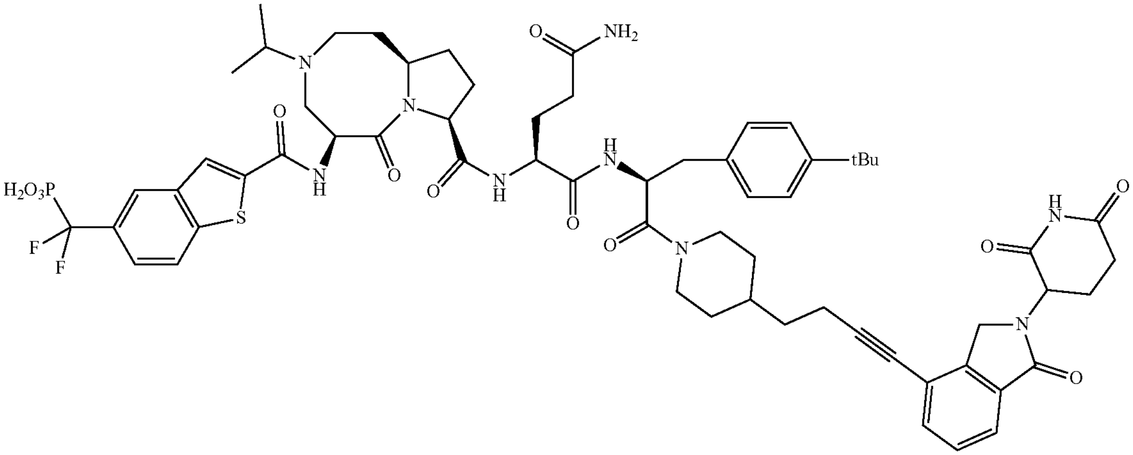 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-isopropyl-6-oxodecahydropyrrolo[1,2-a][1,5]diazocin-5-yl)carbamoyl)benzo[b]thiophen-5-yl)difluoromethyl) phosphonic acid |
| 365 | 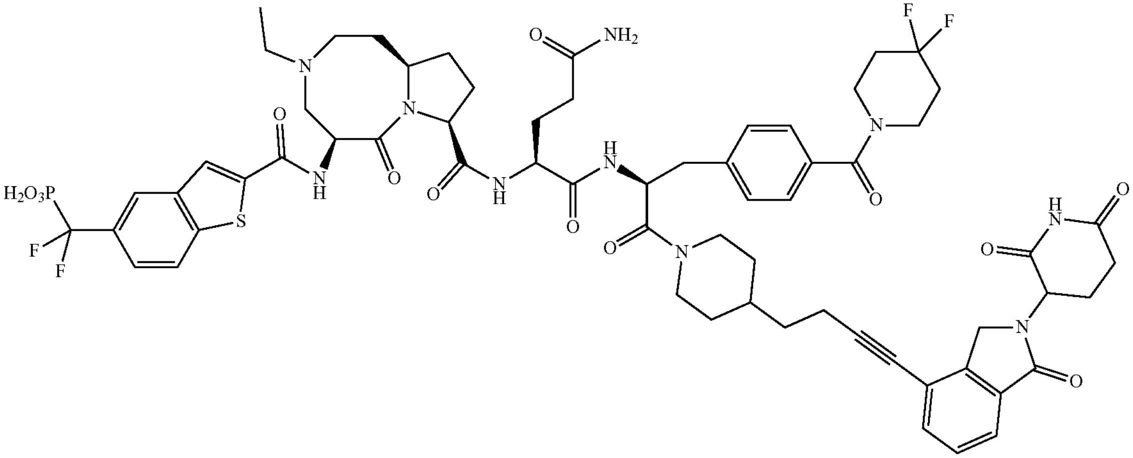 | ((2-(((5S,8S,10aR)-8-(((2S)-5-amino-1-(((2S)-3-(4-(4,4-difluoropiperidine-1-carbonyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl) phosphonic acid |

TABLE 1B-continued

| Cpd. No. | Structure | Name |
|---|---|---|
| 366 | 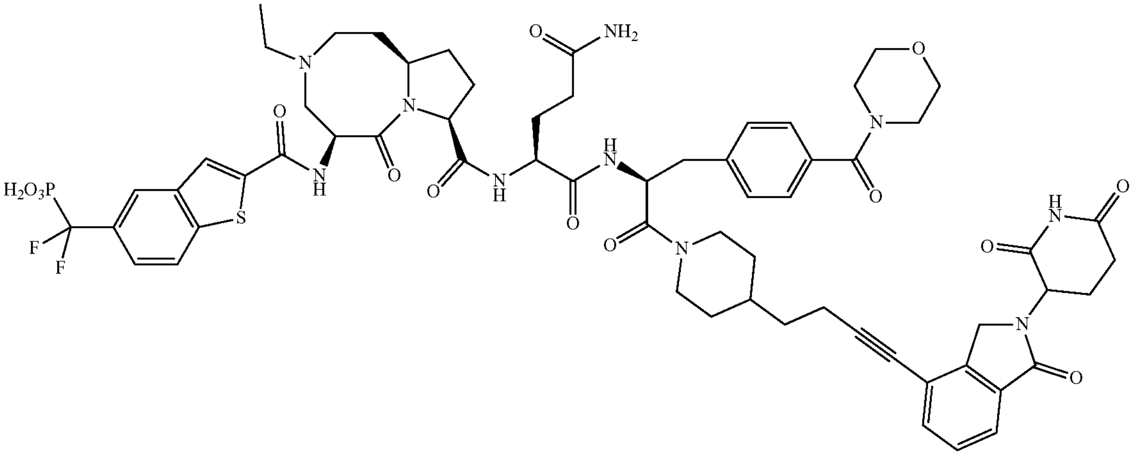 | ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-(morpholine-4-carbonyl)phenyl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl) phosphonic acid |
| 367 | 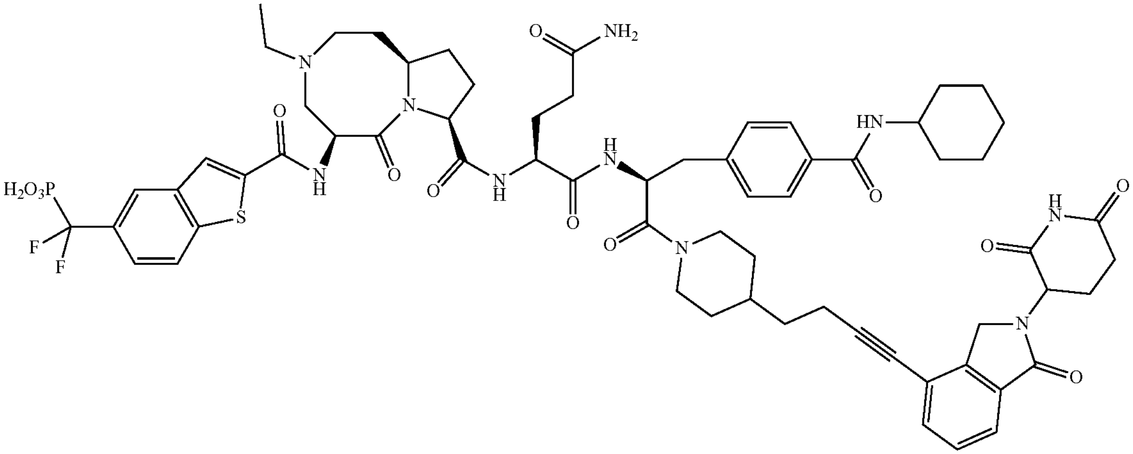 | ((2-(((5S,8S,10aR)-8-(((2S)-5-amino-1-(((2S)-3-(4-(cyclohexylcarbamoyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl) phosphonic acid |

TABLE 1B-continued

| Cpd. No. | Structure | Name |
| --- | --- | --- |
| 368 | 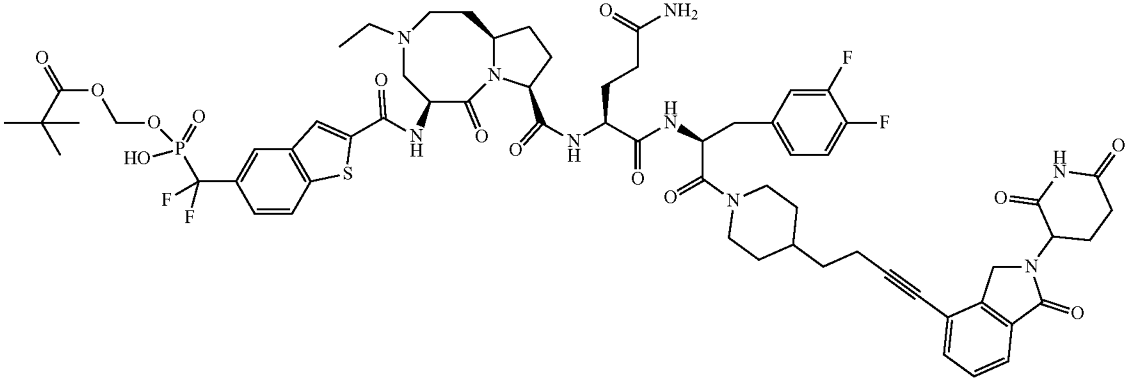 [SMILES: CCN1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(O)OCOC(=O)C(C)(C)C)ccc3s2)C1] | ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)(hydroxy)phosphoryl)oxy) methyl pivalate |
| 369 | 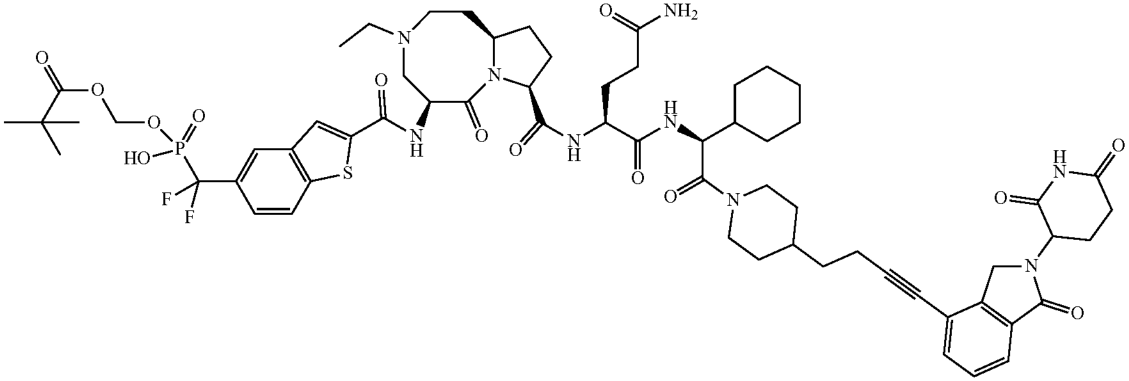 [SMILES: CCN1CC[C@H]2CC[C@@H](C(=O)N[C@@H](CCC(N)=O)C(=O)N[C@H](C(=O)N3CCC(CCC#Cc4cccc5c4CN(C4CCC(=O)NC4=O)C5=O)CC3)C3CCCCC3)N2C(=O)[C@@H](NC(=O)c2cc3cc(C(F)(F)P(=O)(O)OCOC(=O)C(C)(C)C)ccc3s2)C1] | ((((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)(hydroxy)phosphoryl)oxy) methyl pivalate |

TABLE 1B-continued

| Cpd. No. | Structure | Name |
| --- | --- | --- |
| 370 | 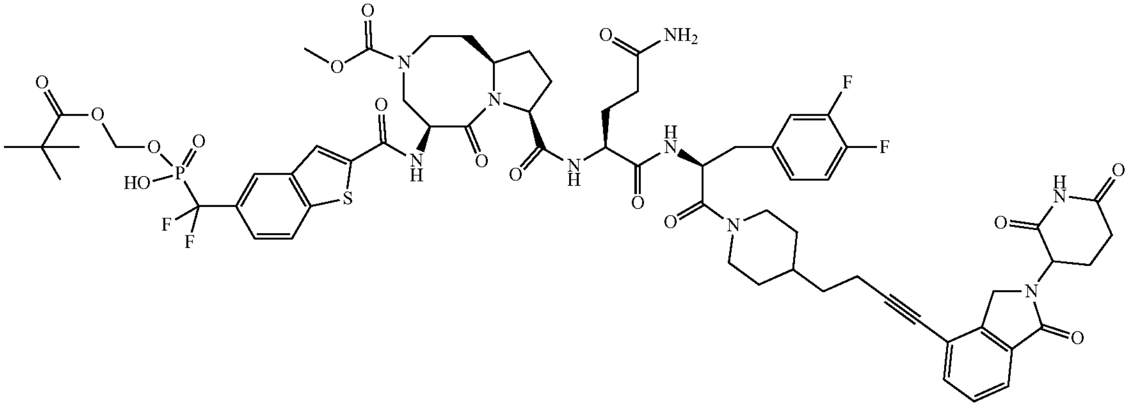 [SMILES: COC(=O)N1CC[C@H]2CC[C@@H](C(=O)N[C@@H](CCC(N)=O)C(=O)N[C@@H](Cc3ccc(F)c(F)c3)C(=O)N3CCC(CCC#Cc4cccc5c4CN(C4CCC(=O)NC4=O)C5=O)CC3)N2C(=O)[C@@H](NC(=O)c2cc3cc(C(F)(F)P(=O)(O)OCOC(=O)C(C)(C)C)ccc3s2)C1] | methyl (5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-5-(5-(difluoro(hydroxy((pivaloyloxy)methoxy)phosphoryl)methyl)benzo[b]thiophene-2-carboxamido)-6-oxooctahydropyrrolo[1,2-a][1,5]diazocine-3(4H)-carboxylate |
| 394 | 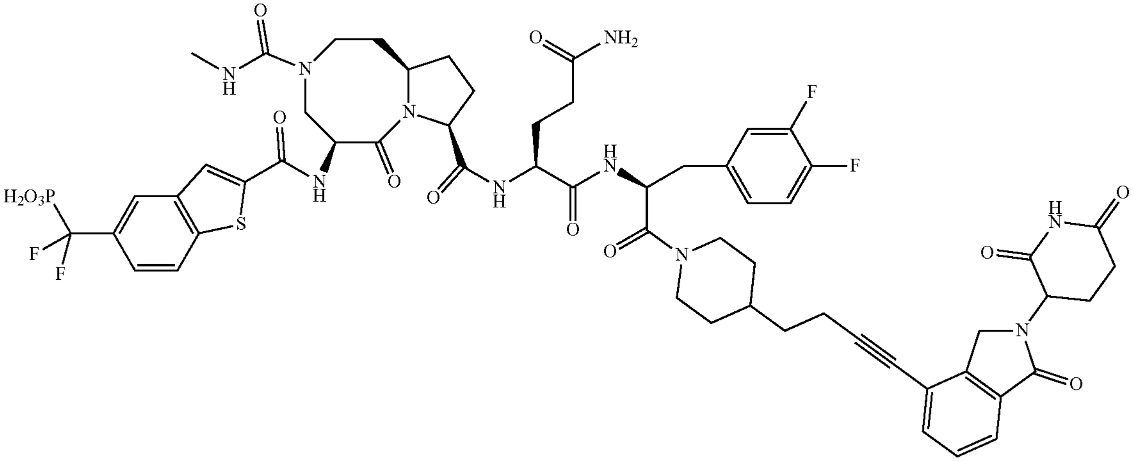 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methylcarbamoyl)-6-oxodecahydropyrrolo[1,2-a][1,5]diazocin-5-yl)carbamoyl)benzo[b]thiophen-5-yl)difluoromethyl)phosphonic acid |

TABLE 1B-continued

| Cpd. No. | Structure | Name |
| --- | --- | --- |
| 395 | 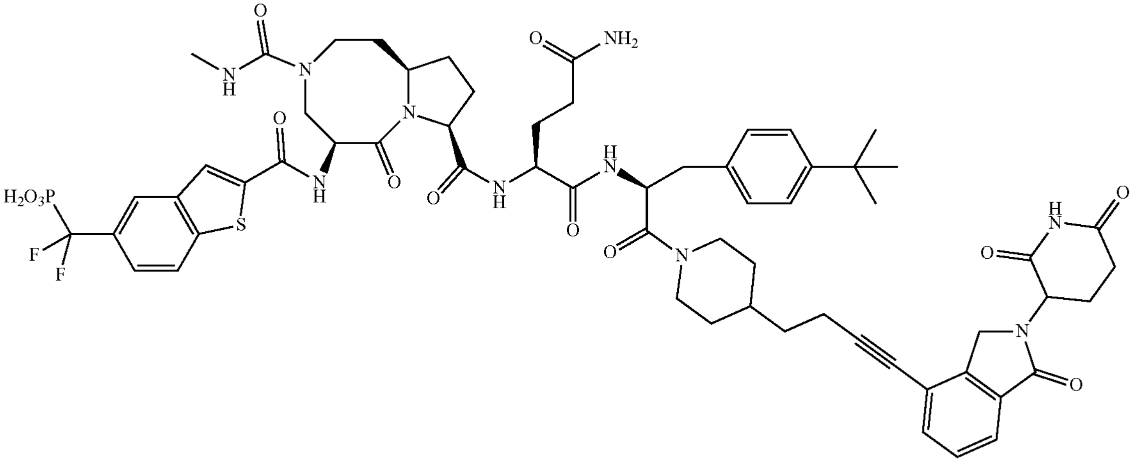 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methylcarbamoyl)-6-oxodecahydropyrrolo[1,2-a][1,5]diazocin-5-yl)carbamoyl)benzo[b]thiophen-5-yl)difluoromethyl)phosphonic acid |
| 396 | 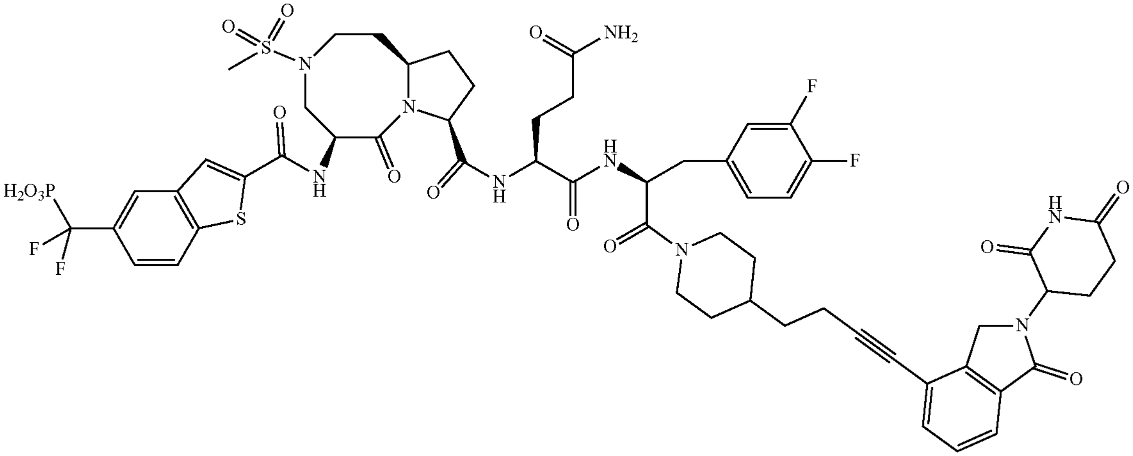 | ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methylsulfonyl)-6-oxodecahydropyrrolo[1,2-a][1,5]diazocin-5-yl)carbamoyl)benzo[b]thiophen-5-yl)difluoromethyl)phosphonic acid |

TABLE 1B-continued
| Cpd. No. | Structure | Name |
| --- | --- | --- |
| 397 | 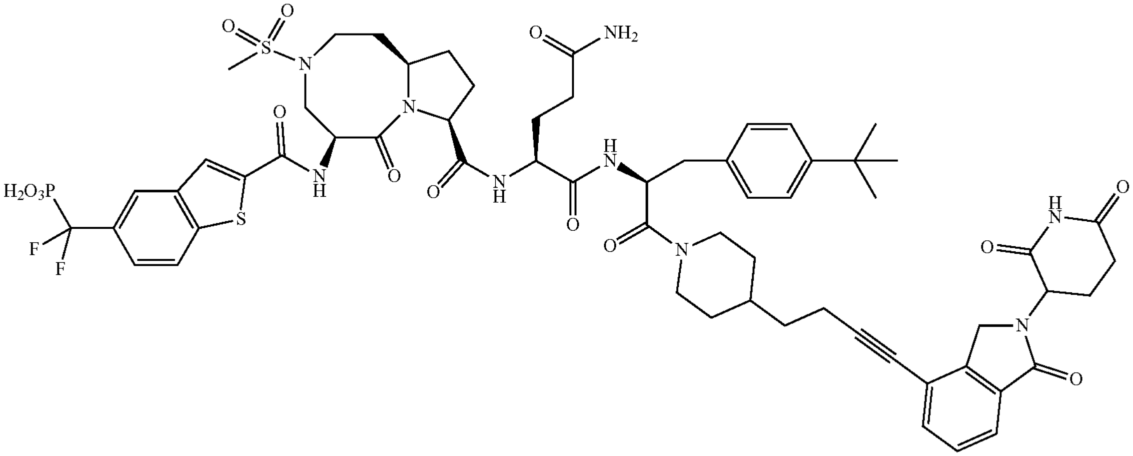 | ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methylsulfonyl)-6-oxodecahydropyrrolo[1,2-a][1,5]diazocin-5-yl)carbamoyl)benzo[b]thiophen-5-yl)difluoromethyl)phosphonic acid |

In another embodiment, Compounds of the Disclosure are compounds of Formula I selected from group consisting of:

((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxo-decahydropyrrolo[1,2-a][1,5]diazocin-5-yl)carbamoyl)-1H-indol-5-yl)difluoromethyl)phosphonic acid;

(2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indole-5-carbonyl)phosphonic acid;

(2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid;

(2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid;

((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxo-decahydropyrrolo[1,2-a][1,5]diazocin-5-yl)carbamoyl)benzo[b]thiophen-5-yl)difluoromethyl)phosphonic acid;

((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid;

((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodeca-hydropyrrolo[1,2-a][1,5]diazocin-5-yl)carbamoyl)benzo[b]thiophene-5-carbonyl)phosphonic acid;

(2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophene-5-carbonyl)phosphonic acid; and (2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)benzo[b]thiophene-5-carbonyl)phosphonic acid, or a pharmaceutically acceptable salt or solvate thereof.

In another embodiment, Compounds of the Disclosure are compounds of Formula I selected from group consisting of:

((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxo-propan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid; and ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid, or a pharmaceutically acceptable salt or solvate thereof.

In another embodiment, a Compound of the Disclosure is ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic acid, or a pharmaceutically acceptable salt thereof.

In another embodiment, the present disclosure provides a compound having the following structure:

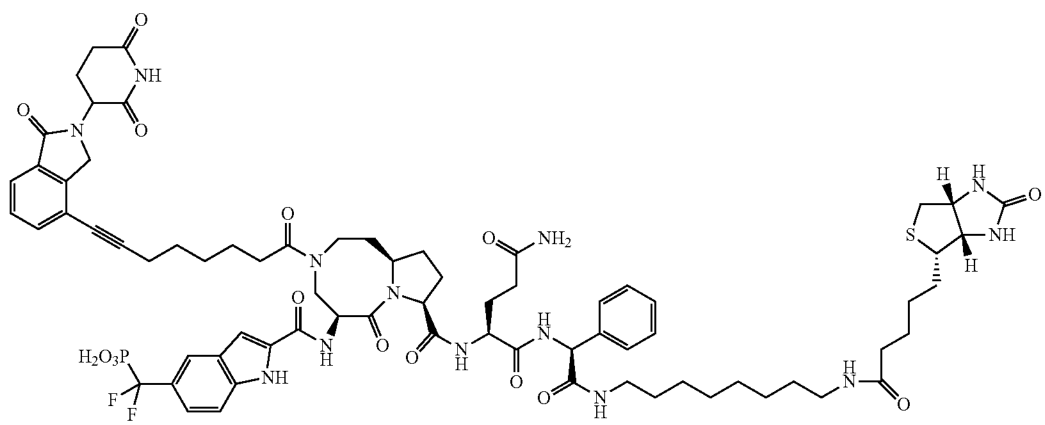

(chemical name: ((2-(((5S,8S,10aR)-8-(((S)-5-amino-1,5-dioxo-1-(((S)-2-oxo-2-((8-(5-((3aS,4S,6aR)-2-oxohexahydro-1H-thieno[3,4-d]imidazol-4-yl)pentanamido)octyl)amino)-1-phenylethyl)amino)pentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid).

In another embodiment, the present disclosure provides a compound having the following structure:

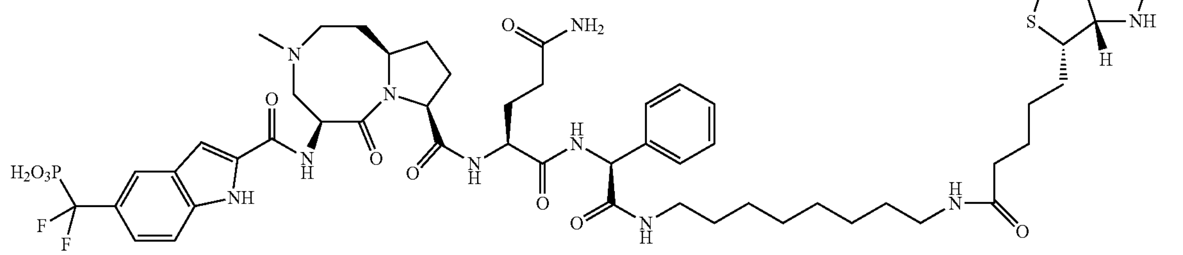

(chemical name: ((2-(((5S,8S,10aR)-8-(((S)-5-amino-1,5-dioxo-1-(((S)-2-oxo-2-((8-(5-((3aS,4S,6aR)-2-oxohexahydro-1H-thieno[3,4-d]imidazol-4-yl)pentanamido)octyl)amino)-1-phenylethyl)amino)pentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid).

In another embodiment, the present disclosure provides a compound having the following structure:

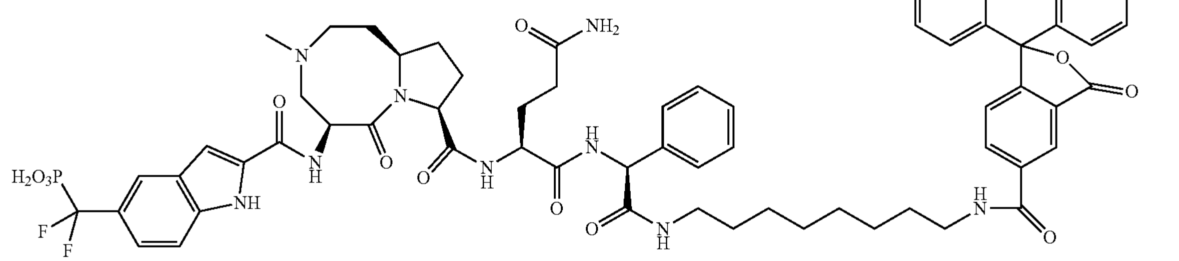

(chemical name: ((2-(((5S,8S,10aR)-8-(((S)-5-amino-1-(((S)-2-((8-(3',6'-dihydroxy-3-oxo-3H-spiro[isobenzofuran-1,9'-xanthene]-5-carboxamido)octyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid).

In another embodiment, Compounds of the Disclosure are compounds of Formula VIII:

VIII

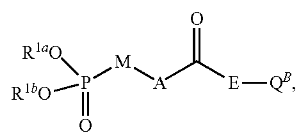

wherein:

$R^{1a}$ and $R^{1b}$ are independently selected from the group consisting of hydrogen, $C_1$-$C_6$ alkyl, and aralkyl;

$R^{2a}$, $R^{2b}$, M, A, and E are as defined in connection with Formula I, except that in A the bond designated with an "*" is attached to —C(═O)-E-$Q^B$ and that in E the bond designated with an "*" is attached to $Q^B$;

$R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$;

$R^9$ is as defined in connection with Formula I;

$Q^B$ is selected from the group consisting of Q-1 and Q-2, wherein Q-1 and Q-2 are as defined in connection with Formula I, or a pharmaceutically acceptable salt or solvate thereof.

In another embodiment, Compounds of the Disclosure are compounds of Formula VIII, with the provisos:

(1) when $X_A$ is —$CH_2CH_2$—, then:

(i) A is selected from the group consisting of A-2, A-5, A-6, A-7, A-8, A-9, A-10, A-11, A-12, A-13, A-14, A-15, A-16, A-17, A-18, A-19, and A-20;

(ii) A is A-4 and $G^1$ is —S—; or (iii) $R^{2a}$ and $R^{2b}$ taken together with the carbon atom to which they are attached form a —C(═O)— group;

(2) when $X_A$ is —N($R^8$)$CH_2$—, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group; or (3) when $X_A$ is —$CH_2$N($R^8$)—, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group, or a pharmaceutically acceptable salt or solvate thereof.

In another embodiment, Compounds of the Disclosure are compounds of Formula VIII, wherein M is —O—, or a pharmaceutically acceptable salt or solvate thereof.

In another embodiment, Compounds of the Disclosure are compounds of Formula VIII, wherein M is —C($R^{2a}$)($R^{2b}$)—, or a pharmaceutically acceptable salt or solvate thereof.

In another embodiment, Compounds of the Disclosure are compounds of Formula IX:

IX

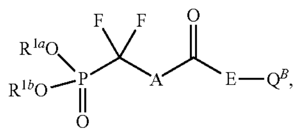

wherein $R^{1a}$, $R^{1b}$, A, E, and $Q^B$ are as defined in connection with Formula VIII, or a pharmaceutically acceptable salt or solvate thereof.

In another embodiment, Compounds of the Disclosure are compounds of Formula X:

X

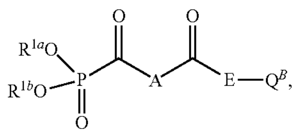

wherein $R^{1a}$, $R^{1b}$, A, E, and $Q^B$ are as defined in connection with Formula VIII, or a pharmaceutically acceptable salt or solvate thereof.

In another embodiment, Compounds of the Disclosure are compounds of any one of Formulae VIII-X, wherein $Q^B$ is Q-1, or a pharmaceutically acceptable salt or solvate thereof. In another embodiment, E is E-1-1. In another embodiment, E is E-2-1. In another embodiment, E is E-3-1. In another embodiment, $X^1$ is selected from the group consisting of —$CH_2$— and —N(H)—. In another embodiment, $X^1$ is —$CH_2$—. In another embodiment, s is 0 or 1. In another embodiment, s is 0.

In another embodiment, Compounds of the Disclosure are compounds of any one of Formulae VIII-X, wherein $Q^B$ is Q-2, or a pharmaceutically acceptable salt or solvate thereof. In another embodiment, E is E-1-1. In another embodiment, E is E-2-1. In another embodiment, E is E-3-1. In another embodiment, Q-2 is Q-2-1 (wherein Q-2-1 is as defined in connection with Formula I). In another embodiment, $X^2$ is selected from the group consisting of —$CH_2$—, —O—, and —N(H)—. In another embodiment, $X^2$ is —$CH_2$—. In another embodiment, t is 0 or 1. In another embodiment, t is 0. In another embodiment, $R^{12b}$ is hydrogen, or a pharmaceutically acceptable salt or solvate thereof. In another embodiment, $R^{12a}$ is aralkyl, or a pharmaceutically acceptable salt or solvate thereof.

In another embodiment, Compounds of the Disclosure are compounds of Formula XI:

XI

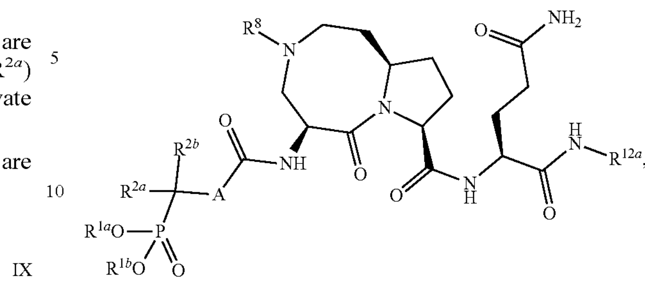

wherein $R^{1a}$, $R^{1b}$, $R^{2a}$, $R^{2b}$, $R^8$, $R^{12a}$, and A are as defined in connection with Formula VIII, or a pharmaceutically acceptable salt or solvate thereof.

In another embodiment, Compounds of the Disclosure are compounds of Formula XII:

XII

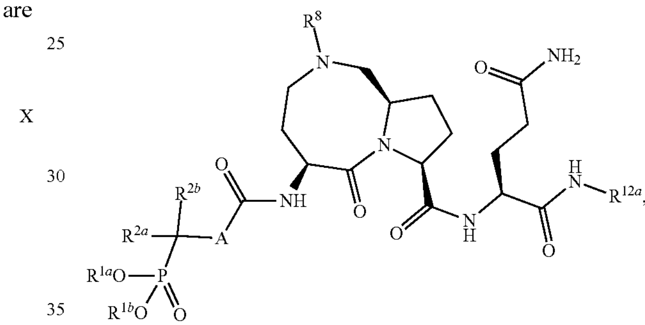

wherein $R^{1a}$, $R^{1b}$, $R^{2a}$, $R^{2b}$, $R^8$, $R^{12a}$, and A are as defined in connection with Formula VIII, or a pharmaceutically acceptable salt or solvate thereof.

In another embodiment, Compounds of the Disclosure are compounds of Formula XI or Formula XII, wherein $R^{2a}$ and $R^{2b}$ are fluoro, or a pharmaceutically acceptable salt or solvate thereof.

In another embodiment, Compounds of the Disclosure are compounds of Formula XI or Formula XII, wherein $R^{2a}$ and $R^{2b}$ taken together with the carbon to which they are attached form a —C(═O)— group, or a pharmaceutically acceptable salt or solvate thereof.

In another embodiment, Compounds of the Disclosure are compounds of Formula XI or Formula XII, wherein A is A-4, or a pharmaceutically acceptable salt or solvate thereof. In another embodiment, $G^1$ is —S—.

In another embodiment, Compounds of the Disclosure are compounds of Formula XI or Formula XII, wherein A is A-8, or a pharmaceutically acceptable salt or solvate thereof. In another embodiment, G, $G^4$, and $G^6$ are —C(H)═; and $R^3$ is hydrogen.

In another embodiment, Compounds of the Disclosure are compounds of Formula XI or Formula XII, wherein $R^8$ is hydrogen, or a pharmaceutically acceptable salt or solvate thereof.

In another embodiment, Compounds of the Disclosure are compounds of Formula XI or Formula XII, wherein $R^8$ is $C_1$-$C_4$ alkyl, or a pharmaceutically acceptable salt or solvate thereof.

In another embodiment, Compounds of the Disclosure are compounds of Formula XI or Formula XII, wherein $R^{12a}$ is aralkyl, or a pharmaceutically acceptable salt or solvate thereof. In another embodiment, $R^{12a}$ is:

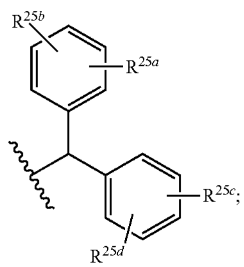

and $R^{25a}$, $R^{25b}$, $R^{25c}$, and $R^{25d}$ are each independently selected from the group consisting of hydrogen, halo, $C_1$-$C_4$ alkyl, and $C_1$-$C_4$ alkoxy, or a pharmaceutically acceptable salt or solvate thereof.

In another embodiment, Compounds of the Disclosure are compounds of Formula XI or Formula XII, wherein $R^{1a}$ and $R^{1b}$ are $C_1$-$C_4$ alkyl, or a pharmaceutically acceptable salt or solvate thereof.

In another embodiment, Compounds of the Disclosure are compounds of Formula XI or Formula XII, wherein $R^{1a}$ and $R^{1b}$ hydrogen, or a pharmaceutically acceptable salt or solvate thereof.

In another embodiment, Compounds of the Disclosure are the compounds of Formula VIII provided in Table 2, or a pharmaceutically acceptable salt or solvate thereof.

TABLE 2

| Cpd. No. | Structure |
| --- | --- |
| 200 | 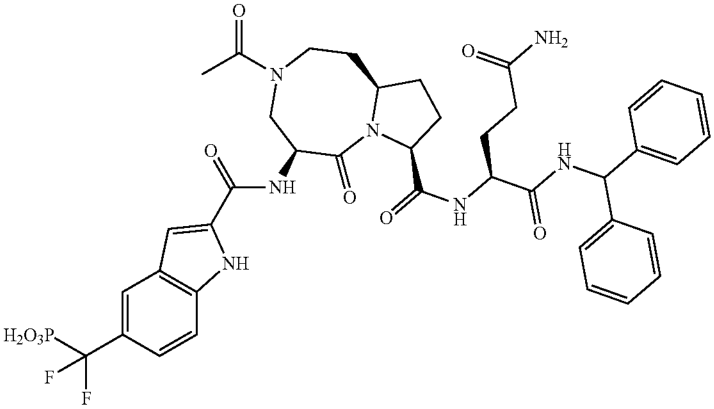 |
| 201 | 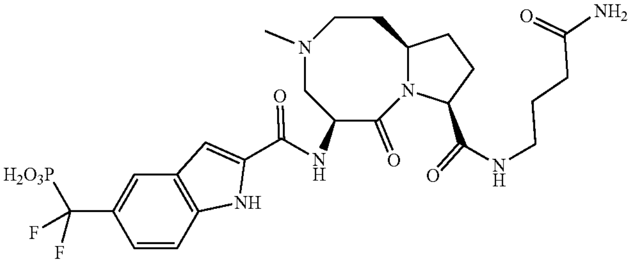 |
| 202 | 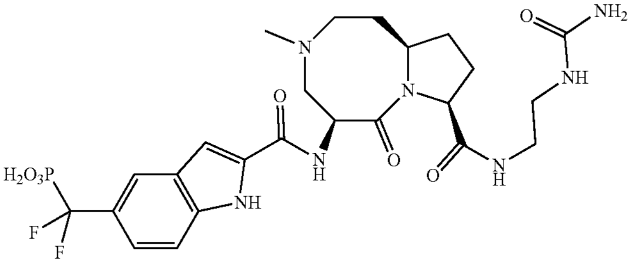 |

TABLE 2-continued
| Cpd. No. | Structure |
|---|---|
| 203 | 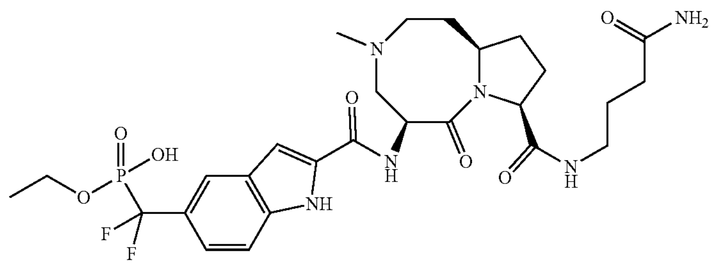 [SMILES: CCOP(=O)(O)C(F)(F)c1ccc2[nH]c(C(=O)N[C@H]3CN(C)CC[C@H]4CC[C@@H](C(=O)NCCCC(N)=O)N4C3=O)cc2c1] |
| 204 | 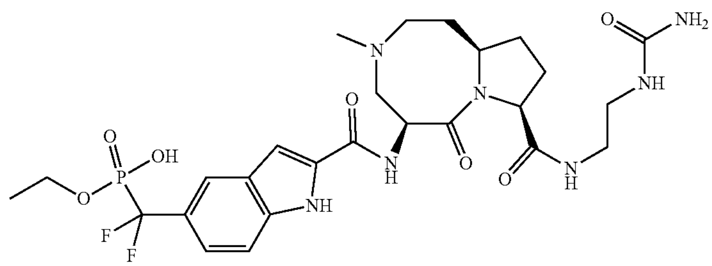 [SMILES: CCOP(=O)(O)C(F)(F)c1ccc2[nH]c(C(=O)N[C@H]3CN(C)CC[C@H]4CC[C@@H](C(=O)NCCNC(N)=O)N4C3=O)cc2c1] |
| 205 | 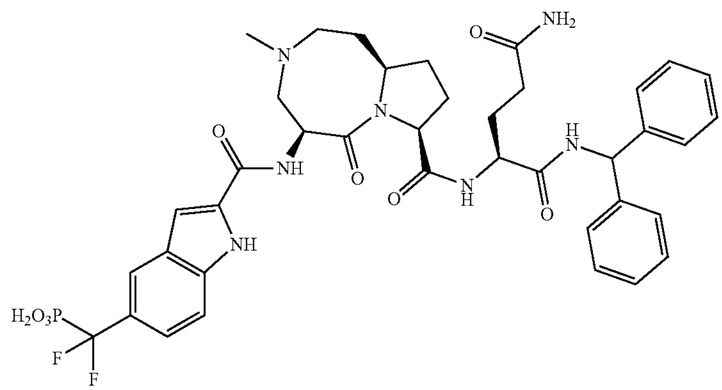 |
| 206 | 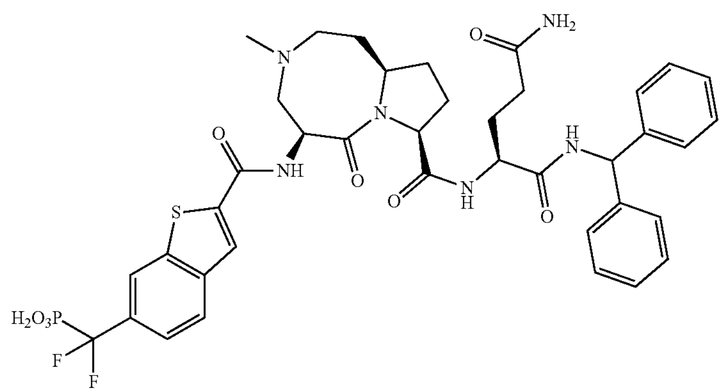 |

TABLE 2-continued
| Cpd. No. | Structure |
|---|---|
| 207 | 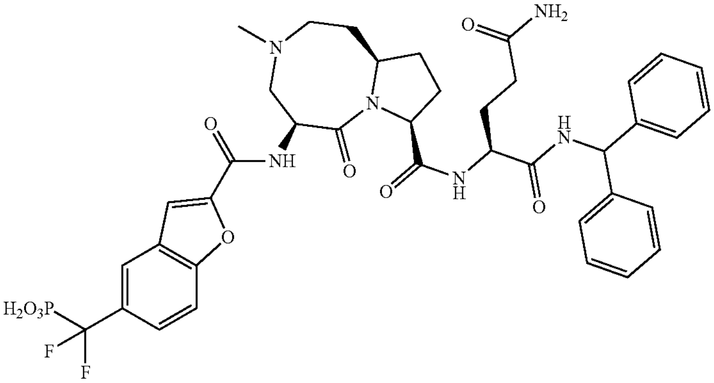 |
| 208 | 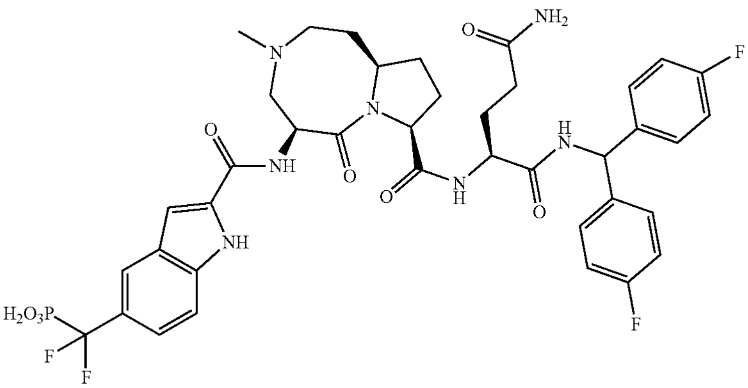 |
| 209 | 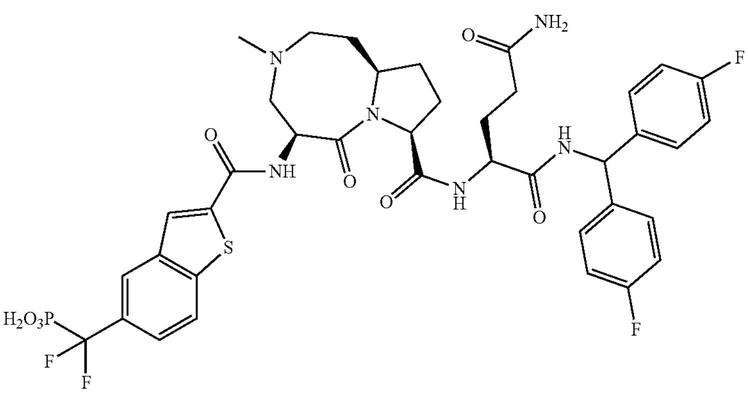 |
| 210 | 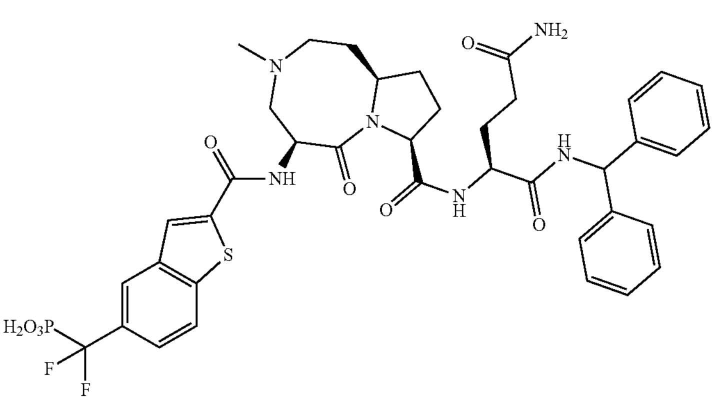 |

TABLE 2-continued
| Cpd. No. | Structure |
|---|---|
| 211 | 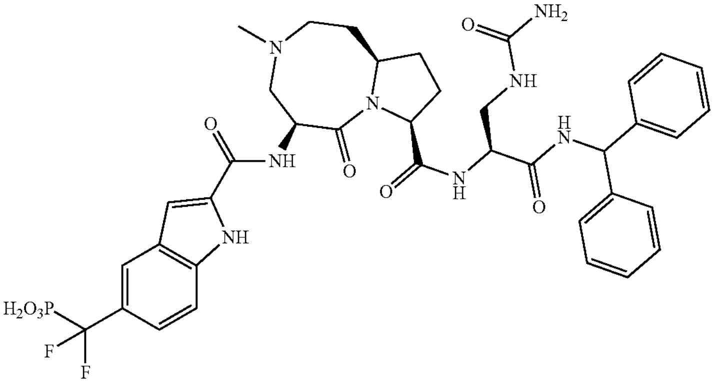 |
| 212 | 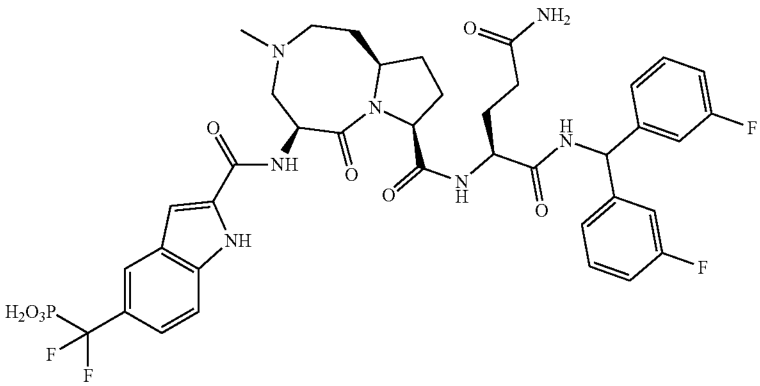 |
| 213 | 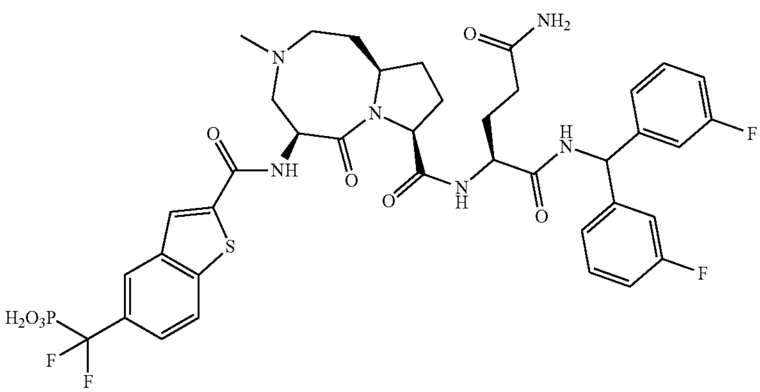 |
| 214 | 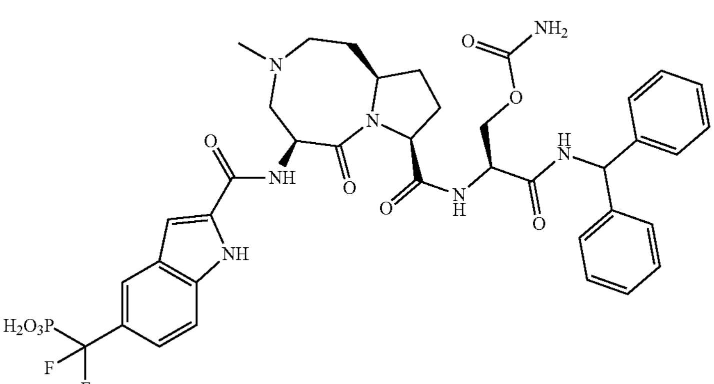 |

TABLE 2-continued
| Cpd. No. | Structure |
|---|---|
| 215 | 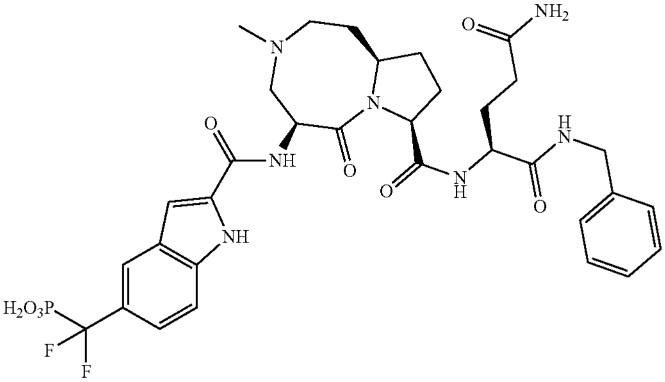 |
| 216 | 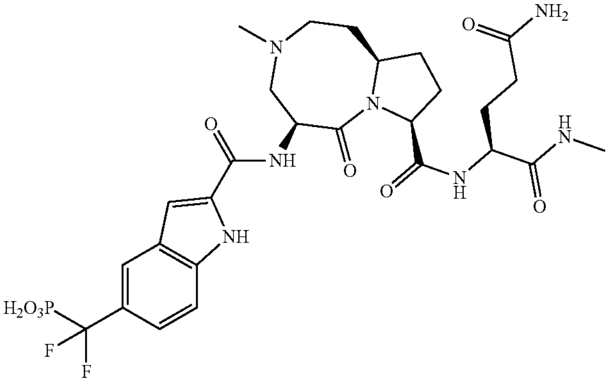 |
| 217 | 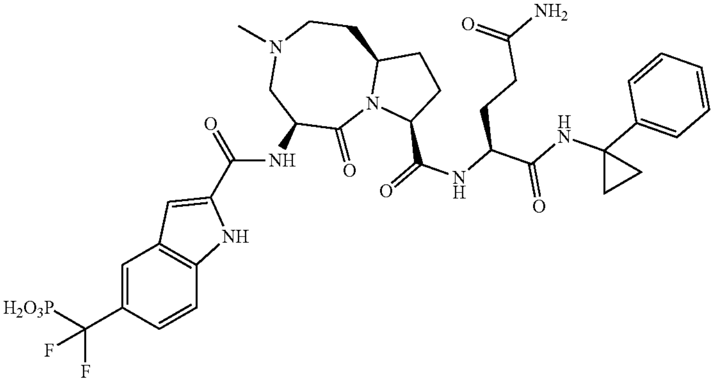 |
| 218 | 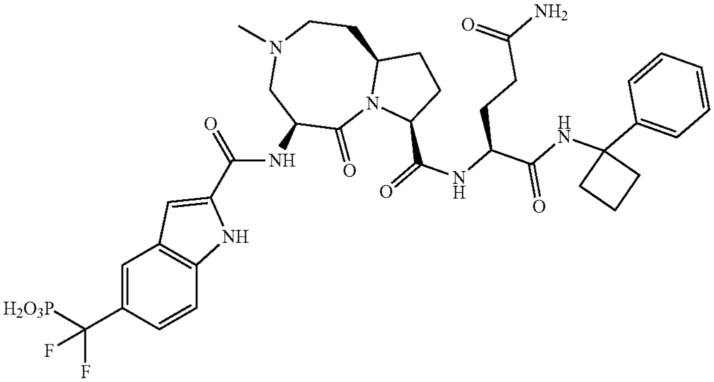 |

TABLE 2-continued
| Cpd. No. | Structure |
|---|---|
| 219 | 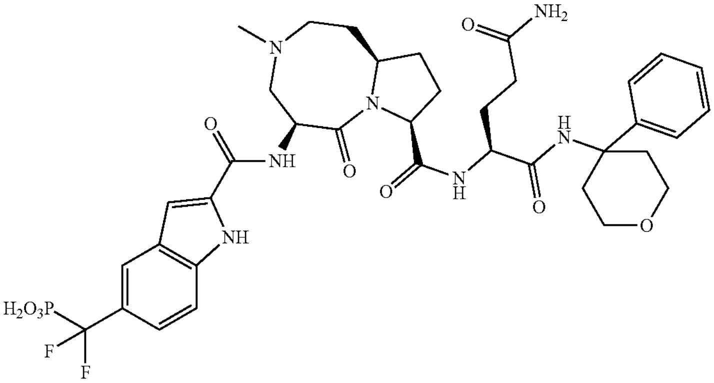 |
| 220 | 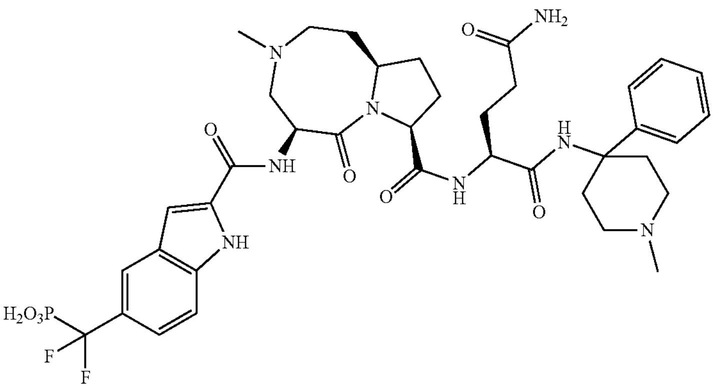 |
| 221 | 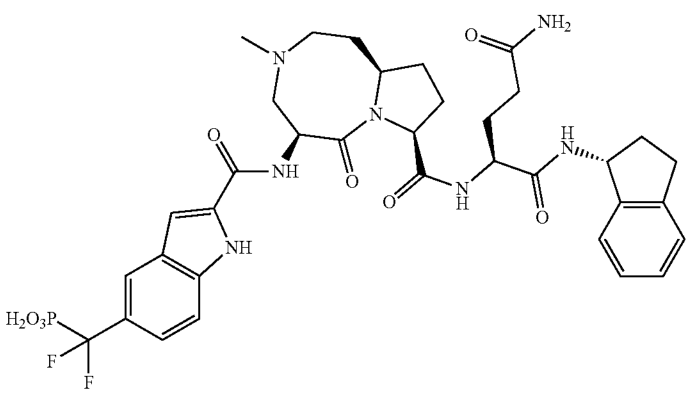 |
| 222 | 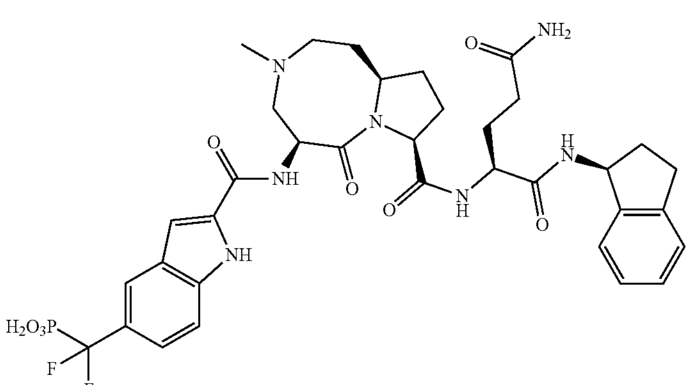 |

TABLE 2-continued
| Cpd. No. | Structure |
|---|---|
| 223 | 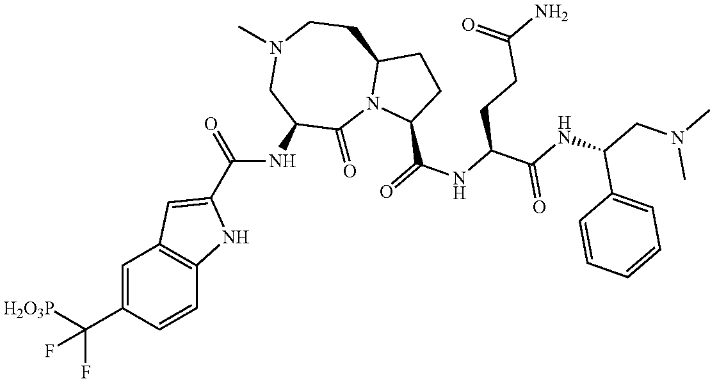 |
| 224 | 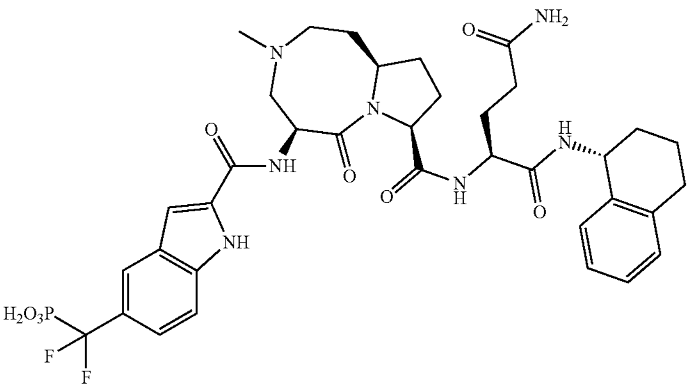 |
| 226 | 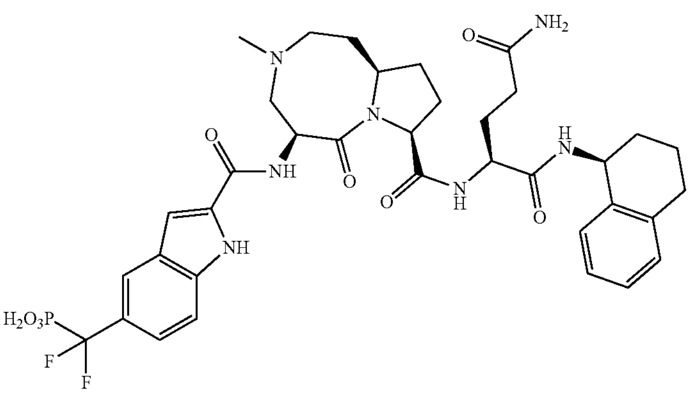 |
| 227 | 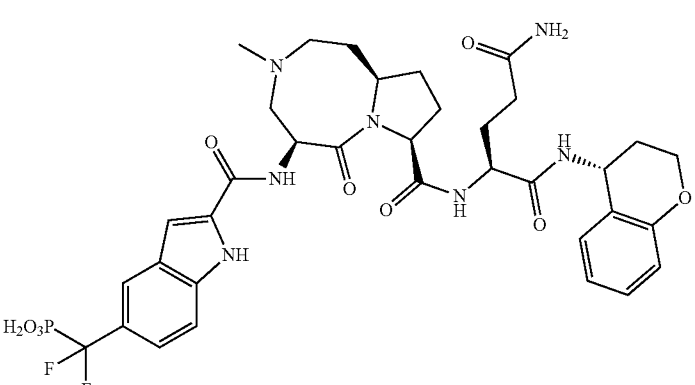 |

TABLE 2-continued
| Cpd. No. | Structure |
|---|---|
| 228 | 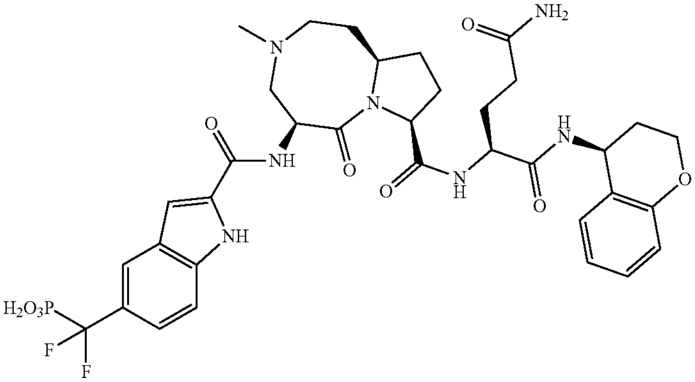 |
| 229 | 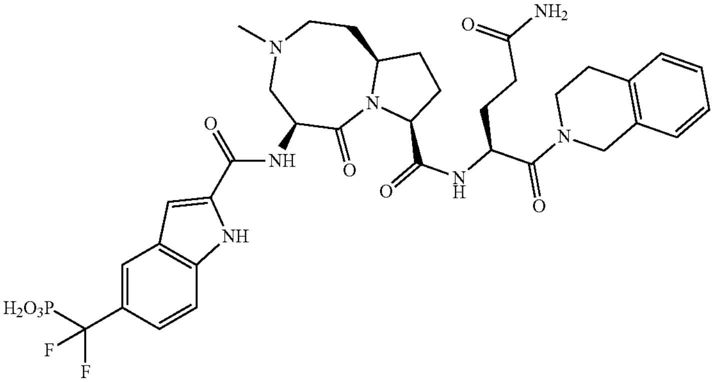 |
| 230 | 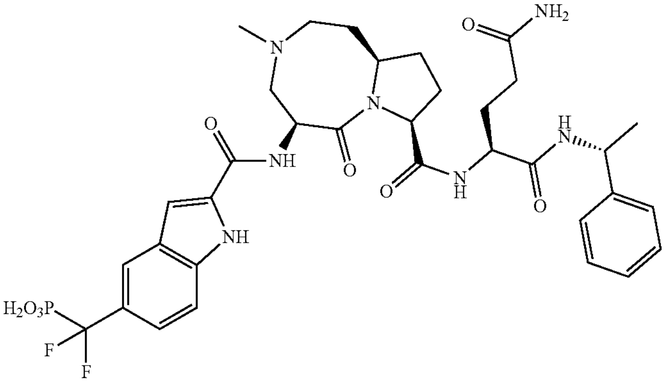 |
| 231 | 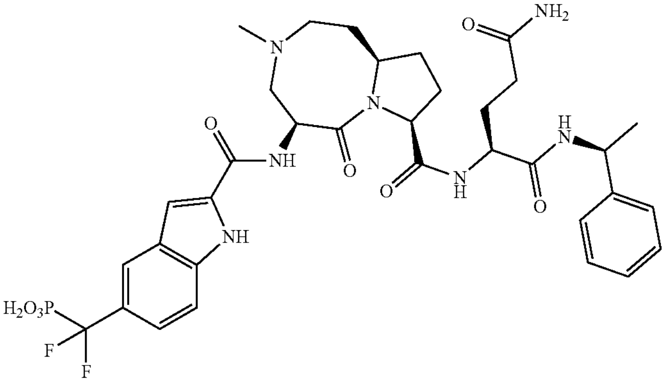 |

TABLE 2-continued
| Cpd. No. | Structure |
|---|---|
| 232 | 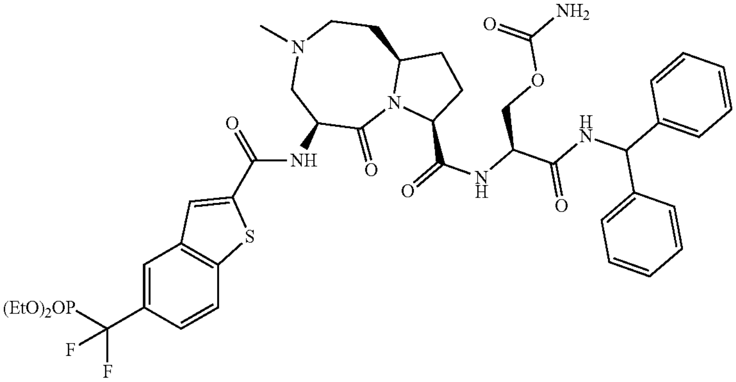 |
| 233 | 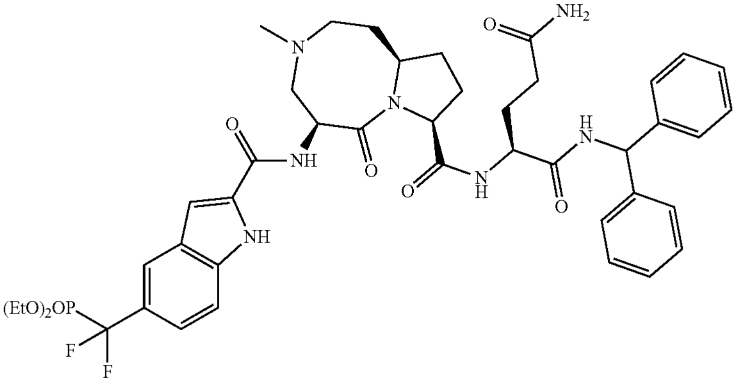 |
| 234 | 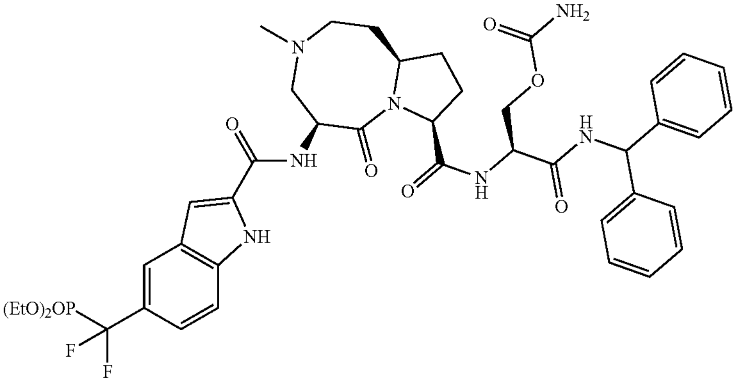 |
| 235 | 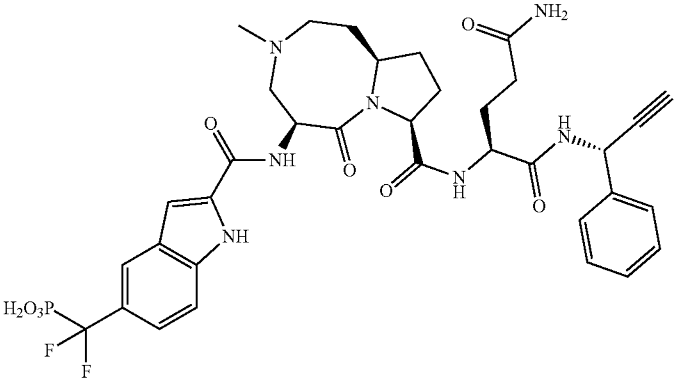 |

TABLE 2-continued
| Cpd. No. | Structure |
|---|---|
| 236 | 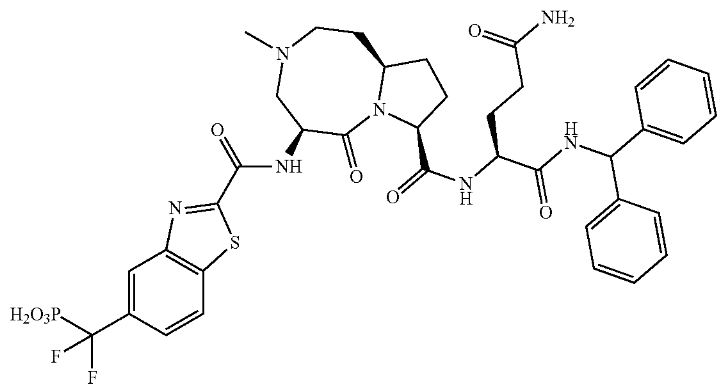 |
| 237 | 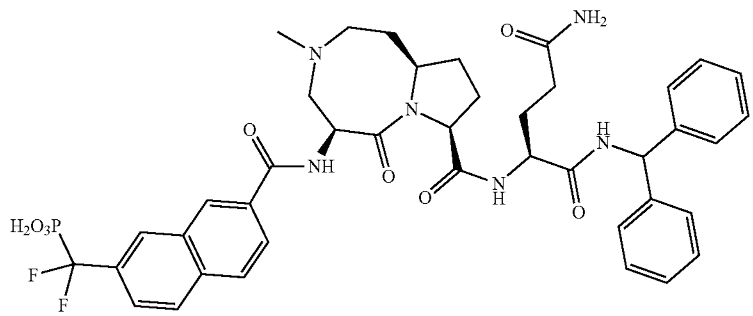 |
| 238 | 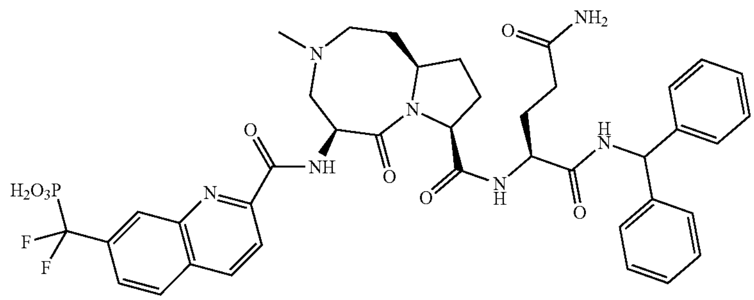 |
| 239 | 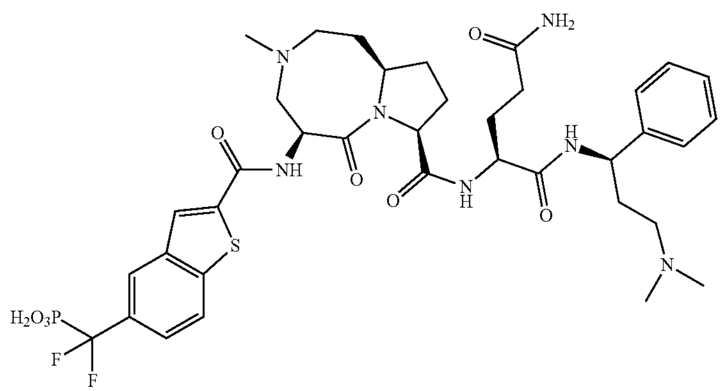 |

TABLE 2-continued

| Cpd. No. | Structure |
| --- | --- |
| 240 | 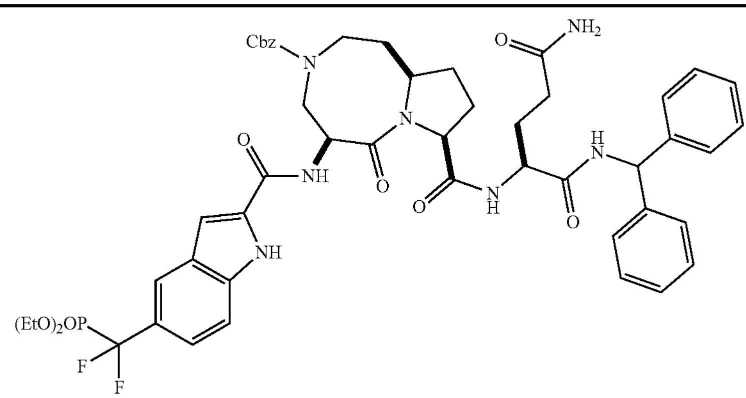 |
| 241 | 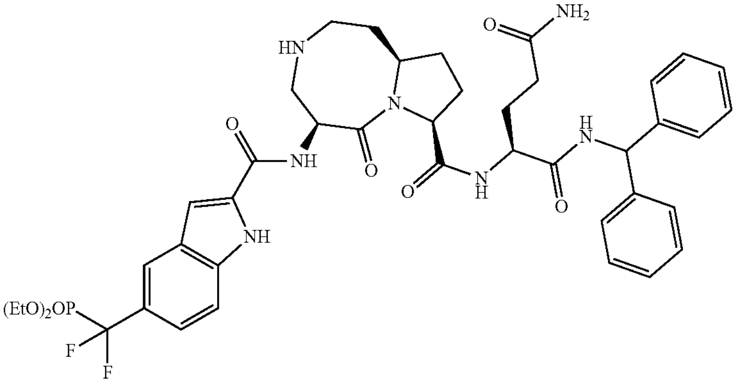 |
| 242 | 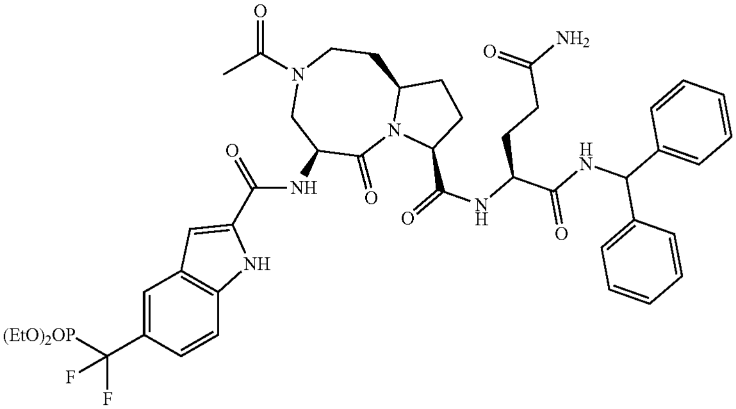 |

In another embodiment, the disclosure provides a pharmaceutical composition comprising a Compound of the Disclosure and a pharmaceutically acceptable carrier.

In another embodiment, Compounds of the Disclosure and Intermediates of the Disclosure are enantiomerically enriched, e.g., the enantiomeric excess or "ee" of the compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

Certain Compounds of the Disclosure are heterobifunctional molecules. In one embodiment, the E portion of the molecule, i.e.,

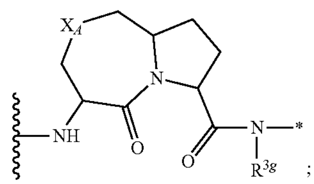

is enantiomerically enriched, e.g., the enantiomeric excess or "ee" of this part of the heterobifunctional compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

In another embodiment, the cereblon binding portion of the molecule, i.e., —B, is enantiomerically enriched. In another embodiment, the cereblon binding portion of the molecule is racemic. The present disclosure encompasses all possible stereoisomeric, e.g., diastereomeric, forms of Compounds of the Disclosure. For example, all possible stereoisomers of Compounds of the Disclosure are encompassed when E portion of the molecule is enantiomerically enriched and the cereblon binding portion of the molecule is racemic.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerophosphate, hemisulfate, heptanoate, hexanoate, formate, succinate, fumarate, maleate, ascorbate, isethionate, salicylate, methanesulfonate, mesitylene sulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a desolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, J. Pharmaceut. Sci., 93(3):601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5(1): Article 12 (2004), and A. L. Bingham et al., Chem. Commun. 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

II. Intermediates of the Disclosure

The disclosure also provides synthetic intermediates, collectively referred to as "Intermediates of the Disclosure," that can be used to prepare Compounds of the Disclosure.

In one embodiment, Intermediates of the Disclosure are compounds of Formula XIII:

XIII

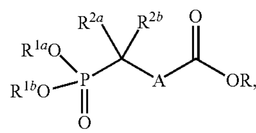

wherein:

R is selected from the group consisting of hydrogen, $C_1$-$C_6$ alkyl, aralkyl, and optionally substituted phenyl;

$R^{1a}$ and $R^{1b}$ are independently selected from the group consisting of hydrogen $C_1$-$C_6$ alkyl, and aralkyl;

$R^{2a}$ and $R^{2b}$ are as defined in connection with Formula I; and

A is as defined in connection with Formula I, wherein the bond designated with an "*" is attached to —C(═O)—OR.

In another embodiment, Intermediates of the Disclosure are compounds of Formula XIII, with the proviso that the compound is not:

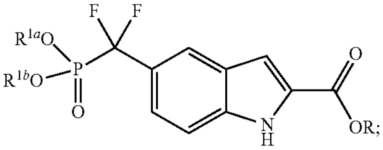

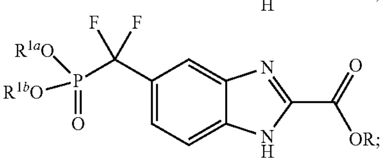

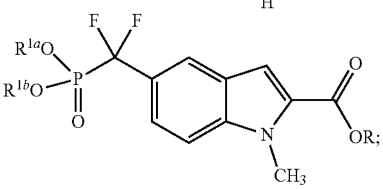

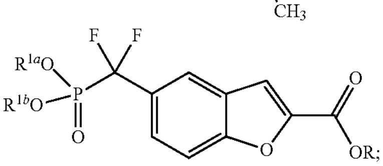

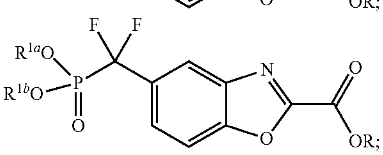

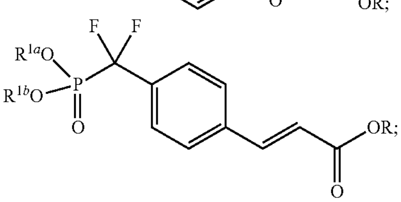

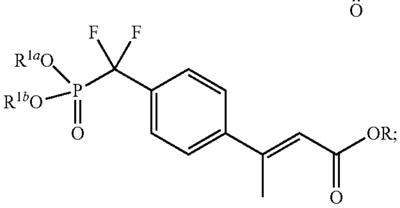 and

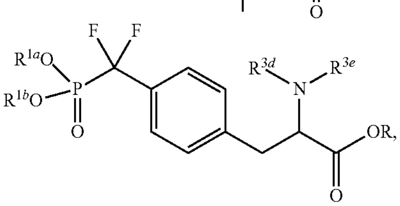

or a salt or solvate thereof.

In another embodiment, Intermediates of the Disclosure are compounds of Formula XIV:

XIV

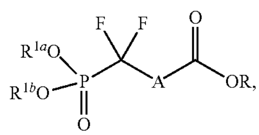

wherein R, $R^{1a}$, $R^{1b}$, and A are as defined in connection with Formula XIII, or a salt or solvate thereof.

In another embodiment, Intermediates of the Disclosure are compounds of Formula XV:

XV

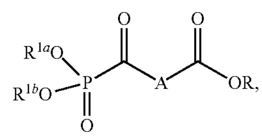

wherein R, $R^{1a}$, $R^{1b}$, and A are as defined in connection with Formula XIII, or a salt or solvate thereof.

In another embodiment, Intermediates of the Disclosure are compounds of Formula XIII selected from the group consisting of:

XIII-A

XIII-B

XIII-C

XIII-D and

XIII-E

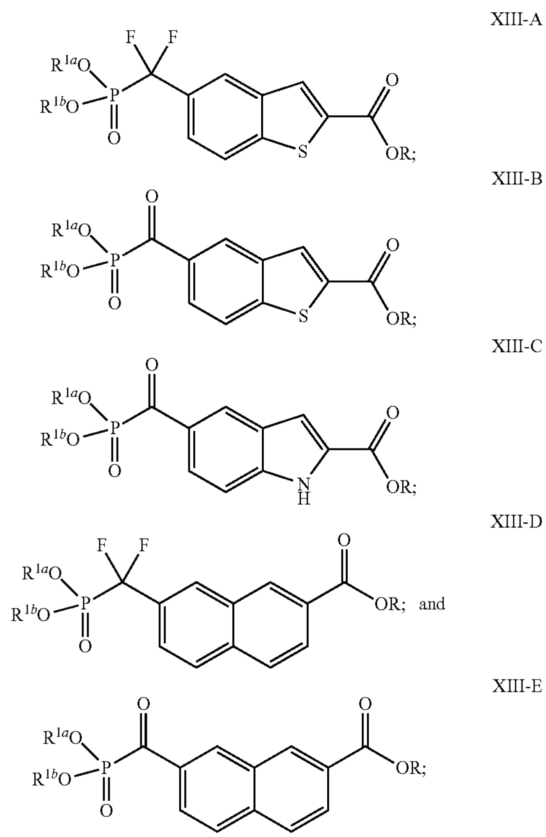

or a salt or solvate thereof.

In another embodiment, Intermediates of the Disclosure are compounds of any one of Formulae XIII, XIII-A, XIII-B, XIII-C, XIII-D, XIII-E, XIV or XV, wherein R is hydrogen, or a salt or solvate thereof.

In another embodiment, Intermediates of the Disclosure are compounds of any one of Formulae XIII, XIII-A, XIII-B, XIII-C, XIII-D, XIII-E, XIV or XV, wherein R is benzyl, or a salt or solvate thereof.

In another embodiment, Intermediates of the Disclosure are compounds of any one of Formulae XIII, XIII-A, XIII-B, XIII-C, XIII-D, XIII-E, XIV or XV, wherein R is selected from the group consisting of pentachlorobenzene and pentafluorobenzene, or a salt or solvate thereof.

In another embodiment, Intermediates of the Disclosure are compounds of any one of Formulae XIII, XIII-A, XIII-B, XIII-C, XIII-D, XIII-E, XIV or XV, wherein $R^{1a}$ and $R^{1b}$ are ethyl, or a salt or solvate thereof.

In another embodiment, Intermediates of the Disclosure are compounds of any one of Formulae XIII, XIII-A, XIII-B, XIII-C, XIII-D, XIII-E, XIV or XV, wherein R is hydrogen; and $R^{1a}$ and $R^{1b}$ are ethyl, or a salt or solvate thereof.

In one embodiment, Intermediates of the Disclosure are compounds of Formula XVI:

XVI

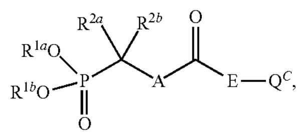

wherein:

$R^{1a}$, $R^{1b}$, $R^{2a}$, $R^{2b}$, A, and E, wherein the bond designated with an "*" is attached to $Q^C$, are as defined in connection with Formula I;

$Q^C$ is:

Q-8

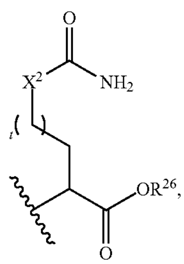

$X^2$ and t are as defined in connection with Formula I; and $R^{26}$ is selected from the group consisting of hydrogen, $C_1$-$C_6$ alkyl, and aralkyl.

In another embodiment, Intermediates of the Disclosure are compounds of Formula XVI, with the provisos that:

(1) when $X_A$ is —$CH_2CH_2$—, then:

(i) A is selected from the group consisting of A-2, A-5, A-6, A-7, A-8, A-9, A-10, A-11, A-12, A-13, A-14, A-15, A-16, A-17, A-18, A-19, and A-20;

(ii) A is A-4 and $G^1$ is —S—; or (iii) $R^{2a}$ and $R^{2b}$ taken together with the carbon atom to which they are attached form a —C(═O)— group;

(2) when $X_A$ is —$N(R^8)CH_2$— and $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group; or (3) when $X_A$ is —$CH_2N(R^8)$— and $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group, or a pharmaceutically acceptable salt or solvate thereof.

In another embodiment, Intermediates of the Disclosure are compounds of Formula XVII:

XVII

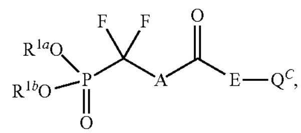

wherein $R^{1a}$, $R^{1b}$, A, E, and $Q^C$ are as defined in connection with Formula XVI, or a salt or solvate thereof.

In another embodiment, Intermediates of the Disclosure are compounds of Formula XVIII:

XVIII

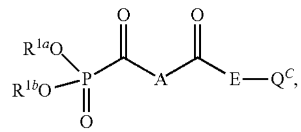

wherein $R^{1a}$, $R^{1b}$, A, E, and $Q^C$ are as defined in connection with Formula XVI, or a salt or solvate thereof.

In another embodiment, Intermediates of the Disclosure are compounds of Formula XVI-A:

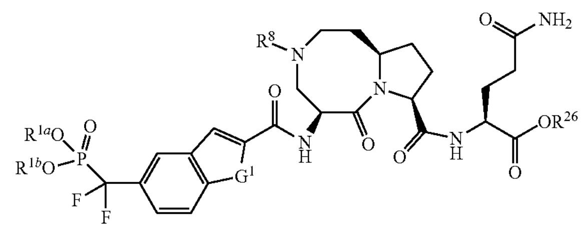

wherein $R^{1a}$ and $R^{1b}$ are independently selected from the group consisting of hydrogen and $C_1$-$C_4$ alkyl; $G^1$ is selected from the group consisting of —S— and —N(H)—; $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$; $R^9$ is selected from the group consisting of $C_1$-$C_6$ alkyl, alkylamino, dialkylamino, and $C_1$-$C_6$ alkoxy; and $R^{26}$ is selected from the group consisting of hydrogen, $C_1$-$C_6$ alkyl, and aralkyl. In another embodiment, $R^{1a}$ and $R^{1b}$ are $C_1$-$C_3$ alkyl. In another embodiment, $R^{1a}$ is $C_1$-$C_3$ alkyl; and $R^{1b}$ is hydrogen. In another embodiment, $R^{1a}$ and $R^{1b}$ are ethyl. In another embodiment, $R^{1a}$ is ethyl; and $R^{1b}$ is hydrogen.

In another embodiment, Intermediates of the Disclosure are compounds of any one of Formulae XVI, XVI-A, XVII, or XVIII, wherein $R^8$ is selected from the group consisting of $C_1$-$C_6$ alkyl, $C_1$-$C_6$ haloalkyl, (heterocyclo)alkyl, and —C(═O)$R^9$, or a salt or solvate thereof. In another embodiment, In another embodiment, $R^8$ is selected from the group consisting of $C_1$-$C_4$ alkyl, $C_1$-$C_4$ haloalkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy. In another embodiment, $R^9$ is selected from the group consisting of $C_1$-$C_3$ alkyl, alkylamino, dialkylamino, and $C_1$-$C_3$ alkoxy. In another embodiment, $R^8$ is methyl, ethyl, isopropyl, —$CH_2CHF_2$, —$CH_2CF_3$, —C(═O)$OCH_3$, —C(═O)$CH_3$, —C(═O)$NHCH_3$, —C(═O)$N(CH_3)_2$, —S(═O)$_2$Me, —S(═O)$_2$Et, or —$SO_2$iPr. In another embodiment, $R^8$ is methyl, ethyl, —$CH_2CHF_2$, or —C(═O)$OCH_3$.

In another embodiment, Intermediates of the Disclosure are compounds of any one of Formulae XVI-XVIII, wherein $R^8$ is -L-B, or a salt or solvate thereof.

In another embodiment, Intermediates of the Disclosure are compounds of any one of Formulae XVI, XVI-A, XVII, or XVIII, wherein $R^{26}$ is $C_1$-$C_6$ alkyl, or a salt or solvate thereof.

In another embodiment, Intermediates of the Disclosure are compounds of any one of Formulae XVI, XVI-A, XVII, or XVIII, $R^{26}$ is hydrogen, or a salt or solvate thereof.

In another embodiment, Intermediates of the Disclosure are compounds of any one of Formulae XVI, XVI-A, XVII, or XVIII, $R^{26}$ is benzyl, or a salt or solvate thereof.

In another embodiment, Intermediates of the Disclosure are compounds of Table 2A, or a salt or solvate thereof.

TABLE 2A

| Cpd. No. | Structure |
| --- | --- |
| 371 | 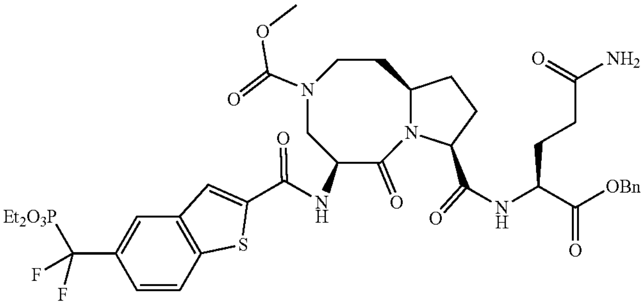 |
| 372 | 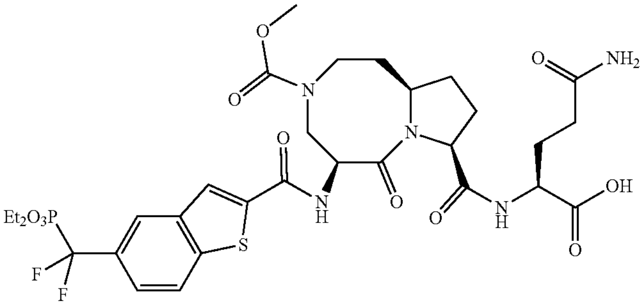 |
| 373 | 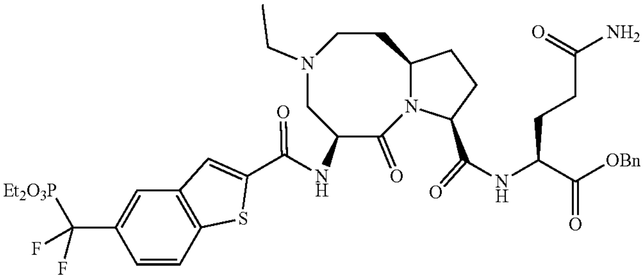 |

TABLE 2A-continued
| Cpd. No. | Structure |
|---|---|
| 374 | 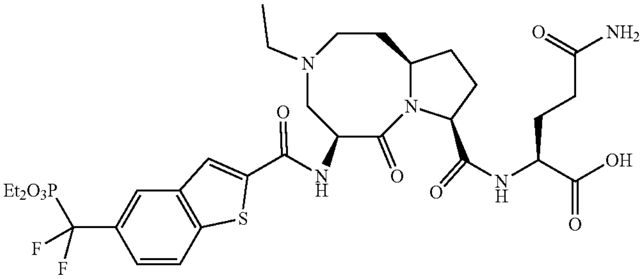 |
| 375 | 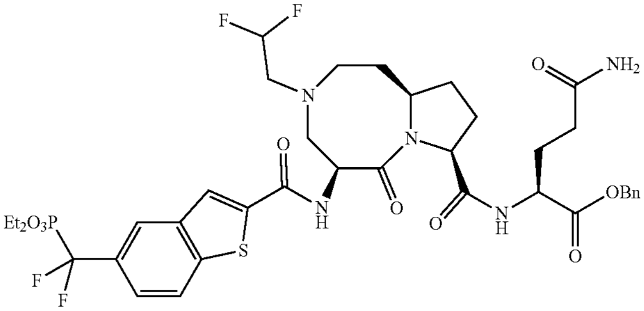 |
| 376 | 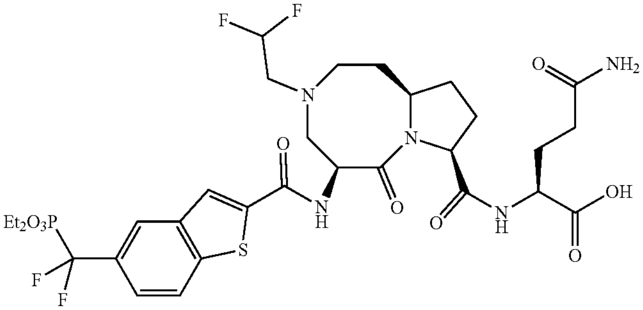 |
| 377 | 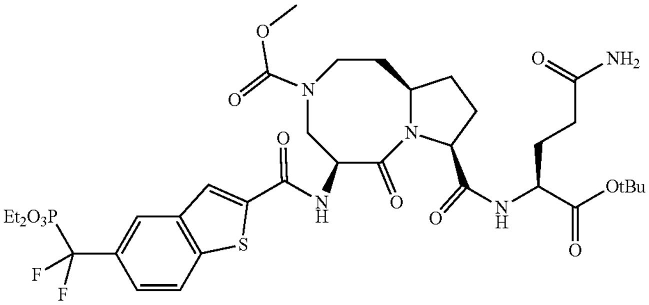 |
| 378 | 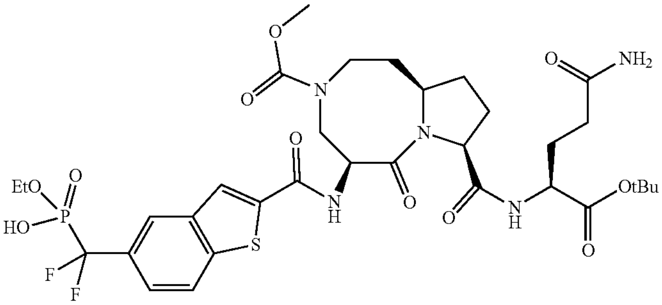 [SMILES: CCOP(=O)(O)C(F)(F)c1ccc2sc(C(=O)N[C@H]3CN(C(=O)OC)CC[C@H]4CC[C@@H](C(=O)N[C@@H](CCC(N)=O)C(=O)OC(C)(C)C)N4C3=O)cc2c1] |

TABLE 2A-continued
| Cpd. No. | Structure |
|---|---|
| 379 | 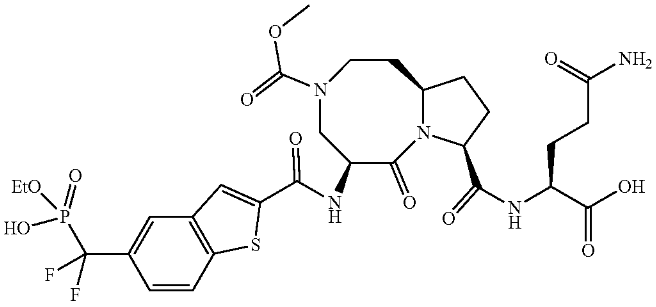 [SMILES: CCOP(=O)(O)C(F)(F)c1ccc2sc(C(=O)N[C@H]3CN(C(=O)OC)CC[C@H]4CC[C@@H](C(=O)N[C@@H](CCC(N)=O)C(=O)O)N4C3=O)cc2c1] |
| 380 | 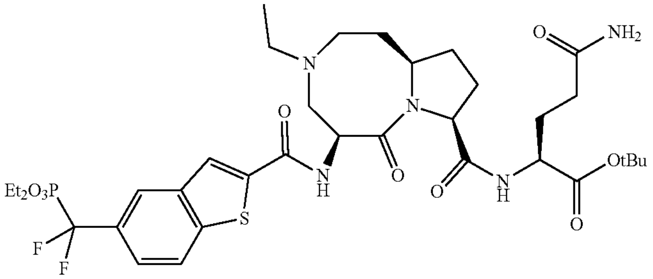 |
| 381 | 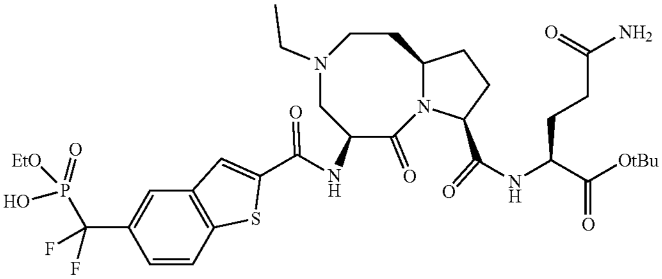 [SMILES: CCOP(=O)(O)C(F)(F)c1ccc2sc(C(=O)N[C@H]3CN(CC)CC[C@H]4CC[C@@H](C(=O)N[C@@H](CCC(N)=O)C(=O)OC(C)(C)C)N4C3=O)cc2c1] |
| 382 | 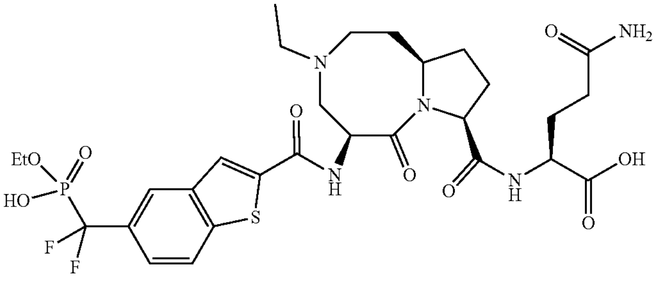 [SMILES: CCOP(=O)(O)C(F)(F)c1ccc2sc(C(=O)N[C@H]3CN(CC)CC[C@H]4CC[C@@H](C(=O)N[C@@H](CCC(N)=O)C(=O)O)N4C3=O)cc2c1] |
In another embodiment, Intermediates of the Disclosure are compounds of Formula XXXIV:

XXXIV

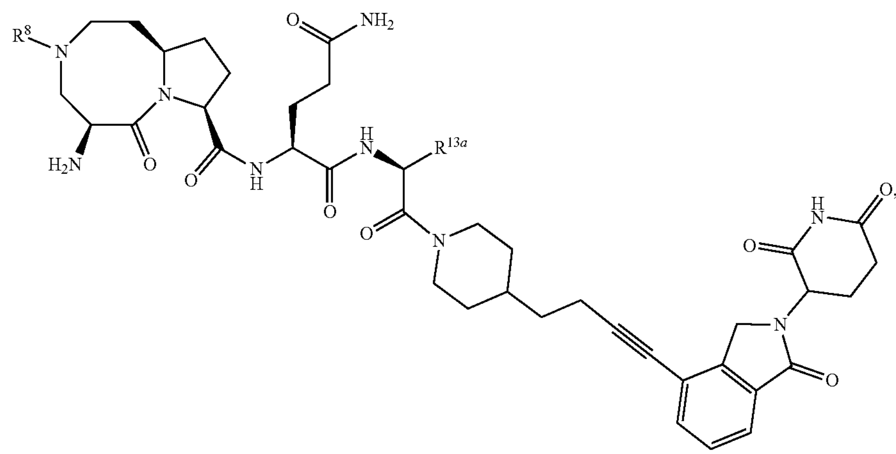

wherein $R^8$ and $R^{13a}$ are as defined in connection with Formula I, or a pharmaceutically acceptable salt or solvate thereof.

In another embodiment, Intermediates of the Disclosure are compounds of Formula XXXIV, wherein $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, or a pharmaceutically acceptable salt or solvate thereof. In another embodiment, $R^8$ is selected from the group consisting of $C_1$-$C_4$ alkyl, $C_1$-$C_4$ haloalkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy. In another embodiment, $R^9$ is selected from the group consisting of $C_1$-$C_3$ alkyl, alkylamino, dialkylamino, and $C_1$-$C_3$ alkoxy. In another embodiment, $R^8$ is methyl, ethyl, isopropyl, —$CH_2CHF_2$, —$CH_2CF_3$, —C(═O)$OCH_3$, —C(═O)$CH_3$, —C(═O)$NHCH_3$, —C(═O)$N(CH_3)_2$, —S(═O)$_2$Me, —S(═O)$_2$Et, or —$SO_2$iPr. In another embodiment, $R^8$ is methyl, ethyl, —$CH_2CHF_2$, or —C(═O)$OCH_3$.

In another embodiment, Intermediates of the Disclosure are compounds of Formula XXXIV, wherein $R^{13a}$ is selected from the group consisting optionally substituted $C_3$-$C_{12}$ cycloalkyl, optionally substituted aryl, aralkyl, (heteroaryl) alkyl, (cycloalkyl)alkyl, and optionally substituted 5- to 9-membered heteroaryl, or a pharmaceutically acceptable salt or solvate thereof. In another embodiment, $R^{13a}$ is aralkyl. In another embodiment, $R^{13a}$ is selected from the group consisting of:

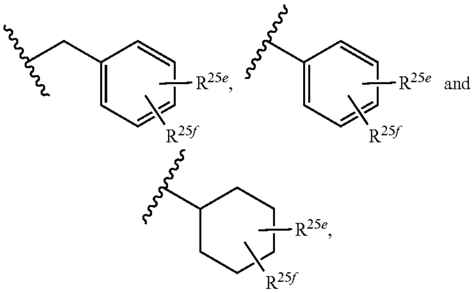

wherein $R^{25e}$ and $R^{25f}$ are independently selected from the group consisting of hydrogen, halo, $C_1$-$C_4$ alkyl, $C_1$-$C_4$ haloalkyl, and $C_1$-$C_4$ alkoxy.

In another embodiment, Intermediates of the Disclosure are compounds of Formula XXXIV, wherein:

$R^{13a}$ is selected from the group consisting of:

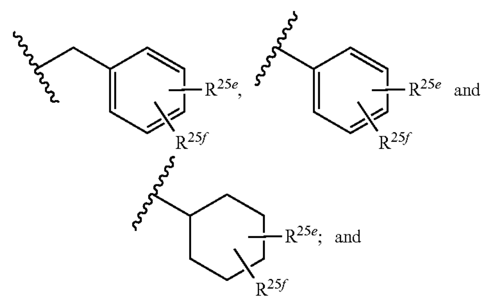

$R^{25e}$ and $R^{25f}$ are independently selected from the group consisting of hydrogen, halo, $C_1$-$C_6$ alkyl, optionally substituted $C_3$-$C_6$ cycloalkyl, optionally substituted aryl, $C_1$-$C_4$ haloalkyl, $C_1$-$C_4$ alkoxy, carboxamido, sulfonamido, alkylsulfonyl, arylsulfonyl, —C(═O)$R^{57}$, —S(═O)$_2R^{58}$, and —N($R^{56c}$)S(═O)$_2R^{56d}$.

In another embodiment, Intermediates of the Disclosure are compounds of Formula XXXIV, wherein:

$R^{13a}$ is:

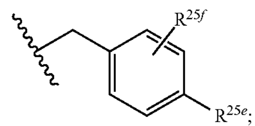

$R^{25e}$ is selected from the group consisting of hydrogen, halo, $C_1$-$C_6$ alkyl, —C(═O)$NR^{50c}R^{50d}$, $C_1$-$C_6$ alkylsulfonyl, arylsulfonyl, —N($R^{56c}$)S(═O)$_2R^{56d}$, and —S(═O)$_2R^{58}$, $R^{25f}$ is selected from the group consisting of hydrogen and halo;

$R^{50c}$ is selected from the group consisting of $C_1$-$C_6$ alkyl, optionally substituted $C_3$-$C_6$ cycloalkyl, optionally substituted 5- or 6-membered heterocyclo, optionally substituted phenyl, optionally substituted 5- to 9-membered heteroaryl, aralkyl, (heteroaryl)$C_1$-$C_4$ alkyl, and (heterocyclo)$C_1$-$C_4$ alkyl;

$R^{50d}$ is selected from the group consisting of hydrogen and $C_1$-$C_3$ alkyl; or $R^{50c}$ and $R^{50d}$ taken together with the nitrogen to which they are attached form a 3- to 8-membered optionally substituted heterocyclo group;

$R^{58}$ is optionally substituted $C_3$-$C_6$ cycloalkyl;

$R^{56c}$ is selected from the group consisting of hydrogen and $C_1$-$C_3$ alkyl; and $R^{56d}$ is selected from the group consisting of optionally substituted $C_3$-$C_6$ cycloalkyl, optionally substituted phenyl, and optionally substituted 5- to 9-membered heteroaryl.

In another embodiment, Intermediates of the Disclosure are compounds of Formula XXXV:

XXXV

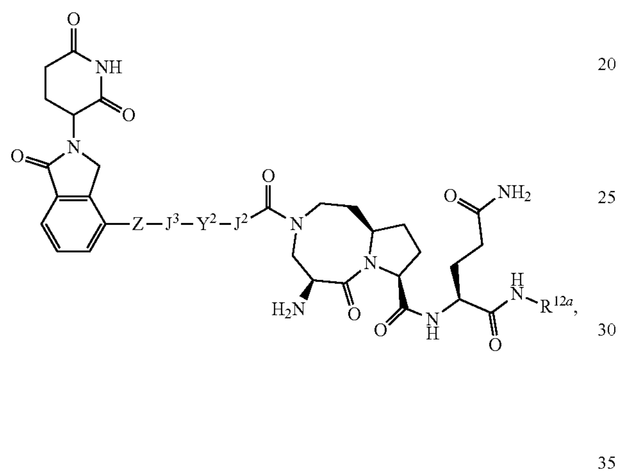

wherein $R^{12a}$, $J^2$, $J^3$, $Y^2$, and Z are as defined in connection with Formula I, or a pharmaceutically acceptable salt or solvate thereof.

In another embodiment, Intermediates of the Disclosure are compounds of Formula XXXVI:

XXXVI

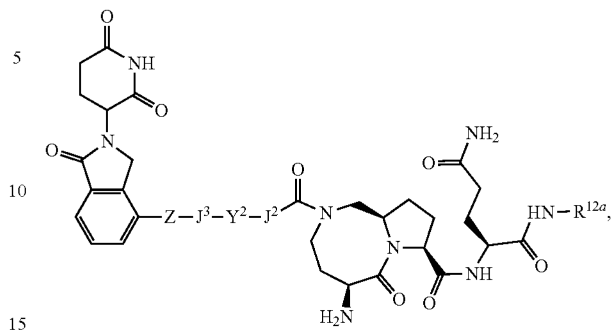

wherein $R^{12a}$, $J^2$, $J^3$, $Y^2$, and Z are as defined in connection with Formula I, or a pharmaceutically acceptable salt or solvate thereof.

In another embodiment, Intermediates of the Disclosure are compounds of Formulae XXXV or XXXVI, wherein $R^{12a}$ is aralkyl, or a pharmaceutically acceptable salt or solvate thereof. In another embodiment, $R^{12}$ is:

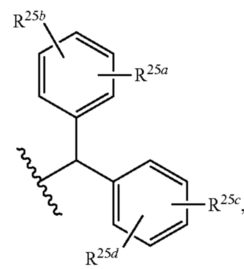

wherein $R^{25a}$, $R^{25b}$, $R^{25c}$, and $R^{25d}$ are each independently selected from the group consisting of hydrogen, halo, $C_1$-$C_4$ alkyl, and $C_1$-$C_4$ alkoxy.

In another embodiment, Intermediates of the Disclosure are compounds of Formula XXXVII:

XXXVII

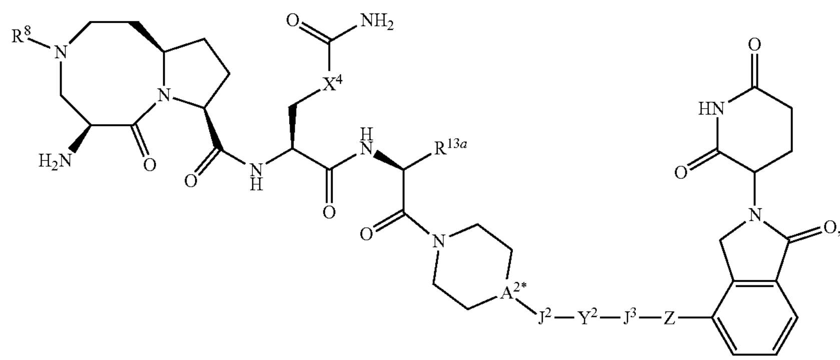

wherein $X^4$ is selected from the group consisting of —$CH_2$— and —O—; and $R^{13a}$, $A^{2*}$, $J^2$, $J^3$, $Y^2$, and Z are as defined in connection with Formula I, or a pharmaceutically acceptable salt or solvate thereof.

In another embodiment, Intermediates of the Disclosure are compounds of Formula XXXVIII:

XXXVIII

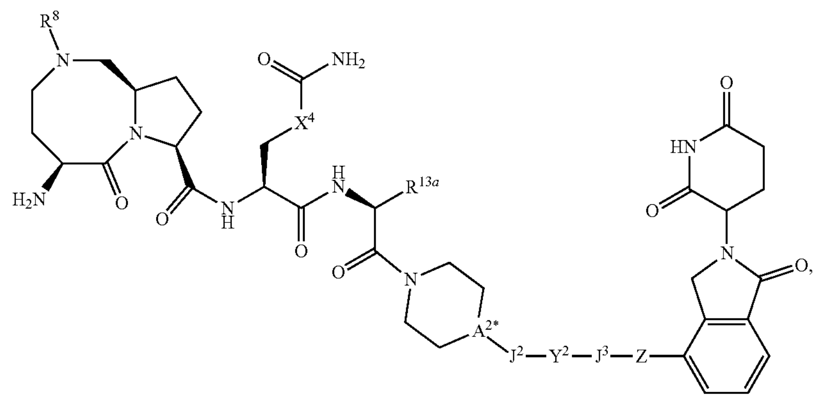

wherein $X^4$ is selected from the group consisting of —$CH_2$— and —O—; and $R^{13a}$, $A^{2*}$, $J^2$, $J^3$, $Y^2$, and Z are as defined in connection with Formula I, or a pharmaceutically acceptable salt or solvate thereof.

In another embodiment, Intermediates of the Disclosure are compounds of Formulae XXXVII or XXXVIII, wherein $R^{13a}$ is selected from the group consisting of optionally substituted cyclohexyl, aralkyl, (heteroaryl)alkyl, and optionally substituted phenyl, or a pharmaceutically acceptable salt or solvate thereof. In another embodiment, $R^{13a}$ is selected from the group consisting of optionally substituted cyclohexyl, aralkyl, and optionally substituted phenyl. In another embodiment, $R^{13a}$ is optionally substituted phenyl. In another embodiment, $R^{13a}$ is aralkyl. In another embodiment, $R^{13a}$ is (heteroaryl)alkyl.

In another embodiment, Intermediates of the Disclosure are compounds Formulae XXXVII or XXXVIII, wherein $R^8$ is selected from the group consisting of $C_1$-$C_4$ alkyl, $C_1$-$C_4$ haloalkyl, (heterocyclo)alkyl, alkylsulfonyl, and —C(═O)$R^9$; and $R^9$ is selected from the group consisting of $C_1$-$C_4$ alkyl, alkylamino, dialkylamino, and $C_1$-$C_4$ alkoxy, or a pharmaceutically acceptable salt or solvate thereof. In another embodiment, $R^8$ is $C_1$-$C_4$ alkyl. In another embodiment, $R^8$ is methyl.

In another embodiment, Intermediates of the Disclosure are compounds of any one of Formulae XXXV-XXXVIII, wherein $J^2$ is absent, $Y^2$ is —$(CH_2)_n$—, n is 3, 4, or 5, and $J^3$ is absent, or a pharmaceutically acceptable salt or solvate thereof.

In another embodiment, Intermediates of the Disclosure are compounds of any one of Formulae XXXV-XXXVIII, wherein Z is —C≡C—, or a pharmaceutically acceptable salt or solvate thereof.

In another embodiment, Intermediates of the Disclosure are compounds of any one of Formulae XXXV-XXXVIII, wherein $A^{2*}$ is —CH—, or a pharmaceutically acceptable salt or solvate thereof.

In another embodiment, Intermediates of the Disclosure are compounds of Formula XXXIX:

XXXIX

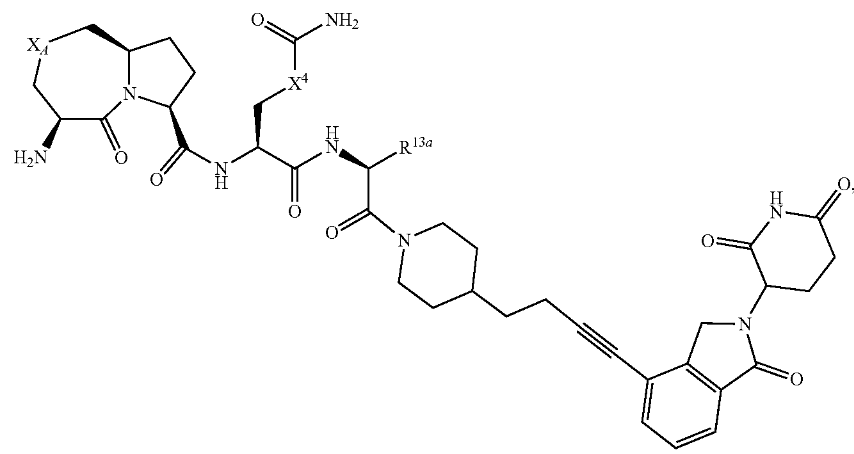

wherein $R^{13a}$, $X_A$, and $X^4$ are as defined in connection with Formula I, or a pharmaceutically acceptable salt or solvate thereof.

In another embodiment, Intermediates of the Disclosure are compounds of Formula XXXIX, wherein $X_A$ is —N($R^8$)$CH_2$—; and $R^8$ is selected from the group consisting of hydrogen, $C_1$-$C_6$ alkyl, $C_1$-$C_6$ haloalkyl, (heterocyclo)alkyl, and —C(═O)$R^9$, or a pharmaceutically acceptable salt or solvate thereof. In another embodiment, $R^9$ is selected from the group consisting of $C_1$-$C_3$ alkyl and $C_1$-$C_3$ alkoxy.

In another embodiment, Intermediates of the Disclosure are compounds of Formula XXXIX, wherein $X_A$ is —$CH_2$N($R^8$)—; and $R^8$ is selected from the group consisting of hydrogen, $C_1$-$C_6$ alkyl, $C_1$-$C_6$ haloalkyl, (heterocyclo)alkyl, alkylsulfonyl, and —C(═O)$R^9$, or a pharmaceutically acceptable salt or solvate thereof. In another embodiment, $R^9$ is selected from the group consisting of $C_1$-$C_3$ alkyl, alkylamino, dialkylamino, and $C_1$-$C_3$ alkoxy.

In another embodiment, Intermediates of the Disclosure are compounds of Formula XXXIX, wherein $X_A$ is —$CH_2CH_2$—, or a pharmaceutically acceptable salt or solvate thereof.

In another embodiment, Intermediates of the Disclosure are compounds of Formula XXXIX, wherein $X^4$ is —$CH_2$—, or a pharmaceutically acceptable salt or solvate thereof.

In another embodiment, Intermediates of the Disclosure are compounds of Formula XXXIX, wherein $X^4$ is —O—, or a pharmaceutically acceptable salt or solvate thereof.

In another embodiment, Intermediates of the Disclosure are compound of Intermediate Formula 2:

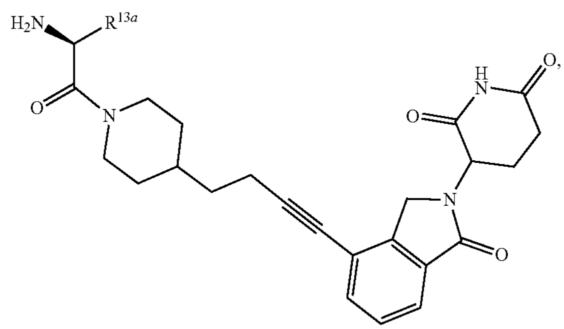

2 wherein $R^{13}$ is as defined in connection with Formula I, or a salt or solvate thereof.

In another embodiment, Intermediates of the Disclosure are compounds of any one of Formulae XXXVII, XXXVIII, XXXIX, or Intermediate Formula 2, wherein $R^{13a}$ is aralkyl.

In another embodiment, Intermediates of the Disclosure are compounds of any one of Formulae XXXVII, XXXVIII, XXXIX, or Intermediate Formula 2, wherein $R^{13a}$ is optionally substituted phenyl.

In another embodiment, Intermediates of the Disclosure are compounds of any one of Formulae XXXVII, XXXVIII, XXXIX, or Intermediate Formula 2, wherein:

$R^{13a}$ is selected from the group consisting of:

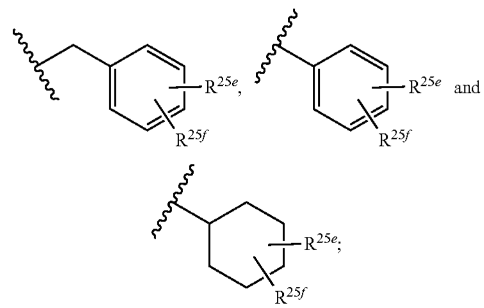

and $R^{25e}$ and $R^{25f}$ are independently selected from the group consisting of hydrogen, halo, $C_1$-$C_6$ alkyl, optionally substituted $C_3$-$C_6$ cycloalkyl, optionally substituted aryl, $C_1$-$C_4$ haloalkyl, $C_1$-$C_4$ alkoxy, carboxamido, sulfonamido, alkylsulfonyl, arylsulfonyl, —C(═O)$R^{57}$, —S(═O)$_2R^{58}$, and —N($R^{56c}$)S(═O)$_2R^{56d}$.

In another embodiment, Intermediates of the Disclosure are compounds of any one of Formulae XXXVII, XXXVIII, XXXIX, or Intermediate Formula 2, wherein:

$R^{13a}$ is:

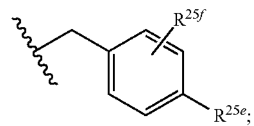

$R^{25e}$ is selected from the group consisting of hydrogen, halo, $C_1$-$C_6$ alkyl, —C(═O)N$R^{50c}R^{50d}$, $C_1$-$C_6$ alkylsulfonyl, arylsulfonyl, —N($R^{56c}$)S(═O)$_2R^{56d}$, and —S(═O)$_2R^{58}$, $R^{25f}$ is selected from the group consisting of hydrogen and halo;

$R^{50c}$ is selected from the group consisting of $C_1$-$C_6$ alkyl, optionally substituted $C_3$-$C_6$ cycloalkyl, optionally substituted 5- or 6-membered heterocyclo, optionally substituted phenyl, optionally substituted 5- to 9-membered heteroaryl, aralkyl, (heteroaryl)$C_1$-$C_4$ alkyl, and (heterocyclo)$C_1$-$C_4$ alkyl;

$R^{50d}$ is selected from the group consisting of hydrogen and $C_1$-$C_3$ alkyl; or $R^{50c}$ and $R^{50d}$ taken together with the nitrogen to which they are attached form a 3- to 8-membered optionally substituted heterocyclo group;

$R^{58}$ is optionally substituted $C_3$-$C_6$ cycloalkyl;

$R^{56c}$ is selected from the group consisting of hydrogen and $C_1$-$C_3$ alkyl; and $R^{56d}$ is selected from the group consisting of optionally substituted $C_3$-$C_6$ cycloalkyl, optionally substituted phenyl, and optionally substituted 5- to 9-membered heteroaryl.

In another embodiment, Intermediates of the Disclosure are compounds of Table 2B, or a salt or solvate thereof.

TABLE 2B
| Cpd. No. | Structure |
|---|---|
| 383 | 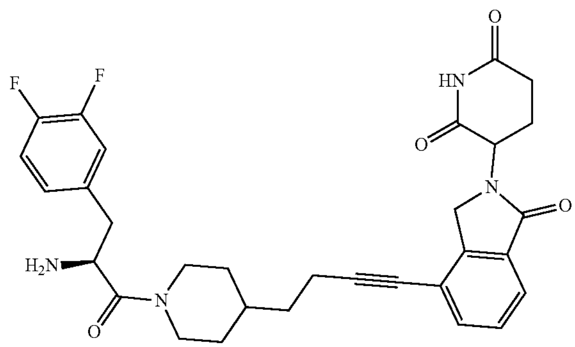 [SMILES: N[C@@H](Cc1ccc(F)c(F)c1)C(=O)N1CCC(CCC#Cc2cccc3c2CN(C2CCC(=O)NC2=O)C3=O)CC1] |
| 384 | 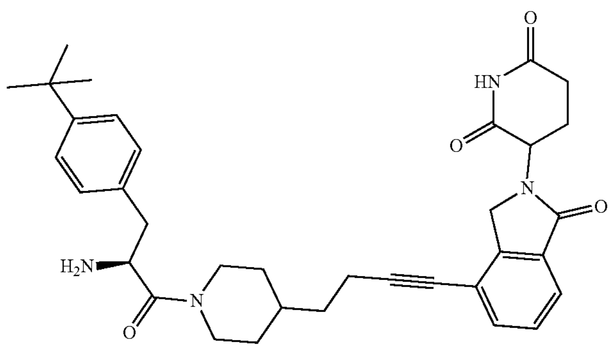 [SMILES: CC(C)(C)c1ccc(C[C@H](N)C(=O)N2CCC(CCC#Cc3cccc4c3CN(C3CCC(=O)NC3=O)C4=O)CC2)cc1] |
| 385 | 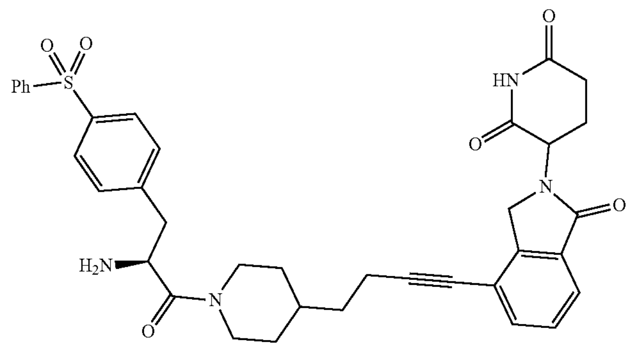 [SMILES: N[C@@H](Cc1ccc(S(=O)(=O)c2ccccc2)cc1)C(=O)N1CCC(CCC#Cc2cccc3c2CN(C2CCC(=O)NC2=O)C3=O)CC1] |
| 386 | 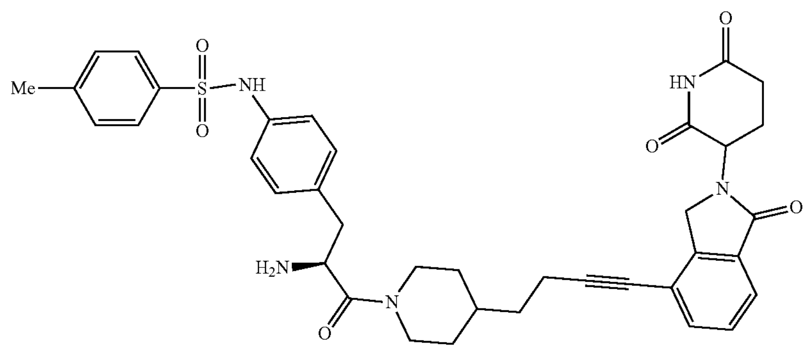 [SMILES: Cc1ccc(S(=O)(=O)Nc2ccc(C[C@H](N)C(=O)N3CCC(CCC#Cc4cccc5c4CN(C4CCC(=O)NC4=O)C5=O)CC3)cc2)cc1] |

TABLE 2B-continued
| Cpd. No. | Structure |
|---|---|
| 387 | 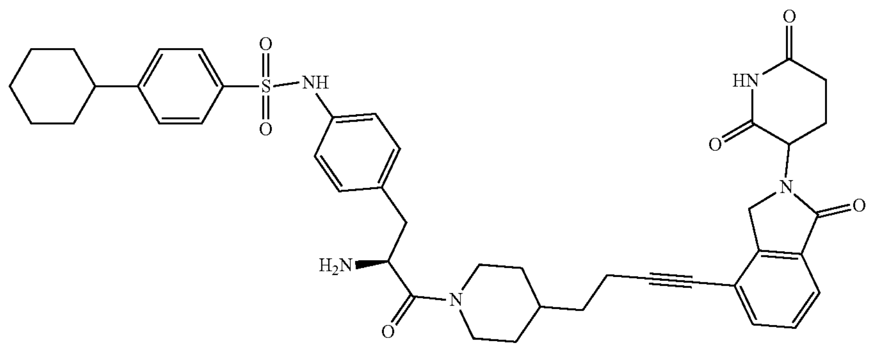 [SMILES: N[C@@H](Cc1ccc(NS(=O)(=O)c2ccc(C3CCCCC3)cc2)cc1)C(=O)N1CCC(CCC#Cc2cccc3c2CN(C2CCC(=O)NC2=O)C3=O)CC1] |
| 388 | 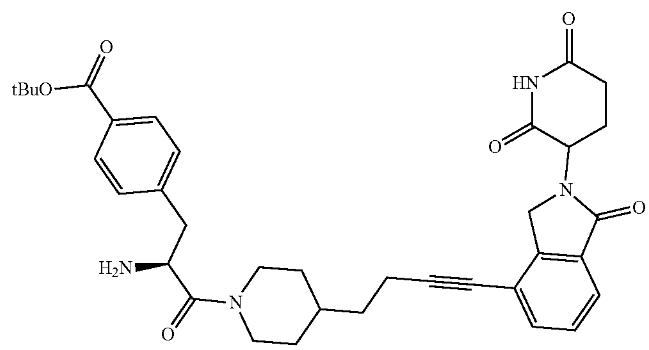 [SMILES: CC(C)(C)OC(=O)c1ccc(C[C@H](N)C(=O)N2CCC(CCC#Cc3cccc4c3CN(C3CCC(=O)NC3=O)C4=O)CC2)cc1] |
| 389 | 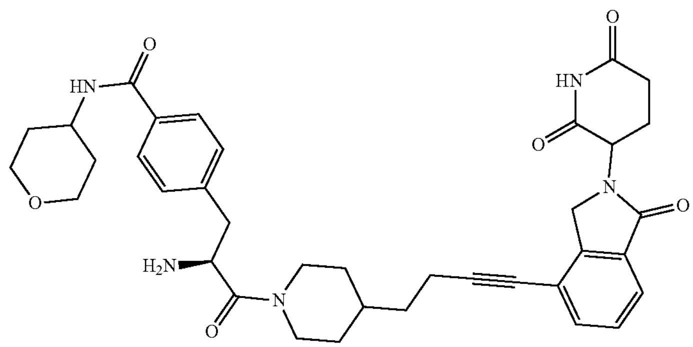 |
| 390 | 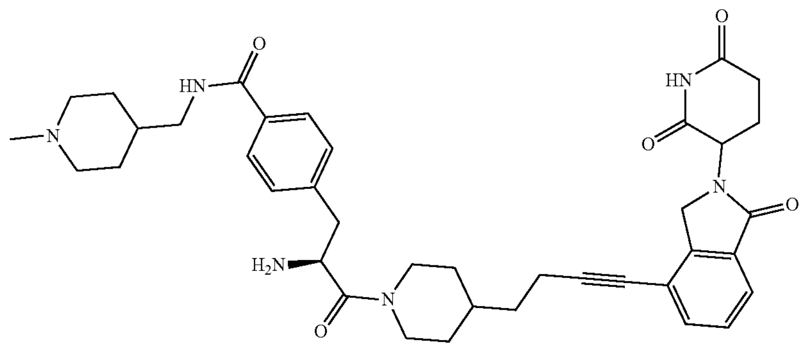 [SMILES: CN1CCC(CNC(=O)c2ccc(C[C@H](N)C(=O)N3CCC(CCC#Cc4cccc5c4CN(C4CCC(=O)NC4=O)C5=O)CC3)cc2)CC1] |

TABLE 2B-continued
| Cpd. No. | Structure |
|---|---|
| 391 | 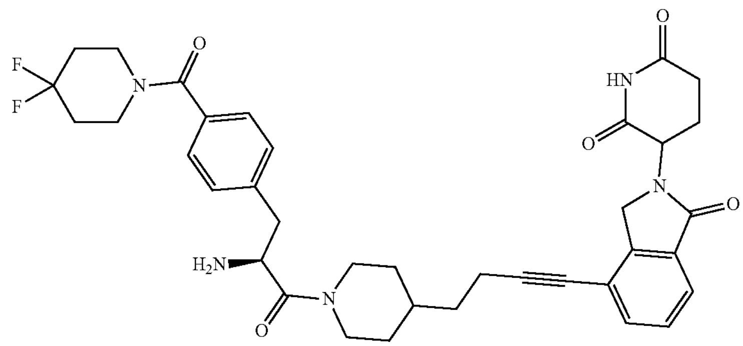 [SMILES: N[C@@H](Cc1ccc(C(=O)N2CCC(F)(F)CC2)cc1)C(=O)N1CCC(CCC#Cc2cccc3c2CN(C2CCC(=O)NC2=O)C3=O)CC1] |
| 392 | 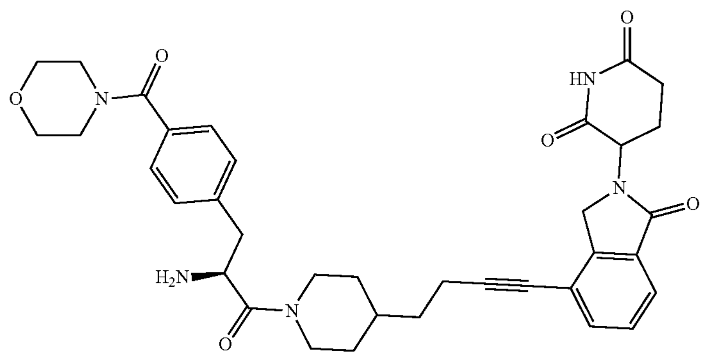 [SMILES: N[C@@H](Cc1ccc(C(=O)N2CCOCC2)cc1)C(=O)N1CCC(CCC#Cc2cccc3c2CN(C2CCC(=O)NC2=O)C3=O)CC1] |
| 393 | 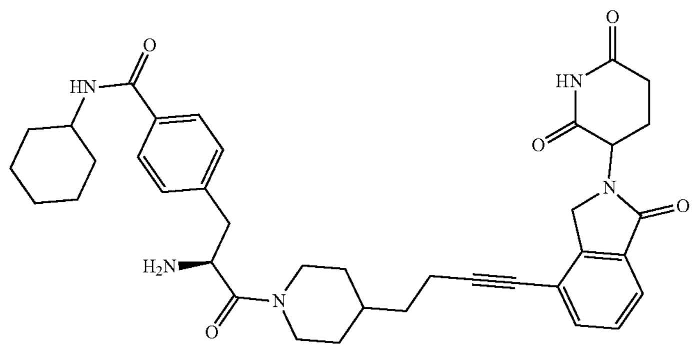 [SMILES: N[C@@H](Cc1ccc(C(=O)NC2CCCCC2)cc1)C(=O)N1CCC(CCC#Cc2cccc3c2CN(C2CCC(=O)NC2=O)C3=O)CC1] |

III. Methods of Preparing Compounds and Intermediates of the Disclosure

The disclosure also provides methods of preparing Compounds of the Disclosure and/or Intermediates of the Disclosure.

In one embodiment, the present disclosure provides a method of making a compound of Formula I, or a pharmaceutically acceptable salt or solvate thereof.

In another embodiment, the present disclosure provides a method of making a compound of Formula XXII:

XXII

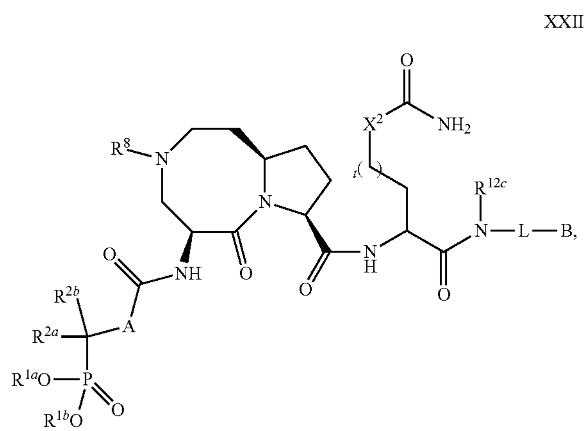

wherein:

$R^{1a}$ and $R^{1b}$ are independently selected from the group consisting of $C_1$-$C_6$ alkyl and aralkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, $R^{12c}$, A, $X^2$, t, L, and B are as defined in connection with Formula I, the method comprising reacting a compound of Formula XXX:

XXX

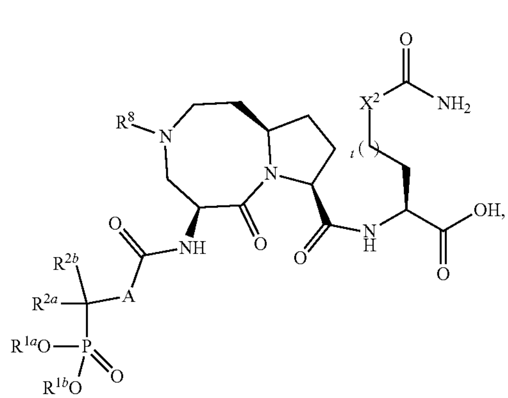

wherein:

$R^{1a}$ and $R^{1b}$ are independently selected from the group consisting of $C_1$-$C_6$ alkyl and aralkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, A, $X^2$, and t are as defined in connection with Formula I, with a compound of Formula XVII:

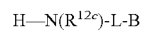

H—N($R^{12c}$)-L-B XVII, wherein $R^{12c}$, L, and B are as defined in connection with Formula I, in presence of a coupling agent in a solvent.

In another embodiment, the present disclosure provides a method of making a compound of Formula XXIII:

XXIII

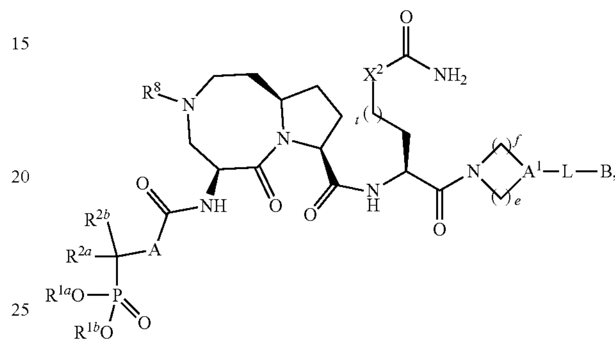

wherein:

$R^{1a}$ and $R^{1b}$ are independently selected from the group consisting of $C_1$-$C_6$ alkyl and aralkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, A, $A^1$, $X^2$, t, e, f, L, and B are as defined in connection with Formula I, the method comprising reacting a compound of Formula XXX:

XXX

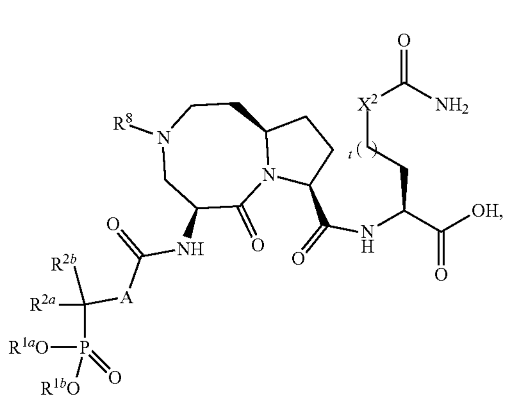

wherein:

$R^{1a}$ and $R^{1b}$ are independently selected from the group consisting of $C_1$-$C_6$ alkyl and aralkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$; and $R^{2a}$, $R^{2b}$, $R^9$, A, $X^2$, and t are as defined in connection with Formula I, with a compound of Formula XVIII:

XVIII

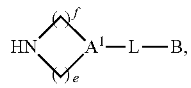

wherein $A^1$, e, f, L, and B are as defined in connection with Formula I, in presence of a coupling agent in a solvent.

In another embodiment, the present disclosure provides a method of making a compound of Formula XXIV:

XXIV

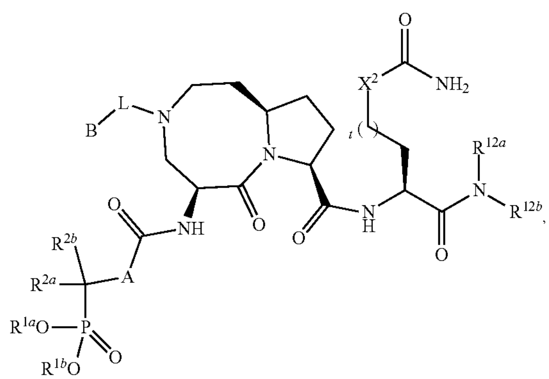

wherein:

$R^{1a}$ and $R^{1b}$ are independently selected from the group consisting of $C_1$-$C_6$ alkyl and aralkyl; and $R^{2a}$, $R^{2b}$, A, $X^2$, $R^{12a}$, $R^{12b}$, t, L, and B are as defined in connection with Formula I, the method comprising reacting a compound of Formula XXXI:

XXXI

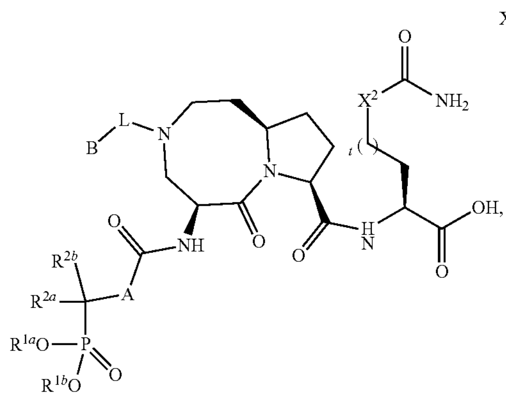

wherein:

$R^{1a}$ and $R^{1b}$ are independently selected from the group consisting of $C_1$-$C_6$ alkyl and aralkyl; and $R^{2a}$, $R^{2b}$, A, $X^2$, t, L, and B are as defined in connection with Formula I, with a compound of Formula XIX:

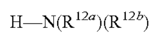

$H—N(R^{12a})(R^{12b})$ XIX, wherein $R^{12a}$ and $R^{12b}$ are as defined in connection with Formula I, in presence of a coupling agent in a solvent.

In another embodiment, the present disclosure provides a compound of Formula XXV:

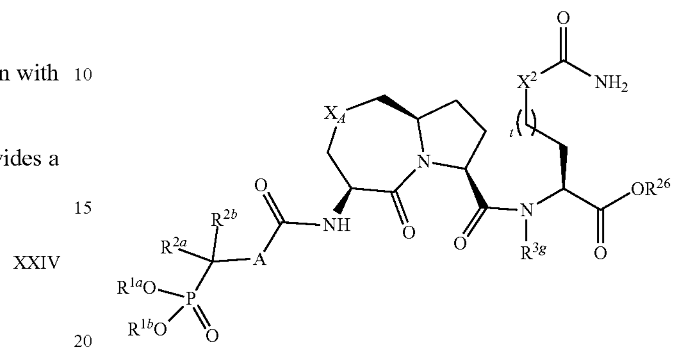

wherein:

$R^{1a}$ and $R^{1b}$ are independently selected from the group consisting of $C_1$-$C_6$ alkyl and aralkyl;

$R^{26}$ is selected from the group consisting of $C_1$-$C_6$ alkyl and aralkyl; and $R^{2a}$, $R^{2b}$, A, $X_A$, $X^2$, t, and $R^{3g}$ are as defined in connection with Formula I.

In another embodiment, the present disclosure provides a method of making a compound of Formula XXV:

XXV

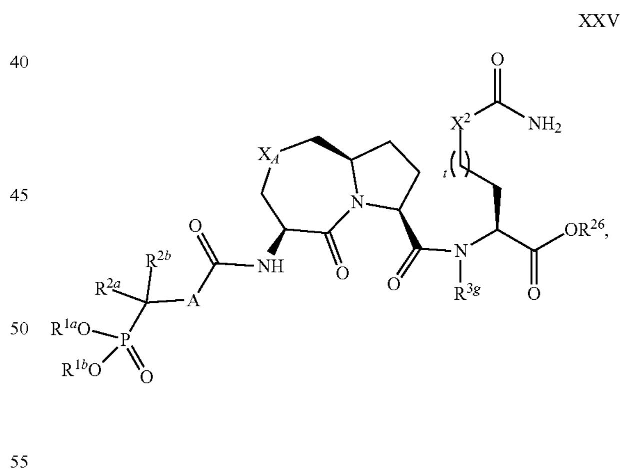

wherein:

$R^{1a}$ and $R^{1b}$ are independently selected from the group consisting of $C_1$-$C_6$ alkyl and aralkyl;

$R^{26}$ is selected from the group consisting of $C_1$-$C_6$ alkyl and aralkyl; and $R^{2a}$, $R^{2b}$, A, $X_A$, $X^2$, t, and $R^{3g}$ are as defined in connection with Formula I, the method comprising reacting a compound of Formula XXXII:

XXXII

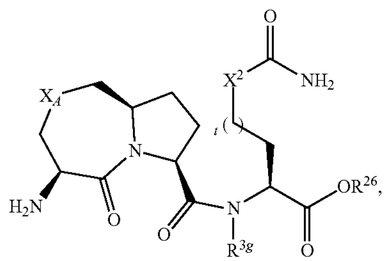

wherein $X_A$, $X^2$, t, and $R^{26}$ are as defined in connection with Formula XVI, with a compound of Formula XIII, wherein $R^{1a}$ and $R^{1b}$ are selected from the group consisting of $C_1$-$C_6$ alkyl and aralkyl; and R is hydrogen, in presence of a coupling agent in a solvent.

In another embodiment, the present disclosure provides a method of making a compound of Formula XXVI:

XXVI

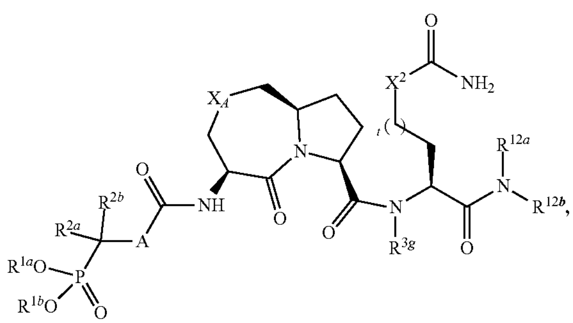

wherein:

$R^{1a}$ and $R^{1b}$ are independently selected from the group consisting of $C_1$-$C_6$ alkyl and aralkyl; and $R^{2a}$, $R^{2b}$, A, $X_A$, t, $R^{3g}$, $R^{12a}$, and $R^{12b}$ are as defined in connection with Formula I, the method comprising reacting a compound of Formula XXXIII:

XXXIII

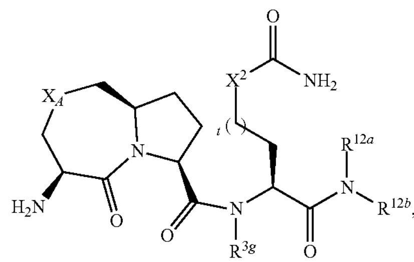

wherein $X_A$, $X^2$, t, $R^{3g}$, $R^{12a}$, and $R^{12b}$ are as defined in connection with Formula I, with a compound of Formula XIII, wherein $R^{1a}$ and $R^{1b}$ are selected from the group consisting of $C_1$-$C_6$ alkyl and aralkyl; and R is hydrogen, in presence of a coupling agent in a solvent.

In another embodiment, the present disclosure provides a method of making a compound of Formula VII-E:

VII-E

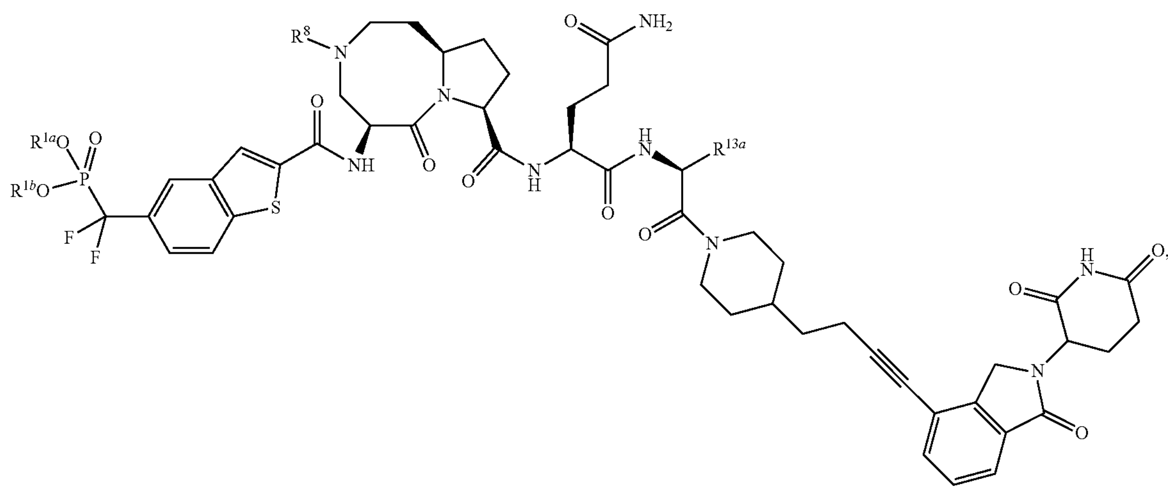

wherein:

$R^{1a}$ and $R^{1b}$ are independently selected from the group consisting of hydrogen and $C_1$-$C_4$ alkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$;

$R^9$ is selected from the group consisting of $C_1$-$C_3$ alkyl, alkylamino, dialkylamino, and $C_1$-$C_3$ alkoxy; and $R^{13a}$ is selected from the group consisting of $C_1$-$C_6$ alkyl, optionally substituted $C_3$-$C_{12}$ cycloalkyl, optionally substituted aryl, aralkyl, (heteroaryl)alkyl, (cycloalkyl) alkyl, and optionally substituted 5- to 9-membered heteroaryl, the method comprising reacting a compound of Formula XVI-A:

XVI-A

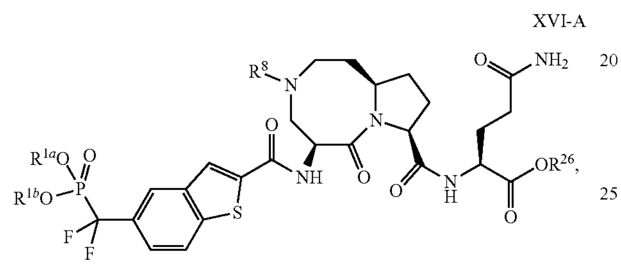

wherein:

$R^{1a}$ and $R^{1b}$ are independently selected from the group consisting of hydrogen and $C_1$-$C_4$ alkyl;

$R^8$ is selected from the group consisting of $C_1$-$C_6$ alkyl, $C_1$-$C_6$ haloalkyl, (heterocyclo)alkyl, alkylsulfonyl, and —C(═O)$R^9$; and $R^9$ is selected from the group consisting of $C_1$-$C_3$ alkyl, alkylamino, dialkylamino, and $C_1$-$C_3$ alkoxy; and $R^{26}$ is hydrogen, with a compound of Intermediate Formula 2:

2

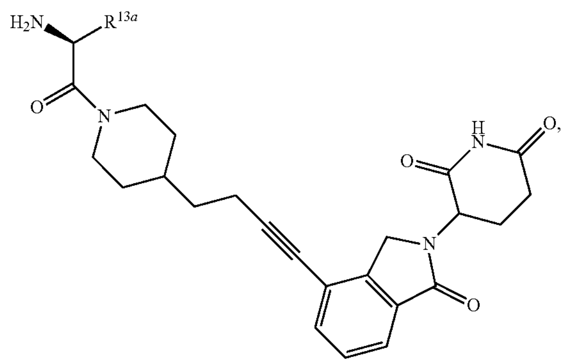

wherein:

$R^{13a}$ is selected from the group consisting of $C_1$-$C_6$ alkyl, optionally substituted $C_3$-$C_{12}$ cycloalkyl, optionally substituted aryl, aralkyl, (heteroaryl)alkyl, (cycloalkyl) alkyl, and optionally substituted 5- to 9-membered heteroaryl, in the presence of a coupling agent in a solvent.

In another embodiment, the present disclosure provides a method of making a compound of Formula VII-E, wherein $R^{13a}$ is aralkyl.

In another embodiment, the present disclosure provides a method of making a compound of Formula VII-E, wherein $R^{13a}$ is optionally substituted phenyl.

In another embodiment, the present disclosure provides a method of making a compound of Formula VII-E, wherein:

$R^{13a}$ is selected from the group consisting of:

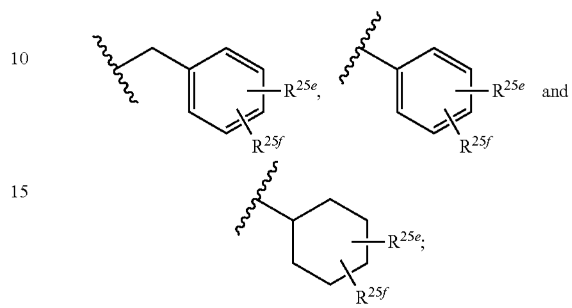

and $R^{25e}$ and $R^{25f}$ are independently selected from the group consisting of hydrogen, halo, $C_1$-$C_6$ alkyl, optionally substituted $C_3$-$C_6$ cycloalkyl, optionally substituted aryl, $C_1$-$C_4$ haloalkyl, $C_1$-$C_4$ alkoxy, carboxamido, sulfonamido, alkylsulfonyl, arylsulfonyl, —C(═O)$R^{57}$, —S(═O)$_2R^{58}$, and —N($R^{56c}$)S(═O)$_2R^{56d}$.

In another embodiment, the present disclosure provides a method of making a compound of Formula VII-E, wherein:

$R^{13a}$ is:

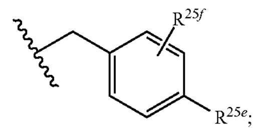

$R^{25e}$ is selected from the group consisting of hydrogen, halo, $C_1$-$C_6$ alkyl, —C(═O)N$R^{50c}R^{50d}$, $C_1$-$C_6$ alkylsulfonyl, arylsulfonyl, —N($R^{56c}$)S(═O)$_2R^{56d}$, and —S(═O)$_2R^{58}$, $R^{25f}$ is selected from the group consisting of hydrogen and halo;

$R^{50c}$ is selected from the group consisting of $C_1$-$C_6$ alkyl, optionally substituted $C_3$-$C_6$ cycloalkyl, optionally substituted 5- or 6-membered heterocyclo, optionally substituted phenyl, optionally substituted 5- to 9-membered heteroaryl, aralkyl, (heteroaryl)$C_1$-$C_4$ alkyl, and (heterocyclo)$C_1$-$C_4$ alkyl;

$R^{50d}$ is selected from the group consisting of hydrogen and $C_1$-$C_3$ alkyl; or $R^{50c}$ and $R^{50d}$ taken together with the nitrogen to which they are attached form a 3- to 8-membered optionally substituted heterocyclo group;

$R^{58}$ is optionally substituted $C_3$-$C_6$ cycloalkyl;

$R^{56c}$ is selected from the group consisting of hydrogen and $C_1$-$C_3$ alkyl; and $R^{56d}$ is selected from the group consisting of optionally substituted $C_3$-$C_6$ cycloalkyl, optionally substituted phenyl, and optionally substituted 5- to 9-membered heteroaryl.

In another embodiment, the present disclosure provides a method of making a compound of Formula VII-E, wherein the compound of Formula XVI-A is selected from one or more of the compounds of Table 2A, or a salt or solvate thereof.

In another embodiment, the present disclosure provides a method of making a compound of Formula VII-E, wherein the compound of Intermediate Formula 2 is selected from one or more of the compounds of Table 2b, or a salt or solvate thereof.

IV. Methods of Treating Disease with Compounds of the Disclosure

Compounds of the Disclosure inhibit or degrade STAT3 and are thus useful in the treatment or prevention of a variety of diseases and conditions. In particular, Compounds of the Disclosure are useful in methods of treating or preventing a disease or condition wherein inhibition or degradation of STAT3 provides a benefit, or wherein degradation of both STAT3 and STAT1 proteins provides a benefit. Foremost among these diseases and conditions are cancers and proliferative diseases. In one embodiment, such a cancer is referred to as a "STAT3 mediated cancer." STAT3 mediated cancers are known in the art. The therapeutic methods of this disclosure comprise administering a therapeutically effective amount of a Compound of the Disclosure to a subject, e.g., human, in need thereof. The present methods also encompass optionally administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

In one embodiment, the present disclosure relates to a method of treating an individual suffering from a disease or condition wherein degradation of STAT3 provides a benefit, the method comprising administering a therapeutically effective amount of a Compound of the Disclosure, e.g., a compound of any one of Formulae I-IV, IV-A, V, V-A, VI, VI-A, VII, VII-A, VII-B, VII-C, VII-D, or VII-E, to an individual in need thereof.

In one embodiment, the present disclosure relates to a method of treating an individual suffering from a disease or condition wherein degradation of STAT3 and STAT1 provides a benefit, the method comprising administering a therapeutically effective amount of a Compound of the Disclosure, e.g., a compound of any one of Formulae I-IV, IV-A, V, V-A, VI, VI-A, VII, VII-A, VII-B, VII-C, VII-D, or VII-E, to an individual in need thereof.

In another embodiment, the present disclosure relates to a method of treating an individual suffering from a disease or condition wherein inhibition of STAT3 provides a benefit, the method comprising administering a therapeutically effective amount of a Compound of the Disclosure, e.g., a compound of any one of Formulae VIII-XII, to an individual in need thereof.

Since Compounds of the Disclosure are inhibitors or degraders of STAT3 protein, or degraders of both STAT3 and STAT1, a number of diseases and conditions mediated by STAT3 can be treated by employing these compounds. The present disclosure is thus directed generally to a method for treating a condition or disorder responsive to STAT3 inhibition or degradation in an animal, e.g., a human subject, suffering from, or at risk of suffering from, the condition or disorder, the method comprising administering to the animal an effective amount of one or more Compounds of the Disclosure.

In another embodiment, the present disclosure is directed to a method of degrading STAT3 in a subject in need thereof, said method comprising administering to the subject an effective amount of at least one Compound of the Disclosure of Formulae I-IV, IV-A, V, V-A, VI, VI-A, VII, VII-A, VII-B, VII-C, VII-D, or VII-E.

In another embodiment, the present disclosure is directed to a method of degrading STAT3 and STAT1 in a subject in need thereof, said method comprising administering to the subject an effective amount of at least one Compound of the Disclosure of Formulae I-IV, IV-A, V, V-A, VI, VI-A, VII, VII-A, VII-B, VII-C, VII-D, or VII-E.

In another embodiment, the present disclosure is directed to a method of inhibiting STAT3 in a subject in need thereof, said method comprising administering to the subject an effective amount of at least one Compound of the Disclosure of Formulae VIII-XII.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein degradation of STAT3 provides a benefit. The second therapeutic agent is different from the Compound of the Disclosure. In one embodiment, a Compound of the Disclosure is administered in conjunction with a second therapeutic agent useful in the treatment of a disease or condition wherein inhibition of STAT3 provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human subject is treated with a Compound of the Disclosure, or a pharmaceutical composition comprising a Compound of the Disclosure, wherein the compound is administered in an amount sufficient to inhibit or degrade STAT3 protein in the patient, or degrade STAT3 and STAT1 protein in the patient.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by degrading STAT3, and in other embodiments Compounds of the Disclosure treat cancer by inhibiting STAT3, and in other embodiments Compounds of the Disclosure treat cancer by degrading STAT3 and STAT1. Examples of treatable cancers include, but are not limited to, any one or more of the cancers of Table 3.

TABLE 3

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |

TABLE 3-continued

| | | | |
|---|---|---|---|
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 4. In another embodiment, the hematological cancer is acute lymphocytic leukemia, chronic lymphocytic leukemia (including B-cell chronic lymphocytic leukemia), or acute myeloid leukemia.

TABLE 4

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the STAT3 inhibitor or degrader that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, rogletimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophyllotoxins, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; colchicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etidronic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and busulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Ax1 receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinolin compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortexolone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

In another embodiment, the second therapeutically active agent is an immune checkpoint inhibitor. Examples of immune checkpoint inhibitors include PD-1 inhibitors, PD-L1 inhibitors, CTLA-4 inhibitors, LAG3 inhibitors, TIM3 inhibitors, cd47 inhibitors, and B7-H1 inhibitors. Thus, in one embodiment, a Compound of the Disclosure is administered in combination with an immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-A1014, and pidilizumab. For a general discussion of the availability, methods of production, mechanism of action, and clinical studies of anti-PD-1 antibodies, see U.S. 2013/0309250, U.S. Pat. Nos. 6,808,710, 7,595,048, 8,008,449, 8,728,474, 8,779,105, 8,952,136, 8,900,587, 9,073,994, 9,084,776, and Naido et al., British Journal of Cancer 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L1 antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., British Journal of Cancer 111:2214-19 (2014).

In another embodiment, the immune checkpoint inhibitor is a CTLA-4 inhibitor. CTLA-4, also known as cytotoxic T-lymphocyte antigen 4, is a protein receptor that down-regulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., British Journal of Cancer 111:2214-19 (2014).

In another embodiment, the immune checkpoint inhibitor is a LAG3 inhibitor. LAG3, Lymphocyte Activation Gene 3, is a negative co-stimulatory receptor that modulates T cell homeostatis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., Immunity 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H1$ and $T_C1$ T-cell responses. The TIM3 pathway is considered a target for anticancer immunotherapy due to its expression on dysfunctional $CD8^+$ T cells and Tregs, which are two reported immune cell populations that constitute immunosuppression in tumor tissue. Anderson, Cancer Immunology Research 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., Cancer Res 71: 6567-71 (2011), Ngiow, et al., Cancer Res 71:3540-51 (2011), and Anderson, Cancer Immunology Res 2:393-98 (2014).

In another embodiment, the immune checkpoint inhibitor is a cd47 inhibitor. See Unanue, E. R., PNAS 110:10886-87 (2013).

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053.

Another class of immune checkpoint inhibitors include inhibitors of certain metabolic enzymes, such as indoleamine 2,3 dioxygenase (IDO), which is expressed by infiltrating myeloid cells and tumor cells. The IDO enzyme inhibits immune responses by depleting amino acids that are necessary for anabolic functions in T cells or through the synthesis of particular natural ligands for cytosolic receptors that are able to alter lymphocyte functions. Pardoll, Nature Reviews. Cancer 12:252-64 (2012); Löb, Cancer Immunol Immunother 58:153-57 (2009). Particular IDO blocking agents include, but are not limited to levo-1-methyl tryptophan (L-1MT) and 1-methyl-tryptophan (1MT). Qian et al., Cancer Res 69:5498-504 (2009); and Löb et al., Cancer Immunol Immunother 58:153-7 (2009).

In one embodiment, the immune checkpoint inhibitor is nivolumab, pembrolizumab, pidilizumab, STI-A1110, avelumab, atezolizumab, durvalumab, STI-A1014, ipilimumab, tremelimumab, GSK2831781, BMS-936559 or MED14736

The above-mentioned second therapeutically active agents, one or more of which can be used in combination with a Compound of the Disclosure, are prepared and administered as described in the art.

Compounds of the Disclosure typically are administered in admixture with a pharmaceutical carrier to give a pharmaceutical composition selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, PA, 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

The disclosure provides the following particular embodiments in connection with treating a disease in a subject Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is any one or more of the cancers of Table 3.

Embodiment IV. The method of Embodiment II, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment V. The method of Embodiment II, wherein the cancer is any one or more of the cancers of Table 4

Embodiment VI. The method of any one of Embodiments I-V further comprising administering a therapeutically effective amount of a second therapeutic agent useful in the treatment of the disease or condition, e.g., an immune checkpoint inhibitor or other anticancer agent.

Embodiment VII. The method of any one of Embodiments I-VI, wherein the Compound of the Disclosure is a compound of any one of Formulae-IV, IV-A, V, V-A, VI, VI-A, VII, VII-A, VII-B, VII-C, VII-D, or VII-E, or a pharmaceutically acceptable salt or solvate thereof.

Embodiment VIII. The method of any one of Embodiments I-VI, wherein the Compound of the Disclosure is a compound of any one of Formulae VIII-XII, or a pharmaceutically acceptable salt or solvate thereof.

Embodiment IX. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment X. The pharmaceutical composition of Embodiment IX for use in treating cancer.

Embodiment XI. The pharmaceutical composition of Embodiment X, wherein the cancer is any one or more of the cancers of Table 3.

Embodiment XII. The pharmaceutical composition of Embodiment X, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XIII The pharmaceutical composition of Embodiment X, wherein the cancer is any one or more of the cancers of Table 4.

Embodiment XIV. The pharmaceutical composition of any one of Embodiments IX-XIII, wherein the Compound of the Disclosure is a compound of any one of Formulae-IV, IV-A, V, V-A, VI, VI-A, VII, VII-A, VII-B, VII-C, VII-D, or VII-E, or a pharmaceutically acceptable salt or solvate thereof.

Embodiment XV. The pharmaceutical composition of any one of Embodiments IX-XIII, wherein the Compound of the Disclosure is a compound of any one of VIII-XII, or a pharmaceutically acceptable salt or solvate thereof.

Embodiment XVI. A Compound of the Disclosure for use in treatment of cancer, a chronic autoimmune disorder, an inflammatory condition, a proliferative disorder, sepsis, or a viral infection.

Embodiment XVII. The compound of Embodiment XVI for use in treating cancer.

Embodiment XVIII. The compound of Embodiment XVII, wherein the cancer is any one or more of the cancers of Table 3.

Embodiment XIX. The compound of Embodiment XVII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XX. The compound of Embodiment XVII, wherein the cancer is any one or more of the cancers of Table 4.

Embodiment XXI. The compound of any one of Embodiments XVI-XX, wherein the Compound of the Disclosure is a compound of any one of Formulae I-IV, IV-A, V, V-A, VI, VI-A, VII, VII-A, VII-B, VII-C, VII-D, or VII-E, or a pharmaceutically acceptable salt or solvate thereof.

Embodiment XXII. The compound of any one of Embodiments XVI-XX, wherein the Compound of the Disclosure is a compound of any one of Formulae VIII-XII, or a pharmaceutically acceptable salt or solvate thereof.

Embodiment XXIII Use of a Compound of the Disclosure for the manufacture of a medicament for treatment of cancer, a chronic autoimmune disorder, an inflammatory condition, a proliferative disorder, sepsis, or a viral infection.

Embodiment XXIV. The use of Embodiment XXIII for the treatment of cancer.

Embodiment XXV. The use of Embodiment XXIV, wherein the cancer is any one or more of the cancers of Table 3.

Embodiment XXVI. The use of Embodiment XXIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XXVII. The use of Embodiment XXIV, wherein the cancer is any one or more of the cancers of Table 4.

Embodiment XXVIII. The use of any one of Embodiments XXIII-XXVII, wherein the Compound of the Disclosure is a compound of any one of Formulae-IV, IV-A, V, V-A, VI, VI-A, VII, VII-A, VII-B, VII-C, VII-D, or VII-E, or a pharmaceutically acceptable salt or solvate thereof.

Embodiment XXIX. The use of any one of Embodiments XXIII-XXVII, wherein the Compound of the Disclosure is a compound of any one of Formulae VIII-XII, or a pharmaceutically acceptable salt or solvate thereof.

Embodiment XXX. A method of reducing STAT3 protein within a cell of a patient in need thereof, the method comprising administering to the patient a compound having any one of Formulae I-IV, IV-A, V, V-A, VI, VI-A, VII, VII-A, VII-B, VII-C, VII-D, or VII-E, or a pharmaceutically acceptable salt or solvate thereof. In one embodiment, the STAT3 protein is reduced by about 50% or less, e.g., 1%, about 2%, about 3%, about 4%, about 5%, about 10%, about 15%, about 20%, about 25%, about 30%, about 35%, about 40%, or about 45%. In one embodiment, the STAT3 protein is reduced by about 51% or more, e.g., about 55%, about 60%, about 65%, about 70%, about 75%, about 80%, about 85%, about 90%, or about 95%.

Embodiment XXXI. A method of reducing STAT3 protein and STAT1 protein within a cell of a patient in need thereof, the method comprising administering to the patient a compound having any one of Formulae I-IV, IV-A, V, V-A, VI, VI-A, VII, VII-A, VII-B, VII-C, VII-D, or VII-E, or a pharmaceutically acceptable salt or solvate thereof. In one embodiment, the STAT3 protein is reduced by about 50% or less, e.g., 1%, about 2%, about 3%, about 4%, about 5%, about 10%, about 15%, about 20%, about 25%, about 30%, about 35%, about 40%, or about 45%. In one embodiment, the STAT3 protein is reduced by about 51% or more, e.g., about 55%, about 60%, about 65%, about 70%, about 75%, about 80%, about 85%, about 90%, or about 95%. In one embodiment, the STAT1 protein is reduced by about 50% or less, e.g., 1%, about 2%, about 3%, about 4%, about 5%, about 10%, about 15%, about 20%, about 25%, about 30%, about 35%, about 40%, or about 45%. In one embodiment, the STAT1 protein is reduced by about 51% or more, e.g., about 55%, about 60%, about 65%, about 70%, about 75%, about 80%, about 85%, about 90%, or about 95%.

Embodiment XXXIII A method of inhibiting STAT3 protein within a cell of a patient in need thereof, the method comprising administering to the patient a compound having any one of Formulae VII-XII, or a pharmaceutically acceptable salt or solvate thereof.

V. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition or degradation of STAT3 provides a benefit" and the like pertains to a disease or condition in which STAT3 is important or necessary, e.g., for the onset, progress, expression of that disease or condition, or a disease or a condition which is known to be treated by an STAT3 inhibitor or degrader. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a STAT3 inhibitor or degrader for any particular cell type, for example, by assays which conveniently can be used to assess the activity of particular compounds. See, e.g., Yue and Turkson, Expert Opinion Invest Drugs 18:45-56 (2009).

The term "STAT3" refers to a protein encoded by the STAT3 gene. STAT3 is a member of the STAT protein family. In response to cytokines and growth factors, STAT3 is phosphorylated by receptor-associated Janus kinases (JAK), form homo- or heterodimers, and translocate to the cell nucleus where they act as transcription activators.

The term "STAT1" refers to a protein encoded by the STAT1 gene. STAT1 is a member of the STAT protein family. STAT1 plays a role in many gene expressions that cause survival of the cell, viability or pathogen response.

The term "STAT3 inhibitor" and the like refers to a Compound of the Disclosure that inhibits STAT3 protein. STAT3 inhibitors typically have a half maximal inhibitory concentration ($IC_{50}$) for inhibiting STAT3 of less than about 100 μM, e.g., less than about 50 μM, less than about 25 μM, and less than 5 μM, less than about 1 less than about 0.5 less than about 0.1 less than about 0.05 or less than about 0.01 STAT3 inhibitors can be used as synthetic intermediates to prepare Compounds of the Disclosure that degrade STAT3. Representative Compounds of the Disclosure that inhibit STAT3 are disclosed in Table 2.

The term "STAT3 degrader" and the like refer to a Compound of the Disclosure that degrades STAT3 protein. STAT3 degraders are heterobifunctional small molecules containing a first ligand which binds to STAT3 protein, a second ligand for an E3 ligase system, and a chemical linker that tethers the first and second ligands. Representative Compounds of the Disclosure that degrade STAT3 are disclosed in Tables 1 1A, and IB. Likewise, a "STAT1" degrader and the like refer to a Compound of the Disclosure that degrades STAT1 protein. Compounds of the Disclosure may preferentially degrade STAT3, or preferentially degrade STAT1, or degrade both STAT3 and STAT1.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. Compounds of the Disclosure are inhibitors or degraders of STAT3 and can be used in treating or preventing diseases and conditions wherein inhibition or degradation of STAT3 provides a benefit. Compounds of the Disclosure may also degrade STAT3 and STAT1 and thus can be used in treating or preventing diseases and conditions wherein degradation of both STAT3 and STAT1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "halo" as used herein by itself or as part of another group refers to —Cl, —F, —Br, or —I.

The term "nitro" as used herein by itself or as part of another group refers to $—NO_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tert-butyl, iso-butyl, 3-pentyl, hexyl, heptyl, octyl, nonyl, and decyl.

The term "optionally substituted alkyl" as used herein by itself or as part of another group refers to an alkyl group that is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkylsulfonyl, arylsulfonyl, ureido, guanidino, carbamate, carboxy, alkoxycarbonyl, carboxyalkyl, $—N(R^{56a})C(=O)R^{56b}$, $—N(R^{56c})S(=O)_2R^{56d}$, $—C(=O)R^{57}$, $—S(=O)R^{56e}$, or $—S(=O)_2R^{58}$; wherein:

$R^{56a}$ is hydrogen or alkyl;

$R^{56b}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56c}$ is hydrogen or alkyl;

$R^{56d}$ is alkyl, haloalkyl, optionally substituted cycloalkyl, alkoxy, (alkoxy)alkyl, (aryl)alkyl, (heteroaryl)alkyl, (amino)

alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56e}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{57}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl; and $R^{58}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl. Non-limiting exemplary optionally substituted alkyl groups include —$CH(CO_2Me)CH_2CO_2Me$ and —$CH(CH_3)CH_2N(H)C({=}O)O(CH_3)_3$.

The term "alkenyl" as used herein by itself or as part of another group refers to an alkyl group containing one, two, or three carbon-to-carbon double bonds. In one embodiment, the alkenyl group is a $C_2$-$C_6$ alkenyl group. In another embodiment, the alkenyl group is a $C_2$-$C_4$ alkenyl group. In another embodiment, the alkenyl group has one carbon-to-carbon double bond. Non-limiting exemplary alkenyl groups include ethenyl, propenyl, isopropenyl, butenyl, sec-butenyl, pentenyl, and hexenyl.

The term "optionally substituted alkenyl" as used herein by itself or as part of another refers to an alkenyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkenyl groups include —CH═CHPh.

The term "alkynyl" as used herein by itself or as part of another group refers to an alkyl group containing one, two, or three carbon-to-carbon triple bonds. In one embodiment, the alkynyl is a $C_2$-$C_6$ alkynyl. In another embodiment, the alkynyl is a $C_2$-$C_4$ alkynyl. In another embodiment, the alkynyl has one carbon-to-carbon triple bond. Non-limiting exemplary alkynyl groups include ethynyl, propynyl, butynyl, 2-butynyl, pentynyl, and hexynyl groups.

The term "optionally substituted alkynyl" as used herein by itself or as part of another group refers to an alkynyl group that is either unsubstituted or substituted with one, two or three substituents, wherein each substituent is independently halo, nitro, cyano, hydroxy, amino, e.g., alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkynyl groups include —C≡CPh and —CH(Ph)C≡CH.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a $C_1$-$C_6$ alkyl. In another embodiment, the alkyl is a $C_1$-$C_4$ alkyl. In another embodiment, the alkyl group is a $C_1$ or $C_2$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The terms "hydroxyalkyl" or "(hydroxy)alkyl" as used herein by themselves or as part of another group refer to an alkyl group substituted with one, two, or three hydroxy groups. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the hydroxyalkyl is a monohydroxyalkyl group, i.e., substituted with one hydroxy group. In another embodiment, the hydroxyalkyl group is a dihydroxyalkyl group, i.e., substituted with two hydroxy groups. Non-limiting exemplary (hydroxyl)alkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "alkoxy" as used herein by itself or as part of another group refers to an alkyl group attached to a terminal oxygen atom. In one embodiment, the alkyl is a $C_1$-$C_6$ alkyl and resulting alkoxy is thus referred to as a "$C_1$-$C_6$ alkoxy." In another embodiment, the alkyl is a $C_1$-$C_4$ alkyl group. Non-limiting exemplary alkoxy groups include methoxy, ethoxy, and tert-butoxy.

The term "haloalkoxy" as used herein by itself or as part of another group refers to a haloalkyl group attached to a terminal oxygen atom. In one embodiment, the haloalkyl group is a $C_1$-$C_6$ haloalkyl. In another embodiment, the haloalkyl group is a $C_1$-$C_4$ haloalkyl group. Non-limiting exemplary haloalkoxy groups include fluoromethoxy, difluoromethoxy, trifluoromethoxy, and 2,2,2-trifluoroethoxy.

The term "alkylthio" as used herein by itself or as part of another group refers to an alkyl group attached to a terminal sulfur atom. In one embodiment, the alkyl group is a $C_1$-$C_4$ alkyl group. Non-limiting exemplary alkylthio groups include —$SCH_3$, and —$SCH_2CH_3$.

The terms "alkoxyalkyl" or "(alkoxy)alkyl" as used herein by themselves or as part of another group refers to an alkyl group substituted with one alkoxy group. In one embodiment, the alkoxy is a $C_1$-$C_6$ alkoxy. In another embodiment, the alkoxy is a $C_1$-$C_4$ alkoxy. In another embodiment, the alkyl is a $C_1$-$C_6$ alkyl. In another embodiment, the alkyl is a $C_1$-$C_4$ alkyl. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "heteroalkyl" as used by itself or part of another group refers to unsubstituted straight- or branched-chain aliphatic hydrocarbons containing from three to twenty chain atoms, i.e., 3- to 20-membered heteroalkyl, or the number of chain atoms designated, wherein at least one —$CH_2$— is replaced with at least one of —O—, —N(H)—, —N($C_1$-$C_4$ alkyl)-, or —S—. The —O—, —N(H)—, —N($C_1$-$C_4$ alkyl)-, or —S— can independently be placed at any interior position of the aliphatic hydrocarbon chain so long as each —O—, —N(H)—, —N($C_1$-$C_4$ alkyl)-, and —S— group is separated by at least two —$CH_2$— groups. In one embodiment, one —$CH_2$— group is replaced with one —O— group. In another embodiment, two —$CH_2$— groups are replaced with two —O— groups. In another embodiment, three —$CH_2$— groups are replaced with three —O— groups. In another embodiment, four —$CH_2$— groups are replaced with four —O— groups. Non-limiting exemplary heteroalkyl groups include —$CH_2OCH_3$, —$CH_2OCH_2CH_2CH_3$, —$CH_2CH_2CH_2OCH_3$, —$CH_2CH_2OCH_2CH_2OCH_2CH_3$, —$CH_2CH_2OCH_2CH_2OCH_2CH_2OCH_2CH_3$.

The term "cycloalkyl" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a $C_{3-12}$ cycloalkyl, or the number of carbons designated, e.g., a $C_3$ cycloalkyl such a cyclopropyl, a $C_4$ cycloalkyl such as cyclobutyl, etc. In one embodiment, the cycloalkyl is bicyclic, i.e., it has two rings. In another embodiment, the cycloalkyl is monocyclic, i.e., it has one ring. In another embodiment, the cycloalkyl is a $C_{3-8}$ cycloalkyl. In another embodiment, the cycloalkyl is a $C_{3-6}$ cycloalkyl, i.e., cyclopropyl, cyclobutyl, cyclopentyl, or cyclohexyl. In another embodiment, the cycloalkyl is a $C_5$ cycloalkyl, i.e., cyclopentyl. In another embodiment, the cycloalkyl is a $C_6$ cycloalkyl, i.e., cyclohexyl. Non-limiting exemplary $C_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro[3.3]heptane.

The term "optionally substituted cycloalkyl" as used herein by itself or as part of another group refers to a cycloalkyl group that is either unsubstituted or substituted with one, two, or three substituents, wherein each substituent is independently halo, nitro, cyano, hydroxy, amino (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(═O)$R^{56b}$, —N($R^{56c}$)S(═O)$_2R^{56d}$, —C(═O)$R^{57}$, —S(═O)$R^{56e}$, —S(═O)$_2R^{58}$, or —O$R^{59}$, wherein $R^{56a}$, $R^{56b}$, $R^{56c}$, $R^{56d}$, $R^{56e}$, $R^{57}$, and $R^{58}$ are as defined in connection with the term "optionally substituted alkyl" and $R^{59}$ is (hydroxy)alkyl or (amino)alkyl. The term optionally substituted cycloalkyl also includes cycloalkyl groups having fused optionally substituted aryl or optionally substituted heteroaryl groups such as

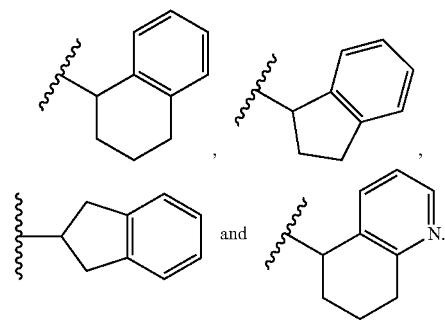

Non-limiting exemplary optionally substituted cycloalkyl groups include:

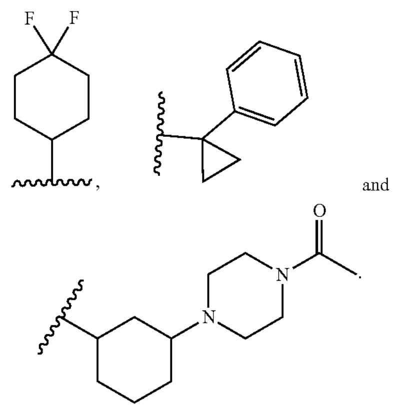

The term "heterocyclo" as used herein by itself or as part of another group refers to saturated and partially unsaturated, e.g., containing one or two double bonds, monocyclic, bicyclic, or tricyclic groups containing three to fourteen ring members, i.e., a 3- to 14-membered heterocyclo, comprising one, two, three, or four heteroatoms. Each heteroatom is independently oxygen, sulfur, or nitrogen. Each sulfur atom is independently oxidized to give a sulfoxide, i.e., S(═O), or sulfone, i.e., S(═O)$_2$.

The term heterocyclo includes groups wherein one or more —$CH_2$— groups is replaced with one or more —C(═O)— groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one —$CH_2$— group is replaced with one —C(═O)— group, e.g., pyrrolidin-2-one or piperazin-2-one. In another embodiment, the heterocyclo group is a 5- to 8-membered cyclic group containing one ring and one or two nitrogen atoms and, optionally, one —$CH_2$— group is replaced with one —C(═O)— group. In another embodiment, the heterocyclo group is a 5- or 6-membered cyclic group containing one ring and one or two nitrogen atoms and, optionally, one —$CH_2$— group is replaced with one —C(═O)— group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

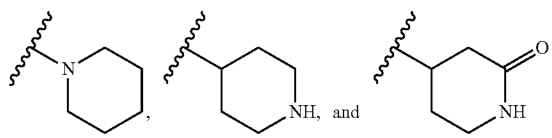

and

The term "optionally substituted heterocyclo" as used herein by itself or part of another group refers to a heterocyclo group that is either unsubstituted or substituted with one to four substituents, wherein each substituent is independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano) alkyl, (carboxamido)alkyl, mercaptoalkyl, (heterocyclo)alkyl, (heteroaryl)alkyl, —$N(R^{56a})C({=}O)R^{56b}$, —$N(R^{56c})S({=}O)_2R^{56d}$, —$C({=}O)R^{57}$, —$S({=}O)R^{56e}$, —$S({=}O)_2R^{58}$, or —$OR^{59}$, wherein $R^{56a}$, $R^{56b}$, $R^{56c}$, $R^{56d}$, $R^{56e}$, $R^{57}$, $R^{58}$, and $R^{59}$ are as defined in connection with the term "optionally substituted cycloalkyl." Substitution may occur on any available carbon or nitrogen atom of the heterocyclo group. Non-limiting exemplary optionally substituted heterocyclo groups include:

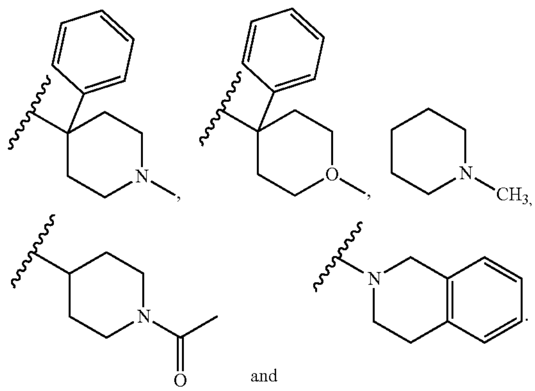

and

The term "aryl" as used herein by itself or as part of another group refers to an aromatic ring system having six to fourteen carbon atoms, i.e., $C_6$-$C_{14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "optionally substituted aryl" as used herein by itself or as part of another group refers to aryl that is either unsubstituted or substituted with one to five substituents, wherein the substituents are each independently halo, nitro, cyano, hydroxy, amino, (e.g., —$NH_2$, alkylamino, dialkylamino, aralkylamino, hydroxyalkylamino, or (heterocyclo) alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C({=}O)R^{56b}$, —$N(R^{56c})S({=}O)_2R^{56d}$, —$C({=}O)R^{57}$, —$S({=}O)R^{56e}$, —$S({=}O)_2R^{58}$, or —$OR^{59}$, wherein $R^{56a}$, $R^{56b}$, $R^{56c}$, $R^{56d}$, $R^{56e}$, $R^{57}$, $R^{58}$, and $R^{59}$ are as defined in connection with the term "optionally substituted cycloalkyl."

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl includes aryl groups having fused optionally substituted cycloalkyl groups and fused optionally substituted heterocyclo groups. Non-limiting examples include: 2,3-dihydro-1H-inden-1-yl, 1,2,3,4-tetrahydronaphthalen-1-yl, 1,3,4,5-tetrahydro-2H-benzo[c]azepin-2-yl, 1,2,3,4-tetrahydroisoquinolin-1-yl, and 2-oxo-2,3,4,5-tetrahydro-1H-benzo[d]azepin-1-yl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "optionally substituted heteroaryl" as used herein by itself or as part of another group refers to a heteroaryl that is either unsubstituted or substituted with one to four substituents, wherein the substituents are independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C(=O)R^{56b}$, —$N(R^{56c})S(=O)_2R^{56d}$, —$C(=O)R^{57}$, —$S(=O)R^{56e}$, —$S(=O)_2R^{58}$, or —$OR^{59}$, wherein $R^{56a}$, $R^{56b}$, $R^{56c}$, $R^{56d}$, $R^{56e}$, $R^{57}$, $R^{58}$, and $R^{59}$ are as defined in connection with the term "optionally substituted cycloalkyl."

In one embodiment, the optionally substituted heteroaryl has two substituents. In another embodiment, the optionally substituted heteroaryl has one substituent. Any available carbon or nitrogen atom can be substituted.

The term "aryloxy" as used herein by itself or as part of another group refers to an optionally substituted aryl attached to a terminal oxygen atom. A non-limiting exemplary aryloxy group is PhO—.

The term "heteroaryloxy" as used herein by itself or as part of another group refers to an optionally substituted heteroaryl attached to a terminal oxygen atom. A non-limiting exemplary aryloxy group is pyridyl-O—.

The term "aralkyloxy" as used herein by itself or as part of another group refers to an aralkyl attached to a terminal oxygen atom. A non-limiting exemplary aralkyloxy group is $PhCH_2O$—.

The term "(cyano)alkyl" as used herein by itself or as part of another group refers to an alkyl substituted with one, two, or three cyano groups. In one embodiment, the alkyl is substituted with one cyano group. In another embodiment, the alkyl is a $C_1$-$C_6$ alkyl In another embodiment, the alkyl is a $C_1$-$C_4$ alkyl. Non-limiting exemplary (cyano)alkyl groups include —$CH_2CH_2CN$ and —$CH_2CH_2CH_2CN$.

The term "(cycloalkyl)alkyl" as used herein by itself or as part of another group refers to an alkyl substituted with one or two optionally substituted cycloalkyl groups. In one embodiment, the cycloalkyl group(s) is an optionally substituted $C_3$-$C_6$ cycloalkyl. In another embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the alkyl is substituted with one optionally substituted cycloalkyl group. In another embodiment, the alkyl is substituted with two optionally substituted cycloalkyl groups. Non-limiting exemplary (cycloalkyl)alkyl groups include:

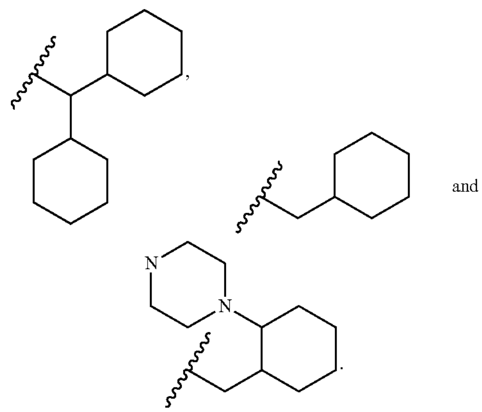

, and .

The term "sulfonamido" as used herein by itself or as part of another group refers to a radical of the formula —$SO_2NR^{50a}R^{50b}$, wherein $R^{50a}$ and $R^{50b}$ are each independently hydrogen, alkyl, optionally substituted cycloalkyl, optionally substituted heterocyclo, optionally substituted aryl, or optionally substituted heteroaryl; or $R^{50a}$ and $R^{50b}$ taken together with the nitrogen to which they are attached form a 3- to 8-membered optionally substituted heterocyclo group. Non-limiting exemplary sulfonamido groups include —$SO_2NH_2$, —$SO_2N(H)CH_3$, and —$SO_2N(H)Ph$.

The term "alkylcarbonyl" as used herein by itself or as part of another group refers to a carbonyl group, i.e., —C(=O)—, substituted by an alkyl group. In one embodiment, the alkyl is a $C_1$-$C_4$ alkyl. A non-limiting exemplary alkylcarbonyl group is —$COCH_3$.

The term "arylcarbonyl" as used herein by itself or as part of another group refers to a carbonyl group, i.e., —C(=O)—, substituted by an optionally substituted aryl group. A non-limiting exemplary arylcarbonyl group is —COPh.

The term "alkylsulfonyl" as used herein by itself or as part of another group refers to a sulfonyl group, i.e., —$SO_2$—, substituted by an alkyl group. A non-limiting exemplary alkylsulfonyl group is —$SO_2CH_3$.

The term "arylsulfonyl" as used herein by itself or as part of another group refers to a sulfonyl group, i.e., —$SO_2$—, substituted by an optionally substituted aryl group. A non-limiting exemplary arylsulfonyl group is —$SO_2Ph$.

The term "mercaptoalkyl" as used herein by itself or as part of another group refers to an alkyl substituted by a —SH group.

The term "carboxy" as used by itself or as part of another group refers to a radical of the formula —C(=O)OH.

The term "carboxamido" as used herein itself or as part of another group refers to a radical of the formula —$C(=O)NR^{50c}R^{50d}$, wherein $R^{50c}$ and $R^{50d}$ are each independently hydrogen, alkyl, optionally substituted cycloalkyl, optionally substituted heterocyclo, optionally substituted aryl, optionally substituted heteroaryl, aralkyl, (heteroaryl)alkyl, or (heterocyclo)alkyl; or $R^{50c}$ and $R^{50d}$ taken together with the nitrogen to which they are attached form a 3- to 8-membered optionally substituted heterocyclo group. Nonlimiting exemplary carboxamido groups include —C(═O)$NH_2$, —C(═O)N(H)$CH_3$, and —C(═O)N(H)Ph The term "ureido" as used herein by itself or as part of another group refers to a radical of the formula —$NR^{51a}$—C(═O)—$NR^{51b}R^{51c}$, wherein $R^{51a}$ is hydrogen or alkyl; and $R^{51b}$ and $R^{51c}$ are each independently hydrogen, alkyl, optionally substituted cycloalkyl, optionally substituted heterocyclo, optionally substituted aryl, or optionally substituted heteroaryl, or $R^{51b}$ and $R^{51c}$ taken together with the nitrogen to which they are attached form a 4- to 8-membered optionally substituted heterocyclo group. Non-limiting exemplary ureido groups include —NH—C(C═O)—$NH_2$ and —NH—C(C═O)—$NHCH_3$.

The term "guanidino" as used herein by itself or as part of another group refers to a radical of the formula —$NR^{52a}$—C(═$NR^{53}$)—$NR^{52b}R^{52c}$, wherein $R^{52a}$ is hydrogen or alkyl; $R^{52b}$ and $R^{53c}$ are each independently hydrogen, alkyl, optionally substituted cycloalkyl, optionally substituted heterocyclo, optionally substituted aryl, or optionally substituted heteroaryl; or $R^{52b}$ and $R^{52c}$ taken together with the nitrogen to which they are attached form a 4- to 8-membered optionally substituted heterocyclo group; and $R^{53}$ is hydrogen, alkyl, cyano, alkylsulfonyl, alkylcarbonyl, carboxamido, or sulfonamido. Non-limiting exemplary guanidino groups include —NH—C(C═NH)—$NH_2$, —NH—C(C═NCN)—$NH_2$, and —NH—C(C═NH)—$NHCH_3$.

The term "(heterocyclo)alkyl" as used herein by itself or as part of another group refers to an alkyl substituted with one, two, or three optionally substituted heterocyclo groups. In one embodiment, the alkyl is substituted with one optionally substituted 5- to 8-membered heterocyclo group. In another embodiment, alkyl is a $C_1$-$C_6$ alkyl. In another embodiment, alkyl is a $C_1$-$C_4$ alkyl. The heterocyclo group can be linked to the alkyl group through a carbon or nitrogen atom. Non-limiting exemplary (heterocyclo)alkyl groups include:

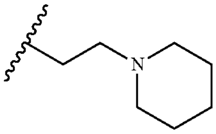, 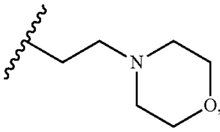

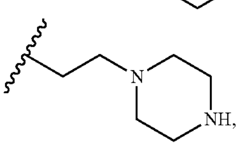, 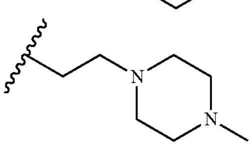

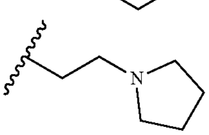, 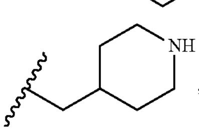,

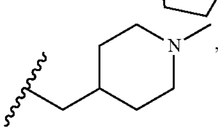, 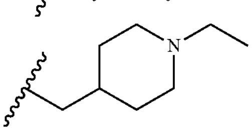,

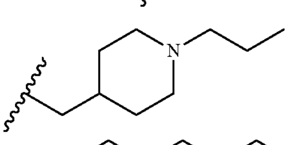,

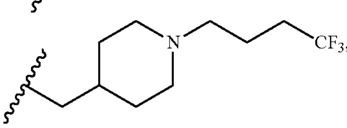,

-continued

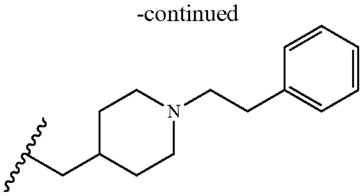,

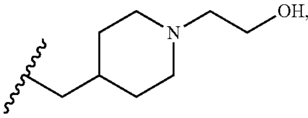, 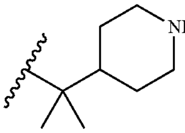 and

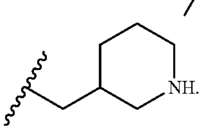.

The term "carbamate" as used herein by itself or as part of another group refers to a radical of the formula —$NR^{54a}$—C(═O)—$OR^{54b}$, wherein $R^{54a}$ is hydrogen or alkyl, and $R^{54b}$ is hydrogen, alkyl, optionally substituted cycloalkyl, optionally substituted heterocyclo, optionally substituted aryl, or optionally substituted heteroaryl. A non-limiting exemplary carbamate group is —NH—(C═O)—OtBu.

The term "(heteroaryl)alkyl" as used herein by itself or as part of another group refers to an alkyl substituted with one or two optionally substituted heteroaryl groups. In one embodiment, the alkyl group is substituted with one optionally substituted 5- to 14-membered heteroaryl group. In another embodiment, the alkyl group is substituted with two optionally substituted 5- to 14-membered heteroaryl groups. In another embodiment, the alkyl group is substituted with one optionally substituted 5- to 9-membered heteroaryl group. In another embodiment, the alkyl group is substituted with two optionally substituted 5- to 9-membered heteroaryl groups. In another embodiment, the alkyl group is substituted with one optionally substituted 5- or 6-membered heteroaryl group. In another embodiment, the alkyl group is substituted with two optionally substituted 5- or 6-membered heteroaryl groups. In one embodiment, the alkyl group is a $C_1$-$C_6$ alkyl. In another embodiment, the alkyl group is a $C_1$-$C_4$ alkyl. In another embodiment, the alkyl group is a $C_1$ or $C_2$ alkyl. Non-limiting exemplary (heteroaryl)alkyl groups include:

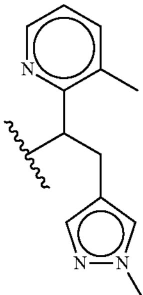, 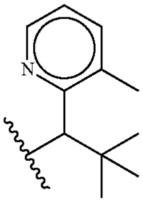, 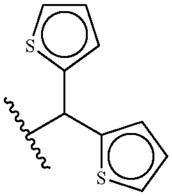,

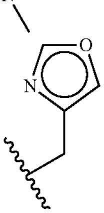 and 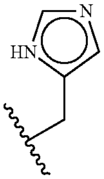.

The term "(amino)(heteroaryl)alkyl" as used herein by itself or as part of another group refers to an alkyl group substituted with one optionally substituted heteroaryl group and one amino group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (amino)(heteroaryl)alkyl group is:

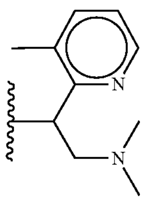

The terms "aralkyl" or "(aryl)alkyl" as used herein by themselves or as part of another group refers to an alkyl substituted with one, two, or three optionally substituted aryl groups. In one embodiment, the alkyl is substituted with one optionally substituted aryl group. In another embodiment, the alkyl is substituted with two optionally substituted aryl groups. In one embodiment, the aryl is an optionally substituted phenyl or optionally substituted naphthyl. In another embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl, phenethyl, $—CHPh_2$, and $—CH(4\text{-}F\text{-}Ph)_2$.

The term "amido" as used herein by itself or as part of another group refers to a radical of formula —C(═O)$NR^{60a}R^{60b}$, wherein $R^{60a}$ and $R^{60b}$ are each independently hydrogen, optionally substituted alkyl, optionally substituted alkenyl, optionally substituted alkynyl, haloalkyl, (alkoxy)alkyl, (hydroxy)alkyl, (cyano)alkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl; or $R^{60a}$ and $R^{60b}$ taken together with the nitrogen to which they are attached from a 4- to 8-membered optionally substituted heterocyclo group. In one embodiment, $R^{60a}$ and $R^{60b}$ are each independently hydrogen or $C_1$-$C_6$ alkyl.

The term "(amido)(aryl)alkyl" as used herein by itself or as part of another group refers to an alkyl group substituted with one amido group and one optionally substituted aryl group. In one embodiment, the aryl group is an optionally substituted phenyl. In one embodiment, the alkyl is a $C_1$-$C_6$ alkyl. In another embodiment, the alkyl is a $C_1$-$C_4$ alkyl. Non-limiting exemplary (amido)(aryl)alkyl groups include:

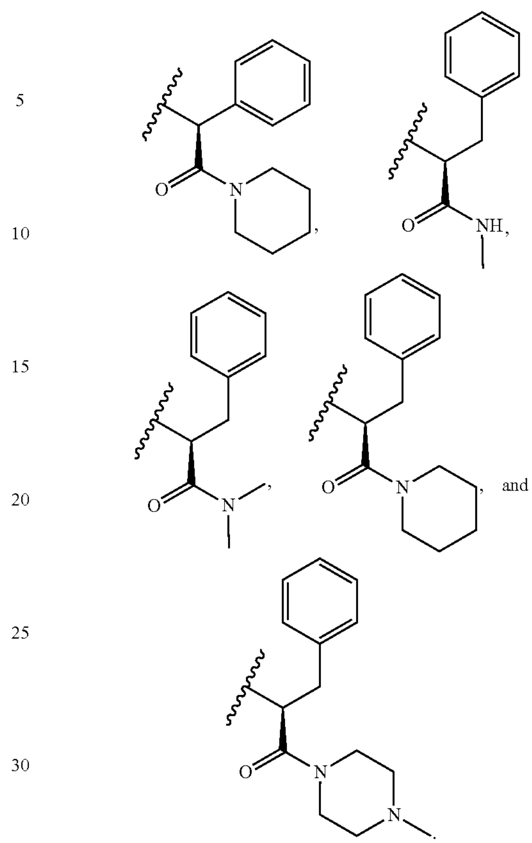

The term "(amino)(aryl)alkyl" as used herein by itself or as part of another group refers to an alkyl group substituted with one amino group and one optionally substituted aryl group. In one embodiment, the amino group is $—NH_2$, alkylamino, or dialkylamino. In one embodiment, the aryl group is an optionally substituted phenyl. In one embodiment, the alkyl is a $C_1$-$C_6$ alkyl. In another embodiment, the alkyl is a $C_1$-$C_4$ alkyl. Non-limiting exemplary (amino)(aryl)alkyl groups include:

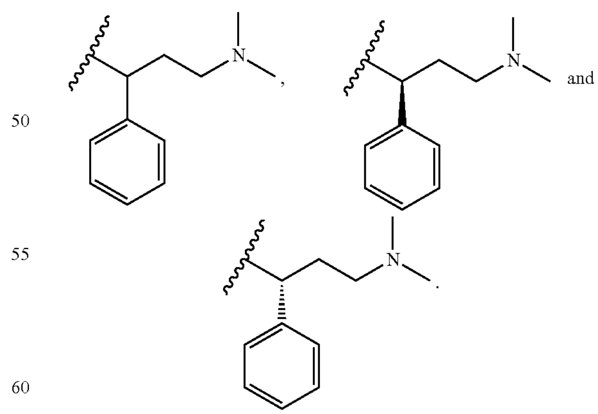

The term "amino" as used by itself or as part of another group refers to a radical of the formula $—NR^{55a}R^{55b}$, wherein $R^{55a}$ and $R^{55b}$ are independently hydrogen, optionally substituted alkyl, haloalkyl, (hydroxy)alkyl, (alkoxy)alkyl, (amino)alkyl, heteroalkyl, optionally substituted cycloalkyl, optionally substituted heterocyclo, optionally substituted aryl, optionally substituted heteroaryl, (aryl) alkyl, (cycloalkyl)alkyl, (heterocyclo)alkyl, or (heteroaryl) alkyl.

In one embodiment, the amino is —$NH_2$.

In another embodiment, the amino is an "alkylamino," i.e., an amino group wherein $R^{55a}$ is $C_{1-6}$ alkyl and $R^{55b}$ is hydrogen. In one embodiment, $R^{55a}$ is $C_1$-$C_4$ alkyl. Non-limiting exemplary alkylamino groups include —N(H)$CH_3$ and —N(H)$CH_2CH_3$.

In another embodiment, the amino is a "dialkylamino," i.e., an amino group wherein $R^{55a}$ and $R^{55b}$ are each independently $C_{1-6}$ alkyl. In one embodiment, $R^{55a}$ and $R^{55b}$ are each independently $C_1$-$C_4$ alkyl. Non-limiting exemplary dialkylamino groups include —N$(CH_3)_2$ and —N$(CH_3)$ $CH_2CH(CH_3)_2$.

In another embodiment, the amino is a "hydroxyalkylamino," i.e., an amino group wherein $R^{55a}$ is (hydroxyl) alkyl and $R^{55b}$ is hydrogen or $C_1$-$C_4$ alkyl.

In another embodiment, the amino is a "cycloalkylamino," i.e., an amino group wherein $R^{55a}$ is optionally substituted cycloalkyl and $R^{55b}$ is hydrogen or $C_1$-$C_4$ alkyl.

In another embodiment, the amino is a "aralkylamino," i.e., an amino group wherein $R^{55a}$ is aralkyl and $R^{55b}$ is hydrogen or $C_1$-$C_4$ alkyl. Non-limiting exemplary aralkylamino groups include —N(H)$CH_2$Ph, —N(H)$CHPh_2$, and —N$(CH_3)CH_2$Ph.

In another embodiment, the amino is a "(cycloalkyl) alkylamino," i.e., an amino group wherein $R^{55a}$ is (cycloalkyl)alkyl and $R^{55b}$ is hydrogen or $C_1$-$C_4$ alkyl. Non-limiting exemplary (cycloalkyl)alkylamino groups include:

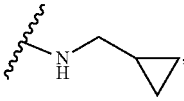,
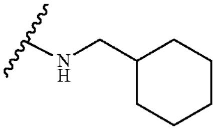
and
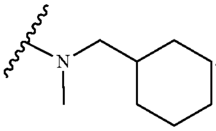.

In another embodiment, the amino is a "(heterocyclo) alkylamino," i.e., an amino group wherein $R^{55a}$ is (heterocyclo)alkyl and $R^{55b}$ is hydrogen or $C_1$-$C_4$ alkyl. Non-limiting exemplary (heterocyclo)alkylamino groups include:

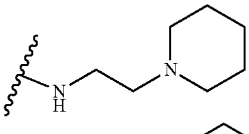
and
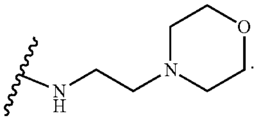.

The term "(amino)alkyl" as used herein by itself or as part of another group refers to an alkyl substituted with one amino group. In one embodiment, the amino group is —$NH_2$. In one embodiment, the amino group is an alkylamino. In another embodiment, the amino group is a dialkylamino. In another embodiment, the alkyl is a $C_1$-$C_6$ alkyl. In another embodiment, the alkyl is a $C_1$-$C_4$ alkyl. Non-limiting exemplary (amino)alkyl groups include —$CH_2NH_2$, $CH_2CH_2$N(H)$CH_3$, —$CH_2CH_2N(CH_3)_2$, $CH_2$N(H)cyclopropyl, —$CH_2$N(H)cyclobutyl, and —$CH_2$N (H)cyclohexyl, and —$CH_2CH_2CH_2$N(H)$CH_2$Ph and —$CH_2CH_2CH_2$N(H)$CH_2$(4-$CF_3$-Ph).

The term "heteroarylenyl" as used herein by itself or part of another group refers to a divalent form of an optionally substituted 5- to 9-membered heteroaryl group. In one embodiment, the heteroarylenyl is a bicyclic 9-membered heteroarylenyl. Exemplary non-limiting exemplary bicyclic 9-membered heteroarylenyl groups include:

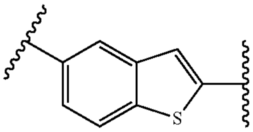,
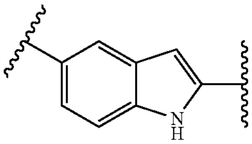,
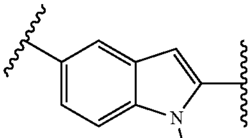,
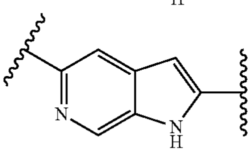,
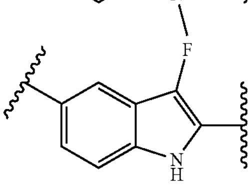,
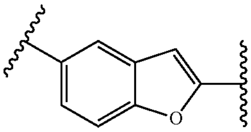,
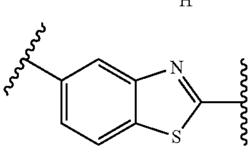
and
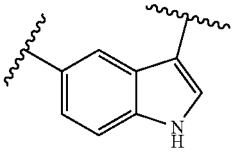.

In the present disclosure, the term "alkylenyl" as used herein by itself or part of another group refers to a divalent form of an alkyl group, wherein the alkyl group is either unsubstituted or substituted with one or two groups independently selected from the group consisting of optionally substituted phenyl and optionally substituted 5- or 6-membered heteroaryl. In one embodiment, the alkylenyl is a divalent form of a $C_{1-12}$ alkyl. In one embodiment, the alkylenyl is a divalent form of a $C_{1-10}$ alkyl. In one embodiment, the alkylenyl is a divalent form of a $C_{1-8}$ alkyl. In one embodiment, the alkylenyl is a divalent form of an unsubstituted $C_{1-6}$ alkyl. In another embodiment, the alkylenyl is a divalent form of an unsubstituted $C_{1-4}$ alkyl. In another embodiment, the alkylenyl is a divalent form of a $C_{1-4}$ alkyl substituted with one or two optionally substituted phenyl groups. Non-limiting exemplary alkylenyl groups include —$CH_2$—, —$CH_2CH_2$—, —CH(Ph)-, —CH(Ph)$CH_2$—, —$CH_2CH_2CH_2$—, —CH(Ph)$CH_2CH_2$—, —$CH_2(CH_2)_2$ $CH_2$—, —$CH(CH_2)_3CH_2$—, and —$CH_2(CH_2)_4CH_2$—.

The term "heteroalkylenyl" as used herein by itself or part of another group refers to a divalent form of a heteroalkyl group. In one embodiment, the heteroalkylenyl is a divalent form of a 3- to 20-membered heteroalkyl. In another embodiment, the heteroalkylenyl is a divalent form of a 3- to 10-membered heteroalkyl. In another embodiment, the heteroalkylenyl is a divalent form of a 3- to 8-membered heteroalkyl. In another embodiment, the heteroalkylenyl is a divalent form of a 3- to 6-membered heteroalkyl. In another embodiment, the heteroalkylenyl is a divalent form of a 3- to 4-membered heteroalkyl. In another embodiment, the heteroalkylenyl is a radical of the formula $-(CH_2CH_2O)_{u1}-$ wherein $u_1$ is 1, 2, 3, 4, 5, or 6. Non-limiting exemplary heteroalkylenyl groups include $-CH_2OCH_2-$, $-CH_2CH_2OCH_2CH_2O-$, $-CH_2OCH_2CH_2CH_2-$, and $-CH_2CH_2OCH_2CH_2OCH_2CH_2O-$.

The term "heterocyclenyl" as used herein by itself or part of another group refers to a divalent form of an optionally substituted 4- to 8-membered heterocyclo group. In one embodiment, the heterocyclenyl is a divalent form of an optionally substituted azetidine. In one embodiment, the heterocyclenyl is a divalent form of an optionally substituted piperidinyl. Non-limiting exemplary heterocyclenyl groups include:

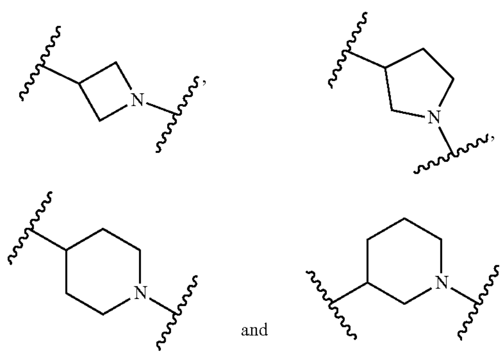

The term "cycloalkylenyl" as used herein by itself or part of another group refers to a divalent form of an optionally substituted $C_4$-$C_6$ cycloalkyl group. In one embodiment, the cycloalkylenyl is a 4-membered cycloalkylenyl. In another embodiment, the cycloalkylenyl is a 5-membered cycloalkylenyl. In another embodiment, the cycloalkylenyl is a 6-membered cycloalkylenyl. Non-limiting exemplary groups include:

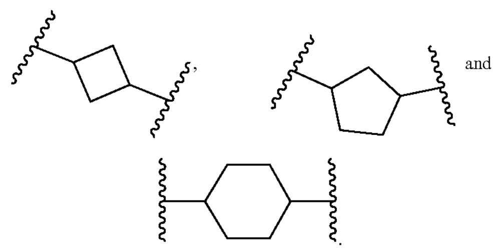

The term "phenylenyl" as used herein by itself or part of another group refers to a divalent form of an optionally substituted phenyl group. Non-limiting examples include:

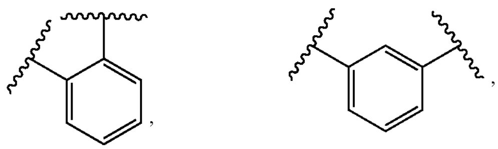

-continued

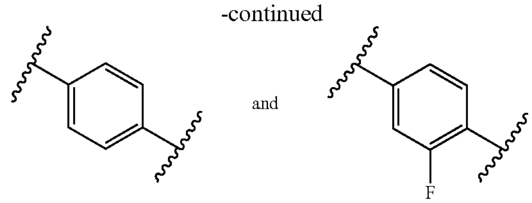

The term "bicyclic 9- or 10-membered heteroarylenyl" as used herein by itself or part of another group refers to a divalent form of an optionally substituted bicyclic 9- or 10-membered heteroaryl group. In one embodiment, bicyclic 9- or 10-membered heteroarylenyl is a bicyclic 9-membered heteroarylenyl. In another embodiment, bicyclic 9- or 10-membered heteroarylenyl is a bicyclic 10-membered heteroarylenyl. Exemplary bicyclic 9-membered heteroarylenyl groups include, but are not limited to,

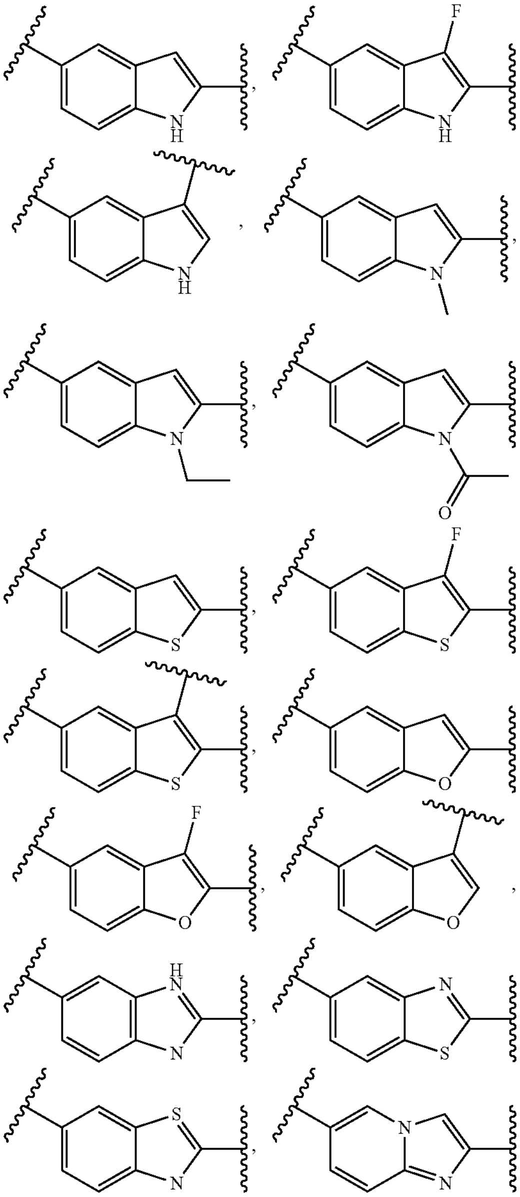

-continued

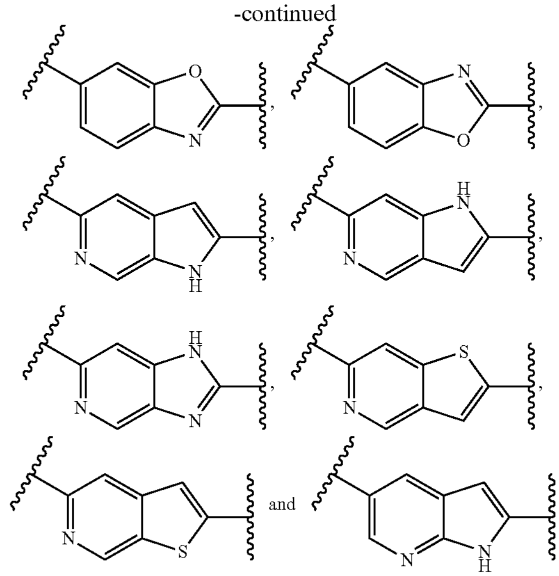

Exemplary bicyclic 10-membered heteroarylenyl groups include, but are not limited to,

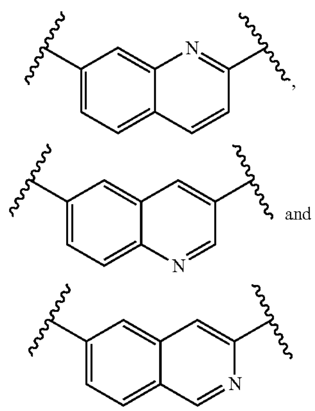

The term "naphthylenyl" as used herein by itself or part of another group refers to a divalent form of an optionally substituted naphthyl group. Exemplary naphthylenyl groups include, but are not limited to,

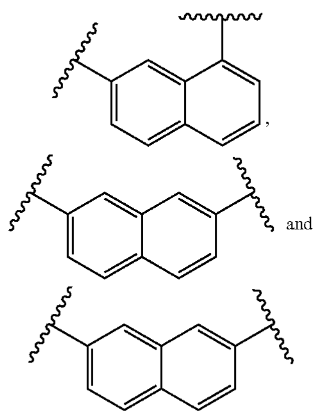

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$ (or deuterium (D)), $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^{3}H$, $^{11}C$, and $^{14}C$. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The term "coupling agent" as used herein refers to the reagent, e.g., activator, or combination of reagents, e.g., activator and base, or activator, base, and additive(s), used to form an amide bond between a carboxylic acid and an amine. Coupling agents are well known in the art. In one embodiment, the coupling agent comprises and activator, e.g., a carbodiimide (dicyclohexylcarbodiimide, diisopropylcarbodiimide, (N-(3-dimethylaminopropyl)-N'-ethylcarbodiimide-HCl) or (N-[(7-Aza-1H-benzotriazol-1-yl)(dimethylamino)-methylene]-N-methylmethanaminium hexafluorophosphate N-oxide (HATU). In another embodiment, the coupling agent comprises and activator, e.g., a carbodiimide or HATU, and a base, e.g., diisopropylethyl amine or 2,4,6-collidine. In another embodiment, the coupling agent comprises and activator, e.g., a carbodiimide, a base, e.g., 2,4,6-collidine, and at least one additive, e.g., 1-hydroxybenzotriazole or OxymaPure®. Solvents used in coupling reactions are also well known in the art. Exemplary solvents include, but are not limited to, dichloromethane, N,N-dimethylformamide, tetrahydrofuran, 2-methyltetrahydrofuran, and N-methyl-2-pyrrolidone.

The term "about," as used herein, includes the recited number ±10%. Thus, "about 10" means 9 to 11.

VII. Specific Embodiments

The present disclosure also provides the following specific Embodiments. The structures of the chemical formula recited in these specific Embodiments are as described above. For example, a compound of Formula I, "A-1," "B-1," etc., in Embodiment 1 are described in "I. Compounds of the Disclosure," a compound of Formula XIII is described in "II. Intermediates of the Disclosure," and so on.

Embodiment 1. A compound of Formula I, wherein $R^{1a}$ and $R^{1b}$ are independently selected from the group consisting of hydrogen $C_1$-$C_4$ alkyl, aralkyl, and —$CH_2OC(=O)R^{1e}$;

$R^{1e}$ is selected from the group consisting of $C_1$-$C_6$ alkyl, $C_3$-$C_6$ cycloalkyl, and $C_1$-$C_6$ alkoxy;

M is selected from the group consisting of —O— and —$C(R^{2a})(R^{2b})$—;

$R^{2a}$ and $R^{2b}$ are independently selected from the group consisting of hydrogen and fluoro; or $R^{2a}$ and $R^{2b}$ taken together with the carbon atom to which they are attached form a —C(=O)— group;

A is selected from the group consisting of A-1, A-2, A-3, A-4, A-5, A-6, A-7, A-8, A-9, A-10, A-11, A-12, A-13, A-14, A-15, A-16, A-17, A-18, A-19, A-20, A-21, and A-22; wherein the bond designated with an "*" is attached to —C(=O)-E-$Q^4$;

$G^1$ is selected from the group consisting of —O—, —S—, and —$NR^{17}$—; $G^2$ is selected from the group consisting of —N= and —$CR^{18a}$=; $G^3$ is selected from the group consisting of —N= and —$CR^{18b}$=; $G^4$ is selected from the group consisting of —N= and —$CR^{18c}$=; $G^5$ is selected from the group consisting of —N= and —$CR^{18d}$=; $G^6$ is selected from the group consisting of —N= and —$CR^{18e}$=; G is selected from the group consisting of —N= and —$CR^{18f}$=;

$R^3$ is selected from the group consisting of hydrogen, halo, $C_1$-$C_4$ alkyl, $C_3$-$C_6$ cycloalkyl, —$C(=O)R^{3a}$, and aralkyl;

$R^{3a}$ is $C_1$-$C_4$ alkyl;

$R^{3b}$ and $R^{3c}$ are independently selected from the group consisting of hydrogen and $C_1$-$C_4$ alkyl;

$R^{3d}$ is selected from the group consisting of hydrogen, $C_1$-$C_6$ alkyl, and —$C(=O)R^{3f}$;

$R^{3e}$ is selected from the group consisting of hydrogen and $C_1$-$C_4$ alkyl;

$R^{3f}$ is selected from the group consisting of $C_1$-$C_{12}$ alkyl, $C_1$-$C_6$ alkoxy, and aralkyloxy;

$R^{17}$ is selected from the group consisting of hydrogen, $C_1$-$C_4$ alkyl, $C_3$-$C_6$ cycloalkyl, aralkyl, and —$C(=O)R^{17a}$;

$R^{17a}$ is $C_1$-$C_4$ alkyl;

$R^{18a}$, $R^{18b}$, $R^{18c}$, $R^{18d}$, $R^{18e}$, and $R^{18f}$ are each independently selected from the group consisting of hydrogen, halo, and $C_1$-$C_4$ alkyl, E is

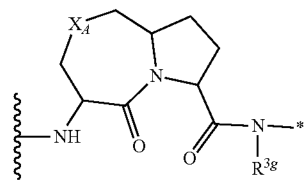

wherein the bond designated with an "*" is attached to $Q^4$;

$R^{3g}$ is selected from the group consisting of hydrogen and $C_1$-$C_4$ alkyl;

$X_A$ is selected from the group consisting of —$N(R^8)CH_2$—, —$CH_2N(R^8)$—, and —$CH—_2CH_2$—;

$R^8$ is selected from the group consisting of hydrogen, $C_1$-$C_6$ alkyl, $C_1$-$C_6$ haloalkyl, (heterocyclo)alkyl, —$C(=O)R^9$, and -L-B;

$R^9$ is selected from the group consisting of $C_1$-$C_6$ alkyl, amino, $C_1$-$C_6$ alkoxy, aralkyloxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

$Q^4$ is selected from the group consisting of Q-1, Q-2, Q-3, Q-4, Q-5, Q-6, and Q-7;

$X^1$ is selected from the group consisting of —$CH_2$—, —O—, and —$N(R^{11a})$—; or $X^1$ is absent;

$R^{10}$ is selected from the group consisting of hydrogen, $C_1$-$C_6$ alkyl, optionally substituted aralkyl, optionally substituted $C_3$-$C_6$ cycloalkyl, optionally substituted 4- to 8-membered heterocyclo, and optionally substituted aryl;

$R^{11a}$ is selected from the group consisting of hydrogen and $C_1$-$C_3$ alkyl;

s is 1, 2, 3, or 4;

$X^2$ is selected from the group consisting of —$CH_2$—, —O—, and —$N(R^{11b})$—; or $X^2$ is absent;

t is 0, 1, 2, 3, or 4;

$R^{11b}$ is selected from the group consisting of hydrogen and $C_1$-$C_3$ alkyl;

$R^{12a}$ is selected from the group consisting of hydrogen, $C_1$-$C_6$ alkyl, optionally substituted $C_2$-$C_6$ alkynyl, aralkyl, (heteroaryl)alkyl, optionally substituted $C_3$-$C_6$ cycloalkyl, optionally substituted 4- to 8-membered heterocyclo, optionally substituted aryl, (amido)(aryl)alkyl, (amino)(aryl)alkyl, (amino)(heteroaryl)alkyl, and (cycloalkyl)alkyl;

$R^{12b}$ is selected from the group consisting of hydrogen, $C_1$-$C_4$ alkyl, optionally substituted aryl, and aralkyl; or $R^{12a}$ and $R^{12b}$ taken together with the nitrogen atom to which they are attached form a 4- to 8-membered optionally substituted heterocyclo, $R^{12c}$ is selected from the group consisting of hydrogen, $C_1$-$C_4$ alkyl, and aralkyl;

$A^1$ is selected from the group consisting of —C($R^{14a}$)— and —N—;

$R^{14a}$ is selected from the group consisting of hydrogen and $C_1$-$C_3$ alkyl;

e is 1, 2, or 3;

f is 1, 2, or 3;

$X^4$ is selected from the group consisting of —$CH_2$—, —O—, and —N($R^{11d}$)—; or $X^4$ is absent;

v is 0, 1, 2, 3, or 4;

$R^{11d}$ is selected from the group consisting of hydrogen and $C_1$-$C_3$ alkyl;

$R^{12d}$ is selected from the group consisting of hydrogen, $C_1$-$C_4$ alkyl, and aralkyl;

$R^{13a}$ is selected from the group consisting of hydrogen, $C_1$-$C_6$ alkyl, optionally substituted $C_3$-$C_{12}$ cycloalkyl, optionally substituted aryl, aralkyl, (heteroaryl)alkyl, (cycloalkyl)alkyl, and optionally substituted 5- to 9-membered heteroaryl;

$R^{13b}$ is selected from the group consisting of hydrogen and $C_1$-$C_4$ alkyl;

$R^{13c}$ is selected from the group consisting of hydrogen and $C_1$-$C_4$ alkyl; or $R^{13a}$ and $R^{13b}$ taken together form a $C_3$-$C_8$ optionally substituted cycloalkyl or $C_4$-$C_9$ optionally substituted heterocyclo; or $R^{13b}$ and $R^{13c}$ taken together form a 4- to 9-membered optionally substituted heterocyclo;

$A^{2*}$ is selected from the group consisting of —C($R^{14b}$)— and —N—;

$R^{14b}$ is selected from the group consisting of hydrogen and $C_1$-$C_3$ alkyl;

g is 1, 2, or 3;

h is 1, 2, or 3;

$X^5$ is selected from the group consisting of —$CH_2$—, —O—, and —N($R^{11e}$)—; or $X^5$ is absent;

y is 0, 1, 2, 3, or 4;

$R^{11e}$ is selected from the group consisting of hydrogen and $C_1$-$C_3$ alkyl;

$R^{15}$ is selected from the group consisting of hydrogen, $C_1$-$C_6$ alkyl, $C_3$-$C_8$ cycloalkyl, optionally substituted aryl, and optionally substituted 5- to 9-membered heteroaryl;

L is -$J^1$-$Y^1$-$J^2$-$Y^2$-$J^3$-Z—;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of —$(CH_2)_m$—, —C≡C—, —CH═CH—, —N($R^{16a}$)—, —C(═O)—, —S(═O)$_2$—, —C(═O)O—, —OC(═O)—, —C(═O)N($R^{16b}$)—, and —N($R^{16b}$)C(═O)—;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of —$(CH_2)_n$—, —C≡C—, —CH═CH—, —N($R^{16a'}$)—, —C(═O)—, —S(═O)$_2$—, —C(═O)O—, —OC(═O)—, —C(═O)N($R^{16b'}$), and —($R^{16b'}$)C(═O)N—;

n is 0, 1, 2, 3, 4, 5, or 6;

$R^{16a'}$ is selected from the group consisting of hydrogen, $C_1$-$C_4$ alkyl, and aralkyl;

$R^{16b'}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of —$(CH_2)_d$—, —C≡C—, —CH═CH—, —C(═O)—, —O—, —S—, —N($R^{16c}$)—, —C(═O)N($R^{16d}$)—, —N($R^{16d}$)C(═O)—, —N($R^{16e}$)C(═O)$CH_2$O—, and —N($R^{16f}$)C(═O)$CH_2$N($R^{16g}$)—;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of B-1, B-2, B-3, B-4, B-5, B-6, B-7, B-8, B-9, and B-10;

$A_5$ is selected from the group consisting of —C($R^{19a}$)═ and —N═; $A^2$ is selected from the group consisting of —C($R^{19b}$)═ and —N═; $A^3$ is selected from the group consisting of —C($R^{19c}$)═ and —N═; $A^4$ is selected from the group consisting of —C($R^{19d}$)═ and —N═;

$Z^1$ is selected from the group consisting of —$CH_2$ and —C(═O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl;

$R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, with the provisos:

(1) when $X_A$ is —$CH_2CH_2$—, then $Q^A$ is selected from the group consisting of Q-3, Q-4, Q-5, Q-6, and Q-7;

(2) when $X_A$ is —N($R^8$)$CH_2$— or —$CH_2$N($R^8$)—, and $R^8$ is selected from the group consisting of hydrogen, $C_1$-$C_6$ alkyl, $C_1$-$C_6$ haloalkyl, (heterocyclo)alkyl, and —C(═O)$R^9$, then $Q^A$ is selected from the group consisting of Q-3, Q-4, Q-5, Q-6, and Q-7;

(3) when $X_A$ is —N($R^8$)$CH_2$— or —$CH_2$N($R^8$)—, and $R^8$ is -L-B, then $Q^A$ is selected from the group consisting of Q-1 and Q-2;

or a pharmaceutically acceptable salt or solvate thereof.

Embodiment 2. The compound of Embodiment 1 of Formula II, or a pharmaceutically acceptable salt or solvate thereof.

Embodiment 3. The compound of Embodiment 1 of Formula III, or a pharmaceutically acceptable salt or solvate thereof.

Embodiment 4. The compound of any one of Embodiments 1-3, wherein A is selected from the group consisting of:

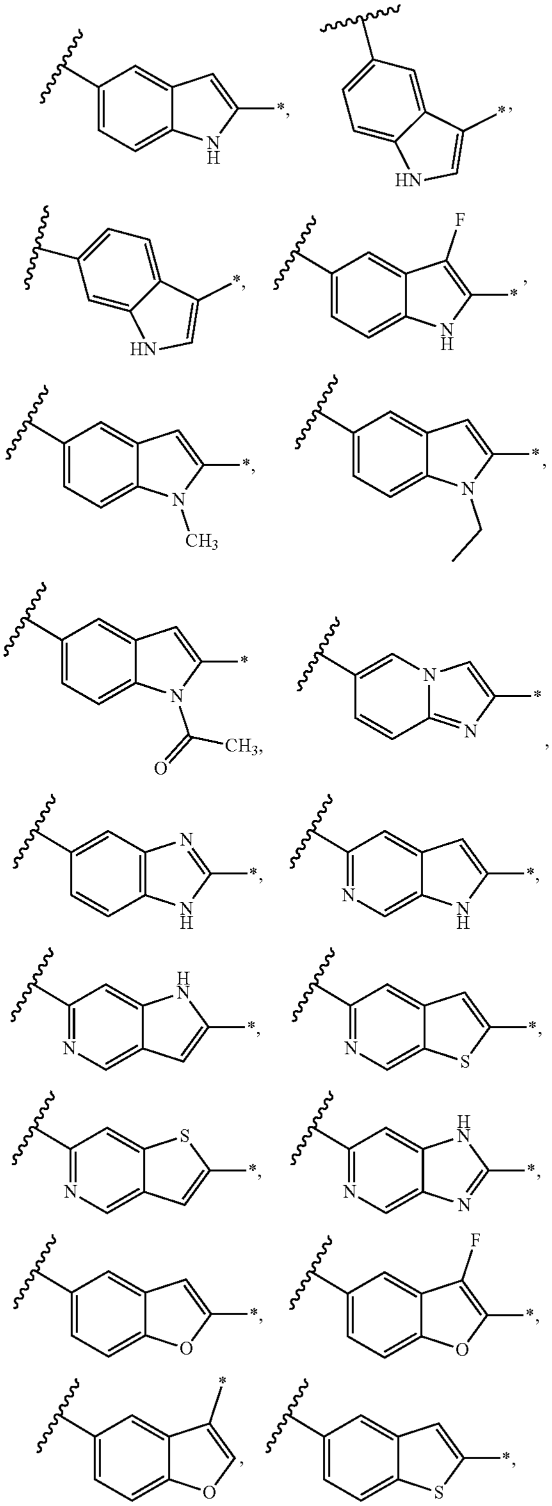

-continued

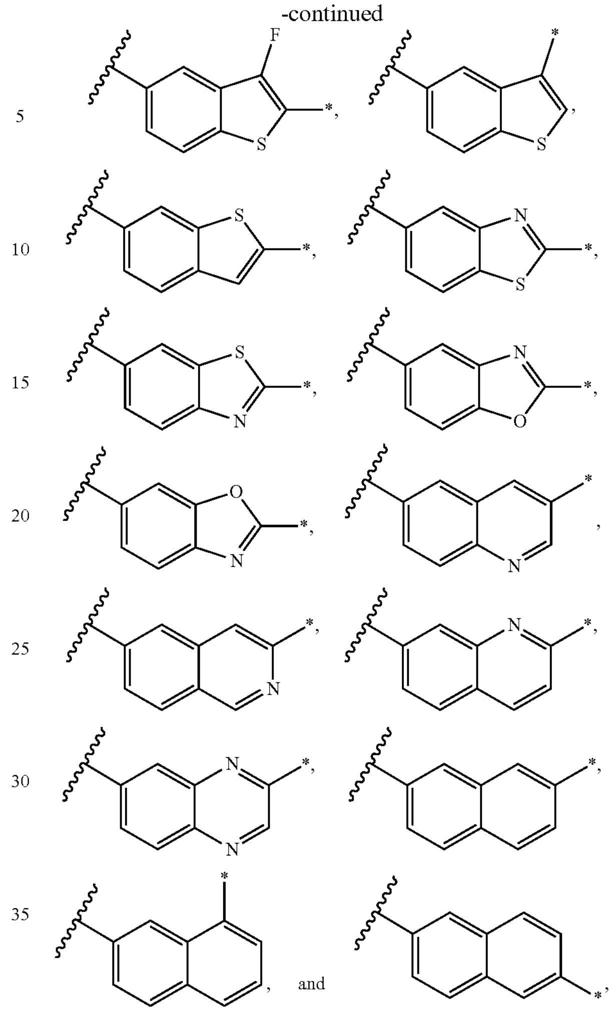

or a pharmaceutically acceptable salt or solvate thereof.

Embodiment 5. The compound of Embodiment 4, wherein A is selected from the group consisting of:

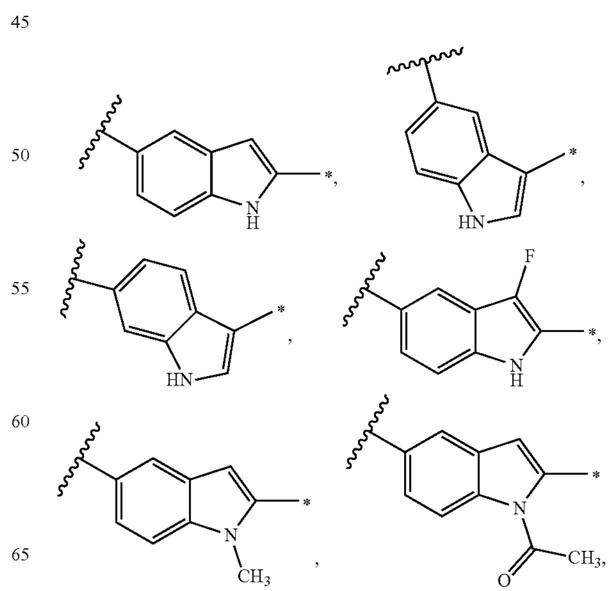

-continued

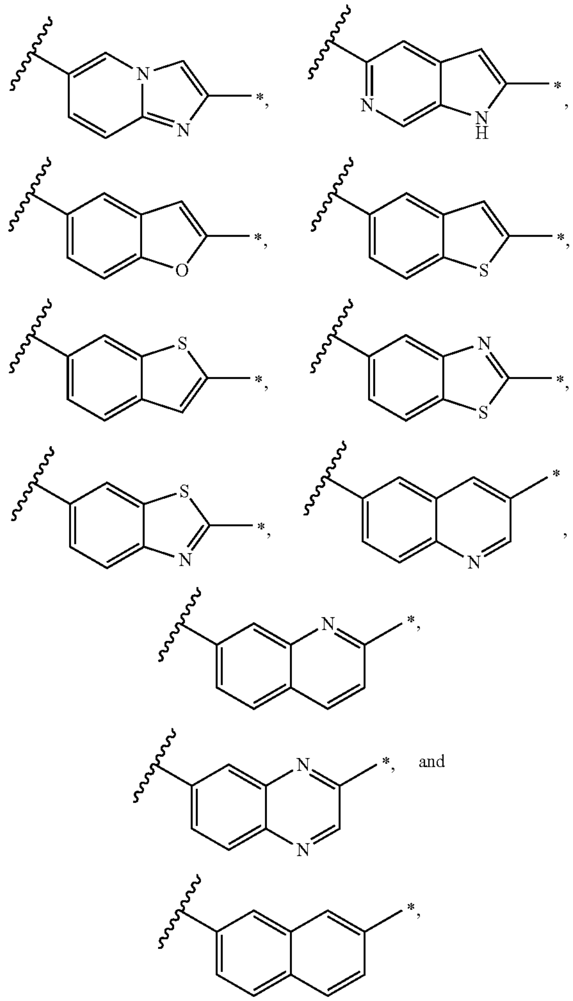

or a pharmaceutically acceptable salt or solvate thereof.

Embodiment 6. The compound of Embodiment 5, wherein A is selected from the group consisting of:

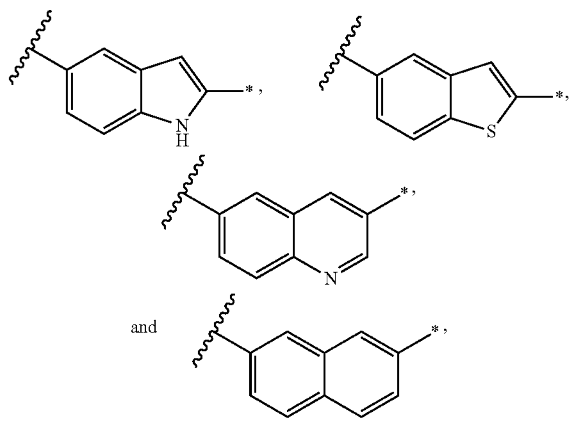

or a pharmaceutically acceptable salt or solvate thereof.

Embodiment 7. The compound of Embodiment 6, wherein A is

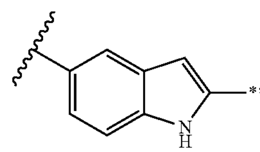

or a pharmaceutically acceptable salt or solvate thereof.

Embodiment 8. The compound of Embodiment 6, wherein A is

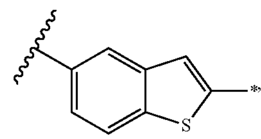 [SMILES: *c1ccc2sc(*)cc2c1]

or a pharmaceutically acceptable salt or solvate thereof.

Embodiment 9. The compound of Embodiment 6, wherein A is

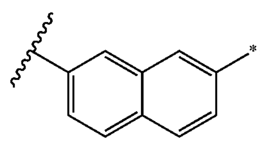

or a pharmaceutically acceptable salt or solvate thereof.

Embodiment 10. The compound of any one of Embodiments 1-9, wherein E is E-1, or a pharmaceutically acceptable salt or solvate thereof.

Embodiment 11. The compound of Embodiment 10, wherein E-1 is E-1-1, or a pharmaceutically acceptable salt or solvate thereof.

Embodiment 12. The compound of any one of Embodiments 1-9, wherein E is E-2, or a pharmaceutically acceptable salt or solvate thereof.

Embodiment 13. The compound of Embodiment 12, wherein E-2 is E-2-1, or a pharmaceutically acceptable salt or solvate thereof.

Embodiment 14. The compound of any one of Embodiments 1-9, wherein E is E-3, or a pharmaceutically acceptable salt or solvate thereof.

Embodiment 15. The compound of Embodiment 14, wherein E-3 is E-3-1, or a pharmaceutically acceptable salt or solvate thereof.

Embodiment 16. The compound of any one of Embodiments 1-13, wherein $R^8$ is -L-B, $Q^A$ is Q-1, and $R^{10}$ is hydrogen, or a pharmaceutically acceptable salt or solvate thereof.

Embodiment 17. The compound of Embodiment 16, wherein $X^1$ is selected from the group consisting of —$CH_2$— and —N(H)—, or a pharmaceutically acceptable salt or solvate thereof.

Embodiment 18. The compound of Embodiments 16 or 17, wherein s is 0 or 1, or a pharmaceutically acceptable salt or solvate thereof.

Embodiment 19. The compound of any one of Embodiments 1-13, wherein $R^8$ is -L-B, $Q^A$ is Q-2, or a pharmaceutically acceptable salt or solvate thereof.

Embodiment 20. The compound of Embodiment 19, wherein Q-2 is Q-2-1, or a pharmaceutically acceptable salt or solvate thereof.

Embodiment 21. The compound of Embodiments 19 or 20, wherein $X^2$ is selected from the group consisting of —$CH_2$—, —O—, and —N(H)—, or a pharmaceutically acceptable salt or solvate thereof.

Embodiment 22. The compound of Embodiment 21, wherein $X^2$ is —$CH_2$—, or a pharmaceutically acceptable salt or solvate thereof.

Embodiment 23. The compound of any one of Embodiments 19-22, wherein t is 0 or 1, or a pharmaceutically acceptable salt or solvate thereof.

Embodiment 24. The compound of any one of Embodiments 19-23, wherein $R^{12b}$ is hydrogen, or a pharmaceutically acceptable salt or solvate thereof.

Embodiment 25. The compound of any one of Embodiments 19-24, wherein $R^{12a}$ is aralkyl, or a pharmaceutically acceptable salt or solvate thereof.

Embodiment 26. The compound of any one of Embodiments 1-13, wherein $R^8$ is selected from the group consisting of hydrogen, $C_1$-$C_6$ alkyl, $C_1$-$C_6$ haloalkyl, (heterocyclo)alkyl, and —C(═O)$R^9$, and $Q^A$ is Q-3, or a pharmaceutically acceptable salt or solvate thereof.

Embodiment 27. The compound of Embodiments 14 or 15, wherein $Q^A$ is Q-3, or a pharmaceutically acceptable salt or solvate thereof, Embodiment 28. The compound of Embodiments 26 or 27, wherein Q-3 is Q-3-1, or a pharmaceutically acceptable salt or solvate thereof.

Embodiment 29. The compound of any one of Embodiments 26-28, wherein $X^2$ is —$CH_2$—, or a pharmaceutically acceptable salt or solvate thereof.

Embodiment 30. The compound of any one of Embodiments 26-29, wherein t is 0, or a pharmaceutically acceptable salt or solvate thereof.

Embodiment 31. The compound of any one of Embodiments 26-30, wherein $R^{12c}$ is hydrogen, or a pharmaceutically acceptable salt or solvate thereof.

Embodiment 32. The compound of any one of Embodiments 26 or 28-31, wherein $R^8$ is $C_1$-$C_4$ alkyl, or a pharmaceutically acceptable salt or solvate thereof.

Embodiment 33. The compound of any one of Embodiments 1-13, wherein $R^8$ is selected from the group consisting of hydrogen, $C_1$-$C_6$ alkyl, $C_1$-$C_6$ haloalkyl, (heterocyclo)alkyl, and —C(═O)$R^9$, and $Q^A$ is Q-4, or a pharmaceutically acceptable salt or solvate thereof.

Embodiment 34. The compound of Embodiments 14 or 15, wherein $Q^A$ is Q-4, or a pharmaceutically acceptable salt or solvate thereof.

Embodiment 35. The compound of Embodiments 33 or 34, wherein Q-4 is Q-4-1, or a pharmaceutically acceptable salt or solvate thereof.

Embodiment 36. The compound of any one of Embodiments 33-35, wherein $X^2$ is —$CH_2$—, or a pharmaceutically acceptable salt or solvate thereof.

Embodiment 37. The compound of any one of Embodiments 33-36, wherein t is 0, or a pharmaceutically acceptable salt or solvate thereof.

Embodiment 38. The compound of any one of Embodiments 33-37, wherein f and e are 2, or a pharmaceutically acceptable salt or solvate thereof.

Embodiment 39. The compound of any one of Embodiments 33-38, wherein $A^1$ is —C(H)—, or a pharmaceutically acceptable salt or solvate thereof.

Embodiment 40. The compound of any one of Embodiments 33 or 35-39, wherein $R^8$ is $C_1$-$C_4$ alkyl, or a pharmaceutically acceptable salt or solvate thereof.

Embodiment 41. The compound of any one of Embodiments 1-13, wherein $R^8$ is selected from the group consisting of hydrogen, $C_1$-$C_6$ alkyl, $C_1$-$C_6$ haloalkyl, (heterocyclo)alkyl, and —C(═O)$R^9$, and $Q^A$ is Q-5, or a pharmaceutically acceptable salt or solvate thereof.

Embodiment 42. The compound of Embodiments 14 or 15, wherein $Q^A$ is Q-5, or a pharmaceutically acceptable salt or solvate thereof.

Embodiment 43. The compound of Embodiments 41 or 42, wherein Q-5 is Q-5-1 or Q-5-2, or a pharmaceutically acceptable salt or solvate thereof.

Embodiment 44. The compound of any one of Embodiments 41-43, wherein $X^4$ is —$CH_2$—, or a pharmaceutically acceptable salt or solvate thereof.

Embodiment 45. The compound of any one of Embodiments 41-44, wherein v is 0, or a pharmaceutically acceptable salt or solvate thereof.

Embodiment 46. The compound of any one of Embodiments 41-45, wherein $R^{12d}$ is hydrogen, or a pharmaceutically acceptable salt or solvate thereof.

Embodiment 47. The compound of any one of Embodiments 41-46, wherein $R^{13a}$ is selected from the group consisting of optionally substituted $C_3$-$C_{12}$ cycloalkyl, aralkyl, and optionally substituted phenyl, or a pharmaceutically acceptable salt or solvate thereof.

Embodiment 48. The compound of any one of Embodiments 41 or 43-47, wherein $R^8$ is $C_1$-$C_4$ alkyl, or a pharmaceutically acceptable salt or solvate thereof.

Embodiment 49. The compound of any one of Embodiments 1-13, wherein $R^8$ is selected from the group consisting of hydrogen, $C_1$-$C_6$ alkyl, $C_1$-$C_6$ haloalkyl, (heterocyclo)alkyl, and —C(═O)$R^9$, and $Q^A$ is Q-6, or a pharmaceutically acceptable salt or solvate thereof.

Embodiment 50. The compound of Embodiments 14 or 15, wherein $Q^A$ is Q-6, or a pharmaceutically acceptable salt or solvate thereof.

Embodiment 51. The compound of Embodiments 49 or 50, wherein Q-6 is Q-6-1 or Q-6-2, or a pharmaceutically acceptable salt or solvate thereof.

Embodiment 52. The compound of any one of Embodiments 49-51, wherein $X^4$ is —$CH_2$—, or a pharmaceutically acceptable salt or solvate thereof.

Embodiment 53. The compound of any one of Embodiments 49-52, wherein v is 0, or a pharmaceutically acceptable salt or solvate thereof.

Embodiment 54. The compound of any one of Embodiments 49-53, wherein g and h are 2, or a pharmaceutically acceptable salt or solvate thereof.

Embodiment 55. The compound of any one of Embodiments 49-54, wherein $A^{2*}$ is —C(H)—, or a pharmaceutically acceptable salt or solvate thereof.

Embodiment 56. The compound of any one of Embodiments 49-55, wherein $R^{13a}$ is selected from the group consisting of optionally substituted $C_3$-$C_{12}$ cycloalkyl, aralkyl, and optionally substituted phenyl, or a pharmaceutically acceptable salt or solvate thereof.

Embodiment 57. The compound of any one of Embodiments 49 or 51-56, wherein $R^8$ is $C_1$-$C_4$ alkyl, or a pharmaceutically acceptable salt or solvate thereof.

Embodiment 58. The compound of any one of Embodiments 1-13, wherein $R^8$ is selected from the group consisting of hydrogen, $C_1$-$C_6$ alkyl, $C_1$-$C_6$ haloalkyl, (heterocyclo)alkyl, and —C(═O)$R^9$, and $Q^A$ is Q-7, or a pharmaceutically acceptable salt or solvate thereof.

Embodiment 59. The compound of Embodiments 14 or 15, wherein $Q^A$ is Q-7, or a pharmaceutically acceptable salt or solvate thereof.

Embodiment 60. The compound of Embodiments 58 or 59, wherein Q-7 is Q-7-1 or Q-7-2, or a pharmaceutically acceptable salt or solvate thereof.

Embodiment 61. The compound of any one of Embodiments 58-60, wherein $X^5$ is —$CH_2$—, or a pharmaceutically acceptable salt or solvate thereof.

Embodiment 62. The compound of any one of Embodiments 58-61, wherein y is 0, or a pharmaceutically acceptable salt or solvate thereof.

Embodiment 63. The compound of any one of Embodiments 58-62, wherein $R^{15}$ is optionally substituted phenyl, or a pharmaceutically acceptable salt or solvate thereof.

Embodiment 64. The compound of any one of Embodiments 58 or 60-63, wherein $R^8$ is $C_1$-$C_4$ alkyl, or a pharmaceutically acceptable salt or solvate thereof.

Embodiment 65. The compound of any one of Embodiments 1-64, wherein L is —$Y^1$-$J^2$-$Y^2$-$J^3$-Z—, or a pharmaceutically acceptable salt or solvate thereof.

Embodiment 66. The compound of any one of Embodiments 1-65, wherein L is —$Y^1$—$Y^2$-$J^3$-Z—, or a pharmaceutically acceptable salt or solvate thereof.

Embodiment 67. The compound of any one of Embodiments 1-65, wherein L is —$Y^1$-$J^2$-$Y^2$—Z—, or a pharmaceutically acceptable salt or solvate thereof.

Embodiment 68. The compound of any one of Embodiments 1-65, wherein L is —$Y^1$—$Y^2$—Z—, or a pharmaceutically acceptable salt or solvate thereof.

Embodiment 69. The compound of Embodiment 68, wherein $Y^1$ is selected from the group consisting of —$(CH_2)_m$— and —C(=O)—; m is 1, 2, or 3; $Y^2$ is —$(CH_2)_n$—; n is 1, 2, 3, 4, 5, or 6; and Z is selected from the group consisting of —$(CH_2)$—, —C≡C—, and —N(H)—, or a pharmaceutically acceptable salt or solvate thereof.

Embodiment 70. The compound of any one of Embodiments 10-13 or 16-25 wherein:

$R^8$ is -L-B;

L is selected from the group consisting of:

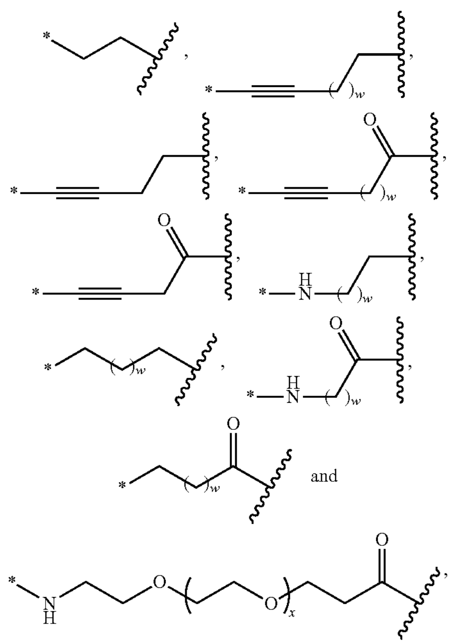

wherein the bond designated with an "*" is attached to B;
w is 1, 2, 3, 4, 5, 6, 7, or 8; and
x is 1, 2, 3, 4, 5, or 6,
or a pharmaceutically acceptable salt or solvate thereof.

Embodiment 71. The compound of any one of Embodiments 14, 15, or 26-64 wherein:

L is selected from the group consisting of:

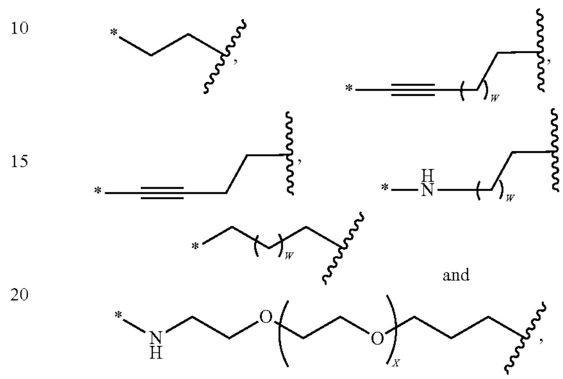

wherein the bond designated with an "*" is attached to B;
w is 1, 2, 3, 4, 5, 6, 7, or 8; and
x is 1, 2, 3, 4, 5, or 6,
or a pharmaceutically acceptable salt or solvate thereof.

Embodiment 72. The compound of any one of Embodiments 1-71, wherein B is B-1, or a pharmaceutically acceptable salt or solvate thereof.

Embodiment 73. The compound of Embodiment 72, wherein B-1 is

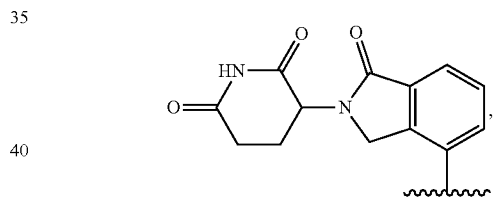

or a pharmaceutically acceptable salt or solvate thereof.

Embodiment 74. The compound of Embodiment 1 of Formula IV-A, or a pharmaceutically acceptable salt or solvate thereof.

Embodiment 75. The compound of Embodiment 1 of Formula V-A, or a pharmaceutically acceptable salt or solvate thereof.

Embodiment 76. The compound of Embodiments 74 or 75, wherein $R^{12a}$ is aralkyl, or a pharmaceutically acceptable salt or solvate thereof.

Embodiment 77. The compound of Embodiment 76, wherein $R^{12a}$ is:

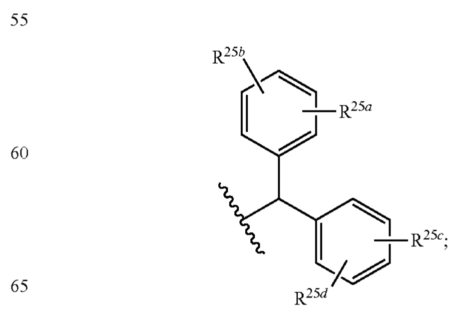

and $R^{25a}$, $R^{25b}$, $R^{25c}$, and $R^{25d}$ are each independently selected from the group consisting of hydrogen, halo, $C_1$-$C_4$ alkyl, and $C_1$-$C_4$ alkoxy, or a pharmaceutically acceptable salt or solvate thereof.

Embodiment 78. The compound of any one of Embodiments 74-77, wherein $G^1$ is —S—, or a pharmaceutically acceptable salt or solvate thereof.

Embodiment 79. The compound of any one of Embodiments 74-77, wherein $G^1$ is —NH—, or a pharmaceutically acceptable salt or solvate thereof.

Embodiment 80. The compound of any one of Embodiments 74-79, wherein $R^{2a}$ and $R^{2b}$ are fluoro, or a pharmaceutically acceptable salt or solvate thereof.

Embodiment 81. The compound of any one of Embodiments 74-79, wherein $R^{2a}$ and $R^{2b}$ taken together with the carbon to which they are attached form a —C(═O)— group, or a pharmaceutically acceptable salt or solvate thereof.

Embodiment 82. The compound of any one of Embodiments 74-81, wherein $J^2$ is absent, $Y^2$ is $—(CH_2)_n—$, n is 3, 4, or 5, and $J^3$ is absent, or a pharmaceutically acceptable salt or solvate thereof.

Embodiment 83. The compound of any one of Embodiments 74-82, wherein Z is —C≡C—, or a pharmaceutically acceptable salt or solvate thereof.

Embodiment 84. The compound of Embodiment 1 of Formula VI-A, or a pharmaceutically acceptable salt or solvate thereof.

Embodiment 85. The compound of Embodiment 1 of Formula VII-A, or a pharmaceutically acceptable salt or solvate thereof.

Embodiment 86. The compound of Embodiments 84 or 85, wherein $R^{13a}$ is selected from the group consisting of optionally substituted cyclohexyl, aralkyl, and optionally substituted phenyl, or a pharmaceutically acceptable salt or solvate thereof.

Embodiment 87. The compound of Embodiment 86, wherein $R^{13a}$ is optionally substituted phenyl, or a pharmaceutically acceptable salt or solvate thereof.

Embodiment 88. The compound of any one of Embodiments 84-86, wherein $R^8$ is $C_1$-$C_4$ alkyl, or a pharmaceutically acceptable salt or solvate thereof.

Embodiment 89. The compound of Embodiment 88, wherein $R^8$ is methyl, or a pharmaceutically acceptable salt or solvate thereof.

Embodiment 90. The compound of any one of Embodiments 84-89, wherein $G^1$ is —S—, or a pharmaceutically acceptable salt or solvate thereof.

Embodiment 91. The compound of any one of Embodiments 84-89, wherein $G^1$ is —NH—, or a pharmaceutically acceptable salt or solvate thereof.

Embodiment 92. The compound of any one of Embodiments 84-91, wherein $R^{2a}$ and $R^{2b}$ are fluoro, or a pharmaceutically acceptable salt or solvate thereof.

Embodiment 93. The compound of any one of Embodiments 84-91, wherein $R^{2a}$ and $R^{2b}$ taken together with the carbon to which they are attached form a —C(═O)— group, or a pharmaceutically acceptable salt or solvate thereof.

Embodiment 94. The compound of any one of Embodiments 84-93, wherein $J^2$ is absent, $Y^2$ is $—(CH_2)_n—$, n is 2, 3, or 4, and $J^3$ is absent, or a pharmaceutically acceptable salt or solvate thereof.

Embodiment 95. The compound of any one of Embodiments 84-94, wherein Z is —C≡C—, or a pharmaceutically acceptable salt or solvate thereof.

Embodiment 96. The compound of Embodiment 1 of Formula VII-D, or a pharmaceutically acceptable salt or solvate thereof.

Embodiment 97. The compound of Embodiment 96, wherein A is selected from the group consisting of

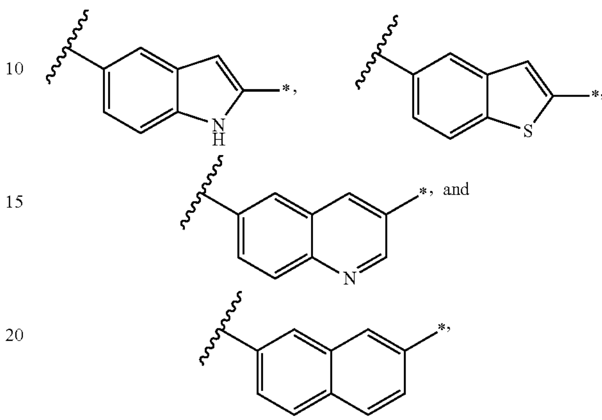

or a pharmaceutically acceptable salt or solvate thereof.

Embodiment 98. The compound of Embodiments 96 or 97, wherein $X_A$ is $—N(R^8)CH_2—$; and $R^8$ is selected from the group consisting of hydrogen, $C_1$-$C_6$ alkyl, $C_1$-$C_6$ haloalkyl, (heterocyclo)alkyl, and $—C(═O)R^9$, or a pharmaceutically acceptable salt or solvate thereof.

Embodiment 99. The compound of Embodiments 96 or 97, wherein $X_A$ is $—CH_2N(R^8)—$; and $R^8$ is selected from the group consisting of hydrogen, $C_1$-$C_6$ alkyl, $C_1$-$C_6$ haloalkyl, (heterocyclo)alkyl, and $—C(═O)R^9$, or a pharmaceutically acceptable salt or solvate thereof.

Embodiment 100. The compound of Embodiments 96 or 97, wherein $X_A$ is $—CH_2CH_2—$, or a pharmaceutically acceptable salt or solvate thereof.

Embodiment 101. The compound of any one of Embodiments 96-100, wherein $X^4$ is $—CH_2—$, or a pharmaceutically acceptable salt or solvate thereof.

Embodiment 102. The compound of any one of Embodiments 96-100, wherein $X^4$ is —O—, or a pharmaceutically acceptable salt or solvate thereof.

Embodiment 103. The compound of any one of Embodiments 96-102, wherein $R^{13a}$ is selected from the group consisting optionally substituted $C_3$-$C_{12}$ cycloalkyl, optionally substituted aryl, aralkyl, (heteroaryl)alkyl, (cycloalkyl)alkyl, and optionally substituted 5- to 9-membered heteroaryl, or a pharmaceutically acceptable salt or solvate thereof.

Embodiment 104. The compound of any one of Embodiments 1-103, wherein $R^{1a}$ and $R^{1b}$ are $C_1$-$C_4$ alkyl, or a pharmaceutically acceptable salt or solvate thereof.

Embodiment 105. The compound of any one of Embodiments 1-103, wherein $R^{1a}$ and $R^{1b}$ are hydrogen, or a pharmaceutically acceptable salt or solvate thereof.

Embodiment 106. The compound of any one of Embodiments 1-103, wherein $R^{1a}$ and $R^{1b}$ are $—CH_2OC(═O)R^{1e}$; and each $R^{1e}$ is independently selected from the group consisting of $C_1$-$C_6$ alkyl and $C_1$-$C_6$ alkoxy.

Embodiment 107. The compound of any one of Embodiments 1-103, wherein $R^{1a}$ and $R^{1b}$ are selected from the group consisting of

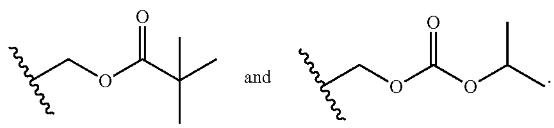

Embodiment 108. The compound of Embodiment 1 selected from one or more of the compounds of Tables 1 and 1A, or a pharmaceutically acceptable salt or solvate thereof.

Embodiment 109. The compound of Embodiment 108 selected from the group consisting of:

((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxo-decahydropyrrolo[1,2-a][1,5]diazocin-5-yl)carbamoyl)-1H-indol-5-yl)difluoromethyl)phosphonic acid;

(2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodeca-hydropyrrolo[1,2-a][1,5]diazocin-5-yl)carbamoyl)-1H-indole-5-carbonyl)phosphonic acid;

(2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-di-oxopentan-2-yl)carbamoyl)-3-methyl-6-oxodecahydropyrrolo[1,2-a][1,5]diazocin-5-yl)carbamoyl)-1H-indole-5-carbonyl)phosphonic acid;

(2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic acid;

((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxo-decahydropyrrolo[1,2-a][1,5]diazocin-5-yl)carbamoyl)benzo[b]thiophen-5-yl)difluoromethyl)phosphonic acid;

((2-(((5S,8S,10aR)-8-(((2S)-5-amino-1-(((1S)-1-cyclo-hexyl-2-(4-(4-(2-(2,6-dioxopiperidin-3-yl)-1-oxoisoindo-lin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid;

((2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-di-oxopentan-2-yl)carbamoyl)-3-methyl-6-oxodecahydropyrrolo[1,2-a][1,5]diazocin-5-yl)carbamoyl)benzo[b]thiophen-5-yl)difluoromethyl)phosphonic acid (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodeca-hydropyrrolo[1,2-a][1,5]diazocin-5-yl)carbamoyl)benzo[b]thiophene-5-carbonyl)phosphonic acid;

(2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-methyl-6-oxodecahydropyrrolo[1,2-a][1,5]diazocin-5-yl)carbamoyl)benzo[b]thiophene-5-carbonyl)phosphonic acid; and (2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-di-oxopentan-2-yl)carbamoyl)-3-methyl-6-oxodecahydropyrrolo[1,2-a][1,5]diazocin-5-yl)carbamoyl)benzo[b]thiophene-5-carbonyl)phosphonic acid, or a pharmaceutically acceptable salt or solvate thereof.

Embodiment 110. The compound of Embodiment 109 that is ((2-(((5S,8S,10aR)-8-(((S)-5-amino-1-(benzhydry-lamino)-1,5-dioxopentan-2-yl)carbamoyl)-3-(8-(2-(2,6-di-oxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic acid, or a pharmaceutically acceptable salt or solvate thereof.

Embodiment 111. A compound of Formula VIII, wherein $R^{1a}$ and $R^{1b}$ are independently selected from the group consisting of hydrogen, $C_1$-$C_6$ alkyl, and aralkyl;

M is selected from the group consisting of —O— and —C($R^{2a}$)($R^{2b}$)—;

$R^{2a}$ and $R^{2b}$ are independently selected from the group consisting of hydrogen and fluoro; or $R^{2a}$ and $R^{2b}$ taken together with the carbon atom to which they are attached form a —C(═O)— group;

A is selected from the group consisting of A-1, A-2, A-3, A-4, A-5, A-6, A-7, A-8, A-9, A-10, A-11, A-12, A-13, A-14, A-15, A-16, A-17, A-18, A-19, and A-20;

wherein the bond designated with an "*" is attached to —C(═O)-E-$Q^B$;

$G^1$ is selected from the group consisting of —O—, —S—, and —$NR^{17}$—; $G^2$ is selected from the group consisting of —N═ and —$CR^{18a}$═; $G^3$ is selected from the group consisting of —N═ and —$CR^{18b}$═; $G^4$ is selected from the group consisting of —N═ and —$CR^{18c}$═; $G^5$ is selected from the group consisting of —N═ and —$CR^{18d}$═; $G^6$ is selected from the group consisting of —N═ and —$CR^{18e}$═; G is selected from the group consisting of —N═ and —$CR^{18f}$═;

$R^3$ is selected from the group consisting of hydrogen, halo, $C_1$-$C_4$ alkyl, $C_3$-$C_6$ cycloalkyl, —C(═O)$R^{3a}$, and aralkyl;

$R^{3a}$ is $C_1$-$C_4$ alkyl;

$R^{3b}$ and $R^{3c}$ are independently selected from the group consisting of hydrogen and $C_1$-$C_4$ alkyl;

$R^{3d}$ is selected from the group consisting of hydrogen, $C_1$-$C_6$ alkyl, and —C(═O)$R^{3f}$;

$R^{3e}$ is selected from the group consisting of hydrogen and $C_1$-$C_4$ alkyl;

$R^{3f}$ is selected from the group consisting of $C_1$-$C_{12}$ alkyl, $C_1$-$C_6$ alkoxy, and aralkyloxy;

$R^{17}$ is selected from the group consisting of hydrogen, $C_1$-$C_4$ alkyl, $C_3$-$C_6$ cycloalkyl, aralkyl, and —C(═O)$R^{17a}$;

$R^{17a}$ is $C_1$-$C_4$ alkyl;

$R^{18a}$, $R^{18b}$, $R^{18c}$, $R^{18d}$, $R^{18e}$, and $R^{18f}$ are each independently selected from the group consisting of hydrogen, halo, and $C_1$-$C_4$ alkyl;

E is

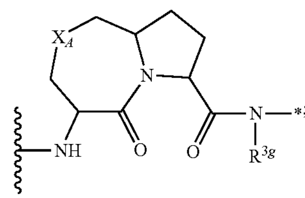

wherein the bond designated with an "*" is attached to $Q^B$;

$R^{3g}$ is selected from the group consisting of hydrogen and $C_1$-$C_4$ alkyl;

$X_A$ is selected from the group consisting of —$N(R^8)CH_2$—, —$CH_2N(R^8)$—, and —$CH—_2CH_2$—;

$R^8$ is selected from the group consisting of hydrogen, $C_1$-$C_6$ alkyl, $C_1$-$C_6$ haloalkyl, (heterocyclo)alkyl, and —C(═O)$R^9$;

$R^9$ is selected from the group consisting of $C_1$-$C_6$ alkyl, amino, $C_1$-$C_6$ alkoxy, aralkyloxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

$Q^B$ is selected from the group consisting of Q-1 and Q-2:

$X^1$ is selected from the group consisting of —$CH_2$—, —O—, and —$N(R^{11a})$—; or $X^1$ is absent;

$R^{10}$ is selected from the group consisting of hydrogen, $C_1$-$C_6$ alkyl, optionally substituted aralkyl, optionally substituted $C_3$-$C_6$ cycloalkyl, optionally substituted 4- to 8-membered heterocyclo, and optionally substituted aryl;

$R^{11a}$ is selected from the group consisting of hydrogen and $C_1$-$C_3$ alkyl;

s is 1, 2, 3, or 4;

$X^2$ is selected from the group consisting of —$CH_2$—, —O—, and —$N(R^{11b})$—; or $X^2$ is absent;

t is 0, 1, 2, 3, or 4;

$R^{11b}$ is selected from the group consisting of hydrogen and $C_1$-$C_3$ alkyl;

$R^{12a}$ is selected from the group consisting of hydrogen, $C_1$-$C_6$ alkyl, optionally substituted $C_2$-$C_6$ alkynyl, aralkyl, (heteroaryl)alkyl, optionally substituted $C_3$-$C_6$ cycloalkyl, optionally substituted 4- to 8-membered heterocyclo, optionally substituted aryl, (amido)(aryl)alkyl, (amino)(aryl)alkyl, (amino)(heteroaryl)alkyl, and (cycloalkyl)alkyl;

$R^{12b}$ is selected from the group consisting of hydrogen, $C_1$-$C_4$ alkyl, optionally substituted aryl, and aralkyl; or $R^{12a}$ and $R^{12b}$ taken together with the nitrogen atom to which they are attached form a 4- to 8-membered optionally substituted heterocyclo, with the provisos:

(1) when $X_A$ is —$CH_2CH_2$—, then:

(i) A is selected from the group consisting of A-2, A-5, A-6, A-7, A-8, A-9, A-10, A-11, A-12, A-13, A-14, A-15, A-16, A-17, A-18, A-19, and A-20;

(ii) A is A-4 and $G^1$ is —S—; or (iii) $R^{2a}$ and $R^{2b}$ taken together with the carbon atom to which they are attached form a —C(═O)— group;

(2) when $X_A$ is —$N(R^8)CH_2$—, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group; or (3) when $X_A$ is —$CH_2N(R^8)$—, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group;

or a pharmaceutically acceptable salt or solvate thereof.

Embodiment 112. The compound of Embodiment 111 of Formula IX, or a pharmaceutically acceptable salt or solvate thereof.

Embodiment 113. The compound of Embodiment 111 of Formula X, or a pharmaceutically acceptable salt or solvate thereof.

Embodiment 114. The compound of any one of Embodiments 111-113, wherein A is selected from the group recited in Embodiment 4, or a pharmaceutically acceptable salt or solvate thereof.

Embodiment 115. The compound of Embodiment 114, wherein A is selected from the group recited in Embodiment 5, or a pharmaceutically acceptable salt or solvate thereof.

Embodiment 116. The compound of Embodiment 115, wherein A is selected from the group recited in Embodiment 6, or a pharmaceutically acceptable salt or solvate thereof.

Embodiment 117. The compound of Embodiment 116, wherein A is

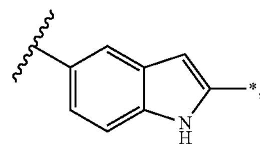

or a pharmaceutically acceptable salt or solvate thereof.

Embodiment 118. The compound of Embodiment 116, wherein A is

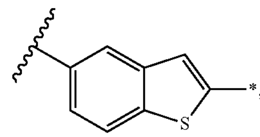

or a pharmaceutically acceptable salt or solvate thereof.

Embodiment 119. The compound of Embodiment 116, wherein A is

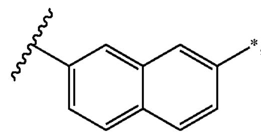

or a pharmaceutically acceptable salt or solvate thereof.

Embodiment 120. The compound of any one of Embodiments 111-119,

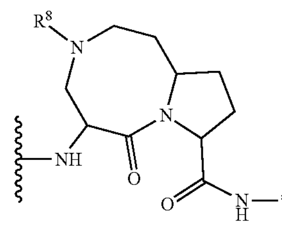

wherein E is E-1, or a pharmaceutically acceptable salt or solvate thereof.

Embodiment 121. The compound of Embodiment 120, wherein E-1 is E-1-1, or a pharmaceutically acceptable salt or solvate thereof.

Embodiment 122. The compound of any one of Embodiments 111-119, wherein E is E-2, or a pharmaceutically acceptable salt or solvate thereof.

Embodiment 123. The compound of Embodiment 122, wherein E-2 is E-2-1, or a pharmaceutically acceptable salt or solvate thereof.

Embodiment 124. The compound of any one of Embodiments 111-119, wherein E is E-3, or a pharmaceutically acceptable salt or solvate thereof.

Embodiment 125. The compound of Embodiment 124, wherein E-3 is E-3-1, or a pharmaceutically acceptable salt or solvate thereof.

Embodiment 126. The compound of any one of Embodiments 111-125, wherein $Q^B$ is Q-1, or a pharmaceutically acceptable salt or solvate thereof.

Embodiment 127. The compound of Embodiment 126, wherein $X^1$ is selected from the group consisting of $—CH_2—$ and —N(H)—, or a pharmaceutically acceptable salt or solvate thereof.

Embodiment 128. The compound of Embodiments 126 or 127, wherein s is 0 or 1, or a pharmaceutically acceptable salt or solvate thereof.

Embodiment 129. The compound of any one of Embodiments 111-125, wherein $Q^B$ is Q-2, or a pharmaceutically acceptable salt or solvate thereof.

Embodiment 130. The compound of Embodiment 129, wherein Q-2 is Q-2-1, or a pharmaceutically acceptable salt or solvate thereof.

Embodiment 131. The compound of Embodiments 129 or 130, wherein $X^2$ is selected from the group consisting of $—CH_2—$, —O—, and —N(H)—, or a pharmaceutically acceptable salt or solvate thereof.

Embodiment 132. The compound of Embodiment 131, wherein $X^2$ is $—CH_2—$, or a pharmaceutically acceptable salt or solvate thereof.

Embodiment 133. The compound of any one of Embodiments 129-132, wherein t is 0 or 1, or a pharmaceutically acceptable salt or solvate thereof.

Embodiment 134. The compound of any one of Embodiments 129-133, wherein $R^{12b}$ is hydrogen, or a pharmaceutically acceptable salt or solvate thereof.

Embodiment 135. The compound of any one of Embodiments 129-134, wherein $R^{12a}$ is aralkyl, or a pharmaceutically acceptable salt or solvate thereof.

Embodiment 136. The compound of Embodiment 111 of Formula XI, or a pharmaceutically acceptable salt or solvate thereof.

Embodiment 137. The compound of Embodiment 111 of Formula XII, or a pharmaceutically acceptable salt or solvate thereof.

Embodiment 138. The compound of Embodiments 136 or 137, wherein $R^{2a}$ and $R^{2b}$ are fluoro, or a pharmaceutically acceptable salt or solvate thereof.

Embodiment 139. The compound of Embodiments 136 or 137, wherein $R^{2a}$ and $R^{2b}$ taken together with the carbon to which they are attached form a —C(═O)— group, or a pharmaceutically acceptable salt or solvate thereof.

Embodiment 140. The compound of any one of Embodiments 136-139, wherein A is A-4, or a pharmaceutically acceptable salt or solvate thereof.

Embodiment 141. The compound of Embodiment 140, wherein $G^1$ is —S—, or a pharmaceutically acceptable salt or solvate thereof.

Embodiment 142. The compound of Embodiment 141, wherein A is A-8, or a pharmaceutically acceptable salt or solvate thereof.

Embodiment 143. The compound of any one of Embodiments 136-142, wherein $R^8$ is hydrogen, or a pharmaceutically acceptable salt or solvate thereof.

Embodiment 144. The compound of any one of Embodiments 136-142, wherein $R^8$ is $C_1$-$C_4$ alkyl, or a pharmaceutically acceptable salt or solvate thereof.

Embodiment 145. The compound of any one of Embodiments 136-144, wherein $R^{12a}$ is aralkyl, or a pharmaceutically acceptable salt or solvate thereof.

Embodiment 146. The compound of Embodiment 145, wherein $R^{12a}$ is

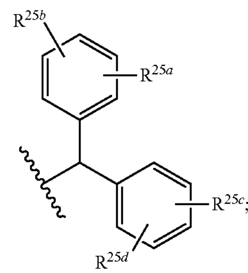

and $R^{25a}$, $R^{25b}$, $R^{25c}$, and $R^{25d}$ are each independently selected from the group consisting of hydrogen, halo, $C_1$-$C_4$ alkyl, and $C_1$-$C_4$ alkoxy, or a pharmaceutically acceptable salt or solvate thereof.

Embodiment 147. The compound of any one of Embodiments 111-146, wherein $R^{1a}$ and $R^{1b}$ are $C_1$-$C_4$ alkyl, or a pharmaceutically acceptable salt or solvate thereof.

Embodiment 148. The compound of any one of Embodiments 111-146, wherein $R^{1a}$ and $R^{1b}$ hydrogen, or a pharmaceutically acceptable salt or solvate thereof.

Embodiment 149. The compound of Embodiment 111 selected from one or more of the compounds of Table 2, or a pharmaceutically acceptable salt or solvate thereof.

Embodiment 150. A pharmaceutical composition comprising the compound of any one of Embodiments 1-149, or a pharmaceutically acceptable salt or solvate thereof, and a pharmaceutically acceptable carrier.

Embodiment 151. A method of treating cancer in a subject in need thereof, the method comprising administering to the subject a therapeutically effective amount of the compound of any one of Embodiments 1-149, or a pharmaceutically acceptable salt or solvate thereof.

Embodiment 152. The method of Embodiment 151, wherein the cancer is any one or more of the cancers of Table 3.

Embodiment 153. The method of Embodiments 151 or 152 further comprising administering a therapeutically effective amount of a second therapeutic agent useful in the treatment of cancer.

Embodiment 154. The pharmaceutical composition of Embodiment 150 for use in treating cancer.

Embodiment 155. The pharmaceutical composition of Embodiment 154, wherein the cancer is any one or more of the cancers of Table 3.

Embodiment 156. A compound of any one of Embodiments 1-149, or a pharmaceutically acceptable salt or solvate thereof, for use in treating of cancer.

Embodiment 157. The compound for use of Embodiment 156, wherein the cancer is any one or more of the cancers of Table 3.

Embodiment 158. Use of a compound of any one of Embodiments 1-149, or a pharmaceutically acceptable salt or solvate thereof, for the manufacture of a medicament for treatment of cancer.

Embodiment 159. The use of Embodiment 158, wherein the cancer is any one or more of the cancers of Table 3.

Embodiment 160. A method of reducing STAT3 protein within a cell of a patient in need thereof, the method comprising administering to the subject a compound of any one of Embodiments 1-110, or a pharmaceutically acceptable salt or solvate thereof.

Embodiment 161. A method of inhibiting STAT3 protein within a cell of a subject in need thereof, the method comprising administering to the patient a compound of any one of Embodiments 111-149, or a pharmaceutically acceptable salt or solvate thereof.

Embodiment 162. A kit comprising the compound of any one of Embodiments 1-149, or a pharmaceutically acceptable salt or solvate thereof, and instructions for administering the compound, or a pharmaceutically acceptable salt or solvate thereof, to a subject having cancer.

Embodiment 163. The kit of Embodiment 162, wherein the cancer is any one or more of the cancers of Table 3.

Embodiment 164. The kit of Embodiments 162 or 163 further comprising one or more additional therapeutic agents.

Embodiment 165. A compound of Formula XIII, wherein R is selected from the group consisting of hydrogen, $C_1$-$C_6$ alkyl, aralkyl, and optionally substituted phenyl;

$R^{1a}$ and $R^{1b}$ are independently selected from the group consisting of hydrogen $C_1$-$C_6$ alkyl, and aralkyl;

$R^{2a}$ and $R^{2b}$ are each fluoro; or $R^{2a}$ and $R^{2b}$ taken together with the carbon atom to which they are attached form a —C(═O)— group;

A is selected from the group consisting of A-1, A-2, A-3, A-4, A-5, A-6, A-7, A-8, A-9, A-10, A-11, A-12, A-13, A-14, A-15, A-16, A-17, A-18, A-19, and A-20;

wherein the bond designated with an "*" is attached to —C(═O)—OR;

$G^1$ is selected from the group consisting of —O—, —S—, and —$NR^{17}$—; $G^2$ is selected from the group consisting of —N═ and —$CR^{18a}$═; $G^3$ is selected from the group consisting of —N═ and —$CR^{18b}$═; $G^4$ is selected from the group consisting of —N═ and —$CR^{18c}$═; $G^5$ is selected from the group consisting of —N═ and —$CR^{18d}$═; $G^6$ is selected from the group consisting of —N═ and —$CR^{18e}$═; G is selected from the group consisting of —N═ and —$CR^{18f}$═;

$R^3$ is selected from the group consisting of hydrogen, halo, $C_1$-$C_4$ alkyl, $C_3$-$C_6$ cycloalkyl, —C(═O)$R^{3a}$, and aralkyl;

$R^{3a}$ is $C_1$-$C_4$ alkyl;

$R^{3b}$ and $R^{3c}$ are each independently selected from the group consisting of hydrogen and $C_1$-$C_4$ alkyl;

$R^{3d}$ is selected from the group consisting of hydrogen, $C_1$-$C_6$ alkyl, and —C(═O)$R^{3f}$;

$R^{3e}$ is selected from the group consisting of hydrogen and $C_1$-$C_4$ alkyl;

$R^{3f}$ is selected from the group consisting of $C_1$-$C_{12}$ alkyl, $C_1$-$C_6$ alkoxy, and aralkyloxy;

$R^{17}$ is selected from the group consisting of hydrogen, $C_1$-$C_4$ alkyl, $C_3$-$C_6$ cycloalkyl, aralkyl, and —C(═O)$R^{17a}$;

$R^{17a}$ is $C_1$-$C_4$ alkyl; and $R^{18a}$, $R^{18b}$, $R^{18c}$, $R^{18d}$, $R^{18e}$, and $R^{18f}$ are each independently selected from the group consisting of hydrogen, halo, and $C_1$-$C_4$ alkyl;

with the proviso that the compound is not:

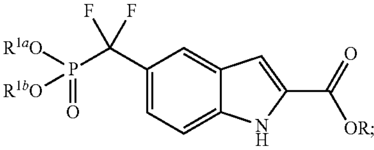

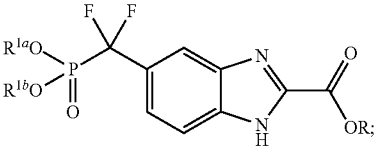

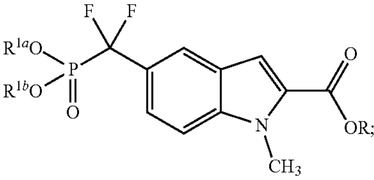

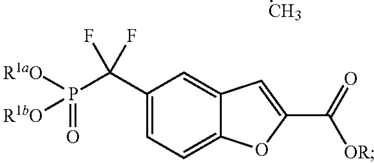

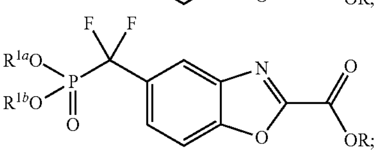

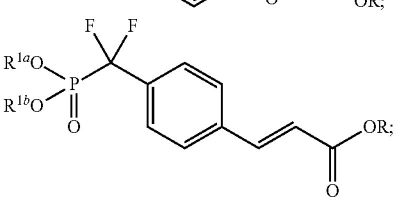

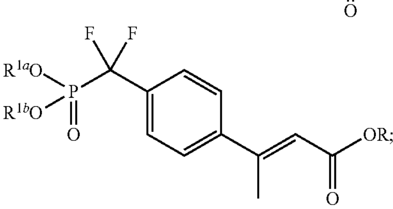

or

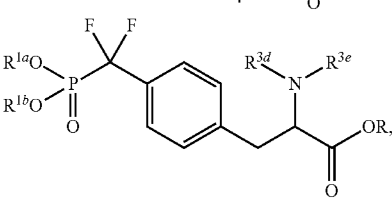

or a pharmaceutically acceptable salt or solvate thereof.

Embodiment 166. The compound of Embodiment 165 of Formula XIV, or a pharmaceutically acceptable salt or solvate thereof.

Embodiment 167. The compound of Embodiment 165 of Formula XV, or a pharmaceutically acceptable salt or solvate thereof.

Embodiment 168. The compound of any one of Embodiments 165-167, wherein A is selected from the group recited in Embodiment 4, or a pharmaceutically acceptable salt or solvate thereof.

Embodiment 169. The compound of Embodiment 168, wherein A is selected from the group recited in Embodiment 5, or a pharmaceutically acceptable salt or solvate thereof.

Embodiment 170. The compound of Embodiment 169, wherein A is selected from the group recited in Embodiment 4, or a pharmaceutically acceptable salt or solvate thereof.

Embodiment 171. The compound of Embodiment 170, wherein A is

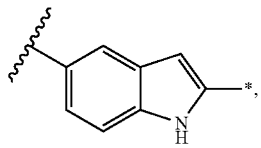

or a pharmaceutically acceptable salt or solvate thereof.

Embodiment 172. The compound of Embodiment 170, wherein A is

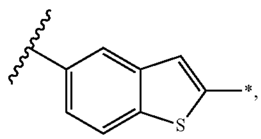

or a pharmaceutically acceptable salt or solvate thereof.

Embodiment 173. The compound of Embodiment 170, wherein A is

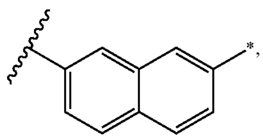

or a pharmaceutically acceptable salt or solvate thereof.

Embodiment 174. The compound of Embodiment 165 selected from the group consisting of:

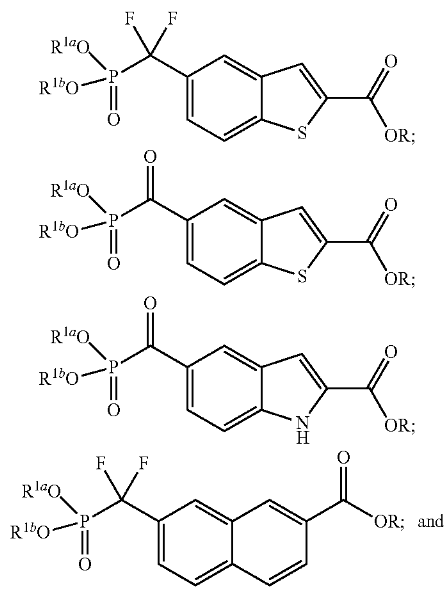

and

-continued

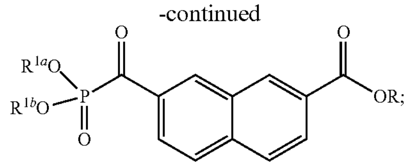

or a pharmaceutically acceptable salt or solvate thereof.

Embodiment 175. The compound of any one of Embodiments 165-174, wherein R is hydrogen, or a pharmaceutically acceptable salt or solvate thereof.

Embodiment 176. The compound of any one of Embodiments 165-174, wherein R is benzyl, or a pharmaceutically acceptable salt or solvate thereof.

Embodiment 177. The compound of any one of Embodiments 165-174, wherein R is selected from the group consisting of pentachlorobenzene and pentafluorobenzene, or a pharmaceutically acceptable salt or solvate thereof.

Embodiment 178. The compound of any one of Embodiments 165-177, wherein $R^{1a}$ and $R^{1b}$ are ethyl, or a pharmaceutically acceptable salt or solvate thereof.

Embodiment 179. A compound of Formula XVI, wherein $R^{1a}$ and $R^{1b}$ are independently selected from the group consisting of hydrogen $C_1$-$C_4$ alkyl, aralkyl, and —$CH_2OC$(═O)$R^{1e}$;

$R^{1e}$ is $C_1$-$C_6$ alkyl;

$R^{2a}$ and $R^{2b}$ are independently selected from the group consisting of hydrogen and fluoro; or $R^{2a}$ and $R^{2b}$ taken together with the carbon atom to which they are attached form a —C(═O)— group;

A is selected from the group consisting of A-1, A-2, A-3, A-4, A-5, A-6, A-7, A-8, A-9, A-10, A-11, A-12, A-13, A-14, A-15, A-16, A-17, A-18, A-19, and A-20;

wherein the bond designated with an "*" is attached to —C(═O)-E-$Q^C$;

$G^1$ is selected from the group consisting of —O—, —S—, and —$NR^{17}$—; $G^2$ is selected from the group consisting of —N═ and —$CR^{18a}$═; $G^3$ is selected from the group consisting of —N═ and —$CR^{18b}$═; $G^4$ is selected from the group consisting of —N═ and —$CR^{18c}$═; $G^5$ is selected from the group consisting of —N═ and —$CR^{18d}$═; $G^6$ is selected from the group consisting of —N═ and —$CR^{18e}$═; G is selected from the group consisting of —N═ and —$CR^{18f}$═;

$R^3$ is selected from the group consisting of hydrogen, halo, $C_1$-$C_4$ alkyl, $C_3$-$C_6$ cycloalkyl, —C(═O)$R^{3a}$, and aralkyl;

$R^{3a}$ is $C_1$-$C_4$ alkyl;

$R^{3b}$ and $R^{3c}$ are independently selected from the group consisting of hydrogen and $C_1$-$C_4$ alkyl;

$R^{3d}$ is selected from the group consisting of hydrogen, $C_1$-$C_6$ alkyl, and —C(═O)$R^{3f}$;

$R^{3e}$ is selected from the group consisting of hydrogen and $C_1$-$C_4$ alkyl;

$R^{3f}$ is selected from the group consisting of $C_1$-$C_{12}$ alkyl, $C_1$-$C_6$ alkoxy, and aralkyloxy;

$R^{17}$ is selected from the group consisting of hydrogen, $C_1$-$C_4$ alkyl, $C_3$-$C_6$ cycloalkyl, aralkyl, and —C(═O)$R^{17a}$;

$R^{17a}$ is $C_1$-$C_4$ alkyl;

$R^{18a}$, $R^{18b}$, $R^{18c}$, $R^{18d}$, $R^{18e}$, and $R^{18f}$ are each independently selected from the group consisting of hydrogen, halo, and $C_1$-$C_4$ alkyl;

E is

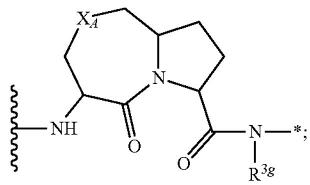

wherein the bond designated with an "*" is attached to $Q^C$;

$R^{3g}$ is selected from the group consisting of hydrogen and $C_1$-$C_4$ alkyl;

$X_A$ is selected from the group consisting of —N($R^8$)$CH_2$—, —$CH_2$N($R^8$)—, and —CH—$_2CH_2$—;

$R^8$ is selected from the group consisting of hydrogen, $C_1$-$C_6$ alkyl, $C_1$-$C_6$ haloalkyl, (heterocyclo)alkyl, —C(═O)$R^9$, and -L-B;

$R^9$ is selected from the group consisting of $C_1$-$C_6$ alkyl, amino, $C_1$-$C_6$ alkoxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

$Q^C$ is Q-8;

$X^2$ is selected from the group consisting of —$CH_2$—, —O—, and —N($R^{11b}$)—; or $X^2$ is absent;

t is 0, 1, 2, 3, or 4;

$R^{11b}$ is selected from the group consisting of hydrogen and $C_1$-$C_3$ alkyl; and $R^{26}$ is selected from the group consisting of hydrogen, $C_1$-$C_6$ alkyl, and aralkyl;

L is -$J^1$-$Y^1$-$J^2$-$Y^2$-$J^3$-Z—;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of —$(CH_2)_m$—, —C≡C—, —CH═CH—, —N($R^{16a}$)—, —C(═O)—, —S(═O)$_2$—, —C(═O)O—, —OC(═O)—, —C(═O)N($R^{16b}$)—, and —N($R^{16b}$)C(═O)—;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of —$(CH_2)_n$—, —C≡C—, —CH═CH—, —N($R^{16a}$)—, —C(═O)—, —S(═O)$_2$—, —C(═O)O—, —OC(═O)—, —C(═O)N($R^{16b}$), and —($R^{16b}$)C(═O)N—;

n is 0, 1, 2, 3, 4, 5, or 6;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of —$(CH_2)_d$—, —C≡C—, —CH═CH—, —C(═O)—, —O—, —S—, —N($R^{16c}$)—, —C(═O)N($R^{16d}$)—, —N($R^{16d}$)C(═O)—, —N($R^{16e}$)C(═O)$CH_2$O—, and —N($R^{16f}$)C(═O)$CH_2$N($R^{16f}$)—;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of -1, B-2, B-3, B-4, B-5, B-6, B-7, B-8, B-9, and B-10;

$A_5$ is selected from the group consisting of —C($R^{19a}$)═ and —N═; $A^2$ is selected from the group consisting of —C($R^{19b}$)═ and —N═; $A^3$ is selected from the group consisting of —C($R^{19c}$)═ and —N═; $A^4$ is selected from the group consisting of —C($R^{19d}$)═ and —N═;

$Z^1$ is selected from the group consisting of —$CH_2$ and —C(═O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl; and $R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, with the provisos that:

(1) when $X_A$ is —$CH_2CH_2$—, then:

(i) A is selected from the group consisting of A-2, A-5, A-6, A-7, A-8, A-9, A-10, A-11, A-12, A-13, A-14, A-15, A-16, A-17, A-18, A-19, and A-20;

(ii) A is A-4 and $G^1$ is —S—; or (iii) $R^{2a}$ and $R^{2b}$ taken together with the carbon atom to which they are attached form a —C(═O)— group;

(2) when $X_A$ is —N($R^8$)$CH_2$— and $R^8$ is selected from the group consisting of hydrogen, $C_1$-$C_6$ alkyl, $C_1$-$C_6$ haloalkyl, (heterocyclo)alkyl, and —C(═O)$R^9$, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group; or (3) when $X_A$ is —$CH_2$N($R^8$)— and $R^8$ is selected from the group consisting of hydrogen, $C_1$-$C_6$ alkyl, $C_1$-$C_6$ haloalkyl, (heterocyclo)alkyl, and —C(═O)$R^9$, then:

(i) A is selected from the group consisting of A-1, A-2, A-4, A-5, A-6, A-7, A-8, A-9, A-10, A-11, A-12, A-13, A-14, A-15, A-16, A-17, A-18, A-19, and A-20; or (ii) $R^{2a}$ and $R^{2b}$ taken together with the carbon atom to which they are attached form a —C(═O)— group, or a salt or solvate thereof.

Embodiment 180. The compound of Embodiment 179 of Formula XVII, or a salt or solvate thereof.

Embodiment 181. The compound of Embodiment 179 of Formula XVIII, or a salt or solvate thereof.

Embodiment 182. The compound of any one of Embodiments 179-181, wherein $R^8$ is selected from the group consisting of hydrogen, $C_1$-$C_6$ alkyl, $C_1$-$C_6$ haloalkyl, (heterocyclo)alkyl, and —C(═O)$R^9$, or a or solvate thereof.

Embodiment 183. The compound of any one of Embodiments 179-181, wherein $R^8$ is -L-B, or a salt or solvate thereof.

Embodiment 184. The compound of any one of Embodiments 179-183, wherein $R^{26}$ is $C_1$-$C_6$ alkyl, or a salt or solvate thereof.

Embodiment 185. The compound of any one of Embodiments 179-183, wherein $R^{26}$ is hydrogen, or a salt or solvate thereof.

Embodiment 186. A compound of Formula XXXIV, wherein $R^8$ is selected from the group consisting of hydrogen, $C_1$-$C_6$ alkyl, $C_1$-$C_6$ haloalkyl, (heterocyclo)alkyl, and —C(═O)$R^9$; and $R^{13a}$ is selected from the group consisting optionally substituted $C_3$-$C_{12}$ cycloalkyl, optionally substituted aryl, aralkyl, (heteroaryl)alkyl, (cycloalkyl)alkyl, and optionally substituted 5- to 9-membered heteroaryl, or a pharmaceutically acceptable salt or solvate thereof.

Embodiment 187. A method of making a compound of Formula XXII, wherein:

$R^{1a}$ and $R^{1b}$ are independently selected from the group consisting of hydrogen $C_1$-$C_6$ alkyl, and aralkyl;

$R^8$ is selected from the group consisting of $C_1$-$C_6$ alkyl, $C_1$-$C_6$ haloalkyl, (heterocyclo)alkyl, and —C(═O)$R^9$;

$R^{2a}$ and $R^{2b}$ are independently selected from the group consisting of hydrogen and fluoro; or $R^{2a}$ and $R^{2b}$ taken together with the carbon atom to which they are attached form a —C(═O)— group;

$R^9$ is selected from the group consisting of $C_1$-$C_6$ alkyl, amino, $C_1$-$C_6$ alkoxy, aralkyloxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

$R^{12c}$ is selected from the group consisting of hydrogen, $C_1$-$C_4$ alkyl, and aralkyl;

$X^2$ is selected from the group consisting of —$CH_2$—, —O—, and —N($R^{11b}$)—; or $X^2$ is absent;

t is 0, 1, 2, 3, or 4;

L is -$J^1$-$Y^1$-$J^2$-$Y^2$-$J^3$-Z—;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of —$(CH_2)_m$—, —C≡C—, —CH═CH—, —N($R^{16a}$)—, —C(═O)—, —S(═O)$_2$—, —C(═O)O—, —OC(═O)—, —C(═O)N($R^{16b}$)—, and —N($R^{16b}$)C(═O)—;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of —$(CH_2)_n$—, —C≡C—, —CH═CH—, —N($R^{16a'}$)—, —C(═O)—, —S(═O)$_2$—, —C(═O)O—, —OC(═O)—, —C(═O)N($R^{16b'}$), and —($R^{16b'}$)C(═O)N—;

n is 0, 1, 2, 3, 4, 5, or 6;

$R^{16a'}$ is selected from the group consisting of hydrogen, $C_1$-$C_4$ alkyl, and aralkyl;

$R^{16b'}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of —$(CH_2)_d$—, —C≡C—, —CH═CH—, —C(═O)—, —O—, —S—, —N($R^{16c}$)—, —C(═O)N($R^{16d}$)—, —N($R^{16d}$)C(═O)—, —N($R^{16e}$)C(═O)$CH_2$O—, and —N($R^{16f}$)C(═O)$CH_2$N($R^{16g}$)—;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of B-1, B-2, B-3, B-4, B-5, B-6, B-7, B-8, B-9, and B-10;

$A_5$ is selected from the group consisting of —C($R^{19a}$)═ and —N═; $A^2$ is selected from the group consisting of —C($R^{19b}$)═ and —N═; $A^3$ is selected from the group consisting of —C($R^{19c}$)═ and —N═; $A^4$ is selected from the group consisting of —C($R^{19d}$)═ and —N═;

$Z^1$ is selected from the group consisting of —$CH_2$ and —C(═O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl;

$R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, the method comprising reacting a compound of Formula XXX, with a compound of Formula XVII in the presence of a coupling agent in a solvent.

Embodiment 188. A method of making a compound of Formula XXIII, wherein:

$R^{1a}$ and $R^{1b}$ are independently selected from the group consisting of hydrogen $C_1$-$C_6$ alkyl, and aralkyl;

$R^8$ is selected from the group consisting of $C_1$-$C_6$ alkyl, $C_1$-$C_6$ haloalkyl, (heterocyclo)alkyl, and —C(═O)$R^9$;

$R^{2a}$ and $R^{2b}$ are independently selected from the group consisting of hydrogen and fluoro; or $R^{2a}$ and $R^{2b}$ taken together with the carbon atom to which they are attached form a —C(═O)— group;

$R^9$ is selected from the group consisting of $C_1$-$C_6$ alkyl, amino, $C_1$-$C_6$ alkoxy, aralkyloxy, optionally substituted $C_3$-$C_{10}$ cycloalkyl, optionally substituted 4- to 8-membered heterocyclo, optionally substituted aryl, optionally substituted 5- to 10-membered heteroaryl, aralkyl, and (heteroaryl)alkyl;

$A^1$ is selected from the group consisting of —C($R^{14a}$)— and —N—;

$R^{14a}$ is selected from the group consisting of hydrogen and $C_1$-$C_3$ alkyl;

e is 1, 2, or 3;

f is 1, 2, or 3;

$X^2$ is selected from the group consisting of —$CH_2$—, —O—, and —N($R^{11b}$)—; or $X^2$ is absent;

t is 0, 1, 2, 3, or 4;

L is $-J^1-Y^1-J^2-Y^2-J^3-Z—$;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of $—(CH_2)_m—$, —C≡C—, —CH═CH—, $—N(R^{16a})—$, —C(═O)—, $—S(═O)_2—$, —C(═O)O—, —OC(═O)—, $—C(═O)N(R^{16b})—$, and $—N(R^{16b})C(═O)—$;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of $—(CH_2)_n—$, —C≡C—, —CH═CH—, $—N(R^{16a'})—$, —C(═O)—, $—S(═O)_2—$, —C(═O)O—, —OC(═O)—, $—C(═O)N(R^{16b'})$, and $—(R^{16b'})C(═O)N—$;

n is 0, 1, 2, 3, 4, 5, or 6;

$R^{16a'}$ is selected from the group consisting of hydrogen, $C_1$-$C_4$ alkyl, and aralkyl;

$R^{16b'}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of $—(CH_2)_d—$, —C≡C—, —CH═CH—, —C(═O)—, —O—, —S—, $—N(R^{16c})—$, $—C(═O)N(R^{16d})—$, $—N(R^{16d})C(═O)—$, $—N(R^{16e})C(═O)CH_2O—$, and $—N(R^{16f})C(═O)CH_2N(R^{16f})—$;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of B-1, B-2, B-3, B-4, B-5, B-6, B-7, B-8, B-9, and B-10;

$A_5$ is selected from the group consisting of $—C(R^{19a})═$ and —N═; $A^2$ is selected from the group consisting of $—C(R^{19b})═$ and —N═; $A^3$ is selected from the group consisting of $—C(R^{19c})═$ and —N═; $A^4$ is selected from the group consisting of $—C(R^{19d})═$ and —N═;

$Z^1$ is selected from the group consisting of $—CH_2$ and —C(═O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl;

$R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, the method comprising reacting a compound of Formula XXX, with a compound of Formula XVII, in the presence of a coupling agent in a solvent.

Embodiment 189. A method of making a compound of Formula XXIV, wherein $R^{1a}$ and $R^{1b}$ are independently selected from the group consisting of hydrogen $C_1$-$C_6$ alkyl, and aralkyl;

$R^{2a}$ and $R^{2b}$ are independently selected from the group consisting of hydrogen and fluoro; or $R^{2a}$ and $R^{2b}$ taken together with the carbon atom to which they are attached form a —C(═O)— group;

$X^2$ is selected from the group consisting of $—CH_2—$, —O—, and $—N(R^{11b})—$; or $X^2$ is absent;

t is 0, 1, 2, 3, or 4;

$R^{12a}$ is selected from the group consisting of hydrogen, $C_1$-$C_6$ alkyl, optionally substituted $C_2$-$C_6$ alkynyl, aralkyl, (heteroaryl)alkyl, optionally substituted $C_3$-$C_6$ cycloalkyl, optionally substituted 4- to 8-membered heterocyclo, optionally substituted aryl, (amido)(aryl)alkyl, (amino)(aryl)alkyl, (amino)(heteroaryl)alkyl, and (cycloalkyl)alkyl;

$R^{12b}$ is selected from the group consisting of hydrogen, $C_1$-$C_4$ alkyl, optionally substituted aryl, and aralkyl; or $R^{12a}$ and $R^{12b}$ taken together with the nitrogen atom to which they are attached form a 4- to 8-membered optionally substituted heterocyclo L is $-J^1-Y^1-J^2-Y^2-J^3-Z—$;

$J^1$ is selected from the group consisting of alkylenyl, heteroalkylenyl, cycloalkylenyl, heterocyclenyl, phenylenyl, and heteroarylenyl; or $J^1$ is absent;

$Y^1$ is selected from the group consisting of $—(CH_2)_m—$, —C≡C—, —CH═CH—, $—N(R^{16a})—$, —C(═O)—, $—S(═O)_2—$, —C(═O)O—, —OC(═O)—, $—C(═O)N(R^{16b})—$, and $—N(R^{16b})C(═O)—$;

m is 0, 1, 2, or 3;

$R^{16a}$ is selected from the group consisting of hydrogen, $C_1$-$C_4$ alkyl, and aralkyl;

$R^{16b}$ is selected from the group consisting of hydrogen and $C_1$-$C_4$ alkyl;

$J^2$ is selected from the group consisting of alkylenyl, heteroalkylenyl, cycloalkylenyl, heterocyclenyl, phenylenyl, and heteroarylenyl; or $J^2$ is absent;

$Y^2$ is selected from the group consisting of $—(CH_2)_n—$, —C≡C—, —CH═CH—, $—N(R^{16a'})—$, —C(═O)—, $—S(═O)_2—$, —C(═O)O—, —OC(═O)—, $—C(═O)N(R^{16b'})$, and $—(R^{16b'})C(═O)N—$;

n is 0, 1, 2, 3, 4, 5, or 6;

$R^{16a'}$ is selected from the group consisting of hydrogen, $C_1$-$C_4$ alkyl, and aralkyl;

$R^{16b'}$ is selected from the group consisting of hydrogen and $C_1$-$C_4$ alkyl;

$J^3$ is selected from the group consisting of alkylenyl, heteroalkylenyl, cycloalkylenyl, heterocyclenyl, phenylenyl, and heteroarylenyl; or $J^3$ is absent;

Z is selected from the group consisting of $—(CH_2)_d—$, —C≡C—, —CH═CH—, —C(═O)—, —O—, —S—, $—N(R^{16c})—$, $—C(═O)N(R^{16d})—$, $—N(R^{16d})C(═O)—$, $—N(R^{16e})C(═O)CH_2O—$, and $—N(R^{16f})C(═O)CH_2N(R^{16g})—$;

d is 0, 1, 2, or 3;

$R^{16c}$, $R^{16d}$, $R^{16e}$, $R^{16f}$, and $R^{16g}$ are each independently selected from the group consisting of hydrogen, $C_1$-$C_4$ alkyl, and aralkyl;

wherein Z is attached to B;

B is selected from the group consisting of B-1, B-2, B-3, B-4, B-5, B-6, B-7, B-8, B-9, and B-10;

$A_5$ is selected from the group consisting of —C($R^{19a}$)═ and —N═; $A^2$ is selected from the group consisting of —C($R^{19b}$)═ and —N═; $A^3$ is selected from the group consisting of —C($R^{19c}$)═ and —N═; $A^4$ is selected from the group consisting of —C($R^{19d}$)═ and —N═;

$Z^1$ is selected from the group consisting of —$CH_2$ and —C(═O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each independently selected from the group consisting of hydrogen, halo, and $C_{1-4}$ alkyl;

$R^{20}$ is $C_1$-$C_6$ alkyl;

$R^{21}$ is selected from the group consisting of hydrogen and $C_1$-$C_4$ alkyl;

$R^{22a}$ is selected from the group consisting of $C_1$-$C_6$ alkyl and optionally substituted $C_3$-$C_6$ cycloalkyl;

$R^{22b}$ is selected from the group consisting of $C_1$-$C_6$ alkyl, optionally substituted $C_3$-$C_6$ cycloalkyl, optionally substituted aryl, and optionally substituted heteroaryl;

$R^{23}$ is selected from the group consisting of $C_1$-$C_6$ alkyl and optionally substituted $C_3$-$C_6$ cycloalkyl; and $R^{24}$ is selected from the group consisting of $C_1$-$C_6$ alkyl, optionally substituted $C_3$-$C_6$ cycloalkyl, optionally substituted aryl, and optionally substituted heteroaryl, the method comprising reacting a compound of Formula XXXI with a compound of Formula XIX in the presence of a coupling agent in a solvent.

EXAMPLES

Example 1

Synthesis of (2-((perchlorophenoxy)carbonyl)-1H-indole-5-carbonyl)phosphonic Acid

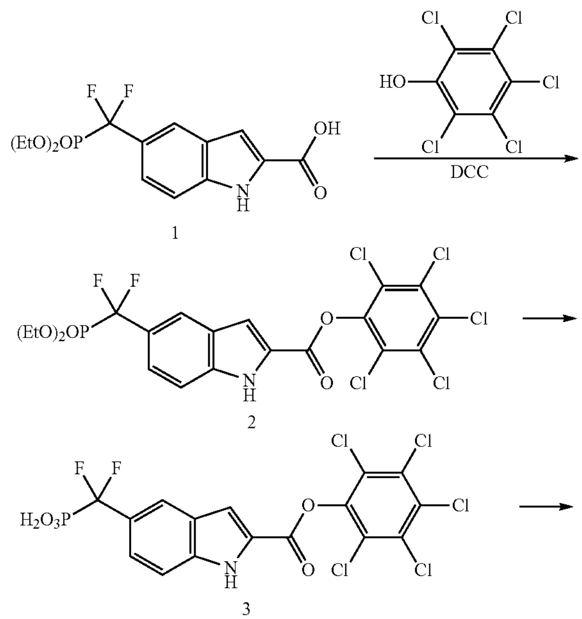

1

2

3

-continued

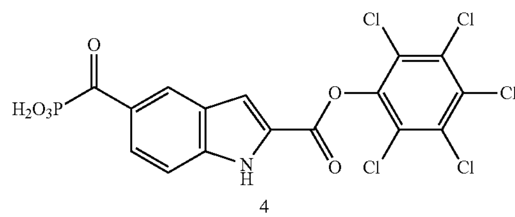

4

A solution of 1 (265 mg, 0.76 mmol, 1 equiv.), pentachlorophenol (223 mg, 0.84 mmol, 1.1 equiv.), DCC (204 mg, 0.99 mmol, 1.3 equiv.), and DMAP (9.3 mg, 0.64 mmol, 0.1 equiv.) in 3 mL of DMF was stirred at room temperature for 24 h. The mixture was purified by HPLC to yield compound 2 (354 mg, yield: 78%). UPLC-MS (ESI-MS) m/z: 597.85.

To a round bottom flask was added 2 (354 mg, 0.59 mmol, 1.0 equiv) and $CH_2Cl_2$ (10 mL). The solution was cooled to 0° C. before adding $CF_3CON(TMS)_2$ (611 mg, 2.37 mmol, 4.0 equiv) and 1M of TMS-I in DCM (1.19 mL, 1.19 mmol, 2.0 equiv). The reaction mixture was allowed to stir at 0° C. until the starting material disappeared. The solvent was removed under vacuum at 0° C. The residue was dissolved in a mixture of $CH_3CN$ and water, and purified by HPLC to yield 3 (254 mg, yield: 79%). UPLC-MS (ESI-MS) m/z: 541.77.

TFA (8 mL) was added to a mixture of compound 3 (450 mg) in $CH_3CN$ (30 mL) and water (45 mL). This mixture was heated to 52° C. for 2 days. The resulting precipitate was collected by filtration to yield compound 4 (350 mg). $^1$H NMR (400 MHz, DMSO) δ 12.90 (d, J=1.4 Hz, 1H), 9.05-8.89 (m, 1H), 8.10 (dd, J=8.9, 1.5 Hz, 1H), 7.86 (dd, J=2.0, 0.8 Hz, 1H), 7.63 (d, J=8.9 Hz, 1H). $^{13}$C NMR (101 MHz, DMSO) δ 203.33 (d, $J_{P—C}$=174.73), 157.31, 143.92, 141.42, 131.89, 131.63, 130.42, 129.83, 128.45, 128.00, 126.41, 126.09, 126.06, 125.97, 114.49, 113.75.

Example 2

Synthesis of 5-((diethoxyphosphoryl)carbonyl)benzo[b]thiophene-2-carboxylic Acid

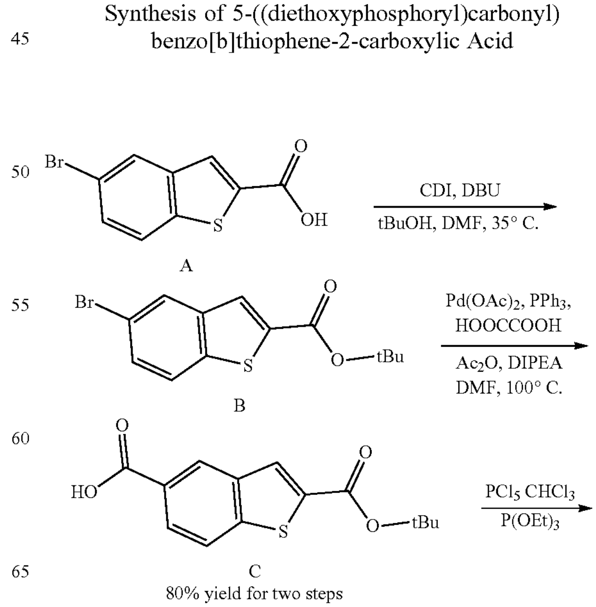

A

B

C

-continued

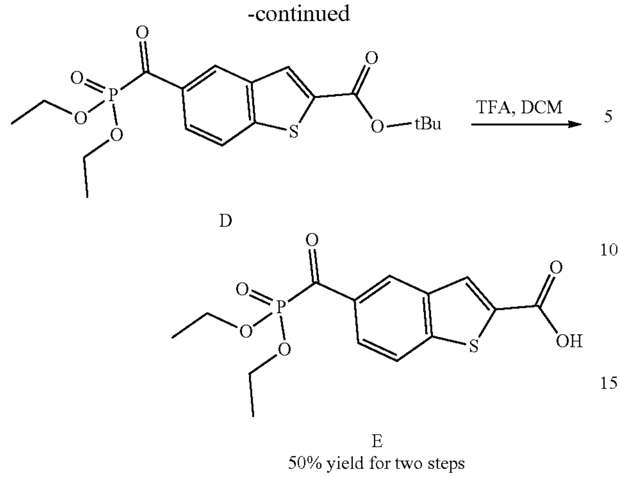

D

E

50% yield for two steps

To a 50 mL round bottom flask equipped with a magnetic stirring bar was added A (1.2 g, 4.66 mmol, 1.0 equiv) and DMF (12 mL). CDI (1.0 g, 6.07 mmol, 1.3 equiv) was added. The solution was stirred at 35° C. for 0.5 hour until LC-MS showed the reaction to be finished. t-BuOH (1.6 ml, 16.3 mmol, 3.5 equiv) and DBU (0.85 ml, 5.60 mmol, 1.2 equiv) was added in sequence. The solution was stirred at 35° C. for another 5 hours until LC-MS showed the reaction to be finished. The reaction was quenched with $H_2O$, extracted with EtOAc (50 mL×3), washed with brine three times, dried with anhydrous sodium sulfate, filtered, and concentrated. The residual crude product B can be directly used in the next step without further purification.

To a 350 mL sealed tube (anti-pressure), was added B (around 4.5 mmol, 1 equiv.), $Pd(OAc)_2$ (0.2 g, 0.9 mmol, 0.2 equiv.), $PPh_3$ (0.7 g, 2.7 mmol, 0.6 equiv.), oxalic acid (1.4 g, 15.7 mmol, 3.5 equiv.), DIPEA (3.2 mL, 18 mmol, 4.0 equiv.), $Ac_2O$ (1.8 mL, 18 mmol, 4.0 equiv.) and DMF (30 mL). The mixture was sealed and allowed to react at 100° C. for 8 hours. After the reaction was complete, the system was cooled to room temperature and quenched with 0.5 M HCl water solution to a pH of 3-5. The reaction mixture was extracted with EtOAc for three times. The organic phase was washed with brine for three times, dried with anhydrous sodium sulfate, filtered and concentrated. The residual crude product was purified by flash column chromatography (DCM:MeOH=20:1) to afford the desired benzothiophene acid C as a white solid (1.03 g, 80% yield for two steps).

To a 50 mL round bottom flask equipped with a magnetic stirring bar was added C (0.3 g, 1.08 mmol, 1.0 equiv) and anhydrous $CHCl_3$ (6.0 mL). $PCl_5$ (0.25 g, 1.2 mmol, 1.1 equiv) was added portionly. The solution was stirred at rt for 5 mins until the solution became clear. $P(OEt)_3$ (0.37 mL, 2.16 mmol, 2.0 equiv) was added slowly. The solution was stirred at rt for another 0.5 hours until LC-MS showed the reaction was finished (about 80% conversion). The reaction was quenched with $H_2O$, extracted with DCM (50 mL×3), washed with brine dried with anhydrous sodium sulfate, filtered and concentrated to give crude product D. The residual crude product D was dissolved in 5 ml DCM, and TFA (5 ml) was added to remove the Boc. After removing all the solvent under vacuum, the crude residue was purified by HPLC ($MeCN/H_2O$ 30%-100%, 70 min, 60 mL/min, the product came out when MeCN is 42%) to afford the desired product E as a white solid (185 mg, 50% yield). $^1H$ NMR (400 MHz, $CD_3CN:D_2O$=1:1) δ 8.74 (s, 1H), 8.15 (s, 1H), 8.06-7.98 (m, 2H), 4.28-4.20 (m, 4H), 1.28 (t, J=7.2 Hz, 6H). UPLC-MS calculated for $C_{14}H_{15}O_6PS$ $[M+H]^+$: 343.03, found: 343.26.

Example 3

Synthesis of 5-(difluoro(phosphono)methyl)benzo[b]thiophene-2-carboxylic Acid

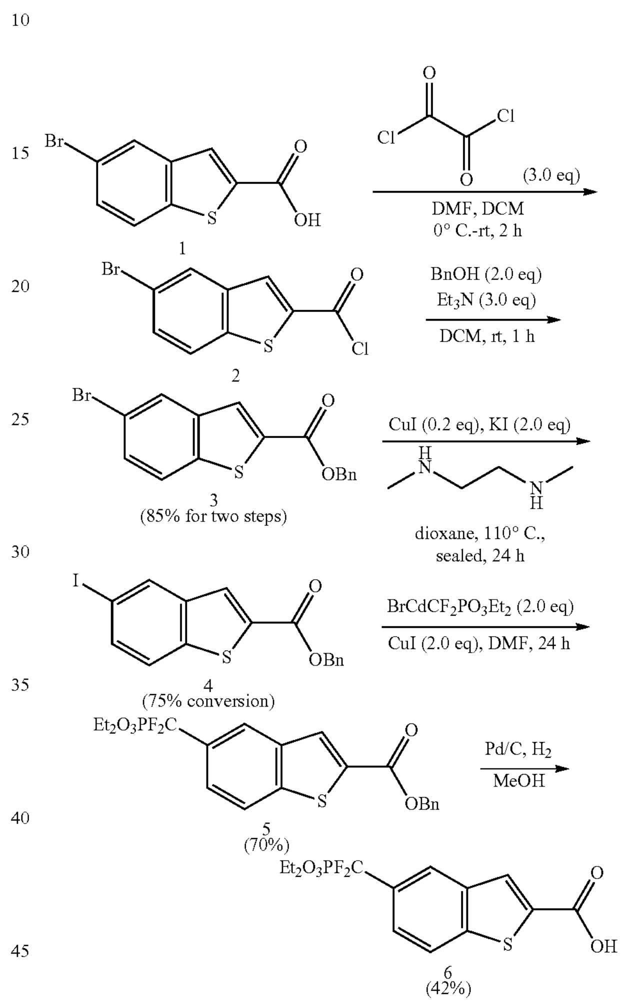

Step 1: Benzyl 5-bromobenzo[b]thiophene-2-carboxylate

To a 100 mL round bottom flask equipped with a magnetic stirring bar was added 5-bromobenzo[b]thiophene-2-carboxylic acid 1 (1.0 g, 3.9 mmol, 1.0 equiv) and anhydrous DCM (50 mL). The suspension was cooled with ice/water bath before adding oxalyl chloride (1.5 g, 11.7 mmol, 3.0 equiv) and DMF (0.3 mL). The solution was stirred at this temperature for 30 minutes and returned to room temperature. The suspension became a clear solution after 1.5 h. All of the solvent and excess oxalyl chloride was removed in vacuum. The residual crude product 2 was used directly for the next step without further purification.

To a 100 mL round bottom flask equipped with a magnetic stirring bar was added previous crude acyl chloride 2 and anhydrous DCM (50 mL). The solution was cooled with ice/water bath before adding benzyl alcohol (0.8 g, 0.8 mL, 7.8 mmol, 2.0 equiv) and triethylamine (1.2 g, 1.6 mL, 11.7 mmol, 3.0 equiv). The solution was returned to room temperature and stirred for 1 h before quenching with ammonium chloride aqueous solution. The reaction was extracted with DCM (50 mL×3), dried with anhydrous sodium sulfate, filtered and concentrated under vacuum. The residual crude product was purified by flash column chromatography (PE: EA=10:1) to afford the desired benzylic ester 3 as a white solid (1.1 g, 85% yield).

Step 2: Benzyl 5-iodobenzo[b]thiophene-2-carboxylate

To a 50 mL sealed bottle equipped with a magnetic stirring bar was filled with argon before adding Benzyl 5-bromobenzo[b]thiophene-2-carboxylate 3 (1.0 g, 2.9 mmol, 1.0 equiv), copper(I) iodide (110 mg, 0.58 mmol, 0.2 equiv), potassium iodide (1.0 g, 5.8 mmol, 2.0 equiv), N,N'-Dimethylethane-1,2-diamine (51 mg, 62 μL, 0.58 mmol, 0.2 equiv) and anhydrous 1,4-dioxane (20 mL). The reaction system was changed to argon atmosphere for another three times before reacting at 110° C. for 24 h. The reaction system was cooled to room temperature and quenched with ammonium chloride aqueous solution. The reaction mixture was extracted with EtOAc (50 mL×3), washed with brine, dried with anhydrous sodium sulfate, filtered and concentrated under vacuum. The residual crude product was purified by flash column chromatography (PE: EA=10:1) to afford the mixture of desired iodide 4 and starting material 3 as a white solid (0.85 g, 4:3=3:1 monitored by LC-MS). This mixture can be used directly for the next step without further purification.

Step 3: Benzyl 5-((diethoxyphosphoryl)difluoromethyl)benzo[b]thiophene-2-carboxylate To a 50 mL round bottom bottle equipped with a magnetic stirring bar was filled with argon before adding the previous mixture of 4 and 3 (0.85 g, 4:3=3:1, 2.1 mmol, 1.0 equiv), copper(I) iodide (0.8 g, 4.2 mmol, 2.0 equiv) and Cadmium reagent DMF solution A (13 mL, 0.33 M, 4.2 mmol, 2.0 equiv). The reaction system was changed to argon atmosphere for another three times before stirring at room temperature for 24 h. The reaction mixture was quenched with ammonium chloride aqueous solution, extracted with EtOAc (50 mL×3), washed with brine for three times, dried with anhydrous sodium sulfate, filtered, and concentrated under vacuum. The residual crude product was purified by flash column chromatography (PE:EA=1:1) to afford the desired phosphate 5 as a colorless oil (0.5 g, 70% yield).

Step 4: 5-((diethoxyphosphoryl)difluoromethyl) benzo[b]thiophene-2-carboxylic Acid To a 50 mL round bottom bottle equipped with a magnetic stirring bar was filled with argon before adding benzyl 5-((diethoxyphosphoryl)difluoromethyl)benzo[b]thiophene-2-carboxylate 5 (130 mg, 0.28 mmol, 1.0 equiv), methanol (5 mL) and 10% Pd/C (150 mg). The reaction system was changed to hydrogen atmosphere for three times before stirring at room temperature for 5 min (a longer reaction time can reduce the yield of this reaction). The reaction mixture was filtered to remove Pd/C and the solvent was removed under vacuum. The residual crude product was purified by HPLC (MeCN/$H_2O$ 35%-100%, 65 min, 60 mL/min, the product came out when MeCN is 46%) to afford the desired carboxylic acid 6 as a white solid (43 mg, 42% yield). $^1$H NMR (400 MHz, Methanol-$d_4$) δ 8.20 (s, 1H), 8.17 (s, 1H), 8.09 (d, J=8.4 Hz, 1H), 7.67 (d, J=8.4 Hz, 1H), 4.29-4.17 (m, 4H), 1.31 (td, J=7.1, 0.7 Hz, 6H). UPLC-MS calculated for $C_{14}H_{16}F_2O_5PS$ [M+H]$^+$: 365.03, found: 365.24.

Example 4

Synthesis of 5-(difluoro(phosphono)methyl)benzo [b]thiophene-2-carboxylic Acid

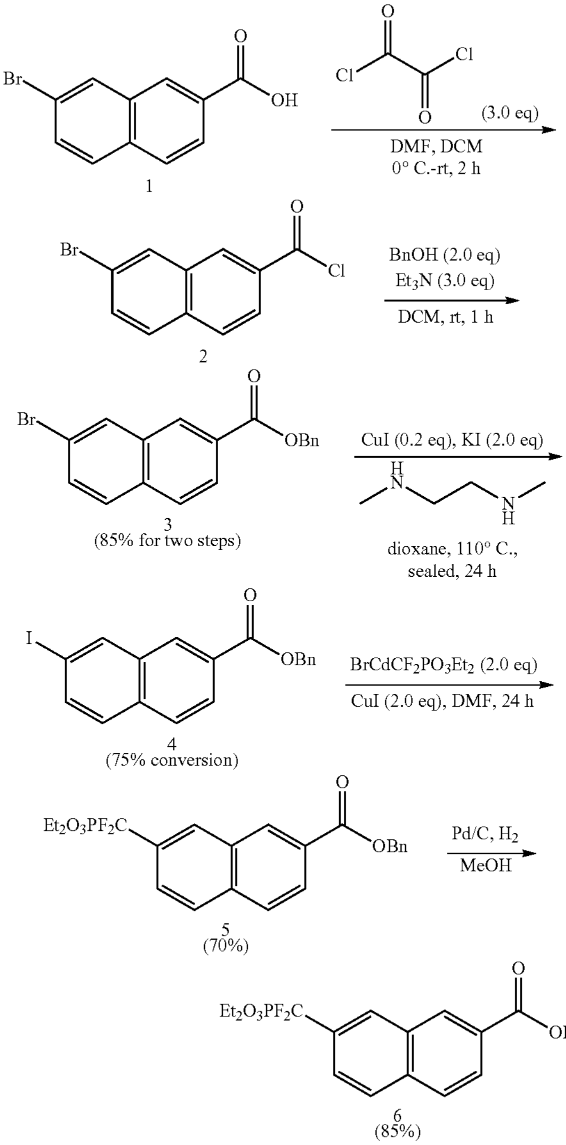

Step 1: Benzyl 7-bromo-2-naphthoate

To a 100 mL round bottom flask equipped with a magnetic stirring bar was added 7-bromo-2-naphthoic acid 1 (1.0 g, 3.9 mmol, 1.0 equiv) and anhydrous DCM (50 mL). The suspension was cooled with an ice/water bath before adding oxalyl chloride (1.5 g, 11.7 mmol, 3.0 equiv) and DMF (0.3 mL). The solution was stirred at this temperature for 30 minutes and returned to room temperature. The suspension became a clear solution after 1.5 h. All the solvent and excess oxalyl chloride was removed in vacuum. The residual crude product 2 was used directly for the next step without further purification.

To a 100 mL round bottom flask equipped with a magnetic stirring bar was added previous crude acyl chloride 2 and anhydrous DCM (50 mL). The solution was cooled with an ice/water bath before adding benzyl alcohol (0.8 g, 0.8 mL, 7.8 mmol, 2.0 equiv) and triethylamine (1.2 g, 1.6 mL, 11.7 mmol, 3.0 equiv). The solution was returned to room temperature and stirred for 1 h before quenching with ammonium chloride aqueous solution. The reaction mixture was extracted with DCM (50 mL×3), dried with anhydrous sodium sulfate, filtered, and concentrated under vacuum. The residual crude product was purified by flash column chromatography (PE:EA=10:1) to afford the desired benzylic ester 3 as a white solid (1.1 g, 85% yield).

Step 2: Benzyl 7-iodo-2-naphthoate

To a 50 mL sealed bottle equipped with a magnetic stirring bar was filled with argon before adding benzyl 7-bromo-2-naphthoate 3 (1.0 g, 2.9 mmol, 1.0 equiv), copper(I) iodide (110 mg, 0.58 mmol, 0.2 equiv), potassium iodide (1.0 g, 5.8 mmol, 2.0 equiv), N,N'-Dimethylethane-1,2-diamine (51 mg, 62 μL, 0.58 mmol, 0.2 equiv) and anhydrous 1,4-dioxane (20 mL). The reaction system was changed to argon atmosphere for another three times before reacting at 110° C. for 24 h. The reaction mixture was cooled to room temperature, quenched with ammonium chloride aqueous solution. extracted with EtOAc (50 mL×3), washed with brine, dried with anhydrous sodium sulfate, filtered and concentrated under vacuum. The residual crude product was purified by flash column chromatography (PE:EA=10:1) to afford the mixture of desired iodide 4 and starting material 3 as a white solid (0.85 g, 4:3=3:1 monitored by LC-MS). This mixture can be used directly for the next step without further purification.

Step 3: Benzyl 7-((diethoxyphosphoryl)difluoromethyl)-2-naphthoate

To a 50 mL round bottom bottle equipped with a magnetic stirring bar was filled with argon before adding the previous mixture of 4 and 3 (0.85 g, 4:3=3:1, 2.1 mmol, 1.0 equiv), copper(I) iodide (0.8 g, 4.2 mmol, 2.0 equiv) and Cadmium reagent DMF solution A (13 mL, 0.33 M, 4.2 mmol, 2.0 equiv). The reaction system was changed to argon atmosphere for another three times before stirring at room temperature for 24 h. The reaction mixture was quenched with ammonium chloride aqueous solution, extracted with EtOAc (50 mL×3), washed with brine three times, dried with anhydrous sodium sulfate, filtered, and concentrated under vacuum. The residual crude product was purified by flash column chromatography (PE:EA=1:1) to afford the desired phosphate 5 as a white solid (0.5 g, 70% yield).

Step 4: 7-((diethoxyphosphoryl)difluoromethyl)-2-naphthoic Acid

To a 50 mL round bottom bottle equipped with a magnetic stirring bar was filled with argon before adding benzyl 7-((diethoxyphosphoryl)difluoromethyl)-2-naphthoate 5 (130 mg, 0.28 mmol, 1.0 equiv), methanol (5 mL) and 10% Pd/C (30 mg). The reaction system was changed to hydrogen atmosphere for three times before stirred at room temperature for 30 min. The reaction mixture was filtered to remove Pd/C and the solvent was removed under vacuum. The residual crude product was purified by HPLC ($MeCN/H_2O$ 35%-100%, 65 min, 60 mL/min, the product came out when MeCN is 46.5%) to afford the desired carboxylic acid 6 as a white solid (86 mg, 85% yield). $^1H$ NMR (400 MHz, Methanol-$d_4$) δ 8.73 (s, 1H), 8.28 (s, 1H), 8.21-8.13 (m, 1H), 8.07 (dd, J=20.0, 8.4 Hz, 2H), 7.82-7.73 (m, 1H), 4.31-4.16 (m, 4H), 1.31 (t, J=7.2 Hz, 6H). UPLC-MS calculated for $C_{16}H_{18}F_2O_5P$ $[M+H]^+$: 359.09, found: 359.38.

Example 5

Synthesis of Intermediates of the Disclosure

Intermediates of the Disclosure of Formula XIII were prepared according to the following schemes and used to make Compounds of the Disclosure.

Scheme 1

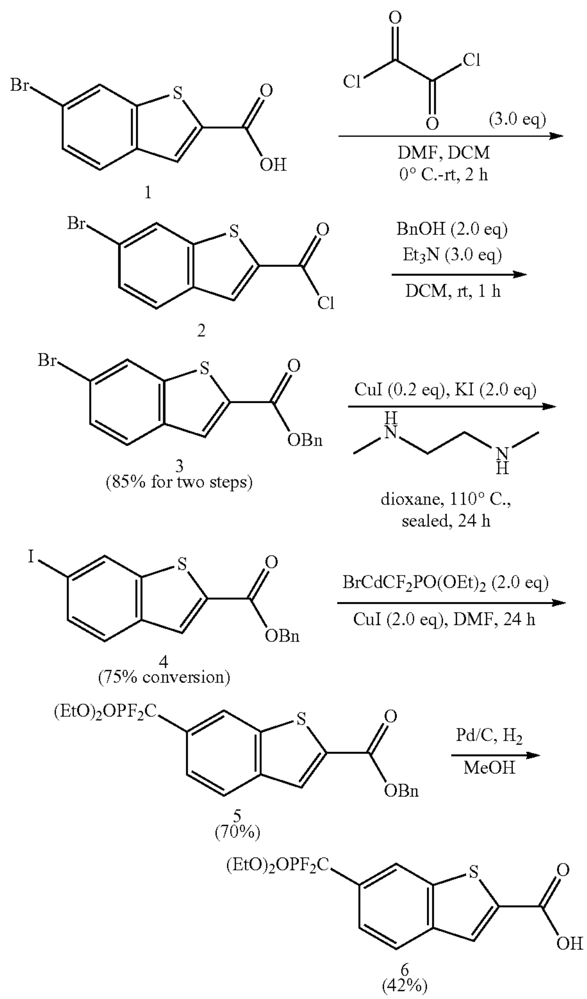

Scheme 2
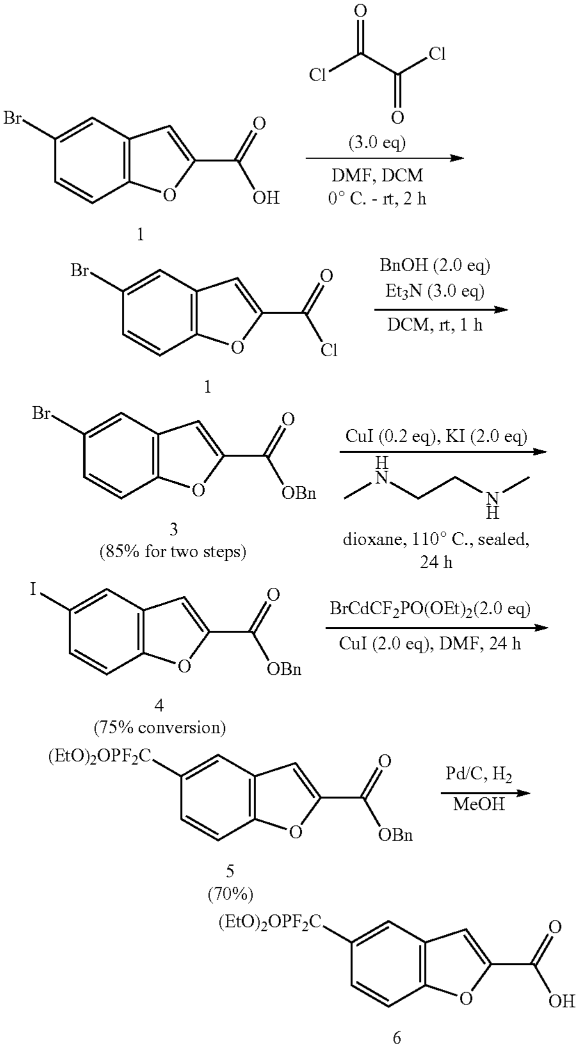
1
1
3
(85% for two steps)
4
(75% conversion)
5
(70%)
6
(42%)
Scheme 3
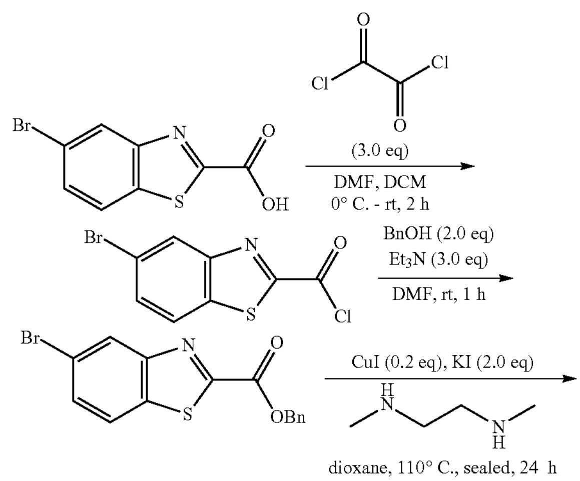
-continued
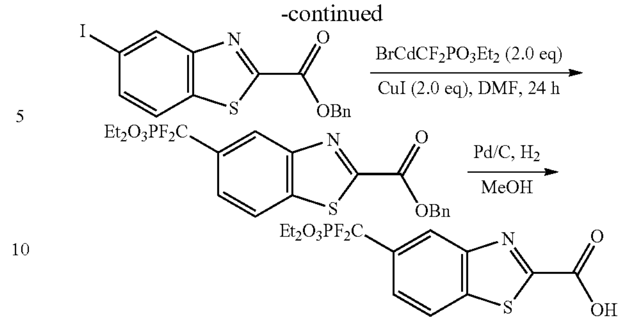
Scheme 4
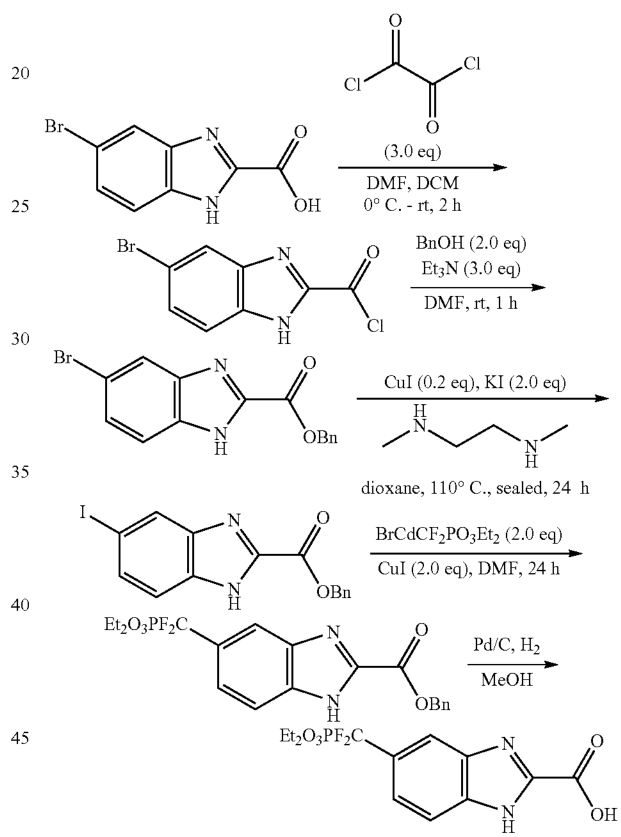
Scheme 5
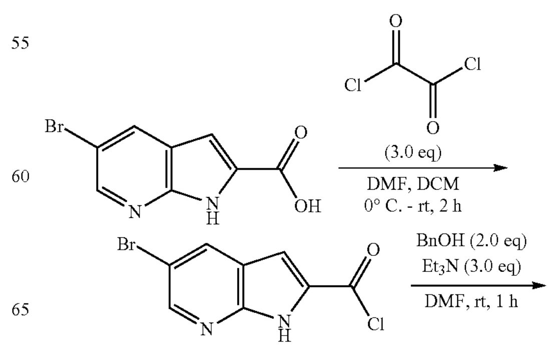

-continued
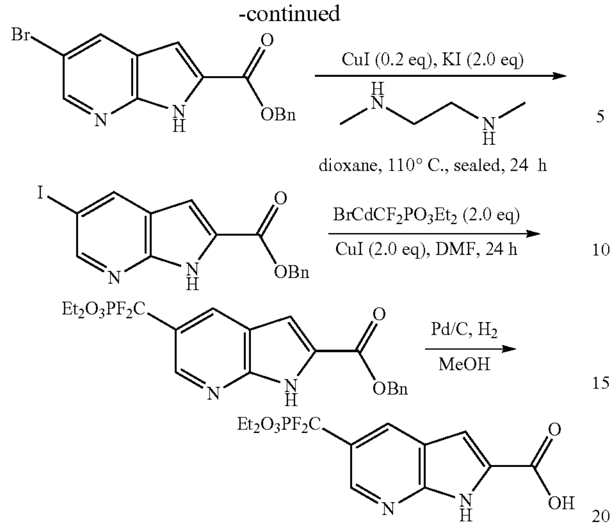
Scheme 6
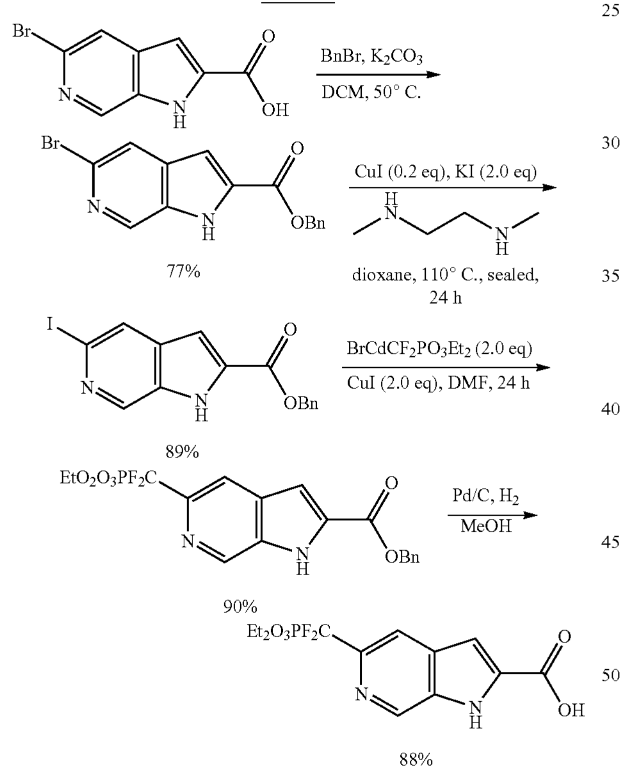
Scheme 7
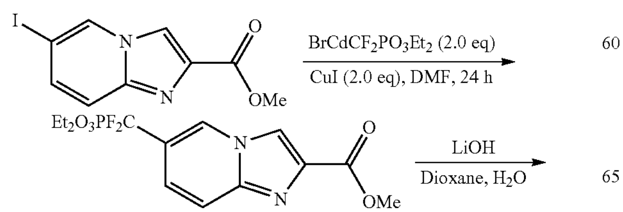
-continued
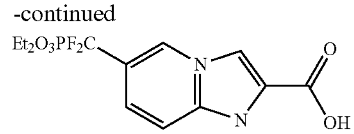
Scheme 8
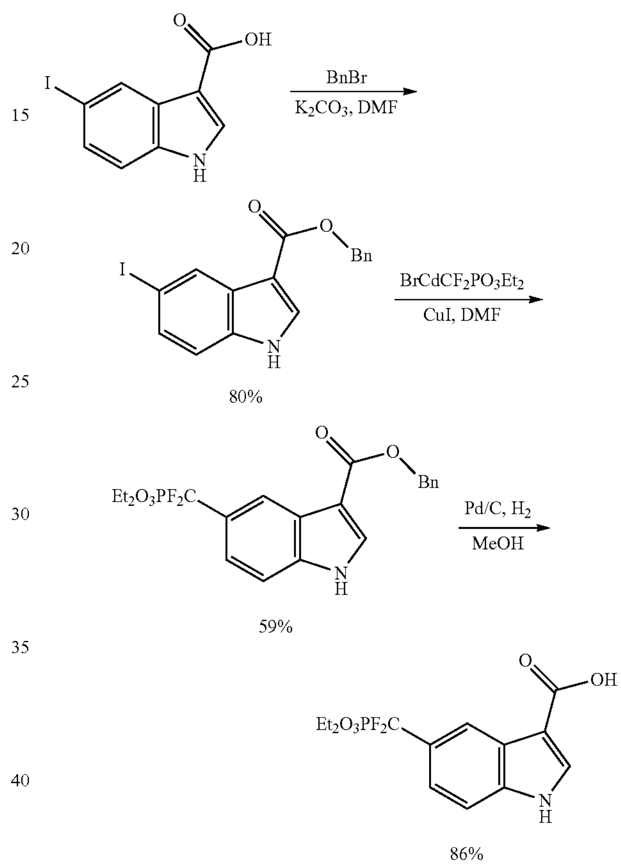
Scheme 9
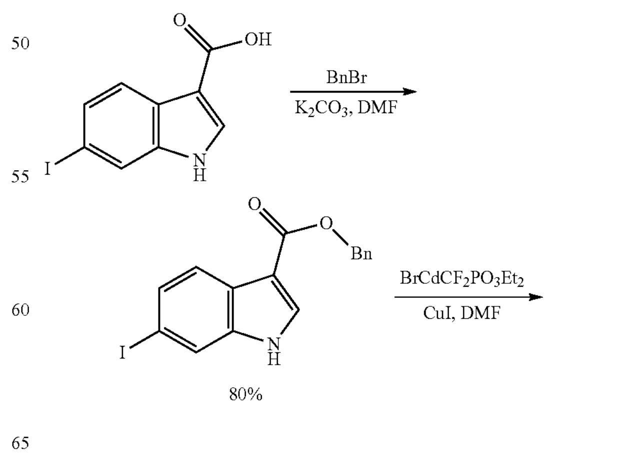

-continued
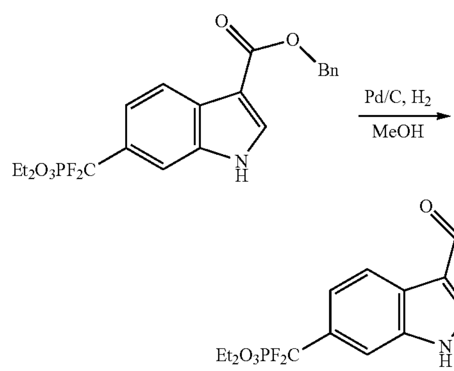
Scheme 10
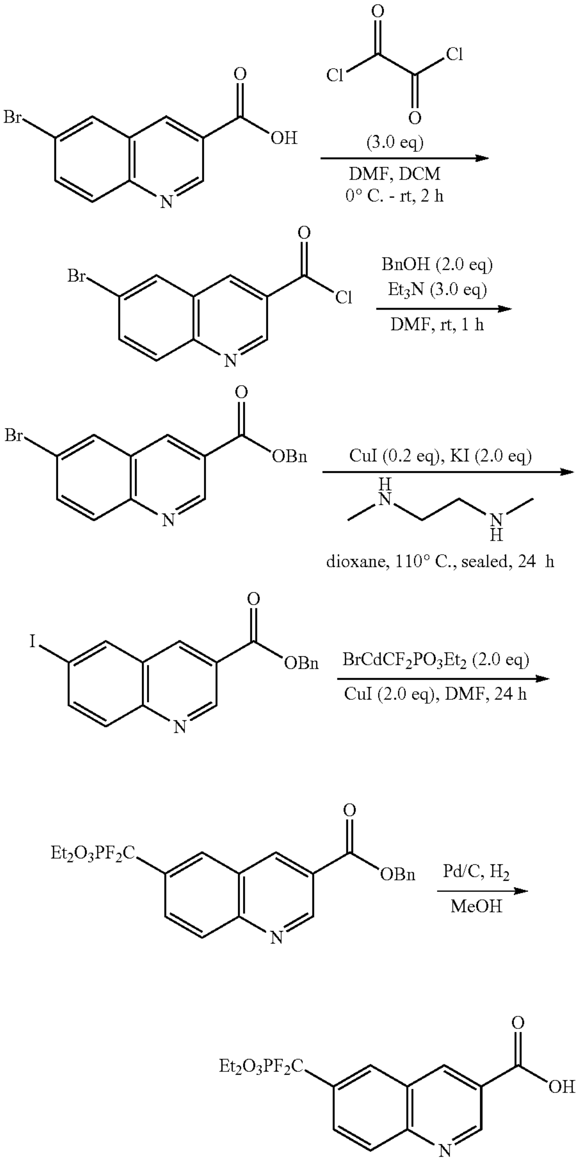
Scheme 11
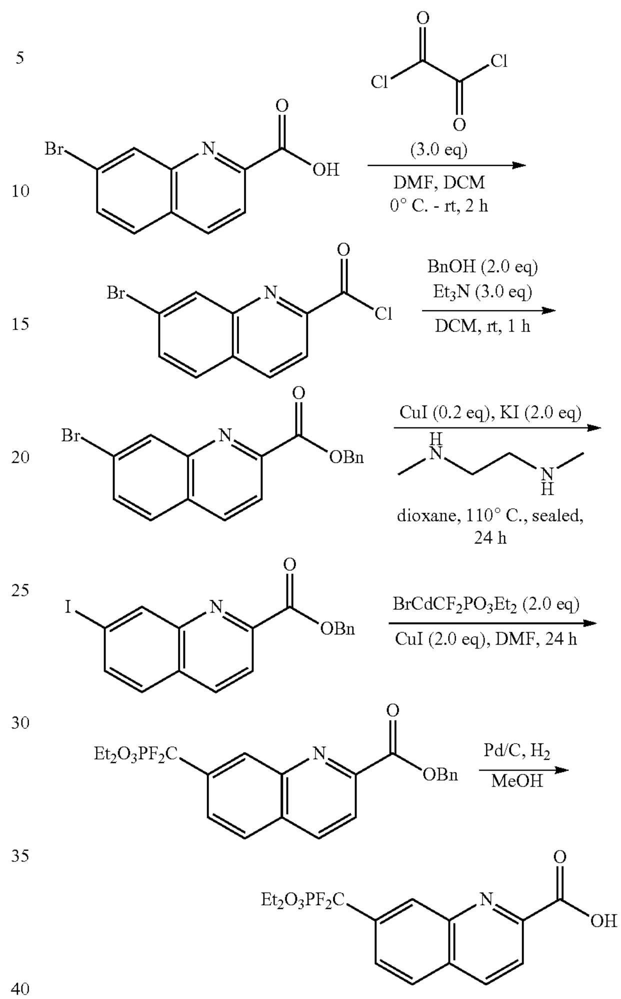
Scheme 12
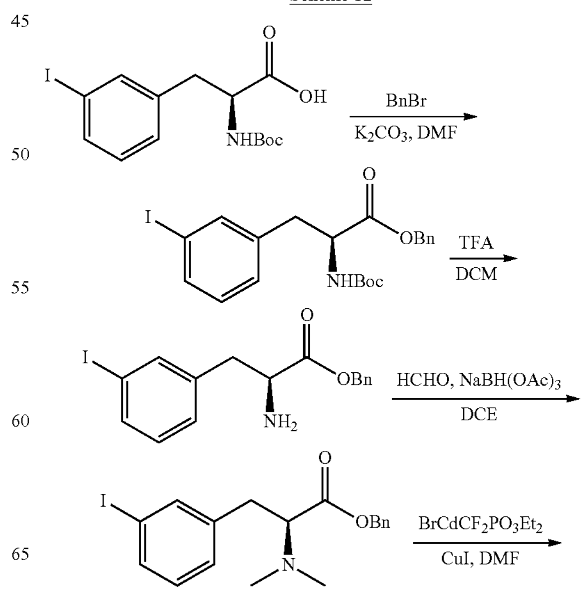

-continued
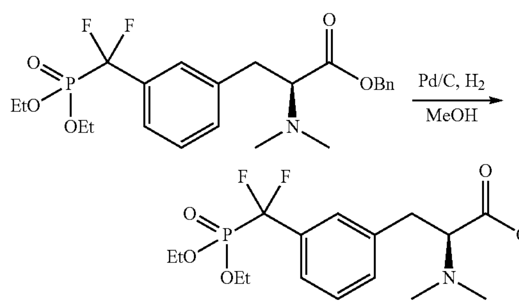
Scheme 13
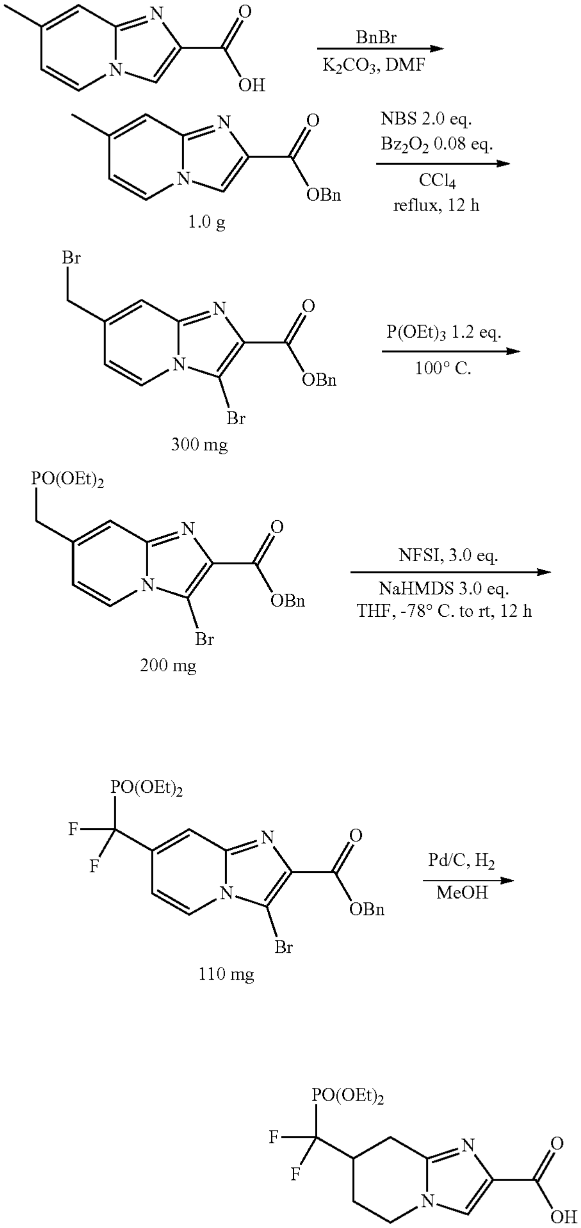
1.0 g
300 mg
200 mg
110 mg
45 mg
Scheme 14
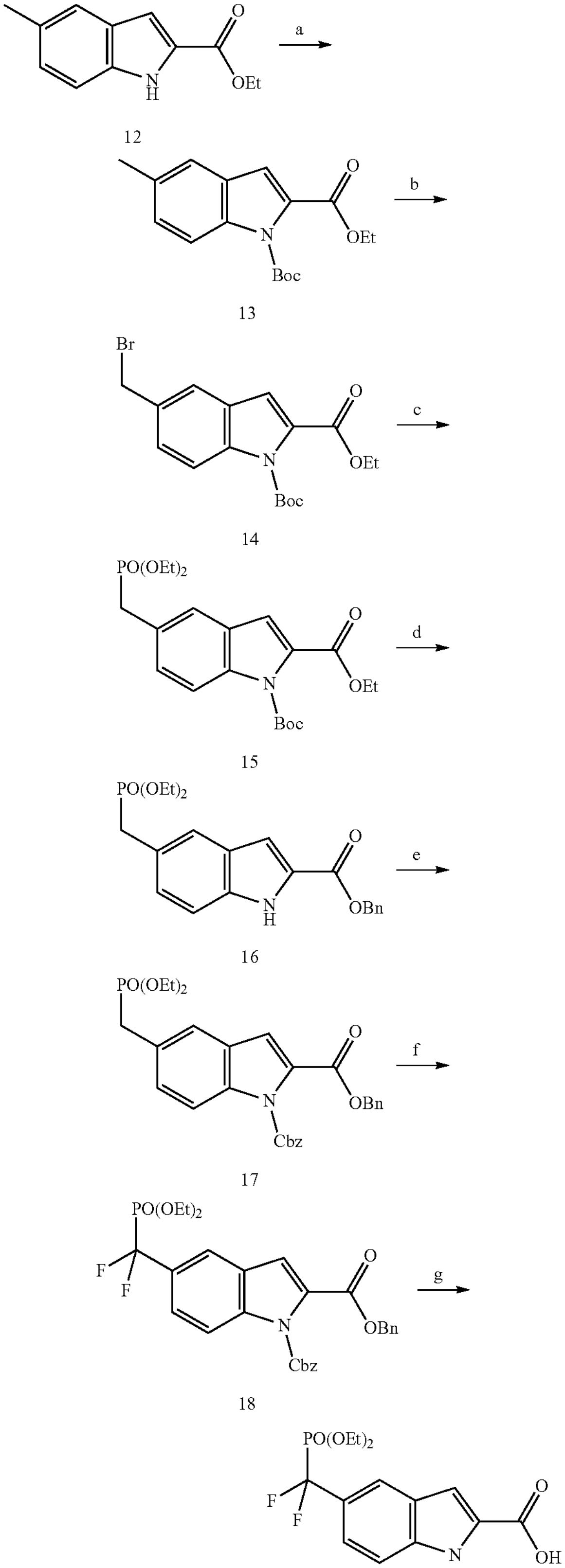
12
13
14
15
16
17
18
19

Reagents and conditions: a. NaH 2.0 equiv., $Boc_2O$ 1.4 equiv., THF, 0° C. to rt, 24 h; b. NBS 1.0 equiv. $Bz_2O_2$ 0.04 equiv. $CCl_4$, reflux 12 h, 77% yield over two steps; c. $P(OEt)_3$ 1.2 equiv., 100° C., 12 h, 84% yield; d. Ti(O-i-$Pr)_4$ 0.25 equiv. BnOH 20.0 equiv. 100° C., 83% yield; e. NaH 3.0 equiv. Cbz-Cl 1.5 equiv. THF, 0° C. to rt, 12 h, 88% yield; f. NFBS 3.0 equiv. NaHMDS 3.0 equiv., THF, −78° C. to rt, 12 h, 95% yield; g. $H_2$/Pd—C, THF, 12 h, 94% yield.

Step 1: 1-tert-Butyl 2-ethyl 5-(bromomethyl)-1H-indole-1,2-dicarboxylate (Compound 14)

To a round bottom flask equipped with a magnetic stirring bar was added NaH (2.2 g, 53 mmol, 2.0 equiv., 60% in mineral oil) and THF (300 mL). The suspension was cooled with an ice/water bath before addition of ethyl 5-methyl-1H-indole-2-carboxylate (compound 12) (5.0 g, 26 mmol, 1.0 equiv.) over 15 min. The solution was stirred at this temperature for 30 min (the color of solution turned red). $Boc_2O$ (8.1 g, 37 mmol, 1.4 equiv) was added to the solution in one portion. The reaction mixture was allowed to stir at room temperature for another 24 h before quenching with ice water. The aqueous layer was extracted with ethyl acetate (200 mL×2) and the combined organic layers were washed with brine (50 mL×2), dried over anhydrous sodium sulphate, and concentrated on a rotary evaporator. The residual crude product compound 13 was used directly in the next step without further purification.

To a round bottom flask equipped with a magnetic stirring bar was added crude product compound 13, $(PhCO)_2O_2$ (242 mg, 1.0 mmol, 0.04 equiv), NBS (4.62 g, 26.0 mmol, 1.0 equiv) and anhydrous $CCl_4$ (150 mL). The reaction mixture was heated at reflux for 12 h. The precipitate was filtered off and the solvent was removed on a rotary evaporator. The residual crude product was purified by flash column chromatography to afford the desired benzylic bromide compound 14 as colorless oil (7.6 g, 77% yield). Monobrominated product (14):Dibrominated product:Starting Material (13)=2:0.15:0.22. The data of major isomer compound 14 is shown as below. $^1H$ NMR (300 MHz, $CDCl_3$): 8.05 (d, J=8.66 Hz, 1H), 7.61 (d, J=1.39 Hz, 1H), 7.44 (dd, J=8.66, 1.81 Hz, 1H), 7.06 (d, J=0.65 Hz, 1H), 5.29 (s, 2H), 4.38 (q, J=7.14 Hz, 2H), 1.62 (s, 9H), 1.40 (t, J=7.14 Hz, 3H). $^{13}C$ NMR (75 MHz, $CDCl_3$): 161.8, 149.2, 146.9, 137.6, 133.0, 131.8, 128.0, 127.9, 122.7, 115.5, 114.5, 85.3, 85.0, 61.7, 34.1, 28.0, 14.4. ESI-MS calculated for $C_{17}H_{21}{}^{79}BrNO_4$ $[M+H]^+$=382.07, Found: 382.42; $C_{17}H_{21}{}^{81}BrNO_4$ $[M+H]^+$: 384.06, Found: 384.08.

Step 2: 1-tert-Butyl 2-ethyl 5-((diethoxyphosphoryl) methyl)-1H-indole-1,2-dicarboxylate (Compound 15)

To a round bottom flask equipped with a magnetic stirring bar was added compound 14 (3 g, 7.9 mmol, 1.0 equiv.) and $(EtO)_3P$ (1.72 mL, 10.0 mmol, 1.2 equiv.). The reaction mixture was heated at 100° C. for 12 h. The reaction mixture was loaded directly to silica gel column and purified by flash column chromatography to afford the desired phosphate compound 15 as colorless oil (2.9 g, 84%). $^1H$ NMR (300 MHz, $CDCl_3$): 8.02 (d, J=8.62 Hz, 1H), 7.53 (s, 1H), 7.35 (d, J=8.63 Hz, 1H), 7.05 (s, 1H), 4.38 (q, J=7.13 Hz, 2H), 4.07-3.92 (m, 4H), 3.23 (d, $J_{P—H}$=21.24 Hz, 2H), 1.63 (s, 9H), 1.39 (t, J=7.13 Hz, 3H), 1.23 (t, J=7.06 Hz, 6H). $^{13}C$ NMR (75 MHz, $CDCl_3$): 161.7, 149.1, 136.7 (d, $J_{P—C}$=2.88 Hz), 131.1, 128.5 (d, $J_{P—C}$=5.88 Hz), 127.7 (d, $J_{P—C}$=2.81), 126.5 (d, $J_{P—C}$=9.12 Hz), 122.9 (d, $J_{P—C}$=7.15 Hz), 114.8 (d, $J_{P—C}$=2.50 Hz), 114.3, 84.5, 62.0 (d, $J_{P—C}$=6.79 Hz), 61.3, 33.3 (d, $J_{P—C}$=128.4), 27.7, 16.3 (d, $J_{P—C}$=5.96 Hz), 14.1. $^{31}P$ NMR (121 M Hz, $CDCl_3$): 26.3 (s). ESI-MS calculated for $C_{21}H_{31}NO_7P$ $[M+H]^+$=440.18, Found: 440.67.

Step 3: Benzyl 5-((diethoxyphosphoryl)methyl)-1H-indole-2-carboxylate (Compound 16)

To a round bottom flask equipped with a magnetic stirring bar was added compound 15 (2.9 g, 6.6 mmol, 1.0 equiv.), BnOH (14 mL, 132 mmol, 20 equiv.), and Ti(Oi-$Pr)_4$ (0.32 mL, 1.6 mmol, 0.25 equiv.). The reaction mixture was heated at 100° C. for 12 h. The reaction mixture was cooled to 35° C. and quenched with 1 N HCl (20 mL). The aqueous layer was extracted with ethyl acetate (200 mL×2) and the combined organic extracts were washed with brine (50 mL×2), dried over anhydrous sodium sulphate, filtered and concentrated in vacuum. The residual crude product was purified by flash column chromatography to afford the desired benzyl carboxylate compound 16 as colorless oil (2.25 g, 83% yield). 80% purity (determined by $^{31}P$ NMR): 10% ethyl carboxylate, 10% unknown. $^1H$ NMR (300 MHz, MeOD-$d_4$): 7.65 (s, 1H), 7.60-7.38 (m, 6H), 7.31 (dt, J=8.57, 1.72 Hz, 1H), 7.24 (s, 1H), 5.43 (s, 2H), 4.15-4.00 (m, 4H), 3.35 (d, $J_{P—H}$=21.03 Hz, 2H), 1.30 (t, J=7.06 Hz, 6H). $^{13}C$ NMR (75 MHz, MeOD-d4): 163.0, 138.2 (d, $J_{P—C}$=2.19 Hz), 137.6, 129.6, 129.3, 129.2, 129.1, 128.8 (d, $J_{P—C}$=2.76 Hz), 128.2 (d, $J_{P—C}$=5.33 Hz), 124.3 (d, $J_{P—C}$=7.95 Hz), 124.1 (d, $J_{P—C}$=9.42 Hz), 113.4 (d, $J_{P—C}$=2.37 Hz), 109.3, 67.4, 63.6 (d, $J_{P—C}$==6.96 Hz), 33.6 (d, $J_{P—C}$=138.3 Hz), 16.7 (d, $J_{P—C}$==5.92 Hz). $^{31}P$ NMR (121 M Hz, MeOD-d4): 28.3 (s), 26.4 (s). ESI-MS calculated for $C_{21}H_{25}NO_5P$ $[M+H]^+$=402.15, Found: 402.50.

Step 4: Dibenzyl 5-((diethoxyphosphoryl)methyl)-1H-indole-1,2-dicarboxylate (Compound 17)

To a round bottom flask equipped with a magnetic stirring bar was added NaH (0.6 g, 15 mmol, 3.0 equiv., 60% in mineral oil) and THF (100 mL). The suspension was cooled with ice/water bath before addition of 16 (2.25 g in THF, 5.5 mmol, 1.0 equiv.) over 5 min. The solution was stirred at this temperature for 10 min before addition of Cbz-Cl (1.12 mL, 8 mmol, 1.5 equiv.) via a syringe. The reaction mixture was stirred at room temperature for another 12 h before quenching with ice water. The aqueous layer was extracted with ethyl acetate (200 mL×2) and the combined organic extracts were washed with brine (50 mL×2), dried over anhydrous sodium sulphate, and concentrated in vacuum. The residual crude product was purified by flash column chromatography to afford the desired compound 17 as colorless oil (2.6 g, 88% yield). $^1H$ NMR (300 MHz, $CDCl_3$): 8.00 (d, J=8.63 Hz, 1H), 7.52 (s, 1H), 7.46-7.26 (m, 11H), 7.11 (s, 1H), 5.33 (s, 2H), 5.20 (s, 2H), 4.10-3.90 (m, 4H), 3.22 (d, $J_{P—H}$=21.30 Hz, 2H), 1.21 (t, J=7.05 Hz, 6H). $^{13}C$ NMR (75 MHz, $CDCl_3$): 161.3, 150.5, 136.6 (d, $J_{P—C}$=2.97 Hz), 135.3, 134.4, 130.6, 129.0 (d, $J_{P—C}$=5.88 Hz) 128.7, 128.6, 128.6, 128.5, 128.3, 128.2, 127.8 (d, $J_{P—C}$=2.82 Hz), 127.0 (d, $J_{P—C}$=9.10 Hz), 123.1 (d, $J_{P—C}$=7.08 Hz), 115.6, 115.0 (d, $J_{P—C}$=2.25 Hz), 69.5, 67.1, 62.1 (d, $J_{P—C}$=6.78 Hz), 33.4 (d, $J_{P—C}$=138.49 Hz), 16.3 (d, $J_{P—C}$=5.87 Hz). $^{31}P$ NMR (121 M Hz, $CDCl_3$): 26.3 (s). ESI-MS calculated for $C_{29}H_{30}NO_7P$ $[M+Na]^+$=558.17, Found: 558.08.

Step 5: Dibenzyl 5-((diethoxyphosphoryl)difluoromethyl)-1H-indole-1,2-dicarboxylate (Compound 18)

To a round bottom flask equipped with a magnetic stirring bar was added compound 17 (9.17 g, 17 mmol, 1.0 equiv.), $(PhSO_2)_2NF$ (known as NFSB, 16 g, 51 mmol, 3.0 equiv.) and THF (300 mL). The reaction mixture was cooled to −78° C. with the aid of an ethanol/dry ice bath. To this solution, NaHMDS (51 mL, 1.0 M in THF, 3.0 equiv.) was added over 10 min. The reaction mixture was allowed to stir at this temperature for 2 h before warming up to room temperature over 3 to 4 h. The reaction was quenched with saturated $NH_4Cl$ aqueous solution (100 mL). The aqueous layer was extracted with ethyl acetate (200 mL×2) and the combined organic extracts were washed with brine (50 mL×2), dried over anhydrous sodium sulphate, and concentrated in vacuum. The residual crude product was purified by flash column chromatography to afford the desired product compound 18 as colorless oil (9.6 g, 95% yield). $^1$H NMR (300 MHz, $CDCl_3$): 8.13 (d, J=8.70 Hz, 1H), 7.88 (s, 1H), 7.65 (d, J=8.90 Hz, 1H), 7.50-7.28 (m, 10H), 7.17 (s, 1H), 5.33 (s, 2H), 5.20 (s, 2H), 4.30-4.00 (m, 4H), 1.27 (t, J=6.85 Hz, 6H). $^{13}$C NMR (75 MHz, $CDCl_3$):161.2, 150.3, 138.6, 135.2, 134.2, 131.5, 129.0, 128.8, 128.7, 128.6, 128.5, 128.4, 128.4-127.6 (m), 127.4, 125.2-124.4 (m), 121.0-120.6 (m), 120.5-119.5 (m), 115.5, 115.2, 70.0, 67.3, 64.9 (d, $J_{P-C}$=6.76 Hz), 16.3 (d, $J_{P-C}$=5.49 Hz). $^{31}$P NMR (121 M Hz, $CDCl_3$): 6.3 (t, $J_{P-F}$=117 Hz). ESI-MS calculated for $C_{29}H_{29}F_2NO_7P$ $[M+H]^+$=572.17, Found: 572.25.

Step 6: 5-((Diethoxyphosphoryl)difluoromethyl)-1H-indole-2-carboxylic Acid (Compound 19)

To a round bottom flask equipped with a magnetic stirring bar was added compound 18 (1 g, 1.7 mmol, 1.0 equiv.) and THF (300 mL). The oxygen was removed with the aid of a vacuum line and a nitrogen balloon. 10% Pd/C (0.1 g, 0.1 mmol, 0.05 equiv.) was added to the reaction mixture. The reaction was stirred at room temperature for 12 h under $H_2$ atmosphere (1 atm $H_2$ balloon). The Pd/C was removed by filtration and the solvent was removed in vacuum. The residual crude product was purified by flash column chromatography to afford the desired compound 19 as a pale green solid (0.56 g, 94% yield). Higher purity can be achieved by recrystallization from $CHCl_3$. $^1$H NMR (300 MHz, MeOD-$d_4$): 11.6 (s, 1H), 7.94 (s, 1H), 7.58 (d, J=8.75 Hz, 1H), 7.48 (d, J=8.75 Hz, 1H), 7.27 (s, 1H), 4.30-4.05 (m, 4H), 1.30 (td, J=7.04 Hz, $J_{P-H}$=0.49 Hz, 6H). $^{13}$C NMR (75 MHz, MeOD-d4): 164.5, 139.7, 131.2, 128.1, 126.0-124.0 (m), 123.4-123.0 (m), 122.4-122.0 (m), 119.0-118.1 (m), 113.5, 109.6, 66.3 (d, $J_{P-C}$=7.09 Hz), 16.6 (d, $J_{P-C}$=5.34 Hz). $^{31}$P NMR (121 M Hz, MeOD-d4): 6.6 (t, $J_{P-F}$=123 Hz). ESI-MS calculated for $C_{14}H_{17}F_2NO_5P$ $[M+H]^+$=348.08, Found: 348.42.

Example 6

Synthesis of ((2-(((5S,8S,10aR)-3-acetyl-8-(((S)-5-amino-1-(benzhydrylamino)-1,5-dioxopentan-2-yl)carbamoyl)-6-oxodecahydropyrrolo[1,2-a][1,5]diazocin-5-yl)carbamoyl)-1H-indol-5-yl)difluoromethyl)phosphonic Acid (Cpd. No. 200)

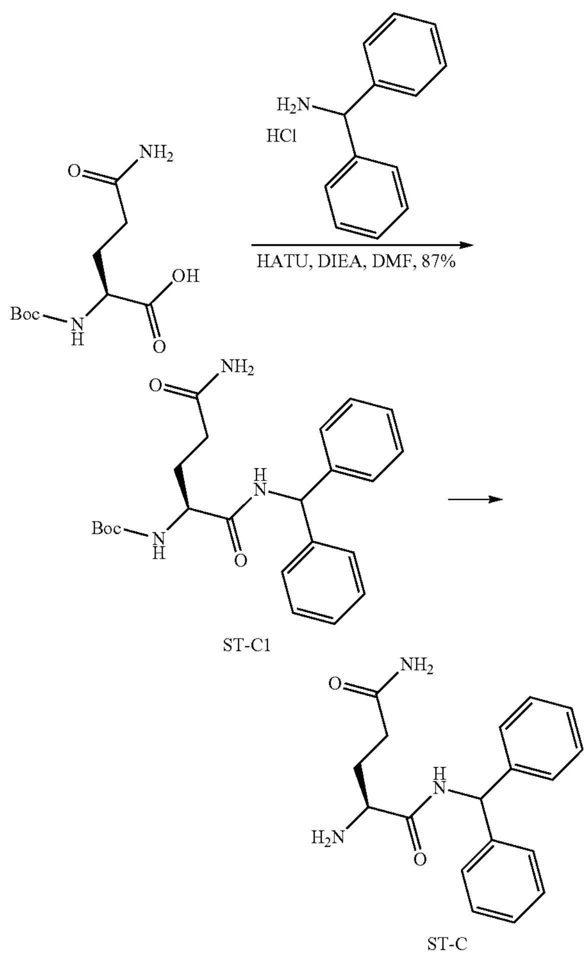

ST-C1

ST-C

ST-C1: To a solution of the Boc-Gln-OH (5.0 g, 20.3 mmol, 1 equiv.), aminodiphenylmethane hydrochloride (4.5 g, 20.3 mmol, 1 equiv.) and DIEA (10.6 mL, 60.9 mmol, 3 equiv.) in DMF (60 mL) was added HATU (8.5 g, 22.3 mmol, 1.1 equiv.) and the resultant mixture was stirred at room temperature for 1 h. The solution was diluted with EtOAc, washed with $H_2O$, saturated sodium bicarbonate aqueous solution, and brine, and dried over sodium sulfate. After removal of the solvent under vacuum, the residue was purified by flash chromatography on silica gel to afford ST-C-1 (7.3 g 87%). $^1$H NMR (400 MHz, $CDCl_3$) δ 7.95 (d, J=6.5 Hz, 1H), 7.35-7.23 (m, 10H), 6.36 (s, 1H), 6.21 (d, J=8.2 Hz, 1H), 5.89 (d, J=5.8 Hz, 1H), 5.74 (s, 1H), 4.24 (s, 1H), 2.33-2.26 (m, 1H), 2.21-2.11 (m, 1H), 2.09-2.00 (m, 1H), 1.92-1.87 (m, 1H), 1.43 (s, 9H). $^{13}$C NMR (101 MHz, $CDCl_3$) δ 175.42, 171.02, 156.26, 141.50, 141.32, 128.63, 127.44, 80.10, 56.92, 53.75, 31.91, 29.10, 28.31.

ST-C: TFA (5 mL) was added slowly in a solution of ST-C-1 (3 g) in DCM (50 mL) and the result reaction solution was stirred at room temperature for 6 hours and then evaporated. The residue was directly used in the next step without purification.

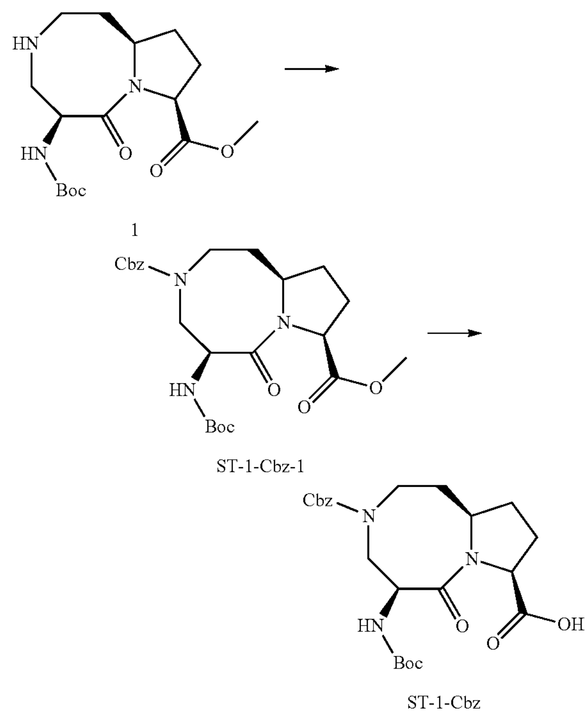

1

ST-1-Cbz-1

ST-1-Cbz

ST-1-Cbz-1: Cbz-Cl (1.36 mL, 9.5 mmol, 1.3 equiv) was added to a mixture of 1 (2.5 g, 7.3 mmol, 1 equiv.) and $NaHCO_3$ (1.85 g, 21.9 mmol, 3 equiv.) in dioxane (100 mL) and the resulting reaction mixture was stirred for 5 h. This reaction mixture was filtered through Celite and the filtrate was evaporated under reduced pressure. The residue was diluted with EA and washed with water and brine, and dried over $Na_2SO_4$. The solvent was then evaporated and the residue was purified by chromatography on silica gel to get compound St-1-Cbz (9-239 acid). $^1$H NMR (400 MHz, MeOD) δ 7.47-7.26 (m, 5H), 5.22-5.10 (m, 2H), 4.78-4.60 (m, 1H), 4.55-4.38 (m, 1H), 4.34-4.19 (m, 1H), 3.83-3.56 (m, 3H), 3.55-3.43 (m, 1H), 2.48-2.32 (m, 1H), 2.24-1.95 (m, 3H), 1.88-1.67 (m, 2H), 1.46-1.45 (m, 9H, two peaks).

ST-1-Cbz: LiOH—$H_2O$ (352 mg, 8.4 mmoL, 2 eqiv) in water (20 mL) was added to a solution of compound 2 (2 g, 4.2 mmol, 1 equiv) in Dioxane (40 mL) and the resulting mixture was stirred for 1 h at room temperature. Most of the organic solvent was removed by evaporation and the PH value of the residue was adjusted to 7 and extracted by EA for several times. The combined organic fractions were dried over $Na_2SO_4$ and the solvent was removed under vacuum and the residue was used directly without purification.

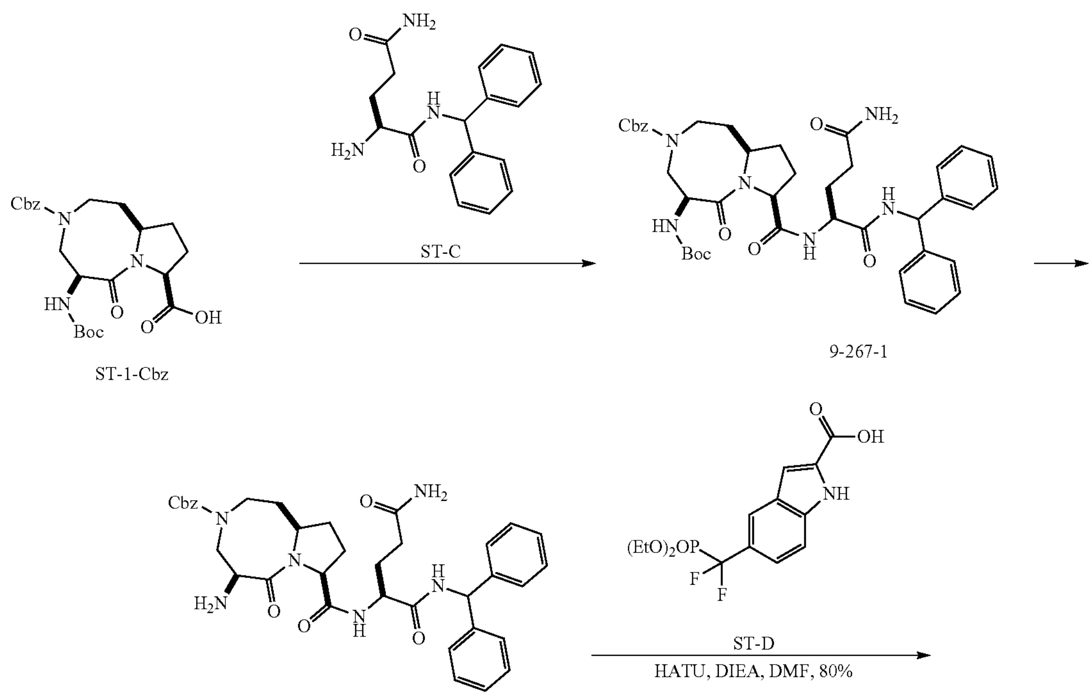

ST-1-Cbz 9-267-1

-continued

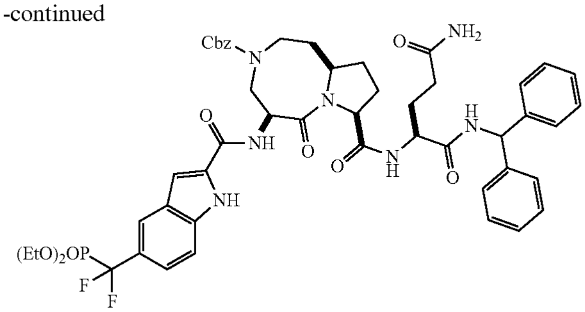

Cpd. No. 240

9-267-1: HATU (1.59 g, 4.2 mmol, 1.1 equiv.) was added to a solution of the ST-1-CBz (1.75 g, 3.8 mmol, 1 equiv.), ST-C (1.61 g, 3.8 mmol, 1 equiv.) and DIEA (1.98 mL, 11.4 mmol, 3 equiv.) in DMF (15 mL) and the resultant mixture was stirred at room temperature for 1 h. The solution was diluted with EtOAc and washed with $H_2O$, saturated sodium bicarbonate aqueous solution and brine, and dried over sodium sulfate. After removal of the solvent under vacuum, the residue was purified by flash chromatography on silica gel to afford 9-267-1 (2.4 g 84%). $^1$H NMR (400 MHz, MeOD) δ 7.46-7.39 (m, 2H), 7.38-7.19 (m, 13H), 6.16-6.15 (m, 1H), 5.20-5.18 (m, 2H), 4.74-4.57 (m, 1H), 4.56-4.37 (m, 2H), 4.25-4.23 (m, 1H), 3.87-3.35 (m, 4H), 2.55-2.28 (m, 2H), 2.27-1.58 (m, 8H), 1.46 (s, 9H). UPLC-MS (ESI-MS) m/z: calculated for $C_{41}H_{51}N_6O_8P^+$ 755.38, found $[M+H]^+$ 755.52.

Cpd. No. 240: TFA (3 mL) was added slowly in a solution of 9-277-1 (2 g, 2.65 mmol) in DCM (30 mL) at room temperature and the result reaction solution was stirred at the same temperature for 6 hours and then evaporated. The crude product was directly used in the next step without purification. To a solution of the crude product of the previous step (2.65 mmol, 1 equiv.), ST-D (0.92 g, 2.65 mmol, 1 equiv.) and DIEA (1.39 mL, 7.95 mmoL, 3 equiv.) in DMF (15 mL) was added HATU (1.1 g, 2.91 mmol, 1.1 equiv.). The resultant mixture was stirred at room temperature for 1 h and diluted with EtOAc, and was washed with $H_2O$, saturated sodium bicarbonate aqueous solution and brine, and dried over sodium sulfate. After removal of the solvent under vacuum, the residue was purified by flash chromatography on silica gel to afford Cpd. No. 240. UPLC-MS (ESI-MS) m/z: calculated for $C_{50}H_{57}F_2N_7O_{10}P^+$ 984.39, found $[M+H]^+$ 984.25.

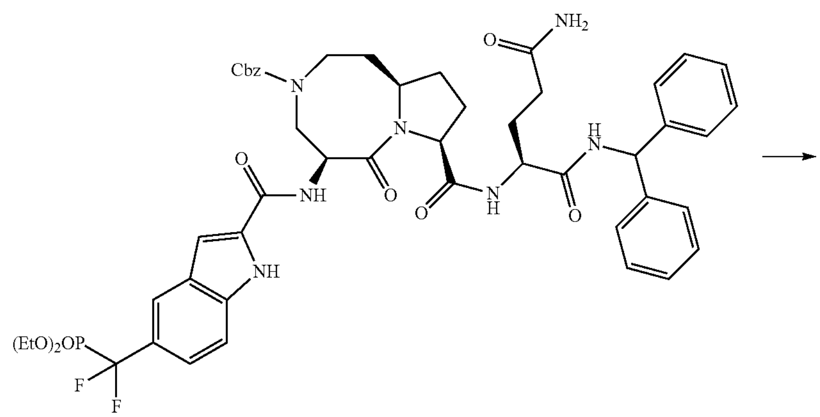

Cpd. No. 240

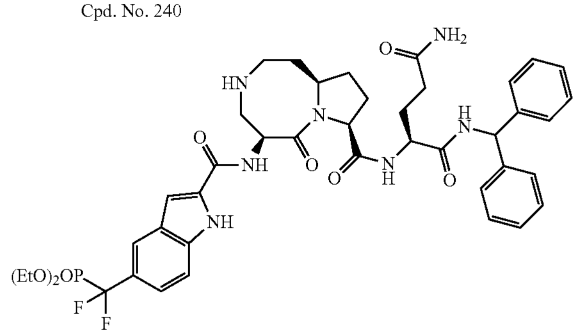

Cpd. No. 241

Cpd. No. 241. To a solution of compound Cpd. No. 240 (1.0 g, 1.02 mmol) in MeOH (40 mL) was added 10% Pd—C (200 mg). The solution was stirred under 1 atm of $H_2$ at room temperature for 3 hours before filtering through celite and being concentrated. The resulting amine was purified by HPLC to afford compound Cpd. No. 241 (0.86 g, 90%). $^1$H NMR (400 MHz, MeOD) δ 7.92 (s, 1H), 7.57 (d, J=8.7 Hz, 1H), 7.46 (d, J=8.8 Hz, 1H), 7.38-7.31 (m, 5H), 7.30-7.24 (m, 6H), 6.19 (s, 1H), 5.61 (dd, J=12.1, 5.6 Hz, 1H), 4.78 (t, J=8.9 Hz, 1H), 4.70-4.66 (m, 1H), 4.59 (dd, J=9.5, 5.0 Hz, 1H), 4.29-4.05 (m, 4H), 3.72-3.61 (m, 2H), 3.54 (t, J=12.6 Hz, 1H), 3.42 (t, J=12.4 Hz, 1H), 2.45-2.27 (m, 3H), 2.24-2.01 (m, 3H), 2.00-1.70 (m, 4H), 1.29 (td, J=7.1, 3.2 Hz, 6H). $^{13}$C NMR (101 MHz, MeOD) δ 176.23, 174.38, 171.02, 168.30, 161.93, 141.49, 141.38, 138.02, 131.42, 128.30, 128.23, 127.29, 127.25, 127.22, 127.16, 127.14, 126.88, 112.17, 104.87, 65.05, 65.03, 64.98, 64.96, (dd) 60.59, 58.41, 57.06, 53.01, 48.95, 46.92, 45.47, 31.53, 30.84, 30.68, 27.78, 26.50, 15.33, 15.28 (d). UPLC-MS (ESI-MS) m/z: calculated for $C_{42}H_{51}F_2N_7O_8P^+$ 850.35, found $[M+H]^+$ 850.37.

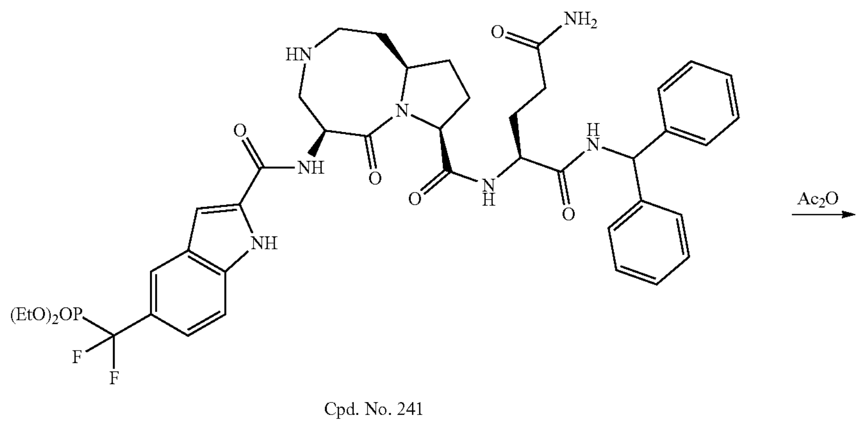

Ac₂O

Cpd. No. 241

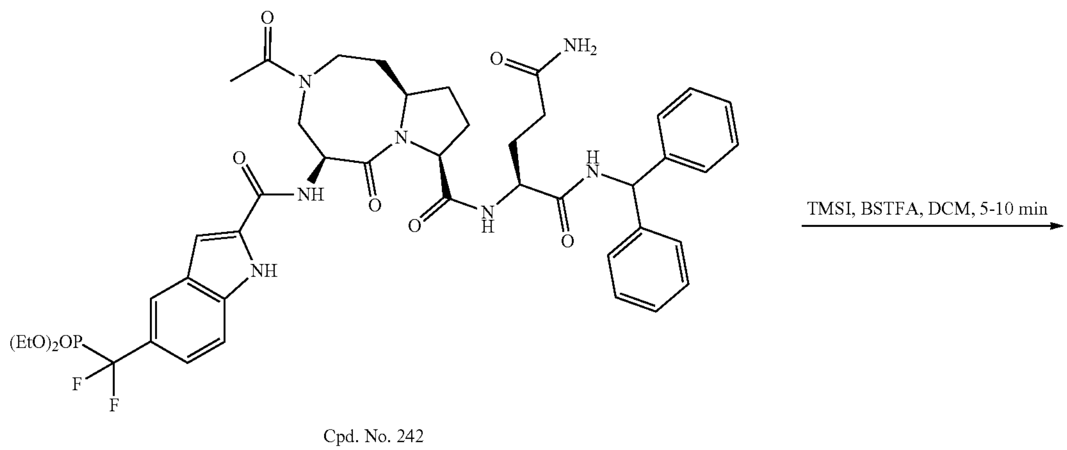

Cpd. No. 242

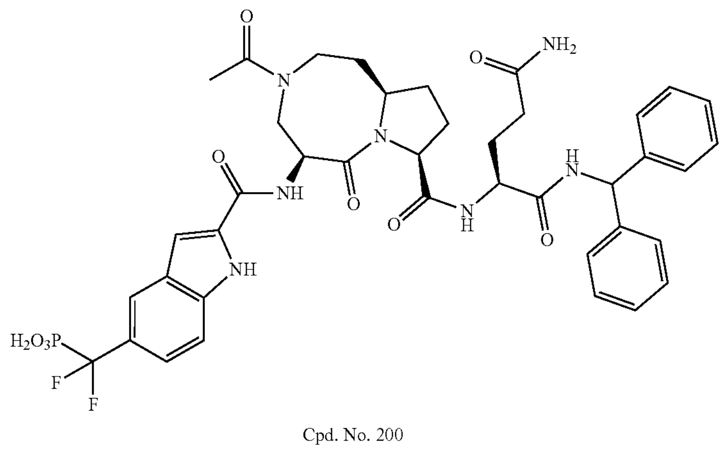

Cpd. No. 200

Cpd. No. 200: Acetic anhydride (24 mg, 0.24 mmoL, 2 equiv.) and DIEA (61 μL, 0.35 mmol, 3 equiv.) were added to a solution of Cpd. No. 241 (100 mg, 0.12 mmol, 1 equiv.) in DCM (5 mL). The resulting reaction mixture was stirred for half an hour and then was evaporated and the residue was purified by flash chromatography on silica gel to afford Cpd. No. 242. Cpd. No. 200 was prepared from Cpd. No. 242 by similar procedures as those for compound Cpd. No. 36 from Cpd. No. 37. The overall yield for these two steps was 69%. $^1$H NMR (400 MHz, $CD_3CN$:$D_2O$=1:1) δ 7.90 (s, 1H), 7.56-7.52 (m, 1H), 7.48-7.46 (m, 1H), 7.35-7.21 (m, 11H), 6.07-6.06 (m, 1H), 5.11-5.02 (m, 1H), 4.42-4.23 (m, 3H), 3.95-3.80 (m, 1H), 3.77-3.53 (m, 2H), 3.49-3.37 (m, 1H), 2.32-2.26 (m, 2H), 2.19-2.14 (m, 4H), 2.11-2.01 (m, 2H), 1.96-1.58 (m, 5H). UPLC-MS (ESI-MS) m/z: calculated for $C_{40}H_{45}F_2N_7O_9P^+$ 836.30, found $[M+H]^+$ 836.4.

Example 7

Synthesis of Intermediates of the Disclosure

The following compounds of Formula VIII were prepared using the techniques described in EXAMPLE 6.

Cpd. No. 216: $^1$H NMR (400 MHz, $CD_3CN$:$D_2O$=1:1) δ 7.91 (s, 1H), 7.53-7.47 (m, 2H), 7.27 (s, 1H), 5.47 (s, 1H), 4.72-4.60 (m, 2H), 4.28-4.26 (m, 1H), 3.94-3.82 (m, 1H), 3.67-3.52 (m, 2H), 3.39-3.33 (m, 1H), 3.04 (s, 3H), 2.68 (s, 3H), 2.50-2.43 (m, 1H), 2.21-1.76 (m, 9H). UPLC-MS (ESI-MS) m/z: calculated for $C_{27}H_{37}F_2N_7O_8P^+$ 656.24, found $[M+H]^+$ 656.15.

Cpd. No. 201: $^1$H NMR (400 MHz, $CD_3CN$) δ 7.91 (s, 1H), 7.553-7.48 (m, 2H), 7.27 (s, 1H), 5.58-5.42 (m, 1H), 4.65-4.59 (m, 2H), 3.93-3.82 (m, 1H), 3.71-3.63 (m, 1H), 3.59-3.49 (m, 1H), 3.37 (t, J=12.0 Hz, 1H), 3.30-3.13 (m, 2H), 3.05 (s, 3H), 2.47-2.40 (m, 1H), 2.24-2.15 (m, 4H), 1.96-1.64 (m, 5H). UPLC-MS (ESI-MS) m/z: calculated for $C_{25}H_{34}F_2N_6O_7P^+$ 599.17, found $[M+H]^+$ 599.22.

Cpd. No. 205: $^1$H NMR (400 MHz, $CD_3CN$:$D_2O$=1:1) δ 7.91 (s, 1H), 7.62-7.43 (m, 2H), 7.42-7.14 (m, 11H), 6.10 (s, 1H), 5.48-5.46 (m, 1H), 4.76-4.57 (m, 2H), 4.42-4.39 (m, 1H), 3.92-3.84 (m, 1H), 3.67-3.65 (m, 1H), 3.49-3.46 (m, 1H), 3.36-3.30 (m, 1H), 2.96 (s, 3H), 2.51-2.23 (m, 3H), 2.17-2.04 (m, 3H), 1.92-1.87 (m, 2H), 1.80-1.72 (m, 2H). UPLC-MS (ESI-MS) m/z: calculated for $C_{39}H_{45}F_2N_7O_8P^+$ 808.30, found $[M+H]^+$ 808.5.

Cpd. No. 206: SI-107: UPLC-MS (ESI-MS) m/z: 825.4.

Cpd. No. 207: UPLC-MS (ESI-MS) m/z: 809.4.

Example 8

Synthesis of ((2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic Acid (Cpd. No. 36)

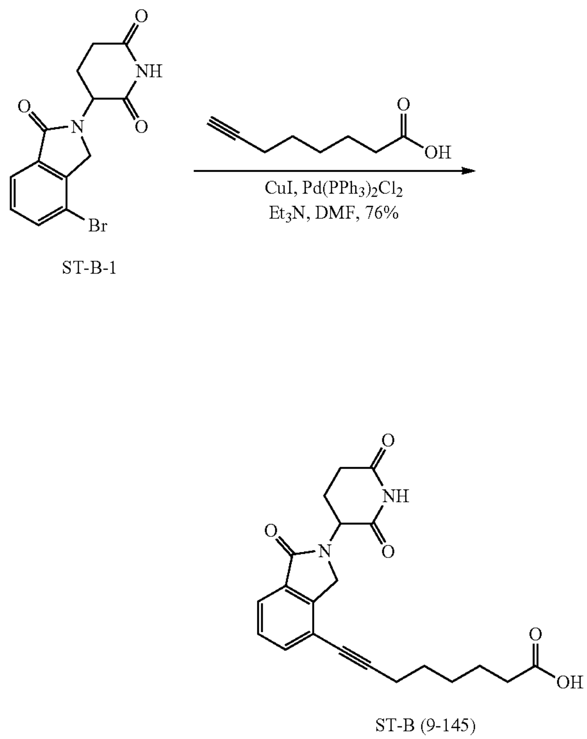

ST-B-1

ST-B (9-145)

9-145: Trimethylamine (10 mL) was added to a mixture of compound ST-B-1 (1.3 g, 4.0 mmol, 1 equiv.), oct-7-ynoic acid (0.56 g, 4.0 mmol, 1 equiv.), CuI (154 mg, 0.8 mmol, 0.2 equiv) and $Pd(PPh_3)_2Cl_2$ (282 mg, 0.4 mmol, 0.1 equiv) in DMF (10 mL). The resulting mixture was purged and refilled with argon three times and stirred at 70-80° C. for 3 h under Argon. The reaction mixture was then cooled to room temperature and evaporated to remove most of the solvent. The residue was purified by HPLC to yield 9-145 (1.18 g, 76%). $^1$H NMR (400 MHz, DMSO) δ 11.99 (s, 1H), 10.99 (s, 1H), 7.77-7.68 (m, 1H), 7.68-7.59 (m, 1H), 7.52 (t, J=7.6 Hz, 1H), 5.15 (dd, J=13.3, 5.0 Hz, 1H), 4.46 (d, J=17.7 Hz, 1H), 4.33 (d, J=17.7 Hz, 1H), 2.97-2.88 (m, 1H), 2.63-2.59 (m, 1H), 2.53-2.47 (m, 3H), 2.24 (t, J=7.2 Hz, 2H), 2.13-1.94 (m, 1H), 1.78-1.27 (m, 6H). $^{13}$C NMR (101 MHz, DMSO) δ 174.90, 173.32, 171.45, 168.14, 144.23, 134.52, 132.46, 129.05, 123.05, 119.32, 96.73, 76.91, 52.14, 47.47, 34.07, 31.68, 28.32, 28.25, 24.50, 22.83, 19.14. UPLC-MS (ESI-MS) m/z: calculated for $C_{21}H_{23}N_2O_5^+$ 383.16, found $[M+H]^+$ 383.28.

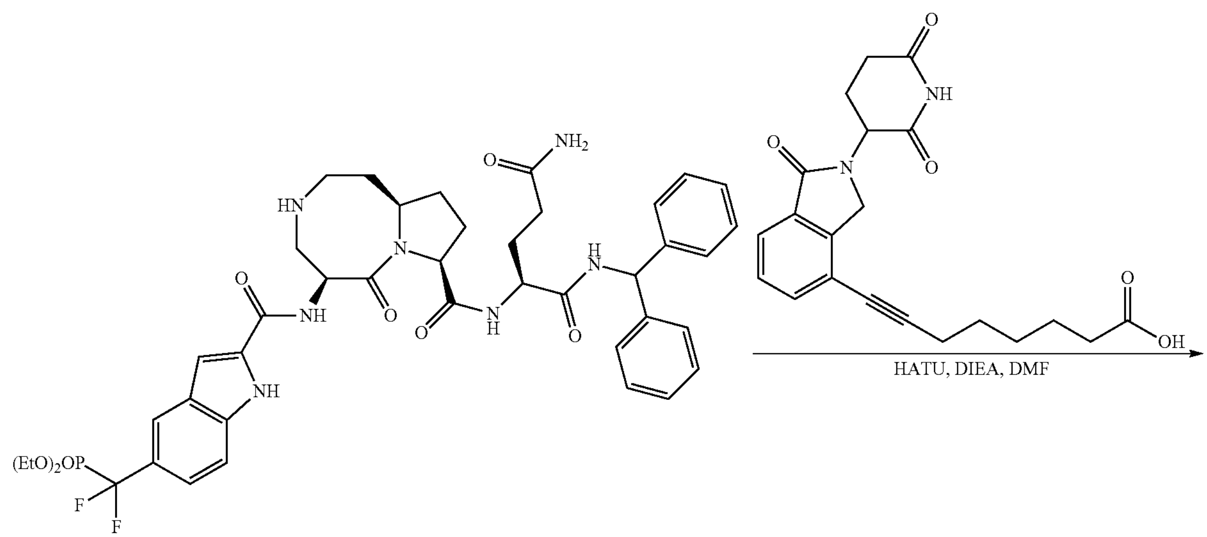
Cpd. No. 241
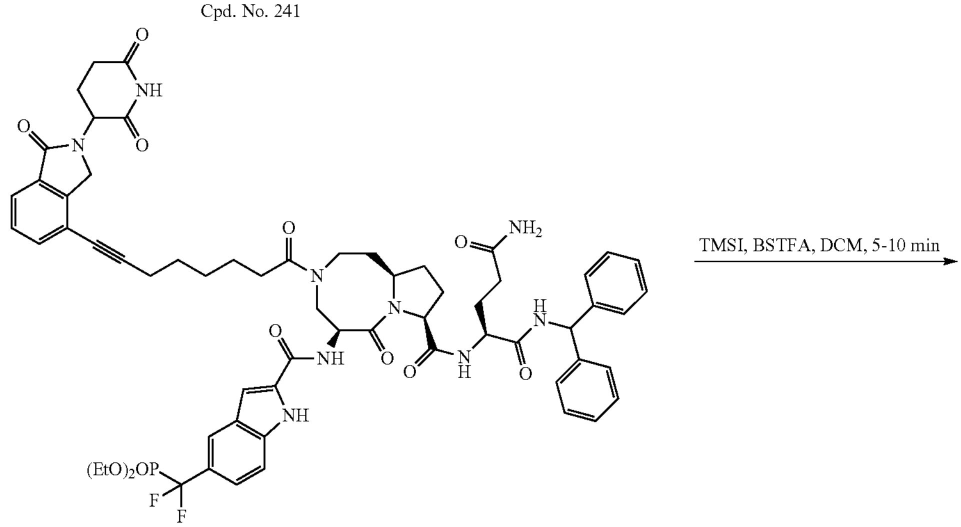
Cpd. No. 102
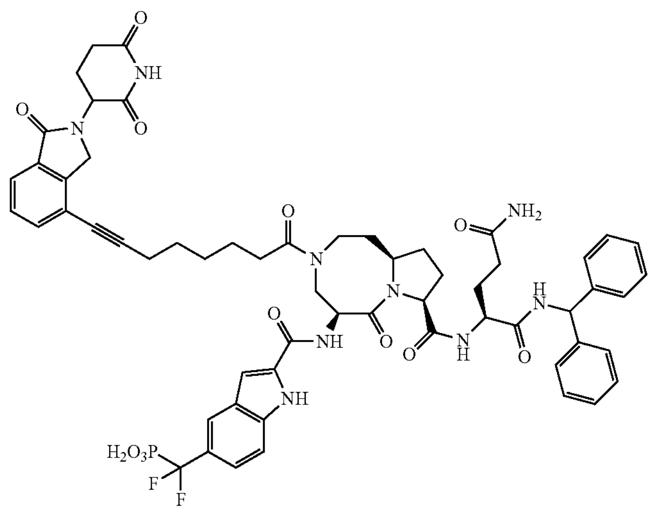
Cpd. No. 36
65
Cpd. No. 102: HATU (295 mg, 0.77 mmol, 1.1 equiv.) was added to a solution of the Cpd. No. 241, See EXAMPLE 6, (600 mg, 0.71 mmol, 1 equiv.), ST-B (270 g, 0.71 mmol, 1 equiv.) and DIEA (0.37 mL, 2.12 mmol, 3 equiv.) in DMF (10 mL) and the resultant mixture was stirred at room temperature for 1 h. The solution was diluted with EtOAc and washed with $H_2O$, saturated sodium bicarbonate aqueous solution and brine, and dried over sodium sulfate. After removal of the solvent under vacuum, the residue was purified by flash chromatography on silica gel to afford Cpd. No. 102 (702 mg 82%). $^1H$ NMR (400 MHz, MeOD: $CDCl_3$=1:1) δ 7.90 (s, 1H), 7.76-7.66 (m, 1H), 7.57-7.51 (m, 2H), 7.47-7.35 (m, 2H), 7.33-7.19 (m, 11H), 6.27-6.06 (m, 1H), 5.33-4.87 (m, 2H), 4.55-4.37 (m, 4H), 4.26-3.75 (m, 7H), 3.71-3.26 (m, 2H), 2.90-2.71 (m, 2H), 2.67-1.85 (m, 14H), 1.83-1.47 (m, 8H), 1.29 (t, J=7.1 Hz, 6H).

Cpd. No. 36: To a round bottom flask was added Cpd. No. 102 (500 mg, 0.41 mmol, 1.0 equiv) and $CH_2Cl_2$ (40 mL). The solution was cooled to 0° C. before adding $CF_3CON(TMS)_2$ (635 mg, 2.5 mmol, 6.0 equiv) and 1M of TMS-I in DCM (1.65 mL, 1.65 mmol, 4.0 equiv). The reaction mixture was allowed to stir at 0° C. for 10 min and the solvent was removed under vacuum at 0° C. The residue was dissolved in a mixture solvent of $CH_3CN$ (5 mL), water (5 mL) and TFA (0.3 mL), and purified by HPLC to yield Cpd. No. 36 (420 mg, 88%). $^1H$ NMR (400 MHz, $CD_3CN$: $D_2O$=1:1) δ δ 7.90-7.85 (m, 1H), 7.73-7.59 (m, 1H), 7.56-7.36 (m, 4H), 7.35-7.05 (m, 11H), 6.06-6.03 (m, 1H), 5.12-4.87 (m, 2H), 4.48-4.19 (m, 5H), 3.98-3.49 (m, 3H), 3.36-3.24 (m, 1H), 2.88-2.64 (m, 2H), 2.61-2.23 (m, 7H), 2.21-1.99 (m, 4H), 1.94-1.35 (m, 11H). $^1H$ NMR (400 MHz, DMSO) δ 11.96-11.76 (d, J=77.6 Hz, 1H), 10.99 (s, 1H), 8.96-8.61 (m, 2H), 8.33 (d, J=6.5 Hz, 1H), 8.24-8.17 (m, 1H), 7.84 (s, 1H), 7.72-7.69 (m, 1H), 7.65-7.62 (m, 1H), 7.54-7.47 (m, 2H), 7.44-7.10 (m, 13H), 6.79-6.71 (m, 1H), 6.13-6.09 (m, 1H), 5.17-5.11 (m, 1H), 4.97-4.88 (m, 1H), 4.60-4.10 (m, 5H), 4.06-3.14 (m, 4H), 2.99-2.82 (m, 1H), 2.78-2.51 (m, 5H), 2.47-2.33 (m, 1H), 2.26-1.12 (m, 17H). $^1H$ NMR (400 MHz, DMSO, added one drop $D_2O$, ageing 3 days) δ 7.84 (s, 1H), 7.72-7.69 (m, 1H), 7.65-7.61 (m, 1H), 7.54-7.47 (m, 2H), 7.40-7.38 (m, 1H), 7.36-7.19 (m, 11H), 6.10-6.08 (m, 1H), 5.15-5.09 (m, 1H), 4.97-4.86 (m, 1H), 4.54-4.15 (m, 5H), 3.98-3.90 (m, 2H), 3.63-3.29 (m, 2H), 2.99-2.80 (m, 1H), 2.74-2.54 (m, 2H), 2.49-2.33 (m, 4H), 2.24-1.43 (m, 17H). $^1H$ NMR (400 MHz, DMSO, added one drop $D_2O$, ageing 3 days, 353K) δ 7.87 (s, 1H), 7.68 (d, J=7.5 Hz, 1H), 7.60 (d, J=7.3 Hz, 1H), 7.57-7.42 (m, 3H), 7.38-7.14 (m, 11H), 6.11 (s, 1H), 5.10-5.06 (m, 1H), 4.96 (d, J=7.8 Hz, 1H), 4.54-4.12 (m, 5H), 3.97 (d, J=12.7 Hz, 1H), 3.80-3.76 (m, 1H), 3.42-3.22 (m, 2H), 2.98-2.80 (m, 1H), 2.75-2.52 (m, 3H), 2.59-2.33 (m, 3H), 2.23-1.44 (m, 17H). UPLC-MS (ESI-MS) m/z: calculated for $C_{59}H_{63}F_2N_9O_{12}P^+$ 1158.43, found $[M+H]^+$ 1158.60.

Example 9

Synthesis of Compounds of the Disclosure

The following Compounds of the Disclosure were prepared using Cpd. No. 241 as a synthetic intermediate according to the following general scheme.

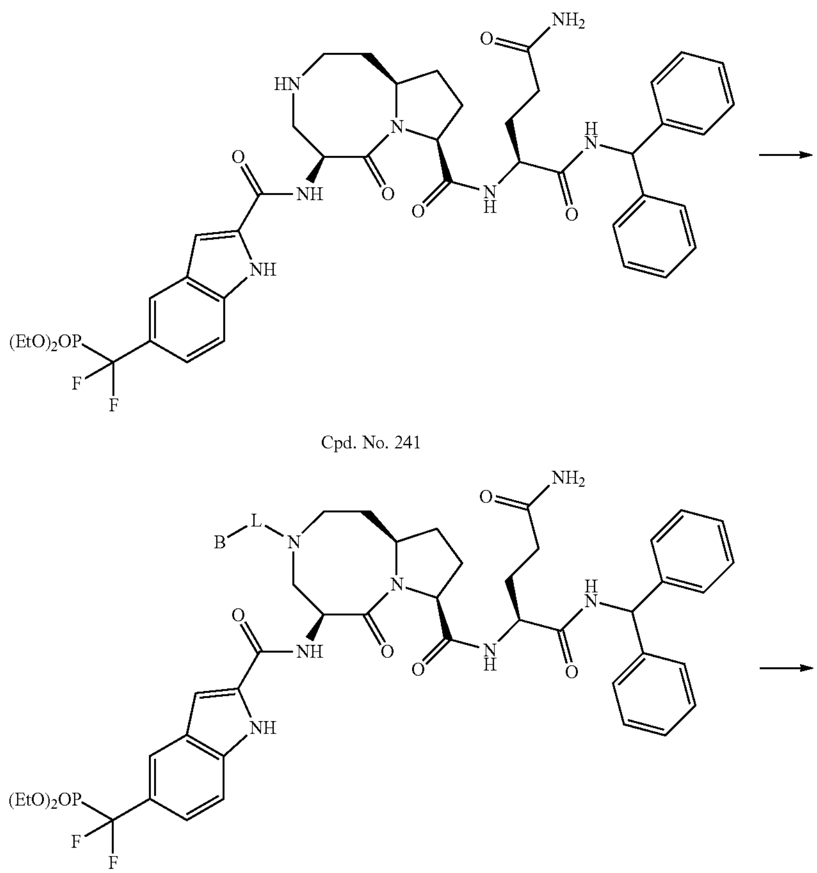

Cpd. No. 241

-continued

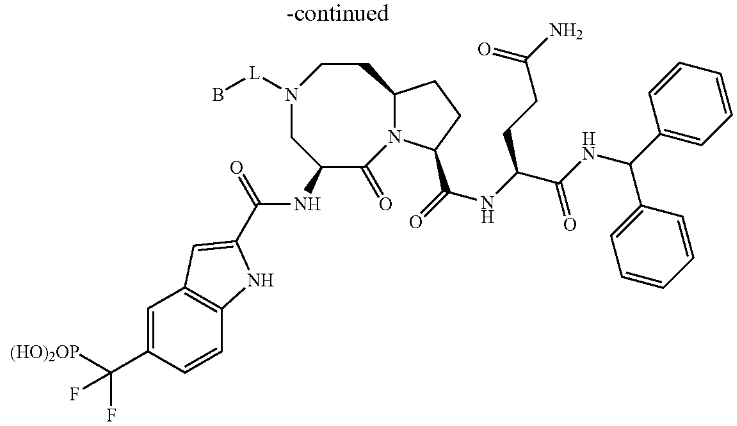

Cpd. No. 35: UPLC-MS (ESI-MS) m/z: 1278.8.

Cpd. No. 38: $^1$H NMR (400 MHz, $CD_3CN:D_2O$=1:1) δ 7.89-7.88 (m, 1H), 7.72-7.67 (m, 1H), 7.60-7.39 (m, 4H), 7.37-7.13 (m, 11H), 6.06-6.03 (m, 1H), 5.17-4.86 (m, 2H), 4.47-4.19 (m, 5H), 3.95-3.53 (m, 3H), 3.38-3.27 (m, 1H), 2.90-2.67 (m, 2H), 2.57-2.01 (m, 11H), 1.93-1.20 (m, 17H). UPLC-MS (ESI-MS) m/z: calculated for $C_{62}H_{70}F_2N_9O_{12}P^{2+}$ 600.74, found $[M+2H]^{2+}$ 600.88.

Cpd. No. 47: UPLC-MS (ESI-MS) m/z: 1158.9.

Cpd. No. 50: $^1$H NMR (400 MHz, $CD_3CN:D_2O$=1:1) δ 7.90-7.88 (m, 1H), 7.69-7.41 (m, 4H), 7.41-7.07 (m, 12H), 6.07-6.03 (m, 1H), 5.13-4.90 (m, 2H), 4.51-4.18 (m, 5H), 3.99-3.55 (m, 3H), 3.36-3.27 (m, 1H), 3.01-2.02 (m, 13H), 1.91-1.09 (m, 15H). UPLC-MS (ESI-MS) m/z: calculated for $C_{59}H_{67}F_2N_9O_{12}P^+$ 1162.46, found $[M+H]^+$ 1162.44.

Cpd. No. 51: $^1$H NMR (400 MHz, $CD_3CN:D_2O$=1:1) δ 7.99-7.81 (m, 1H), 7.76-7.43 (m, 4H), 7.43-7.00 (m, 12H), 6.06-6.03 (m, 1H), 5.19-4.88 (m, 2H), 4.45-4.18 (m, 5H), 3.95-3.65 (m, 3H), 3.37-3.28 (m, 1H), 3.02-1.99 (m, 14H), 1.93-1.51 (m, 8H). UPLC-MS (ESI-MS) m/z: calculated for $C_{58}H_{61}F_2N_9O_{12}P^+$ 1144.41, found $[M+H]^+$ 1144.45.

Cpd. No. 52: $^1$H NMR (400 MHz, $CD_3CN:D_2O$=1:1) δ 7.99-7.79 (m, 1H), 7.78-7.43 (m, 4H), 7.42-6.93 (m, 12H), 6.09-5.98 (m, 1H), 5.11-4.89 (m, 2H), 4.50-4.24 (m, 5H), 3.91-3.15 (m, 4H), 2.86-2.47 (m, 6H), 2.42-1.99 (m, 8H), 1.93-1.45 (m, 6H). UPLC-MS (ESI-MS) m/z: calculated for $C_{57}H_{60}F_2N_9O_{12}P^{2+}$ 565.71, found $[M+H]^{2+}$ 565.96.

Cpd. No. 56: $^1$H NMR (400 MHz, $CD_3CN:D_2O$=1:1) 7.89-7.87 (m, 1H), 7.61-7.41 (m, 4H), 7.38-7.08 (m, 12H), 6.06-6.03 (m, 1H), 5.13-4.90 (m, 2H), 4.50-4.18 (m, 5H), 3.97-3.50 (m, 3H), 3.41-3.33 (m, 1H), 3.26-3.30 (m, 2H), 2.90-2.65 (m, 2H), 2.56-2.00 (m, 9H), 1.92-1.84 (m, 2H), 1.73-1.55 (m, 7H), 1.42-1.21 (m, 4H). UPLC-MS (ESI-MS) m/z: calculated for $C_{57}H_{60}F_2N_9O_{12}P^{2+}$ 565.71, found $[M+H]^{2+}$ 582.65.

Cpd. No. 67: UPLC-MS (ESI-MS) m/z: 1184.7.

Cpd. No. 68: $^1$H NMR (400 MHz, $CD_3CN:D_2O$=1:1) δ 7.99-7.87 (m, 1H), 7.73-7.41 (m, 5H), 7.40-6.99 (m, 11H), 6.07-6.04 (m, 1H), 5.12-4.91 (m, 2H), 4.46-4.21 (m, 5H), 3.98-3.53 (m, 3H), 3.34-3.26 (m, 1H), 2.88-2.68 (m, 2H), 2.57-2.06 (m, 10H), 1.90-1.21 (m, 14H). UPLC-MS (ESI-MS) m/z: calculated for $C_{60}H_{66}F_2N_9O_{12}P^{2+}$ 586.73, found $[M+2H]^{2+}$ 586.95.

Example 10

Synthesis of ((2-(((5S,8S,10aR)-8-(((S)-5-amino-1-(benzhydrylamino)-1,5-dioxopentan-2-yl)carbamoyl)-3-(((6-(2-(2,6-dioxopiperidin-3-yl)-1-oxoisoindolin-4-yl)hex-5-yn-1-yl)oxy)carbonyl)-6-oxodecahydropyrrolo[1,2-a][1,5]diazocin-5-yl)carbamoyl)-1H-indol-5-yl)difluoromethyl)phosphonic Acid (Cpd. No. 69)

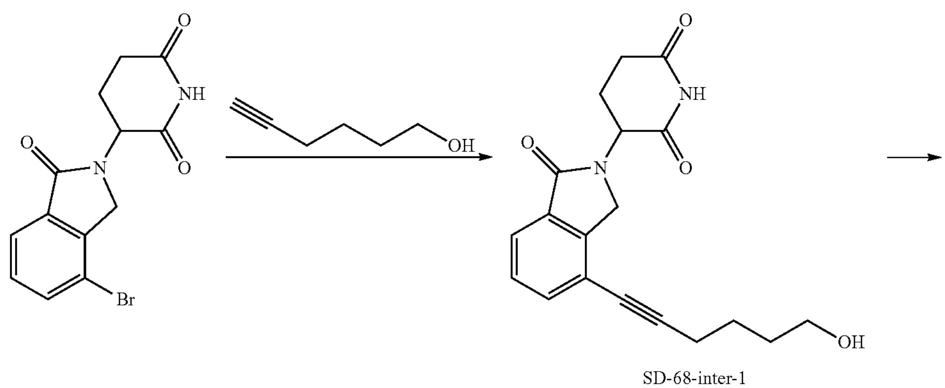

SD-68-inter-1

-continued
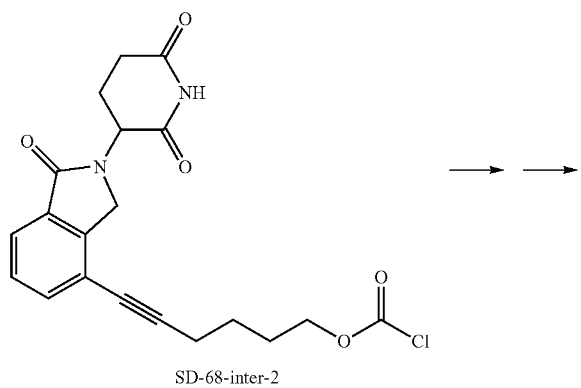
SD-68-inter-2
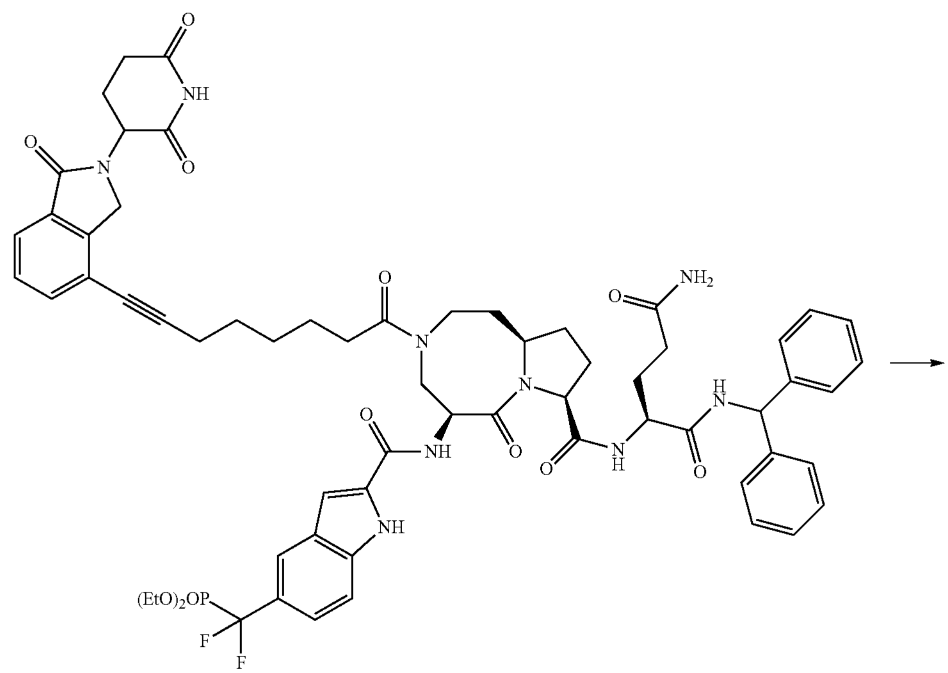
Cpd. No. 69E

-continued

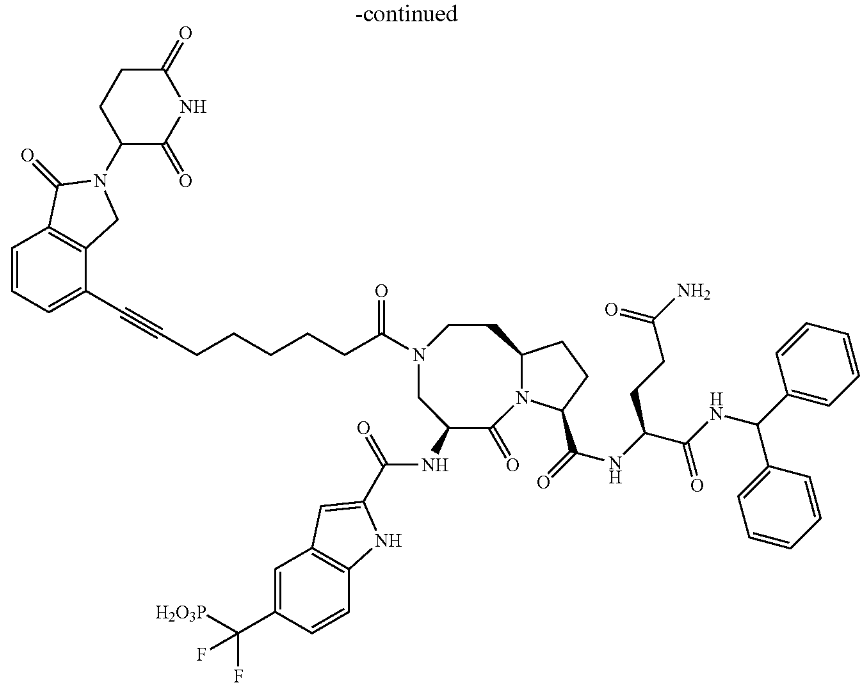

Cpd. No. 69

Cpd. No. 69: Cpd. No. 69E was made using the same method as for 9-145. See EXAMPLE 8. A solution of SD-68-inter-1 (1.1 mmol) in dichloromethane (5 mL) was cooled to 0° C. and a solution of triphosgene (0.5 mmol) in dichloromethane (3 mL) was added dropwise. The resultant solution was stirred for 10 min before pyridine (0.09 ml, 1.1 mmol) was added dropwise. The resultant solution was stirred for 10 min at 0° C. and then the reaction was poured in water (10 mL). The product was extracted with dichloromethane (3×10 mL) and the combined organic phase was washed with brine (20 mL), dried over $Na_2SO_4$ and concentrated under reduced pressure providing SD-68-inter-2 that was used for the next step without further purification. One equivalent of triethylamine (1 mmol) and Cpd. No. 241 (1 mmol) was added dropwise to a solution of a SD-68-inter-2 (1 mmol) in 5 mL of $CH_2Cl_2$ cooled with an ice bath. The reaction mixture was allowed to warm to room temperature and stirred for 2 h. The solution was washed with brine, and the organic layer was dried over $Na_2SO_4$, then concentrated to afford SD-68-inter-3. SD-68-inter-3 was transformed to Cpd. No. 69 by using the same method as for Cpd. No. 36. $^1$H NMR (400 MHz, $CD_3CN:D_2O$=1:1) δ 7.90 (s, 1H), 7.72 (d, J=7.5 Hz, 1H), 7.65-7.39 (m, 4H), 7.38-6.99 (m, 11H), 6.05-6.03 (m, 1H), 5.12-4.90 (m, 2H), 4.46-4.16 (m, 6H), 4.07-3.97 (m, 1H), 3.68-3.31 (m, 4H), 2.86-2.69 (m, 2H), 2.56-1.98 (m, 10H), 1.90-1.43 (m, 8H). UPLC-MS (ESI-MS) m/z: calculated for $C_{58}H_{63}F_2N_9O_{13}P^{2+}$ 580.71, found $[M+H]^{2+}$ 581.11.

Example 11

Synthesis of ((2-(((5S,8S,10aR)-8-(((S)-5-amino-1-(benzhydrylamino)-1,5-dioxopentan-2-yl)carbamoyl)-3-((6-(2-(2,6-dioxopiperidin-3-yl)-1-oxoisoindolin-4-yl)hex-5-yn-1-yl)carbamoyl)-6-oxodecahydropyrrolo[1,2-a][1,5]diazocin-5-yl)carbamoyl)-1H-indol-5-yl)difluoromethyl)phosphonic Acid (Cpd. No. 70)

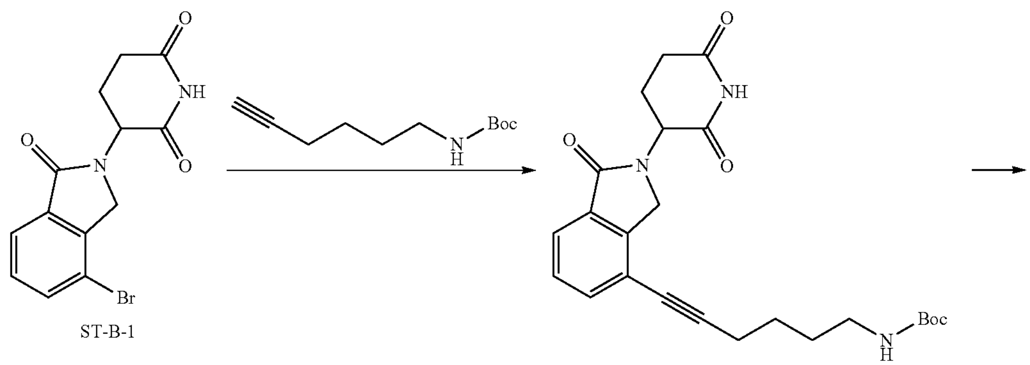

ST-B-1

-continued
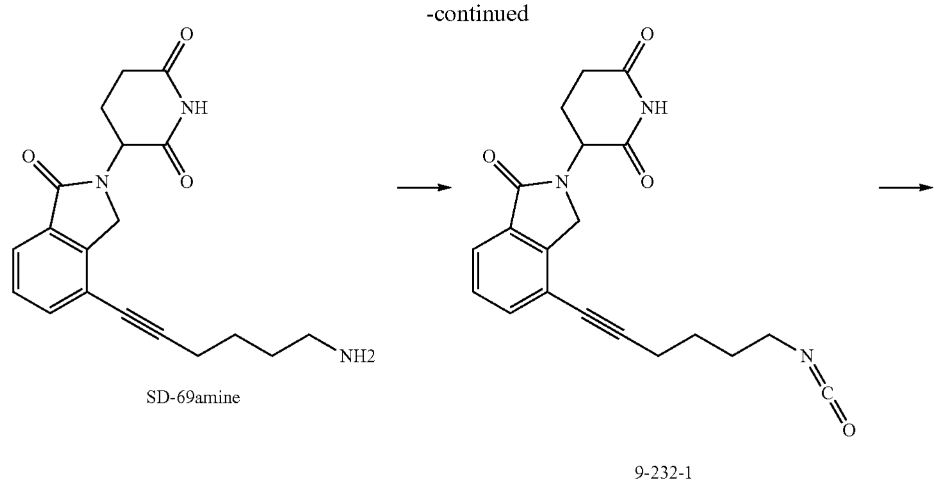
SD-69amine
9-232-1
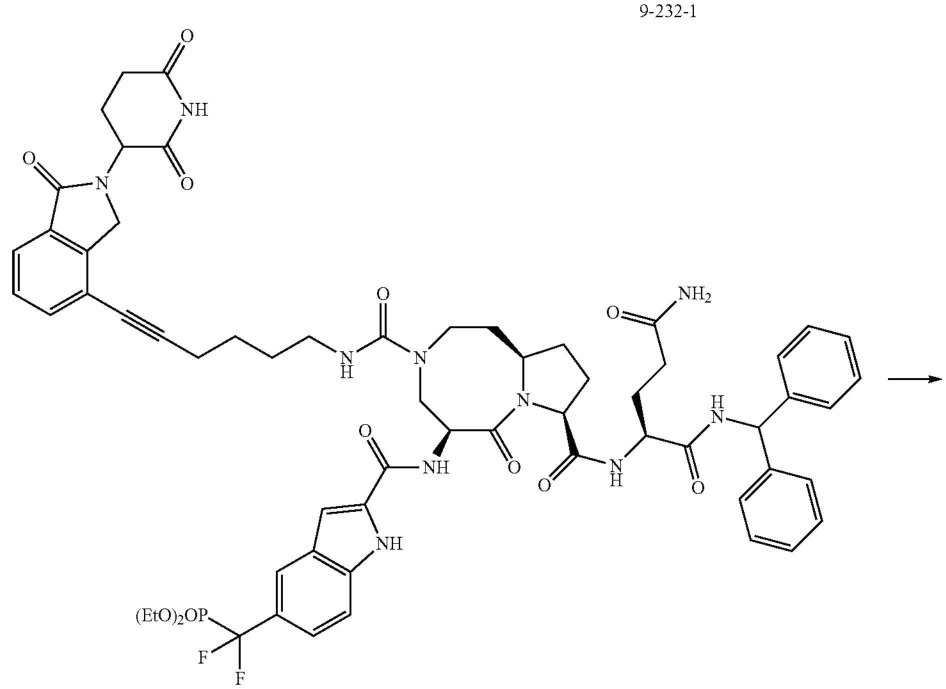
Cpd. No. 70E
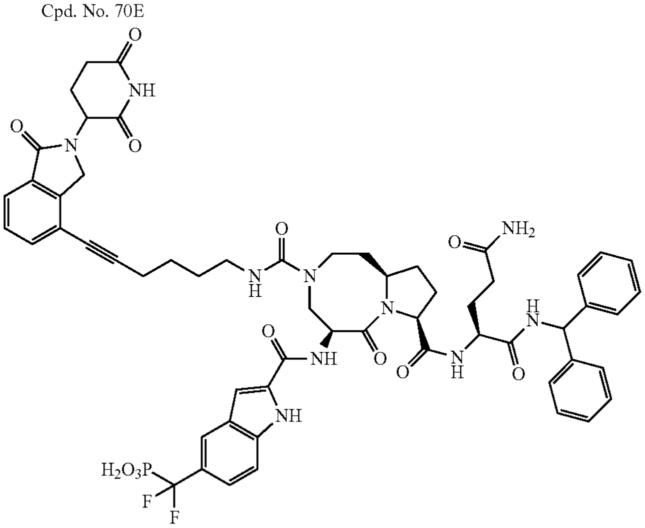
Cpd. No. 70

SD-69amine: Trimethylamine (5 mL) was added to a mixture of compound ST-B-1 (0.5 g, 1.54 mmol, 1 equiv.), N-Boc-hex-5-yn-1-amine (0.31 g, 1.54 mmol, 1 equiv.), CuI (59 mg, 0.31 mmol, 0.2 equiv) and $Pd(PPh_3)_3Cl_2$ (109 mg, 0.15 mmol, 0.1 equiv) in DMF (5 mL). The resulting mixture was purged and refilled with argon three times and stirred at 70-80° C. for 3 h under Argon. The reaction mixture was then cooled to room temperature and evaporated to remove most of the solvent. The residue was purified by HPLC and the yielded product was dissolved in DCM (10 mL) before adding TFA (2 mL). The reaction was stirred at room temperature for 3 h and the content was evaporated under reduced pressure to yield SD-69amine (373 mg, 71% over two steps). $^1H$ NMR (400 MHz, MeOD) δ 7.77 (dd, J=7.6, 0.9 Hz, 1H), 7.63 (dd, J=7.7, 1.0 Hz, 1H), 7.52 (t, J=7.6 Hz, 1H), 5.19 (dd, J=13.3, 5.2 Hz, 1H), 4.62-4.33 (m, 2H), 3.09-2.99 (m, 2H), 2.93 (ddd, J=17.8, 13.5, 5.4 Hz, 1H), 2.84-2.77 (ddd, J=17.6, 4.6, 2.4 Hz, 1H), 2.59 (t, J=6.8 Hz, 2H), 2.57-2.45 (m, 1H), 2.24-2.18 (m, 1H), 1.94-1.82 (m, 2H), 1.80-1.65 (m, 2H). $^{13}C$ NMR (101 MHz, MeOD) δ 173.21, 170.82, 169.58, 143.91, 134.47, 131.58, 128.24, 122.47, 119.32, 94.75, 76.44, 52.34, 47.51, 38.96, 30.96, 26.47, 25.14, 22.68, 18.26.

9-232-1: Triphosgene (131 mg, 0.44 mmol, ½ equiv.) was added to a mixture of SD-69amine (400 g, 0.88 mmol, 1 equiv.) and potassium hydrogen carbonate solution (260 mg, 2.6 mmmol, 3 equiv.) in dichloromethane (5 mL) and water (5 mL) at 0° C. The mixture was stirred at 0° C. for 2 hour and diluted with dichloromethane. The organic fraction was separated and the aqueous layer washed with additional dichloromethane. The combined organic fractions were dried over $Na_2SO_4$ and the solvent was removed under vacuum and the residue was used directly without purification.

Cpd. No. 70E: To a solution of crude product 9-232-1 (140 mg, 0.38 mmol, 1 equiv.) and Cpd. No. 241 (326 mg, 0.38 mmol, 1 equiv.) in DCM (10 mL) was added DIEA (0.2 mL, 1.15 mmol, 3 equiv.). The reaction was stirred at room temperature overnight and concentrated. The residue was purified by HPLC to get compound SD-69ester (218 mg, 47%). $^1H$ NMR (400 MHz, MeOD:CDCl3=1:1) δ 7.88 (s, 1H), 7.66 (t, J=8.0 Hz, 1H), 7.57-7.48 (m, 2H), 7.45 (d, J=8.8 Hz, 1H), 7.36-7.20 (m, 11H), 7.11 (d, J=4.8 Hz, 1H), 6.18 (s, 1H), 5.16-5.07 (m, 1H), 4.77-4.73 (m, 1H), 4.59-4.37 (m, 4H), 4.25-3.93 (m, 7H), 3.53-3.34 (m, 2H), 3.27-3.10 (m, 2H), 2.87-2.69 (m, 2H), 2.56 (t, J=6.7 Hz, 2H), 2.48-2.31 (m, 3H), 2.30-1.92 (m, 7H), 1.90-1.57 (m, 6H), 1.29 (td, J=7.1, 0.8 Hz, 6H). UPLC-MS (ESI-MS) m/z: calculated for $C_{62}H_{71}F_2N_{10}O_{12}P^{2+}$ 608.25, found $[M+H]^{2+}$ 607.82.

Cpd. No. 70: Cpd. No. 70 was prepared from Cpd. No. 70E in 81% yield by a similar procedure as that used for compound Cpd. No. 36 prepared from Cpd. No. 102. $^1H$ NMR (400 MHz, $CD_3CN:D_2O$=1:1) δ 7.84 (d, J=4.8 Hz, 1H), 7.63-7.55 (m, 1H), 7.53-7.42 (m, 3H), 7.41-7.01 (m, 12H), 6.07 (s, 1H), 5.04-4.92 (m, 1H), 4.78 (d, J=8.1 Hz, 1H), 4.45-4.32 (m, 4H), 4.09-4.04 (m, 1H), 3.87 (d, J=13.5 Hz, 2H), 3.43-3.22 (m, 2H), 3.15-3.09 (m, 2H), 2.88-2.63 (m, 2H), 2.51 (t, J=6.4 Hz, 2H), 2.39-2.16 (m, 4H), 2.12-2.02 (m, 4H), 1.96-1.90 (m, 1H), 1.83-1.43 (m, 7H). UPLC-MS (ESI-MS) m/z: calculated for $C_{58}H_{62}F_2N_{10}O_{12}P^+$ 1159.42, found $[M+H]^+$ 1159.44.

Example 12

Synthesis of Compounds of the Disclosure

The following Compounds of the Disclosure were prepared using Cpd. No. 241 as a synthetic intermediate according to the following general scheme.

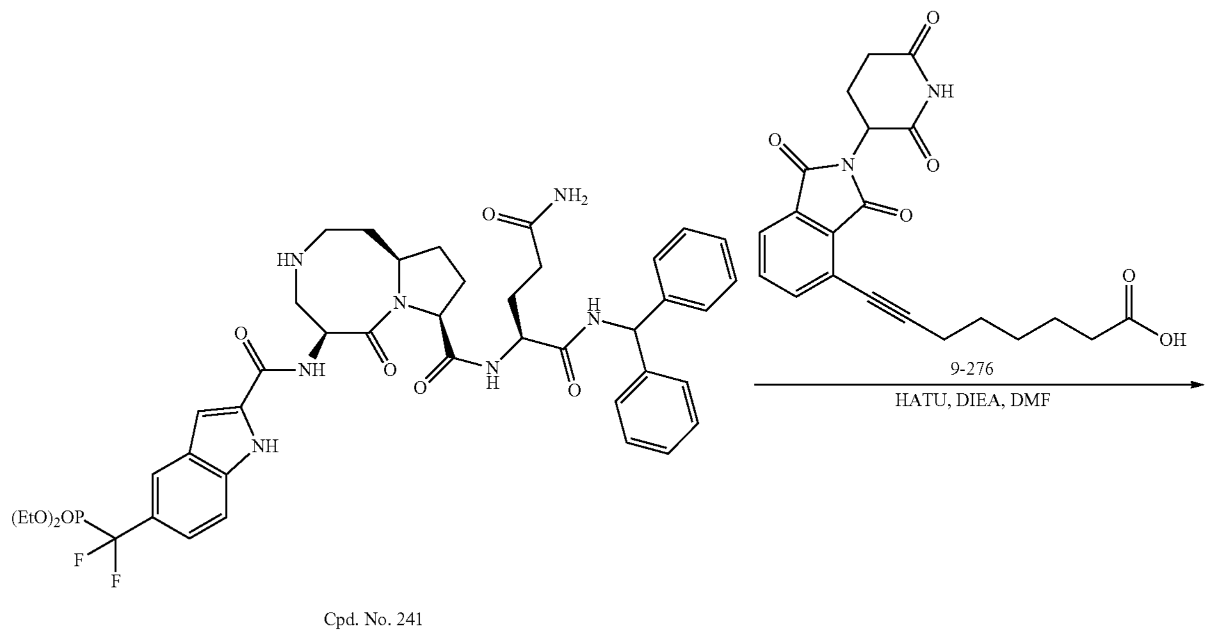

Cpd. No. 241

-continued

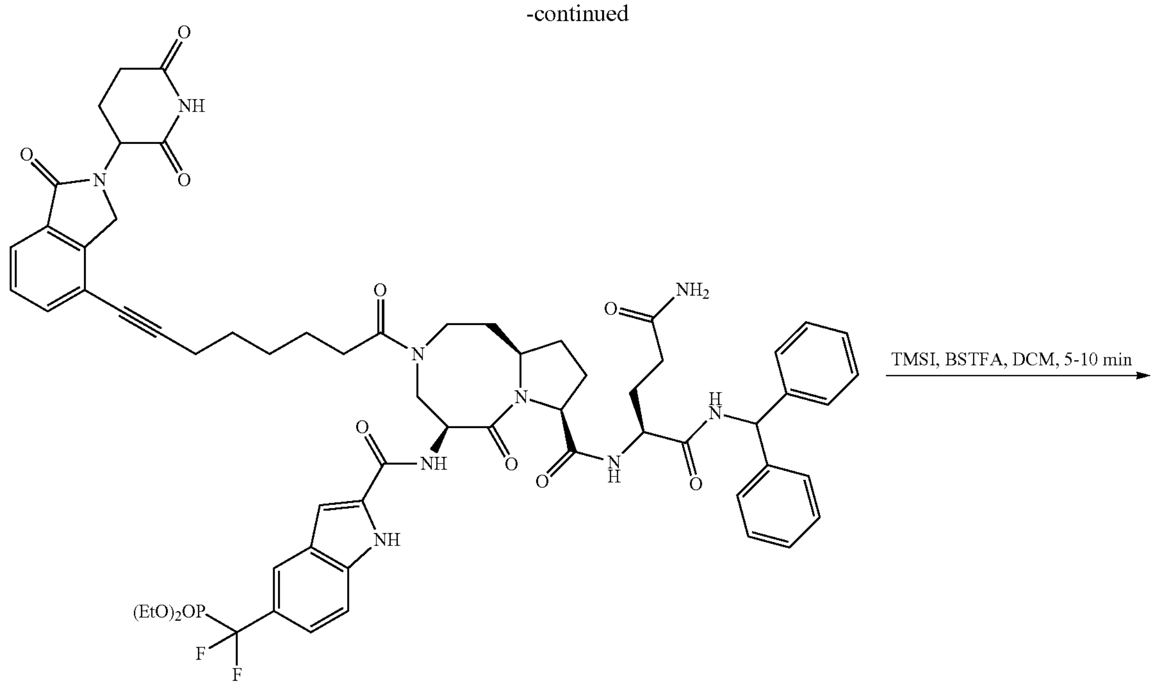

Cpd. No. 88E

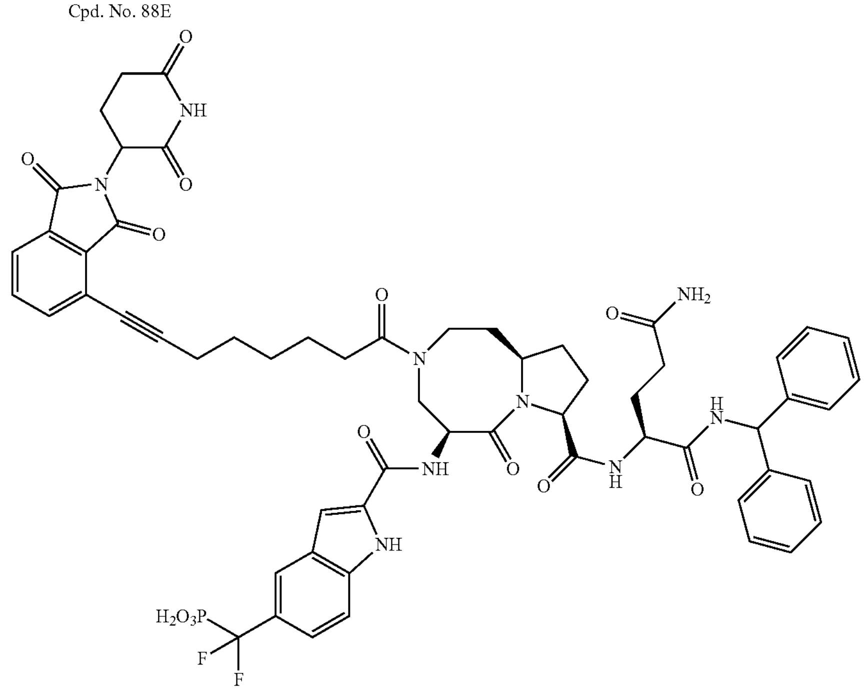

Cpd. No. 88

Cpd. No. 88: $^1H$ NMR (400 MHz, $CD_3CN:D_2O$=1:1) δ 7.89-7.85 (m, 1H), 7.76-7.65 (m, 3H), 7.57-7.41 (m, 2H), 7.38-7.08 (m, 11H), 6.06-6.03 (m, 1H), 5.13-4.84 (m, 2H), 4.35-4.21 (m, 3H), 3.3.95-3.65 (m, 3H), 3.38-3.26 (m, 1H), 2.87-2.68 (m, 2H), 2.65-2.36 (m, 5H), 2.33-2.00 (m, 6H), 1.96-1.36 (m, 11H). UPLC-MS (ESI-MS) m/z: calculated for $C_{59}H_{61}F_2N_9O_{13}P^+$ 1172.41, found $[M+H]^+$ 1172.29.

Cpd. No. 140: $^1H$ NMR (400 MHz, $CD_3CN:D_2O$=1:1) δ 7.86 (s, 1H), 7.67-7.64 (m, 1H), 7.48-7.37 (m, 4H), 7.29-7.14 (m, 11H), 6.01 (s, 1H), 5.45 (br, 1H), 5.02-4.96 (m, 1H), 4.68-4.53 (m, 2H), 4.32-4.21 (m, 3H), 3.73-3.70 (m, 1H), 3.54-3.49 (m, 2H), 3.29 (t, J=1.2 Hz, 1H), 3.14-3.08 (m, 2H), 2.82-2.64 (m, 2H), 2.38-2.15 (m, 6H), 2.14-1.95 (m, 3H), 1.93-1.23 (m, 13H). UPLC-MS calculated for $C_{59}H_{64}F_2N_8O_{11}PS$ $[M+H]^+$: 1144.45, found: 1144.50. UPLC-retention time: 3.89 min.

Cpd. No. 156: $^1H$ NMR (400 MHz, $CD_3CN:D_2O$=1:1) δ 7.89-7.78 (m, 2H), 7.71-7.60 (m, 2H), 7.50-7.34 (m, 4H), 7.27-7.13 (m, 11H), 6.01-5.96 (m, 1H), 5.05-4.88 (m, 2H), 4.37-4.21 (m, 7H), 3.75-3.29 (m, 4H), 2.82-2.70 (m, 2H), 2.65-1.94 (m, 11H), 1.93-1.65 (m, 5H). UPLC-MS calculated for $C_{60}H_{61}F_2N_{11}O_{12}P$ $[M+H]^+$: 1196.42, found: 1196.44. UPLC-retention time: 3.71 min.

Cpd. No. 157: $^1H$ NMR (400 MHz, $CD_3CN:D_2O$=1:1) δ 7.93-7.83 (m, 1H), 7.65-7.54 (m, 1H), 7.47-7.10 (m, 15H), 6.03-5.99 (m, 1H), 5.00-4.90 (m, 2H), 4.30-4.18 (m, 6H), 3.91-3.63 (m, 3H), 3.29-3.26 (m, 1H), 2.76-2.57 (m, 3H), 2.45-1.94 (m, 10H), 1.93-1.44 (m, 10H). UPLC-MS calculated for $C_{59}H_{63}F_2N_9O_{12}P$ $[M+H]^+$: 1158.43, found: 1158.48. UPLC-retention time: 4.00 min.

Cpd. No. 158: $^1H$ NMR (400 MHz, $CD_3CN:D_2O$=1:1) δ 7.95-7.82 (m, 1H), 7.68-7.61 (m, 1H), 7.53-7.09 (m, 15H), 6.03-5.99 (m, 1H), 4.99-4.90 (m, 2H), 4.31-4.15 (m, 6H), 3.93-3.64 (m, 3H), 3.29-3.28 (m, 1H), 2.78-2.69 (m, 2H), 2.57-2.13 (m, 7H), 2.03-1.94 (m, 4H), 1.92-1.47 (m, 10H). UPLC-MS calculated for $C_{59}H_{63}F_2N_9O_{12}P$ $[M+H]^+$: 1158.43, found: 1158.45. UPLC-retention time: 3.99 min.

Cpd. No. 160: $^1H$ NMR (400 MHz, $CD_3CN:D_2O$=1:1) δ 8.14-8.03 (m, 1H), 7.86-7.60 (m, 3H), 7.51-7.10 (m, 15H), 6.00-5.99 (m, 1H), 5.15-4.95 (m, 2H), 4.27-4.18 (m, 7H), 3.82-3.48 (m, 3H), 2.74-2.66 (m, 2H), 2.38-1.95 (m, 11H), 1.92-1.54 (m, 5H). UPLC-MS calculated for $C_{60}H_{61}F_2N_{11}O_{12}P$ $[M+H]^+$: 1196.42, found: 1196.28. UPLC-retention time: 3.50 min.

Cpd. No. 165: $^1H$ NMR (400 MHz, $CD_3CN:D_2O$=1:1) δ 7.84 (s, 1H), 7.70-7.68 (m, 1H), 7.55-7.41 (m, 4H), 7.29-7.13 (m, 11H), 6.02 (s, 1H), 5.14-5.02 (m, 2H), 4.44-4.13 (m, 6H), 3.64-3.52 (m, 4H), 3.27-3.15 (m, 2H), 2.83-2.61 (m, 4H), 2.45-2.02 (m, 9H), 1.92-1.49 (m, 9H), 1.20-1.05 (m, 2H). UPLC-MS calculated for $C_{61}H_{66}F_2N_{10}O_{12}P$ $[M+H]^+$: 1199.46, found: 1199.48. UPLC-retention time: 4.35 min.

Example 13

Synthesis of ((2-(((5S,8S,10aR)-8-(((S)-5-amino-1-(benzhydrylamino)-1,5-dioxopentan-2-yl)carbamoyl)-3-(8-(2-(1-methyl-2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic Acid (Cpd. No. 37)

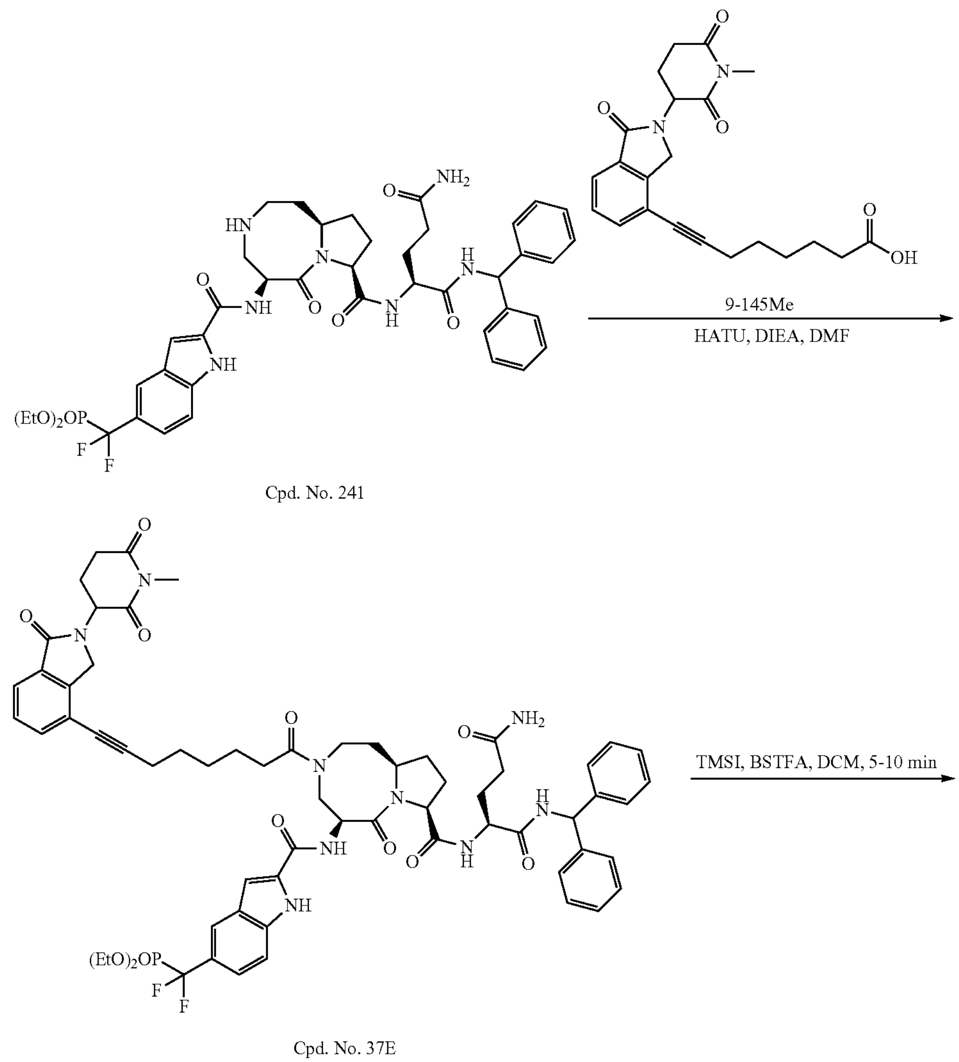

Cpd. No. 241

Cpd. No. 37E

-continued

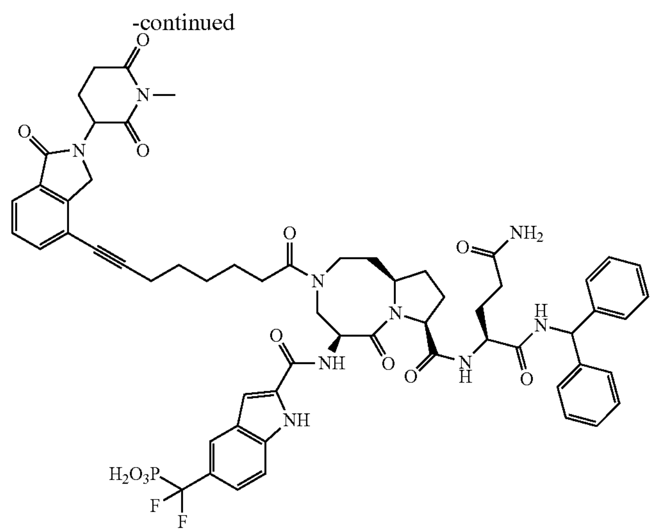

Cpd. No. 37

9-145Me: UPLC-MS (ESI-MS) m/z: calculated for $C_{22}H_{25}N_2O_5^+$ 397.18, found [M+H]+ 397.31.

Cpd. No. 37: $^1$H NMR (400 MHz, $CD_3CN:D_2O$=1:1) δ 7.88 (d, J=16.1 Hz, 1H), 7.72-7.59 (m, 1H), 7.56-7.36 (m, 4H), 7.35-7.06 (m, 11H), 6.06-6.03 (m, 1H), 5.12-4.87 (m, 2H), 4.45-4.20 (m, 5H), 3.98-3.50 (m, 3H), 3.37-3.22 (m, 1H), 3.08-2.94 (m, 3H), 2.88-2.73 (m, 2H), 2.61-2.37 (m, 4H), 2.34-1.99 (m, 7H), 1.95-1.81 (m, 2H), 1.79-1.40 (m, 9H). UPLC-MS (ESI-MS) m/z: calculated for $C_{60}H_{65}F_2N_9O_{12}P^+$ 1172.45, found $[M+H]^+$ 1172.45.

Example 14

Synthesis of Compounds of the Disclosure

The following Compounds of the Disclosure were prepared using a compound of Formula XVI, wherein $R^{26}$ is hydrogen, e.g., 9-247 (((5S,8S,10aR)-5-(5-((diethoxyphosphoryl)difluoromethyl)-1H-indole-2-carboxamido)-3-(8-(2-(2,6-dioxopiperidin-3-yl)-1-oxoisoindolin-4-yl)oct-7-ynoyl)-6-oxodecahydropyrrolo[1,2-a][1,5]diazocine-8-carbonyl)-L-glutamine), as a synthetic intermediate according to the following general scheme.

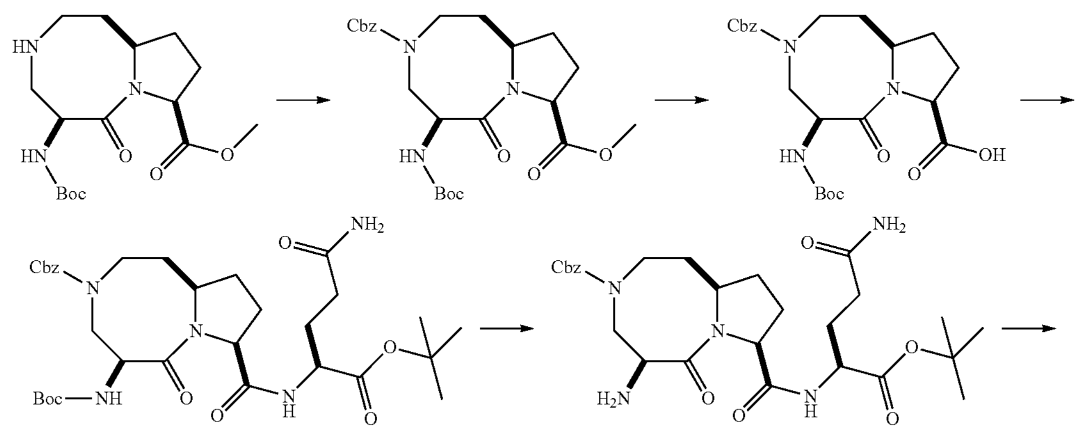

9-243

-continued
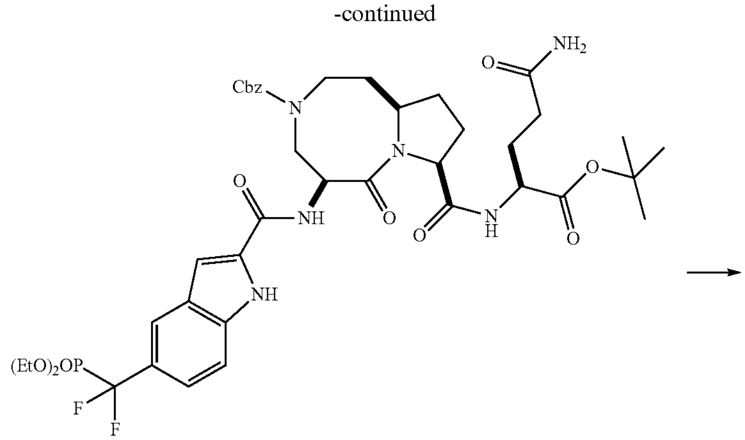
9-244
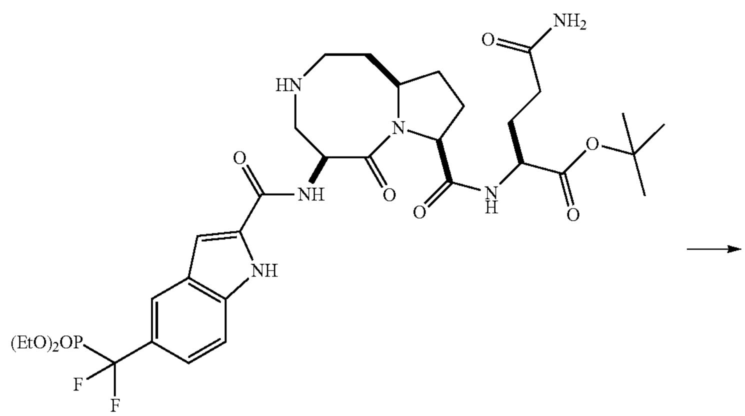
9-245amine
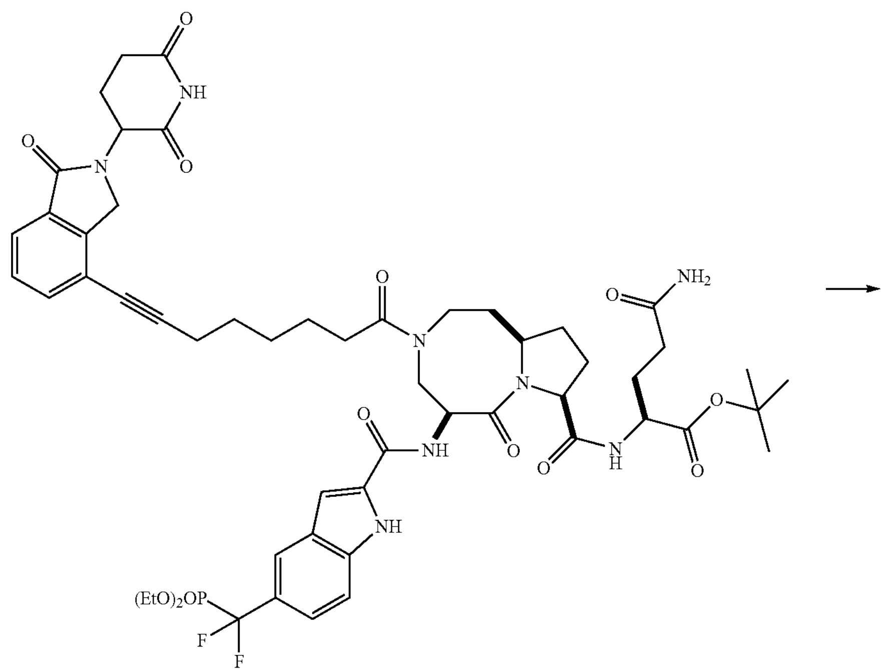

-continued

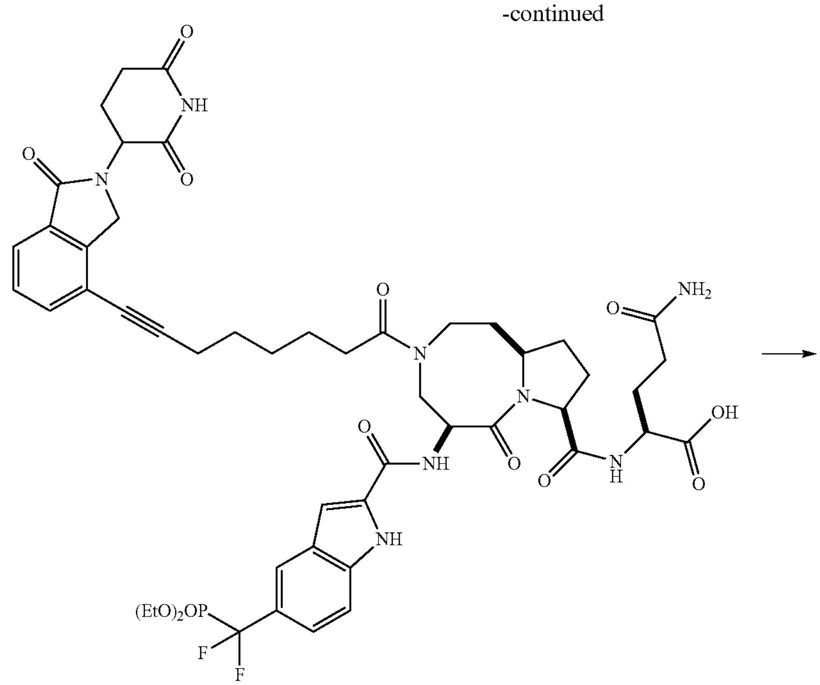

9-247

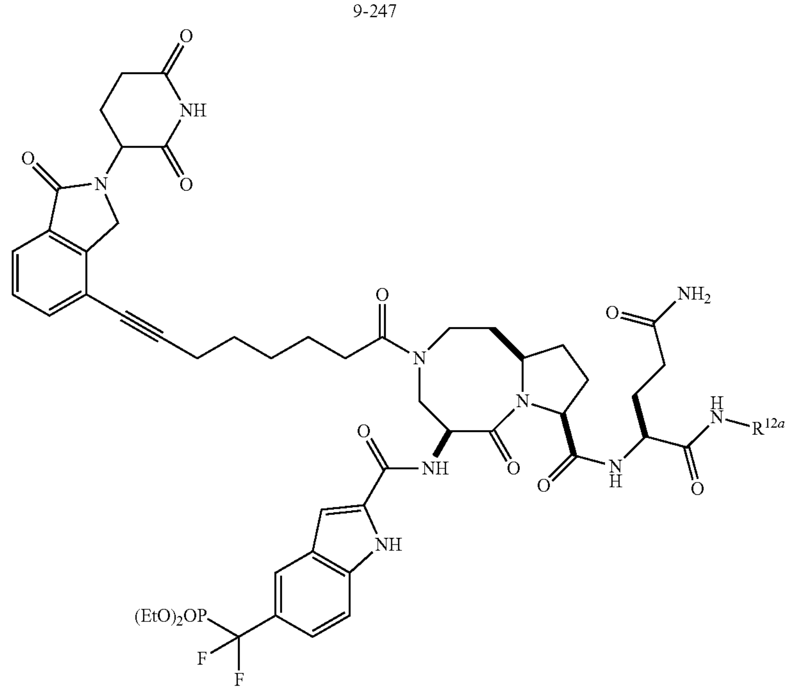

(wherein $R^{12a}$ is as defined in connection with Formula I)

9-243: $^1$H NMR (400 MHz, MeOD) δ 7.44-7.33 (m, 5H), 5.33-5.14 (m, 2H), 4.53 (t, J=8.6 Hz, 1H), 4.45-4.29 (m, 2H), 4.18-4.11 (m, 2H), 3.83-3.63 (m, 1H), 3.55-3.36 (m, 2H), 2.38 (tt, J=7.3, 6.0 Hz, 3H), 2.28-2.03 (m, 3H), 2.01-1.72 (m, 4H), 1.50-1.44 m, 9H). UPLC-MS (ESI-MS) m/z: calculated for $C_{27}H_{40}N_5O_7^+$ 546.29, found $[M+H]^+$ 546.47.

9-244: $^1$H NMR (400 MHz, MeOD) δ 7.90 (s, 1H), 7.61-7.18 (m, 8H), 5.29-5.06 (m, 3H), 4.49 (t, J=8.5 Hz, 1H), 4.39-4.30 (m, 2H), 4.26-4.08 (m, 4H), 4.01-3.44 (m, 4H), 2.52-1.62 (m, 10H), 1.50-1.43 (m, 9H), 1.29 (t, J=7.1 Hz, 6H). UPLC-MS (ESI-MS) m/z: calculated for $C_{41}H_{54}F_2N_6O_{11}P^+$ 875.36, found $[M+H-]^+$ 819.59.

9-245: $^1$H NMR (400 MHz, MeOD) δ 7.91 (s, 1H), 7.56 (d, J=8.7 Hz, 1H), 7.46 (d, J=8.8 Hz, 1H), 7.33 (d, J=0.6 Hz, 1H), 5.64 (dd, J=12.1, 5.6 Hz, 1H), 4.84-4.67 (m, 2H), 4.39 (dd, J=9.2, 5.3 Hz, 1H), 4.29-4.04 (m, 4H), 3.79-3.50 (m, 3H), 3.43 (t, J=12.4 Hz, 1H), 2.53-2.41 (m, 1H), 2.37 (t,

J=7.4 Hz, 2H), 2.28-1.80 (m, 7H), 1.48 (s, 9H), 1.36-1.23 (m, 6H). UPLC-MS (ESI-MS) m/z: calculated for $C_{33}H_{48}F_2N_6O_9P^+$ 741.32, found $[M+H]^+$ 741.44.

9-247: $^1$H NMR (400 MHz, MeOD) δ 7.91 (s, 1H), 7.76-7.67 (m, 1H), 7.64-7.53 (m, 2H), 7.51-7.40 (m, 2H), 7.33-7.24 (m, 1H), 5.27-5.07 (m, 2H), 4.59-4.40 (m, 4H), 4.35-4.25 (m, 1H), 4.25-4.09 (m, 4H), 4.02-3.99 (m, 1H), 3.82-3.54 (m, 3H), 2.95-2.47 (m, 7H), 2.45-1.85 (m, 10H), 1.83-1.49 (m, 7H), 1.30 (t, J=7.1 Hz, 6H). UPLC-MS (ESI-MS) m/z: calculated for $C_{50}H_{60}F_2N_8O_{13}P^+$ 1049.40, found $[M+H]^+$ 1049.53.

Cpd. No. 64: $^1$H NMR (400 MHz, $CD_3CN$:$D_2O$=1:1) δ 7.98-7.87 (m, 1H), 7.79-7.45 (m, 4H), 7.44-7.35 (m, 1H), 7.35-6.92 (m, 6H), 5.12-4.93 (m, 2H), 4.46-4.21 (m, 6H), 3.94-3.28 (m, 5H), 2.81-2.73 (m, 2H), 2.63-1.99 (m, 12H), 1.92-1.38 (m, 10H). UPLC-MS (ESI-MS) m/z: $[M+H]^+$ 1082.4.

Cpd. No. 65: $^1$H NMR (400 MHz, $CD_3CN$:D2O=1:1) δ 7.97-7.82 (m, 1H), 7.81-6.96 (m, 6H), 5.16-4.93 (m, 2H), 4.49-4.18 (m, 5H), 3.95-3.18 (m, 4H), 3.00-1.99 (m, 14H), 1.95-1.08 (m, 13H). UPLC-MS (ESI-MS) m/z: $[M+H]^+$ 1006.5.

Cpd. No. 66: UPLC-MS (ESI-MS) m/z: $[M+2H]^{2+}$ 475.4.

Cpd. No. 54: $^1$H NMR (400 MHz, $CD_3CN$) δ 7.90-7.86 (m, 1H), 7.73-7.60 (m, 1H), 7.55-7.35 (m, 4H), 7.31-6.92 (m, 9H), 6.06-6.04 (m, 1H), 5.13-4.93 (m, 2H), 4.48-4.19 (m, 5H), 3.98-3.56 (m, 3H), 3.39-3.31 (m, 1H), 2.89-2.66 (m, 2H), 2.62-2.01 (m, 11H), 1.95-1.35 (m, 11H). UPLC-MS (ESI-MS) m/z: $[M+2H]^{2+}$ 598.1.

Cpd. No. 60: $^1$H NMR (400 MHz, $CD_3CN$) δ 7.90-7.85 (m, 1H), 7.77-7.17 (m, 8H), 7.13-6.94 (m, 6H), 6.09-6.06 (m, 1H), 5.22-4.83 (m, 2H), 4.47-4.19 (m, 5H), 3.94-3.57 (m, 3H), 3.35-3.27 (m, 1H), 2.85-2.68 (m, 2H), 2.63-2.02 (m, 11H), 1.92-1.44 (m, 11H). UPLC-MS (ESI-MS) m/z: $[M+2H]^{2+}$ 598.1.

Cpd. No. 71: UPLC-MS (ESI-MS) m/z: $[M+2H]^{2+}$ 555.4.

Cpd. No. 72: UPLC-MS (ESI-MS) m/z: 1122.5.

Cpd. No. 73: UPLC-MS (ESI-MS) m/z: 1152.4.

Cpd. No. 74: UPLC-MS (ESI-MS) m/z: $[M+2H]^{2+}$ 583.3.

Cpd. No. 75: UPLC-MS (ESI-MS) m/z: $[M+2H]^{2+}$ 555.0.

Cpd. No. 76: UPLC-MS (ESI-MS) m/z: $[M+2H]^{2+}$ 554.9.

Cpd. No. 77: UPLC-MS (ESI-MS) m/z: $[M+2H]^{2+}$ 570.5.

Cpd. No. 78: UPLC-MS (ESI-MS) m/z: $[M+2H]^{2+}$ 561.7.

Cpd. No. 79: UPLC-MS (ESI-MS) m/z: $[M+2H]^{2+}$ 562.0.

Cpd. No. 80: UPLC-MS (ESI-MS) m/z: 1124.4.

Cpd. No. 81: UPLC-MS (ESI-MS) m/z: 1124.6.

Cpd. No. 82: UPLC-MS (ESI-MS) m/z: 1108.7.

Cpd. No. 83: UPLC-MS (ESI-MS) m/z: 1096.5.

Cpd. No. 84: UPLC-MS (ESI-MS) m/z: 1097.3.

Cpd. No. 91: UPLC-MS (ESI-MS) m/z: 1106.8.

Example 15

Synthesis of Compounds of the Disclosure

The following Compounds of the Disclosure were prepared using a compound of Formula XVI, wherein $R^{26}$ is hydrogen, e.g., SD-2-inter (((5S,8S,10aR)-5-(5-((diethoxyphosphoryl)difluoromethyl)-1H-indole-2-carboxamido)-3-methyl-6-oxodecahydropyrrolo[1,2-a][1,5]diazocine-8-carbonyl)-L-glutamine), as a synthetic intermediate according to the following general scheme

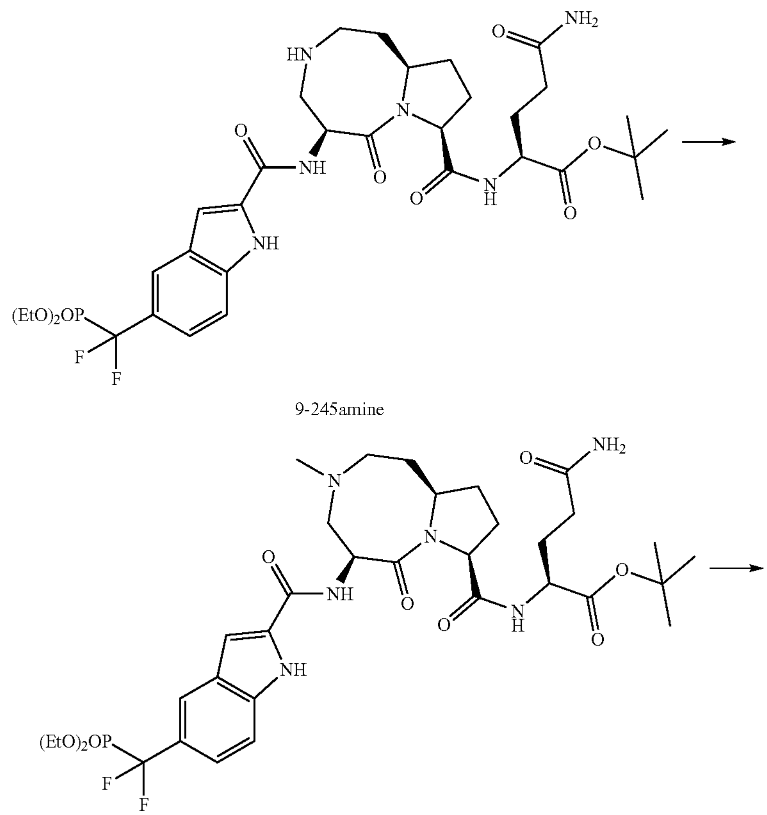

9-245amine

-continued

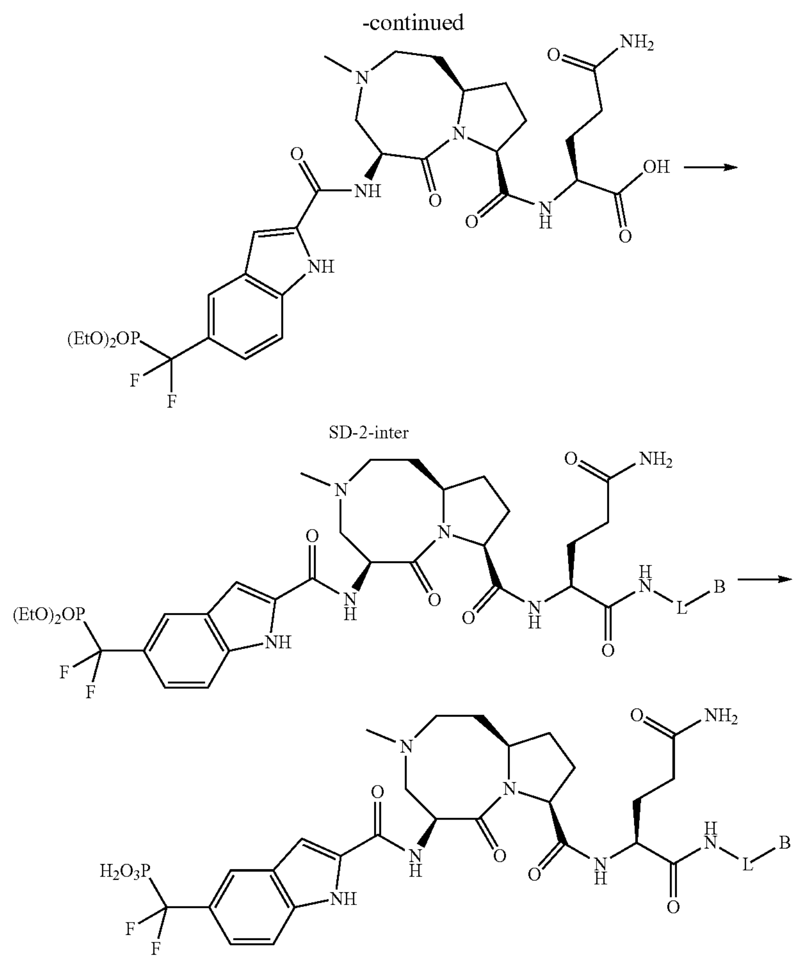

SD-2-inter

SD-2inter: Compound 9-245amine (1 mmol) and a formaldehyde solution 37 wt. % in $H_2O$ (4 mmol) were mixed in 1,2-dichloroethane (25 mL) and then treated with sodium triacetoxyborohydride (2 mmol). The mixture was stirred at room temperature for 3 h. Then the reaction mixture was quenched by adding 1N NaOH, and concentrated. The resultant crud product was dissolved in DCM (20 mL) and treated with TFA (5 mL) and the resultant solution was stirred for 5 h until the starting material disappeared. The reaction was concentrated to give product SD-2inter. UPLC-MS (ESI-MS) m/z: 699.1.

Cpd. No. 2: UPLC-MS (ESI-MS) m/z: 1101.9.
Cpd. No. 9: UPLC-MS (ESI-MS) m/z: 950.7.
Cpd. No. 10: UPLC-MS (ESI-MS) m/z: 954.5.
Cpd. No. 11: UPLC-MS (ESI-MS) m/z: 1034.4.
Cpd. No. 12: UPLC-MS (ESI-MS) m/z: 1038.5.
Cpd. No. 13: UPLC-MS (ESI-MS) m/z: 1060.5.
Cpd. No. 14: UPLC-MS (ESI-MS) m/z: 1094.8.
Cpd. No. 15: UPLC-MS (ESI-MS) m/z: 1052.9.
Cpd. No. 16: UPLC-MS (ESI-MS) m/z: 1011.4.
Cpd. No. 17: UPLC-MS (ESI-MS) m/z: 1059.7.
Cpd. No. 18: UPLC-MS (ESI-MS) m/z: 1142.6.
Cpd. No. 19: UPLC-MS (ESI-MS) m/z: 1067.5.
Cpd. No. 20: UPLC-MS (ESI-MS) m/z: 1150.6.
Cpd. No. 24: UPLC-MS (ESI-MS) m/z: 1101.6.
Cpd. No. 25: UPLC-MS (ESI-MS) m/z: 1124.6.
Cpd. No. 26: UPLC-MS (ESI-MS) m/z: 1006.0.
Cpd. No. 27: UPLC-MS (ESI-MS) m/z: 1103.7.
Cpd. No. 32: UPLC-MS (ESI-MS) m/z: $[M+H]^{2+}$ 617.9.
Cpd. No. 33: UPLC-MS (ESI-MS) m/z: 1153.7.
Cpd. No. 34: UPLC-MS (ESI-MS) m/z: 1153.7.
Cpd. No. 39: UPLC-MS (ESI-MS) m/z: 1111.9.
Cpd. No. 40: UPLC-MS (ESI-MS) m/z: 1111.9.
Cpd. No. 41: UPLC-MS (ESI-MS) m/z: 1139.7.
Cpd. No. 42: UPLC-MS (ESI-MS) m/z: 1167.5.
Cpd. No. 43: UPLC-MS (ESI-MS) m/z: $[M+H]^{2+}$ 601.6.
Cpd. No. 44: UPLC-MS (ESI-MS) m/z: $[M+H]^{2+}$ 601.5.

Example 16

Synthesis of ((2-(((5S,8S,10aR)-8-(((2S)-5-amino-1-(((1S)-2-((11-(2-(2,6-dioxopiperidin-3-yl)-1-oxoisoindolin-4-yl)undec-10-yn-1-yl)oxy)-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic Acid (Cpd. No. 21) and Related Compounds

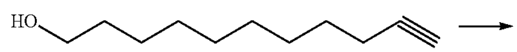

-continued
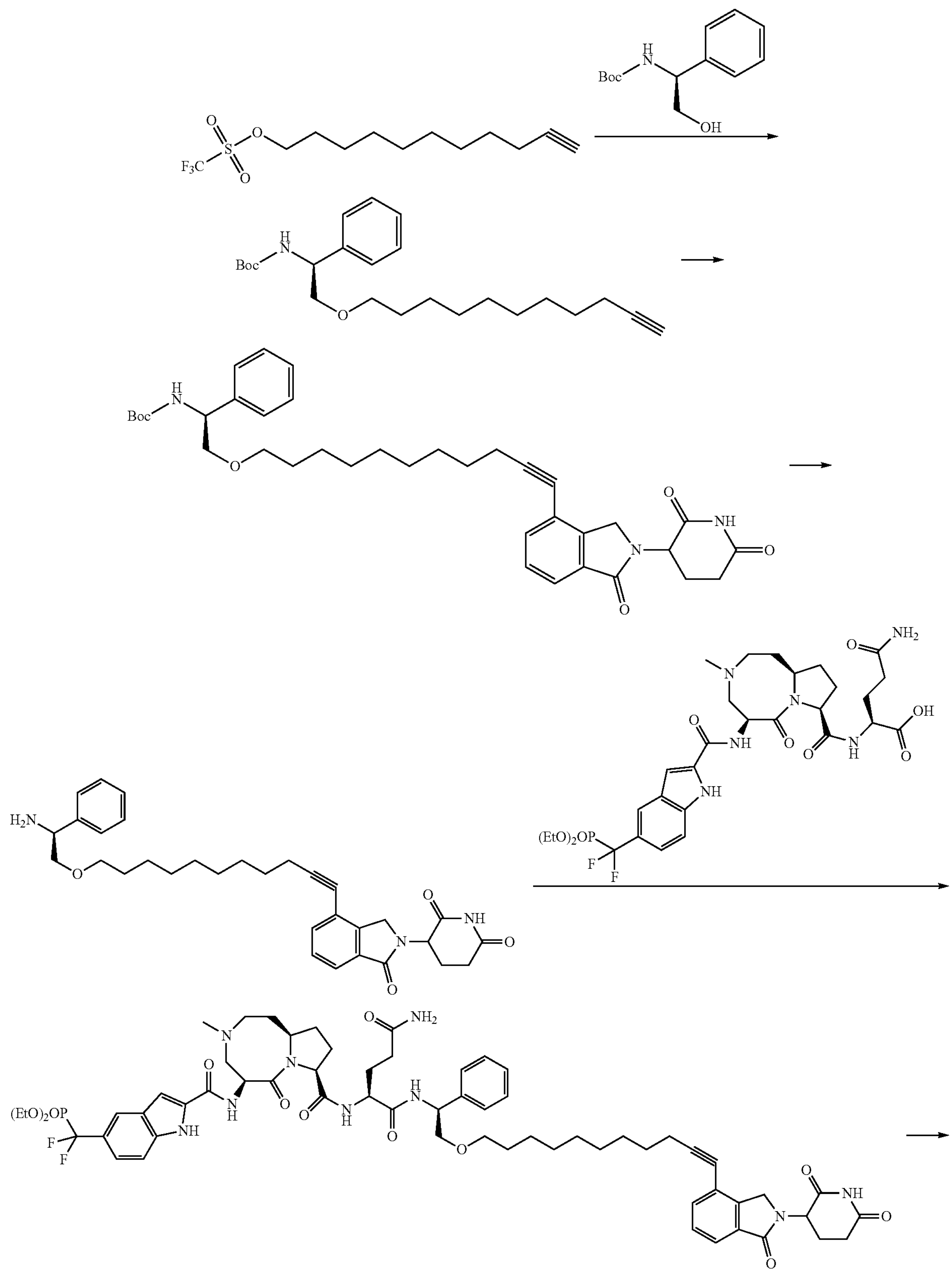

-continued

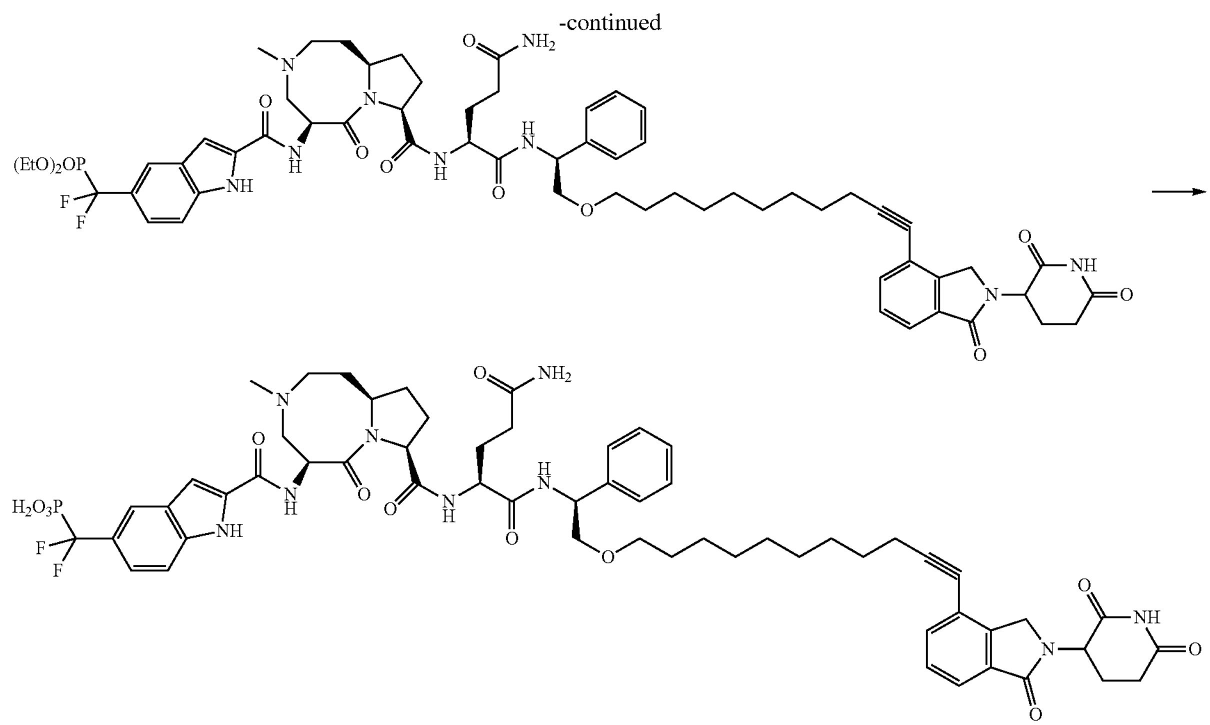

Cpd. No. 21

Cpd. No. 21: UPLC-MS (ESI-MS) m/z: 1154.5.
Cpd. No. 23: UPLC-MS (ESI-MS) m/z: 1154.7.
Cpd. No. 28: UPLC-MS (ESI-MS) m/z: 1168.9.
Cpd. No. 29: UPLC-MS (ESI-MS) m/z: 1070.7.
Cpd. No. 30: UPLC-MS (ESI-MS) m/z: 1098.5.
Cpd. No. 31: UPLC-MS (ESI-MS) m/z: 1126.8.

Example 17

Synthesis of ((2-(((3S,6S,10aS)-3-(((16S)-19-amino-1-((2-(2,6-dioxopiperidin-3-yl)-1,3-dioxoisoindolin-4-yl)amino)-15,19-dioxo-4,7,10-trioxa-14-azanonadecan-16-yl)carbamoyl)-5-oxodecahydropyrrolo[1,2-a]azocin-6-yl)carbamoyl)-1H-indol-5-yl)difluoromethyl)phosphonic Acid (Cpd. No. 1) and Related Compounds

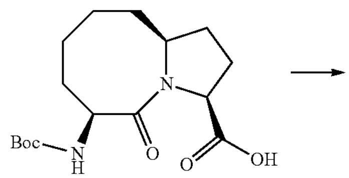

-continued

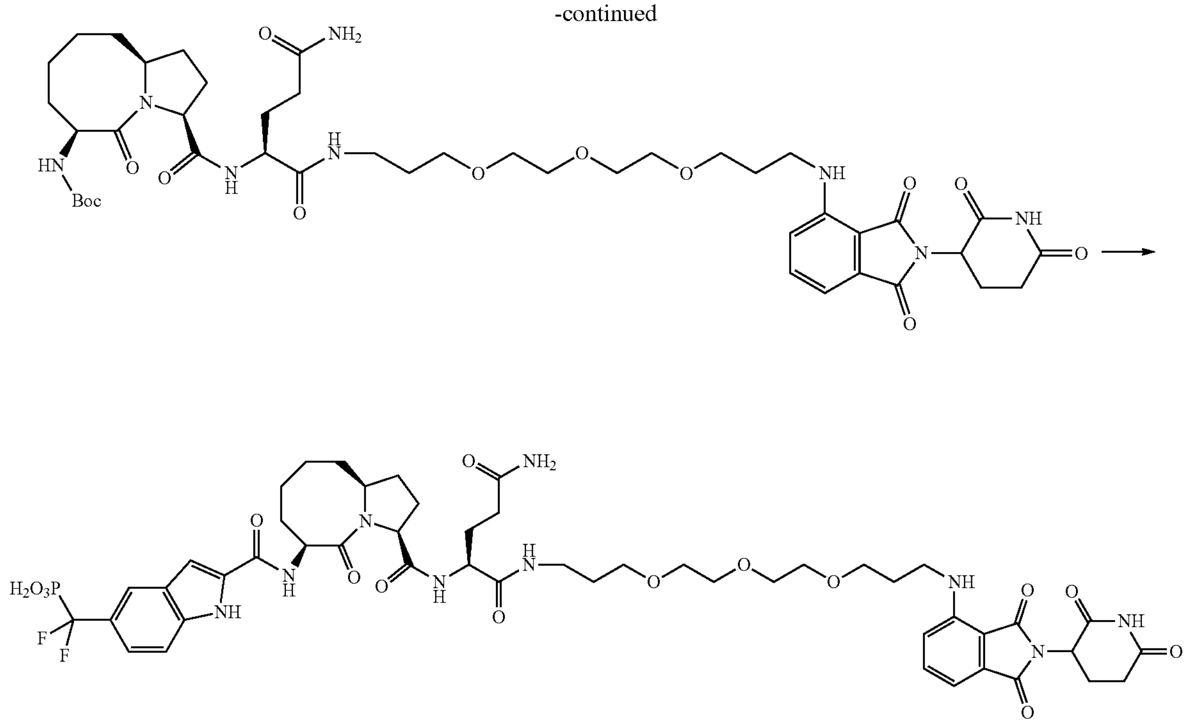

Cpd. No. 1

Cpd. No. 1: UPLC-MS (ESI-MS) m/z: 1186.7.
Cpd. No. 3: UPLC-MS (ESI-MS) m/z: 1044.9.
Cpd. No. 4: UPLC-MS (ESI-MS) m/z: 1045.5.
Cpd. No. 5: UPLC-MS (ESI-MS) m/z: 1016.8.
Cpd. No. 6: UPLC-MS (ESI-MS) m/z: 1017.4.
Cpd. No. 7: UPLC-MS (ESI-MS) m/z: 1044.8.
Cpd. No. 8: UPLC-MS (ESI-MS) m/z: 1045.9.
Cpd. No. 58: UPLC-MS (ESI-MS) m/z: 1159.8.

Example 18

Synthesis of ((2-(((5S,8S,10aR)-8-(((S)-1-(benzhydrylamino)-3-(carbamoyloxy)-1-oxopropan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indol-5-yl)difluoromethyl)phosphonic Acid (Cpd. No. 62) and Related Compounds

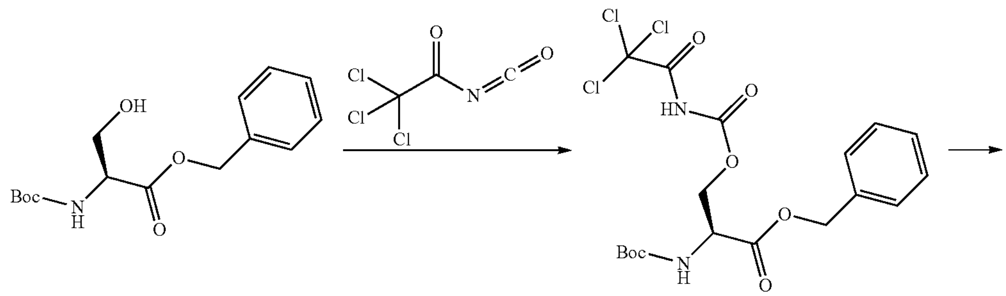

-continued
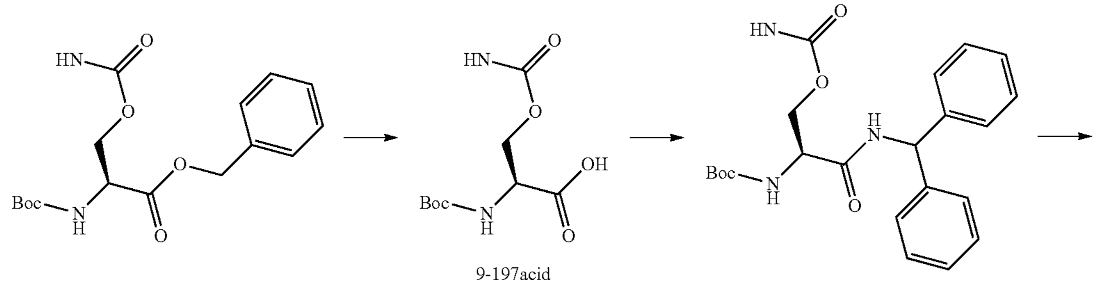
9-197acid
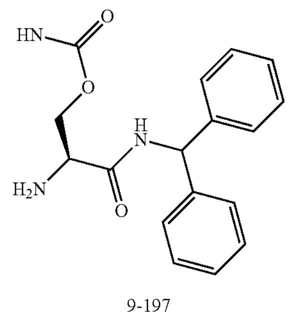
9-197
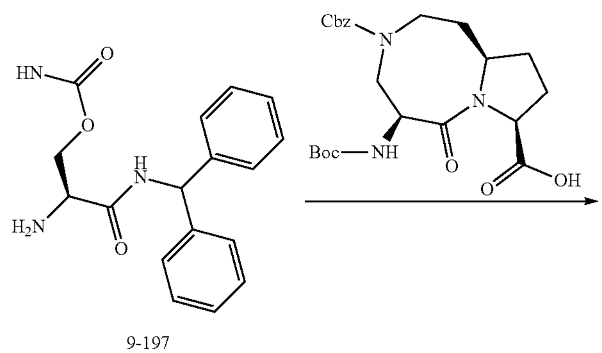
9-197
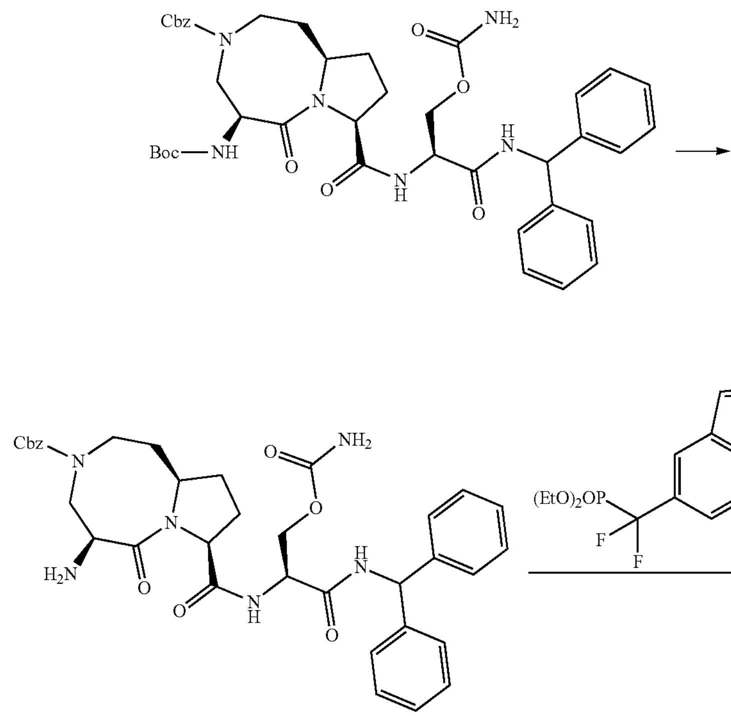

-continued
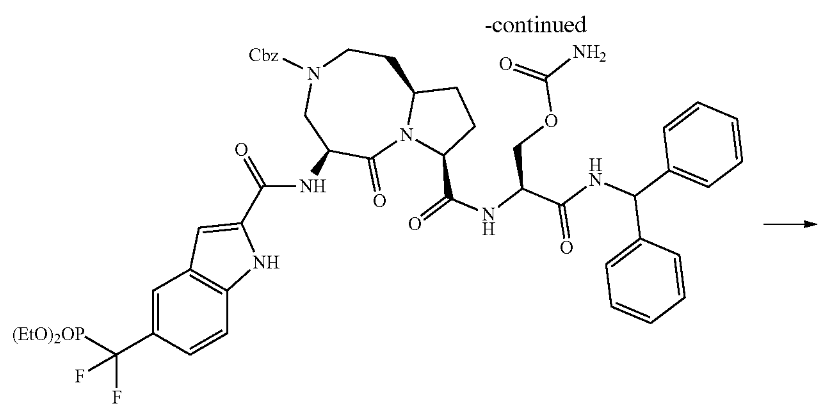
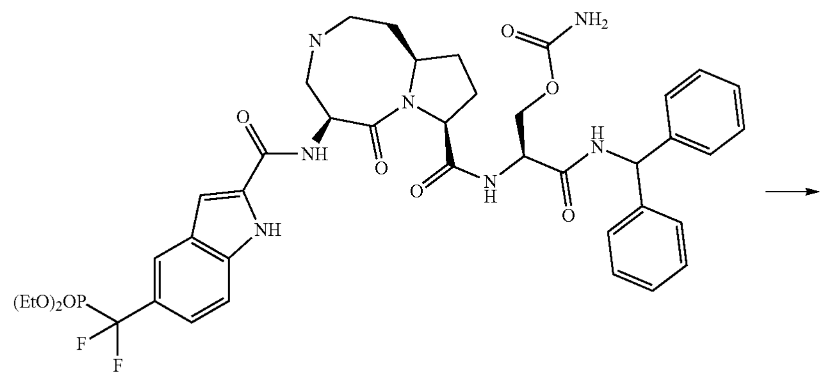
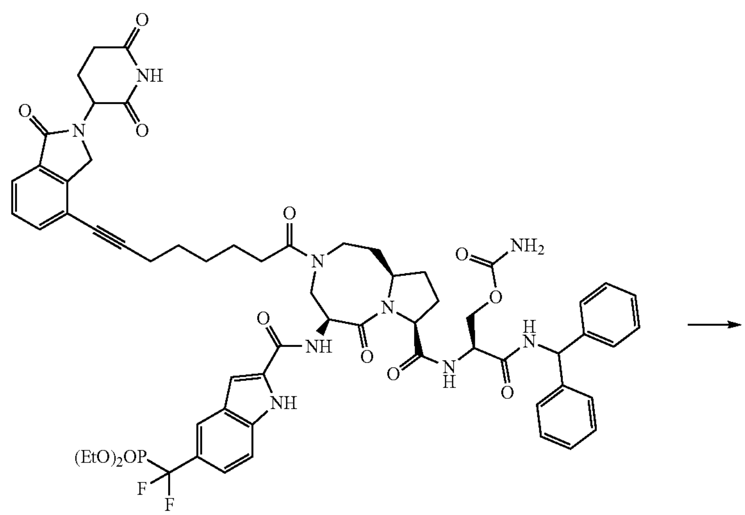

-continued

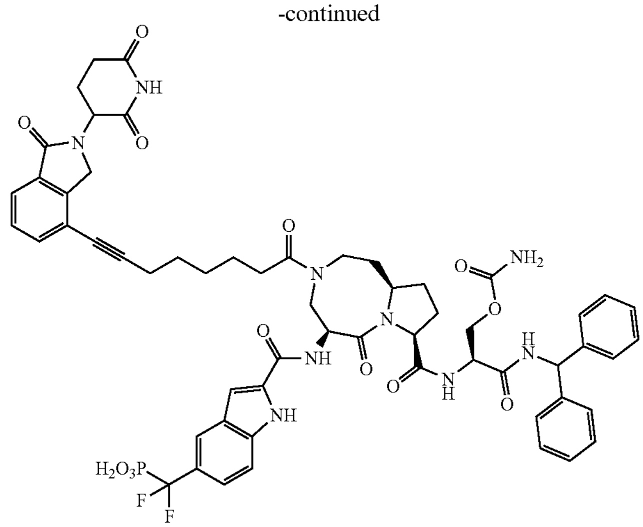

Cpd. No. 62

N-(tert-butoxycarbonyl)-O-carbamoyl-L-serine (9-197 acid): Boc-Ser-OBzl (1 g, 3.39 mmol, 1 equiv.) was dissolved in DCM (10 mL) and this solution was cooled to 0° C. before slowly adding trichloroacetyl isocyanate (0.76 g, 4.06 mmol, 1.2 equiv.). This reaction was then warmed to room temperature and stirred for 5 h before the solvent was removed under reduced pressure. The residue was dissolved in MeOH and $K_2CO_3$ (47 mg, 0.34 mmol, 0.1 equiv) was added. The resulting mixture was stirred at room temperature for 4 h before the solvent was removed under reduced pressure. The residue was dissolved in DCM and saturated aqueous $NH_4Cl$, the organic layer was collected, and the aqueous layer was extracted with additional DCM. The combined organic extracts were washed with saturated aqueous NaCl, dried with $MgSO_4$, and evaporated under reduced pressure to afford the crude product. This crude product was re-dissolved in MeOH to which 10% Pd—C (200 mg) was added. The solution was stirred under 1 atm of $H_2$ at room temperature for 3 hours before filtering through celite and being concentrated. The resulting acid was purified by HPLC to afford compound N-(tert-butoxycarbonyl)-O-carbamoyl-L-serine (9-197 acid). $^1H$ NMR (400 MHz, MeOD) δ 7.46-7.12 (m, 10H), 6.23 (s, 1H), 4.56-4.37 (m, 2H), 4.28 (dd, J=5.3, 3.9 Hz, 1H). $^{13}C$ NMR (101 MHz, MeOD) δ 165.06, 156.86, 140.99, 140.93, 128.29, 128.29, 127.45, 127.30, 127.17, 127.05, 62.57, 57.38, 52.64.

Cpd. No. 62: All the other steps were used similar procedures as for synthesis of Cpd. No. 36. $^1H$ NMR (400 MHz, $CD_3CN:D_2O$=1:1) δ 7.87 (d, J=14.6 Hz, 1H), 7.70-7.58 (m, 1H), 7.56-7.41 (m, 3H), 7.40-7.01 (m, 12H), 6.08-6.04 (m, 1H), 5.11-4.88 (m, 2H), 4.64-4.52 (m, 1H), 4.47-4.19 (m, 6H), 3.89-3.27 (m, 4H), 2.79-2.70 (m, 2H), 2.58-1.98 (m, 8H), 1.94-1.36 (m, 10H). UPLC-MS (ESI-MS) m/z: 1160.4.

Cpd. No. 89: UPLC-MS (ESI-MS) m/z: 1161.8.

Cpd. No. 106: UPLC-MS (ESI-MS) m/z: $[M+2H]^{2+}$ 693.9.

Example 19

Synthesis of (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)-1H-indole-5-carbonyl)phosphonic Acid (Cpd. No. 92)

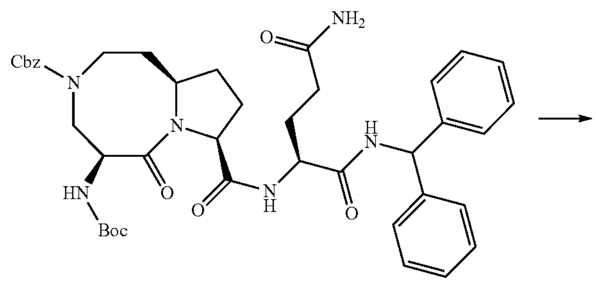

9-267-1

-continued

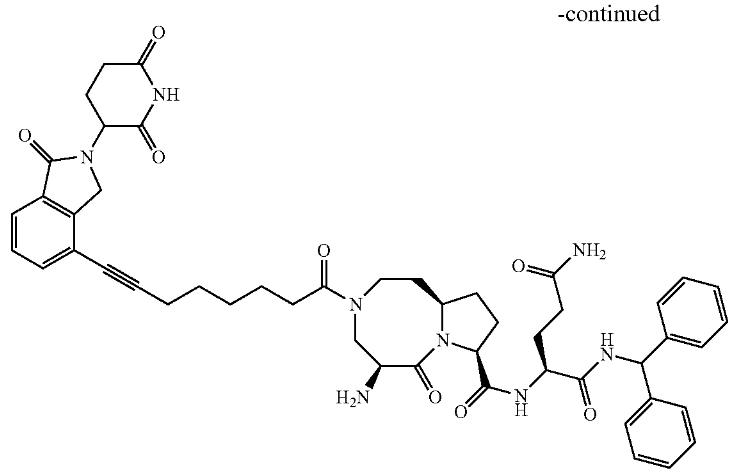

9-208

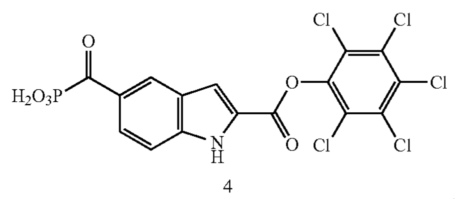

4

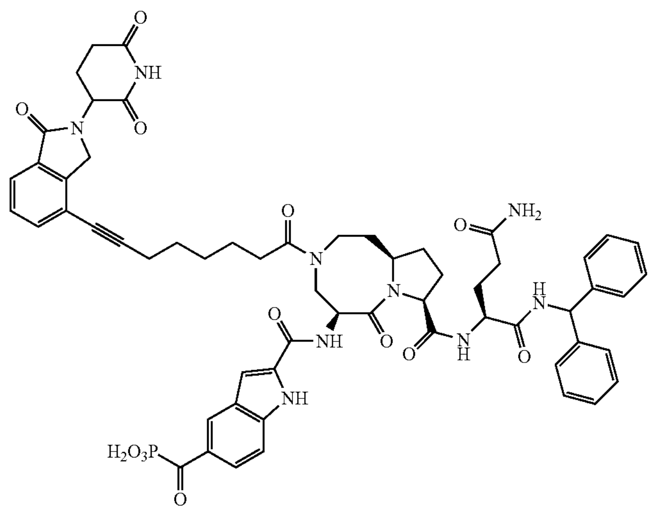

Cpd. No. 92

To a solution of compound 9-267-1 (500 mg, 0.66 mmol) in THF (30 mL) was added 10% Pd—C (150 mg). The solution was stirred under 1 atm of $H_2$ at room temperature for 3 hours before filtering through celite and being concentrated. The resulting amine was used for the next step without further purification.

HATU (276 mg, 0.73 mmol, 1.1 equiv.) was added to a solution of this amine, ST-B (253 g, 0.66 mmol, 1 equiv.) and DIEA (0.34 mL, 1.98 mmol, 3 equiv.) in DMF (10 mL) and the resultant mixture was stirred at room temperature for 1 h. The solution was diluted with EtOAc and washed with $H_2O$, saturated sodium bicarbonate aqueous solution and brine, and dried over sodium sulfate. After removal of the solvent under vacuum, the residue was dissolved in DCM (10 mL) and TFA (2 mL) was added to this solution. The resultant mixture was stirred for 1 h and then concentrated. The residue was purified by HPLC to afford 9-208.

DIEA (12 μL, 0.068 mmol, 3 equiv.) was added to the mixture of compound 4 (14 mg, 0.027 mmol, 1.2 equiv.), compound 5 (20 mg, 0.023 mmol, 1 equiv.) and HOBt (6 mg, 0.045 mmol, 2 equiv.) in DMF (2 mL). The resulting mixture was stirred at room temperature for 0.5 hour. Purification by HPLC gave Cpd. No. 92 (20 mg, 80%). $^1H$ NMR (400 MHz, $CD_3CN:D_2O$=1:1) δ 8.79-8.66 (m, 1H), 8.06-7.93 (m, 1H), 7.80-7.43 (m, 4H), 7.42-7.05 (m, 11H), 6.06-6.02 (m, 1H), 5.14-4.89 (m, 2H), 4.49-4.24 (m, 4H), 3.96-3.24 (m, 5H), 2.88-2.68 (m, 2H), 2.64-2.25 (m, 7H), 2.22-2.00 (m, 4H), 1.94-1.38 (m, 11H). UPLC-MS (ESI-MS) m/z: $[M+H]^+$ 1136.5.

Example 20
Synthesis of (2-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)carbamoyl)benzo[b]thiophene-5-carbonyl)phosphonic Acid (Cpd. No. 191) and Related Compounds
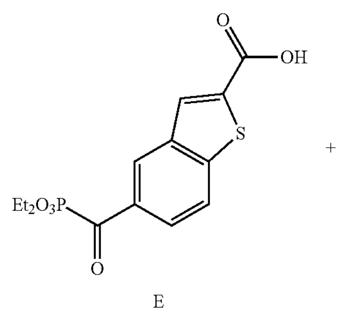
E
+
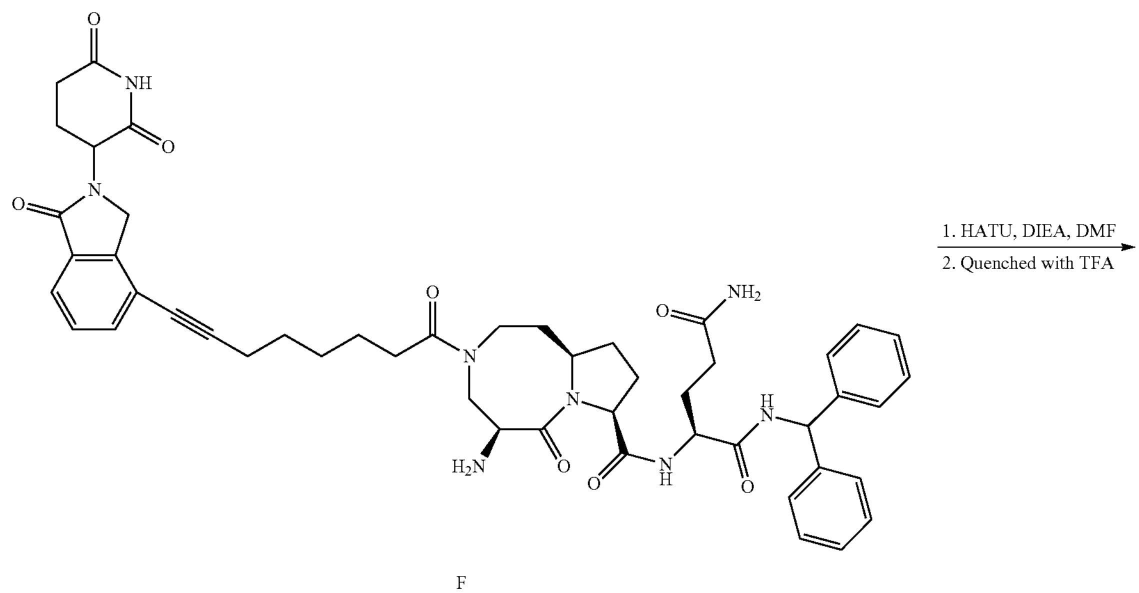
F -continued

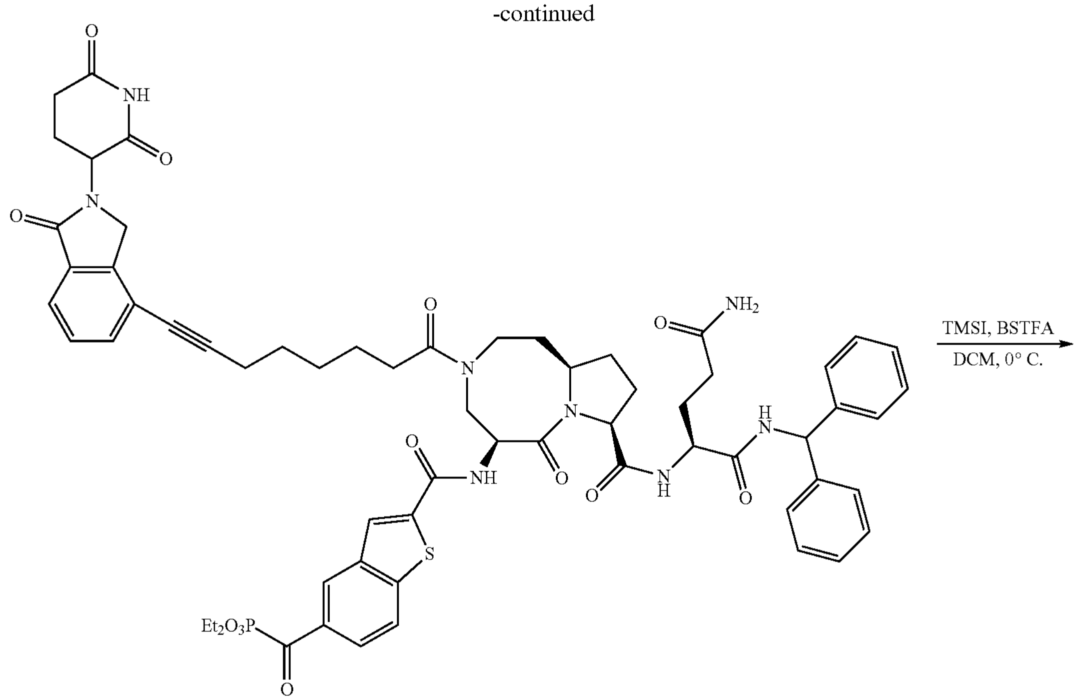

Cpd. No. 191E

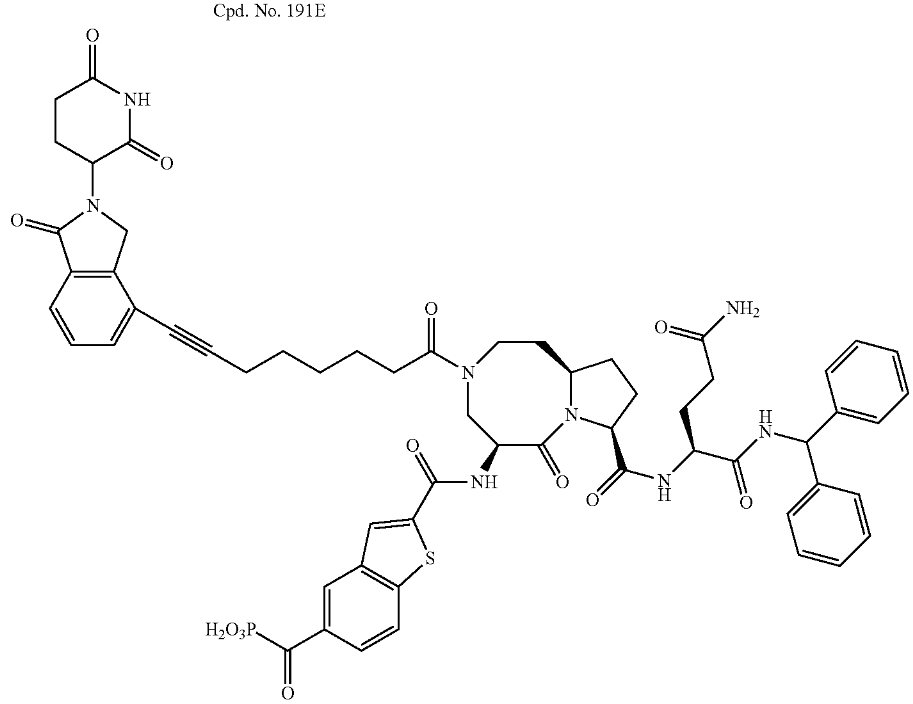

Cpd. No. 191

Cpd. No. 191E: DIEA (0.07 mL, 0.36 mmol, 3 equiv.) was added to a solution of E (42 mg, 0.12 mmol, 1.0 equiv.), F (120 mg, 0.132 mmol, 1.1 equiv.) and HATU (51 mg, 0.132 mmol, 1.1 equiv.) in DMF (1.0 mL), and the resultant mixture was stirred at room temperature for 10 min until LC-MS showed the reaction to be finished. The reaction was quenched with TFA (0.2 mL) (this step is important because Cpd. No. 191E is not stable in basic conditions). The residual crude product was purified by HPLC (MeCN/$H_2O$ 50%-100%, 50 min, 40 mL/min, the product came out when MeCN is 58.5%) to give Cpd. No. 191E as a white solid (102 mg, 70% yield).

Cpd. No. 191: To a round bottom flask was added Cpd. No. 191E (102 mg, 0.085 mmol, 1.0 equiv) and $CH_2Cl_2$ (5.0 mL). The solution was cooled to 0° C. before adding $CF_3CON(TMS)_2$ (0.13 mL, 0.42 mmol, 5.0 equiv) and 1M of TMS-I in DCM (0.34 mL, 0.34 mmol, 4.0 equiv). The reaction mixture was allowed to stir at 0° C. for 10 min and the solvent was removed under vacuum at 0° C. The residue was dissolved in $CH_3CN$, water, and TFA, and purified by HPLC ($MeCN/H_2O$ 35%-100%, 65 min, 60 mL/min, the product came out when MeCN is 43.2%) to yield Cpd. No. 191 (70 mg, 70% yield). $^1H$ NMR (400 MHz, $CD_3CN$:$D_2O$=1:1) δ 8.76-8.67 (m, 1H), 8.06-7.78 (m, 1H), 7.65-7.15 (m, 13H), 6.02-5.98 (m, 1H), 5.03-4.81 (m, 2H), 4.36-4.19 (m, 4H), 4.18-4.10 (m, 1H), 3.91-3.57 (m, 3H), 3.26-3.16 (m, 1H), 2.77-2.62 (m, 2H), 2.65-2.22 (m, 7H), 2.16-1.96 (m, 4H). 1.92-1.38 (m, 11H). UPLC-MS calculated for $C_{59}H_{62}N_8O_{13}PS$ $[M+H]^+$: 1153.39, found: 1153.44. UPLC-retention time: 4.01 min.

Cpd. No. 48: UPLC-MS (ESI-MS) m/z: 1175.4.

Cpd. No. 49: UPLC-MS (ESI-MS) m/z: 1160.4.

Cpd. No. 55: UPLC-MS (ESI-MS) m/z: $[M+2H]^{2+}$ 607.0.

Cpd. No. 57: UPLC-MS (ESI-MS) m/z: 1180.9.

Cpd. No. 59: UPLC-MS (ESI-MS) m/z: $[M+H]^{2+}$ 589.07.

Cpd. No. 61: UPLC-MS (ESI-MS) m/z: $[M+2H]^{2+}$ 606.38.

Cpd. No. 63: $^1H$ NMR (400 MHz, $CD_3CN$) δ 8.16-7.83 (m, 3H), 7.71-7.43 (m, 3H), 7.41-7.14 (m, 11H), 6.09-6.04 (m, 1H), 5.13-4.82 (m, 2H), 4.65-4.53 (m, 1H), 4.46-4.18 (m, 6H), 4.03-3.12 (m, 4H), 2.90-2.63 (m, 2H), 2.61-1.99 (m, 8H), 1.95-1.33 (m, 10H). UPLC-MS (ESI-MS) m/z: 1177.39.

Cpd. No. 85: UPLC-MS (ESI-MS) m/z: $[M+2H]^{2+}$ 589.1.

Cpd. No. 87: UPLC-MS (ESI-MS) m/z: $[M+H]^+$ 1178.4.

Cpd. No. 93: UPLC-MS (ESI-MS) m/z: 1172.6.

Cpd. No. 94: UPLC-MS (ESI-MS) m/z: 1174.6.

Cpd. No. 95: UPLC-MS (ESI-MS) m/z: $[M+H]^{2+}$ 570.4.

Cpd. No. 96: UPLC-MS (ESI-MS) m/z: $[M+2H]^{2+}$ 607.4.

Cpd. No. 97: UPLC-MS (ESI-MS) m/z: $[M+2H]^{2+}$ 601.9.

Cpd. No. 98: UPLC-MS (ESI-MS) m/z: 1042.7.

Cpd. No. 99: UPLC-MS (ESI-MS) m/z: 1072.5.

Cpd. No. 136: $^1H$ NMR (400 MHz, $CD_3CN$:$D_2O$=1:1) δ 8.10-7.83 (m, 3H), 7.68-7.57 (m, 2H), 7.49-7.17 (m, 12H), 6.04-5.99 (m, 1H), 5.05-4.83 (m, 2H), 4.40-4.25 (m, 5H), 4.20-3.66 (m, 3H), 3.26-3.18 (m, 1H), 2.79-2.64 (m, 2H), 2.55-1.96 (m, 11H), 1.93-1.42 (m, 11H). UPLC-MS calculated for $C_{59}H_{62}F_2N_8O_{12}PS$ $[M+H]^+$: 1175.39, found: 1175.55. UPLC-retention time: 4.28 min.

Cpd. No. 142: $^1H$ NMR (400 MHz, $CD_3CN$:$D_2O$=1:1) δ 8.40-8.30 (m, 1H), 8.17-8.09 (m, 1H), 7.95-7.63 (m, 4H), 7.57-7.36 (m, 2H), 7.32-7.15 (m, 11H), 6.01-5.98 (m, 1H), 5.07-4.88 (m, 2H), 4.35-4.24 (m, 5H), 4.22-3.57 (m, 3H), 3.26-3.19 (m, 1H), 2.76-2.61 (m, 2H), 2.54-2.16 (m, 7H), 2.14-1.96 (m, 4H), 1.92-1.40 (m, 11H). UPLC-MS calculated for $C_{61}H_{64}F_2N_8O_{12}P$ $[M+H]^+$: 1169.43, found: 1169.73. UPLC-retention time: 4.31 min.

Cpd. No. 181: $^1H$ NMR (400 MHz, $CD_3CN$:$D_2O$=1:1) δ 8.38-8.28 (m, 1H), 8.16-8.09 (m, 1H), 7.95-7.69 (m, 4H), 7.64-7.12 (m, 13H), 6.03-5.99 (m, 1H), 5.02-4.88 (m, 2H), 4.55-4.50 (m, 1H), 4.37-4.27 (m, 3H), 4.23-4.13 (m, 3H), 3.90-3.59 (m, 3H), 3.22-3.20 (m, 1H), 2.76-2.36 (m, 6H), 2.30-1.94 (m, 4H), 1.87-1.40 (m, 10H). UPLC-MS calculated for $C_{60}H_{62}F_2N_8O_{13}P$ $[M+H]^+$: 1171.41, found: 1171.54. UPLC-retention time: 4.40 min.

Example 21

Synthesis of Compounds of the Disclosure

I. Synthesis of Intermediate 1

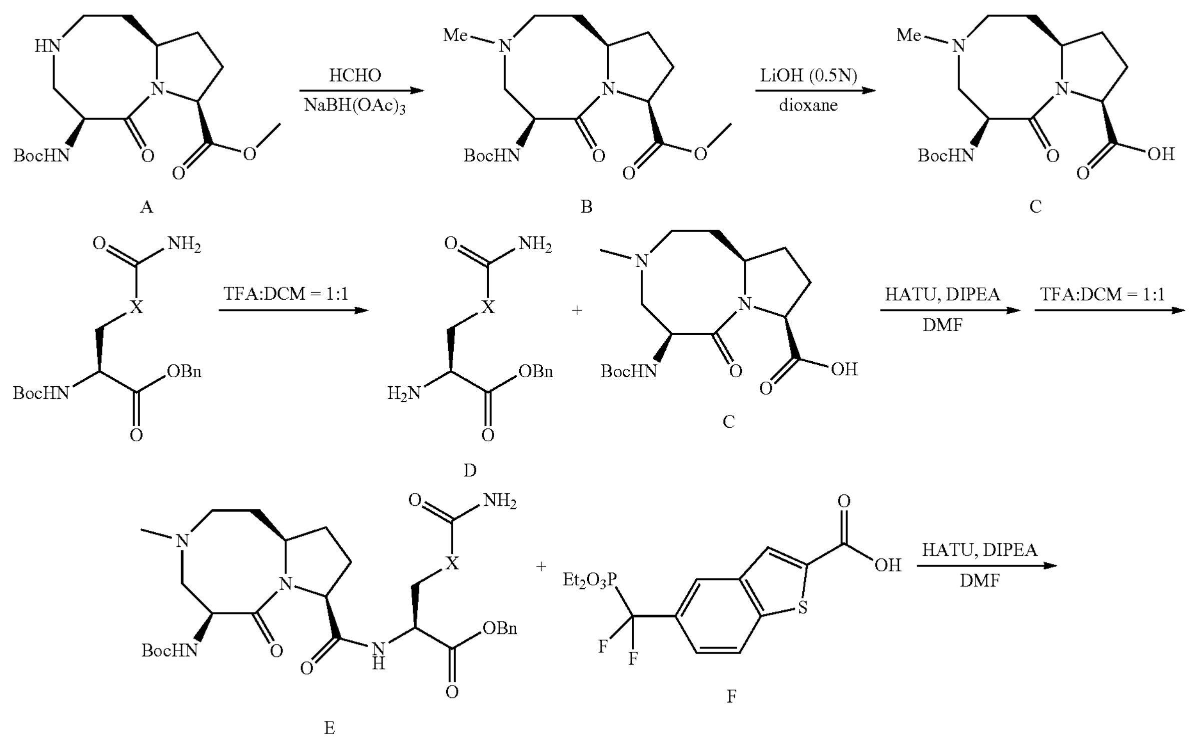

-continued

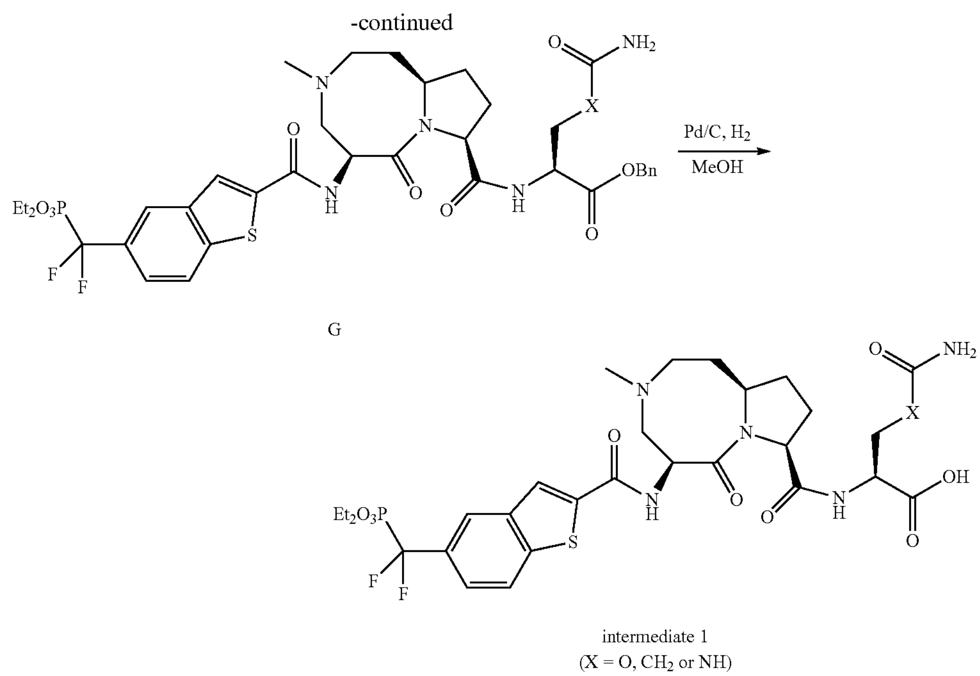

G intermediate 1
(X = O, $CH_2$ or NH)

The following procedure is for intermediate 1 when X is O.

Compound C: To a 100 mL round bottom flask equipped with a magnetic stirring bar was added A (1.1 g, 3.2 mmol, 1.0 equiv), HCHO (37%, 2.2 mL, 25.6 mmol, 8.0 equiv) and DCE (50 mL). $NaBH(OAc)_3$ (5.6 g, 25.6 mmol, 8.0 equiv) was added portion by portion. The solution was stirred room temperature for 2 hours until LC-MS showed the reaction to be finished. Water (40 ml) was added to quench the reaction. The reaction mixture was extracted with DCM (50 mL×3), dried with anhydrous sodium sulfate, filtered, and concentrated under vacuum. The residual crude product B was dissolved in dioxane (60 ml) and water (30 ml), LiOH—$H_2O$ (270 mg, 6.4 mmol, 2 equiv) was added, The resulting mixture was stirred for 1 h at room temperature until LC-MS showed the reaction to be finished. Most of the organic solvent was removed by evaporation, then the residue was purified by HPLC ($MeCN/H_2O$ 10%-100%, 90 min, 60 mL/min, the product came out when MeCN is 18%) to afford the desired acid C as a white solid (0.9 g, 82% yield).

Compound E: HATU (0.5 g, 1.3 mmol, 1.1 equiv.) was added to a solution of D (0.29 g, 1.2 mmol, 1 equiv.), C (0.4 g, 1.2 mmol, 1 equiv.) and DIEA (1.25 mL, 7.2 mmol, 6 equiv.) in DMF (10 mL) and the resultant mixture was stirred at room temperature for 30 min. The reaction was quenched with $NaHCO_3$ aqueous solution, extracted with EtOAc (75 mL×3), washed with brine for three times, dried with anhydrous sodium sulfate, filtered, and concentrated under vacuum. The residual crude product was purified by flash column chromatography (DCM:MeOH=20:1) to afford the desired Boc protected E as a white solid (0.6 g, 88% yield). The Boc group was removed before the next step.

Compound G: HATU (0.42 g, 1.1 mmol, 1.1 equiv.) was added to a solution of the E (0.46 g, 1.0 mmol, 1 equiv.), F (0.36 g, 1.0 mmol, 1 equiv.) and DIEA (1.0 mL, 6 mmol, 6 equiv.) in DMF (10 mL) and the resultant mixture was stirred at room temperature for 30 min, quenched with $NaHCO_3$ aqueous solution, extracted with EtOAc (75 mL×3), washed with brine for three times, dried with anhydrous sodium sulfate, filtered, and concentrated under vacuum. The residual crude product was purified by flash column chromatography (DCM:MeOH=20:1) to afford G (0.6 g, 80% yield).

Intermediate 1: To a 50 mL round bottom bottle equipped with a magnetic stirring bar was filled with argon before adding G (0.45 g), methanol (30 mL) and 10% Pd/C (500 mg). The reaction system was changed to hydrogen atmosphere for three times before stirred at room temperature for 30 min. The reaction mixture was filtered to remove Pd/C and the solvent was removed under vacuum. The residual crude product was purified by HPLC ($MeCN/H_2O$ 25%-100%, 75 min, 60 mL/min, the product came out when MeCN is 31.6%) to afford the desired Intermediate 1 as a light yellow solid (280 mg, 71% yield).

II. Synthesis of Intermediate 2

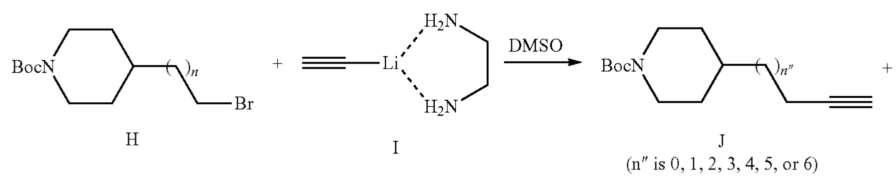

H

I

J
(n″ is 0, 1, 2, 3, 4, 5, or 6)

-continued

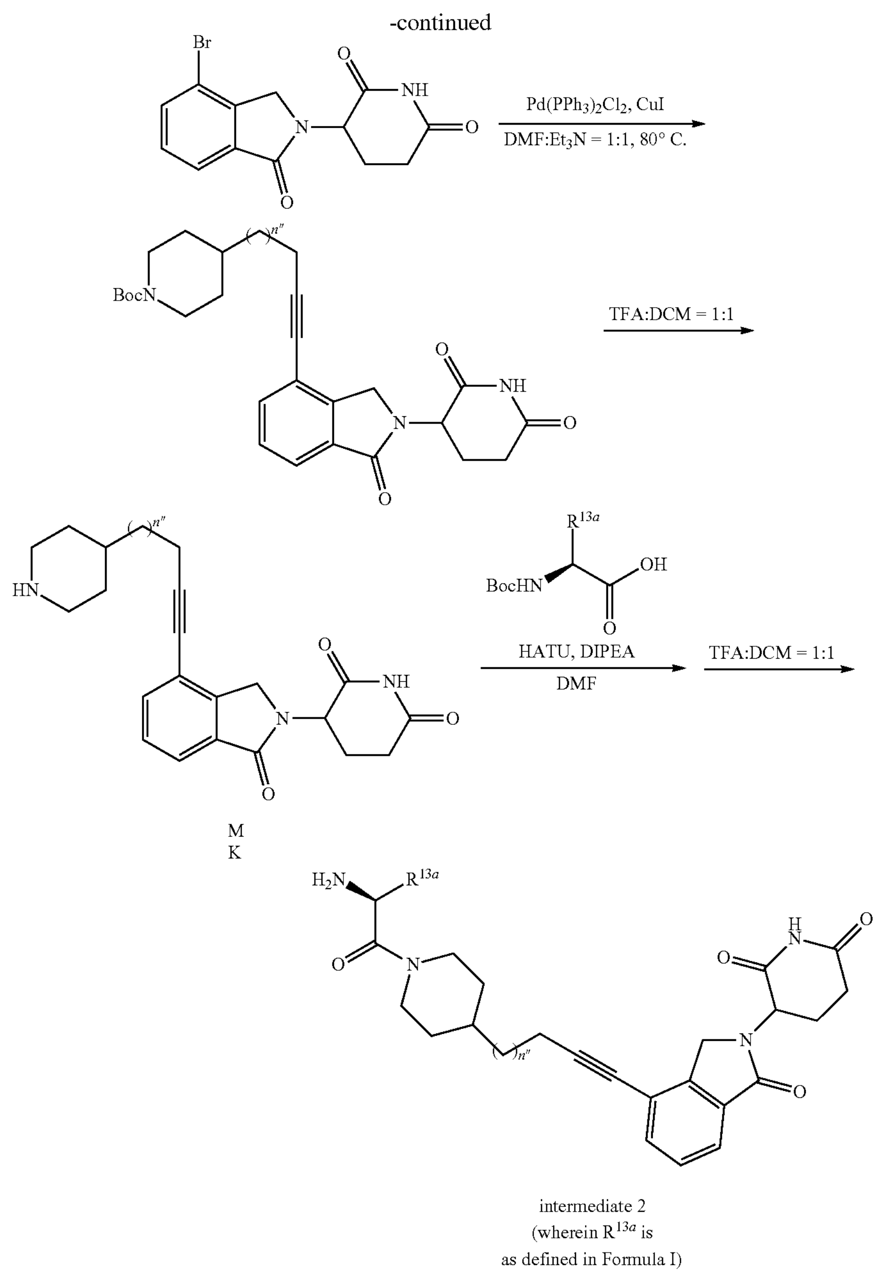

M
K intermediate 2
(wherein $R^{13a}$ is
as defined in Formula I)

The following procedure is for intermediate 2 when n is 1 and $R^{13a}$ is cyclohexyl.

Compound J: To a 25 mL round bottom flask equipped with a magnetic stirring bar was added H (0.25 g, 0.85 mmol, 1.0 equiv), DMSO (5.0 mL) and I (90%, 0.13 g, 1.3 mmol, 1.5 equiv). The suspension was stirred at room temperature for 4 hours monitored by TLC (PE:EA=4:1). Water (10 ml) was added to quench the reaction. Extracted with EtOAc (20 mL×3), washed with brine for three times and dried with anhydrous sodium sulfate. Filtered and the solvent was removed under vacuum. The residual was purified by flash column chromatography (PE:EA=10:1 TO PE:EA=5:1) to afford J as a colorless oil (0.15 g, 75% yield).

Compound M: Trimethylamine (4 mL) was added to a mixture of compound J (0.15 g, 0.63 mmol, 1 equiv.), K (0.2 g, 0.63 mmol, 1 equiv.), CuI (24 mg, 0.126 mmol, 0.2 equiv) and $Pd(PPh_3)_2Cl_2$ (44 mg, 0.063 mmol, 0.1 equiv) in DMF (4 mL). The resulting mixture was purged and refilled with argon for three times and stirred at 80° C. for 3 h under Argon. The reaction mixture was then cooled to room temperature and quenched with $NH_4Cl$ aqueous solution. Extracted with EtOAc (50 mL×3), washed with brine for three times and dried with anhydrous sodium sulfate. Filtered and the solvent was removed under vacuum. The residual was purified by flash column chromatography (PE:EA=1:2) to afford Boc protected M as a light yellow solid (0.2 g, 66% yield). Before the next step use TFA to remove Boc.

Intermediate 2 (n=1, $R^{13a}$=cyclohexyl): HATU (13 mg, 0.033 mmol, 1.1 equiv.) was added to a solution of the amino acid L (8.5 mg, 0.033 mmol, 1.1 equiv.), M (15 mg, 0.03 mmol, 1 equiv.) and DIEA (0.03 mL, 0.18 mmol, 6 equiv.) in DMF (1.0 mL) and the resultant mixture was stirred at room temperature for 30 min. The residual crude product was purified by HPLC (MeCN/$H_2O$ 50%-100%, 50 min, 60 mL/min, the product came out when MeCN is 61.3%), then use TFA to remove Boc to afford Intermediate 2 (14 mg, 90% yield).
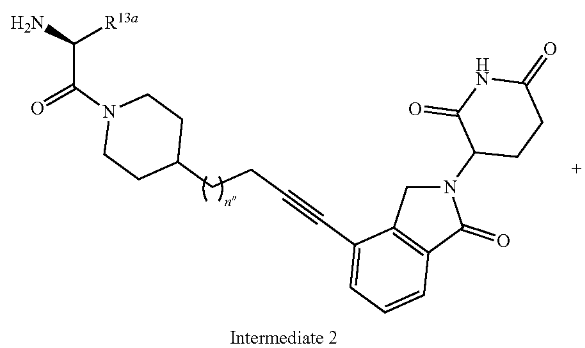
Intermediate 2
+
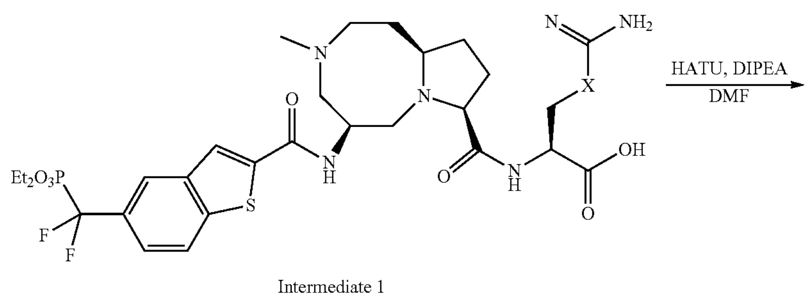
Intermediate 1
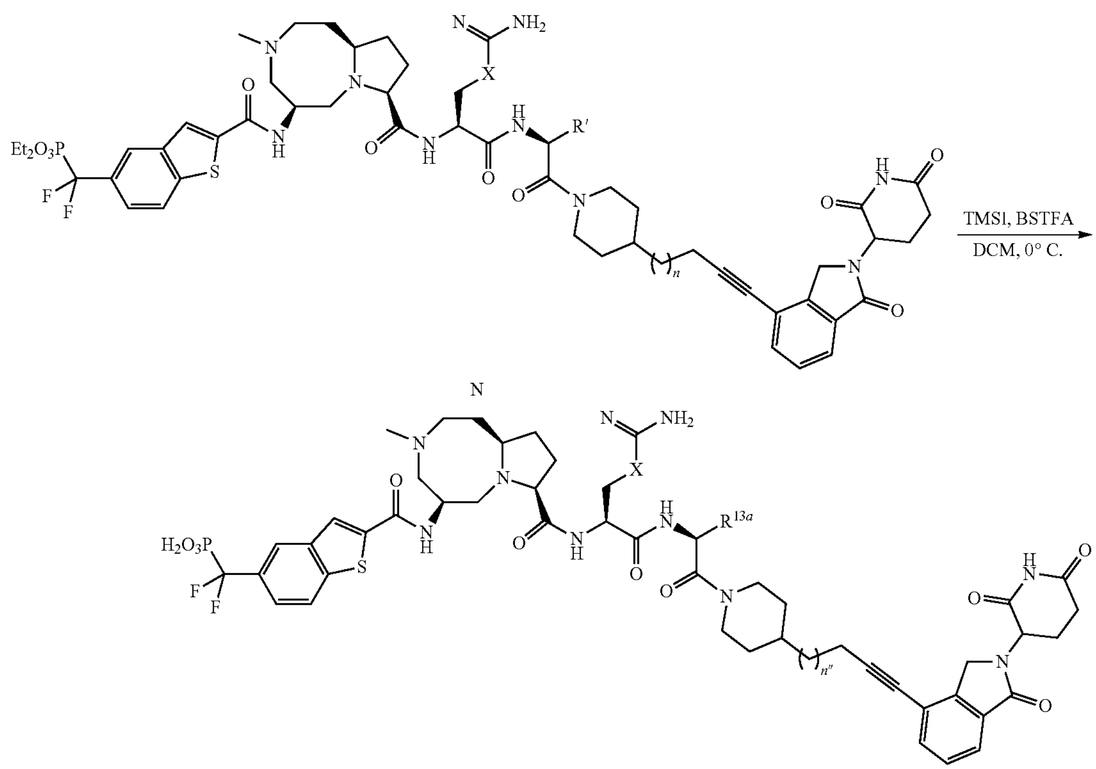
(wherein $R^{13a}$ is as defined in Formula I;
X is —O—, —NH—, or —$CH_2$—;
and n″ is 0, 1, 2, 3, 4, 5, or 6)

Compound N (X=O, n"=1, and $R^{13a}$=cyclohexyl): HATU (12 mg, 0.03 mmol, 1.1 equiv.) was added to a solution of the Intermediate 2 (14 mg, 0.027 mmol, 1 equiv.), Intermediate 1 (21 mg, 0.03 mmol, 1.1 equiv.) and DIEA (0.03 mL, 0.18 mmol, 6 equiv.) in DMF (1.0 mL) and the resultant mixture was stirred at room temperature for 30 min. The residual crude product was purified by HPLC (MeCN/$H_2O$ 40%-100%, 60 min, 60 mL/min, the product came out when MeCN is 45.3%) to afford N (23.8 mg, 72% yield).

Cpd. No. 180 (X=O, n"=1, and $R^{13a}$=cyclohexyl): To a round bottom flask was added N (23.8 mg, 0.02 mmol, 1.0 equiv) and $CH_2Cl_2$ (1.5 mL). The solution was cooled to 0° C. before adding $CF_3CON(TMS)_2$ (0.036 mL, 0.12 mmol, 6.0 equiv) and 1M of TMS-I in DCM (0.1 mL, 0.1 mmol, 5.0 equiv). The reaction mixture was allowed to stir at 0° C. for 10 min and the solvent was removed under vacuum at 0° C. The residue was dissolved in a mixture solvent of $CH_3CN$ (1.5 mL), water (1.5 mL) and TFA (0.1 mL), and purified by HPLC (MeCN/$H_2O$ 30%-100%, 70 min, 60 mL/min, the product came out when MeCN is 38.3%) to yield Cpd. No. 180 (14 mg, 63%).

Cpd. No. 182: was also purified by HPLC (MeCN/$H_2O$ 30%-100%, 70 min, 60 mL/min, the product came out when MeCN is 38.5%). $^1$H NMR (400 MHz, DMSO-$d_6$:$D_2O$=4:1) δ 8.17-8.07 (m, 2H), 7.70-7.68 (m, 1H), 7.60-7.58 (m, 1H), 7.52-7.48 (m, 1H), 5.34 (br, 1H), 5.05-5.01 (m, 1H), 4.66-4.58 (m, 3H), 4.46-4.41 (m, 1H), 4.32-4.16 (m, 3H), 3.98-3.36 (m, 5H), 2.96-2.93 (m, 4H), 2.87-2.78 (m, 1H), 2.65-2.51 (m, 2H), 2.18-1.44 (m, 21H), 1.06-0.92 (m, 7H). UPLC-MS calculated for $C_{56}H_{69}F_2N_9O_{12}PS$ $[M+H]^+$: 1160.45, found: 1160.48. UPLC-retention time: 3.74 min.

Cpd. No. 183: $^1$H NMR (400 MHz, DMSO-d6:$D_2O$=4:1) δ 8.16 (s, 1H), 8.09-8.06 (m, 2H), 7.70-7.67 (m, 1H), 7.60-7.47 (m, 3H), 7.36-7.27 (m, 5H), 5.79-5.74 (m, 1H), 5.33 (br, 1H), 5.05-5.01 (m, 1H), 4.63-4.55 (m, 2H), 4.44-4.24 (m, 4H), 4.06-3.33 (m, 5H), 2.96-2.79 (m, 5H), 2.66-2.55 (m, 2H), 2.49-0.98 (m, 21H). UPLC-MS calculated for $C_{56}H_{63}F_2N_9O_{12}PS$ $[M+H]^+$: 1154.40, found: 1154.58. UPLC-retention time: 3.40 min.

Cpd. No. 199: $^1$H NMR (400 MHz, $CD_3CN$:$D_2O$=1:1) δ 8.79 (s, 1H), 8.03-7.91 (m, 3H), 7.70-7.67 (m, 1H), 7.53-7.43 (m, 2H), 7.30-7.27 (m, 5H), 5.81-5.76 (m, 1H), 5.38 (br, 1H), 5.08-5.02 (m, 1H), 4.66-4.55 (m, 2H), 4.40-4.21 (m, 5H), 3.81-3.63 (m, 3H), 3.43-3.32 (m, 2H), 2.99-2.63 (m, 7H), 2.56-1.97 (m, 10H), 1.87-1.27 (m, 10H). UPLC-MS calculated for $C_{56}H_{63}N_9O_{13}PS$ $[M+H]^+$: 1132.40, found: 1132.97. UPLC-retention time: 3.29 min.

Cpd. No. 192: $^1$H NMR (400 MHz, $CD_3CN$:$D_2O$=1:1) δ 8.10-8.04 (m, 2H), 7.97-7.94 (m, 1H), 7.70-7.67 (m, 1H), 7.61-7.59 (m, 1H), 7.54-7.49 (m, 1H), 7.46-7.42 (m, 1H), 7.31-7.24 (m, 5H), 5.78-5.72 (m, 1H), 5.07-4.95 (m, 2H), 4.39-4.25 (m, 6H), 3.84-3.76 (m, 2H), 3.68-3.35 (m, 3H), 2.98-2.55 (m, 4H), 2.43-1.99 (m, 12H), 2.99-2.63 (m, 7H), 1.92-1.06 (m, 12H). UPLC-MS calculated for $C_{57}H_{63}F_2N_9O_{13}PS$ $[M+H]^+$: 1182.40, found: 1182.56. UPLC-retention time: 3.89 min.

Cpd. No. 194: $^1$H NMR (400 MHz, $CD_3CN$:$D_2O$=1:1) δ 8.09-8.02 (m, 2H), 7.96-7.94 (m, 1H), 7.69-7.67 (m, 1H), 7.61-7.59 (m, 1H), 7.54-7.42 (m, 2H), 7.31-7.26 (m, 5H), 5.78-5.72 (m, 1H), 5.07-4.90 (m, 2H), 4.38-4.21 (m, 6H), 3.84-3.36 (m, 8H), 2.98-2.54 (m, 4H), 2.43-2.02 (m, 9H), 1.78-1.05 (m, 12H). UPLC-MS calculated for $C_{57}H_{63}F_2N_9O_{14}PS$ $[M+H]^+$: 1198.39, found: 1198.45. UPLC-retention time: 3.85 min.

Cpd. No. 196: $^1$H NMR (400 MHz, $CD_3CN$:$D_2O$=1:1) δ 8.09-8.04 (m, 2H), 7.95-7.93 (m, 1H), 7.70-7.67 (m, 1H), 7.62-7.60 (m, 1H), 7.54-7.43 (m, 2H), 7.33-7.25 (m, 5H), 5.81-5.76 (m, 1H), 5.45-5.41 (m, 1H), 5.08-5.02 (m, 1H), 4.68-4.56 (m, 2H), 4.40-4.26 (m, 6H), 3.76-3.72 (m, 1H), 3.52-3.18 (m, 4H), 3.21-3.15 (m, 1H), 2.98-2.55 (m, 4H), 2.44-2.24 (m, 6H), 2.12-1.94 (m, 3H), 1.87-1.05 (m, 16H). UPLC-MS calculated for $C_{58}H_{67}F_2N_9O_{12}PS$ $[M+H]^+$: 1182.43, found: 1182.55. UPLC-retention time: 3.57 min.

Example 22

Synthesis of Compounds of the Disclosure

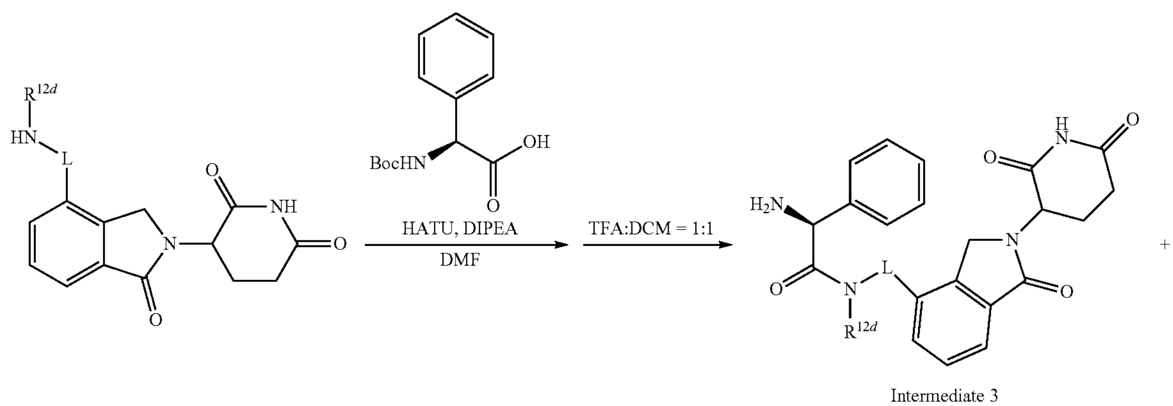

Intermediate 3

-continued
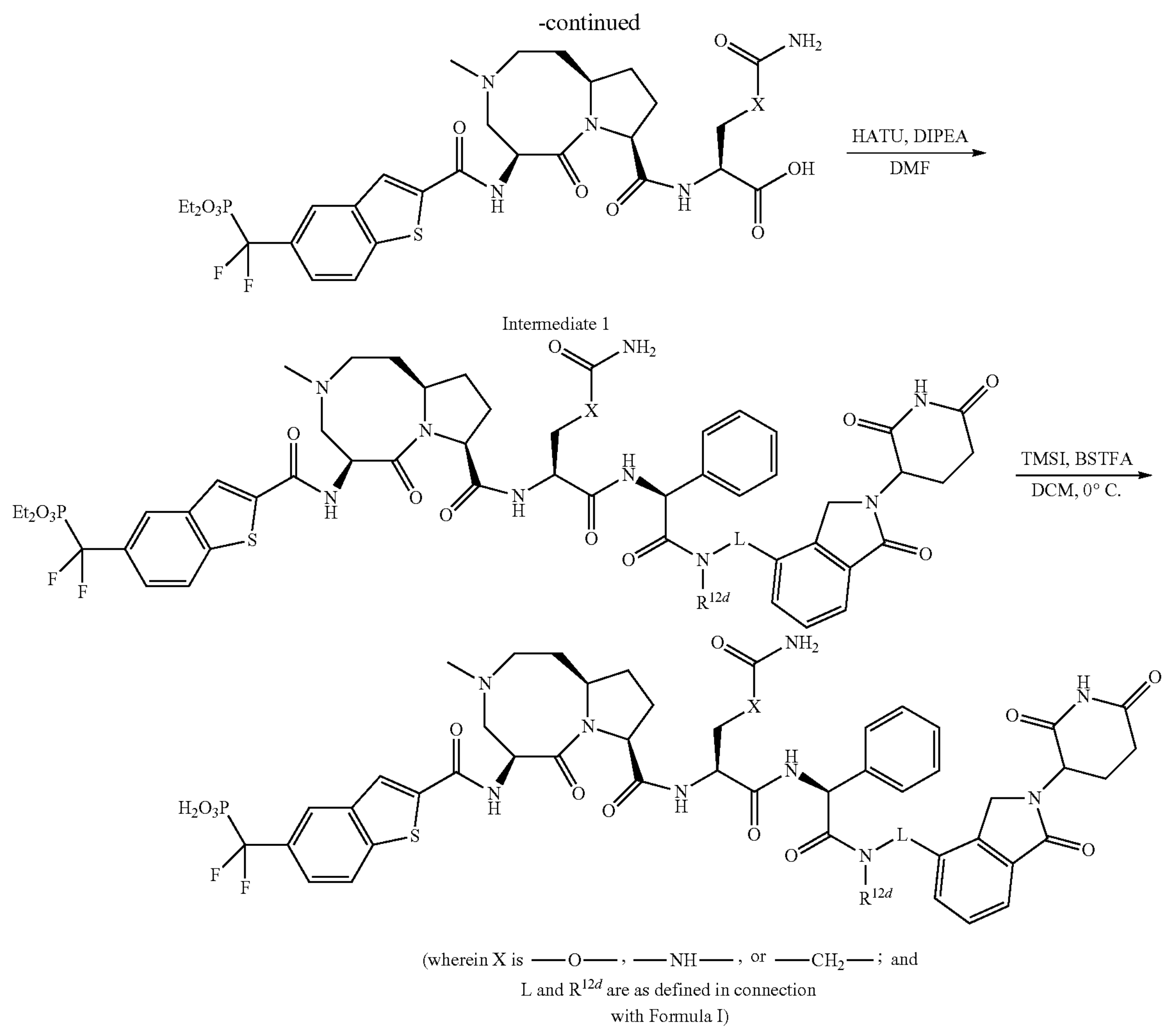
Cpd. No. 53: UPLC-MS (ESI-MS) m/z: 1156.7.4.
Example 23
Synthesis of (2-(((5S,8S,10aR)-8-(((2S)-5-amino-1-(((1S)-2-(4-(4-(2-(2,6-dioxopiperidin-3-yl)-1-oxoisoindolin-4-yl)but-3-yn-1-yl)piperidin-1-yl)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indole-5-carbonyl)phosphonic Acid (Cpd. No. 100) and Related Compounds
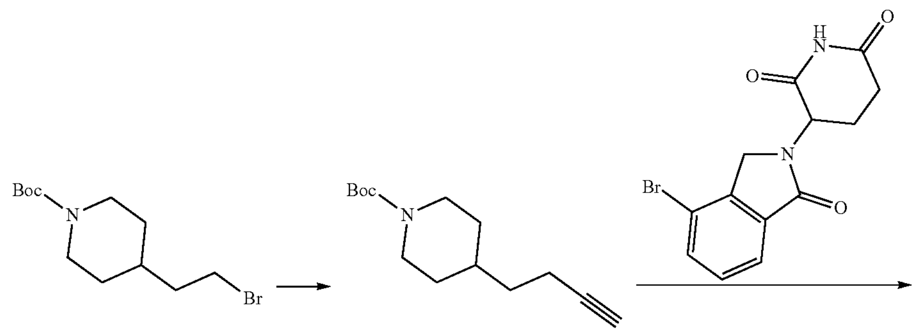

-continued
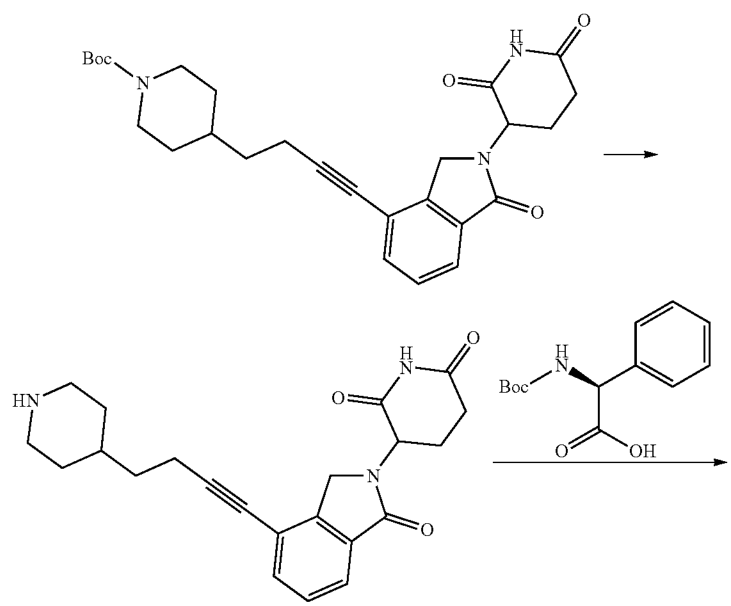
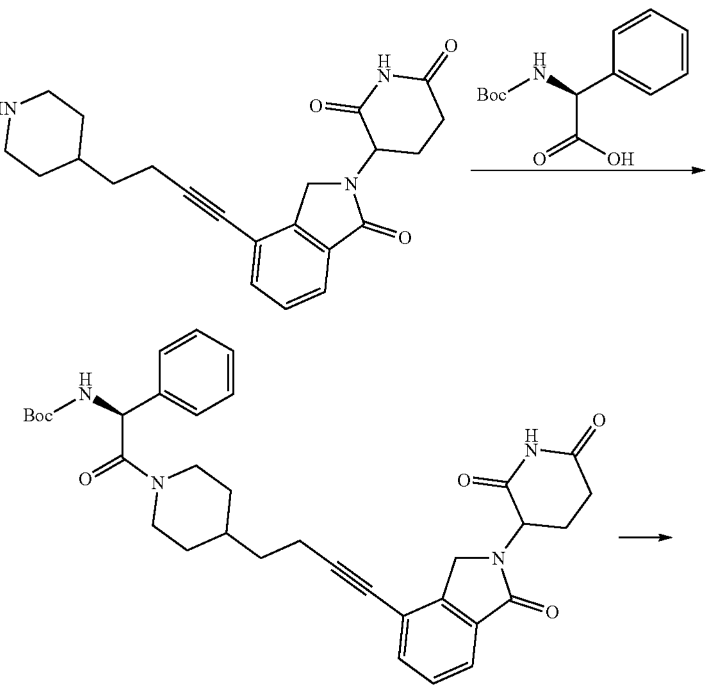
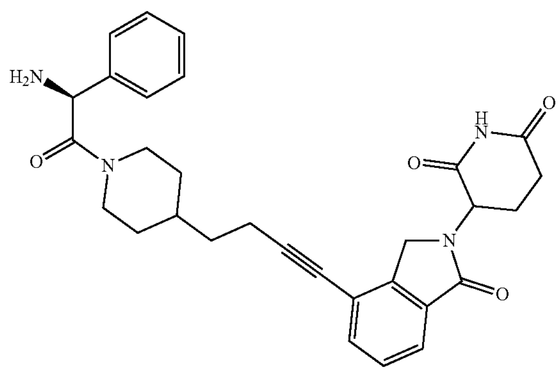
10-66
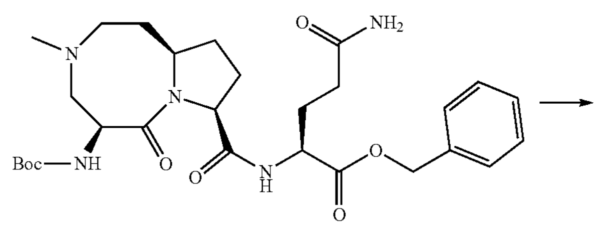
10-65

-continued
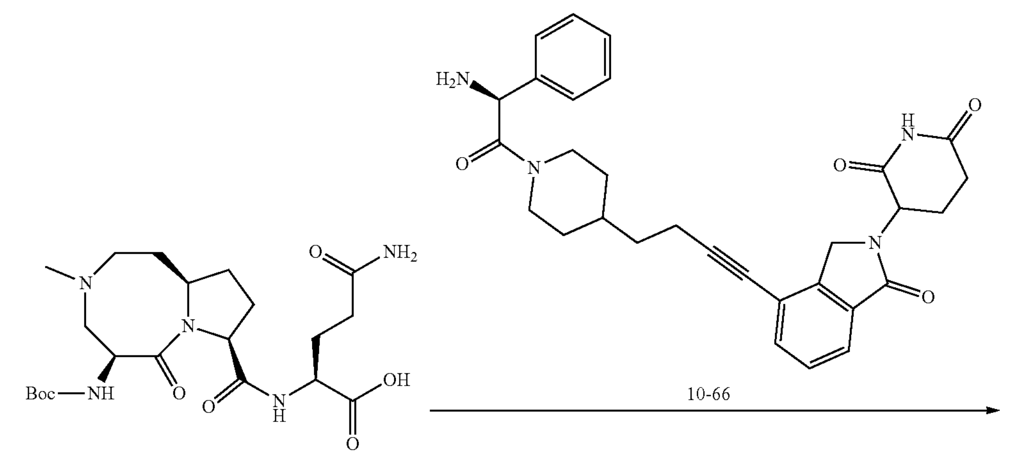
10-69
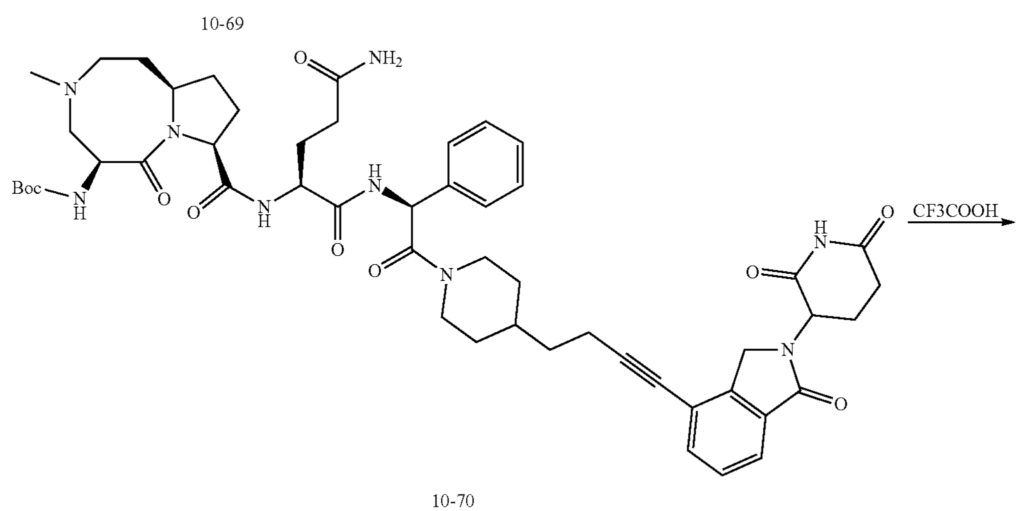
10-70
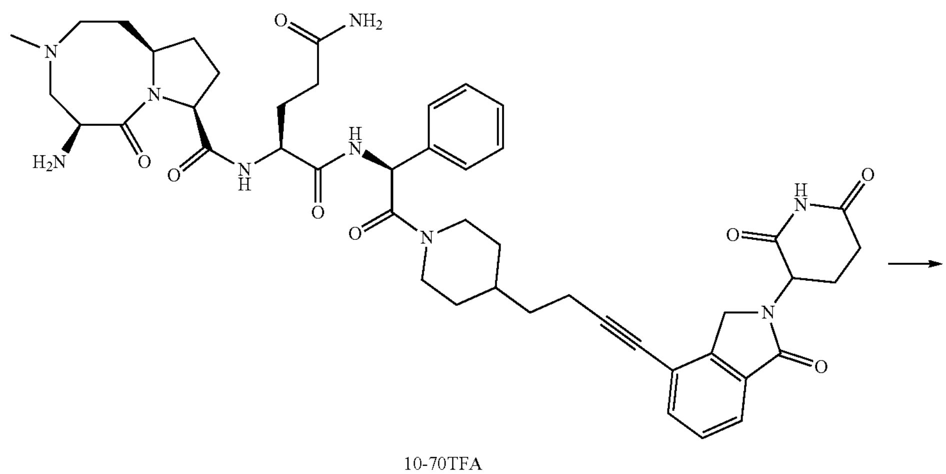
10-70TFA

-continued

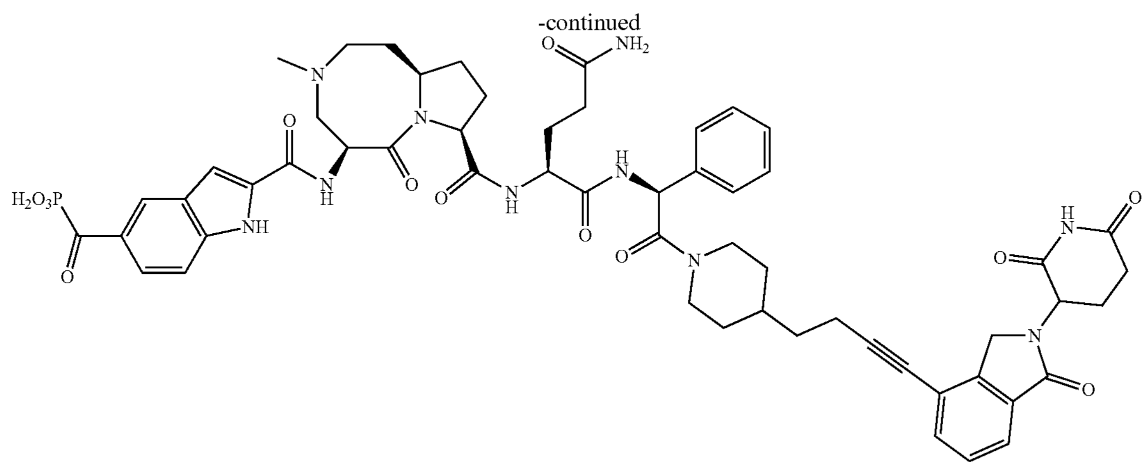

Cpd. No. 100
(as TFA salt)

Cpd. No. 100: Compound 10-66 was made using similar method described above. To a solution of compound 10-65 (210 mg, 0.38 mmol) in THF (20 mL) was added 10% Pd—C (100 mg). The solution was stirred under 1 atm of $H_2$ at room temperature for 3 hours before filtering through celite. The filtrate was concentrated to yield 10-69 (160 mg, 91%). UPLC-MS (ESI-MS) m/z: 470.3.

HATU (53 mg, 0.14 mmol, 1.1 equiv.) and 10-69 (60 mg, 0.13 mmol, 1 equiv.) were added to a solution of the 10-66 (65 mg, 0.13 mmol, 1 equiv.) and DIEA (67 μL, 0.38 mmol, 3 equiv.) in DMF (2 mL) and the resultant mixture was stirred at room temperature for 1 h. Purified by HPLC to yield 10-70 (95 mg, 77%). UPLC-MS (ESI-MS) m/z: 1964.5.

TFA (0.5 mL) was added slowly in a solution of 10-70 (60 mg, 0.06 mmol) in DCM (5 mL) at room temperature and the result reaction solution was stirred at the same temperature for 1 hour and then evaporated. The crude product 10-70TFA was directly used in the next step without purification. DIEA (11 μL, 0.061 mmol, 3 equiv.) was added to the mixture of (2-((perchlorophenoxy)carbonyl)-1H-indole-5-carbonyl)phosphonic acid (13 mg, 0.025 mmol, 1.2 equiv.), compound 10-70TFA (20 mg, 0.02 mmol, 1 equiv.) and HOBt (6 mg, 0.045 mmol, 2 equiv.) in DMF (2 mL). The resulting mixture was stirred at room temperature for 10 min. Purification of this reaction mixture by HPLC gave the compound Cpd. No. 100 (18 mg, 81%). $^1$H NMR (400 MHz, $CD_3CN:D_2O$=1:1) δ 8.73 (s, 1H), 7.96 (d, J=8.8 Hz, 1H), 7.75-7.72 (m, 1H), 7.57-7.48 (m, 3H), 7.36-7.33 (m, 6H), 5.86-5.81 (m, 1H), 5.50-5.39 (m, 1H), 5.13-5.08 (m, 1H), 4.70-4.59 (m, 2H), 4.49-4.28 (m, 4H), 3.85-3.29 (m, 5H), 3.11-2.56 (m, 7H), 2.50-2.01 (m, 10H), 1.94-1.48 (m, 7H), 1.45-1.14 (m, 4H). UPLC-MS (ESI-MS) m/z: 1115.5.

Cpd. No. 101: $^1$H NMR (400 MHz, $CD_3CN:D_2O$=1:1) δ 8.75 (s, 1H), 7.97 (d, J=8.8 Hz, 1H), 7.74 (d, J=7.6 Hz, 1H), 7.60 (d, J=7.4 Hz, 1H), 7.53-7.49 (m, 2H), 7.35 (s, 1H), 5.46 (s, 1H), 5.24-5.03 (m, 1H), 4.85-4.56 (m, 3H), 4.48-4.31 (m, 4H), 4.06-3.90 (m, 2H), 3.73-3.47 (m, 2H), 3.38 (t, J=11.9 Hz, 1H), 3.13-2.42 (m, 13H), 2.33-2.15 (m, 5H), 1.86-1.49 (m, 13H), 1.27-0.97 (m, 8H). UPLC-MS (ESI-MS) m/z: 1121.7.

Cpd. No. 243: UPLC-MS (ESI-MS) m/z: $[M+H]^+$ 1117.50.

Cpd. No. 244: UPLC-MS (ESI-MS) m/z: 1130.6.

Cpd. No. 245: UPLC-MS (ESI-MS) m/z: 1135.8.

Cpd. No. 246: UPLC-MS (ESI-MS) m/z: 1169.5.

Cpd. No. 247: UPLC-MS (ESI-MS) m/z: 1174.6.

Cpd. No. 248: UPLC-MS (ESI-MS) m/z: 1174.8.

Cpd. No. 249: UPLC-MS (ESI-MS) m/z: 1174.6.

Example 24

Synthesis of (5S,8S,10aR)-5-((tert-butoxycarbonyl)amino)-3-ethyl-6-oxodecahydropyrrolo[1,2-a][1,5]diazocine-8-carboxylic Acid (Compound B) and Related Compounds

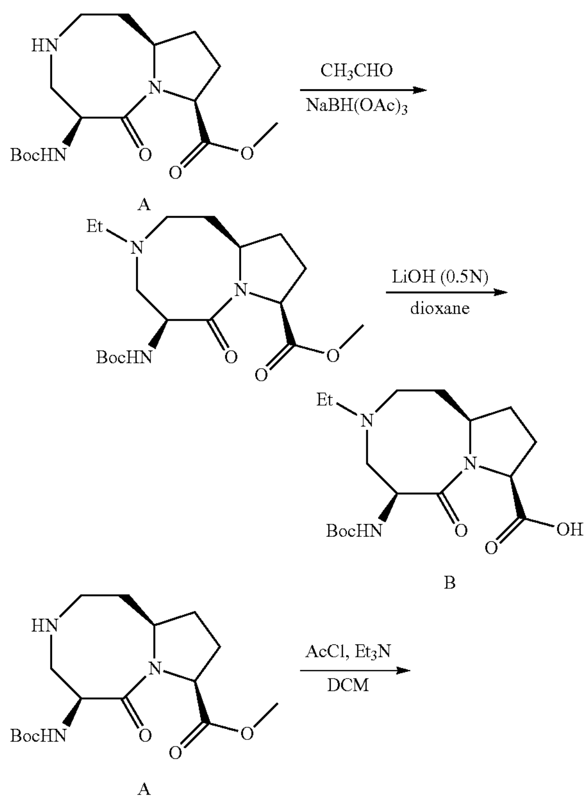

A

B

A

-continued

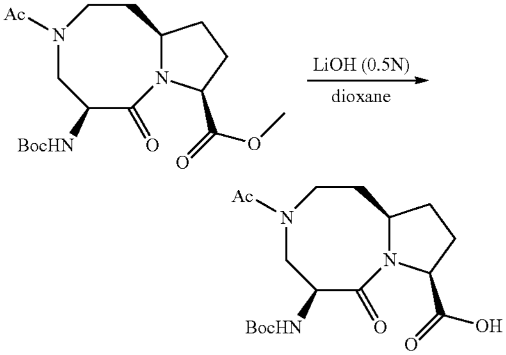

C

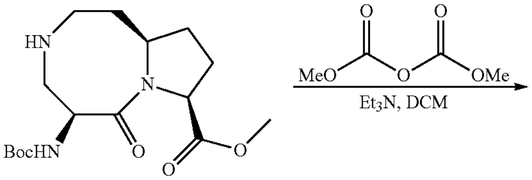

A

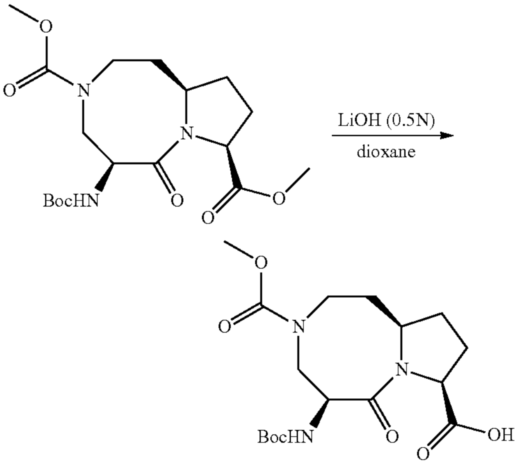

D

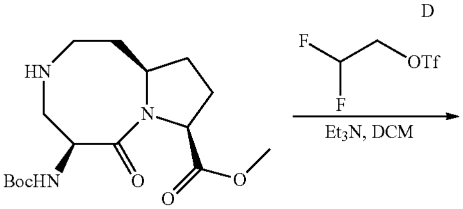

A

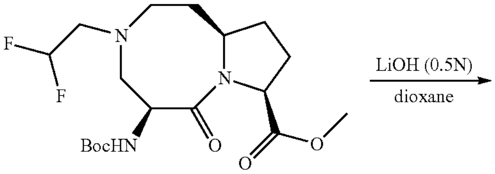

-continued

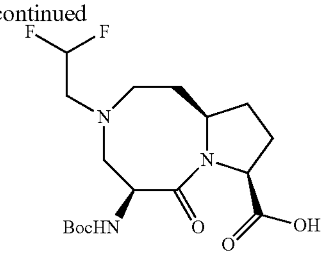

E

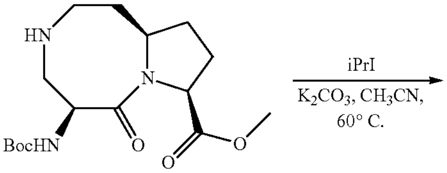

A

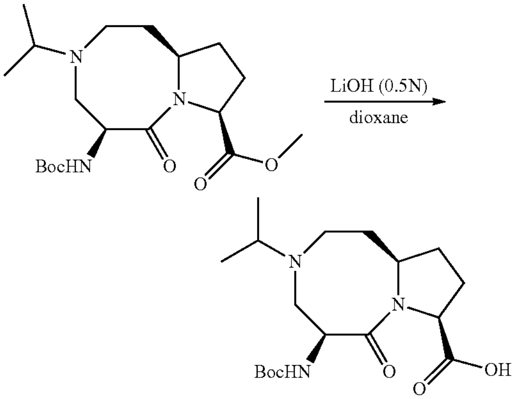

F

Compound B: To a 100 mL round bottom flask equipped with a magnetic stirring bar was added Compound A (1.1 g, 3.2 mmol, 1.0 equiv), $CH_3CHO$ (1.4 mL, 25.6 mmol, 8.0 equiv) and DCE (50 mL). $NaBH(OAc)_3$ (5.6 g, 25.6 mmol, 8.0 equiv) was added portion by portion. The resulting solution was stirred room temperature for 2 h until LC-MS showed that the reaction was complete. Water (40 ml) was added to quench the reaction. The reaction mixture was extracted with DCM (50 mL×3), dried with anhydrous sodium sulfate, filtered, and concentrated under vacuum. The residual crude product was dissolved in dioxane (60 ml) and water (30 ml), and LiOH—$H_2O$ (270 mg, 6.4 mmol, 2 equiv) was added. The resulting mixture was stirred for 1 h at room temperature until LC-MS showed that the reaction was complete. Most of the organic solvent was removed by evaporation, and the residue was purified by HPLC (MeCN/$H_2O$ 10%-100%, 90 min, 60 mL/min). The desired product eluted off the column when the MeCN concentration reached 19%. Compound B was obtained as a white solid (0.9 g, 82% yield).

Compound C: To a 100 mL round bottom flask equipped with a magnetic stirring bar was added Compound A (1.1 g, 3.2 mmol, 1.0 equiv) and DCM (50 mL). $Et_3N$ (0.7 mL, 4.8 mmol, 1.5 equiv) was added to the mixture followed by AcCl (0.3 mL, 3.8 mmol, 1.2 equiv). The solution was stirred room temperature for 1 h until LC-MS showed that the reaction was complete. The reaction solvent was removed under vacuum. The residual product was dissolved in dioxane (60 ml) and water (30 ml), and LiOH—$H_2O$ (270 mg, 6.4 mmol, 2 equiv) was added. The resulting mixture was stirred for 1 h at room temperature until LC-MS showed that the reaction was complete. Most of the organic solvent was removed by evaporation, and residue was purified by HPLC to afford Compound C as a white solid (1.0 g, 90% yield).

Compound F: To a 100 mL round bottom flask equipped with a magnetic stirring bar was added Compound A (1.1 g, 3.2 mmol, 1.0 equiv) and MeCN (50 mL). $K_2CO_3$ (0.7 g, 4.8 mmol, 1.5 equiv) and was added to the mixture followed by iPrI (0.5 mL, 4.8 mmol, 1.5 equiv). The solution was heated at 60° C. for 8 h until LC-MS showed that the reaction was complete. The reaction solvent was removed under vacuum. The residual product was dissolved in dioxane (60 ml) and water (30 ml), and LiOH—$H_2O$ (270 mg, 6.4 mmol, 2 equiv) was added. The resulting mixture was stirred for 1 h at room temperature until LC-MS showed that the reaction was complete. Most of the organic solvent was removed by evaporation, and the residue was purified by HPLC to afford Compound F as a white solid (0.7 g, 61% yield).

Compounds D and E were made using similar synthetic methods.

Example 25

Synthesis of Intermediate Formula 1 and Intermediate Formula 2

Intermediate Formula 1

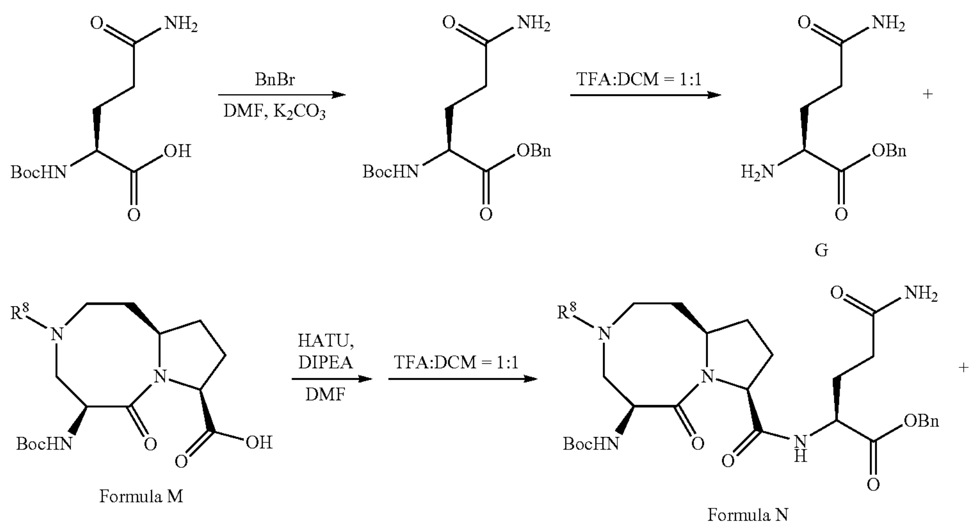

G

Formula M

Formula N

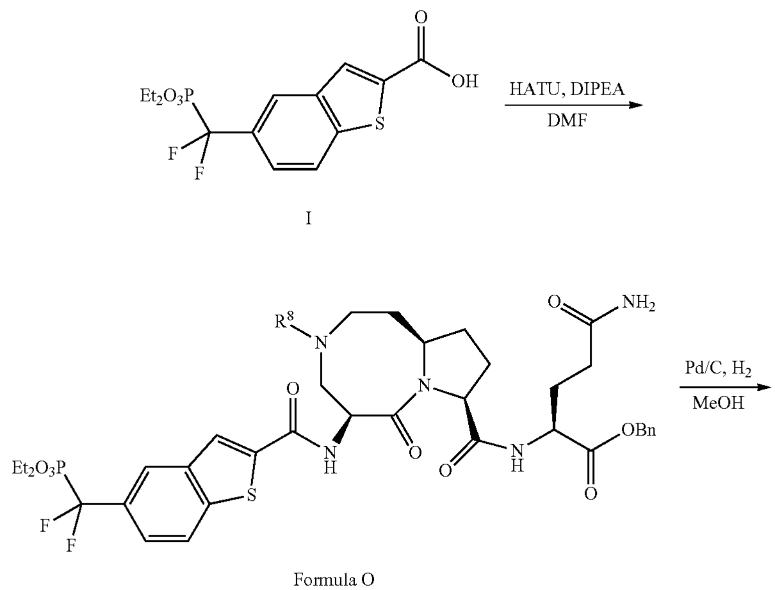

I

Formula O

-continued

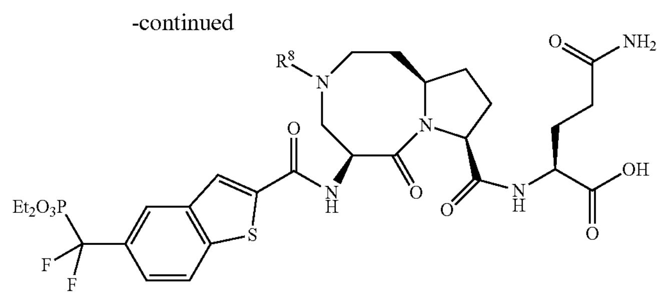

Intermediate Formula 1

Synthesis of Formula N (wherein $R^8$ is as defined in connection with Formula XXX): HATU (0.5 g, 1.3 mmol, 1.1 equiv.) was added to a solution of Compound G (0.29 g, 1.2 mmol, 1 equiv.), Formula M (1.2 mmol, 1 equiv.), and DIEA (1.25 mL, 7.2 mmol, 6 equiv.) in DMF (10 mL) and the resultant mixture was stirred at room temperature for 30 min. The reaction was quenched with $NaHCO_3$ aqueous solution, extracted with EtOAc (75 mL×3), washed with brine for three times, dried with anhydrous sodium sulfate, filtered, and concentrated under vacuum. The residual crude product was purified by flash column chromatography (DCM:MeOH=20:1) to afford the desired Boc protected product as a white solid (85-90% yield). The Boc group was removed before the next step to give a compound of Formula N.

Synthesis of Formula O: HATU (0.42 g, 1.1 mmol, 1.1 equiv.) was added to a solution of Formula N (0.46 g, 1.0 mmol, 1 equiv.), Compound I (0.36 g, 1.0 mmol, 1 equiv.), and DIEA (1.0 mL, 6 mmol, 6 equiv.) in DMF (10 mL) and the resultant mixture was stirred at room temperature for 30 min. The reaction was quenched with $NaHCO_3$ aqueous solution, extracted with EtOAc (75 mL×3), washed with brine for three times, dried with anhydrous sodium sulfate, filtered, and concentrated under vacuum. The residual crude product was purified by flash column chromatography (DCM:MeOH=20:1) to afford Formula O (around 80% yield).

Synthesis of Intermediate 1: A 50 mL round bottom bottle equipped with a magnetic stirring bar was filled with argon before adding Formula O (0.45 g), methanol (30 mL) and 10% Pd/C (500 mg). The reaction system was changed to hydrogen atmosphere three times and stirred at room temperature for 30 min. The reaction mixture was filtered to remove Pd/C and the solvent was removed under vacuum. The residual crude product was purified by HPLC to afford Intermediate Formula 1 as a light yellow solid (around 50-70% yield).

Synthesis of Intermediate Formula 2

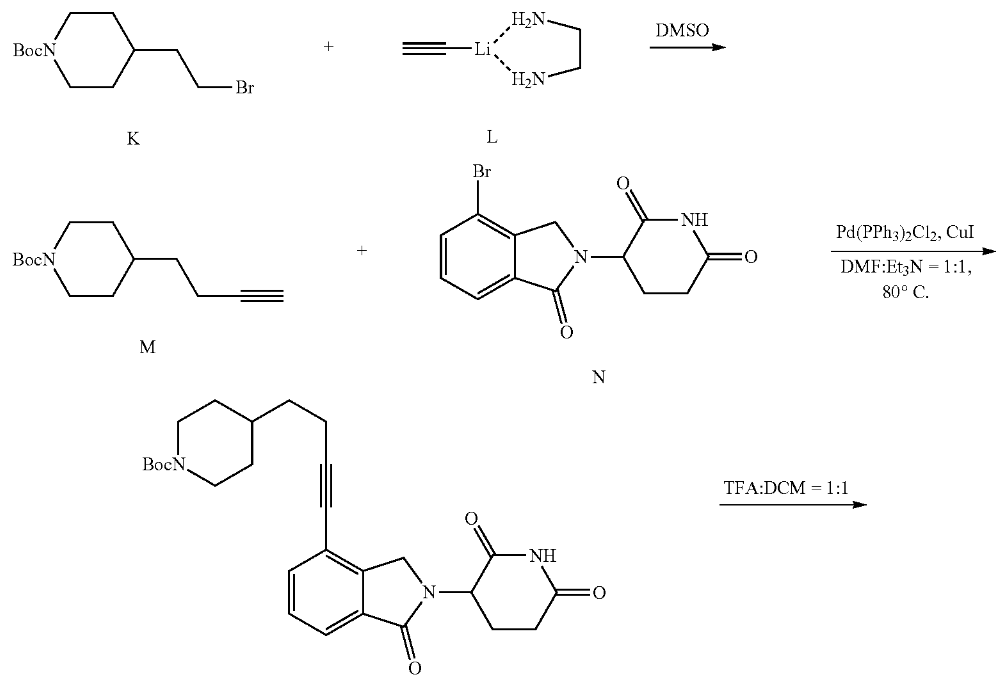

K

L

M

N

-continued

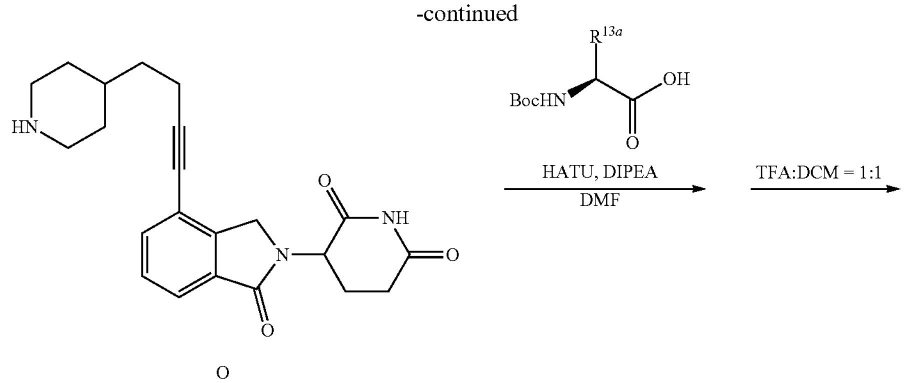

O

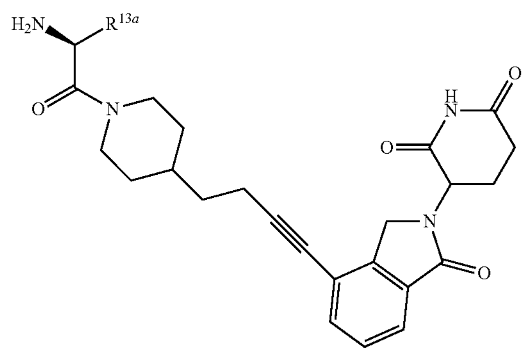

Intermediate Formula 2

Synthesis of Compound M: To a 25 mL round bottom flask equipped with a magnetic stirring bar was added Compound K (0.25 g, 0.85 mmol, 1.0 equiv), DMSO (5.0 mL) and Compound L (90%, 0.13 g, 1.3 mmol, 1.5 equiv). The suspension was stirred at room temperature for 4 h and monitored by TLC (PE:EA=4:1). Water (10 ml) was added to quench the reaction. The reaction was extracted with EtOAc (20 mL×3), washed with brine three times, dried with anhydrous sodium sulfate, filtered, and concentrated. The residual was purified by flash column chromatography (PE:EA=10:1 TO PE:EA=5:1) to afford Compound M as a colorless oil (0.15 g, 75% yield).

Synthesis of Compound O: Trimethylamine (4 mL) was added to a mixture of Compound M (0.15 g, 0.63 mmol, 1 equiv.), Compound N (0.2 g, 0.63 mmol, 1 equiv.), CuI (24 mg, 0.126 mmol, 0.2 equiv), and $Pd(PPh_3)_2Cl_2$ (44 mg, 0.063 mmol, 0.1 equiv) in DMF (4 mL). The resulting mixture was purged, refilled with argon three times, and stirred at 80° C. for 3 h under Argon. The reaction mixture was then cooled to room temperature and quenched with $NH_4Cl$ aqueous solution. The reaction mixture was extracted with EtOAc (50 mL×3), washed with brine three times, dried with anhydrous sodium sulfate, filtered, and concentrated. The residual crude product was purified by flash column chromatography (PE:EA=1:2) to afford Boc-protected compound as a light yellow solid (0.2 g, 66% yield). Compound O was obtained by using TFA to remove Boc group.

Synthesis of Intermediate Formula 2 (wherein $R^{13a}$ is as defined in connection with Formula I): HATU (13 mg, 0.033 mmol, 1.1 equiv.) was added to a solution of the cyclohexyl amino acid (($R^{13a}$=cyclohexyl, as an example: 8.5 mg, 0.033 mmol, 1.1 equiv.), Compound O (15 mg, 0.03 mmol, 1 equiv.) and DIEA (0.03 mL, 0.18 mmol, 6 equiv.) in DMF (1.0 mL). The resultant mixture was stirred at room temperature for 30 min. The residual crude product was purified by HPLC (MeCN/$H_2O$ 50%-100%, 50 min, 60 mL/min). The desired product eluted off the column when the MeCN concentration reached 61.3%). Intermediate Formula 2 was obtained by using TFA to remove the Boc group (14 mg, 90% yield).

Example 26
General Synthesis of STAT3 Degraders of Formula VII-E
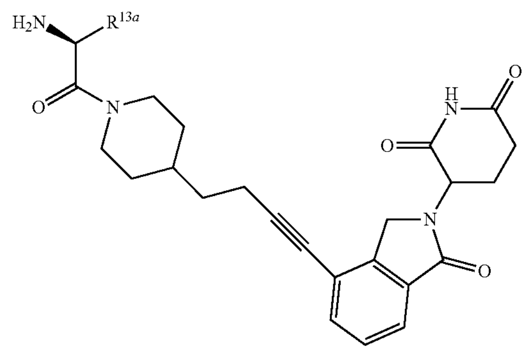
Intermediate Formula 2
+
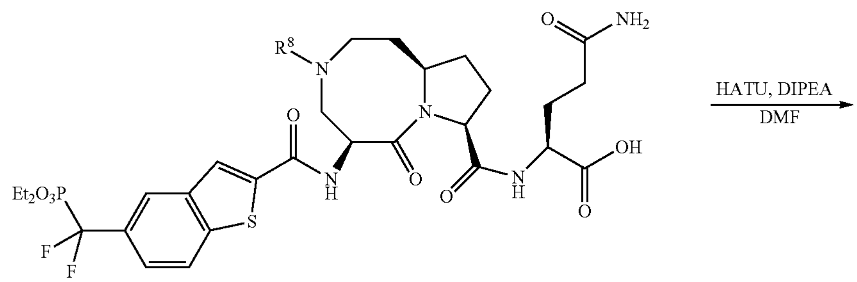
Intermediate Formula 1
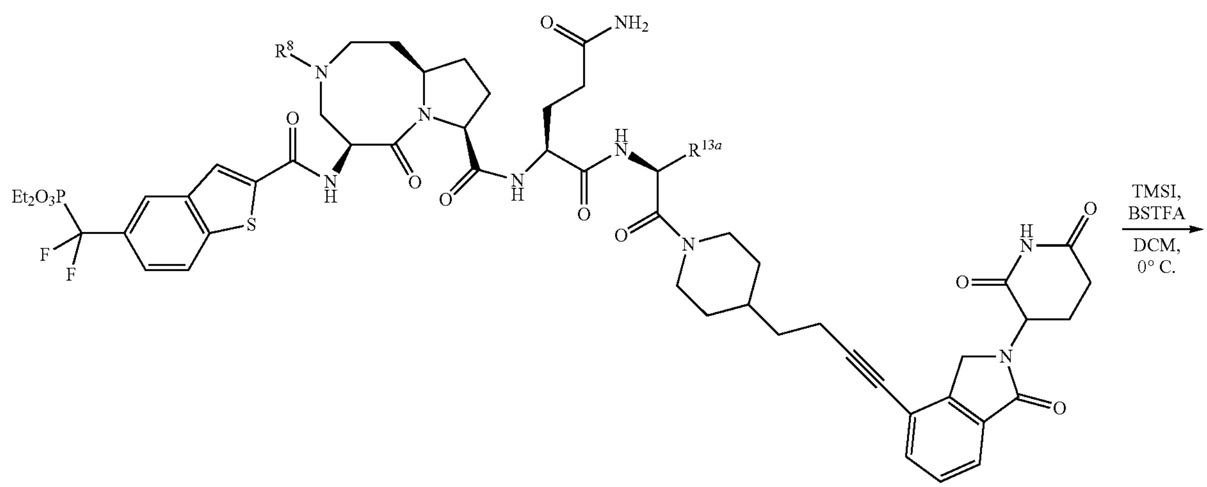
Formula VII-E
(wherein $R^{1a}$ and $R^{1b}$ are ethyl)

-continued

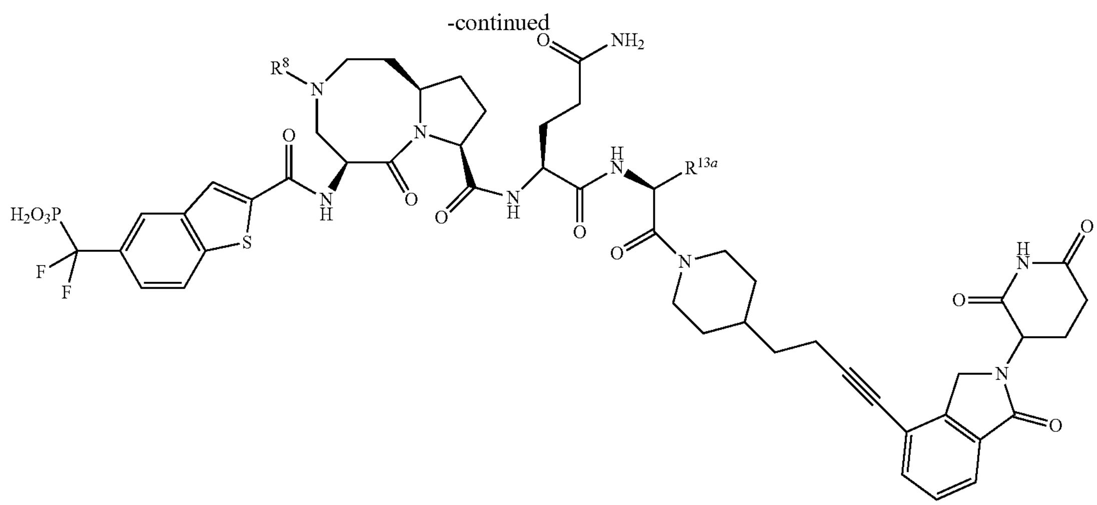

Formula VII-E
(wherein $R^{1a}$ and $R^{1b}$ are hydrogen

Synthesis of ((2-(((5S,8S,10aR)-8-(((2S)-5-amino-1-(((1S)-1-cyclohexyl-2-(4-(4-(2-(2,6-dioxopiperidin-3-yl)-1-oxoisoindolin-4-yl)but-3-yn-1-yl)piperidin-1-yl)-2-oxoethyl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic Acid (Cpd. No. 195)

Step 1: HATU (12 mg, 0.03 mmol, 1.1 equiv.) was added to a solution of Intermediate Formula 2 (wherein $R^{13}$=cyclohexyl, 11 mg, 0.013 mmol, 1 equiv.), Intermediate Formula 1 (wherein $R^8$=methoxycarbonyl and $R^{1a}$ and $R^{1b}$=ethyl, 9 mg, 0.013 mmol, 1 equiv.) and DIEA (0.014 mL, 0.078 mmol, 6 equiv.) in DMF (1.0 mL) and the resultant mixture was stirred at room temperature for 10 min. The residual crude product was purified by HPLC ($MeCN/H_2O$ 50%-100%, 50 min, 40 mL/min). The desired product eluted off the column when the MeCN concentration reached 58.5% to afford the desired product (14.6 mg, 89% yield).

Step 2: To a round bottom flask was the product of Step 1 (14.6 mg, 0.011 mmol, 1.0 equiv) and $CH_2Cl_2$ (1.0 mL). The solution was cooled to 0° C. before adding $CF_3CON(TMS)_2$ (0.021 mL, 0.066 mmol, 6.0 equiv) and 1M of TMS-I in DCM (0.055 mL, 0.055 mmol, 5.0 equiv). The reaction mixture was allowed to stir at 0° C. for 10 min and the solvent was removed under vacuum at 0° C. The residue was dissolved in a mixture of $CH_3CN$ (1.5 mL), water (1.5 mL) and TFA (0.1 mL), and purified by HPLC ($MeCN/H_2O$ 40%-100%, 60 min, 40 mL/min). The product eluted off the column when the MeCN concentration reached 45.3% to yield Cpd. No. 195 (10.5 mg, 80%). $^1H$ NMR (400 MHz, $CD_3CN:D_2O$=1:1) δ 8.09 (s, 1H), 8.03 (d, J=6.8 Hz, 1H), 7.95 (d, J=8.8 Hz, 1H), 7.69 (d, J=7.6 Hz, 1H), 7.60 (d, J=8.8 Hz, 1H), 7.54 (d, J=8.0 Hz, 1H), 7.45 (t, J=7.6 Hz, 1H), 5.09-4.92 (m, 2H), 4.64-4.62 (m, 1H), 4.42-4.23 (m, 7H), 3.99-3.73 (m, 2H), 3.66-3.43 (m, 6H), 3.01 (t, J=13.2 Hz, 1H), 2.87-2.71 (m, 2H), 2.62-2.53 (m, 1H), 2.45-2.34 (m, 3H), 2.27-2.01 (m, 5H), 1.88-1.46 (m, 16H), 1.10-0.93 (m, 7H). UPLC-MS calculated for $C_{57}H_{69}F_2N_9O_{14}PS$ [M+H]+: 1204.44, found: 603.04. UPLC-retention time: 4.1 min.

The following compounds were prepared using methods similar to those used to prepare Cpd. No. 195 and other compounds described in the EXAMPLES above. All compounds were purified by HPLC.

Cpd. No. 193: UPLC-MS calculated [M+H]+: 1188.45, found: 1188.68. UPLC-retention time: 3.7 min.

Cpd. No. 278: UPLC-MS calculated [M+H]+: 1186.41, found: 1186.48. UPLC-retention time: 3.6 min.

Cpd. No. 305: UPLC-MS calculated [M+H]+: 1169.42, found: 1169.64. UPLC-retention time: 2.5 min.

Cpd. No. 306: UPLC-MS calculated [M+H]+: 1174.47, found: 1174.58. UPLC-retention time: 4.0 min.

Cpd. No. 307: UPLC-MS calculated [M+H]+: 1204.40, found: 602.75. UPLC-retention time: 3.6 min.

Cpd. No. 308: UPLC-MS calculated for [M+H]+: 1182.44, found: 1182.49. UPLC-retention time: 3.8 min.

Cpd. No. 309: UPLC-MS calculated for [M+H]+: 1202.38, found: 601.69. UPLC-retention time: 3.9 min.

Cpd. No. 310: UPLC-MS calculated for [M+H]+: 1170.40, found: 1170.59. UPLC-retention time: 3.6 min.

Cpd. No. 311: UPLC-MS calculated for [M+H]+: 1271.56, found: 636.83. UPLC-retention time: 3.3 min.

Cpd. No. 312: UPLC-MS calculated for [M+H]+: 1313.49, found: 657.83. UPLC-retention time: 3.4 min.

Cpd. No. 313: UPLC-MS calculated for [M+H]+: 1204.36, found: 602.77. UPLC-retention time: 3.9 min.

Cpd. No. 314: UPLC-MS calculated for [M+H]+: 1206.38, found: 603.95. UPLC-retention time: 3.8 min.

Cpd. No. 315: UPLC-MS calculated for [M+H]+: 1162.34, found: 1163.50. UPLC-retention time: 3.4 min.

Cpd. No. 316: UPLC-MS calculated for [M+H]+: 1182.44, found: 1182.58. UPLC-retention time: 3.7 min.

Cpd. No. 317: UPLC-MS calculated for [M+H]+: 1224.48, found: 613.21. UPLC-retention time: 4.5 min.

Cpd. No. 318: UPLC-MS calculated for [M+H]+: 1236.41, found: 618.92. UPLC-retention time: 4.1 min.

Cpd. No. 319: UPLC-MS calculated for [M+H]+: 1226.46, found: 614.04. UPLC-retention time: 4.5 min.

Cpd. No. 320: UPLC-MS calculated for [M+H]+: 1238.39, found: 619.98. UPLC-retention time: 4.1 min.

Cpd. No. 321: UPLC-MS calculated for [M+H]+: 1244.45, found: 622.83. UPLC-retention time: 4.2 min.

Cpd. No. 322: UPLC-MS calculated for [M+H]+: 1226.37, found: 613.91. UPLC-retention time: 4.0 min.

Cpd. No. 323: UPLC-MS calculated for [M+H]+: 1238.32, found: 621.19. UPLC-retention time: 4.1 min.

Cpd. No. 324: $^1$H NMR (400 MHz, $CD_3CN:D_2O$=1:1) δ 8.10 (s, 1H), 8.04 (s, 1H), 7.94 (d, J=8.0 Hz, 1H), 7.70 (d, J=8.0 Hz, 1H), 7.62 (d, J=8.0 Hz, 1H), 7.55 (d, J=8.0 Hz, 1H), 7.46 (t, J=8.0 Hz, 1H), 5.48-5.45 (m, 1H), 5.10-5.04 (m, 1H), 4.72-4.60 (m, 3H), 4.43-4.25 (m, 7H), 4.01-3.97 (m, 1H), 3.76-3.72 (m, 1H), 3.61-3.54 (m, 2H), 3.40-3.25 (m, 3H), 3.03-2.99 (m, 1H), 2.88-2.72 (m, 2H), 2.64-2.53 (m, 1H), 2.46-2.00 (m, 9H), 1.87-1.48 (m, 13H), 1.34-1.28 (m, 3H), 1.14-0.93 (m, 7H). UPLC-MS calculated for [M+H]+: 1174.47, found: 1174.72. UPLC-retention time: 3.8 min.

Cpd. No. 325: UPLC-MS calculated for [M+H]+: 1238.39, found: 619.76. UPLC-retention time: 4.1 min.

Cpd. No. 326: $^1$H NMR (400 MHz, $CD_3CN:D_2O$=1:1) δ 8.09 (s, 1H), 8.02 (s, 1H), 7.92 (d, J=8.4 Hz, 1H), 7.69 (d, J=7.6 Hz, 1H), 7.61 (d, J=8.8 Hz, 1H), 7.53 (d, J=7.6 Hz, 1H), 7.45 (t, J=7.6 Hz, 1H), 7.16-7.05 (m, 2H), 6.98-6.95 (m, 1H), 5.46 (s, 1H), 5.10-4.94 (m, 2H), 4.70-4.58 (m, 2H), 4.41-4.25 (m, 5H), 3.80-3.71 (m, 2H), 3.58-3.53 (m, 2H), 3.39-3.26 (m, 3H), 2.94-2.66 (m, 5H), 2.55-2.34 (m, 5H), 2.24-1.97 (m, 7H), 1.87-1.27 (m, 12H). UPLC-MS calculated for [M+H]+: 1218.42, found: 610.28. UPLC-retention time: 4.5 min.

Cpd. No. 327: UPLC-MS calculated for [M+H]+: 1232.43, found: 617.05. UPLC-retention time: 4.5 min.

Cpd. No. 328: $^1$H NMR (400 MHz, $CD_3CN:D_2O$=1:1) δ 8.09 (s, 1H), 8.03 (s, 1H), 7.95 (d, J=8.4 Hz, 1H), 7.68 (d, J=7.6 Hz, 1H), 7.60 (d, J=8.4 Hz, 1H), 7.53 (d, J=7.6 Hz, 1H), 7.44 (t, J=7.6 Hz, 1H), 7.13-7.04 (m, 2H), 6.97-6.94 (m, 1H), 5.08-4.93 (m, 3H), 4.40-4.25 (m, 7H), 3.86-3.75 (m, 2H), 3.70-3.41 (m, 3H), 2.93-2.67 (m, 5H), 2.50-2.00 (m, 13H), 1.92-0.90 (m, 11H). UPLC-MS calculated for [M+H]+: 1232.40, found: 616.82. UPLC-retention time: 3.8 min.

Cpd. No. 330: UPLC-MS calculated for [M+H]+: 1220.40, found: 610.60. UPLC-retention time: 4.7 min.

Cpd. No. 332: UPLC-MS calculated for [M+H]+: 1254.40, found: 628.42. UPLC-retention time: 4.2 min.

Cpd. No. 333: $^1$H NMR (400 MHz, $CD_3CN:D_2O$=1:1) δ 8.09 (s, 1H), 8.03 (s, 1H), 7.98-7.93 (m, 1H), 7.71-7.68 (m, 1H), 7.62-7.59 (m, 1H), 7.55-7.42 (m, 4H), 7.38-7.31 (m, 1H), 5.10-4.98 (m, 3H), 4.37-4.25 (m, 7H), 3.88-3.43 (m, 8H), 2.99-2.91 (m, 5H), 2.49-2.06 (m, 10H), 1.87-0.99 (m, 11H). UPLC-MS calculated for [M+H]+: 1280.40, found: 640.89. UPLC-retention time: 4.5 min.

Cpd. No. 334: $^1$H NMR (400 MHz, $CD_3CN:D_2O$=1:1) δ 8.44 (s, 1H), 8.20 (s, 1H), 7.97 (d, J=8.4 Hz, 1H), 7.88 (d, J=8.4 Hz, 1H), 7.74-7.69 (m, 2H), 7.55 (d, J=7.6 Hz, 1H), 7.46 (t, J=7.6 Hz, 1H), 5.09-4.99 (m, 2H), 4.64-4.62 (m, 1H), 4.43-4.22 (m, 7H), 3.99-3.76 (m, 2H), 3.67-3.30 (m, 6H), 3.05-2.99 (m, 1H), 2.86-2.71 (m, 2H), 2.62-2.53 (m, 1H), 2.46-2.34 (m, 3H), 2.25-2.10 (m, 5H), 1.88-1.48 (m, 11H), 1.11-0.91 (m, 7H). UPLC-MS calculated for [M+H]+: 1198.48, found: 1198.55. UPLC-retention time: 4.2 min.

Cpd. No. 335: UPLC-MS calculated for [M+H]+: 1240.42, found: 620.88. UPLC-retention time: 4.5 min.

Cpd. No. 336: $^1$H NMR (400 MHz, $CD_3CN:D_2O$=1:1) δ 8.08 (s, 1H), 8.01 (s, 1H), 7.94 (d, J=8.4 Hz, 1H), 7.69 (d, J=7.6 Hz, 1H), 7.59 (d, J=8.4 Hz, 1H), 7.54 (d, J=7.6 Hz, 1H), 7.45 (t, J=7.6 Hz, 1H), 7.13-7.07 (m, 2H), 6.97-6.95 (m, 1H), 5.10-4.91 (m, 2H), 4.76-4.75 (m, 1H), 4.44-4.24 (m, 9H), 3.96-3.88 (m, 1H), 3.76-3.59 (m, 5H), 3.49-3.41 (m, 1H), 3.17-3.07 (m, 1H), 2.93-2.71 (m, 5H), 2.48-2.35 (m, 5H), 2.25-2.13 (m, 5H), 1.88-1.34 (m, 9H). UPLC-MS calculated for [M+H]+: 1248.39, found: 625.04. UPLC-retention time: 3.9 min.

Cpd. No. 284: UPLC-MS (ESI-MS) m/z: calculated for $C_{64}H_{64}F_2N_8O_{12}PS^+$ 1189.41, found $[M+H]^+$ 1189.50. UPLC-retention time: 4.4 min.

Cpd. No. 285: MS (ESI-MS) m/z: 1188.9.

Cpd. No. 286: MS (ESI-MS) m/z: 1200.3.

Cpd. No. 287: UPLC-MS (ESI-MS) m/z: calculated for $C_{56}H_{62}F_3N_9O_{13}PS^+$ 1188.39, found $[M+H]^+$ 1188.51. UPLC-retention time: 3.7 min.

Cpd. No. 288: UPLC-MS (ESI-MS) m/z: calculated for $C_{57}H_{64}F_3N_8O_{12}PS^{2+}$ 586.20, found $[M+H]^{2+}$ 586.76. UPLC-retention time: 4.3 min.

Cpd. No. 289: MS (ESI-MS) m/z: 1227.1.

Cpd. No. 290: $^1$H NMR (400 MHz, $CD_3CN:D_2O$=1:1) δ 8.10 (s, 1H), 8.04 (s, 1H), 7.94 (d, J=8.6 Hz, 1H), 7.70 (d, J=7.6 Hz, 1H), 7.62 (d, J=8.6 Hz, 1H), 7.55 (d, J=7.6 Hz, 1H), 7.48-7.44 (m, 1H), 7.24-7.10 (m, 2H), 7.04-6.86 (m, 2H), 5.47-5.41 (m, 1H), 5.15-4.90 (m, 2H), 4.70-4.52 (m, 2H), 4.44-4.22 (m, 4H), 3.76-3.66 (m, 2H), 3.63-3.45 (m, 2H), 3.38-3.22 (m, 3H), 2.99-2.62 (m, 5H), 2.54-1.96 (m, 11H), 1.90-0.92 (m, 14H). MS (ESI-MS) m/z: 1200.5.

Cpd. No. 291: $^1$H NMR (400 MHz, $CD_3CN:D_2O$=1:1) δ 8.12 (s, 1H), 8.08 (s, 1H), 7.97 (d, J=8.6 Hz, 1H), 7.72 (dd, J=7.6, 1.3 Hz, 1H), 7.63 (d, J=8.6 Hz, 1H), 7.57 (d, J=7.7 Hz, 1H), 7.48 (td, J=7.6, 2.0 Hz, 1H), 7.25-7.10 (m, 2H), 7.06-6.90 (m, 2H), 5.51-5.44 (m, 1H), 5.14-4.88 (m, 2H), 4.79-4.22 (m, 6H), 3.74 (d, J=13.0 Hz, 2H), 3.61-3.54 (m, 2H), 3.38-3.23 (m, 3H), 3.00-2.55 (m, 5H), 2.52-1.96 (m, 8H), 1.87-0.63 (m, 15H). MS (ESI-MS) m/z: 1202.7.

Cpd. No. 279: MS (ESI-MS) m/z: 1145.8.

Cpd. No. 293: $^1$H NMR (400 MHz, $CD_3CN:D_2O$=1:1) δ $^1$H NMR (400 MHz, $CD_3CN$) δ 8.12 (s, 1H), 8.08 (s, 1H), 7.97 (d, J=8.6 Hz, 1H), 7.71 (d, J=7.6 Hz, 1H), 7.64 (d, J=8.6 Hz, 1H), 7.57 (d, J=7.5 Hz, 1H), 7.50-7.46 (m, 1H), 7.31-7.06 (m, 4H), 5.50-5.45 (m, 1H), 5.15-4.90 (m, 2H), 4.75-4.54 (m, 2H), 4.47-4.22 (m, 4H), 3.79-3.73 (m, 2H), 3.62-3.54 (m, 2H), 3.43-3.17 (m, 3H), 2.98-2.64 (m, 5H), 2.61-1.96 (m, 11H), 1.89-0.89 (m, 14H). MS (ESI-MS) m/z: 1216.6.

Cpd. No. 294: MS (ESI-MS) m/z: 1218.7.

Cpd. No. 295: $^1$H NMR (400 MHz, $CD_3CN:D_2O$=1:1) δ 8.14 (s, 1H), 8.10 (s, 1H), 7.99 (d, J=8.6 Hz, 1H), 7.74 (d, J=7.5 Hz, 1H), 7.66 (d, J=8.6 Hz, 1H), 7.59 (d, J=7.6 Hz, 1H), 7.50 (t, J=7.7 Hz, 1H), 7.30-7.11 (m, 2H), 7.04-6.95 (m, 2H), 6.37 (t, J=53.8 Hz, 1H), 5.51-5.38 (m, 1H), 5.14-5.07 (m, 1H), 5.03-4.96 (m, 1H), 4.74-4.64 (m, 1H), 4.61-4.54 (m, 1H), 4.46-4.29 (m, 3H), 3.86-3.63 (m, 5H), 3.46-3.40 (m, 1H), 3.01-2.67 (m, 4H), 2.64-2.34 (m, 4H), 2.32-1.99 (m, 4H), 1.91-1.03 (m, 10H). UPLC-MS (ESI-MS) m/z: calculated for $C_{58}H_{65}F_5N_9O_{12}PS^{2+}$ 618.71, found $[M+H]^{2+}$ 618.97. UPLC-retention time: 4.6 min.

Cpd. No. 296: $^1$H NMR (400 MHz, $CD_3CN:D_2O$=1:1) δ 8.10 (s, 1H), 8.04 (d, J=6.6 Hz, 1H), 7.96 (d, J=8.6 Hz, 1H), 7.70 (d, J=7.6 Hz, 1H), 7.61 (d, J=8.6 Hz, 1H), 7.55 (d, J=7.6 Hz, 1H), 7.46 (t, J=7.6 Hz, 1H), 7.19-7.12 (m, 2H), 6.99-6.91 (m, 2H), 5.10-5.03 (m, 1H), 4.97-4.93 (m, 2H), 4.53-4.21 (m, 6H), 3.93-3.31 (m, 8H), 2.98-2.56 (m, 5H), 2.54-1.98 (m, 10H), 1.88-0.88 (m, 12H). UPLC-MS (ESI-MS) m/z: calculated for $C_{58}H_{65}F_3N_9O_{14}PS^{2+}$ 615.70, found $[M+H]^{2+}$ 615.93. UPLC-retention time: 4.5 min.

Cpd. No. 297: $^1$H NMR (400 MHz, $CD_3CN:D_2O$=1:1) δ 8.15 (s, 1H), 8.11 (d, J=2.8 Hz, 1H), 8.00 (d, J=8.7 Hz, 1H), 7.74 (d, J=7.4 Hz, 1H), 7.66 (d, J=8.6 Hz, 1H), 7.61 (d, J=7.7 Hz, 1H), 7.51 (t, J=7.5 Hz, 1H), 6.33 (t, J=53.8 Hz, 1H), 5.40 (s, 1H), 5.20-5.02 (m, 1H), 4.75-4.41 (m, 5H), 3.81-3.34 (m,

5H), 3.19-1.99 (m, 16H), 1.90-0.75 (m, 18H). UPLC-MS (ESI-MS) m/z: calculated for $C_{57}H_{70}F_4N_9O_{12}PS^{2+}$ 605.73, found $[M+H]^{2+}$ 606.27. UPLC-retention time: 4.9 min.

Cpd. No. 298: $^1H$ NMR (400 MHz, $CD_3CN:D_2O$=1:1) δ 8.12 (s, 1H), 8.07 (s, 1H), 7.97 (d, J=8.6 Hz, 1H), 7.75-7.67 (m, 1H), 7.63 (d, J=8.7 Hz, 1H), 7.56-7.44 (m, 2H), 7.41-7.07 (m, 5H), 6.43-6.16 (m, 1H), 5.80-5.75 (m, 1H), 5.45 (dd, J=11.5, 5.1 Hz, 1H), 5.09-5.03 (m, 1H), 4.69-4.65 (m, 1H), 4.59-4.54 (m, 1H), 4.44-4.25 (m, 4H), 3.92-3.62 (m, 6H), 3.42-3.36 (m, 1H), 3.01-2.56 (m, 4H), 2.51-1.96 (m, 10H), 1.89-0.88 (m, 11H). MS (ESI-MS) m/z: 1204.7.

Cpd. No. 299: $^1H$ NMR (400 MHz, $CD_3CN:D_2O$=1:1) δ 8.11 (s, 1H), 8.06 (s, 1H), 7.96 (d, J=8.6 Hz, 1H), 7.71 (d, J=7.5 Hz, 1H), 7.63 (d, J=8.6 Hz, 1H), 7.56-7.45 (m, 2H), 7.39-7.19 (m, 5H), 5.82-5.77 m, 1H), 5.47-5.39 (m, 1H), 5.09-5.03 (m, 1H), 4.70-4.56 (m, 2H), 4.40-4.27 (m, 4H), 3.80-3.69 (m, 2H), 3.61-3.43 (m, 2H), 3.30 (t, J=12.0 Hz, 1H), 3.20-3.15 (m, 2H), 3.02-2.54 (m, 4H), 2.49-1.95 (m, 10H), 1.90-0.98 (m, 14H). MS (ESI-MS) m/z: 1168.5.

Cpd. No. 300: $^1H$ NMR (400 MHz, $CD_3CN:D_2O$=1:1) δ 8.08 (d, J=14.4 Hz, 2H), 7.96 (d, J=8.6 Hz, 1H), 7.71 (d, J=7.6 Hz, 1H), 7.63 (d, J=8.6 Hz, 1H), 7.56 (dd, J=7.6, 0.9 Hz, 1H), 7.47 (td, J=7.6, 2.2 Hz, 1H), 7.20-7.12 (m, 2H), 7.01-6.91 (m, 2H), 6.47-6.19 (m, 1H), 5.45-5.41 (m, 1H), 5.13-4.93 (m, 2H), 4.72-4.68 (m, 1H), 4.55-4.50 (m, 2H), 4.44-4.24 (m, 3H), 3.83-3.64 (m, 5H), 3.44-3.37 (m, 1H), 2.98-2.69 (m, 4H), 2.65-1.95 (m, 9H), 1.91-0.80 (m, 10H). MS (ESI-MS) m/z: 1238.9.

Cpd. No. 301: UPLC-MS (ESI-MS) m/z: calculated for $C_{58}H_{65}F_3N_9O_{13}PS^{2+}$ 607.71, found $[M+H]^{2+}$ 607.73. UPLC-retention time: 4.2 min.

Example 27

Synthesis of ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphoryl)bis(oxy))bis(methylene)bis(2,2-dimethylpropanoate) (Cpd. No. 340) and Related Compounds

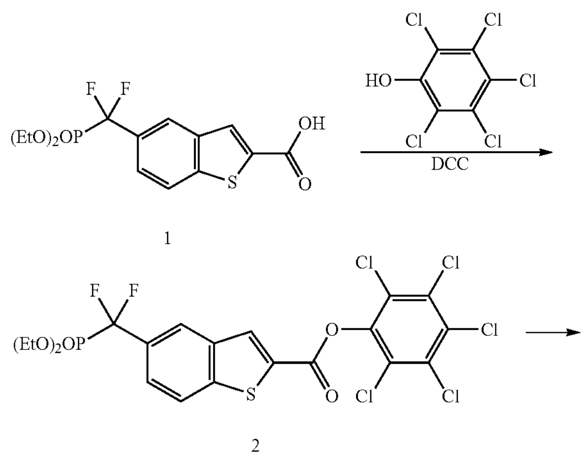

1

2

-continued

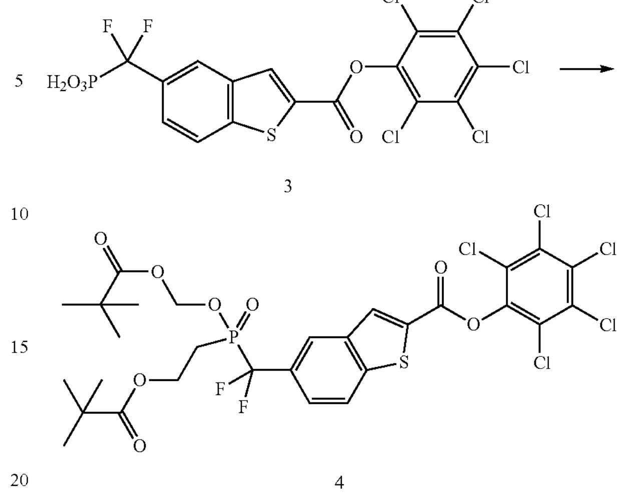

3

4

Step 1: Synthesis of Compound 4

A solution of Compound 1 (364 mg, 1 mmol, 1 equiv.), pentachlorophenol (193 mg, 1.1 mmol, 1.1 equiv.), DCC (268 mg, 1.3 mmol, 1.3 equiv.), and DMAP (12.2 mg, 0.1 mmol, 0.1 equiv.) in 10 mL of DMF was stirred at room temperature for 24 h. The reaction mixture was filtered through celite and the filtrate was diluted with EtOAc, washed with $H_2O$ and brine, and dried over sodium sulfate. After removal of the solvent under vacuum, the residue was purified by flash chromatography on silica gel to afford Compound 2 (410 mg, 67%). UPLC-MS (ESI-MS) m/z: 612.8.

To a round bottom flask was added Compound 2 (330 mg, 0.54 mmol, 1.0 equiv) and $CH_2Cl_2$ (10 mL). The solution was cooled to 0° C. before adding $CF_3CON(TMS)_2$ (555 mg, 2.16 mmol, 4.0 equiv) and 1M of TMS-I in DCM (1.08 mL, 1.08 mmol, 2.0 equiv). The reaction mixture was allowed to stir at 0° C. until the starting material disappeared. The solvent was removed under vacuum at 0° C. The crude product Compound 3 was used without further purification.

1 N NaOH solution (1.1 mL) was added to a stirred suspension of the crude Compound 3 in 10 mL of $H_2O$ to adjust pH to be 9~10. After 5 minutes, $AgNO_3$ (275 mg, 1.6 mmol, 3 equiv) aqueous solution was added and the reaction mixture was allowed to stir at room temperature for 2 hours. The precipitate (silver salt) was collected by filtration, washed with ether (20 mL×4) and dried on lyophilizer.

The silver salt was place in a round bottom flask equipped with a magnetic stirring bar and anhydrous toluene was added. After that, iodomethyl pivalate (392 mg, 1.6 mmol, 3.0 equiv) was added via syringe and the reaction mixture was allowed to stir for 24 hours in dark. The reaction mixture was filtered and the solution was collected. The solvent was remove under vacuum and the residual crude product was purified by flash column chromatography to afford Compound 4 as a white solid (207 mg, 49% yield over three steps). MS (ESI-MS) m/z: 785.1.

Step 2: Synthesis of Cpd. No. 340

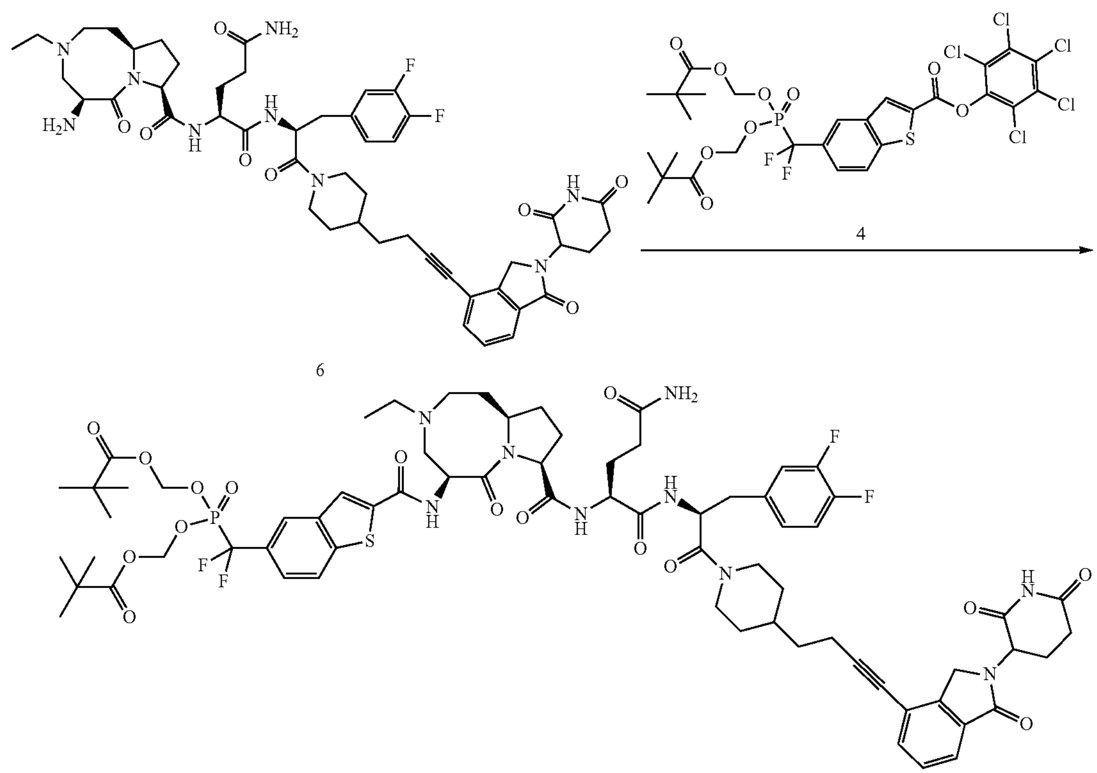

6

Cpd. No. 340

DIEA (12 μL, 0.068 mmol, 3 equiv.) was added to the mixture of Compound 4 (25 mg, 0.032 mmol, 1.2 equiv.), Compound 6 (25 mg, 0.027 mmol, 1 equiv.) and HOBt (7.2 mg, 0.054 mmol, 2 equiv.) in DMF (2 mL). The resulting mixture was stirred at room temperature for 0.5 hour. Purification HPLC gave the compound Cpd. No. 340 (30 mg, 78%). MS (ESI-MS) m/z: 1446.8. UPLC-retention time: 5.5 min.

Compound 5 was made used the similar method for Compound 4. MS (ESI-MS) m/z: 788.7.

5

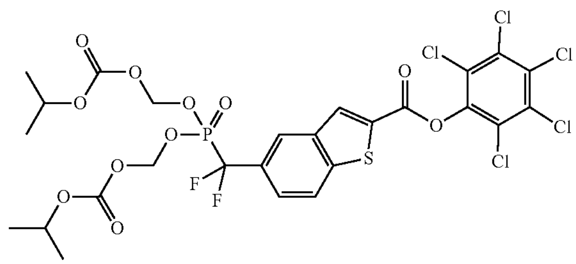

The following compounds were prepared by a procedure similar to the one used to prepare Cpd. No. 340, e.g., using Compounds 4 or 5 as starting materials.

Cpd. No. 341: UPLC-MS (ESI-MS) m/z: calculated for $C_{68}H_{82}F_4N_9O_{18}PS^{2+}$ 726.24, found $[M+H]^{2+}$ 726.06. UPLC-retention time: 5.1 min.

Cpd. No. 342: MS (ESI-MS) m/z: 1402.9. UPLC-retention time: 5.3 min.

Cpd. No. 343: UPLC-MS (ESI-MS) m/z: calculated for C67H88F2N9O18PS$^{2+}$ 703.78, found $[M+H]^{2+}$ 704.21. UPLC-retention time: 5.1 min.

Cpd. No. 344: MS (ESI-MS) m/z: 1476.6. UPLC-retention time: 6.4 min.

Cpd. No. 345: UPLC-MS (ESI-MS) m/z: calculated for $C_{68}H_{80}F_4N_9O_{20}PS^{2+}$ 740.75, found $[M+H]^{2+}$ 741.38. UPLC-retention time: 5.9 min.

Cpd. No. 346: MS (ESI-MS) m/z: 1432.5. UPLC-retention time: 6.5 min.

Cpd. No. 347: MS (ESI-MS) m/z: 1436.9. UPLC-retention time: 6.4 min.

Cpd. No. 348: $^1$H NMR (400 MHz, $CD_3CN:D_2O$=1:1) δ 7.86 (s, 1H), 7.69 (d, J=7.6 Hz, 1H), 7.54 (d, J=7.6 Hz, 1H), 7.48-7.42 (m, 1H), 7.34-7.25 (m, 1H), 7.20 (s, 1H), 5.26 (s, 1H), 5.08-5.03 (m, 2H), 4.70-4.54 (m, 2H), 4.41-4.22 (m, 4H), 3.31-3.30 (m, 2H), 3.18-2.68 (m, 8H), 2.40-2.01 (m, 11H), 1.82-1.70 (m, 3H), 1.54-1.47 (m, 2H), 1.38-1.00 (m, 12H). UPLC-MS calculated for [M+H]+: 1167.49, found: 1167.81. UPLC-retention time: 4.1 min.

Example 28

Synthesis of ((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-(methoxycarbonyl)-6-oxodecahydropyrrolo[1,2-a][1,5]diazocin-5-yl)carbamoyl)benzo[b]thiophen-5-yl)difluoromethyl)phosphonic Acid (Cpd. No. 329)

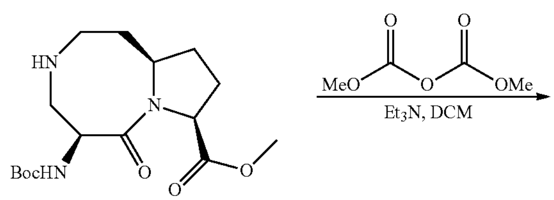

A

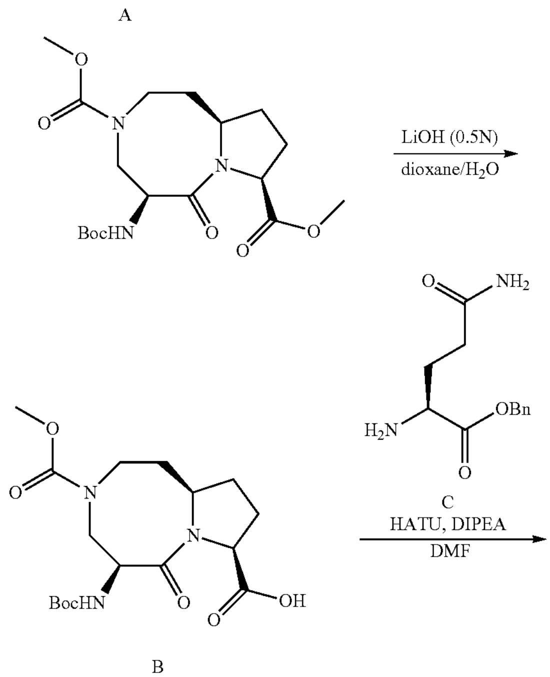

C

B

-continued

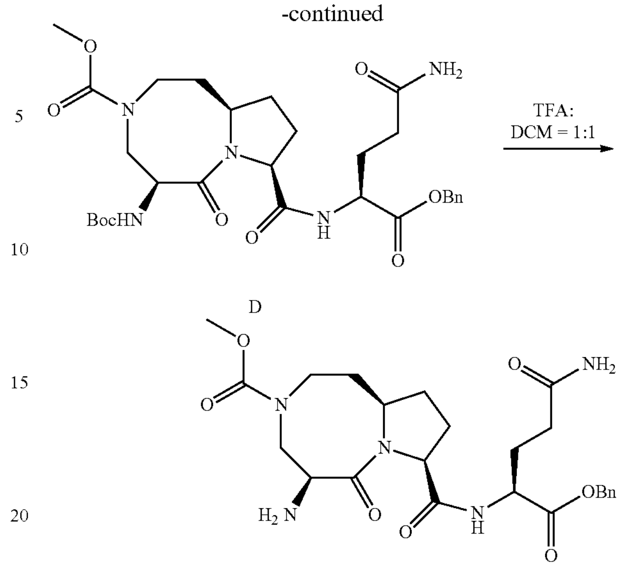

D

E

Compound B: To a 100 mL round bottom flask equipped with a magnetic stirring bar was added compound A (1.1 g, 3.2 mmol, 1.0 equiv) and DCM (50 mL). $Et_3N$ (0.7 mL, 4.8 mmol, 1.5 equiv) and was added to the mixture followed by dimethyl dicarbonate (0.5 g, 3.8 mmol, 1.2 equiv). The solution was stirred room temperature for 1 h until LC-MS showed the reaction to be finished. The reaction solvent was removed under vacuum. The residual crude compound B was dissolved in dioxane (60 ml) and water (30 ml), and LiOH—$H_2O$ (670 mg, 16 mmol, 5 equiv) was added. The resulting mixture was stirred for 30 min at room temperature until LC-MS showed the reaction finished. Most of the organic solvent was removed by evaporation, then the residue was purified by HPLC to afford compound B as a white solid (0.95 g, 77% yield for two steps).

Compound D: HATU (0.42 g, 1.1 mmol, 1.1 equiv.) was added to a solution of compound C (0.26 g, 1.1 mmol, 1.1 equiv.), compound B (0.38 g, 1.0 mmol, 1 equiv.) and DIEA (1.0 mL, 6.0 mmol, 6 equiv.) in DMF (8 mL) and the resultant mixture was stirred at room temperature for 15 min until LC-MS showed the reaction finished. The residue was purified by HPLC (MeCN/$H_2O$ 30%-100%, 70 min, 60 mL/min. Compound D eluted off the column when MeCN reached 41.0% to give a white solid (0.54 g, 90% yield). The Boc group was removed in TFA/DCM=1/1 solution to give compound E.

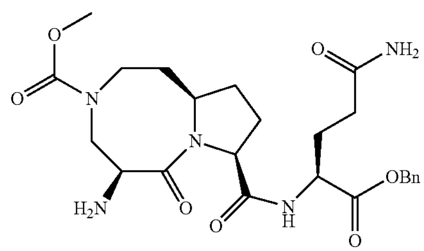

E

+

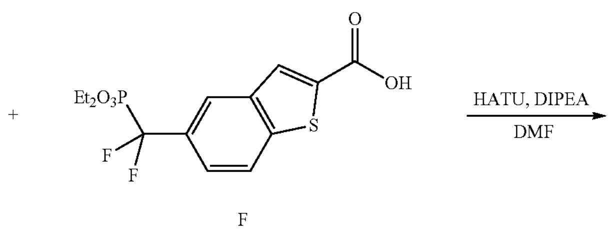

F

-continued

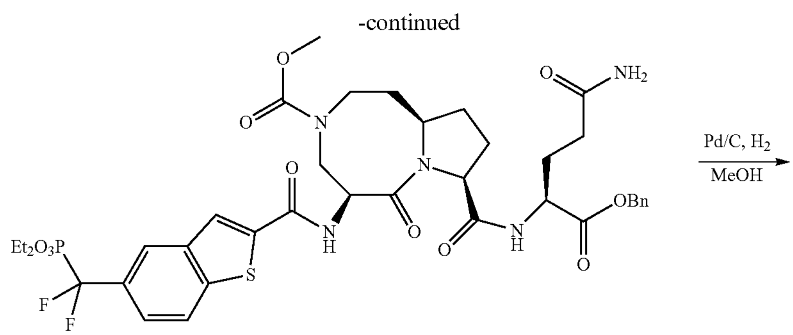

Cpd. No. 371

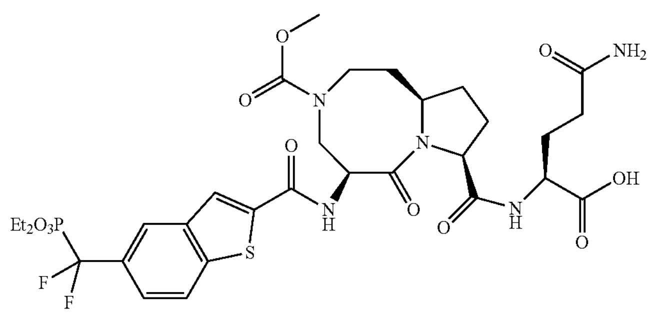

Cpd. No. 372

Cpd. No. 371: HATU (0.14 g, 0.36 mmol, 1.1 equiv.) was added to a solution of compound E (0.16 g, 0.33 mmol, 1 equiv.), compound F (0.12 g, 0.33 mmol, 1 equiv.) and DIEA (0.34 mL, 2 mmol, 6 equiv.) in DMF (3 mL), and the resultant mixture was stirred at room temperature for 30 min until LC-MS showed the reaction finished (LC-MS: 5.0 min $[M+H/Na]^+$: 850/872). The reaction was quenched with $NaHCO_3$ aqueous solution, extracted with EtOAc (75 mL×3), washed with brine three times, dried with anhydrous sodium sulfate, filtered, and concentrated under vacuum. The residual crude product was purified by flash column chromatography (DCM:MeOH=20:1) to afford Cpd. No. 371 (0.23 g, 85% yield).

Cpd. No. 372: A 50 mL round bottom bottle equipped with a magnetic stirring bar was filled with argon and Cpd. No. 371 (0.23 g, 0.28 mmol), methanol (30 mL) and 10% Pd/C (300 mg) was added. The reaction system was changed to hydrogen atmosphere for three times, and stirred at room temperature for 30 min. The reaction mixture was filtered to remove Pd/C and the solvent was removed under vacuum. The residual crude product was purified by HPLC (MeCN/$H_2O$ 35%-100%, 65 min, 60 mL/min, the product came out when MeCN is 40.4%) to afford Cpd. No. 372 as a light yellow solid (0.15 g, 70% yield).

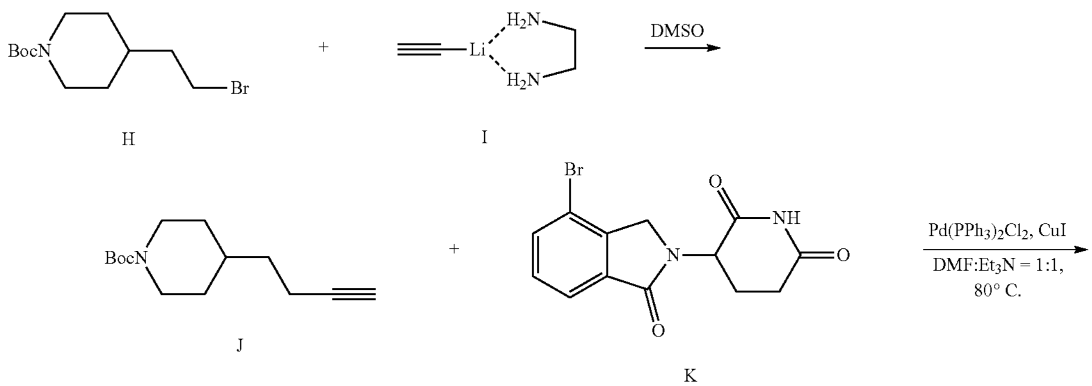

H I

J K

-continued

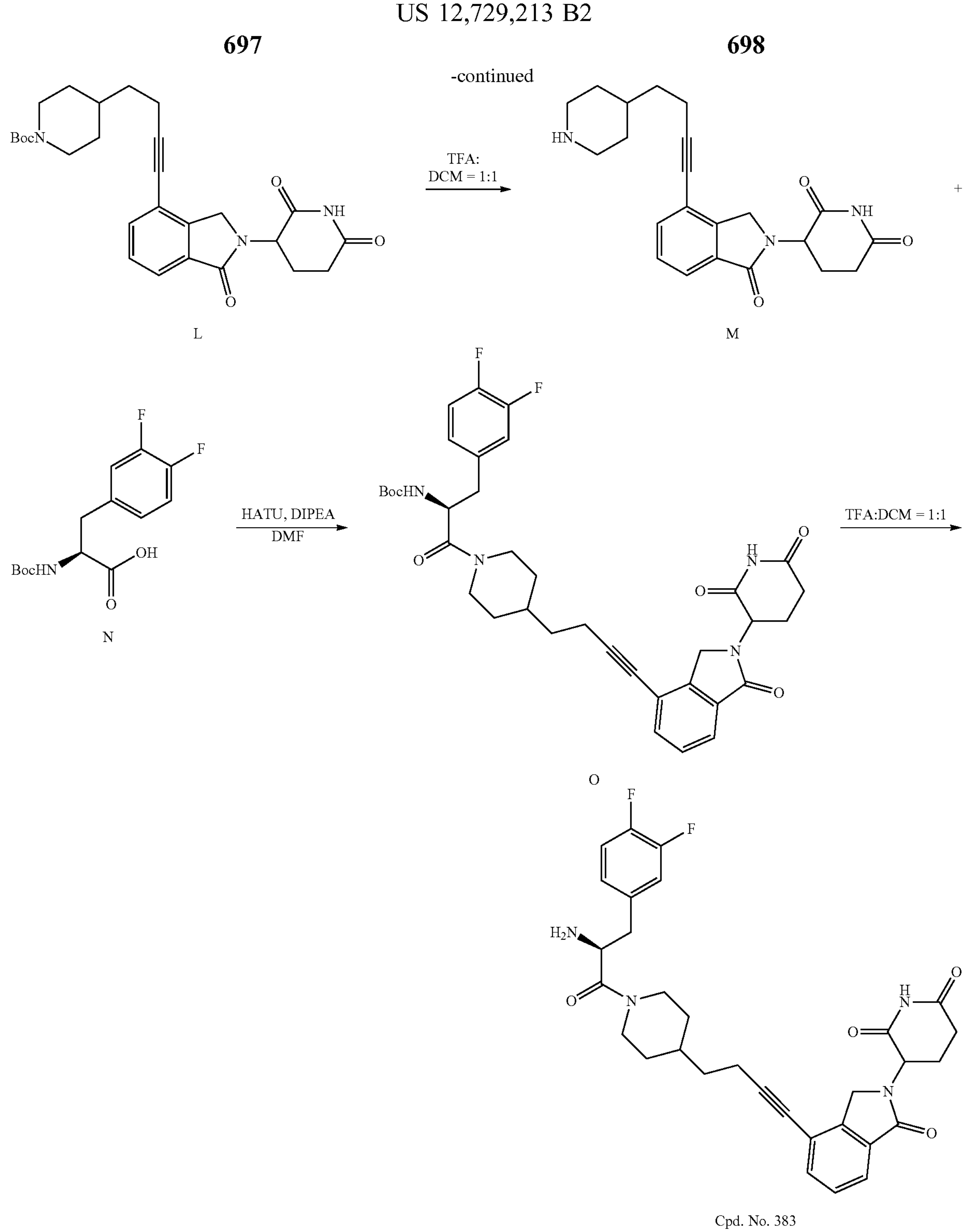

L

M

N

O

Cpd. No. 383

Compound J: To a 25 mL round bottom flask equipped with a magnetic stirring bar was added compound H (0.25 g, 0.85 mmol, 1.0 equiv), DMSO (5.0 mL) and compound I (90%, 0.13 g, 1.3 mmol, 1.5 equiv). The suspension was stirred at room temperature for 4 hours and monitored by TLC (PE:EA=4:1). Water (10 ml) was added to quench the reaction. The reaction mixture was extracted with EtOAc (20 mL×3), washed with brine for three times, dried with anhydrous sodium sulfate, filtered and concentrated under vacuum. The residual product was purified by flash column chromatography (PE:EA=10:1 TO PE:EA=5:1) to afford compound J as a colorless oil (0.15 g, 75% yield).

Compound L: Trimethylamine (4 mL) was added to a mixture of compound J (0.15 g, 0.63 mmol, 1 equiv.), compound K (0.2 g, 0.63 mmol, 1 equiv.), CuI (24 mg, 0.126 mmol, 0.2 equiv) and $Pd(PPh_3)_2Cl_2$ (44 mg, 0.063 mmol, 0.1 equiv) in DMF (4 mL). The resulting mixture was purged and refilled with argon three times, and stirred at 80° C. for 5 h under Argon. The reaction mixture was then cooled to room temperature and quenched with $NH_4Cl$ aqueous solution, extracted with EtOAc (50 mL×3), washed with brine for three times, and dried with anhydrous sodium sulfate, filtered and concentrated under vacuum. The residual product was purified by flash column chromatography (PE: EA=1:2) to afford compound L as a light yellow solid (0.2 g, 66% yield). The Boc group was removed in TFA/DCM=1/1 solution to give compound M before the next step.

Cpd. No. 383: HATU (69 mg, 0.18 mmol, 1.1 equiv.) was added to a solution of amino acid compound N (49 mg, 0.16 mmol, 1.0 equiv.), compound M (61 mg, 0.16 mmol, 1.0 equiv.) and DIEA (0.17 mL, 1.0 mmol, 6 equiv.) in DMF (1.0 mL) and the resultant mixture was stirred at room temperature for 30 min. The residual crude product was purified by HPLC (MeCN/$H_2O$ 55%-100%, 45 min, 60 mL/min, the product came out when MeCN is 62.1%), and then TFA/DCM=1/1 solution was used to remove the Boc group to afford Cpd. No. 383 (77 mg, 86% yield).

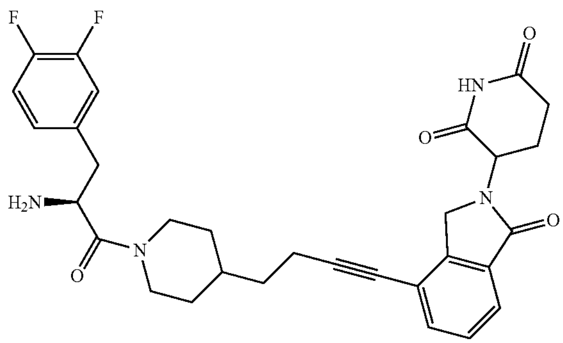

+

Cpd. No. 383

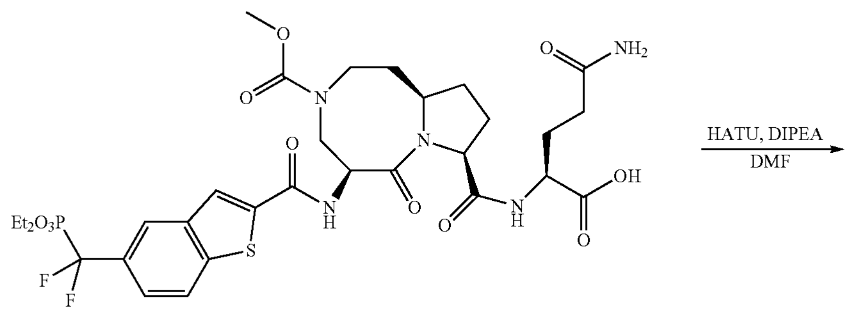

Cpd. No. 372

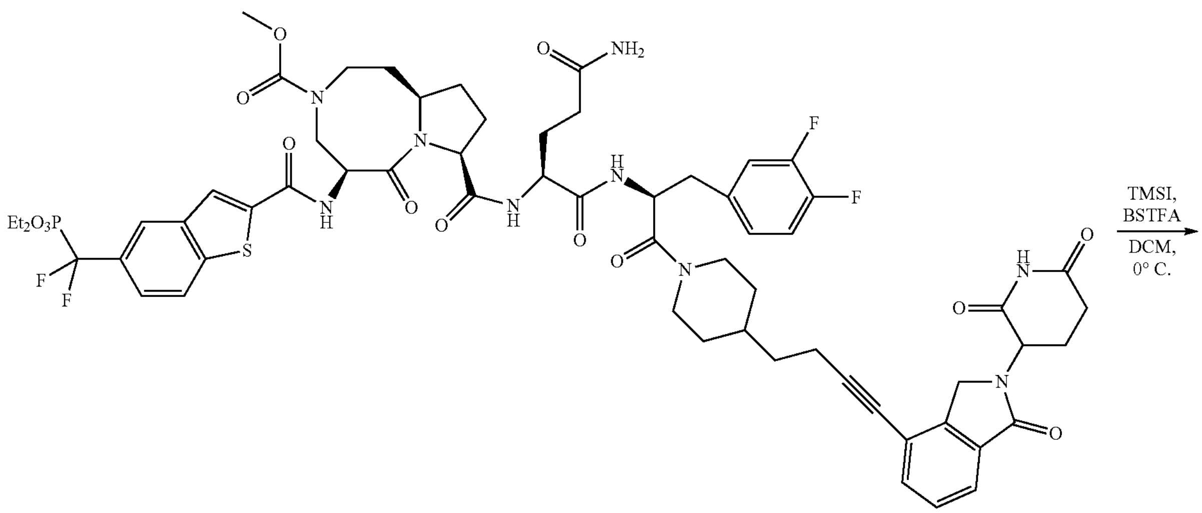

Cpd. No. 329E

-continued

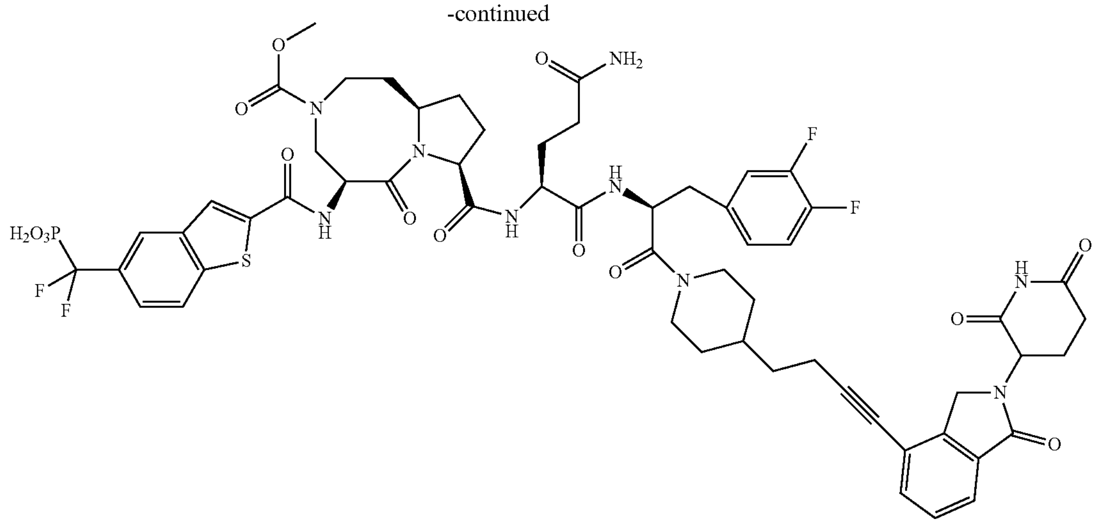

Cpd. No. 329

Cpd. No. 329E: HATU (12 mg, 0.033 mmol, 1.1 equiv.) was added to a solution of the Cpd. No. 383 (17 mg, 0.03 mmol, 1.0 equiv.), Cpd. No. 372 (23 mg, 0.03 mmol, 1.0 equiv.) and DIEA (0.03 mL, 0.18 mmol, 6 equiv.) in DMF (1.0 mL) and the resultant mixture was stirred at room temperature for 10 min. The residual crude product was purified by HPLC (MeCN/$H_2O$ 45%-100%, 55 min, 60 mL/min, the product came out when MeCN is 53.5%) to Cpd. No. 329E (27.1 mg, 70% yield).

Cpd. No. 329: To a round bottom flask was added Cpd. No. 329E (27.1 mg, 0.02 mmol, 1.0 equiv) and $CH_2Cl_2$ (1.0 mL). The solution was cooled to 0° C. before adding $CF_3CON(TMS)_2$ (31 mg, 0.12 mmol, 6.0 equiv) and 1M of TMS-I in DCM (0.1 mL, 0.1 mmol, 5.0 equiv). The reaction mixture was allowed to stir at 0° C. for 10 min and the solvent was removed under vacuum at 0° C. The residue was dissolved in a mixture solvent of $CH_3CN$ (1.5 mL), water (1.5 mL) and TFA (0.1 mL), and purified by HPLC (MeCN/$H_2O$ 35%-100%, 65 min, 60 mL/min, the product came out when MeCN is 43.5%) to yield Cpd. No. 329 (21 mg, 87%).

$^1H$ NMR (400 MHz, $CD_3CN$:$D_2O$=1:1) δ 8.10 (s, 1H), 8.05 (d, J=6.0 Hz, 1H), 7.96 (d, J=8.4 Hz, 1H), 7.70 (d, J=7.2 Hz, 1H), 7.61 (d, J=8.4 Hz, 1H), 7.56 (d, J=7.6 Hz, 1H), 7.47 (t, J=7.6 Hz, 1H), 7.12-7.06 (m, 2H), 6.99-6.95 (m, 1H), 5.10-4.93 (m, 3H), 4.43-4.25 (m, 7H), 3.87-3.30 (m, 9H), 2.94-2.68 (m, 5H), 2.51-2.31 (m, 4H), 2.22-2.00 (m, 5H), 1.87-1.35 (m, 11H). UPLC-MS calculated for $C_{58}H_{63}F_4N_9O_{14}PS$ [M H]+: 1248.39, found: 625.28. UPLC-retention time: 4.0 min.

Example 29

Synthesis of ((2-(((5S,8S,10aR)-8-(((2S)-5-amino-1-(((2S)-3-(4-(tert-butyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic Acid (Cpd. No. 331)

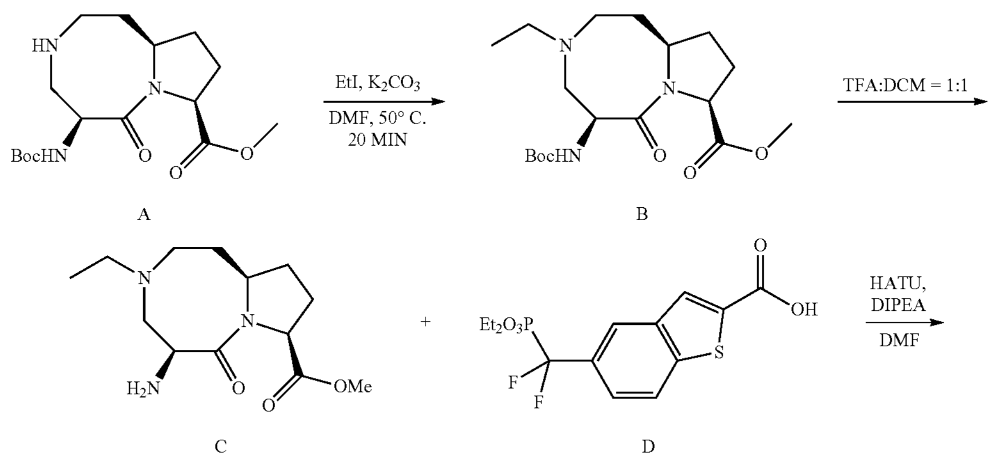

A B C D

-continued

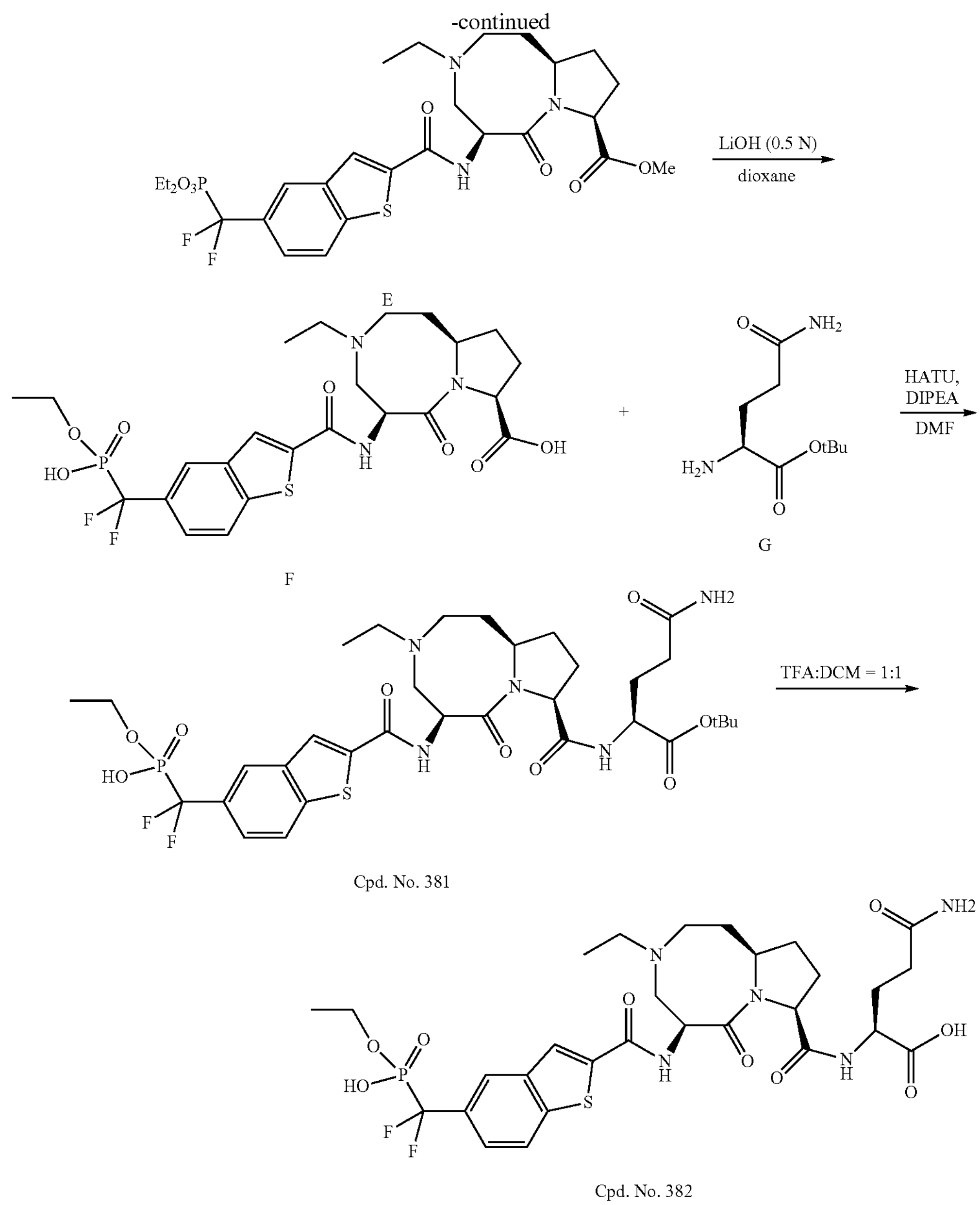

E

F

G

Cpd. No. 381

Cpd. No. 382

Compound B: To a 25 mL round bottom flask equipped with a magnetic stirring bar was added compound A (0.5 g, 1.46 mmol, 1.0 equiv), $K_2CO_3$ (0.8 g, 5.84 mmol, 4.0 equiv) and DMF (6 mL). EtI (0.36 mL, 4.4 mmol, 3.0 equiv) was added. The solution was stirred at 50° C. for 20 min until LC-MS detected the reaction to be finished. The reaction was cooled to room temperature, and water and MeCN were added. The crude product was directly purified by HPLC ($MeCN/H_2O$ 15%-100%, 85 min, 60 mL/min, the product came out when MeCN is 22.3%) to afford compound B. The Boc was removed by TFA/DCM=1/1 before the next step.

Compound E: HATU (0.58 g, 1.54 mmol, 1.1 equiv.) was added to a solution of compound B (0.7 g, 1.4 mmol, 1 equiv.), compound D (0.5 g, 1.4 mmol, 1 equiv.) and DIEA (1.5 mL, 8.4 mmol, 6 equiv.) in DMF (10 mL), and the resultant mixture was stirred at room temperature for 15 min. The reaction was quenched with $NaHCO_3$ aqueous solution, extracted with EtOAc (75 mL×3), washed with brine for three times, dried with anhydrous sodium sulfate, filtered, and concentrated under vacuum. The crude product was directly used in the next step without further purification.

Compound F: The residual crude compound E was dissolved in THF (10 ml) and water (5 ml), and LiOH—$H_2O$ (300 mg, 7 mmoL, 5 equiv) was added, The resulting mixture was stirred for 1 h at room temperature until LC-MS detected the reaction to be finished. Most of the organic solvent was removed by evaporation, then the residual product was purified by HPLC ($MeCN/H_2O$ 10%-100%, 90 min, 60 mL/min, the product came out when MeCN is 22.0%) to afford the desired acid compound F as a white solid (0.6 g, 80% yield).

Cpd. No. 382: HATU (0.11 g, 0.29 mmol, 1.1 equiv.) was added to a solution of compound F (0.15 g, 0.26 mmol, 1 equiv.), compound G (0.069 g, 0.29 mmol, 1.1 equiv.) and DIEA (0.26 mL, 1.5 mmol, 6 equiv.) in DMF (2 mL), and the resultant mixture was stirred at room temperature for 20 min. The residual product was purified by HPLC (MeCN/$H_2O$ 20%-100%, 80 min, 60 mL/min, the product came out when MeCN is 28.0%) to afford the desired tBu ester Cpd. No. 381. The tBu group was removed by TFA/DCM=1/1 before lyophilization to give Cpd. No. 382.
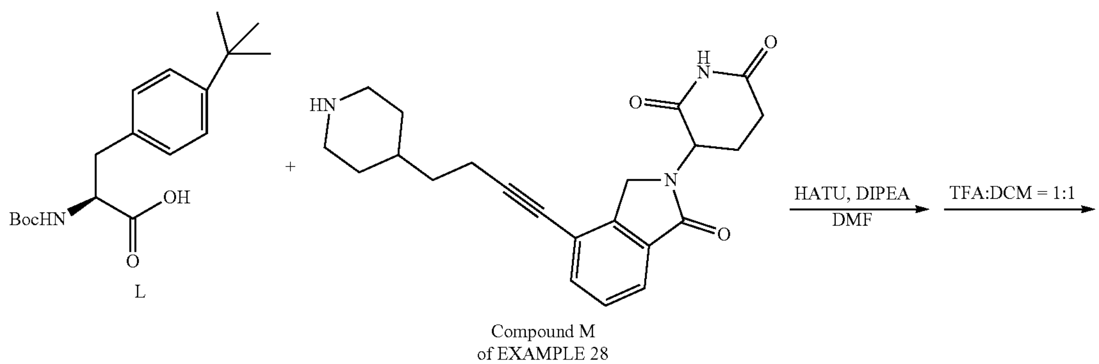
L
Compound M
of EXAMPLE 28
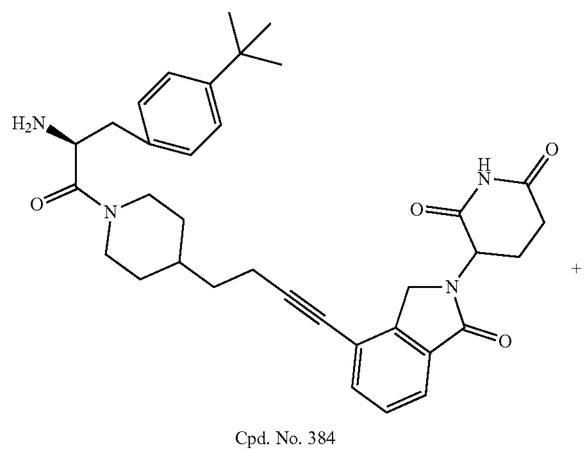
+
Cpd. No. 384
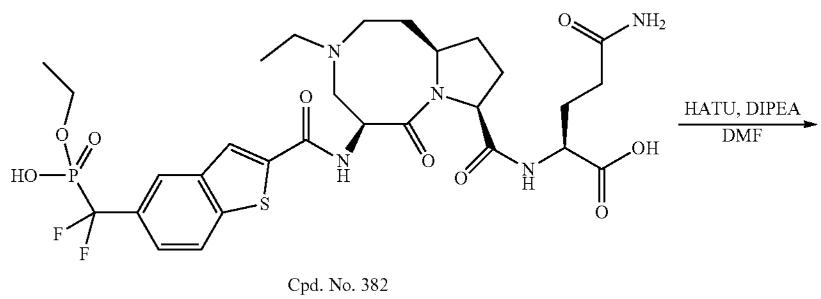
Cpd. No. 382
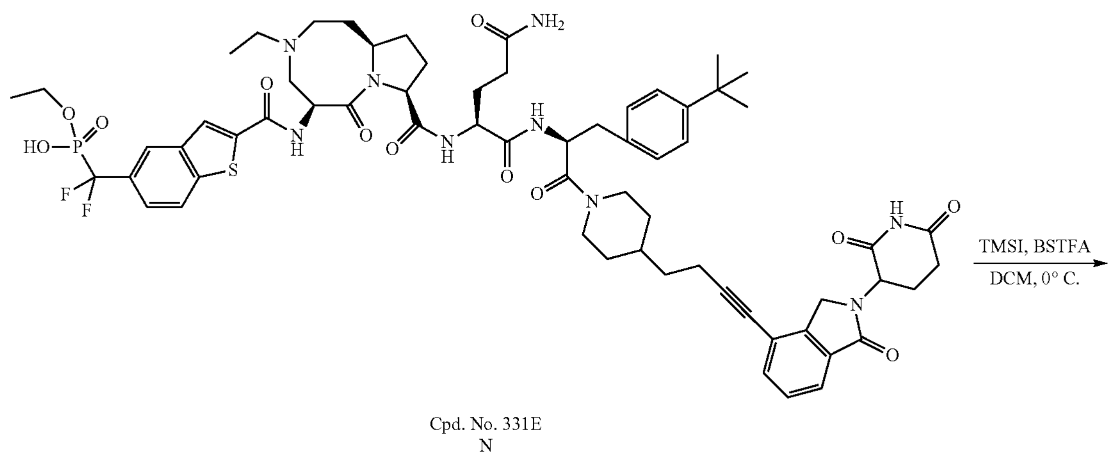
Cpd. No. 331E
N -continued

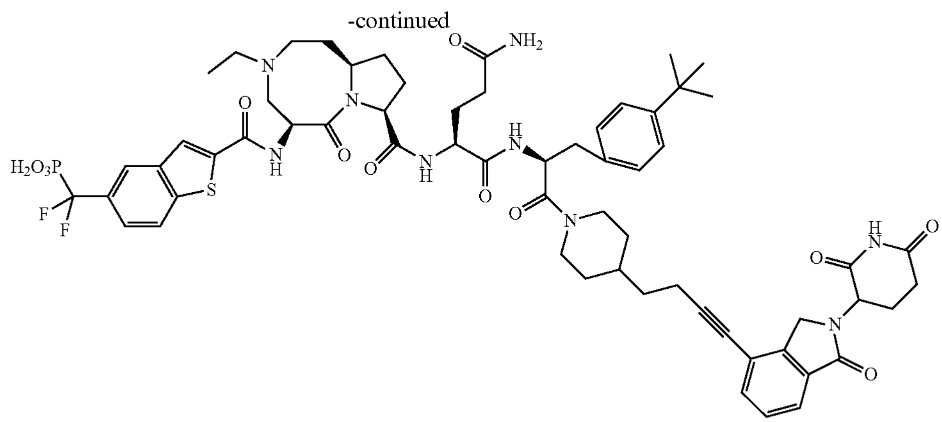

Cpd. No. 331

Cpd. No. 384: HATU (13 mg, 0.033 mmol, 1.1 equiv.) was added to a solution of the amino acid L (10.5 mg, 0.033 mmol, 1.1 equiv.), Compound M (see EXAMPLE 28) (12 mg, 0.03 mmol, 1 equiv.) and DIEA (0.03 mL, 0.18 mmol, 6 equiv.) in DMF (1.0 mL), and the resultant mixture was stirred at room temperature for 30 min. The residual crude product was purified by HPLC (MeCN/$H_2O$ 50%-100%, 50 min, 60 mL/min, the product came out when MeCN is 59.5%). TFA was used to remove the Boc group to afford Cpd. No. 384 (14 mg, 90% yield).

Cpd. No. 331E: HATU (12 mg, 0.03 mmol, 1.1 equiv.) was added to a solution of compound M (16 mg, 0.028 mmol, 1 equiv.), Cpd. No. 382 (21 mg, 0.03 mmol, 1.1 equiv.) and DIEA (0.03 mL, 0.18 mmol, 6 equiv.) in DMF (1.0 mL), and the resultant mixture was stirred at room temperature for 30 min. The residual crude product was purified by HPLC (MeCN/$H_2O$ 35%-100%, 65 min, 60 mL/min, the product came out when MeCN is 44.1%) to afford Cpd. No. 331E.

Cpd. No. 331: To a round bottom flask was added Cpd. No. 331E (25.3 mg, 0.02 mmol, 1.0 equiv) and $CH_2Cl_2$ (1.5 mL). The solution was cooled to 0° C. before adding $CF_3CON(TMS)_2$ (0.03 mL, 0.10 mmol, 5.0 equiv) and 1M of TMS-I in DCM (0.08 mL, 0.08 mmol, 4.0 equiv). The reaction mixture was allowed to stir at 0° C. for 10 min and the solvent was removed under vacuum at 0° C. The residue was dissolved in a mixture of $CH_3CN$ (1.5 mL), water (1.5 mL) and TFA (0.1 mL), and purified by HPLC (MeCN/$H_2O$ 40%-100%, 60 min, 60 mL/min, the product came out when MeCN is 44.7%) to yield Cpd. No. 331. UPLC-MS calculated for [M+H]+: 1238.50, found: 619.97. UPLC-retention time: 5.4 min.

Example 30

Synthesis of ((2-(((5S,8S,10aR)-8-(((2S)-5-amino-1-(((2S)-3-(4-(cyclopropylsulfonyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl) phosphonic Acid (Cpd. No. 352)

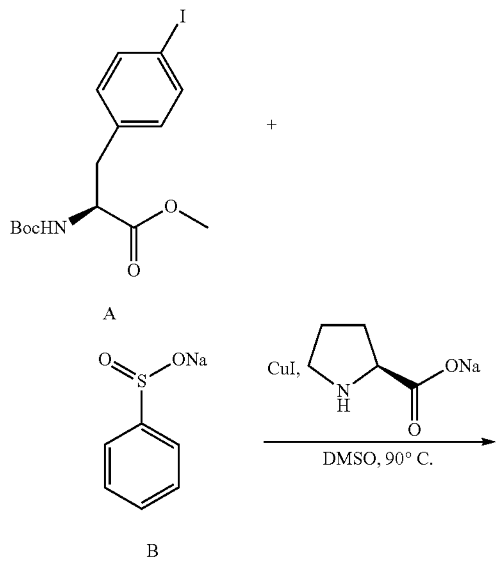

-continued

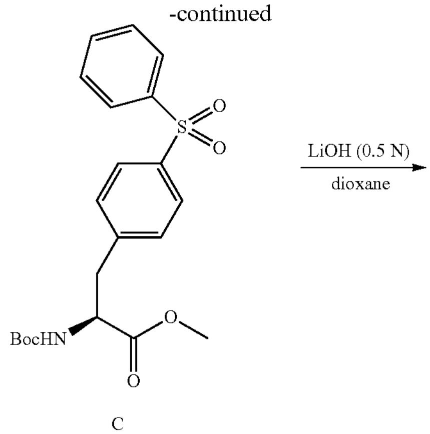

C

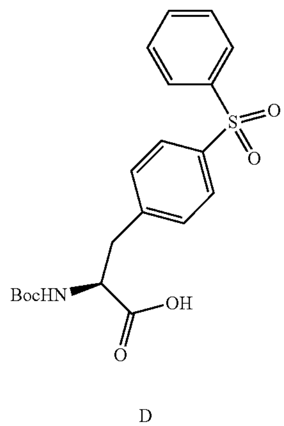

D

Compound C: A mixture of aryl halide compound A (1 mmol), sodium benzenesulfonate compound B (1.2 mmol), copper iodide (0.1 mmol), L-proline sodium salt (0.2 mmol), and 2 mL of DMSO in a sealed tube was heated at 90° C. under argon. After 24 h, the cooled mixture purified by HPLC (MeCN/$H_2O$ 40%-100%, 60 min, 60 mL/min, the product came out when MeCN is 54.1%) to yield compound C.

Compound D: Compound C (0.5 mmol) was dissolved in THF (3 ml) and water (1.5 ml), LiOH—$H_2O$ (200 mg, 5 mmoL, 10 equiv) was added. The resulting mixture was stirred for 1 h at room temperature until LC-MS detected the reaction to be finished. The residue was purified by HPLC (MeCN/$H_2O$ 35%-100%, 65 min, 60 mL/min, the product came out when MeCN is 45.7%) to afford the desired acid compound D.

Cpd. No. 352 was prepared using compound D in place of compound L as described in EXAMPLE 29. Cpd. No. 352 was purified by HPLC (MeCN/$H_2O$ 30%-100%, 70 min, 60 mL/min, the product came out when MeCN is 37.6%). (ESI-MS) $[M+H]^+$: 1322.8.

Example 31

Synthesis of ((2-(((5S,8S,10aR)-8-(((2S)-5-amino-1-(((2S)-3-(4-(cyclopropylsulfonyl)phenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic Acid (Cpd. No. 353)

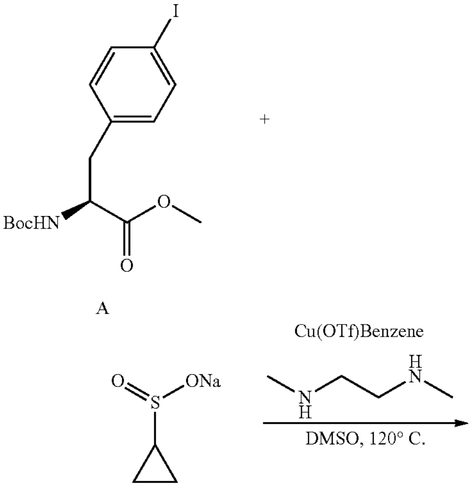

A

B

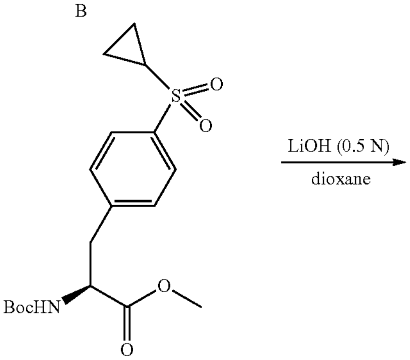

C

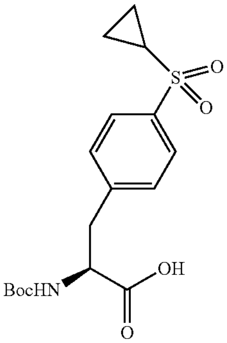

D

Compound C: A mixture of aryl halide compound A (202 mg, 0.5 mmol, 1 equiv.), sodium sulfonate compound B (77 mg, 0.6 mmol, 1.2 equiv.), Cu(OTf)Benzene (50 mg, 0.1 mmol, 0.2 equiv.), $N^1$,$N^2$-dimethylethane-1,2-diamine (17.6 mg, 0.2 mmol, 0.4 equiv.), and 2.5 mL of DMSO in a sealed tube was heated at 120° C. under argon. After 24 h, the cooled mixture was purified by HPLC ($MeCN/H_2O$ 30%-100%, 70 min, 60 mL/min, the product came out when MeCN is 46.0%) to yield compound C.

Compound D: Compound C (0.25 mmol) was dissolved in THF (2 ml) and water (1 ml), and $LiOH—H_2O$ (100 mg, 2.5 mmoL, 10 equiv) was added. The resulting mixture was stirred for 1 h at room temperature until LC-MS detected the reaction to be finished. The residue was purified by HPLC ($MeCN/H_2O$ 25%-100%, 75 min, 60 mL/min, the product came out when MeCN is 38.4%) to afford the desired acid compound D.

Cpd. No. 353 was prepared using compound D in place of compound L as described in EXAMPLE 29. Cpd. No. 353 was purified by HPLC ($MeCN/H_2O$ 25%-100%, 75 min, 60 mL/min, the product came out when MeCN is 34.7%). (ESI-MS) $[M+H]^+$: 1286.8.

Example 32

Synthesis of ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-3-(4-((4-methylphenyl)sulfonamido)phenyl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic Acid (Cpd. No. 354)

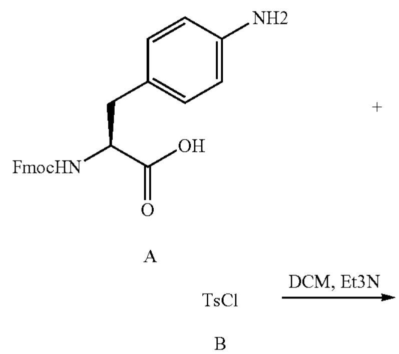

A

TsCl

B

-continued

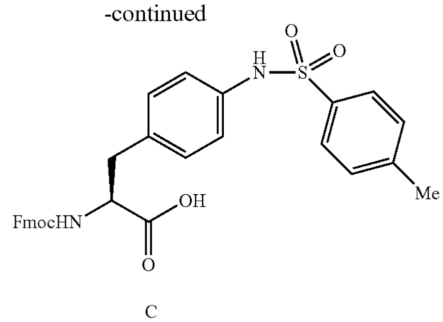

C

Compound C: To a 10 mL round bottom flask equipped with a magnetic stirring bar was added compound A (100 mg, 0.25 mmol, 1.0 equiv), $Et_3N$ (101 mg, 0.14 mL, 1 mmol, 4 equiv) and DCM (3 mL). TsCl (51 mg, 0.28 mmol, 1.1 equiv) was added. The solution was stirred at room temperature for 1 h until LC-MS detected the reaction to be finished. The crude product was directly purified by HPLC ($MeCN/H_2O$ 45%-100%, 55 min, 60 mL/min, the product came out when MeCN is 58.3%) to afford compound C (about 15% yield)

Cpd. No. 354 was prepared using compound C in place of compound L as described in EXAMPLE 29. Cpd. No. 354 was purified by HPLC ($MeCN/H_2O$ 30%-100%, 70 min, 60 mL/min, the product came out when MeCN is 38.5%). (ESI-MS) $[M+H]^+$: 1351.6.

Cpd. No. 357 made using the similar route as Cpd. No. 354. Cpd. No. 357 was purified by HPLC ($MeCN/H_2O$ 45%-100%, 55 min, 60 mL/min, the product came out when MeCN is 50.6%). (ESI-MS) $[M+H]^+$: 1419.7.

Example 33

Synthesis of ((2-(((5S,8S,10aR)-8-(((2S)-5-amino-1-(((2S)-1-(4-(4-(2-(2,6-dioxopiperidin-3-yl)-1-oxoisoindolin-4-yl)but-3-yn-1-yl)piperidin-1-yl)-1-oxo-3-(4-((tetrahydro-2H-pyran-4-yl)carbamoyl)phenyl)propan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)phosphonic Acid (Cpd. No. 359)

I. General Synthesis of Cpd. No. 358

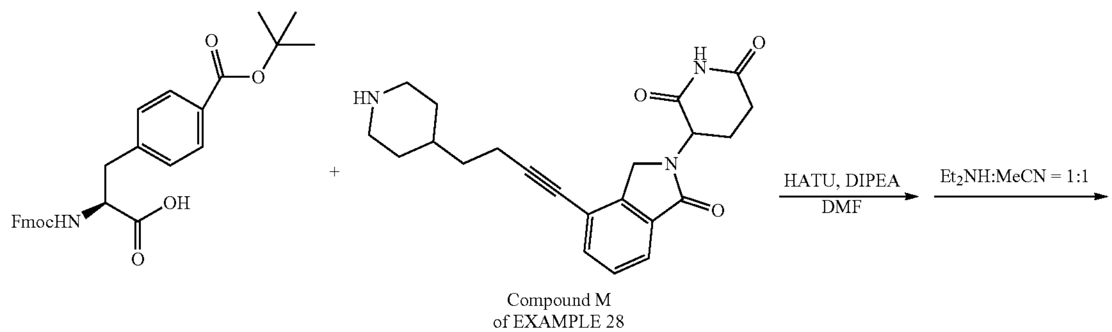

Compound M of EXAMPLE 28

-continued
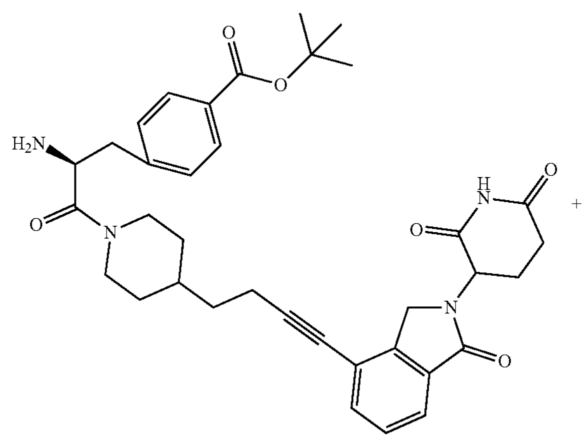
Cpd. No. 388
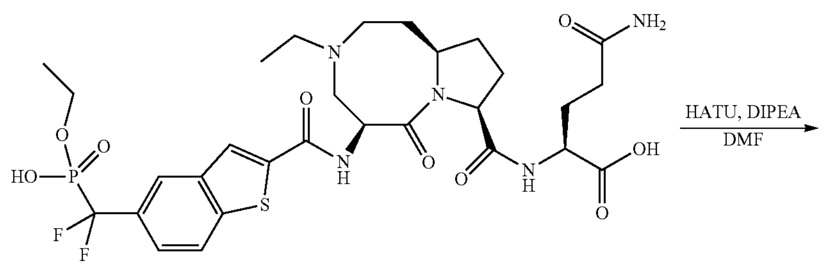
Cpd. No. 382
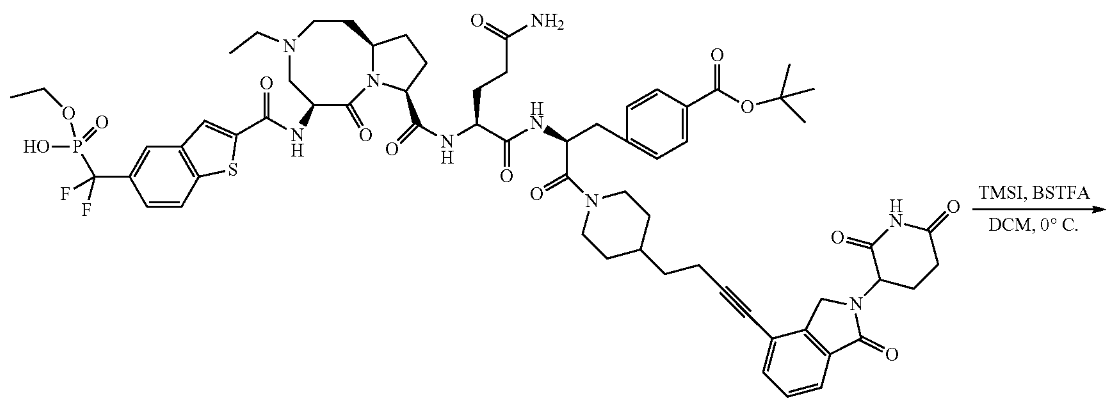
Cpd. No. 358E
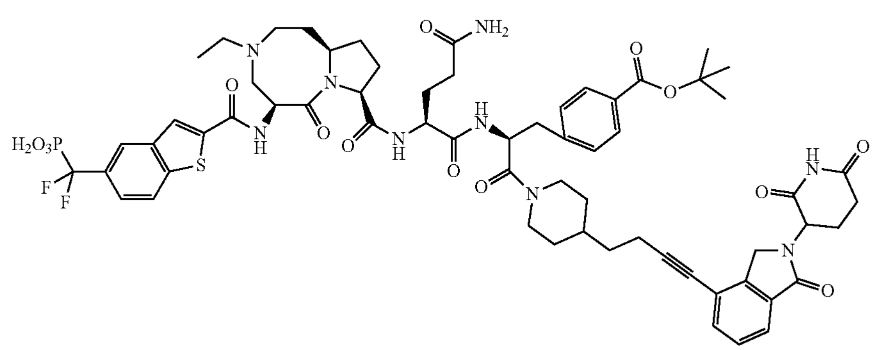
Cpd. No. 358

Cpd. No. 358 was purified by HPLC (MeCN/$H_2O$ 40%-100%, 60 min, 40 mL/min, the product came out when MeCN is 45.3%). (ESI-MS) $[M+H]^+$: 1226.5.
II. General Synthesis of Cpd. No. 359
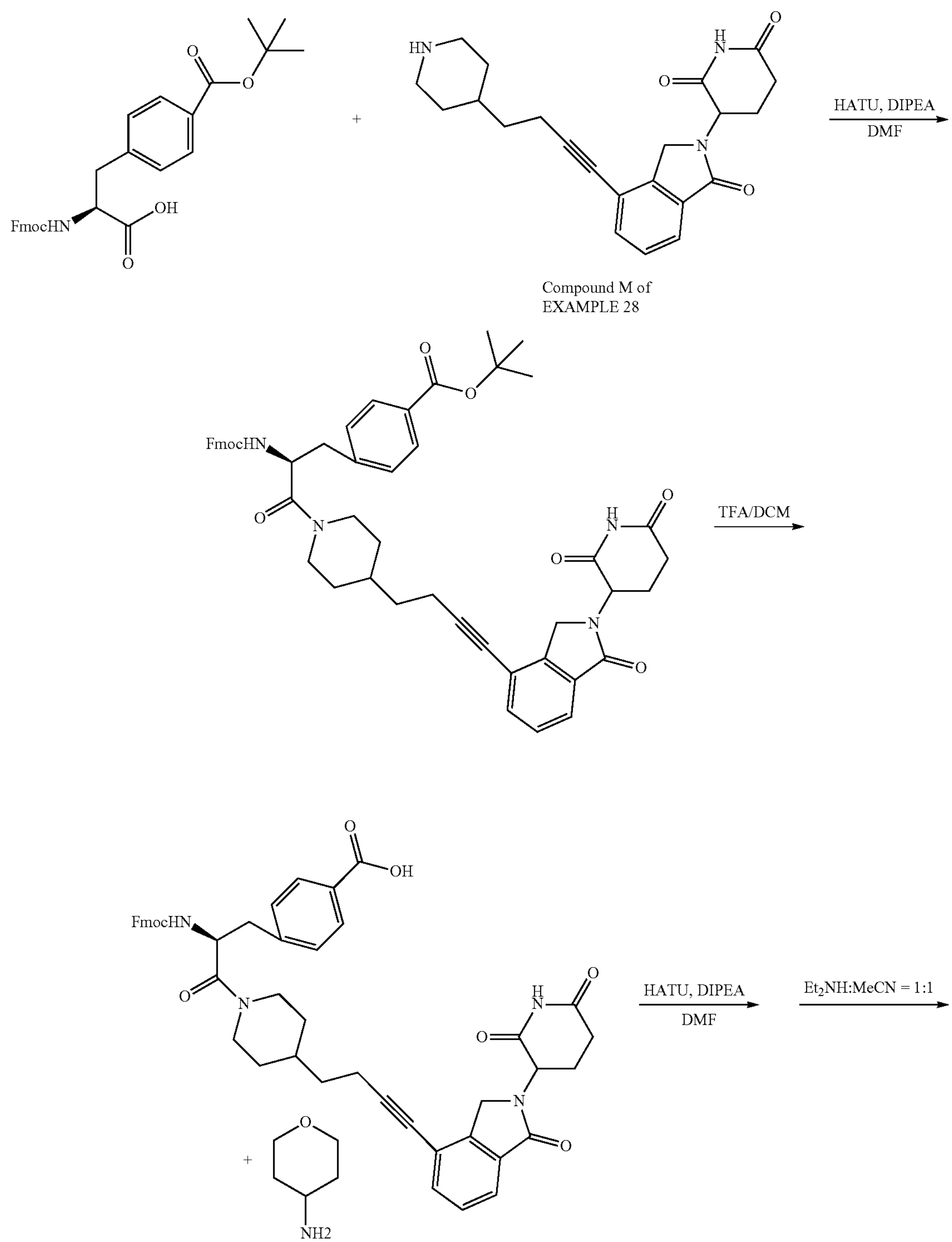

-continued
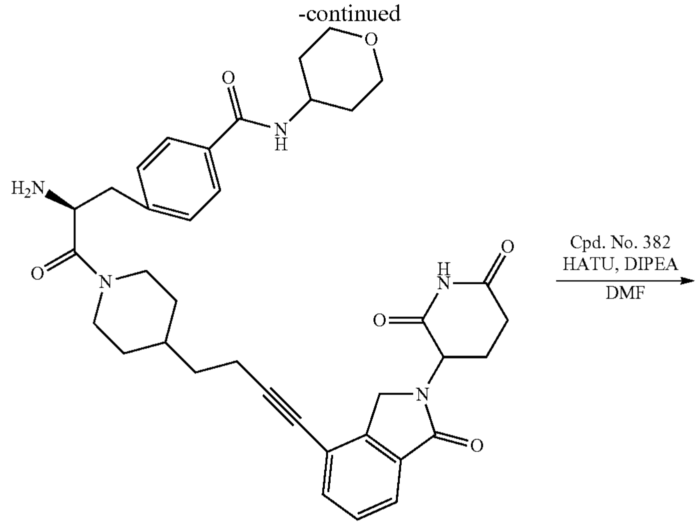
Cpd. No. 389
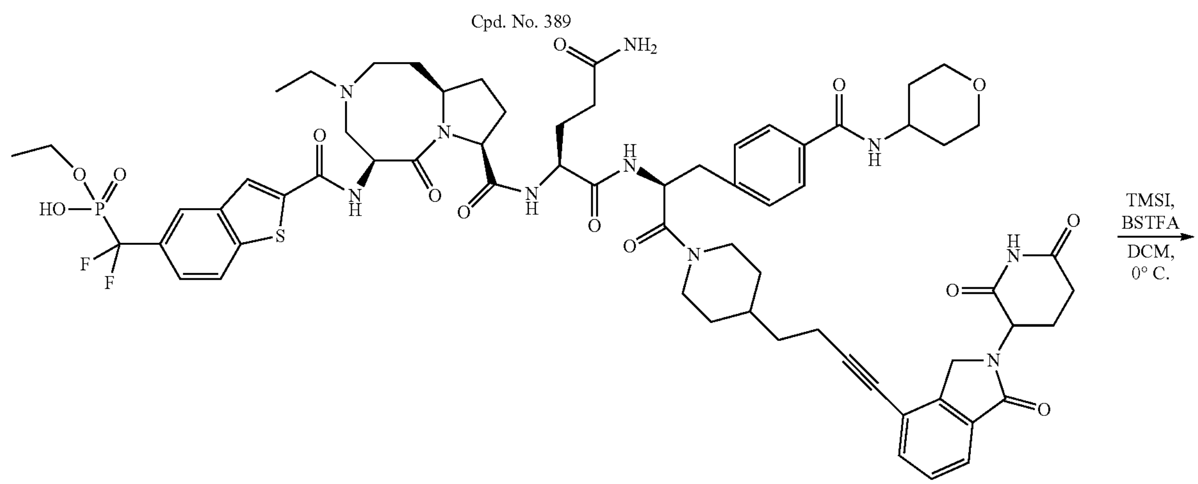
Cpd. No. 359E
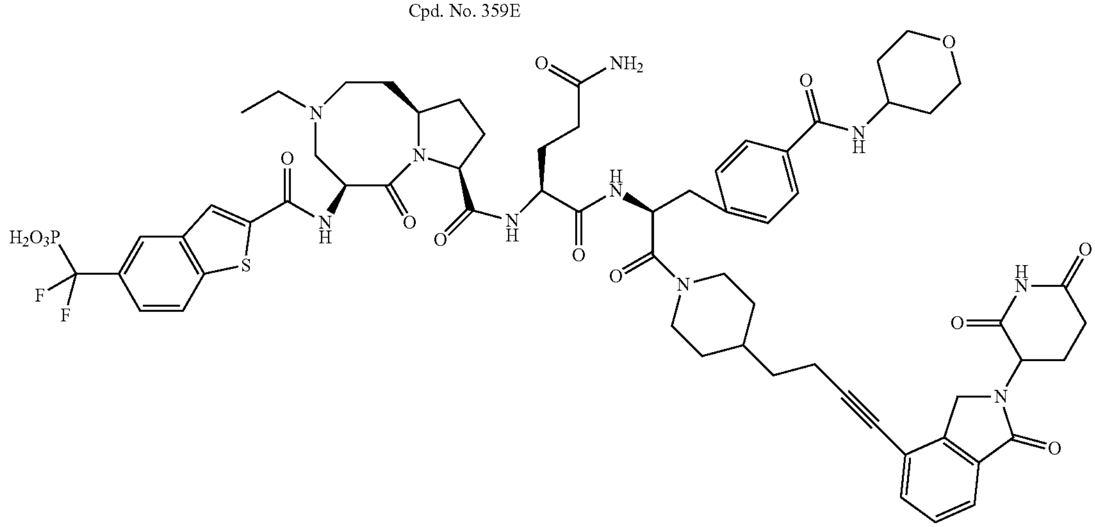
Cpd. No. 359
Cpd. No. 359 was purified by HPLC (MeCN/$H_2O$ 25%-100%, 75 min, 60 mL/min, the product came out when MeCN is 32.6%). (ESI-MS) $[M+H]^+$: 1309.6.

Example 34

The following compounds were prepared using the methods described in the EXAMPLEs above.

Cpd. No. 360 was purified by HPLC (MeCN/$H_2O$ 20%-100%, 80 min, 60 mL/min, the product came out when MeCN is 25.9%). (ESI-MS) $[M+H]^+$: 1336.7.

Cpd. No. 365 was purified by HPLC (MeCN/$H_2O$ 30%-100%, 70 min, 60 mL/min, the product came out when MeCN is 37.3%). (ESI-MS) $[M+H]^+$: 1329.6.

Cpd. No. 366 was purified by HPLC (MeCN/$H_2O$ 25%-100%, 75 min, 60 mL/min, the product came out when MeCN is 32.3%). (ESI-MS) $[M+H]^+$: 1295.5.

Cpd. No. 367 was purified by HPLC (MeCN/$H_2O$ 30%-100%, 70 min, 60 mL/min, the product came out when MeCN is 38.0%). (ESI-MS) $[M+H]^+$: 1307.8.

Cpd. No. 361 was purified by HPLC (MeCN/$H_2O$ 45%-100%, 55 min, 60 mL/min, the product came out when MeCN is 50.9%). (ESI-MS) $[M+H]^+$: 1268.7.

Cpd. No. 362 was purified by HPLC (MeCN/$H_2O$ 45%-100%, 55 min, 60 mL/min, the product came out when MeCN is 49.0%). (ESI-MS) $[M+H]^+$: 1274.8.

Cpd. No. 363 was purified by HPLC (MeCN/$H_2O$ 40%-100%, 60 min, 60 mL/min, the product came out when MeCN is 46.6%). (ESI-MS) $[M+H]^+$: 1252.6.

Cpd. No. 364 was purified by HPLC (MeCN/$H_2O$ 40%-100%, 60 min, 60 mL/min, the product came out when MeCN is 44.6%). (ESI-MS) $[M+H]^+$: 1252.7.

Cpd. No. 349 was purified by HPLC (MeCN/$H_2O$ 35%-100%, 65 min, 60 mL/min, the product came out when MeCN is 44.5%). (ESI-MS) $[M+H]^+$: 1203.7.

Cpd. No. 350 purified by HPLC (MeCN/$H_2O$ 35%-100%, 65 min, 60 mL/min, the product came out when MeCN is 44.8%). (ESI-MS) $[M+H]^+$: 1250.7.

Cpd. No. 351 was purified by HPLC (MeCN/$H_2O$ 40%-100%, 60 min, 60 mL/min, the product came out when MeCN is 44.6%). (ESI-MS) $[M+H]^+$: 1226.8.

Example 35

Synthesis of ((((2-(((5S,8S,10aR)-8-(((2S)-5-amino-1-(((2S)-3-(3,4-difluorophenyl)-1-(4-(4-(2-(2,6-dioxopiperidin-3-yl)-1-oxoisoindolin-4-yl)but-3-yn-1-yl)piperidin-1-yl)-1-oxopropan-2-yl)amino)-1,5-dioxopentan-2-yl)carbamoyl)-3-ethyl-6-oxodecahydropyrrolo[1,2-a][1,5]diazocin-5-yl)carbamoyl)benzo[b]thiophen-5-yl)difluoromethyl)(hydroxy)phosphoryl)oxy)methyl Pivalate (Cpd. No. 368)

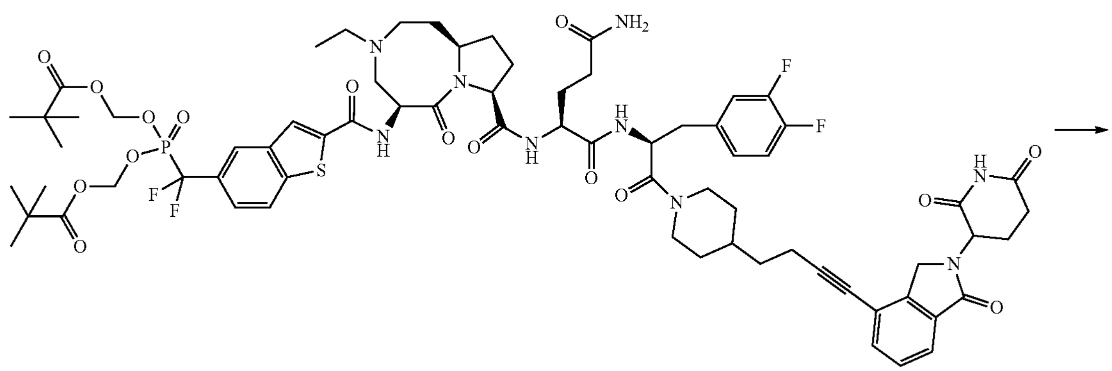

Cpd. No. 340

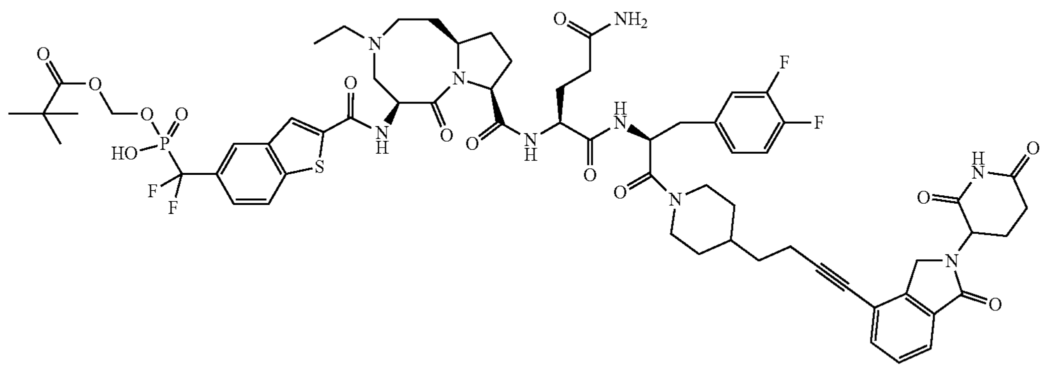

Cpd. No. 368

Cpd. No. 368: 0.04 mL of TFA was added slowly to a solution of Cpd. No. 340 (10 mg) in $CH^3CN$ (4 mL) and the resultant solution was stirred for 5 min. After removal the solvent, the residue was purified by HPLC to afford Cpd. No. 368 (4 mg). MS (ESI-MS) m/z: 1332.7.

Cpd. No. 369 was synthesized by a procedure similar to that used for SD-255. MS (ESI-MS) m/z: 1288.9.

Cpd. No. 370 was synthesized by a procedure similar to that used for SD-255. MS (ESI-MS) m/z: 1362.8.

Example 36

STAT3 Assays

Fluorescence Polarization (FP) Assay

The FP assay was performed to determine dissociation constants ($K_d$) for the interactions between STAT3 SH2 domain binder ((2-(((5S,8S,10aR)-8-(((S)-5-amino-1-(((S)-2-((8-(3',6'-dihydroxy-3-oxo-3H-spiro[isobenzofuran-1,9'-xanthene]-5-carboxamido)octyl)amino)-2-oxo-1-phenylethyl)amino)-1,5-dioxopentan-2-yl)carbamoyl)-3-methyl-6-oxodecahydropyrrolo[1,2-a][1,5]diazocin-5-yl)carbamoyl)-1H-indol-5-yl)difluoromethyl)phosphonic acid (SD-FL) and STATs, in which 5 nM of SD-FL, the 5-FAM labeled Cpd. No. 200, was incubated with serially diluted recombinant STAT proteins in FP buffer (50 mM NaCl, 10 mM Hepes pH 7.5, 1 mM EDTA pH 8.0, 0.01% Triton X-100, 2 mM DTT). FP was measured after 1 h of incubation on a Tecan Infinite microplate reader. $K_d$ values were determined from the binding isotherm derived from curves of mP vs protein concentrations. For the competitive assays, STAT3 recombinant protein was first combined with SD-FL, then added to the serially diluted compounds. FP was measured after 1 h of incubation at room temperature. $IC_{50}$ values of SD-FL displacement were calculated by nonlinear regression analysis using GraphPad Prism software. The $K_i$ values of competitive inhibitors were calculated as described by Cer, R. Z., et al., IC50-to-Ki: a web-based tool for converting IC50 to Ki values for inhibitors of enzyme activity and ligand binding. Nucleic Acids Res, 2009. 37 (Web Server issue): p. W441-5).

Biolayer Interferometry (BLI) Assay

Purified recombinant STAT proteins were biotinylated using the EZ-Link biotinylation reagent (Thermo Fisher Scientific). Briefly, protein and biotinylation reagent were mixed with 1:1 molar ratio in PBS at 4° C. Low biotinylation reagent concentration was applied to avoid protein over-biotinylation. These reaction mixtures were incubated at 4° C. for 2 hours to allow reaction being finished. Reaction mixture was then dialyzed using 10K MWCO dialysis cassettes (Thermo Fisher Scientific) to remove unreacted biotinylation reagent.

BLI experiments were performed using an OctetRED96 instrument from ForteBio. All assays were run at 30° C. with continuous 1000 RPM shaking. PBS with 0.1% BSA, 0.01% Tween-20 and 1% DMSO was used as the assay buffer. Biotinylated STAT proteins were tethered on Super Streptavidin (SSA) biosensors (ForteBio) by dipping sensors into 10 μg/mL protein solutions. Average saturation response levels of 10-15 nm were achieved in 15 minutes for all STAT proteins. Sensors with proteins tethered were washed in assay buffer for 10 minutes to eliminate loose nonspecific protein molecules bounded and establish stable base lines before starting association-dissociation cycles with compound being tested. DMSO only references were included in all assays. Raw kinetic data collected were processed in the Data Analysis software provided by the manufacturer using double reference subtraction in which both DMSO only reference and inactive reference were subtracted. Resulting data were analyzed based on 1:1 binding model from which Kon and Koff values were obtained and then Kd values were calculated.

Immunoblotting

In vitro cultured cells or xenograft tumors were lysed 1× Cell Lysis Buffer (Cell Signaling Technology, #9803), resolved by SDS-PAGE NuPAGE gel (Thermo Fisher Scientific), and transferred to a PVDF membrane (Bio Rad). For chemiluminescence immunoblotting, membranes were blocked for 1 h using 5% Blotting-Grade Blocker (#1706404, Bio Rad) in 1× Tris-buffered saline with Tween 20 (TBST, Pierce). Antibodies used were: rabbit mAbs for STAT3 (Cell Signaling Technology, #4368, #12640) and p-STAT3 (Y705) (Cell Signaling Technology, #9245, #52075). HRP conjugated goat anti-rabbit IgG (H+L) (#A27036) secondary antibodies was from Thermo Fisher Scientific. GAPDH (Santa Cruz Technology, sc-47724HRP) and actin (Santa Cruz Technology, sc-8432HRP, sc-47778HRP) were loading controls. For fluorescent immunoblotting, membranes were blocked using Odyssey TBS Blocker Buffer (LI-COR). IRDye 680RD and 800CW Dye-labeled secondary antibodies (LI-COR) were used. The washed membranes were scanned using Odyssey CLx imager (LI-COR). The intensity of Western blot signaling was quantitated using the Odyssey software.

Pharmacodynamic Studies in the Xenograft Models in Mice

All animal experiments were performed under the guidelines of the University of Michigan Committee for Use and Care of Animals and using an approved animal protocol. Xenograft tumors were established by injecting $5\times10^6$ cells in 50% Matrigel subcutaneously on the dorsal side of severe combined immunodeficient (SCID) mice, one tumor per mouse. When tumors reached ~100 $mm^3$, mice were randomly assigned to treatment and vehicle control groups. The size of tumors growing in the mice was measured in two dimensions using calipers. Tumor volume ($mm^3$)=$(A\times B^2)/2$ where A and B are the tumor length and width (in mm), respectively. During treatment, tumor volume and body weight was measured two or three times a week. After the treatment was stopped, tumor volume and body weight was measured at least once a week. Before treatment began, tumors were allowed to grow to 100-200 $mm^3$ in volume. Mice with tumors within acceptable size range were randomized into treatment groups of 7 mice per group. Representative Compounds of the Disclosure were administered intravenously to determine antitumor activity.

The estimated $DC_{50}$ in MOLM-16 cells of representative Compounds of the Disclosure against STAT3 and STAT1 is provide in Table 5.

TABLE 5

| | Estimated DC50 (μM) (MOLM-16, 4 h) ND = not determined | |
|---|---|---|
| Cpd. No. | STAT3 | STAT1 |
| 349 | 0.2 | ND |
| 352 | <0.25 | 0.25 |

TABLE 5-continued

| Cpd. No. | Estimated DC50 (μM) (MOLM-16, 4 h) ND = not determined STAT3 | STAT1 |
|---|---|---|
| 353 | <0.25 | 0.5 |
| 354 | <0.25 | 0.25 |
| 355 | >1 | >1 |
| 356 | <0.25 | >1 |
| 357 | 0.5 | >1 |
| 356 | <0.25 | >1 |
| 359 | 1 | >1 |
| 360 | >1 | >1 |
| 361 | <0.25 | 0.25 |
| 362 | <0.25 | <0.25 |
| 363 | <0.25 | <0.25 |
| 364 | <0.25 | <0.25 |
| 365 | <0.25 | <0.25 |
| 366 | <0.25 | <0.25 |
| 367 | <1 | <1 |

REFERENCES

Yu, H.; Jove, R. The STATs of cancer—new molecular targets come of age. Nat Rev Cancer 2004, 4, 97-105.

Wang, X.; Crowe, P. J.; Goldstein, D.; Yang, J. L. STAT3 inhibition, a novel approach to enhancing targeted therapy in human cancers (review). Int J Oncol 2012, 41, 1181-91.

Johnson, D. E.; O'Keefe, R. A.; Grandis, J. R. Targeting the IL-6/JAK/STAT3 signalling axis in cancer. Nat Rev Clin Oncol 2018, 15, 234-248.

Banerjee, K.; Resat, H. Constitutive activation of STAT3 in breast cancer cells: A review. Int J Cancer 2016, 138, 2570-8.

Kortylewski, M.; Jove, R.; Yu, H. Targeting STAT3 affects melanoma on multiple fronts. Cancer Metastasis Rev 2005, 24, 315-27.

Haura, E. B.; Turkson, J.; Jove, R. Mechanisms of disease: Insights into the emerging role of signal transducers and activators of transcription in cancer. Nat Clin Pract Oncol 2005, 2, 315-24.

Sakamoto, K. M.; Kim, K. B.; Kumagai, A.; Mercurio, F.; Crews, C. M.; Deshaies, R. J. Protacs: Chimeric molecules that target proteins to the Skp1-Culling-F box complex for ubiquitination and degradation. Proceedings of the National Academy of Sciences 2001, 98, 8554-8559.

Raina, K.; Crews, C. M. Chemical Inducers of Targeted Protein Degradation. Journal of Biological Chemistry 2010, 285, 11057-11060.

Bondeson, D. P.; Mares, A.; Smith, I. E. D.; Ko, E.; Campos, S.; Miah, A. H.; Mulholland, K. E.; Routly, N.; Buckley, D. L.; Gustafson, J. L.; Zinn, N.; Grandi, P.; Shimamura, S.; Bergamini, G.; Faelth-Savitski, M.; Bantscheff, M.; Cox, C.; Gordon, D. A.; Willard, R. R.; Flanagan, J. J.; Casillas, L. N.; Votta, B. J.; den Besten, W.; Famm, K.; Kruidenier, L.; Carter, P. S.; Harling, J. D.; Churcher, I.; Crews, C. M. Catalytic in vivo protein knockdown by small-molecule PROTACs. Nat Chem Biol 2015, 11, 611-617.

Toure, M.; Crews, C. M. Small-Molecule PROTACS: New Approaches to Protein Degradation. Angewandte Chemie International Edition 2016, 55, 1966-1973.

Raina, K.; Lu, J.; Qian, Y.; Altieri, M.; Gordon, D.; Rossi, A. M. K.; Wang, J.; Chen, X.; Dong, H.; Siu, K.; Winkler, J. D.; Crew, A. P.; Crews, C. M.; Coleman, K. G. PROTAC-induced BET protein degradation as a therapy for castration-resistant prostate cancer. Proceedings of the National Academy of Sciences 2016, 113, 7124-7129.

Chen, J.; Bai, L.; Bernard, D.; Nikolovska-Coleska, Z.; Gomez, C.; Zhang, J.; Yi, H.; Wang, S. Structure-Based Design of Conformationally Constrained, Cell-Permeable STAT3 Inhibitors. ACS Med Chem Lett 2010, 1, 85-89.

Chen, J. Y.; Bai, L. C.; Bernard, D.; Nikolovska-Coleska, Z.; Gomez, C.; Zhang, J. A.; Yi, H.; Wang, S. M. Structure-Based Design of Conformationally Constrained, Cell-Permeable STAT3 Inhibitors. ACS Med. Chem. Lett. 2010, 1, 85-89.

Mandal, P. K.; Liao, W. S. L.; McMurray, J. S. Synthesis of Phosphatase-Stable, Cell-Permeable Peptidomimetic Prodrugs That Target the SH2 Domain of Stat3. Org. Lett. 2009, 11, 3394-3397.

Mandal, P. K.; Gao, F. Q.; Lu, Z.; Ren, Z. Y.; Ramesh, R.; Birtwistle, J. S.; Kaluarachchi, K. K.; Chen, X. M.; Bast, R. C.; Liao, W. S.; McMurray, J. S. Potent and Selective Phosphopeptide Mimetic Prodrugs Targeted to the Src Homology 2 (SH2) Domain of Signal Transducer and Activator of Transcription 3. J. Med. Chem. 2011, 54, 3549-3563.

Morlacchi, P.; Mandal, P. K.; McMurray, J. S. Synthesis and in Vitro Evaluation of a Peptidomimetic Inhibitor Targeting the Src Homology 2 (SH2) Domain of STAT6. ACS Med. Chem. Lett. 2014, 5, 69-72.

Mandal, P. K.; Morlacchi, P.; Knight, J. M.; Link, T. M.; Lee, G. R.; Nurieva, R.; Singh, D.; Dhanik, A.; Kavraki, L.; Corry, D. B.; Ladbury, J. E.; McMurray, J. S. Targeting the Src Homology 2 (SH2) Domain of Signal Transducer and Activator of Transcription 6 (STAT6) with Cell-Permeable, Phosphatase-Stable Phosphopeptide Mimics Potently Inhibits Tyr641 Phosphorylation and Transcriptional Activity. J. Med. Chem. 2015, 58, 8970-8984.

Toure, M.; Crews, C. M. Small-Molecule PROTACS: New Approaches to Protein Degradation. Angew. Chem. Int. Edit. 2016, 55, 1966-1973.

Bai, L. C.; Zhou, B.; Yang, C. Y.; Ji, J.; McEachern, D.; Przybranowski, S.; Jiang, H.; Hu, J. T.; Xu, F. M.; Zhao, Y. J.; Liu, L.; Fernandez-Salas, E.; Xu, J.; Dou, Y. L.; Wen, B.; Sun, D. X.; Meagher, J.; Stuckey, J.; Hayes, D. F.; Li, S. Q.; Ellis, M. J.; Wang, S. M. Targeted Degradation of BET Proteins in Triple-Negative Breast Cancer. Cancer Res. 2017, 77, 2476-2487.

Zhou, B.; Hu, J. T.; Xu, F. M.; Chen, Z.; Bai, L. C.; Fernandez-Salas, E.; Lin, M.; Liu, L.; Yang, C. Y.; Zhao, Y. J.; McEachern, D.; Przybranowski, S.; Wen, B.; Sun, D. X.; Wang, S. M. Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481.

Qin, C.; Hu, Y.; Zhou, B.; Fernandez-Salas, E.; Yang, C. Y.; Liu, L.; McEachern, D.; Przybranowski, S.; Wang, M.; Stuckey, J.; Meagher, J.; Bai, L. C.; Chen, Z.; Lin, M.; Yang, J. L.; Ziazadeh, D. N.; Xu, F. M.; Hu, J. T.; Xiang, W. G.; Huang, L. Y.; Li, S. W.; Wen, B.; Sun, D. X.; Wang, S. M. Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression. J. Med. Chem. 2018, 61, 6685-6704.

Li, Y.; Yang, J.; Aguilar, A.; McEachern, D.; Przybranowski, S.; Liu, L.; Yang, C. Y.; Wang, M.; Han, X.; Wang, S. Discovery of MD-224 as a First-in-Class, Highly Potent, and Efficacious Proteolysis Targeting Chimera Murine Double Minute 2 Degrader Capable of Achieving Complete and Durable Tumor Regression. J Med Chem 2018.

Qin, C.; Hu, Y.; Zhou, B.; Fernandez-S alas, E.; Yang, C. Y.; Liu, L.; McEachern, D.; Przybranowski, S.; Wang, M.; Stuckey, J.; Meagher, J.; Bai, L.; Chen, Z.; Lin, M.; Yang, J.; Ziazadeh, D. N.; Xu, F.; Hu, J.; Xiang, W.; Huang, L.; Li, S.; Wen, B.; Sun, D.; Wang, S. Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression. J Med Chem 2018, 61, 6685-6704.

Zhou, B.; Hu, J.; Xu, F.; Chen, Z.; Bai, L.; Fernandez-S alas, E.; Lin, M.; Liu, L.; Yang, C. Y.; Zhao, Y.; McEachern, D.; Przybranowski, S.; Wen, B.; Sun, D.; Wang, S. Discovery of a Small-Molecule Degrader of Bromodomain and Extra-Terminal (BET) Proteins with Picomolar Cellular Potencies and Capable of Achieving Tumor Regression. J Med Chem 2018, 61, 462-481.

Li, Y.; Yang, J.; Aguilar, A.; McEachern, D.; Przybranowski, S.; Liu, L.; Yang, C.-Y.; Wang, M.; Han, X.; Wang, S. Discovery of MD-224 as a First-in-Class, Highly Potent, and Efficacious Proteolysis Targeting Chimera Murine Double Minute 2 Degrader Capable of Achieving Complete and Durable Tumor Regression. Journal of Medicinal Chemistry 2019, 62, 448-466.

Fischer, E. S.; Bohm, K.; Lydeard, J. R.; Yang, H. D.; Stadler, M. B.; Cavadini, S.; Nagel, J.; Serluca, F.; Acker, V.; Lingaraju, G. M.; Tichkule, R. B.; Schebesta, M.; Forrester, W. C.; Schirle, M.; Hassiepen, U.; Ottl, J.; Hild, M.; Beckwith, R. E. J.; Harper, J. W.; Jenkins, J. L.; Thoma, N. H. Structure of the DDBI-CRBN E3 ubiquitin ligase in complex with thalidomide. Nature 2014, 512, 49.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound of Formula I:

I

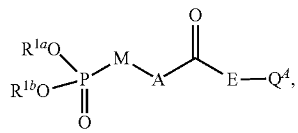

or a pharmaceutically acceptable salt or solvate thereof, wherein:

$R^{1a}$ and $R^{1b}$ are independently selected from the group consisting of hydrogen, $C_1$-$C_4$ alkyl, and —$CH_2OC(=O)R^{1e}$;

$R^{1e}$ is $C_1$-$C_6$ alkyl;

M is selected from the group consisting of —O— and —$C(R^{2a})(R^{2b})$—;

$R^{2a}$ and $R^{2b}$ are independently selected from the group consisting of hydrogen and fluoro; or $R^{2a}$ and $R^{2b}$ taken together with the carbon atom to which they are attached form a —C(=O)— group;

A is selected from the group consisting of:

A-1

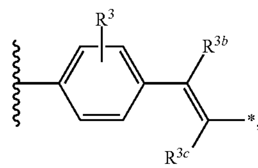

A-4

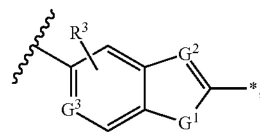

A-6

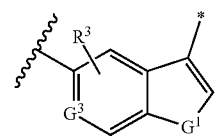

A-7

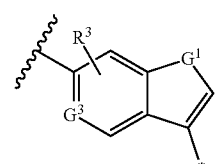

A-8

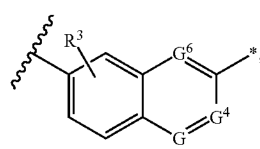

A-9

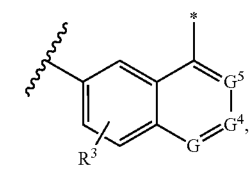

A-10

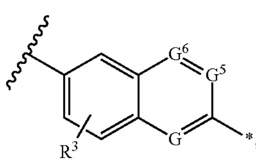

A-11

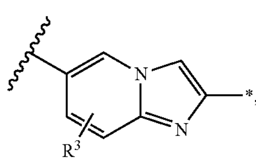

A-21

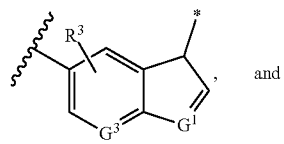

and

A-22

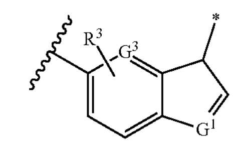

wherein the bond designated with an "*" is attached to —C(═O)-E-$Q^A$, $G^1$ is selected from the group consisting of —O—, —S—, and —$NR_{17}$—;

$G^2$ is —$CR^{18a}$═;

$G^3$ is —$CR^{18b}$═;

$G^4$ is —$CR^{18c}$═;

$G^5$ is —$CR^{18d}$═;

$G^6$ is —$CR^{18e}$═;

G is selected from the group consisting of —N═ and —$CR^{18f}$═;

$R^3$ is hydrogen;

$R^{3b}$ is $C_1$-$C_4$ alkyl;

$R^{3c}$ is hydrogen;

$R^{17}$ is selected from the group consisting of hydrogen and $C_1$-$C_4$ alkyl;

$R^{18a}$, $R^{18b}$, $R^{18c}$, $R^{18d}$, $R^{18e}$, and $R^{18f}$ are hydrogen;

E is:

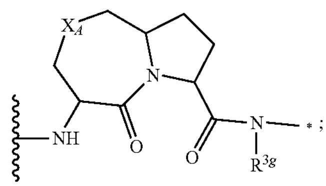

wherein the bond designated with an "*" is attached to $Q^A$;

$R^{3g}$ is hydrogen;

$X_A$ is selected from the group consisting of —N($R^8$)$CH_2$—, —$CH_2N(R^8)$—, and —$CH_2CH_2$—;

$R^8$ is selected from the group consisting of hydrogen, $C_1$-$C_6$ alkyl, $C_1$-$C_6$ haloalkyl, (optionally substituted 5- to 8-membered heterocyclo)$C_1$-$C_6$ alkyl-, $C_1$-$C_6$ alkylsulfonyl, —C(═O)$R^9$, and -L-B;

$R^9$ is selected from the group consisting of $C_1$-$C_6$ alkyl, amino, $C_1$-$C_6$ alkoxy, optionally substituted 4- to 8-membered heterocyclo, and optionally substituted 5- to 10-membered heteroaryl;

$Q^A$ is selected from the group consisting of:

Q-1

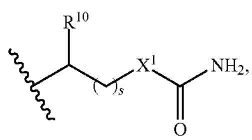

Q-2

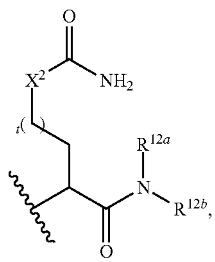

-continued

Q-3

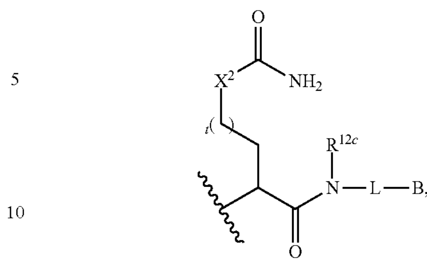

Q-5

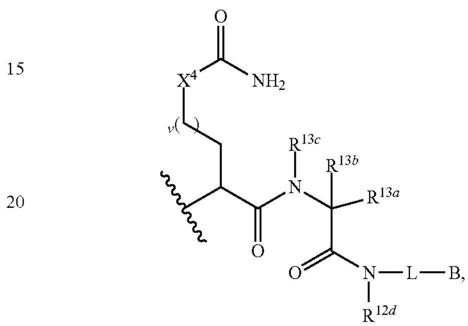

Q-6

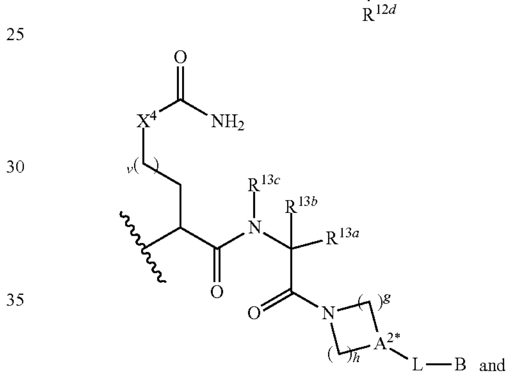

and

Q-7

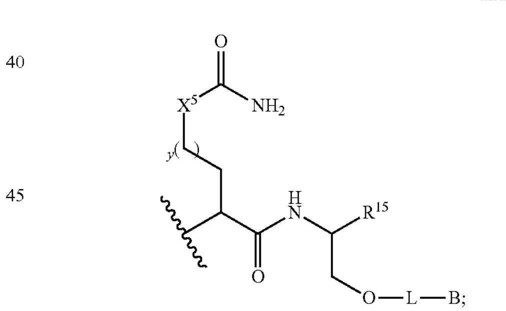

$X^1$ is selected from the group consisting of —$CH_2$—, —O—, and —N($R^{11a}$)—; or $X^1$ is absent;

$R^{10}$ is hydrogen;

$R^{11a}$ is hydrogen;

s is 2 or 3;

$X^2$ is selected from the group consisting of —$CH_2$—, —O—, and —N($R^{11b}$)—; or $X^2$ is absent;

t is 2 or 3;

$R^{11b}$ is hydrogen;

$R^{12a}$ is selected from the group consisting of hydrogen, $C_1$-$C_6$ alkyl, optionally substituted $C_2$-$C_6$ alkynyl, optionally substituted $C_3$-$C_6$-cycloalkyl, optionally substituted 4- to 8-membered heterocyclo, and (amino)($C_6$-$C_{14}$ aryl)$C_1$-$C_6$ alkyl-;

$R^{12b}$ is selected from the group consisting of hydrogen, $C_1$-$C_4$ alkyl, optionally substituted $C_6$-$C_{14}$ aryl, and (optionally substituted $C_6$-$C_{14}$ aryl)$C_1$-$C_6$ alkyl; or $R^{12a}$ and $R^{12b}$ taken together with the nitrogen atom to which they are attached form a 4- to 8-membered optionally substituted heterocyclo, $R^{12c}$ is hydrogen;

$X^4$ is —$CH_2$—; or $X^4$ is absent;

v is 0, 1, or 2;

$R^{12d}$ is hydrogen;

$R^{13a}$ is selected from the group consisting of hydrogen, optionally substituted $C_6$-$C_{14}$ aryl, (optionally substituted $C_6$-$C_{14}$ aryl) $C_1$-$C_6$ alkyl-, (optionally substituted $C_3$-$C_6$ cycloalkyl)$C_1$-$C_6$ alkyl-, and optionally substituted 5- to 9-membered heteroaryl;

$R^{13b}$ is hydrogen;

$R^{13c}$ is hydrogen; or $R^{13a}$ and $R^{13b}$ taken together form an optionally substituted $C_3$-$C_8$ cycloalkyl or an optionally substituted $C_4$-$C_9$ heterocyclo; or $R^{13b}$ and $R^{13c}$ taken together form an optionally substituted 4- to 9-membered heterocyclo;

$A^{2*}$ is selected from the group consisting of —C($R^{14b}$)— and —N—;

$R^{14b}$ is hydrogen;

g is 2;

h is 2;

$X^5$ is —$CH_2$—; or $X^5$ is absent;

y is 1 or 2;

$R^{15}$ is optionally substituted $C_6$-$C_{14}$ aryl;

L is -$J^1$-$Y^1$-$J^2$-$Y^2$-$J^3$-Z—;

$J^1$ is selected from the group consisting of $C_{1-12}$ alkylenyl, 4- to 8-membered heterocyclenyl, and 5- to 9-membered heteroarylenyl; or $J^1$ is absent;

$Y^1$ is selected from the group consisting of —$(CH_2)_m$— and —C≡C—;

m is 0, 1, or 2;

$J^2$ is $C_{1-12}$ alkylenyl; or $J^2$ is absent;

$Y^2$ is selected from the group consisting of —$(CH_2)_n$—;

n is 0, 1, 2, 3, or 4;

$J^3$ is $C_{1-12}$ alkylenyl, 4- to 8-membered heterocyclenyl, and 5- to 9-membered heteroarylenyl; or $J^3$ is absent;

Z is selected from the group consisting of —$(CH_2)_d$—, —C≡C—, and, —N($R^{16c}$);

d is 0, 1, 2, or 3;

$R^{16c}$ is hydrogen;

wherein Z is attached to B;

B is selected from the group consisting of:

B-1

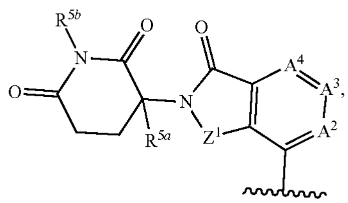

-continued

B-4

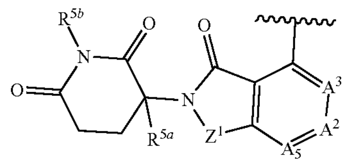

B-5

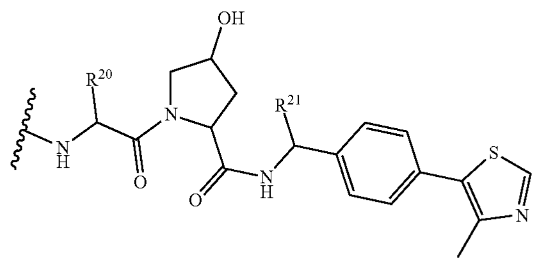

B-6

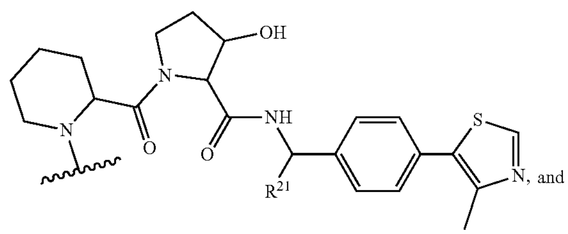

and

B-8

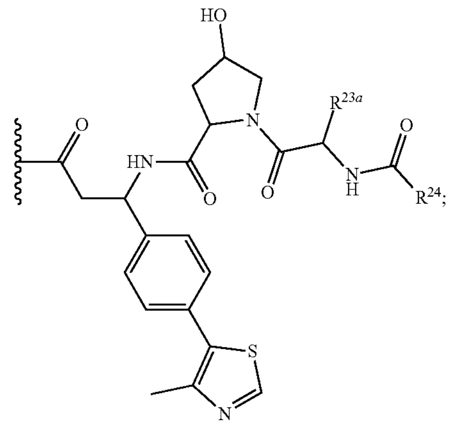

$A_5$ is —C($R^{19a}$)=;

$A^2$ is —C($R^{19a}$)±;

$A^3$ is —C($R^{19a}$)=;

$A^4$ is —C($R^{19a}$)=;

$Z^1$ is —$CH_2$ and —C(=O)—;

$R^{5a}$ is selected from the group consisting of hydrogen, methyl, and fluoro;

$R^{5b}$ is selected from the group consisting of hydrogen and methyl;

$R^{19a}$, $R^{19b}$, $R^{19c}$, and $R^{19d}$ are each hydrogen;

$R^{20}$ is $C_4$ alkyl;

$R^{21}$ is $C_1$ alkyl;

$R^{23}$ is $C_1$-$C_6$ alkyl; and $R^{24}$ is selected from the group consisting of, optionally substituted $C_3$-$C_6$ cycloalkyl and optionally substituted 5- to 14-membered heteroaryl, with the provisos:

(1) when $X_A$ is —$CH_2CH_2$—, then $Q^A$ is selected from the group consisting of Q-3, Q-5, Q-6, and Q-7;

(2) when $X_A$ is —N($R^8$)$CH_2$— or —$CH_2$N($R^8$)—, and $R^8$ is selected from the group consisting of hydrogen, $C_1$-$C_6$ alkyl, $C_1$-$C_6$ haloalkyl, (optionally substituted 5- to 8-membered heterocyclo)$C_1$-$C_6$ alkyl-, $C_1$-$C_6$ alkylsulfonyl, and —C(═O) $R^9$, then $Q^A$ is selected from the group consisting of Q-3, Q-4, Q-5, Q-6, and Q-7; and (3) when $X_A$ is —N($R^8$)$CH_2$— or —$CH_2$N($R^8$)—, and $R^8$ is-L-B, then $Q^A$ is selected from the group consisting of Q-1 and Q-2.

2. The compound of claim 1, wherein the compound is Formula II:

II

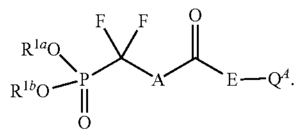

3. The compound of claim 1, wherein A is selected from the group consisting of:

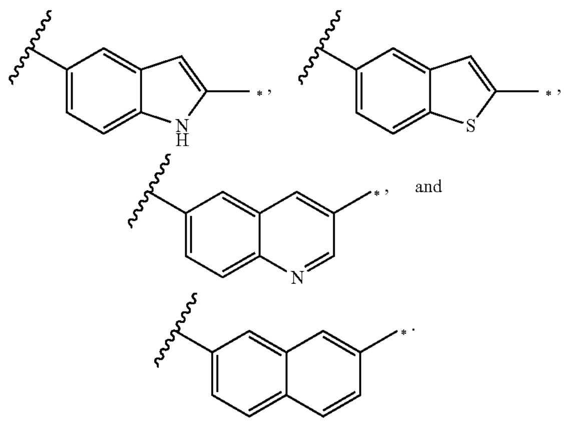

4. The compound of claim 1, wherein E is:

E-1-1

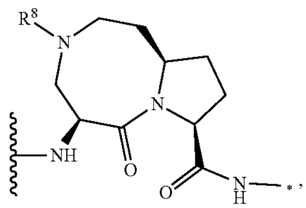

E-2-1

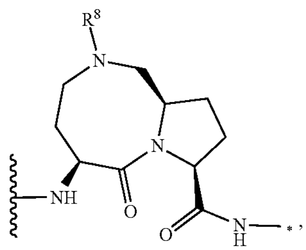

or

E-3-1

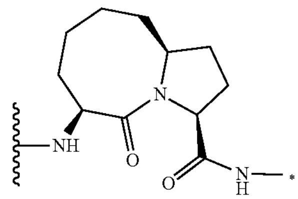

5. The compound of claim 1, wherein $X_A$ is —N($R^8$)$CH_2$— or —$CH_2$N($R^8$)—, $R^8$ is selected from the group consisting of hydrogen, $C_1$-$C_6$ alkyl, $C_1$-$C_6$ haloalkyl, (optionally substituted 5- to 8-membered heterocyclo) $C_1$-$C_6$ alkyl-, $C_1$-$C_6$ alkylsulfonyl, and —C(═O)$R^9$, and $Q^A$ is Q-6.

6. The compound of claim 5, wherein $Q^A$ is Q-6-1 or Q-6-2:

Q-6-1

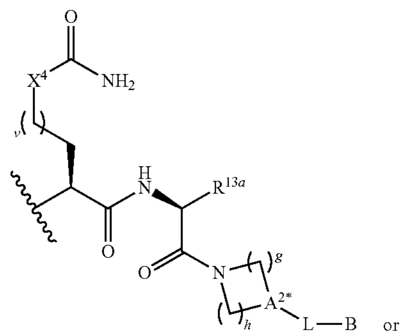

or

Q-6-2

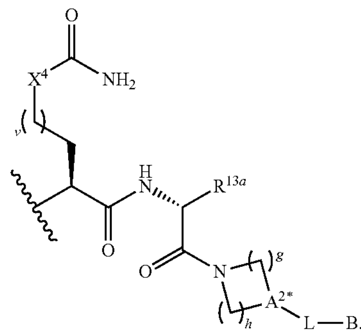

7. The compound of claim 1, wherein L is —$Y^1$-$Y^2$—Z—.

8. The compound of claim 7, wherein $Y^1$ is selected from the group consisting of —$(CH_2)_m$— and —C(═O)—; m is 1, 2, or 3; $Y^2$ is —$(CH_2)_n$—; n is 1, 2, 3, or 4; and Z is selected from the group consisting of —($CH_2$)—, —C≡C—, and —N(H)—.

9. The compound of claim 8, wherein Z is —C≡C—.

10. The compound of claim 1, wherein:

L is selected from the group consisting of:

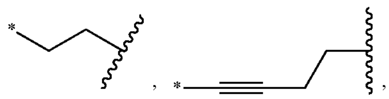

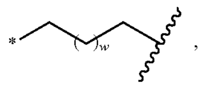

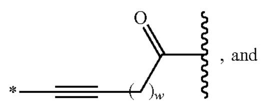

, and

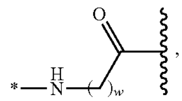

wherein the bond designated with an "*" is attached to B;

w is 1, 2, 3, 4, 5, 6, 7, or 8; and x is 1, 2, 3, 4, 5, or 6.

11. The compound of claim 1, wherein B is B-1.

12. The compound of claim 1, wherein the compound is Formula VII-E:

VII-E

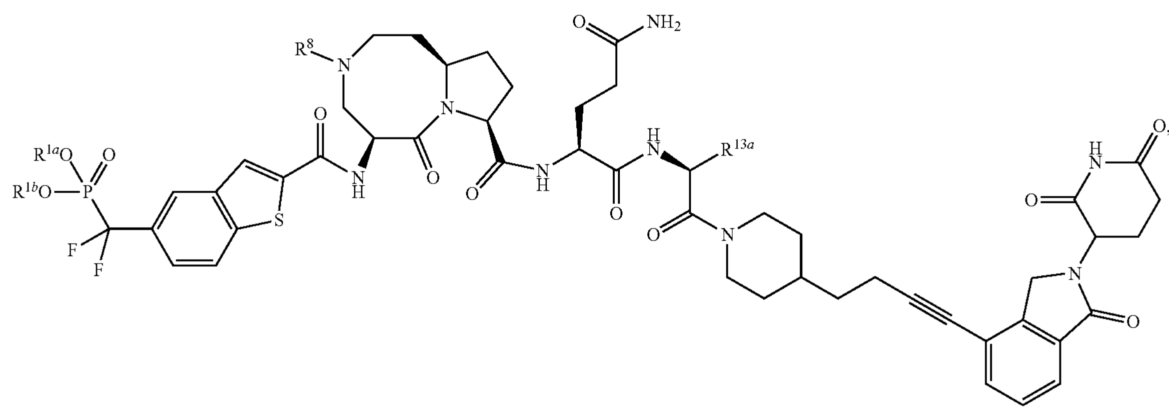

or a pharmaceutically acceptable salt or solvate thereof.

13. The compound of claim 12, wherein:

$R^{13a}$ is:

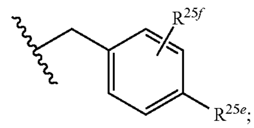

$R^{25e}$ is selected from the group consisting of hydrogen, halo, $C_1$-$C_6$ alkyl, —C(═O)$NR^{50c}R^{50d}$, $C_1$-$C_6$ alkylsulfonyl, $C_6$-$C_{14}$ arylsulfonyl, —N($R^{56c}$)S(═O)$_2R^{56d}$, and —S(═O)$_2R^{58}$;

$R^{25f}$ is selected from the group consisting of hydrogen and halo;

$R^{50c}$ is selected from the group consisting of $C_1$-$C_6$ alkyl, optionally substituted $C_3$-$C_6$ cycloalkyl, optionally substituted 5- or 6-membered heterocyclo, optionally substituted phenyl, optionally substituted 5- to 9-membered heteroaryl, (optionally substituted $C_6$-$C_{14}$ aryl) $C_1$-$C_6$ alkyl-, (optionally substituted 5- to 14-membered heteroaryl)$C_1$-$C_4$ alkyl-, and (3- to 14-membered heterocyclo)$C_1$-$C_4$ alkyl-;

$R^{50d}$ is selected from the group consisting of hydrogen and $C_1$-$C_3$ alkyl; or $R^{50c}$ and $R^{50d}$ taken together with the nitrogen to which they are attached form an optionally substituted 3- to 8-membered heterocyclo group;

$R^{56c}$ is selected from the group consisting of hydrogen and $C_1$-$C_3$ alkyl;

$R^{56d}$ is selected from the group consisting of optionally substituted $C_3$-$C_6$ cycloalkyl, optionally substituted phenyl, and optionally substituted 5- to 9-membered heteroaryl; and $R^{58}$ is optionally substituted $C_3$-$C_6$ cycloalkyl.

14. The compound of claim 12, wherein $R^8$ is selected from the group consisting of $C_1$-$C_4$ alkyl, $C_1$-$C_4$ haloalkyl, $C_1$-$C_6$ alkylsulfonyl, and —C(═O)$R^9$; and $R^9$ is selected from the group consisting of $C_1$-$C_4$ alkyl, $C_1$-$C_6$ alkylamino, di$C_1$-$C_6$ alkylamino, and $C_1$-$C_4$ alkoxy.

15. The compound of claim 1, wherein each of $R^{1a}$ and $R^{1b}$ is hydrogen.

16. A compound selected from the group consisting of:
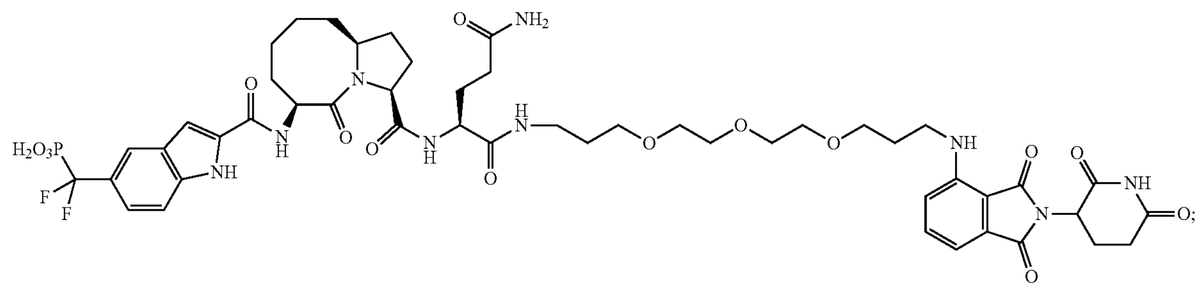
;
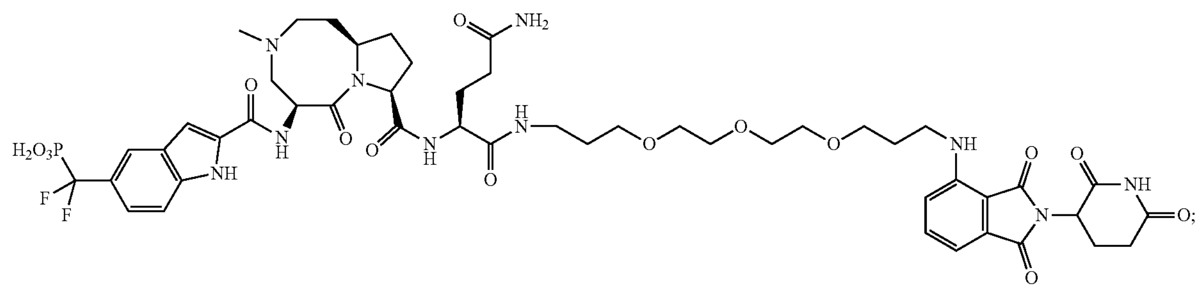
;
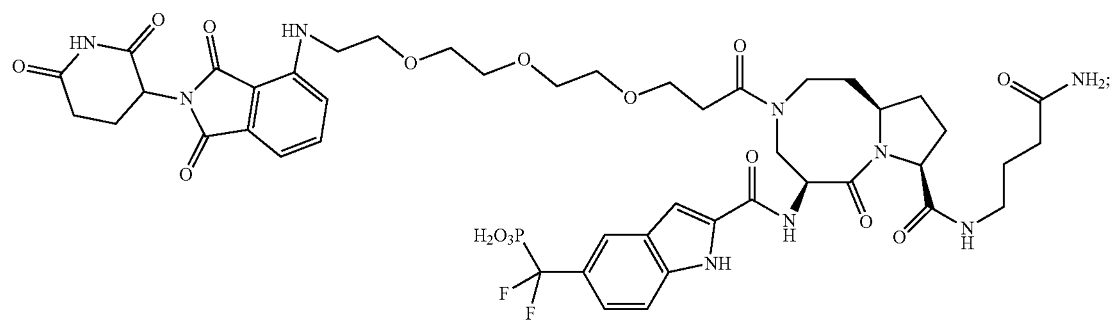
;
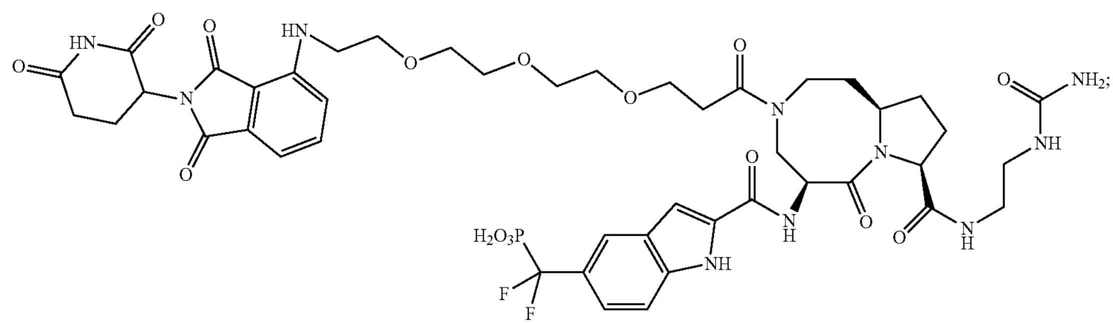
;
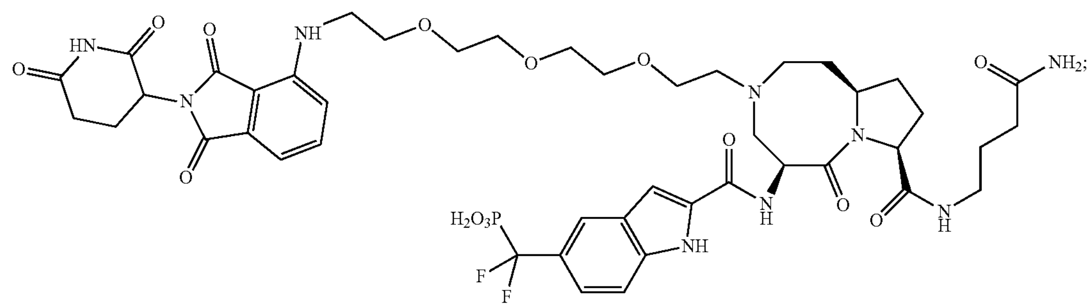
;

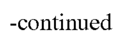
-continued
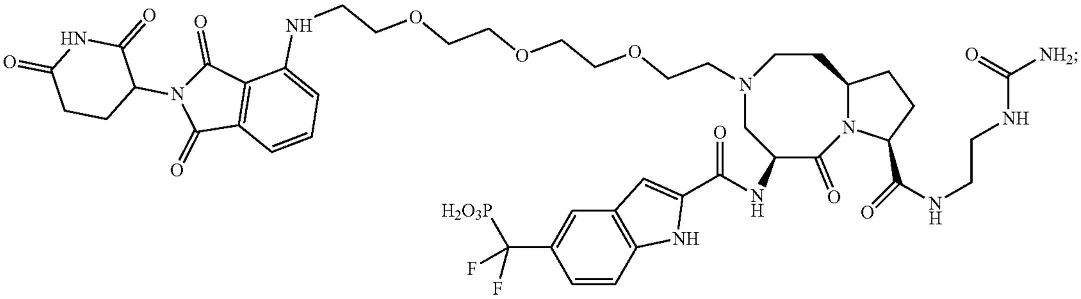
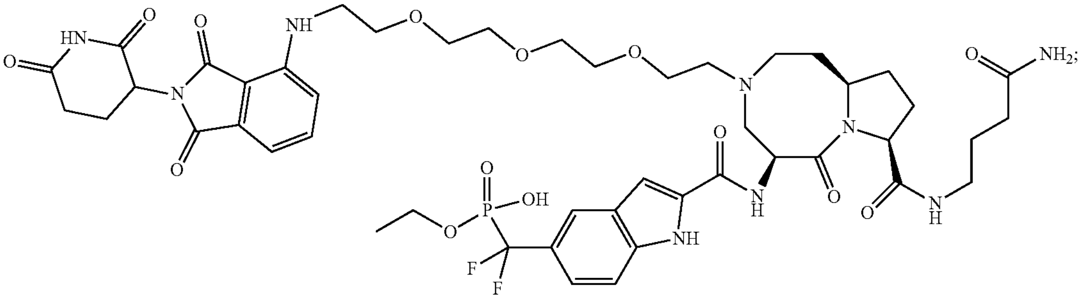
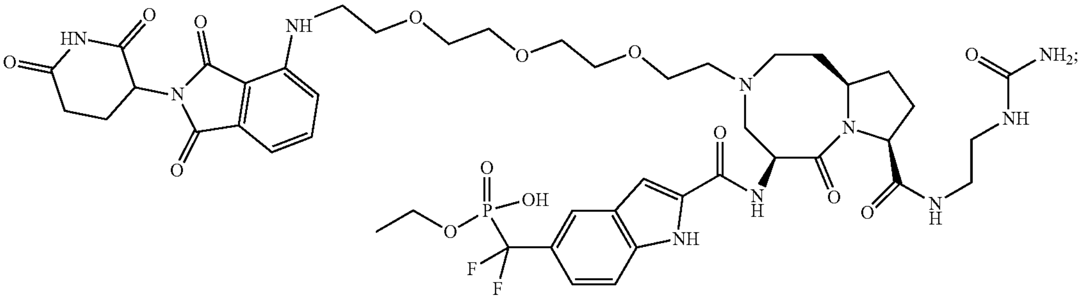
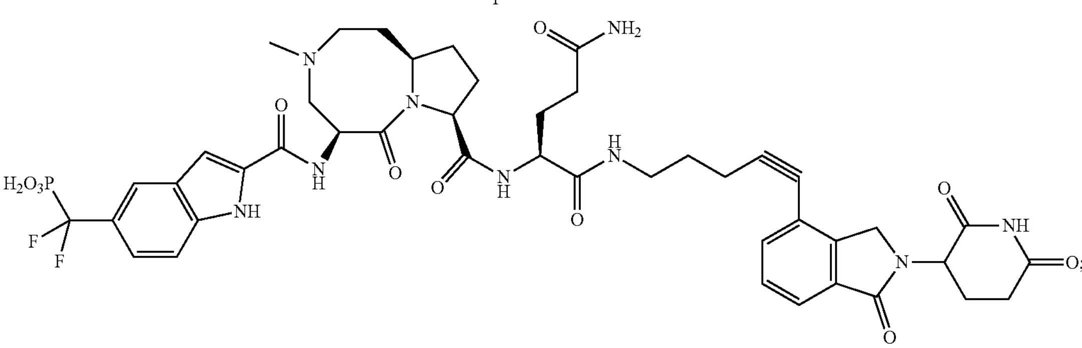
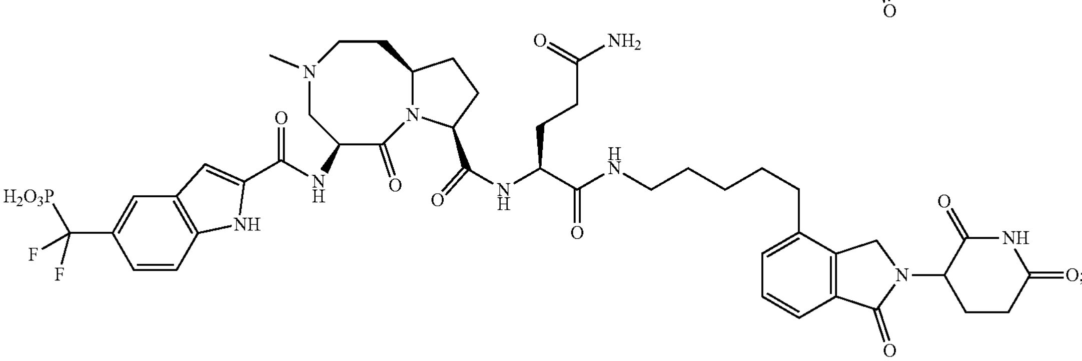

-continued
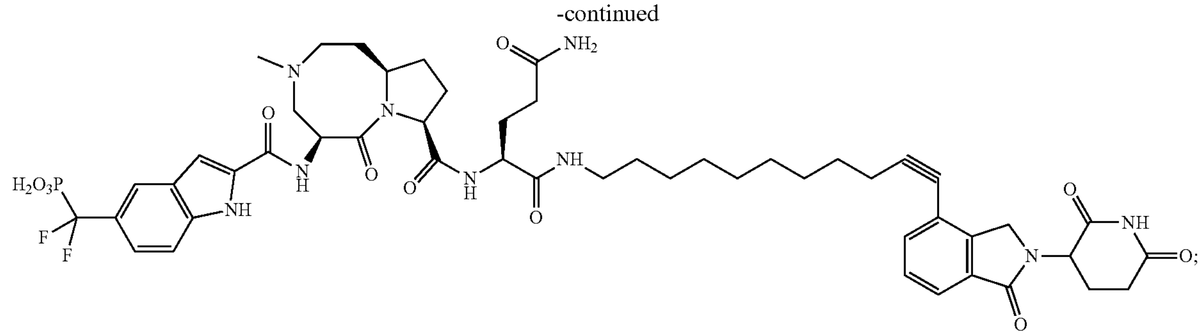
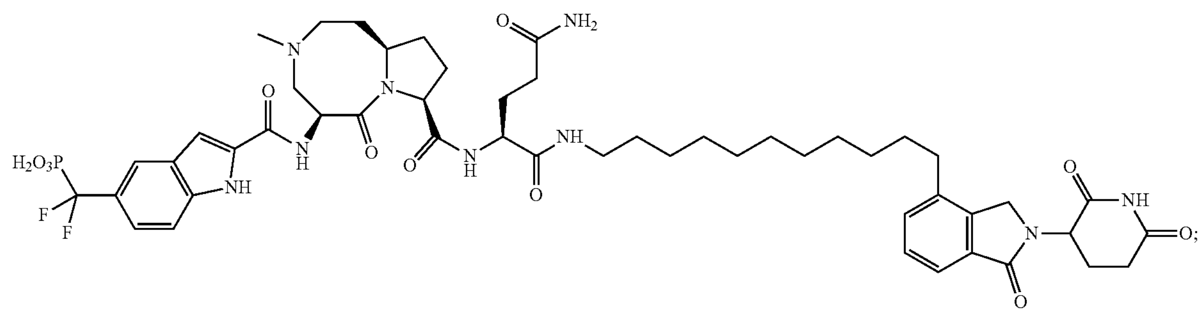
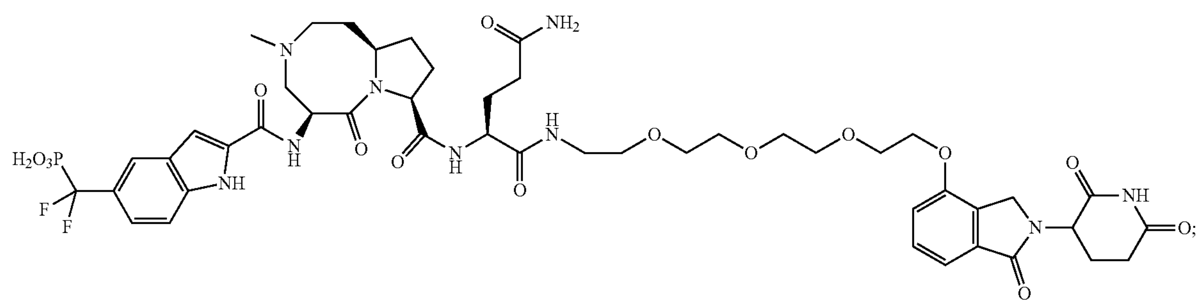
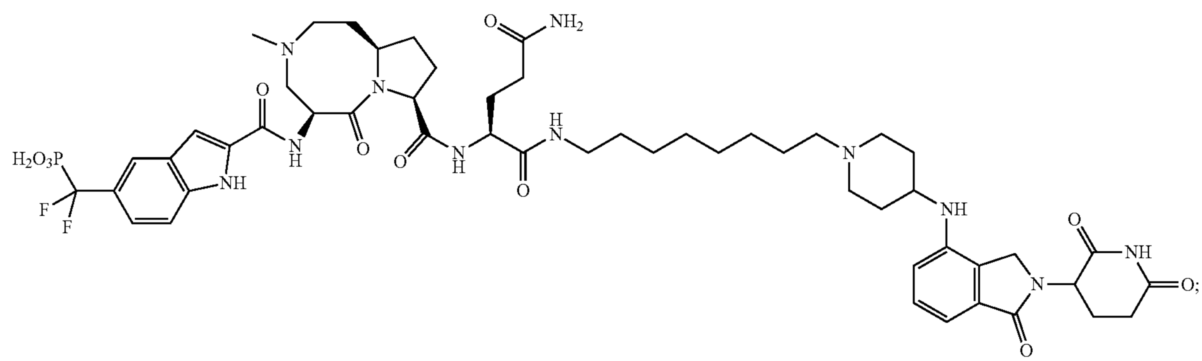
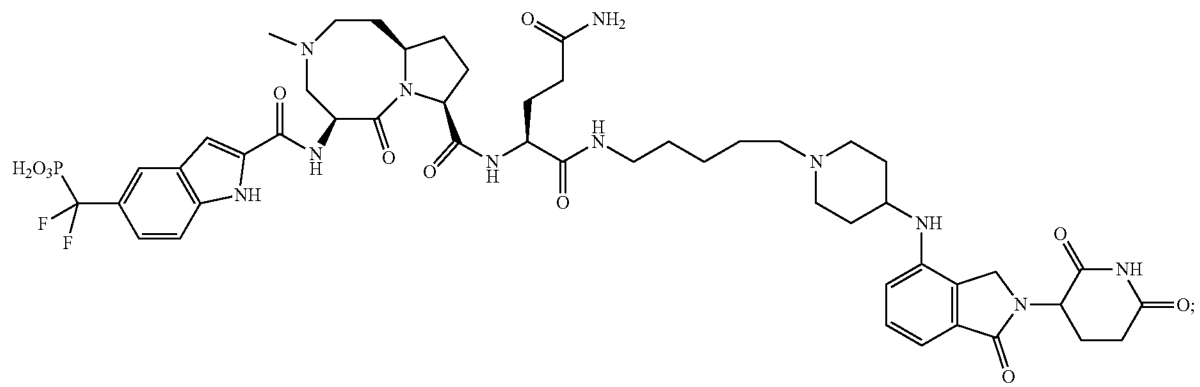

-continued
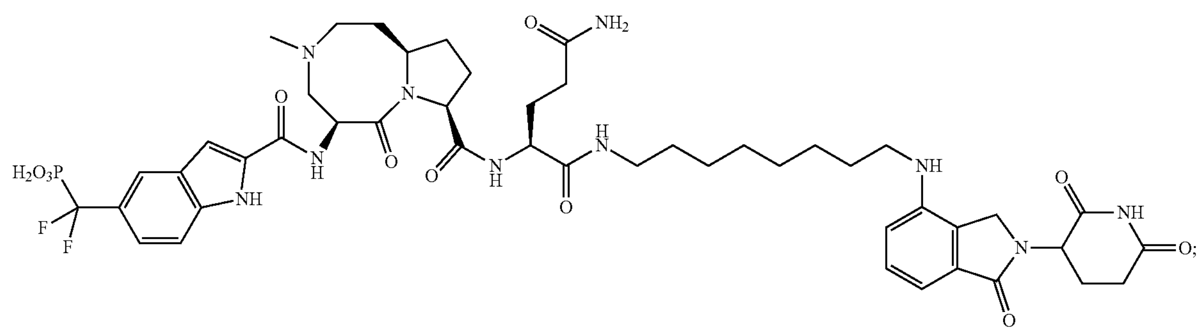
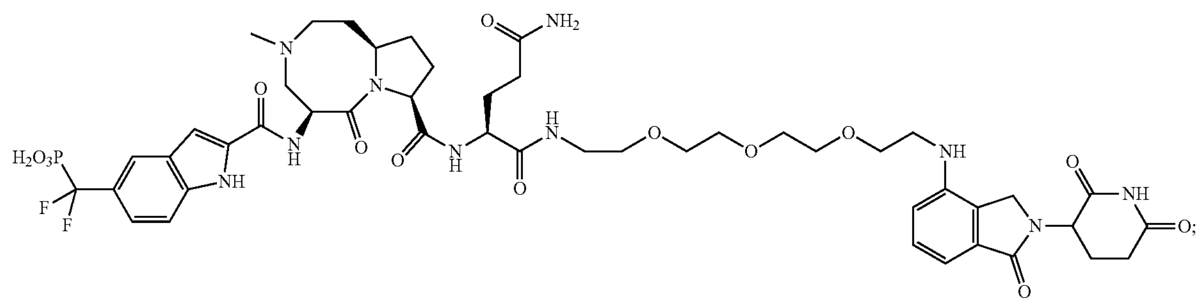
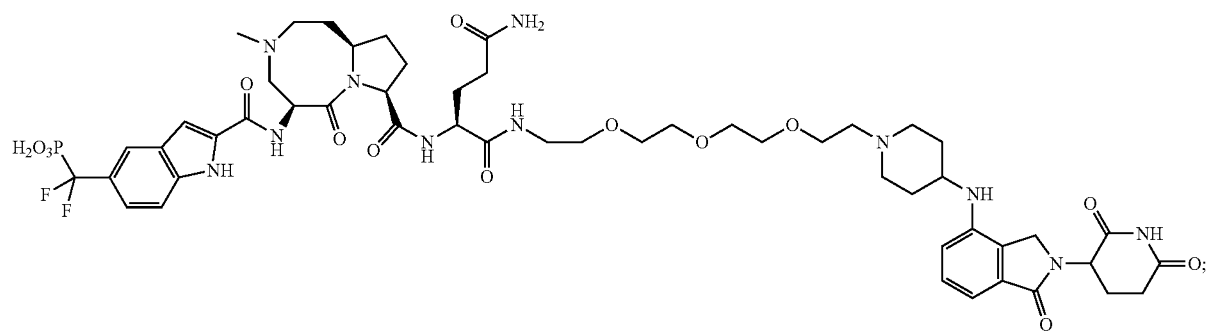
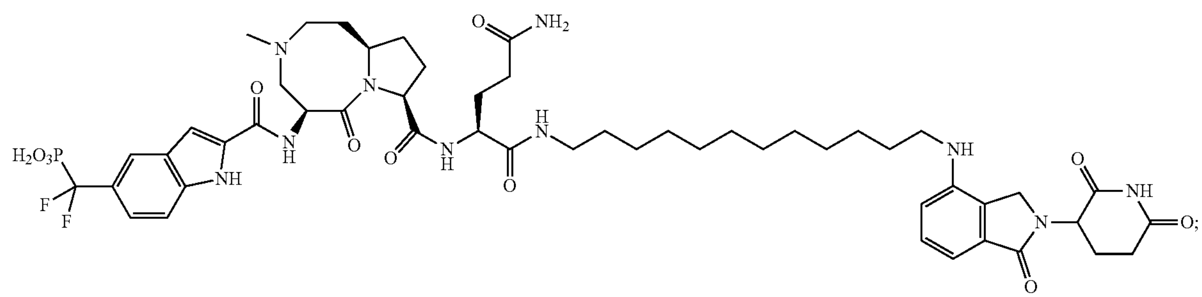
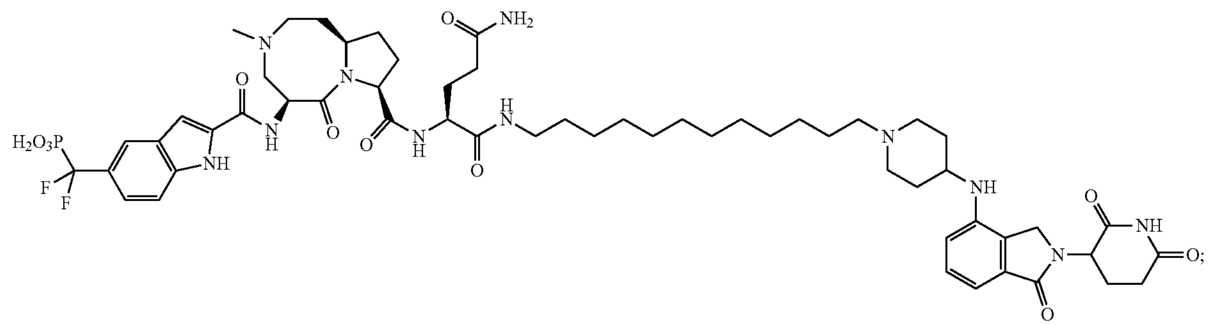

-continued
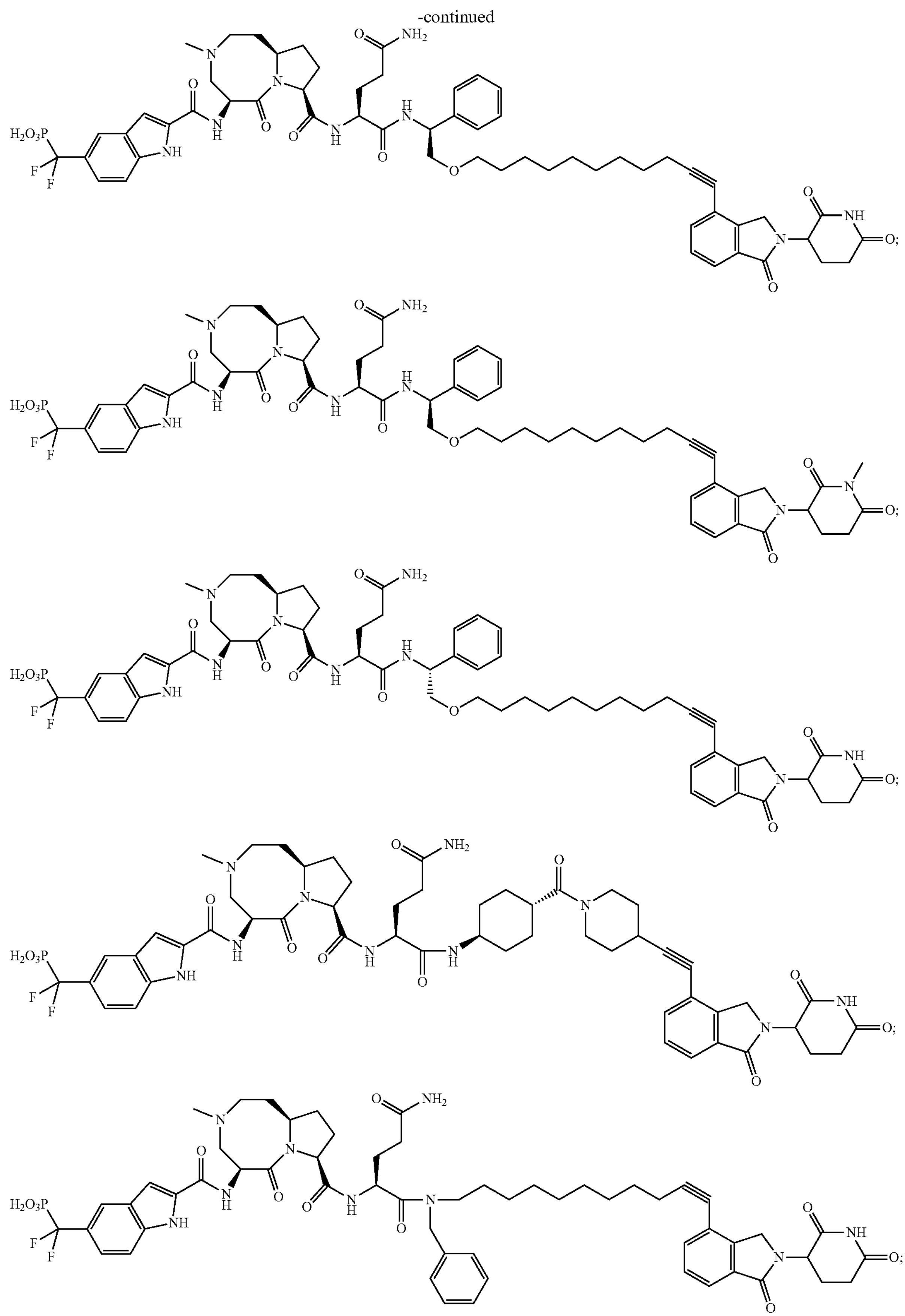

-continued
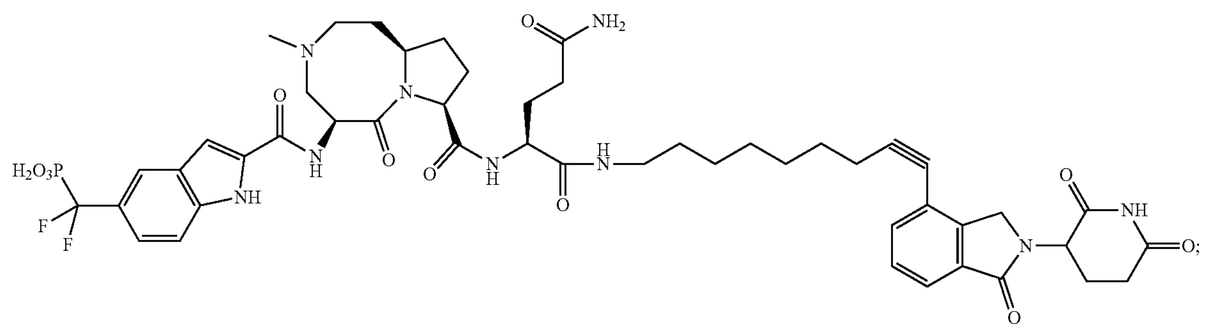
;
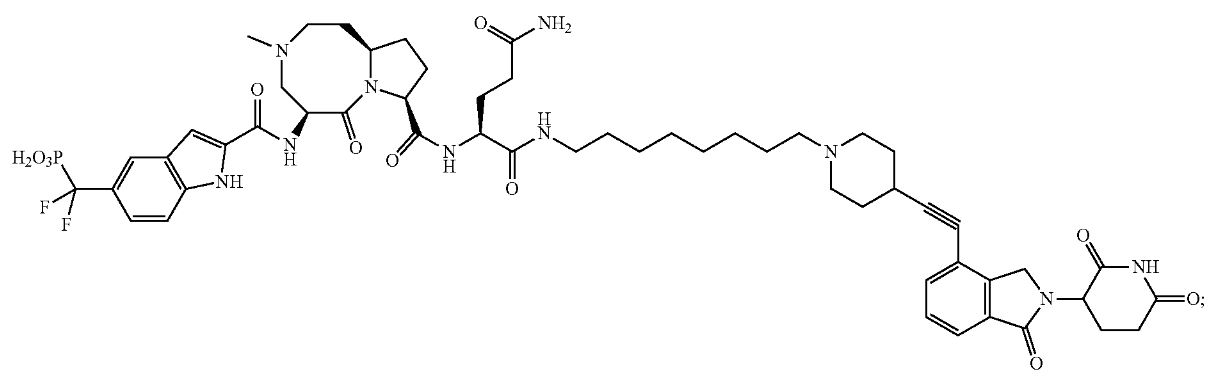
;
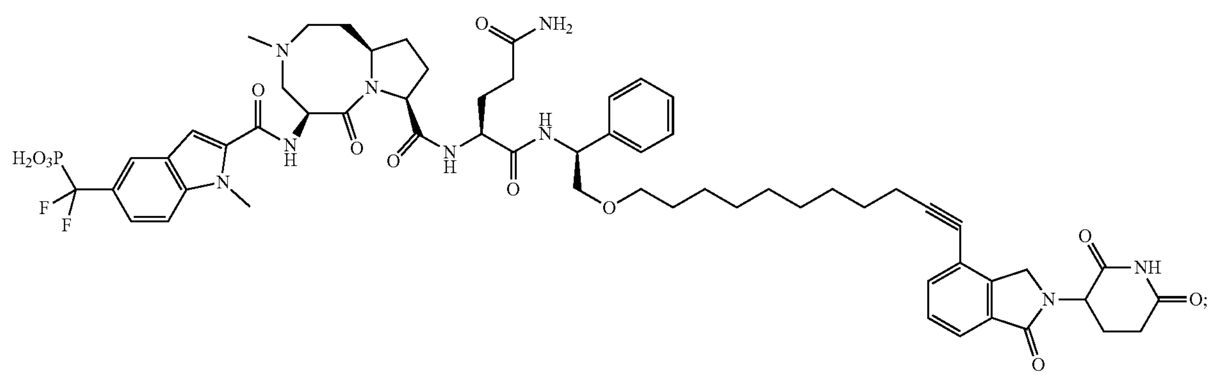
;
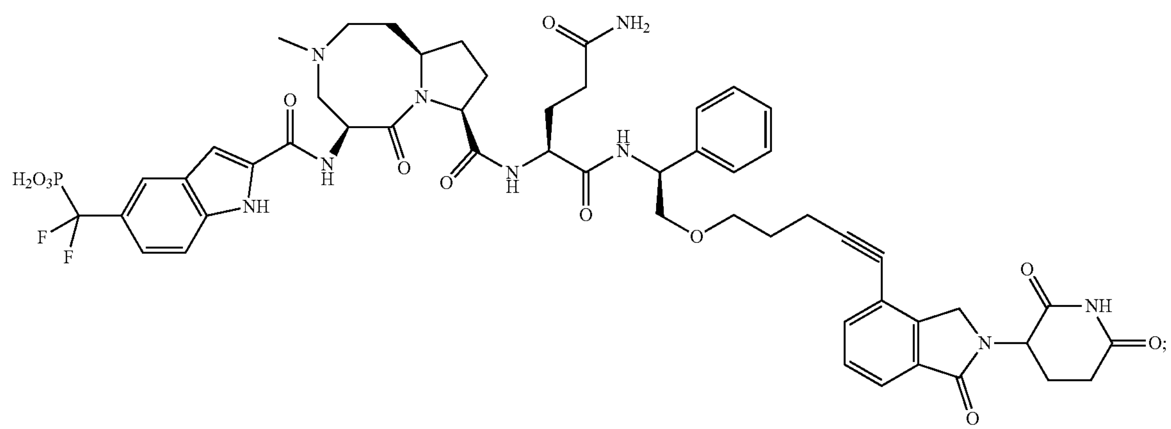
;

-continued
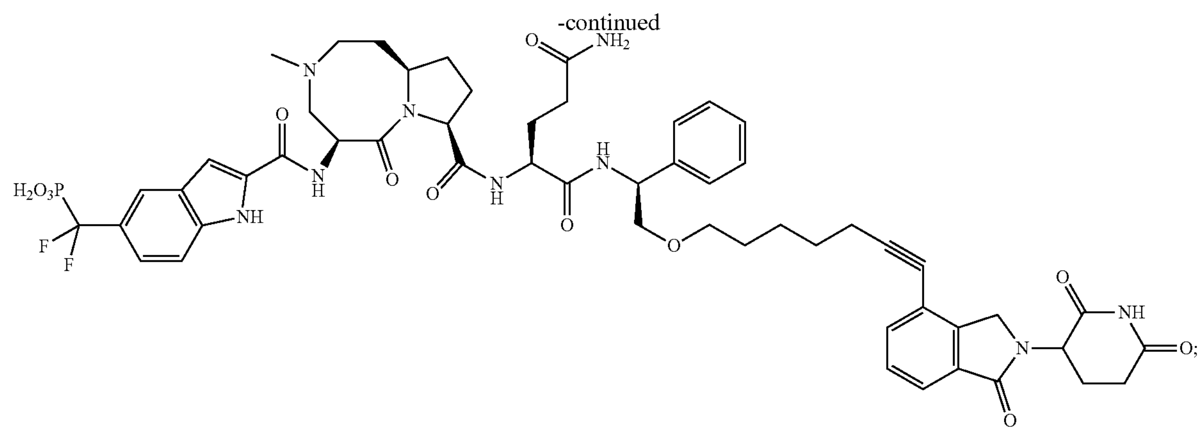
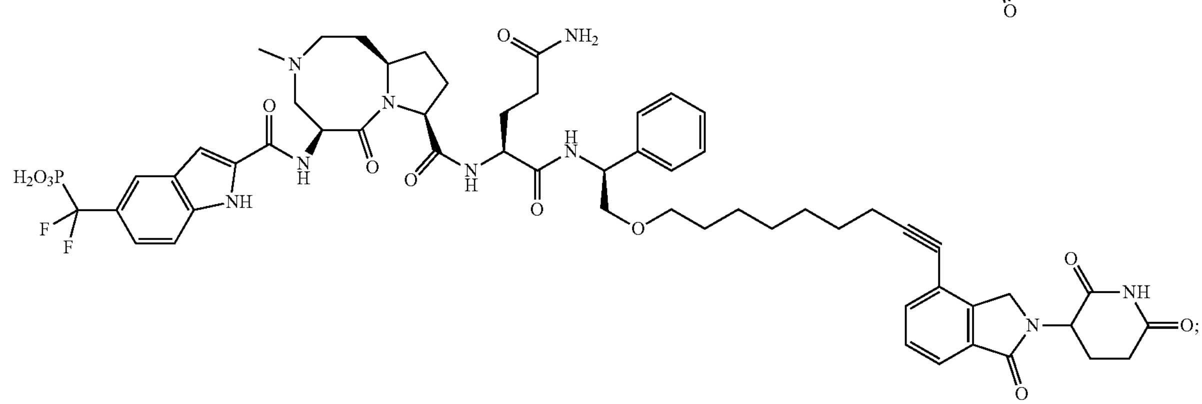
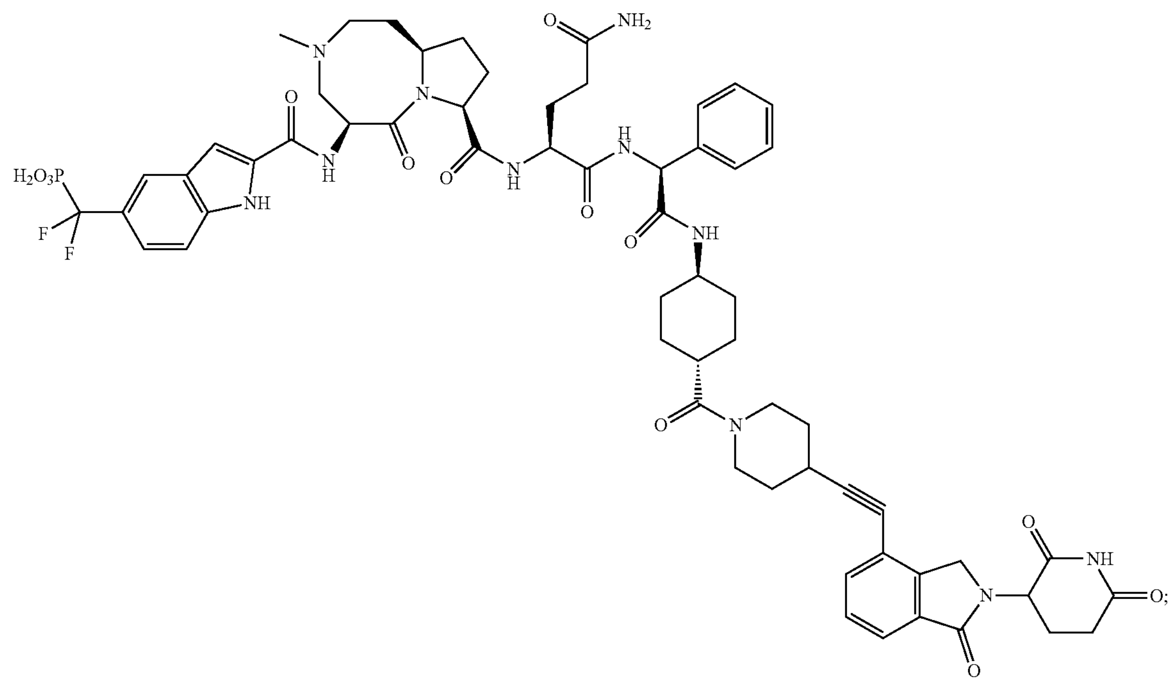

-continued
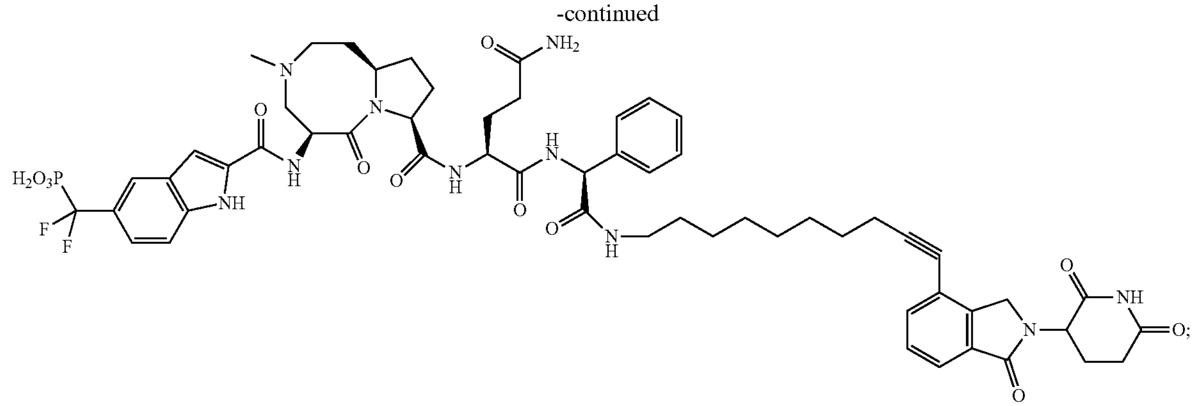
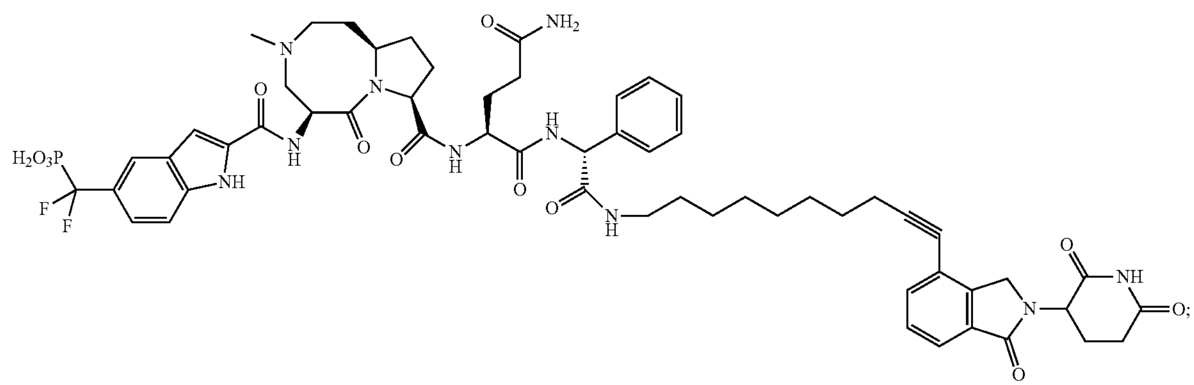
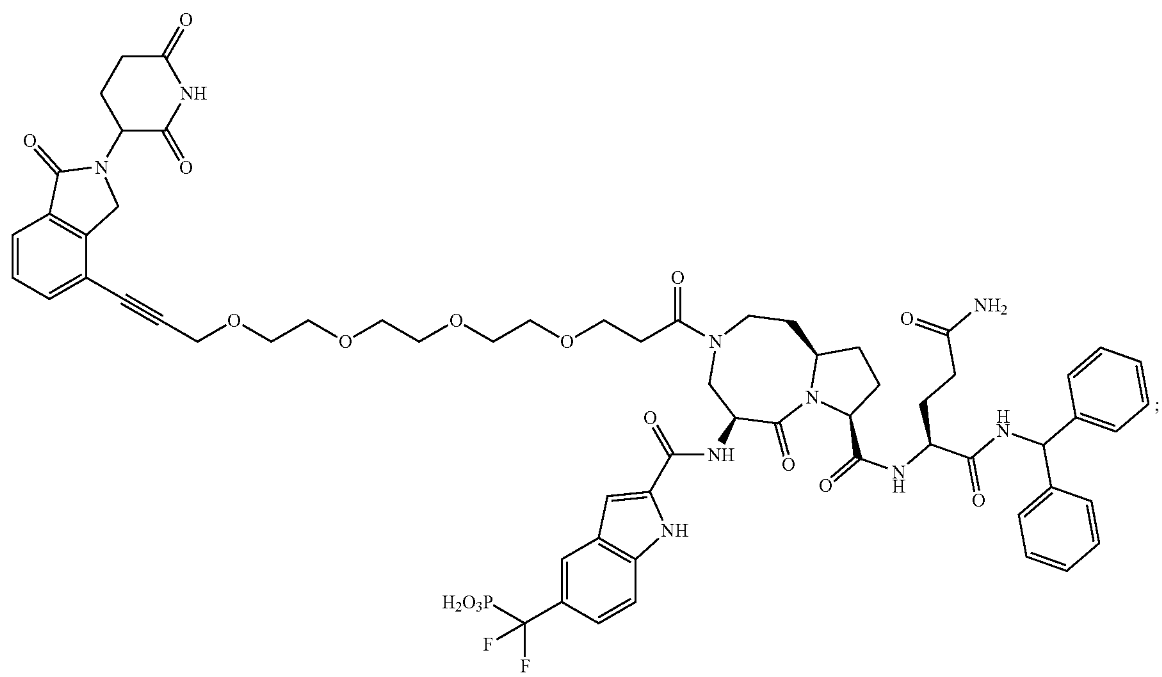

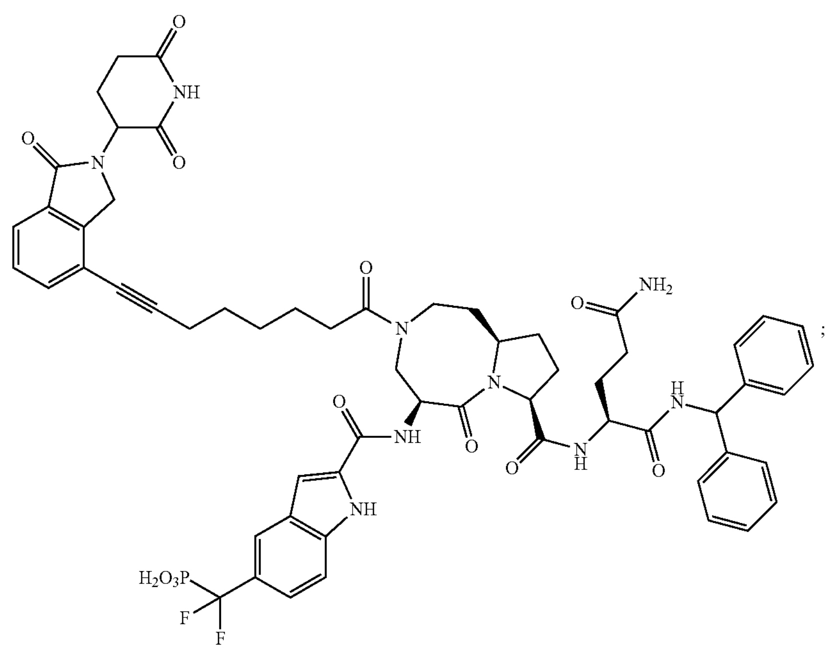
;
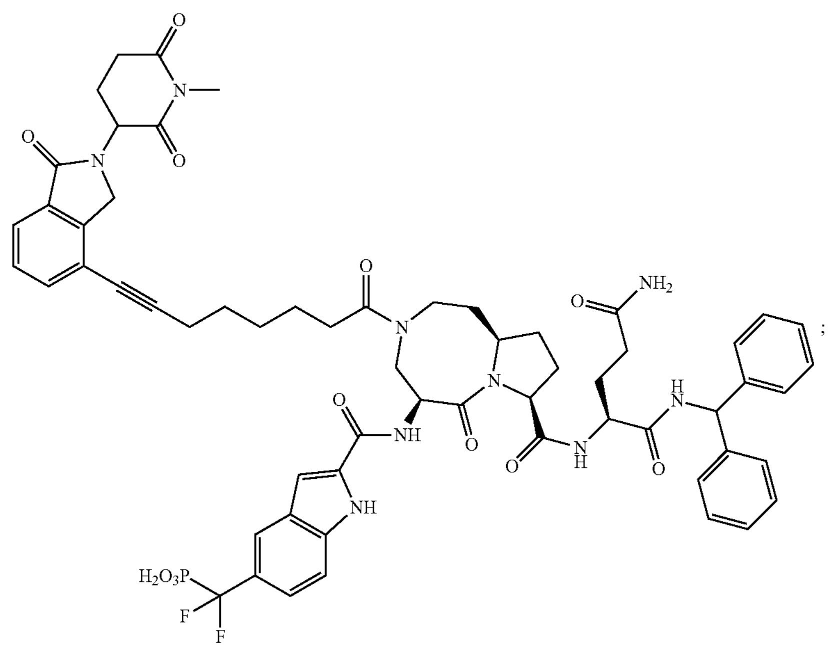
;

-continued
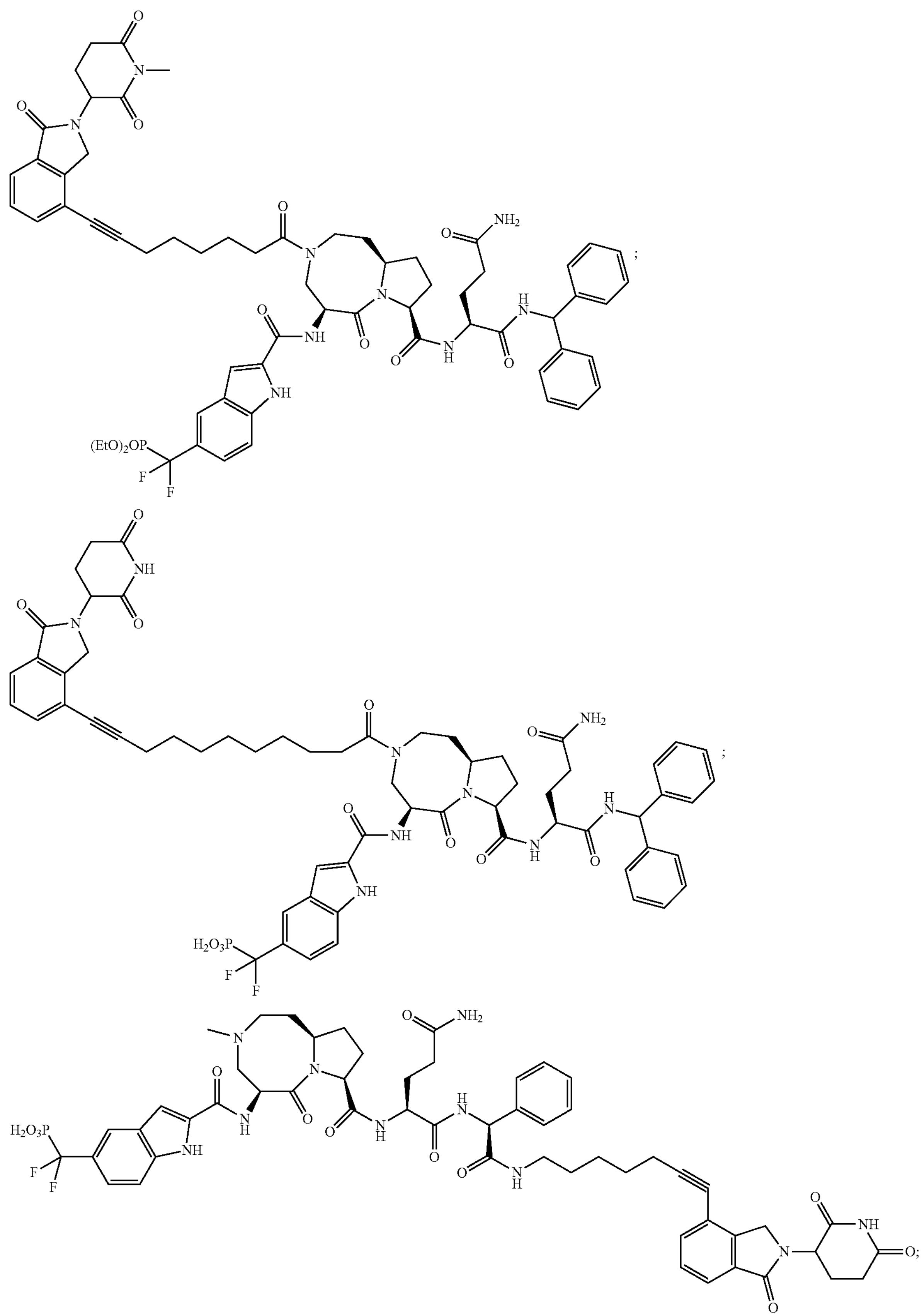
;
;
;

-continued
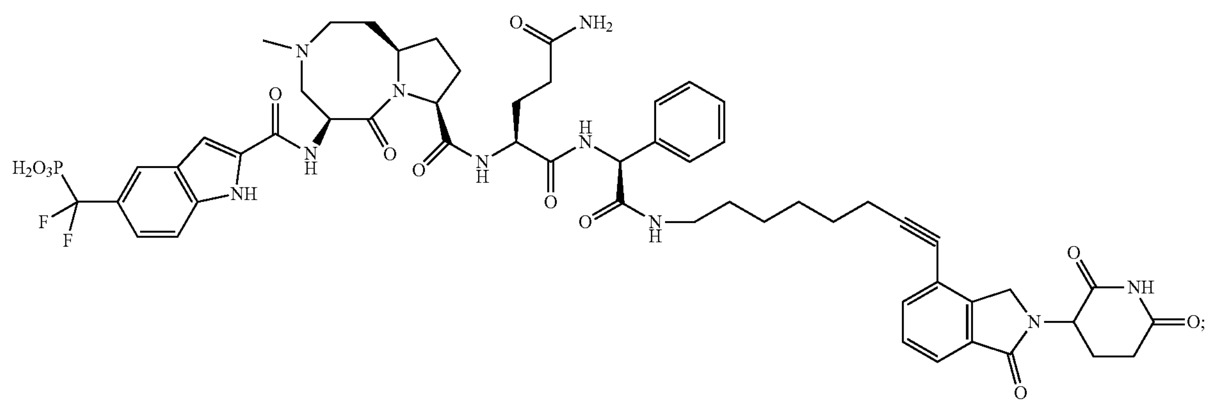
;
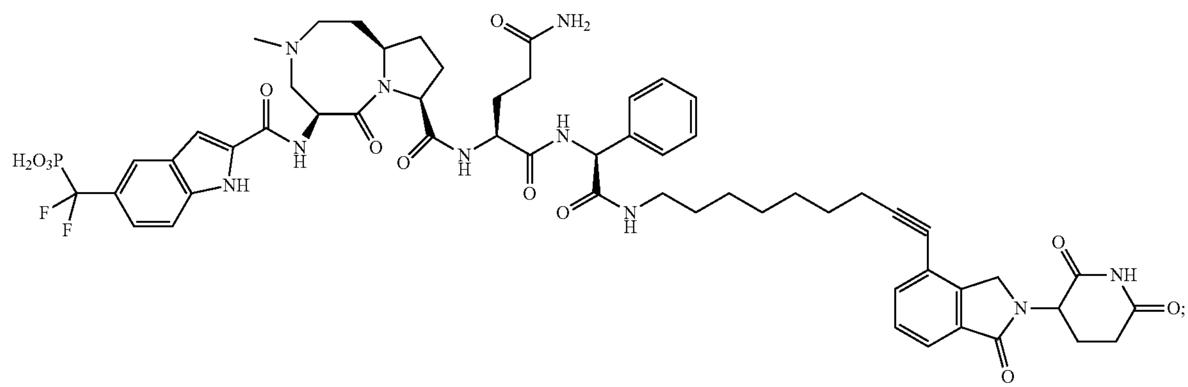
;
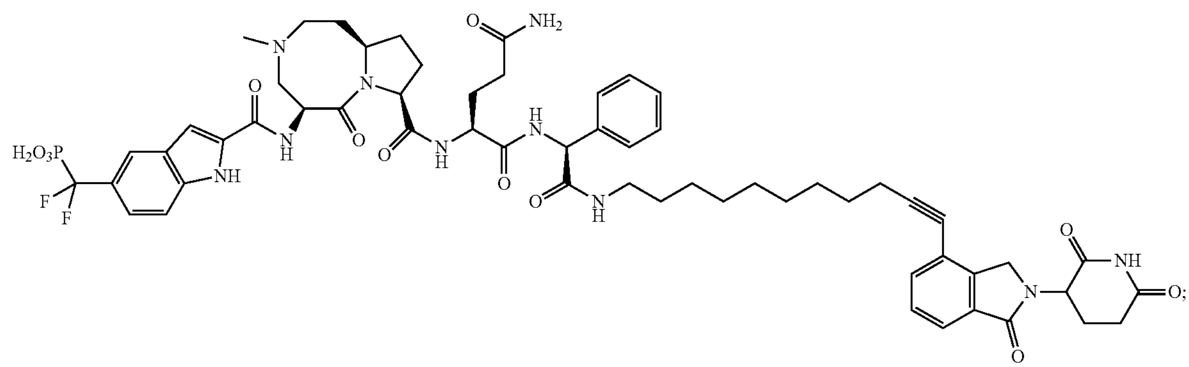
;
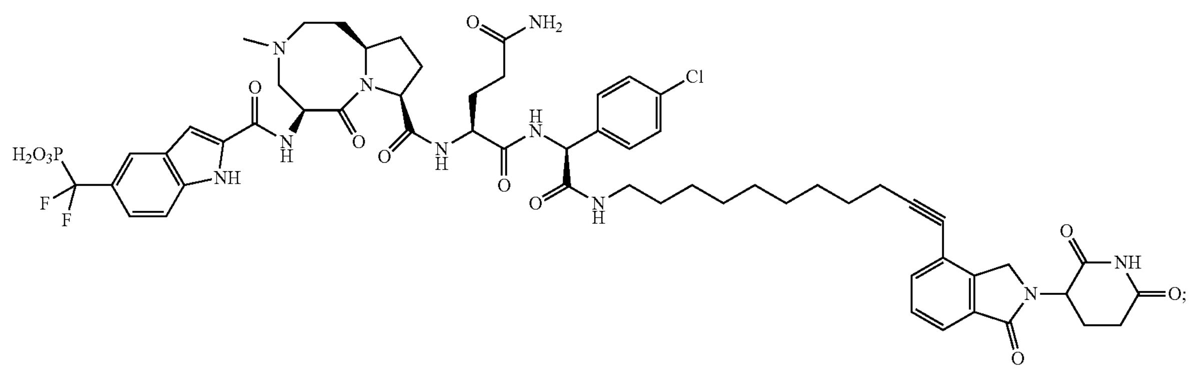
;

-continued
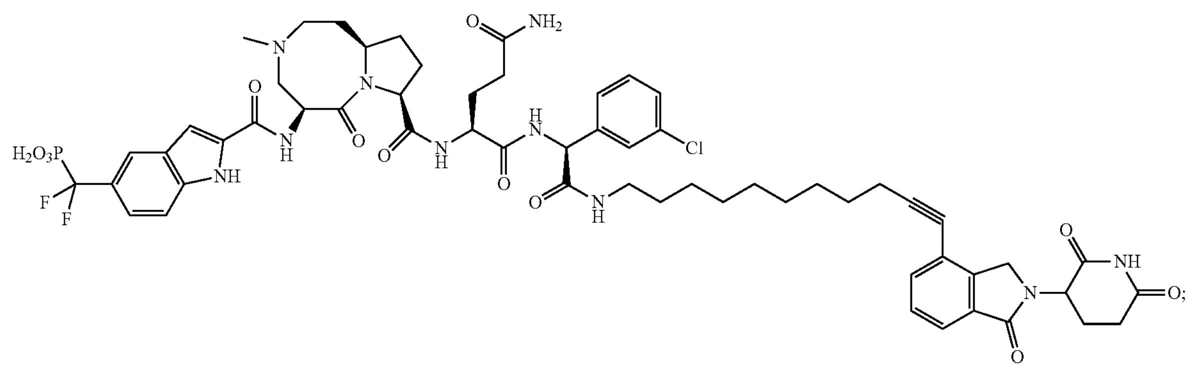
;
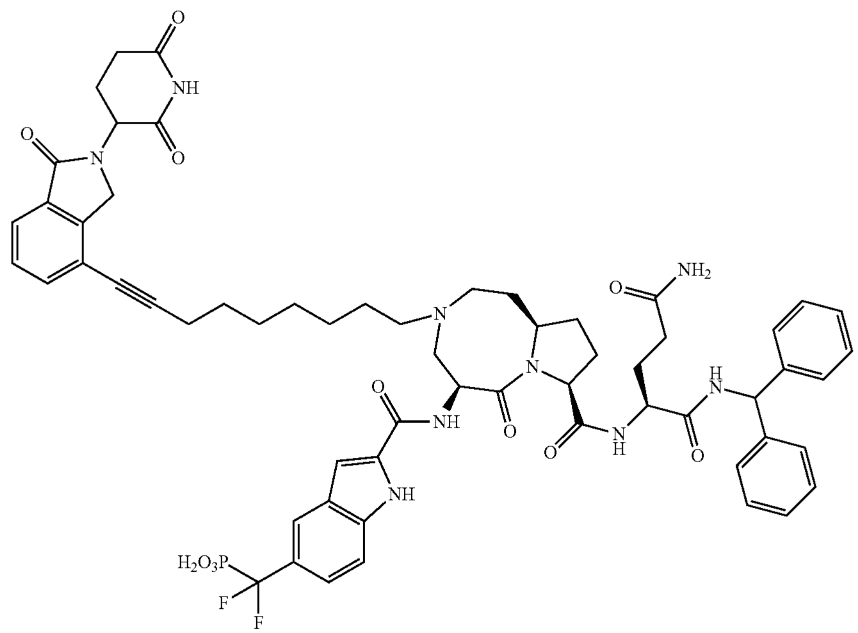
;
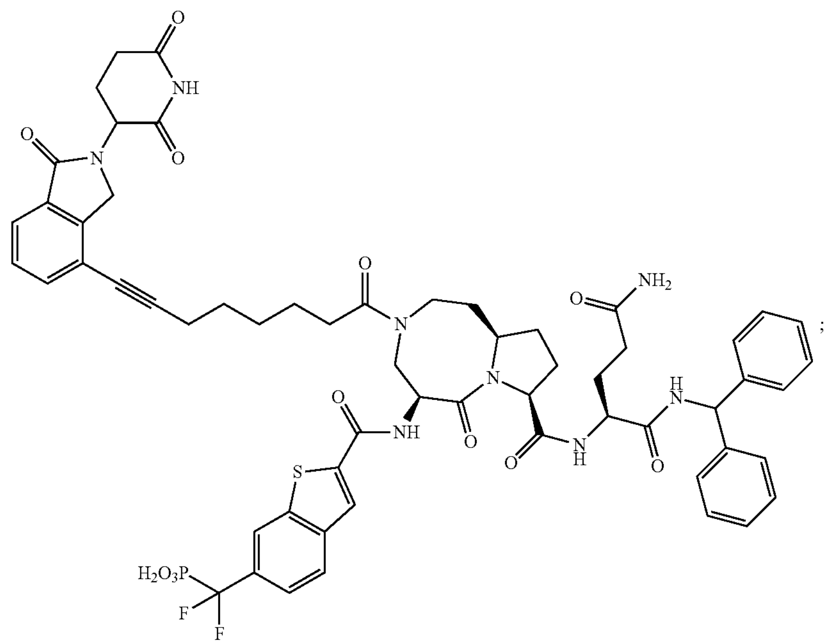
;

-continued
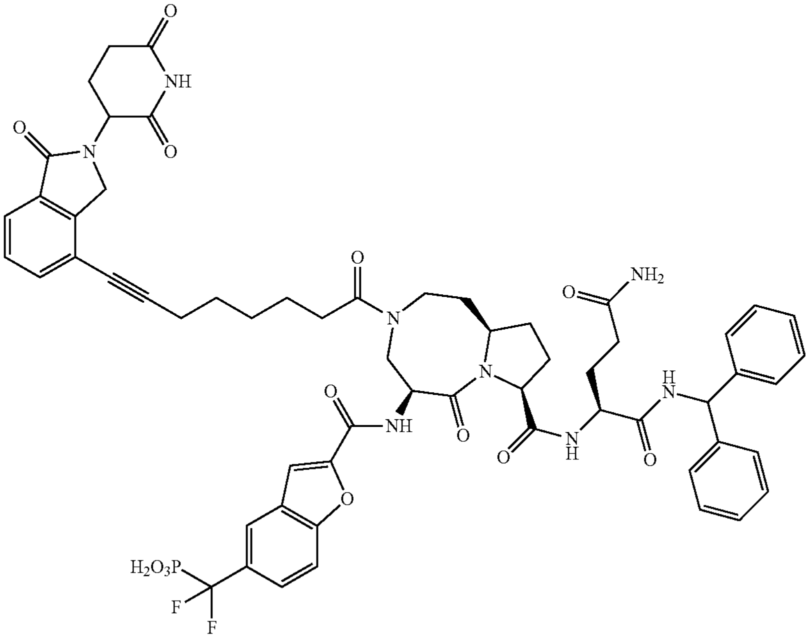
;
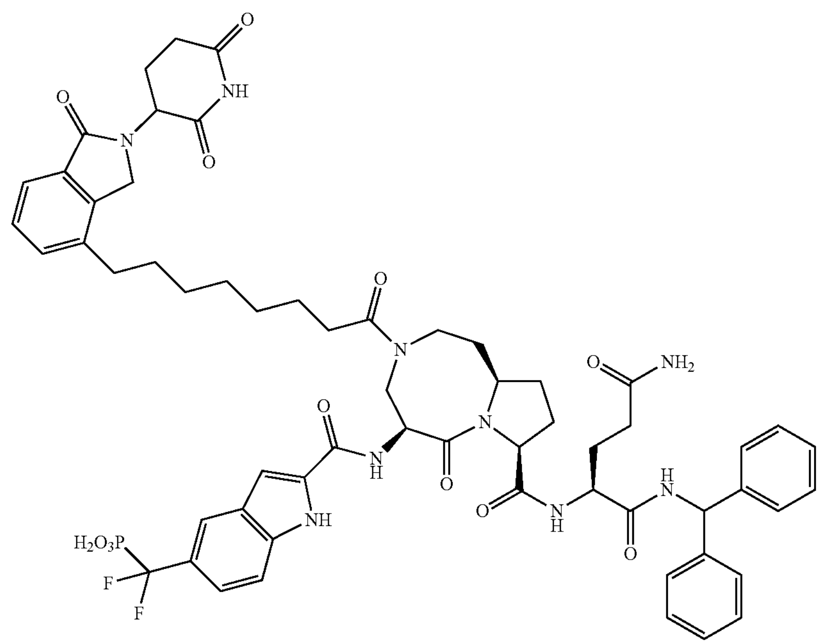
;

-continued
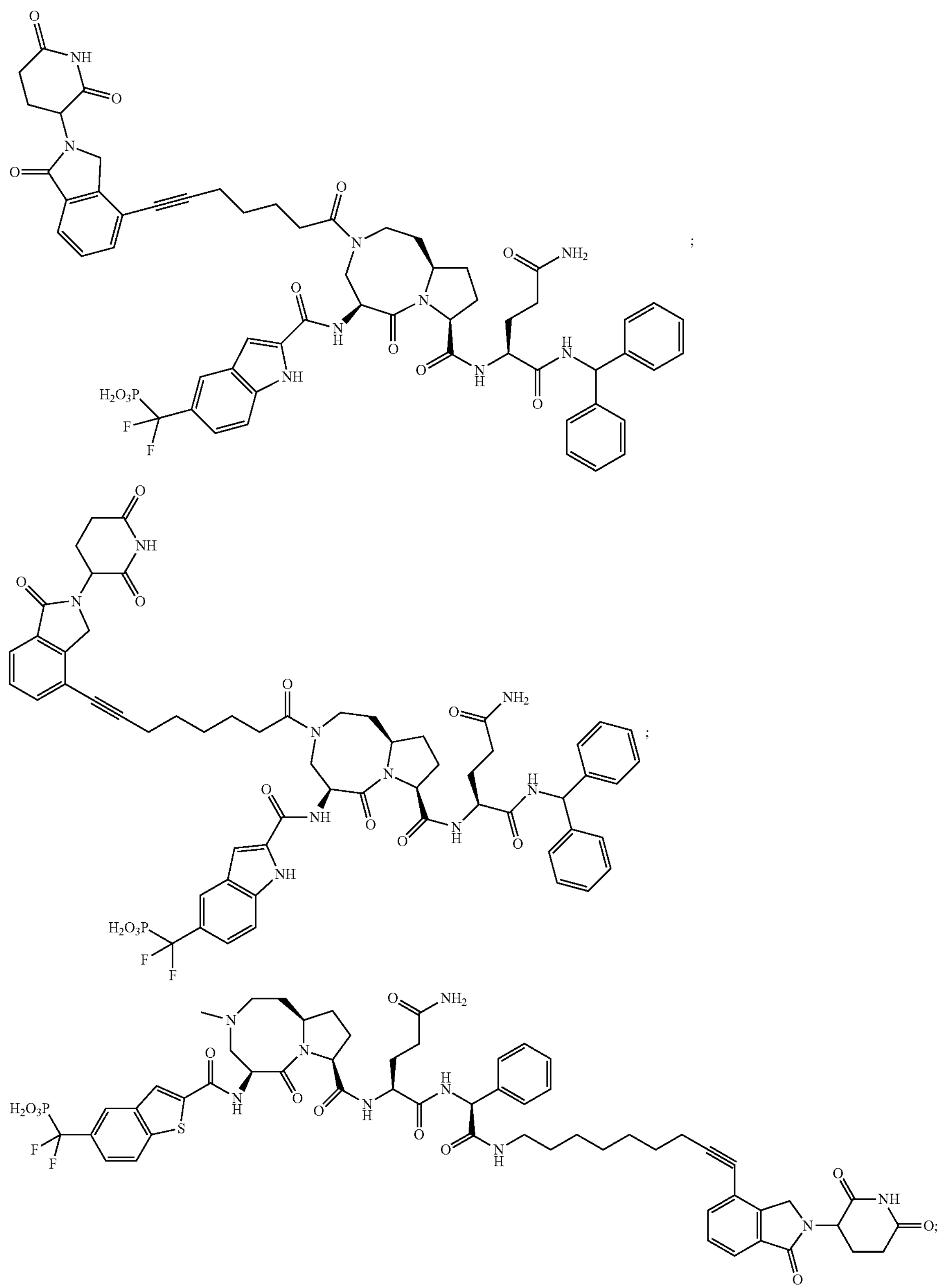
;
;
;

-continued
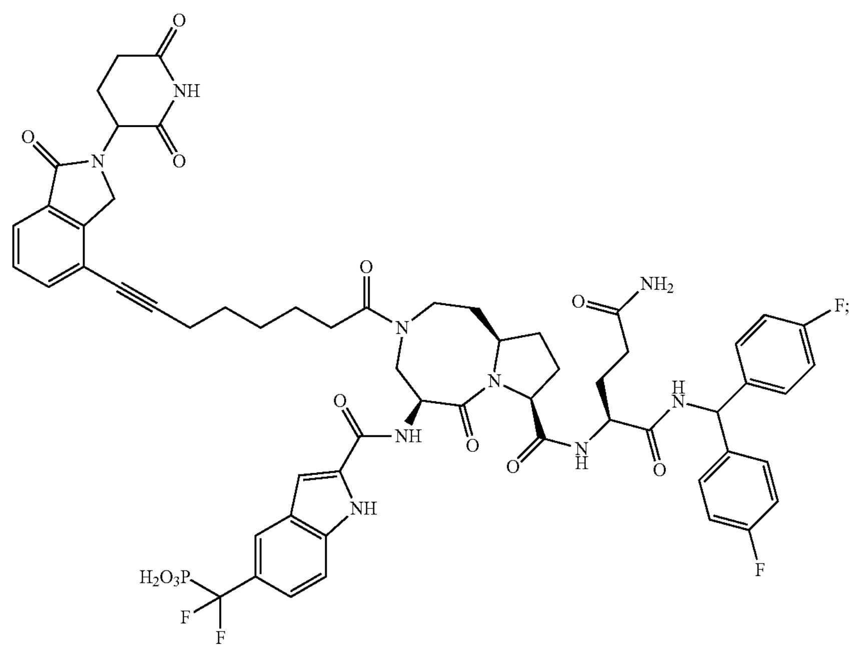
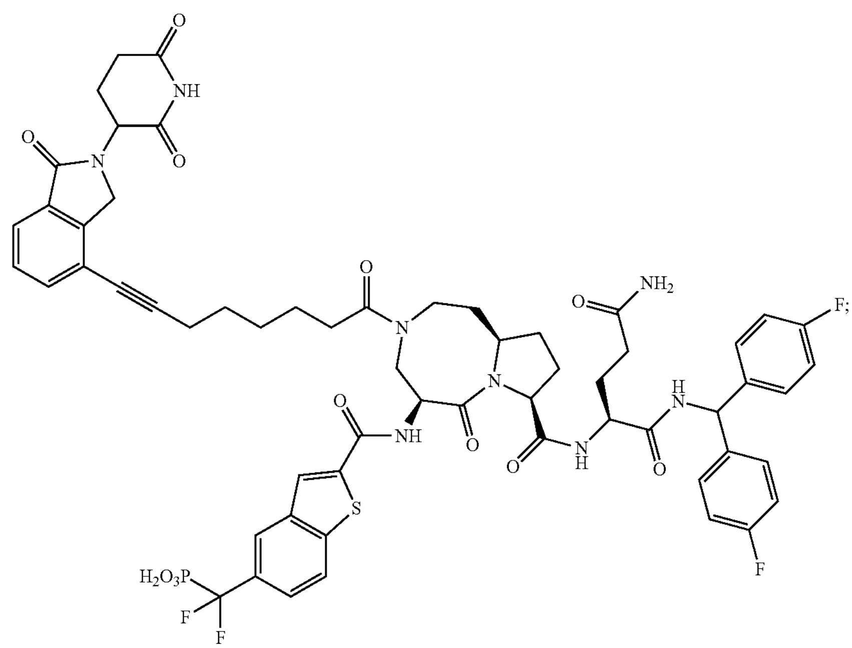

-continued
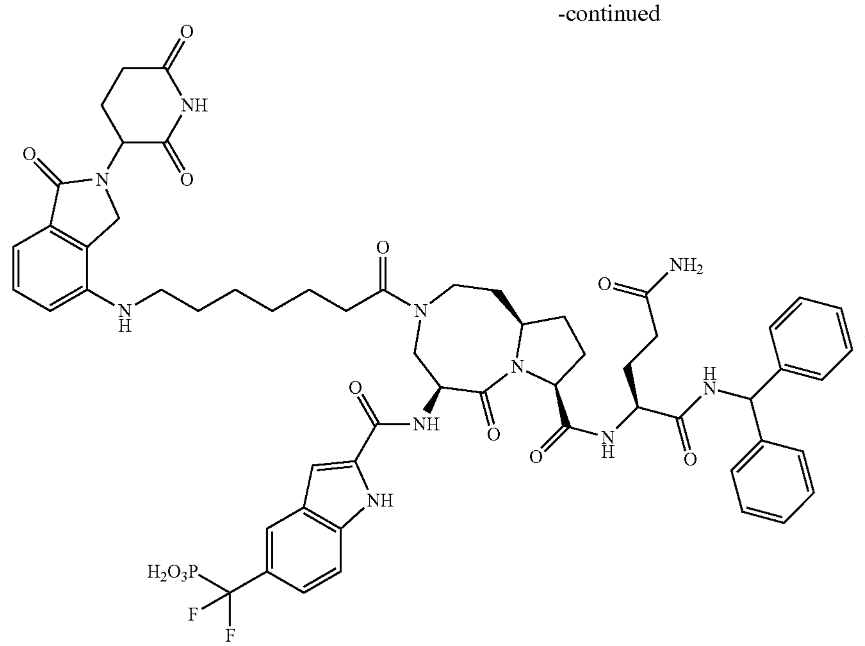
;
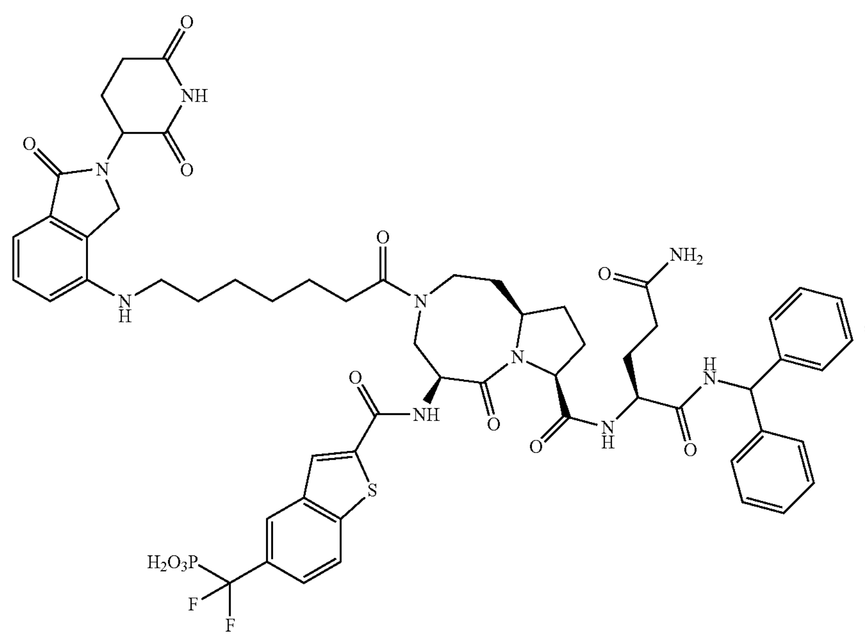
;

-continued
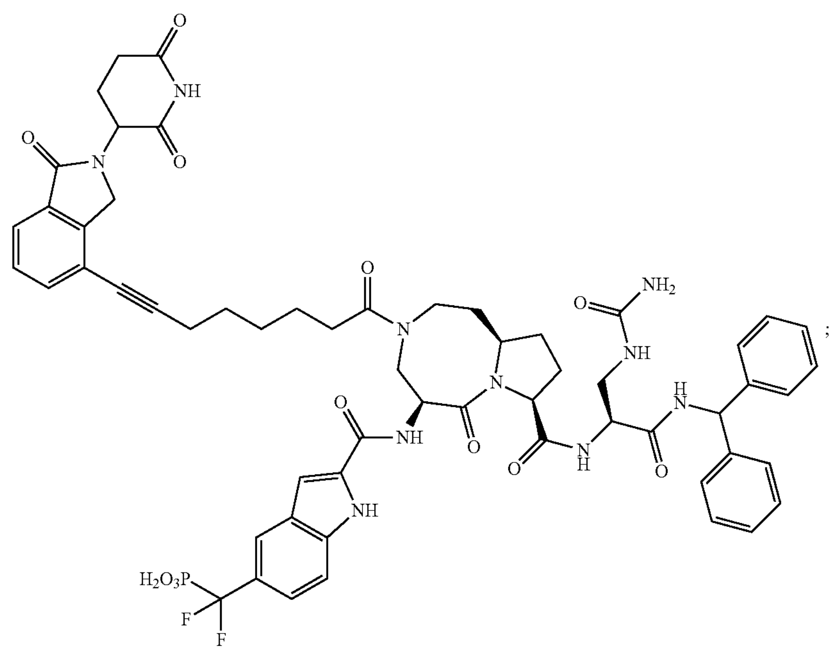
;
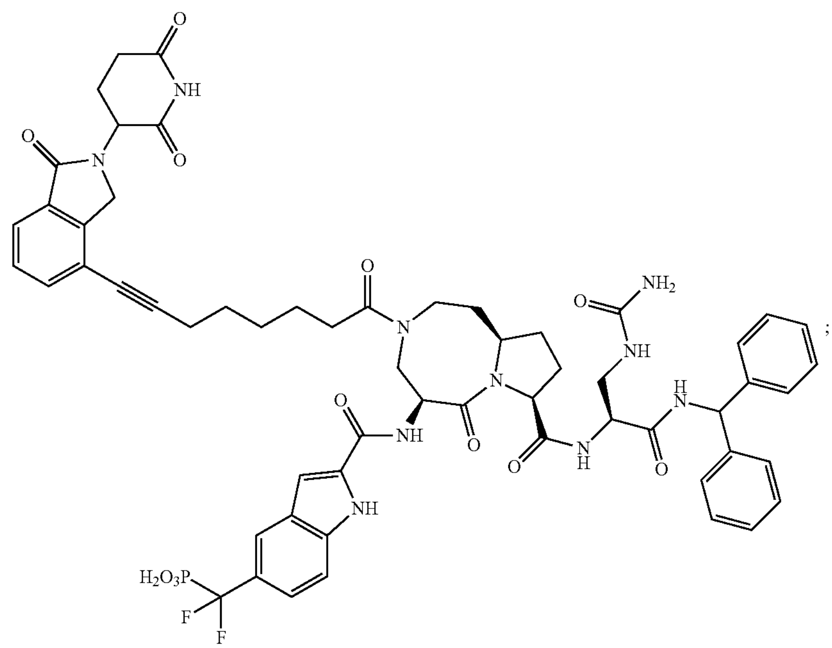
;

-continued
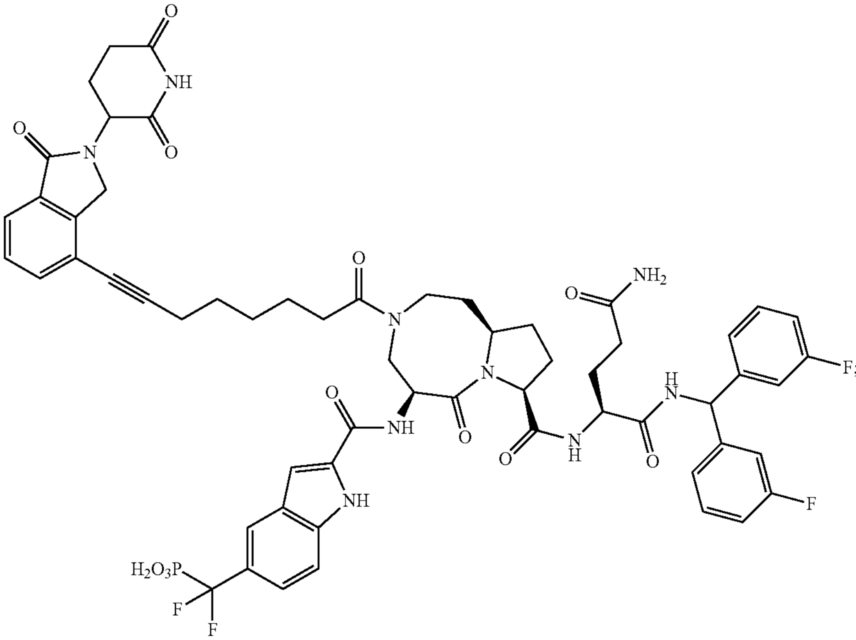
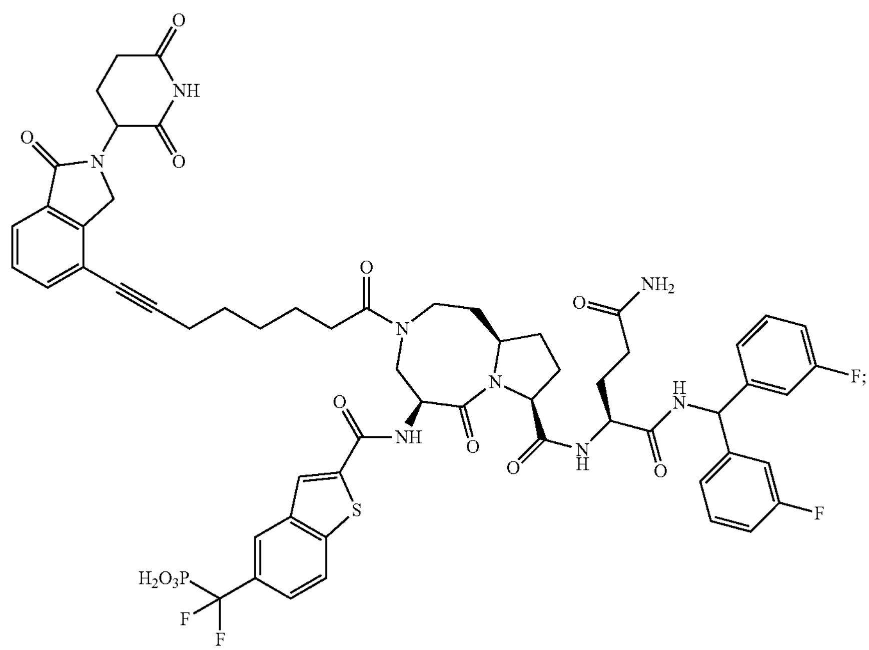

-continued
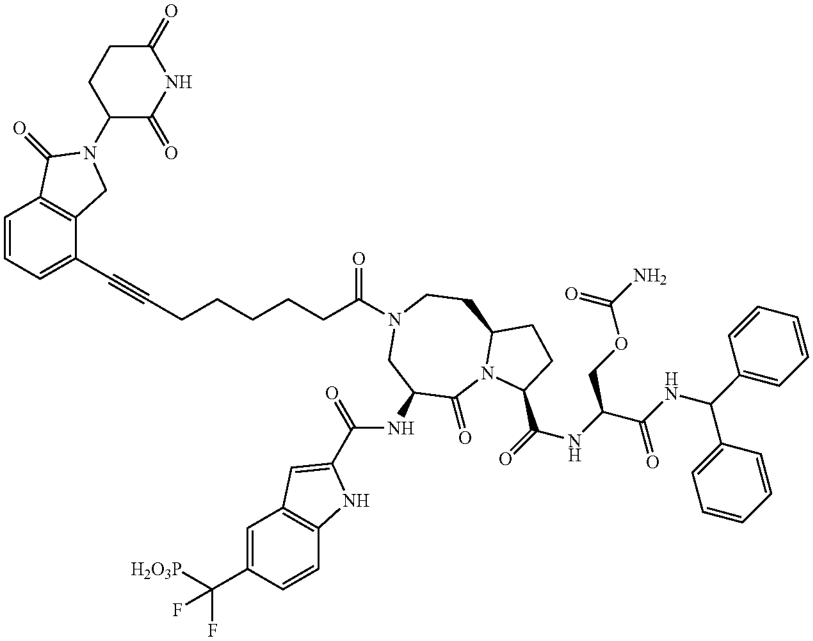
;
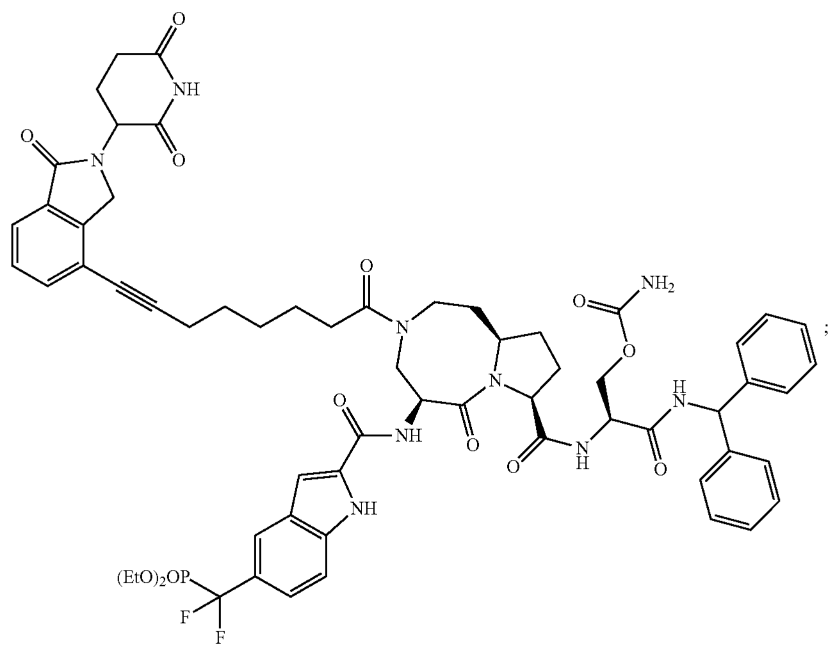
;

-continued
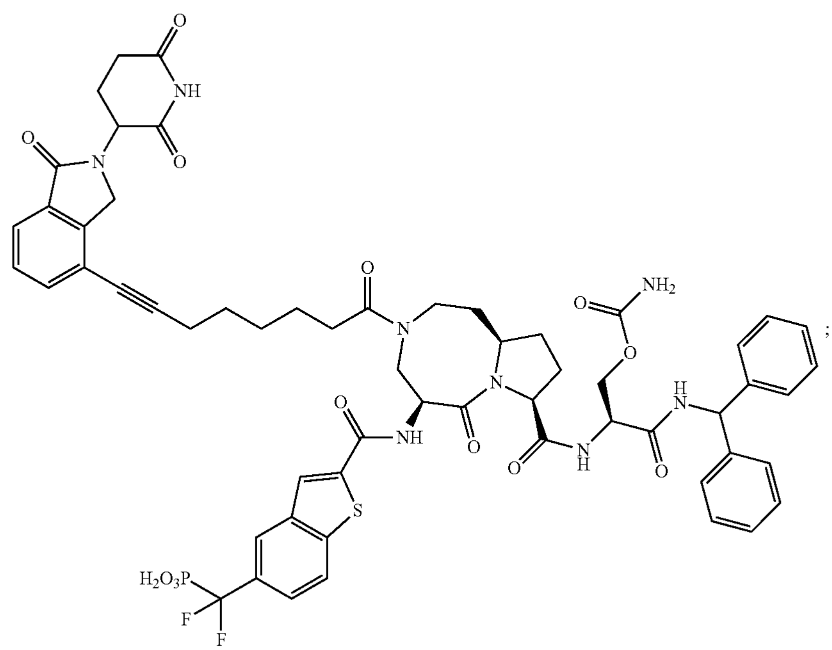
;
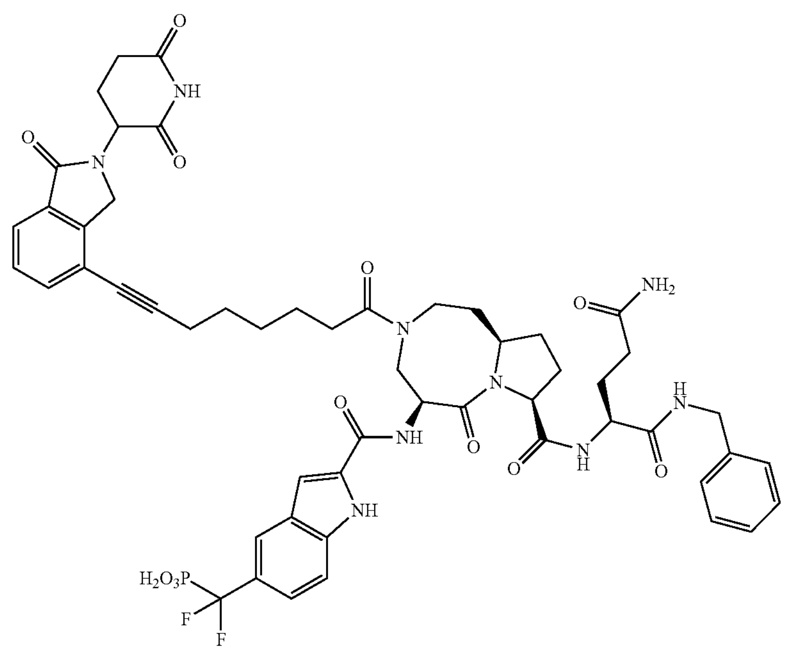
;

-continued
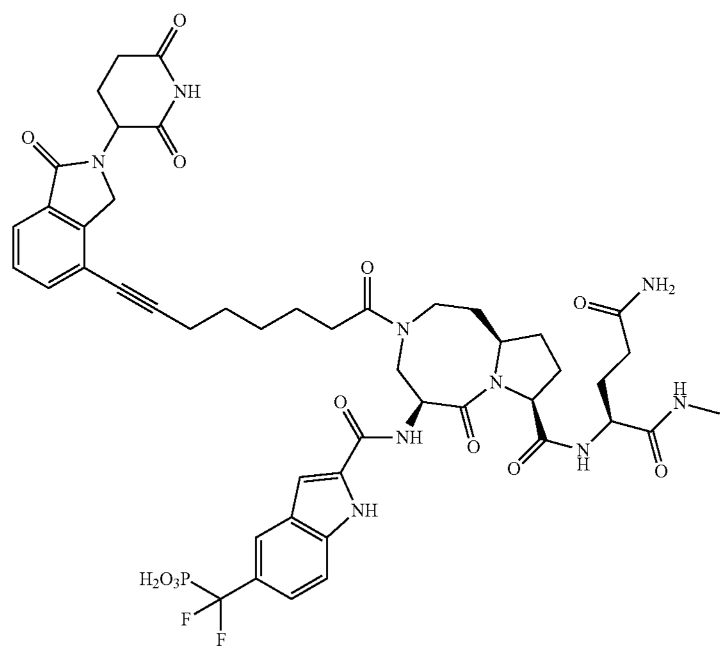
;
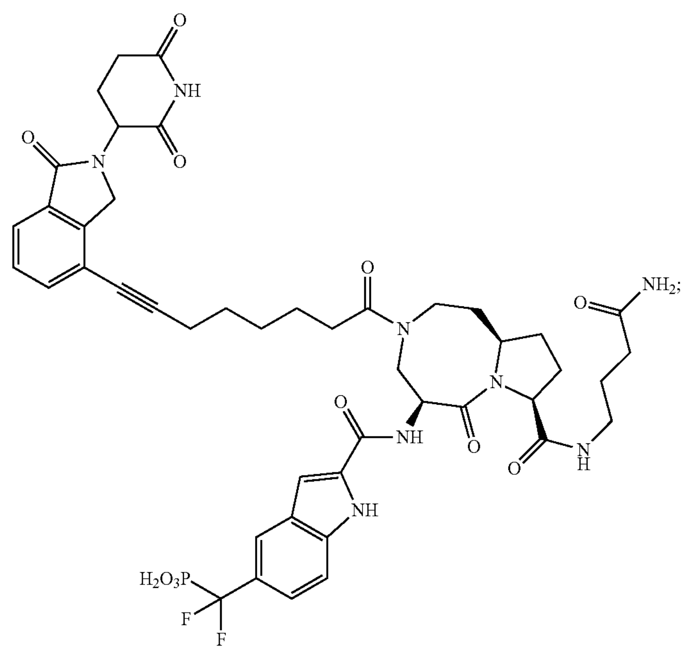
;

-continued
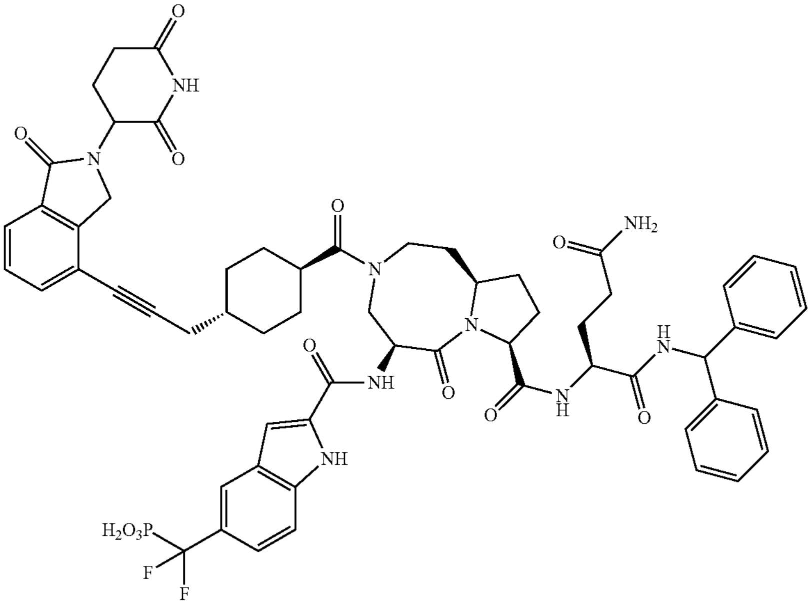
;
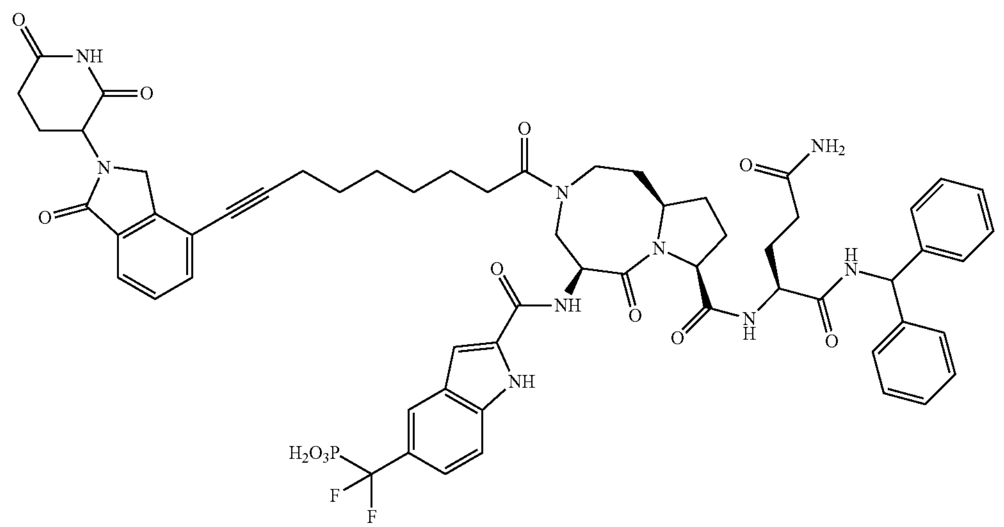
;

-continued
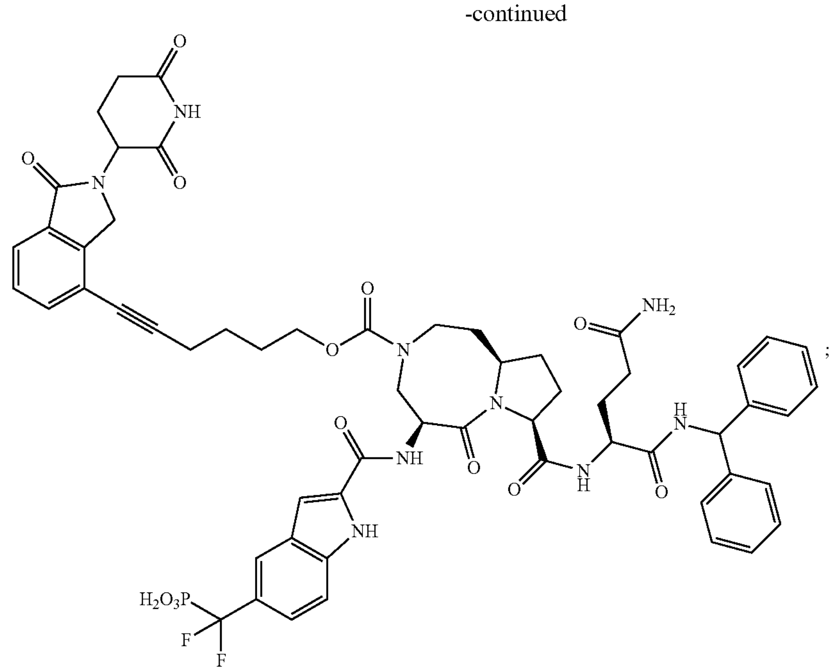
;
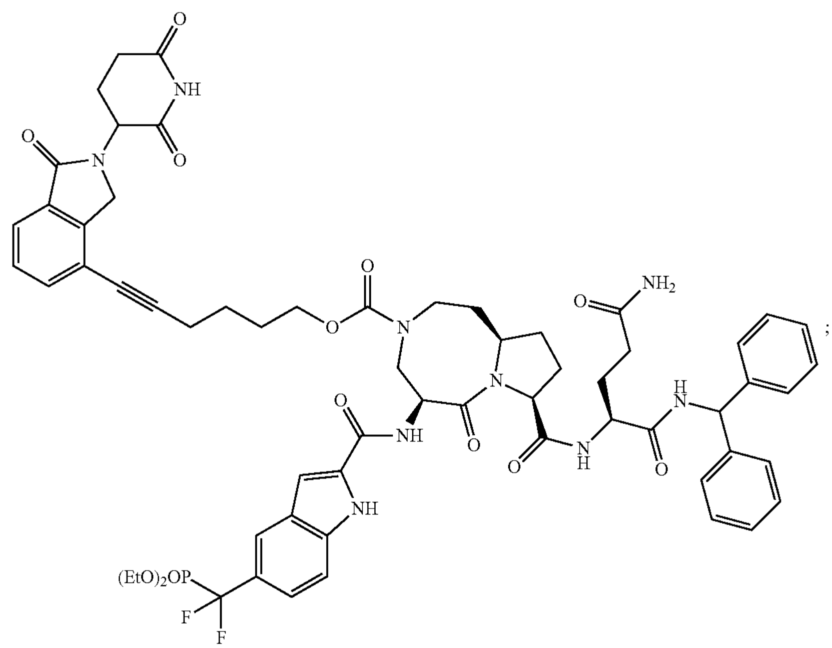
;

-continued
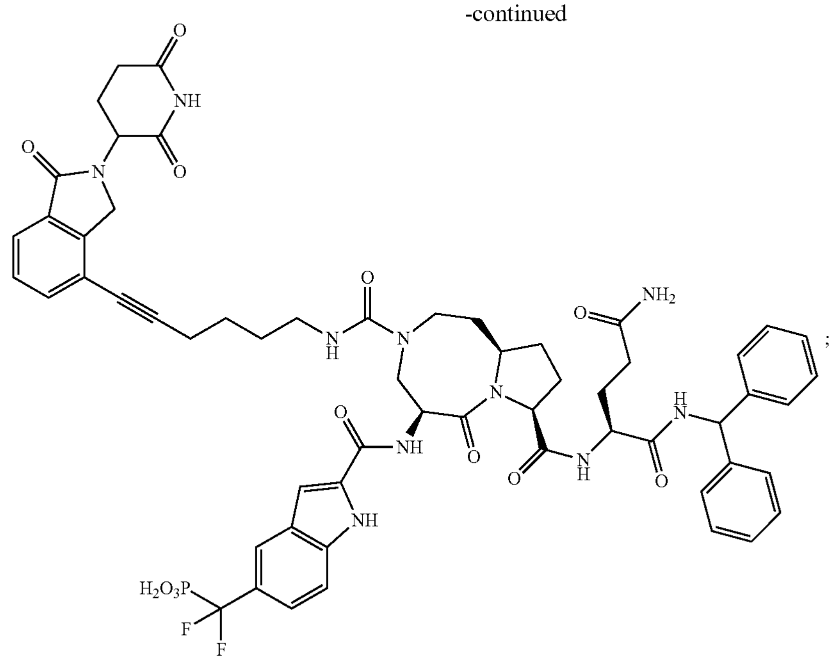
;
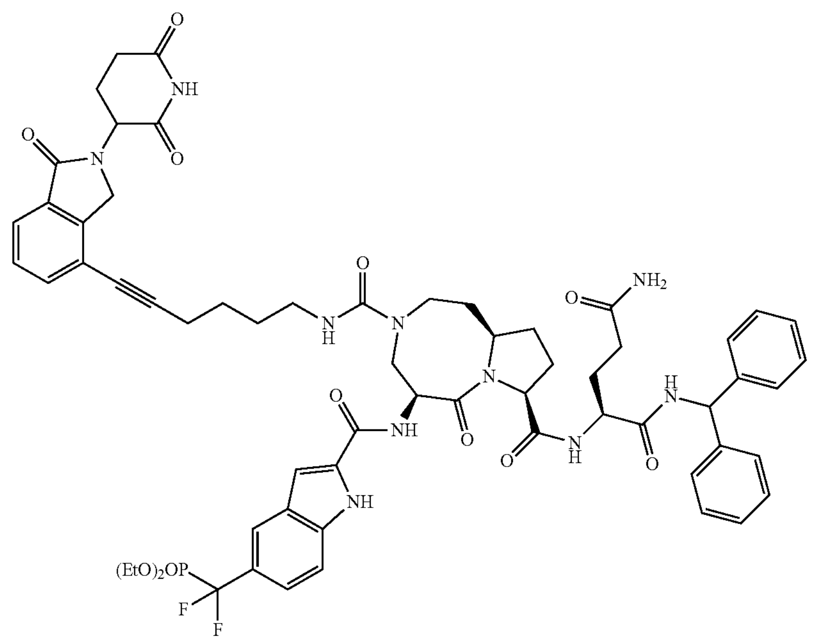
;

-continued
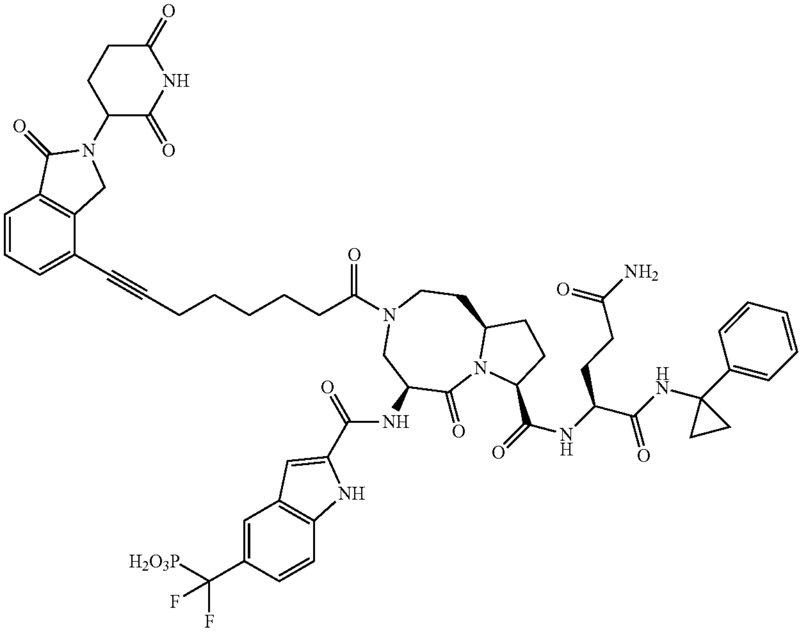
;
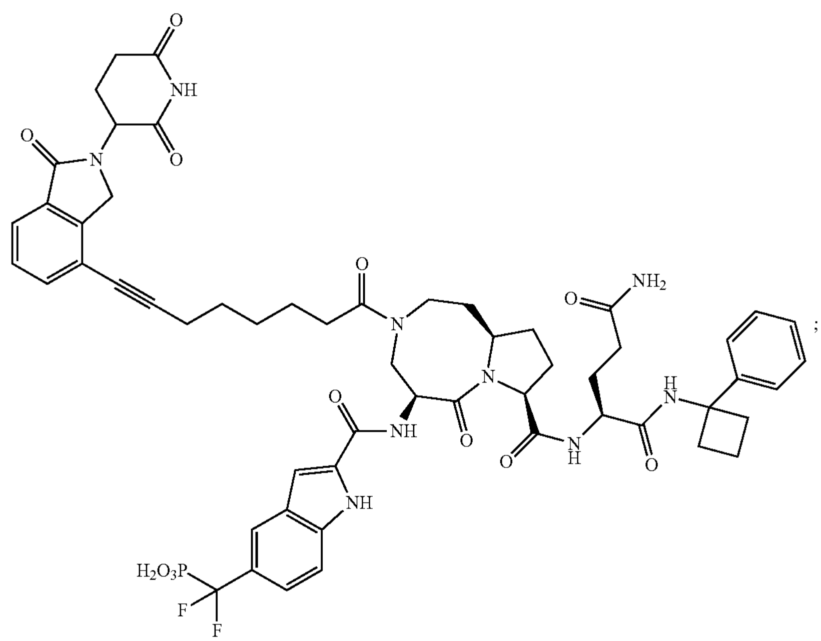
;

-continued
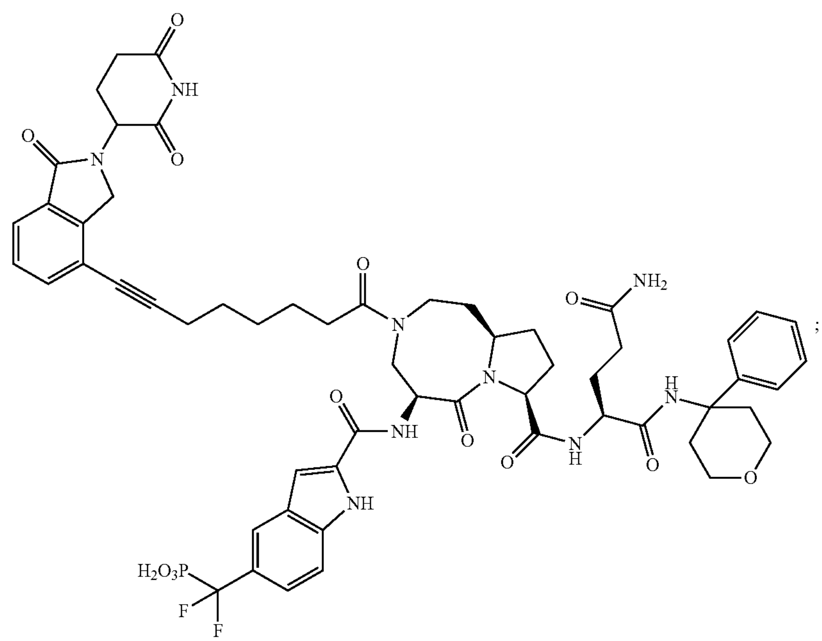
;
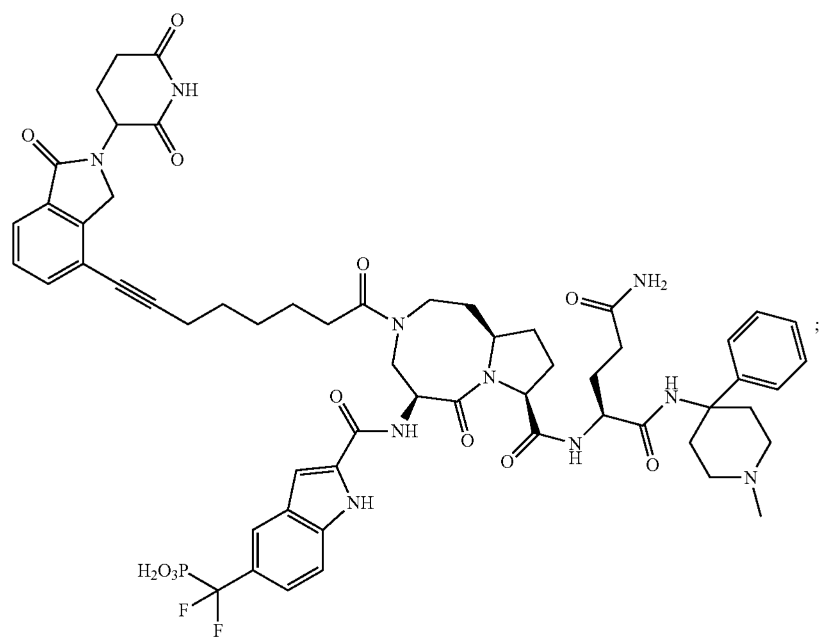
;

-continued
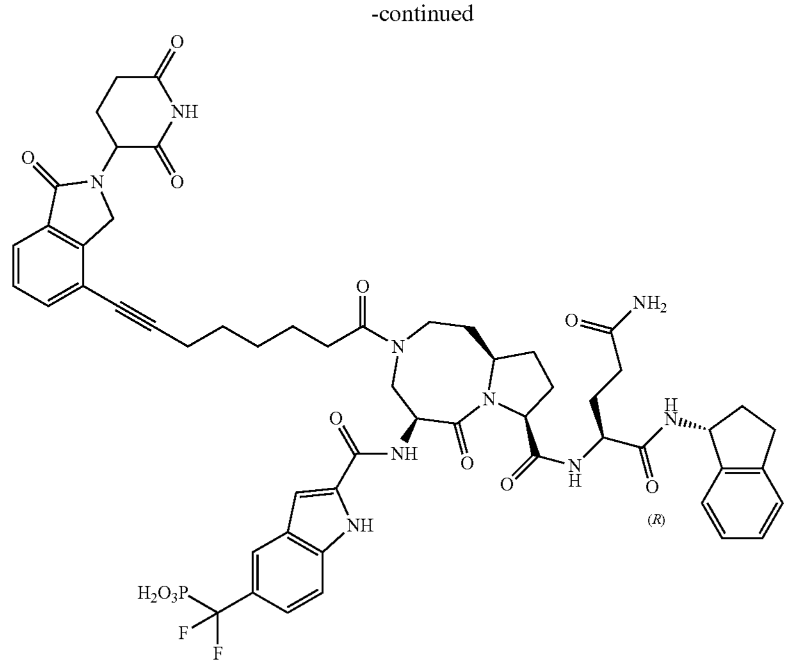
;
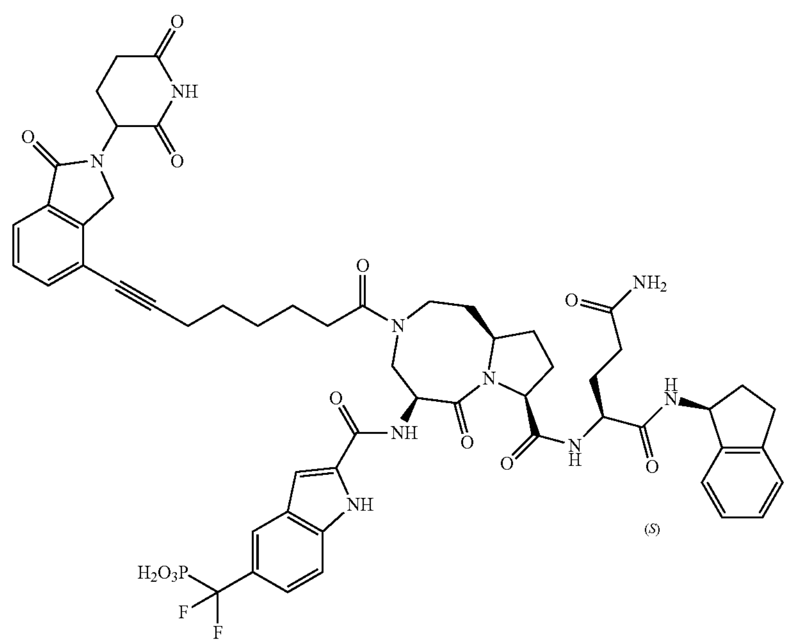
;

-continued
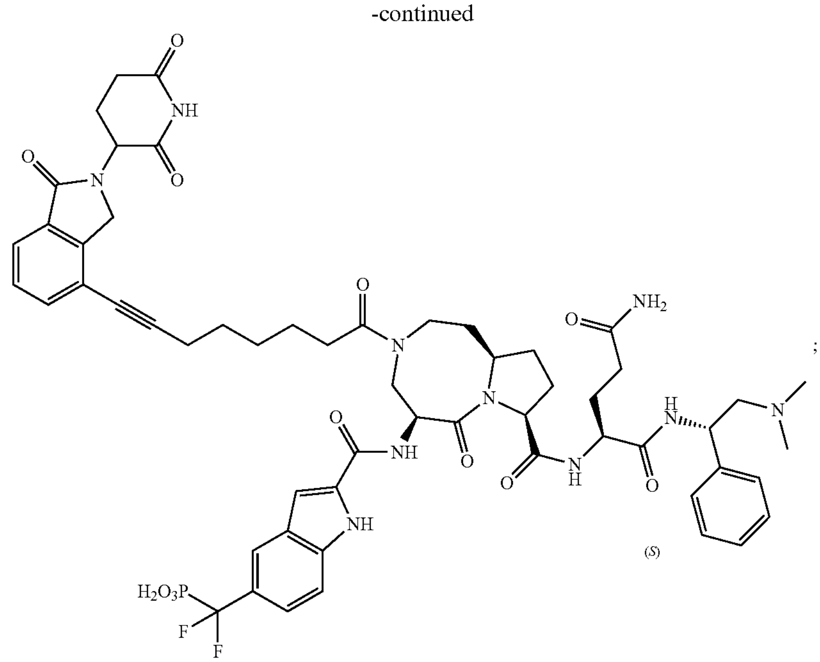
;
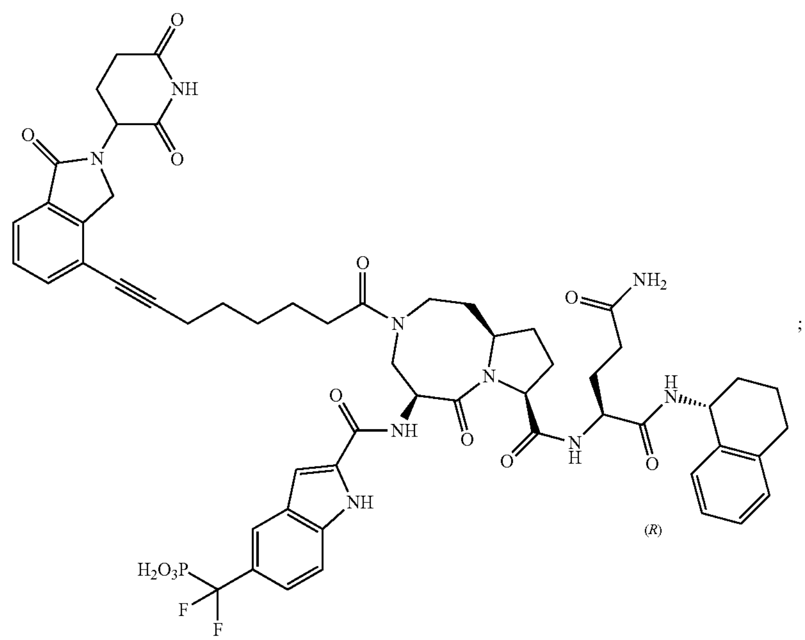
;

-continued
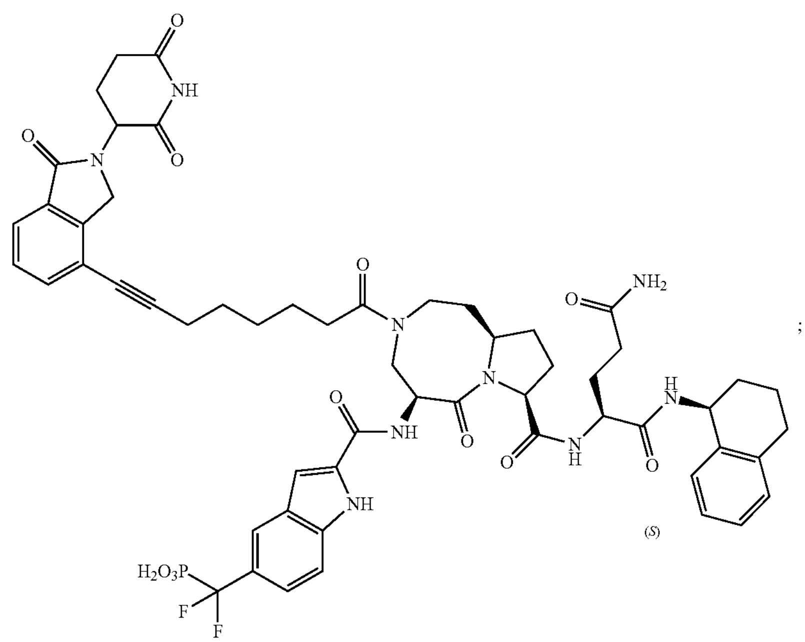
;
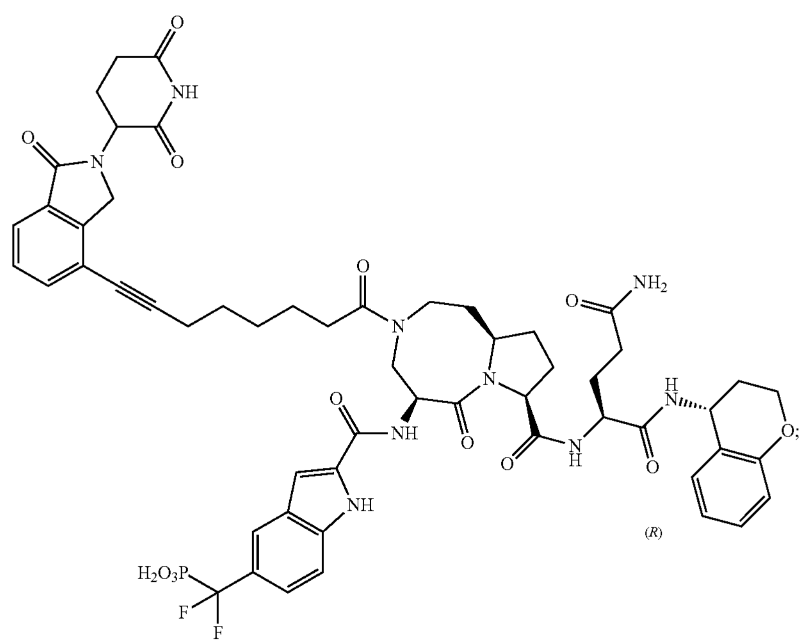

-continued
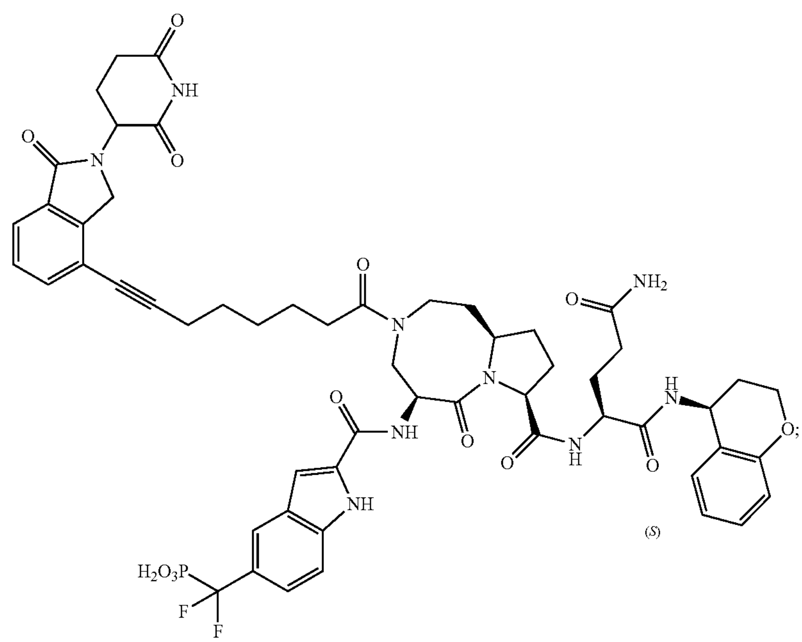
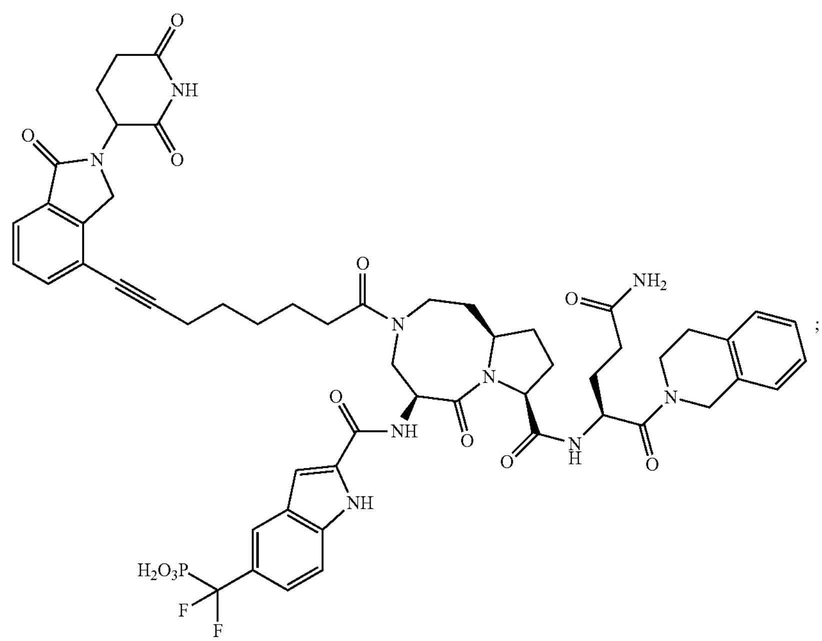
;

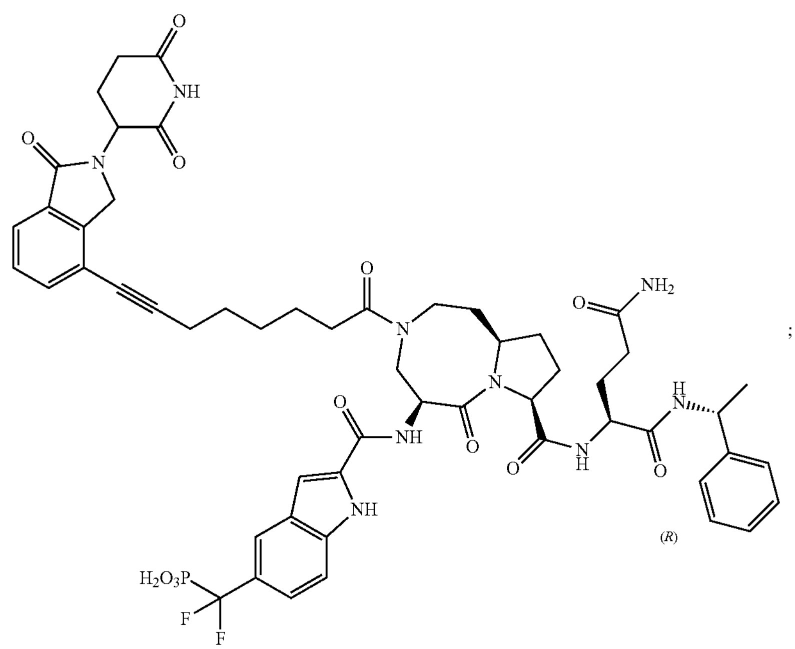
;
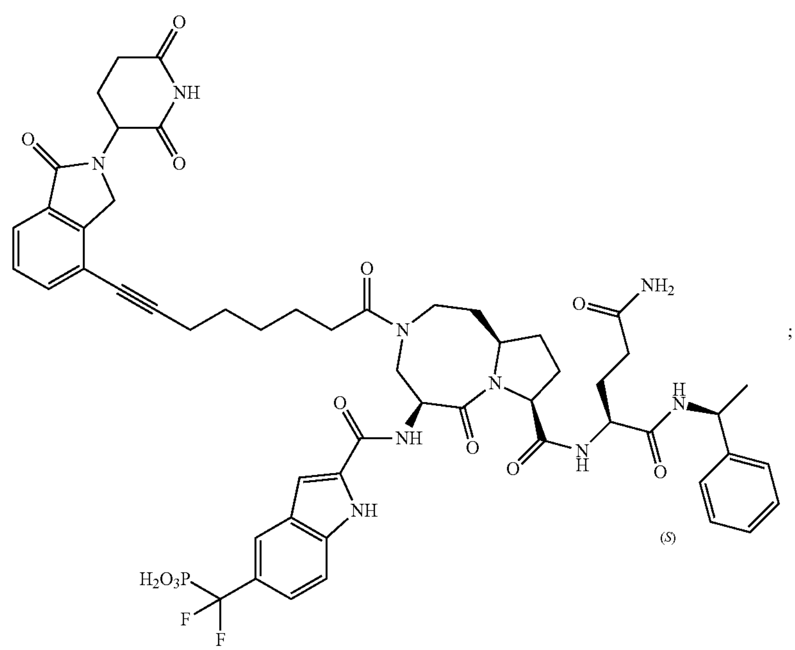
;

-continued
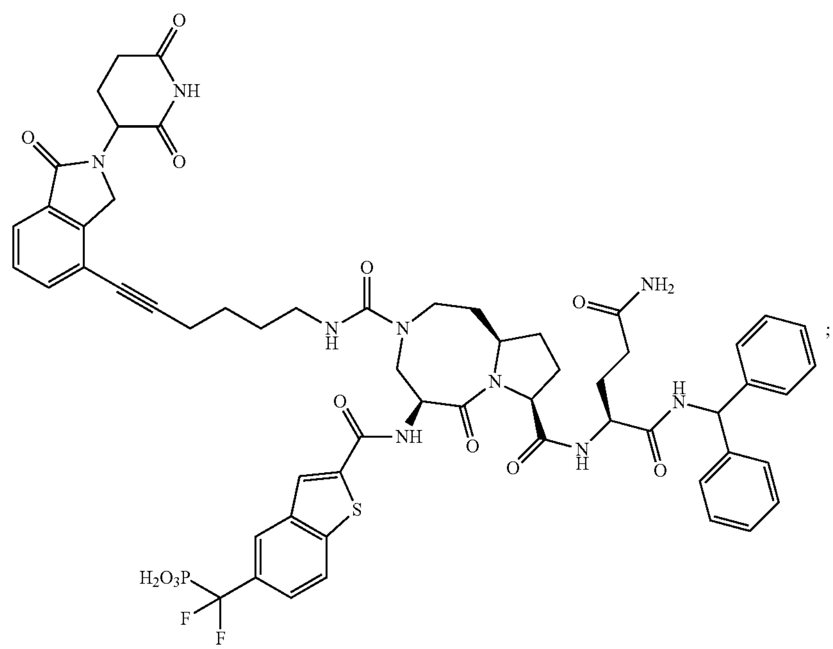
;
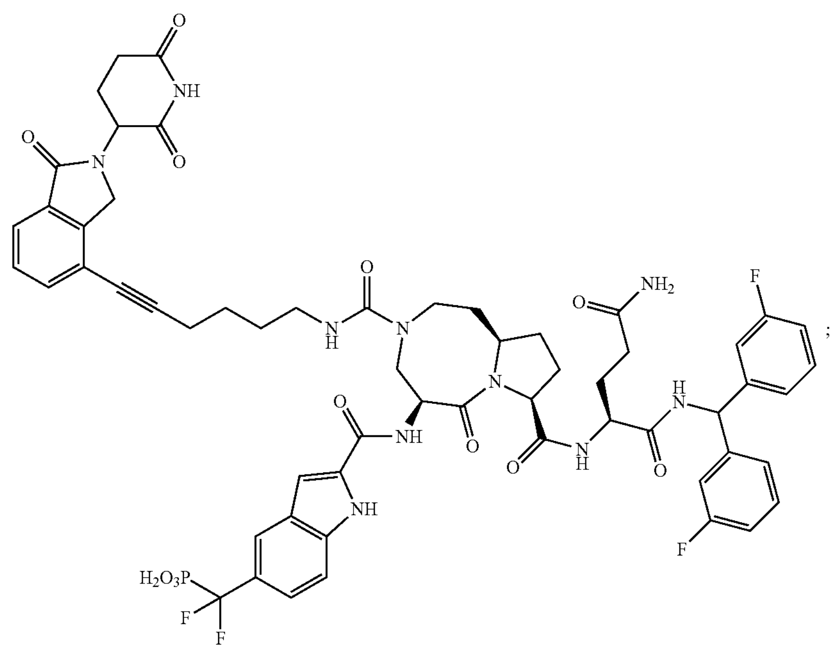
;

-continued
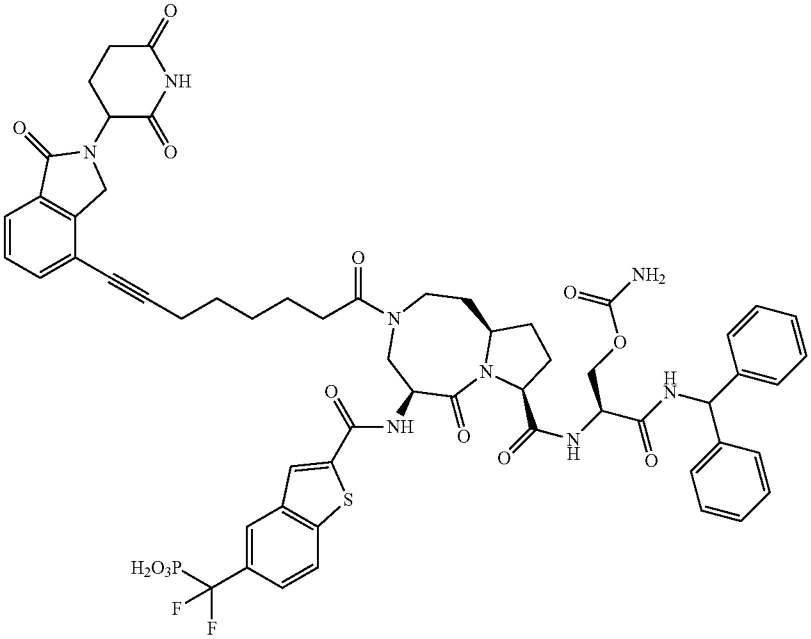
;
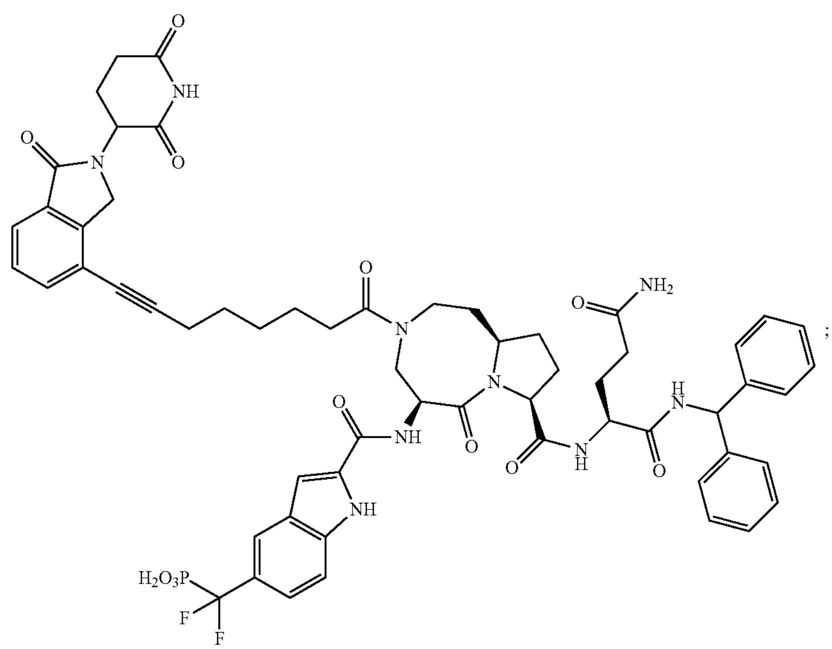
;

-continued
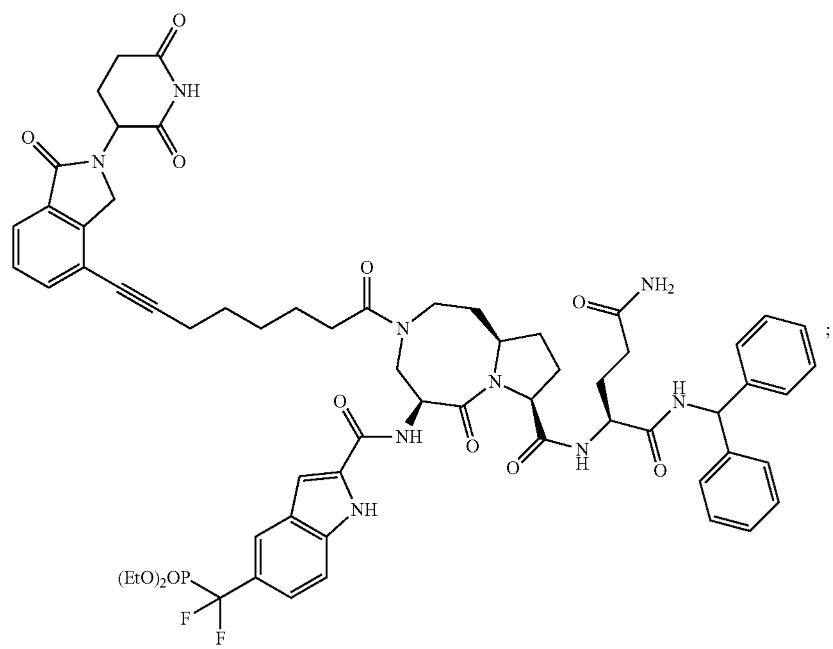
;
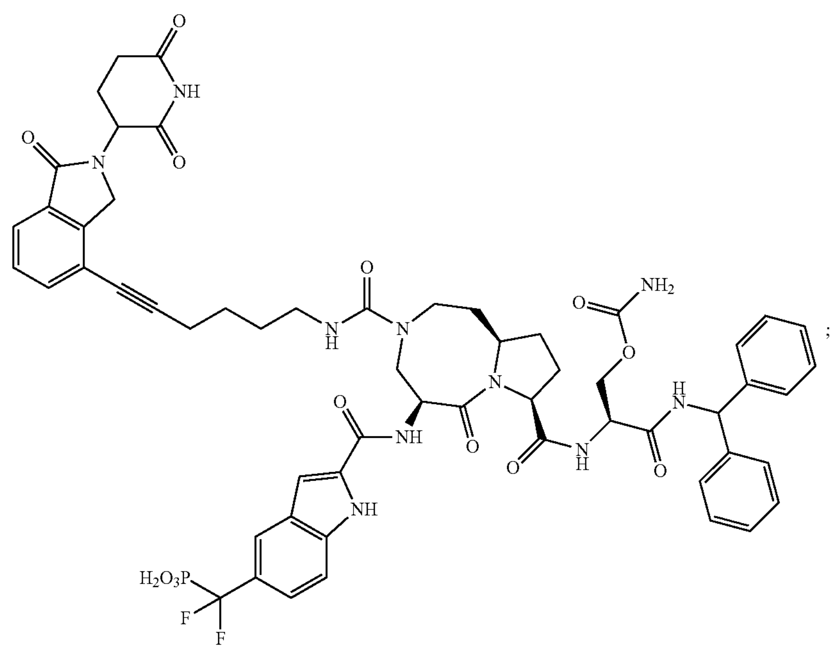
;

-continued
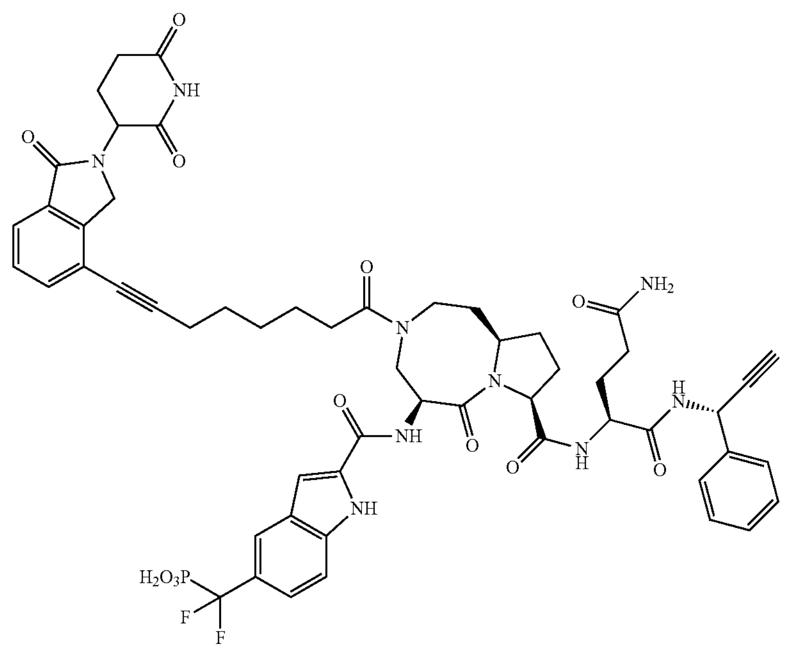
;
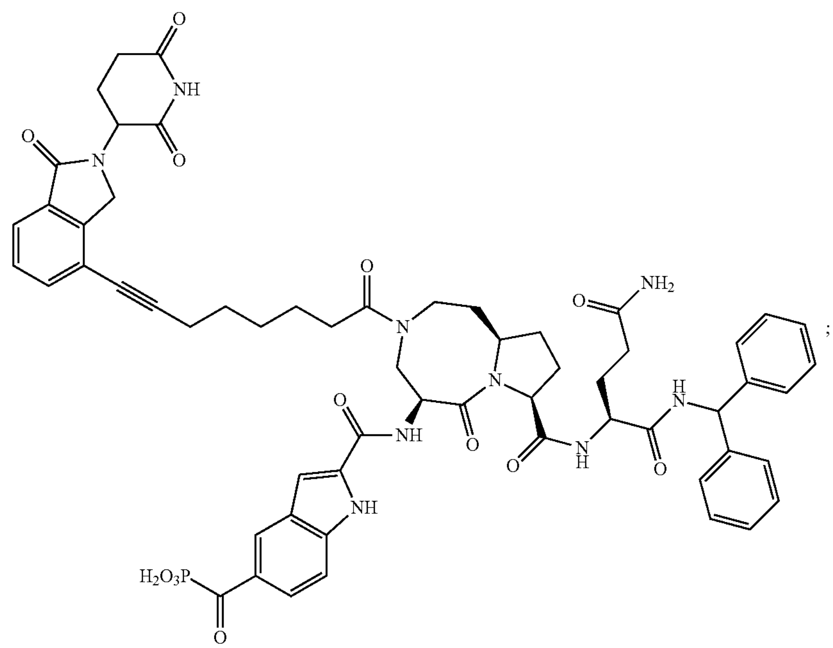
;

-continued
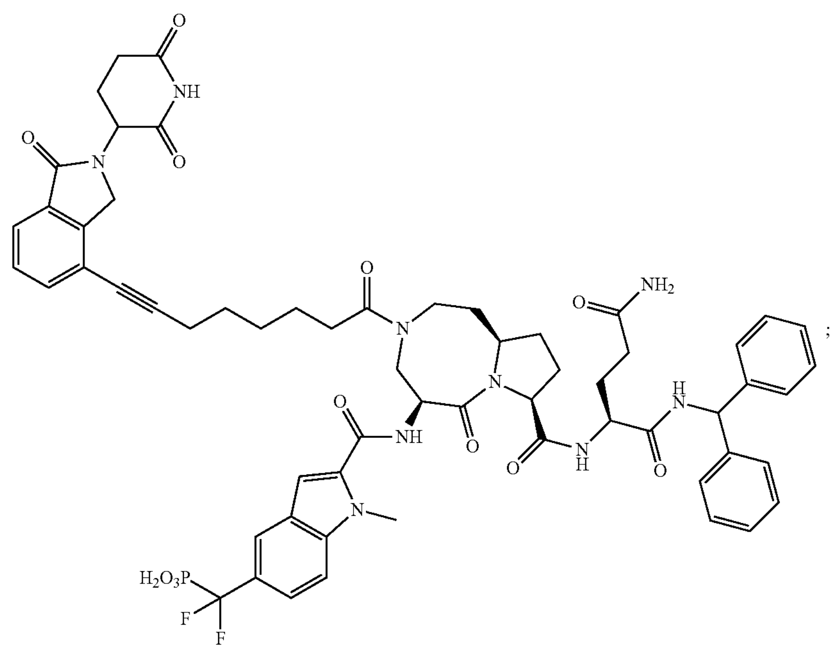
;
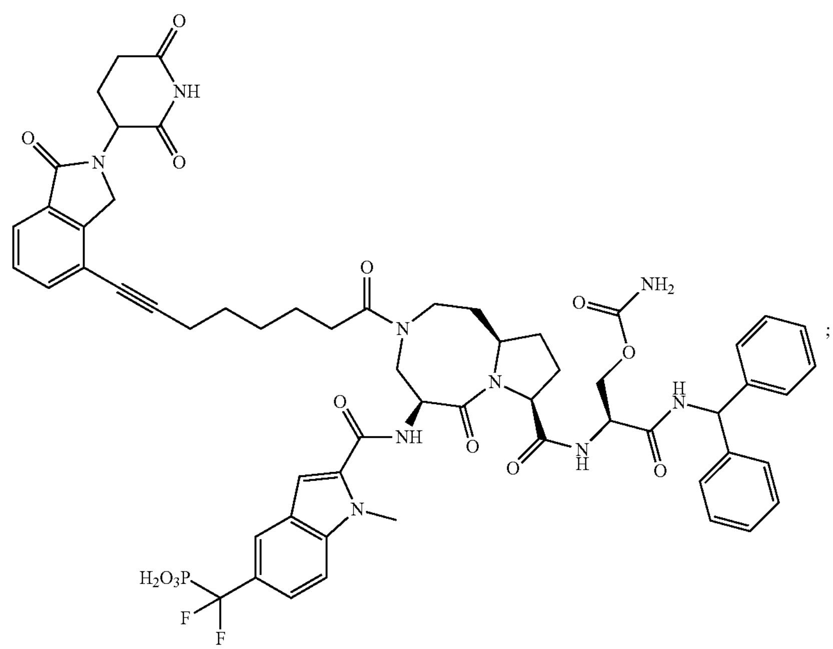
;

-continued
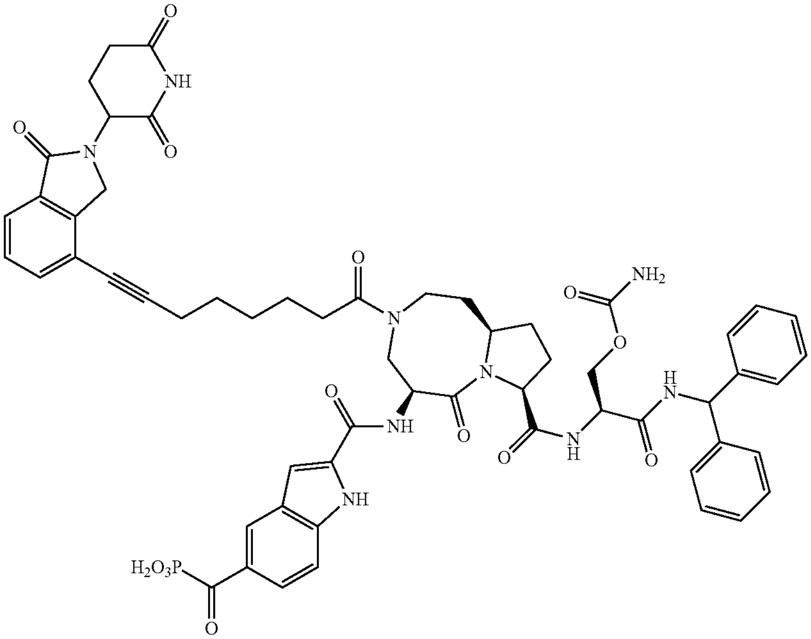
;
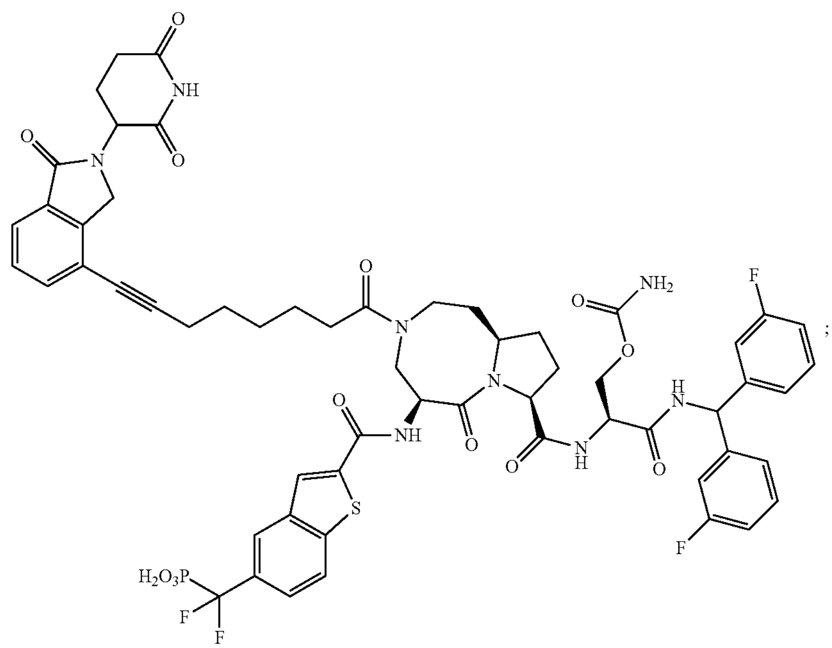
;

-continued
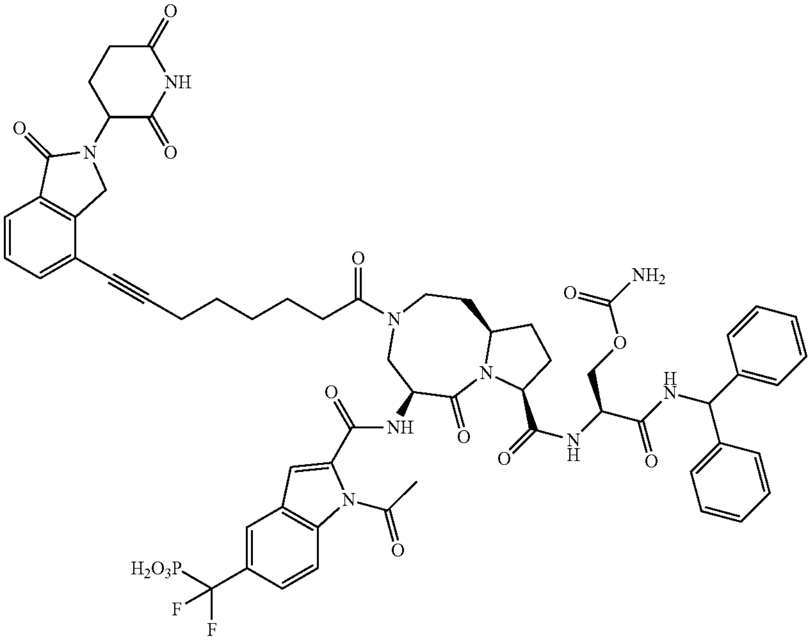
;
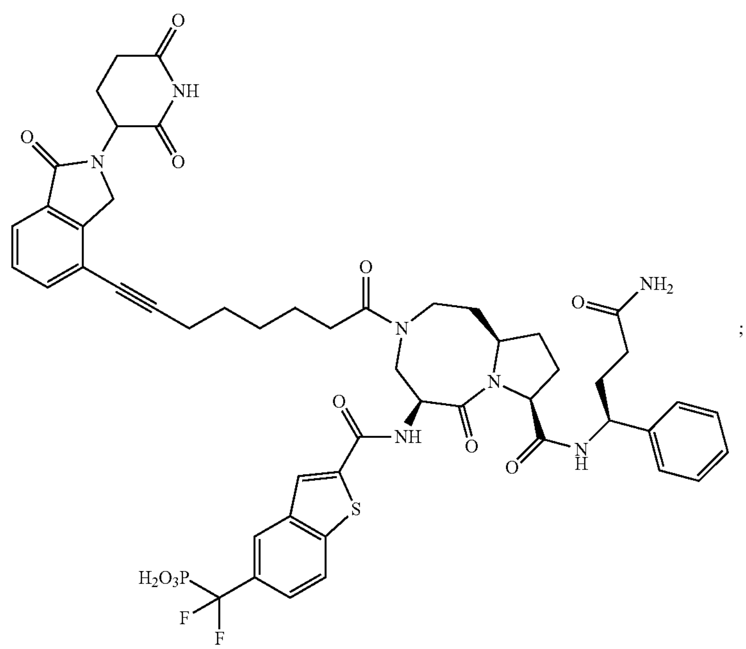
;

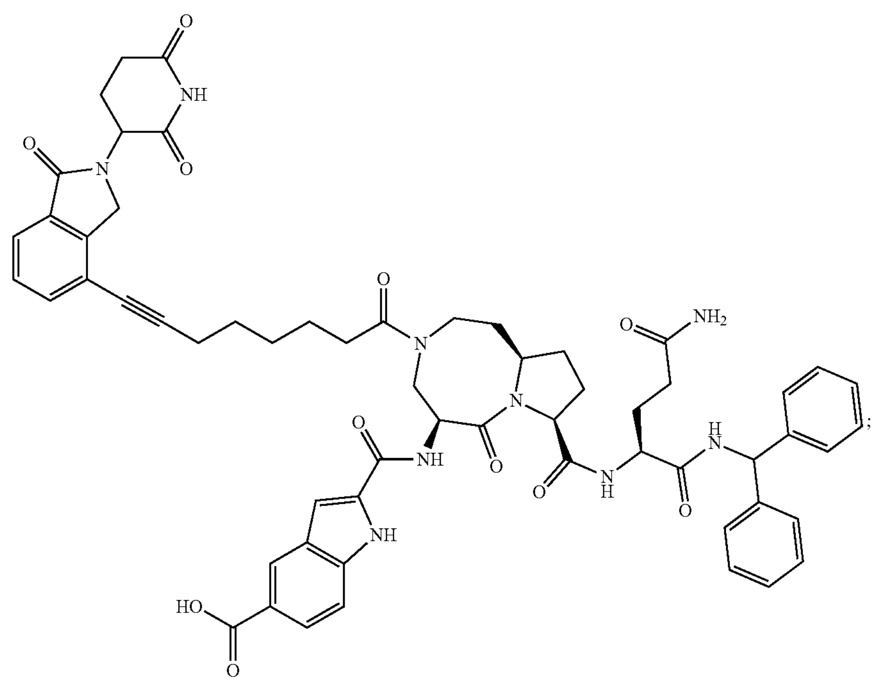
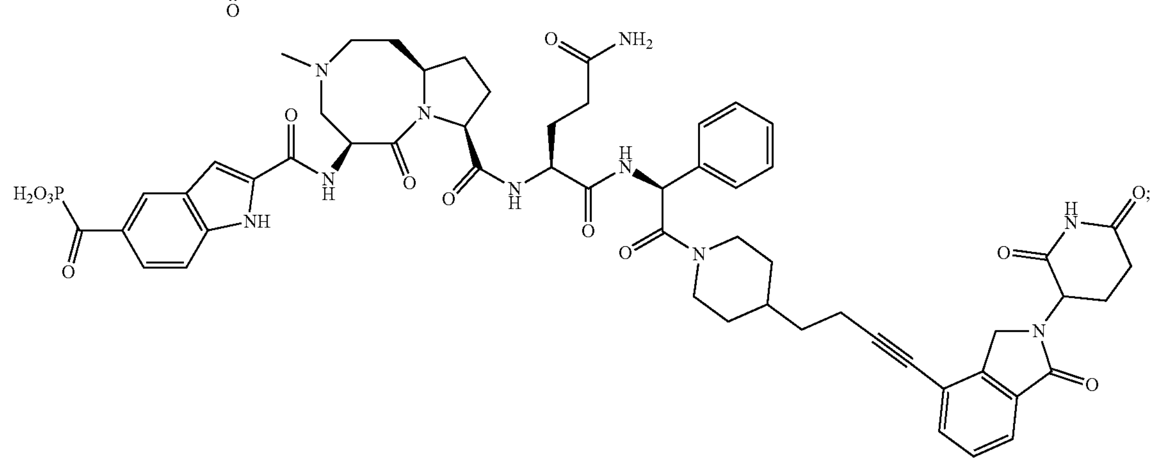
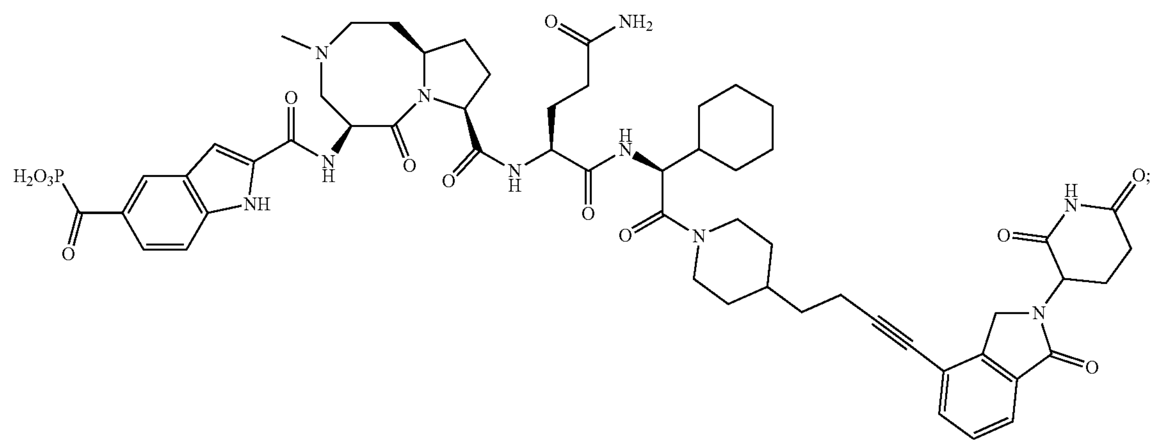

-continued
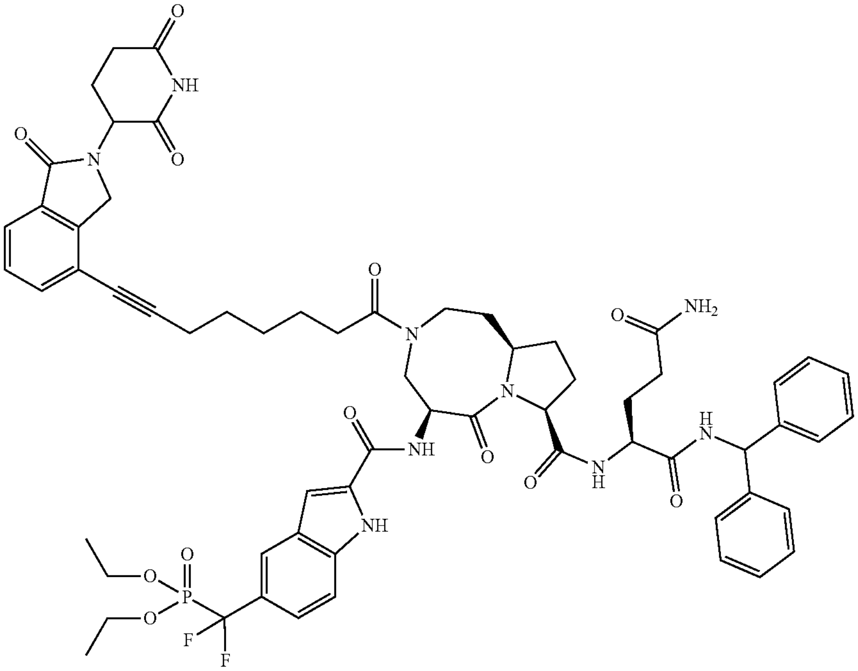
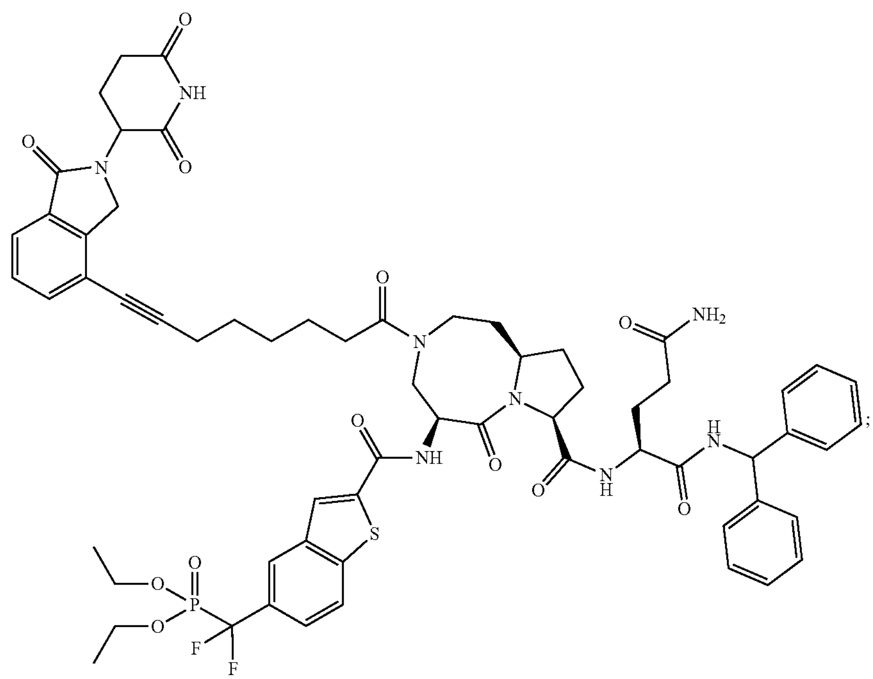

-continued
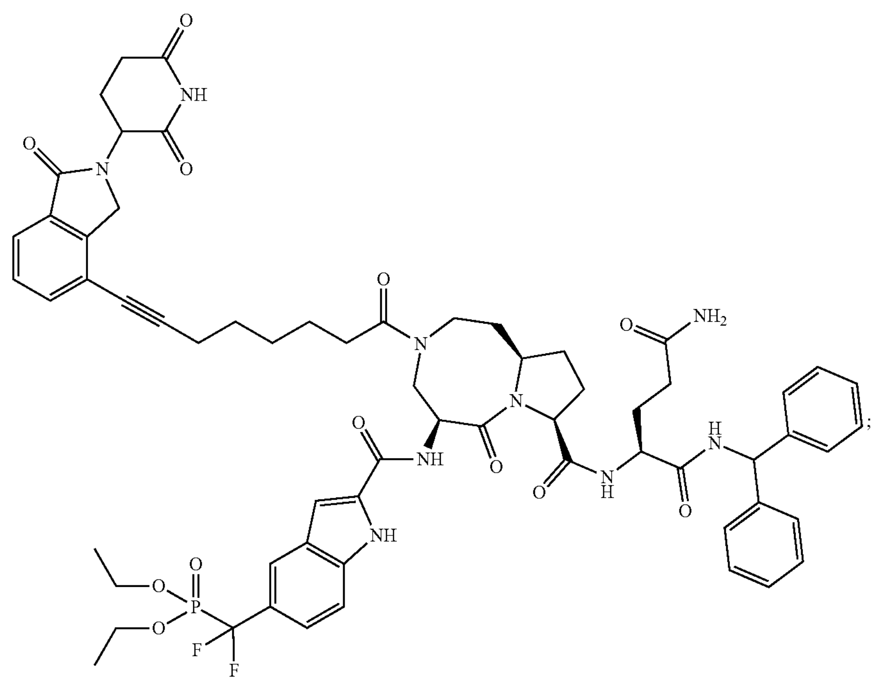
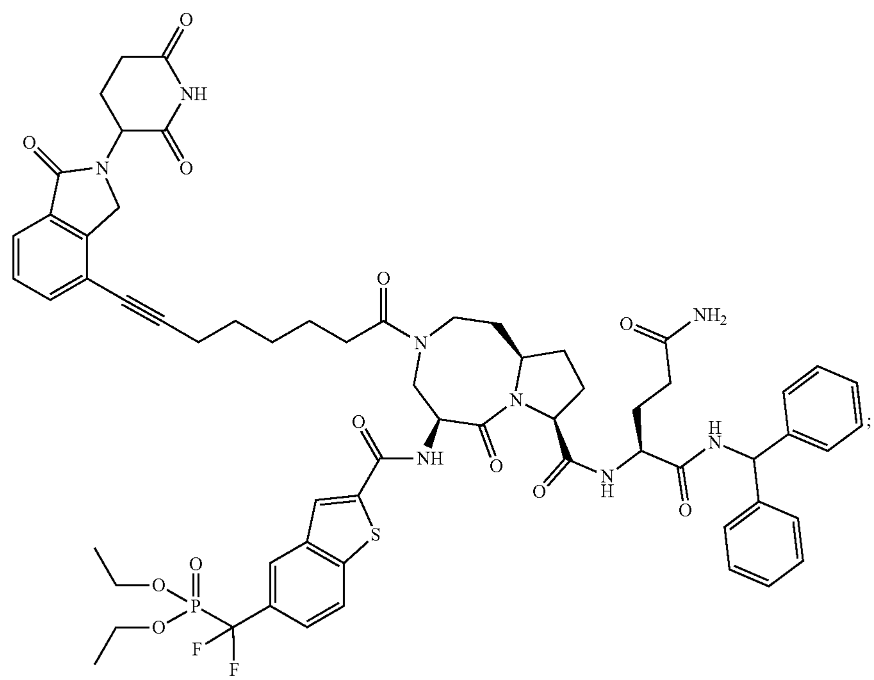

-continued
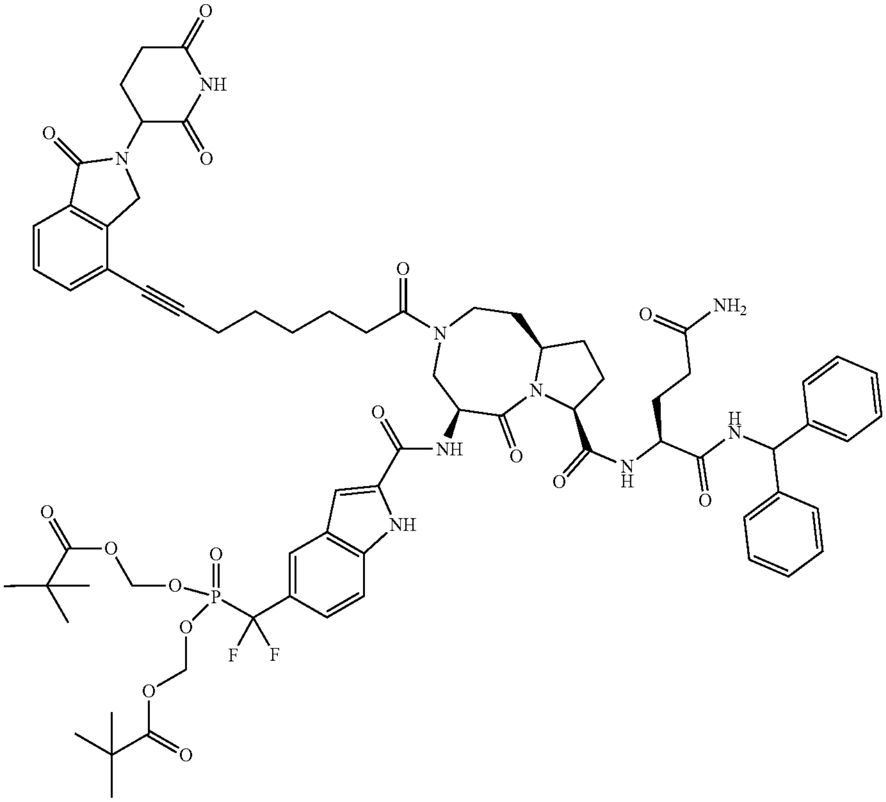
;
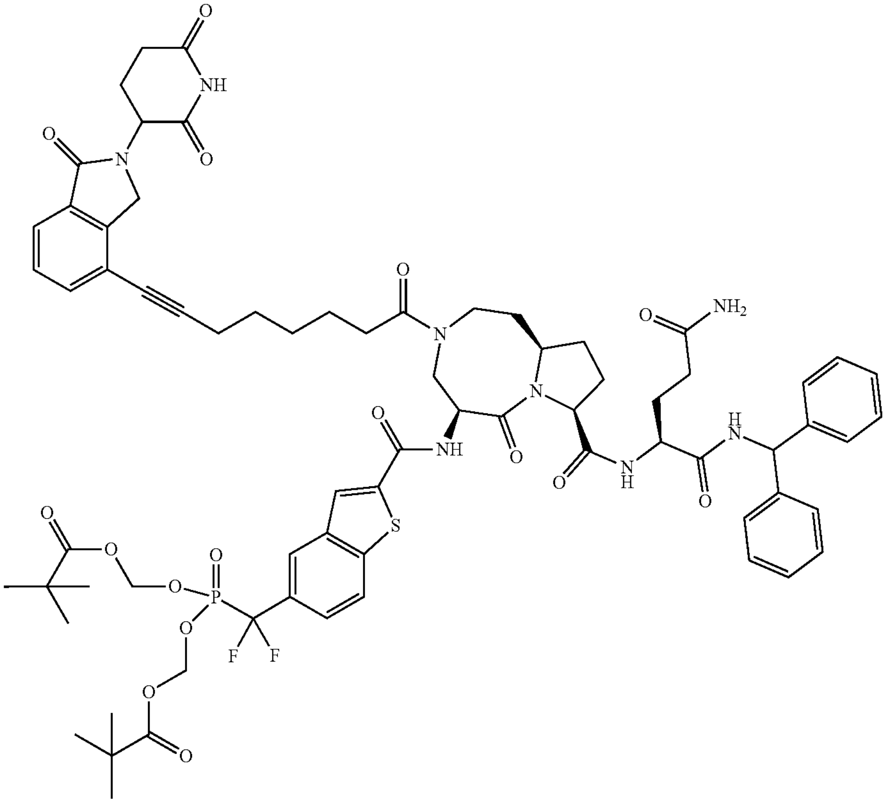
;

-continued
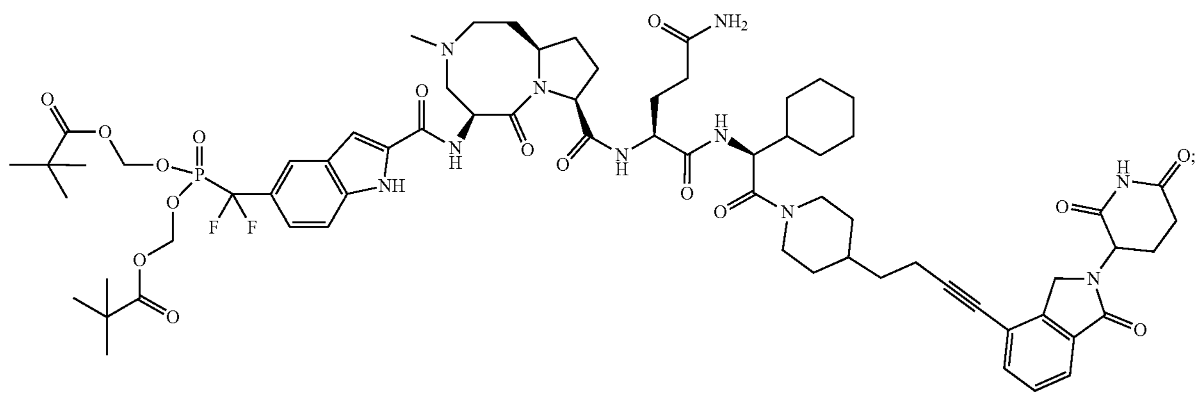
;
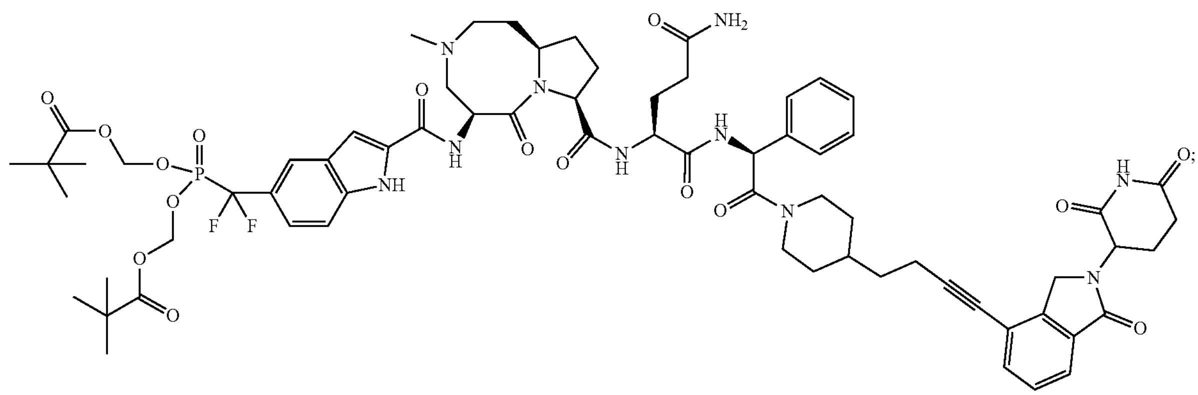
;
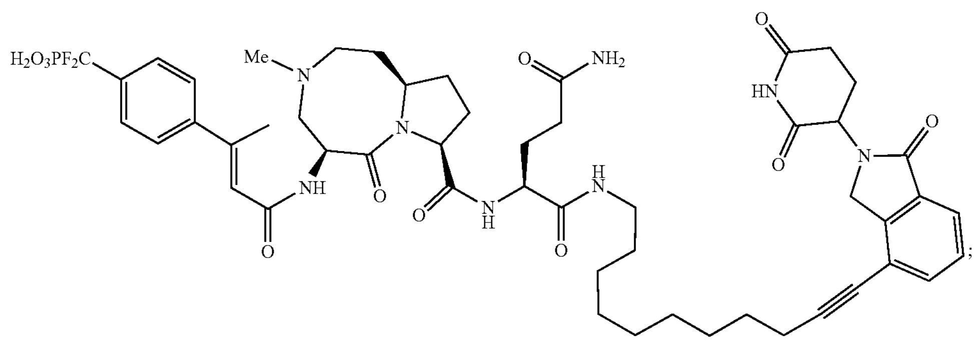
;
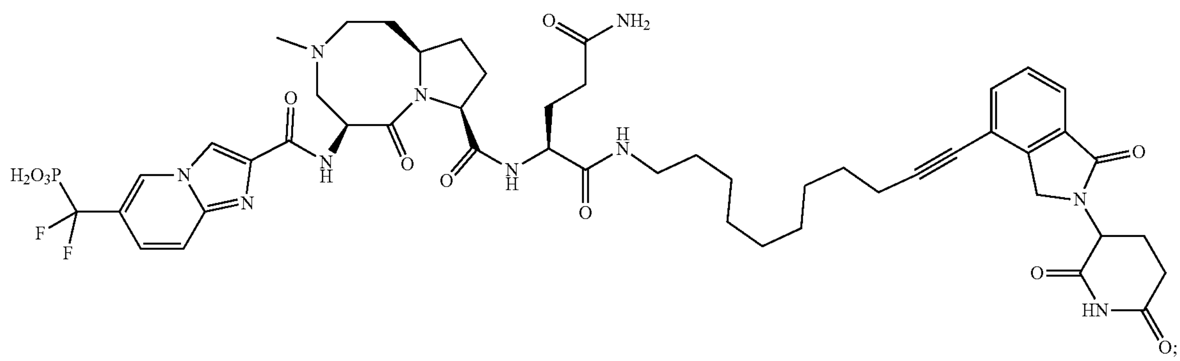
;

-continued
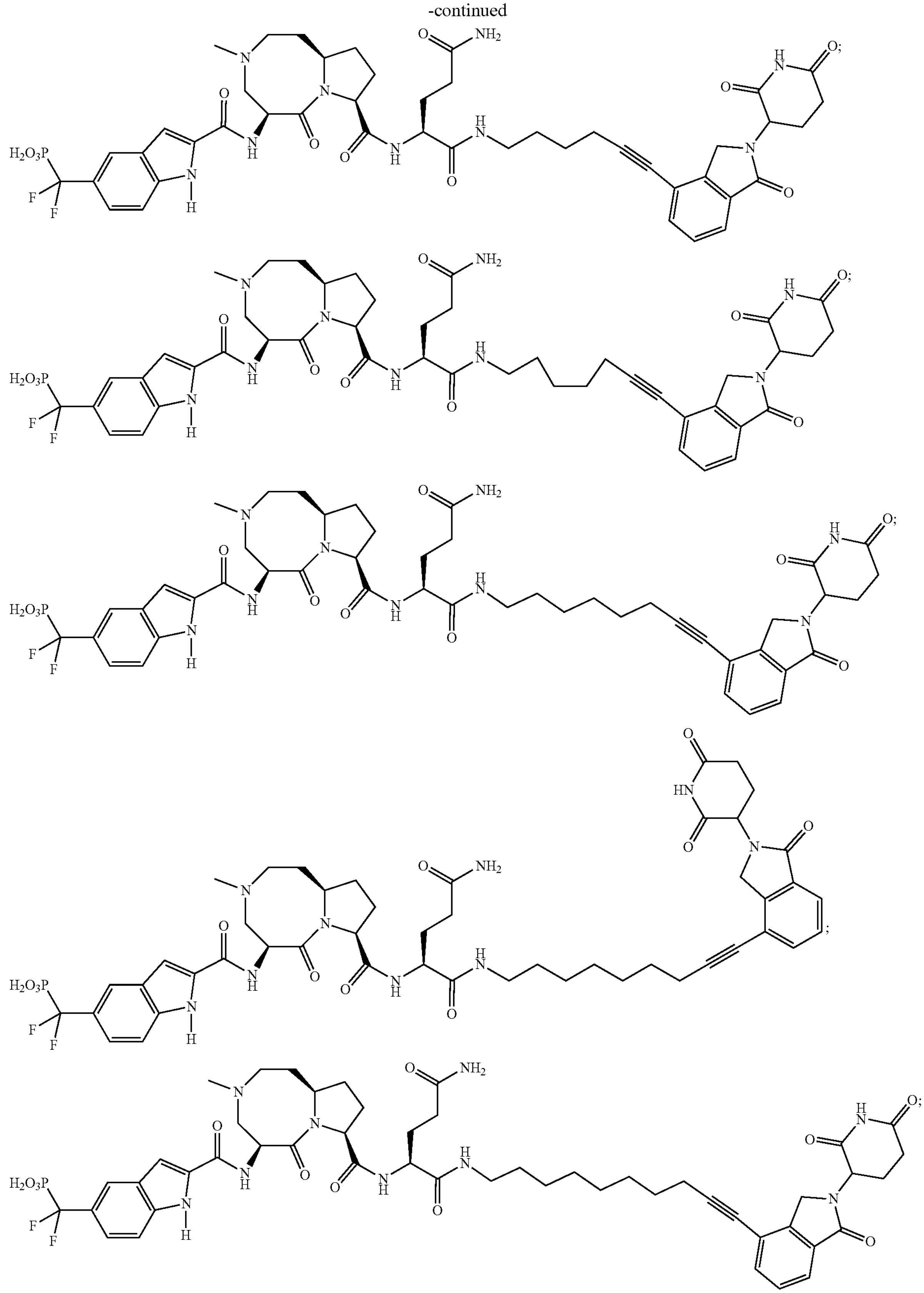

-continued
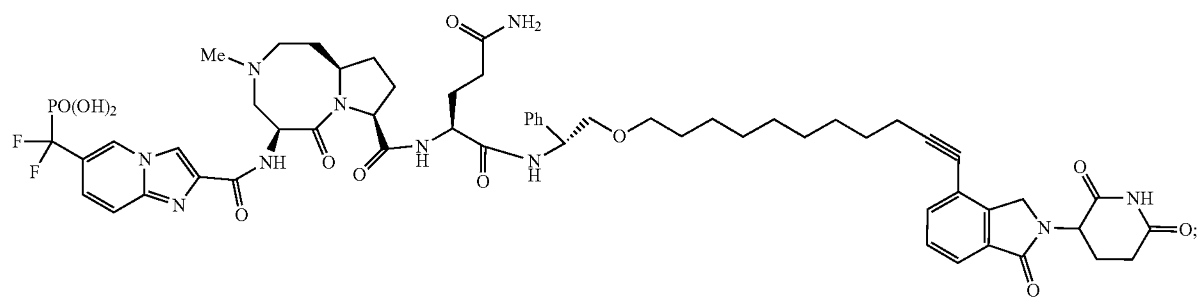
;
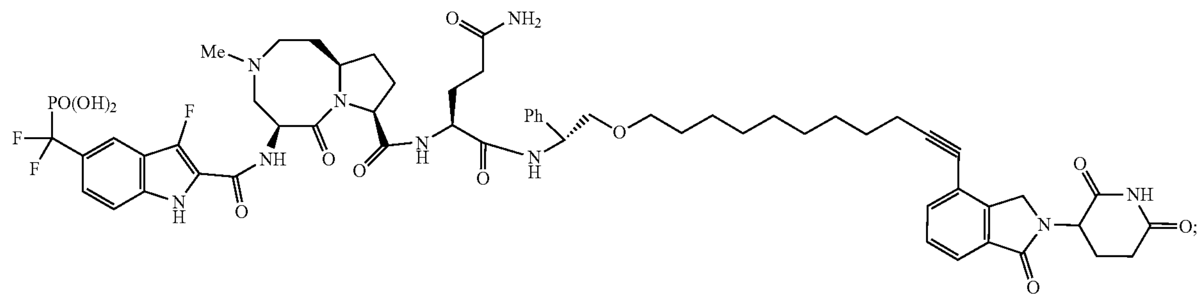
;
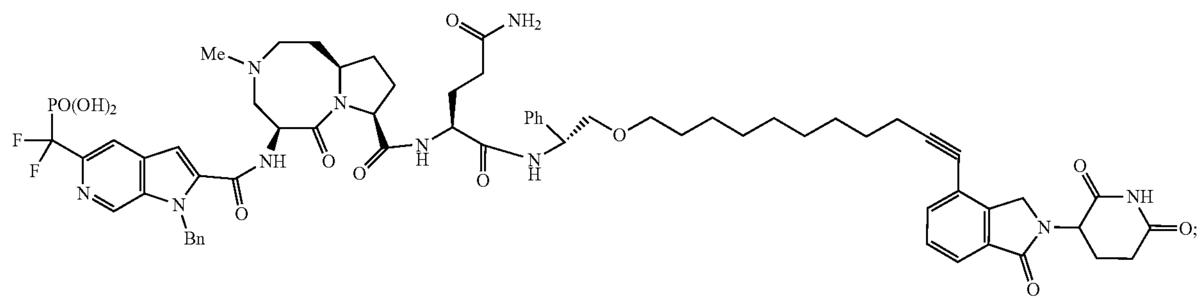
;
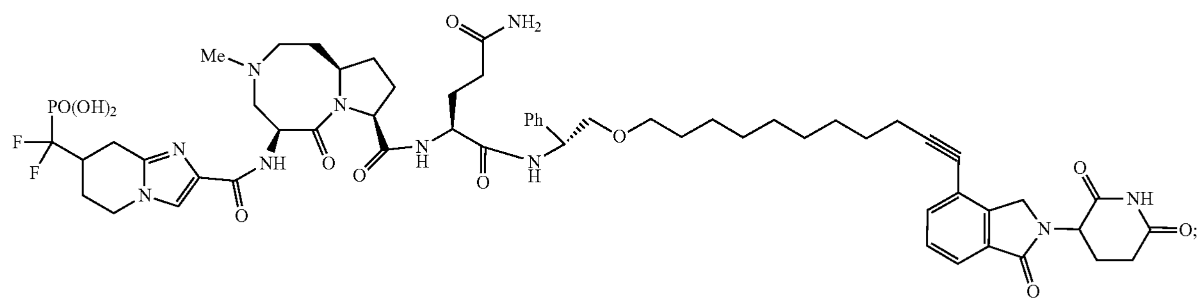
;
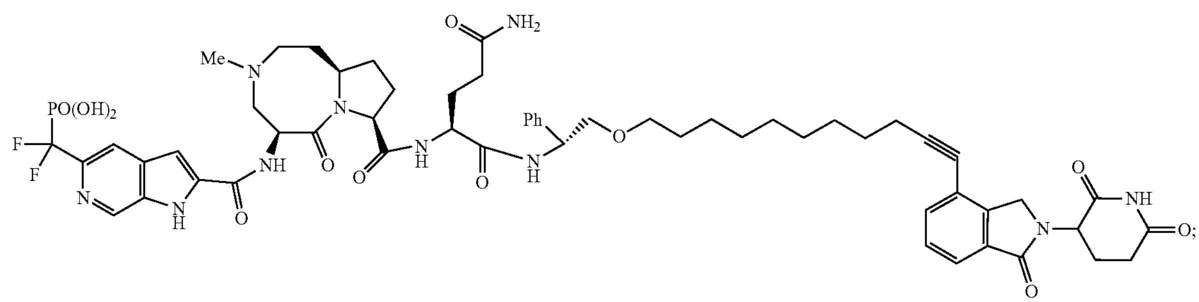
;

-continued
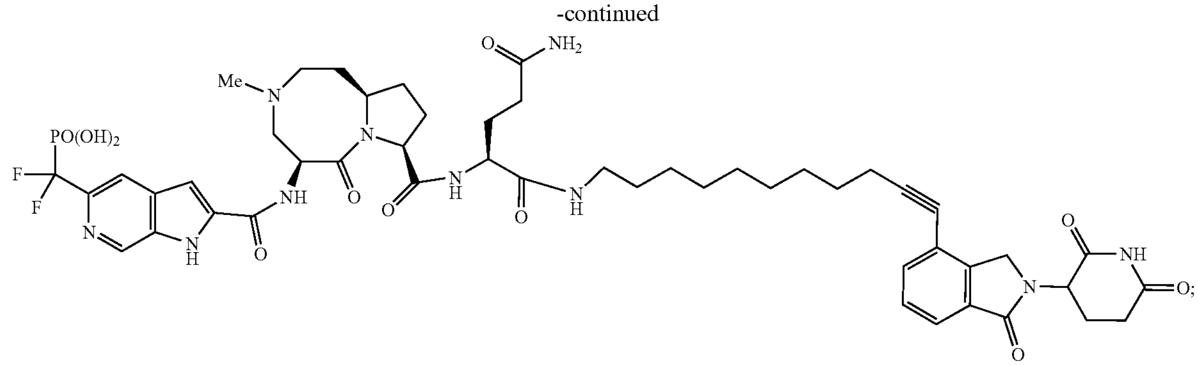
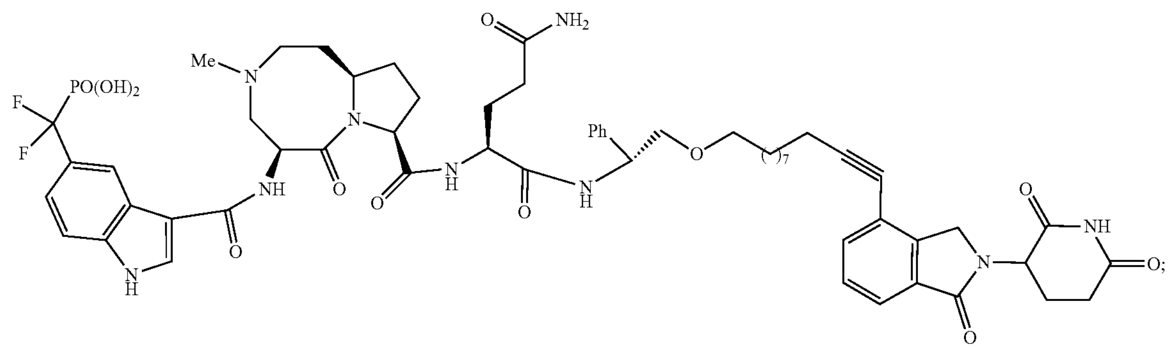
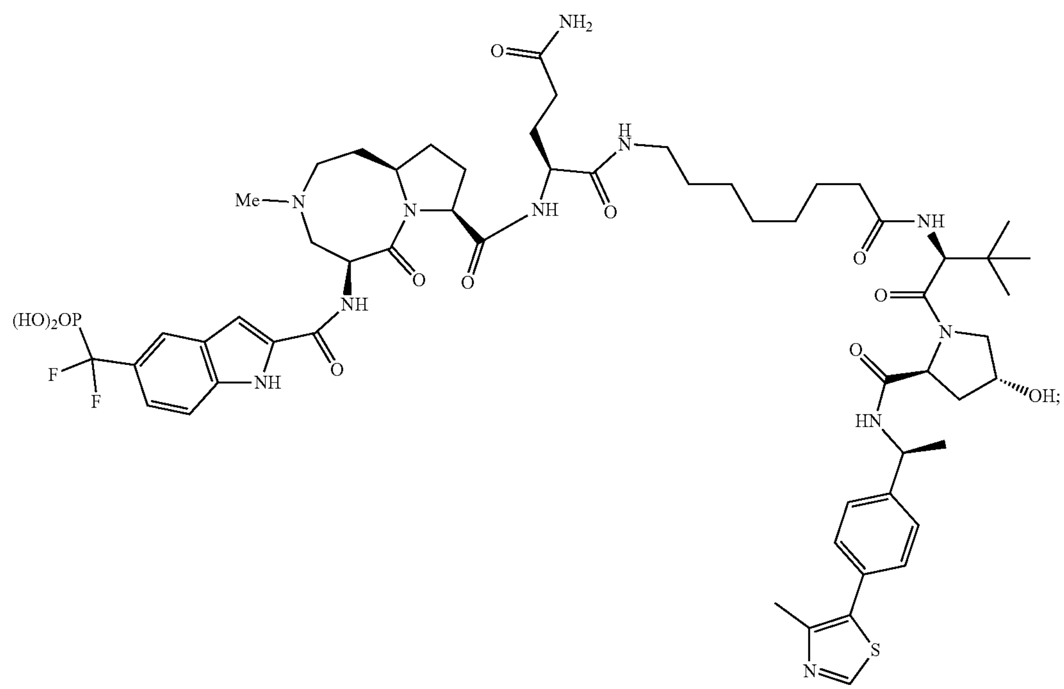

-continued
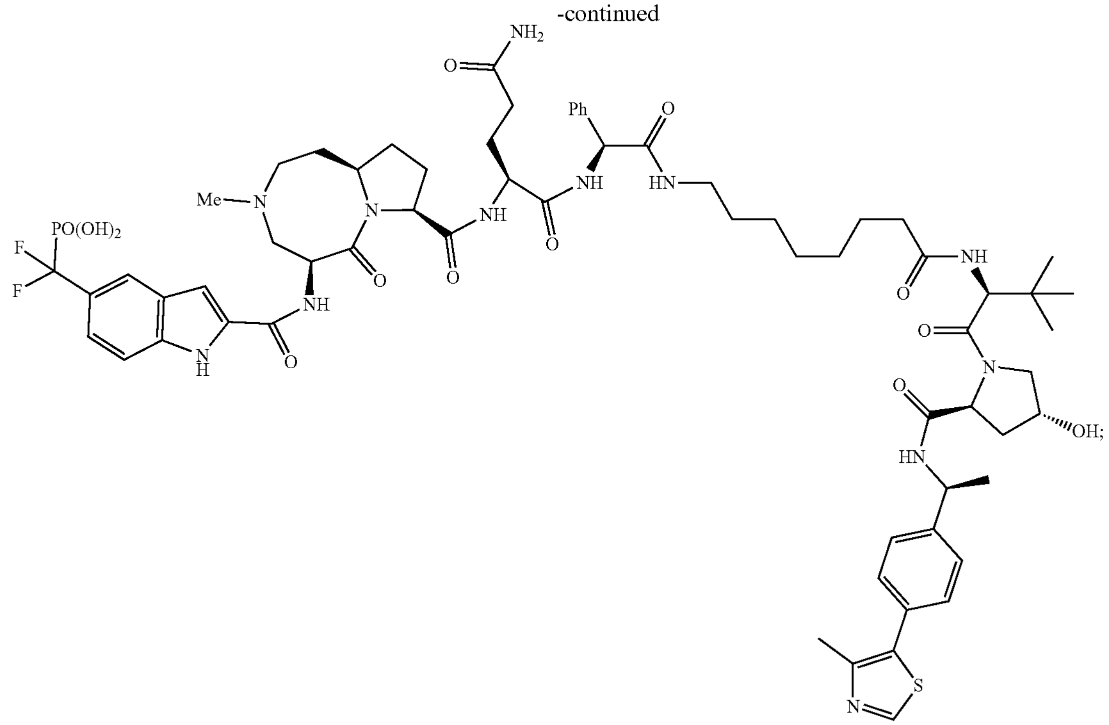
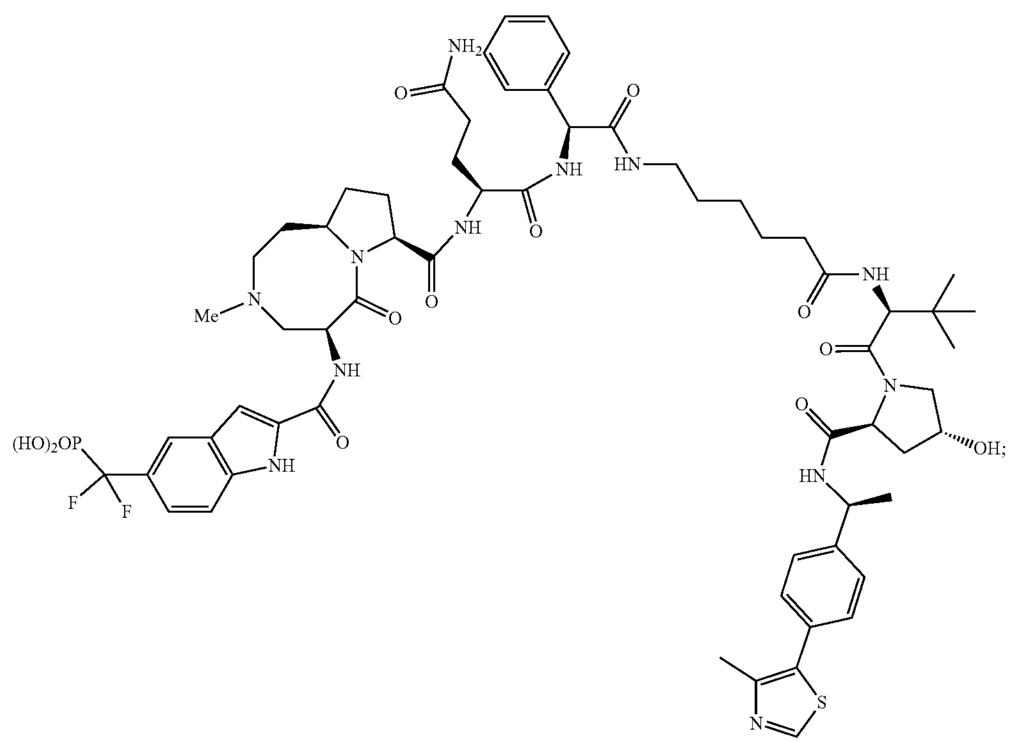

-continued
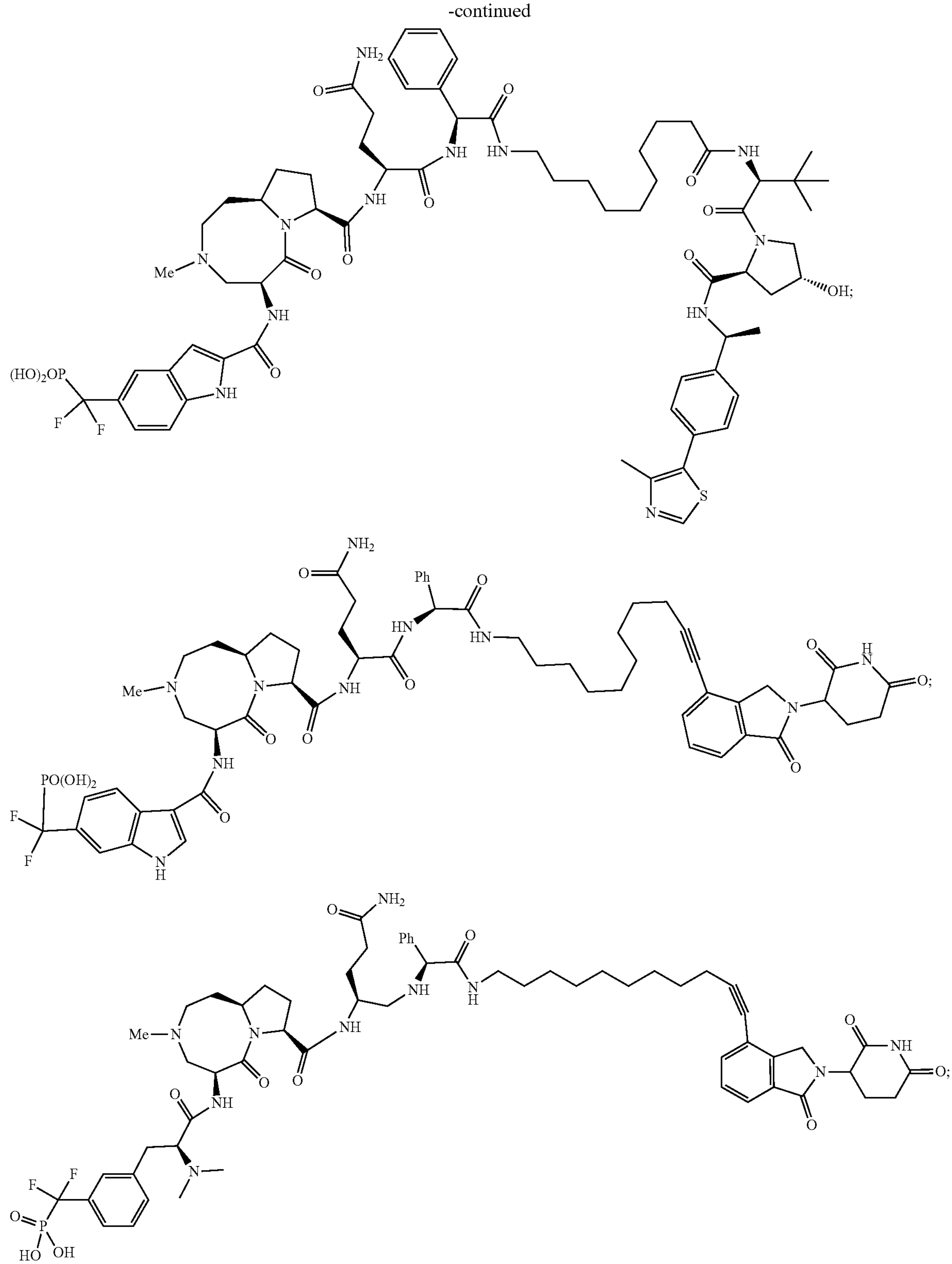

-continued
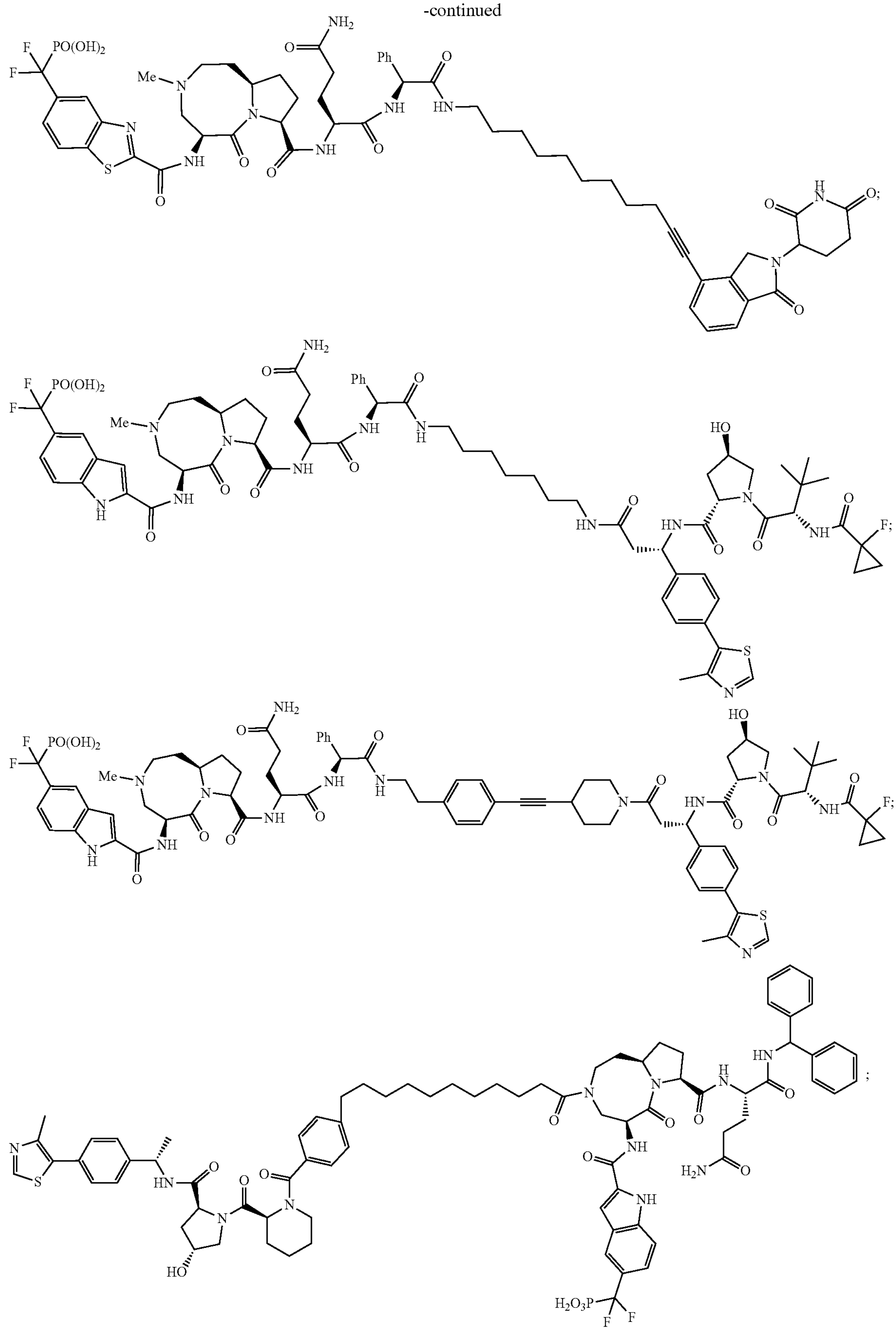

-continued
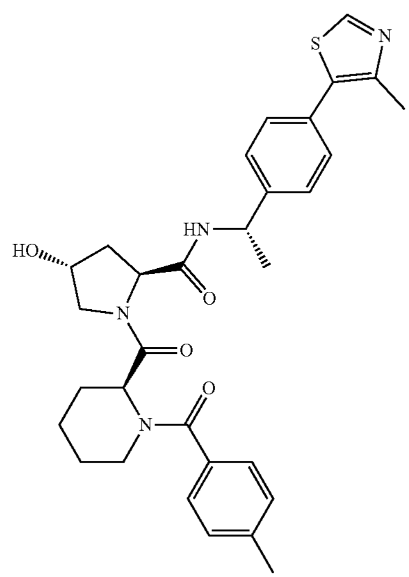
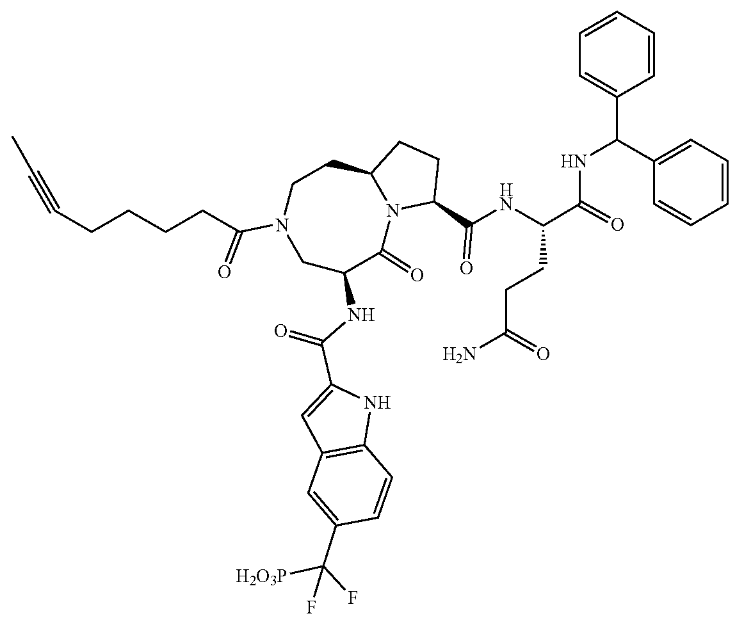
;
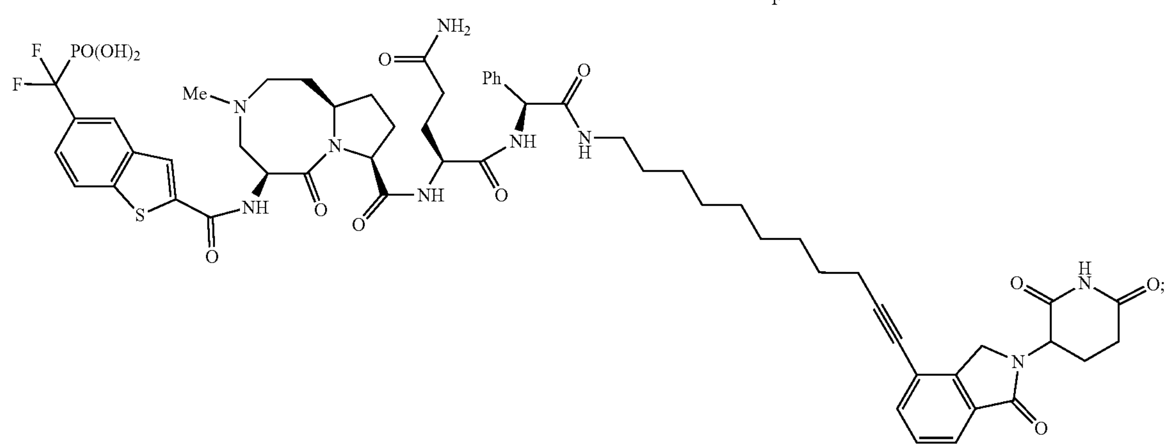
;

-continued
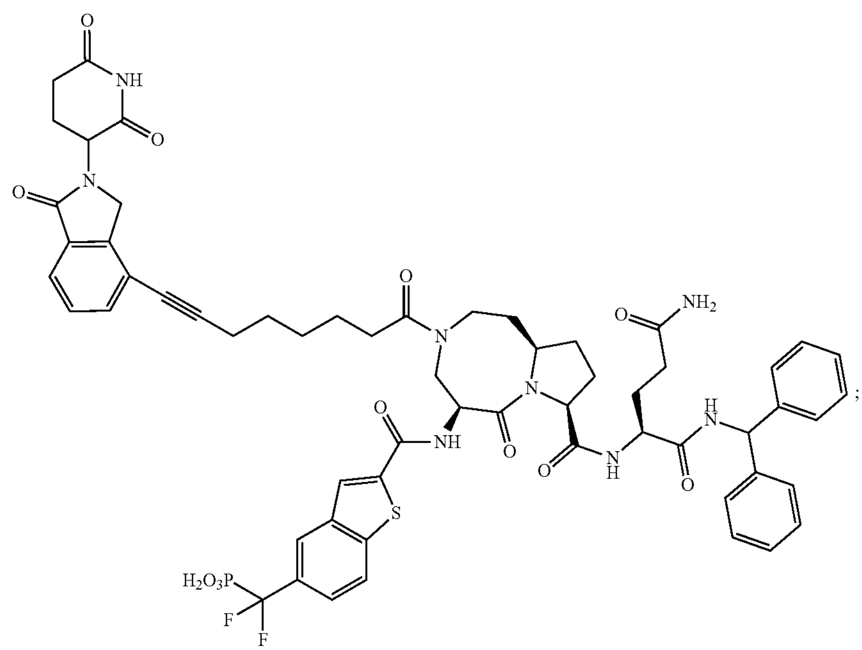
;
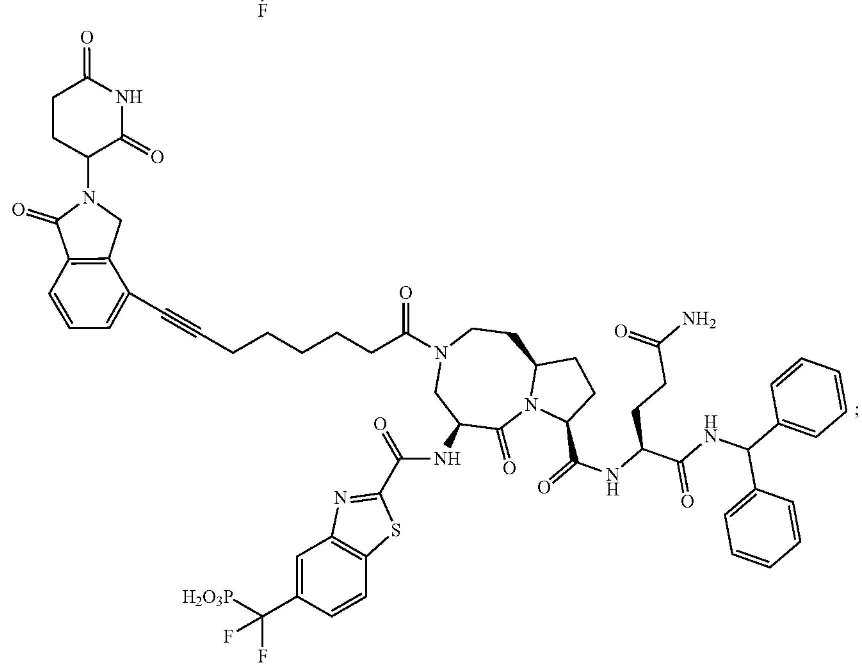
;
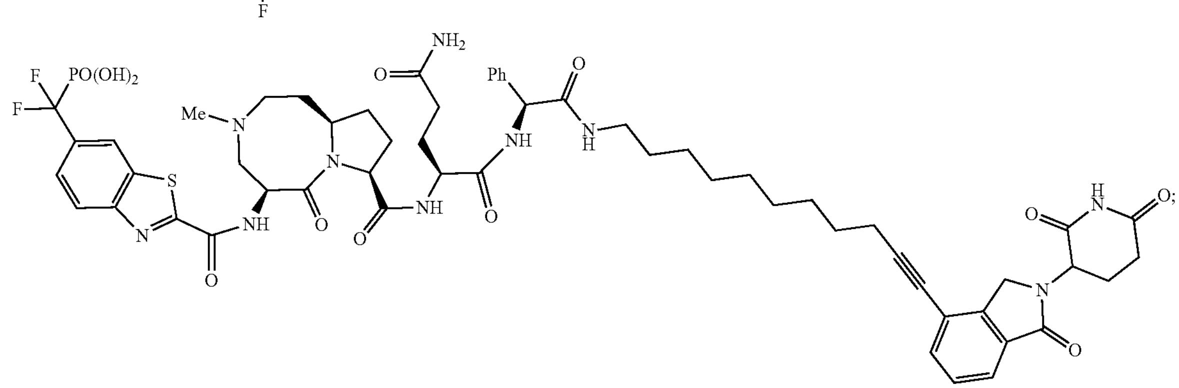
;

-continued
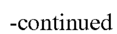
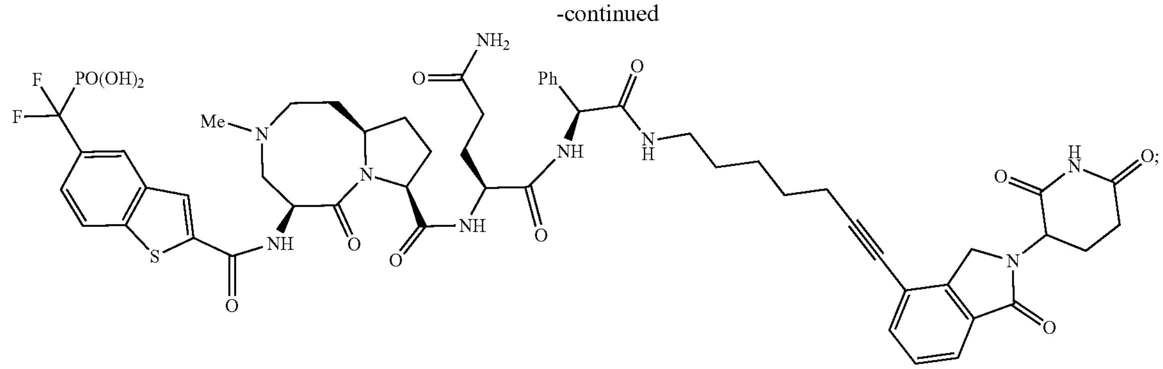
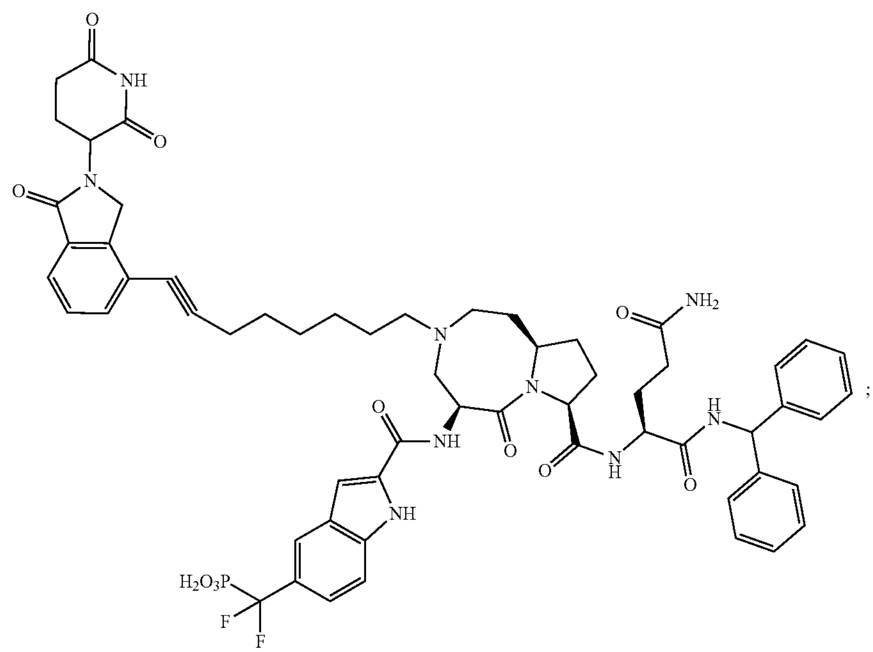
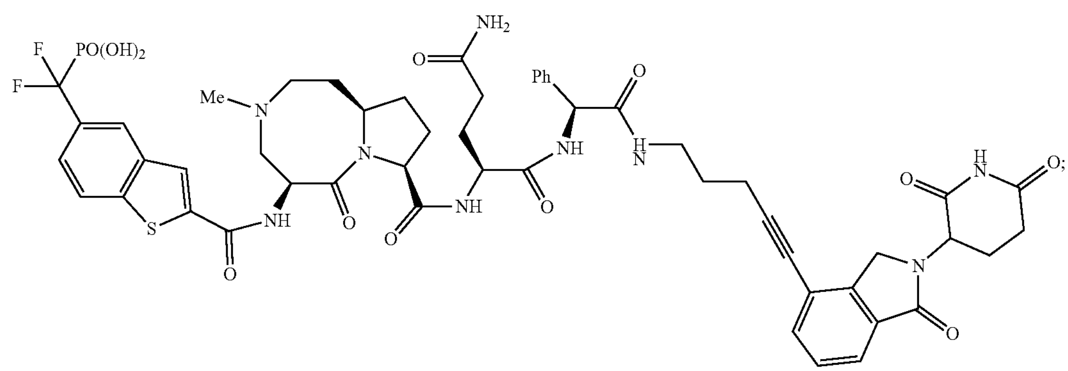

-continued
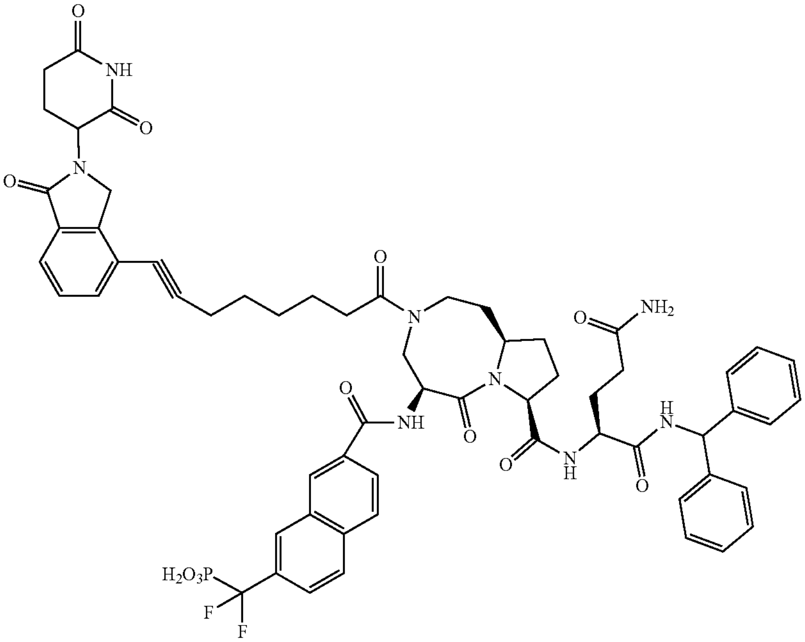
;
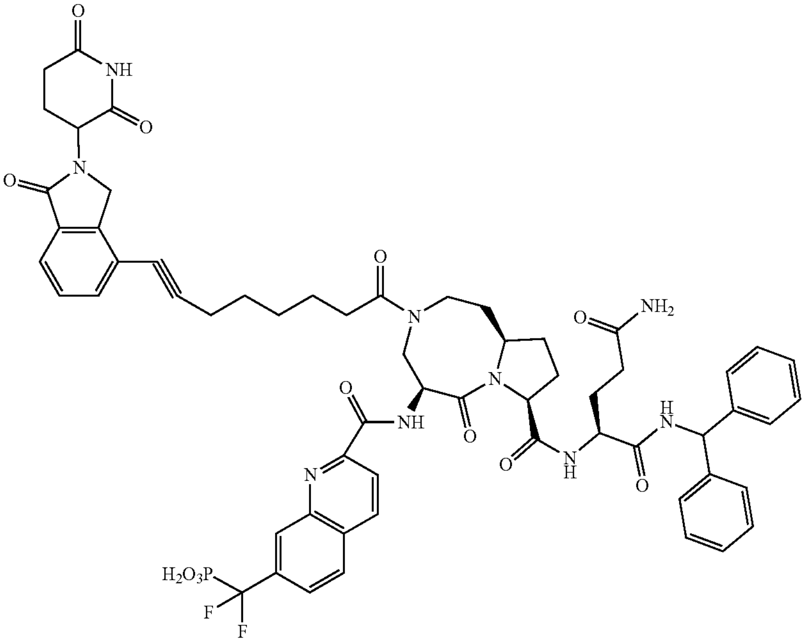
;
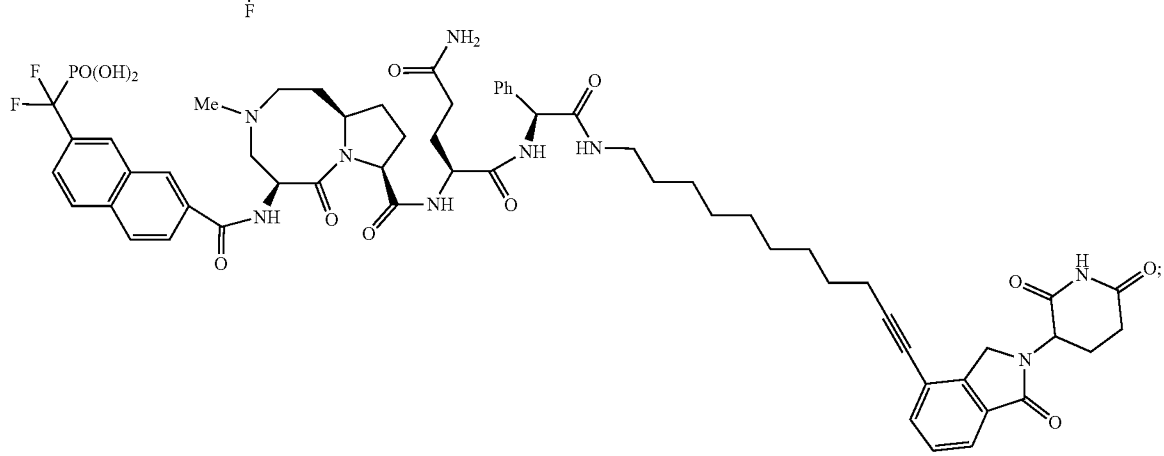
;

-continued
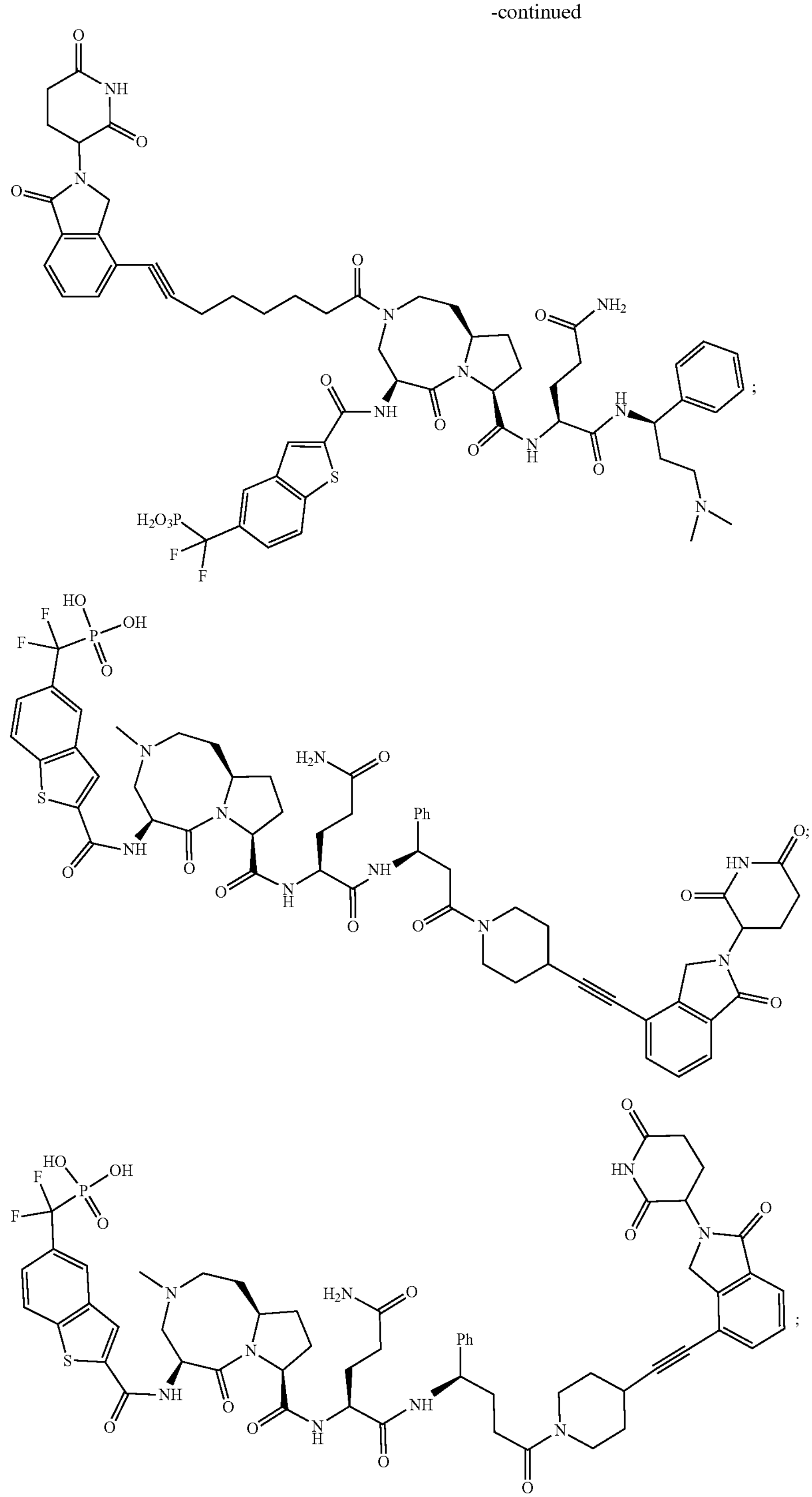

-continued
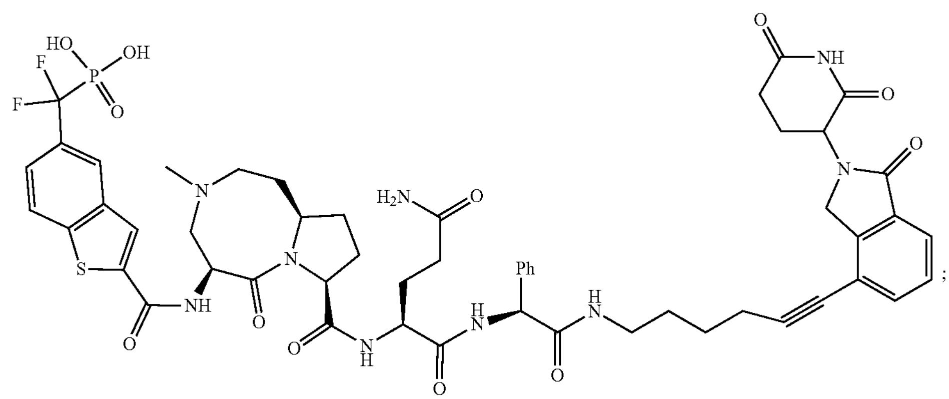
;
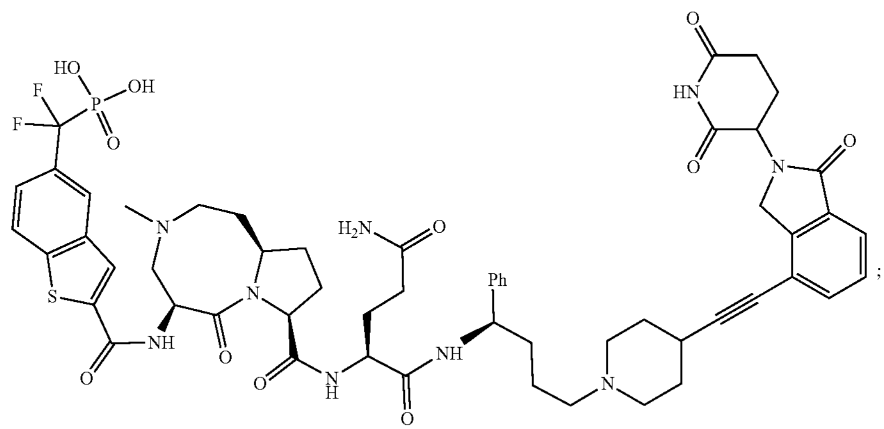
;
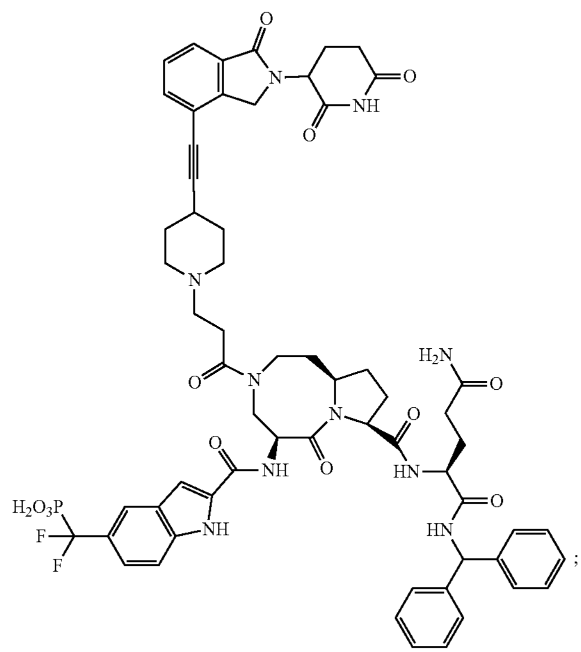
;

-continued
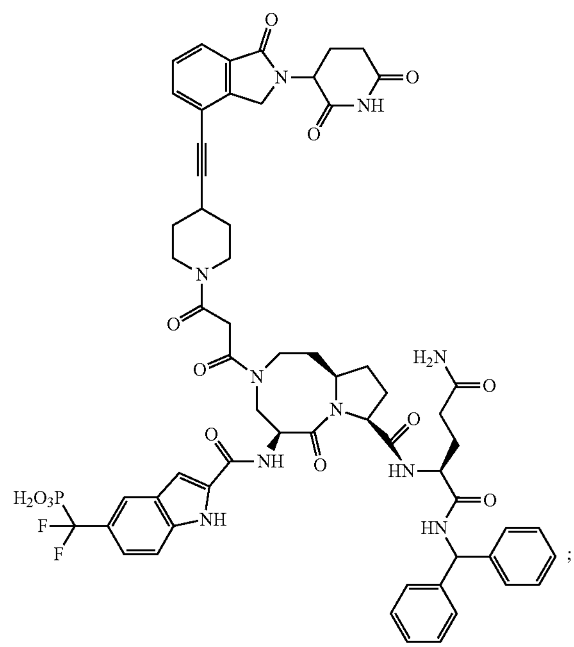
;
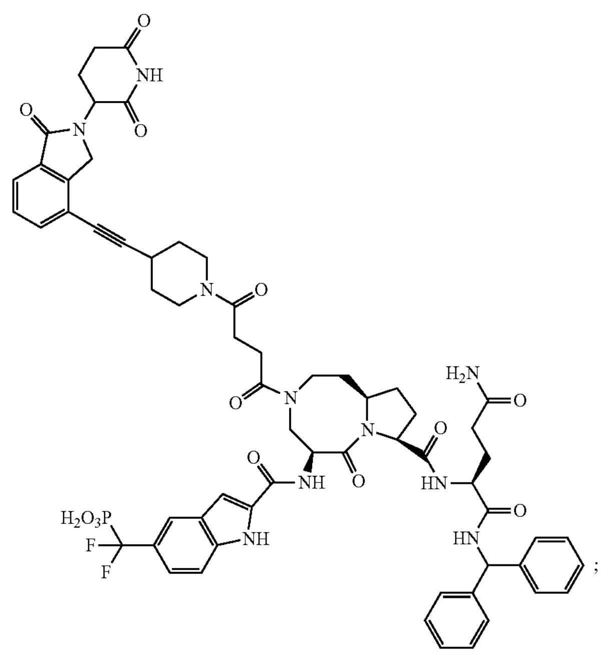
;

-continued
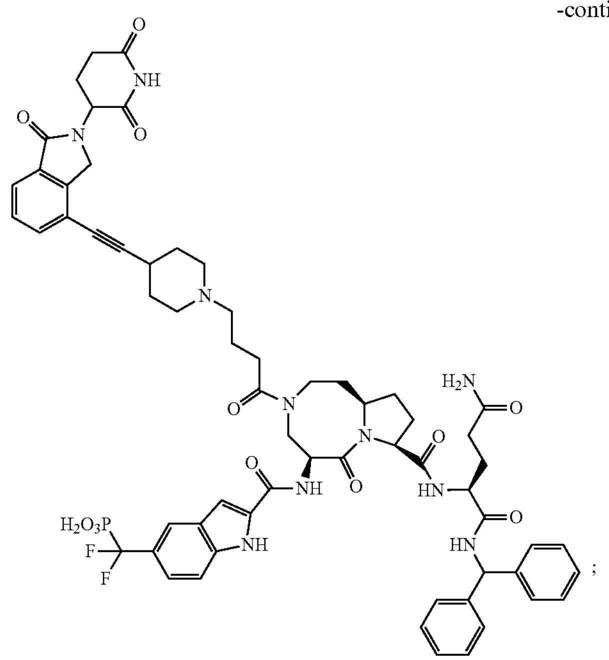
;
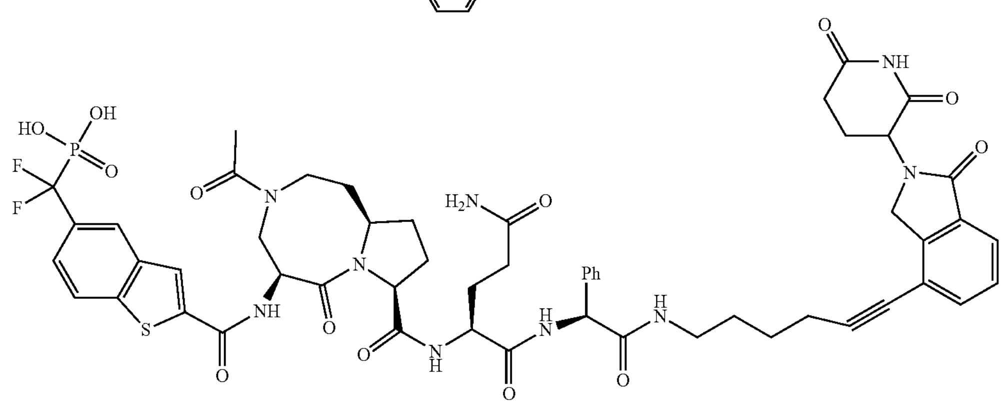
;
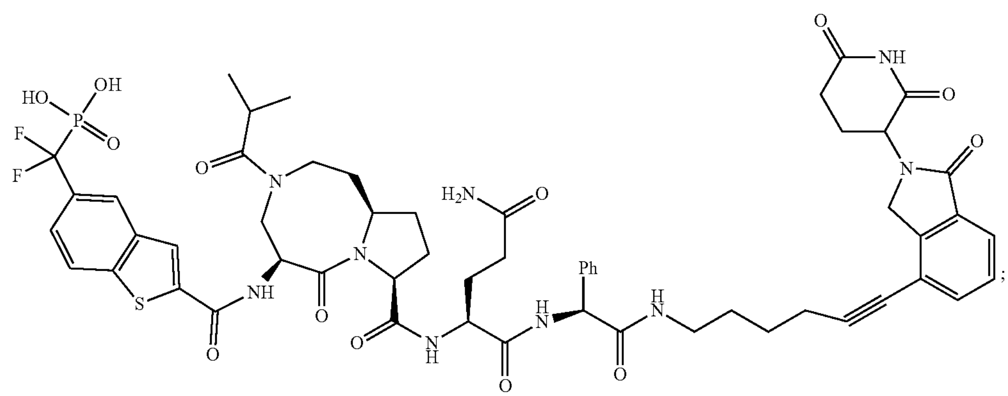
;

-continued
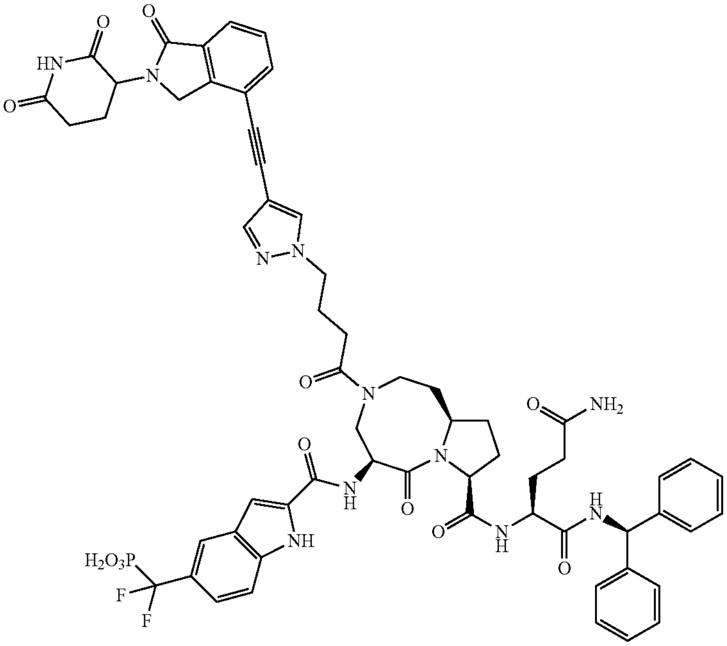
;
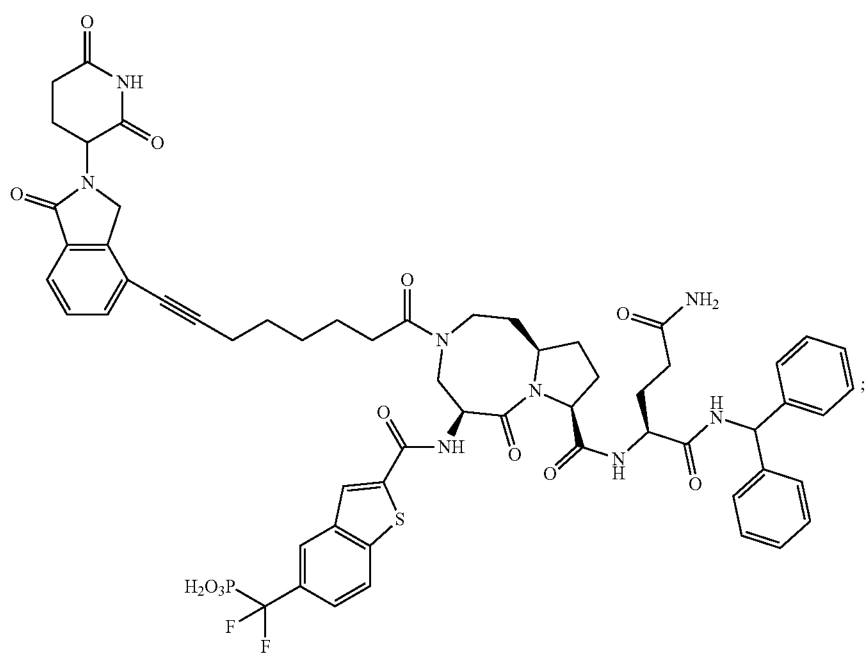
;

-continued
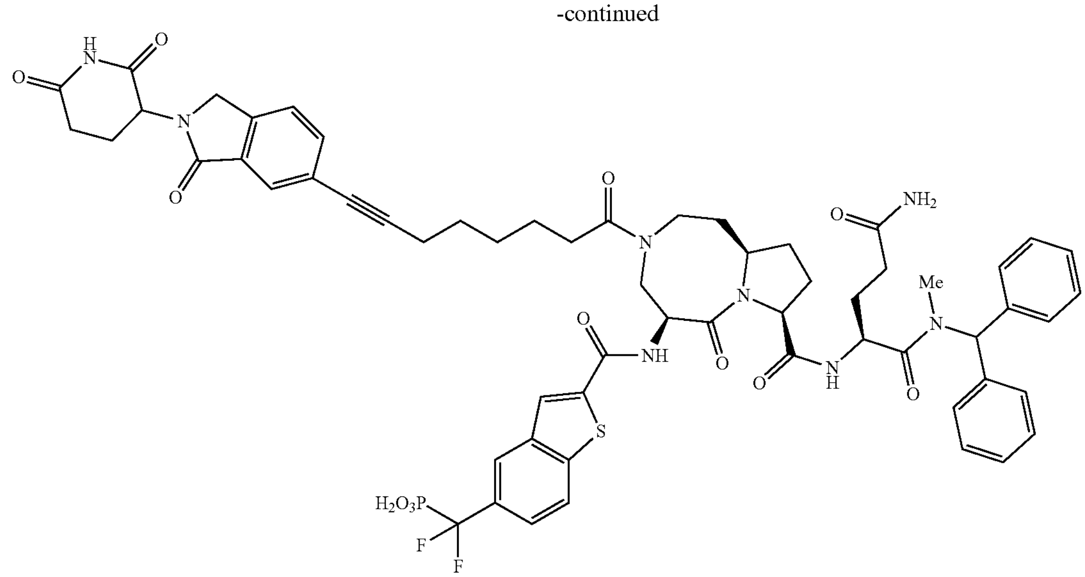
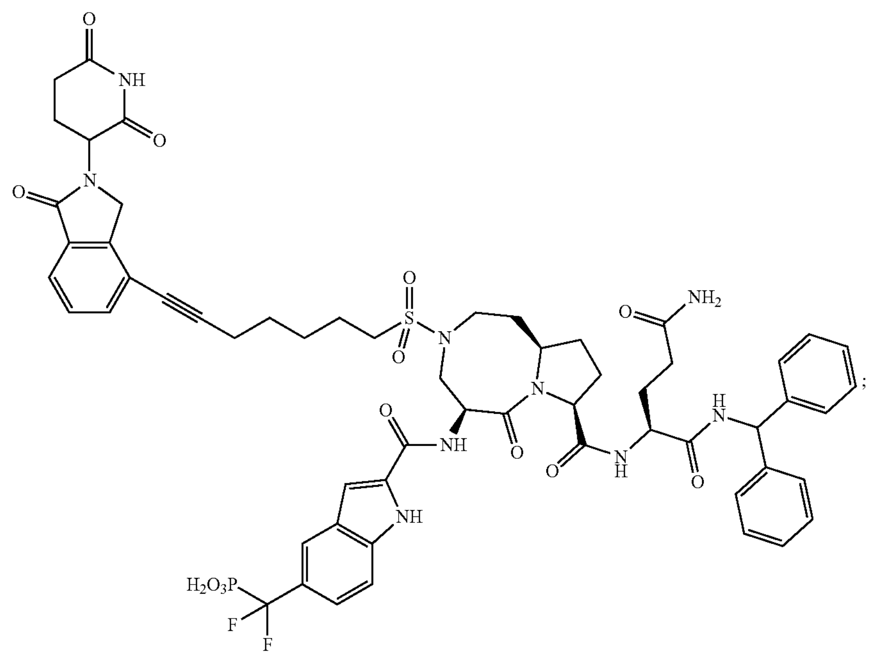

-continued
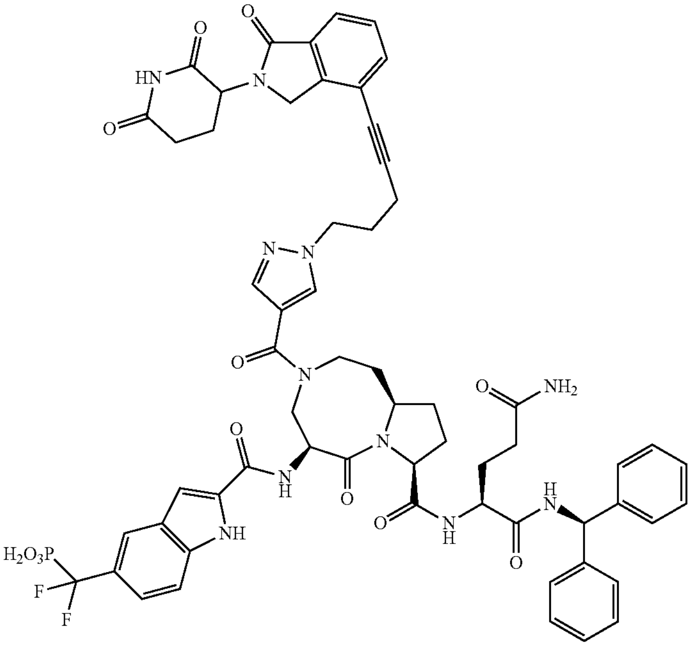
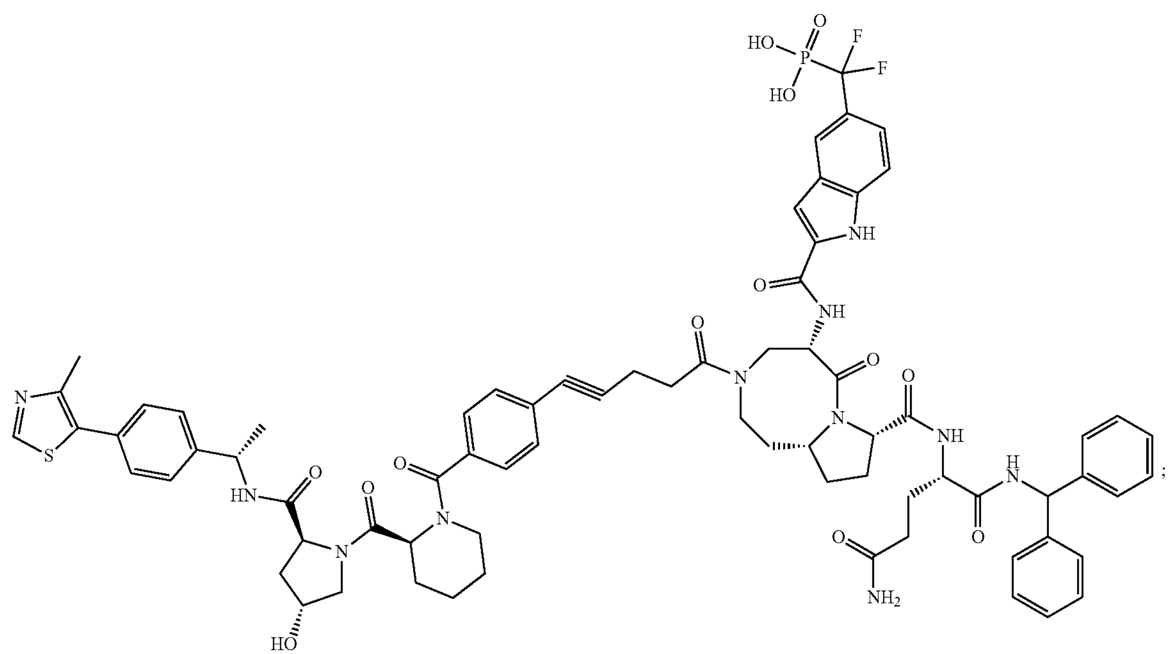

-continued
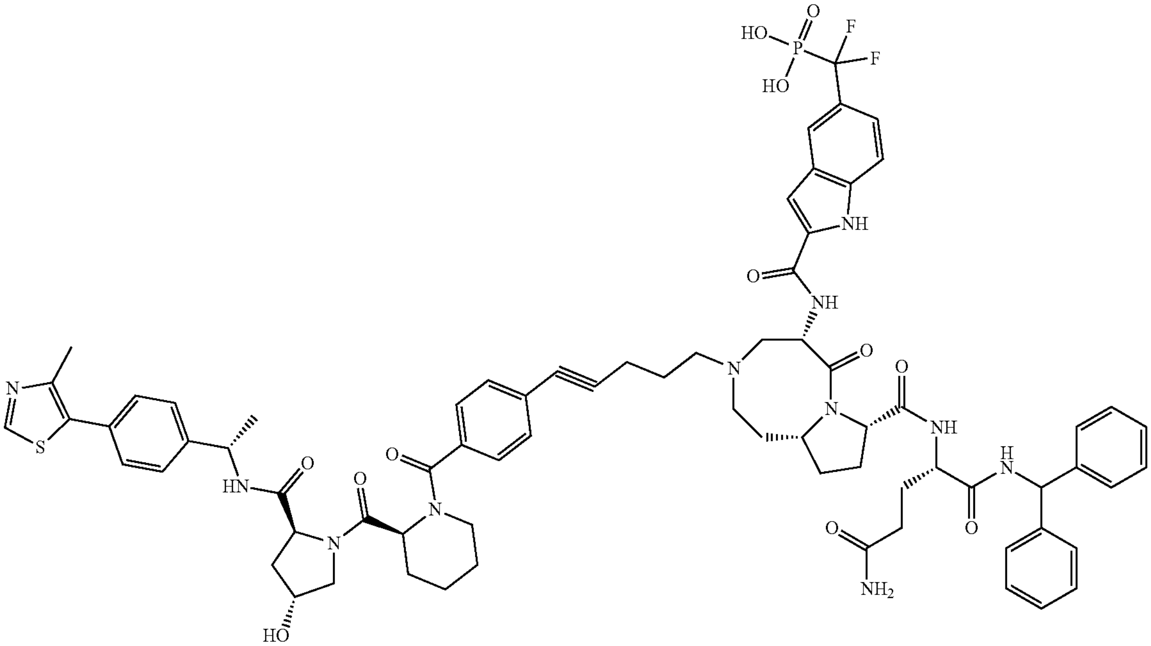
;
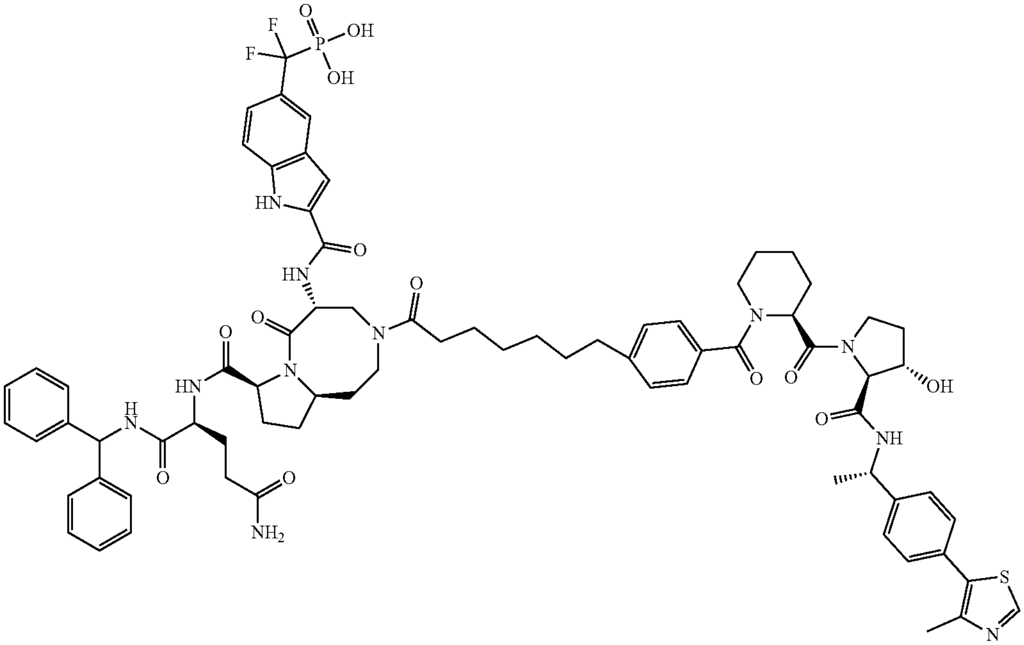
;
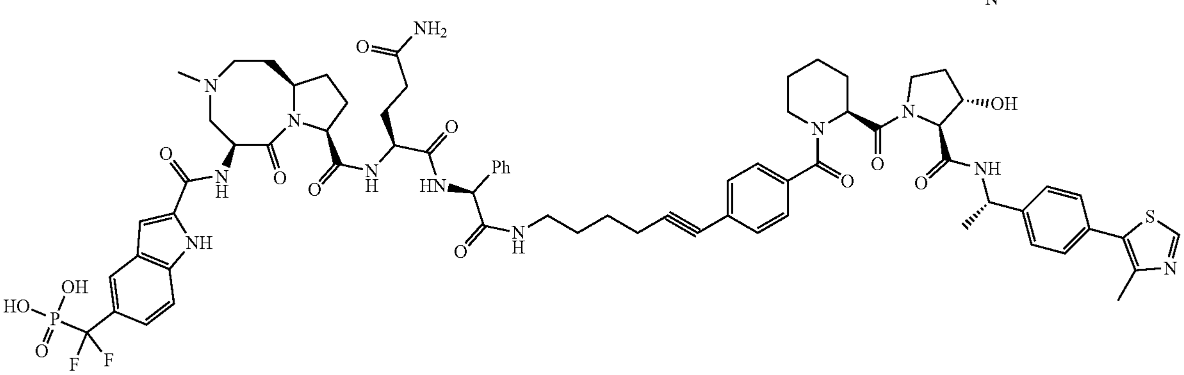
;

-continued
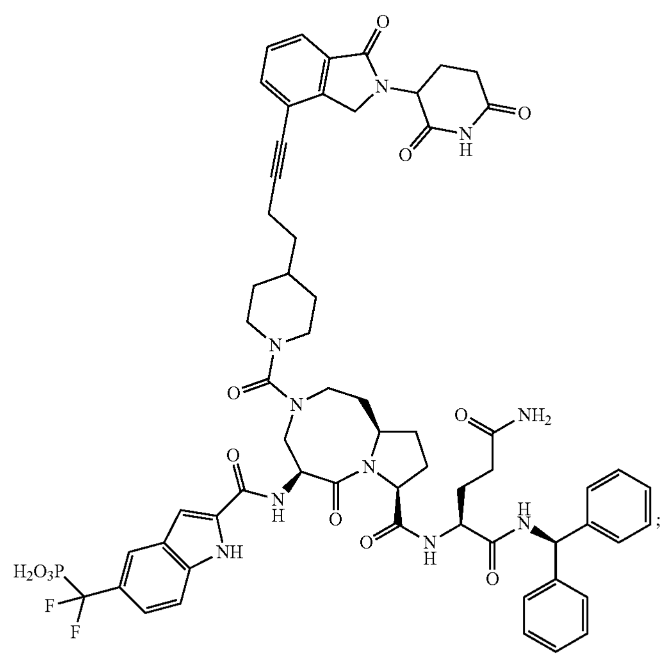
;
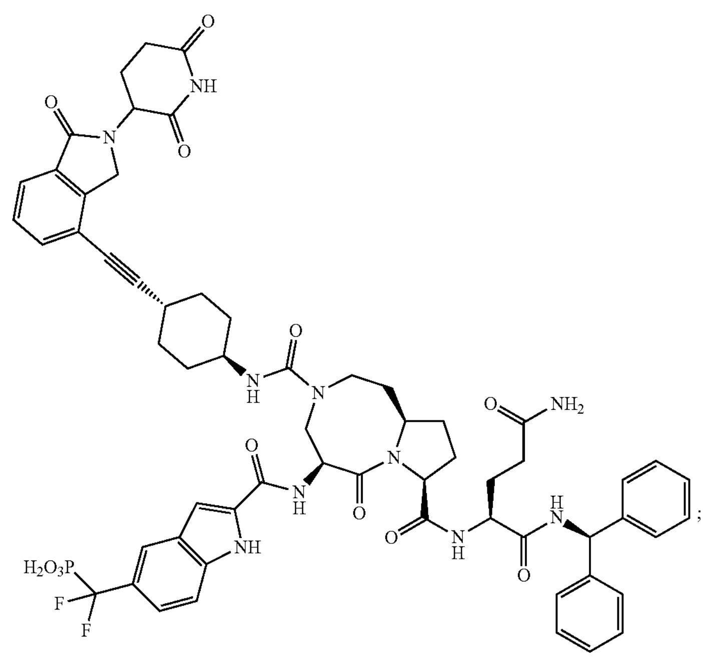
;

-continued
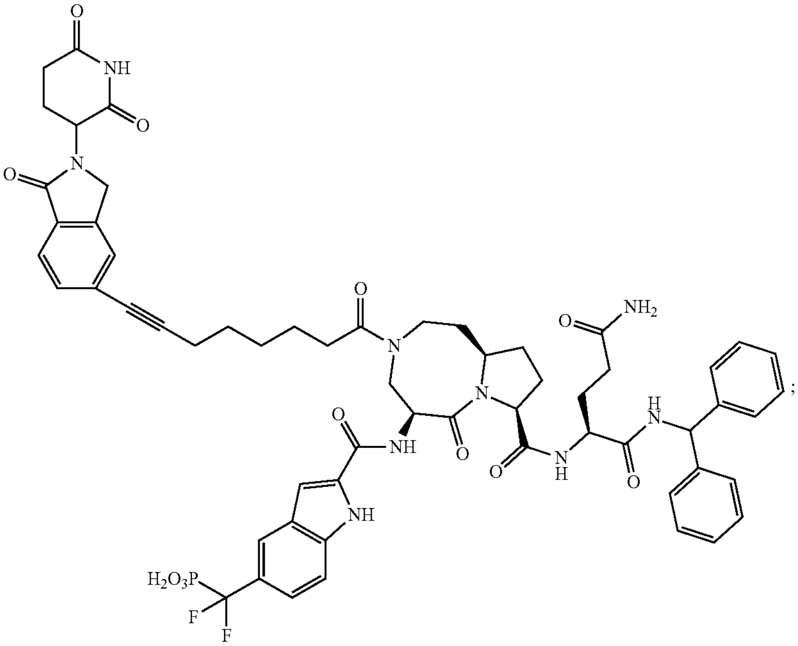
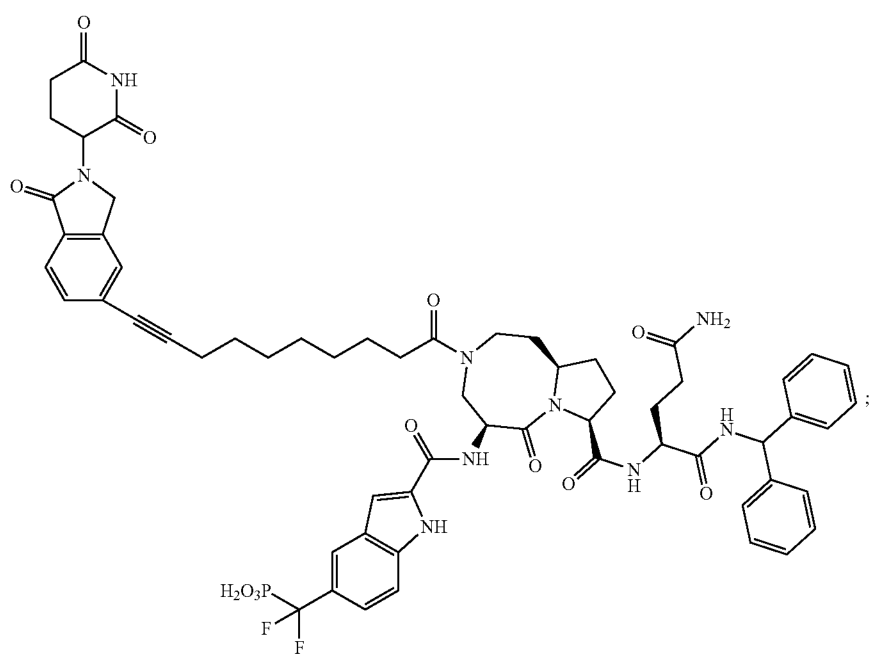

-continued
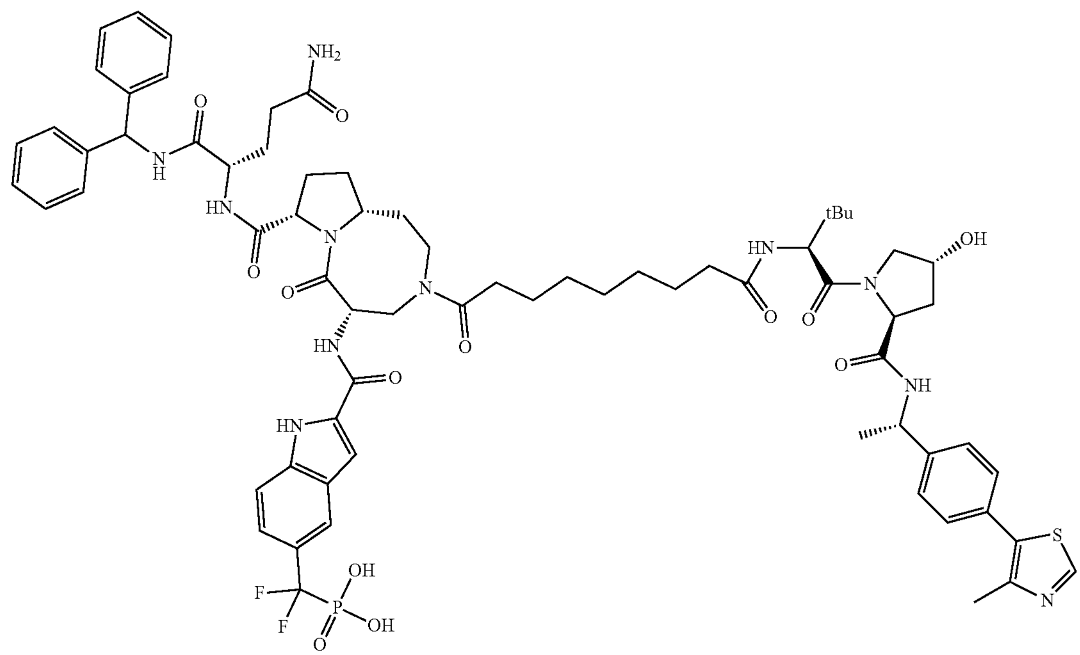
;
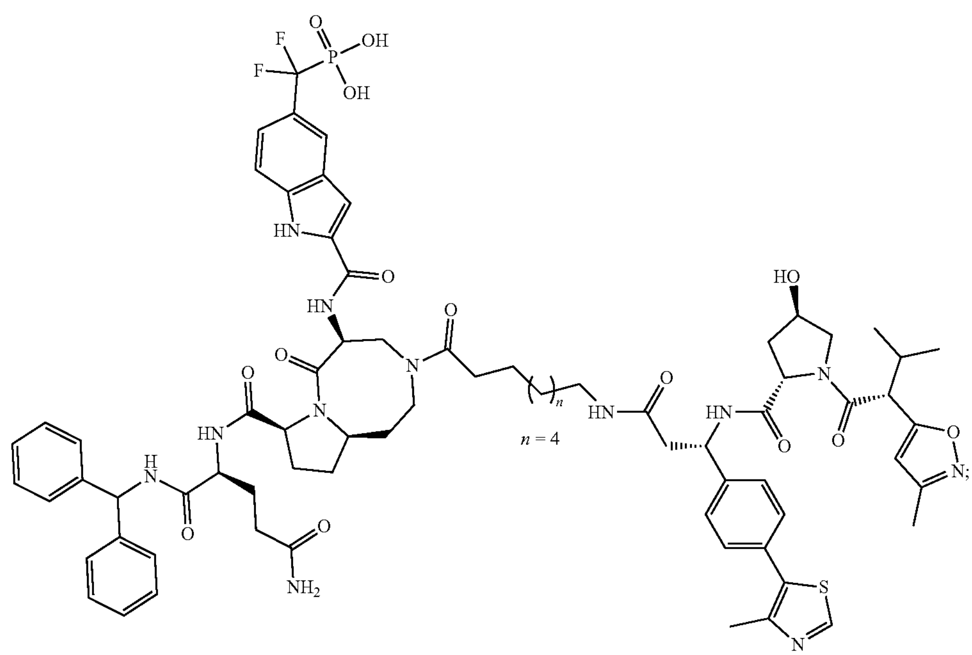
;

-continued
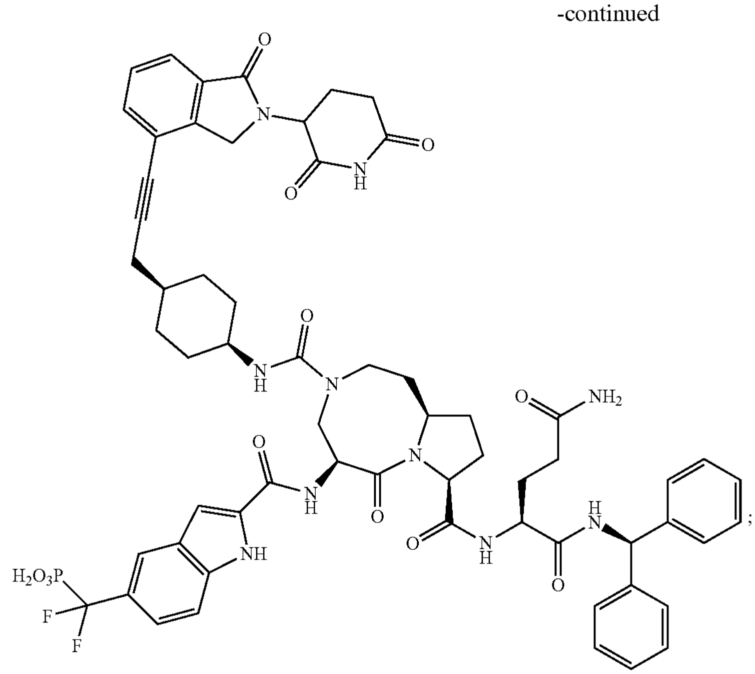
;
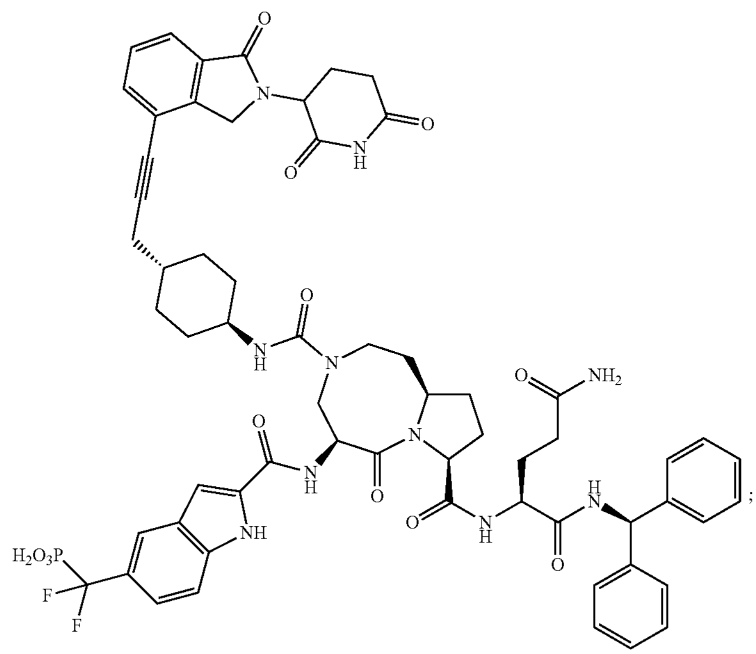
;
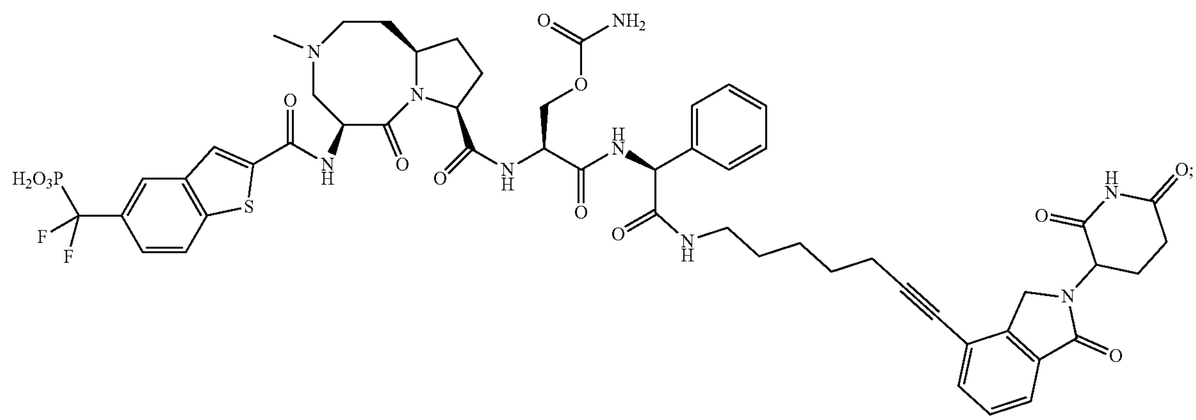
;

-continued
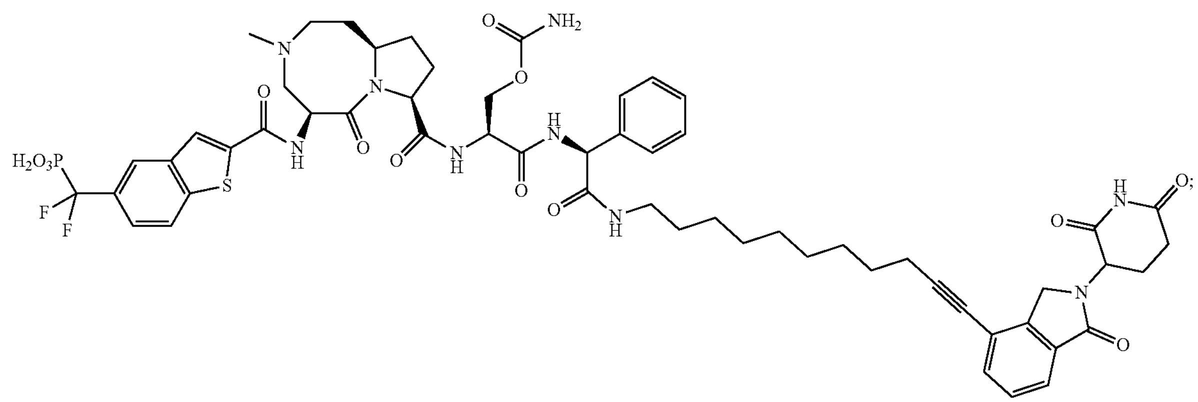
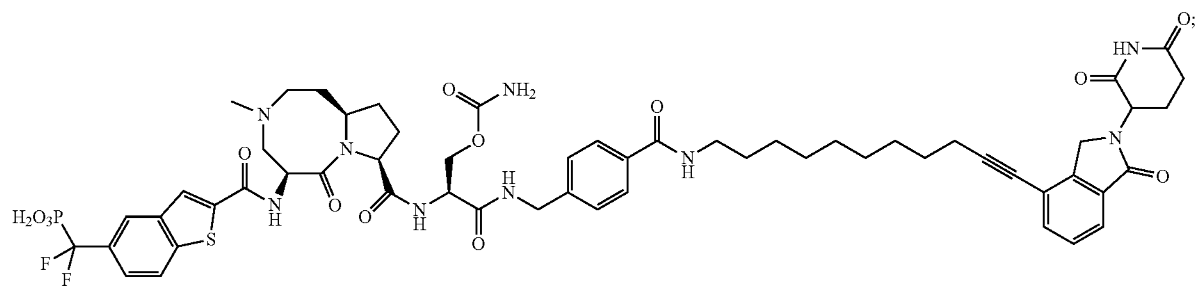
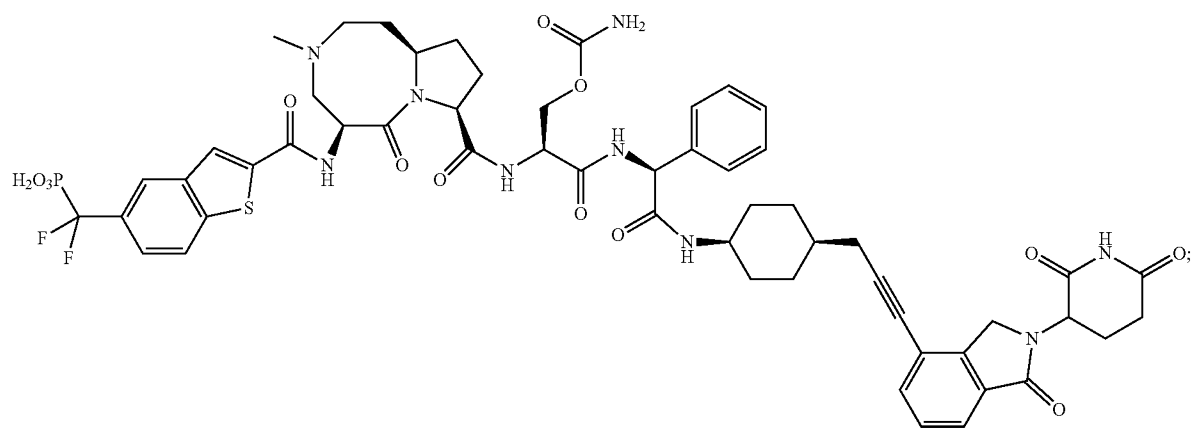
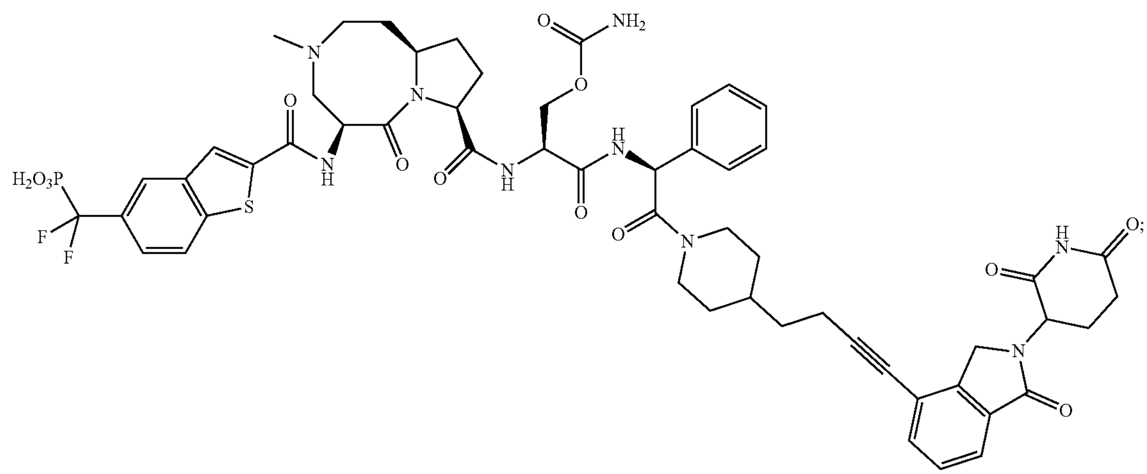

-continued
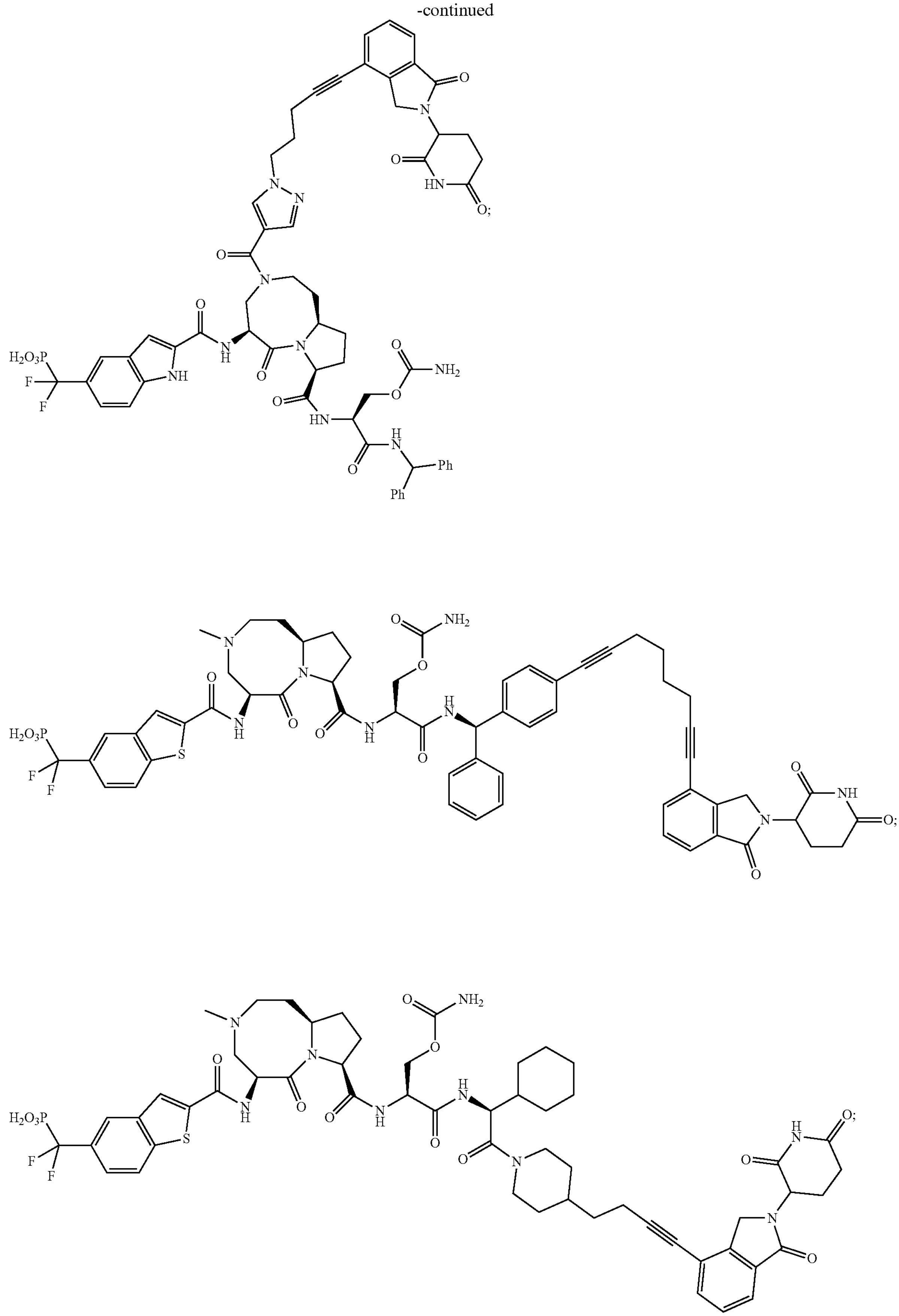

-continued
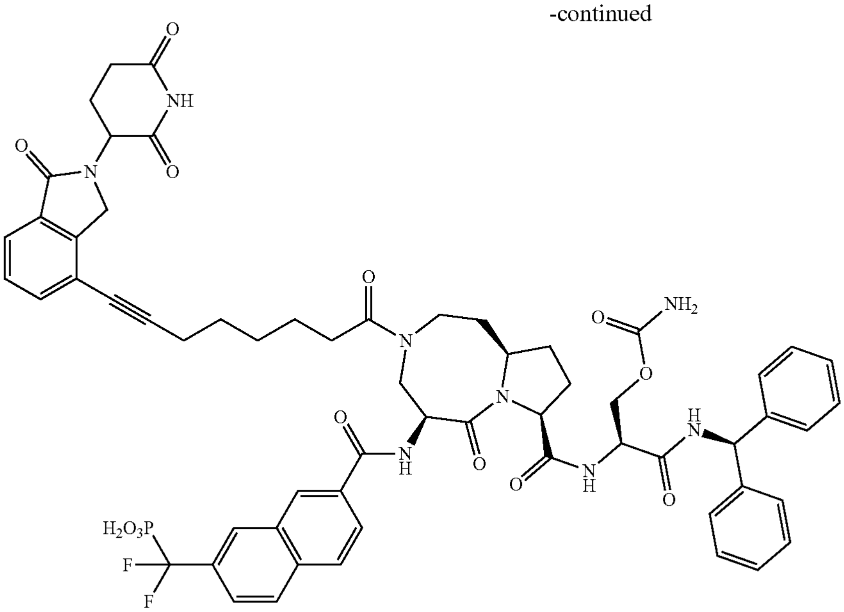
;
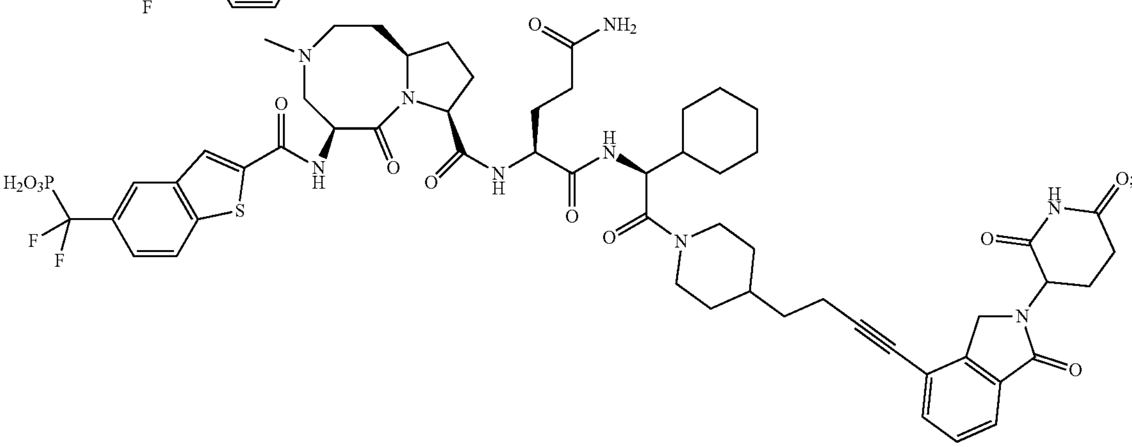
;
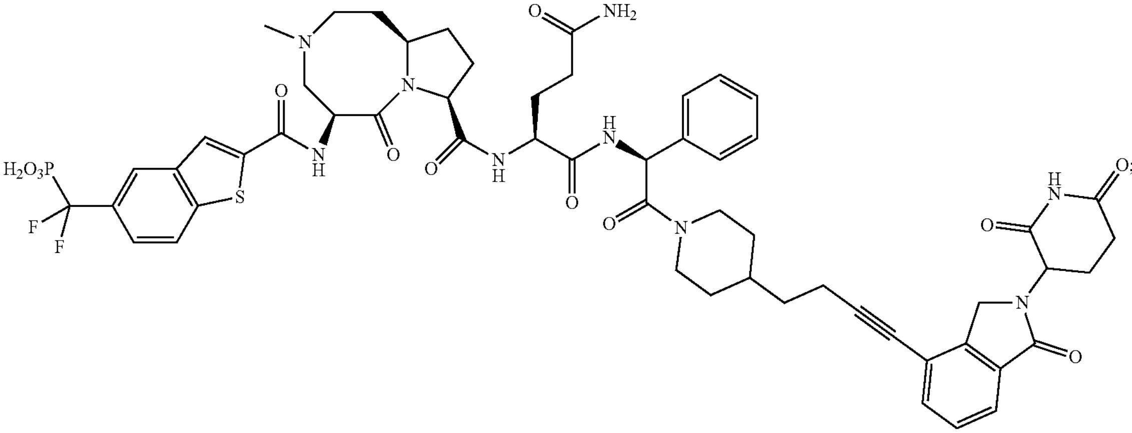
;

-continued
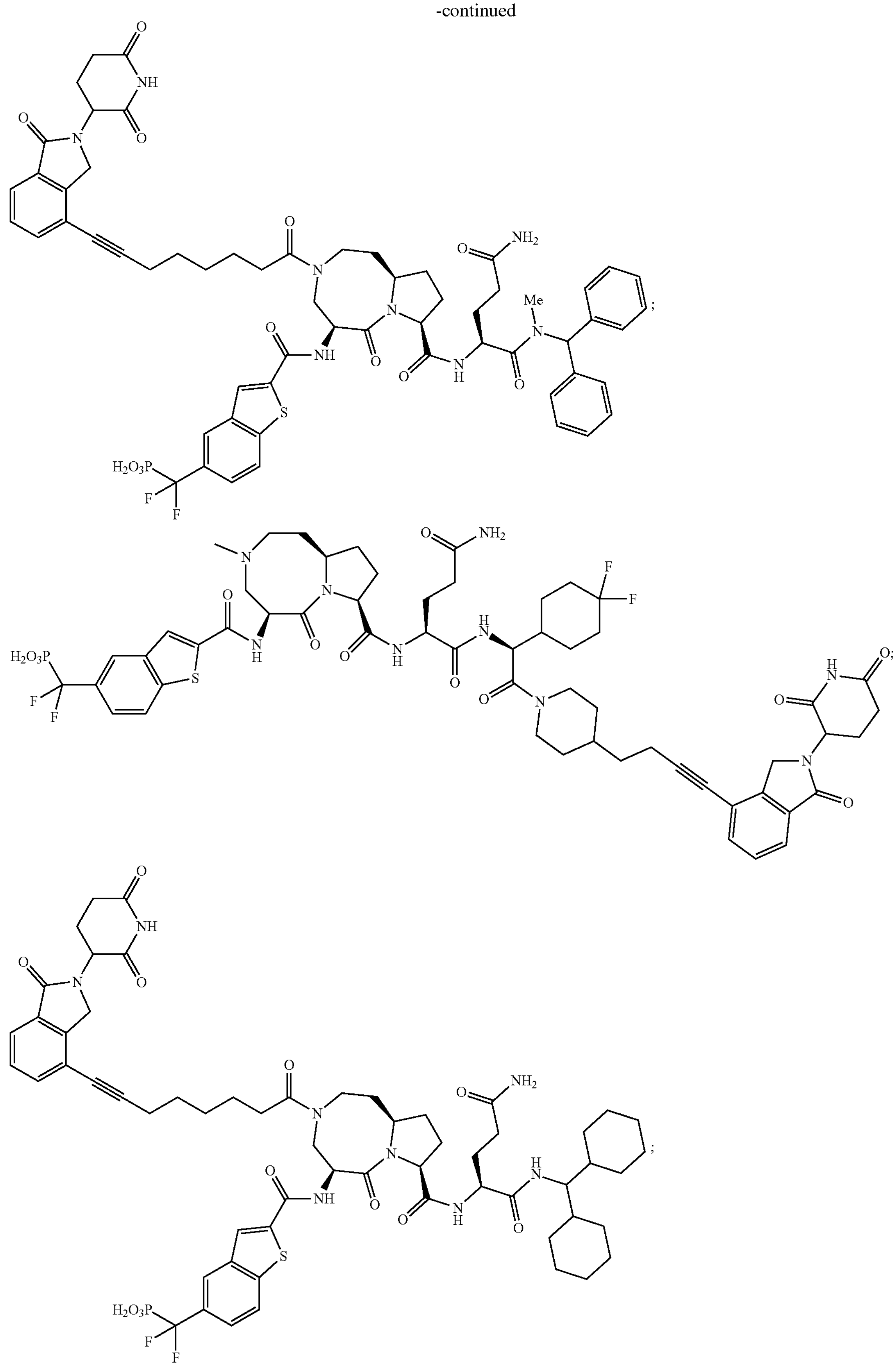

-continued
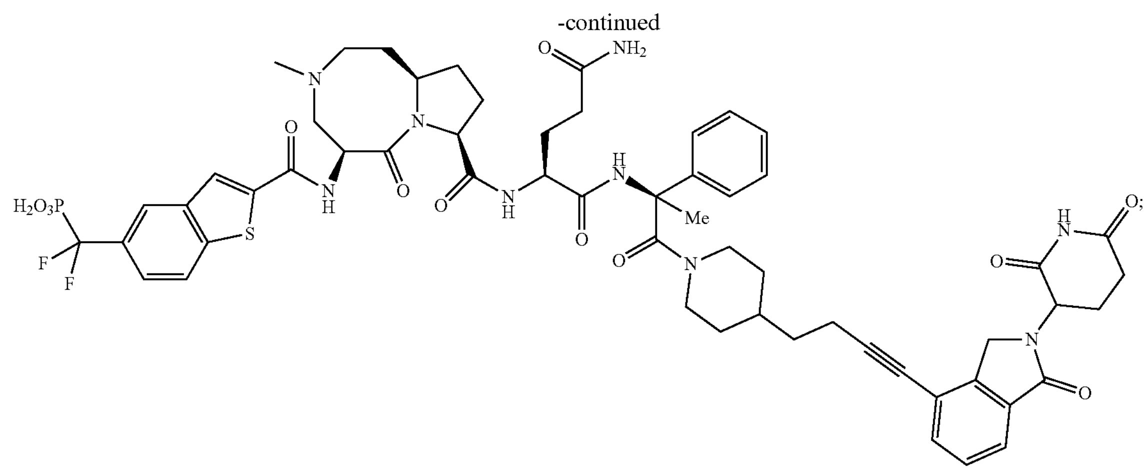
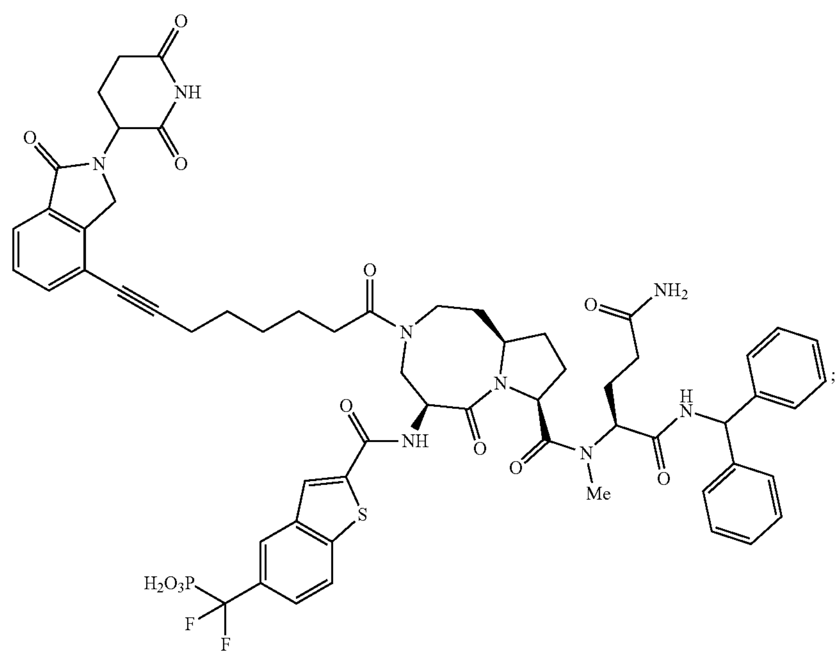
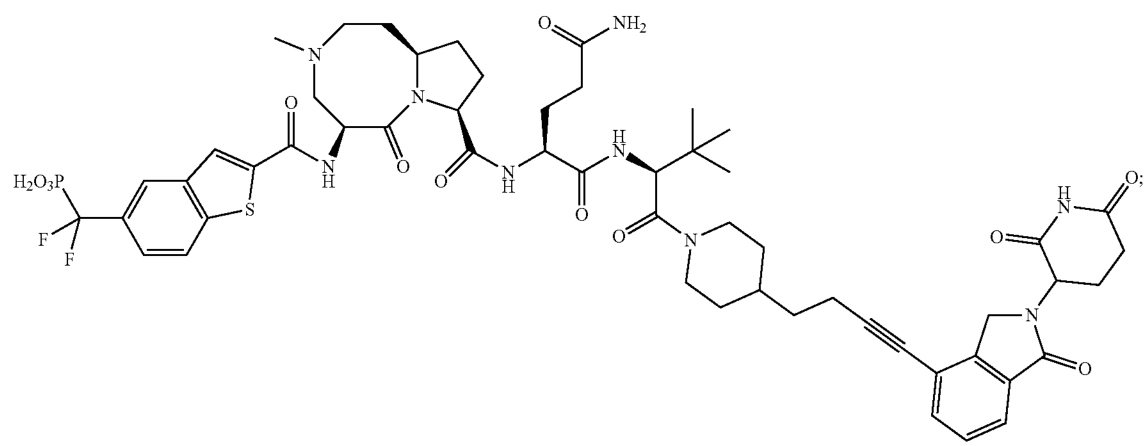

-continued
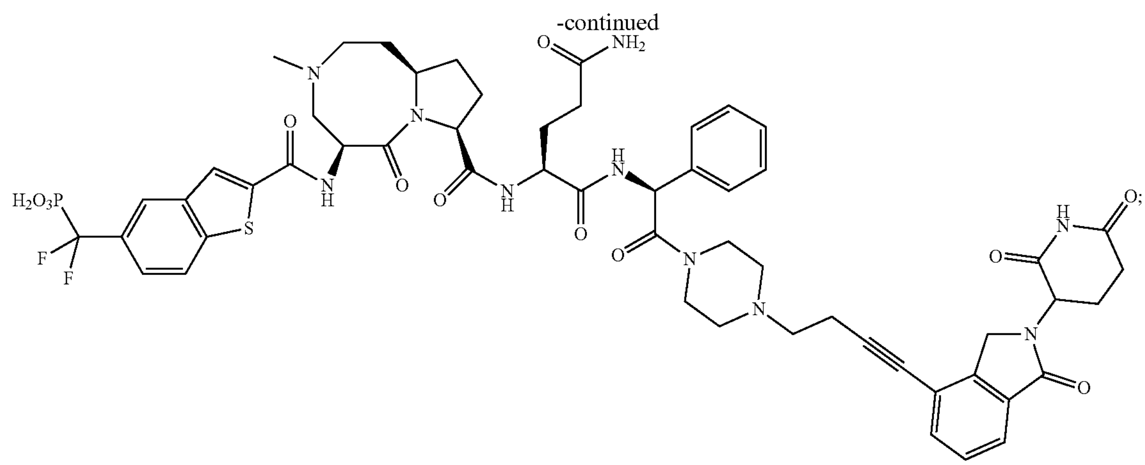
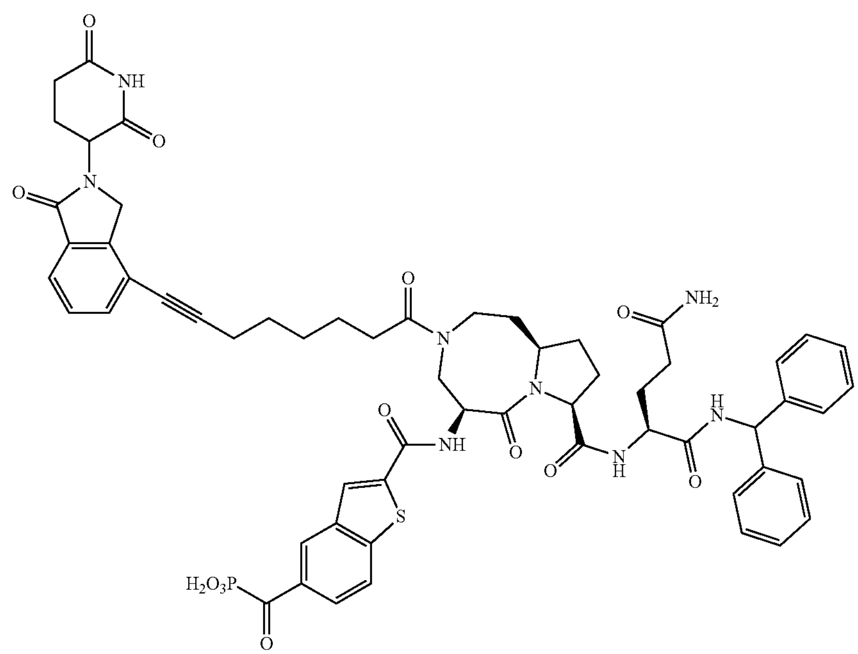
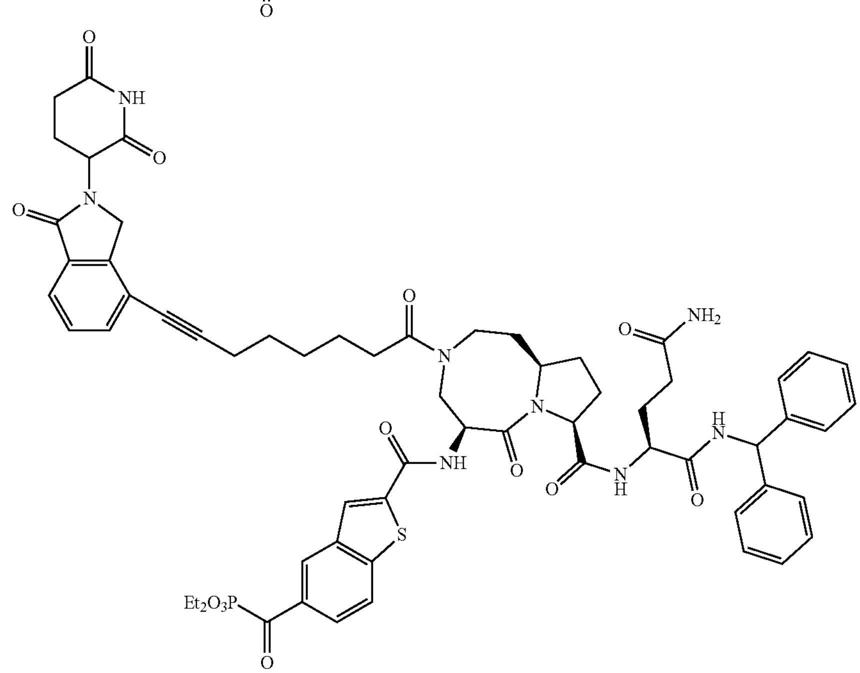

-continued
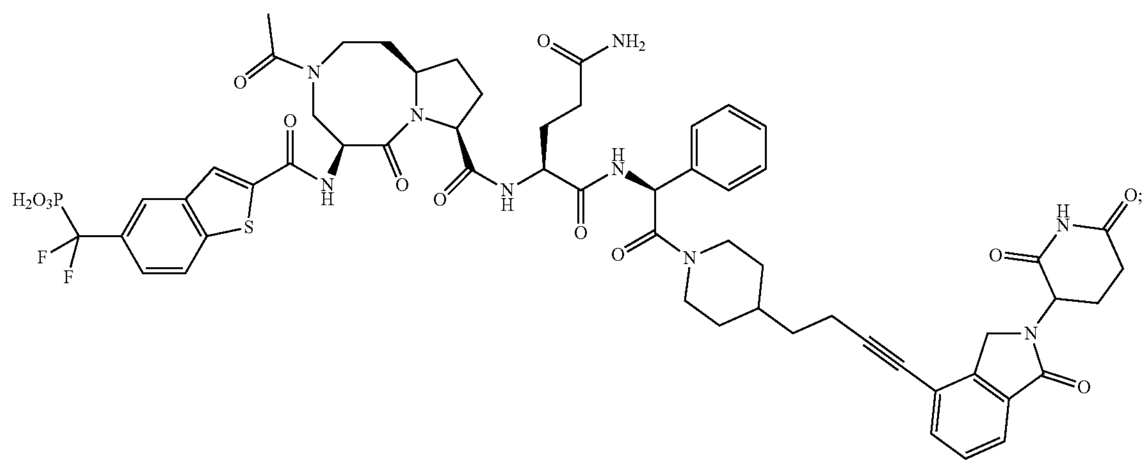
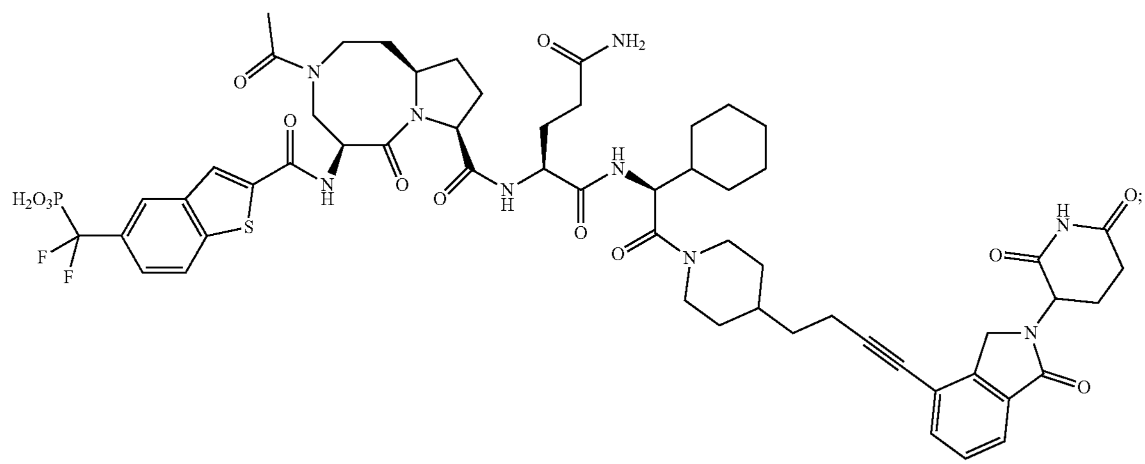
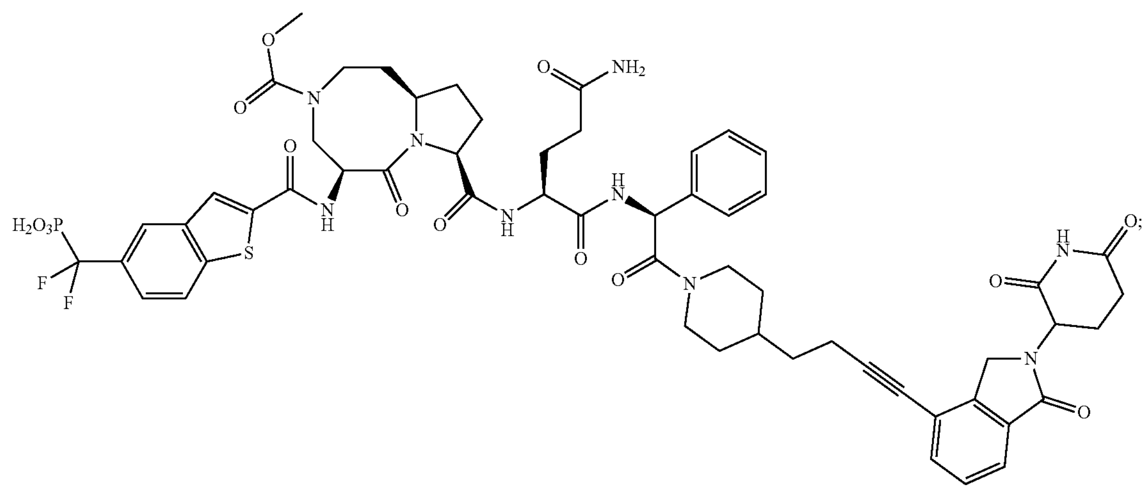

-continued
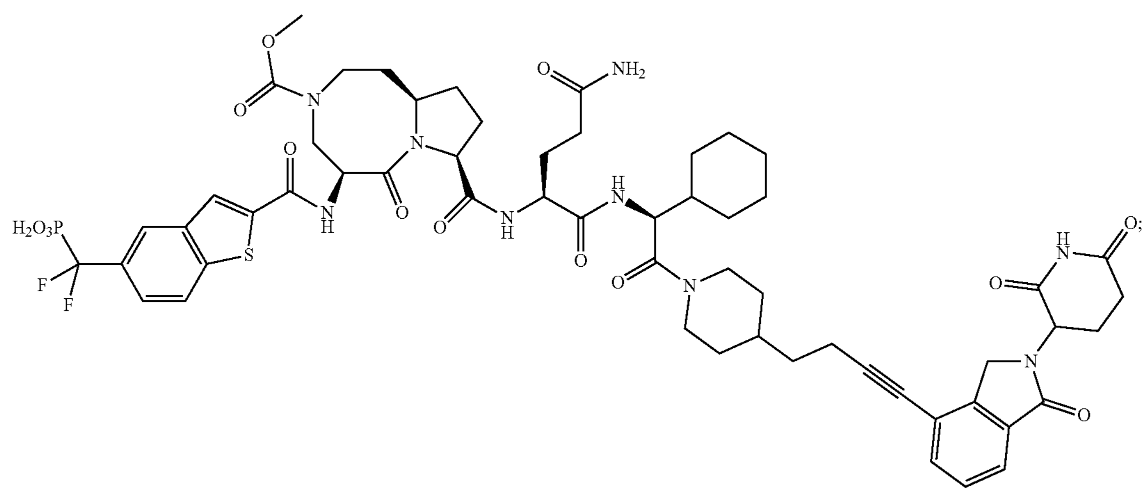
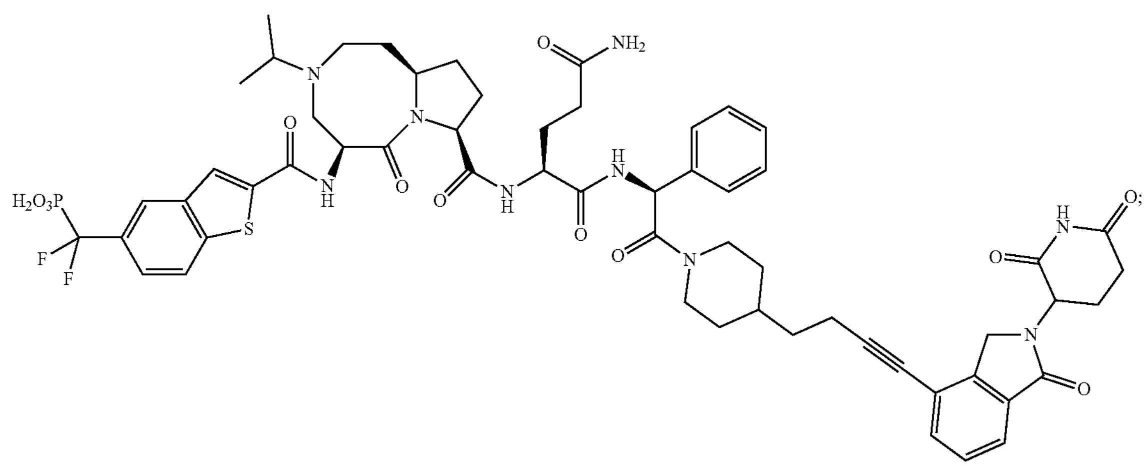
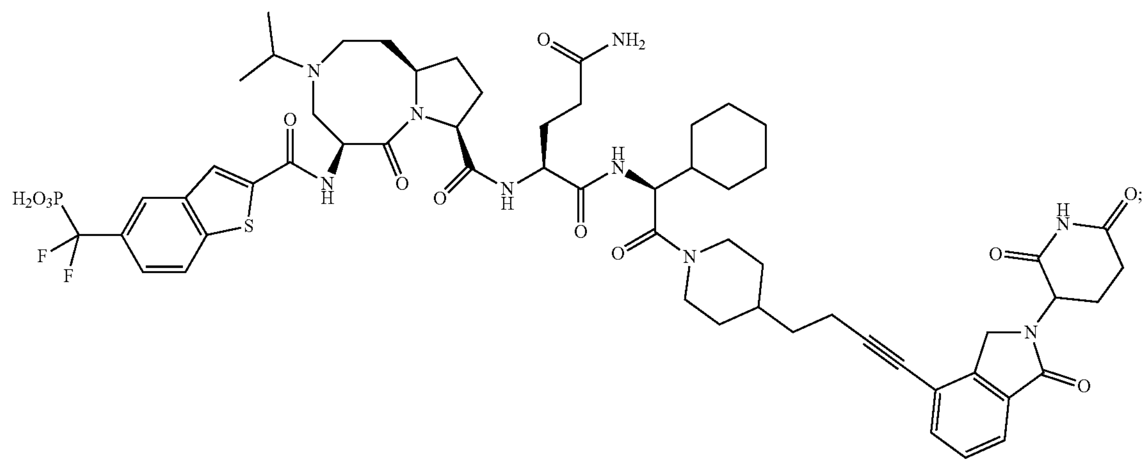

-continued
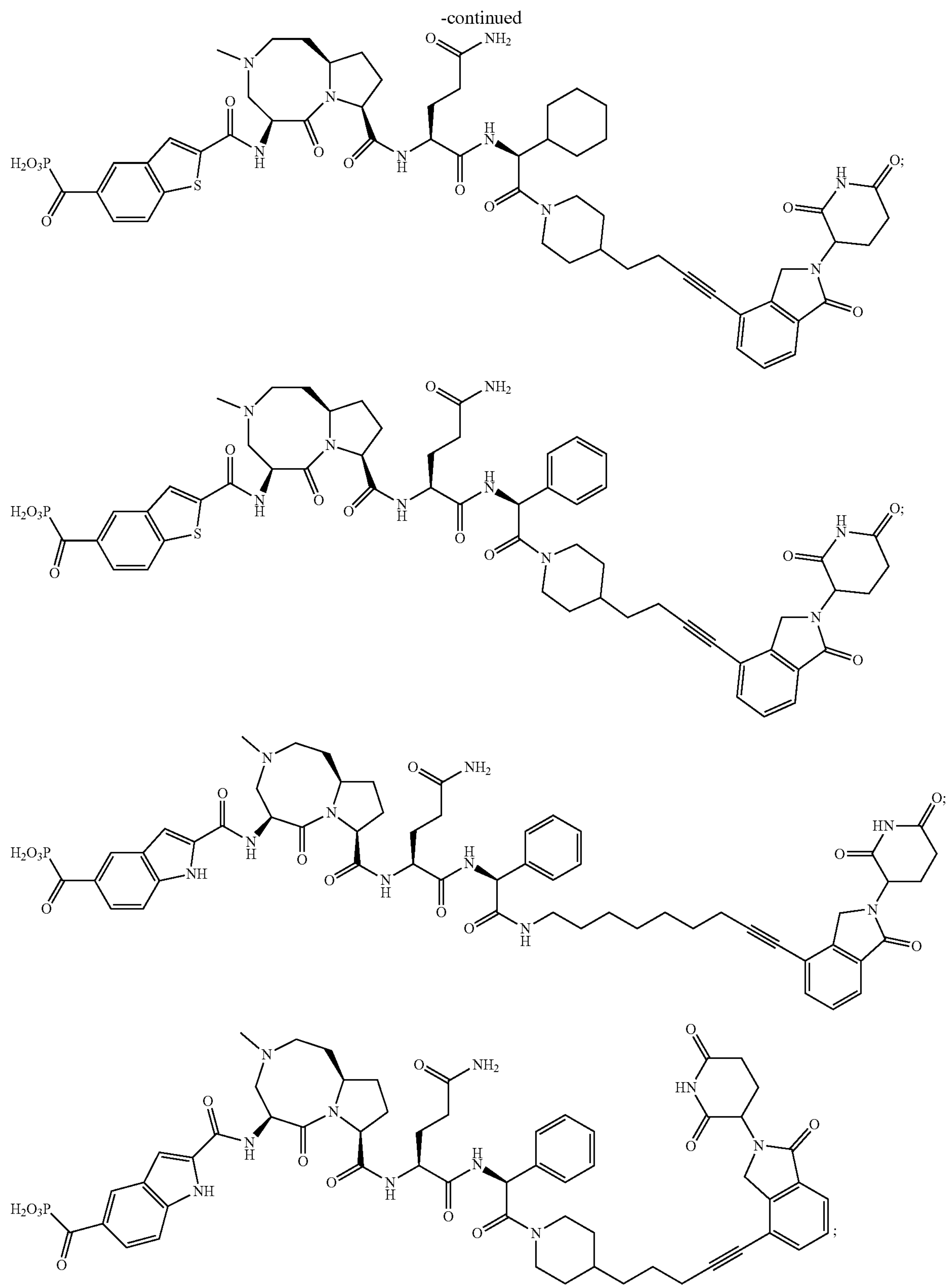
;
;
;
;

-continued
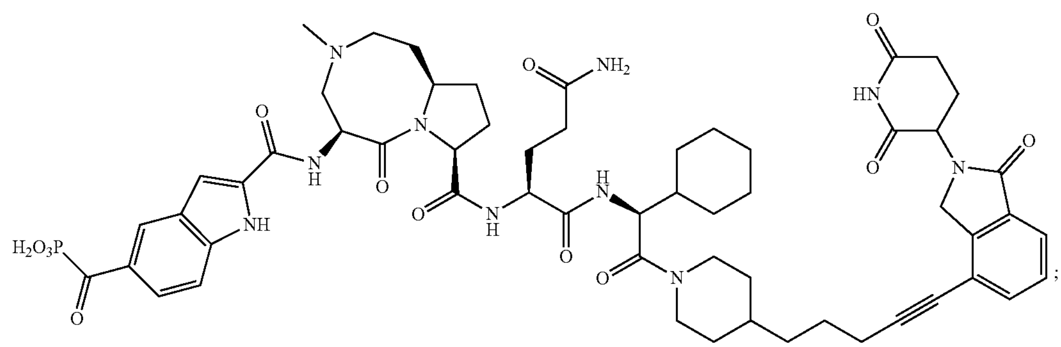
;
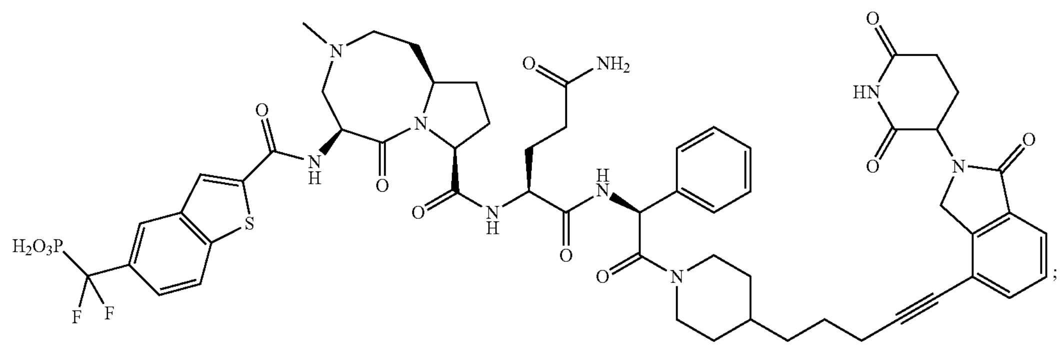
;
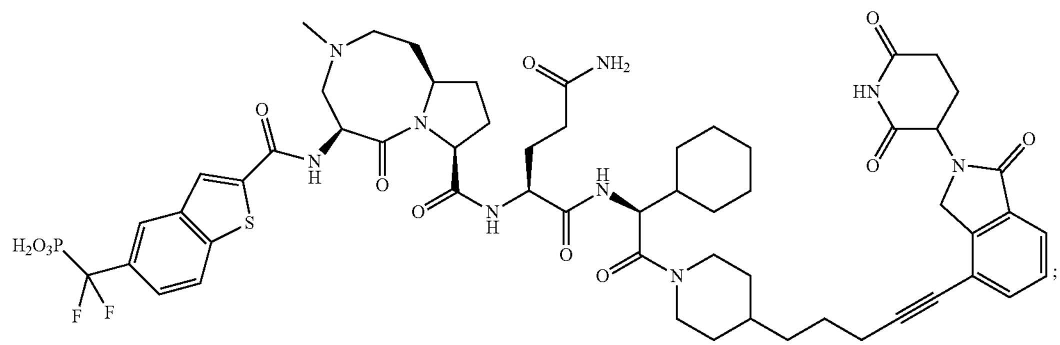
;
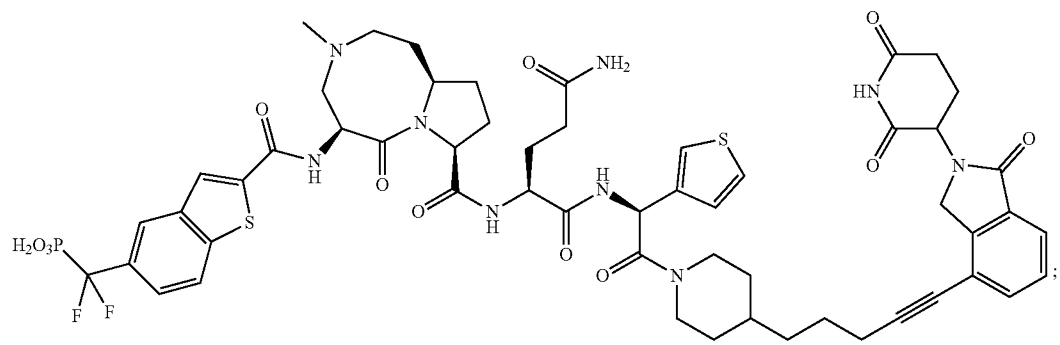
;
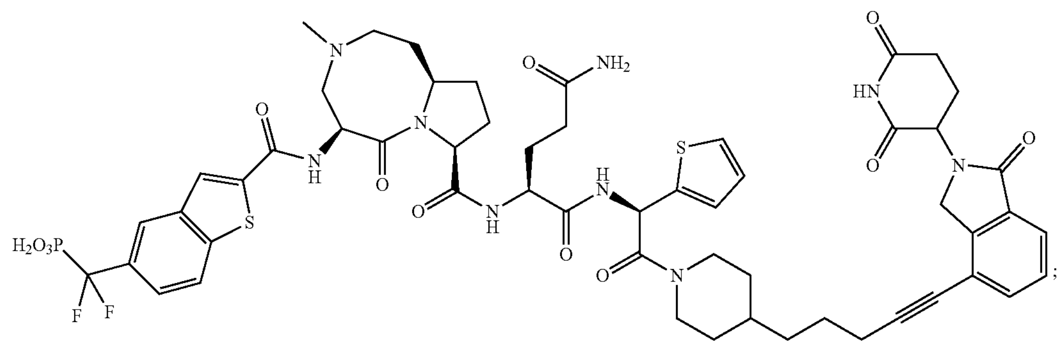
;

-continued
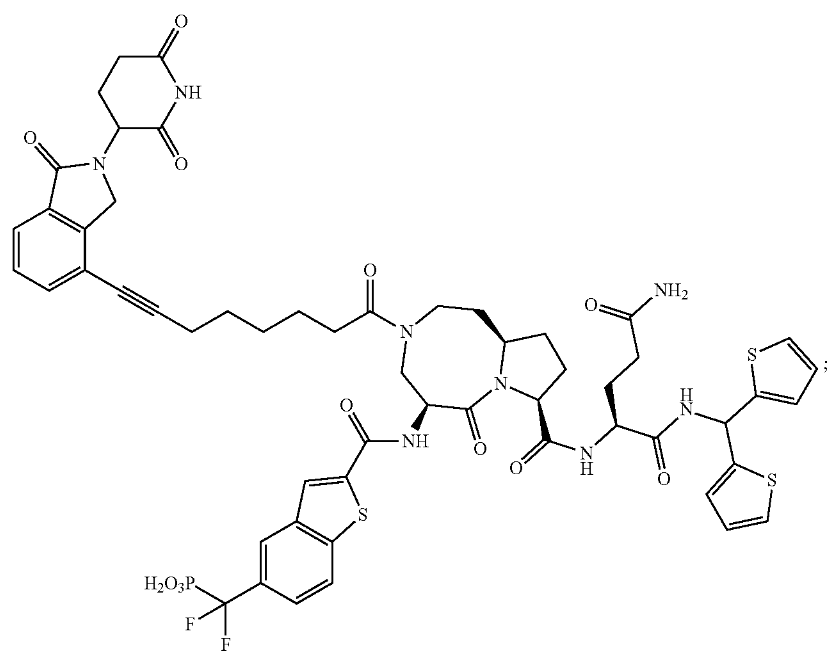
;
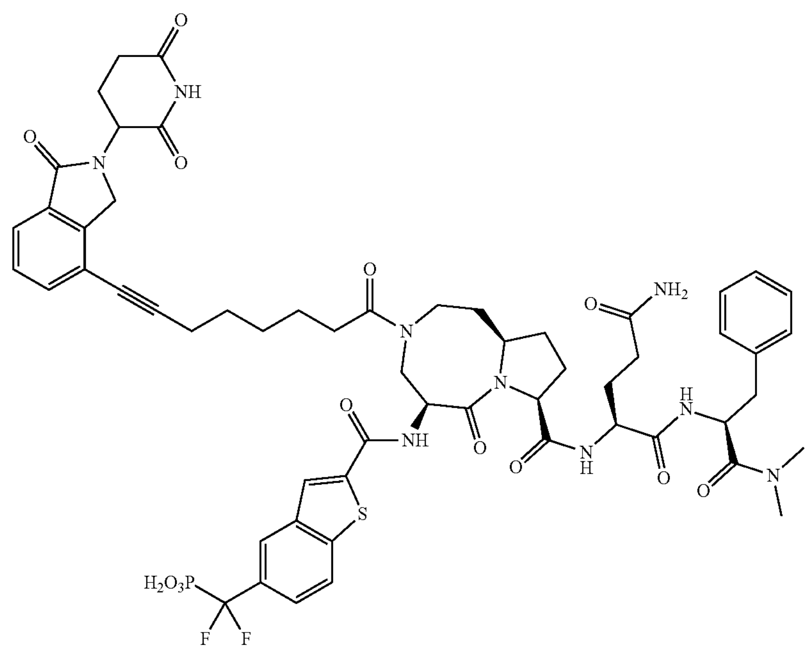
;

-continued
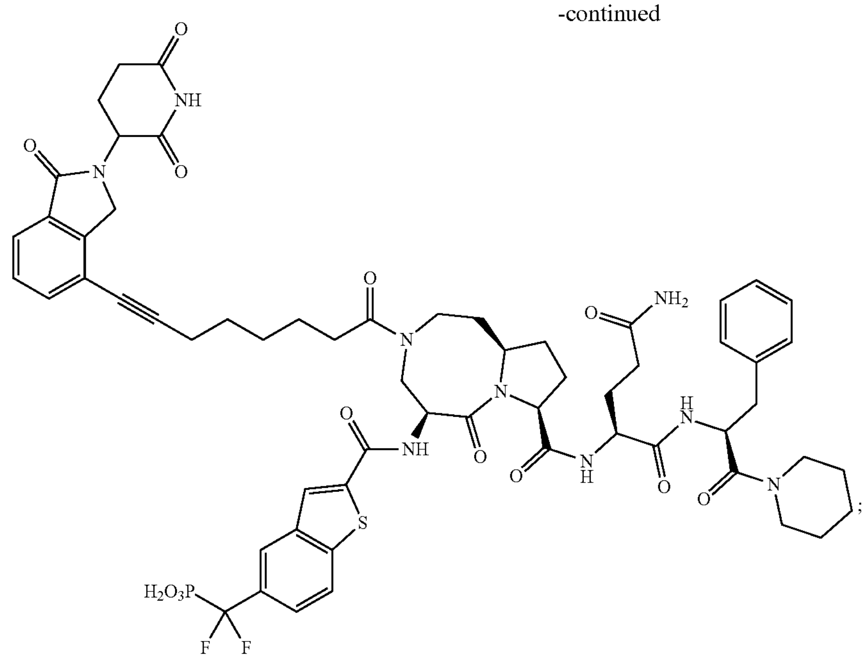
;
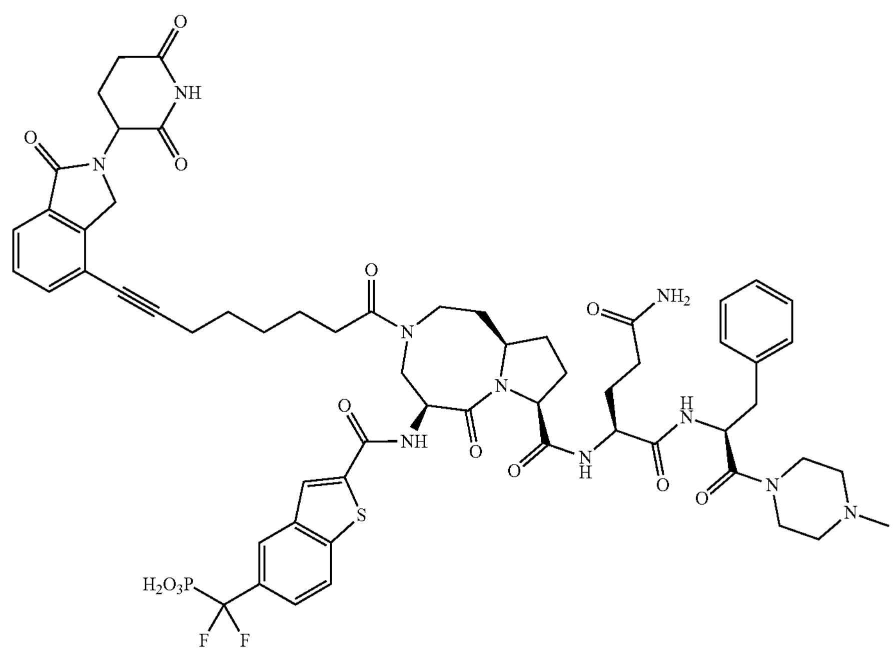
;

-continued
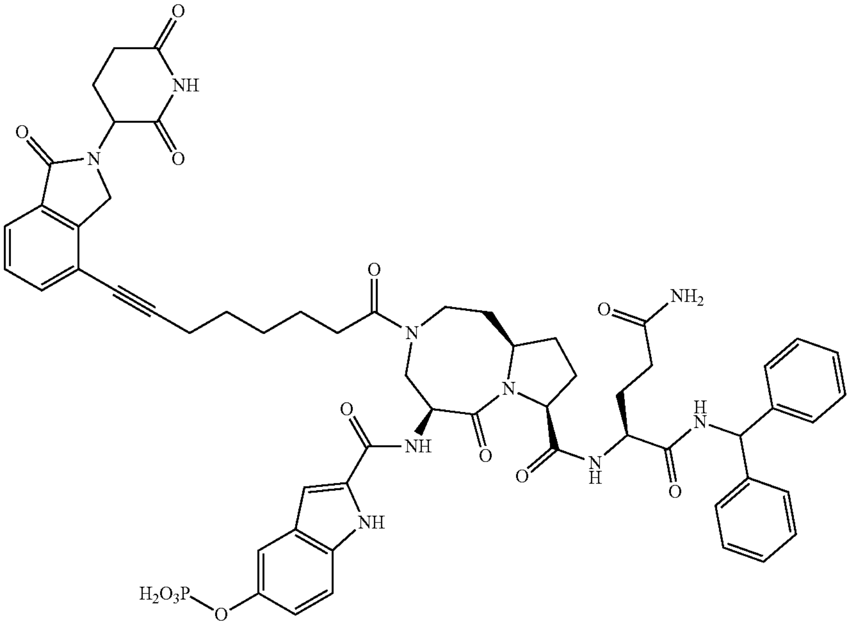
;
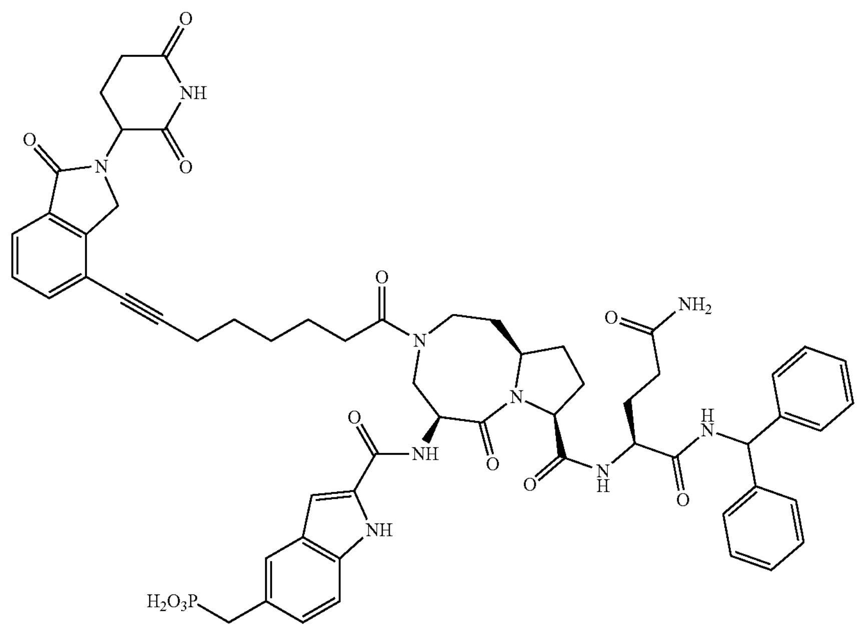
;

-continued
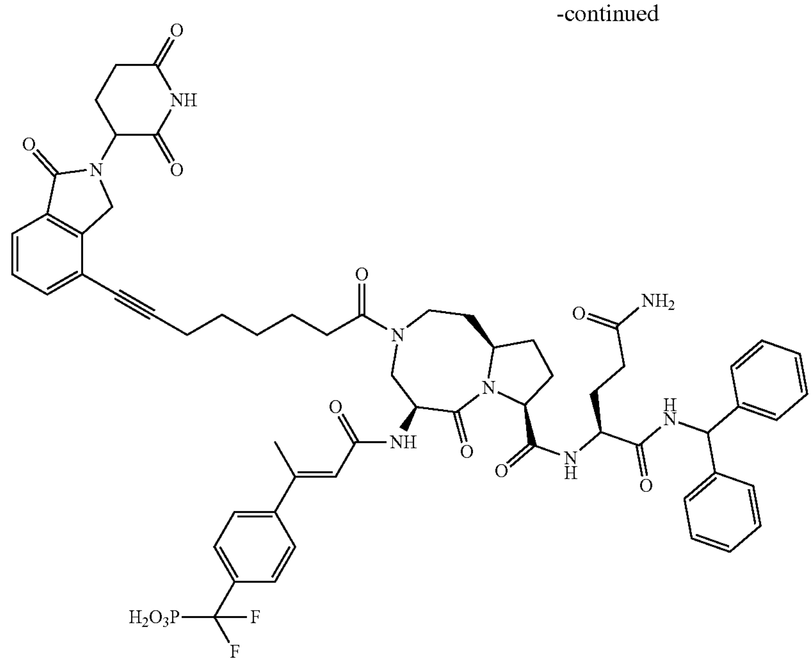
;
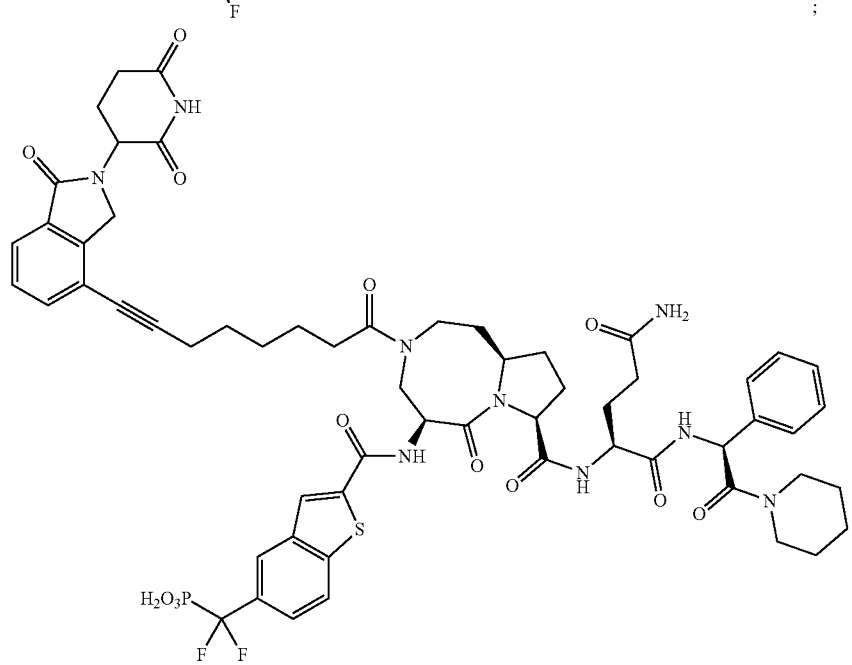
;
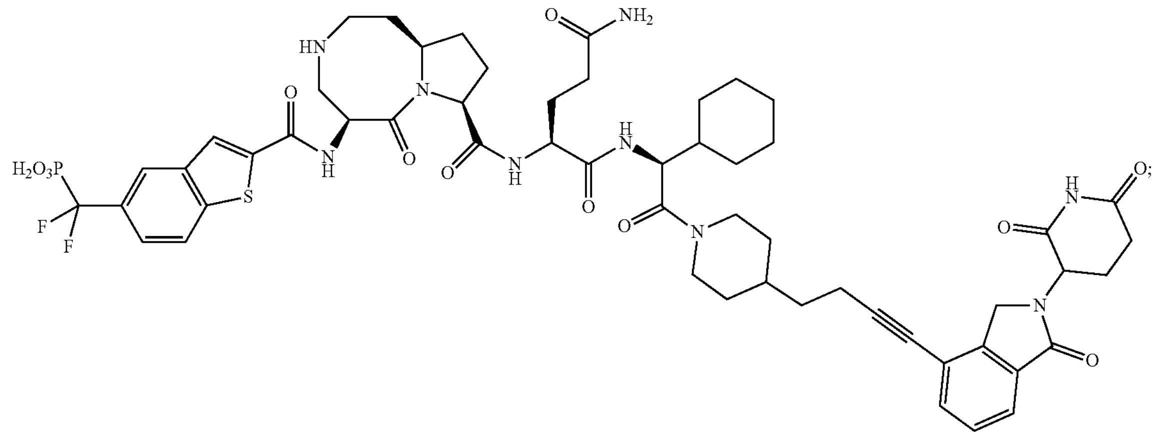
;

-continued
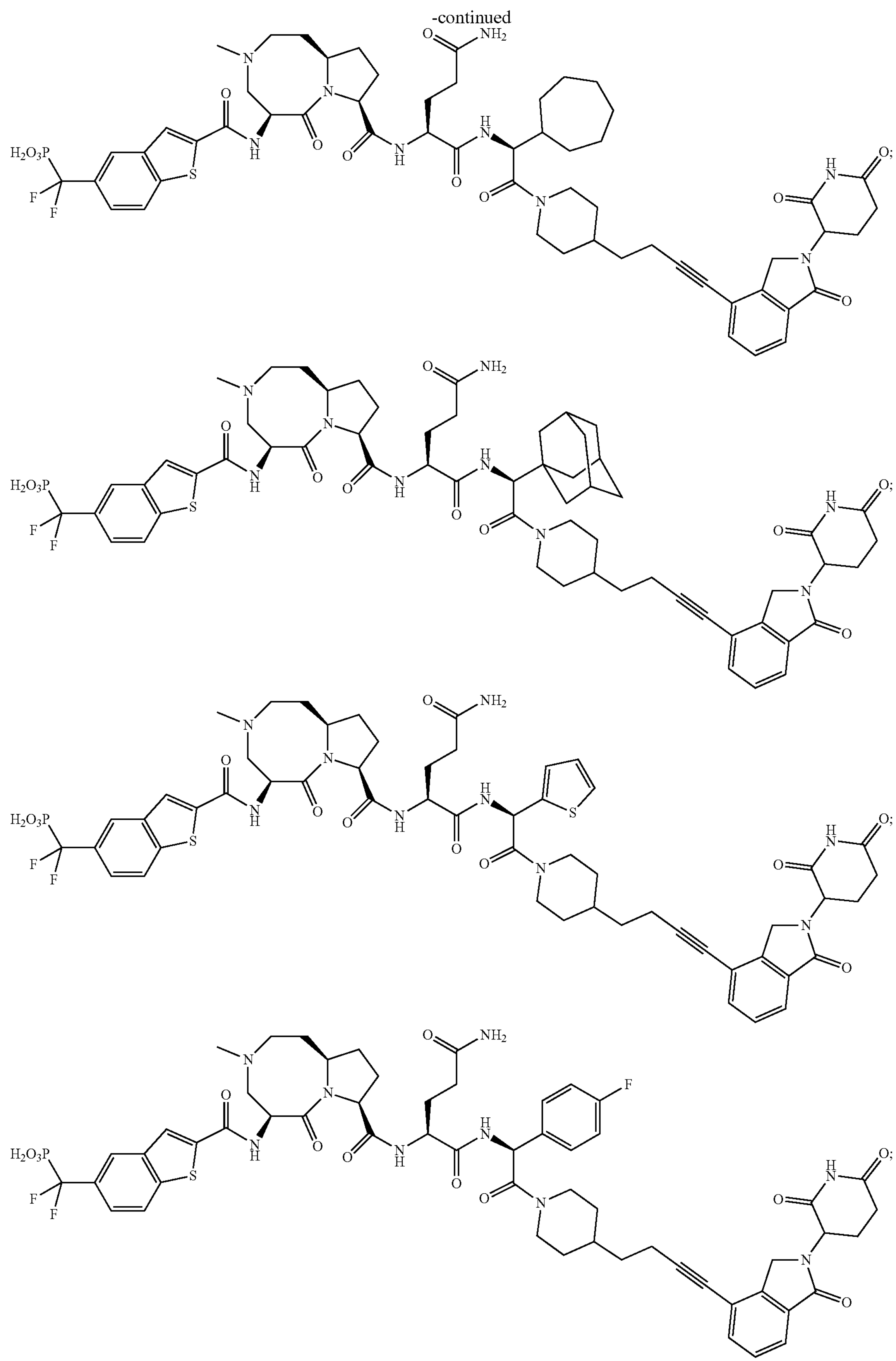

-continued
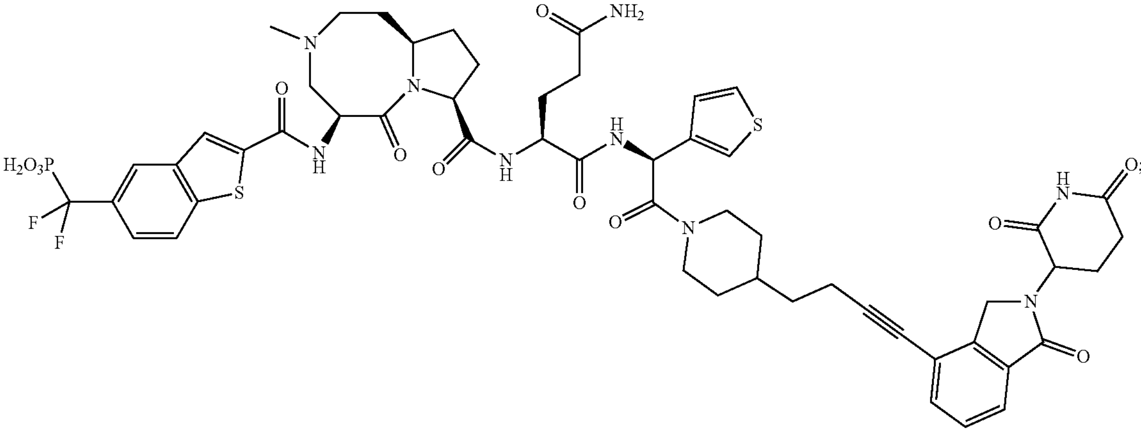
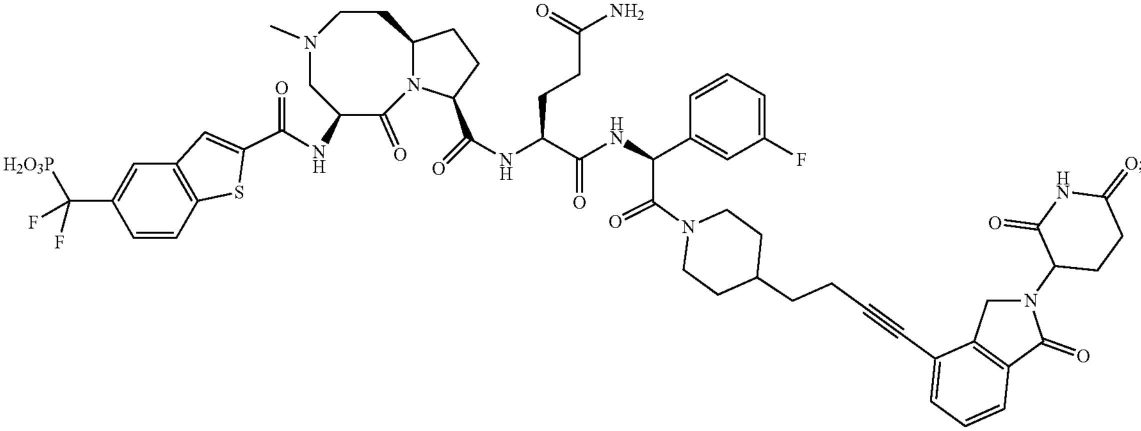
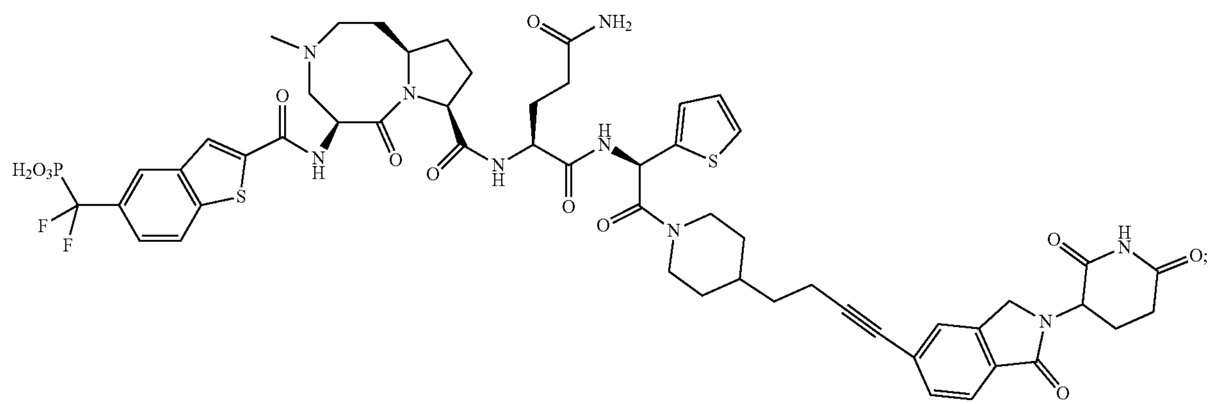

-continued
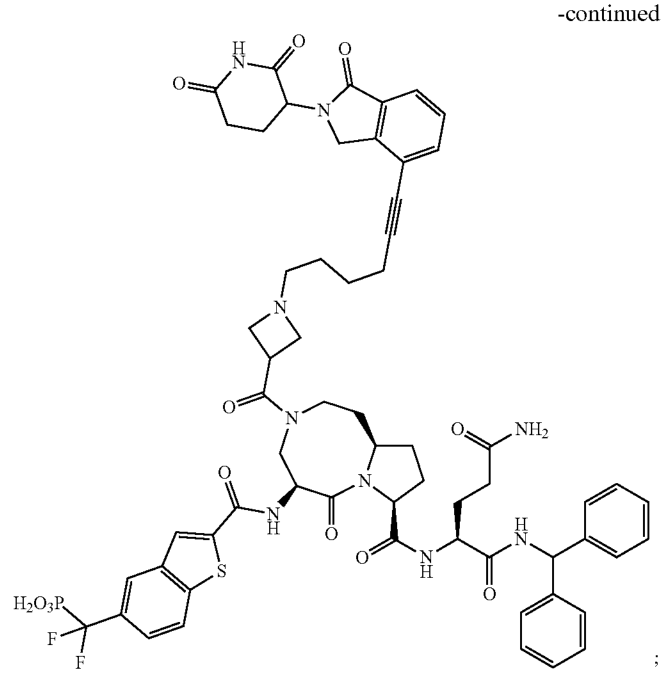
;
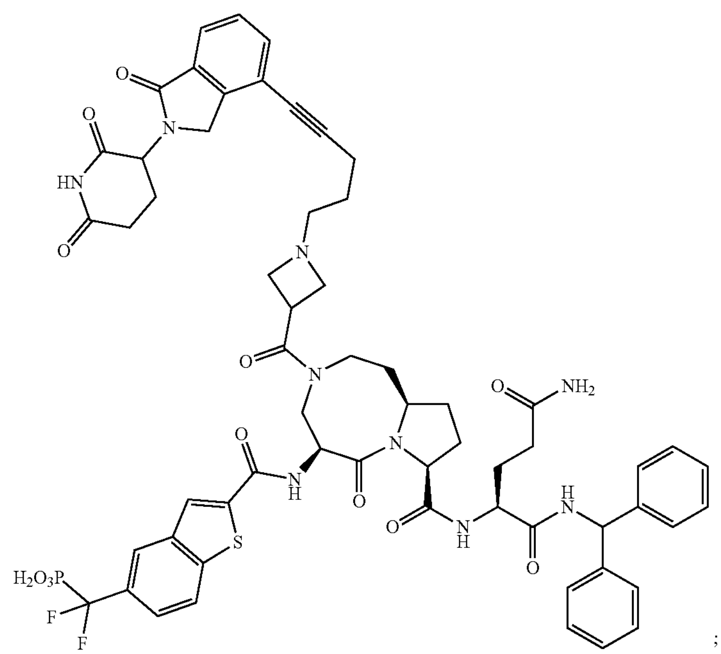
;

-continued
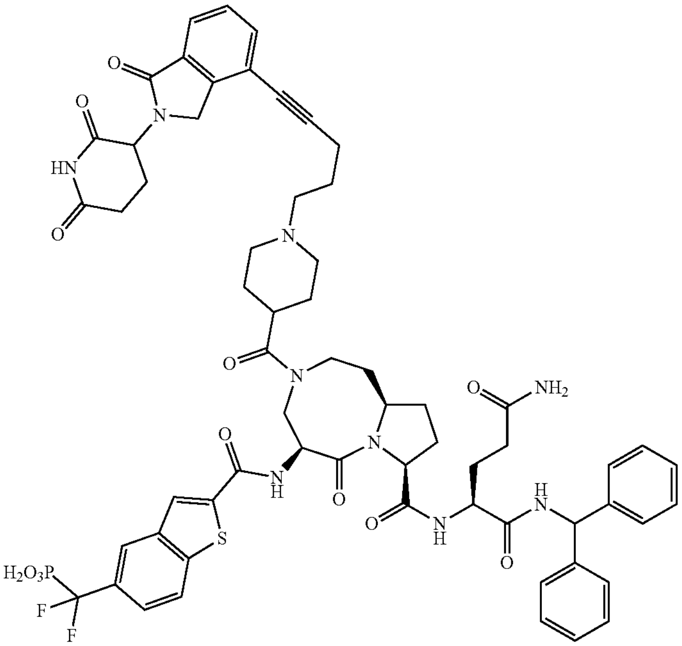
;
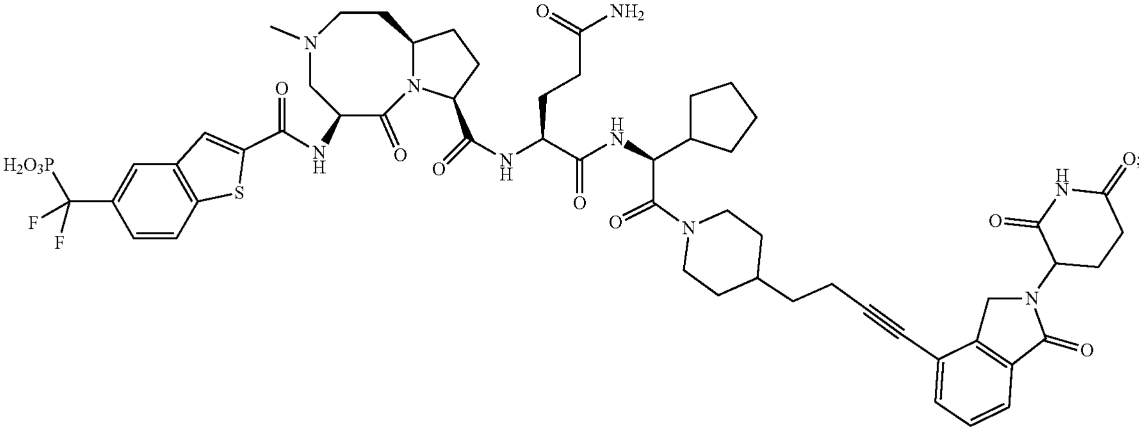
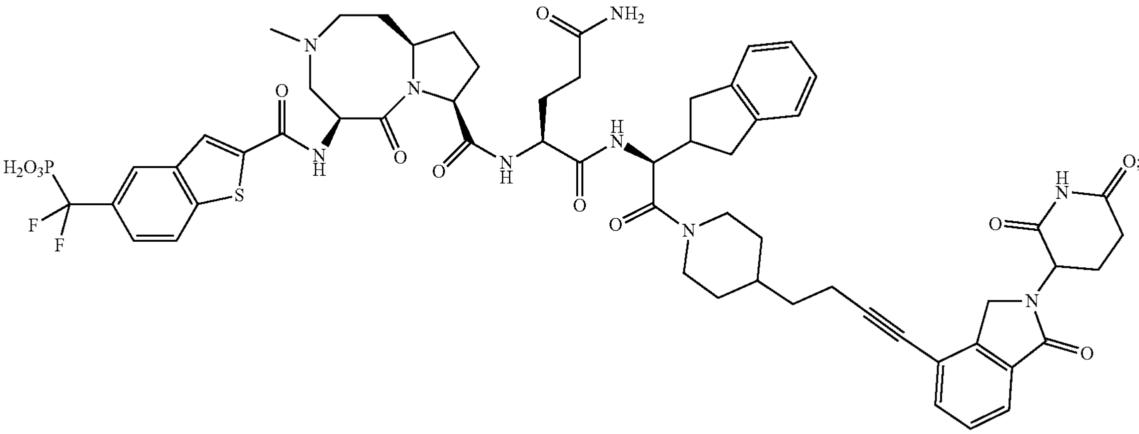

-continued
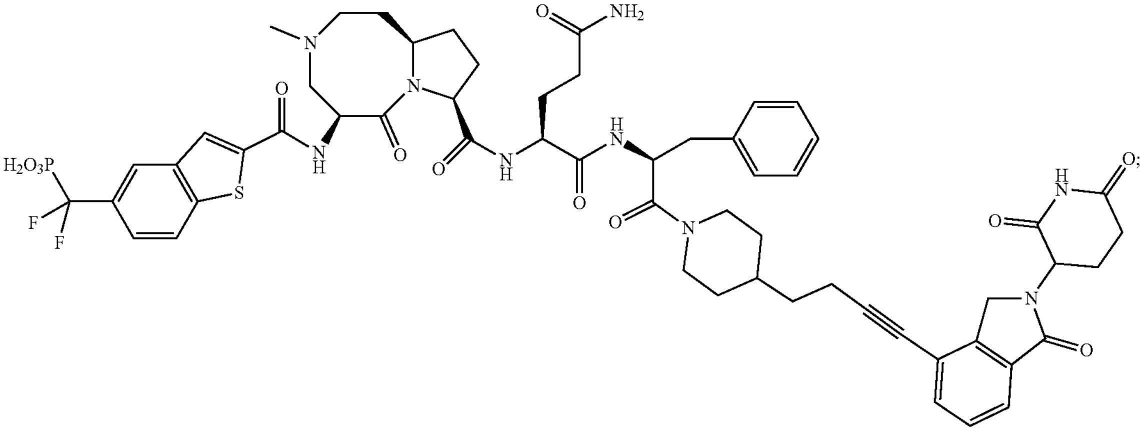
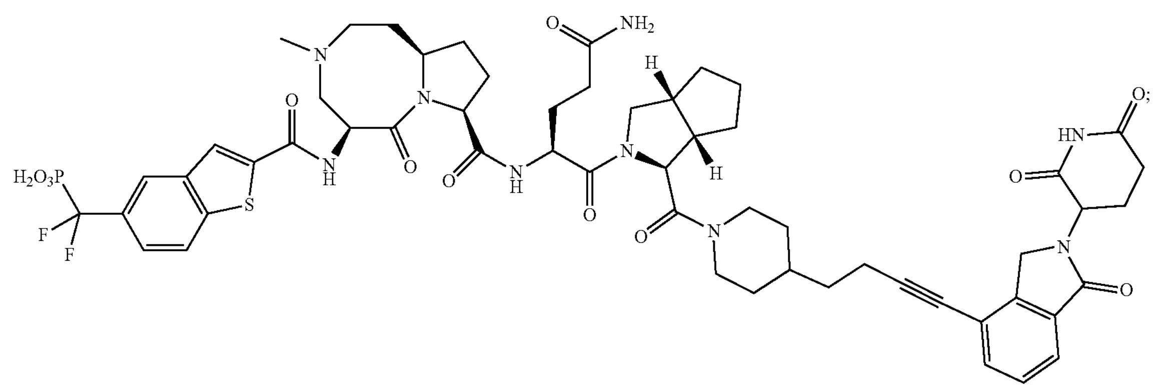
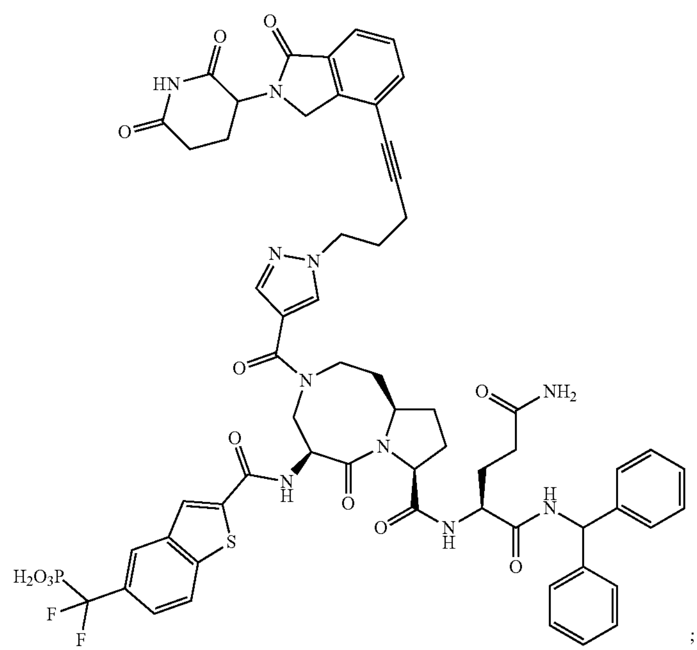
;

-continued
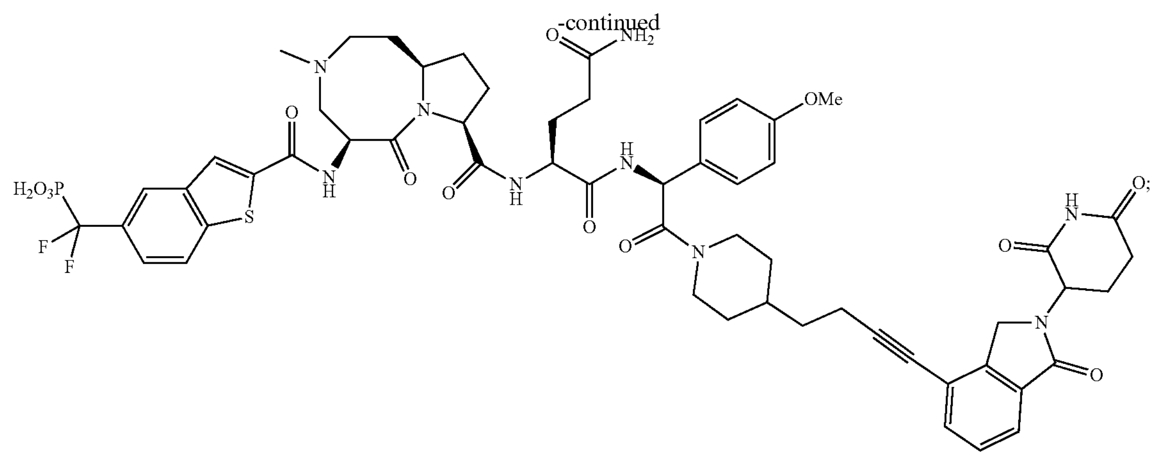
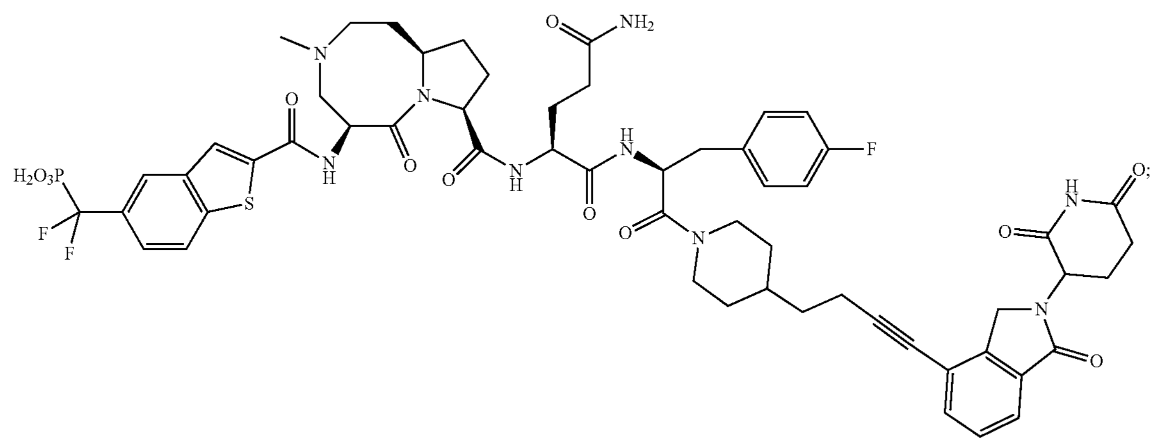
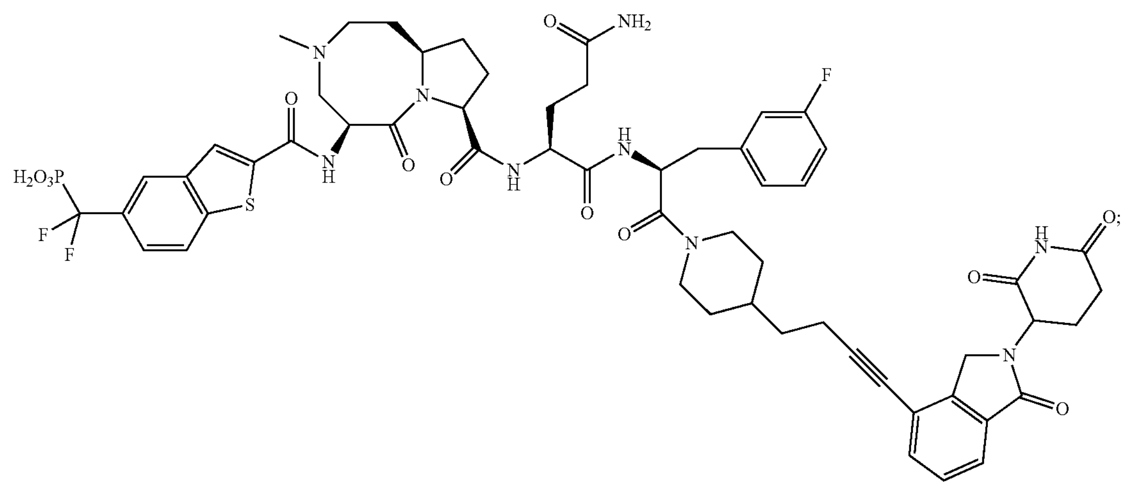

-continued
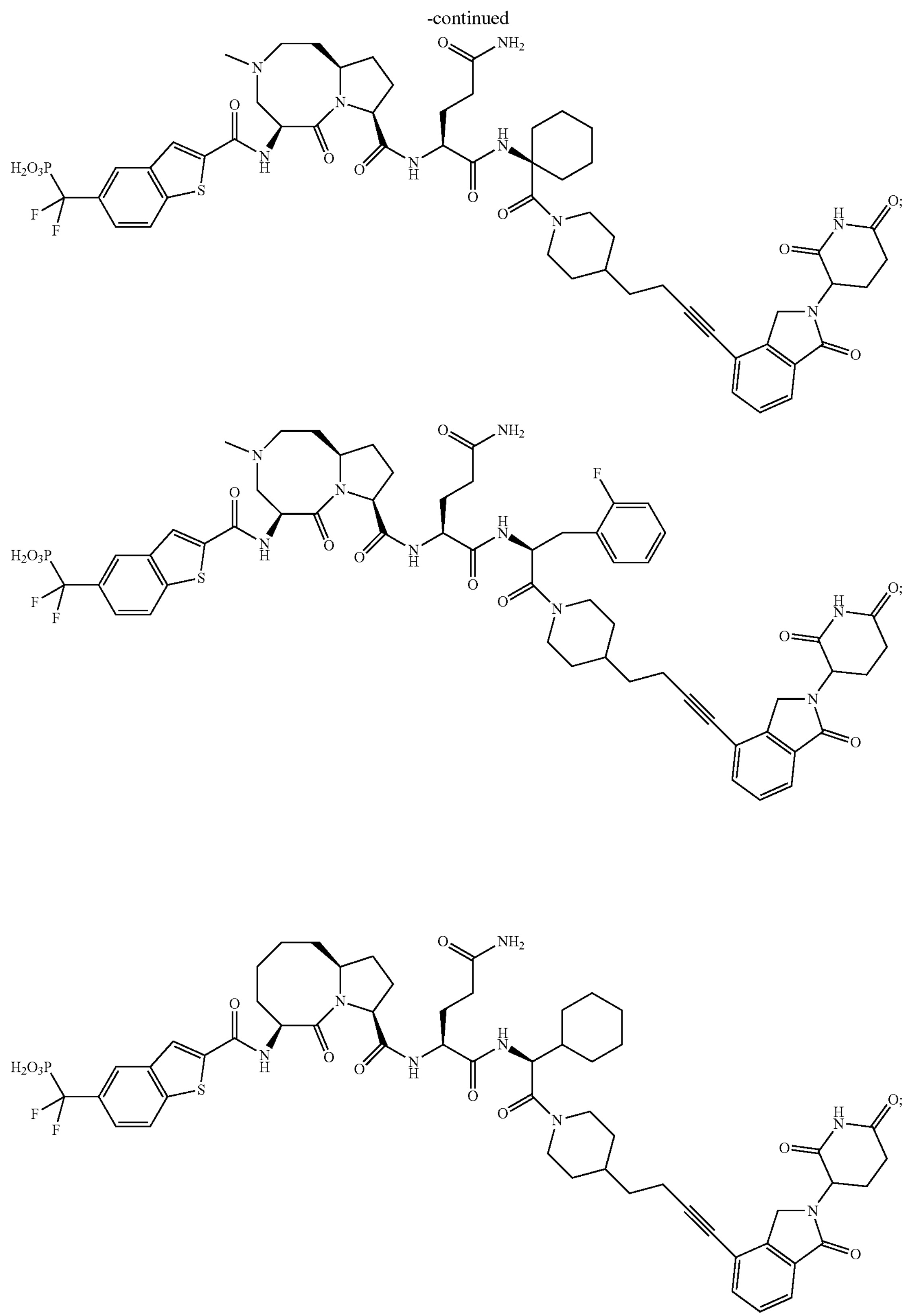

-continued
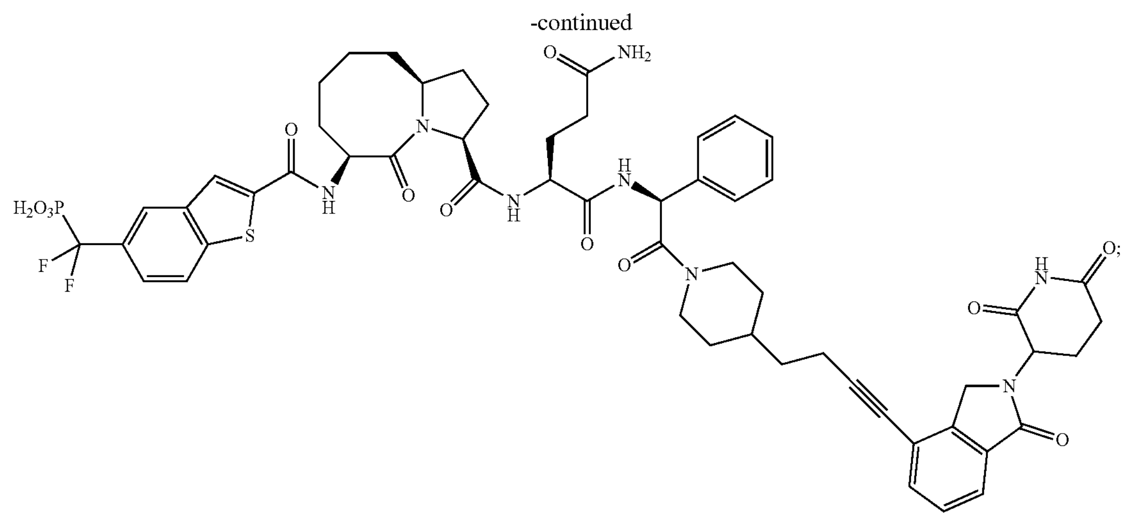
;
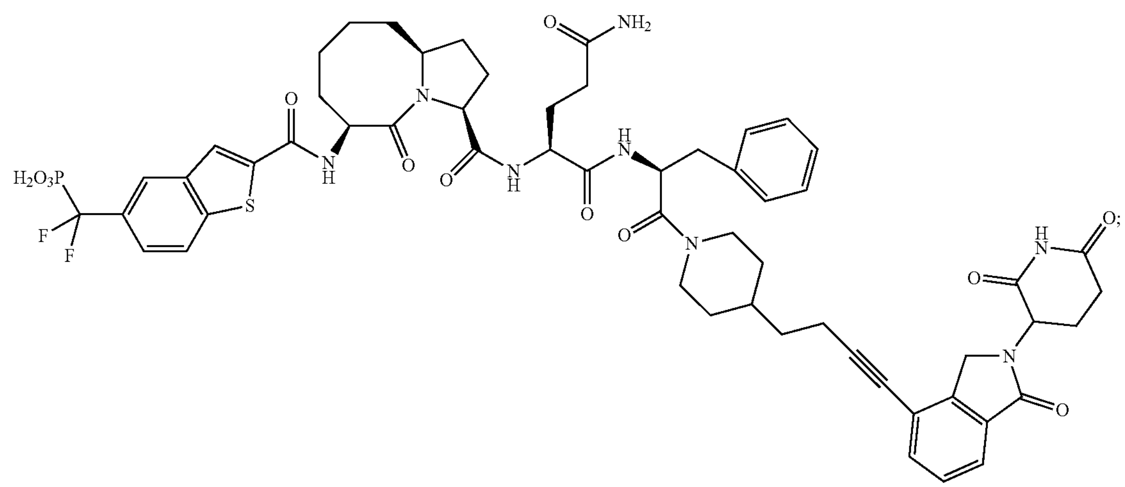
;
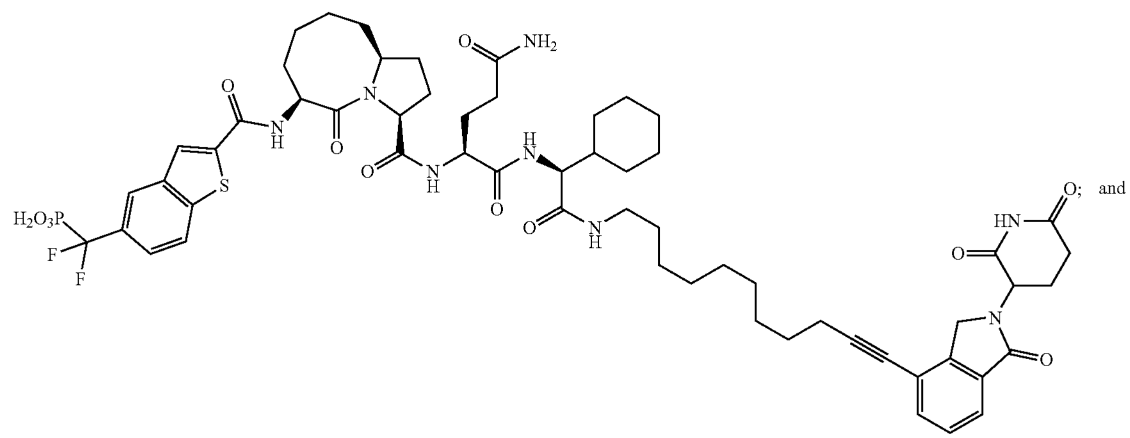
; and

-continued
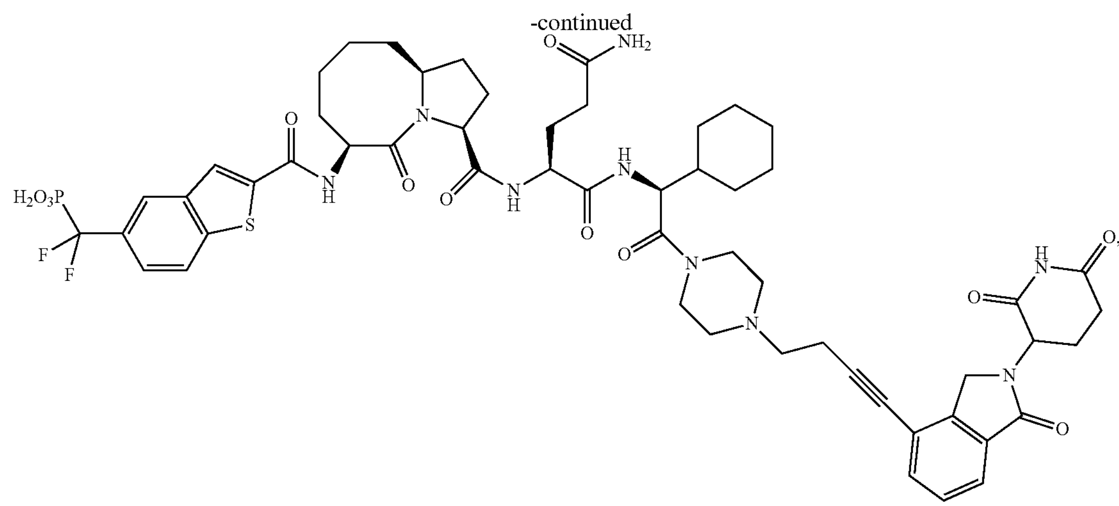
or a pharmaceutically acceptable salt or solvate thereof.
17. A pharmaceutical composition comprising the compound of claim 1, and a pharmaceutically acceptable carrier.
* * * * *